US012435087B2

(12) United States Patent
Nicewonger et al.

(10) Patent No.: US 12,435,087 B2
(45) Date of Patent: Oct. 7, 2025

(54) MODULATORS OF DCN-1 AND METHODS OF USE THEREOF

(71) Applicant: Cellarity, Inc., Somerville, MA (US)

(72) Inventors: Robert Brian Nicewonger, Tyngsboro, MA (US); Mauricio Cortes, Wellesley, MA (US); Colin Diner, Somerville, MA (US); Sriram Krishnamoorthy, Acton, MA (US); Na Li, Winchester, MA (US); Frank Lovering, Acton, MA (US); Kristen Marino, Stoneham, MA (US); Samuel Miller, Cambridge, MA (US); Qing Tang, Boxborough, MA (US); Atli Thorarensen, Stow, MA (US); Ravi Ujjinamatada, Lexington, MA (US); David Zhang, West Roxbury, MA (US)

(73) Assignee: Cellarity, Inc., Somerville, MA (US)

( * ) Notice: Subject to any disclaimer, the term of this patent is extended or adjusted under 35 U.S.C. 154(b) by 0 days.

(21) Appl. No.: 18/935,253

(22) Filed: Nov. 1, 2024

(65) Prior Publication Data

US 2025/0163058 A1 May 22, 2025

Related U.S. Application Data

(60) Provisional application No. 63/661,523, filed on Jun. 18, 2024, provisional application No. 63/655,542, filed on Jun. 3, 2024, provisional application No. 63/547,254, filed on Nov. 3, 2023.

(51) Int. Cl.

*C07D 471/04* (2006.01)
*C07D 519/00* (2006.01)

(52) U.S. Cl.

CPC ......... *C07D 471/04* (2013.01); *C07D 519/00* (2013.01)

(58) Field of Classification Search

CPC .................................................... C07D 471/04
USPC ......................................................... 546/112
See application file for complete search history.

(56) References Cited

U.S. PATENT DOCUMENTS

| | | | | |
|---|---|---|---|---|
| 10,525,048 | B2 * | 1/2020 | Min | C07D 401/06 |
| 2014/0057938 | A1 | 2/2014 | Dounay et al. | |
| 2022/0017908 | A1 | 1/2022 | Rahl et al. | |

FOREIGN PATENT DOCUMENTS

| | | | |
|---|---|---|---|
| EP | 3609876 | B1 | 3/2022 |
| WO | 2017049295 | A1 | 3/2017 |
| WO | 2018183411 | A1 | 10/2018 |
| WO | 2020257790 | A1 | 12/2020 |

OTHER PUBLICATIONS

Kim et al., "Improvement of Oral Bioavailability of Pyrazolo-Pyridone Inhibitors of the Interaction of DCN1/2 and UBE2M," J. Med. Chem. 2021;64:5850-5862.

Kim et al., "Discovery of Novel Pyrazolo-pyridone DCN1 Inhibitors Controlling Cullin Neddylation," J. Med. Chem. 2019;62(18):8429-8442.

Zhou et al., "Selective inhibition of cullin 3 neddylation through covalent targeting DCN1 protects mice from acetaminophen-induced liver toxicity," Nature Communications 2021; 12:2621.

Scott et al., "Blocking an N-terminal acetylation-dependent protein interaction inhibits an E3 ligase," Nature Chemical Biology 2017;13:850-857.

Hammill et al. "Discovery of an Orally Bioavailable Inhibitor of Defective in Cullin Neddylation 1 (DCN1)-Mediated Cullin Neddylation," J. Med. Chem. 2018;61:2694-2706.

Hammill et al., "Piperidinyl Ureas Chemically Control Defective in Cullin Neddylation 1 (DCN1)-Mediated Cullin Neddylation," J. Med. Chem. 2018;61:2680-2693.

Shi et al., "An efficient synthesis of new class of pyrazolo[3,4-b]pyridine-6-one derivatives by a novel cascade reaction," Journal of Heterocyclic Chemistry 2007;44(5):1013-1017.

PCT International Search Report for PCT/US2024/054169 dated Feb. 12, 2025.

PCT International Search Report for PCT/US2024054133 dated Feb. 18, 2025.

PCT International Search Report for PCT/US2024/054278 dated Feb. 20, 2025.

PubChem_CID_155415365, create date: Jan. 30, 2021, p. 2 formula.

* cited by examiner

*Primary Examiner* — Niloofar Rahmani

(74) *Attorney, Agent, or Firm* — Dechert LLP; John P. Rearick; Joseph W. Arico

(57) ABSTRACT

The present disclosure provides DCN-1 modulating compounds, pharmaceutically acceptable salts thereof, pharmaceutical compositions, and their use for treating sickle cell disorders, diseases, and conditions. Such compounds are of Formula Ia:

Ia

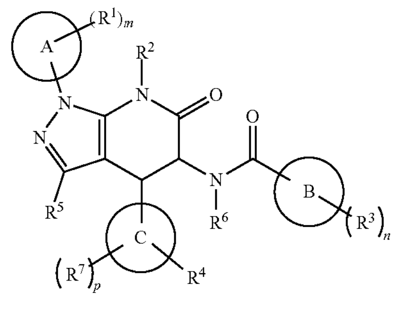

or a pharmaceutically acceptable salt thereof.

27 Claims, 5 Drawing Sheets

MODULATORS OF DCN-1 AND METHODS OF USE THEREOF

CROSS-REFERENCE TO RELATED APPLICATIONS

This application claims the benefit of United States Provisional Patent Application Nos. 63/661,523, filed Jun. 18, 2024; 63/655,542, filed Jun. 3, 2024; and 63/547,254, filed Nov. 3, 2023; the entire contents each of which are hereby incorporated by reference.

TECHNICAL FIELD OF THE INVENTION

The present disclosure relates generally to various compounds and compositions useful in the treatment of hemoglobin-related disorders including sickle cell disorders, diseases, and conditions, and thalassemia.

BACKGROUND OF THE INVENTION

Hemoglobinopathies are diseases that affect hemoglobin that include sickle cell disease and thalassemia. Sickle cell disease or disorder is a group of inherited red blood cell disorders that affect hemoglobin and can block blood flow to the body. Specifically, a defective beta hemoglobin chain in sickle cell patients twists and changes the shape of each red blood cell from a doughnut-like shape into a “sickled” or croissant shape that can clog small blood vessels and prevent the delivery of oxygen around the body. Sickle-cell disease is characterized by various acute and chronic complications, which are associated with significant morbidity and mortality in an afflicted subject. Thalassemia is also an inherited red blood cell disorder that is caused by a defect in the beta-globin gene, controlling the production of the beta-globin chains of hemoglobin. Accordingly, a patient suffering from thalassemia can’t make enough normal hemoglobin and thus has relatively fewer red blood cells and lower blood oxygen levels than people who do not suffer from the disease. Thalassemia patients may not make enough of either or both of the alpha or beta proteins in hemoglobin.

The cullin family of ubiquitination E3s are the most well-characterized substrates of neddylation. Upon neddylation, the cullins constellate the cullin-RING E3 UB ligase family (CRLs), which has approximately 300 members. The CRLs regulate diverse biological processes including cell cycle, signal transduction, DNA replication, and viral modulation. CRL dysfunction is implicated in a number of human diseases, including cancer. Drug discovery efforts targeting the CRLs and the associated proteasomal protein degradation machinery have been extensive and continue to grow. The neddylation pathway has been successfully targeted by MLN4924 (Pevonedistat), an inhibitor of NEDD8’s E1 enzyme, that completely blocks NEDD8 ligation to substrates. MLN4924 is currently being tested in oncology clinical trials. An inhibitor of the COP9 signalosome, responsible for de-neddylation of the CRLs, has been reported and also displays anti-tumor activity. Defective in cullin neddylation 1 (DCN-1) is a protein that interacts with cullins and is required for neddylation. DCN-1 is also known as DCUN1D1, DCNL1 or Squamous Cell Carcinoma-related Oncogene (SCCRO). DCN-1 is the most well characterized isoform due to its common amplification as part of a large 3q26.3 amplicon in squamous cell carcinomas (SCC) and other tumors. DCN-1 amplification in SCC negatively correlates with cause-specific survival, suggesting that targeting DCN-1 may be of clinical utility in cancers. Its role in other diseases remains under-explored.

There remains a need to find therapeutic agents, methods, and therapies for the treatment of hemoglobin-related disorders including sickle cell disorders, diseases and conditions and thalassemia. The present invention fulfils this need and provides other related advantages.

DETAILED DESCRIPTION OF CERTAIN EMBODIMENTS

Figure 1A:
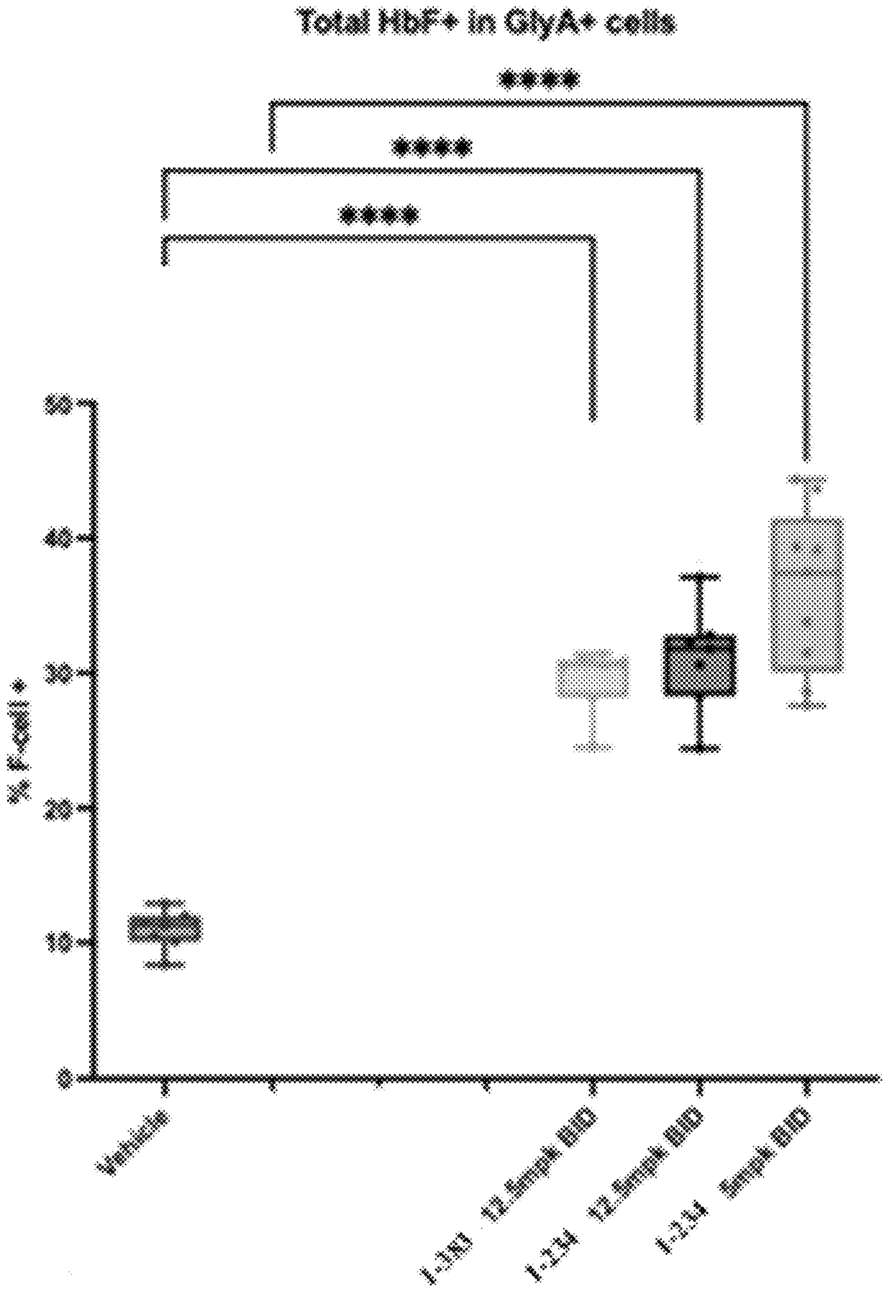
FIGS. 1A, 1B, 2A, 2B and 2C show compounds I-383 and I-234 that were evaluated for their ability to induce fetal hemoglobin protein as shown by percentage F-cells (flow-cytometry) and HPLC. HBG1 expression, is shown both as HBG1 alone or as HBG1 to total beta hemoglobin mRNA (fetal HBG1 plus adult-type HBB), both measured by NanoString.

1. General Description of Certain Embodiments of the Invention; Definitions

It has now been found that the compounds and compositions of the disclosure can modulate DCN-1, induce fetal hemoglobin and are useful in treating hemoglobin-related disorders including sickle cell disorders, diseases and conditions, and thalassemia.

In one aspect, the present disclosure provides a compound of Formula Ia:

Ia

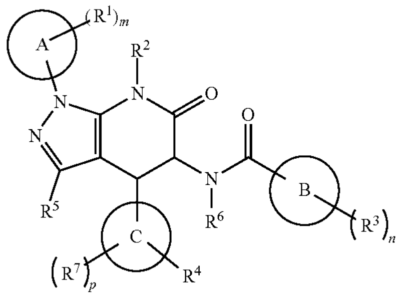

or a pharmaceutically acceptable salt thereof, wherein:

Ring A is phenyl, 3-8 membered saturated or partially unsaturated monocyclic carbocyclic ring, and a 5-6 membered monocyclic heteroaromatic ring having 1-4 heteroatoms independently selected from nitrogen, oxygen, and sulfur;

Ring B is phenyl, or a 5-6 membered monocyclic heteroaromatic ring having 1-4 heteroatoms independently selected from nitrogen, oxygen, and sulfur;

Ring C is phenyl, or a 5-6 membered monocyclic heteroaromatic ring having 1-4 heteroatoms independently selected from nitrogen, oxygen, and sulfur;

each occurrence of $R^1$ is independently an optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, or —NRS(O)$_2$R; or two instances of $R^1$ together form a 4-6 membered optionally substituted heterocyclic ring having 1-4 heteroatoms selected from nitrogen, oxygen, and sulfur, or two instances of $R^1$ together form a 4-6 membered optionally substituted carbocyclic ring;

$R^2$ is an optionally substituted group selected from $C_{1-6}$ aliphatic, or a 3-8 membered saturated or partially unsaturated monocyclic carbocyclic ring;

each occurrence of $R^3$ is independently an optionally substituted $C_{1-6}$ aliphatic, $C_{3-6}$ cycloalkyl, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, or —NRS(O)$_2$R;

$R^4$ is a substituent comprising a warhead group;

$R^5$ is hydrogen; or an optionally substituted group selected from $C_{1-6}$ aliphatic;

$R^6$ is hydrogen or an optionally substituted $C_{1-6}$ aliphatic group;

each occurrence of $R^7$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, —NRS(O)$_2$R, phenyl, or a 5-6 membered heteroaromatic ring having 1-3 heteroatoms selected from nitrogen, sulfur, and oxygen;

each occurrence of R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

m is 0, 1, 2, 3, 4, or 5;

n is 0, 1, 2, 3, 4, or 5; and p is 0, 1, 2, 3, 4, or 5.

In one aspect, the present disclosure provides a compound of Formula I:

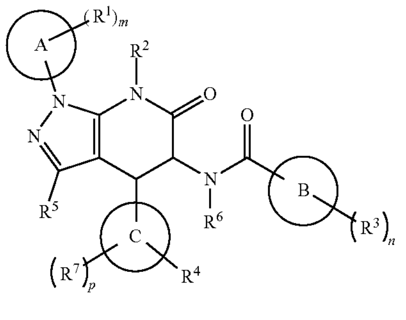

I or a pharmaceutically acceptable salt thereof, wherein:

Ring A is phenyl, 3-8 membered saturated or partially unsaturated monocyclic carbocyclic ring, and a 5-6 membered monocyclic heteroaromatic ring having 1-4 heteroatoms independently selected from nitrogen, oxygen, and sulfur;

Ring B is phenyl, or a 5-6 membered monocyclic heteroaromatic ring having 1-4 heteroatoms independently selected from nitrogen, oxygen, and sulfur;

Ring C is phenyl, or a 5-6 membered monocyclic heteroaromatic ring having 1-4 heteroatoms independently selected from nitrogen, oxygen, and sulfur;

each occurrence of $R^1$ is independently an optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, or —NRS(O)$_2$R;

$R^2$ is an optionally substituted group selected from $C_{1-6}$ aliphatic, or a 3-8 membered saturated or partially unsaturated monocyclic carbocyclic ring;

each occurrence of $R^3$ is independently an optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, or —NRS(O)$_2$R;

$R^4$ is a substituent comprising a warhead group;

$R^5$ is hydrogen; or an optionally substituted group selected from $C_{1-6}$ aliphatic;

$R^6$ is hydrogen or an optionally substituted $C_{1-6}$ aliphatic group;

each occurrence of $R^7$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, —NRS(O)$_2$R, phenyl, or a 5-6 membered heteroaromatic ring having 1-3 heteroatoms selected from nitrogen, sulfur, and oxygen;

each occurrence of R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

m is 0, 1, 2, 3, 4, or 5;

n is 0, 1, 2, 3, 4, or 5; and p is 0, 1, 2, 3, 4, or 5.

As defined generally above, Ring A is selected from phenyl, 3-8 membered saturated or partially unsaturated monocyclic carbocyclic ring, and a 5-6 membered monocyclic heteroaromatic ring having 1-4 heteroatoms independently selected from nitrogen, oxygen, and sulfur.

In some embodiments, Ring A is phenyl. In some embodiments, Ring A is a 3-8 membered saturated monocyclic carbocyclic ring. In some embodiments, Ring A is a 3-8 membered partially unsaturated monocyclic carbocyclic ring. In some embodiments, Ring A is a 5-6 membered monocyclic heteroaromatic ring having 1-4 heteroatoms independently selected from nitrogen, oxygen, and sulfur.

In some embodiments, Ring A is phenyl.

In some embodiments, Ring A is selected from those depicted in Table 1, below.

As defined generally above, Ring B is selected from phenyl, and a 5-6 membered monocyclic heteroaromatic ring having 1-4 heteroatoms independently selected from nitrogen, oxygen, and sulfur.

In some embodiments, Ring B is phenyl. In some embodiments, Ring B is a 5-6 membered monocyclic heteroaromatic ring having 1-4 heteroatoms independently selected from nitrogen, oxygen, and sulfur.

In some embodiments, Ring B, taken together with $(R^3)_n$, is selected from

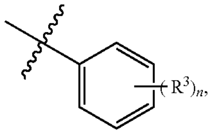

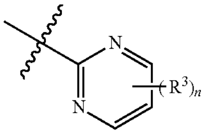

and

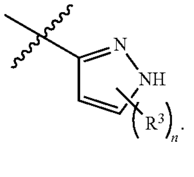

In some embodiments, Ring B, taken together with $(R^3)_n$, is

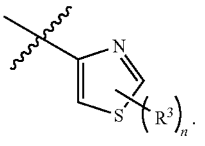

In some embodiments, Ring B is a thiazole, pyridyl, or pyrimidinyl ring.

In some embodiments, Ring B, taken together with $R^3$, is selected from

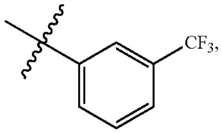

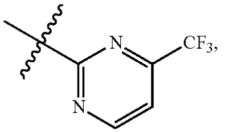

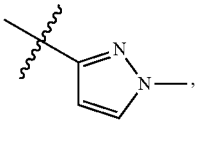

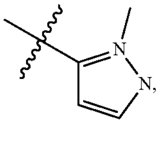

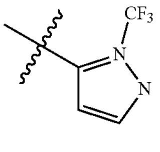

and

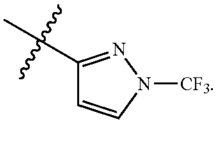

In some embodiments, Ring B, taken together with $R^3$, is

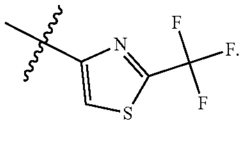 [SMILES: *c1csc(C(F)(F)F)n1]

In some embodiments, Ring B, taken together with $R^3$, is

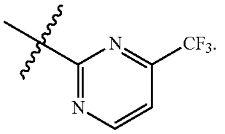 [SMILES: *c1nccc(C(F)(F)F)n1]

In some embodiments, Ring B is selected from those depicted in Table 1, below.

As defined generally above, Ring C is selected from phenyl, and a 5-6 membered monocyclic heteroaromatic ring having 1-4 heteroatoms independently selected from nitrogen, oxygen, and sulfur.

In some embodiments, Ring C is phenyl. In some embodiments, Ring C is a 5-6 membered monocyclic heteroaromatic ring having 1-4 heteroatoms independently selected from nitrogen, oxygen, and sulfur.

In some embodiments, Ring C is phenyl.

In some embodiments, Ring C is selected from those depicted in Table 1, below.

As defined generally above, each occurrence of $R^1$ is independently an optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, or —NRS(O)$_2$R; or two instances of $R^1$ together form a 4-6 membered optionally substituted heterocyclic ring having 1-4 heteroatoms selected from nitrogen, oxygen, and sulfur, or two instances of $R^1$ together form a 4-6 membered optionally substituted carbocyclic ring.

In some embodiments, each occurrence of $R^1$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, or —NRS(O)$_2$R.

In some embodiments, $R^1$ is a $C_{1-6}$ aliphatic group. In some embodiments, $R^1$ is a substituted $C_{1-6}$ aliphatic group. In some embodiments, $R^1$ is halogen. In some embodiments, $R^1$ is —CN. In some embodiments, $R^1$ is —C(O)R. In some embodiments, $R^1$ is —C(O)OR. In some embodiments, $R^1$ is —OC(O)R. In some embodiments, $R^1$ is —C(O)N(R)$_2$. In some embodiments, $R^1$ is —N(R)C(O)R. In some embodiments, $R^1$ is —N(R)C(O)N(R)$_2$. In some embodiments, $R^1$ is —OC(O)N(R)$_2$. In some embodiments, $R^1$ is —N(R)C(O)OR. In some embodiments, $R^1$ is —OR. In some embodiments, $R^1$ is —N(R)$_2$. In some embodiments, $R^1$ is —$NO_2$. In some embodiments, $R^1$ is —SR. In some embodiments, $R^1$ is —S(O)R. In some embodiments, $R^1$ is —S(O)$_2$R. In some embodiments, $R^1$ is —S(O)$_2$N(R)$_2$. In some embodiments, $R^1$ is —NRS(O)$_2$R.

In some embodiments, $R^1$ is selected from those depicted in Table 1, below.

As defined generally above, $R^2$ is an optionally substituted group selected from $C_{1-6}$ aliphatic, or a 3-8 membered saturated or partially unsaturated monocyclic carbocyclic ring.

In some embodiments, $R^2$ is a $C_{1-6}$ aliphatic group. In some embodiments, $R^2$ is a substituted $C_{1-6}$ aliphatic group. In some embodiments, $R^2$ is a 3-8 membered saturated monocyclic carbocyclic ring. In some embodiments, $R^2$ is a 3-8 membered partially unsaturated monocyclic carbocyclic ring. In some embodiments, $R^2$ is a substituted 3-8 membered saturated monocyclic carbocyclic ring. In some embodiments, $R^2$ is a substituted 3-8 membered partially unsaturated monocyclic carbocyclic ring.

In some embodiments, $R^2$ is selected from

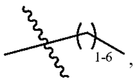,
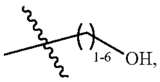,
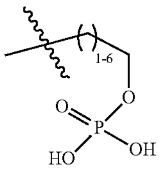
and
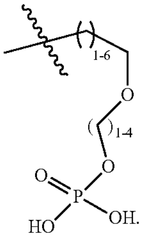

In some embodiments, $R^2$ is selected from ethyl,

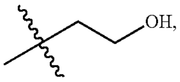,
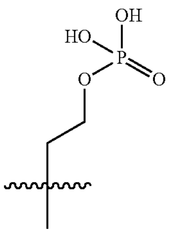
and
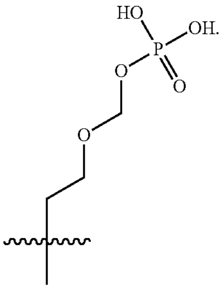

In some embodiments, $R^2$ is selected from $C_{1-6}$ alkyl optionally substituted with 1, 2, 3, 4, 5, or 6 halogen or deuterium atoms.

In some embodiments, $R^2$ is selected from methyl, —$CD_3$, —$CF_3$, ethyl, —$CH_2CF_3$, n-propyl, isopropyl, n-butyl, and s-butyl.

In some embodiments, $R^2$ is ethyl.

In some embodiments, $R^2$ is selected from those depicted in Table 1, below.

As defined generally above, each occurrence of $R^3$ is independently an optionally substituted $C_{1-6}$ aliphatic, $C_{3-6}$ cycloalkyl, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, or —NRS(O)$_2$R.

In some embodiments, each occurrence of $R^3$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, or —NRS(O)$_2$R.

In some embodiments, $R^3$ is a $C_{1-6}$ aliphatic group. In some embodiments, $R^3$ is a substituted $C_{1-6}$ aliphatic group. In some embodiments, $R^3$ is halogen. In some embodiments, $R^3$ is —CN. In some embodiments, $R^3$ is —C(O)R. In some embodiments, $R^3$ is —C(O)OR. In some embodiments, $R^3$ is —OC(O)R. In some embodiments, $R^3$ is —C(O)N(R)$_2$. In some embodiments, $R^3$ is —N(R)C(O)R. In some embodiments, $R^3$ is —N(R)C(O)N(R)$_2$. In some embodiments, $R^3$ is —OC(O)N(R)$_2$. In some embodiments, $R^3$ is —N(R)C(O)OR. In some embodiments, $R^3$ is —OR. In some embodiments, $R^3$ is —N(R)$_2$. In some embodiments, $R^3$ is —$NO_2$. In some embodiments, $R^3$ is —SR. In some embodiments, $R^3$ is —S(O)R. In some embodiments, $R^3$ is —S(O)$_2$R. In some embodiments, $R^3$ is —S(O)$_2$N(R)$_2$. In some embodiments, $R^3$ is —NRS(O)$_2$R.

In some embodiments, $R^3$ is a $C_{1-6}$ aliphatic group substituted with 1, 2, or 3 halogen atoms. In some embodiments, $R^3$ is a $C_{1-6}$ alkyl group substituted with 1, 2, or 3 halogen atoms.

In some embodiments, $R^3$ is a $C_{1-6}$ alkyl group, —$C_{1-6}$ alkylene, —OR, —$C_{2-4}$ alkenyl, —$C_{2-4}$ alkynyl, halogen, —OR, —C(O)R, —CN, —C(O)$NR_2$, —NHMe, —$NMe_2$, or —$NH_2$.

In some embodiments, $R^3$ is —$CF_3$.

In some embodiments, $R^3$ is selected from those depicted in Table 1, below.

As defined generally above, $R^4$ is a substituent comprising a warhead group.

In some embodiments, the warhead group comprises an electrophilic group capable of reacting with a nucleophile under biological conditions to form a covalent bond to the nucleophile.

In some embodiments, the warhead group comprises an electrophilic group capable of reacting with the thiol group of a cysteine under biological conditions to form a covalent bond to the cysteine. In some embodiments, the warhead group comprises an epoxide, a Michael acceptor (e.g., substituted or unsubstituted acrylamide, substituted or unsubstituted acrylate, substituted or unsubstituted alpha halo acetamide), an alkyl chloride, alkyl bromide, alkyl iodide, a sulfonyl halide, an alpha-halo ketone, an alpha-halo amide, an aldehyde, an aminonitrile, an N-cyanamide, a nitrile, a vinyl sulfone, a vinyl sulfonamide, or an anhydride. In some embodiments, the warhead groups comprise those described in Table 1c.

In some embodiments, the warhead group is -$L^2$-Y, wherein:

- $L^2$ is a covalent bond or a bivalent $C_{1-8}$ saturated or unsaturated, straight or branched, hydrocarbon chain, wherein one, two, or three methylene units of $L^2$ are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —O—P(O)(OR)O—, —C(=S)—, —C(=NR)—, —N=N—, or —C(=$N_2$)—;
- Y is hydrogen, $C_{1-6}$ aliphatic optionally substituted with oxo, halogen, $NO_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and
- each $R^e$ is independently selected from -Q-Z, oxo, $NO_2$, halogen, CN, a suitable leaving group, or a $C_{1-6}$ aliphatic optionally substituted with oxo, halogen, $NO_2$, or CN, wherein:

- Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and
- Z is hydrogen or $C_{1-6}$ aliphatic optionally substituted with oxo, halogen, $NO_2$, or CN.

In certain embodiments, $L^2$ is a covalent bond. In certain embodiments, $L^2$ is a bivalent $C_{1-8}$ saturated or unsaturated, straight or branched, hydrocarbon chain. In certain embodiments, $L^2$ is —$CH_2$.

In certain embodiments, $L^2$ is a covalent bond, —$CH_2$—, —NH—, —$CH_2$NH—, —NH$CH_2$—, —NHC(O)—, —NHC(O)$CH_2$OC(O)—, —$CH_2$NHC(O)—, —NH$SO_2$—, —NH$SO_2CH_2$—, —NHC(O)$CH_2$OC(O)—, or —$SO_2$NH—.

In some embodiments, $L^2$ is a bivalent $C_{2-8}$ straight or branched, hydrocarbon chain wherein $L^2$ has at least one double bond and one or two additional methylene units of $L^2$ are optionally and independently replaced by —NRC(O)—, —C(O)NR—, —N(R)$SO_2$—, —$SO_2$N(R)—, —S—, —S(O)—, —$SO_2$—, —OC(O)—, —C(O)O—, cyclopropylene, —O—, —N(R)—, —O—P(O)(OR)O—, or —C(O)—.

In certain embodiments, $L^2$ is a bivalent $C_{2-8}$ straight or branched, hydrocarbon chain wherein $L^2$ has at least one double bond and at least one methylene unit of $L^2$ is replaced by —C(O)—, 13 NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of $L^2$ are optionally and independently replaced by cyclopropylene, —O—, —N(R)—, or —C(O)—.

In some embodiments, $L^2$ is a bivalent $C_{2-8}$ straight or branched, hydrocarbon chain wherein $L^2$ has at least one double bond and at least one methylene unit of $L^2$ is replaced by —C(O)—, and one or two additional methylene units of $L^2$ are optionally and independently replaced by cyclopropylene, —O—, —N(R)—, —O—P(O)(OR)O—, or —C(O)—. In some embodiments, $L^2$ is a bivalent $C_{2-8}$ straight or branched, hydrocarbon chain wherein $L^2$ has at least one double bond and at least one methylene unit of $L^2$ is replaced by —C(O)—, and one or two additional methylene units of $L^2$ are optionally and independently replaced by cyclopropylene, —O—, —N(R)—, —O—P(O)(OR)O—, or —C(O)—, wherein at least one double bond is located in an alpha-beta position relative to a —C(O)—.

As described above, in certain embodiments, $L^2$ is a bivalent $C_{2-8}$ straight or branched, hydrocarbon chain wherein $L^2$ has at least one double bond. One of ordinary skill in the art will recognize that such a double bond may exist within the hydrocarbon chain backbone or may be "exo" to the backbone chain and thus forming an alkylidene group. By way of example, such an $L^2$ group having an alkylidene branched chain includes —$CH_2$C(=$CH_2$)$CH_2$—. Thus, in some embodiments, $L^2$ is a bivalent $C_{2-8}$ straight or branched, hydrocarbon chain wherein $L^2$ has at least one alkylidenyl double bond. In some embodiments, $L^2$ is a bivalent $C_{2-8}$ straight or branched, hydrocarbon chain wherein $L^2$ has at least one alkylidenyl double bond located in an alpha-beta position relative to a —C(O)—. Exemplary $L^2$ groups include —NHC(O)C(=$CH_2$)$CH_2$.

In certain embodiments, $L^2$ is a bivalent $C_{2-8}$ straight or branched, hydrocarbon chain wherein $L^2$ has at least one double bond and at least one methylene unit of $L^2$ is replaced by —C(O)—. In certain embodiments, $L^2$ is —C(O)CH=CH($CH_3$)—, —C(O)CH=CH$CH_2$NH($CH_3$)—, —C(O)CH=CH($CH_3$)—, —C(O)CH=CH—, —$CH_2$C(O)CH=CH—, —$CH_2$C(O)CH=CH($CH_3$)—, —$CH_2CH_2$C(O)CH=CH—, —$CH_2CH_2$C(O)CH=CH$CH_2$—, —$CH_2CH_2$C(O)CH=CH$CH_2$NH($CH_3$)—, —$CH_2CH_2$C(O)CH=CH($CH_3$)—, or —CH($CH_3$)OC(O)CH=CH.

In certain embodiments, $L^2$ is a bivalent $C_{2-8}$ straight or branched, hydrocarbon chain wherein $L^2$ has at least one double bond and at least one methylene unit of $L^2$ is replaced by OC(O).

In some embodiments, $L^2$ is a bivalent $C_{2-8}$ straight or branched, hydrocarbon chain wherein $L^2$ has at least one double bond and at least one methylene unit of $L^2$ is replaced by —NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of $L^2$ are optionally and independently replaced by cyclopropylene, —O—, —N(R)—, or —C(O)—. In some embodiments, $L^2$ is $CH_2$OC(O)CH=CH$CH_2$—, —$CH_2$—OC(O)CH=CH—, or CH(CH=$CH_2$)OC(O)CH=CH.

In certain embodiments, $L^2$ is —NRC(O)CH=CH—, —NRC(O)CH=CH$CH_2$N($CH_3$)—, —NRC(O)CH=CH$CH_2$O—, —$CH_2$NRC(O)CH=CH—, —NR$SO_2$CH=CH—, —NR$SO_2$CH=CH$CH_2$—, —NRC(O)(C=$N_2$)C(O)—, —NRC(O)CH=CH$CH_2$N($CH_3$)—, —NR$SO_2$CH=CH—, —NR$SO_2$CH=CH$CH_2$—, —NRC(O)CH=CH$CH_2$O—, —NRC(O)C(=$CH_2$)$CH_2$—, —$CH_2$NRC(O)—, —$CH_2$NRC(O)CH=CH—, —$CH_2CH_2$NRC(O)—, or —$CH_2$NRC(O)cyclopropylene-, wherein each R is independently hydrogen or optionally substituted $C_{1-6}$ aliphatic.

In certain embodiments, $L^2$ is —NHC(O)CH=CH, —NHC(O)CH=CH$CH_2$N($CH_3$)—, —NHC(O)CH=CH$CH_2$O—, —$CH_2$NHC(O)CH=CH—, —NH$SO_2$CH=CH—, —NH$SO_2$CH=CH$CH_2$—, —NHC(O)(C=$N_2$)C(O)—, —NHC(O)CH=CH$CH_2$N($CH_3$)—, —NH$SO_2$CH=CH—, —NH$SO_2$CH=CH$CH_2$—, —NHC(O)CH=CH$CH_2$O—, —NHC(O)C(=$CH_2$)$CH_2$—, —$CH_2$NHC(O)—, —$CH_2$NHC(O)CH=CH, —$CH_2CH_2$NHC(O)—, or —$CH_2$NHC(O)cyclopropylene-.

In some embodiments, $L^2$ is a bivalent $C_{2-8}$ straight or branched, hydrocarbon chain wherein $L^2$ has at least one triple bond. In certain embodiments, $L^2$ is a bivalent $C_{2-8}$ straight or branched, hydrocarbon chain wherein $L^2$ has at least one triple bond and one or two additional methylene units of $L^2$ are optionally and independently replaced by —NRC(O)—, —C(O)NR—, —S—, —S(O)—, —$SO_2$—, —C(=S)—, —C(=NR), —O—, —N(R)—, or —C(O)—. In some embodiments, $L^2$ has at least one triple bond and at least one methylene unit of $L^2$ is replaced by —N(R)—, —N(R)C(O)—, —C(O)—, —C(O)O—, or —OC(O)—, or —O—. In some embodiments, $L^2$ has at least one triple bond and at least one methylene unit of $L^2$ is replaced by —N(R)—, —N(R)C(O)—, —C(O)—, —C(O)O—, or —OC(O)—, or —O—, wherein at least one triple bond is located in an alpha-beta position relative to a —C(O)—.

Exemplary $L^2$ groups include —C≡C—, —C≡C$CH_2$N(isopropyl)-, —NHC(O)C≡C$CH_2CH_2$—, —$CH_2$—C≡C≡$CH_2$—, —C≡C$CH_2$O—, —$CH_2$C(O)C≡C—, —C(O)C≡C—, or —$CH_2$OC(=O)C≡C—.

In certain embodiments, $L^2$ is a bivalent $C_{2-8}$ straight or branched, hydrocarbon chain wherein one methylene unit of $L^2$ is replaced by cyclopropylene and one or two additional methylene units of $L^2$ are independently replaced by —C(O)—, —NRC(O)—, —C(O)NR—, —N(R)$SO_2$—, or —$SO_2$N(R). Exemplary $L^2$ groups include —NHC(O)-cyclopropylene-$SO_2$— and —NHC(O)-cyclopropylene-.

In certain embodiments, $L^2$ is a bivalent $C_{2-8}$ straight or branched, hydrocarbon chain wherein one methylene unit of $L^2$ is replaced by —O—P(O)(OR)O—.

As defined generally above, Y is hydrogen, $C_{1-6}$ aliphatic optionally substituted with oxo, halogen, $NO_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 $R^e$ groups, each $R^e$ is independently selected from -Q-Z, oxo, $NO_2$, halogen, CN, a suitable leaving group, or $C_{1-6}$ aliphatic, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and, Z is hydrogen or $C_{1-6}$ aliphatic optionally substituted with oxo, halogen, $NO_2$, or CN.

In certain embodiments, Y is hydrogen. In some embodiments, when L is a covalent bond, Y is other than hydrogen.

In certain embodiments, Y is $C_{1-6}$ aliphatic optionally substituted with oxo, halogen, $NO_2$, or CN. In some embodiments, Y is $C_{2-6}$alkenyl optionally substituted with oxo, halogen, $NO_2$, or CN. In other embodiments, Y is $C_{2-6}$alkynyl optionally substituted with oxo, halogen, $NO_2$, or CN. In some embodiments, Y is $C_{2-6}$alkenyl. In other embodiments, Y is $C_{2-4}$ alkynyl.

In other embodiments, Y is $C_{1-6}$ alkyl substituted with oxo, halogen, $NO_2$, or CN. Such Y groups include $CH_2F$, —$CH_2Cl$, —$CH_2CN$, and —$CH_2NO_2$.

In certain embodiments, Y is a saturated 3-6 membered monocyclic ring having 0-3 heteroatoms independently selected from nitrogen, oxygen, or sulfur, wherein Y is substituted with 1-4 $R^e$ groups, wherein each $R^e$ is as defined above in warhead group -$L^2$-Y.

In some embodiments, Y is a saturated 3-4 membered heterocyclic ring having 1 heteroatom selected from oxygen or nitrogen wherein said ring is substituted with 1-2 $R^e$ groups, wherein each $R^e$ is as defined above in warhead group is -$L^2$-Y. Exemplary such rings are epoxide and oxetane rings, wherein each ring is substituted with 1-2 $R^e$ groups, wherein each $R^e$ is as defined above in warhead group is -$L^2$-Y.

In other embodiments, Y is a saturated 5-6 membered heterocyclic ring having 1-2 heteroatom selected from oxygen or nitrogen wherein said ring is substituted with 1-4 $R^e$ groups, wherein each $R^e$ is as defined above in warhead group -$L^2$-Y. Such rings include piperidine and pyrrolidine, wherein each ring is substituted with 1-4 $R^e$ groups, wherein each $R^e$ is as defined above in warhead group is -$L^2$-Y. In certain embodiments, Y is

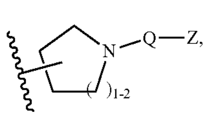,
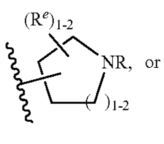, or
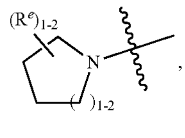, wherein each R, Q, Z, and R is as defined above in warhead group -$L^2$-Y.

In some embodiments, Y is a saturated 3-6 membered carbocyclic ring, wherein said ring is substituted with 1-4 $R^e$ groups, wherein each $R^e$ is as defined above in warhead group -$L^2$-Y. In certain embodiments, Y is cyclopropyl, cyclobutyl, cyclopentyl, or cyclohexyl, wherein each ring is substituted with 1-4 $R^e$ groups, wherein each $R^e$ is as defined above in warhead group -$L^2$-Y. In certain embodiments, Y is

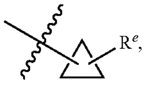

wherein $R^e$ is as defined above in warhead group -$L^2$-Y.

In certain embodiments, Y is cyclopropyl optionally substituted with halogen, CN or $NO_2$.

In certain embodiments, Y is a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above in warhead group -$L^2$-Y.

In some embodiments, Y is a partially unsaturated 3-6 membered carbocyclic ring, wherein said ring is substituted with 1-4 $R^e$ groups, wherein each $R^e$ is as defined above in warhead group -$L^2$-Y. In some embodiments, Y is cyclopropenyl, cyclobutenyl, cyclopentenyl, or cyclohexenyl wherein each ring is substituted with 1-4 $R^e$ groups, wherein each $R^e$ is as defined above in warhead group -$L^2$-Y. In certain embodiments, Y is

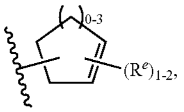

wherein each $R^e$ is as defined above in warhead group -$L^2$-Y.

In certain embodiments, Y is a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above in warhead group -$L^2$-Y. In certain embodiments, Y is selected from:

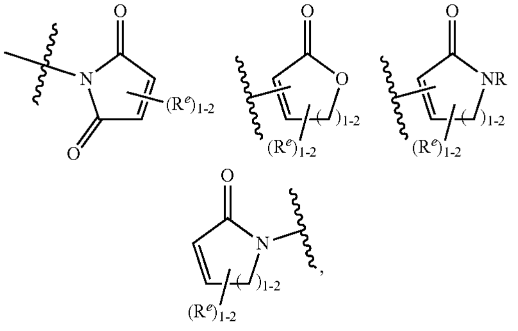

wherein each R is as defined above and described herein and $R^e$ is as defined above in warhead group -$L^2$-Y.

In certain embodiments, Y is a 6-membered aromatic ring having 0-2 nitrogens wherein said ring is substituted with 1-4 $R^e$ groups, wherein each $R^e$ group is as defined above in warhead group -$L^2$-Y. In certain embodiments, Y is phenyl, pyridyl, or pyrimidinyl, wherein each ring is substituted with 1-4 $R^e$ groups, wherein each $R^e$ is as defined above in warhead group -$L^2$-Y.

In some embodiments, Y is selected from:

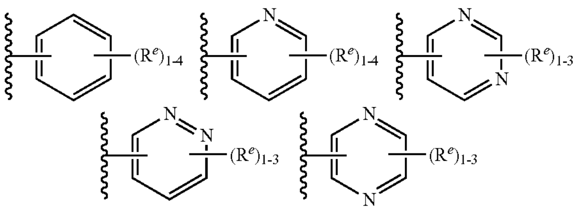

wherein each $R^e$ is as defined above in warhead group $-L^2$-Y.

In other embodiments, Y is a 5-membered heteroaryl ring having 1-3 heteroatoms independently selected from nitrogen, oxygen, or sulfur, wherein said ring is substituted with 1-3 $R^e$ groups, wherein each $R^e$ group is as defined above in warhead group $-L^2$-Y. In some embodiments, Y is a 5 membered partially unsaturated or aryl ring having 1-3 heteroatoms independently selected from nitrogen, oxygen, and sulfur, wherein said ring is substituted with 1-4 $R^e$ groups, wherein each $R^e$ group is as defined above in warhead group $-L^2$-Y. Exemplary such rings are isoxazolyl, oxazolyl, thiazolyl, imidazolyl, pyrazolyl, pyrrolyl, furanyl, thienyl, triazole, thiadiazole, and oxadiazole, wherein each ring is substituted with 1-3 $R^e$ groups, wherein each $R^e$ group is as defined above in warhead group $-L^2$-Y. In certain embodiments, Y is selected from:

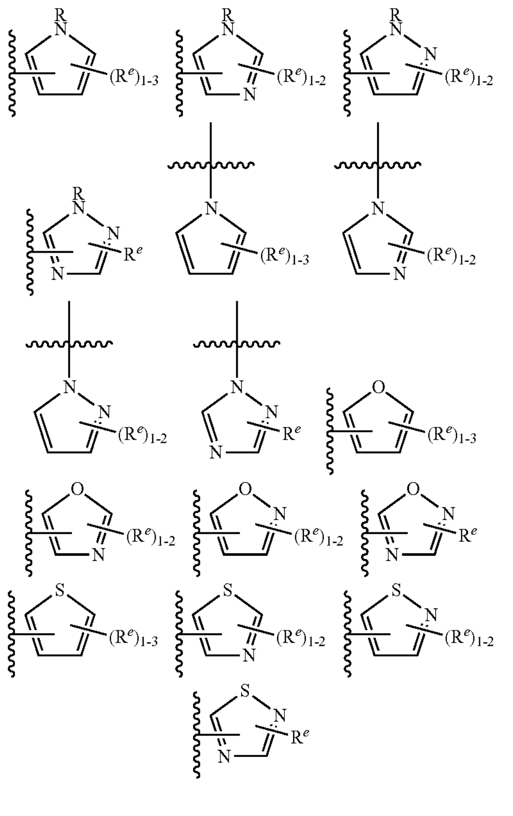

wherein each R is as defined above and described herein and $R^e$ is as defined above in warhead group $-L^2$-Y.

In certain embodiments, Y is an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above in warhead group $-L^2$-Y. According to another aspect, Y is a 9-10 membered bicyclic, partially unsaturated, or aryl ring having 1-3 heteroatoms independently selected from nitrogen, oxygen, or sulfur, wherein said ring is substituted with 1-4 $R^e$ groups, wherein $R^e$ is as defined above in warhead group $-L^2$-Y. Exemplary such bicyclic rings include 2,3-dihydrobenzo[d]isothiazole, wherein said ring is substituted with 1-4 $R^e$ groups, wherein $R^e$ is as defined above in warhead group $-L^2$-Y.

As defined generally above, each $R^e$ group is independently selected from -Q-Z, oxo, $NO_2$, halogen, CN, a suitable leaving group, or $C_{1-6}$ aliphatic optionally substituted with oxo, halogen, $NO_2$, or CN, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

In certain embodiments, $R^e$ is $C_{1-6}$ aliphatic optionally substituted with oxo, halogen, $NO_2$, or CN. In other embodiments, $R^e$ is oxo, $NO_2$, halogen, or CN.

In some embodiments, $R^e$ is -Q-Z, wherein Q is a covalent bond and Z is hydrogen (i.e., $R^e$ is hydrogen). In other embodiments, $R^e$ is -Q-Z, wherein Q is a bivalent $C_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —$SO_2$—. In other embodiments, Q is a bivalent $C_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —$SO_2$—. In certain embodiments, the Z moiety of the $R^e$ group is hydrogen. In some embodiments, -Q-Z is —NHC(O)CH═$CH_2$ or —C(O)CH═$CH_2$.

In certain embodiments, each $R^e$ is independently selected from oxo, $NO_2$, CN, fluoro, chloro, —NHC(O)CH═$CH_2$, —C(O)CH═$CH_2$, —$CH_2$CH═$CH_2$, —C≡CH, —C(O)O$CH_2$Cl, —C(O)O$CH_2$F, —C(O)O$CH_2$CN, —C(O)$CH_2$Cl, —C(O)$CH_2$F, —C(O)$CH_2$CN, or —$CH_2$C(O)$CH_3$.

In certain embodiments, $R^e$ is a suitable leaving group, i.e., a group that is subject to nucleophilic displacement. A "suitable leaving" is a chemical group that is readily displaced by a desired incoming chemical moiety such as the thiol moiety of a cysteine of interest. In some embodiments, the warhead group modifies a cysteine of DCN-1. In some embodiments, the cysteine of DCN-1 is Cys115. Suitable leaving groups are well known in the art, e.g., see, "Advanced Organic Chemistry," Jerry March, $5^{th}$ Ed., pp. 351-357, John Wiley and Sons, N.Y. Such leaving groups include, but are not limited to, halogen, alkoxy, sulfonyloxy, optionally substituted alkylsulfonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methanesulfonyloxy (mesyloxy), tosyloxy, triflyloxy, nitrophenylsulfonyloxy (nosyloxy), and bromo-phenylsulfonyloxy (brosyloxy).

In certain embodiments, the following embodiments, and combinations of $-L^2$-Y apply:

(a) $L^2$ is a bivalent $C_{2-8}$ straight or branched, hydrocarbon chain wherein $L^2$ has at least one double bond and one or two additional methylene units of $L^2$ are optionally and independently replaced by —NRC(O)—, —C(O)

NR—, —N(R)$SO_2$—, —$SO_2$N(R)—, —S—, —S(O)—, —$SO_2$—, —OC(O)—, —C(O)O, cyclopropylene, —O—, —N(R)—, —O—P(O)(OR)O—, or —C(O)—; and Y is hydrogen, or $C_{1-6}$ aliphatic optionally substituted with oxo, halogen, $NO_2$, or CN; wherein -$L^2$-Y comprises an alpha, beta-unsaturated carbonyl moiety; or (b) $L^2$ is a bivalent $C_{2-8}$ straight or branched, hydrocarbon chain wherein $L^2$ has at least one double bond and at least one methylene unit of $L^2$ is replaced by —C(O)—, —NRC(O)—, —C(O)NR—, —N(R)$SO_2$—, —$SO_2$N(R)—, —S—, S(O)—, —$SO_2$—, —OC(O)—, or C(O)O—, and one or two additional methylene units of $L^2$ are optionally and independently replaced by cyclopropylene, —O—, —N(R)—, or —C(O)—; and Y is hydrogen, halogen or $C_{1-6}$ aliphatic optionally substituted with oxo, halogen, $NO_2$, or CN; wherein -$L^2$-Y comprises an alpha, beta-unsaturated carbonyl moiety; or (c) $L^2$ is a bivalent $C_{2-8}$ straight or branched, hydrocarbon chain wherein $L^2$ has at least one double bond and at least one methylene unit of $L^2$ is replaced by —C(O)—, and one or two additional methylene units of $L^2$ are optionally and independently replaced by cyclopropylene, —O—, —N(R)—, or —C(O)—; and Y is hydrogen, or $C_{1-6}$ aliphatic optionally substituted with oxo, halogen, $NO_2$, or CN; wherein -$L^2$-Y comprises an alpha, beta-unsaturated carbonyl moiety; or (d) $L^2$ is a bivalent $C_{2-8}$ straight or branched, hydrocarbon chain wherein $L^2$ has at least one double bond and at least one methylene unit of $L^2$ is replaced by —C(O)—; and Y is hydrogen, or $C_{1-6}$ aliphatic optionally substituted with oxo, halogen, $NO_2$, or CN; wherein -$L^2$-Y comprises an alpha, beta-unsaturated carbonyl moiety; or (e) $L^2$ is a bivalent $C_{2-8}$ straight or branched, hydrocarbon chain wherein $L^2$ has at least one double bond and at least one methylene unit of $L^2$ is replaced by OC(O)—; and Y is hydrogen, or $C_{1-6}$ aliphatic optionally substituted with oxo, halogen, $NO_2$—, or CN; wherein -$L^2$-Y comprises an alpha, beta-unsaturated carbonyl moiety; or (f) $L^2$ is —NRC(O)CH═CH—, —NRC(O)CH═CH$CH_2$N($CH_3$)—, —NRC(O)CH═CH$CH_2$O—, —$CH_2$NRC(O)CH═CH—, —NR$SO_2$CH═CH—, —NR$SO_2$CH═CH$CH_2$—, —NRC(O)(C═$N_2$)—, —NRC(O)(C═$N_2$)C(O)—, —NRC(O)CH═CH$CH_2$N($CH_3$)—, —NR$SO_2$CH═CH—, —NR$SO_2$CH═CH$CH_2$—, —NRC(O)CH═CH$CH_2$O—, —NRC(O)C(═$CH_2$)$CH_2$—, —$CH_2$NRC(O)—, $CH_2$NRC(O)CH═CH, —$CH_2CH_2$NRC(O)—, or —$CH_2$NRC(O)cyclopropylene-; wherein R is H or optionally substituted $C_{1-6}$ aliphatic; and Y is hydrogen, or $C_{1-6}$ aliphatic optionally substituted with oxo, halogen, $NO_2$—, or CN; wherein -$L^2$-Y comprises an alpha, beta-unsaturated carbonyl moiety; or (g) $L^2$ is —NHC(O)CH═CH—, —NHC(O)CH═CH$CH_2$N($CH_3$)—, —NHC(O)CH═CH$CH_2$O—, —$CH_2$NHC(O)CH═CH—, —NH$SO_2$CH═CH—, —NH$SO_2$CH═CH$CH_2$—, —NHC(O)(C═$N_2$)—, —NHC(O)(C═$N_2$)C(O)—, —NHC(O)CH═CH$CH_2$N($CH_3$)—, —NH$SO_2$CH═CH—, —NH$SO_2$CH═CH$CH_2$—, —NHC(O)CH═CH$CH_2$O—, —NHC(O)C(═$CH_2$)$CH_2$—, —$CH_2$NHC(O)—, —$CH_2$NHC(O)CH═CH, —$CH_2CH_2$NHC(O)—, or —$CH_2$NHC(O)cyclopropylene-; and Y is hydrogen, or $C_{1-6}$ aliphatic optionally substituted with oxo, halogen, $NO_2$, or CN; wherein -$L^2$-Y comprises an alpha, beta-unsaturated carbonyl moiety; or (h) $L^2$ is a bivalent $C_{2-8}$ straight or branched, hydrocarbon chain wherein $L^2$ has at least one alkylidenyl double bond and at least one methylene unit of $L^2$ is replaced by —C(O)—, —NRC(O)—, —C(O)NR—, —N(R)$SO_2$—, $SO_2$N(R)—, —S—, S(O)—, —$SO_2$—, —OC(O)—, or —C(O)O—, and one or two additional methylene units of $L^2$ are optionally and independently replaced by cyclopropylene, —O—, —N(R)—, or —C(O)—; and Y is hydrogen, or $C_{1-6}$ aliphatic optionally substituted with oxo, halogen, $NO_2$—, or CN; wherein -$L^2$-Y comprises an alpha, beta-unsaturated carbonyl moiety; or (i) $L^2$ is a bivalent $C_{2-8}$ straight or branched, hydrocarbon chain wherein $L^2$ has at least one triple bond and one or two additional methylene units of $L^2$ are optionally and independently replaced by —NRC(O)—, —C(O)NR—, —N(R)$SO_2$—, $SO_2$N(R)—, —S—, —S(O)—, —$SO_2$—, —OC(O)—, or —C(O)O—, and Y is hydrogen, or $C_{1-6}$ aliphatic optionally substituted with oxo, halogen, $NO_2$—, or CN; wherein -$L^2$-Y comprises an alpha, beta-unsaturated carbonyl moiety; or (j) $L^2$ is —C≡C—, —C≡C$CH_2$N(isopropyl)-, —NHC(O)C≡C$CH_2CH_2$, —$CH_2$—C≡C≡$CH_2$—, —C≡C$CH_2$O—, —$CH_2$C(O)C≡C—, —C(O)C≡C—, or —$CH_2$C(═O)C≡C—; and Y is hydrogen, or $C_{1-6}$ aliphatic optionally substituted with oxo, halogen, $NO_2$, or CN; wherein -L-Y comprises an alpha, beta-unsaturated carbonyl moiety; or (k) $L^2$ is a bivalent $C_{2-8}$ straight or branched, hydrocarbon chain wherein one methylene unit of $L^2$ is replaced by cyclopropylene and one or two additional methylene units of $L^2$ are independently replaced by —NRC(O)—, —C(O)NR—, —N(R)$SO_2$—, $SO_2$N(R)—, —S—, —S(O)—, —$SO_2$—, —OC(O)—, or —C(O)O—; and Y is hydrogen, or $C_{1-6}$ aliphatic optionally substituted with oxo, halogen, $NO_2$—, or CN; wherein -$L^2$-Y comprises an alpha, beta-unsaturated carbonyl moiety; or (l) $L^2$ is a covalent bond and Y is selected from:

(i) $C_{1-6}$ alkyl substituted with oxo, halogen, $NO_2$, or CN;

(ii) $C_{2-6}$alkenyl optionally substituted with oxo, halogen, $NO_2$, or CN; or (iii) $C_{2-6}$alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above in warhead group -$L^2$-Y; or (v) a saturated 5-6 membered heterocyclic ring having 1-2 heteroatom selected from oxygen or nitrogen wherein said ring is substituted with 1-4 R groups, wherein each $R^e$ is as defined above in warhead group -$L^2$-Y; or (vi)

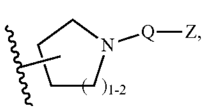

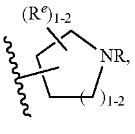

or

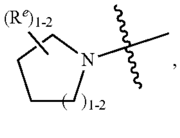

, wherein each R, Q, Z, and $R^e$ is as defined above in warhead group $-L^2$-Y; or (vii) a saturated 3-6 membered carbocyclic ring, wherein said ring is substituted with 1-4 $R^e$ groups, wherein each $R^e$ is as defined above in warhead group $-L^2$-Y; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each R is as defined above in warhead group $-L^2$-Y; or (ix) a partially unsaturated 3-6 membered carbocyclic ring, wherein said ring is substituted with 1-4 $R^e$ groups, wherein each $R^e$ is as defined above in warhead group $-L^2$-Y; or (x)

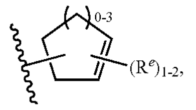

wherein each $R^e$ is as defined above in warhead group $-L^2$-Y; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each R is as defined above in warhead group $-L^2$-Y; or (xii)

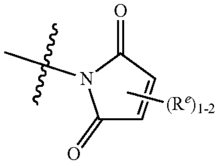
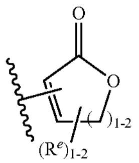
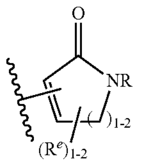
or
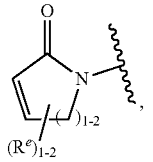

wherein each R is as defined above and described herein and $R^e$ is as defined above in warhead group $-L^2$-Y; or (xiii) a 6-membered aromatic ring having 0-2 nitrogens wherein said ring is substituted with 1-4 $R^e$ groups, wherein each $R^e$ group is as defined above in warhead group $-L^2$-Y; or (xiv)

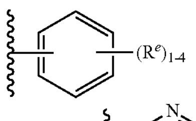
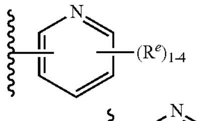
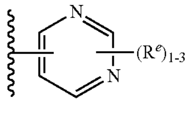
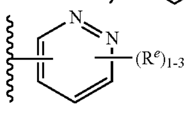
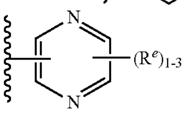

wherein each $R^e$ is as defined above in warhead group $-L^2$-Y; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above in warhead group $-L^2$-Y; or (xvi)

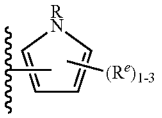
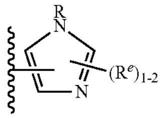
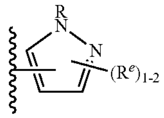
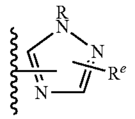
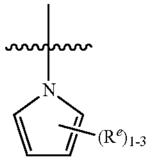
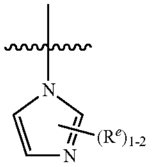
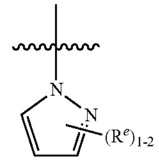
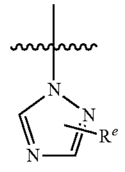
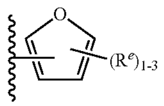
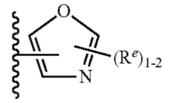
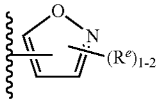
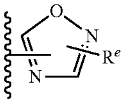
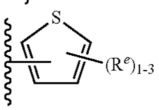
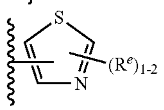
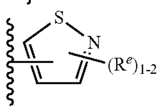
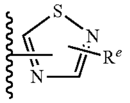

wherein each R is as defined above and described herein and $R^e$ is as defined above in warhead group $-L^2$-Y; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above in warhead group $-L^2$-Y;

(m) $L^2$ is —C(O)— and Y is selected from:

(i) $C_{1-6}$ alkyl substituted with oxo, halogen, $NO_2$, or CN; or (ii) $C_{2-6}$alkenyl optionally substituted with oxo, halogen, $NO_2$, or CN; or (iii) $C_{2-6}$alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above in warhead group $-L^2$-Y; or (v) a saturated 5-6 membered heterocyclic ring having 1-2 heteroatom selected from oxygen or nitrogen wherein said ring is substituted with 1-4 $R^e$ groups, wherein each $R^e$ is as defined above in warhead group $-L^2$-Y; or (vi)

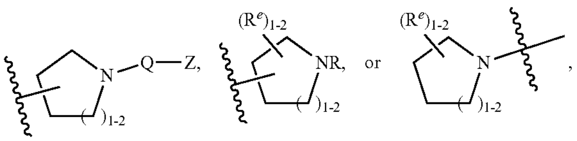

wherein each R, Q, Z, and $R^e$ is as defined above in warhead group $-L^2-Y$; or (vii) a saturated 3-6 membered carbocyclic ring, wherein said ring is substituted with 1-4 $R^e$ groups, wherein each $R^e$ is as defined above in warhead group $-L^2-Y$; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above in warhead group $-L^2-Y$; or (ix) a partially unsaturated 3-6 membered carbocyclic ring, wherein said ring is substituted with 1-4 $R^e$ groups, wherein each $R^e$ is as defined above in warhead group $-L^2-Y$; or (x)

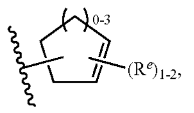

wherein each $R^e$ is as defined above in warhead group $-L^2-Y$; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above in warhead group $-L^2-Y$; or (xii)

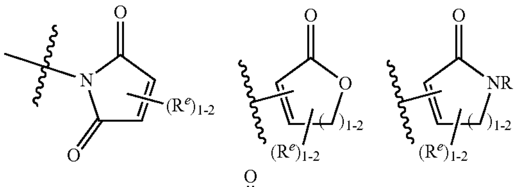

or

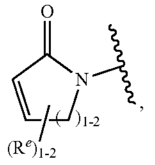

wherein each R is as defined above and described herein and $R^e$ is as defined above in warhead group $-L^2-Y$; or (xiii) a 6-membered aromatic ring having 0-2 nitrogens wherein said ring is substituted with 1-4 $R^e$ groups, wherein each $R^e$ group is as defined above in warhead group $-L^2-Y$; or (xiv)

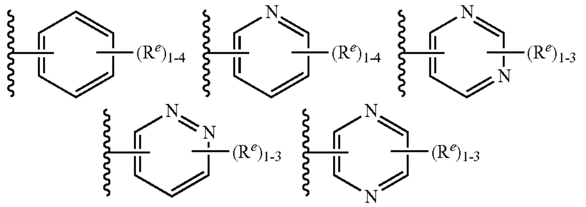

wherein each $R^e$ is as defined above in warhead group $-L^2-Y$; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above in warhead group $-L^2-Y$; or (xvi)

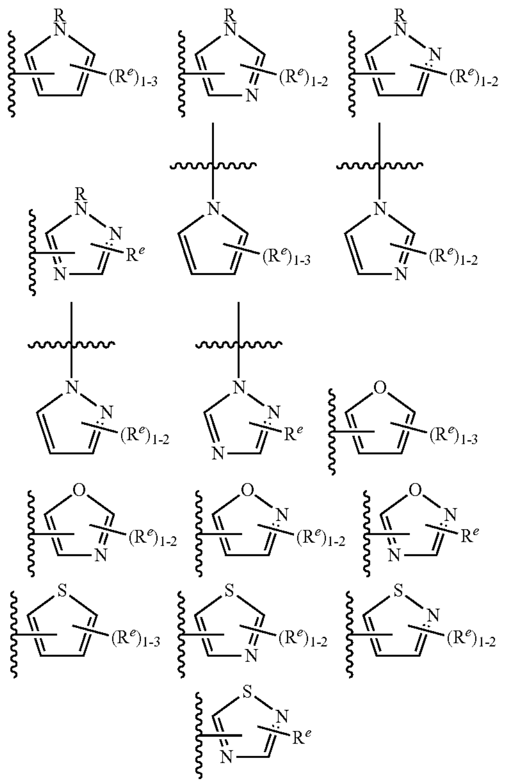

wherein each R is as defined above and described herein and $R^e$ is as defined above in warhead group $-L^2-Y$; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above in warhead group $-L^2-Y$;

(n) $L^2$ is N(R)C(O) and Y is selected from:

(i) $C_{1-6}$ alkyl substituted with oxo, halogen, $NO_2$, or CN; or (ii) $C_{2-6}$alkenyl optionally substituted with oxo, halogen, $NO_2$, or CN; or (iii) $C_{2-6}$alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above in warhead group $-L^2$-Y; or (v) a saturated 5-6 membered heterocyclic ring having 1-2 heteroatom selected from oxygen or nitrogen wherein said ring is substituted with 1-4 $R^e$ groups, wherein each $R^e$ is as defined above in warhead group $-L^2$-Y; or (vi)

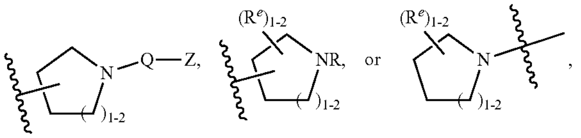

wherein each R, Q, Z, and $R^e$ is as defined above in warhead group $-L^2$-Y; or (vii) a saturated 3-6 membered carbocyclic ring, wherein said ring is substituted with 1-4 $R^e$ groups, wherein each $R^e$ is as defined above in warhead group $-L^2$-Y; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above in warhead group $-L^2$-Y; or (ix) a partially unsaturated 3-6 membered carbocyclic ring, wherein said ring is substituted with 1-4 $R^e$ groups, wherein each $R^e$ is as defined above in warhead group $-L^2$-Y; or (x)

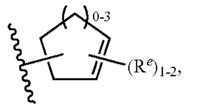

wherein each $R^e$ is as defined above in warhead group $-L^2$-Y; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above in warhead group $-L^2$-Y; or (xii)

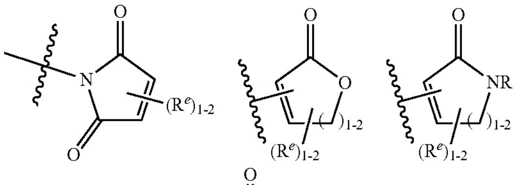

or

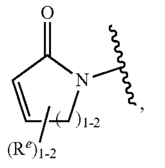

wherein each R and $R^e$ is as defined above in warhead group $-L^2$-Y; or (xiii) a 6-membered aromatic ring having 0-2 nitrogens wherein said ring is substituted with 1-4 $R^e$ groups, wherein each $R^e$ group is as defined above in warhead group $-L^2$-Y; or (xiv)

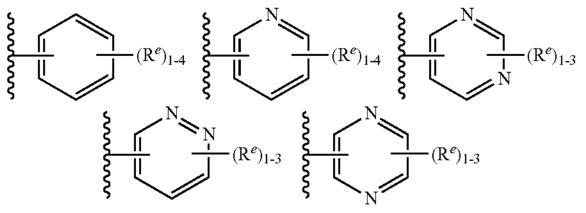

wherein each $R^e$ is as defined above in warhead group $-L^2$-Y; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above in warhead group $-L^2$-Y; or (xvi)

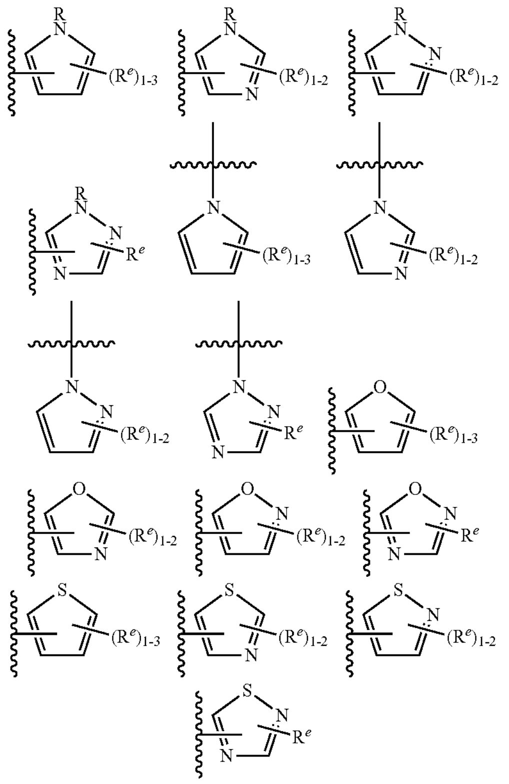

wherein each R is as defined above and described herein and $R^e$ is as defined above in warhead group $-L^2$-Y; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above in warhead group $-L^2$-Y;

(o) $L^2$ is a bivalent $C_{1-8}$ saturated or unsaturated, straight or branched, hydrocarbon chain; and Y is selected from:

(i) $C_{1-6}$ alkyl substituted with oxo, halogen, $NO_2$, or CN;

(ii) $C_{2-6}$alkenyl optionally substituted with oxo, halogen, $NO_2$, or CN; or (iii) $C_{2-6}$alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above in warhead group $-L^2$-Y; or (v) a saturated 5-6 membered heterocyclic ring having 1-2 heteroatom selected from oxygen or nitrogen wherein said ring is substituted with 1-4 $R^e$ groups, wherein each $R^e$ is as defined above in warhead group $-L^2$-Y; or (vi)

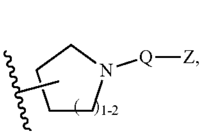
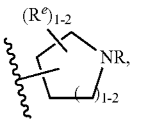
or
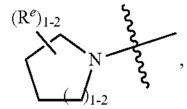
, wherein each R, Q, Z, and $R^e$ is as defined above in warhead group $-L^2$-Y; or (vii) a saturated 3-6 membered carbocyclic ring, wherein said ring is substituted with 1-4 $R^e$ groups, wherein each $R^e$ is as defined above in warhead group $-L^2$-Y; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above in warhead group $-L^2$-Y; or (ix) a partially unsaturated 3-6 membered carbocyclic ring, wherein said ring is substituted with 1-4 $R^e$ groups, wherein each $R^e$ is as defined above in warhead group $-L^2$-Y; or (x)

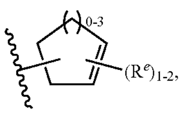

wherein each $R^e$ is as defined above in warhead group $-L^2$-Y; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above in warhead group $-L^2$-Y; or (xii)

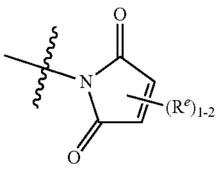
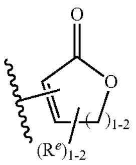
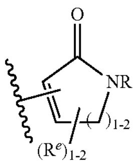
or

-continued

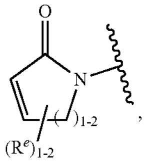
, wherein each R is as defined above and described herein and $R^e$ is as defined above in warhead group $-L^2$-Y; or (xiii) a 6-membered aromatic ring having 0-2 nitrogens wherein said ring is substituted with 1-4 $R^e$ groups, wherein each $R^e$ group is as defined above in warhead group $-L^2$-Y; or (xiv)

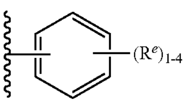
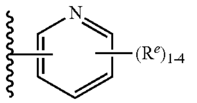
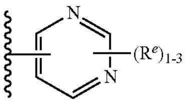
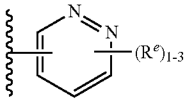
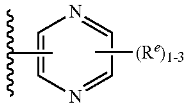

wherein each $R^e$ is as defined above in warhead group $-L^2$-Y; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above in warhead group $-L^2$-Y; or (xvi)

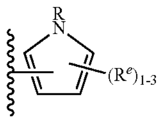
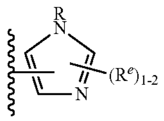
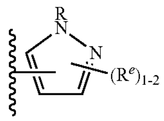
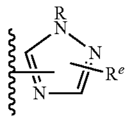
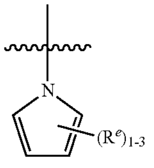
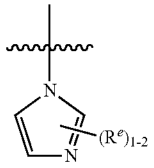
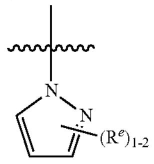
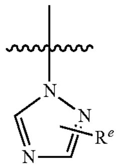
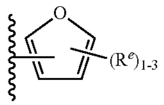
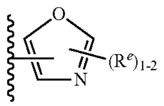
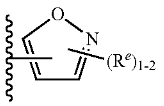
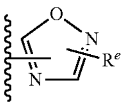
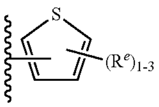
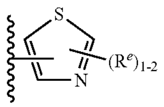
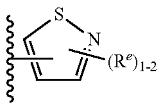

-continued

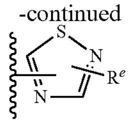

wherein each R is as defined above and described herein and $R^e$ is as defined above in warhead group $-L^2$-Y; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above in warhead group $-L^2$-Y;

(p) $L^2$ is a covalent bond, —$CH_2$—, —NH—, —C(O)—, —$CH_2$NH—, —NH$CH_2$—, —NHC(O)—, —NHC(O)$CH_2$OC(O)—, —$CH_2$NHC(O)—, —NH$SO_2$—, —NH$SO_2CH_2$—, —NHC(O)$CH_2$OC(O)—, or —$SO_2$NH—; and Y is selected from.

(i) $C_{1-6}$ alkyl substituted with oxo, halogen, $NO_2$, or CN; or (ii) $C_{2-6}$alkenyl optionally substituted with oxo, halogen, $NO_2$, or CN; or (iii) $C_{2-6}$alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above in warhead group $-L^2$-Y; or (v) a saturated 5-6 membered heterocyclic ring having 1-2 heteroatom selected from oxygen or nitrogen wherein said ring is substituted with 1-4 $R^e$ groups, wherein each $R^e$ is as defined above in warhead group $-L^2$-Y; or (vi)

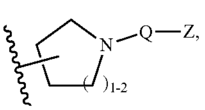 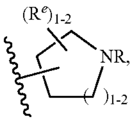 or 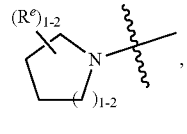 , wherein each R, Q, Z, and $R^e$ is as defined above in warhead group $-L^2$-Y; or (vii) a saturated 3-6 membered carbocyclic ring, wherein said ring is substituted with 1-4 $R^e$ groups, wherein each $R^e$ is as defined above in warhead group $-L^2$-Y; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above in warhead group $-L^2$-Y; or (ix) a partially unsaturated 3-6 membered carbocyclic ring, wherein said ring is substituted with 1-4 $R^e$ groups, wherein each $R^e$ is as defined above in warhead group $-L^2$-Y;

(x)

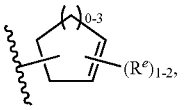

wherein each $R^e$ is as defined above in warhead group $-L^2$-Y; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above in warhead group $-L^2$-Y; or (xii)

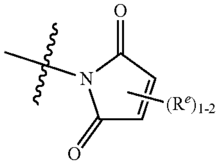 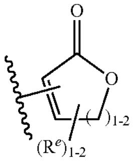 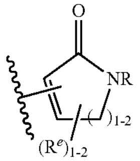 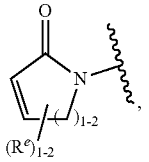 , wherein each R and $R^e$ is as defined above in warhead group $-L^2$-Y; or (xiii) a 6-membered aromatic ring having 0-2 nitrogens wherein said ring is substituted with 1-4 $R^e$ groups, wherein each $R^e$ group is as defined above in warhead group $-L^2$-Y; or (xiv)

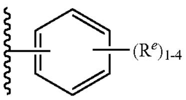 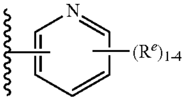 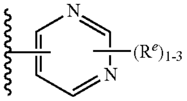 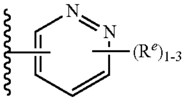 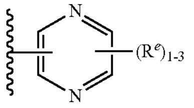

wherein each $R^e$ is as defined above in warhead group $-L^2$-Y; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above in warhead group $-L^2$-Y; or (xvi)

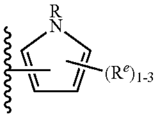 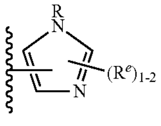 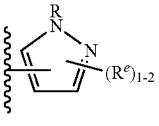

-continued

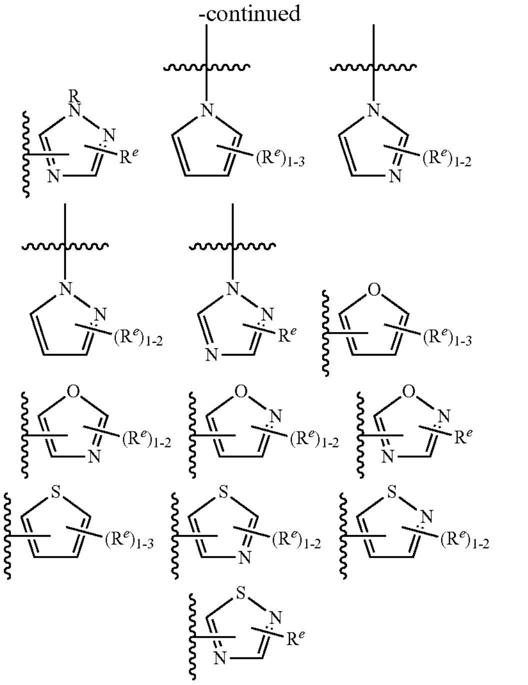

wherein each R is as defined above and described herein and $R^e$ is as defined above in warhead group $-L^2$-Y; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above in warhead group $-L^2$-Y;

(q) $L^2$ is a bivalent $C_{1-8}$ saturated or unsaturated, straight or branched, hydrocarbon chain, wherein one, two, or three methylene units of $L^2$ are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O, —S—, —SO—, —$SO_2$—, —O—P(O)(OR)O—, —C(═S)—, —C(═NR)—, —N═N—, or —C(═$N_2$)—; and Y is hydrogen or $C_{1-6}$ aliphatic optionally substituted with oxo, halogen, $NO_2$—, or CN, wherein $-L^2$-Y comprises an alpha, beta-unsaturated carbonyl moiety;

(r) $L^2$ is a bivalent $C_{1-8}$ saturated or unsaturated, straight or branched, hydrocarbon chain, wherein one, two, or three methylene units of $L^2$ are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O, —S—, —SO—, —$SO_2$—, —O—P(O)(OR)O—, —C(═S)—, —C(═NR)—, —N═N—, or —C(═$N_2$)—; and Y is hydrogen or $C_{1-6}$ aliphatic optionally substituted with oxo, halogen, $NO_2$—, or CN, wherein $-L^2$-Y comprises an alpha halo carbonyl moiety.

In certain embodiments, a Y group is selected from those set forth in Table 1a, below.

In certain embodiments, $R^4$ is $L^2$-Y. In certain embodiments, the following embodiments, and combinations of $-L^2$-Y apply:

$L^2$ is a covalent bond or a bivalent $C_{2-8}$ straight or branched, hydrocarbon chain wherein one or two methylene units of $L^2$ are optionally and independently replaced by —NRC(O)—, —C(O)NR—, —N(R)$SO_2$—, $SO_2$N(R)—, —S—, —O—, —NR—, S(O)—, —$SO_2$—, —C(O)—, —OC(O)—, or —C(O)O—; and additionally one methylene unit of $L^2$ is optionally replaced by an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur; and Y is hydrogen, halogen, —COOR, —CN, —CON$(R)_2$, —NRCN, $NO_2$—, —N$(R)_2$, optionally substituted $C_{1-8}$ aliphatic, or an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, and an 8-10 membered bicyclic heteroaromatic ring having 1-5 heteroatoms independently selected from nitrogen, oxygen, and sulfur; wherein $-L^2$-Y comprises an alpha, beta-unsaturated carbonyl moiety, amide, cyano group, halogen, carbonyl, alkynyl group, sulfonyl group, or epoxide.

In certain embodiments, $R^4$ is $L^2$-Y. In certain embodiments, the following embodiments, and combinations of $-L^2$-Y apply:

$L^2$ is a covalent bond or a bivalent $C_{2-8}$ straight or branched, hydrocarbon chain wherein one or two methylene units of $L^2$ are optionally and independently replaced by —NRC(O)—, —C(O)NR—, —N(R)$SO_2$—, —$SO_2$N(R)—, —S—, —O—, —NR—, —S(O)—, —$SO_2$—, —C(O)—, —OC(O)—, or —C(O)O—; and additionally one methylene unit of $L^2$ is optionally replaced by an optionally substituted ring selected from a 3-8 membered saturated or partially unsaturated monocyclic carbocyclic ring, or a 3-8 membered saturated or partially unsaturated monocyclic heterocyclic ring having 1-2 heteroatoms independently selected from nitrogen, oxygen, and sulfur; and Y is hydrogen, halogen, —COO$R^f$, —CN, —CON$R_2$, —N$R^f$CN, $NO_2$—, —N$R_2$, $C_{1-8}$ aliphatic optionally substituted with halogen, $NO_2$—, or CN, or an optionally substituted ring selected from a 3-8 membered saturated or partially unsaturated monocyclic carbocyclic ring, phenyl, a 3-8 membered saturated or partially unsaturated monocyclic heterocyclic ring having 1-2 heteroatoms independently selected from nitrogen, oxygen, and sulfur, and a 5-10 membered bicyclic heterocyclic ring having 1-4 heteroatoms independently selected from nitrogen, oxygen, and sulfur;

wherein $-L^2-Y$ comprises an alpha, beta-unsaturated carbonyl moiety, amide, cyano group, halogen, carbonyl, alkynyl group, sulfonyl group, or epoxide; and wherein each occurrence of R is independently H, or straight or branched $C_{1-6}$ alkyl, $C_{2-6}$ alkenyl, or $C_{2-6}$ alkynyl group optionally substituted with 1, 2 or 3 halogen atoms.

In certain embodiments, $R^4$ is $L^2$-Y. In certain embodiments, the following embodiments, and combinations of -L-Y apply:

$L^2$ is a covalent bond or a bivalent $C_{2-8}$ straight or branched, hydrocarbon chain wherein one or two methylene units of $L^2$ are optionally and independently replaced by —NRC(O)—, —C(O)NR—, —N(R) $SO_2$—, $SO_2N(R)$—, —S—, S(O)—, —$SO_2$—, —C(O)—, —OC(O)—, or —C(O)O—; and additionally one methylene unit of $L^2$ is optionally replaced by a ring selected from

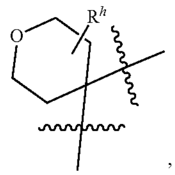, 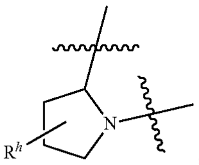, 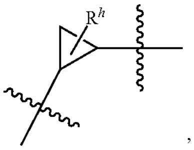, 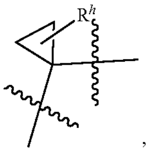, 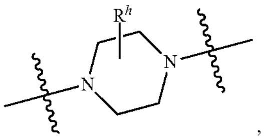, 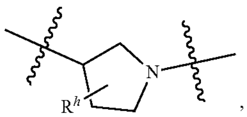, 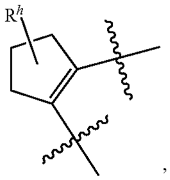, 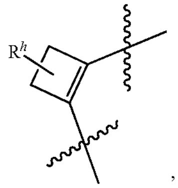, 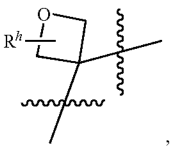, and 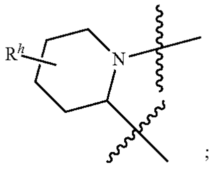;

and Y is hydrogen, halogen, —$COOR^f$, —CN, —$CONR_2$, —$NR^fCN$, $NO_2$—, —$NR^f_2$, epoxide, $C_{1-8}$ aliphatic optionally substituted with halogen, $NO_2$ or CN or a ring selected from

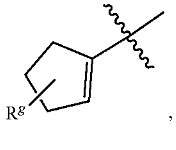, 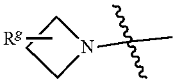, 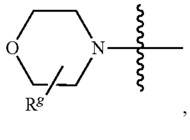,

-continued

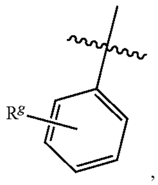, 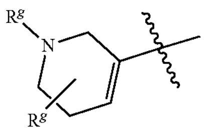, 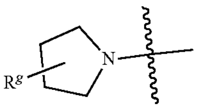, 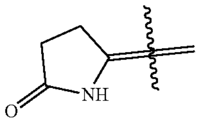, 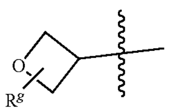, 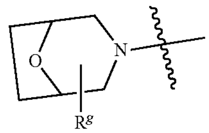, 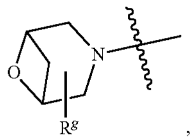, 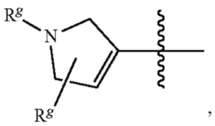, 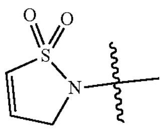, 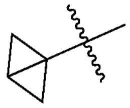, 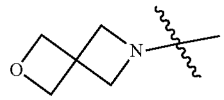, 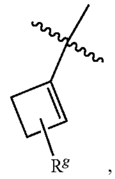, 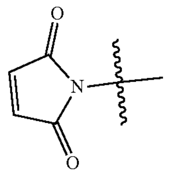, 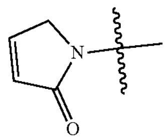, 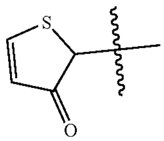, 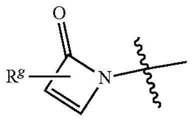, 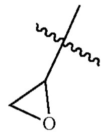, 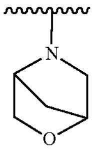, 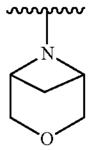, 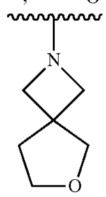, 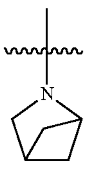, 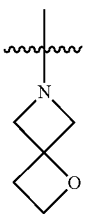, 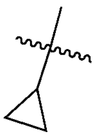, and 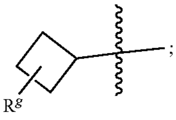;

wherein $-L^2-Y$ comprises an alpha, beta-unsaturated carbonyl moiety, amide, cyano group, halogen, carbonyl, $C_{2-6}$ alkynyl group, sulfonyl group, or epoxide; wherein each occurrence of $R^f$ is independently H, or straight or branched $C_{1-6}$ alkyl, $C_{2-6}$ alkenyl, or $C_{2-6}$ alkynyl group optionally substituted with 1, 2 or 3 halogen atoms; and wherein each occurrence of $R^g$ and $R^h$ is independently H, halogen, or OH, or straight or branched $C_{1-6}$ alkyl, $C_{2-6}$ alkenyl, or $C_{2-6}$ alkynyl group optionally substituted with 1, 2 or 3 halogen atoms.

In certain embodiments, a $L^2$-Y group is selected from those set forth in Table 1c, Table 1d and Table 1e below. In certain embodiments, a warhead group is selected from those set forth in Table 1c, Table 1d and Table 1e below.

TABLE la

| Exemplary Y groups | |
|---|---|
| 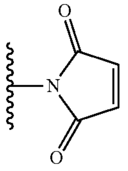 [SMILES: *N1C(=O)C=CC1=O] | a |
| 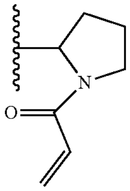 [SMILES: *C1CCCN1C(=O)C=C] | b |
| 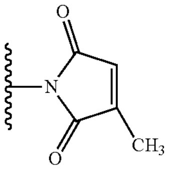 [SMILES: *N1C(=O)C=C(C)C1=O] | c |
| 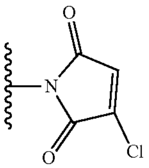 | d |
| 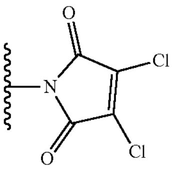 [SMILES: *N1C(=O)C(Cl)=C(Cl)C1=O] | e |
| 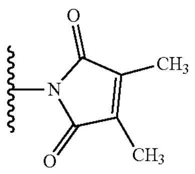 [SMILES: *N1C(=O)C(C)=C(C)C1=O] | f |
| 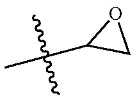 [SMILES: *C1CO1] | g |
| 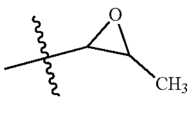 [SMILES: *C1OC1C] | h |

TABLE la-continued

| Exemplary Y groups | |
|---|---|
| 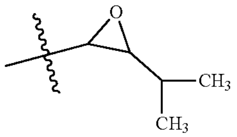 [SMILES: *C1OC1C(C)C] | i |
| 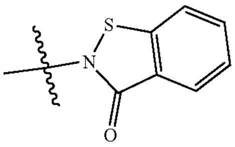 [SMILES: *n1sc2ccccc2c1=O] | j |
| 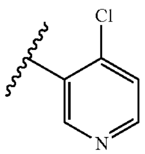 [SMILES: *c1cnccc1Cl] | k |
| 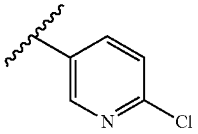 [SMILES: *c1ccc(Cl)nc1] | l |
| 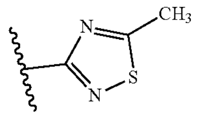 [SMILES: *c1nsc(C)n1] | m |
| 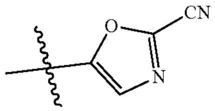 [SMILES: *c1cnc(C#N)o1] | n |
| 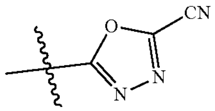 [SMILES: *c1nnc(C#N)o1] | o |
| 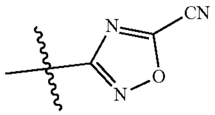 [SMILES: *c1noc(C#N)n1] | p |
| 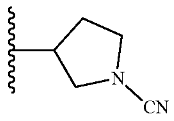 [SMILES: *C1CCN(C#N)C1] | q |
| 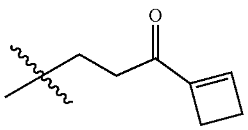 [SMILES: *CCC(=O)C1=CCC1] | r |
| 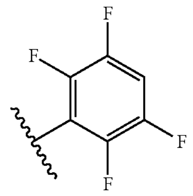 [SMILES: *c1c(F)c(F)cc(F)c1F] | s |

TABLE Ia-continued
Exemplary Y groups
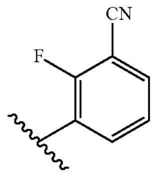 [SMILES: *c1cccc(C#N)c1F]
t
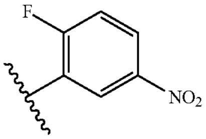 [SMILES: *c1cc([N+](=O)[O-])ccc1F]
u
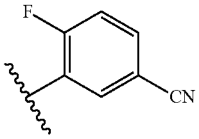 [SMILES: *c1cc(C#N)ccc1F]
v
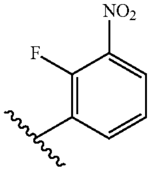 [SMILES: *c1cccc([N+](=O)[O-])c1F]
w
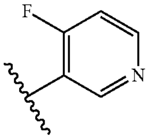 [SMILES: *c1cnccc1F]
x
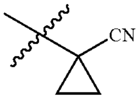 [SMILES: *C1(C#N)CC1]
y
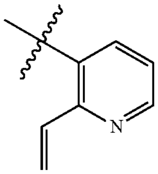 [SMILES: *c1cccnc1C=C]
z
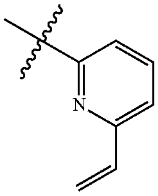 [SMILES: *c1cccc(C=C)n1]
aa
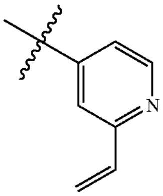 [SMILES: *c1ccnc(C=C)c1]
bb
TABLE Ia-continued
Exemplary Y groups
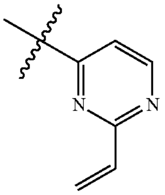 [SMILES: *c1ccnc(C=C)n1]
cc
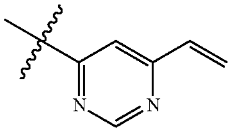 [SMILES: *c1cc(C=C)ncn1]
dd
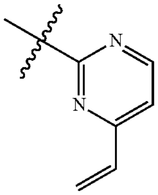 [SMILES: *c1nccc(C=C)n1]
ee
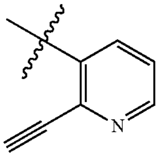 [SMILES: *c1cccnc1C#C]
ff
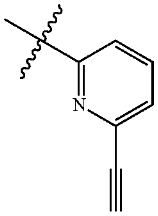 [SMILES: *c1cccc(C#C)n1]
gg
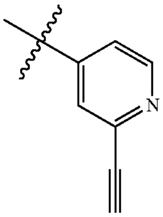 [SMILES: *c1ccnc(C#C)c1]
hh
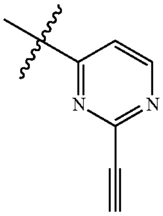 [SMILES: *c1ccnc(C#C)n1]
ii
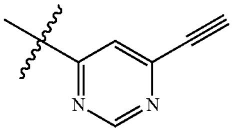 [SMILES: *c1cc(C#C)ncn1]
jj TABLE la-continued
| Exemplary Y groups | |
|---|---|
| 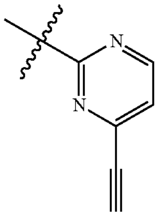 [SMILES: *c1nccc(C#C)n1] | kk |
| 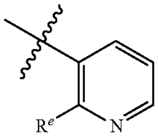 | ll |
| 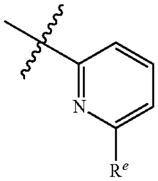 | mm |
| 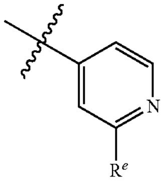 | nn |
| 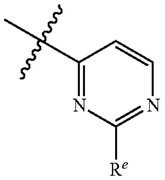 | oo |
| 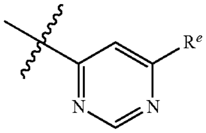 | pp |
| 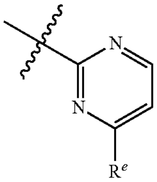 | qq |
| 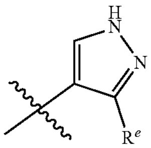 | rr |
| 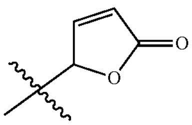 [SMILES: *C1C=CC(=O)O1] | ss |
TABLE la-continued
| Exemplary Y groups | |
|---|---|
| 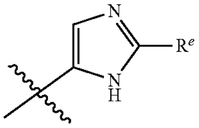 | tt |
| 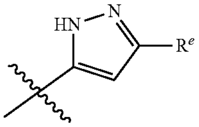 | uu |
| 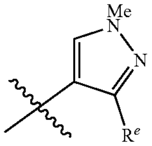 | vv |
| 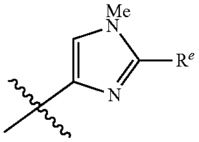 | ww |
| 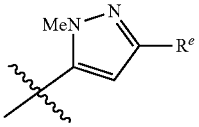 | xx |
| 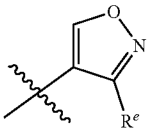 | yy |
| 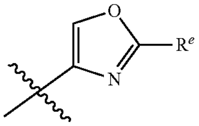 | zz |
| 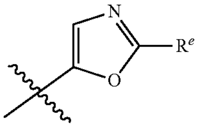 | aaa |
| 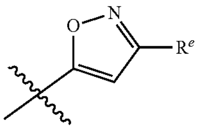 | bbb |
| 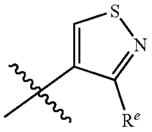 | ccc |
| 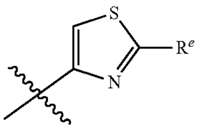 | ddd |

TABLE la-continued
| Exemplary Y groups | |
|---|---|
| 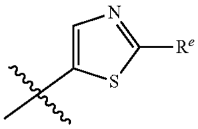 | eee |
| 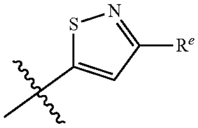 | fff |
| 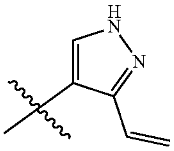 [SMILES: *c1c[nH]nc1C=C] | ggg |
| 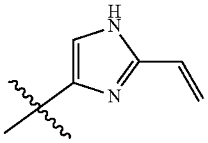 [SMILES: *c1c[nH]c(C=C)n1] | hhh |
| 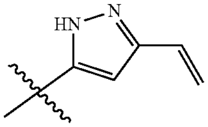 [SMILES: *c1cc(C=C)n[nH]1] | iii |
| 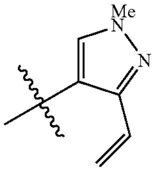 [SMILES: *c1cn(C)nc1C=C] | jjj |
| 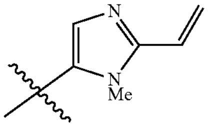 [SMILES: *c1cnc(C=C)n1C] | kkk |
| 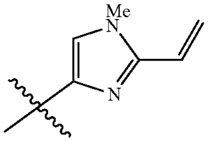 [SMILES: *c1cn(C)c(C=C)n1] | lll |
| 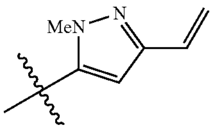 [SMILES: *c1cc(C=C)nn1C] | mmm |
| 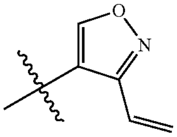 [SMILES: *c1conc1C=C] | nnn |
TABLE la-continued
| Exemplary Y groups | |
|---|---|
| 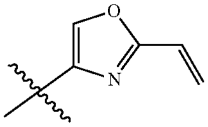 [SMILES: *c1coc(C=C)n1] | ooo |
| 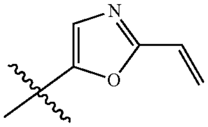 [SMILES: *c1cnc(C=C)o1] | ppp |
| 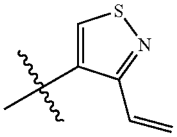 [SMILES: *c1csnc1C=C] | qqq |
| 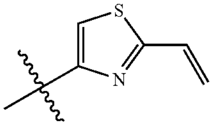 [SMILES: *c1csc(C=C)n1] | rrr |
| 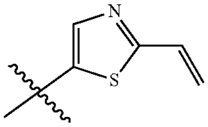 [SMILES: *c1cnc(C=C)s1] | sss |
| 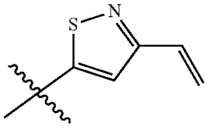 [SMILES: *c1cc(C=C)ns1] | ttt |
| 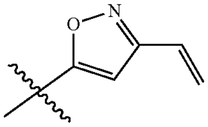 [SMILES: *c1cc(C=C)no1] | uuu |
| 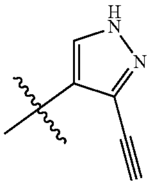 [SMILES: *c1c[nH]nc1C#C] | vvv |
| 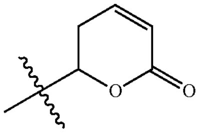 | qqq |
| 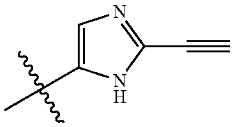 [SMILES: *c1cnc(C#C)[nH]1] | www |

TABLE Ia-continued
| Exemplary Y groups | |
|---|---|
| 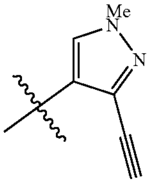 [SMILES: *c1cn(C)nc1C#C] | xxx |
| 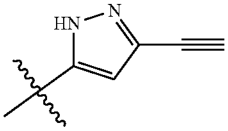 [SMILES: *c1cc(C#C)n[nH]1] | yyy |
| 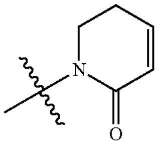 [SMILES: *N1CCC=CC1=O] | zzz |
| 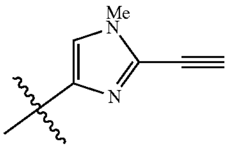 [SMILES: *c1cn(C)c(C#C)n1] | aaaa |
| 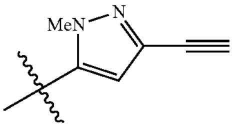 [SMILES: *c1cc(C#C)nn1C] | bbbb |
| 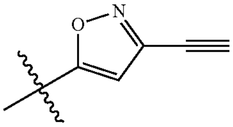 [SMILES: *c1cc(C#C)no1] | cccc |
| 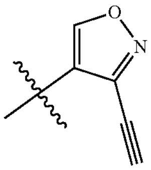 [SMILES: *c1conc1C#C] | dddd |
| 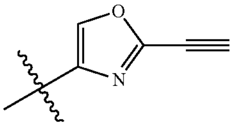 [SMILES: *c1coc(C#C)n1] | eeee |
| 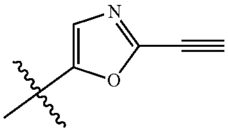 | ffff |
| 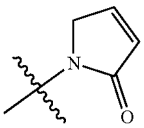 [SMILES: *N1CC=CC1=O] | gggg |
TABLE Ia-continued
| Exemplary Y groups | |
|---|---|
| 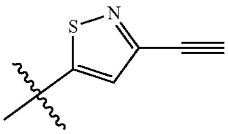 | hhhh |
| 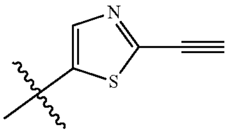 [SMILES: *c1cnc(C#C)s1] | iiii |
| 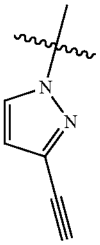 [SMILES: *n1ccc(C#C)n1] | jjjj |
| 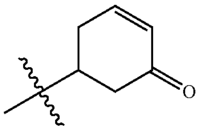 [SMILES: *C1CC=CC(=O)C1] | kkkk |
| 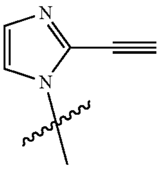 [SMILES: *n1ccnc1C#C] | llll |
| 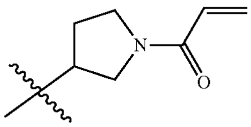 [SMILES: *C1CCN(C(=O)C=C)C1] | mmmm |
| 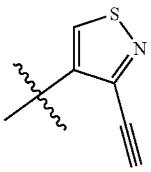 [SMILES: *c1csnc1C#C] | nnnn |
| 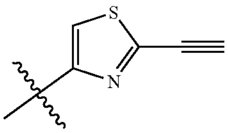 [SMILES: *c1csc(C#C)n1] | oooo |
| 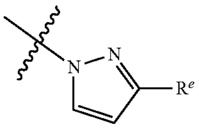 | pppp |

TABLE la-continued

| Exemplary Y groups | |
|---|---|
| 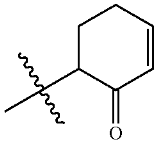 [SMILES: *C1CCC=CC1=O] | qqqq |
| 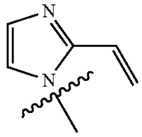 | rrrr |
| 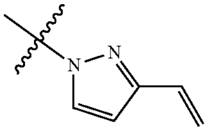 [SMILES: *n1ccc(C=C)n1] | ssss |
| 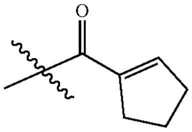 [SMILES: *C(=O)C1=CCCC1] | tttt |
| 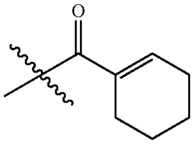 [SMILES: *C(=O)C1=CCCCC1] | uuuu |
| 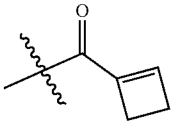 [SMILES: *C(=O)C1=CCC1] | vvvv |
| 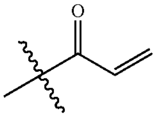 [SMILES: *C(=O)C=C] | wwww |
| 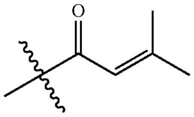 [SMILES: *C(=O)C=C(C)C] | xxxx |
| 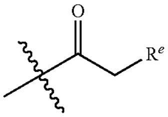 | yyyy |
| 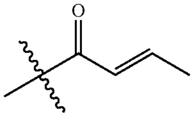 [SMILES: *C(=O)/C=C/C] | zzzz |
| 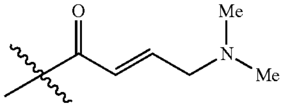 [SMILES: *C(=O)/C=C/CN(C)C] | aaaaa |

TABLE la-continued

| Exemplary Y groups | |
|---|---|
| 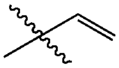 | bbbbb |
| 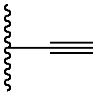 | ccccc |

wherein each $R^e$ is independently a suitable leaving group, $NO_2$, CN or oxo.

In certain embodiments, a warhead group is —C≡CH, —C≡CCH$_2$NH(isopropyl), —NHC(O)C≡CCH$_2$CH$_3$, —CH$_2$—C≡C≡CH$_3$, —C≡CCH$_2$OH, —CH$_2$C(O)C≡CH, —C(O)C≡CH, or —CH$_2$C(═O)C≡CH. In some embodiments, a warhead group is selected from —NHC(O)CH═CH$_2$, —NHC(O)CH═CHCH$_2$N(CH$_3$)$_2$, or —CH$_2$NHC(O)CH═CH$_2$.

In certain embodiments, a warhead group is selected from those set forth in Table 1b, below, wherein each wavy line indicates the point of attachment to the rest of the molecule. In certain embodiments, $R^4$ is selected from those set forth in Table 1b.

TABLE 1b

| Exemplary Warhead Groups | |
|---|---|
| 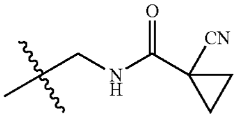 [SMILES: *CNC(=O)C1(C#N)CC1] | a |
| 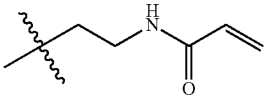 [SMILES: *CCNC(=O)C=C] | b |
| 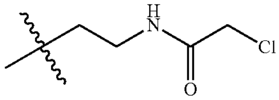 [SMILES: *CCNC(=O)CCl] | c |
| 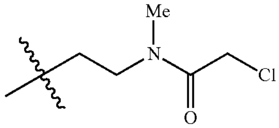 [SMILES: *CCN(C)C(=O)CCl] | d |
| 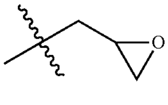 | e |
| 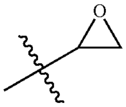 [SMILES: *C1CO1] | f |
| 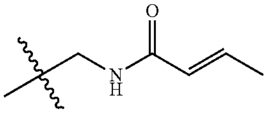 [SMILES: *CNC(=O)/C=C/C] | g |

TABLE 1b-continued
| Exemplary Warhead Groups | |
|---|---|
| 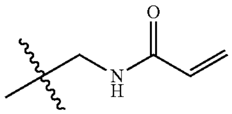 [SMILES: *CNC(=O)C=C] | h |
| 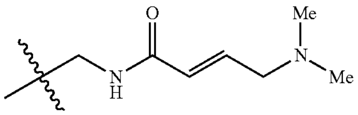 [SMILES: *CNC(=O)/C=C/CN(C)C] | i |
| 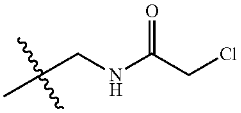 [SMILES: *CNC(=O)CCl] | j |
| 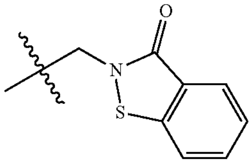 [SMILES: *Cn1sc2ccccc2c1=O] | k |
| 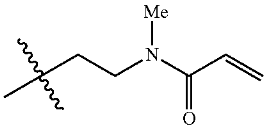 [SMILES: *CCN(C)C(=O)C=C] | l |
| 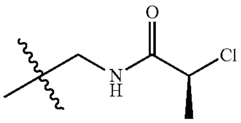 [SMILES: *CNC(=O)[C@H](C)Cl] | m |
| 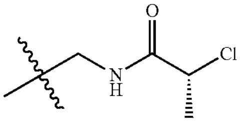 [SMILES: *CNC(=O)[C@@H](C)Cl] | n |
| 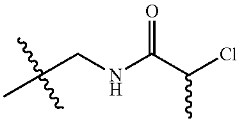 [SMILES: *CNC(=O)C(C)Cl] | o |
| 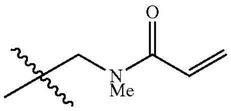 [SMILES: *CN(C)C(=O)C=C] | p |
| 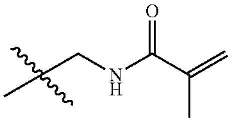 [SMILES: *CNC(=O)C(=C)C] | q |
| 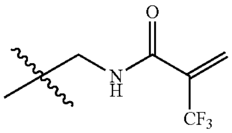 [SMILES: *CNC(=O)C(=C)C(F)(F)F] | r |
TABLE 1b-continued
| Exemplary Warhead Groups | |
|---|---|
| 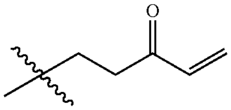 [SMILES: *CCC(=O)C=C] | s |
| 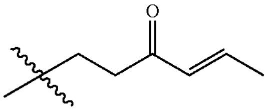 | t |
| 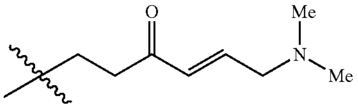 [SMILES: *CCC(=O)/C=C/CN(C)C] | u |
| 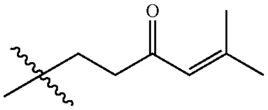 [SMILES: *CCC(=O)C=C(C)C] | v |
| 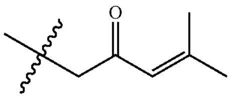 [SMILES: *CC(=O)C=C(C)C] | w |
| 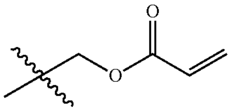 | x |
| 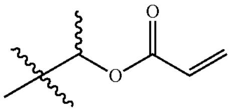 [SMILES: *C(C)OC(=O)C=C] | y |
| 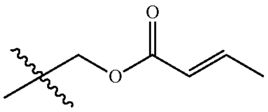 | z |
| 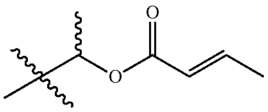 [SMILES: *C(C)OC(=O)/C=C/C] | aa |
| 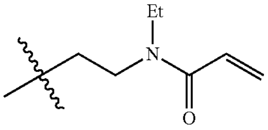 [SMILES: *CCN(CC)C(=O)C=C] | bb |
| 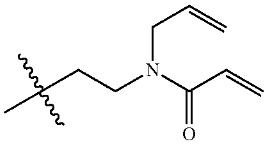 [SMILES: *CCN(CC=C)C(=O)C=C] | cc |
| 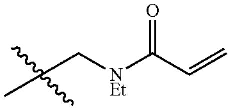 | dd |

TABLE 1b-continued
| Exemplary Warhead Groups | |
|---|---|
| 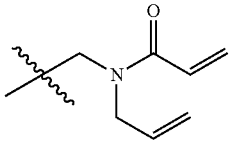 [SMILES: *CN(CC=C)C(=O)C=C] | ee |
| 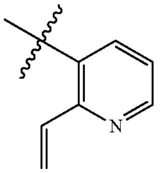 [SMILES: *c1cccnc1C=C] | ff |
| 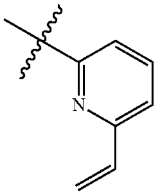 [SMILES: *c1cccc(C=C)n1] | gg |
| 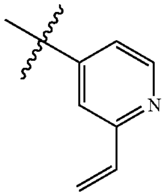 [SMILES: *c1ccnc(C=C)c1] | hh |
| 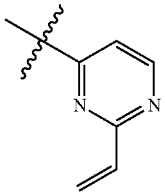 [SMILES: *c1ccnc(C=C)n1] | ii |
| 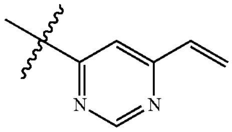 [SMILES: *c1cc(C=C)ncn1] | jj |
| 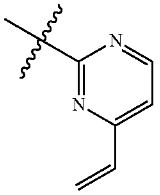 [SMILES: *c1nccc(C=C)n1] | kk |
| 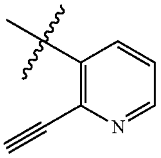 [SMILES: *c1cccnc1C#C] | ll |
TABLE 1b-continued
| Exemplary Warhead Groups | |
|---|---|
| 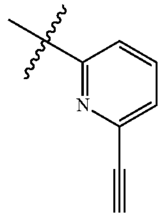 [SMILES: *c1cccc(C#C)n1] | mm |
| 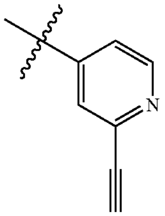 [SMILES: *c1ccnc(C#C)c1] | nn |
| 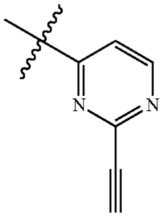 [SMILES: *c1ccnc(C#C)n1] | oo |
| 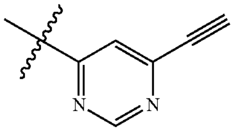 [SMILES: *c1cc(C#C)ncn1] | pp |
| 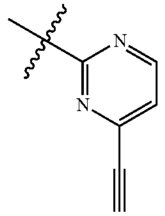 [SMILES: *c1nccc(C#C)n1] | qq |
| 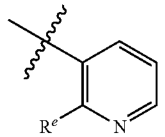 | rr |
| 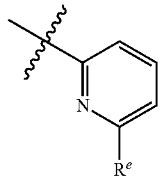 | ss |
| 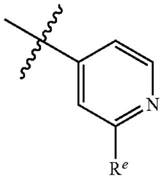 | tt |

TABLE 1b-continued
Exemplary Warhead Groups
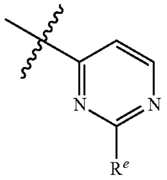
uu
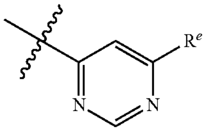
vv
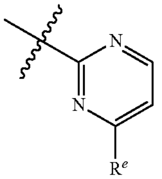
ww
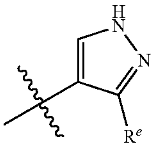
xx
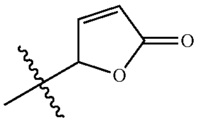 [SMILES: *C1C=CC(=O)O1]
yy
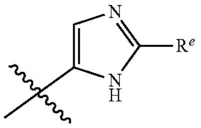
zz
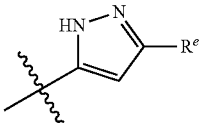
aaa
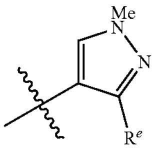
bbb
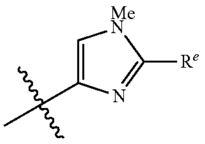
ccc
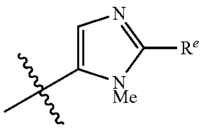
ddd
TABLE 1b-continued
Exemplary Warhead Groups
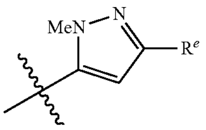
eee
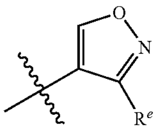
fff
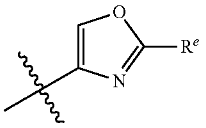
ggg
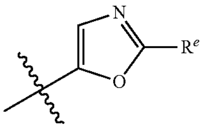
hhh
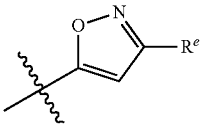
iii
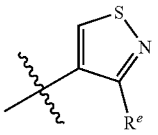
jjj
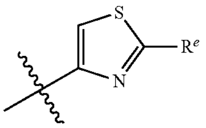
kkk
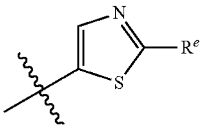
lll
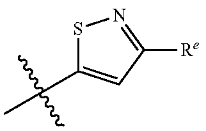
mmm
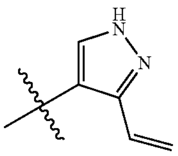 [SMILES: *c1c[nH]nc1C=C]
nnn TABLE 1b-continued
Exemplary Warhead Groups
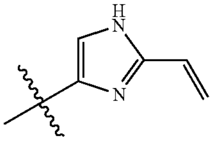 [SMILES: *c1c[nH]c(C=C)n1]
ooo
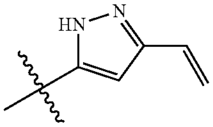 [SMILES: *c1cc(C=C)n[nH]1]
ppp
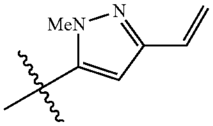 [SMILES: *c1cc(C=C)nn1C]
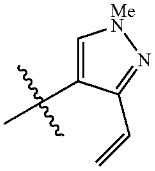 [SMILES: *c1cn(C)nc1C=C]
qqq
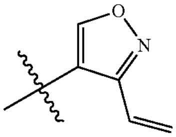 [SMILES: *c1conc1C=C]
rrr
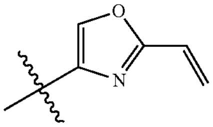 [SMILES: *c1coc(C=C)n1]
sss
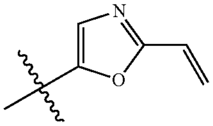 [SMILES: *c1cnc(C=C)o1]
ttt
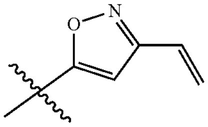 [SMILES: *c1cc(C=C)no1]
uuu
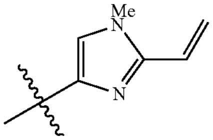 [SMILES: *c1cn(C)c(C=C)n1]
vvv
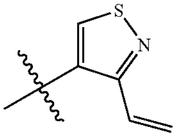 [SMILES: *c1csnc1C=C]
www
TABLE 1b-continued
Exemplary Warhead Groups
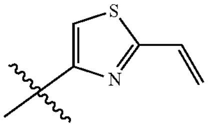 [SMILES: *c1csc(C=C)n1]
xxx
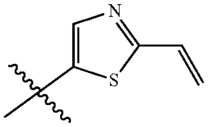 [SMILES: *c1cnc(C=C)s1]
yyy
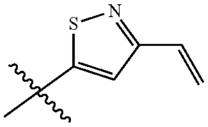 [SMILES: *c1cc(C=C)ns1]
zzz
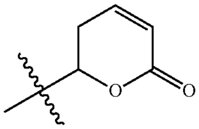 [SMILES: *C1CC=CC(=O)O1]
aaaa
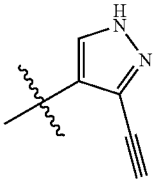 [SMILES: *c1c[nH]nc1C#C]
bbbb
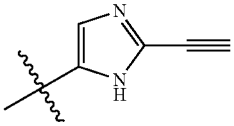 [SMILES: *c1cnc(C#C)[nH]1]
cccc
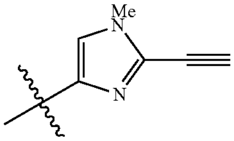 [SMILES: *c1cn(C)c(C#C)n1]
dddd
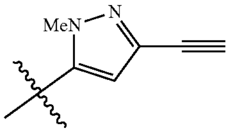 [SMILES: *c1cc(C#C)nn1C]
eeee
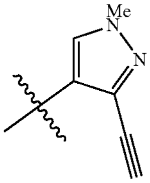 [SMILES: *c1cn(C)nc1C#C]
ffff
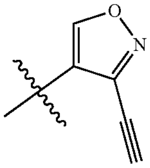 [SMILES: *c1conc1C#C]
gggg TABLE 1b-continued
Exemplary Warhead Groups
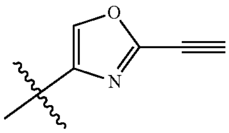 [SMILES: *c1coc(C#C)n1]
hhhh
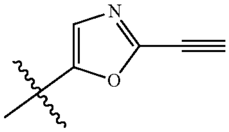 [SMILES: *c1cnc(C#C)o1]
iiii
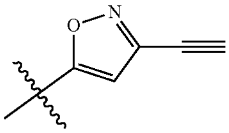 [SMILES: *c1cc(C#C)no1]
jjjj
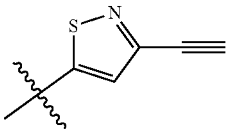 [SMILES: *c1cc(C#C)ns1]
kkkk
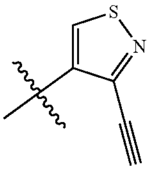 [SMILES: *c1csnc1C#C]
llll
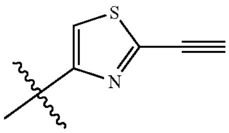 [SMILES: *c1csc(C#C)n1]
mmmm
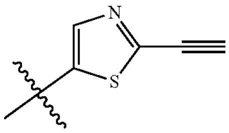 [SMILES: *c1cnc(C#C)s1]
nnnn
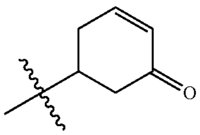 [SMILES: *C1CC=CC(=O)C1]
oooo
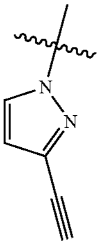 [SMILES: *n1ccc(C#C)n1]
pppp
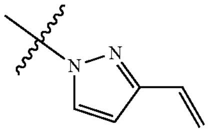 [SMILES: *n1ccc(C=C)n1]
qqqq
TABLE 1b-continued
Exemplary Warhead Groups
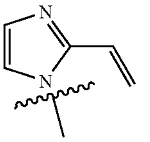
rrrr
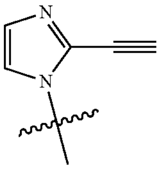 [SMILES: *n1ccnc1C#C]
ssss
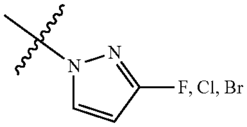
tttt
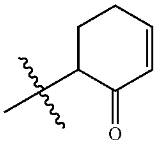 [SMILES: *C1CCC=CC1=O]
uuuu
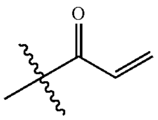 [SMILES: *C(=O)C=C]
vvvv
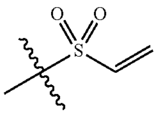 [SMILES: *S(=O)(=O)C=C]
wwww
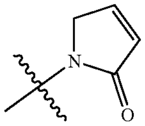 [SMILES: *N1CC=CC1=O]
xxxx
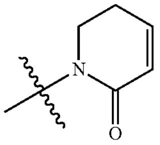 [SMILES: *N1CCC=CC1=O]
yyyy
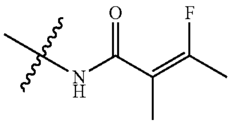 [SMILES: *NC(=O)/C(C)=C(/C)F]
zzzz
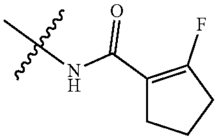 [SMILES: *NC(=O)C1=C(F)CCC1]
aaaaa TABLE 1b-continued
| Exemplary Warhead Groups | |
|---|---|
| 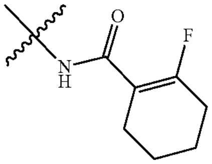 [SMILES: *NC(=O)C1=C(F)CCCC1] | bbbbb |
| 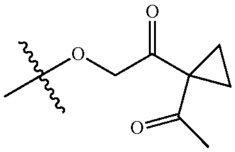 [SMILES: *OCC(=O)C1(C(C)=O)CC1] | ccccc |
| 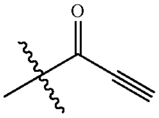 [SMILES: *C(=O)C#C] | ddddd |
| 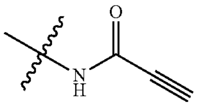 [SMILES: *NC(=O)C#C] | eeeee |
| 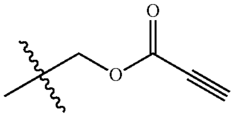 [SMILES: *COC(=O)C#C] | fffff |
| 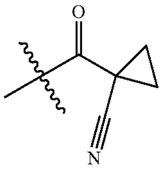 [SMILES: *C(=O)C1(C#N)CC1] | ggggg |
| 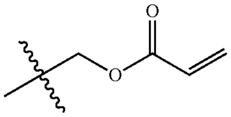 [SMILES: *COC(=O)C=C] | hhhhh |
| 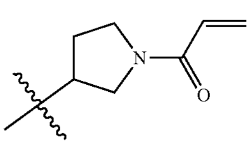 [SMILES: *C1CCN(C(=O)C=C)C1] | iiiii |
| 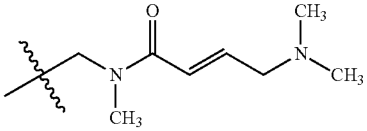 | jjjjj |
| 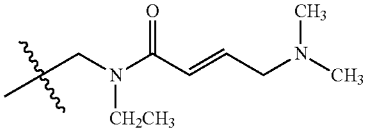 | kkkkk |
TABLE 1b-continued
| Exemplary Warhead Groups | |
|---|---|
| 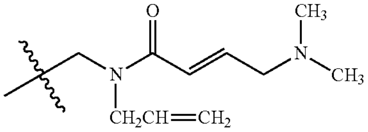 | lllll |
| 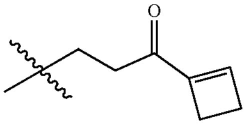 | mmmmm |
| 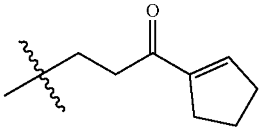 [SMILES: *CCC(=O)C1=CCCC1] | nnnnn |
| 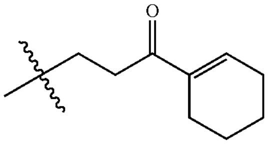 [SMILES: *CCC(=O)C1=CCCCC1] | ooooo |
| 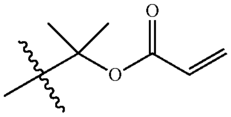 [SMILES: *C(C)(C)OC(=O)C=C] | ppppp |
| 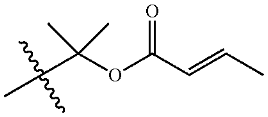 [SMILES: *C(C)(C)OC(=O)/C=C/C] | qqqqq |
| 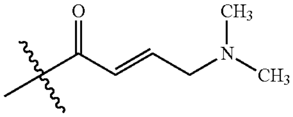 [SMILES: *C(=O)/C=C/CN(C)C] | rrrrr |
| 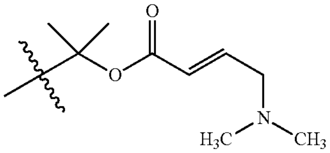 [SMILES: *C(C)(C)OC(=O)/C=C/CN(C)C] | sssss |
| 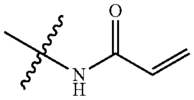 [SMILES: *NC(=O)C=C] | ttttt |
| 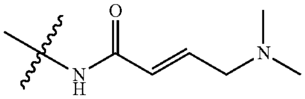 [SMILES: *NC(=O)/C=C/CN(C)C] | uuuuu |
| 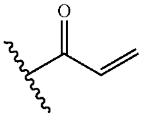 [SMILES: *C(=O)C=C] | vvvvv |

TABLE 1b-continued
| Exemplary Warhead Groups | |
|---|---|
| 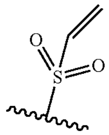 [SMILES: *S(=O)(=O)C=C] | wwwww |
| 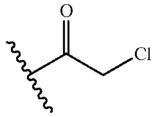 [SMILES: *C(=O)CCl] | xxxxx |
| 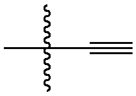 [SMILES: *C#C] | yyyyy |
| 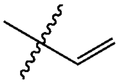 [SMILES: *C=C] | zzzzz |
| 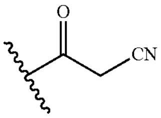 [SMILES: *C(=O)CC#N] | aaaaaa |
| 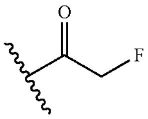 [SMILES: *C(=O)CF] | bbbbbb |
| 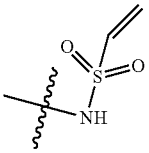 [SMILES: *NS(=O)(=O)C=C] | cccccc |
| 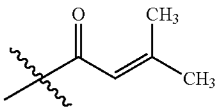 [SMILES: *C(=O)C=C(C)C] | dddddd |
| 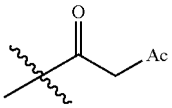 [SMILES: *C(=O)CC(C)=O] | eeeeee |
| 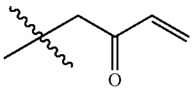 [SMILES: *CC(=O)C=C] | ffffff |
| 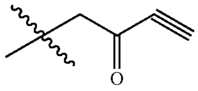 [SMILES: *CC(=O)C#C] | gggggg |
| 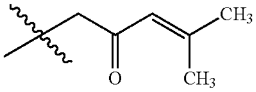 | hhhhhh |
TABLE 1b-continued
| Exemplary Warhead Groups | |
|---|---|
| 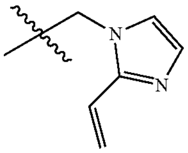 [SMILES: *Cn1ccnc1C=C] | iiiii |
| 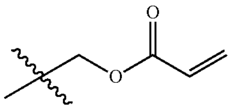 [SMILES: *COC(=O)C=C] | jjjjj |
| 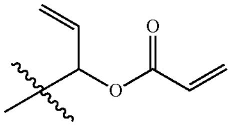 [SMILES: *C(C=C)OC(=O)C=C] | kkkkkk |
| 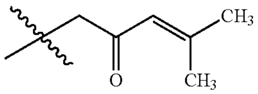 | llllll |
| 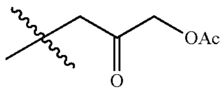 [SMILES: *CC(=O)COC(C)=O] | mmmmmm |
| 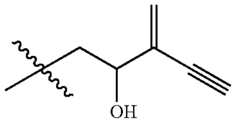 [SMILES: *CC(O)C(=C)C#C] | nnnnnn |
| 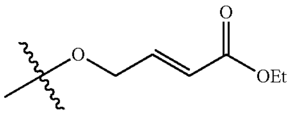 [SMILES: *OC/C=C/C(=O)OCC] | oooooo |
| 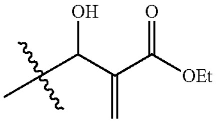 [SMILES: *C(O)C(=C)C(=O)OCC] | pppppp |
| 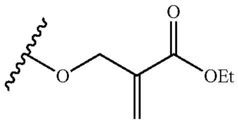 [SMILES: *OCC(=C)C(=O)OCC] | qqqqqq |
| 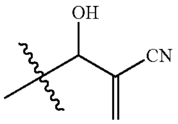 [SMILES: *C(O)C(=C)C#N] | rrrrrr |
| 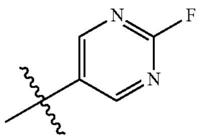 [SMILES: *c1cnc(F)nc1] | ssssss |
| 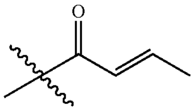 [SMILES: *C(=O)/C=C/C] | tttttt |

TABLE 1b-continued

| Exemplary Warhead Groups | |
|---|---|
| 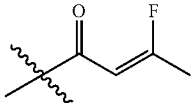 [SMILES: *C(=O)/C=C(/C)F] | uuuuuu |
| 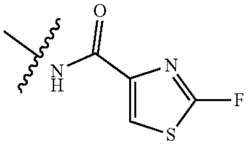 | vvvvvv |
| 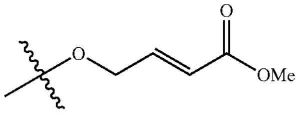 [SMILES: *OC/C=C/C(=O)OC] | wwwwww |
| 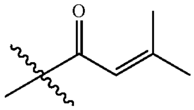 [SMILES: *C(=O)C=C(C)C] | xxxxxx |

wherein each $R^e$ is independently a suitable leaving group, $NO_2$, CN, or oxo.

In some embodiments, Y of a warhead group is an isoxazoline compound or derivative capable of covalently binding to serine. In some embodiments, Y of a warhead group is an isoxazoline compound or derivative described in WO 2010135360, the entire content of which is incorporated herein by reference. As understood by one skilled in the art, an isoxazoline compound or derivative described in WO 2010135360, as Y of a warhead group, can covalently connect to $L^2$ of the warhead group at any reasonable position of the isoxazoline compound or derivative. In some embodiments, Y of a warhead group is:

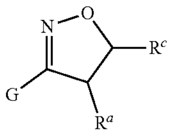

wherein G, Ra, and $R^e$ are:

| G | $R^a$ | $R^c$ |
|---|---|---|
| —Br | —H | —H |
| —Cl | —H | —H |
| 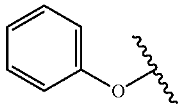 [SMILES: *Oc1ccccc1] | —H | —H |
| 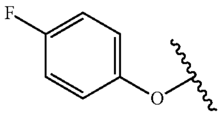 [SMILES: *Oc1ccc(F)cc1] | —H | —H |

-continued

| G | $R^a$ | $R^c$ |
|---|---|---|
| 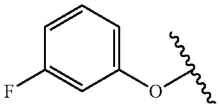 | —H | —H |
| 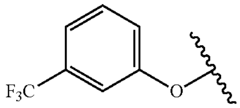 [SMILES: *Oc1cccc(C(F)(F)F)c1] | —H | —H |
| 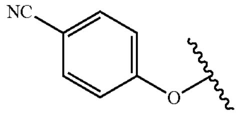 [SMILES: *Oc1ccc(C#N)cc1] | —H | —H |
| 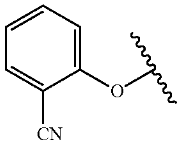 [SMILES: *Oc1ccccc1C#N] | —H | —H |
| 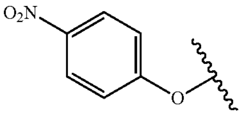 [SMILES: *Oc1ccc([N+](=O)[O-])cc1] | —H | —H |
| 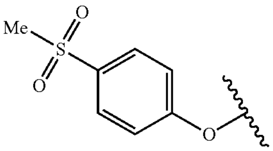 [SMILES: *Oc1ccc(S(C)(=O)=O)cc1] | —H | —H |
| 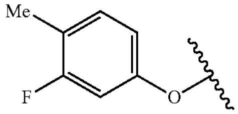 [SMILES: *Oc1ccc(C)c(F)c1] | —H | —H |
| 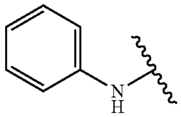 [SMILES: *Nc1ccccc1] | —H | —H |
| 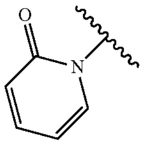 [SMILES: *n1ccccc1=O] | —H | —H |
| 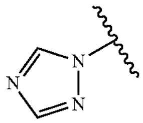 [SMILES: *n1cncn1] | —H | —H |
| 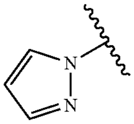 [SMILES: *n1cccn1] | —H | —H |

-continued
| G | $R^a$ | $R^c$ |
|---|---|---|
| 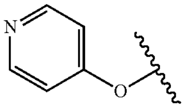 [SMILES: *Oc1ccncc1] | —H | —H |
| 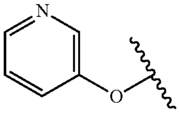 [SMILES: *Oc1cccnc1] | —H | —H |
| 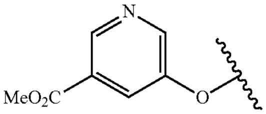 [SMILES: *Oc1cncc(C(=O)OC)c1] | —H | —H |
| 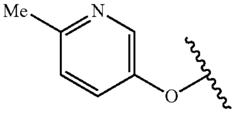 [SMILES: *Oc1ccc(C)nc1] | —H | —H |
| 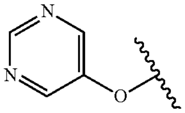 [SMILES: *Oc1cncnc1] | —H | —H |
| 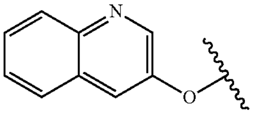 [SMILES: *Oc1cnc2ccccc2c1] | —H | —H |
| 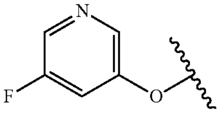 [SMILES: *Oc1cncc(F)c1] | —H | —H |
| 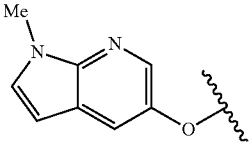 [SMILES: *Oc1cnc2c(ccn2C)c1] | —H | —H |
| —OMe | —H | —H |
| 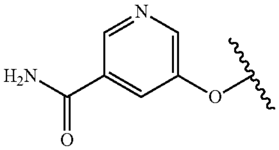 [SMILES: *Oc1cncc(C(N)=O)c1] | —H | —H |
| 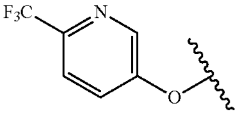 [SMILES: *Oc1ccc(C(F)(F)F)nc1] | —H | —H |
| 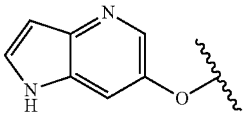 [SMILES: *Oc1cnc2cc[nH]c2c1] | —H | —H |
-continued
| G | $R^a$ | $R^c$ |
|---|---|---|
| 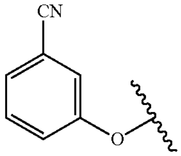 [SMILES: *Oc1cccc(C#N)c1] | —H | —H |
| 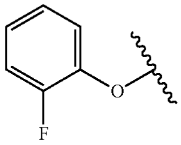 [SMILES: *Oc1ccccc1F] | —H | —H |
| 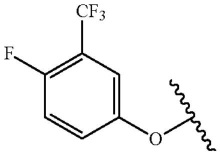 [SMILES: *Oc1ccc(F)c(C(F)(F)F)c1] | —H | —H |
| 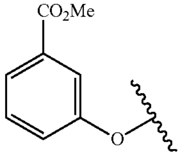 [SMILES: *Oc1cccc(C(=O)OC)c1] | —H | —H |
| 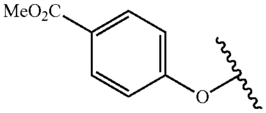 [SMILES: *Oc1ccc(C(=O)OC)cc1] | —H | —H |
| 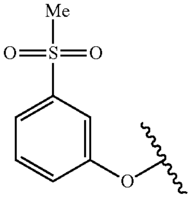 [SMILES: *Oc1cccc(S(C)(=O)=O)c1] | —H | —H |
| 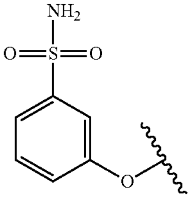 [SMILES: *Oc1cccc(S(N)(=O)=O)c1] | —H | —H |
| 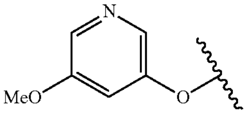 [SMILES: *Oc1cncc(OC)c1] | —H | —H |
| 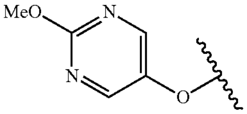 [SMILES: *Oc1cnc(OC)nc1] | —H | —H |

-continued
| G | $R^a$ | $R^c$ |
|---|---|---|
| 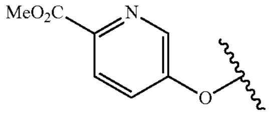 [SMILES: *Oc1ccc(C(=O)OC)nc1] | —H | —H |
| 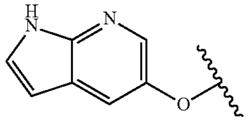 [SMILES: *Oc1cnc2[nH]ccc2c1] | —H | —H |
| 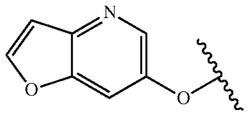 [SMILES: *Oc1cnc2ccoc2c1] | —H | —H |
| 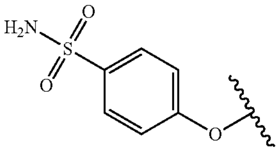 [SMILES: *Oc1ccc(S(N)(=O)=O)cc1] | —H | —H |
| 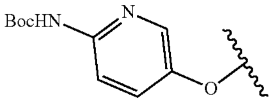 [SMILES: *Oc1ccc(NC(=O)OC(C)(C)C)nc1] | —H | —H |
| 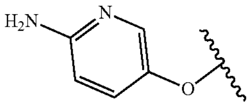 [SMILES: *Oc1ccc(N)nc1] | —H | —H |
| 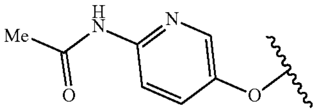 [SMILES: *Oc1ccc(NC(C)=O)nc1] | —H | —H |
| 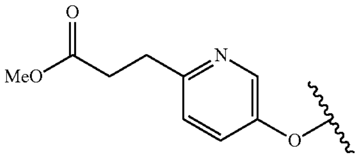 [SMILES: *Oc1ccc(CCC(=O)OC)nc1] | —H | —H |
| 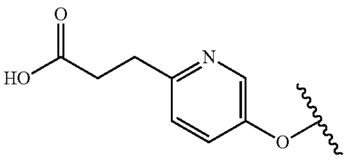 [SMILES: *Oc1ccc(CCC(=O)O)nc1] | —H | —H |
| 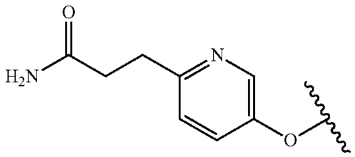 [SMILES: *Oc1ccc(CCC(N)=O)nc1] | —H | —H |
| 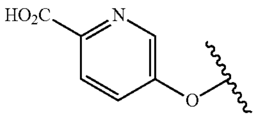 [SMILES: *Oc1ccc(C(=O)O)nc1] | —H | —H |
-continued
| G | $R^a$ | $R^c$ |
|---|---|---|
| 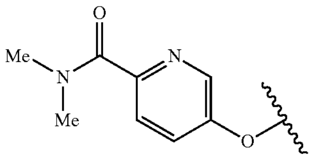 [SMILES: *Oc1ccc(C(=O)N(C)C)nc1] | —H | —H |
| 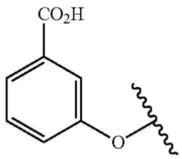 [SMILES: *Oc1cccc(C(=O)O)c1] | —H | —H |
| 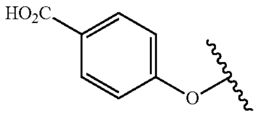 [SMILES: *Oc1ccc(C(=O)O)cc1] | —H | —H |
| 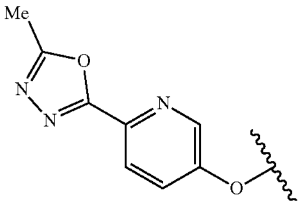 [SMILES: *Oc1ccc(-c2nnc(C)o2)nc1] | —H | —H |
| 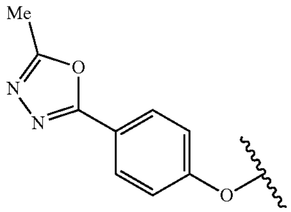 [SMILES: *Oc1ccc(-c2nnc(C)o2)cc1] | —H | —H |
| 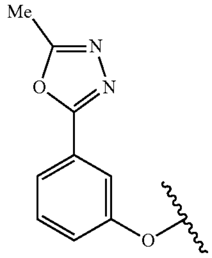 [SMILES: *Oc1cccc(-c2nnc(C)o2)c1] | —H | —H |
| 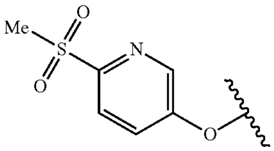 [SMILES: *Oc1ccc(S(C)(=O)=O)nc1] | —H | —H |
| 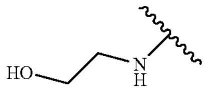 [SMILES: *NCCO] | —H | —H |
| 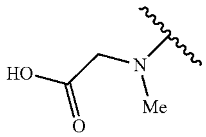 [SMILES: *N(C)CC(=O)O] | —H | —H |

-continued

| G | $R^a$ | $R^c$ |
|---|---|---|
| 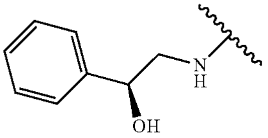 [SMILES: *NC[C@@H](O)c1ccccc1] | —H | —H |
| 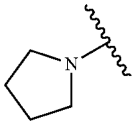 | —H | —H |
| 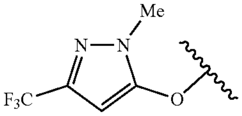 | —H | —H |
| 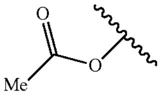 [SMILES: *OC(C)=O] | —H | —H |
| —Br | $—CH_3$ | —H |
| —Br | $—CH_3$ | —H |
| 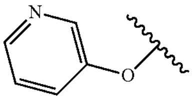 [SMILES: *Oc1cccnc1] | $—CH_3$ | — |
| —Br | —H | $—CH_3$ |
| 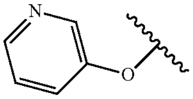 [SMILES: *Oc1cccnc1] | —H | $—CH_3$ |
| —Br | —H | $—CF_3$ |
| 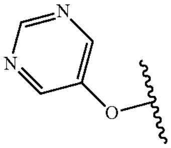 [SMILES: *Oc1cncnc1] | —H | $—CF_3$ |
| —Br | —H | $—CH_2CH_3$ |

In some embodiments, a warhead group is selected from those set forth in Table 1c, below, wherein each wavy line indicates the point of attachment to the rest of the molecule. In some embodiments, $R^4$ is selected from those set forth in Table 1c.

TABLE 1c

| Exemplary Warhead Groups | |
|---|---|
| 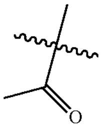 , | (A1) |

TABLE 1c-continued

| Exemplary Warhead Groups | |
|---|---|
| 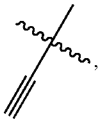 [SMILES: *C#C] , | (A2) |
| 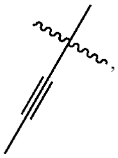 [SMILES: *C#CC] , | (A3) |
| 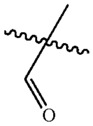 [SMILES: *C=O] , | (A4) |
| 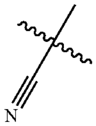 [SMILES: *C#N] , | (A5) |
| 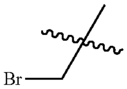 , | (A6) |
| 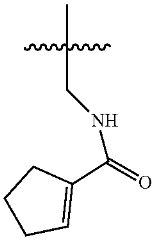 [SMILES: *CNC(=O)C1=CCCC1] , | (A7) |
| 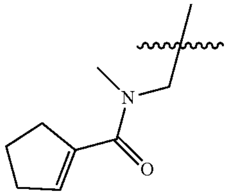 [SMILES: *CN(C)C(=O)C1=CCCC1] , | (A8) |
| 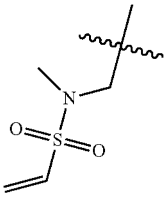 [SMILES: *CN(C)S(=O)(=O)C=C] , | (A9) |

TABLE 1c-continued
| Exemplary Warhead Groups |
| --- |
(A10)
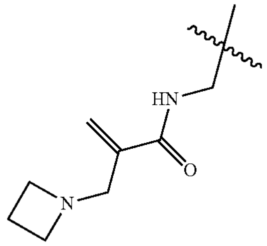 [SMILES: *CNC(=O)C(=C)CN1CCC1]
,
(A11)
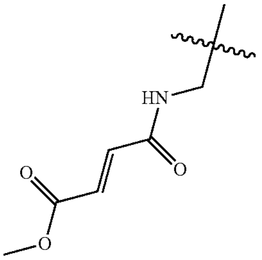 [SMILES: *CNC(=O)/C=C/C(=O)OC]
,
(A12)
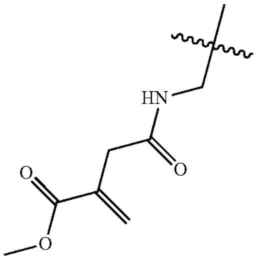 [SMILES: *CNC(=O)CC(=C)C(=O)OC]
,
(A13)
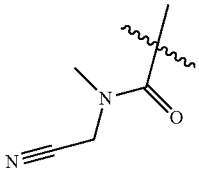 [SMILES: *C(=O)N(C)CC#N]
,
(A14)
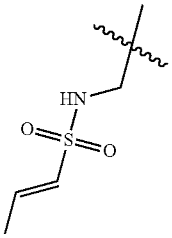 [SMILES: *CNS(=O)(=O)/C=C/C]
,
(A15)
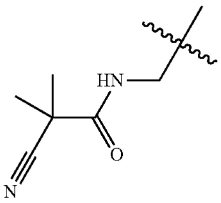 [SMILES: *CNC(=O)C(C)(C)C#N]
,
TABLE 1c-continued
| Exemplary Warhead Groups |
| --- |
(A16)
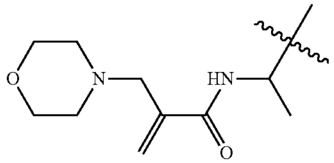 [SMILES: *C(C)NC(=O)C(=C)CN1CCOCC1]
,
(A17)
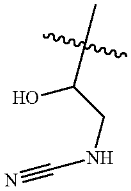 [SMILES: *C(O)CNC#N]
,
(A18)
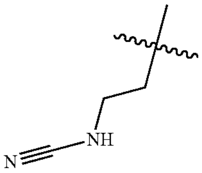 [SMILES: *CCNC#N]
,
(A19)
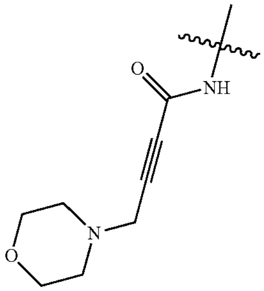 [SMILES: *NC(=O)C#CCN1CCOCC1]
,
(A20)
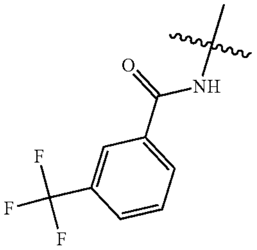 [SMILES: *NC(=O)c1cccc(C(F)(F)F)c1]
,
(A21)
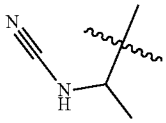 [SMILES: *C(C)NC#N]
, TABLE 1c-continued
Exemplary Warhead Groups
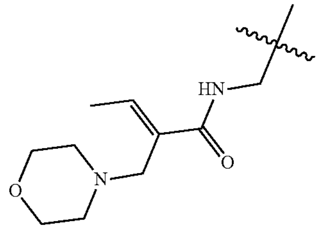 [SMILES: *CNC(=O)/C(=C/C)CN1CCOCC1]
(A22)
,
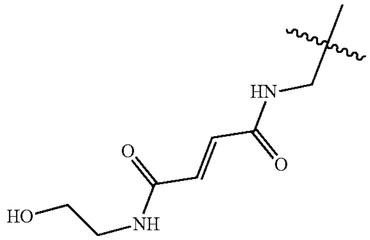 [SMILES: *CNC(=O)/C=C/C(=O)NCCO]
(A23)
,
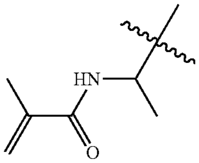 [SMILES: *C(C)NC(=O)C(=C)C]
(A24)
,
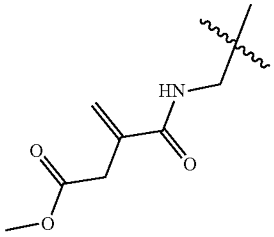 [SMILES: *CNC(=O)C(=C)CC(=O)OC]
(A25)
,
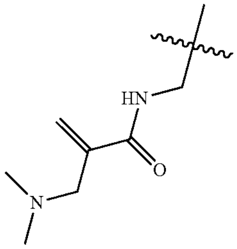 [SMILES: *CNC(=O)C(=C)CN(C)C]
(A26)
,
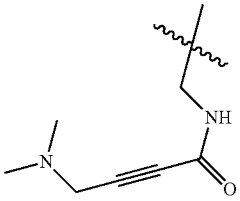 [SMILES: *CNC(=O)C#CCN(C)C]
(A27)
,
TABLE 1c-continued
Exemplary Warhead Groups
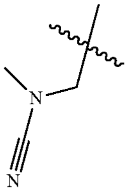 [SMILES: *CN(C)C#N]
(A28)
,
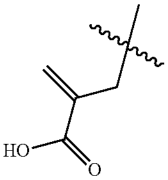 [SMILES: *CC(=C)C(=O)O]
(A29)
,
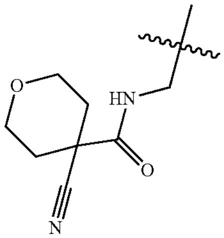 [SMILES: *CNC(=O)C1(C#N)CCOCC1]
(A30)
,
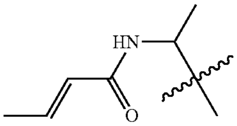 [SMILES: *C(C)NC(=O)/C=C/C]
(A31)
,
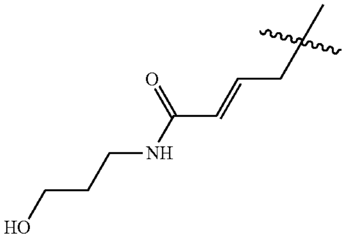 [SMILES: *C/C=C/C(=O)NCCCO]
(A32)
,
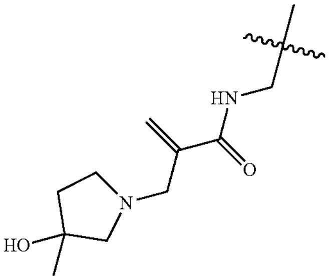 [SMILES: *CNC(=O)C(=C)CN1CCC(C)(O)C1]
(A33)
, TABLE 1c-continued
| Exemplary Warhead Groups |
|---|
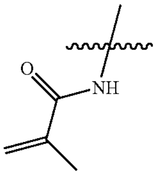 [SMILES: *NC(=O)C(=C)C]
(A34)
,
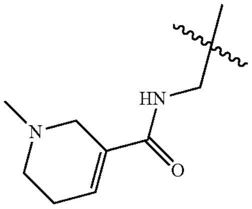 [SMILES: *CNC(=O)C1=CCCN(C)C1]
(A35)
,
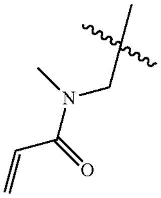 [SMILES: *CN(C)C(=O)C=C]
(A36)
,
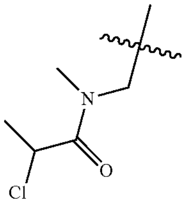 [SMILES: *CN(C)C(=O)C(C)Cl]
(A37)
,
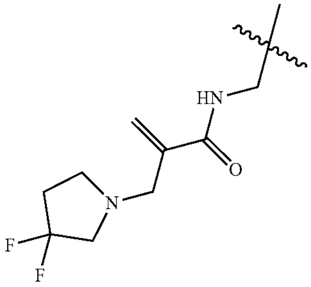 [SMILES: *CNC(=O)C(=C)CN1CCC(F)(F)C1]
(A38)
,
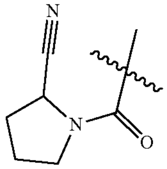 [SMILES: *C(=O)N1CCCC1C#N]
(A39)
,
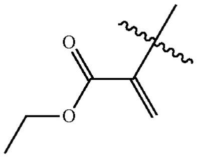 [SMILES: *C(=C)C(=O)OCC]
(A40)
,
TABLE 1c-continued
| Exemplary Warhead Groups |
|---|
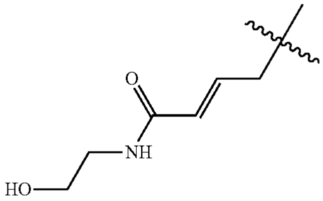 [SMILES: *C/C=C/C(=O)NCCO]
(A41)
,
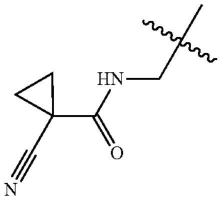 [SMILES: *CNC(=O)C1(C#N)CC1]
(A42)
,
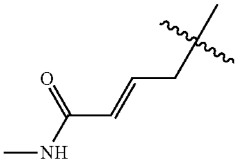 [SMILES: *C/C=C/C(=O)NC]
(A43)
,
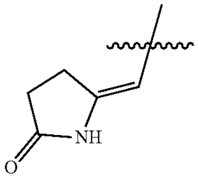 [SMILES: */C=C1\CCC(=O)N1]
(A44)
,
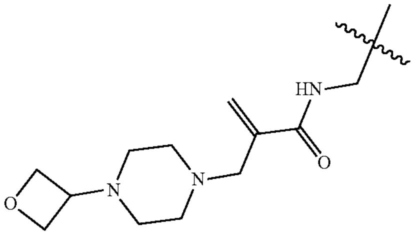 [SMILES: *CNC(=O)C(=C)CN1CCN(C2COC2)CC1]
(A45)
,
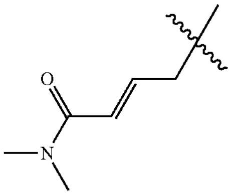 [SMILES: *C/C=C/C(=O)N(C)C]
(A46)
,
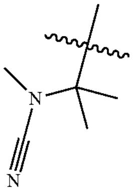 [SMILES: *C(C)(C)N(C)C#N]
(A47)
, TABLE 1c-continued
| Exemplary Warhead Groups |
|---|
| 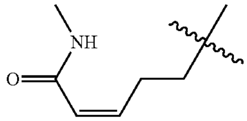 [SMILES: *CC/C=C\C(=O)NC] , (A48) |
| 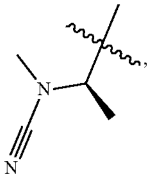 [SMILES: *[C@@H](C)N(C)C#N] (A49) |
| 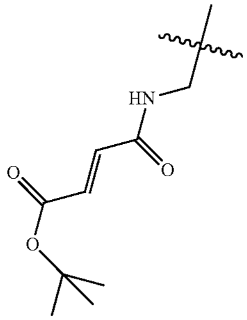 , (A50) |
| 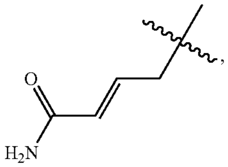 [SMILES: *C/C=C/C(N)=O] (A51) |
| 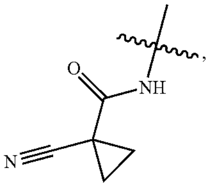 [SMILES: *NC(=O)C1(C#N)CC1] (A52) |
| 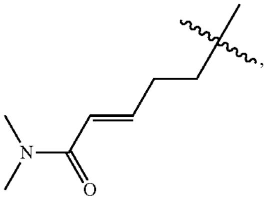 [SMILES: *CC/C=C/C(=O)N(C)C] (A53) |
| 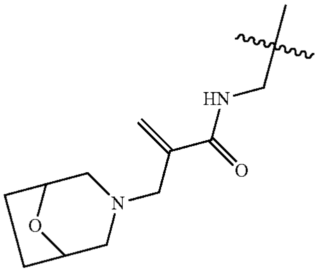 , (A54) |
TABLE 1c-continued
| Exemplary Warhead Groups |
|---|
| 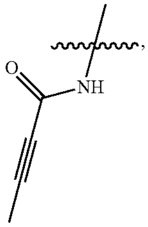 [SMILES: *NC(=O)C#CC] (A55) |
| 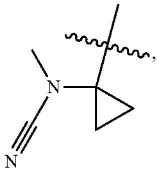 (A56) |
| 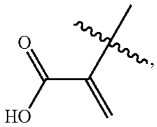 [SMILES: *C(=C)C(=O)O] (A57) |
| 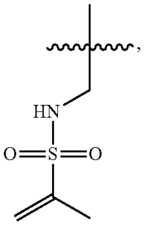 [SMILES: *CNS(=O)(=O)C(=C)C] (A58) |
| 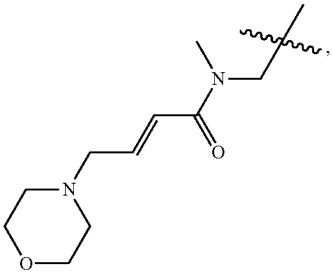 [SMILES: *CN(C)C(=O)/C=C/CN1CCOCC1] (A59) |
| 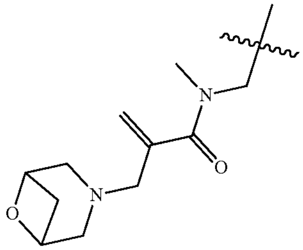 , (A60) |
| 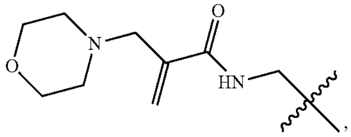 [SMILES: *CNC(=O)C(=C)CN1CCOCC1] (A61) |

TABLE 1c-continued
| Exemplary Warhead Groups |
|---|
(A62)
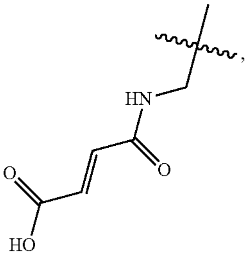 [SMILES: *CNC(=O)/C=C/C(=O)O]
(A63)
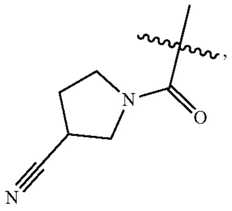 [SMILES: *C(=O)N1CCC(C#N)C1]
(A64)
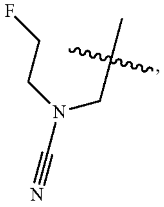 [SMILES: *CN(C#N)CCF]
(A65)
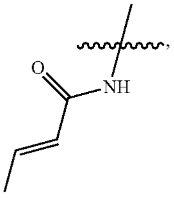 [SMILES: *NC(=O)/C=C/C]
(A66)
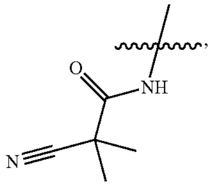 [SMILES: *NC(=O)C(C)(C)C#N]
(A67)
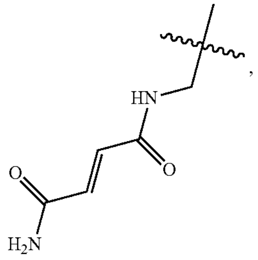 [SMILES: *CNC(=O)/C=C/C(N)=O]
(A68)
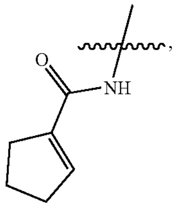 [SMILES: *NC(=O)C1=CCCC1]
TABLE 1c-continued
| Exemplary Warhead Groups |
|---|
(A69)
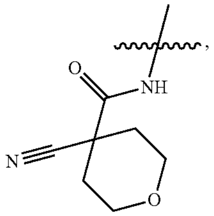 [SMILES: *NC(=O)C1(C#N)CCOCC1]
(A70)
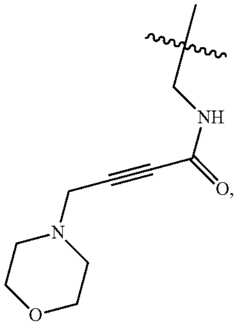 [SMILES: *CNC(=O)C#CCN1CCOCC1]
(A71)
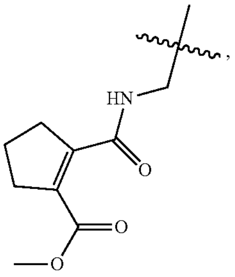 [SMILES: *CNC(=O)C1=C(C(=O)OC)CCC1]
(A72)
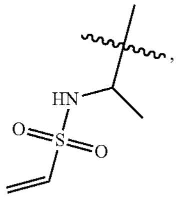 [SMILES: *C(C)NS(=O)(=O)C=C]
(A73)
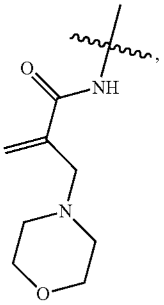 [SMILES: *NC(=O)C(=C)CN1CCOCC1]
(A74)
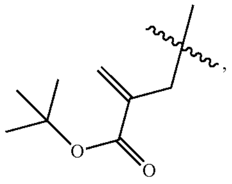 [SMILES: *CC(=C)C(=O)OC(C)(C)C]

TABLE 1c-continued
Exemplary Warhead Groups
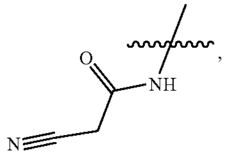 [SMILES: *NC(=O)CC#N]
(A75)
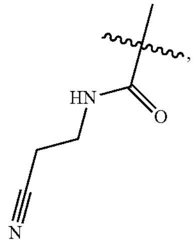 [SMILES: *C(=O)NCCC#N]
(A76)
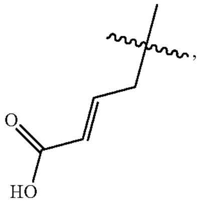 [SMILES: *C/C=C/C(=O)O]
(A77)
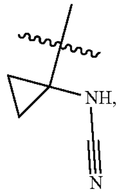
(A78)
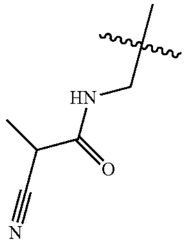 [SMILES: *CNC(=O)C(C)C#N]
(A79)
,
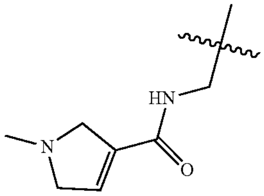 [SMILES: *CNC(=O)C1=CCN(C)C1]
(A80)
,
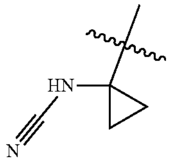 [SMILES: *C1(NC#N)CC1]
(A81)
,
TABLE 1c-continued
Exemplary Warhead Groups
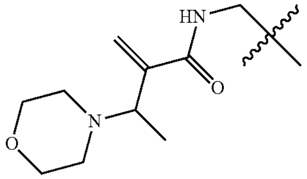 [SMILES: *CNC(=O)C(=C)C(C)N1CCOCC1]
(A82)
,
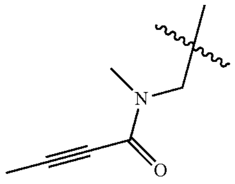 [SMILES: *CN(C)C(=O)C#CC]
(A83)
,
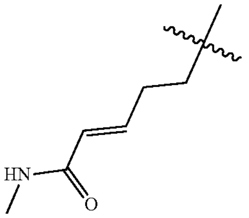 [SMILES: *CC/C=C/C(=O)NC]
(A84)
,
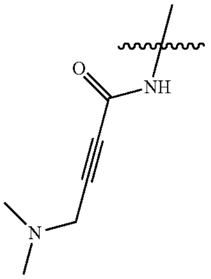 [SMILES: *NC(=O)C#CCN(C)C]
(A85)
,
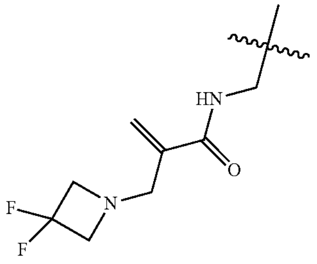 [SMILES: *CNC(=O)C(=C)CN1CC(F)(F)C1]
(A86)
,
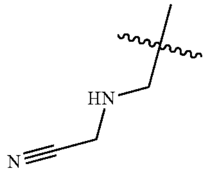 [SMILES: *CNCC#N]
(A87)
, TABLE 1c-continued
| Exemplary Warhead Groups |
| --- |
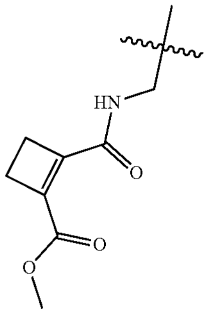 [SMILES: *CNC(=O)C1=C(C(=O)OC)CC1]
(A88)
,
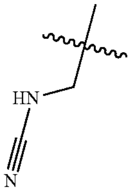 [SMILES: *CNC#N]
(A89)
,
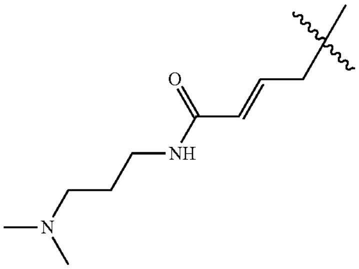 [SMILES: *C/C=C/C(=O)NCCCN(C)C]
(A90)
,
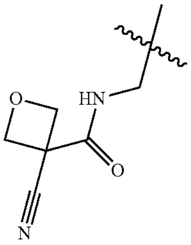 [SMILES: *CNC(=O)C1(C#N)COC1]
(A91)
,
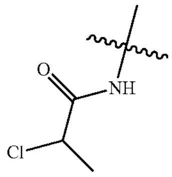 [SMILES: *NC(=O)C(C)Cl]
(A92)
,
TABLE 1c-continued
| Exemplary Warhead Groups |
| --- |
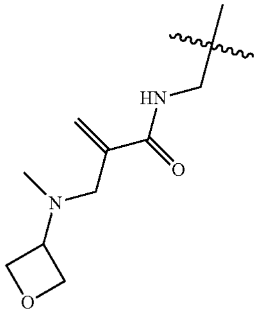 [SMILES: *CNC(=O)C(=C)CN(C)C1COC1]
(A93)
,
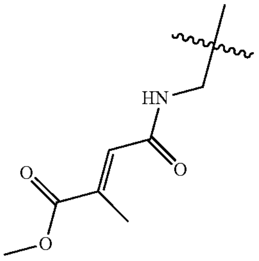 [SMILES: *CNC(=O)/C=C(\C)C(=O)OC]
(A94)
,
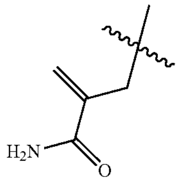 [SMILES: *CC(=C)C(N)=O]
(A95)
,
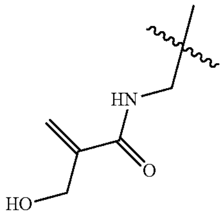 [SMILES: *CNC(=O)C(=C)CO]
(A96)
,
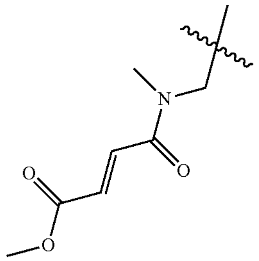 [SMILES: *CN(C)C(=O)/C=C/C(=O)OC]
(A97)
, TABLE 1c-continued
| Exemplary Warhead Groups |
| --- |
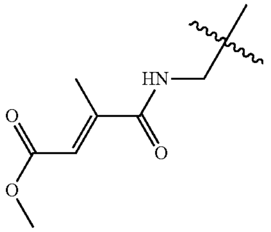 [SMILES: *CNC(=O)/C(C)=C/C(=O)OC]
(A98)
,
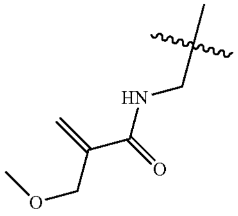 [SMILES: *CNC(=O)C(=C)COC]
(A99)
,
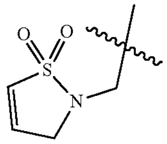 [SMILES: *CN1CC=CS1(=O)=O]
(A100)
,
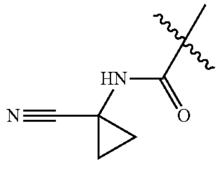 [SMILES: *C(=O)NC1(C#N)CC1]
(A101)
,
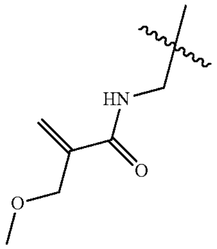 [SMILES: *CNC(=O)C(=C)COC]
(A102)
,
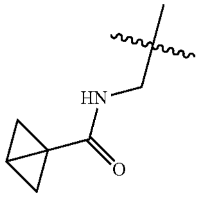 [SMILES: *CNC(=O)C12CC1C2]
(A103)
,
TABLE 1c-continued
| Exemplary Warhead Groups |
| --- |
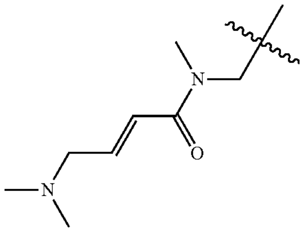 [SMILES: *CN(C)C(=O)/C=C/CN(C)C]
(A104)
,
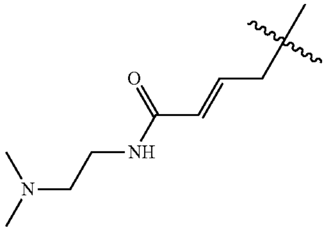 [SMILES: *C/C=C/C(=O)NCCN(C)C]
(A105)
,
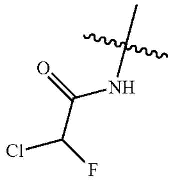 [SMILES: *NC(=O)C(F)Cl]
(A106)
,
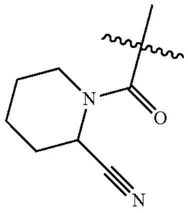 [SMILES: *C(=O)N1CCCCC1C#N]
(A107)
,
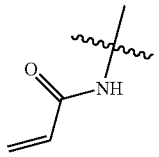 [SMILES: *NC(=O)C=C]
(A108)
,
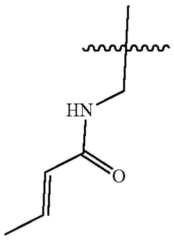 [SMILES: *CNC(=O)/C=C/C]
(A109)
, TABLE 1c-continued
| Exemplary Warhead Groups |
|---|
| 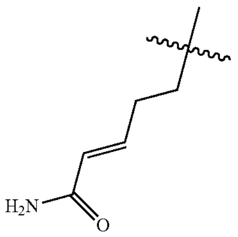 [SMILES: *CC/C=C/C(N)=O] (A110) , |
| 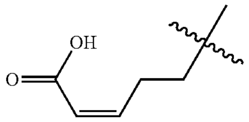 [SMILES: *CC/C=C\C(=O)O] (A111) , |
| 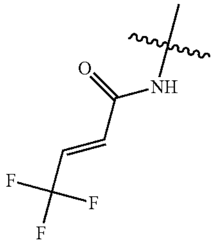 [SMILES: *NC(=O)/C=C/C(F)(F)F] (A112) , |
| 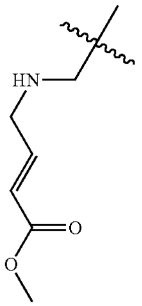 [SMILES: *CNC/C=C/C(=O)OC] (A113) , |
| 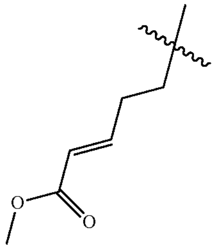 [SMILES: *CC/C=C/C(=O)OC] (A114) , |
| 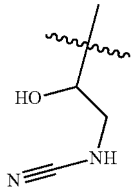 (A115) , |
TABLE 1c-continued
| Exemplary Warhead Groups |
|---|
| 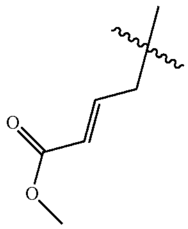 [SMILES: *C/C=C/C(=O)OC] (A116) , |
| 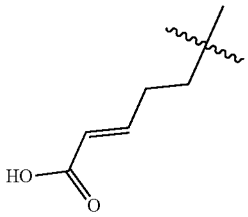 [SMILES: *CC/C=C/C(=O)O] (A117) , |
| 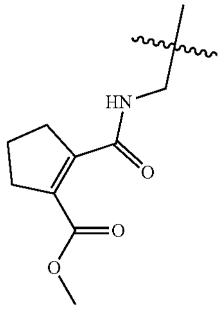 [SMILES: *CNC(=O)C1=C(C(=O)OC)CCC1] (A118) , |
| 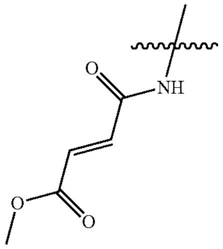 [SMILES: *NC(=O)/C=C/C(=O)OC] (A119) , |
| 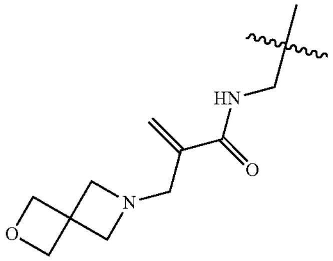 [SMILES: *CNC(=O)C(=C)CN1CC2(COC2)C1] (A120) , |
| 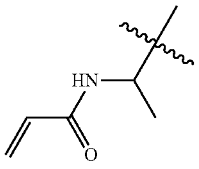 [SMILES: *C(C)NC(=O)C=C] (A121) , |

TABLE 1c-continued
Exemplary Warhead Groups
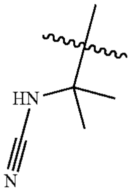 [SMILES: *C(C)(C)NC#N]
(A122)
,
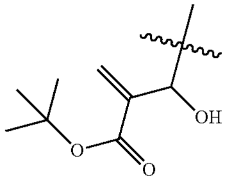 [SMILES: *C(O)C(=C)C(=O)OC(C)(C)C]
(A123)
,
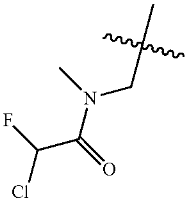 [SMILES: *CN(C)C(=O)C(F)Cl]
(A124)
,
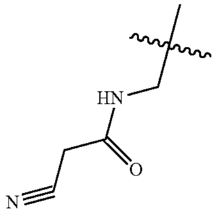 [SMILES: *CNC(=O)CC#N]
(A125)
,
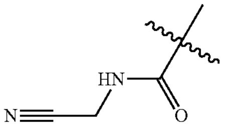 [SMILES: *C(=O)NCC#N]
(A126)
,
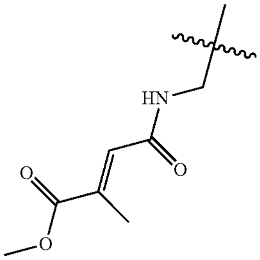 [SMILES: *CNC(=O)/C=C(\C)C(=O)OC]
(A127)
,
TABLE 1c-continued
Exemplary Warhead Groups
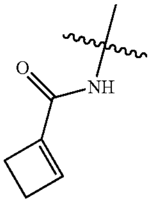 [SMILES: *NC(=O)C1=CCC1]
(A128)
,
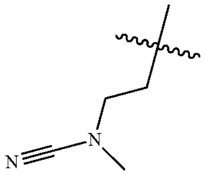 [SMILES: *CCN(C)C#N]
(A129)
,
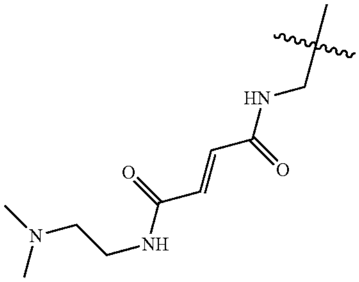 [SMILES: *CNC(=O)/C=C/C(=O)NCCN(C)C]
(A130)
,
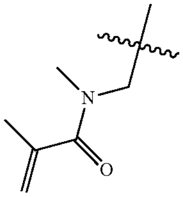 [SMILES: *CN(C)C(=O)C(=C)C]
(A131)
,
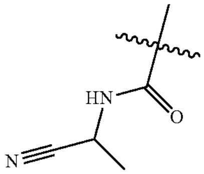 [SMILES: *C(=O)NC(C)C#N]
(A132)
,
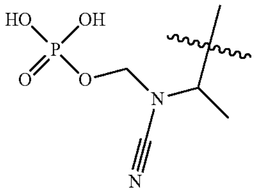 [SMILES: *C(C)N(C#N)COP(=O)(O)O]
(A133)
, TABLE 1c-continued
Exemplary Warhead Groups
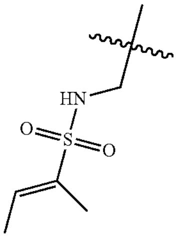 [SMILES: *CNS(=O)(=O)/C(C)=C/C]
(A134)
,
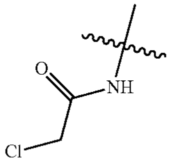 [SMILES: *NC(=O)CCl]
(A135)
,
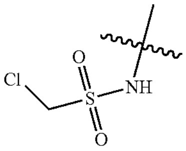 [SMILES: *NS(=O)(=O)CCl]
(A136)
,
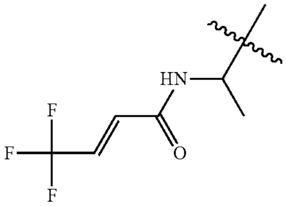 [SMILES: *C(C)NC(=O)/C=C/C(F)(F)F]
(A137)
,
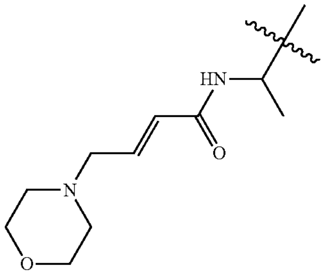 [SMILES: *C(C)NC(=O)/C=C/CN1CCOCC1]
(A138)
,
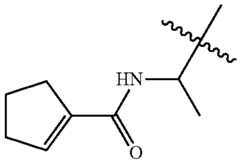 [SMILES: *C(C)NC(=O)C1=CCCC1]
(A139)
,
TABLE 1c-continued
Exemplary Warhead Groups
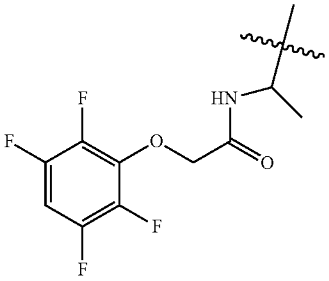 [SMILES: *C(C)NC(=O)COc1c(F)c(F)cc(F)c1F]
(A140)
,
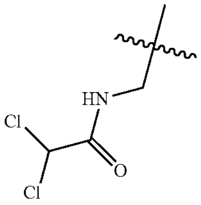 [SMILES: *CNC(=O)C(Cl)Cl]
(A141)
,
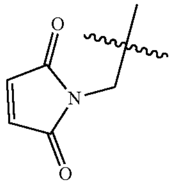 [SMILES: *CN1C(=O)C=CC1=O]
(A142)
,
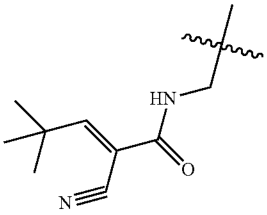 [SMILES: *CNC(=O)/C(C#N)=C/C(C)(C)C]
(A143)
,
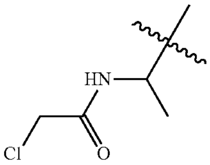 [SMILES: *C(C)NC(=O)CCl]
(A144)
,
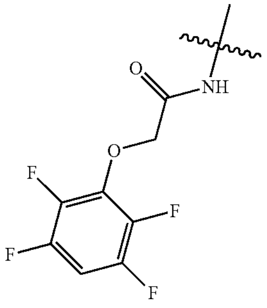 [SMILES: *NC(=O)COc1c(F)c(F)cc(F)c1F]
(A145)
, TABLE 1c-continued
| Exemplary Warhead Groups |
|---|
| 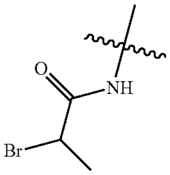 [SMILES: *NC(=O)C(C)Br] (A146) , |
| 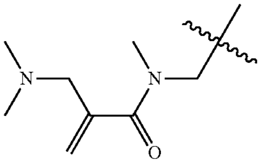 [SMILES: *CN(C)C(=O)C(=C)CN(C)C] (A147) , |
| 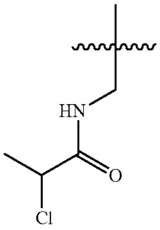 [SMILES: *CNC(=O)C(C)Cl] (A148) , |
| 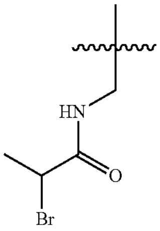 [SMILES: *CNC(=O)C(C)Br] (A149) , |
| 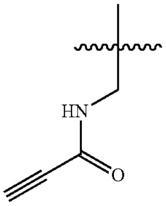 [SMILES: *CNC(=O)C#C] (A150) , |
| 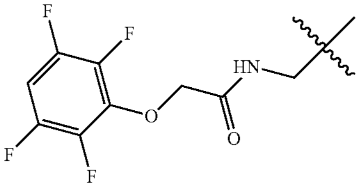 [SMILES: *CNC(=O)COc1c(F)c(F)cc(F)c1F] (A151) , |
TABLE 1c-continued
| Exemplary Warhead Groups |
|---|
| 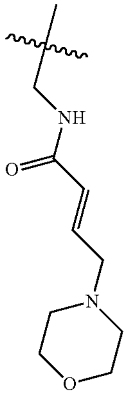 [SMILES: *CNC(=O)/C=C/CN1CCOCC1] (A152) , |
| 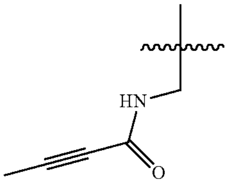 [SMILES: *CNC(=O)C#CC] (A153) , |
| 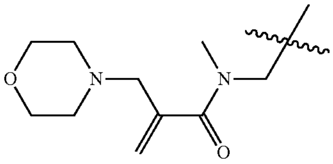 [SMILES: *CN(C)C(=O)C(=C)CN1CCOCC1] (A154) , |
| 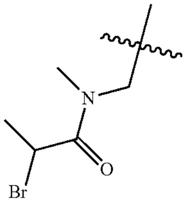 [SMILES: *CN(C)C(=O)C(C)Br] (A155) , |
| 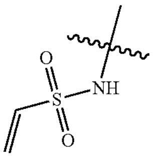 [SMILES: *NS(=O)(=O)C=C] (A156) , |
| 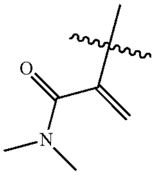 [SMILES: *C(=C)C(=O)N(C)C] (A157) , |

TABLE 1c-continued
| Exemplary Warhead Groups |
| --- |
| 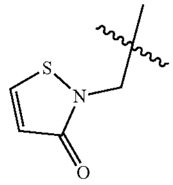 [SMILES: *Cn1sccc1=O] (A158) , |
| 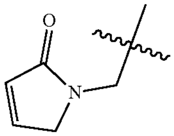 [SMILES: *CN1CC=CC1=O] (A159) , |
| 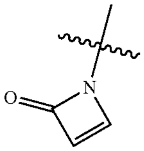 [SMILES: *N1C=CC1=O] (A160) , |
| 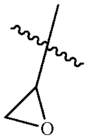 [SMILES: *C1CO1] (A161) , |
| 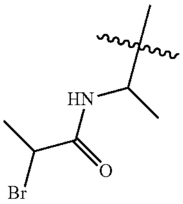 [SMILES: *C(C)NC(=O)C(C)Br] (A162) , |
| 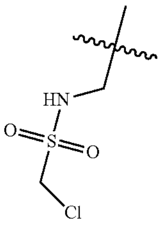 [SMILES: *CNS(=O)(=O)CCl] (A163) , |
| 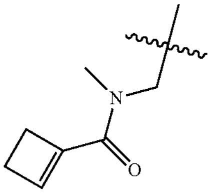 [SMILES: *CN(C)C(=O)C1=CCC1] (A164) , |
TABLE 1c-continued
| Exemplary Warhead Groups |
| --- |
| 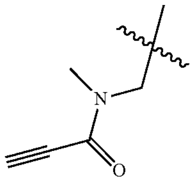 [SMILES: *CN(C)C(=O)C#C] (A165) , |
| 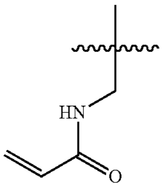 [SMILES: *CNC(=O)C=C] (A166) , |
| 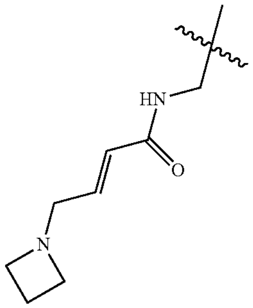 [SMILES: *CNC(=O)/C=C/CN1CCC1] (A167) , |
| 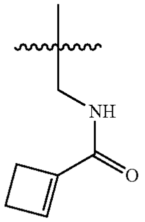 [SMILES: *CNC(=O)C1=CCC1] (A168) , |
| 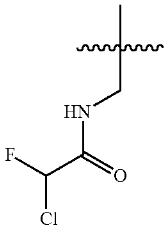 [SMILES: *CNC(=O)C(F)Cl] (A169) , |
| 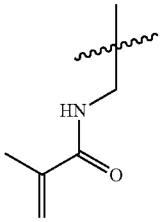 [SMILES: *CNC(=O)C(=C)C] (A170) , |

TABLE 1c-continued
| Exemplary Warhead Groups |
| --- |
(A171)
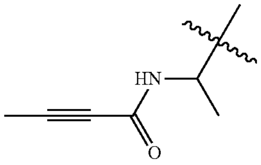 [SMILES: *C(C)NC(=O)C#CC]
,
(A172)
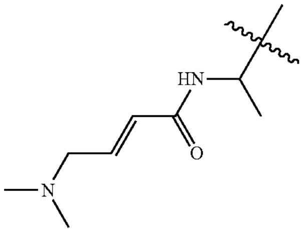 [SMILES: *C(C)NC(=O)/C=C/CN(C)C]
,
(A173)
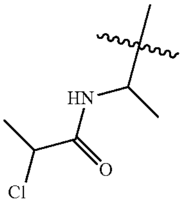 [SMILES: *C(C)NC(=O)C(C)Cl]
,
(A174)
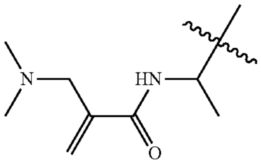 [SMILES: *C(C)NC(=O)C(=C)CN(C)C]
,
(A175)
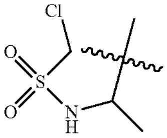 [SMILES: *C(C)NS(=O)(=O)CCl]
,
(A176)
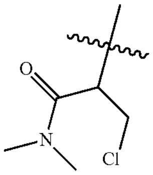 [SMILES: *C(CCl)C(=O)N(C)C]
,
(A177)
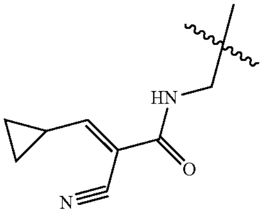 [SMILES: *CNC(=O)/C(C#N)=C/C1CC1]
,
TABLE 1c-continued
| Exemplary Warhead Groups |
| --- |
(A178)
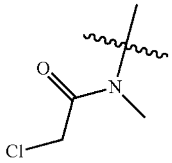 [SMILES: *N(C)C(=O)CCl]
,
(A179)
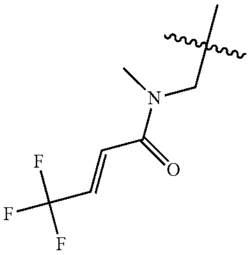 [SMILES: *CN(C)C(=O)/C=C/C(F)(F)F]
,
(A180)
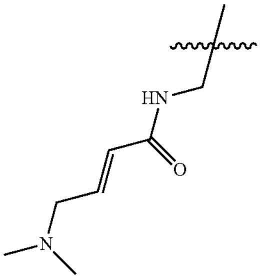 [SMILES: *CNC(=O)/C=C/CN(C)C]
,
(A181)
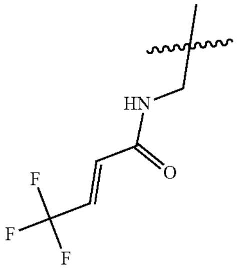 [SMILES: *CNC(=O)/C=C/C(F)(F)F]
,
(A182)
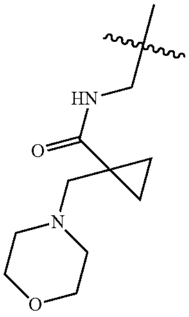 [SMILES: *CNC(=O)C1(CN2CCOCC2)CC1]
,
(A183)
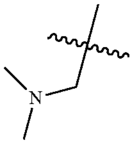 [SMILES: *CN(C)C]
, TABLE 1c-continued
| Exemplary Warhead Groups |
|---|
(A184)
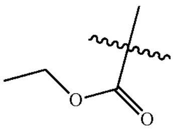 [SMILES: *C(=O)OCC]
,
(A185)
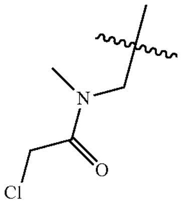 [SMILES: *CN(C)C(=O)CCl]
,
(A186)
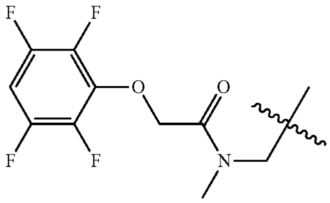 [SMILES: *CN(C)C(=O)COc1c(F)c(F)cc(F)c1F]
,
(A187)
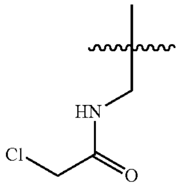 [SMILES: *CNC(=O)CCl]
,
(A188)
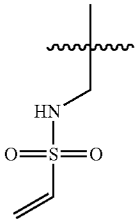 [SMILES: *CNS(=O)(=O)C=C]
,
(A189)
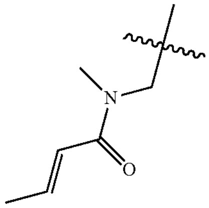 [SMILES: *CN(C)C(=O)/C=C/C]
,
(A190)
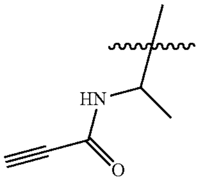 [SMILES: *C(C)NC(=O)C#C]
,
TABLE 1c-continued
| Exemplary Warhead Groups |
|---|
(A191)
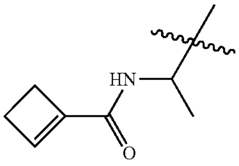 [SMILES: *C(C)NC(=O)C1=CCC1]
,
(A192)
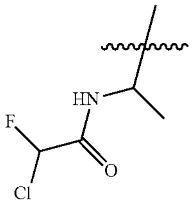 [SMILES: *C(C)NC(=O)C(F)Cl]
,
(A193)
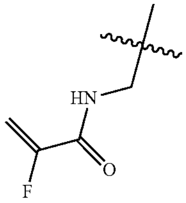 [SMILES: *CNC(=O)C(=C)F]
,
(A194)
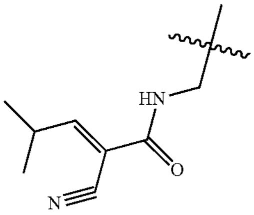 [SMILES: *CNC(=O)/C(C#N)=C/C(C)C]
,
(A195)
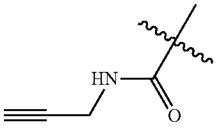
,
(A196)
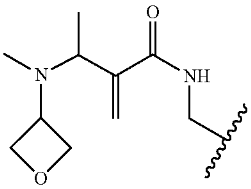 [SMILES: *CNC(=O)C(=C)C(C)N(C)C1COC1]
,
(A197)
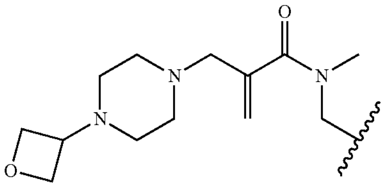 [SMILES: *CN(C)C(=O)C(=C)CN1CCN(C2COC2)CC1]
, TABLE 1c-continued
Exemplary Warhead Groups
(A198)
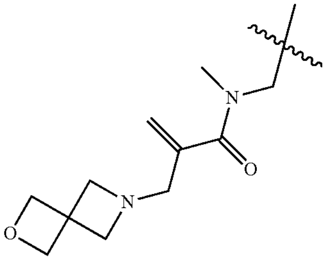 [SMILES: *CN(C)C(=O)C(=C)CN1CC2(COC2)C1]
,
(A199)
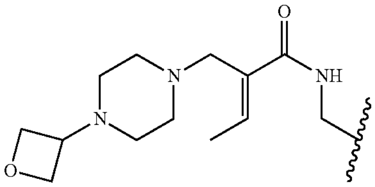 [SMILES: *CNC(=O)/C(=C/C)CN1CCN(C2COC2)CC1]
,
(A200)
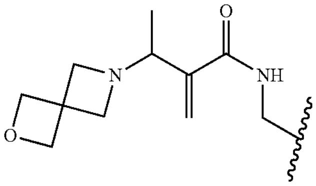 [SMILES: *CNC(=O)C(=C)C(C)N1CC2(COC2)C1]
,
(A201)
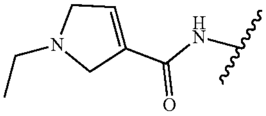 [SMILES: *NC(=O)C1=CCN(CC)C1]
,
(A202)
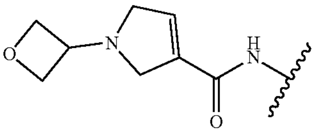 [SMILES: *NC(=O)C1=CCN(C2COC2)C1]
,
(A203)
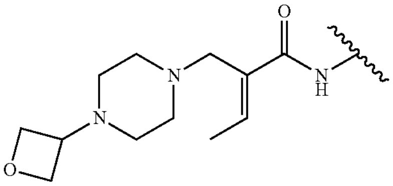 [SMILES: *NC(=O)/C(=C/C)CN1CCN(C2COC2)CC1]
,
(A204)
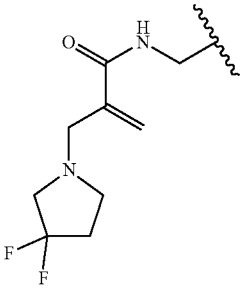 [SMILES: *CNC(=O)C(=C)CN1CCC(F)(F)C1]
,
TABLE 1c-continued
Exemplary Warhead Groups
(A205)
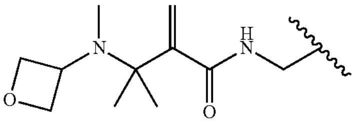 [SMILES: *CNC(=O)C(=C)C(C)(C)N(C)C1COC1]
,
(A206)
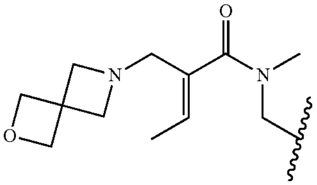 [SMILES: *CN(C)C(=O)/C(=C/C)CN1CC2(COC2)C1]
,
(A207)
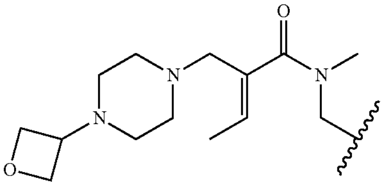 [SMILES: *CN(C)C(=O)/C(=C/C)CN1CCN(C2COC2)CC1]
,
(A208)
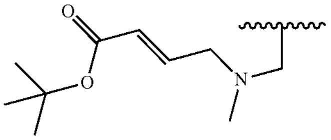 [SMILES: *CN(C)C/C=C/C(=O)OC(C)(C)C]
,
(A210)
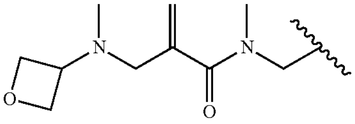 [SMILES: *CN(C)C(=O)C(=C)CN(C)C1COC1]
,
(A211)
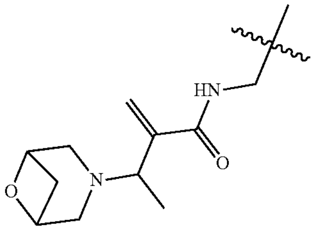 [SMILES: *CNC(=O)C(=C)C(C)N1CC2CC(C1)O2]
,
(A212)
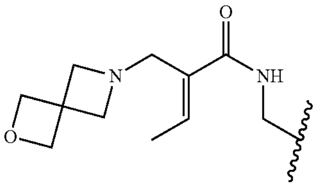 [SMILES: *CNC(=O)/C(=C/C)CN1CC2(COC2)C1]
, TABLE 1c-continued
| Exemplary Warhead Groups |
|---|
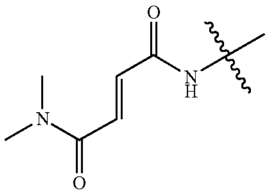 [SMILES: *NC(=O)/C=C/C(=O)N(C)C]
(A213)
,
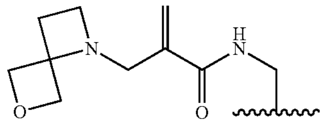
(A214)
,
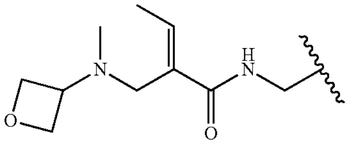 [SMILES: *CNC(=O)/C(=C/C)CN(C)C1COC1]
(A215)
,
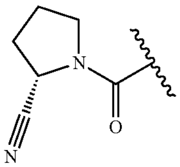 [SMILES: *C(=O)N1CCC[C@H]1C#N]
(A216)
,
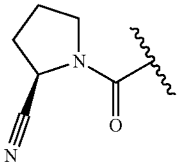 [SMILES: *C(=O)N1CCC[C@@H]1C#N]
(A217)
,
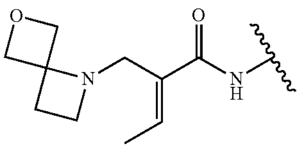 [SMILES: *NC(=O)/C(=C/C)CN1CCC12COC2]
(A218)
,
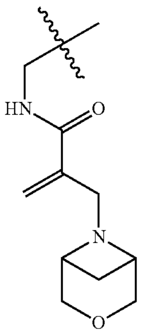 [SMILES: *CNC(=O)C(=C)CN1C2COCC1C2]
(A219)
,
TABLE 1c-continued
| Exemplary Warhead Groups |
|---|
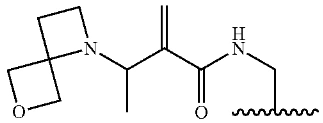 [SMILES: *CNC(=O)C(=C)C(C)N1CCC12COC2]
(A220)
,
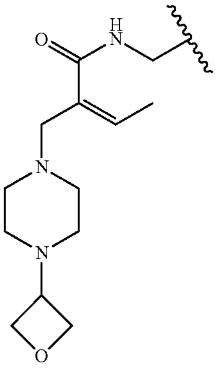 [SMILES: *CNC(=O)/C(=C\C)CN1CCN(C2COC2)CC1]
(A221)
,
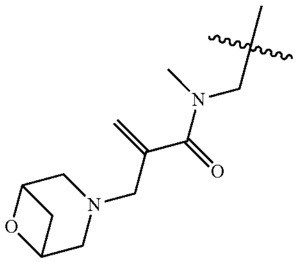 [SMILES: *CN(C)C(=O)C(=C)CN1CC2CC(C1)O2]
(A222)
,
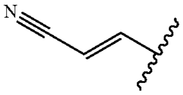 [SMILES: */C=C/C#N]
(A223)
,
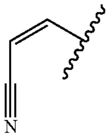 [SMILES: */C=C\C#N]
(A224)
,
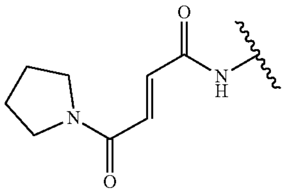 [SMILES: *NC(=O)/C=C/C(=O)N1CCCC1]
(A225)
,
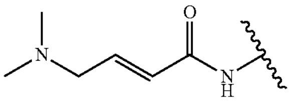 [SMILES: *NC(=O)/C=C/CN(C)C]
(A226)
, TABLE 1c-continued
| Exemplary Warhead Groups |
| --- |
| 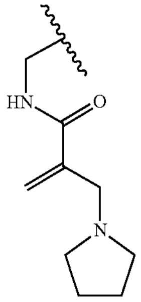 [SMILES: *CNC(=O)C(=C)CN1CCCC1] (A227) |
| , |
| 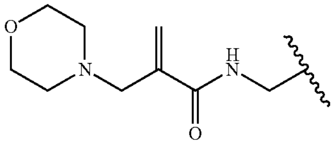 [SMILES: *CNC(=O)C(=C)CN1CCOCC1] (A228) |
| , |
| 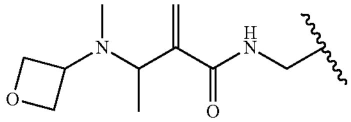 [SMILES: *CNC(=O)C(=C)C(C)N(C)C1COC1] (A229) |
| , |
| 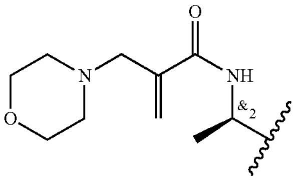 [SMILES: *[C@@H](C)NC(=O)C(=C)CN1CCOCC1] (A230) |
| , |
| 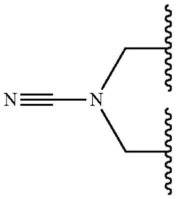 [SMILES: *CN(C#N)C*] (A231) |
| , |
| 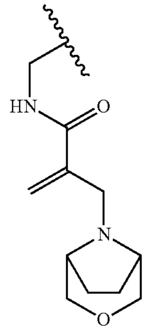 [SMILES: *CNC(=O)C(=C)CN1C2CCC1COC2] (A232) |
| , |
TABLE 1c-continued
| Exemplary Warhead Groups |
| --- |
| 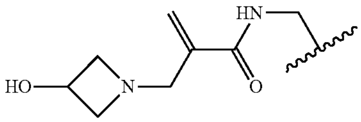 [SMILES: *CNC(=O)C(=C)CN1CC(O)C1] (A233) |
| , |
| 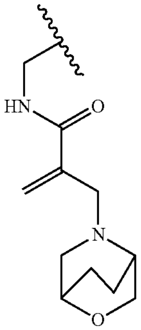 [SMILES: *CNC(=O)C(=C)CN1CC2CCC1CO2] (A234) |
| , |
| 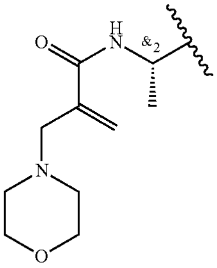 [SMILES: *[C@H](C)NC(=O)C(=C)CN1CCOCC1] (A235) |
| , |
| 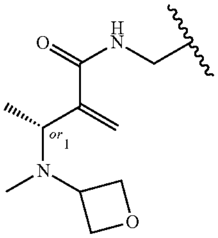 [SMILES: *CNC(=O)C(=C)[C@@H](C)N(C)C1COC1] (A236) |
| , |
| 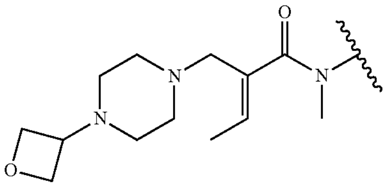 [SMILES: *N(C)C(=O)/C(=C/C)CN1CCN(C2COC2)CC1] (A237) |
| , |

TABLE 1c-continued
| Exemplary Warhead Groups |
|---|
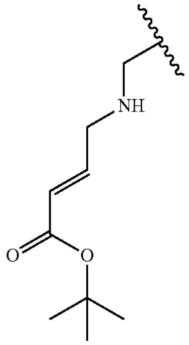 [SMILES: *CNC/C=C/C(=O)OC(C)(C)C]
(A238)
,
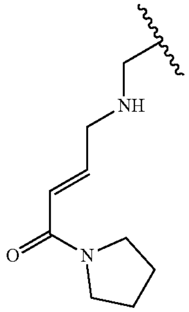 [SMILES: *CNC/C=C/C(=O)N1CCCC1]
(A239)
,
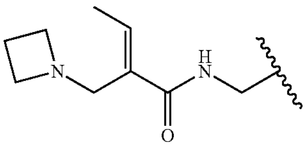 [SMILES: *CNC(=O)/C(=C/C)CN1CCC1]
(A240)
,
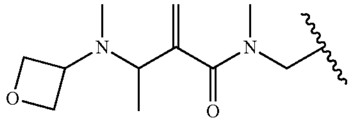 [SMILES: *CN(C)C(=O)C(=C)C(C)N(C)C1COC1]
(A241)
,
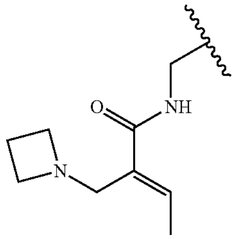 [SMILES: *CNC(=O)/C(=C/C)CN1CCC1]
(A242)
,
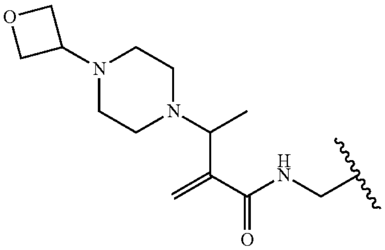 [SMILES: *CNC(=O)C(=C)C(C)N1CCN(C2COC2)CC1]
(A243)
,
TABLE 1c-continued
| Exemplary Warhead Groups |
|---|
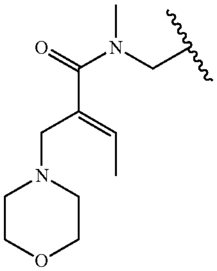 [SMILES: *CN(C)C(=O)/C(=C/C)CN1CCOCC1]
(A244)
,
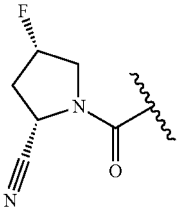 [SMILES: *C(=O)N1C[C@@H](F)C[C@H]1C#N]
(A245)
,
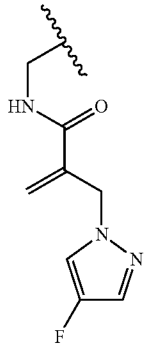 [SMILES: *CNC(=O)C(=C)Cn1cc(F)cn1]
(A246)
,
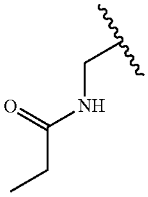 [SMILES: *CNC(=O)CC]
(A247)
,
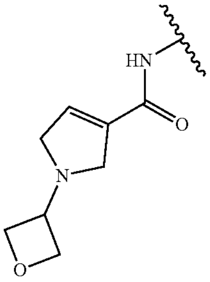 [SMILES: *NC(=O)C1=CCN(C2COC2)C1]
(A248)
, TABLE 1c-continued
Exemplary Warhead Groups
(A249)
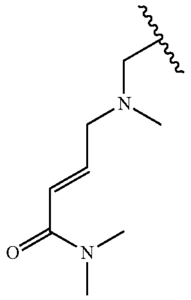 [SMILES: *CN(C)C/C=C/C(=O)N(C)C]
,
(A250)
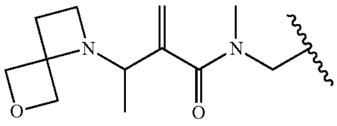 [SMILES: *CN(C)C(=O)C(=C)C(C)N1CCC12COC2]
,
(A251)
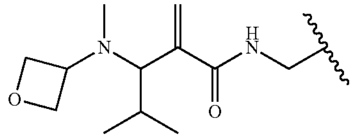 [SMILES: *CNC(=O)C(=C)C(C(C)C)N(C)C1COC1]
,
(A252)
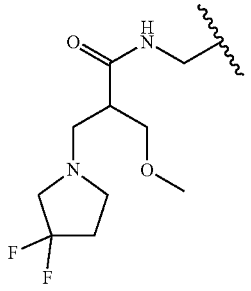 [SMILES: *CNC(=O)C(COC)CN1CCC(F)(F)C1]
,
(A253)
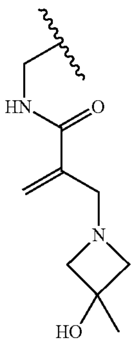 [SMILES: *CNC(=O)C(=C)CN1CC(C)(O)C1]
,
TABLE 1c-continued
Exemplary Warhead Groups
(A254)
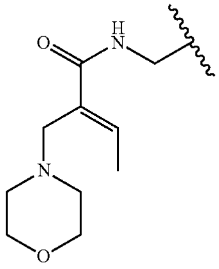 [SMILES: *CNC(=O)/C(=C/C)CN1CCOCC1]
,
(A255)
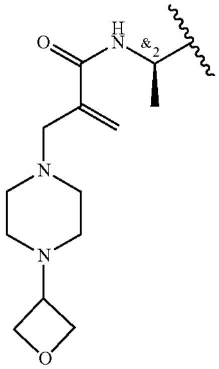 [SMILES: *[C@@H](C)NC(=O)C(=C)CN1CCN(C2COC2)CC1]
,
(A256)
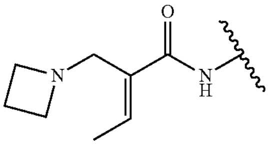 [SMILES: *NC(=O)/C(=C/C)CN1CCC1]
,
(A257)
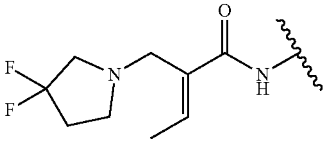 [SMILES: *NC(=O)/C(=C/C)CN1CCC(F)(F)C1]
,
(A258)
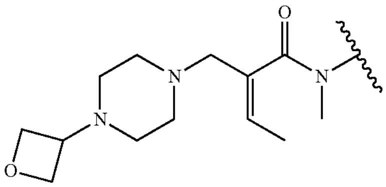 [SMILES: *N(C)C(=O)/C(=C\C)CN1CCN(C2COC2)CC1]
,
(A259)
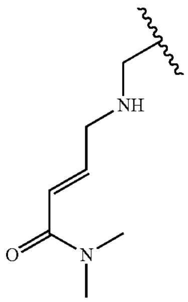 [SMILES: *CNC/C=C/C(=O)N(C)C]
, TABLE 1c-continued

| Exemplary Warhead Groups |
|---|

(A260)

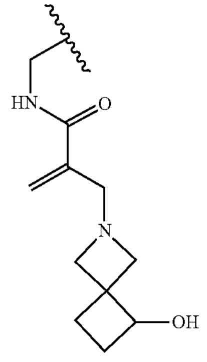 [SMILES: *CNC(=O)C(=C)CN1CC2(CCC2O)C1]

, (A261)

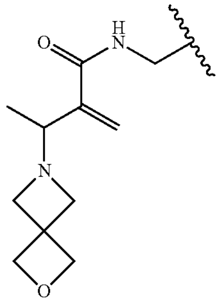 [SMILES: *CNC(=O)C(=C)C(C)N1CC2(COC2)C1]

, (A262)

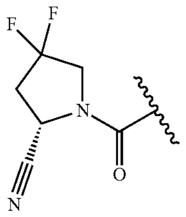 [SMILES: *C(=O)N1CC(F)(F)C[C@H]1C#N]

, (A263)

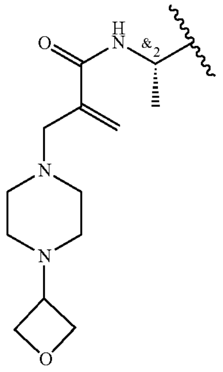 [SMILES: *[C@H](C)NC(=O)C(=C)CN1CCN(C2COC2)CC1]

, (A264)

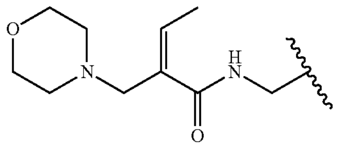 [SMILES: *CNC(=O)/C(=C\C)CN1CCOCC1]

,

TABLE 1c-continued

| Exemplary Warhead Groups |
|---|

(A265)

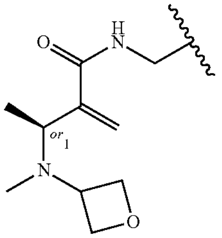 [SMILES: *CNC(=O)C(=C)[C@H](C)N(C)C1COC1]

, (A266)

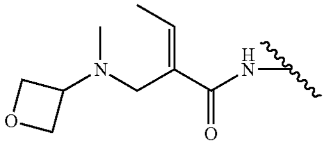 [SMILES: *NC(=O)/C(=C/C)CN(C)C1COC1]

, (A267)

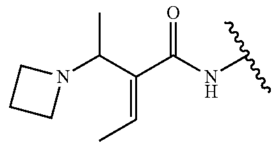 [SMILES: *NC(=O)/C(=C/C)C(C)N1CCC1]

.

In some embodiments, a warhead group is selected from those set forth in Table 1d, below, wherein each wavy line indicates the point of attachment to the rest of the molecule. In some embodiments, $R^4$ is selected from those set forth in Table 1d.

TABLE 1d

| Exemplary Warhead Groups |
|---|

(B1)

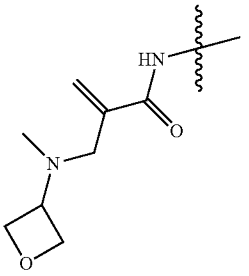 [SMILES: *NC(=O)C(=C)CN(C)C1COC1]

(B2)

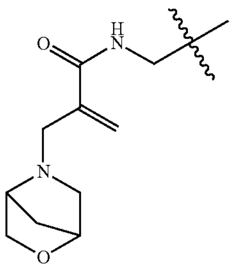 [SMILES: *CNC(=O)C(=C)CN1CC2CC1CO2]

,

TABLE 1d-continued
Exemplary Warhead Groups
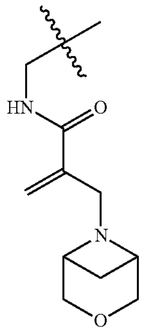 [SMILES: *CNC(=O)C(=C)CN1C2COCC1C2]
(B3)
,
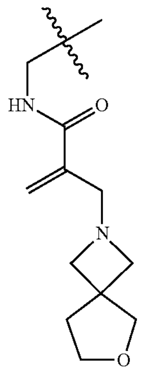 [SMILES: *CNC(=O)C(=C)CN1CC2(CCOC2)C1]
(B4)
,
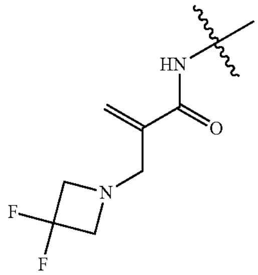 [SMILES: *NC(=O)C(=C)CN1CC(F)(F)C1]
(B5)
,
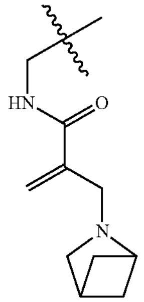 [SMILES: *CNC(=O)C(=C)CN1CC2CC1C2]
(B6)
,
TABLE 1d-continued
Exemplary Warhead Groups
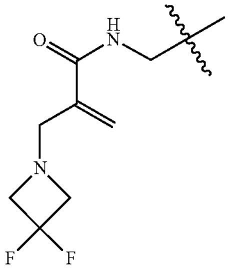 [SMILES: *CNC(=O)C(=C)CN1CC(F)(F)C1]
(B7)
,
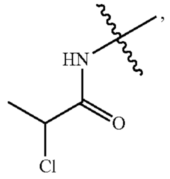 [SMILES: *NC(=O)C(C)Cl]
(B8)
,
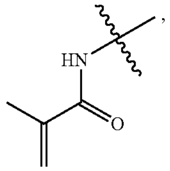 [SMILES: *NC(=O)C(=C)C]
(B9)
,
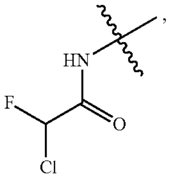 [SMILES: *NC(=O)C(F)Cl]
(B10)
,
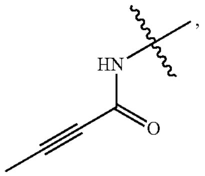 [SMILES: *NC(=O)C#CC]
(B11)
,
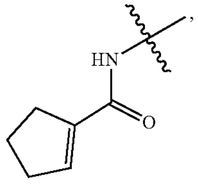 [SMILES: *NC(=O)C1=CCCC1]
(B12)
,
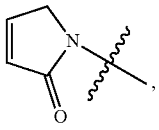 [SMILES: *N1CC=CC1=O]
(B13)
, TABLE 1d-continued
Exemplary Warhead Groups
(B14)
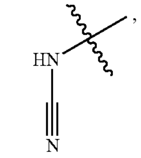
,
(B15)
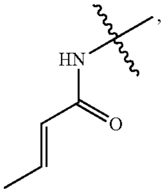 [SMILES: *NC(=O)/C=C/C]
,
(B16)
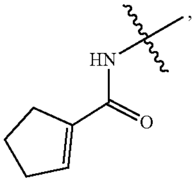
,
(B17)
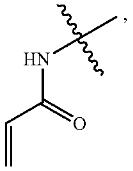 [SMILES: *NC(=O)C=C]
,
(B18)
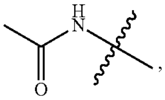 [SMILES: *NC(C)=O]
,
(B19)
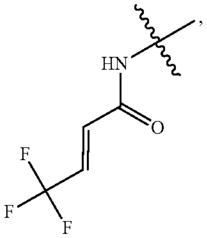 [SMILES: *NC(=O)/C=C/C(F)(F)F]
,
(B20)
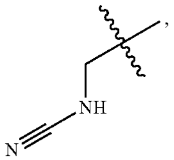 [SMILES: *CNC#N]
,
(B21)
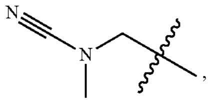 [SMILES: *CN(C)C#N]
,
TABLE 1d-continued
Exemplary Warhead Groups
(B22)
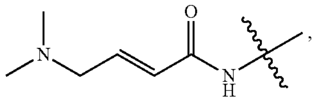 [SMILES: *NC(=O)/C=C/CN(C)C]
,
(B23)
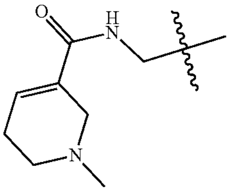 [SMILES: *CNC(=O)C1=CCCN(C)C1]
,
(B24)
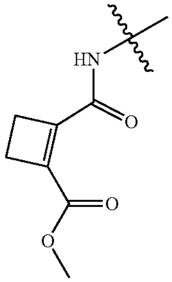 [SMILES: *NC(=O)C1=C(C(=O)OC)CC1]
,
(B25)
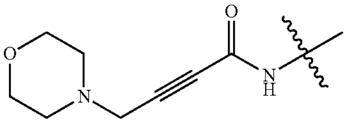 [SMILES: *NC(=O)C#CCN1CCOCC1]
,
(B26)
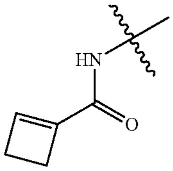 [SMILES: *NC(=O)C1=CCC1]
,
(B27)
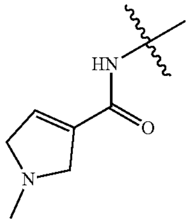 [SMILES: *NC(=O)C1=CCN(C)C1]
,
(B28)
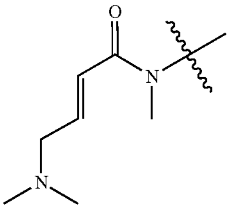 [SMILES: *N(C)C(=O)/C=C/CN(C)C]
, TABLE 1d-continued
Exemplary Warhead Groups
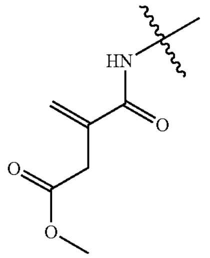 [SMILES: *NC(=O)C(=C)CC(=O)OC]
(B29)
,
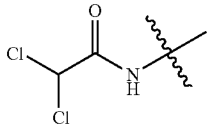 [SMILES: *NC(=O)C(Cl)Cl]
(B30)
,
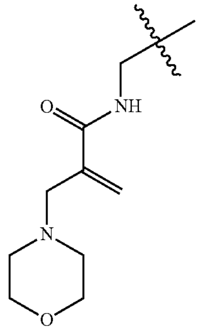 [SMILES: *CNC(=O)C(=C)CN1CCOCC1]
(B31)
,
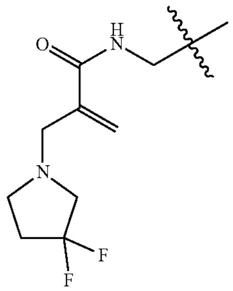 [SMILES: *CNC(=O)C(=C)CN1CCC(F)(F)C1]
(B32)
,
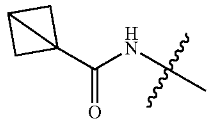 [SMILES: *NC(=O)C12CC1C2]
(B33)
,
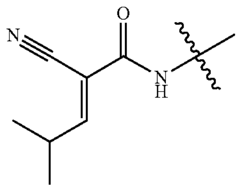 [SMILES: *NC(=O)/C(C#N)=C/C(C)C]
(B34)
,
TABLE 1d-continued
Exemplary Warhead Groups
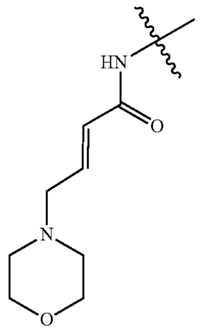 [SMILES: *NC(=O)/C=C/CN1CCOCC1]
(B35)
,
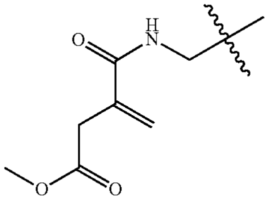 [SMILES: *CNC(=O)C(=C)CC(=O)OC]
(B36)
,
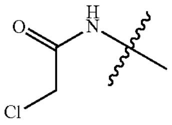 [SMILES: *NC(=O)CCl]
(B37)
,
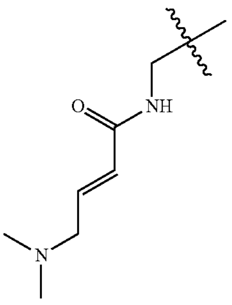 [SMILES: *CNC(=O)/C=C/CN(C)C]
(B38)
,
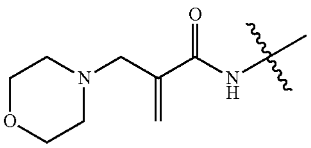 [SMILES: *NC(=O)C(=C)CN1CCOCC1]
(B39)
,
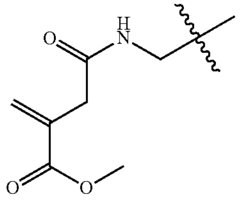 [SMILES: *CNC(=O)CC(=C)C(=O)OC]
(B40)
, TABLE 1d-continued
Exemplary Warhead Groups
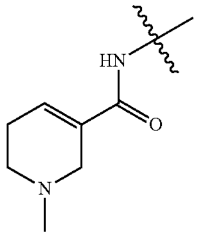 [SMILES: *NC(=O)C1=CCCN(C)C1]
(B41)
,
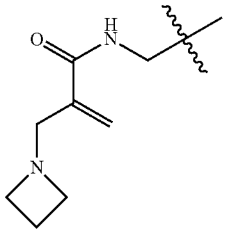 [SMILES: *CNC(=O)C(=C)CN1CCC1]
(B42)
,
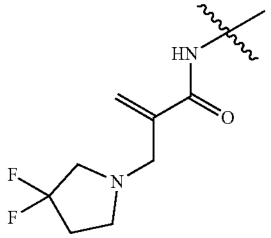 [SMILES: *NC(=O)C(=C)CN1CCC(F)(F)C1]
(B43)
,
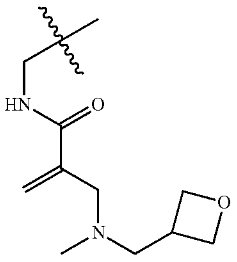 [SMILES: *CNC(=O)C(=C)CN(C)CC1COC1]
(B44)
,
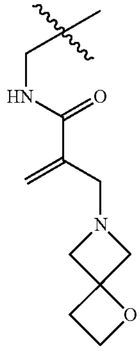 [SMILES: *CNC(=O)C(=C)CN1CC2(CCO2)C1]
(B45)
,
TABLE 1d-continued
Exemplary Warhead Groups
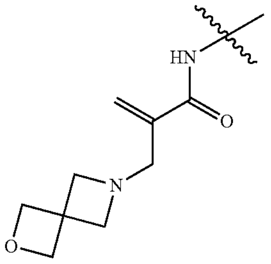 [SMILES: *NC(=O)C(=C)CN1CC2(COC2)C1]
(B46)
,
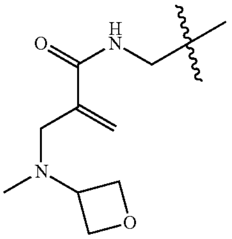 [SMILES: *CNC(=O)C(=C)CN(C)C1COC1]
(B47)
,
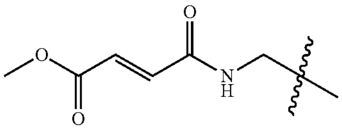 [SMILES: *CNC(=O)/C=C/C(=O)OC]
(B48)
,
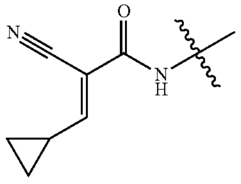 [SMILES: *NC(=O)/C(C#N)=C/C1CC1]
(B49)
,
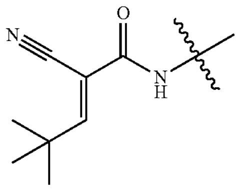 [SMILES: *NC(=O)/C(C#N)=C/C(C)(C)C]
(B50)
,
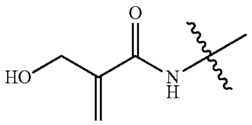 [SMILES: *NC(=O)C(=C)CO]
(B51)
,
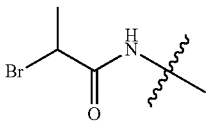 [SMILES: *NC(=O)C(C)Br]
(B52)
, TABLE 1d-continued
| Exemplary Warhead Groups |
|---|
(B53)
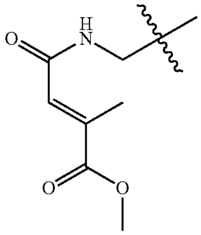 [SMILES: *CNC(=O)/C=C(\C)C(=O)OC]
,
(B54)
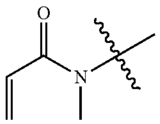 [SMILES: *N(C)C(=O)C=C]
,
(B55)
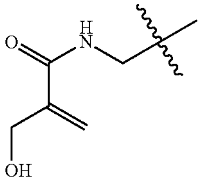 [SMILES: *CNC(=O)C(=C)CO]
,
(B56)
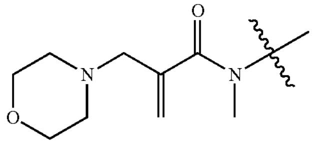 [SMILES: *N(C)C(=O)C(=C)CN1CCOCC1]
,
(B57)
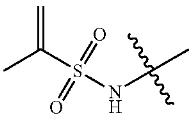 [SMILES: *NS(=O)(=O)C(=C)C]
,
(B58)
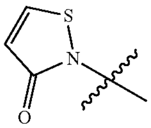
,
(B59)
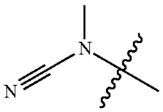 [SMILES: *N(C)C#N]
,
(B60)
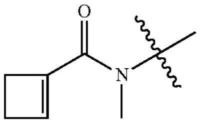 [SMILES: *N(C)C(=O)C1=CCC1]
,
TABLE 1d-continued
| Exemplary Warhead Groups |
|---|
(B61)
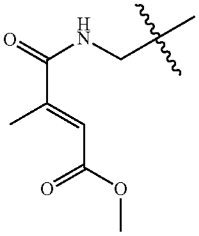 [SMILES: *CNC(=O)/C(C)=C/C(=O)OC]
,
(B62)
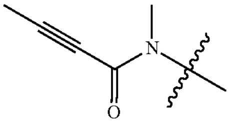 [SMILES: *N(C)C(=O)C#CC]
,
(B63)
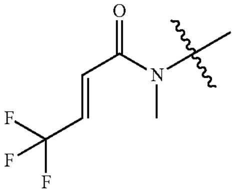 [SMILES: *N(C)C(=O)/C=C/C(F)(F)F]
,
(B64)
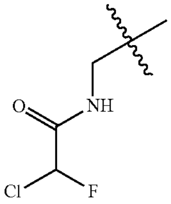 [SMILES: *CNC(=O)C(F)Cl]
,
(B65)
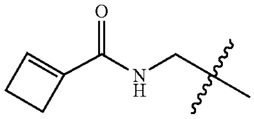 [SMILES: *CNC(=O)C1=CCC1]
,
(B66)
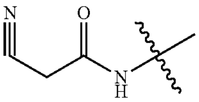 [SMILES: *NC(=O)CC#N]
,
(B67)
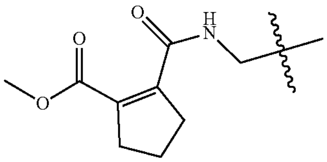 [SMILES: *CNC(=O)C1=C(C(=O)OC)CCC1]
,
(B68)
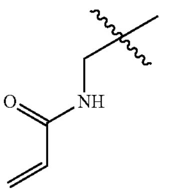 [SMILES: *CNC(=O)C=C]
, TABLE 1d-continued
| Exemplary Warhead Groups |
|---|
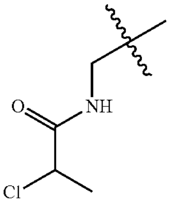 [SMILES: *CNC(=O)C(C)Cl]
(B69)
,
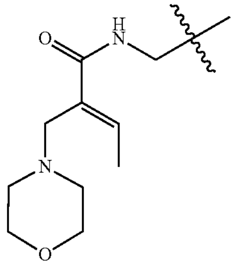 [SMILES: *CNC(=O)/C(=C/C)CN1CCOCC1]
(B70)
,
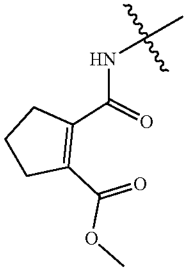 [SMILES: *NC(=O)C1=C(C(=O)OC)CCC1]
(B71)
,
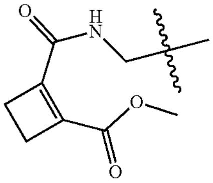 [SMILES: *CNC(=O)C1=C(C(=O)OC)CC1]
(B72)
,
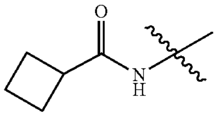 [SMILES: *NC(=O)C1CCC1]
(B73)
,
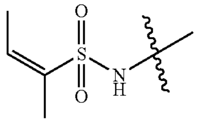 [SMILES: *NS(=O)(=O)/C(C)=C\C]
(B74)
,
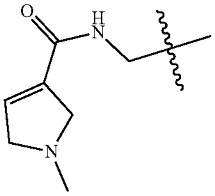 [SMILES: *CNC(=O)C1=CCN(C)C1]
(B75)
,
TABLE 1d-continued
| Exemplary Warhead Groups |
|---|
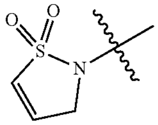 [SMILES: *N1CC=CS1(=O)=O]
(B76)
,
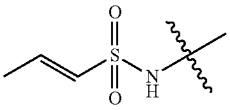 [SMILES: *NS(=O)(=O)/C=C/C]
(B77)
,
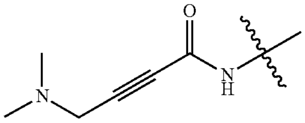 [SMILES: *NC(=O)C#CCN(C)C]
(B78)
,
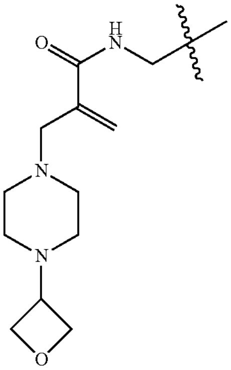 [SMILES: *CNC(=O)C(=C)CN1CCN(C2COC2)CC1]
(B79)
,
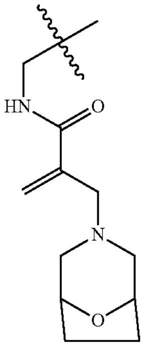 [SMILES: *CNC(=O)C(=C)CN1CC2CCC(C1)O2]
(B80)
,
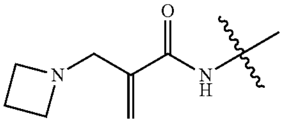 [SMILES: *NC(=O)C(=C)CN1CCC1]
(B81)
,
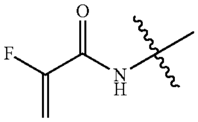 [SMILES: *NC(=O)C(=C)F]
(B82)
, TABLE 1d-continued
| Exemplary Warhead Groups |
|---|
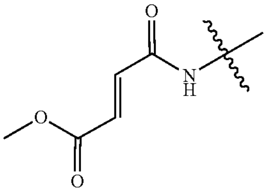 [SMILES: *NC(=O)/C=C/C(=O)OC]
(B83)
,
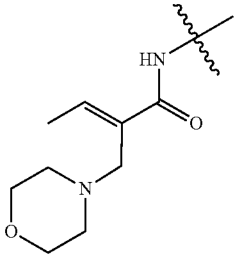 [SMILES: *NC(=O)/C(=C/C)CN1CCOCC1]
(B84)
,
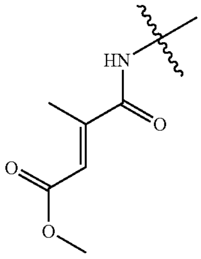 [SMILES: *NC(=O)/C(C)=C/C(=O)OC]
(B85)
,
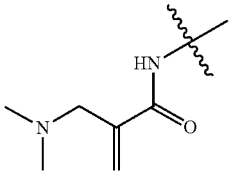 [SMILES: *NC(=O)C(=C)CN(C)C]
(B86)
,
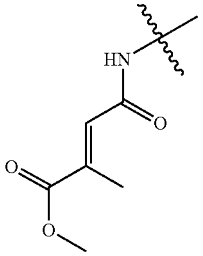 [SMILES: *NC(=O)/C=C(\C)C(=O)OC]
(B87)
,
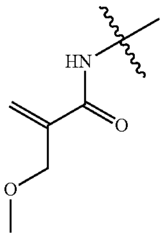 [SMILES: *NC(=O)C(=C)COC]
(B88)
,
TABLE 1d-continued
| Exemplary Warhead Groups |
|---|
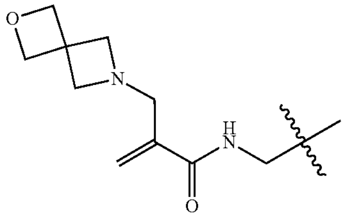 [SMILES: *CNC(=O)C(=C)CN1CC2(COC2)C1]
(B89)
,
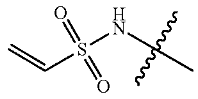 [SMILES: *NS(=O)(=O)C=C]
(B90)
,
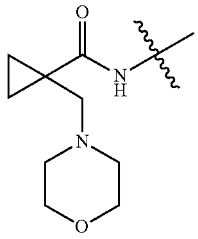 [SMILES: *NC(=O)C1(CN2CCOCC2)CC1]
(B91)
,
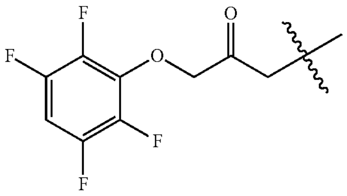 [SMILES: *CC(=O)COc1c(F)c(F)cc(F)c1F]
(B92)
,
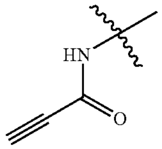 [SMILES: *NC(=O)C#C]
(B93)
,
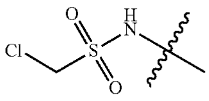 [SMILES: *NS(=O)(=O)CCl]
(B94)
,
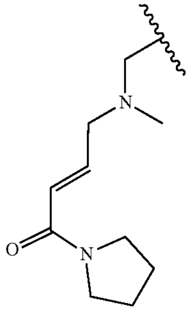 [SMILES: *CN(C)C/C=C/C(=O)N1CCCC1]
(B95)
, TABLE 1d-continued

| Exemplary Warhead Groups |
| --- |
| 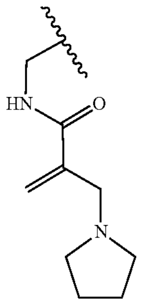 [SMILES: *CNC(=O)C(=C)CN1CCCC1] (B96) , |
| 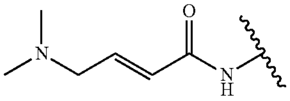 [SMILES: *NC(=O)/C=C/CN(C)C] (B97) , |
| 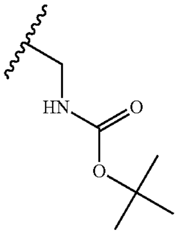 [SMILES: *CNC(=O)OC(C)(C)C] (B98) , |
| 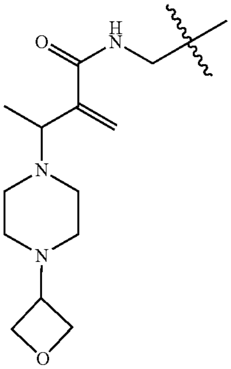 [SMILES: *CNC(=O)C(=C)C(C)N1CCN(C2COC2)CC1] (B99) , |
| 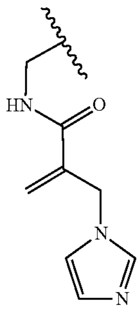 [SMILES: *CNC(=O)C(=C)Cn1ccnc1] (B100) , |

TABLE 1d-continued

| Exemplary Warhead Groups |
| --- |
| 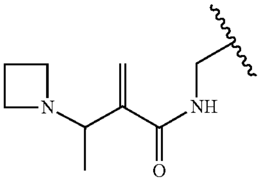 [SMILES: *CNC(=O)C(=C)C(C)N1CCC1] (B101) , |
| 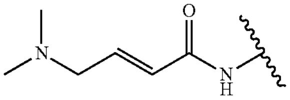 [SMILES: *NC(=O)/C=C/CN(C)C] (B102) , |
| 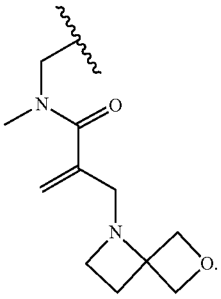 [SMILES: *CN(C)C(=O)C(=C)CN1CCC12COC2] (B103) . |

In some embodiments, $R^4$ is selected from those set forth in Table 1d.

In some embodiments, a warhead group is selected from those set forth in Table 1e, below, wherein each wavy line indicates the point of attachment to the rest of the molecule. In some embodiments, $R^4$ is selected from those set forth in Table 1e.

TABLE 1e

| Exemplary Warhead Groups |
| --- |
| 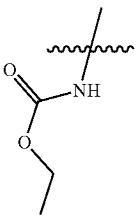 , |
| 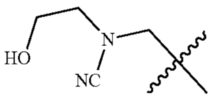 , |
| 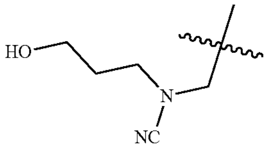 , |

TABLE 1e-continued

| Exemplary Warhead Groups |
| --- |
| 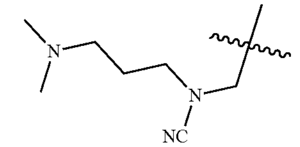 , |
| 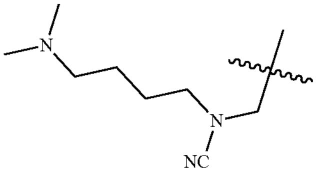 , |
| 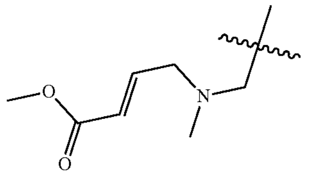 , |
| 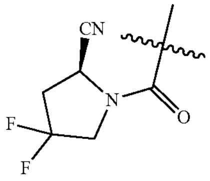 , |
| 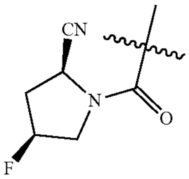 and |
| 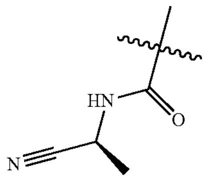 . |

In some embodiments, $R^4$ is selected from those set forth in Table 1e.

In some embodiments, $R^4$ is selected from those depicted in Table 1, below.

As defined generally above, $R^5$ is hydrogen; or an optionally substituted group selected from $C_{1-6}$ aliphatic.

In some embodiments, $R^5$ is hydrogen. In some embodiments, $R^5$ is a $C_{1-6}$ aliphatic group. In some embodiments, $R^5$ is a substituted $C_{1-6}$ aliphatic group.

In some embodiments, $R^5$ is selected from hydrogen,

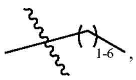 , 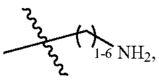 and 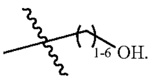

In some embodiments, $R^5$ is selected from hydrogen,

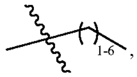 , 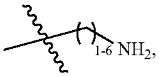 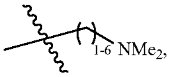 and

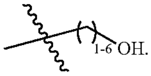

In some embodiments, $R^5$ is selected from hydrogen, ethyl, and

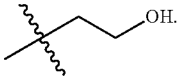 [SMILES: *CCO]

In some embodiments, $R^3$ is selected from hydrogen, ethyl,

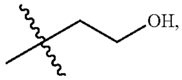 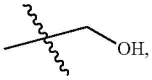 and

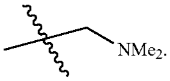

In some embodiments, $R^5$ is selected from those depicted in Table 1, below.

As defined generally $R^6$ is hydrogen or an optionally substituted $C_{1-6}$ aliphatic group.

In some embodiments, $R^6$ is hydrogen. In some embodiments, $R^6$ is an optionally substituted $C_{1-6}$ aliphatic group. In some embodiments, $R^6$ is an optionally substituted $C_{1-6}$ aliphatic group.

In some embodiments, $R^6$ is selected from hydrogen,

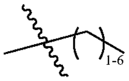 , 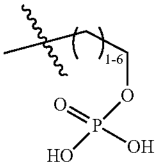 and

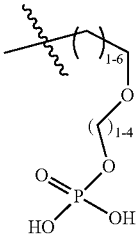

or a pharmaceutically acceptable salt thereof.

In some embodiments, $R^6$ is selected from hydrogen and

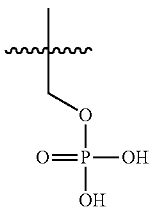 [SMILES: *COP(=O)(O)O]

or a pharmaceutically acceptable salt thereof.

In some embodiments, $R^6$ is selected from those depicted in Table 1, below.

As defined generally above, each occurrence of $R^7$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$—, —SR, —S(O)R, —S(O)$_2$R, —S(O)$_2$N(R)$_2$, —NRS(O)$_2$R, phenyl, or a 5-6 membered heteroaromatic ring having 1-3 heteroatoms selected from nitrogen, sulfur, and oxygen.

In some embodiments, $R^7$ is $C_{1-6}$ aliphatic group. In some embodiments, $R^7$ is substituted $C_{1-6}$ aliphatic group. In some embodiments, $R^7$ is halogen. In some embodiments, $R^7$ is —CN. In some embodiments, $R^7$ is —C(O)R. In some embodiments, $R^7$ is —C(O)OR. In some embodiments, $R^7$ is —OC(O)R. In some embodiments, $R^7$ is —C(O)N(R)$_2$. In some embodiments, $R^7$ is —N(R)C(O)R. In some embodiments, $R^7$ is —N(R)C(O)N(R)$_2$. In some embodiments, $R^7$ is —OC(O)N(R)$_2$. In some embodiments, $R^7$ is —N(R)C(O)OR. In some embodiments, $R^7$ is —OR. In some embodiments, $R^7$ is —N(R)$_2$. In some embodiments, $R^7$ is —NO$_2$. In some embodiments, $R^7$ is —SR. In some embodiments, $R^7$ is —S(O)R. In some embodiments, $R^7$ is —S(O)$_2$R. In some embodiments, $R^7$ is —S(O)$_2$N(R)$_2$. In some embodiments, $R^7$ is —NRS(O)$_2$R. In some embodiments, $R^7$ is phenyl. In some embodiments, $R^7$ is a 5-6 membered heteroaromatic ring having 1-3 heteroatoms selected from nitrogen, sulfur, and oxygen.

In some embodiments, $R^7$ is halogen. In some embodiments, $R^7$ is selected from F, $C_1$ or Br. In some embodiments, $R^7$ is F.

In some embodiments, $R^7$ is selected from those depicted in Table 1, below.

As defined generally above, each occurrence of R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur.

In some embodiments, R is hydrogen. In some embodiments, R is a $C_{1-6}$ aliphatic group. In some embodiments, R is a substituted $C_{1-6}$ aliphatic group. In some embodiments, R is a 3-8 membered saturated monocyclic carbocyclic ring. In some embodiments, R is a 3-8 membered partially unsaturated monocyclic carbocyclic ring. In some embodiments, R is a substituted 3-8 membered saturated monocyclic carbocyclic ring. In some embodiments, R is a substituted 3-8 membered partially unsaturated monocyclic carbocyclic ring. In some embodiments, R is phenyl. In some embodiments, R is a substituted phenyl. In some embodiments, R is an 8-10 membered bicyclic aromatic carbocyclic ring. In some embodiments, R is a substituted 8-10 membered bicyclic aromatic carbocyclic ring. In some embodiments, R is a 4-8 membered saturated monocyclic heterocyclic ring having 1-2 heteroatoms independently selected from nitrogen, oxygen, and sulfur. In some embodiments, R is a 4-8 membered partially unsaturated monocyclic heterocyclic ring having 1-2 heteroatoms independently selected from nitrogen, oxygen, and sulfur. In some embodiments, R is a substituted 4-8 membered saturated monocyclic heterocyclic ring having 1-2 heteroatoms independently selected from nitrogen, oxygen, and sulfur. In some embodiments, R is a substituted 4-8 membered partially unsaturated monocyclic heterocyclic ring having 1-2 heteroatoms independently selected from nitrogen, oxygen, and sulfur. In some embodiments, R is a 5-6 membered monocyclic heteroaromatic ring having 1-4 heteroatoms independently selected from nitrogen, oxygen, and sulfur. In some embodiments, R is a substituted 5-6 membered monocyclic heteroaromatic ring having 1-4 heteroatoms independently selected from nitrogen, oxygen, and sulfur. In some embodiments, R is an 8-10 membered bicyclic heteroaromatic ring having 1-5 heteroatoms independently selected from nitrogen, oxygen, and sulfur. In some embodiments, R is a substituted 8-10 membered bicyclic heteroaromatic ring having 1-5 heteroatoms independently selected from nitrogen, oxygen, and sulfur.

In some embodiments, R is selected from those depicted in Table 1, below.

As defined generally above, m is 0, 1, 2, 3, 4 or 5. In some embodiments, m is 0. In some embodiments, m is 1. In some embodiments, m is 2. In some embodiments, m is 3. In some embodiments, m is 4. In some embodiments, m is 5.

In some embodiments, m is selected from those depicted in Table 1, below.

As defined generally above, n is 0, 1, 2, 3, 4 or 5. In some embodiments, n is 0. In some embodiments, n is 1. In some embodiments, n is 2. In some embodiments, n is 3. In some embodiments, n is 4. In some embodiments, n is 5.

In some embodiments, n is selected from those depicted in Table 1, below.

As defined generally above, p is 0, 1, 2, 3, 4 or 5. In some embodiments, p is 0. In some embodiments, p is 1. In some embodiments, p is 2. In some embodiments, p is 3. In some embodiments, p is 4. In some embodiments, p is 5.

In some embodiments, p is selected from those depicted in Table 1, below.

In some embodiments, the present disclosure provides a compound of Formula II:

II

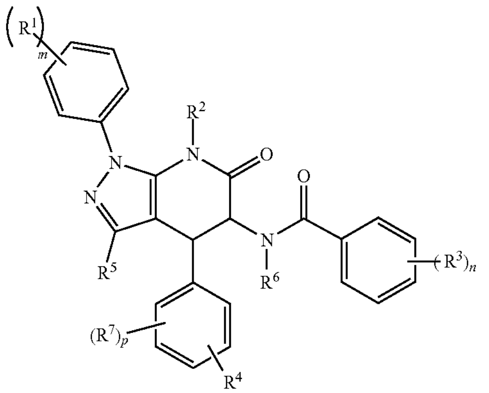

or a pharmaceutically acceptable salt thereof, wherein: each of $R^1$, $R^2$, $R^3$, $R^4$, $R^5$, $R^6$, $R^7$, m, n, and p are as defined above and described in embodiments herein, both singly and in combination.

In some embodiments, the present disclosure provides a compound of Formula III:

III

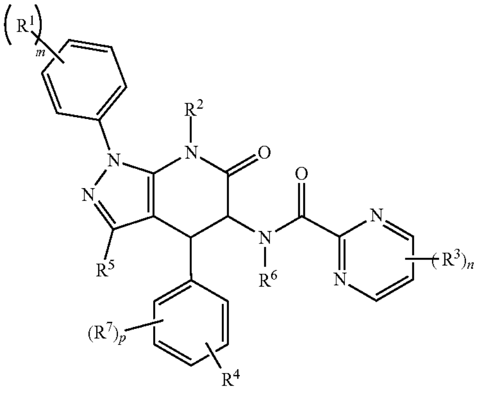

or a pharmaceutically acceptable salt thereof, wherein: each of $R^1$, $R^2$, $R^3$, $R^4$, $R^5$, $R^6$, $R^7$, m, n, and p are as defined above and described in embodiments herein, both singly and in combination.

In some embodiments, the present disclosure provides compounds of Formula IVa, Formula IVb, Formula IVc or Formula IVd:

IVa

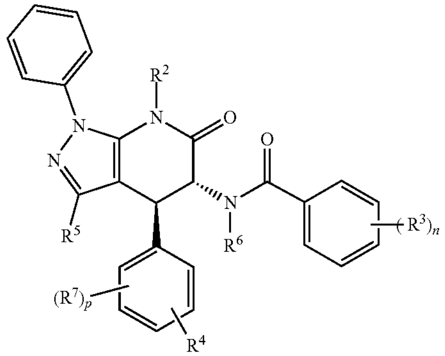

IVb

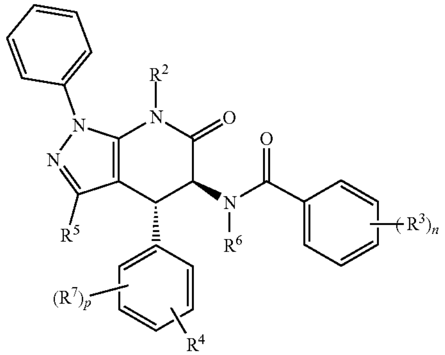

IVc

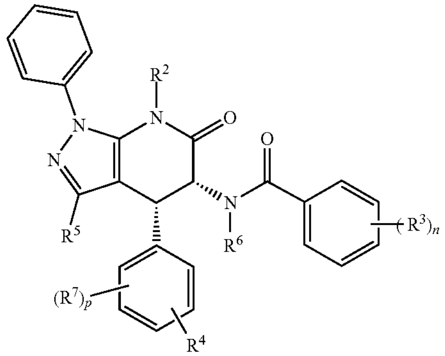

IVd

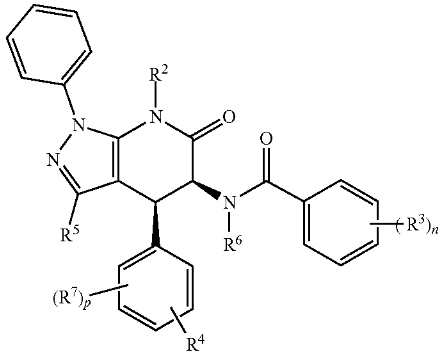

or a pharmaceutically acceptable salt thereof, wherein: each of $R^2$, $R^3$, $R^4$, $R^5$, $R^6$, $R^7$, n, and p are as defined above and described in embodiments herein, both singly and in combination.

In some embodiments, the present disclosure provides compounds of Formula Va, Formula Vb, Formula Vc or Formula Vd:

Va

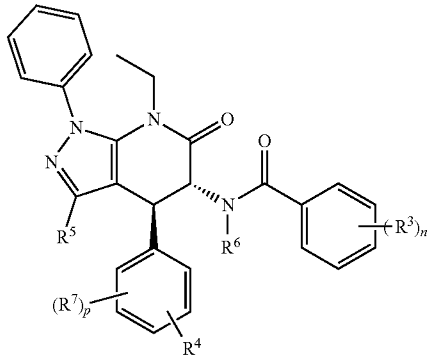

Vb

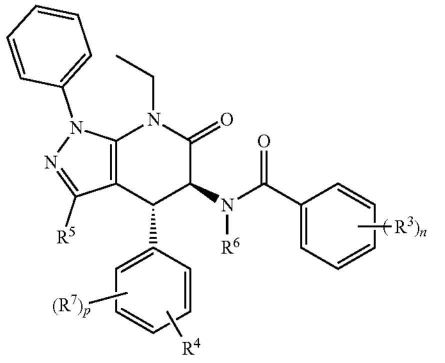

Vc

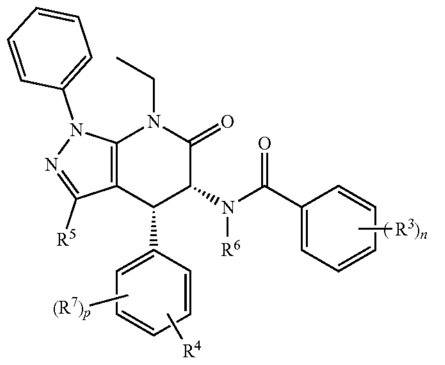

Vd

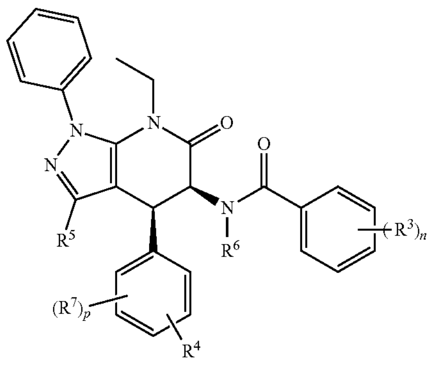

or a pharmaceutically acceptable salt thereof, wherein:

each of $R^3$, $R^4$, $R^5$, $R^6$, $R^7$, n, and p are as defined above and described in embodiments herein, both singly and in combination.

In some embodiments, the present disclosure provides compounds of Formula Va-i, Formula Vb-i, Formula Vc-i or Formula Vd-i:

Va-i

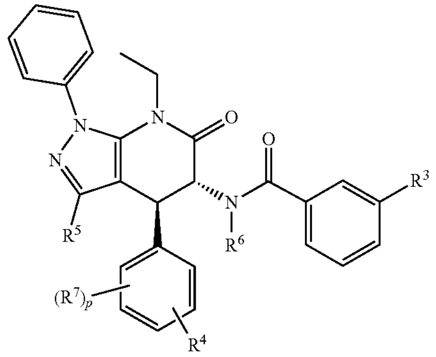

Vb-i

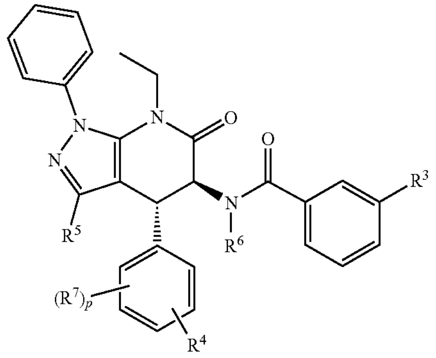

Vc-i

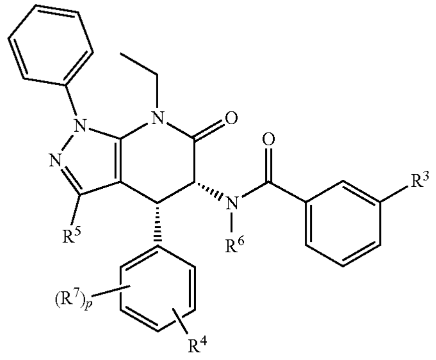

Vd-i

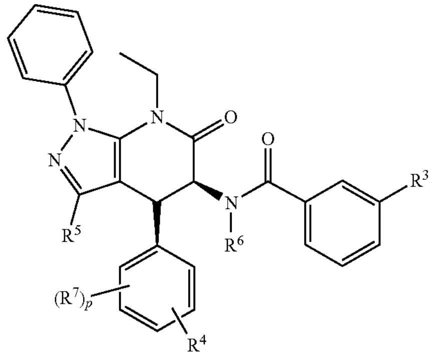

or a pharmaceutically acceptable salt thereof, wherein:

each of $R^3$, $R^4$, $R^5$, $R^6$, $R^7$, and p are as defined above and described in embodiments herein, both singly and in combination.

In some embodiments, the present disclosure provides compounds of Formula VIa, Formula VIb, Formula VIc or Formula VId:

VIa

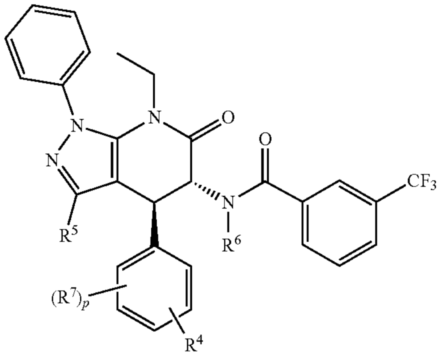

VIb

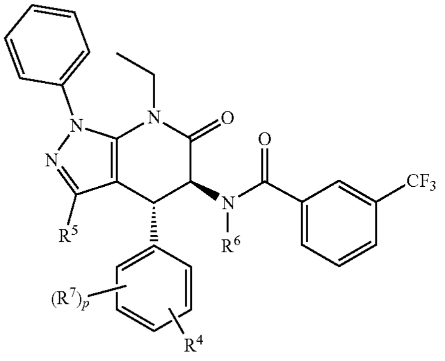

VIc

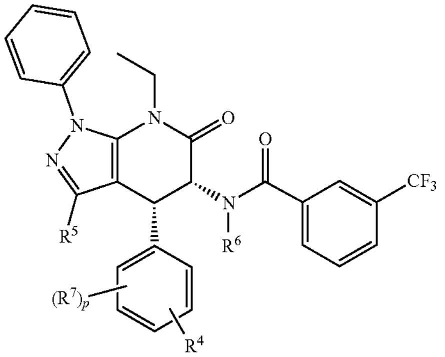

VId

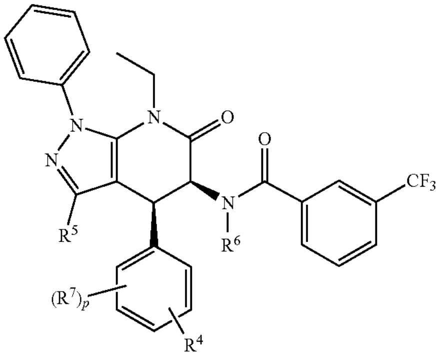

or a pharmaceutically acceptable salt thereof, wherein:

each of $R^4$, $R^5$, $R^6$, $R^7$, and p are as defined above and described in embodiments herein, both singly and in combination.

In some embodiments, the present disclosure provides compounds of Formula VIIa, Formula VIIb, Formula VIIc or Formula VIId:

VIIa

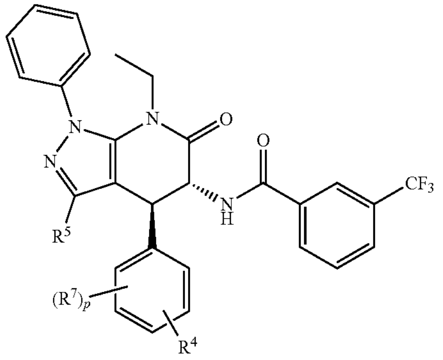

VIIb

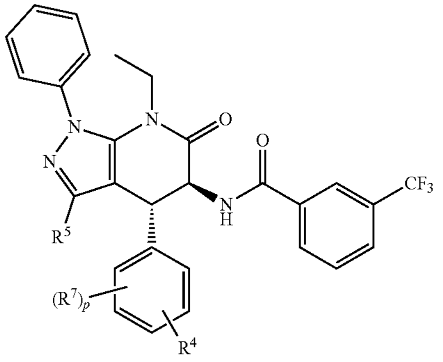

VIIc

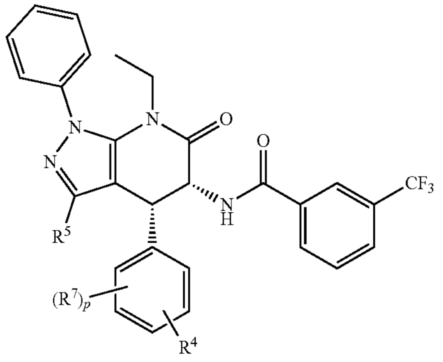

VIId

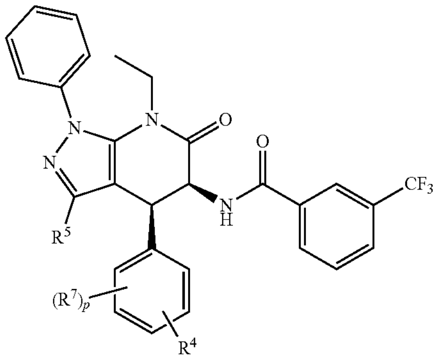

or a pharmaceutically acceptable salt thereof, wherein:

each of $R^4$, $R^5$, $R^7$, and p are as defined above and described in embodiments herein, both singly and in combination.

In some embodiments, the present disclosure provides compounds of Formula VIIIa, Formula VIIIb, Formula VIIIc or Formula VIIId:

VIIIa

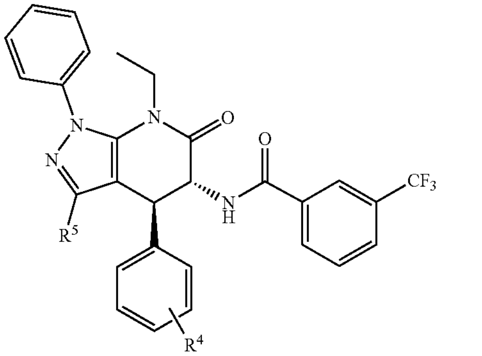

VIIIb

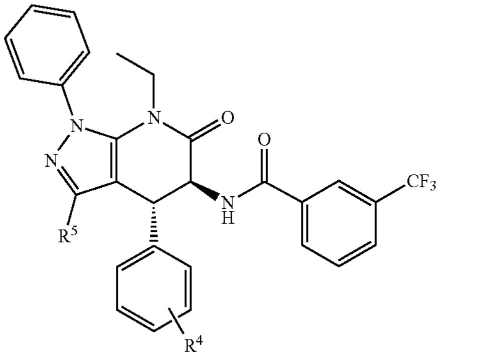

VIIIc

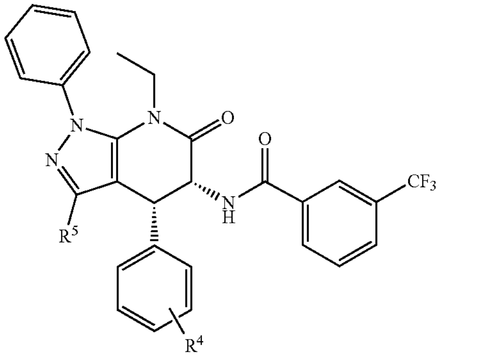

VIIId

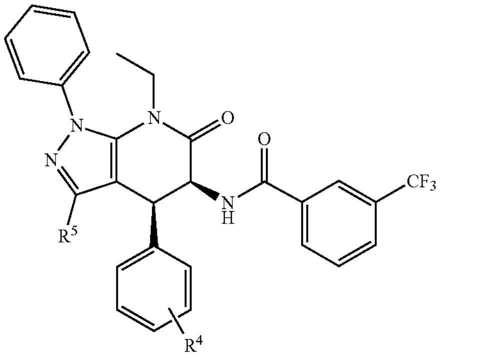

or a pharmaceutically acceptable salt thereof, wherein:

each of $R^4$ and $R^5$ is as defined above and described in embodiments herein, both singly and in combination.

In some embodiments, the present disclosure provides compounds of Formula IXa, Formula IXb, Formula IXc or Formula IXd:

IXa

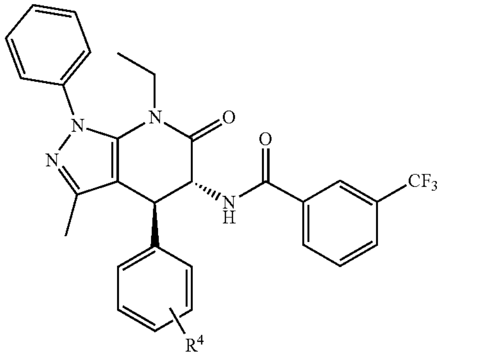

IXb

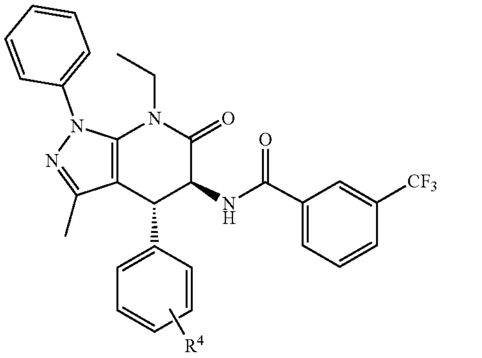

IXc

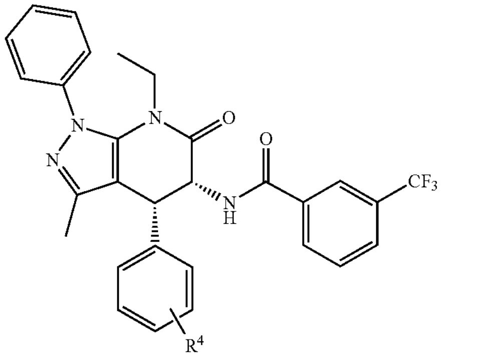

IXd

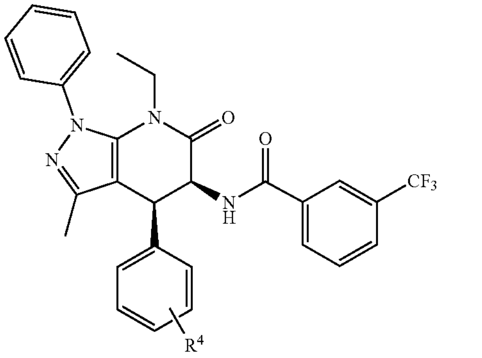

or a pharmaceutically acceptable salt thereof, wherein $R^4$ is as defined above and described in embodiments herein.

In some embodiments, the present disclosure provides compounds of Formula IXa-i, Formula IXb-i, Formula IXc-i or Formula IXd-i:

IXa-i

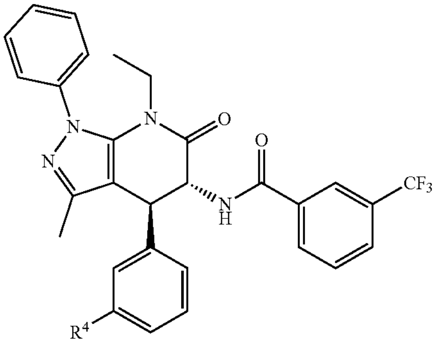

IXb-i

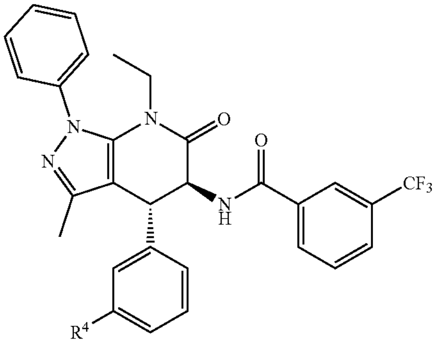

IXc-i

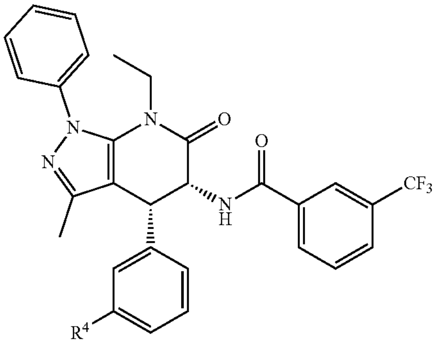

IXd-i

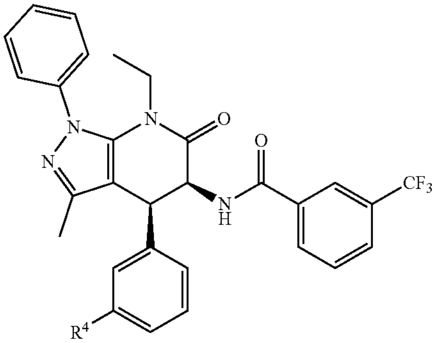

or a pharmaceutically acceptable salt thereof, wherein $R^4$ is as defined above and described in embodiments herein.

In some embodiments, the present disclosure provides compounds of Formula Xa, Formula Xb, Formula Xc or Formula Xd:

Xa

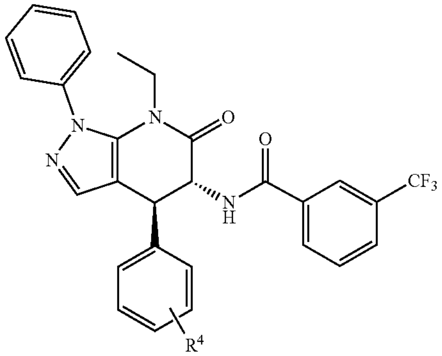

Xb

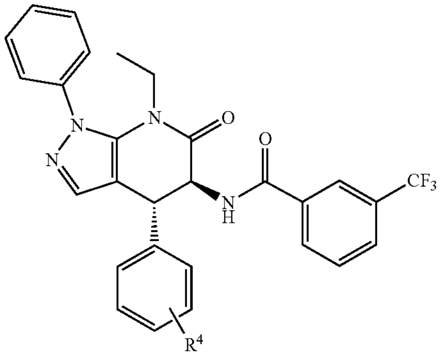

Xc

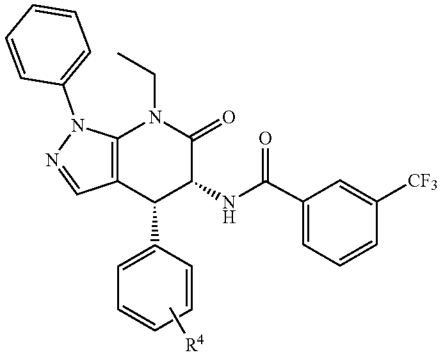

Xd

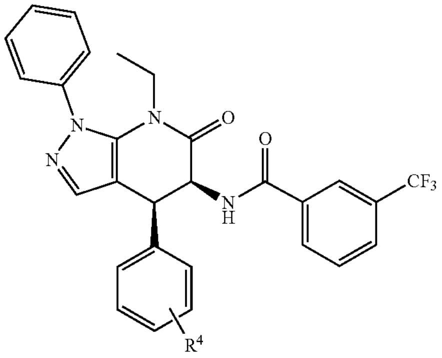

or a pharmaceutically acceptable salt thereof, wherein $R^4$ is as defined above and described in embodiments herein.

In some embodiments, the present disclosure provides compounds of Formula Xa-i, Formula Xb-i, Formula Xc-i or Formula Xd-i:

Xa-i

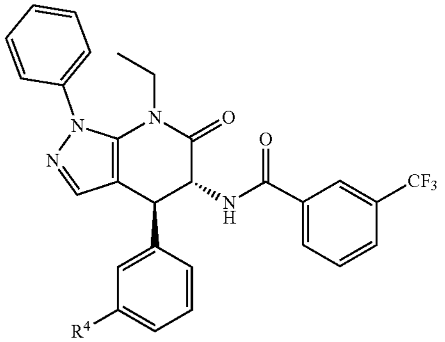

Xb-i

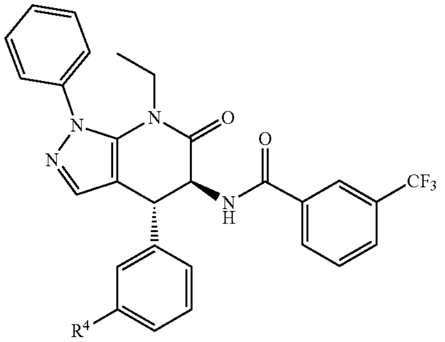

Xc-i

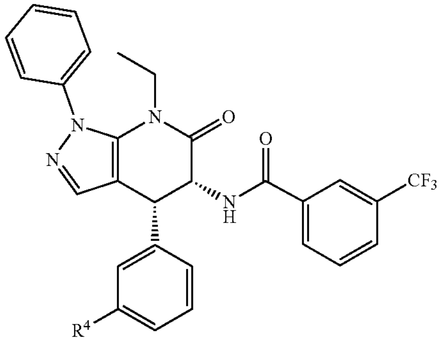

Xd-i

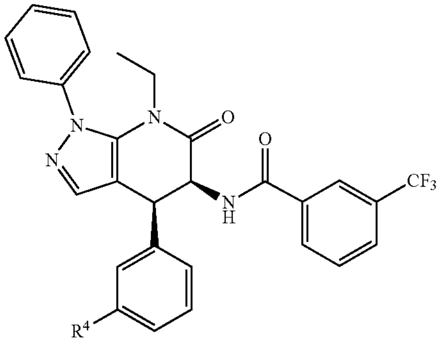

or a pharmaceutically acceptable salt thereof, wherein $R^4$ is as defined above and described in embodiments herein.

In some embodiments, the present disclosure provides compounds of Formula XIa, Formula XIb, Formula XIc or Formula XId:

XIa

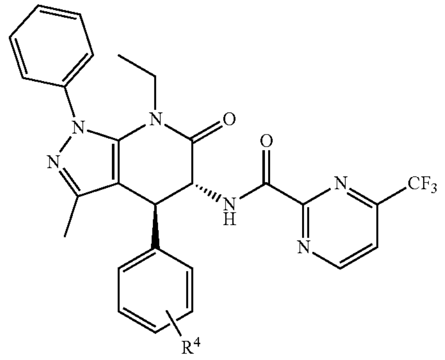

XIb

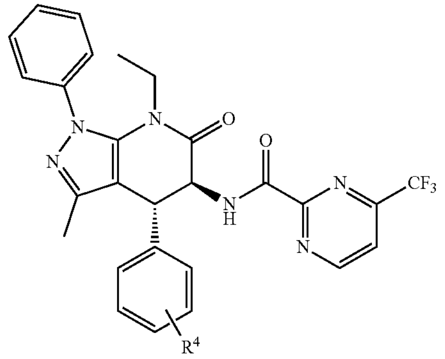

XIc

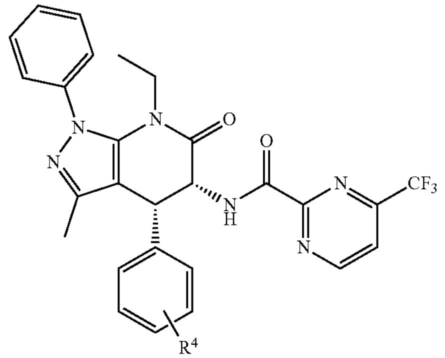

XId

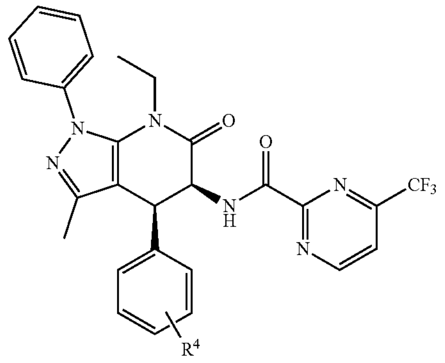

or a pharmaceutically acceptable salt thereof, wherein $R^4$ is as defined above and described in embodiments herein.

In some embodiments, the present disclosure provides compounds of Formula Xia-i, Formula XIb-i, Formula XIc-i or Formula XId-i:

XIa-i

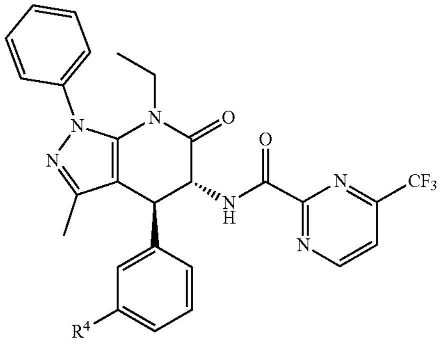

XIb-i

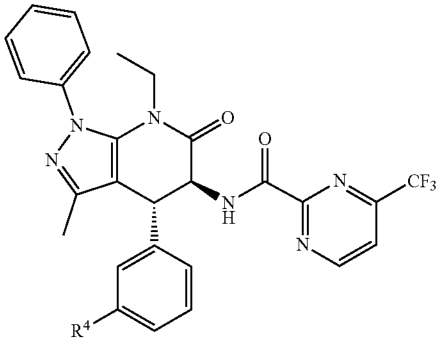

XIc-i

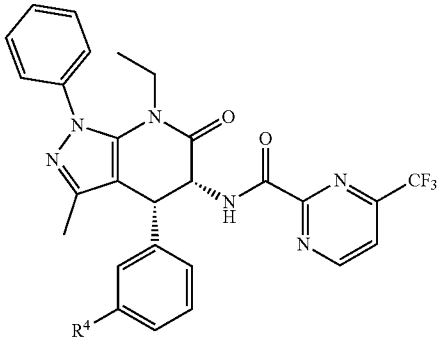

XId-i

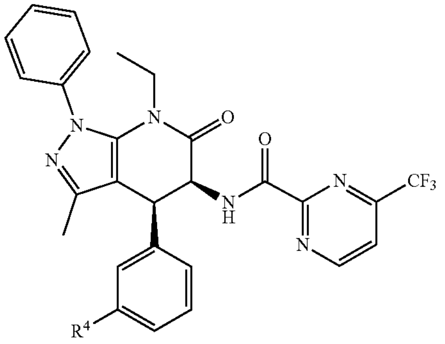

or a pharmaceutically acceptable salt thereof, wherein $R^4$ is as defined above and described in embodiments herein.

In some embodiments, the present disclosure provides compounds of Formula XIIa, Formula XIIb, Formula XIIc or Formula XIId:

XIIa

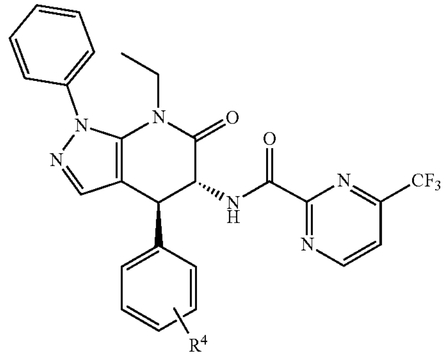

XIIb

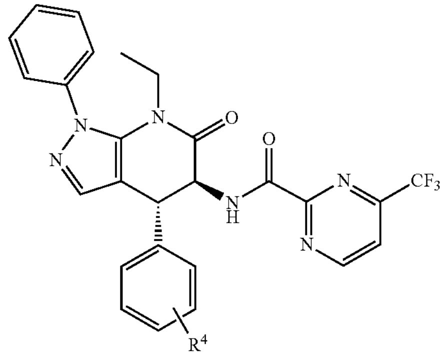

XIIc

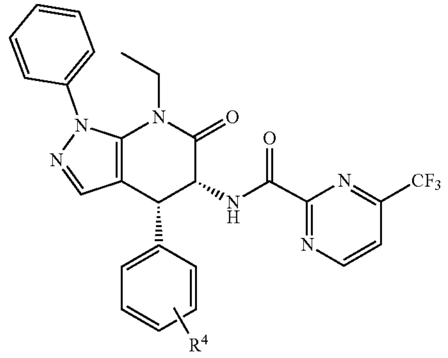

XIId

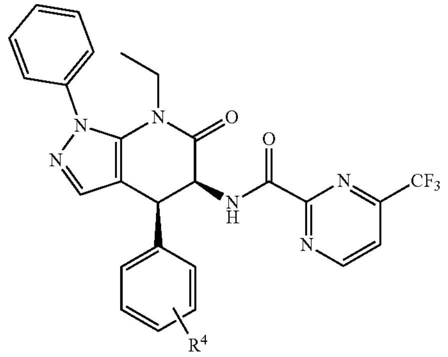

or a pharmaceutically acceptable salt thereof, wherein $R^4$ is as defined above and described in embodiments herein.

In some embodiments, the present disclosure provides compounds of Formula XIIa-i, Formula XIIb-i, Formula XIIc-i or Formula XIId-i:

XIIa-i

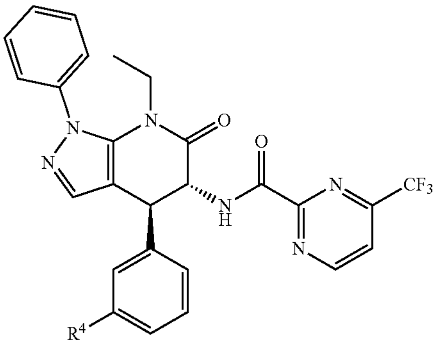

XIIb-i

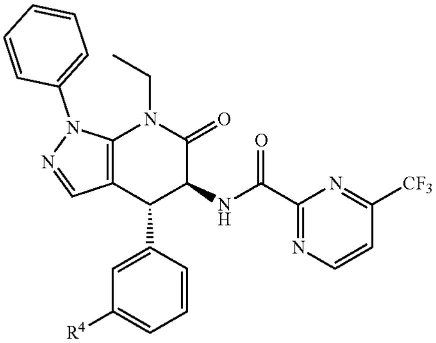

XIIc-i

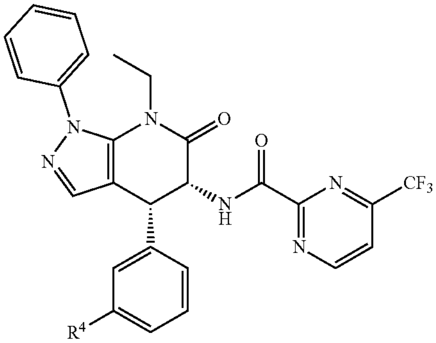

XIId-i

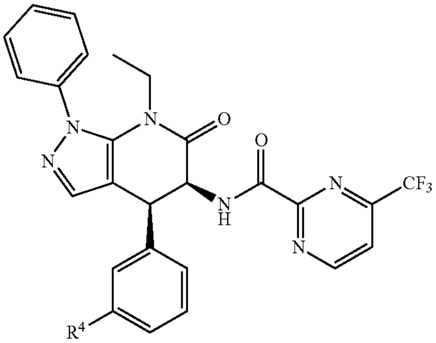

or a pharmaceutically acceptable salt thereof, wherein $R^4$ is as defined above and described in embodiments herein.

In some embodiments, the present disclosure provides compounds of Formula XIIIa, Formula XIIIb, Formula XIIIc or Formula XIIId:

XIIIa

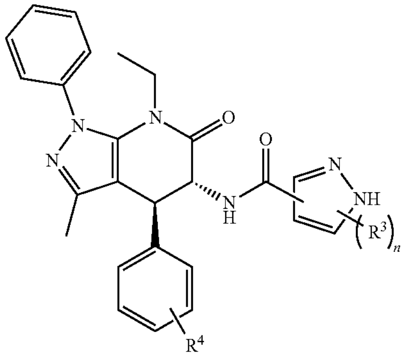

XIIIb

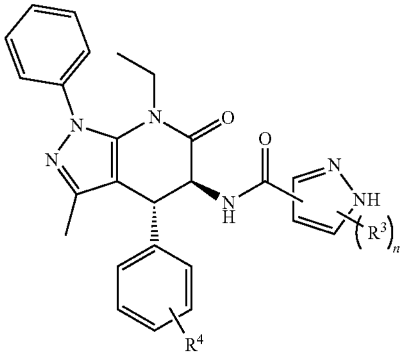

XIIIc

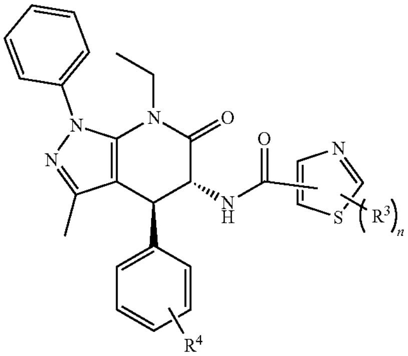

XIIId

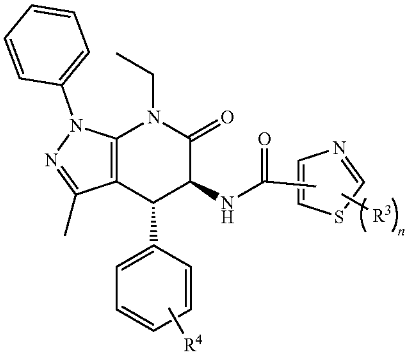

or a pharmaceutically acceptable salt thereof, wherein $R^4$ is as defined above and described in embodiments herein.

In some embodiments of Formula IXa, Formula IXb, Formula IXc, Formula IXd, Formula IXa-i, Formula IXb-i, Formula IXc-i, Formula IXd-i, Formula Xa, Formula Xb, Formula Xc, Formula Xd, Formula Xa-i, Formula Xb-i, Formula Xc-i, Formula Xd-i, Formula XIa, Formula XIb, Formula XIc, Formula XId, Formula XIa-i, Formula XIb-i, Formula XIc-i, Formula XId-i, Formula XIIa, Formula XIIb, Formula XIIc, Formula XIId, Formula XIIa-i, Formula XIIb-i, Formula XIIc-i, Formula XIId-i, Formula XIIIa, Formula XIIIb, Formula XIIIc or Formula XIIId, $R^4$ is $L^2$-Y, wherein $L^2$ is a covalent bond, bivalent $C_{2-8}$ straight or branched, hydrocarbon chain wherein one or two methylene units of $L^2$ are optionally independently replaced by —NRC(O)—, —C(O)NR—, —N(R)$SO_2$—, $SO_2$N(R)—, —S—, S(O)—, —$SO_2$—, —C(O)—, —OC(O)—, or C(O)O—; and additionally one methylene unit of $L^2$ is optionally replaced by an optionally substituted 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur; and Y is hydrogen, halogen, —COOR$^f$, —CN, —CONR$^f_2$, —NRCN, $NO_2$, —NR$^f_2$, epoxide, or a ring selected from an optionally substituted 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, and an 8-10 membered bicyclic heteroaromatic ring having 1-5 heteroatoms independently selected from nitrogen, oxygen, and sulfur, or $C_{1-8}$ aliphatic optionally substituted with halogen, $NO_2$, or CN; wherein -$L^2$-Y comprises an alpha, beta-unsaturated carbonyl moiety, amide, cyano group, halogen, carbonyl, alkynyl group, sulfonyl group, or epoxide; and wherein each occurrence of $R^f$, $R^g$ and $R^h$ is independently H, halogen, OH, or straight or branched $C_{1-6}$ alkyl, $C_{2-6}$ alkenyl, or $C_{2-6}$ alkynyl group optionally substituted with 1, 2 or 3 halogen atoms.

In some embodiments of Formula IXa, Formula IXb, Formula IXc, Formula IXd, Formula IXa-i, Formula IXb-i, Formula IXc-i, Formula IXd-i, Formula Xa, Formula Xb, Formula Xc, Formula Xd, Formula Xa-i, Formula Xb-i, Formula Xc-i, Formula Xd-i, Formula XIa, Formula XIb, Formula XIc, Formula XId, Formula XIa-i, Formula XIb-i, Formula XIc-i, Formula XId-i, Formula XIIa, Formula XIIb, Formula XIIc, Formula XIId, Formula XIIa-i, Formula XIIb-i, Formula XIIc-i, and Formula XIId-i, $R^4$ is $L^2$-Y, wherein $L^2$ is a covalent bond, bivalent $C_{2-8}$ straight or branched, hydrocarbon chain wherein one or two methylene units of $L^2$ are optionally independently replaced by —NRC(O)—, —C(O)NR—, —N(R)$SO_2$—, $SO_2$N(R)—, —S—, S(O)—, —$SO_2$—, —C(O)—, —OC(O)—, or —C(O)O—; and additionally one methylene unit of $L^2$ is optionally replaced by an optionally substituted 3-8 membered saturated or partially unsaturated monocyclic carbocyclic ring, or a 3-8 membered saturated or partially unsaturated monocyclic heterocyclic ring having 1-2 heteroatoms independently selected from nitrogen, oxygen, and sulfur; and Y is hydrogen, halogen, —COOR$^f$, —CN, —CONR$^f_2$, —NRCN, —$NO_2$—, —NR$^f_2$, epoxide, or a ring selected from an optionally substituted 3-8 membered saturated or partially unsaturated monocyclic carbocyclic ring, phenyl, a 3-8 membered saturated or partially unsaturated monocyclic heterocyclic ring having 1-2 heteroatoms independently selected from nitrogen, oxygen, and sulfur, and a 5-10 membered bicyclic heterocyclic ring having 1-4 heteroatoms independently selected from nitrogen, oxygen, and sulfur, or $C_{1-8}$ aliphatic optionally substituted with halogen, $NO_2$, or CN; wherein -$L^2$-Y comprises an alpha, beta-unsaturated carbonyl moiety, amide, cyano group, halogen, carbonyl, alkynyl group, sulfonyl group, or epoxide; and wherein each occurrence of $R^f$, $R^g$ and $R^h$ is independently H, halogen, OH, or straight or branched $C_{1-6}$ alkyl, $C_{2-6}$ alkenyl, or $C_{2-6}$ alkynyl group optionally substituted with 1, 2 or 3 halogen atoms.

In some embodiments of Formula IXa, Formula IXb, Formula IXc, Formula IXd, Formula IXa-i, Formula IXb-i, Formula IXc-i, Formula IXd-i, Formula Xa, Formula Xb, Formula Xc, Formula Xd, Formula Xa-i, Formula Xb-i, Formula Xc-i, Formula Xd-i, Formula XIa, Formula XIb, Formula XIc, Formula XId, Formula XIa-i, Formula XIb-i, Formula XIc-i, Formula XId-i, Formula XIIa, Formula XIIb, Formula XIIc, Formula XIId, Formula XIIa-i, Formula XIIb-i, Formula XIIc-i, and Formula XIId-i, $R^4$ is $L^2$-Y, wherein $L^2$ is a covalent bond, bivalent $C_{2-8}$ straight or branched, hydrocarbon chain wherein one or two methylene units of $L^2$ are optionally independently replaced by —NRC(O)—, —C(O)NR—, —N(R)$SO_2$—, —$SO_2$N(R)—, —S—, S(O)—, —$SO_2$—, —C(O)—, —OC(O)—, or —C(O)O—; and additionally one methylene unit of L is optionally replaced by a ring selected from

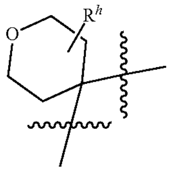
,
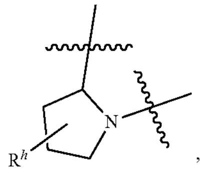
,
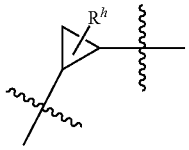
,
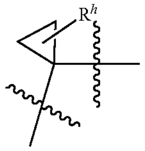
,
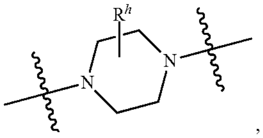
,
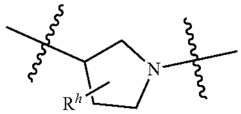
,
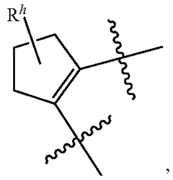
,
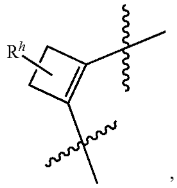
, -continued

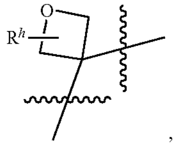, and 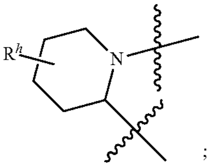;

and Y is hydrogen, halogen, —COOR$^f$, —CN, —CONR$_2$, —NRCN, NO$_2$, —NR$^f_2$, epoxide, or a ring selected from

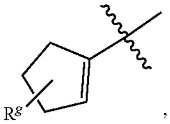, 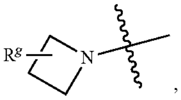, 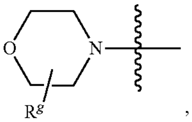,

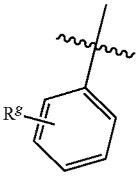, 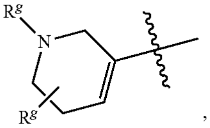,

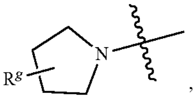, 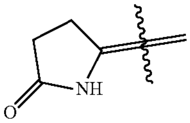,

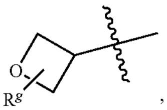, 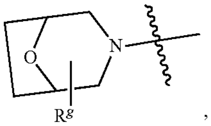,

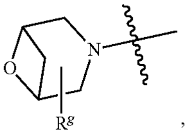, 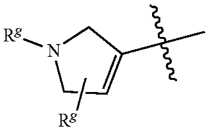,

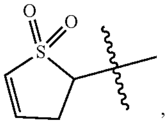, 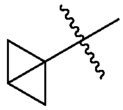, 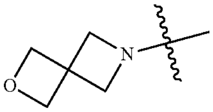,

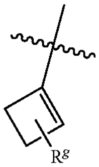, 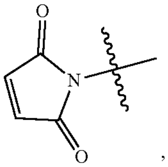, 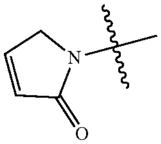,

-continued

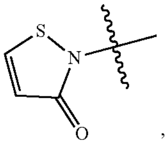, 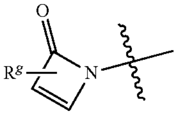, 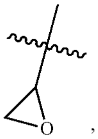,

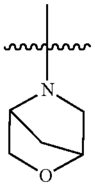, 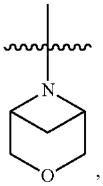, 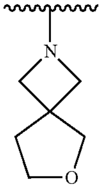, 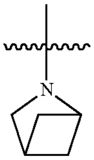,

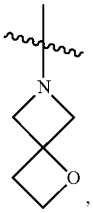, 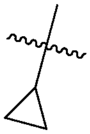, and 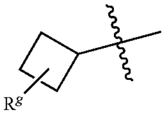, or $C_{1-8}$ aliphatic optionally substituted with halogen, NO$_2$, or CN; wherein -L$^2$-Y comprises an alpha, beta-unsaturated carbonyl moiety, amide, cyano group, halogen, carbonyl, alkynyl group, sulfonyl group, or epoxide; and wherein each occurrence of R$^f$, R$^g$ and R$^h$ is independently H, halogen, OH, or C$_1$-6 straight or branched alkyl, $C_{2-6}$ alkenyl, or $C_{2-6}$ alkynyl group optionally substituted with 1, 2 or 3 halogen atoms.

In some embodiments, the present disclosure provides a compound selected from the following:

I-9a

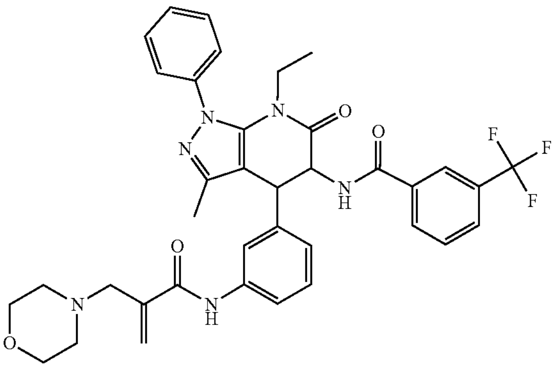

I-15a

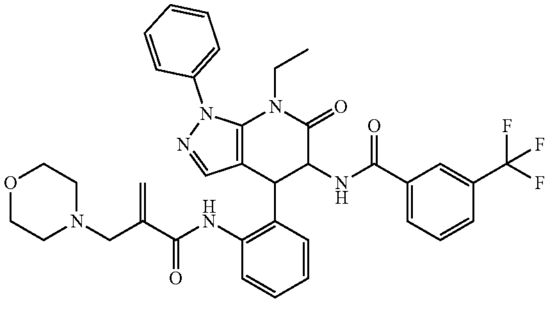

-continued
I-66a
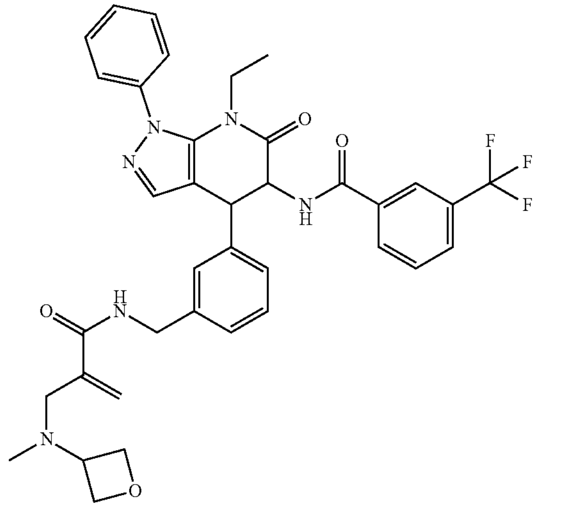
I-153a
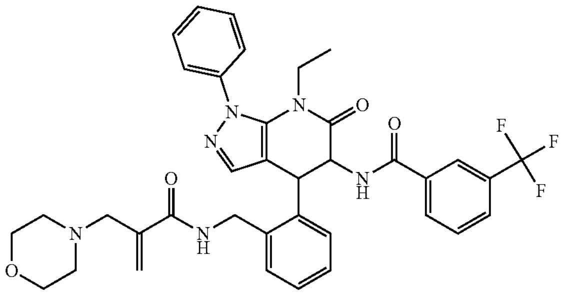
I-160a
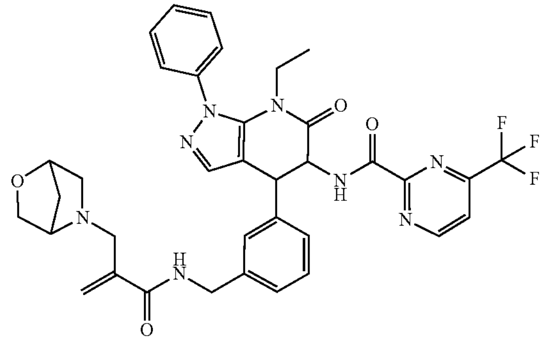
I-161a
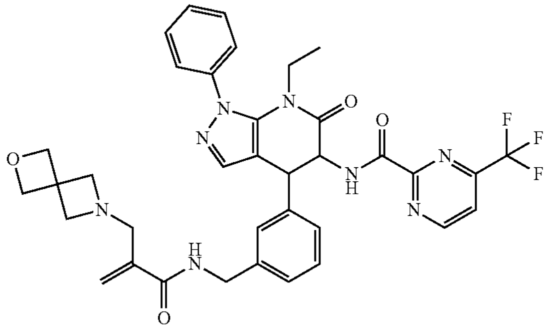
-continued
I-162a
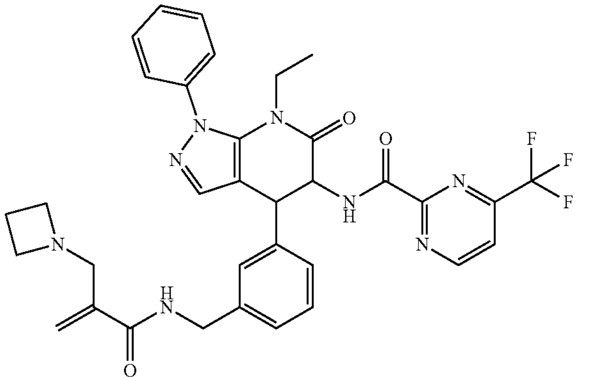
I-163a
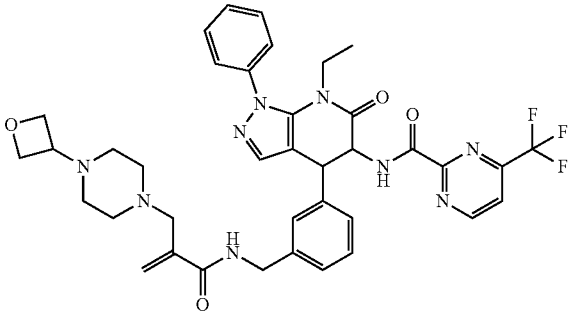
I-177a
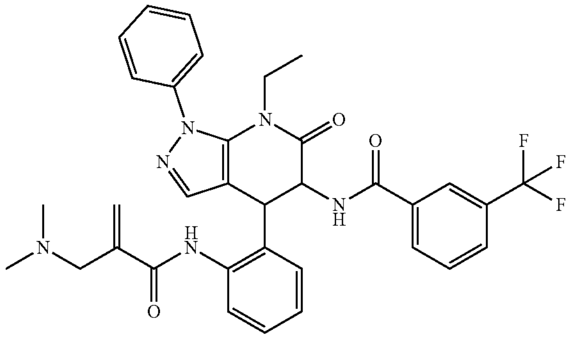
I-234a
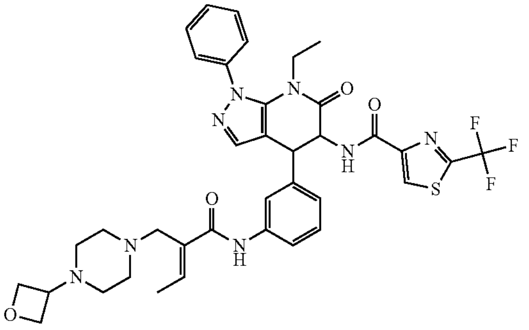
and -continued
I-383a
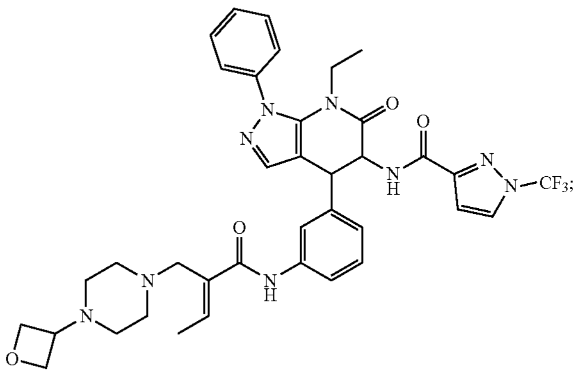
or a pharmaceutically acceptable salt thereof.
In some embodiments, the present disclosure provides a compound selected from the following:
I-9
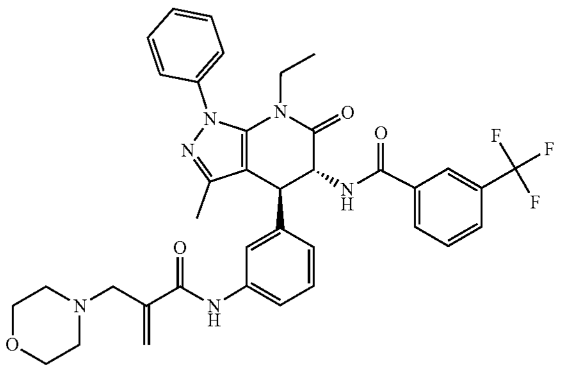
I-2
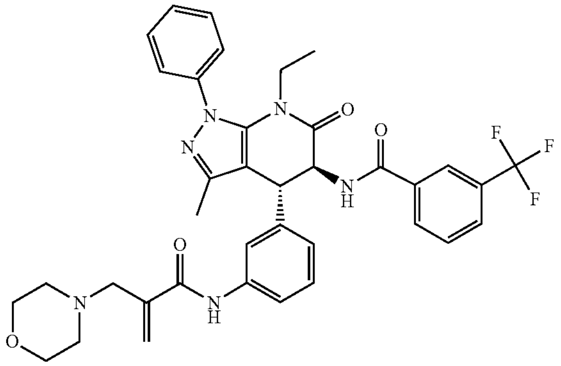
-continued
I-15
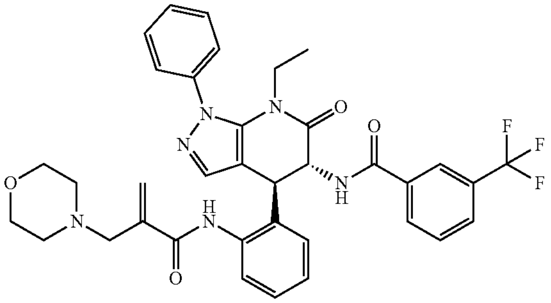
I-15b
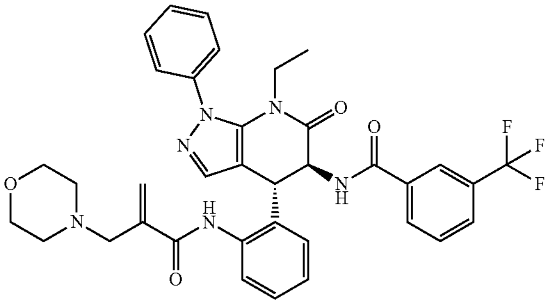
I-66
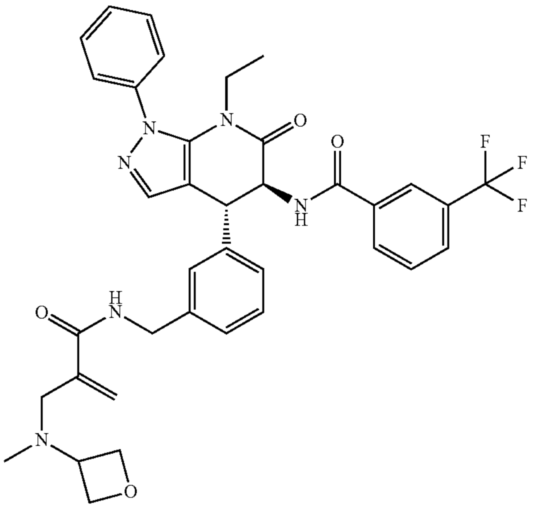

-continued
I-154
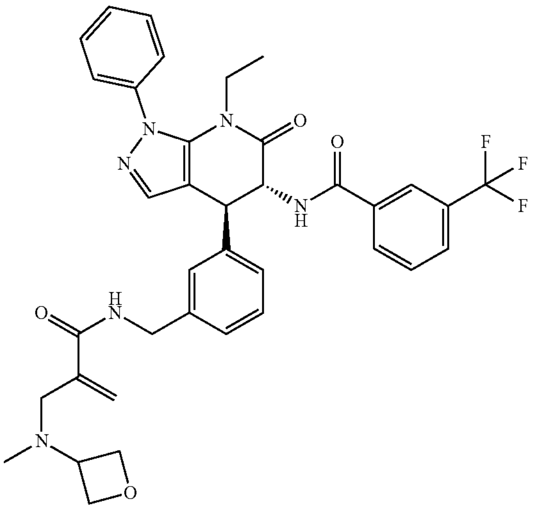
I-153
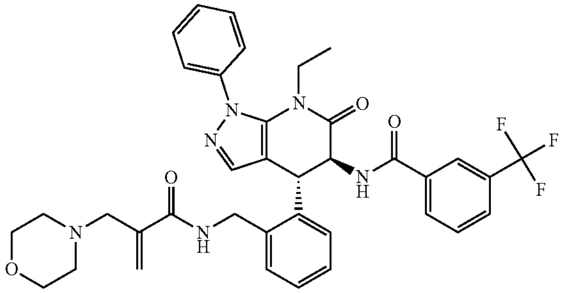
I-153b
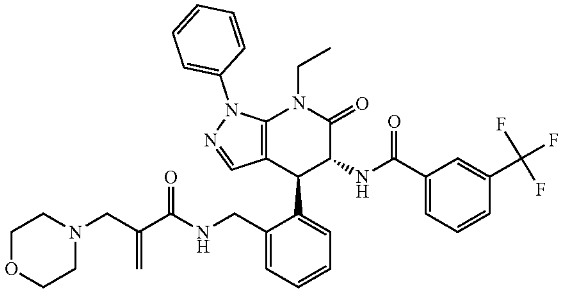
I-160
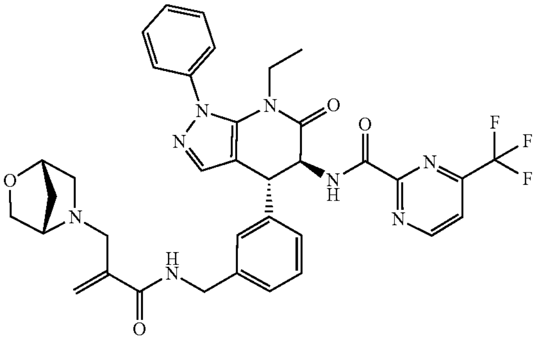
-continued
I-160b
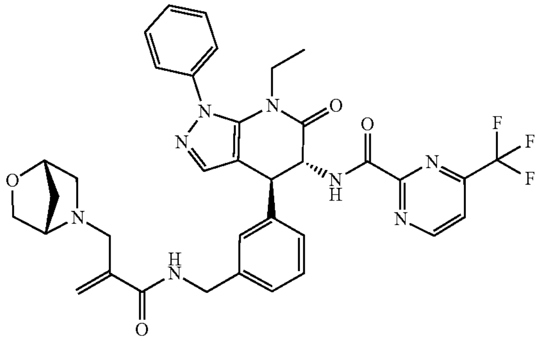
I-160c
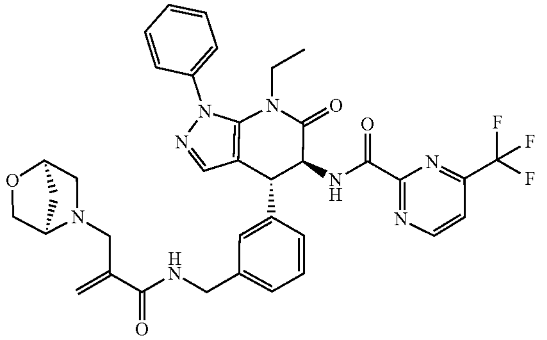
I-160d
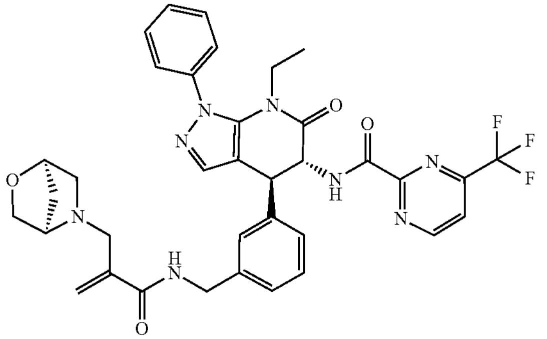
I-161
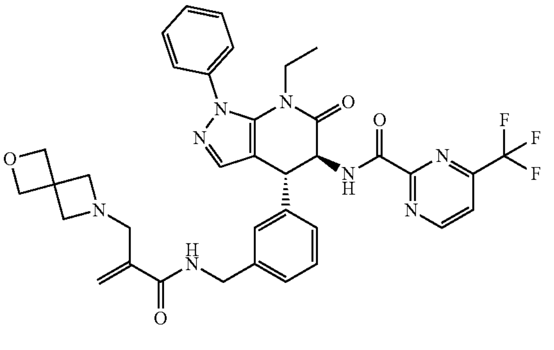

I-161b
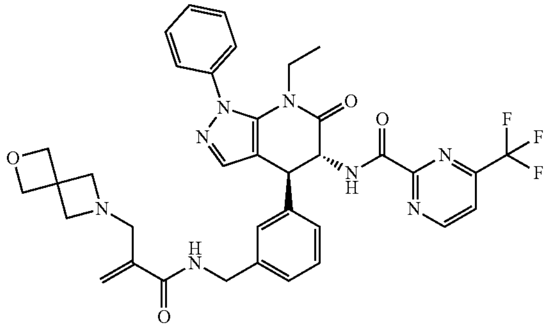
I-162
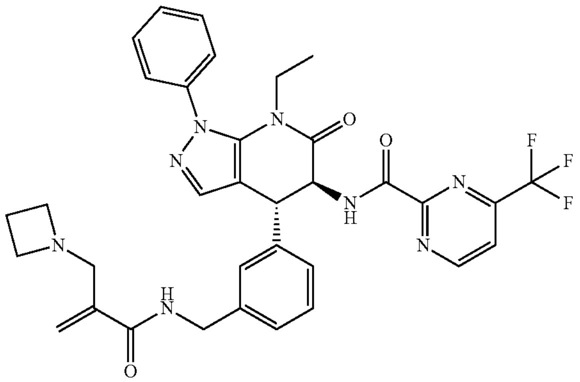
I-162b
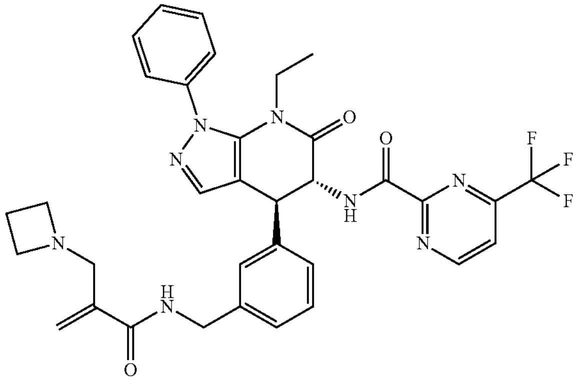
I-163
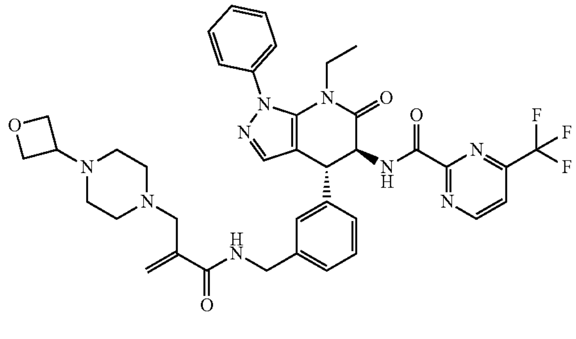
I-163b
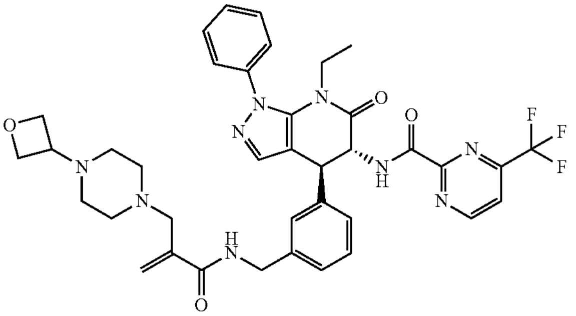
I-177
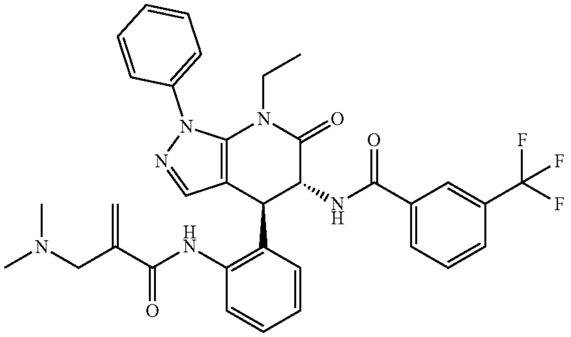
I-177b
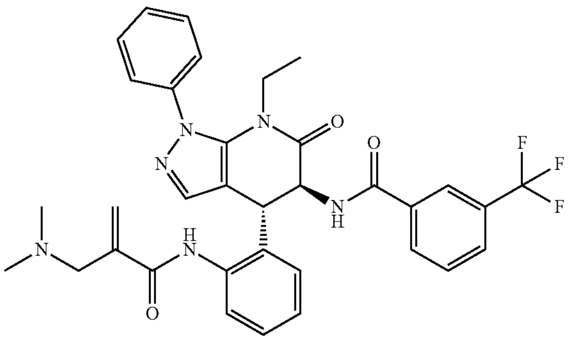
I-234
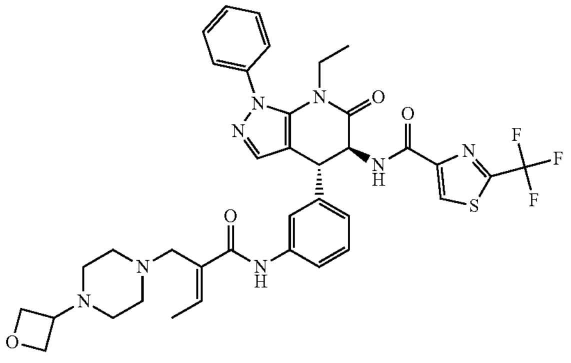

-continued
I-234b
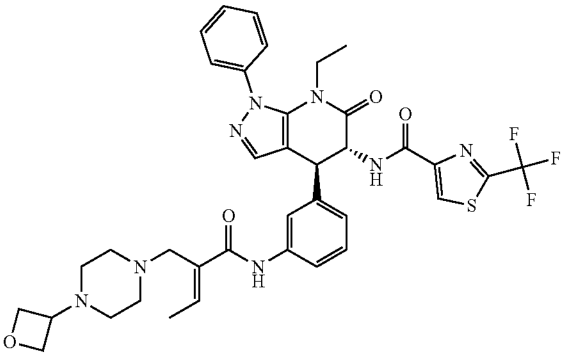
I-383
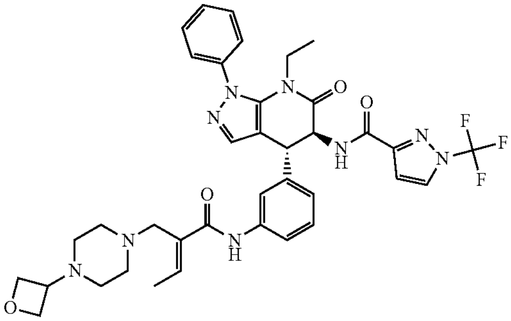
and
-continued
I-383b
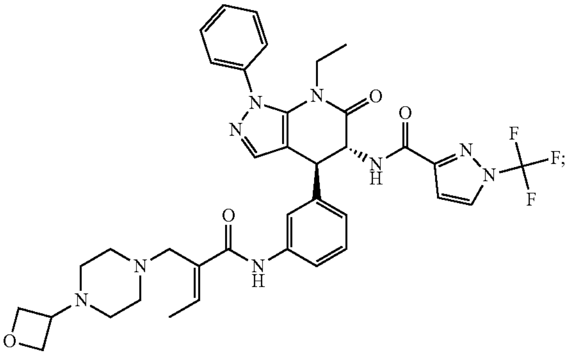
or a pharmaceutically acceptable salt thereof.
Exemplary compounds of the disclosure are set forth in Table 1, below.
In some embodiments, the present disclosure provides a compound shown in Table 1, below, or a pharmaceutically acceptable salt thereof.
TABLE 1
| Exemplary Compounds |
| --- |
| I-1 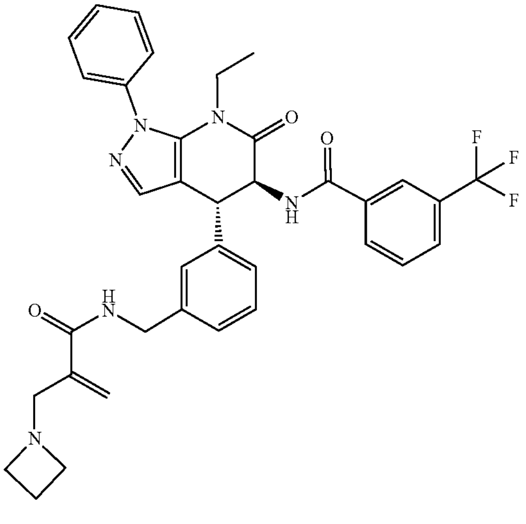 [SMILES: C=C(CN1CCC1)C(=O)NCc1cccc([C@@H]2c3cnn(-c4ccccc4)c3N(CC)C(=O)[C@H]2NC(=O)c2cccc(C(F)(F)F)c2)c1] |

TABLE 1-continued
| Exemplary Compounds | |
|---|---|
| 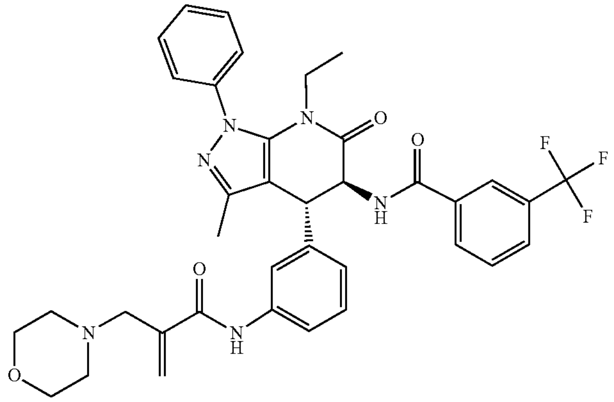 [SMILES: C=C(CN1CCOCC1)C(=O)Nc1cccc([C@@H]2c3c(C)nn(-c4ccccc4)c3N(CC)C(=O)[C@H]2NC(=O)c2cccc(C(F)(F)F)c2)c1] | I-2 |
| 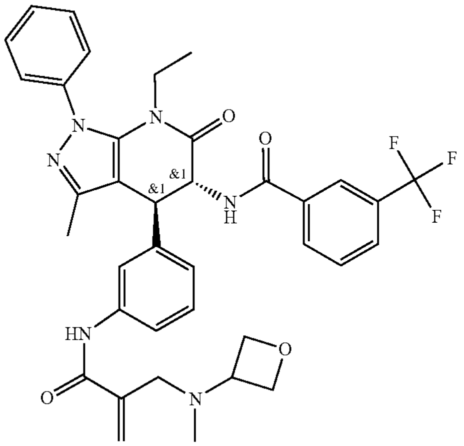 [SMILES: C=C(CN(C)C1COC1)C(=O)Nc1cccc([C@H]2c3c(C)nn(-c4ccccc4)c3N(CC)C(=O)[C@@H]2NC(=O)c2cccc(C(F)(F)F)c2)c1] | I-3 |
| 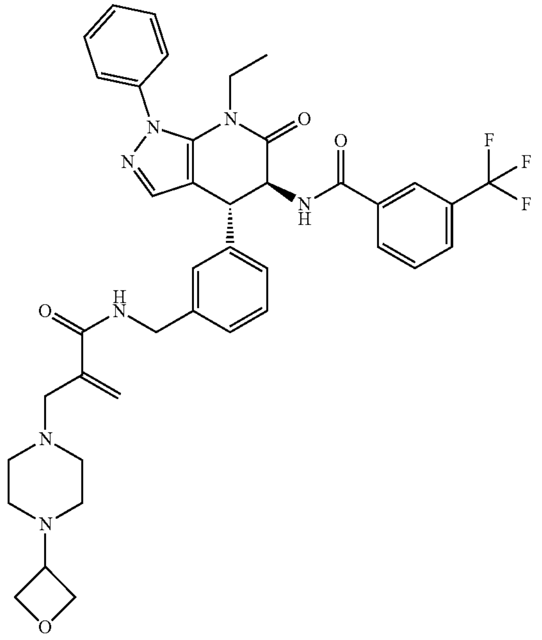 [SMILES: C=C(CN1CCN(C2COC2)CC1)C(=O)NCc1cccc([C@@H]2c3cnn(-c4ccccc4)c3N(CC)C(=O)[C@H]2NC(=O)c2cccc(C(F)(F)F)c2)c1] | I-4 |

TABLE 1-continued
| Exemplary Compounds |
| --- |
| I-5<br>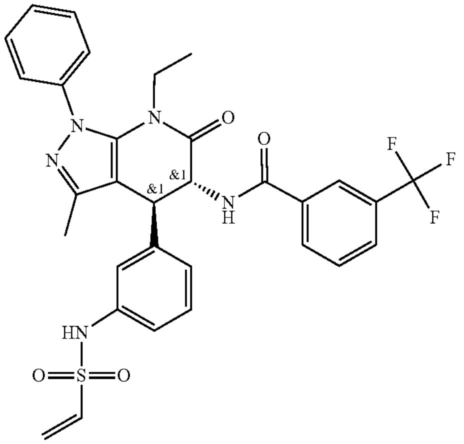 [SMILES: C=CS(=O)(=O)Nc1cccc([C@H]2c3c(C)nn(-c4ccccc4)c3N(CC)C(=O)[C@@H]2NC(=O)c2cccc(C(F)(F)F)c2)c1] |
| I-6<br>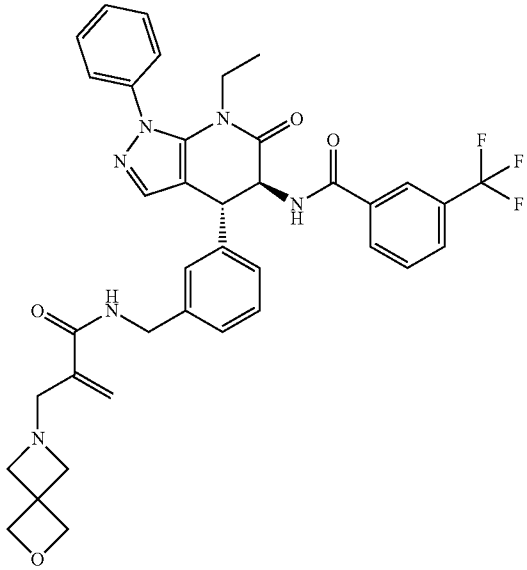 [SMILES: C=C(CN1CC2(COC2)C1)C(=O)NCc1cccc([C@@H]2c3cnn(-c4ccccc4)c3N(CC)C(=O)[C@H]2NC(=O)c2cccc(C(F)(F)F)c2)c1] |
| I-7<br>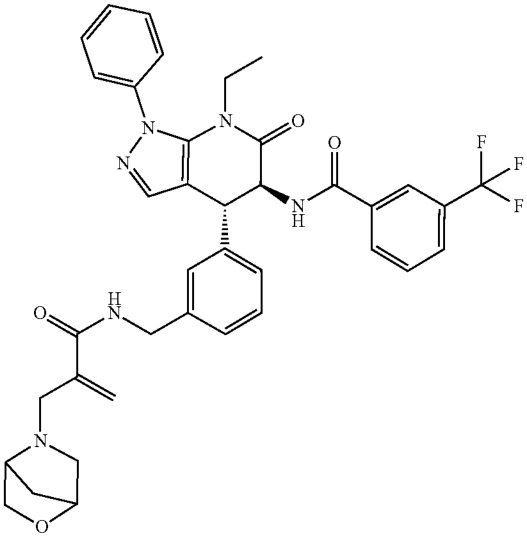 [SMILES: C=C(CN1CC2CC1CO2)C(=O)NCc1cccc([C@@H]2c3cnn(-c4ccccc4)c3N(CC)C(=O)[C@H]2NC(=O)c2cccc(C(F)(F)F)c2)c1] |

TABLE 1-continued
| Exemplary Compounds |
| --- |
| 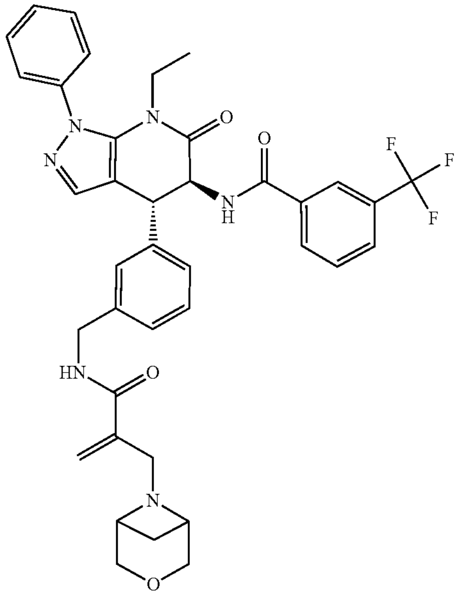 [SMILES: C=C(CN1C2COCC1C2)C(=O)NCc1cccc([C@@H]2c3cnn(-c4ccccc4)c3N(CC)C(=O)[C@H]2NC(=O)c2cccc(C(F)(F)F)c2)c1] I-8 |
| 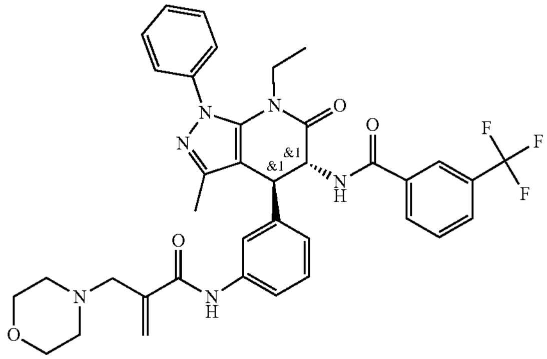 [SMILES: C=C(CN1CCOCC1)C(=O)Nc1cccc([C@H]2c3c(C)nn(-c4ccccc4)c3N(CC)C(=O)[C@@H]2NC(=O)c2cccc(C(F)(F)F)c2)c1] I-9 |
| 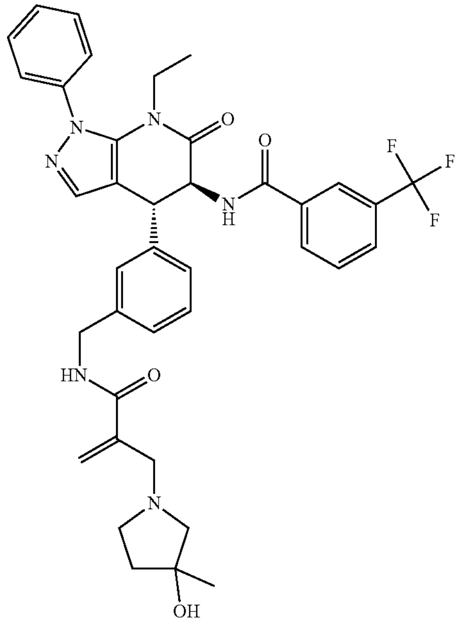 [SMILES: C=C(CN1CCC(C)(O)C1)C(=O)NCc1cccc([C@@H]2c3cnn(-c4ccccc4)c3N(CC)C(=O)[C@H]2NC(=O)c2cccc(C(F)(F)F)c2)c1] I-10 |

TABLE 1-continued
| Exemplary Compounds |
|---|
| 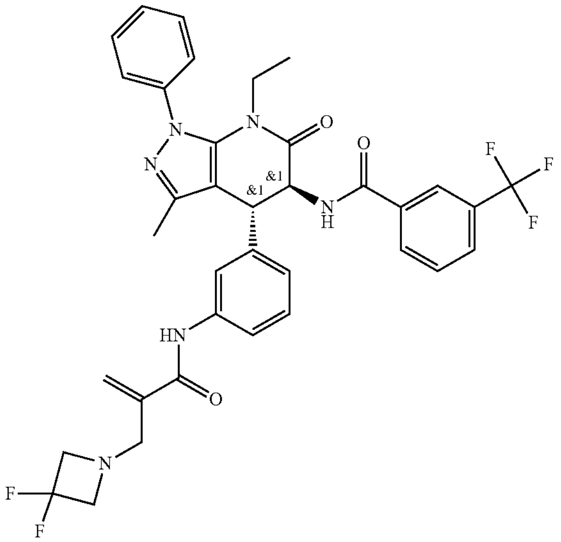 [SMILES: C=C(CN1CC(F)(F)C1)C(=O)Nc1cccc([C@@H]2c3c(C)nn(-c4ccccc4)c3N(CC)C(=O)[C@H]2NC(=O)c2cccc(C(F)(F)F)c2)c1] I-11 |
| 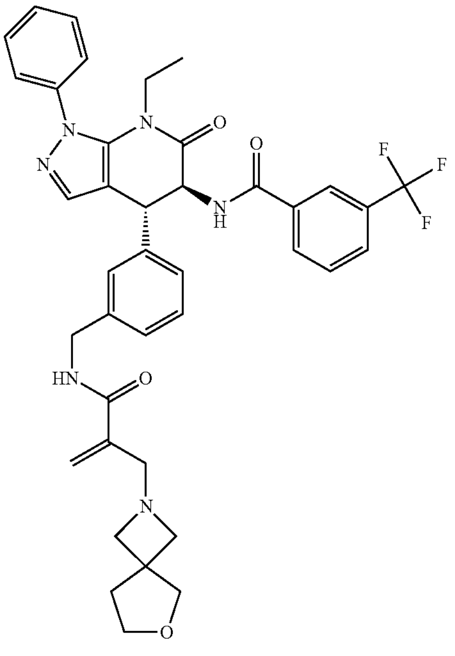 [SMILES: C=C(CN1CC2(CCOC2)C1)C(=O)NCc1cccc([C@@H]2c3cnn(-c4ccccc4)c3N(CC)C(=O)[C@H]2NC(=O)c2cccc(C(F)(F)F)c2)c1] I-12 |

TABLE 1-continued
| Exemplary Compounds |
| --- |
| 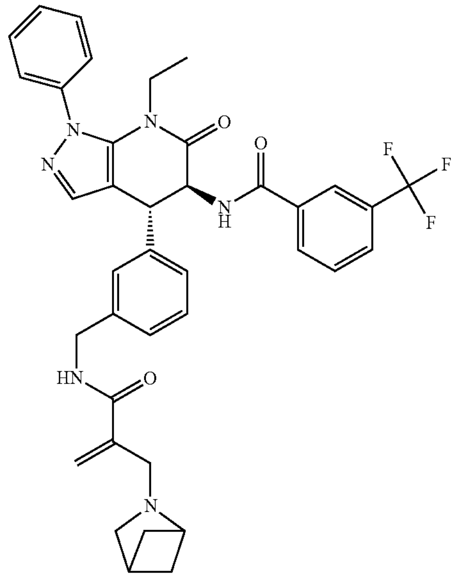 [SMILES: C=C(CN1CC2CC1C2)C(=O)NCc1cccc([C@@H]2c3cnn(-c4ccccc4)c3N(CC)C(=O)[C@H]2NC(=O)c2cccc(C(F)(F)F)c2)c1] I-13 |
| 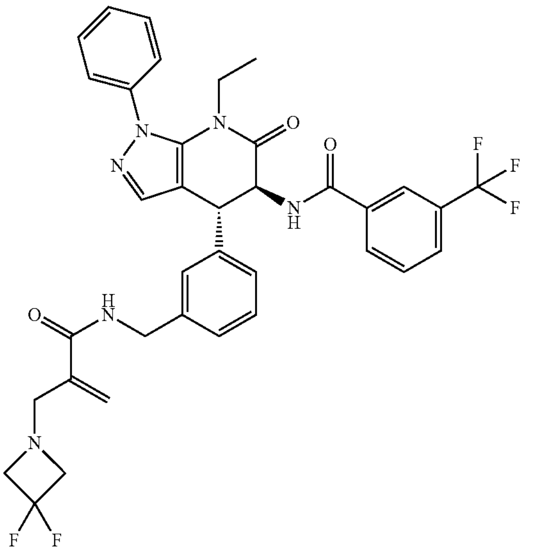 [SMILES: C=C(CN1CC(F)(F)C1)C(=O)NCc1cccc([C@@H]2c3cnn(-c4ccccc4)c3N(CC)C(=O)[C@H]2NC(=O)c2cccc(C(F)(F)F)c2)c1] I-14 |
| 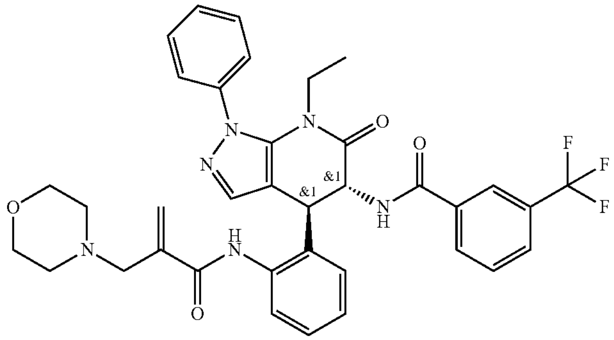 [SMILES: C=C(CN1CCOCC1)C(=O)Nc1ccccc1[C@H]1c2cnn(-c3ccccc3)c2N(CC)C(=O)[C@@H]1NC(=O)c1cccc(C(F)(F)F)c1] I-15 |

TABLE 1-continued
Exemplary Compounds
I-16
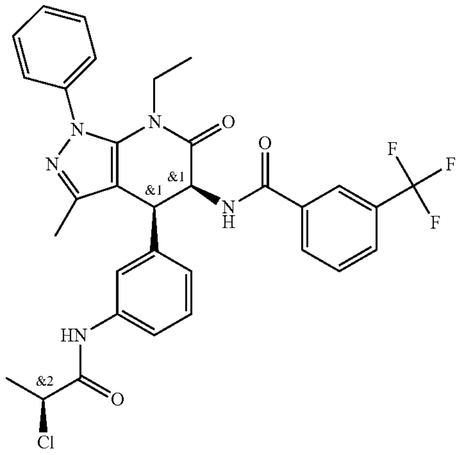 [SMILES: CCN1C(=O)[C@@H](NC(=O)c2cccc(C(F)(F)F)c2)[C@@H](c2cccc(NC(=O)[C@H](C)Cl)c2)c2c(C)nn(-c3ccccc3)c21]
I-17
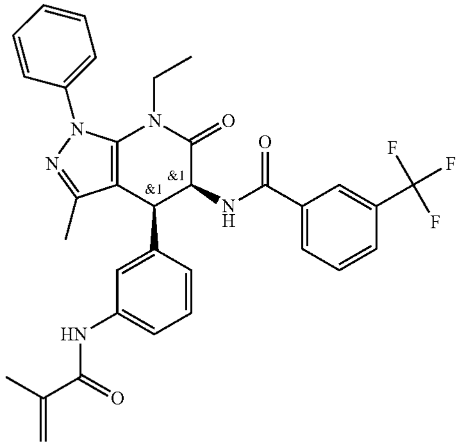 [SMILES: C=C(C)C(=O)Nc1cccc([C@H]2c3c(C)nn(-c4ccccc4)c3N(CC)C(=O)[C@H]2NC(=O)c2cccc(C(F)(F)F)c2)c1]
I-18
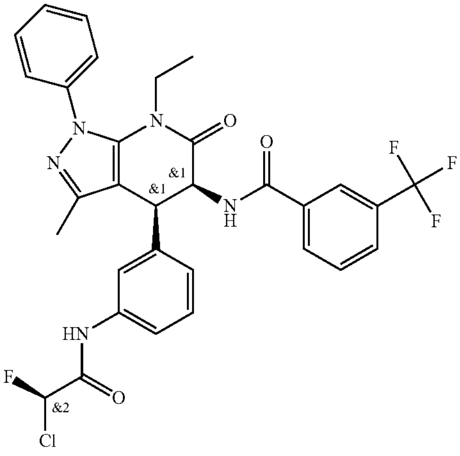 [SMILES: CCN1C(=O)[C@@H](NC(=O)c2cccc(C(F)(F)F)c2)[C@@H](c2cccc(NC(=O)[C@H](F)Cl)c2)c2c(C)nn(-c3ccccc3)c21]

TABLE 1-continued
| Exemplary Compounds |
| --- |
| 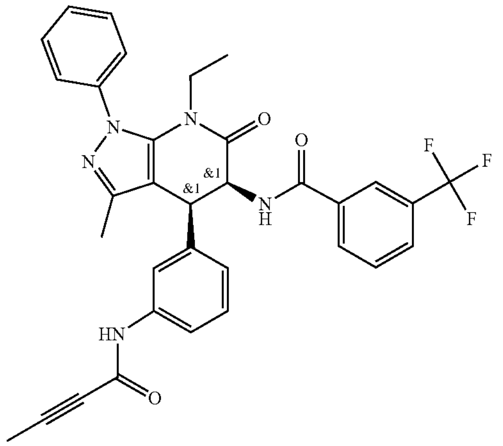 [SMILES: CC#CC(=O)Nc1cccc([C@H]2c3c(C)nn(-c4ccccc4)c3N(CC)C(=O)[C@H]2NC(=O)c2cccc(C(F)(F)F)c2)c1] I-19 |
| 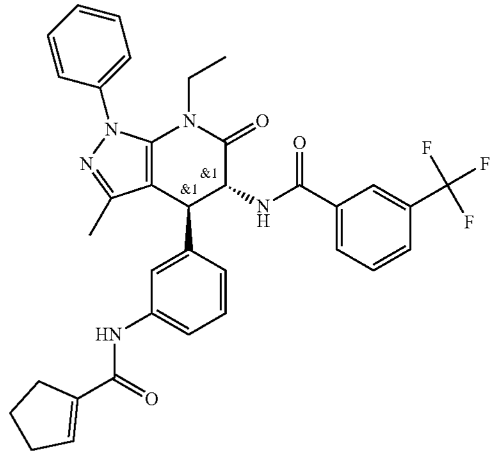 [SMILES: CCN1C(=O)[C@H](NC(=O)c2cccc(C(F)(F)F)c2)[C@@H](c2cccc(NC(=O)C3=CCCC3)c2)c2c(C)nn(-c3ccccc3)c21] I-20 |
| 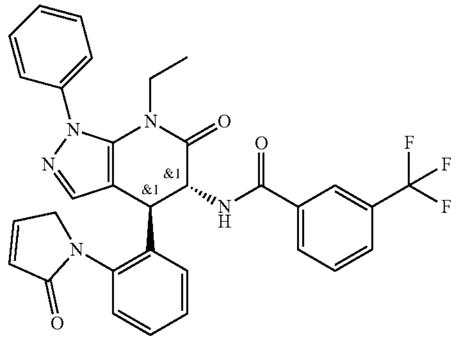 [SMILES: CCN1C(=O)[C@H](NC(=O)c2cccc(C(F)(F)F)c2)[C@@H](c2ccccc2N2CC=CC2=O)c2cnn(-c3ccccc3)c21] I-21 |

TABLE 1-continued
| Exemplary Compounds |
| --- |
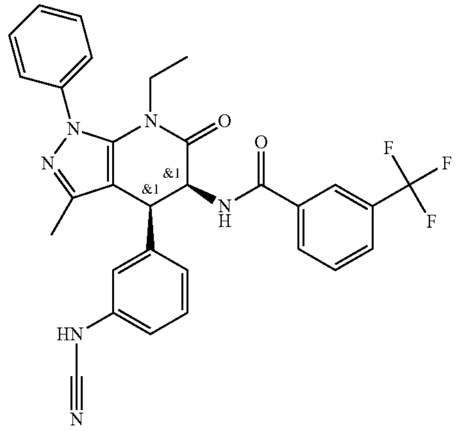 [SMILES: CCN1C(=O)[C@@H](NC(=O)c2cccc(C(F)(F)F)c2)[C@@H](c2cccc(NC#N)c2)c2c(C)nn(-c3ccccc3)c21]
I-22
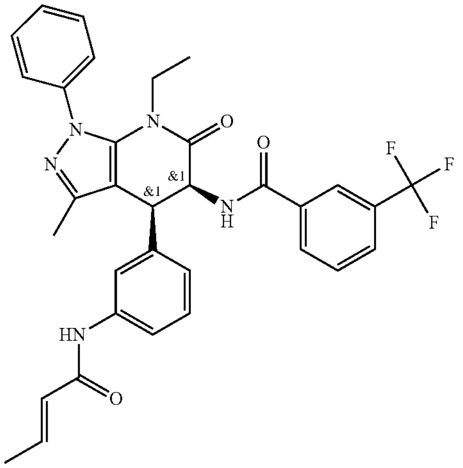 [SMILES: C/C=C/C(=O)Nc1cccc([C@H]2c3c(C)nn(-c4ccccc4)c3N(CC)C(=O)[C@H]2NC(=O)c2cccc(C(F)(F)F)c2)c1]
I-23
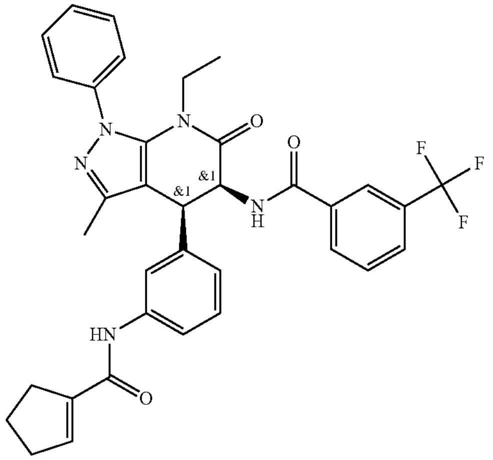 [SMILES: CCN1C(=O)[C@@H](NC(=O)c2cccc(C(F)(F)F)c2)[C@@H](c2cccc(NC(=O)C3=CCCC3)c2)c2c(C)nn(-c3ccccc3)c21]
I-24

TABLE 1-continued
| Exemplary Compounds |
|---|
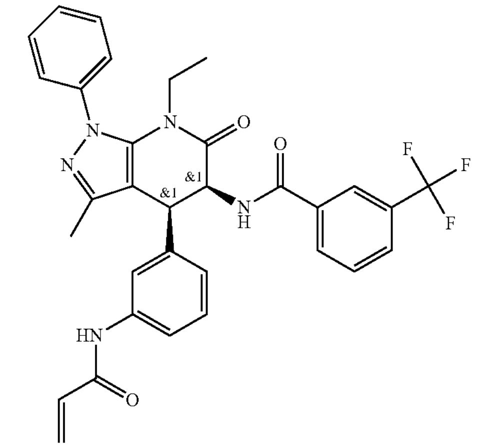 [SMILES: C=CC(=O)Nc1cccc([C@H]2c3c(C)nn(-c4ccccc4)c3N(CC)C(=O)[C@H]2NC(=O)c2cccc(C(F)(F)F)c2)c1]
I-25
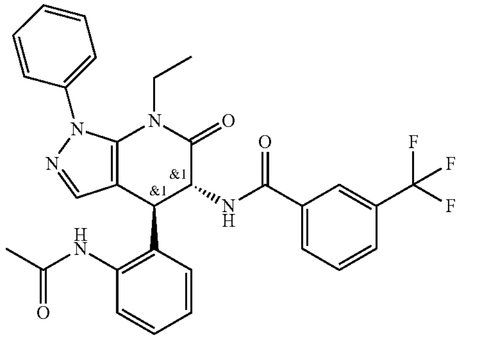 [SMILES: CCN1C(=O)[C@H](NC(=O)c2cccc(C(F)(F)F)c2)[C@@H](c2ccccc2NC(C)=O)c2cnn(-c3ccccc3)c21]
I-26
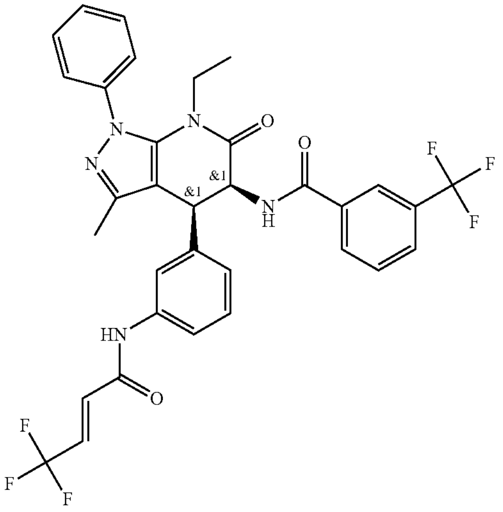 [SMILES: CCN1C(=O)[C@@H](NC(=O)c2cccc(C(F)(F)F)c2)[C@@H](c2cccc(NC(=O)/C=C/C(F)(F)F)c2)c2c(C)nn(-c3ccccc3)c21]
I-27

TABLE 1-continued
| Exemplary Compounds |
|---|
| 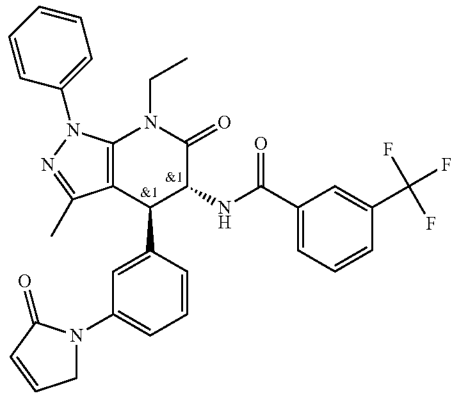 [SMILES: CCN1C(=O)[C@H](NC(=O)c2cccc(C(F)(F)F)c2)[C@@H](c2cccc(N3CC=CC3=O)c2)c2c(C)nn(-c3ccccc3)c21] I-28 |
| 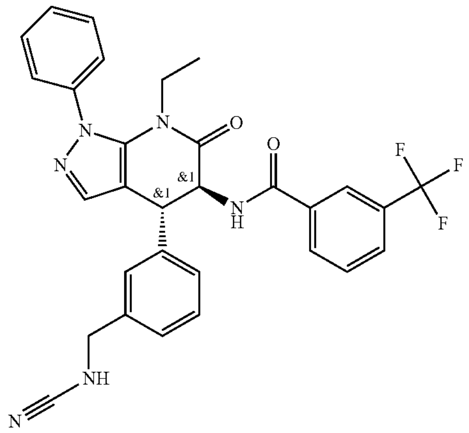 [SMILES: CCN1C(=O)[C@@H](NC(=O)c2cccc(C(F)(F)F)c2)[C@H](c2cccc(CNC#N)c2)c2cnn(-c3ccccc3)c21] I-29 |
| 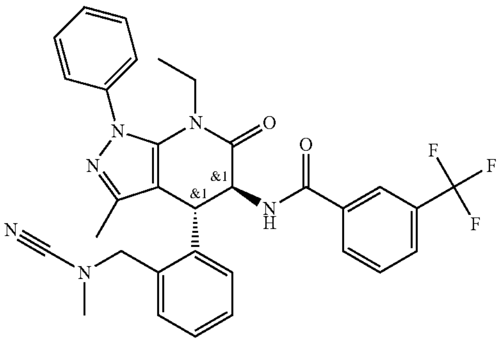 [SMILES: CCN1C(=O)[C@@H](NC(=O)c2cccc(C(F)(F)F)c2)[C@H](c2ccccc2CN(C)C#N)c2c(C)nn(-c3ccccc3)c21] I-30 |
| 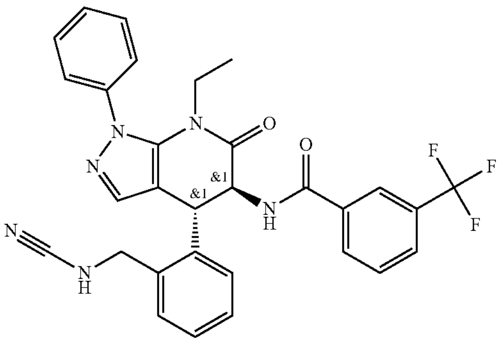 [SMILES: CCN1C(=O)[C@@H](NC(=O)c2cccc(C(F)(F)F)c2)[C@H](c2ccccc2CNC#N)c2cnn(-c3ccccc3)c21] I-31 |

TABLE 1-continued
Exemplary Compounds
I-32
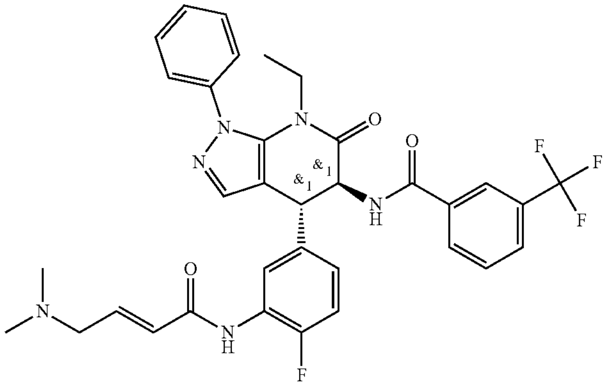 [SMILES: CCN1C(=O)[C@@H](NC(=O)c2cccc(C(F)(F)F)c2)[C@H](c2ccc(F)c(NC(=O)/C=C/CN(C)C)c2)c2cnn(-c3ccccc3)c21]
I-33
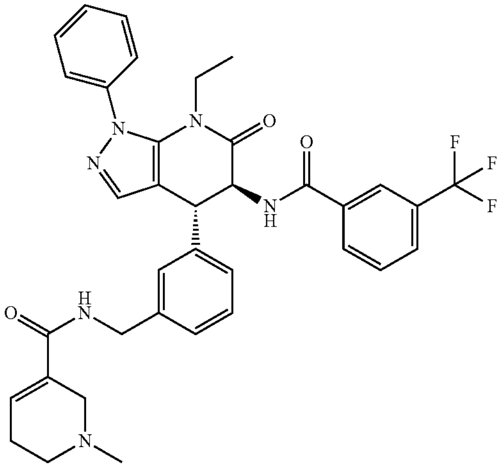 [SMILES: CCN1C(=O)[C@@H](NC(=O)c2cccc(C(F)(F)F)c2)[C@H](c2cccc(CNC(=O)C3=CCCN(C)C3)c2)c2cnn(-c3ccccc3)c21]
I-34
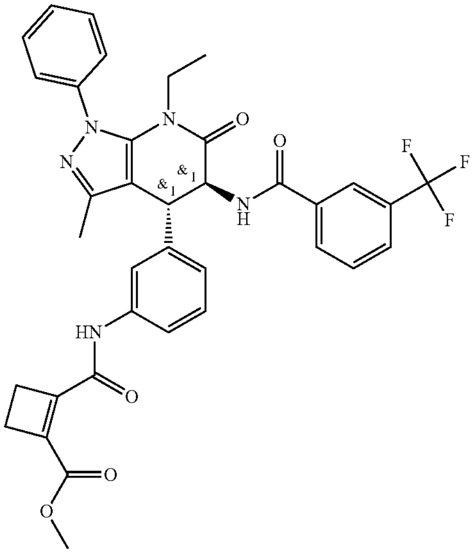 [SMILES: CCN1C(=O)[C@@H](NC(=O)c2cccc(C(F)(F)F)c2)[C@H](c2cccc(NC(=O)C3=C(C(=O)OC)CC3)c2)c2c(C)nn(-c3ccccc3)c21]

TABLE 1-continued
| Exemplary Compounds |
|---|
| 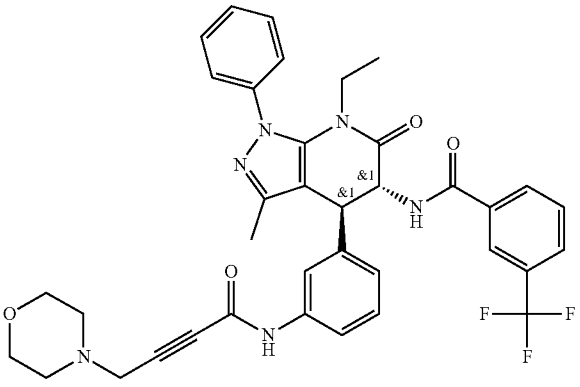 [SMILES: CCN1C(=O)[C@H](NC(=O)c2cccc(C(F)(F)F)c2)[C@@H](c2cccc(NC(=O)C#CCN3CCOCC3)c2)c2c(C)nn(-c3ccccc3)c21] I-35 |
| 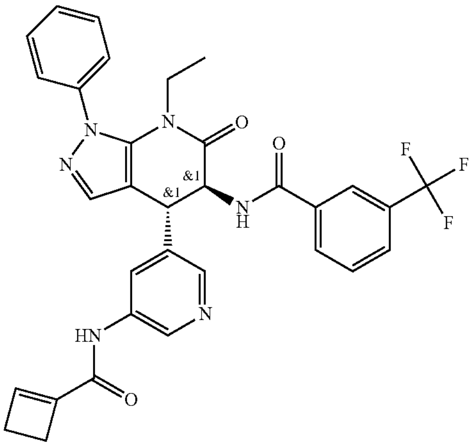 [SMILES: CCN1C(=O)[C@@H](NC(=O)c2cccc(C(F)(F)F)c2)[C@H](c2cncc(NC(=O)C3=CCC3)c2)c2cnn(-c3ccccc3)c21] I-36 |
| 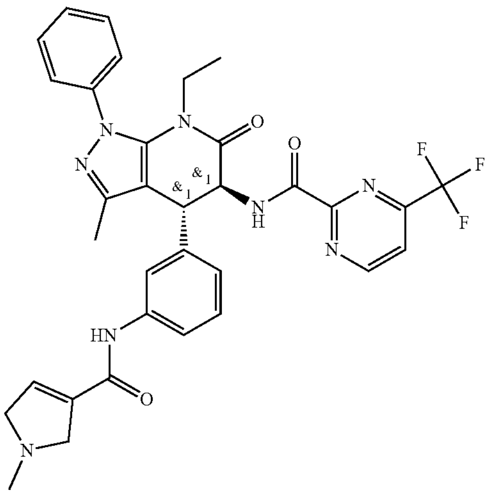 [SMILES: CCN1C(=O)[C@@H](NC(=O)c2nccc(C(F)(F)F)n2)[C@H](c2cccc(NC(=O)C3=CCN(C)C3)c2)c2c(C)nn(-c3ccccc3)c21] I-37 |

TABLE 1-continued
| Exemplary Compounds |
|---|
| 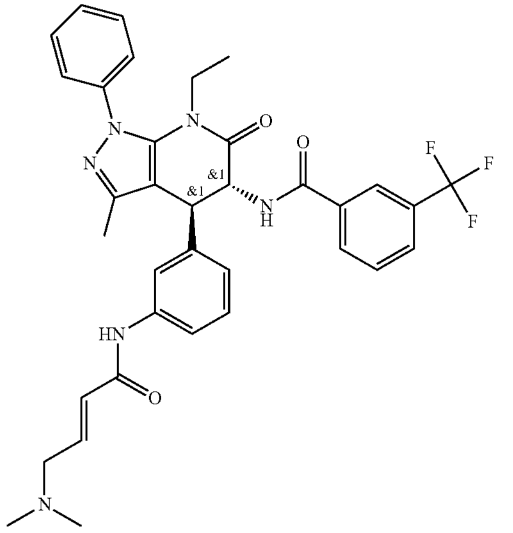 [SMILES: CCN1C(=O)[C@H](NC(=O)c2cccc(C(F)(F)F)c2)[C@@H](c2cccc(NC(=O)/C=C/CN(C)C)c2)c2c(C)nn(-c3ccccc3)c21] I-38 |
| 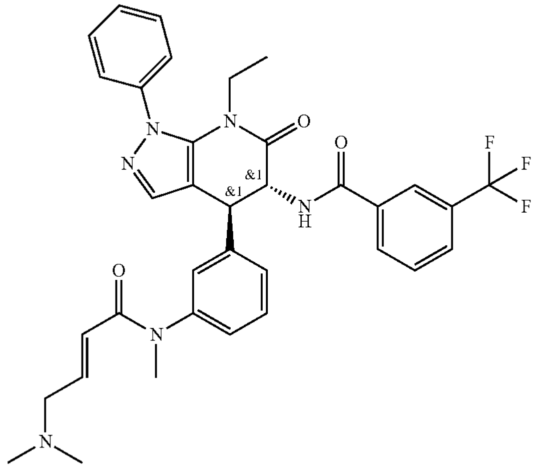 [SMILES: CCN1C(=O)[C@H](NC(=O)c2cccc(C(F)(F)F)c2)[C@@H](c2cccc(N(C)C(=O)/C=C/CN(C)C)c2)c2cnn(-c3ccccc3)c21] I-39 |
| 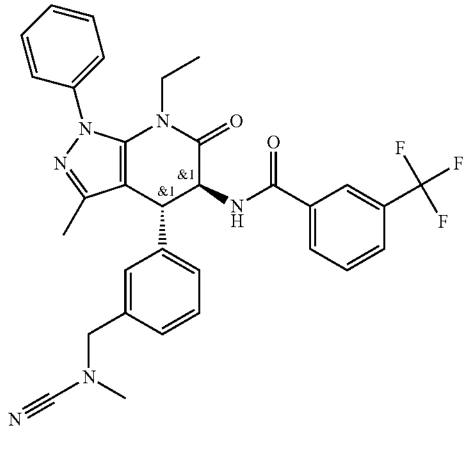 [SMILES: CCN1C(=O)[C@@H](NC(=O)c2cccc(C(F)(F)F)c2)[C@H](c2cccc(CN(C)C#N)c2)c2c(C)nn(-c3ccccc3)c21] I-40 |

TABLE 1-continued
| Exemplary Compounds |
| --- |
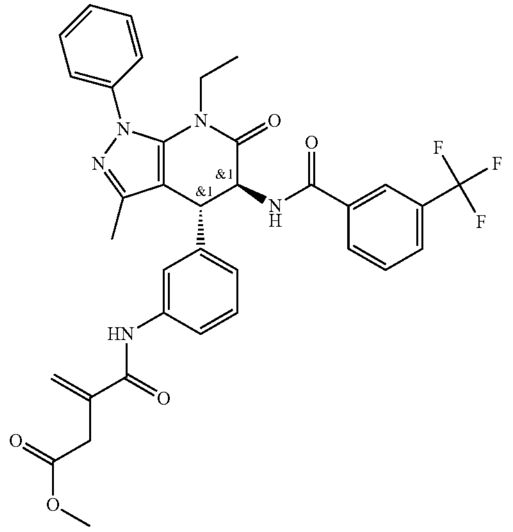 [SMILES: C=C(CC(=O)OC)C(=O)Nc1cccc([C@@H]2c3c(C)nn(-c4ccccc4)c3N(CC)C(=O)[C@H]2NC(=O)c2cccc(C(F)(F)F)c2)c1]
I-41
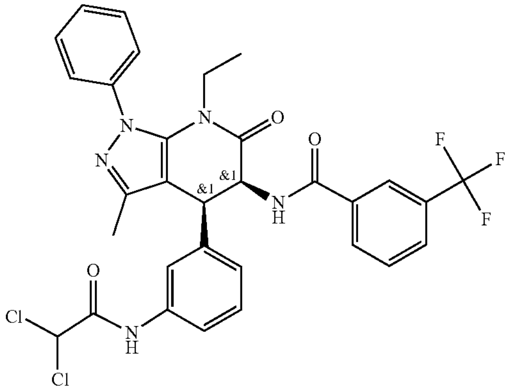 [SMILES: CCN1C(=O)[C@@H](NC(=O)c2cccc(C(F)(F)F)c2)[C@@H](c2cccc(NC(=O)C(Cl)Cl)c2)c2c(C)nn(-c3ccccc3)c21]
I-42
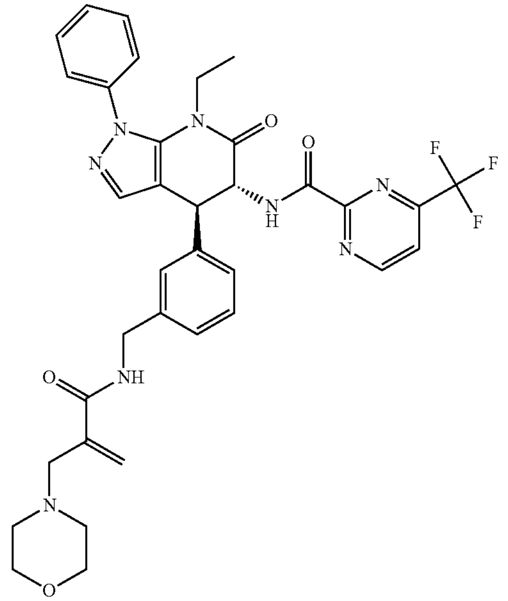 [SMILES: C=C(CN1CCOCC1)C(=O)NCc1cccc([C@H]2c3cnn(-c4ccccc4)c3N(CC)C(=O)[C@@H]2NC(=O)c2nccc(C(F)(F)F)n2)c1]
I-43

TABLE 1-continued
Exemplary Compounds
I-44
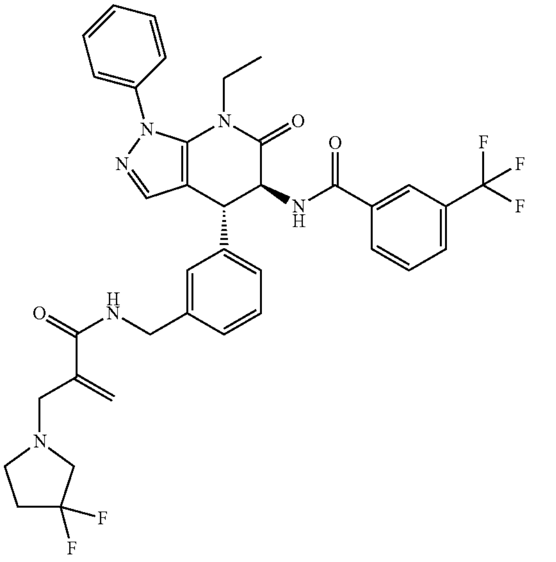 [SMILES: C=C(CN1CCC(F)(F)C1)C(=O)NCc1cccc([C@@H]2c3cnn(-c4ccccc4)c3N(CC)C(=O)[C@H]2NC(=O)c2cccc(C(F)(F)F)c2)c1]
I-45
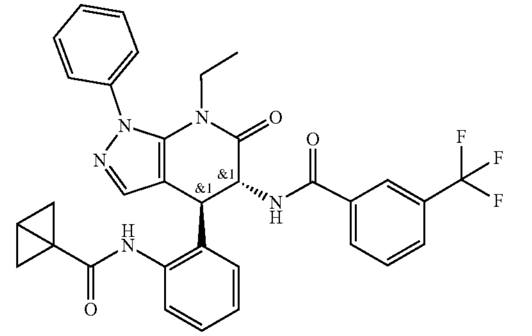 [SMILES: CCN1C(=O)[C@H](NC(=O)c2cccc(C(F)(F)F)c2)[C@@H](c2ccccc2NC(=O)C23CC2C3)c2cnn(-c3ccccc3)c21]
I-46
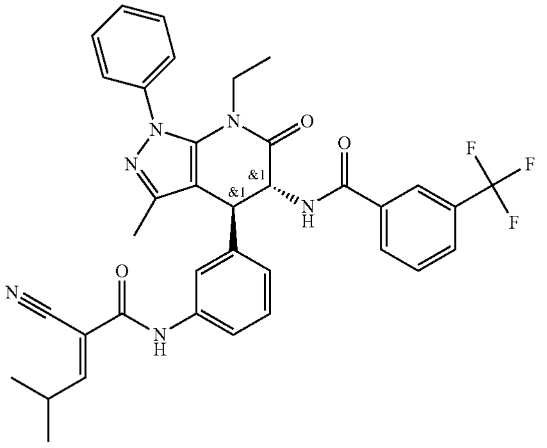 [SMILES: CCN1C(=O)[C@H](NC(=O)c2cccc(C(F)(F)F)c2)[C@@H](c2cccc(NC(=O)/C(C#N)=C/C(C)C)c2)c2c(C)nn(-c3ccccc3)c21]

TABLE 1-continued
| Exemplary Compounds |
| --- |
| 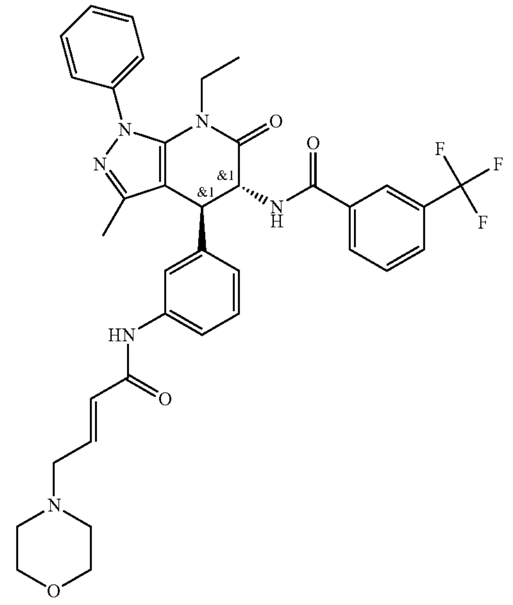 [SMILES: CCN1C(=O)[C@H](NC(=O)c2cccc(C(F)(F)F)c2)[C@@H](c2cccc(NC(=O)/C=C/CN3CCOCC3)c2)c2c(C)nn(-c3ccccc3)c21] I-47 |
| 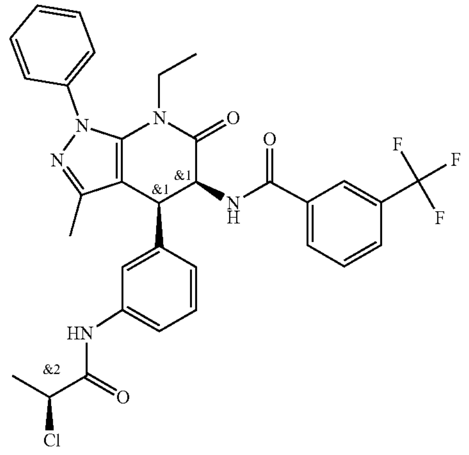 [SMILES: CCN1C(=O)[C@@H](NC(=O)c2cccc(C(F)(F)F)c2)[C@@H](c2cccc(NC(=O)[C@H](C)Cl)c2)c2c(C)nn(-c3ccccc3)c21] I-48 |
| 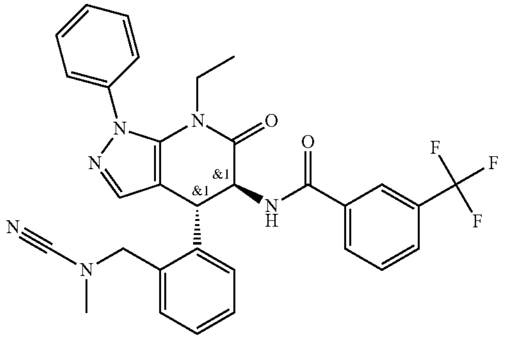 [SMILES: CCN1C(=O)[C@@H](NC(=O)c2cccc(C(F)(F)F)c2)[C@H](c2ccccc2CN(C)C#N)c2cnn(-c3ccccc3)c21] I-49 |

TABLE 1-continued
| Exemplary Compounds |
|---|
I-50
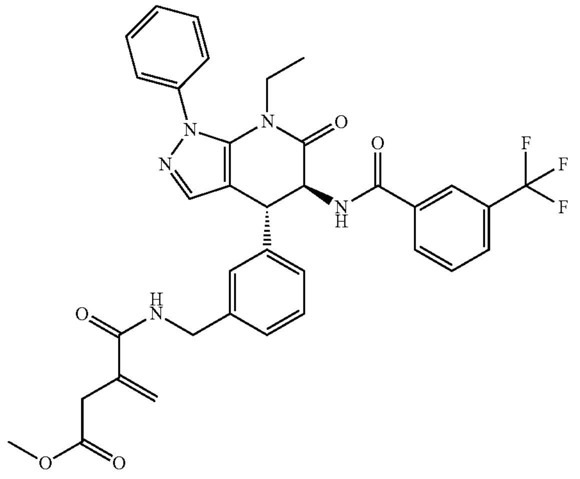 [SMILES: C=C(CC(=O)OC)C(=O)NCc1cccc([C@@H]2c3cnn(-c4ccccc4)c3N(CC)C(=O)[C@H]2NC(=O)c2cccc(C(F)(F)F)c2)c1]
I-51
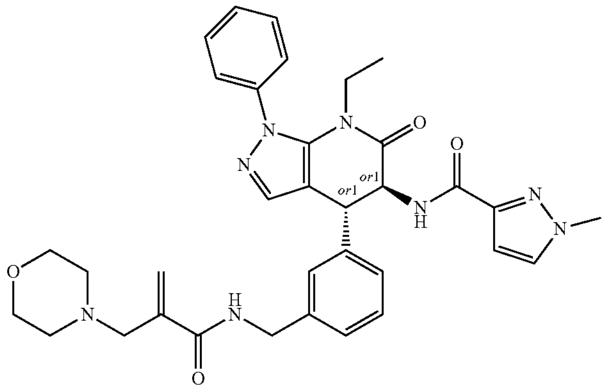 [SMILES: C=C(CN1CCOCC1)C(=O)NCc1cccc([C@@H]2c3cnn(-c4ccccc4)c3N(CC)C(=O)[C@H]2NC(=O)c2ccn(C)n2)c1]
I-52
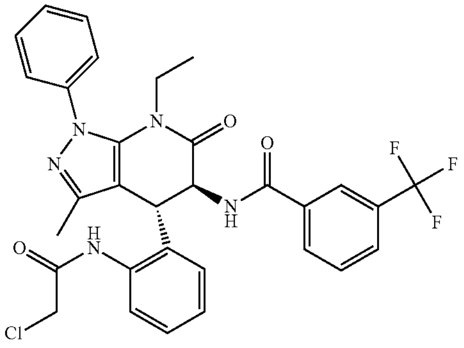 [SMILES: CCN1C(=O)[C@@H](NC(=O)c2cccc(C(F)(F)F)c2)[C@H](c2ccccc2NC(=O)CCl)c2c(C)nn(-c3ccccc3)c21]

TABLE 1-continued
| Exemplary Compounds |
| --- |
I-53
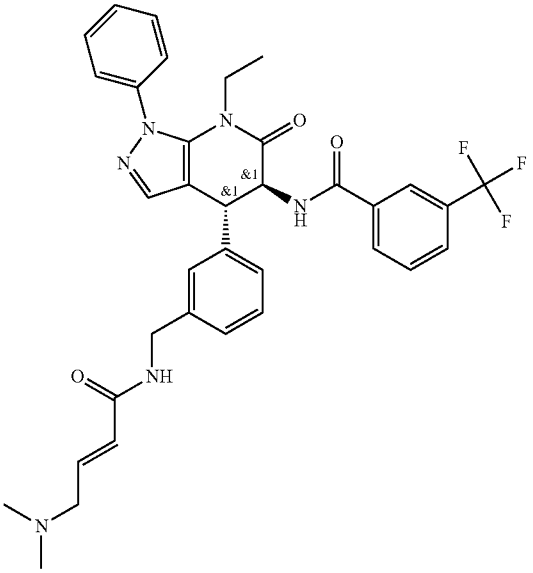 [SMILES: CCN1C(=O)[C@@H](NC(=O)c2cccc(C(F)(F)F)c2)[C@H](c2cccc(CNC(=O)/C=C/CN(C)C)c2)c2cnn(-c3ccccc3)c21]
I-54
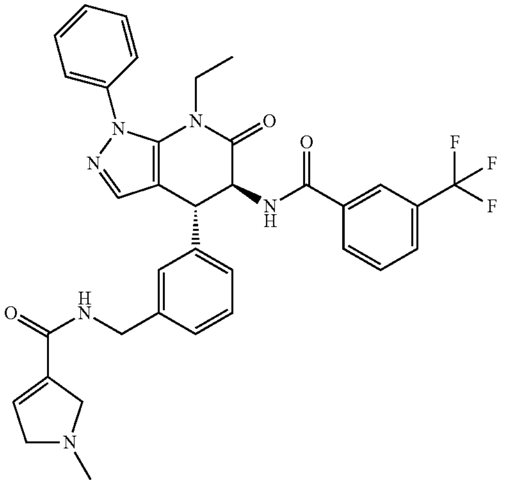 [SMILES: CCN1C(=O)[C@@H](NC(=O)c2cccc(C(F)(F)F)c2)[C@H](c2cccc(CNC(=O)C3=CCN(C)C3)c2)c2cnn(-c3ccccc3)c21]
I-55
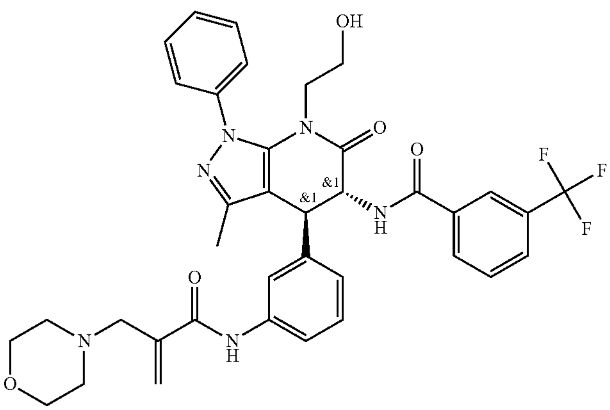 [SMILES: C=C(CN1CCOCC1)C(=O)Nc1cccc([C@H]2c3c(C)nn(-c4ccccc4)c3N(CCO)C(=O)[C@@H]2NC(=O)c2cccc(C(F)(F)F)c2)c1]

TABLE 1-continued
Exemplary Compounds
I-56
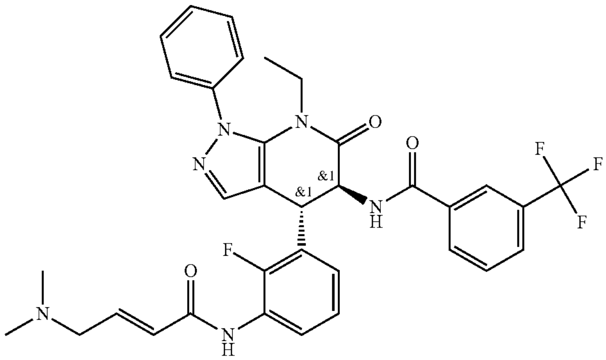 [SMILES: CCN1C(=O)[C@@H](NC(=O)c2cccc(C(F)(F)F)c2)[C@H](c2cccc(NC(=O)/C=C/CN(C)C)c2F)c2cnn(-c3ccccc3)c21]
I-57
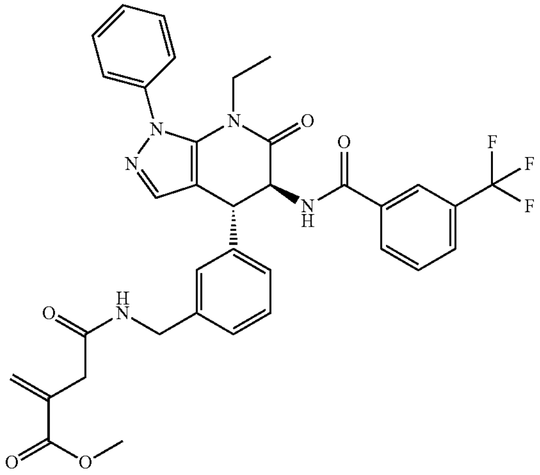 [SMILES: C=C(CC(=O)NCc1cccc([C@@H]2c3cnn(-c4ccccc4)c3N(CC)C(=O)[C@H]2NC(=O)c2cccc(C(F)(F)F)c2)c1)C(=O)OC]
I-58
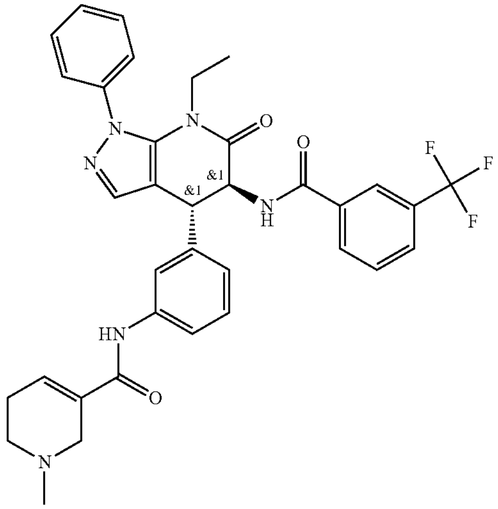 [SMILES: CCN1C(=O)[C@@H](NC(=O)c2cccc(C(F)(F)F)c2)[C@H](c2cccc(NC(=O)C3=CCCN(C)C3)c2)c2cnn(-c3ccccc3)c21]

TABLE 1-continued
| Exemplary Compounds |
|---|
I-59
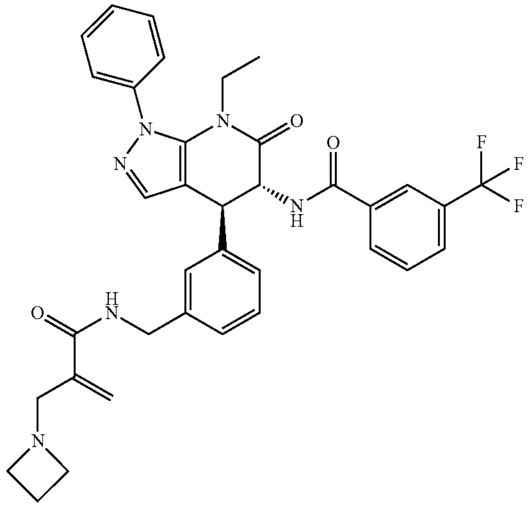 [SMILES: C=C(CN1CCC1)C(=O)NCc1cccc([C@H]2c3cnn(-c4ccccc4)c3N(CC)C(=O)[C@@H]2NC(=O)c2cccc(C(F)(F)F)c2)c1]
I-60
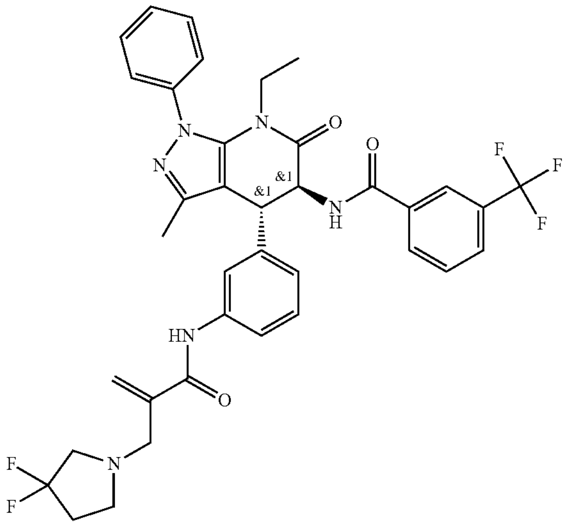 [SMILES: C=C(CN1CCC(F)(F)C1)C(=O)Nc1cccc([C@@H]2c3c(C)nn(-c4ccccc4)c3N(CC)C(=O)[C@H]2NC(=O)c2cccc(C(F)(F)F)c2)c1]
I-61
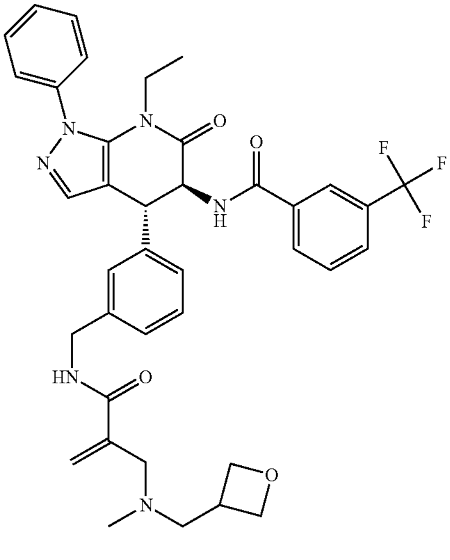 [SMILES: C=C(CN(C)CC1COC1)C(=O)NCc1cccc([C@@H]2c3cnn(-c4ccccc4)c3N(CC)C(=O)[C@H]2NC(=O)c2cccc(C(F)(F)F)c2)c1]

TABLE 1-continued
Exemplary Compounds
I-62
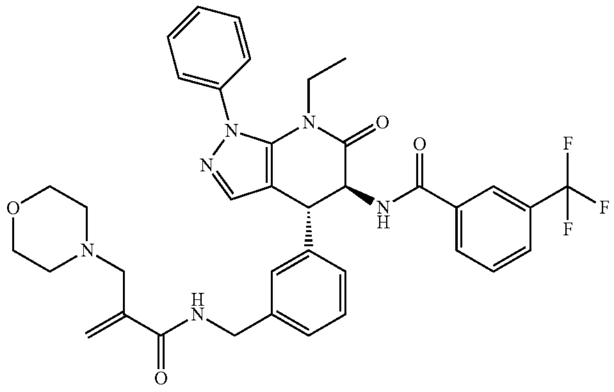 [SMILES: C=C(CN1CCOCC1)C(=O)NCc1cccc([C@@H]2c3cnn(-c4ccccc4)c3N(CC)C(=O)[C@H]2NC(=O)c2cccc(C(F)(F)F)c2)c1]
I-63
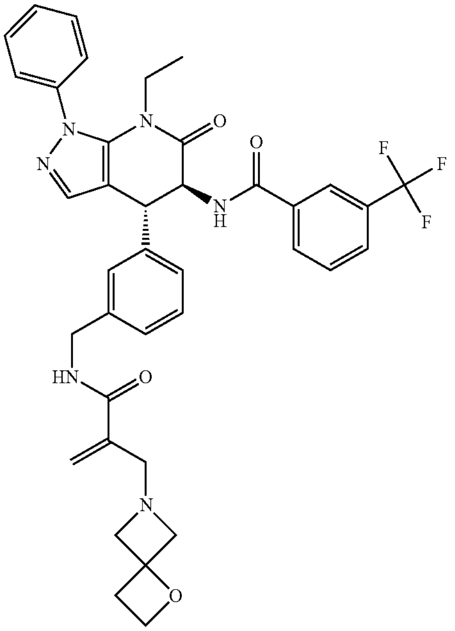 [SMILES: C=C(CN1CC2(CCO2)C1)C(=O)NCc1cccc([C@@H]2c3cnn(-c4ccccc4)c3N(CC)C(=O)[C@H]2NC(=O)c2cccc(C(F)(F)F)c2)c1]
I-64
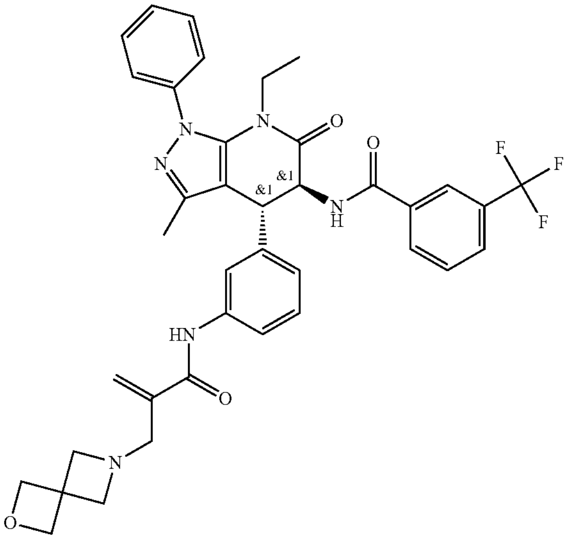 [SMILES: C=C(CN1CC2(COC2)C1)C(=O)Nc1cccc([C@@H]2c3c(C)nn(-c4ccccc4)c3N(CC)C(=O)[C@H]2NC(=O)c2cccc(C(F)(F)F)c2)c1]

TABLE 1-continued
| Exemplary Compounds |
| --- |
I-65
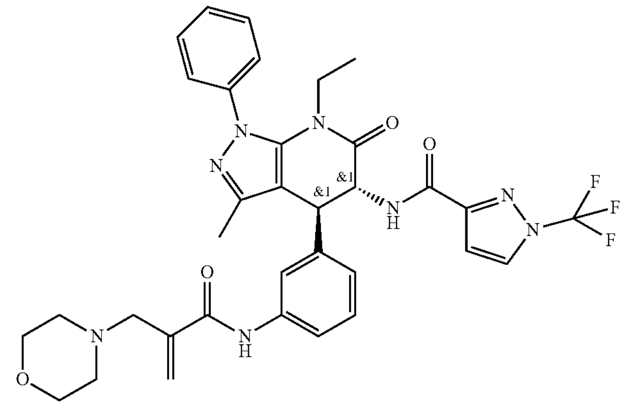 [SMILES: C=C(CN1CCOCC1)C(=O)Nc1cccc([C@H]2c3c(C)nn(-c4ccccc4)c3N(CC)C(=O)[C@@H]2NC(=O)c2ccn(C(F)(F)F)n2)c1]
I-66
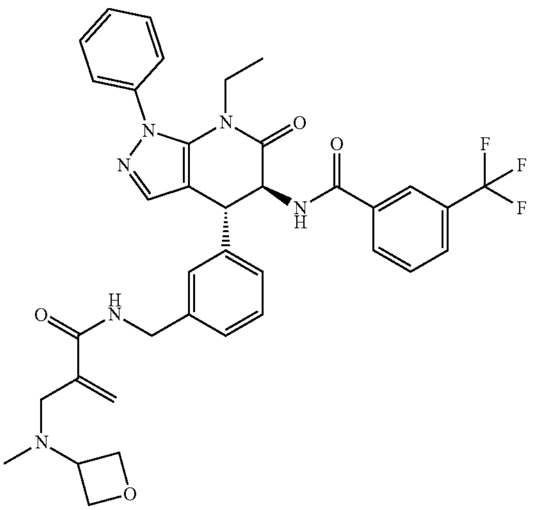 [SMILES: C=C(CN(C)C1COC1)C(=O)NCc1cccc([C@@H]2c3cnn(-c4ccccc4)c3N(CC)C(=O)[C@H]2NC(=O)c2cccc(C(F)(F)F)c2)c1]
I-67
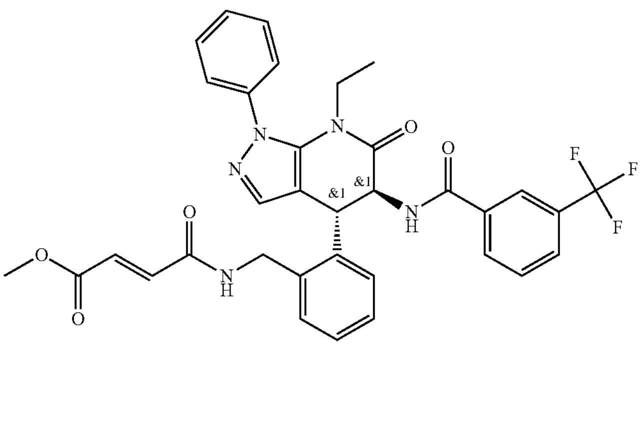 [SMILES: CCN1C(=O)[C@@H](NC(=O)c2cccc(C(F)(F)F)c2)[C@H](c2ccccc2CNC(=O)/C=C/C(=O)OC)c2cnn(-c3ccccc3)c21]

TABLE 1-continued
| Exemplary Compounds |
|---|
I-68
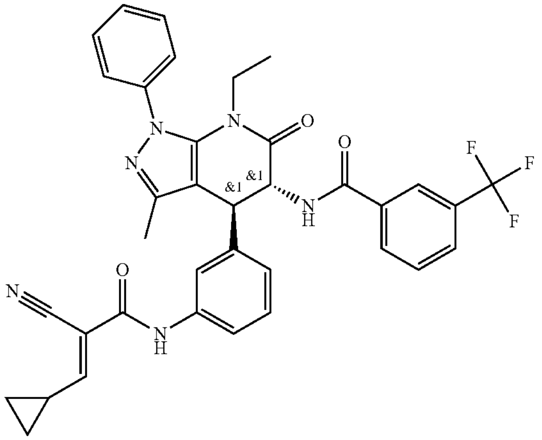 [SMILES: CCN1C(=O)[C@H](NC(=O)c2cccc(C(F)(F)F)c2)[C@@H](c2cccc(NC(=O)/C(C#N)=C/C3CC3)c2)c2c(C)nn(-c3ccccc3)c21]
I-69
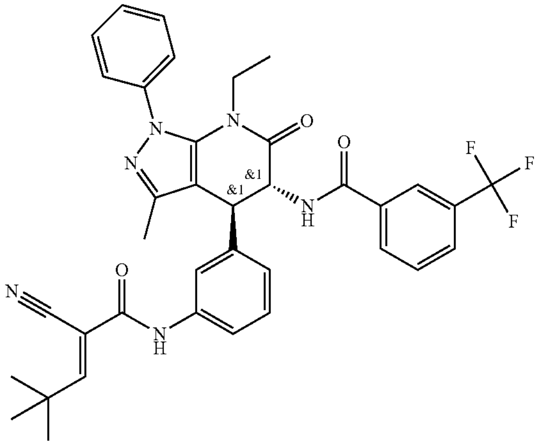 [SMILES: CCN1C(=O)[C@H](NC(=O)c2cccc(C(F)(F)F)c2)[C@@H](c2cccc(NC(=O)/C(C#N)=C/C(C)(C)C)c2)c2c(C)nn(-c3ccccc3)c21]
I-70
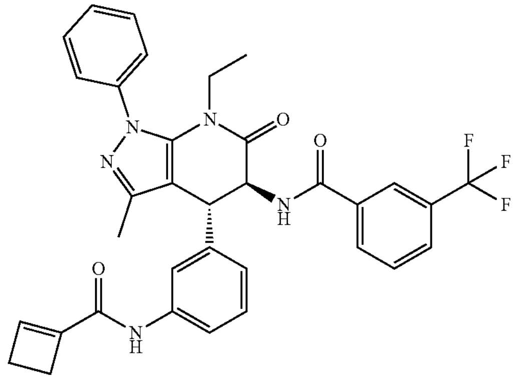 [SMILES: CCN1C(=O)[C@@H](NC(=O)c2cccc(C(F)(F)F)c2)[C@H](c2cccc(NC(=O)C3=CCC3)c2)c2c(C)nn(-c3ccccc3)c21]

TABLE 1-continued
| Exemplary Compounds |
| --- |
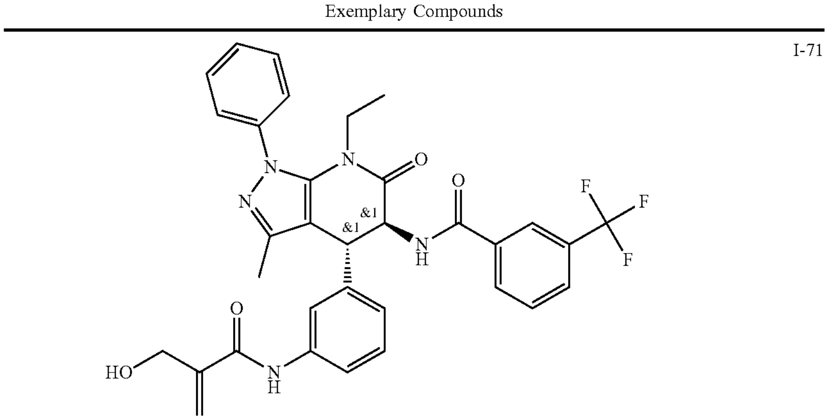
I-71
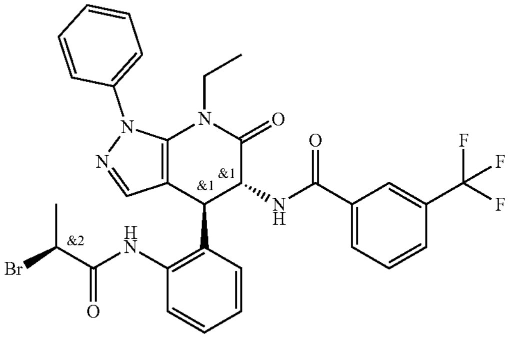 [SMILES: CCN1C(=O)[C@H](NC(=O)c2cccc(C(F)(F)F)c2)[C@@H](c2ccccc2NC(=O)[C@H](C)Br)c2cnn(-c3ccccc3)c21]
I-72
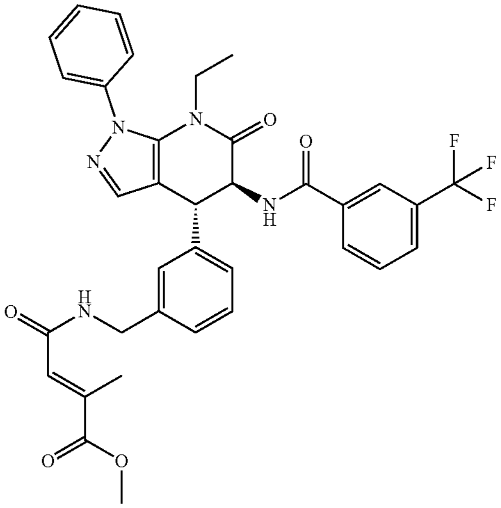 [SMILES: CCN1C(=O)[C@@H](NC(=O)c2cccc(C(F)(F)F)c2)[C@H](c2cccc(CNC(=O)/C=C(\C)C(=O)OC)c2)c2cnn(-c3ccccc3)c21]
I-73
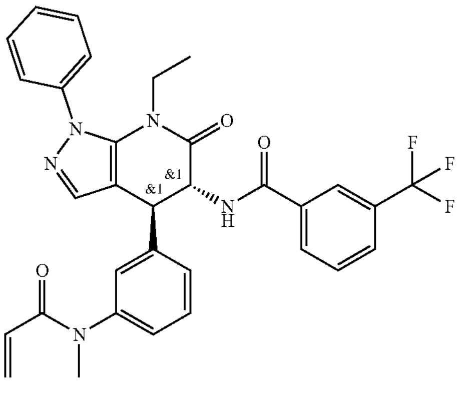 [SMILES: C=CC(=O)N(C)c1cccc([C@H]2c3cnn(-c4ccccc4)c3N(CC)C(=O)[C@@H]2NC(=O)c2cccc(C(F)(F)F)c2)c1]
I-74

TABLE 1-continued
| Exemplary Compounds |
| --- |
I-75
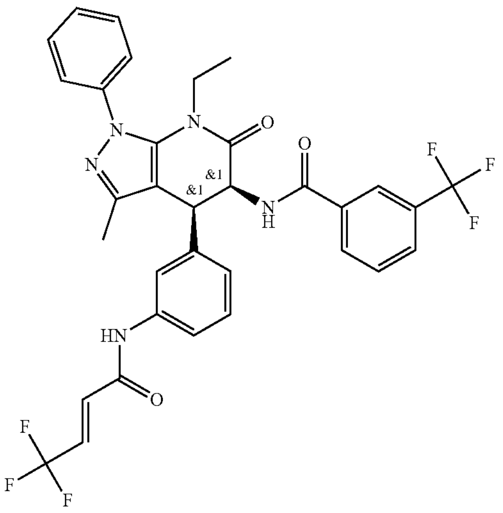 [SMILES: CCN1C(=O)[C@@H](NC(=O)c2cccc(C(F)(F)F)c2)[C@@H](c2cccc(NC(=O)/C=C/C(F)(F)F)c2)c2c(C)nn(-c3ccccc3)c21]
I-76
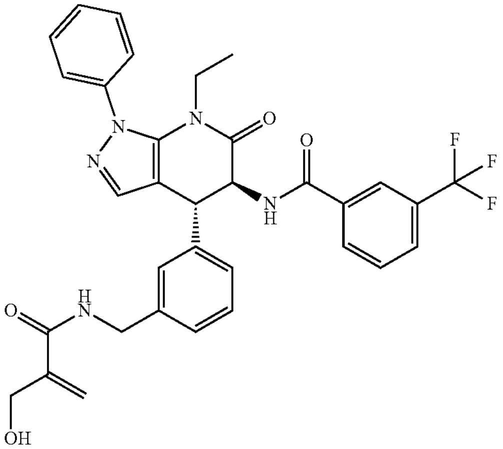 [SMILES: C=C(CO)C(=O)NCc1cccc([C@@H]2c3cnn(-c4ccccc4)c3N(CC)C(=O)[C@H]2NC(=O)c2cccc(C(F)(F)F)c2)c1]
I-77
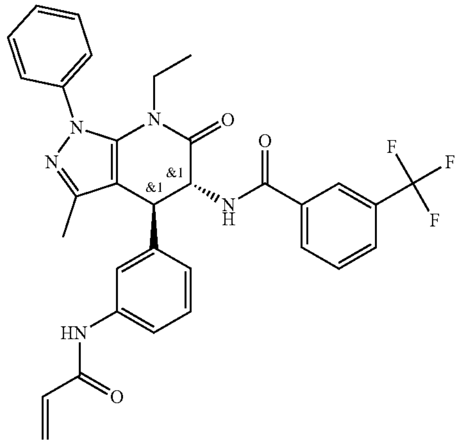 [SMILES: C=CC(=O)Nc1cccc([C@H]2c3c(C)nn(-c4ccccc4)c3N(CC)C(=O)[C@@H]2NC(=O)c2cccc(C(F)(F)F)c2)c1]

TABLE 1-continued
| Exemplary Compounds |
|---|
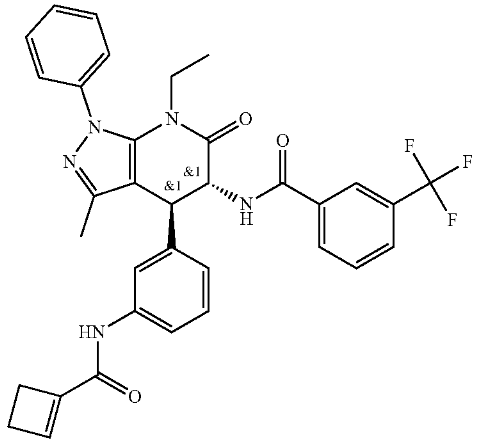 [SMILES: CCN1C(=O)[C@H](NC(=O)c2cccc(C(F)(F)F)c2)[C@@H](c2cccc(NC(=O)C3=CCC3)c2)c2c(C)nn(-c3ccccc3)c21]
I-78
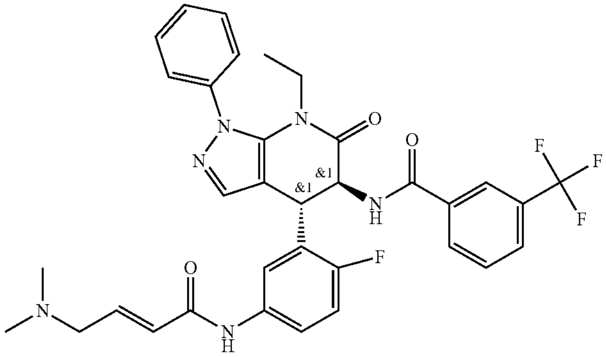 [SMILES: CCN1C(=O)[C@@H](NC(=O)c2cccc(C(F)(F)F)c2)[C@H](c2cc(NC(=O)/C=C/CN(C)C)ccc2F)c2cnn(-c3ccccc3)c21]
I-79
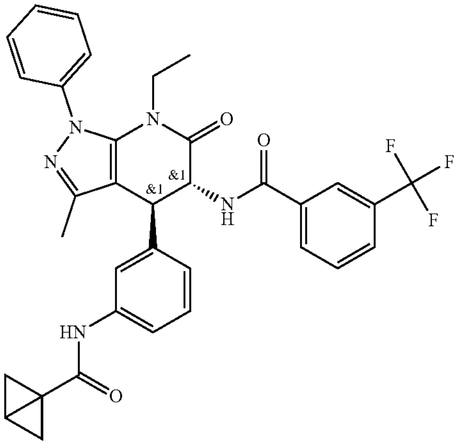 [SMILES: CCN1C(=O)[C@H](NC(=O)c2cccc(C(F)(F)F)c2)[C@@H](c2cccc(NC(=O)C34CC3C4)c2)c2c(C)nn(-c3ccccc3)c21]
I-80

TABLE 1-continued
| Exemplary Compounds |
|---|
I-81
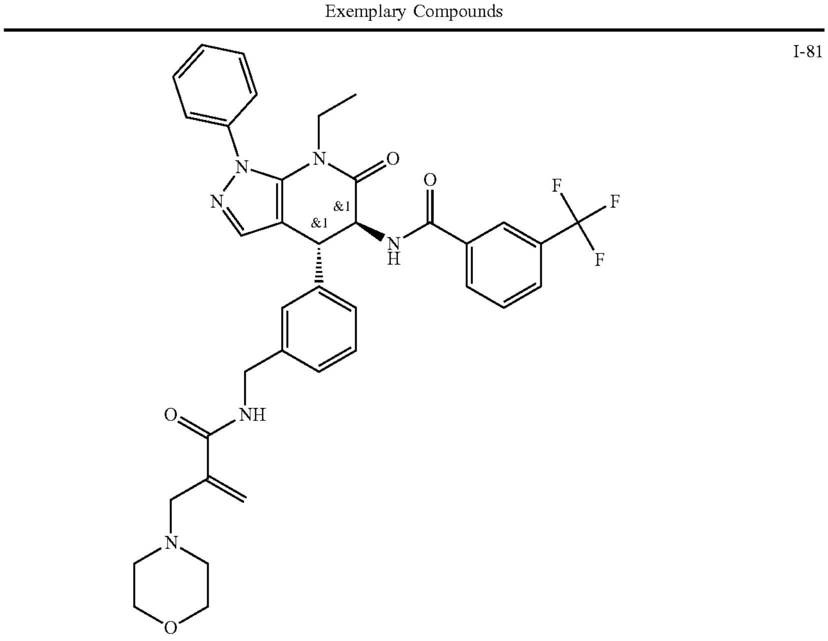
I-82
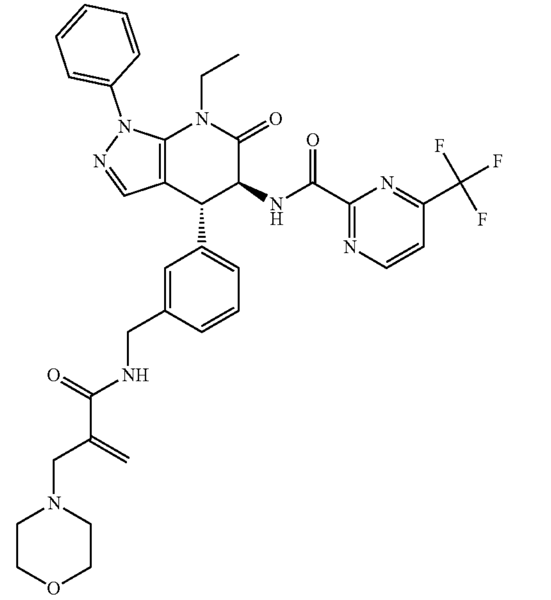 [SMILES: C=C(CN1CCOCC1)C(=O)NCc1cccc([C@@H]2c3cnn(-c4ccccc4)c3N(CC)C(=O)[C@H]2NC(=O)c2nccc(C(F)(F)F)n2)c1]
I-83
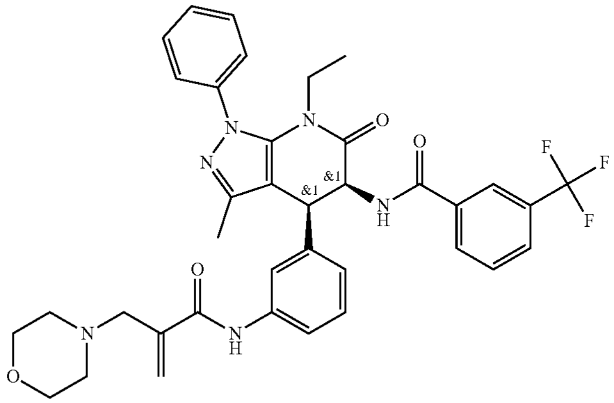 [SMILES: C=C(CN1CCOCC1)C(=O)Nc1cccc([C@H]2c3c(C)nn(-c4ccccc4)c3N(CC)C(=O)[C@H]2NC(=O)c2cccc(C(F)(F)F)c2)c1]

TABLE 1-continued
| Exemplary Compounds |
| --- |
| I-84 |
| 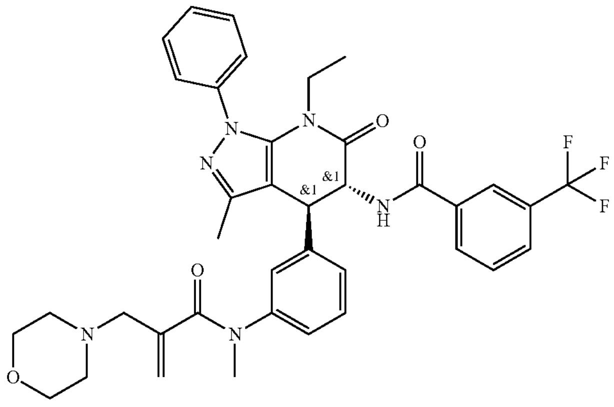 [SMILES: C=C(CN1CCOCC1)C(=O)N(C)c1cccc([C@H]2c3c(C)nn(-c4ccccc4)c3N(CC)C(=O)[C@@H]2NC(=O)c2cccc(C(F)(F)F)c2)c1] |
| I-85 |
| 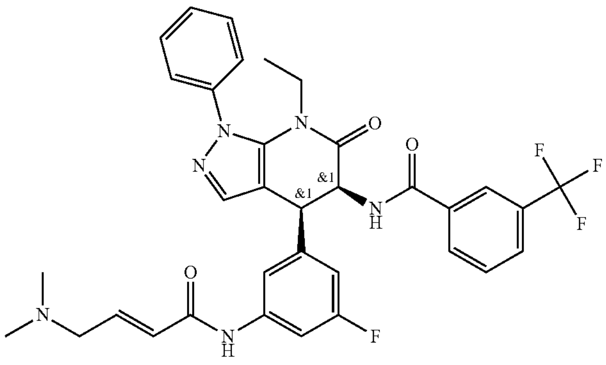 [SMILES: CCN1C(=O)[C@@H](NC(=O)c2cccc(C(F)(F)F)c2)[C@@H](c2cc(F)cc(NC(=O)/C=C/CN(C)C)c2)c2cnn(-c3ccccc3)c21] |
| I-86 |
| 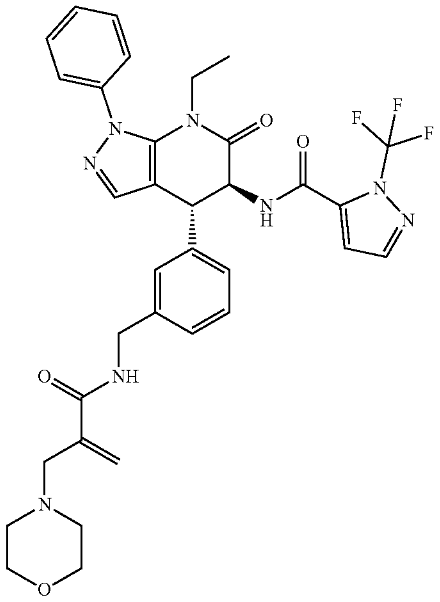 [SMILES: C=C(CN1CCOCC1)C(=O)NCc1cccc([C@@H]2c3cnn(-c4ccccc4)c3N(CC)C(=O)[C@H]2NC(=O)c2ccnn2C(F)(F)F)c1] |

TABLE 1-continued
Exemplary Compounds
I-87
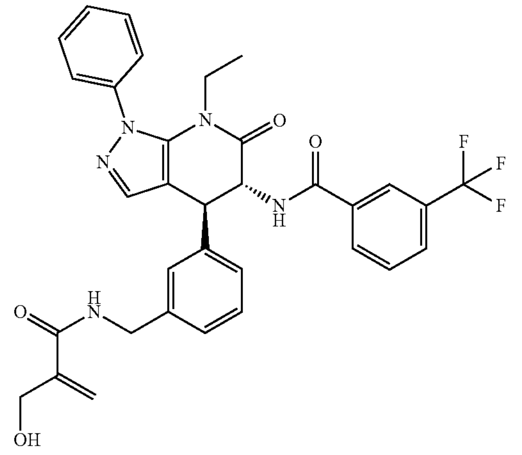 [SMILES: C=C(CO)C(=O)NCc1cccc([C@H]2c3cnn(-c4ccccc4)c3N(CC)C(=O)[C@@H]2NC(=O)c2cccc(C(F)(F)F)c2)c1]
I-88
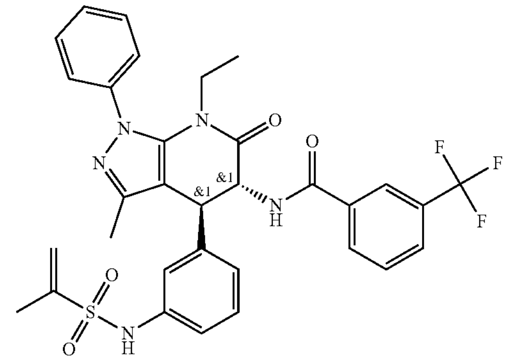 [SMILES: C=C(C)S(=O)(=O)Nc1cccc([C@H]2c3c(C)nn(-c4ccccc4)c3N(CC)C(=O)[C@@H]2NC(=O)c2cccc(C(F)(F)F)c2)c1]
I-89
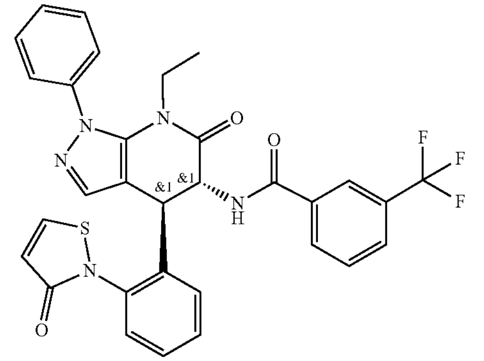 [SMILES: CCN1C(=O)[C@H](NC(=O)c2cccc(C(F)(F)F)c2)[C@@H](c2ccccc2-n2sccc2=O)c2cnn(-c3ccccc3)c21]
I-90
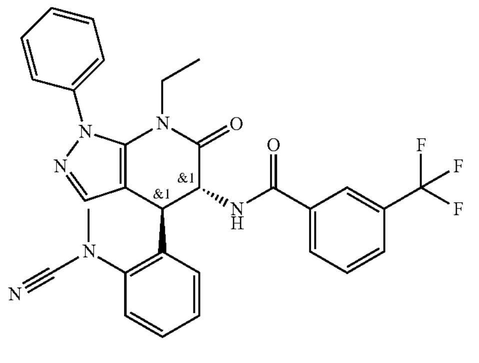 [SMILES: CCN1C(=O)[C@H](NC(=O)c2cccc(C(F)(F)F)c2)[C@@H](c2ccccc2N(C)C#N)c2cnn(-c3ccccc3)c21]

TABLE 1-continued
| Exemplary Compounds |
| --- |
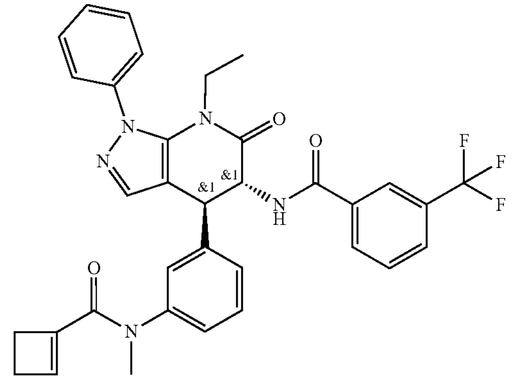 [SMILES: CCN1C(=O)[C@H](NC(=O)c2cccc(C(F)(F)F)c2)[C@@H](c2cccc(N(C)C(=O)C3=CCC3)c2)c2cnn(-c3ccccc3)c21]
I-91
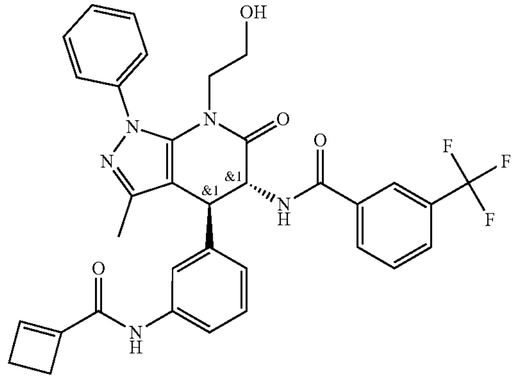 [SMILES: Cc1nn(-c2ccccc2)c2c1[C@H](c1cccc(NC(=O)C3=CCC3)c1)[C@@H](NC(=O)c1cccc(C(F)(F)F)c1)C(=O)N2CCO]
I-92
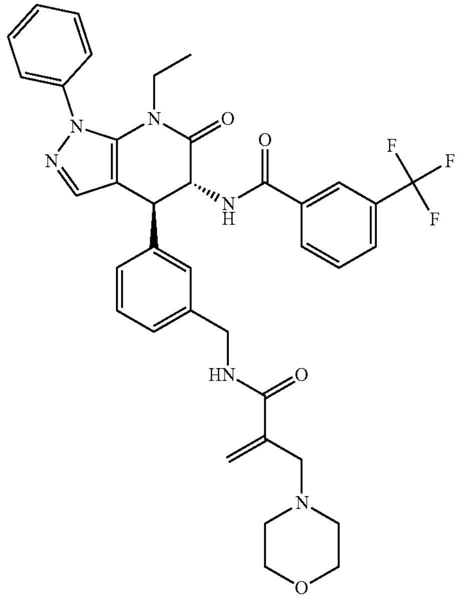 [SMILES: C=C(CN1CCOCC1)C(=O)NCc1cccc([C@H]2c3cnn(-c4ccccc4)c3N(CC)C(=O)[C@@H]2NC(=O)c2cccc(C(F)(F)F)c2)c1]
I-93

TABLE 1-continued
| Exemplary Compounds |
|---|
| 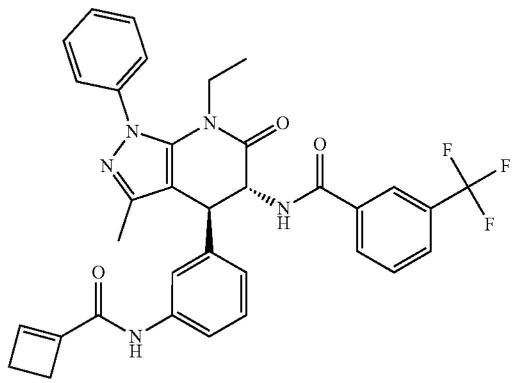 [SMILES: CCN1C(=O)[C@H](NC(=O)c2cccc(C(F)(F)F)c2)[C@@H](c2cccc(NC(=O)C3=CCC3)c2)c2c(C)nn(-c3ccccc3)c21] I-94 |
| 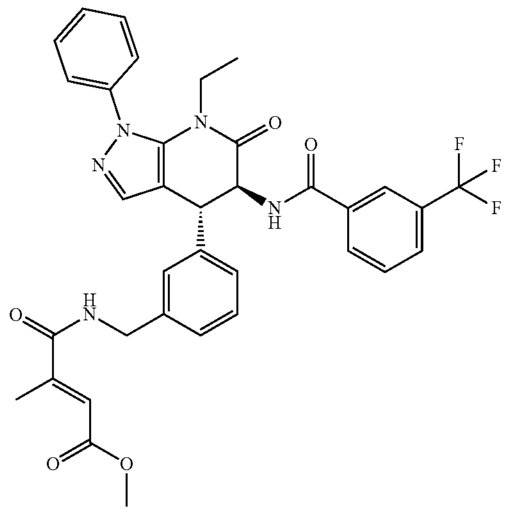 [SMILES: CCN1C(=O)[C@@H](NC(=O)c2cccc(C(F)(F)F)c2)[C@H](c2cccc(CNC(=O)/C(C)=C/C(=O)OC)c2)c2cnn(-c3ccccc3)c21] I-95 |
| 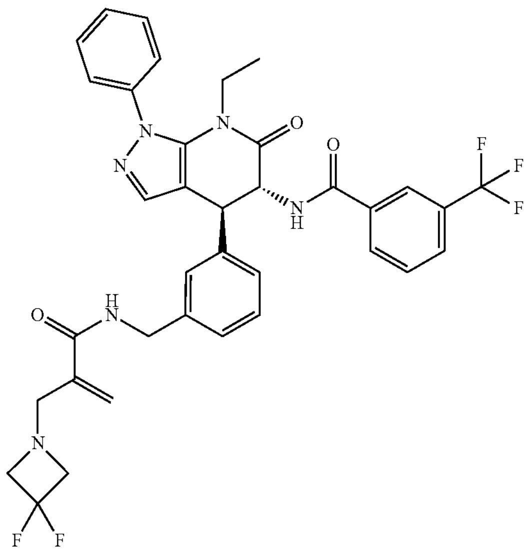 [SMILES: C=C(CN1CC(F)(F)C1)C(=O)NCc1cccc([C@H]2c3cnn(-c4ccccc4)c3N(CC)C(=O)[C@@H]2NC(=O)c2cccc(C(F)(F)F)c2)c1] I-96 |

TABLE 1-continued
| Exemplary Compounds |
|---|
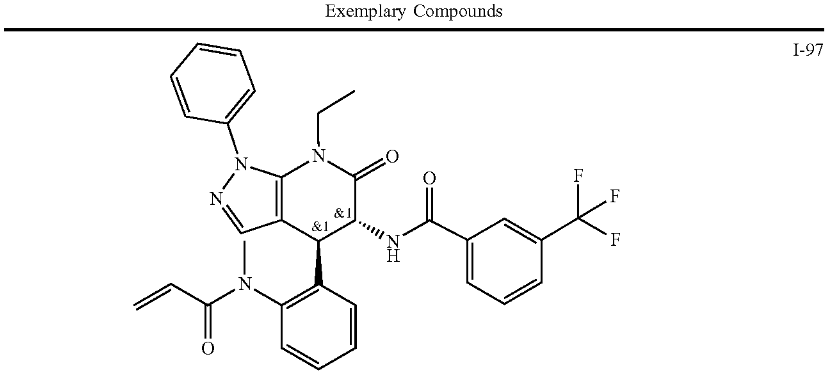
I-97
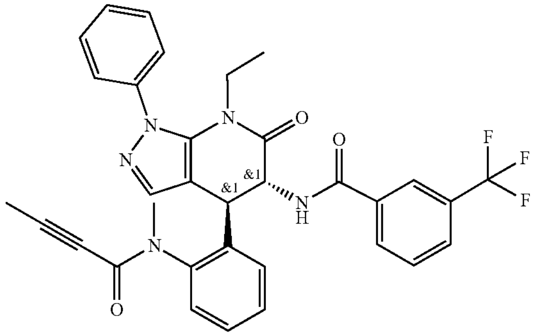 [SMILES: CC#CC(=O)N(C)c1ccccc1[C@H]1c2cnn(-c3ccccc3)c2N(CC)C(=O)[C@@H]1NC(=O)c1cccc(C(F)(F)F)c1]
I-98
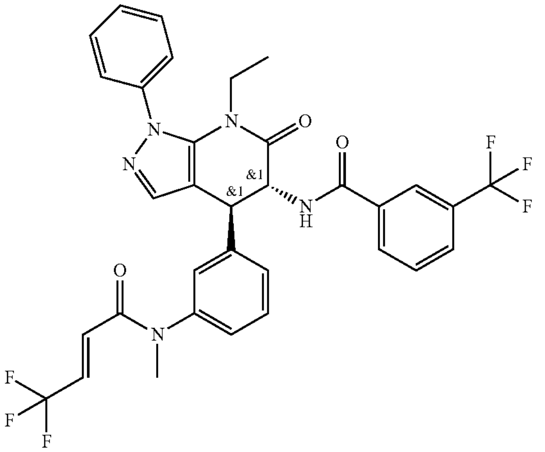 [SMILES: CCN1C(=O)[C@H](NC(=O)c2cccc(C(F)(F)F)c2)[C@@H](c2cccc(N(C)C(=O)/C=C/C(F)(F)F)c2)c2cnn(-c3ccccc3)c21]
I-99
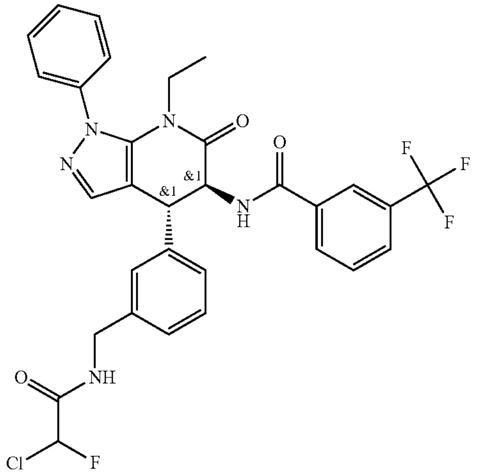 [SMILES: CCN1C(=O)[C@@H](NC(=O)c2cccc(C(F)(F)F)c2)[C@H](c2cccc(CNC(=O)C(F)Cl)c2)c2cnn(-c3ccccc3)c21]
I-100

TABLE 1-continued
| Exemplary Compounds |
|---|
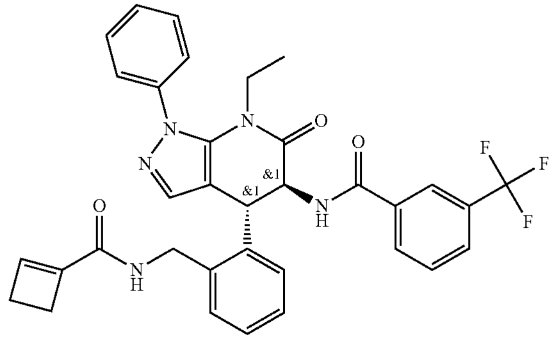 [SMILES: CCN1C(=O)[C@@H](NC(=O)c2cccc(C(F)(F)F)c2)[C@H](c2ccccc2CNC(=O)C2=CCC2)c2cnn(-c3ccccc3)c21]
I-101
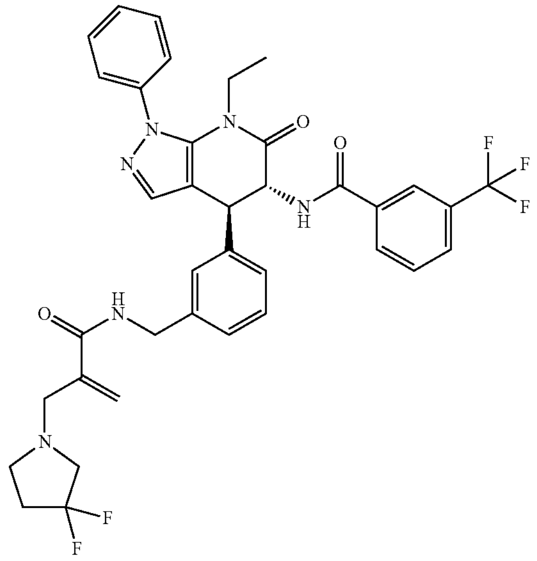 [SMILES: C=C(CN1CCC(F)(F)C1)C(=O)NCc1cccc([C@H]2c3cnn(-c4ccccc4)c3N(CC)C(=O)[C@@H]2NC(=O)c2cccc(C(F)(F)F)c2)c1]
I-102
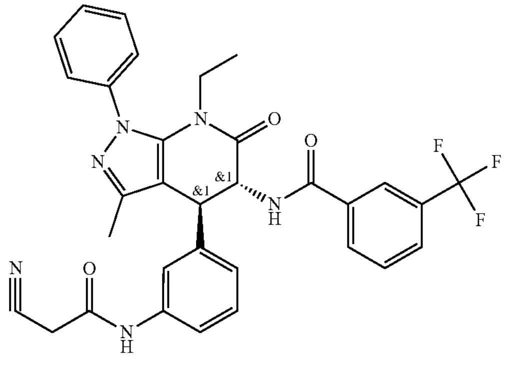 [SMILES: CCN1C(=O)[C@H](NC(=O)c2cccc(C(F)(F)F)c2)[C@@H](c2cccc(NC(=O)CC#N)c2)c2c(C)nn(-c3ccccc3)c21]
I-103

TABLE 1-continued
| Exemplary Compounds |
| --- |
| I-104 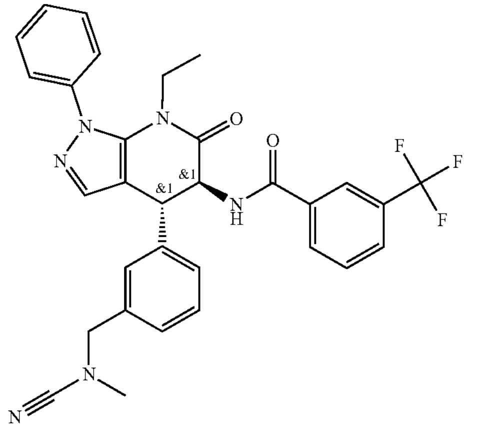 [SMILES: CCN1C(=O)[C@@H](NC(=O)c2cccc(C(F)(F)F)c2)[C@H](c2cccc(CN(C)C#N)c2)c2cnn(-c3ccccc3)c21] |
| I-105 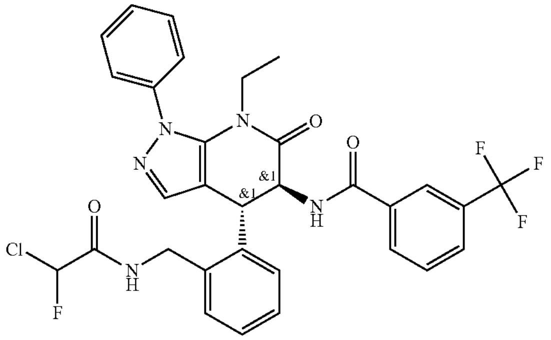 [SMILES: CCN1C(=O)[C@@H](NC(=O)c2cccc(C(F)(F)F)c2)[C@H](c2ccccc2CNC(=O)C(F)Cl)c2cnn(-c3ccccc3)c21] |
| I-106 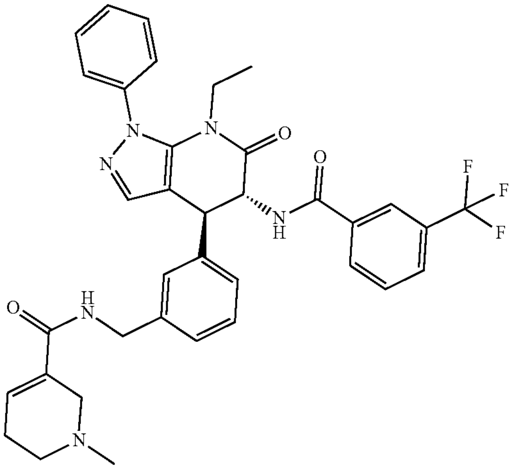 [SMILES: CCN1C(=O)[C@H](NC(=O)c2cccc(C(F)(F)F)c2)[C@@H](c2cccc(CNC(=O)C3=CCCN(C)C3)c2)c2cnn(-c3ccccc3)c21] |
| I-107 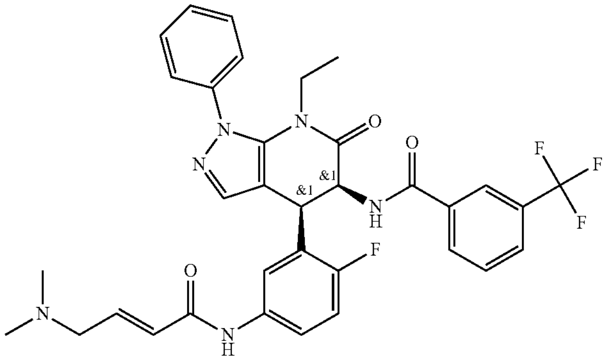 [SMILES: CCN1C(=O)[C@@H](NC(=O)c2cccc(C(F)(F)F)c2)[C@@H](c2cc(NC(=O)/C=C/CN(C)C)ccc2F)c2cnn(-c3ccccc3)c21] |

TABLE 1-continued
| Exemplary Compounds |
|---|
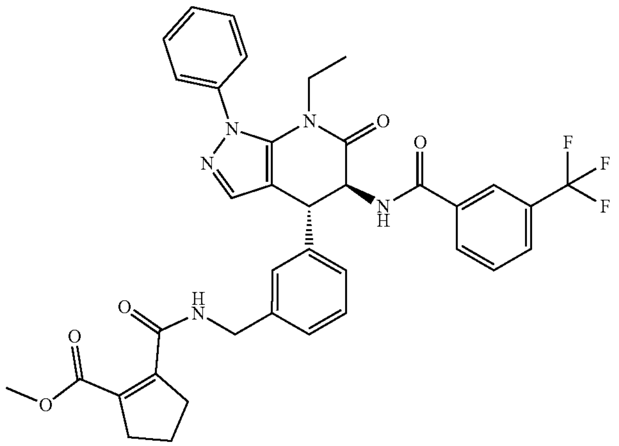 [SMILES: CCN1C(=O)[C@@H](NC(=O)c2cccc(C(F)(F)F)c2)[C@H](c2cccc(CNC(=O)C3=C(C(=O)OC)CCC3)c2)c2cnn(-c3ccccc3)c21]
I-108
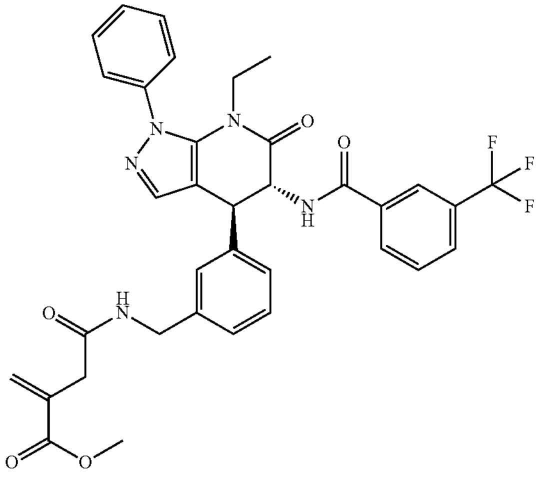 [SMILES: C=C(CC(=O)NCc1cccc([C@H]2c3cnn(-c4ccccc4)c3N(CC)C(=O)[C@@H]2NC(=O)c2cccc(C(F)(F)F)c2)c1)C(=O)OC]
I-109
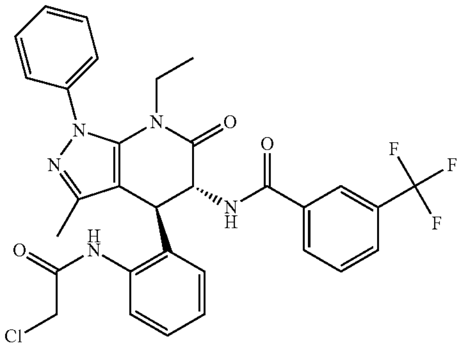 [SMILES: CCN1C(=O)[C@H](NC(=O)c2cccc(C(F)(F)F)c2)[C@@H](c2ccccc2NC(=O)CCl)c2c(C)nn(-c3ccccc3)c21]
I-110

TABLE 1-continued
| Exemplary Compounds |
|---|
I-111
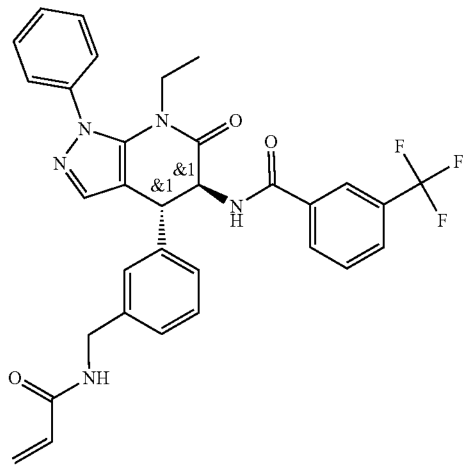 [SMILES: C=CC(=O)NCc1cccc([C@@H]2c3cnn(-c4ccccc4)c3N(CC)C(=O)[C@H]2NC(=O)c2cccc(C(F)(F)F)c2)c1]
I-112
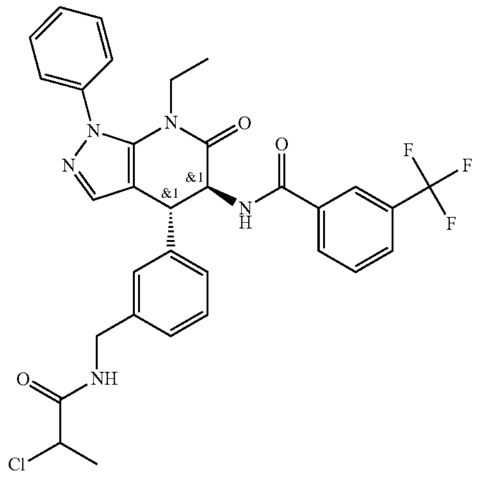 [SMILES: CCN1C(=O)[C@@H](NC(=O)c2cccc(C(F)(F)F)c2)[C@H](c2cccc(CNC(=O)C(C)Cl)c2)c2cnn(-c3ccccc3)c21]
I-113
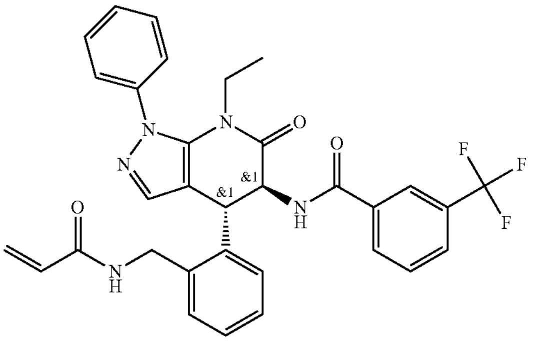 [SMILES: C=CC(=O)NCc1ccccc1[C@@H]1c2cnn(-c3ccccc3)c2N(CC)C(=O)[C@H]1NC(=O)c1cccc(C(F)(F)F)c1]

TABLE 1-continued
| Exemplary Compounds |
| --- |
| I-114 |
| 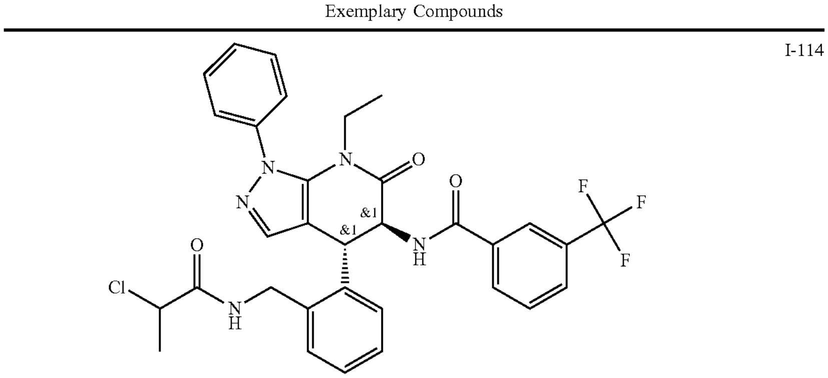 |
| I-115 |
| 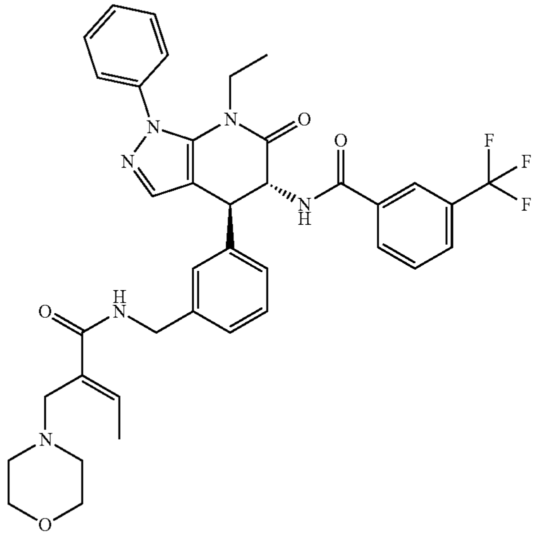 [SMILES: C/C=C(\CN1CCOCC1)C(=O)NCc1cccc([C@H]2c3cnn(-c4ccccc4)c3N(CC)C(=O)[C@@H]2NC(=O)c2cccc(C(F)(F)F)c2)c1] |
| I-116 |
| 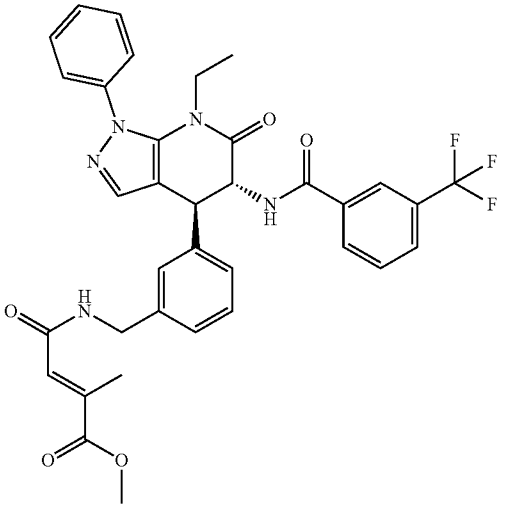 [SMILES: CCN1C(=O)[C@H](NC(=O)c2cccc(C(F)(F)F)c2)[C@@H](c2cccc(CNC(=O)/C=C(\C)C(=O)OC)c2)c2cnn(-c3ccccc3)c21] |

TABLE 1-continued
| Exemplary Compounds |
|---|
I-117
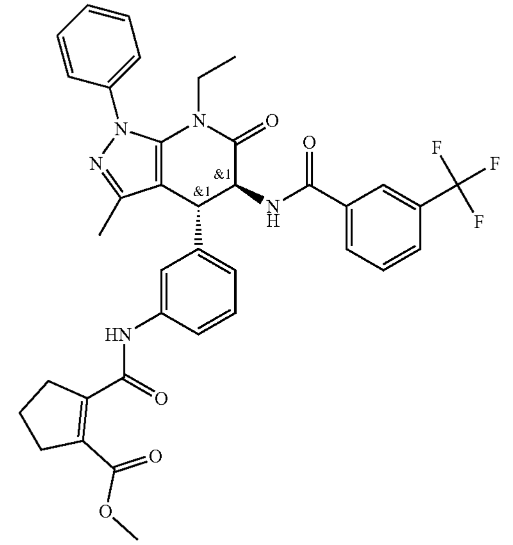 [SMILES: CCN1C(=O)[C@@H](NC(=O)c2cccc(C(F)(F)F)c2)[C@H](c2cccc(NC(=O)C3=C(C(=O)OC)CCC3)c2)c2c(C)nn(-c3ccccc3)c21]
I-118
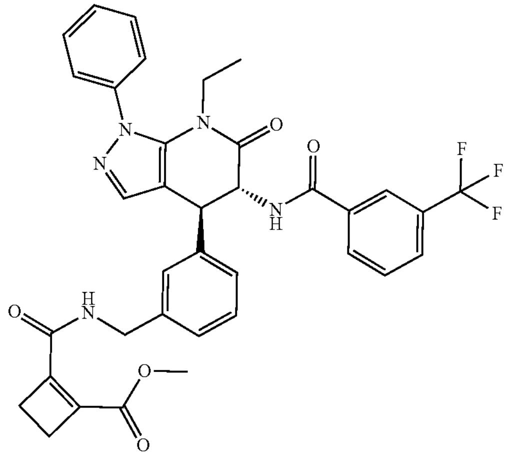 [SMILES: CCN1C(=O)[C@H](NC(=O)c2cccc(C(F)(F)F)c2)[C@@H](c2cccc(CNC(=O)C3=C(C(=O)OC)CC3)c2)c2cnn(-c3ccccc3)c21]
I-119
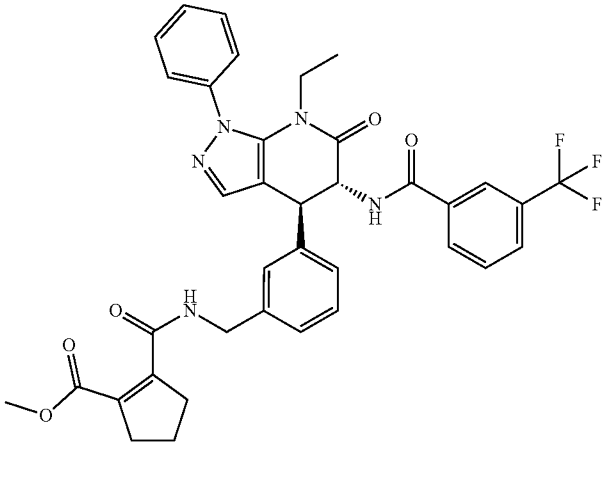 [SMILES: CCN1C(=O)[C@H](NC(=O)c2cccc(C(F)(F)F)c2)[C@@H](c2cccc(CNC(=O)C3=C(C(=O)OC)CCC3)c2)c2cnn(-c3ccccc3)c21]

TABLE 1-continued
| Exemplary Compounds |
|---|
| 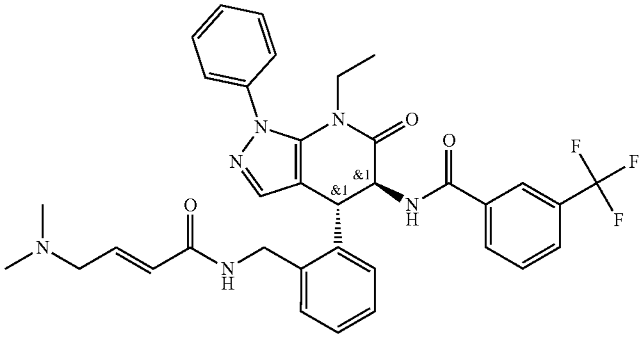 [SMILES: CCN1C(=O)[C@@H](NC(=O)c2cccc(C(F)(F)F)c2)[C@H](c2ccccc2CNC(=O)/C=C/CN(C)C)c2cnn(-c3ccccc3)c21] I-120 |
| 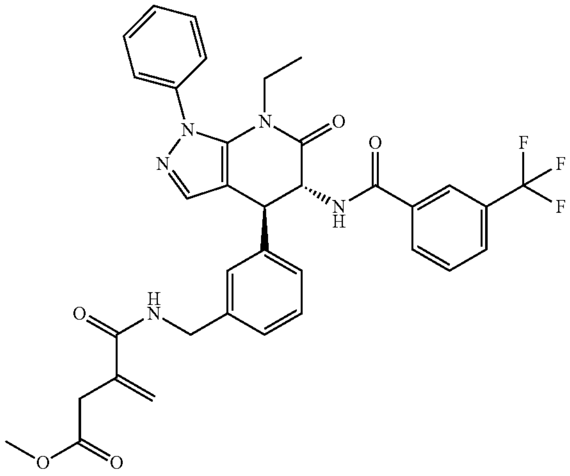 [SMILES: C=C(CC(=O)OC)C(=O)NCc1cccc([C@H]2c3cnn(-c4ccccc4)c3N(CC)C(=O)[C@@H]2NC(=O)c2cccc(C(F)(F)F)c2)c1] I-121 |
| 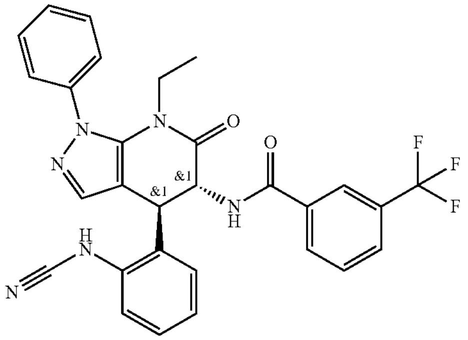 [SMILES: CCN1C(=O)[C@H](NC(=O)c2cccc(C(F)(F)F)c2)[C@@H](c2ccccc2NC#N)c2cnn(-c3ccccc3)c21] I-122 |
| 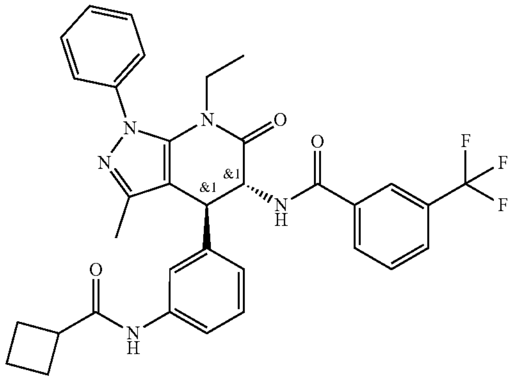 [SMILES: CCN1C(=O)[C@H](NC(=O)c2cccc(C(F)(F)F)c2)[C@@H](c2cccc(NC(=O)C3CCC3)c2)c2c(C)nn(-c3ccccc3)c21] I-123 |

TABLE 1-continued
| Exemplary Compounds |
| --- |
| I-124 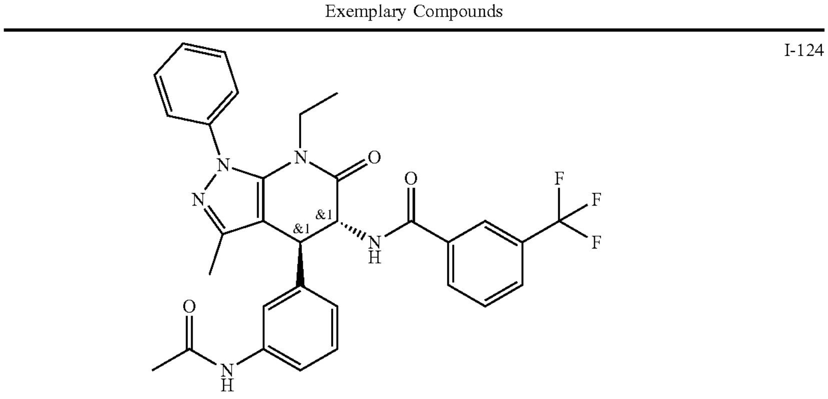 |
| I-125 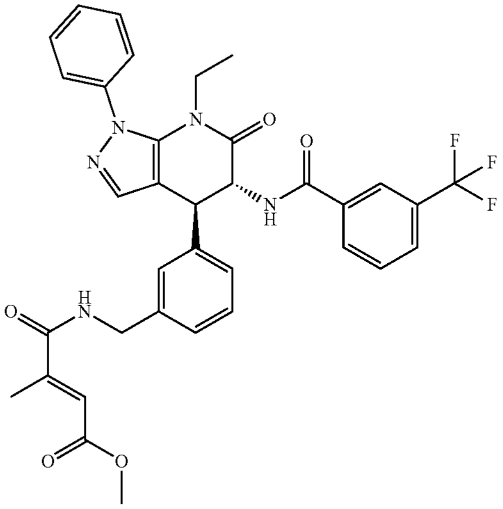 [SMILES: CCN1C(=O)[C@H](NC(=O)c2cccc(C(F)(F)F)c2)[C@@H](c2cccc(CNC(=O)/C(C)=C/C(=O)OC)c2)c2cnn(-c3ccccc3)c21] |
| I-126 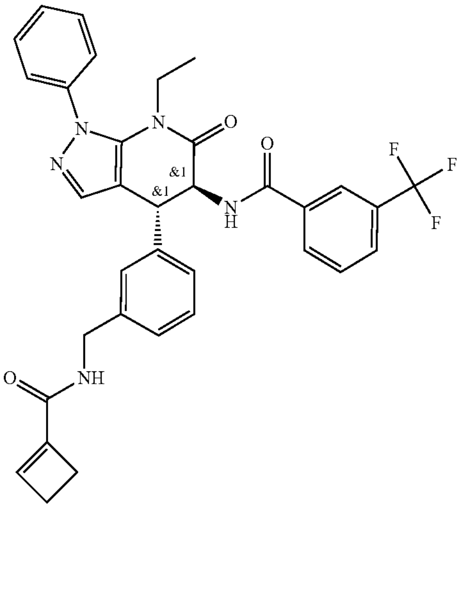 [SMILES: CCN1C(=O)[C@@H](NC(=O)c2cccc(C(F)(F)F)c2)[C@H](c2cccc(CNC(=O)C3=CCC3)c2)c2cnn(-c3ccccc3)c21] |

TABLE 1-continued
| Exemplary Compounds |
| --- |
| 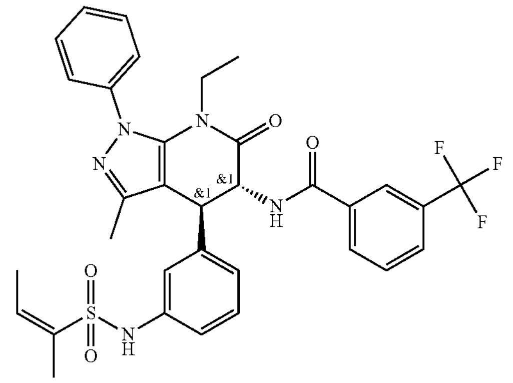 [SMILES: C/C=C(/C)S(=O)(=O)Nc1cccc([C@H]2c3c(C)nn(-c4ccccc4)c3N(CC)C(=O)[C@@H]2NC(=O)c2cccc(C(F)(F)F)c2)c1] I-127 |
| 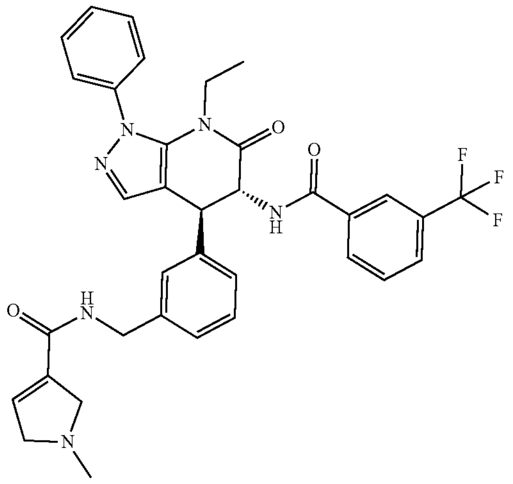 [SMILES: CCN1C(=O)[C@H](NC(=O)c2cccc(C(F)(F)F)c2)[C@@H](c2cccc(CNC(=O)C3=CCN(C)C3)c2)c2cnn(-c3ccccc3)c21] I-128 |
| 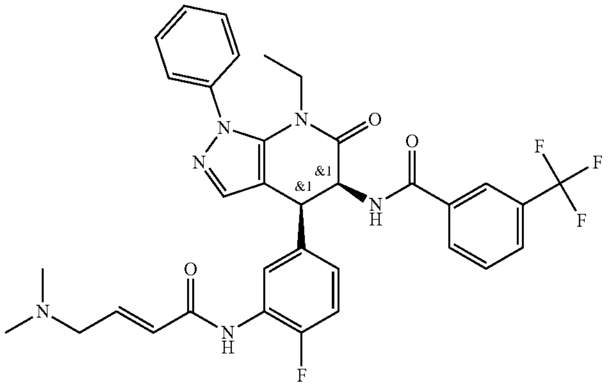 [SMILES: CCN1C(=O)[C@@H](NC(=O)c2cccc(C(F)(F)F)c2)[C@@H](c2ccc(F)c(NC(=O)/C=C/CN(C)C)c2)c2cnn(-c3ccccc3)c21] I-129 |

TABLE 1-continued
| Exemplary Compounds |
| --- |
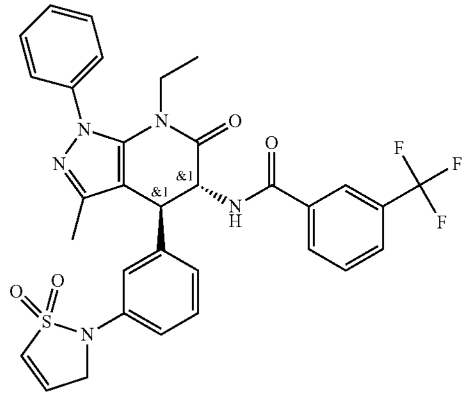 [SMILES: CCN1C(=O)[C@H](NC(=O)c2cccc(C(F)(F)F)c2)[C@@H](c2cccc(N3CC=CS3(=O)=O)c2)c2c(C)nn(-c3ccccc3)c21]
I-130
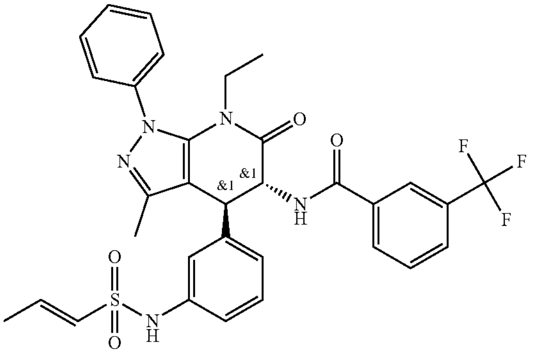 [SMILES: C/C=C/S(=O)(=O)Nc1cccc([C@H]2c3c(C)nn(-c4ccccc4)c3N(CC)C(=O)[C@@H]2NC(=O)c2cccc(C(F)(F)F)c2)c1]
I-131
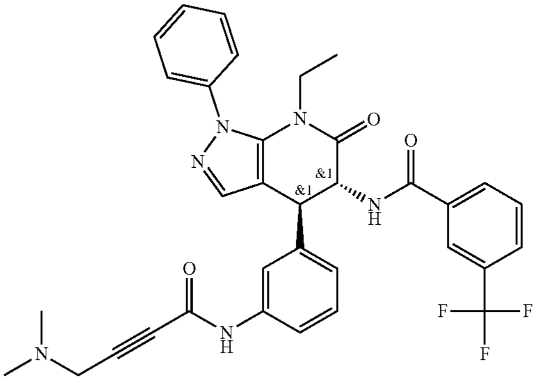 [SMILES: CCN1C(=O)[C@H](NC(=O)c2cccc(C(F)(F)F)c2)[C@@H](c2cccc(NC(=O)C#CCN(C)C)c2)c2cnn(-c3ccccc3)c21]
I-132

TABLE 1-continued
| Exemplary Compounds |
| --- |
I-133
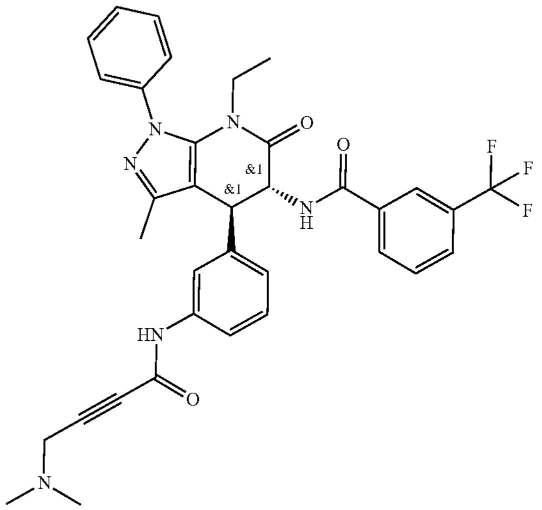 [SMILES: CCN1C(=O)[C@H](NC(=O)c2cccc(C(F)(F)F)c2)[C@@H](c2cccc(NC(=O)C#CCN(C)C)c2)c2c(C)nn(-c3ccccc3)c21]
I-134
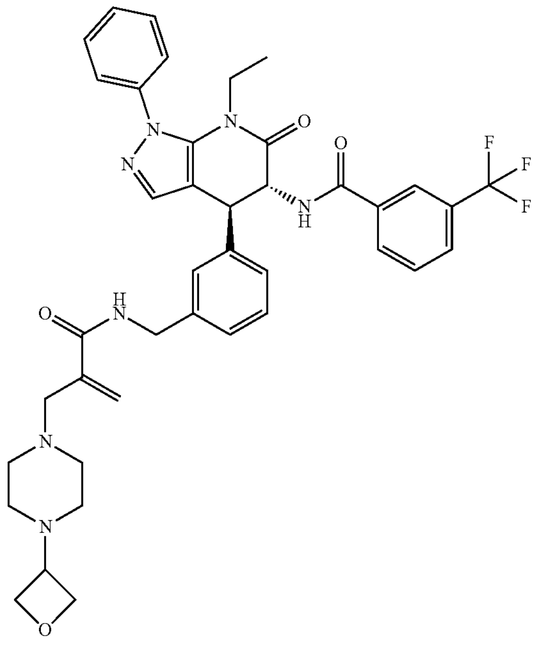 [SMILES: C=C(CN1CCN(C2COC2)CC1)C(=O)NCc1cccc([C@H]2c3cnn(-c4ccccc4)c3N(CC)C(=O)[C@@H]2NC(=O)c2cccc(C(F)(F)F)c2)c1]

TABLE 1-continued
| Exemplary Compounds |
|---|
I-135
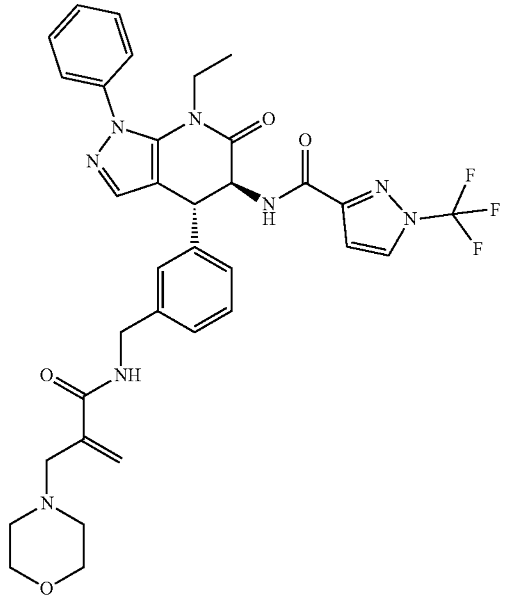 [SMILES: C=C(CN1CCOCC1)C(=O)NCc1cccc([C@@H]2c3cnn(-c4ccccc4)c3N(CC)C(=O)[C@H]2NC(=O)c2ccn(C(F)(F)F)n2)c1]
I-136
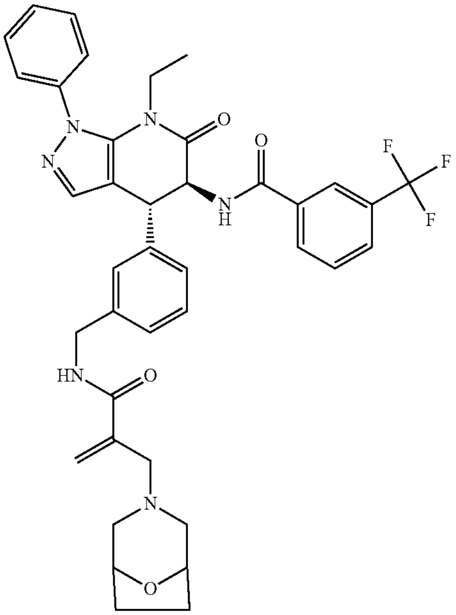
I-137
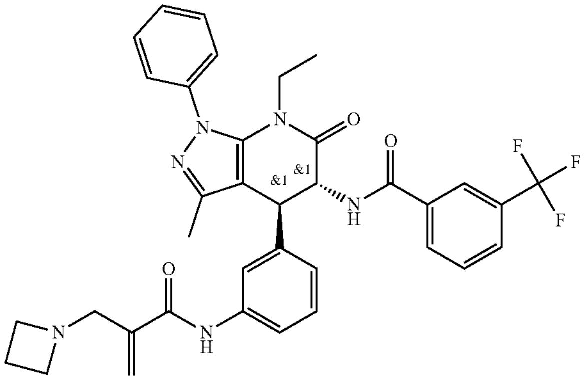 [SMILES: C=C(CN1CCC1)C(=O)Nc1cccc([C@H]2c3c(C)nn(-c4ccccc4)c3N(CC)C(=O)[C@@H]2NC(=O)c2cccc(C(F)(F)F)c2)c1]

TABLE 1-continued
Exemplary Compounds
I-138
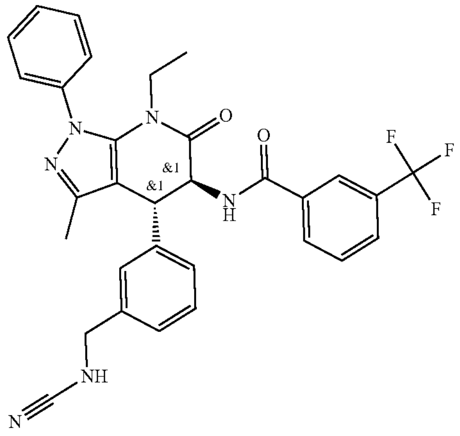 [SMILES: CCN1C(=O)[C@@H](NC(=O)c2cccc(C(F)(F)F)c2)[C@H](c2cccc(CNC#N)c2)c2c(C)nn(-c3ccccc3)c21]
I-139
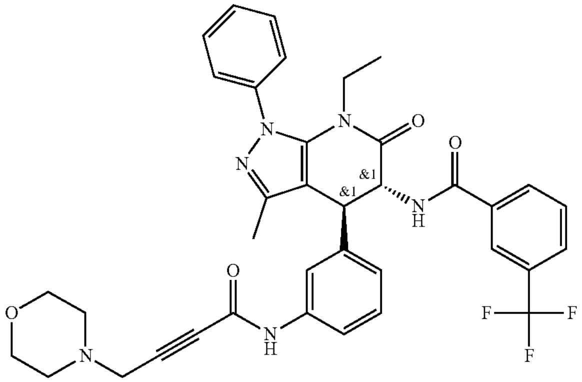 [SMILES: CCN1C(=O)[C@H](NC(=O)c2cccc(C(F)(F)F)c2)[C@@H](c2cccc(NC(=O)C#CCN3CCOCC3)c2)c2c(C)nn(-c3ccccc3)c21]
I-140
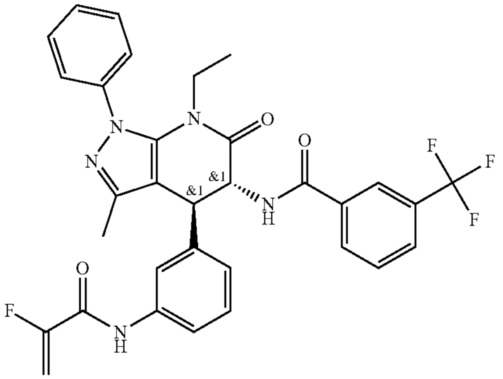 [SMILES: C=C(F)C(=O)Nc1cccc([C@H]2c3c(C)nn(-c4ccccc4)c3N(CC)C(=O)[C@@H]2NC(=O)c2cccc(C(F)(F)F)c2)c1]

TABLE 1-continued
Exemplary Compounds
I-141
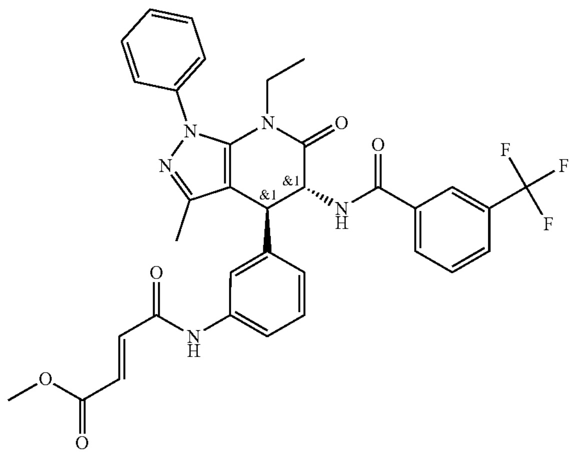 [SMILES: CCN1C(=O)[C@H](NC(=O)c2cccc(C(F)(F)F)c2)[C@@H](c2cccc(NC(=O)/C=C/C(=O)OC)c2)c2c(C)nn(-c3ccccc3)c21]
I-142
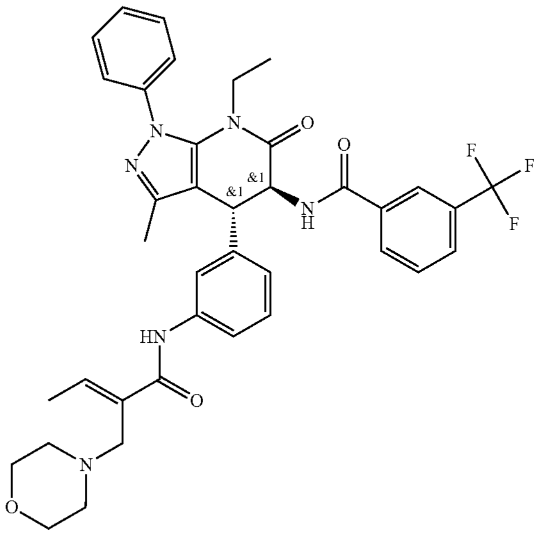 [SMILES: C/C=C(\CN1CCOCC1)C(=O)Nc1cccc([C@@H]2c3c(C)nn(-c4ccccc4)c3N(CC)C(=O)[C@H]2NC(=O)c2cccc(C(F)(F)F)c2)c1]
I-143
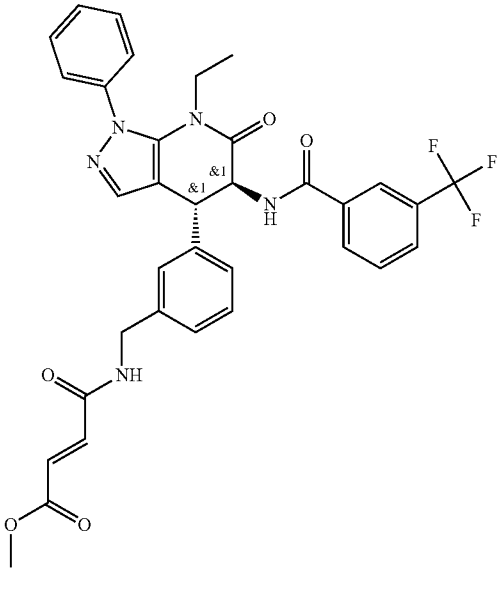 [SMILES: CCN1C(=O)[C@@H](NC(=O)c2cccc(C(F)(F)F)c2)[C@H](c2cccc(CNC(=O)/C=C/C(=O)OC)c2)c2cnn(-c3ccccc3)c21]

TABLE 1-continued
| Exemplary Compounds |
| --- |
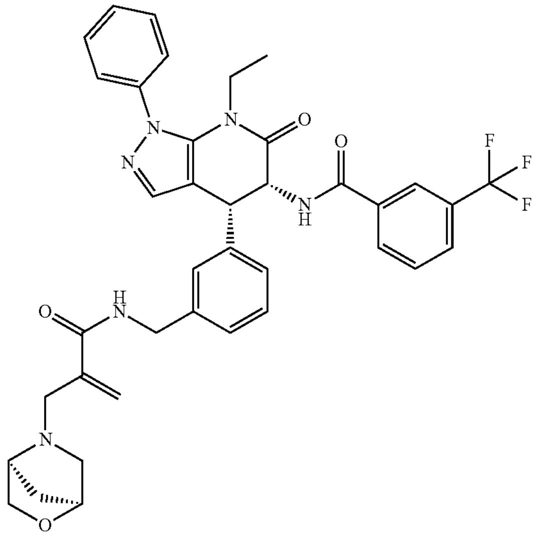 [SMILES: C=C(CN1C[C@@H]2C[C@H]1CO2)C(=O)NCc1cccc([C@@H]2c3cnn(-c4ccccc4)c3N(CC)C(=O)[C@@H]2NC(=O)c2cccc(C(F)(F)F)c2)c1]
I-144
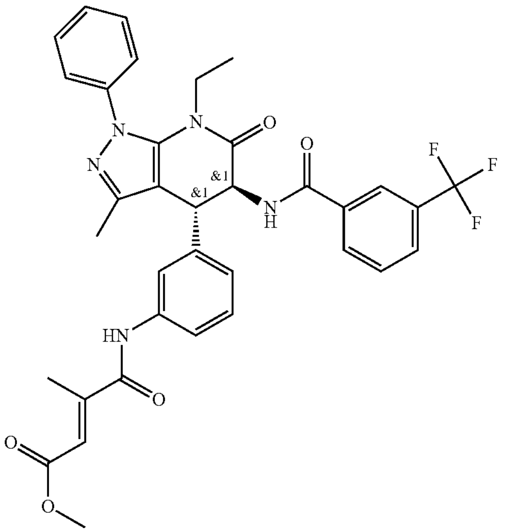 [SMILES: CCN1C(=O)[C@@H](NC(=O)c2cccc(C(F)(F)F)c2)[C@H](c2cccc(NC(=O)/C(C)=C/C(=O)OC)c2)c2c(C)nn(-c3ccccc3)c21]
I-145
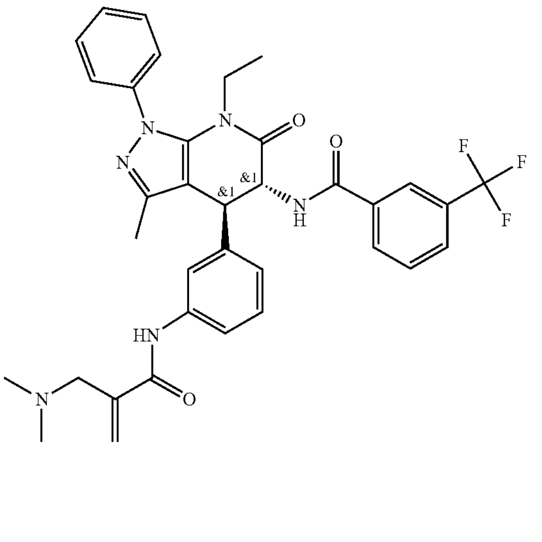 [SMILES: C=C(CN(C)C)C(=O)Nc1cccc([C@H]2c3c(C)nn(-c4ccccc4)c3N(CC)C(=O)[C@@H]2NC(=O)c2cccc(C(F)(F)F)c2)c1]
I-146

TABLE 1-continued
| Exemplary Compounds |
| --- |
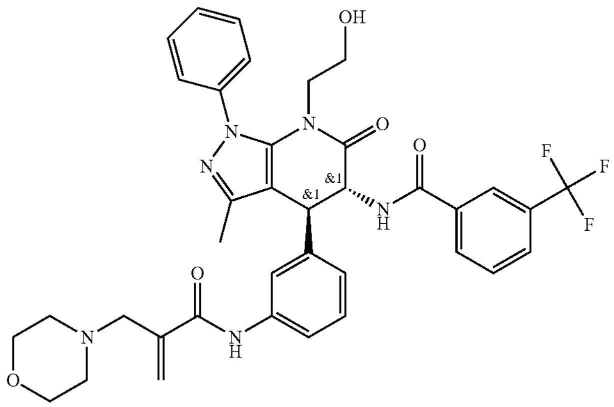 [SMILES: C=C(CN1CCOCC1)C(=O)Nc1cccc([C@H]2c3c(C)nn(-c4ccccc4)c3N(CCO)C(=O)[C@@H]2NC(=O)c2cccc(C(F)(F)F)c2)c1]
I-147
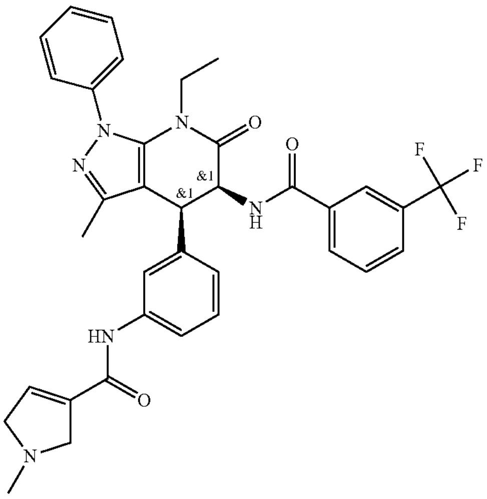 [SMILES: CCN1C(=O)[C@@H](NC(=O)c2cccc(C(F)(F)F)c2)[C@@H](c2cccc(NC(=O)C3=CCN(C)C3)c2)c2c(C)nn(-c3ccccc3)c21]
I-148
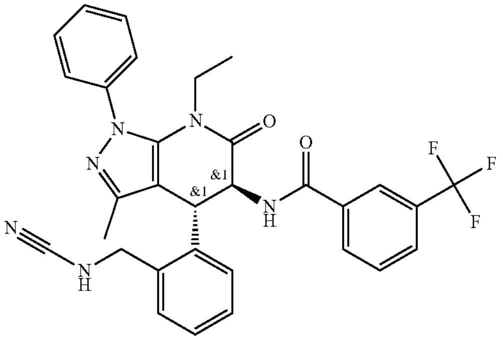 [SMILES: CCN1C(=O)[C@@H](NC(=O)c2cccc(C(F)(F)F)c2)[C@H](c2ccccc2CNC#N)c2c(C)nn(-c3ccccc3)c21]
I-149

TABLE 1-continued
| Exemplary Compounds |
|---|
I-150
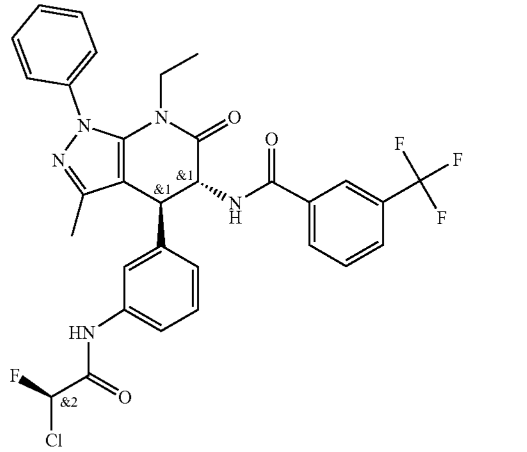 [SMILES: CCN1C(=O)[C@H](NC(=O)c2cccc(C(F)(F)F)c2)[C@@H](c2cccc(NC(=O)[C@H](F)Cl)c2)c2c(C)nn(-c3ccccc3)c21]
I-151
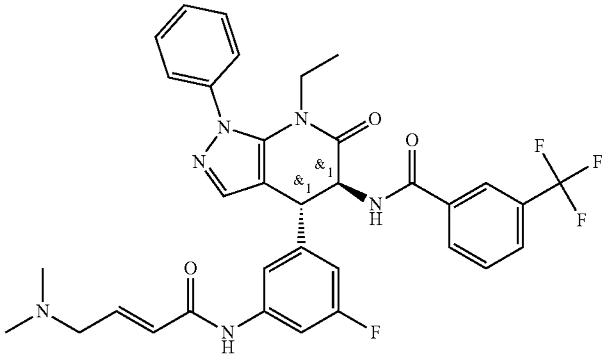 [SMILES: CCN1C(=O)[C@@H](NC(=O)c2cccc(C(F)(F)F)c2)[C@H](c2cc(F)cc(NC(=O)/C=C/CN(C)C)c2)c2cnn(-c3ccccc3)c21]
I-152
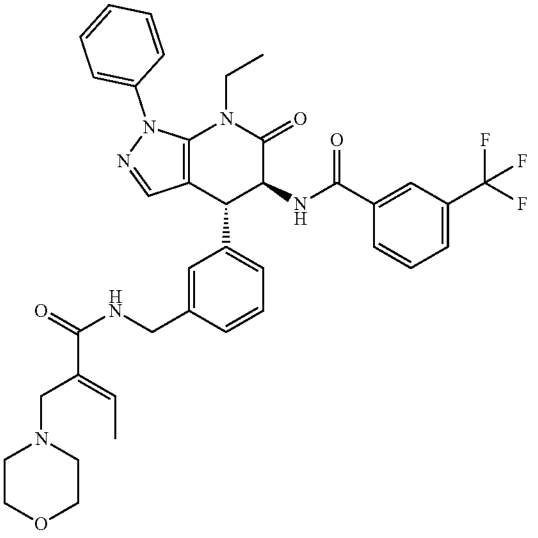 [SMILES: C/C=C(\CN1CCOCC1)C(=O)NCc1cccc([C@@H]2c3cnn(-c4ccccc4)c3N(CC)C(=O)[C@H]2NC(=O)c2cccc(C(F)(F)F)c2)c1]

TABLE 1-continued
| Exemplary Compounds |
|---|
I-153
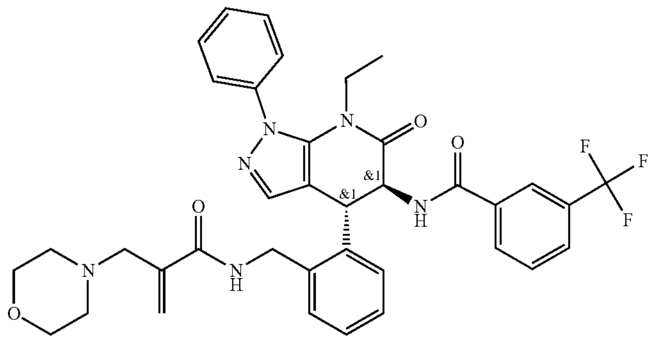 [SMILES: C=C(CN1CCOCC1)C(=O)NCc1ccccc1[C@@H]1c2cnn(-c3ccccc3)c2N(CC)C(=O)[C@H]1NC(=O)c1cccc(C(F)(F)F)c1]
I-154
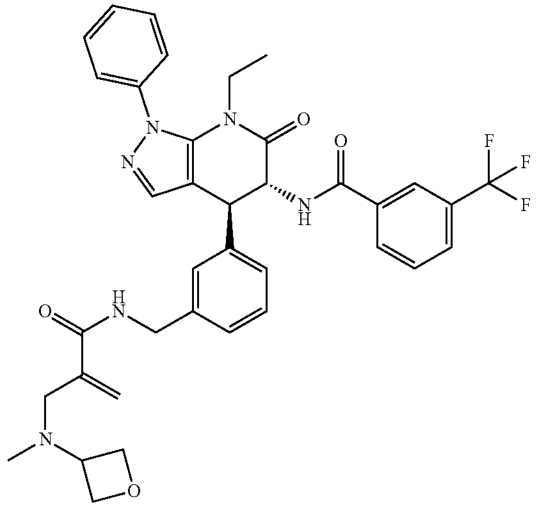 [SMILES: C=C(CN(C)C1COC1)C(=O)NCc1cccc([C@H]2c3cnn(-c4ccccc4)c3N(CC)C(=O)[C@@H]2NC(=O)c2cccc(C(F)(F)F)c2)c1]
I-155
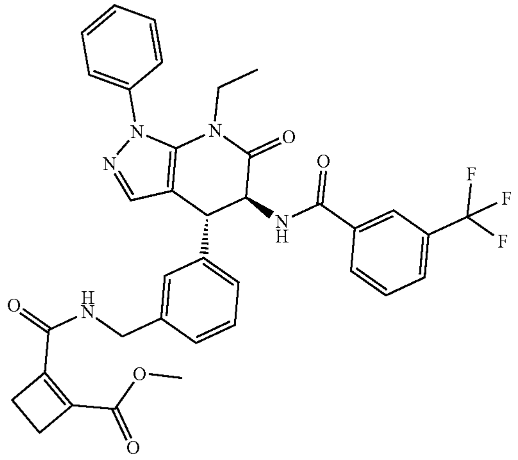 [SMILES: CCN1C(=O)[C@@H](NC(=O)c2cccc(C(F)(F)F)c2)[C@H](c2cccc(CNC(=O)C3=C(C(=O)OC)CC3)c2)c2cnn(-c3ccccc3)c21]

TABLE 1-continued
| Exemplary Compounds |
|---|
I-156
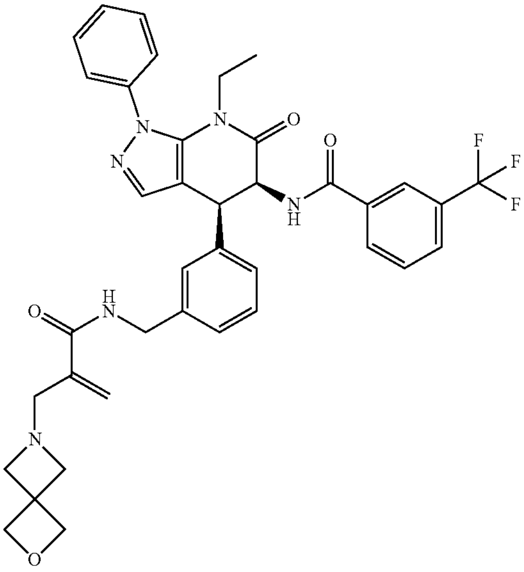 [SMILES: C=C(CN1CC2(COC2)C1)C(=O)NCc1cccc([C@H]2c3cnn(-c4ccccc4)c3N(CC)C(=O)[C@H]2NC(=O)c2cccc(C(F)(F)F)c2)c1]
I-157
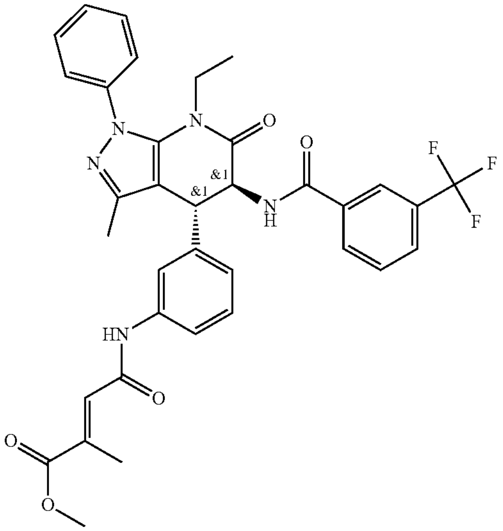 [SMILES: CCN1C(=O)[C@@H](NC(=O)c2cccc(C(F)(F)F)c2)[C@H](c2cccc(NC(=O)/C=C(\C)C(=O)OC)c2)c2c(C)nn(-c3ccccc3)c21]
I-158
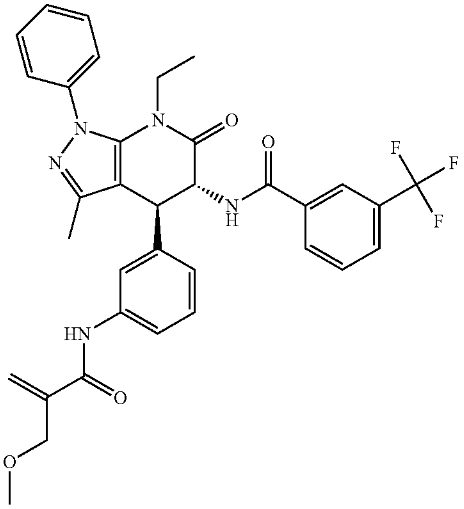 [SMILES: C=C(COC)C(=O)Nc1cccc([C@H]2c3c(C)nn(-c4ccccc4)c3N(CC)C(=O)[C@@H]2NC(=O)c2cccc(C(F)(F)F)c2)c1]

TABLE 1-continued
| Exemplary Compounds |
|---|
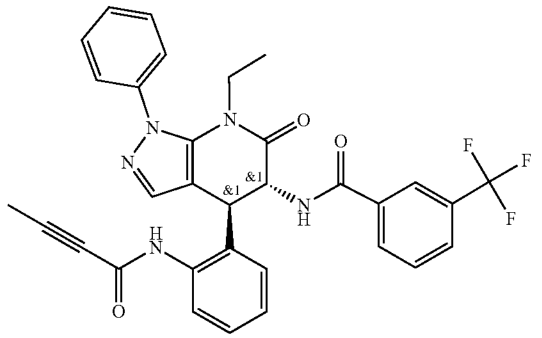 [SMILES: CC#CC(=O)Nc1ccccc1[C@H]1c2cnn(-c3ccccc3)c2N(CC)C(=O)[C@@H]1NC(=O)c1cccc(C(F)(F)F)c1]
I-159
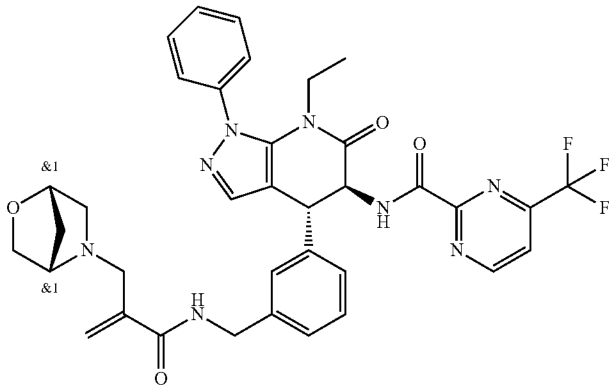
I-160
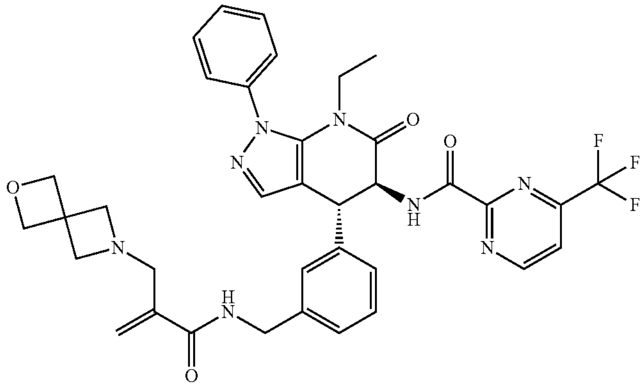 [SMILES: C=C(CN1CC2(COC2)C1)C(=O)NCc1cccc([C@@H]2c3cnn(-c4ccccc4)c3N(CC)C(=O)[C@H]2NC(=O)c2nccc(C(F)(F)F)n2)c1]
I-161
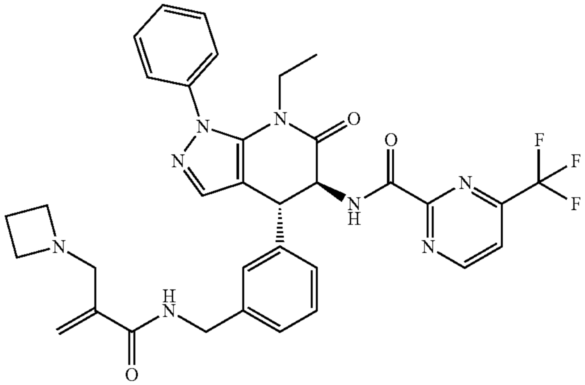 [SMILES: C=C(CN1CCC1)C(=O)NCc1cccc([C@@H]2c3cnn(-c4ccccc4)c3N(CC)C(=O)[C@H]2NC(=O)c2nccc(C(F)(F)F)n2)c1]
I-162

TABLE 1-continued
| Exemplary Compounds |
| --- |
I-163
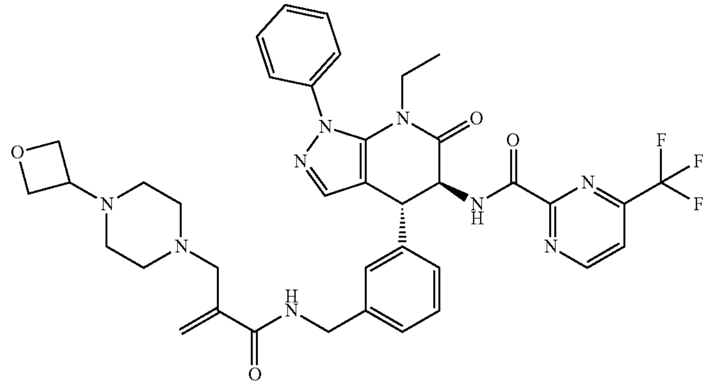 [SMILES: C=C(CN1CCN(C2COC2)CC1)C(=O)NCc1cccc([C@@H]2c3cnn(-c4ccccc4)c3N(CC)C(=O)[C@H]2NC(=O)c2nccc(C(F)(F)F)n2)c1]
I-164
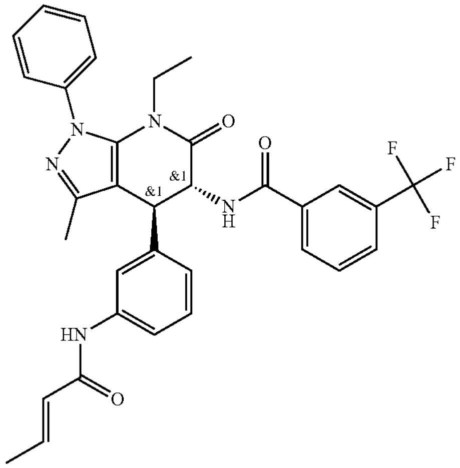 [SMILES: C/C=C/C(=O)Nc1cccc([C@H]2c3c(C)nn(-c4ccccc4)c3N(CC)C(=O)[C@@H]2NC(=O)c2cccc(C(F)(F)F)c2)c1]
I-165
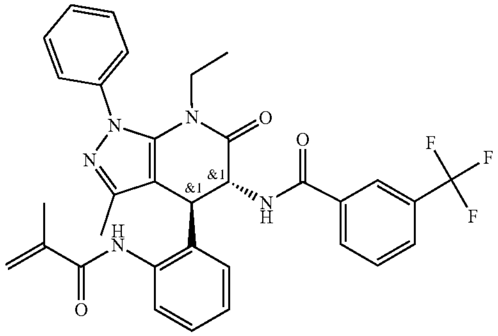 [SMILES: C=C(C)C(=O)Nc1ccccc1[C@H]1c2c(C)nn(-c3ccccc3)c2N(CC)C(=O)[C@@H]1NC(=O)c1cccc(C(F)(F)F)c1]
I-166
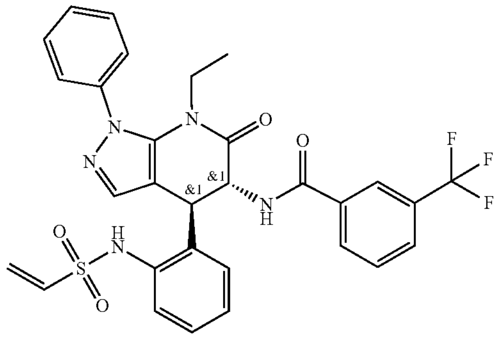 [SMILES: C=CS(=O)(=O)Nc1ccccc1[C@H]1c2cnn(-c3ccccc3)c2N(CC)C(=O)[C@@H]1NC(=O)c1cccc(C(F)(F)F)c1]

TABLE 1-continued
Exemplary Compounds
I-167
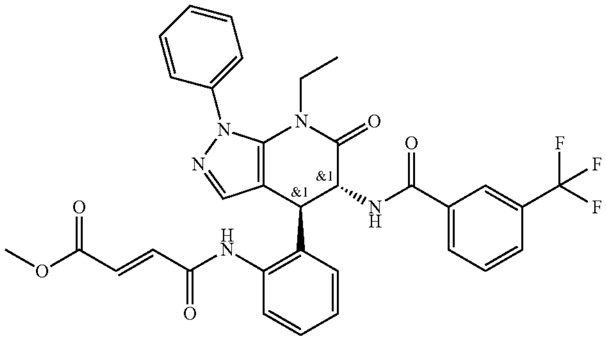 [SMILES: CCN1C(=O)[C@H](NC(=O)c2cccc(C(F)(F)F)c2)[C@@H](c2ccccc2NC(=O)/C=C/C(=O)OC)c2cnn(-c3ccccc3)c21]
I-168
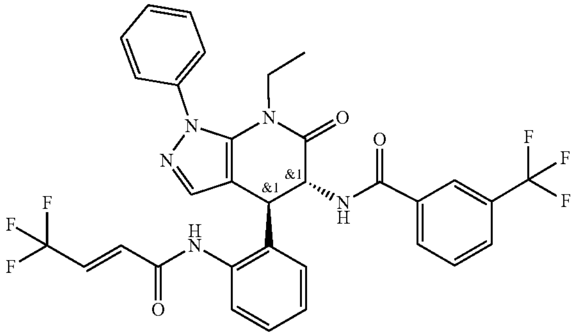 [SMILES: CCN1C(=O)[C@H](NC(=O)c2cccc(C(F)(F)F)c2)[C@@H](c2ccccc2NC(=O)/C=C/C(F)(F)F)c2cnn(-c3ccccc3)c21]
I-169
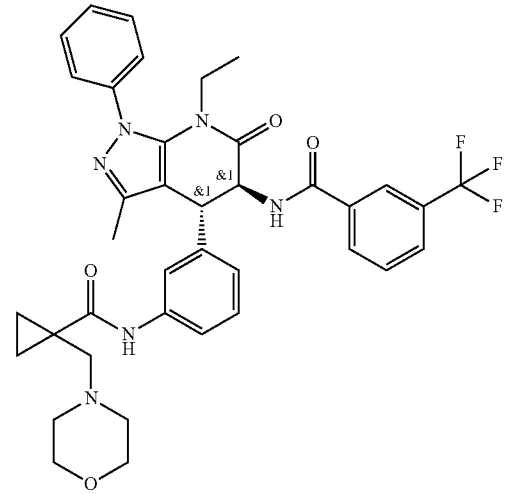 [SMILES: CCN1C(=O)[C@@H](NC(=O)c2cccc(C(F)(F)F)c2)[C@H](c2cccc(NC(=O)C3(CN4CCOCC4)CC3)c2)c2c(C)nn(-c3ccccc3)c21]
I-170
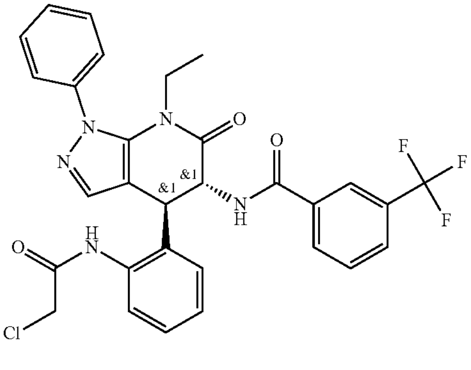 [SMILES: CCN1C(=O)[C@H](NC(=O)c2cccc(C(F)(F)F)c2)[C@@H](c2ccccc2NC(=O)CCl)c2cnn(-c3ccccc3)c21]

TABLE 1-continued
| Exemplary Compounds |
| --- |
| 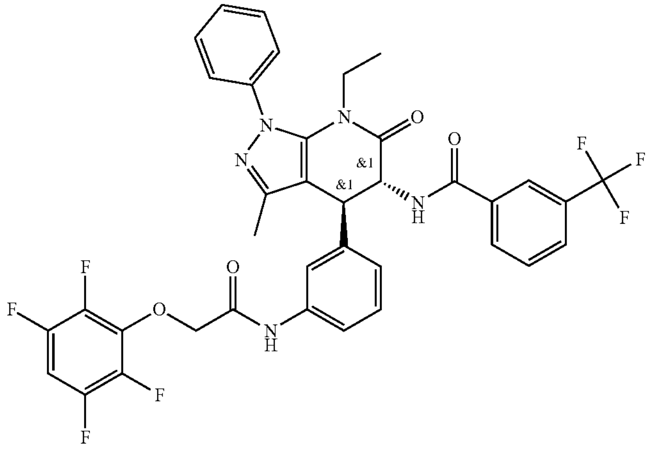 [SMILES: CCN1C(=O)[C@H](NC(=O)c2cccc(C(F)(F)F)c2)[C@@H](c2cccc(NC(=O)COc3c(F)c(F)cc(F)c3F)c2)c2c(C)nn(-c3ccccc3)c21] I-171 |
| 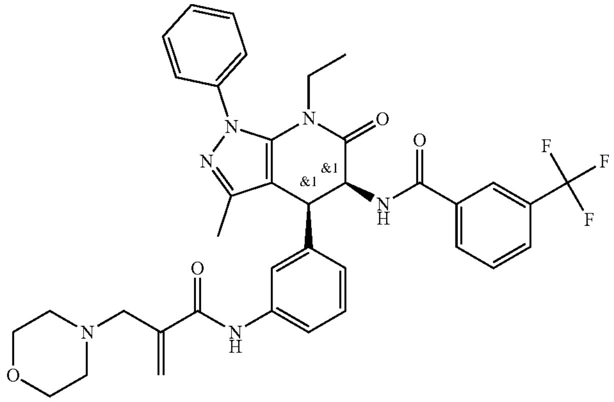 [SMILES: C=C(CN1CCOCC1)C(=O)Nc1cccc([C@H]2c3c(C)nn(-c4ccccc4)c3N(CC)C(=O)[C@H]2NC(=O)c2cccc(C(F)(F)F)c2)c1] I-172 |
| 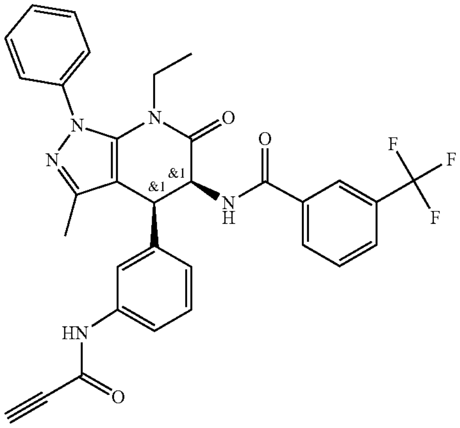 [SMILES: C#CC(=O)Nc1cccc([C@H]2c3c(C)nn(-c4ccccc4)c3N(CC)C(=O)[C@H]2NC(=O)c2cccc(C(F)(F)F)c2)c1] I-173 |

TABLE 1-continued
| Exemplary Compounds |
| --- |
I-174
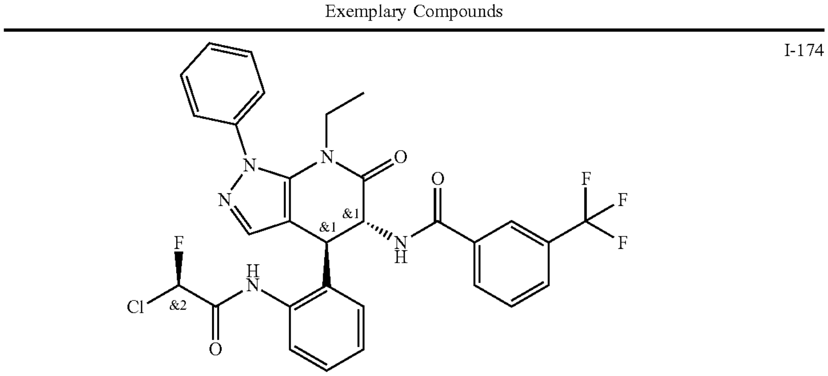
I-175
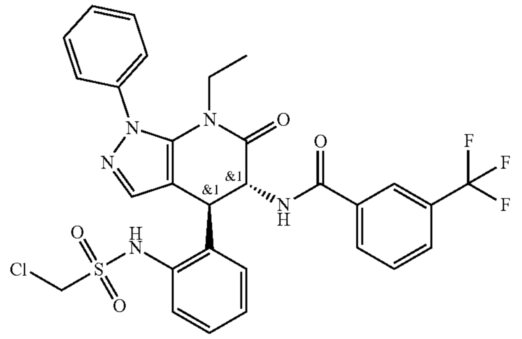 [SMILES: CCN1C(=O)[C@H](NC(=O)c2cccc(C(F)(F)F)c2)[C@@H](c2ccccc2NS(=O)(=O)CCl)c2cnn(-c3ccccc3)c21]
I-176
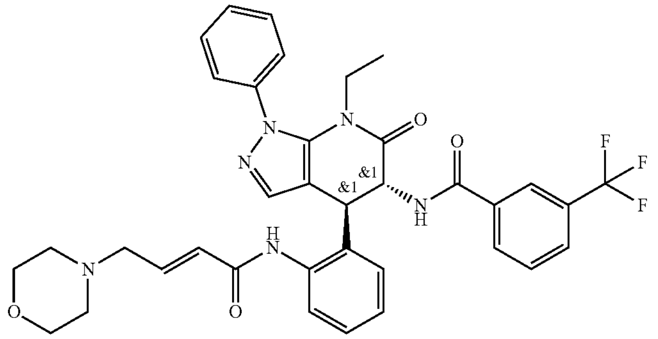 [SMILES: CCN1C(=O)[C@H](NC(=O)c2cccc(C(F)(F)F)c2)[C@@H](c2ccccc2NC(=O)/C=C/CN2CCOCC2)c2cnn(-c3ccccc3)c21]
I-177
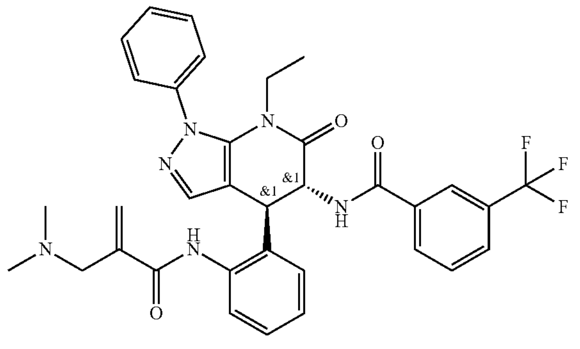 [SMILES: C=C(CN(C)C)C(=O)Nc1ccccc1[C@H]1c2cnn(-c3ccccc3)c2N(CC)C(=O)[C@@H]1NC(=O)c1cccc(C(F)(F)F)c1]

TABLE 1-continued
| Exemplary Compounds |
| --- |
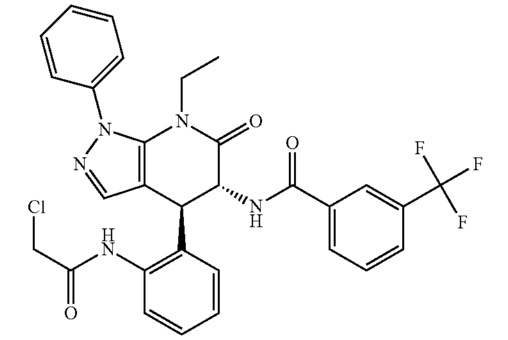 [SMILES: CCN1C(=O)[C@H](NC(=O)c2cccc(C(F)(F)F)c2)[C@@H](c2ccccc2NC(=O)CCl)c2cnn(-c3ccccc3)c21]
I-178
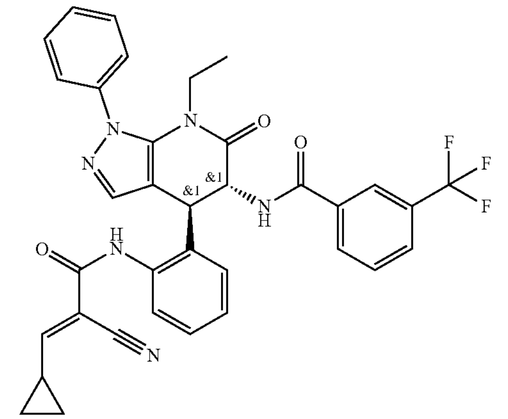 [SMILES: CCN1C(=O)[C@H](NC(=O)c2cccc(C(F)(F)F)c2)[C@@H](c2ccccc2NC(=O)/C(C#N)=C/C2CC2)c2cnn(-c3ccccc3)c21]
I-179
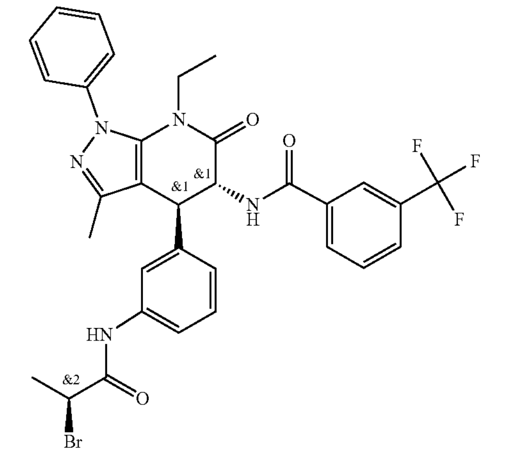 [SMILES: CCN1C(=O)[C@H](NC(=O)c2cccc(C(F)(F)F)c2)[C@@H](c2cccc(NC(=O)[C@H](C)Br)c2)c2c(C)nn(-c3ccccc3)c21]
I-180
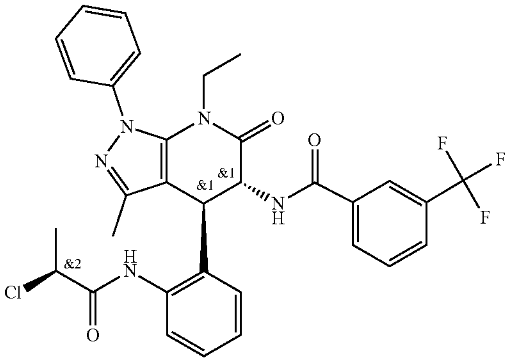 [SMILES: CCN1C(=O)[C@H](NC(=O)c2cccc(C(F)(F)F)c2)[C@@H](c2ccccc2NC(=O)[C@H](C)Cl)c2c(C)nn(-c3ccccc3)c21]
I-181

TABLE 1-continued
| Exemplary Compounds |
| --- |
| 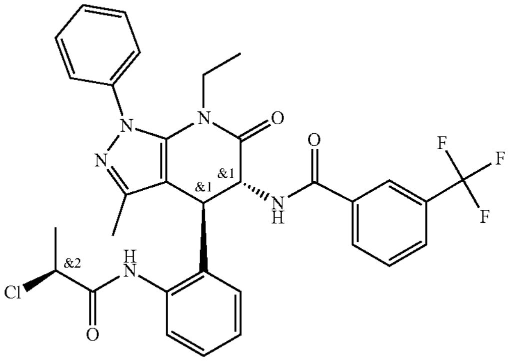 [SMILES: CCN1C(=O)[C@H](NC(=O)c2cccc(C(F)(F)F)c2)[C@@H](c2ccccc2NC(=O)[C@H](C)Cl)c2c(C)nn(-c3ccccc3)c21] I-182 |
| 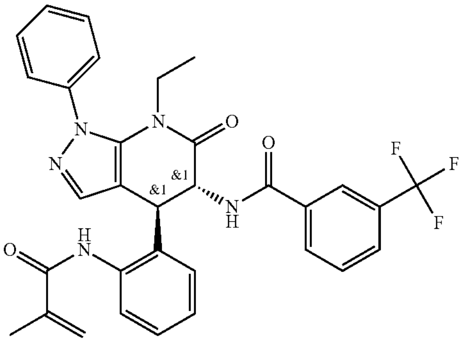 [SMILES: C=C(C)C(=O)Nc1ccccc1[C@H]1c2cnn(-c3ccccc3)c2N(CC)C(=O)[C@@H]1NC(=O)c1cccc(C(F)(F)F)c1] I-183 |
| 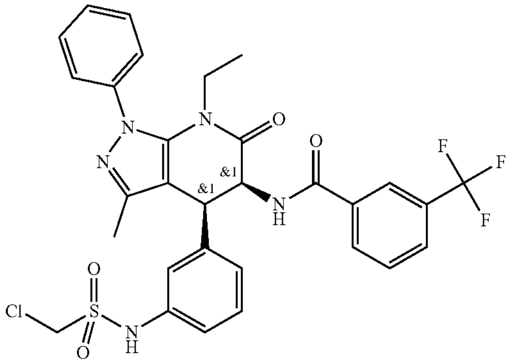 [SMILES: CCN1C(=O)[C@@H](NC(=O)c2cccc(C(F)(F)F)c2)[C@@H](c2cccc(NS(=O)(=O)CCl)c2)c2c(C)nn(-c3ccccc3)c21] I-184 |
| 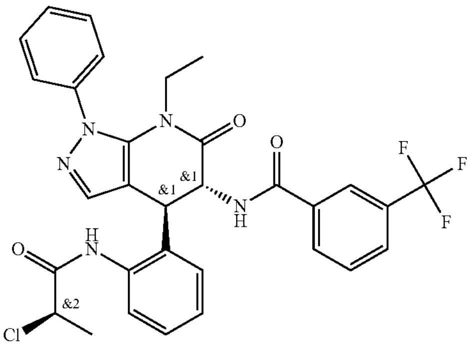 I-185 |

TABLE 1-continued
| Exemplary Compounds |
| --- |
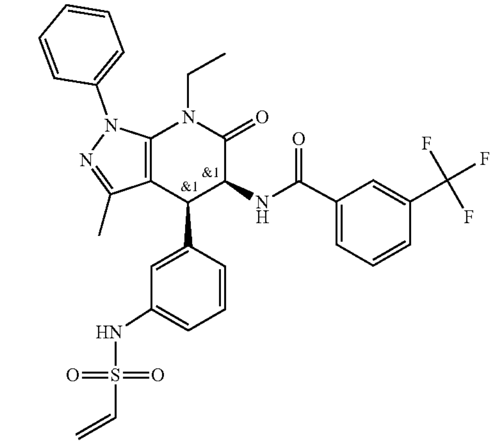 [SMILES: C=CS(=O)(=O)Nc1cccc([C@H]2c3c(C)nn(-c4ccccc4)c3N(CC)C(=O)[C@H]2NC(=O)c2cccc(C(F)(F)F)c2)c1]
I-186
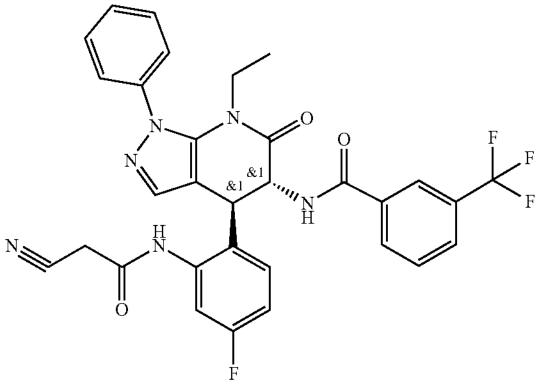 [SMILES: CCN1C(=O)[C@H](NC(=O)c2cccc(C(F)(F)F)c2)[C@@H](c2ccc(F)cc2NC(=O)CC#N)c2cnn(-c3ccccc3)c21]
I-187
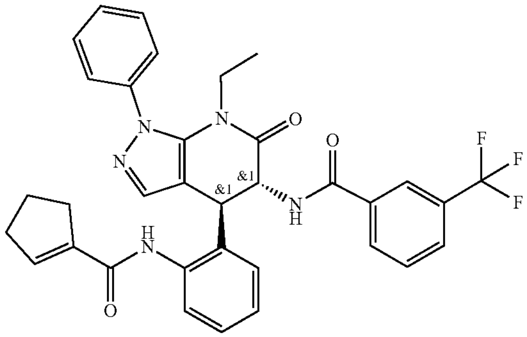 [SMILES: CCN1C(=O)[C@H](NC(=O)c2cccc(C(F)(F)F)c2)[C@@H](c2ccccc2NC(=O)C2=CCCC2)c2cnn(-c3ccccc3)c21]
I-188
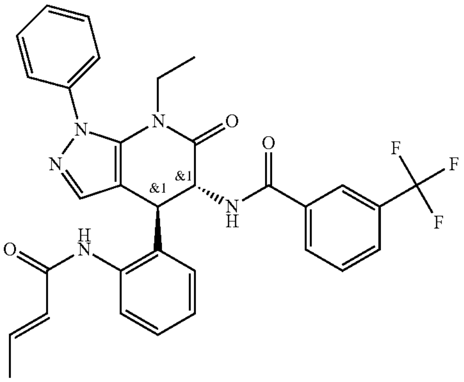 [SMILES: C/C=C/C(=O)Nc1ccccc1[C@H]1c2cnn(-c3ccccc3)c2N(CC)C(=O)[C@@H]1NC(=O)c1cccc(C(F)(F)F)c1]
I-189

TABLE 1-continued
| Exemplary Compounds |
| --- |
| 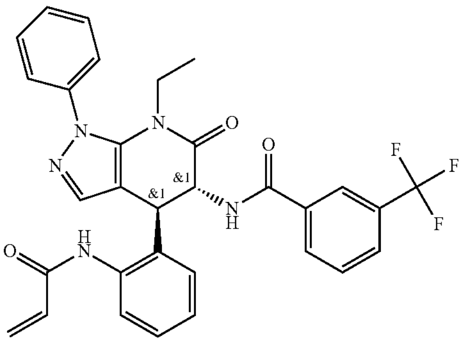 [SMILES: C=CC(=O)Nc1ccccc1[C@H]1c2cnn(-c3ccccc3)c2N(CC)C(=O)[C@@H]1NC(=O)c1cccc(C(F)(F)F)c1] I-190 |
| 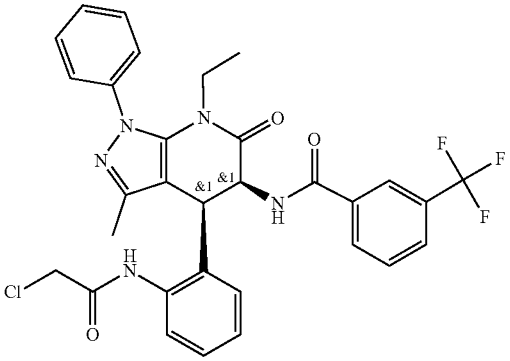 [SMILES: CCN1C(=O)[C@@H](NC(=O)c2cccc(C(F)(F)F)c2)[C@@H](c2ccccc2NC(=O)CCl)c2c(C)nn(-c3ccccc3)c21] I-191 |
| 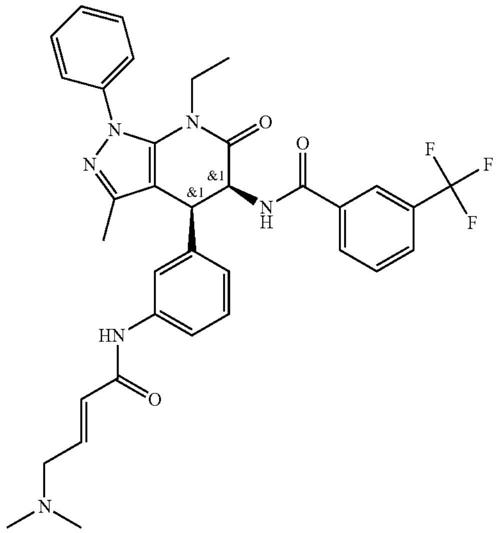 [SMILES: CCN1C(=O)[C@@H](NC(=O)c2cccc(C(F)(F)F)c2)[C@@H](c2cccc(NC(=O)/C=C/CN(C)C)c2)c2c(C)nn(-c3ccccc3)c21] I-192 |

TABLE 1-continued
| Exemplary Compounds |
|---|
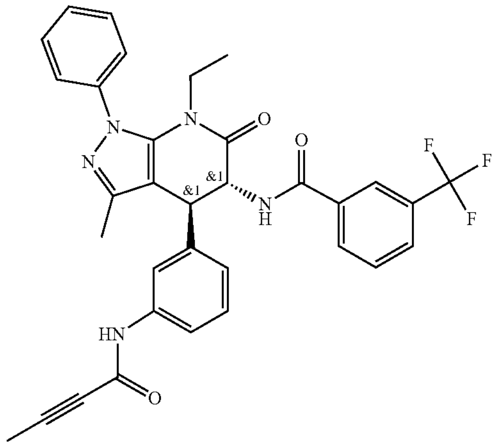 [SMILES: CC#CC(=O)Nc1cccc([C@H]2c3c(C)nn(-c4ccccc4)c3N(CC)C(=O)[C@@H]2NC(=O)c2cccc(C(F)(F)F)c2)c1]
I-193
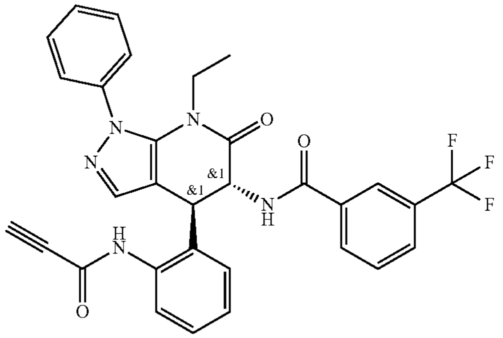 [SMILES: C#CC(=O)Nc1ccccc1[C@H]1c2cnn(-c3ccccc3)c2N(CC)C(=O)[C@@H]1NC(=O)c1cccc(C(F)(F)F)c1]
I-194
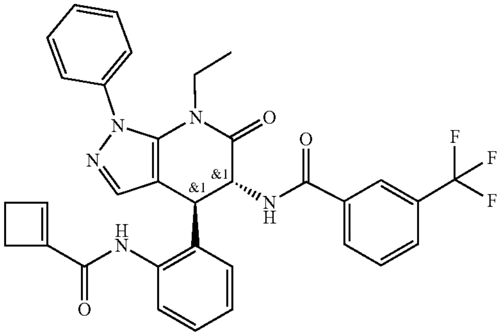 [SMILES: CCN1C(=O)[C@H](NC(=O)c2cccc(C(F)(F)F)c2)[C@@H](c2ccccc2NC(=O)C2=CCC2)c2cnn(-c3ccccc3)c21]
I-195
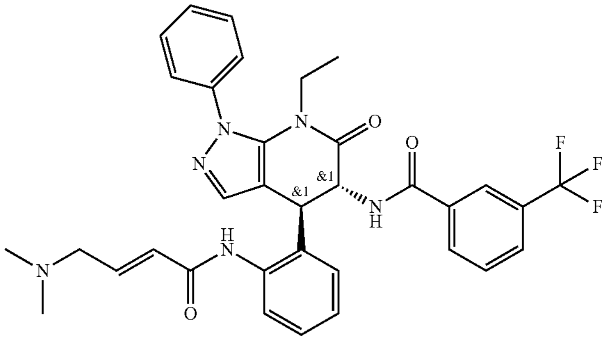 [SMILES: CCN1C(=O)[C@H](NC(=O)c2cccc(C(F)(F)F)c2)[C@@H](c2ccccc2NC(=O)/C=C/CN(C)C)c2cnn(-c3ccccc3)c21]
I-196

TABLE 1-continued
| Exemplary Compounds |
|---|
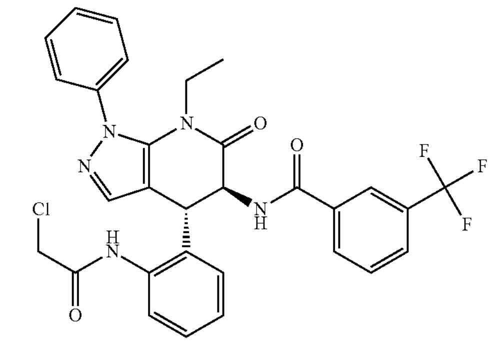 [SMILES: CCN1C(=O)[C@@H](NC(=O)c2cccc(C(F)(F)F)c2)[C@H](c2ccccc2NC(=O)CCl)c2cnn(-c3ccccc3)c21]
I-197
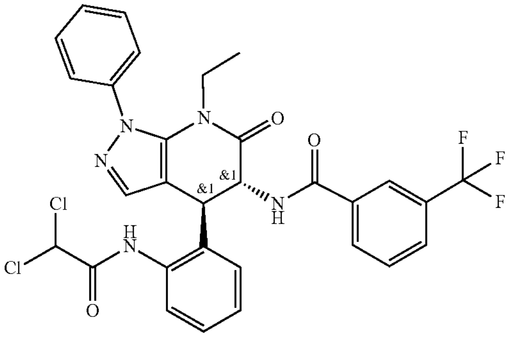 [SMILES: CCN1C(=O)[C@H](NC(=O)c2cccc(C(F)(F)F)c2)[C@@H](c2ccccc2NC(=O)C(Cl)Cl)c2cnn(-c3ccccc3)c21]
I-198
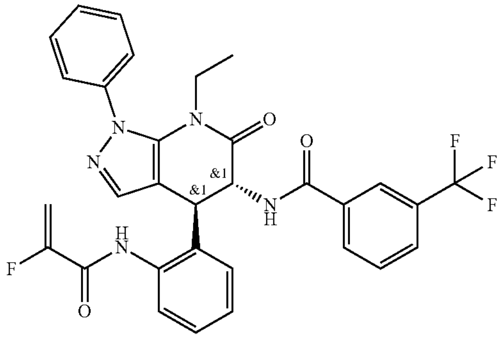 [SMILES: C=C(F)C(=O)Nc1ccccc1[C@H]1c2cnn(-c3ccccc3)c2N(CC)C(=O)[C@@H]1NC(=O)c1cccc(C(F)(F)F)c1]
I-199
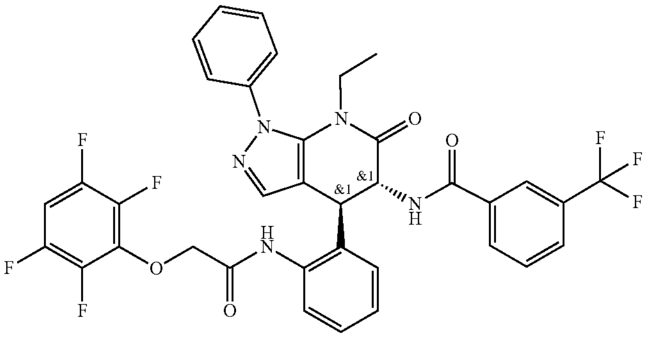 [SMILES: CCN1C(=O)[C@H](NC(=O)c2cccc(C(F)(F)F)c2)[C@@H](c2ccccc2NC(=O)COc2c(F)c(F)cc(F)c2F)c2cnn(-c3ccccc3)c21]
I-200

TABLE 1-continued
| Exemplary Compounds |
| --- |
| I-201 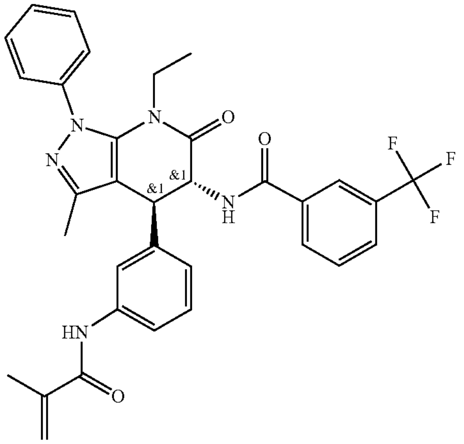 [SMILES: C=C(C)C(=O)Nc1cccc([C@H]2c3c(C)nn(-c4ccccc4)c3N(CC)C(=O)[C@@H]2NC(=O)c2cccc(C(F)(F)F)c2)c1] |
| I-202 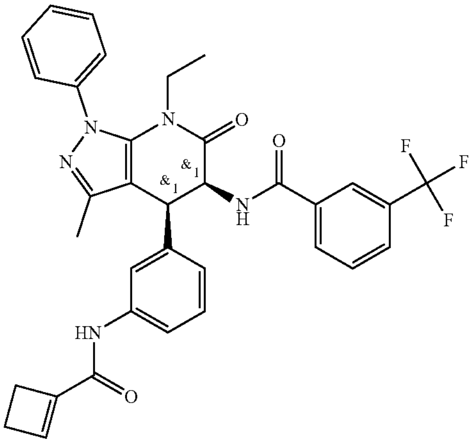 [SMILES: CCN1C(=O)[C@@H](NC(=O)c2cccc(C(F)(F)F)c2)[C@@H](c2cccc(NC(=O)C3=CCC3)c2)c2c(C)nn(-c3ccccc3)c21] |
| I-203 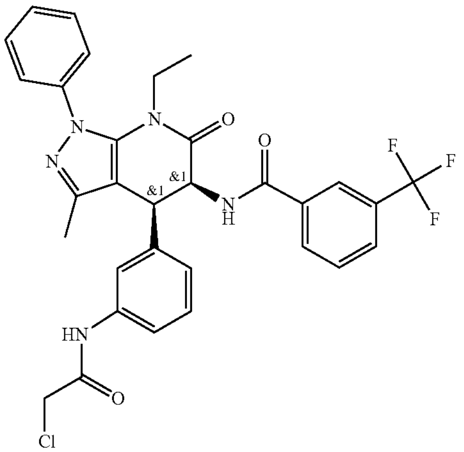 [SMILES: CCN1C(=O)[C@@H](NC(=O)c2cccc(C(F)(F)F)c2)[C@@H](c2cccc(NC(=O)CCl)c2)c2c(C)nn(-c3ccccc3)c21] |

TABLE 1-continued
| Exemplary Compounds |
| --- |
| I-204 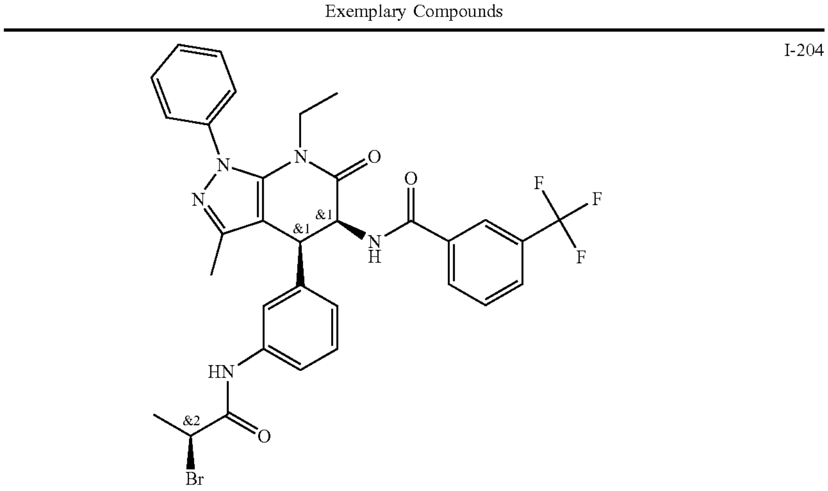 |
| I-205 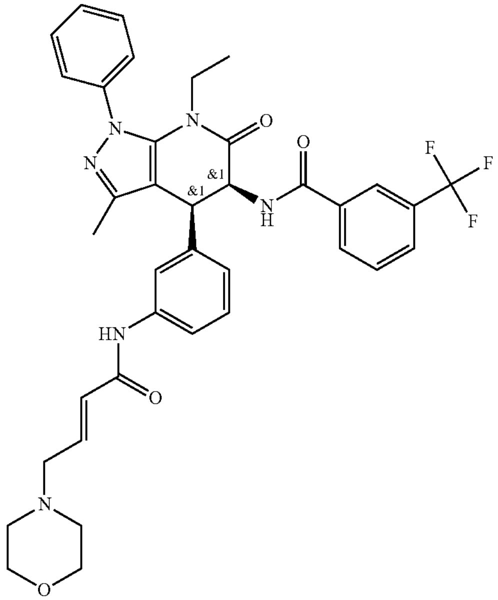 [SMILES: CCN1C(=O)[C@@H](NC(=O)c2cccc(C(F)(F)F)c2)[C@@H](c2cccc(NC(=O)/C=C/CN3CCOCC3)c2)c2c(C)nn(-c3ccccc3)c21] |
| I-206 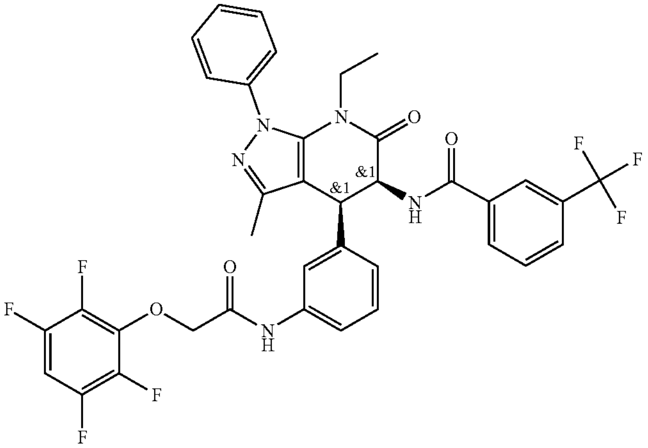 [SMILES: CCN1C(=O)[C@@H](NC(=O)c2cccc(C(F)(F)F)c2)[C@@H](c2cccc(NC(=O)COc3c(F)c(F)cc(F)c3F)c2)c2c(C)nn(-c3ccccc3)c21] |

TABLE 1-continued
| Exemplary Compounds |
|---|
| 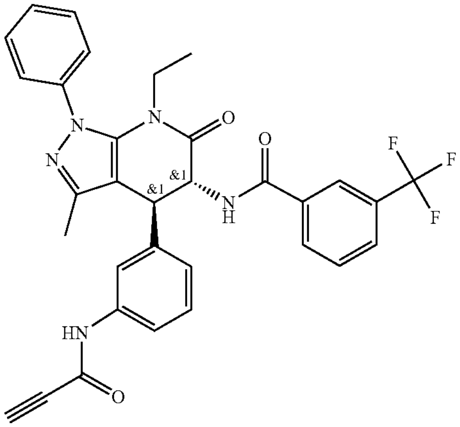 [SMILES: C#CC(=O)Nc1cccc([C@H]2c3c(C)nn(-c4ccccc4)c3N(CC)C(=O)[C@@H]2NC(=O)c2cccc(C(F)(F)F)c2)c1] I-207 |
| 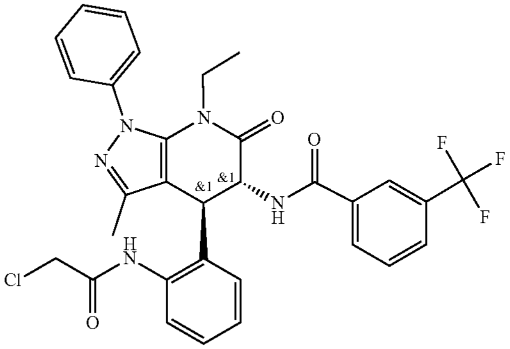 [SMILES: CCN1C(=O)[C@H](NC(=O)c2cccc(C(F)(F)F)c2)[C@@H](c2ccccc2NC(=O)CCl)c2c(C)nn(-c3ccccc3)c21] I-208 |
| 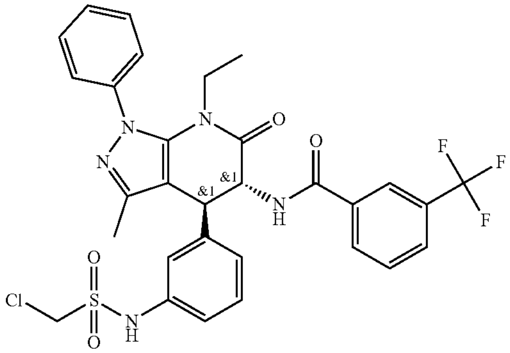 [SMILES: CCN1C(=O)[C@H](NC(=O)c2cccc(C(F)(F)F)c2)[C@@H](c2cccc(NS(=O)(=O)CCl)c2)c2c(C)nn(-c3ccccc3)c21] I-209 |
| 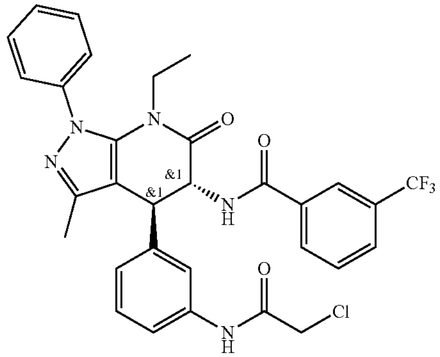 [SMILES: CCN1C(=O)[C@H](NC(=O)c2cccc(C(F)(F)F)c2)[C@@H](c2cccc(NC(=O)CCl)c2)c2c(C)nn(-c3ccccc3)c21] I-210 |

TABLE 1-continued
| Exemplary Compounds |
| --- |
I-211
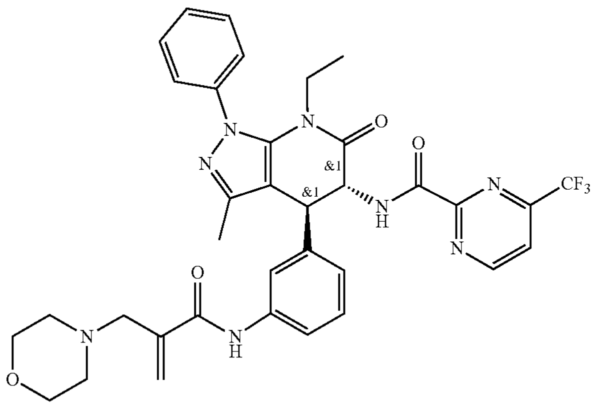 [SMILES: C=C(CN1CCOCC1)C(=O)Nc1cccc([C@H]2c3c(C)nn(-c4ccccc4)c3N(CC)C(=O)[C@@H]2NC(=O)c2nccc(C(F)(F)F)n2)c1]
I-212
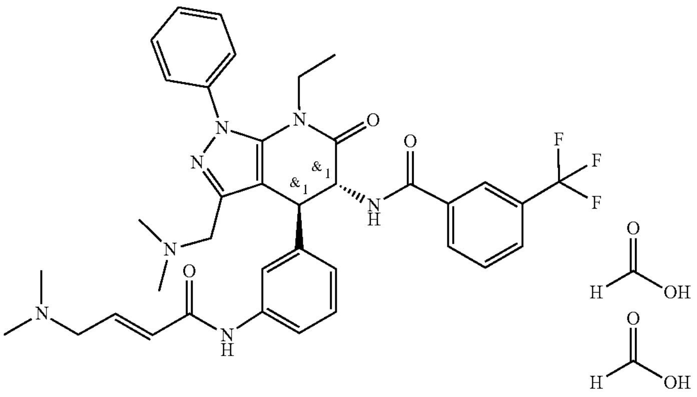
I-213
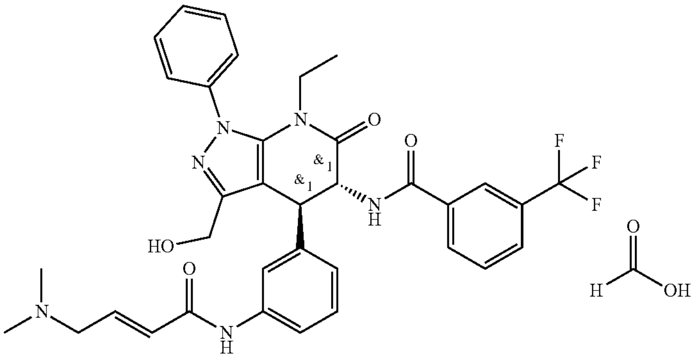
I-214
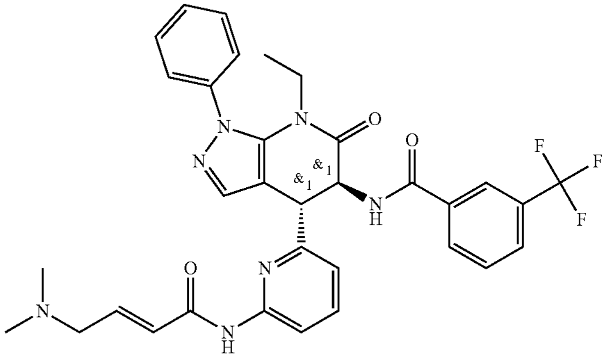 [SMILES: CCN1C(=O)[C@@H](NC(=O)c2cccc(C(F)(F)F)c2)[C@H](c2cccc(NC(=O)/C=C/CN(C)C)n2)c2cnn(-c3ccccc3)c21]

TABLE 1-continued
| Exemplary Compounds |
| --- |
| I-215 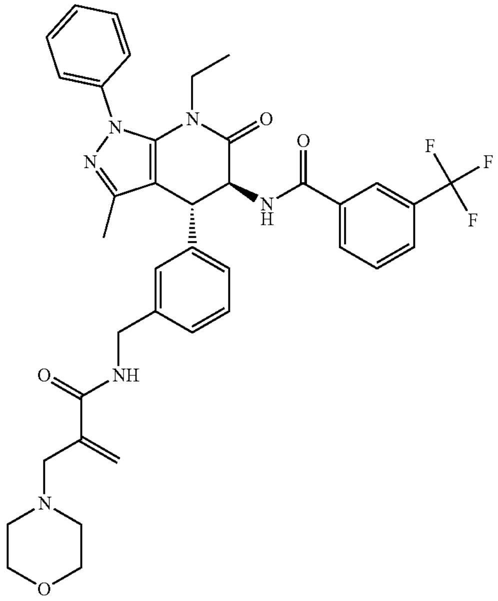 [SMILES: C=C(CN1CCOCC1)C(=O)NCc1cccc([C@@H]2c3c(C)nn(-c4ccccc4)c3N(CC)C(=O)[C@H]2NC(=O)c2cccc(C(F)(F)F)c2)c1] |
| I-216 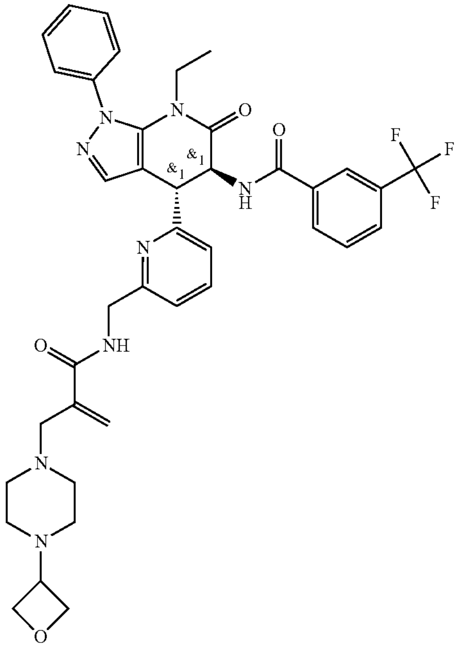 [SMILES: C=C(CN1CCN(C2COC2)CC1)C(=O)NCc1cccc([C@@H]2c3cnn(-c4ccccc4)c3N(CC)C(=O)[C@H]2NC(=O)c2cccc(C(F)(F)F)c2)n1] |

TABLE 1-continued
| Exemplary Compounds |
|---|
| I-217 |
| 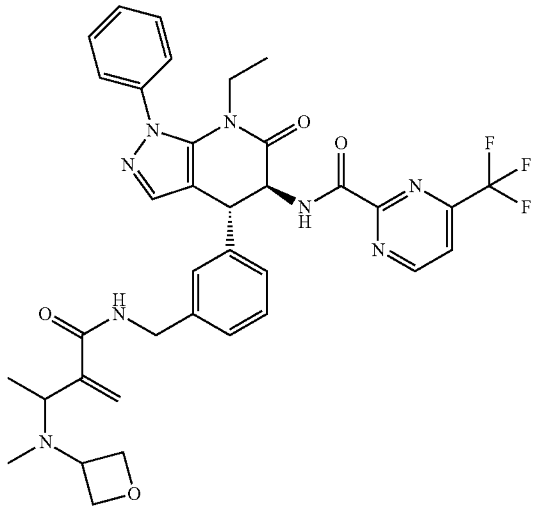 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N(C)C1COC1] |
| I-218 |
| 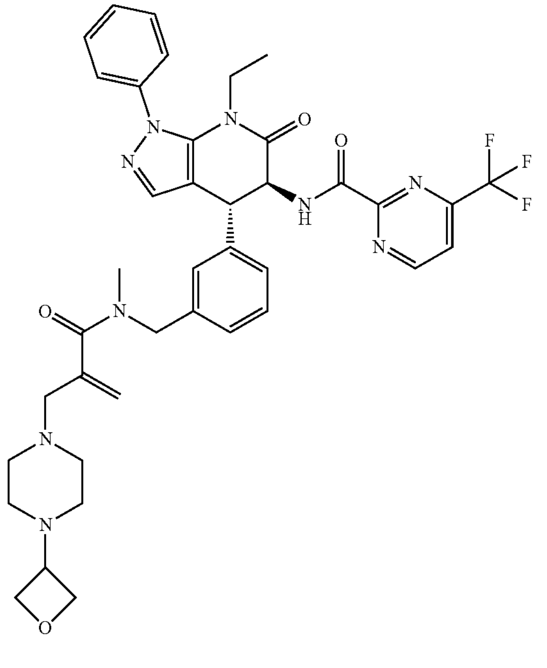 [SMILES: C=C(CN1CCN(C2COC2)CC1)C(=O)N(C)Cc1cccc([C@@H]2c3cnn(-c4ccccc4)c3N(CC)C(=O)[C@H]2NC(=O)c2nccc(C(F)(F)F)n2)c1] |

TABLE 1-continued
| Exemplary Compounds |
| --- |
I-219
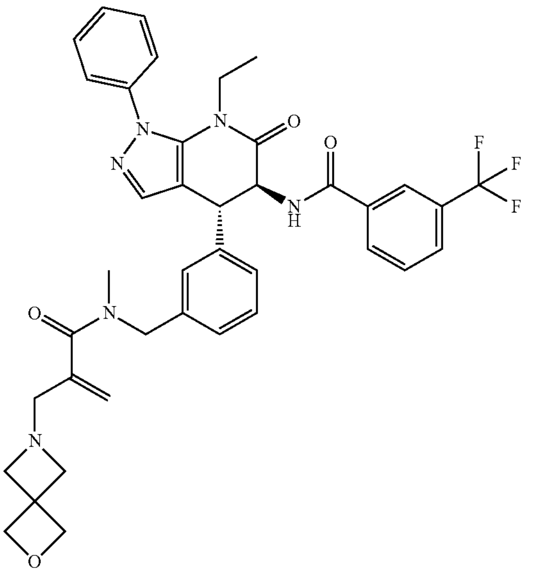
I-220
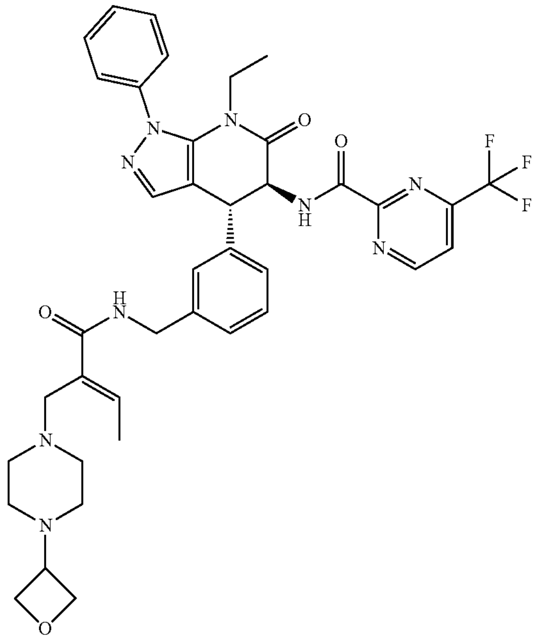 [SMILES: C/C=C(\CN1CCN(C2COC2)CC1)C(=O)NCc1cccc([C@@H]2c3cnn(-c4ccccc4)c3N(CC)C(=O)[C@H]2NC(=O)c2nccc(C(F)(F)F)n2)c1]

TABLE 1-continued
| Exemplary Compounds |
|---|
I-221
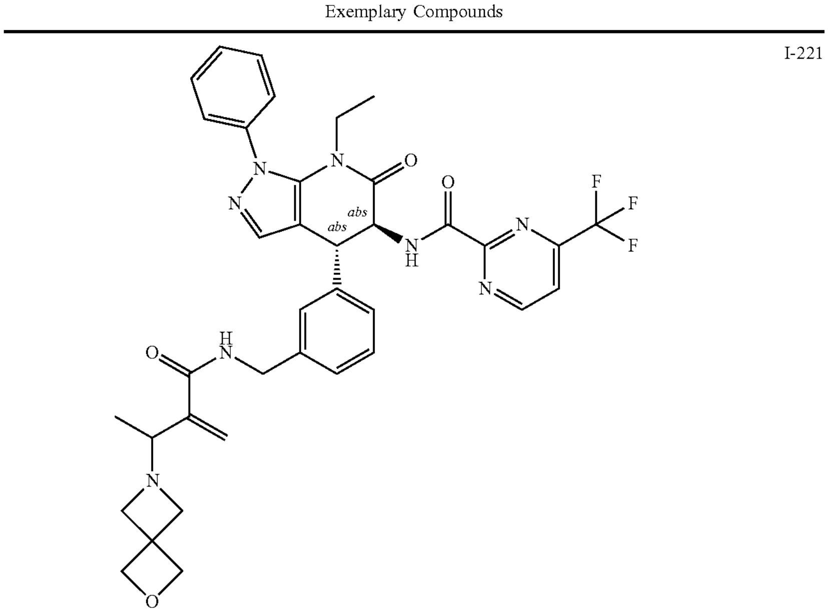
I-222
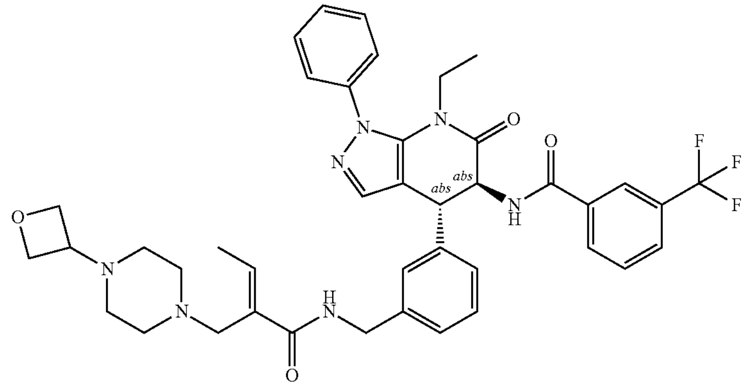 [SMILES: C/C=C(\CN1CCN(C2COC2)CC1)C(=O)NCc1cccc([C@@H]2c3cnn(-c4ccccc4)c3N(CC)C(=O)[C@H]2NC(=O)c2cccc(C(F)(F)F)c2)c1]
I-223
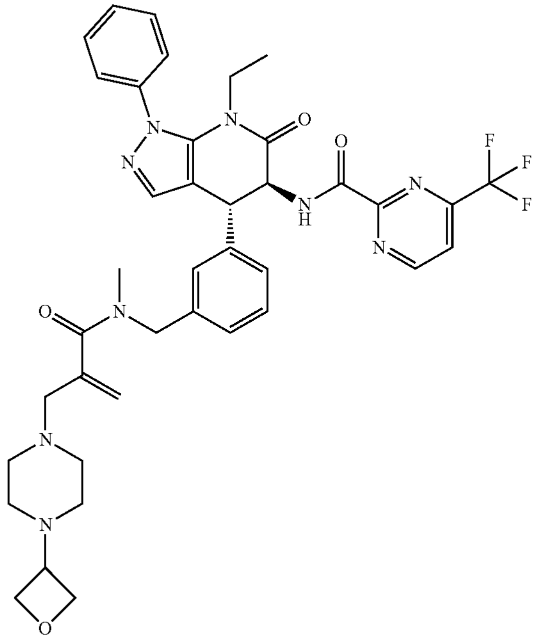 [SMILES: C=C(CN1CCN(C2COC2)CC1)C(=O)N(C)Cc1cccc([C@@H]2c3cnn(-c4ccccc4)c3N(CC)C(=O)[C@H]2NC(=O)c2nccc(C(F)(F)F)n2)c1]

TABLE 1-continued
Exemplary Compounds
I-224
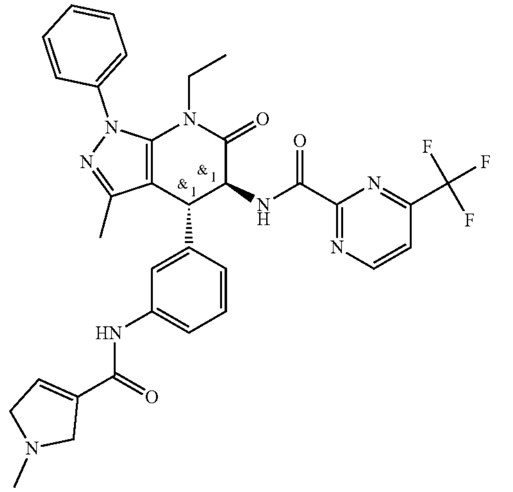 [SMILES: CCN1C(=O)[C@@H](NC(=O)c2nccc(C(F)(F)F)n2)[C@H](c2cccc(NC(=O)C3=CCN(C)C3)c2)c2c(C)nn(-c3ccccc3)c21]
I-225
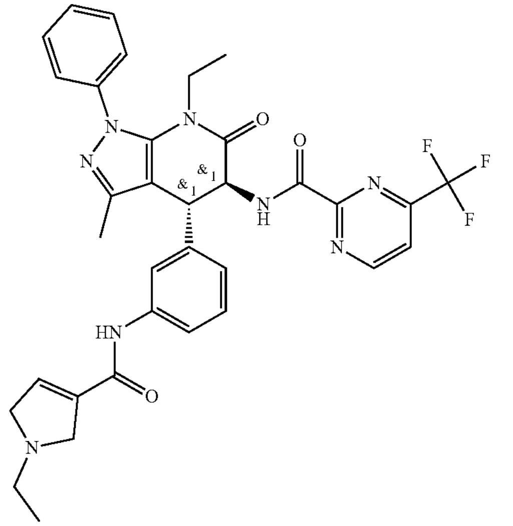 [SMILES: CCN1CC=C(C(=O)Nc2cccc([C@@H]3c4c(C)nn(-c5ccccc5)c4N(CC)C(=O)[C@H]3NC(=O)c3nccc(C(F)(F)F)n3)c2)C1]
I-226
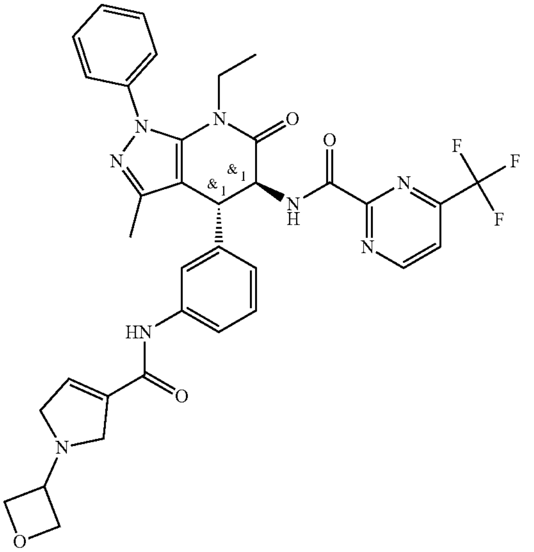 [SMILES: CCN1C(=O)[C@@H](NC(=O)c2nccc(C(F)(F)F)n2)[C@H](c2cccc(NC(=O)C3=CCN(C4COC4)C3)c2)c2c(C)nn(-c3ccccc3)c21]

TABLE 1-continued
Exemplary Compounds
I-227
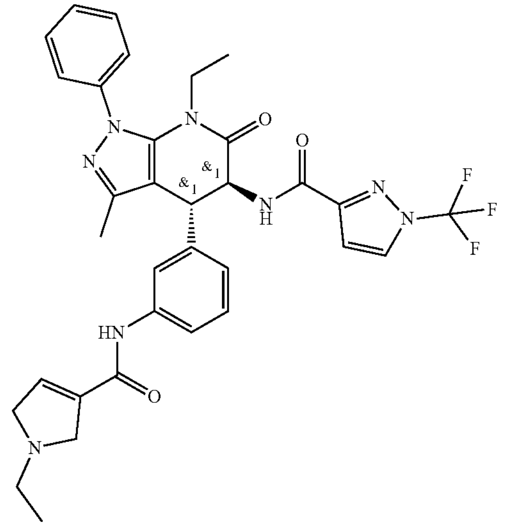 [SMILES: CCN1CC=C(C(=O)Nc2cccc([C@@H]3c4c(C)nn(-c5ccccc5)c4N(CC)C(=O)[C@H]3NC(=O)c3ccn(C(F)(F)F)n3)c2)C1]
I-228
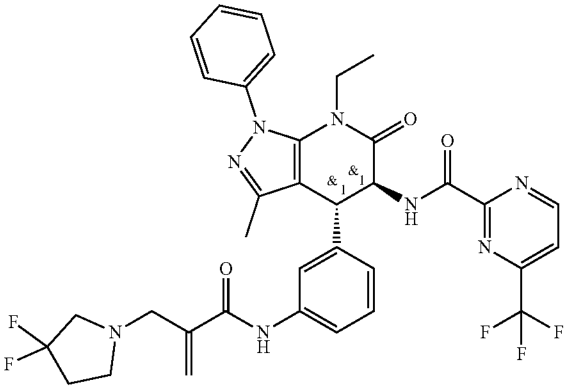 [SMILES: C=C(CN1CCC(F)(F)C1)C(=O)Nc1cccc([C@@H]2c3c(C)nn(-c4ccccc4)c3N(CC)C(=O)[C@H]2NC(=O)c2nccc(C(F)(F)F)n2)c1]
I-229
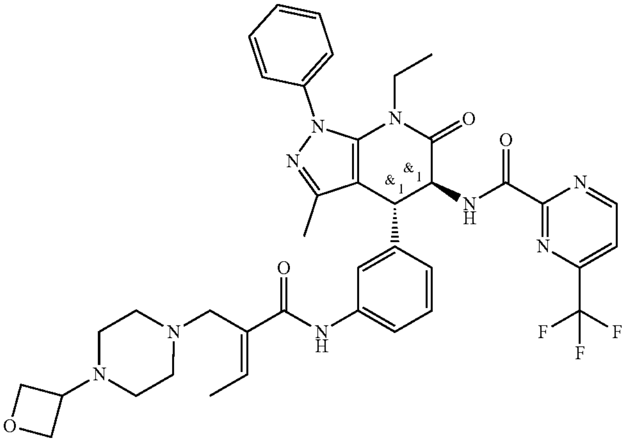 [SMILES: C/C=C(\CN1CCN(C2COC2)CC1)C(=O)Nc1cccc([C@@H]2c3c(C)nn(-c4ccccc4)c3N(CC)C(=O)[C@H]2NC(=O)c2nccc(C(F)(F)F)n2)c1]

TABLE 1-continued
| Exemplary Compounds |
|---|
I-230A
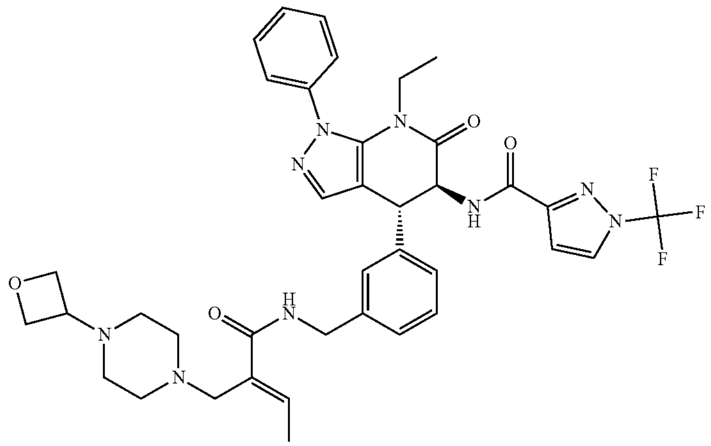 [SMILES: C/C=C(\CN1CCN(C2COC2)CC1)C(=O)NCc1cccc([C@@H]2c3cnn(-c4ccccc4)c3N(CC)C(=O)[C@H]2NC(=O)c2ccn(C(F)(F)F)n2)c1]
I-230B
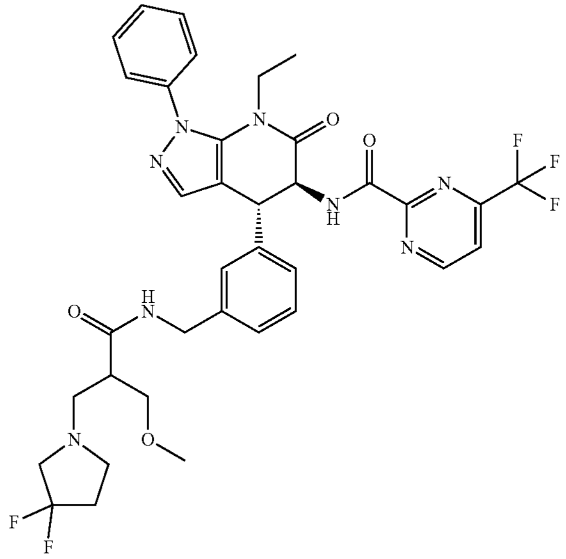 [SMILES: CCN1C(=O)[C@@H](NC(=O)c2nccc(C(F)(F)F)n2)[C@H](c2cccc(CNC(=O)C(COC)CN3CCC(F)(F)C3)c2)c2cnn(-c3ccccc3)c21]
I-231
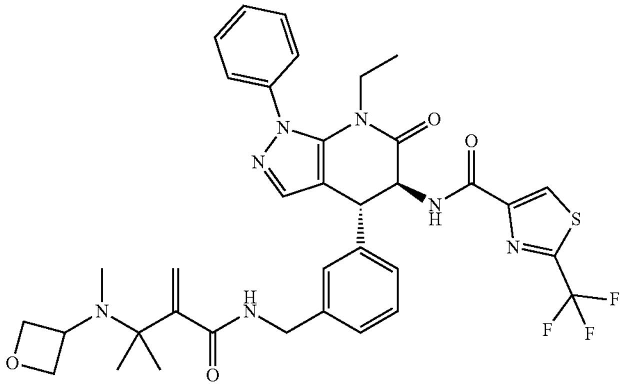 [SMILES: C=C(C(=O)NCc1cccc([C@@H]2c3cnn(-c4ccccc4)c3N(CC)C(=O)[C@H]2NC(=O)c2csc(C(F)(F)F)n2)c1)C(C)(C)N(C)C1COC1]

TABLE 1-continued
| Exemplary Compounds |
|---|
I-232
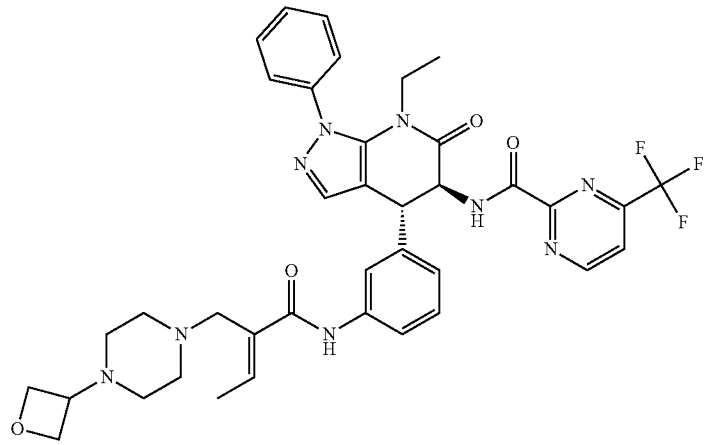 [SMILES: C/C=C(\CN1CCN(C2COC2)CC1)C(=O)Nc1cccc([C@@H]2c3cnn(-c4ccccc4)c3N(CC)C(=O)[C@H]2NC(=O)c2nccc(C(F)(F)F)n2)c1]
I-233
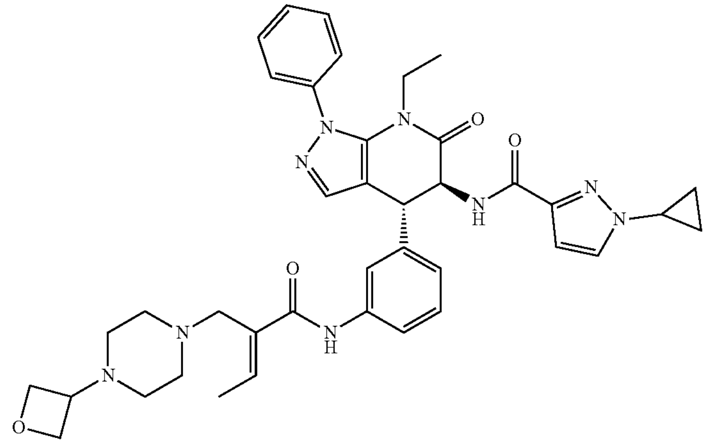 [SMILES: C/C=C(\CN1CCN(C2COC2)CC1)C(=O)Nc1cccc([C@@H]2c3cnn(-c4ccccc4)c3N(CC)C(=O)[C@H]2NC(=O)c2ccn(C3CC3)n2)c1]
I-234
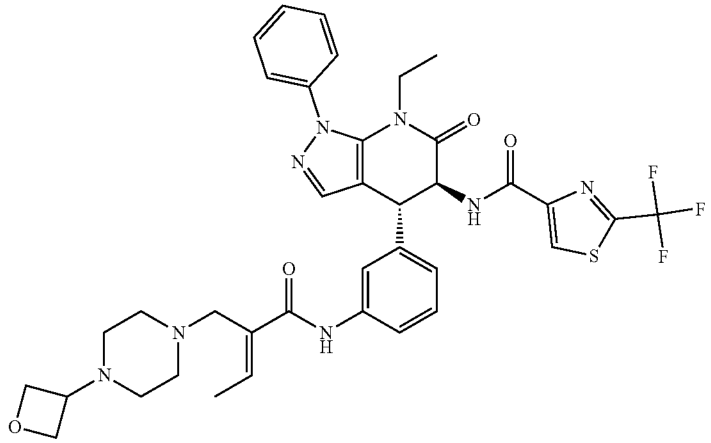 [SMILES: C/C=C(\CN1CCN(C2COC2)CC1)C(=O)Nc1cccc([C@@H]2c3cnn(-c4ccccc4)c3N(CC)C(=O)[C@H]2NC(=O)c2csc(C(F)(F)F)n2)c1]

TABLE 1-continued
| Exemplary Compounds |
|---|
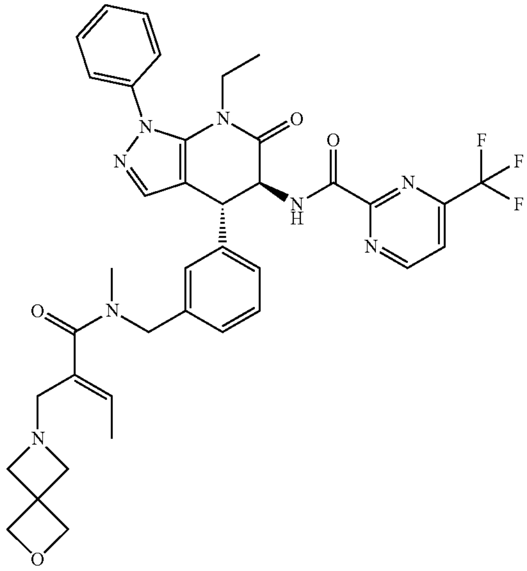 [SMILES: C/C=C(\CN1CC2(COC2)C1)C(=O)N(C)Cc1cccc([C@@H]2c3cnn(-c4ccccc4)c3N(CC)C(=O)[C@H]2NC(=O)c2nccc(C(F)(F)F)n2)c1]
I-235
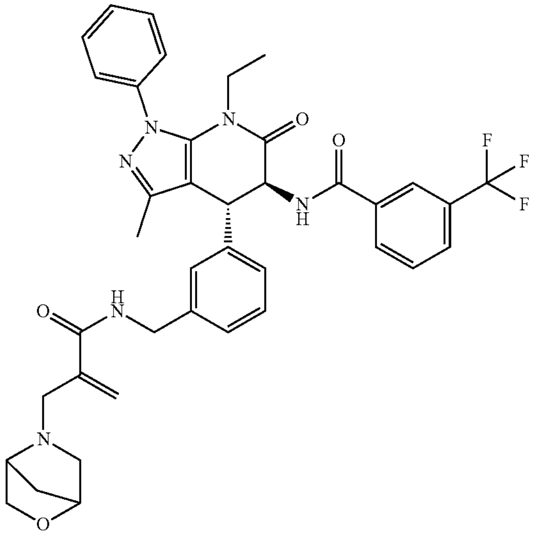 [SMILES: C=C(CN1CC2CC1CO2)C(=O)NCc1cccc([C@@H]2c3c(C)nn(-c4ccccc4)c3N(CC)C(=O)[C@H]2NC(=O)c2cccc(C(F)(F)F)c2)c1]
I-236
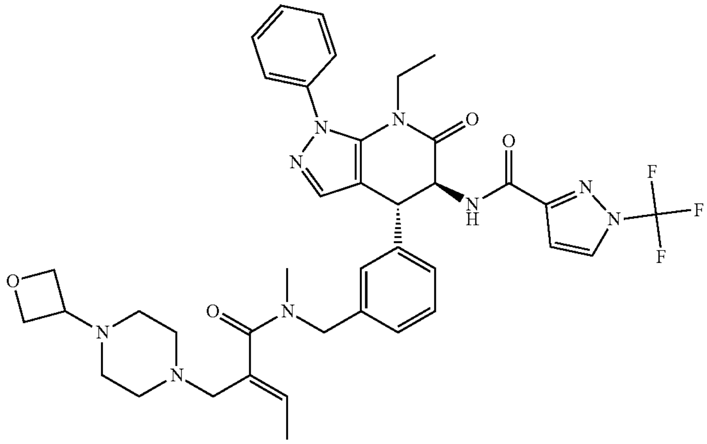 [SMILES: C/C=C(\CN1CCN(C2COC2)CC1)C(=O)N(C)Cc1cccc([C@@H]2c3cnn(-c4ccccc4)c3N(CC)C(=O)[C@H]2NC(=O)c2ccn(C(F)(F)F)n2)c1]
I-237

TABLE 1-continued
| Exemplary Compounds |
| --- |
| 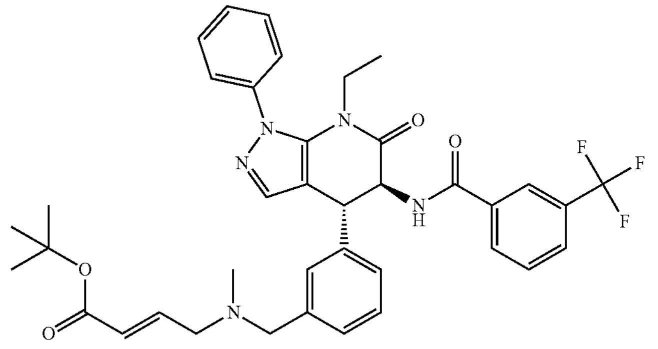 [SMILES: CCN1C(=O)[C@@H](NC(=O)c2cccc(C(F)(F)F)c2)[C@H](c2cccc(CN(C)C/C=C/C(=O)OC(C)(C)C)c2)c2cnn(-c3ccccc3)c21] I-238 |
| 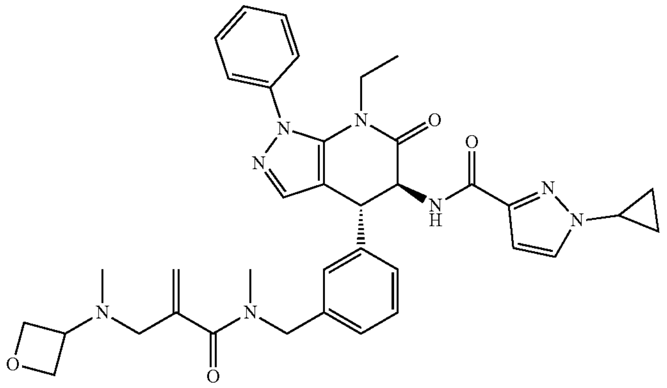 [SMILES: C=C(CN(C)C1COC1)C(=O)N(C)Cc1cccc([C@@H]2c3cnn(-c4ccccc4)c3N(CC)C(=O)[C@H]2NC(=O)c2ccn(C3CC3)n2)c1] I-239 |
| 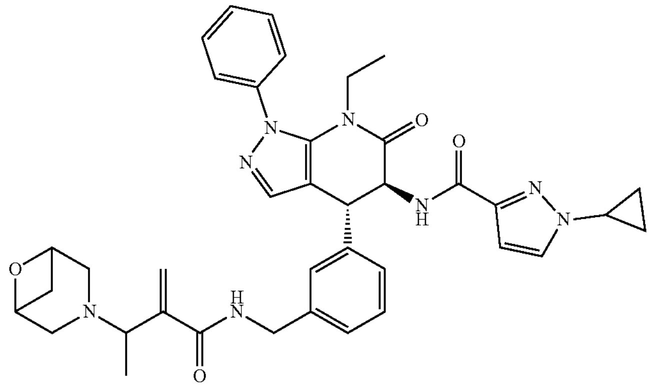 [SMILES: C=C(C(=O)NCc1cccc([C@@H]2c3cnn(-c4ccccc4)c3N(CC)C(=O)[C@H]2NC(=O)c2ccn(C3CC3)n2)c1)C(C)N1CC2CC(C1)O2] I-240 |
| 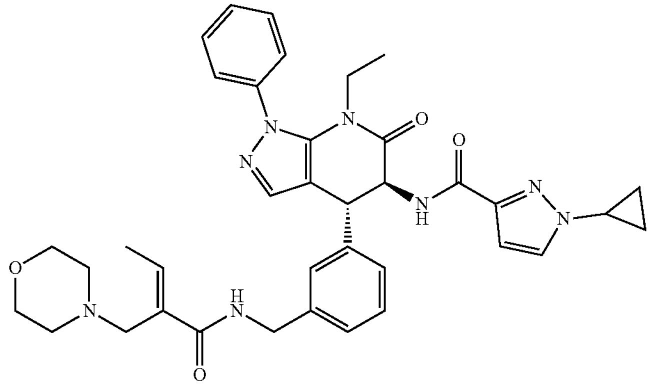 [SMILES: C/C=C(\CN1CCOCC1)C(=O)NCc1cccc([C@@H]2c3cnn(-c4ccccc4)c3N(CC)C(=O)[C@H]2NC(=O)c2ccn(C3CC3)n2)c1] I-241 |

TABLE 1-continued
| Exemplary Compounds |
|---|
| I-242 |
| 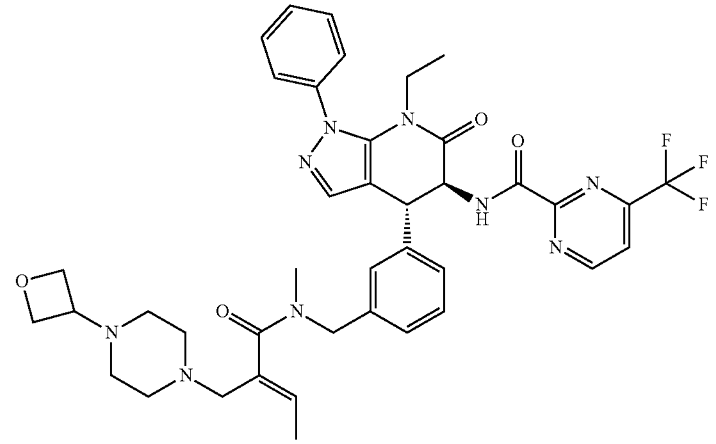 [SMILES: C/C=C(\CN1CCN(C2COC2)CC1)C(=O)N(C)Cc1cccc([C@@H]2c3cnn(-c4ccccc4)c3N(CC)C(=O)[C@H]2NC(=O)c2nccc(C(F)(F)F)n2)c1] |
| I-243 |
| 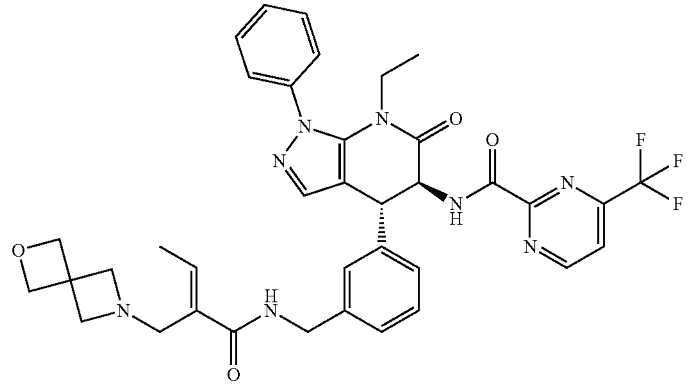 [SMILES: C/C=C(\CN1CC2(COC2)C1)C(=O)NCc1cccc([C@@H]2c3cnn(-c4ccccc4)c3N(CC)C(=O)[C@H]2NC(=O)c2nccc(C(F)(F)F)n2)c1] |
| I-244 |
| 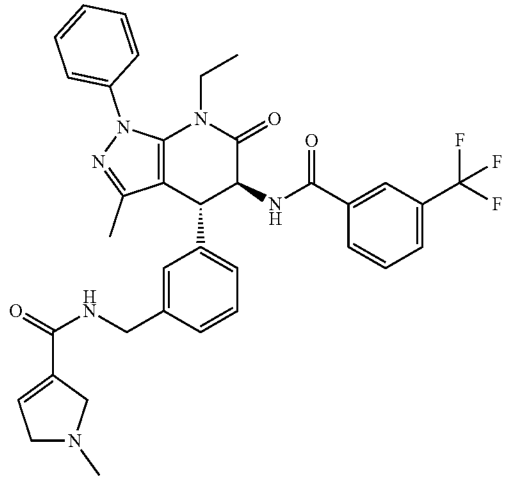 [SMILES: CCN1C(=O)[C@@H](NC(=O)c2cccc(C(F)(F)F)c2)[C@H](c2cccc(CNC(=O)C3=CCN(C)C3)c2)c2c(C)nn(-c3ccccc3)c21] |

TABLE 1-continued
| Exemplary Compounds |
| --- |
I-245
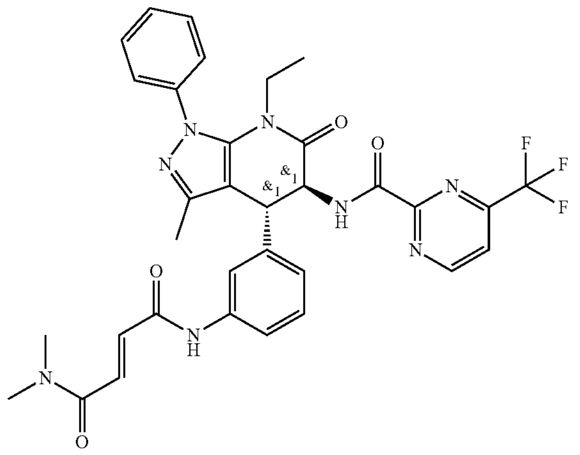 [SMILES: CCN1C(=O)[C@@H](NC(=O)c2nccc(C(F)(F)F)n2)[C@H](c2cccc(NC(=O)/C=C/C(=O)N(C)C)c2)c2c(C)nn(-c3ccccc3)c21]
I-246
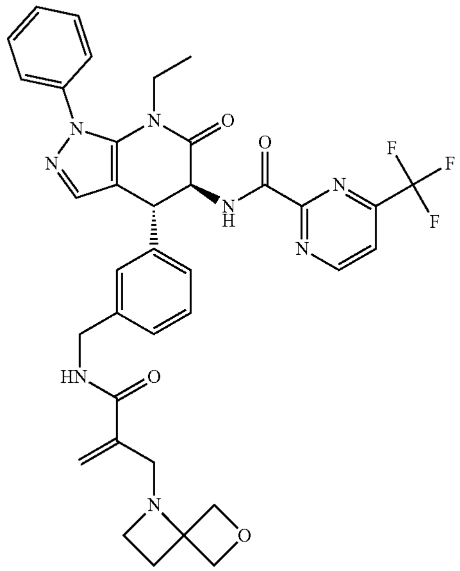 [SMILES: C=C(CN1CCC12COC2)C(=O)NCc1cccc([C@@H]2c3cnn(-c4ccccc4)c3N(CC)C(=O)[C@H]2NC(=O)c2nccc(C(F)(F)F)n2)c1]
I-247
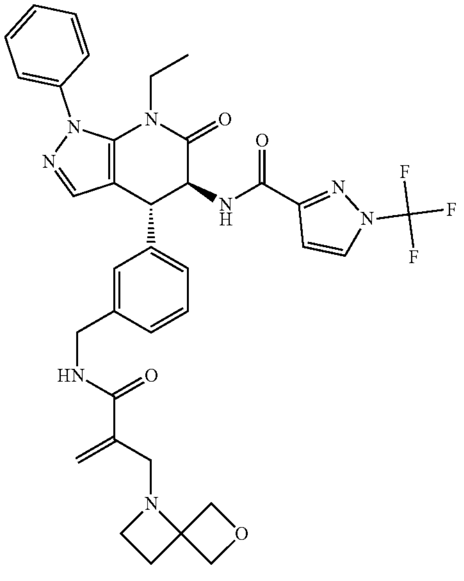 [SMILES: C=C(CN1CCC12COC2)C(=O)NCc1cccc([C@@H]2c3cnn(-c4ccccc4)c3N(CC)C(=O)[C@H]2NC(=O)c2ccn(C(F)(F)F)n2)c1]

TABLE 1-continued
| Exemplary Compounds |
| --- |
| I-248 |
| 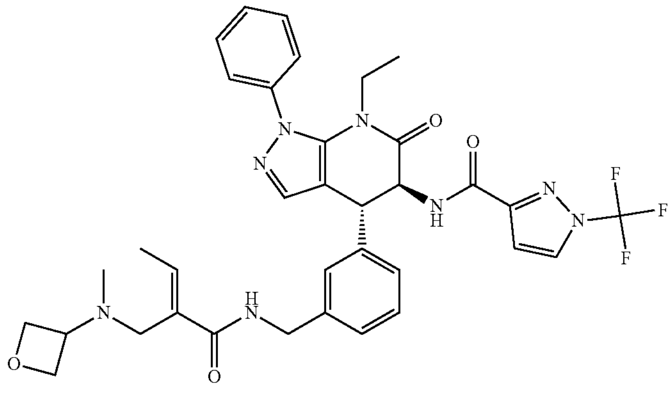 [SMILES: C/C=C(\CN(C)C1COC1)C(=O)NCc1cccc([C@@H]2c3cnn(-c4ccccc4)c3N(CC)C(=O)[C@H]2NC(=O)c2ccn(C(F)(F)F)n2)c1] |
| I-249 |
| 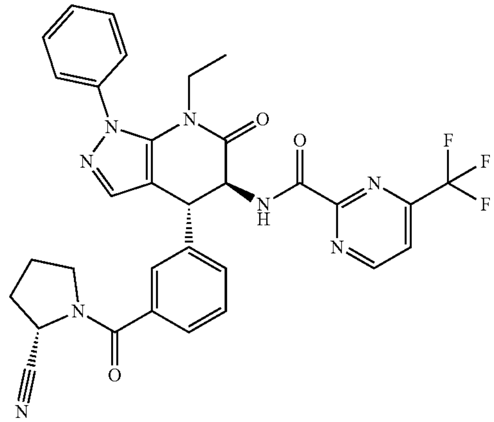 [SMILES: CCN1C(=O)[C@@H](NC(=O)c2nccc(C(F)(F)F)n2)[C@H](c2cccc(C(=O)N3CCC[C@H]3C#N)c2)c2cnn(-c3ccccc3)c21] |
| I-250 |
| 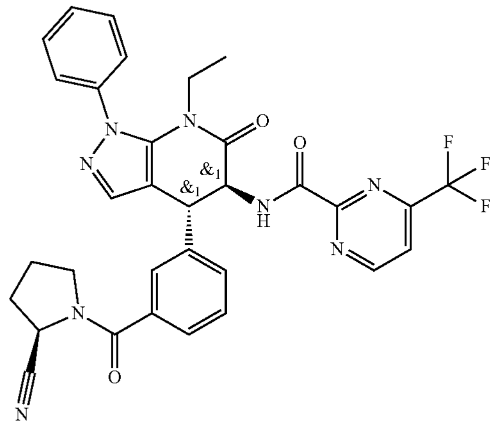 [SMILES: CCN1C(=O)[C@@H](NC(=O)c2nccc(C(F)(F)F)n2)[C@H](c2cccc(C(=O)N3CCC[C@@H]3C#N)c2)c2cnn(-c3ccccc3)c21] |

TABLE 1-continued
| Exemplary Compounds |
|---|
I-251
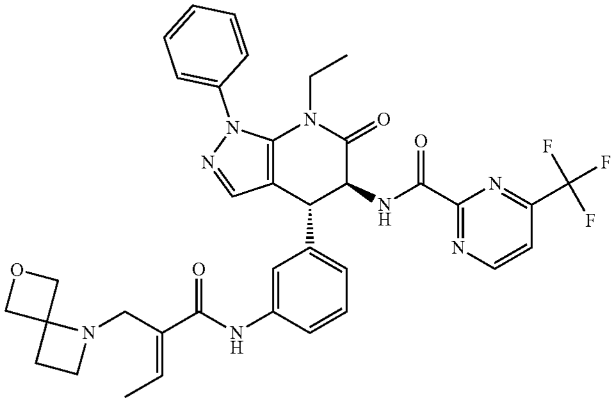 [SMILES: C/C=C(\CN1CCC12COC2)C(=O)Nc1cccc([C@@H]2c3cnn(-c4ccccc4)c3N(CC)C(=O)[C@H]2NC(=O)c2nccc(C(F)(F)F)n2)c1]
I-252
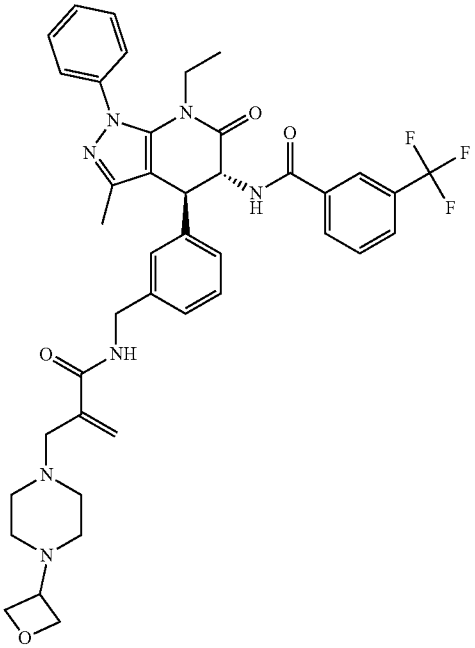 [SMILES: C=C(CN1CCN(C2COC2)CC1)C(=O)NCc1cccc([C@H]2c3c(C)nn(-c4ccccc4)c3N(CC)C(=O)[C@@H]2NC(=O)c2cccc(C(F)(F)F)c2)c1]

TABLE 1-continued
Exemplary Compounds
I-253
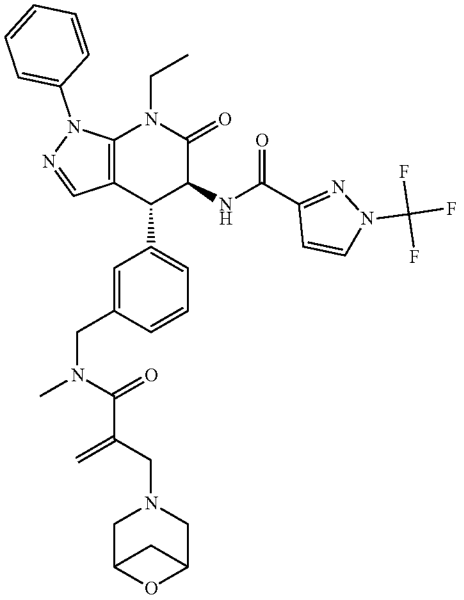 [SMILES: C=C(CN1CC2CC(C1)O2)C(=O)N(C)Cc1cccc([C@@H]2c3cnn(-c4ccccc4)c3N(CC)C(=O)[C@H]2NC(=O)c2ccn(C(F)(F)F)n2)c1]
I-254
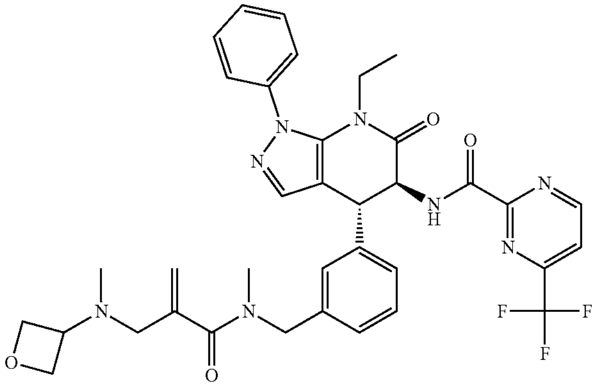 [SMILES: C=C(CN(C)C1COC1)C(=O)N(C)Cc1cccc([C@@H]2c3cnn(-c4ccccc4)c3N(CC)C(=O)[C@H]2NC(=O)c2nccc(C(F)(F)F)n2)c1]
I-255
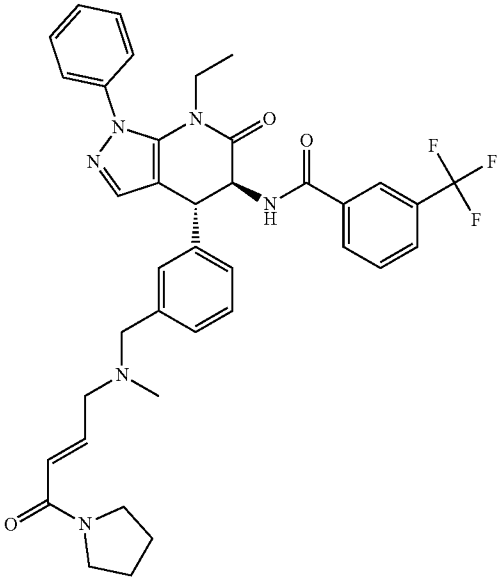 [SMILES: CCN1C(=O)[C@@H](NC(=O)c2cccc(C(F)(F)F)c2)[C@H](c2cccc(CN(C)C/C=C/C(=O)N3CCCC3)c2)c2cnn(-c3ccccc3)c21]

TABLE 1-continued
| Exemplary Compounds |
| --- |
| I-256 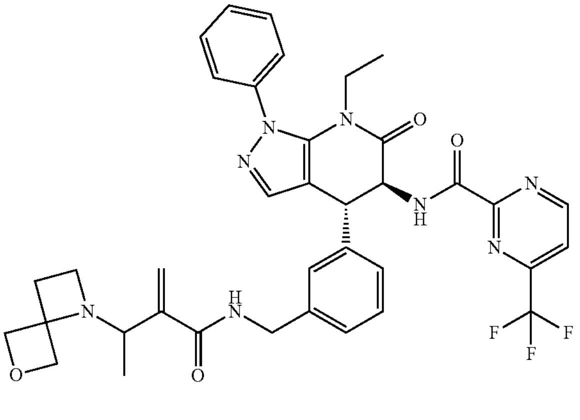 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N1CCC12COC2] |
| I-257 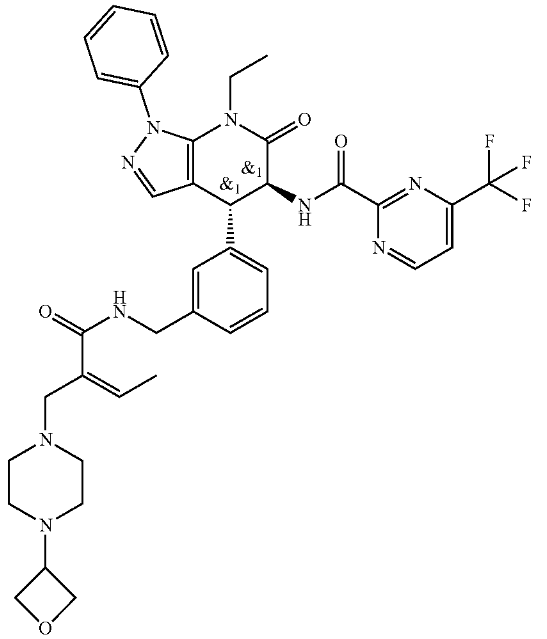 [SMILES: C/C=C(/CN1CCN(C2COC2)CC1)C(=O)NCc1cccc([C@@H]2c3cnn(-c4ccccc4)c3N(CC)C(=O)[C@H]2NC(=O)c2nccc(C(F)(F)F)n2)c1] |
| I-258 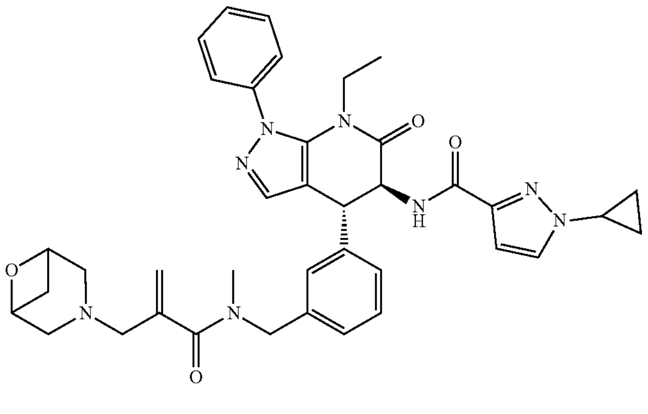 [SMILES: C=C(CN1CC2CC(C1)O2)C(=O)N(C)Cc1cccc([C@@H]2c3cnn(-c4ccccc4)c3N(CC)C(=O)[C@H]2NC(=O)c2ccn(C3CC3)n2)c1] |

TABLE 1-continued
| Exemplary Compounds |
|---|
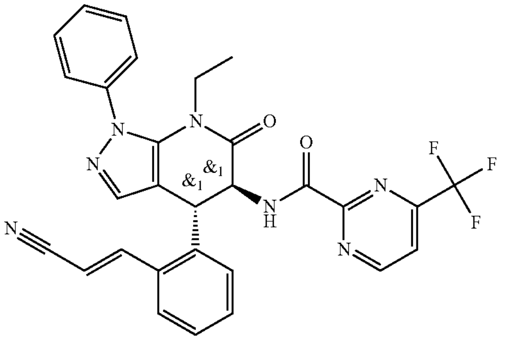 [SMILES: CCN1C(=O)[C@@H](NC(=O)c2nccc(C(F)(F)F)n2)[C@H](c2ccccc2/C=C/C#N)c2cnn(-c3ccccc3)c21]
I-259
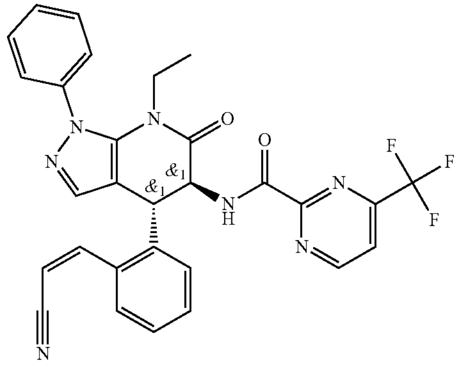 [SMILES: CCN1C(=O)[C@@H](NC(=O)c2nccc(C(F)(F)F)n2)[C@H](c2ccccc2/C=C\C#N)c2cnn(-c3ccccc3)c21]
I-260
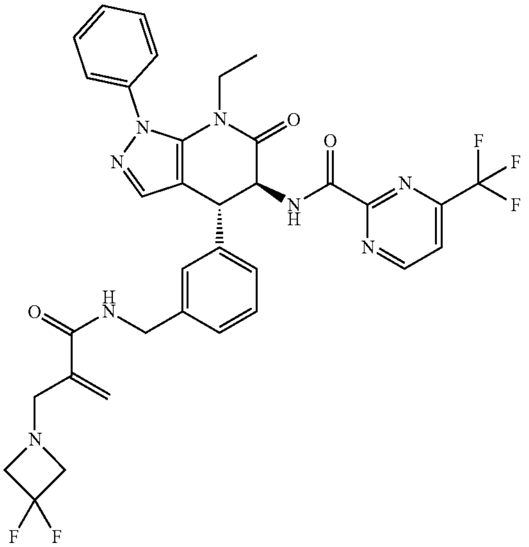 [SMILES: C=C(CN1CC(F)(F)C1)C(=O)NCc1cccc([C@@H]2c3cnn(-c4ccccc4)c3N(CC)C(=O)[C@H]2NC(=O)c2nccc(C(F)(F)F)n2)c1]
I-261

TABLE 1-continued
| Exemplary Compounds |
|---|
I-262
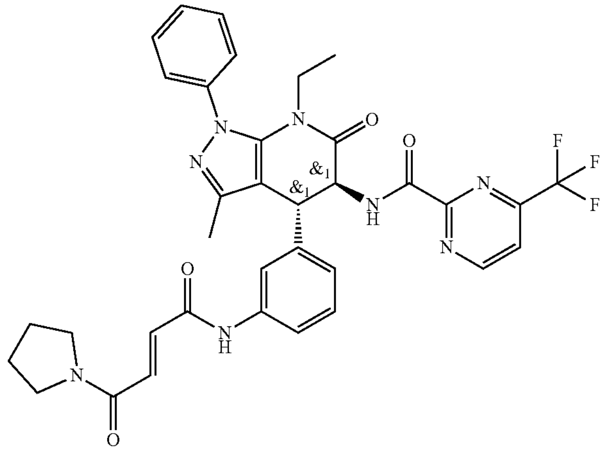 [SMILES: CCN1C(=O)[C@@H](NC(=O)c2nccc(C(F)(F)F)n2)[C@H](c2cccc(NC(=O)/C=C/C(=O)N3CCCC3)c2)c2c(C)nn(-c3ccccc3)c21]
I-263
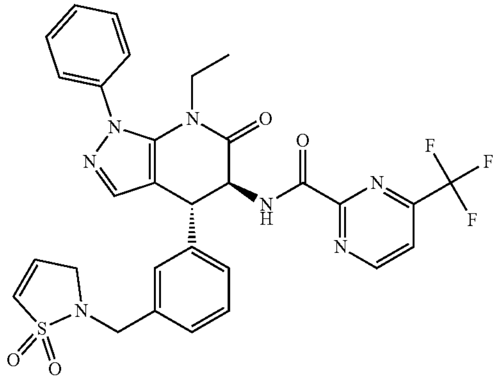 [SMILES: CCN1C(=O)[C@@H](NC(=O)c2nccc(C(F)(F)F)n2)[C@H](c2cccc(CN3CC=CS3(=O)=O)c2)c2cnn(-c3ccccc3)c21]
I-264
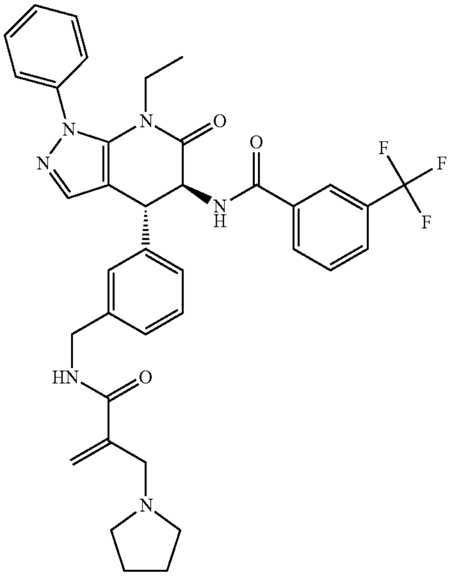 [SMILES: C=C(CN1CCCC1)C(=O)NCc1cccc([C@@H]2c3cnn(-c4ccccc4)c3N(CC)C(=O)[C@H]2NC(=O)c2cccc(C(F)(F)F)c2)c1]

TABLE 1-continued
Exemplary Compounds
I-265
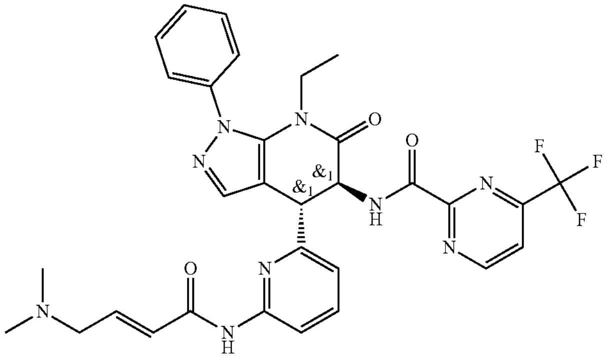 [SMILES: CCN1C(=O)[C@@H](NC(=O)c2nccc(C(F)(F)F)n2)[C@H](c2cccc(NC(=O)/C=C/CN(C)C)n2)c2cnn(-c3ccccc3)c21]
I-266
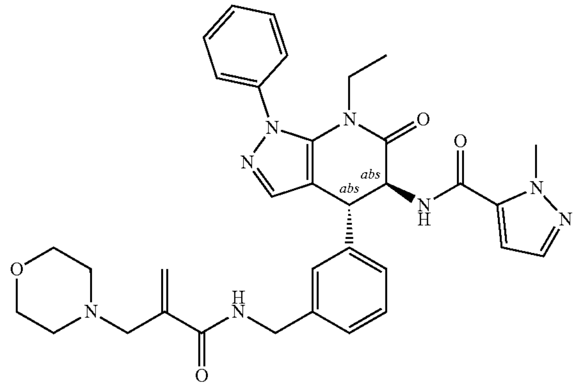 [SMILES: C=C(CN1CCOCC1)C(=O)NCc1cccc([C@@H]2c3cnn(-c4ccccc4)c3N(CC)C(=O)[C@H]2NC(=O)c2ccnn2C)c1]
I-277
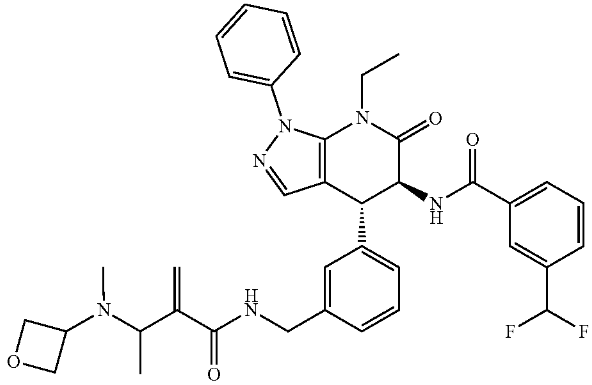 [SMILES: C=C(C(=O)NCc1cccc([C@@H]2c3cnn(-c4ccccc4)c3N(CC)C(=O)[C@H]2NC(=O)c2cccc(C(F)F)c2)c1)C(C)N(C)C1COC1]
I-278
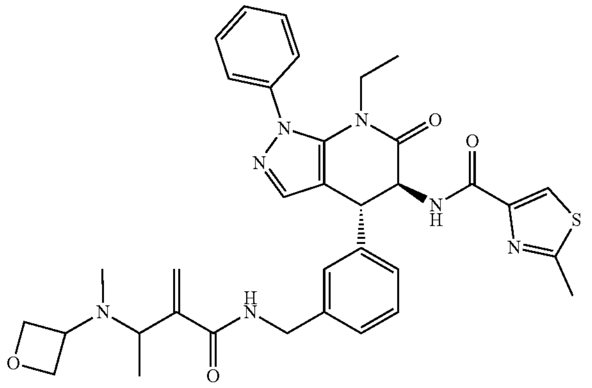 [SMILES: C=C(C(=O)NCc1cccc([C@@H]2c3cnn(-c4ccccc4)c3N(CC)C(=O)[C@H]2NC(=O)c2csc(C)n2)c1)C(C)N(C)C1COC1]

TABLE 1-continued
| Exemplary Compounds |
|---|
I-279
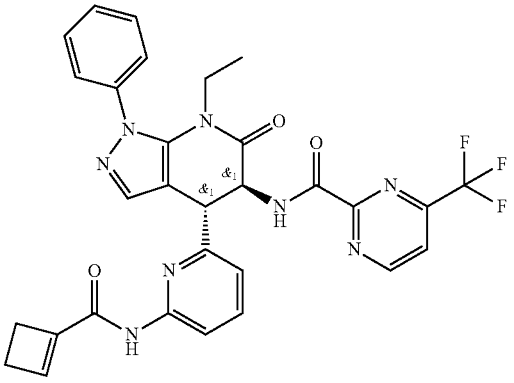 [SMILES: CCN1C(=O)[C@@H](NC(=O)c2nccc(C(F)(F)F)n2)[C@H](c2cccc(NC(=O)C3=CCC3)n2)c2cnn(-c3ccccc3)c21]
I-280
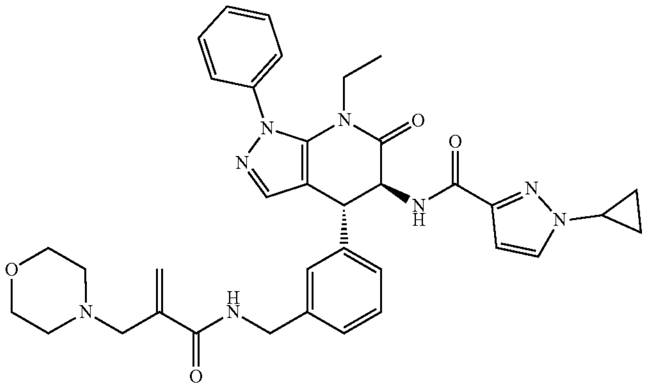 [SMILES: C=C(CN1CCOCC1)C(=O)NCc1cccc([C@@H]2c3cnn(-c4ccccc4)c3N(CC)C(=O)[C@H]2NC(=O)c2ccn(C3CC3)n2)c1]
I-281
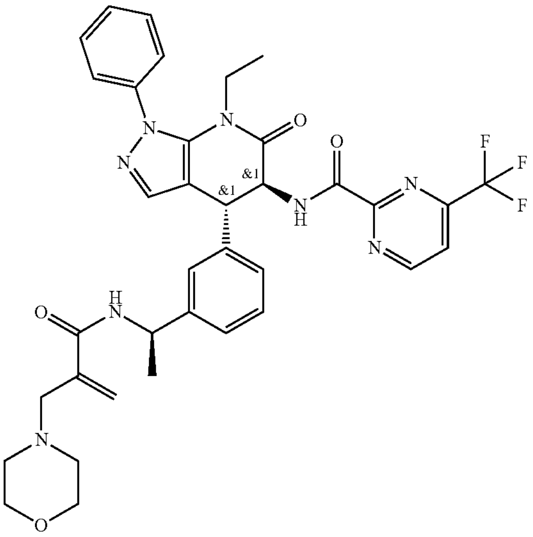 [SMILES: C=C(CN1CCOCC1)C(=O)N[C@H](C)c1cccc([C@@H]2c3cnn(-c4ccccc4)c3N(CC)C(=O)[C@H]2NC(=O)c2nccc(C(F)(F)F)n2)c1]

TABLE 1-continued
| Exemplary Compounds |
| --- |
| I-282 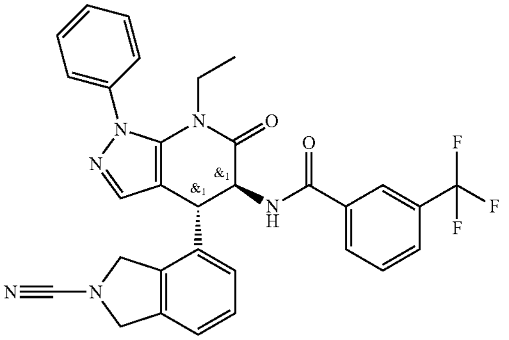 [SMILES: CCN1C(=O)[C@@H](NC(=O)c2cccc(C(F)(F)F)c2)[C@H](c2cccc3c2CN(C#N)C3)c2cnn(-c3ccccc3)c21] |
| I-283 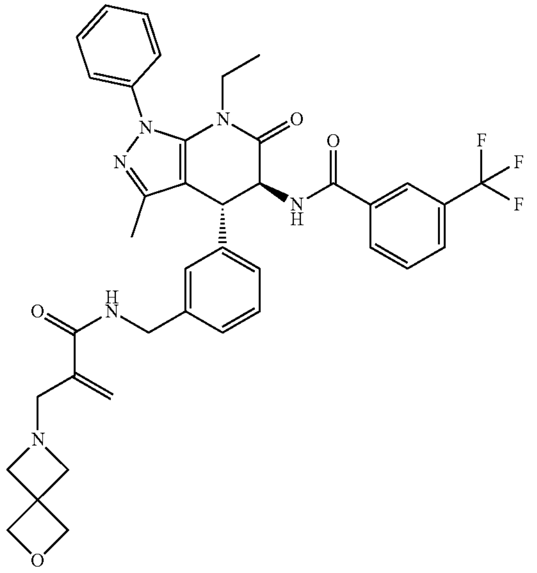 [SMILES: C=C(CN1CC2(COC2)C1)C(=O)NCc1cccc([C@@H]2c3c(C)nn(-c4ccccc4)c3N(CC)C(=O)[C@H]2NC(=O)c2cccc(C(F)(F)F)c2)c1] |
| I-284 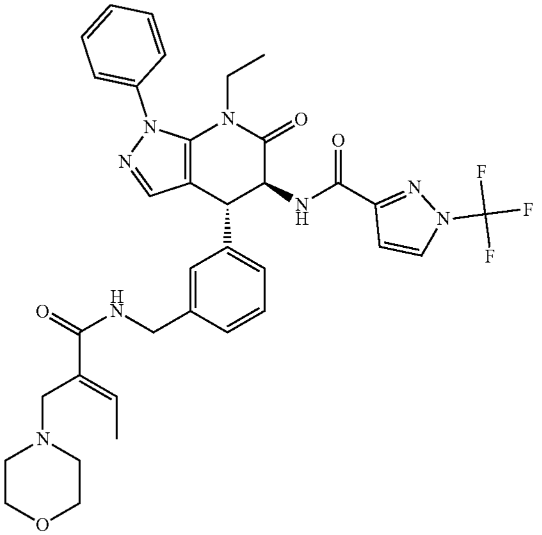 [SMILES: C/C=C(\CN1CCOCC1)C(=O)NCc1cccc([C@@H]2c3cnn(-c4ccccc4)c3N(CC)C(=O)[C@H]2NC(=O)c2ccn(C(F)(F)F)n2)c1] |

TABLE 1-continued
| Exemplary Compounds |
|---|
I-285
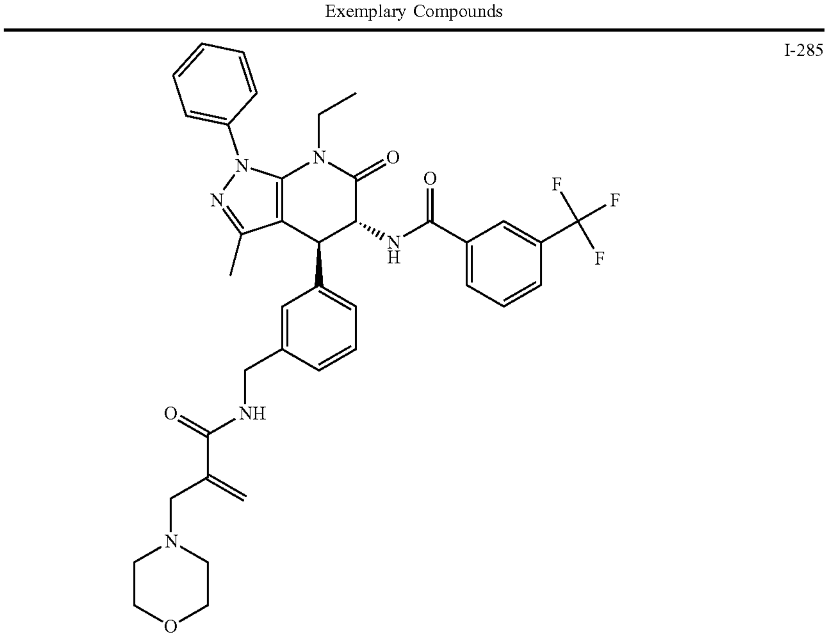
I-286
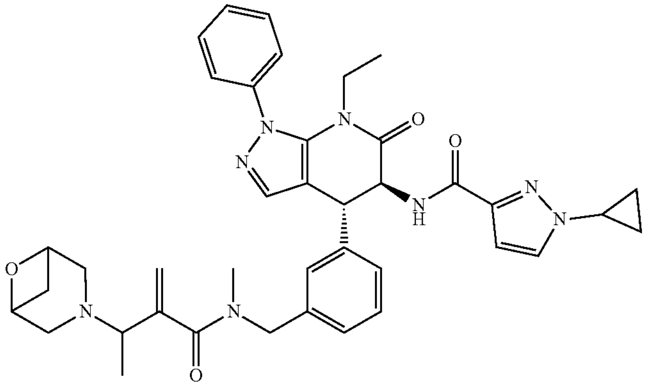 [SMILES: C=C(C(=O)N(C)Cc1cccc([C@@H]2c3cnn(-c4ccccc4)c3N(CC)C(=O)[C@H]2NC(=O)c2ccn(C3CC3)n2)c1)C(C)N1CC2CC(C1)O2]
I-287
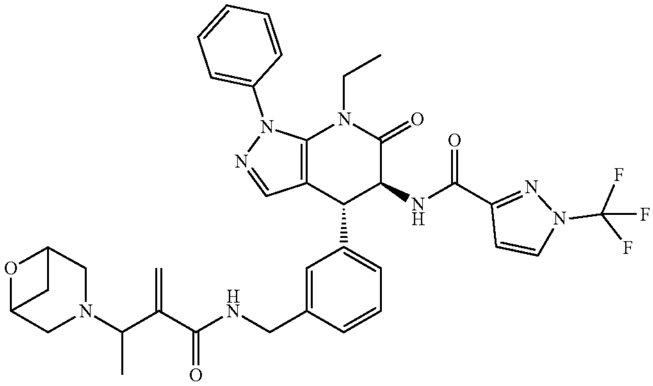 [SMILES: C=C(C(=O)NCc1cccc([C@@H]2c3cnn(-c4ccccc4)c3N(CC)C(=O)[C@H]2NC(=O)c2ccn(C(F)(F)F)n2)c1)C(C)N1CC2CC(C1)O2]

TABLE 1-continued
| Exemplary Compounds |
| --- |
| I-288 |
| 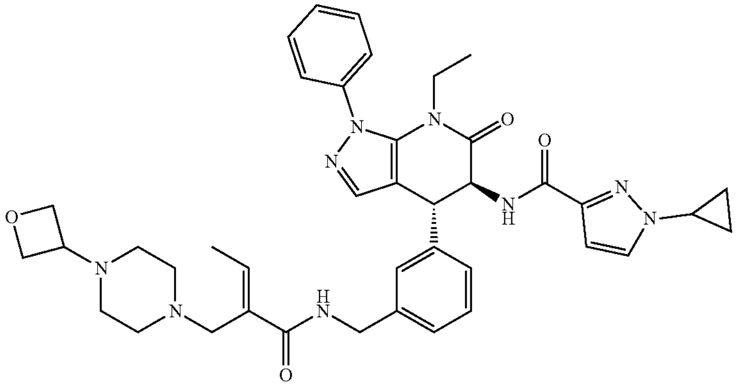 [SMILES: C/C=C(\CN1CCN(C2COC2)CC1)C(=O)NCc1cccc([C@@H]2c3cnn(-c4ccccc4)c3N(CC)C(=O)[C@H]2NC(=O)c2ccn(C3CC3)n2)c1] |
| I-289 |
| 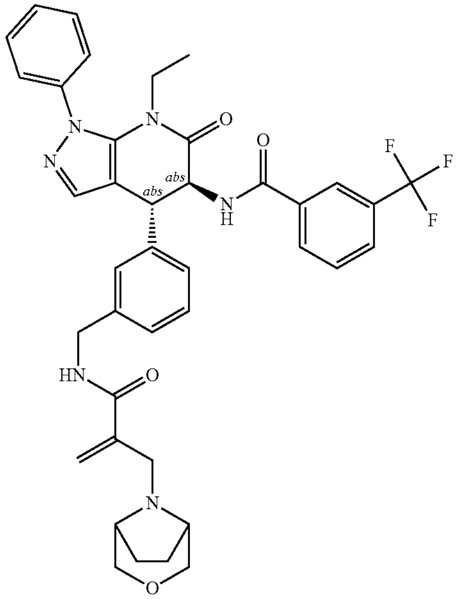 [SMILES: C=C(CN1C2CCC1COC2)C(=O)NCc1cccc([C@@H]2c3cnn(-c4ccccc4)c3N(CC)C(=O)[C@H]2NC(=O)c2cccc(C(F)(F)F)c2)c1] |
| I-290 |
| 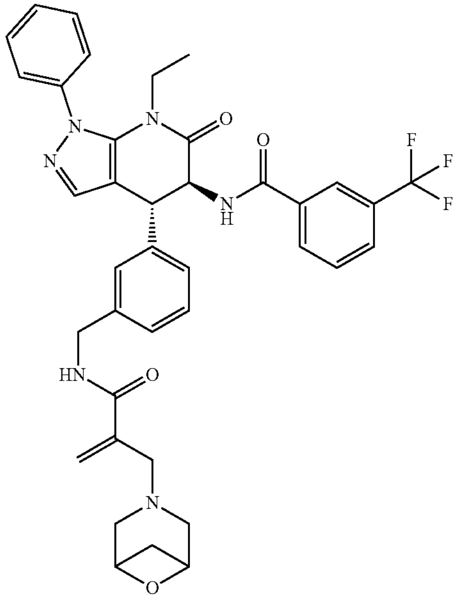 [SMILES: C=C(CN1CC2CC(C1)O2)C(=O)NCc1cccc([C@@H]2c3cnn(-c4ccccc4)c3N(CC)C(=O)[C@H]2NC(=O)c2cccc(C(F)(F)F)c2)c1] |

TABLE 1-continued
| Exemplary Compounds |
|---|
I-291
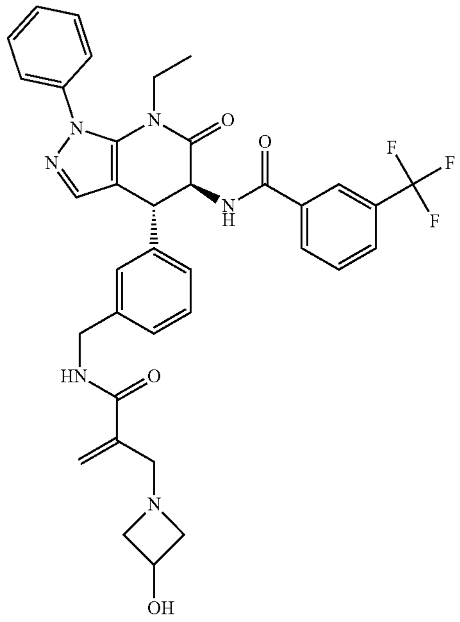 [SMILES: C=C(CN1CC(O)C1)C(=O)NCc1cccc([C@@H]2c3cnn(-c4ccccc4)c3N(CC)C(=O)[C@H]2NC(=O)c2cccc(C(F)(F)F)c2)c1]
I-292
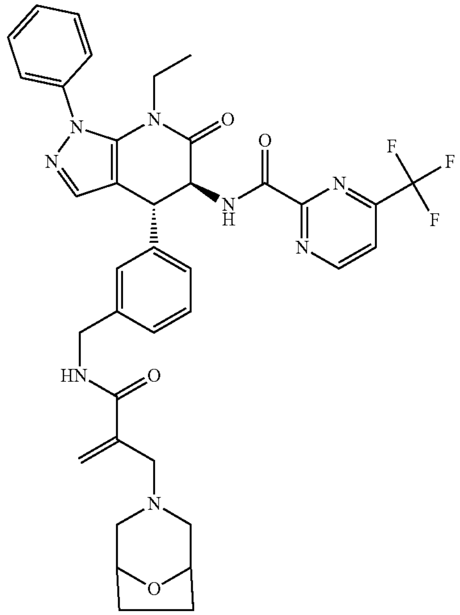 [SMILES: C=C(CN1CC2CCC(C1)O2)C(=O)NCc1cccc([C@@H]2c3cnn(-c4ccccc4)c3N(CC)C(=O)[C@H]2NC(=O)c2nccc(C(F)(F)F)n2)c1]

TABLE 1-continued
| Exemplary Compounds |
| --- |
I-293
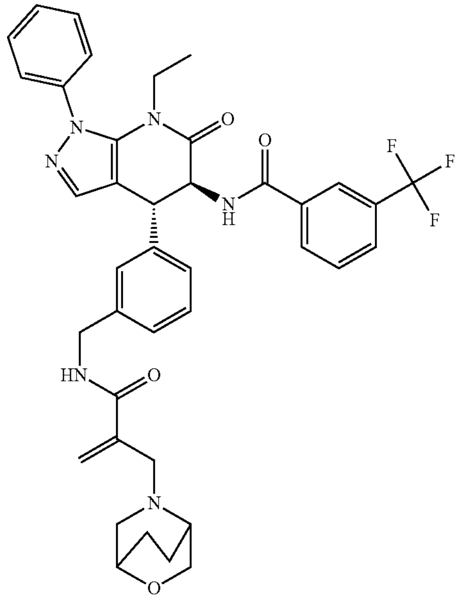 [SMILES: C=C(CN1CC2CCC1CO2)C(=O)NCc1cccc([C@@H]2c3cnn(-c4ccccc4)c3N(CC)C(=O)[C@H]2NC(=O)c2cccc(C(F)(F)F)c2)c1]
I-294
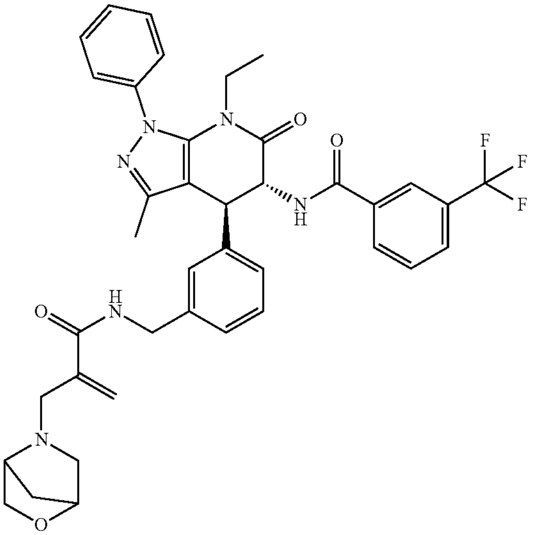 [SMILES: C=C(CN1CC2CC1CO2)C(=O)NCc1cccc([C@H]2c3c(C)nn(-c4ccccc4)c3N(CC)C(=O)[C@@H]2NC(=O)c2cccc(C(F)(F)F)c2)c1]

TABLE 1-continued
| Exemplary Compounds |
|---|
| I-295<br>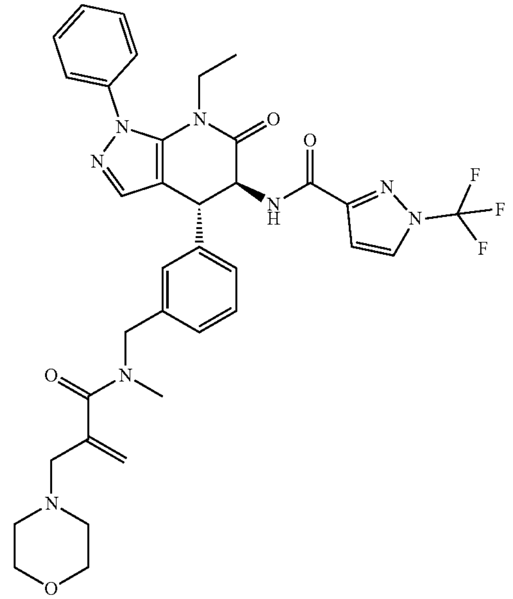 [SMILES: C=C(CN1CCOCC1)C(=O)N(C)Cc1cccc([C@@H]2c3cnn(-c4ccccc4)c3N(CC)C(=O)[C@H]2NC(=O)c2ccn(C(F)(F)F)n2)c1] |
| I-296<br>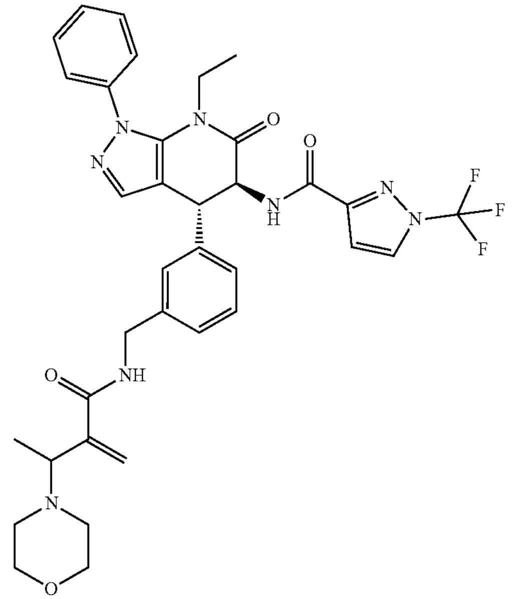 [SMILES: C=C(C(=O)NCc1cccc([C@@H]2c3cnn(-c4ccccc4)c3N(CC)C(=O)[C@H]2NC(=O)c2ccn(C(F)(F)F)n2)c1)C(C)N1CCOCC1] |
| I-297<br>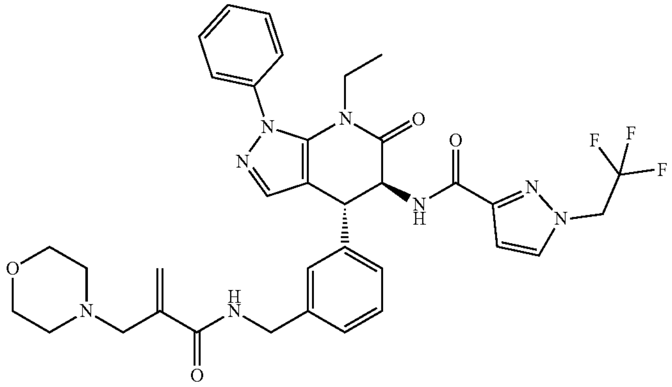 [SMILES: C=C(CN1CCOCC1)C(=O)NCc1cccc([C@@H]2c3cnn(-c4ccccc4)c3N(CC)C(=O)[C@H]2NC(=O)c2ccn(CC(F)(F)F)n2)c1] |

TABLE 1-continued
| Exemplary Compounds |
|---|
| I-298 |
| 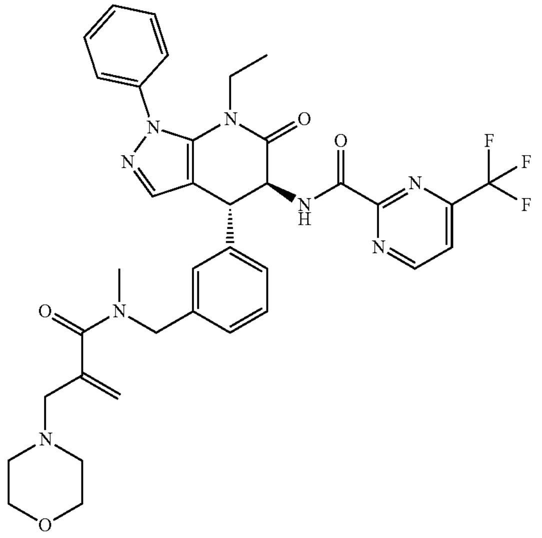 [SMILES: C=C(CN1CCOCC1)C(=O)N(C)Cc1cccc([C@@H]2c3cnn(-c4ccccc4)c3N(CC)C(=O)[C@H]2NC(=O)c2nccc(C(F)(F)F)n2)c1] |
| I-299 |
| 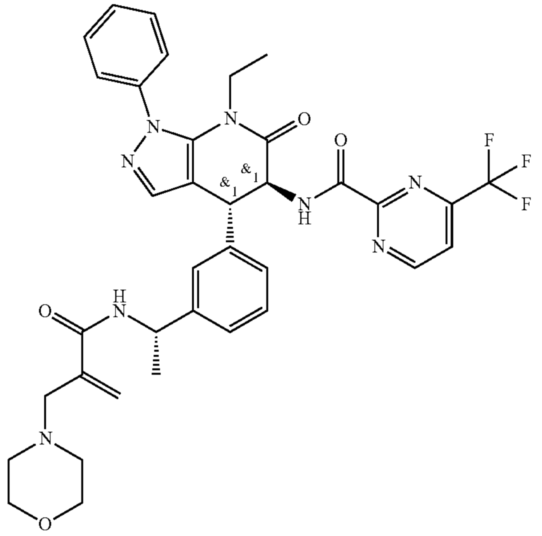 [SMILES: C=C(CN1CCOCC1)C(=O)N[C@@H](C)c1cccc([C@@H]2c3cnn(-c4ccccc4)c3N(CC)C(=O)[C@H]2NC(=O)c2nccc(C(F)(F)F)n2)c1] |
| I-300 |
| 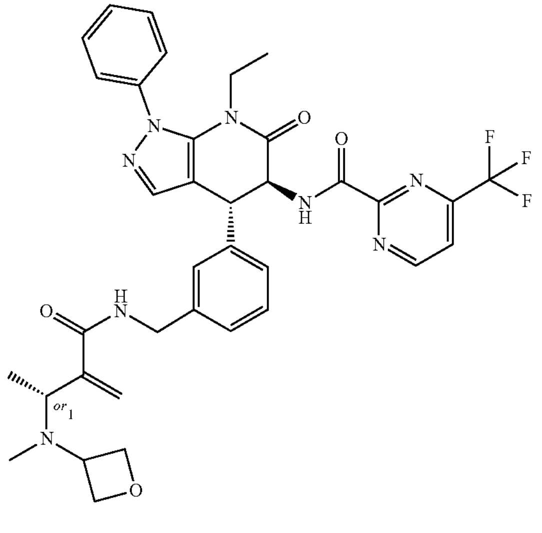 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)[C@@H](C)N(C)C1COC1] |

TABLE 1-continued
| Exemplary Compounds |
| --- |
I-301'
I-301
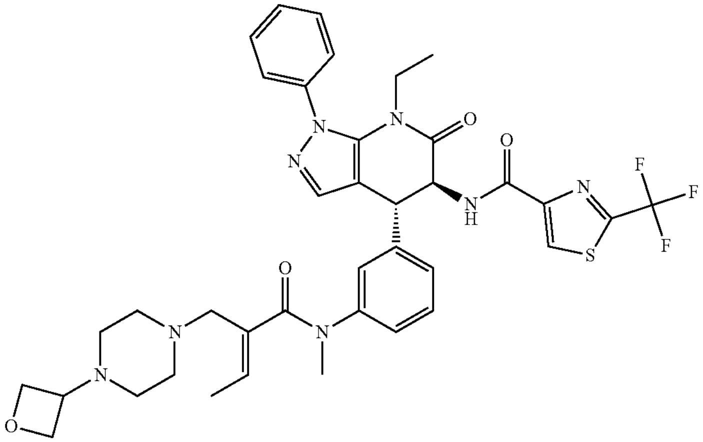
I-301'trans I-301 cis
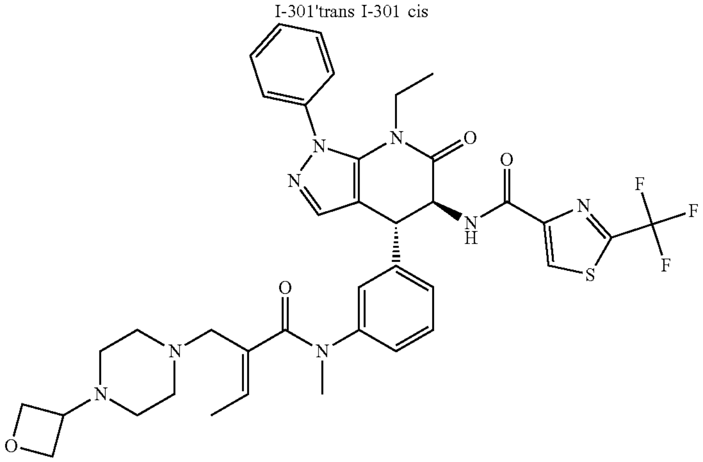
I-302
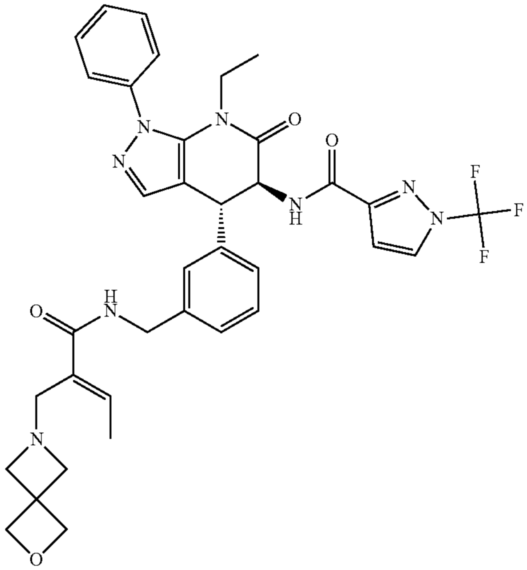 [SMILES: C/C=C(\CN1CC2(COC2)C1)C(=O)NCc1cccc([C@@H]2c3cnn(-c4ccccc4)c3N(CC)C(=O)[C@H]2NC(=O)c2ccn(C(F)(F)F)n2)c1]

TABLE 1-continued
| Exemplary Compounds |
|---|
I-303
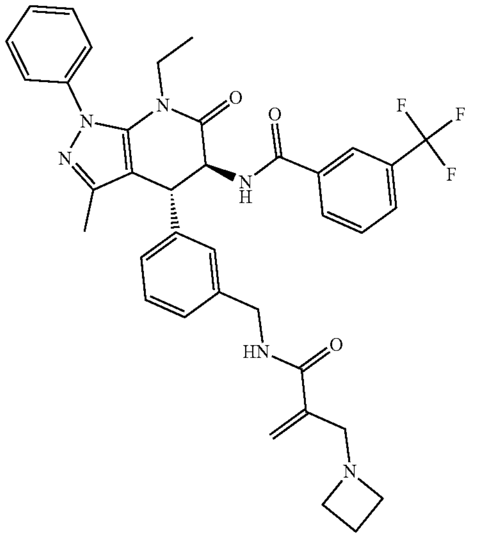 [SMILES: C=C(CN1CCC1)C(=O)NCc1cccc([C@@H]2c3c(C)nn(-c4ccccc4)c3N(CC)C(=O)[C@H]2NC(=O)c2cccc(C(F)(F)F)c2)c1]
I-304
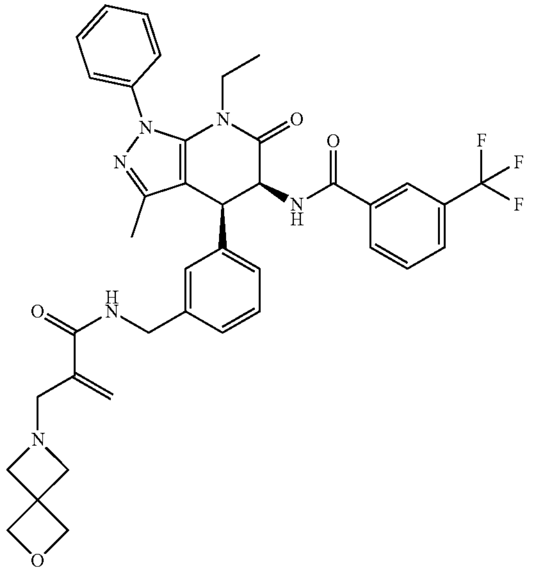 [SMILES: C=C(CN1CC2(COC2)C1)C(=O)NCc1cccc([C@H]2c3c(C)nn(-c4ccccc4)c3N(CC)C(=O)[C@H]2NC(=O)c2cccc(C(F)(F)F)c2)c1]
I-305
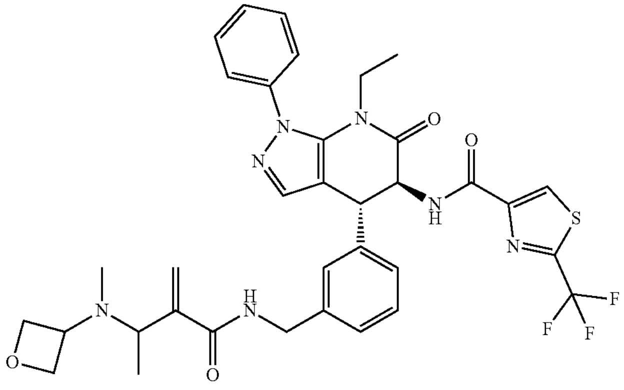 [SMILES: C=C(C(=O)NCc1cccc([C@@H]2c3cnn(-c4ccccc4)c3N(CC)C(=O)[C@H]2NC(=O)c2csc(C(F)(F)F)n2)c1)C(C)N(C)C1COC1]

TABLE 1-continued
| Exemplary Compounds |
|---|
| I-306 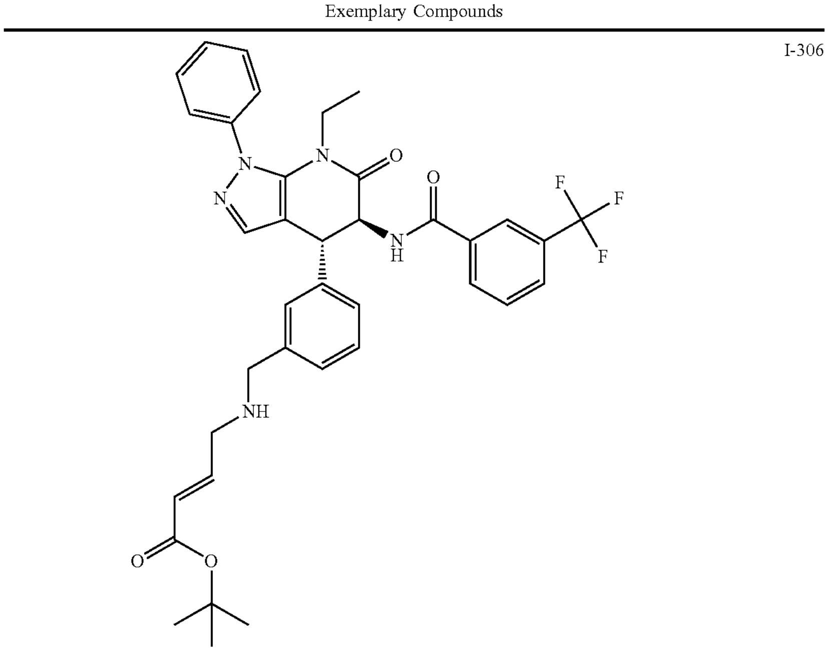 |
| I-307 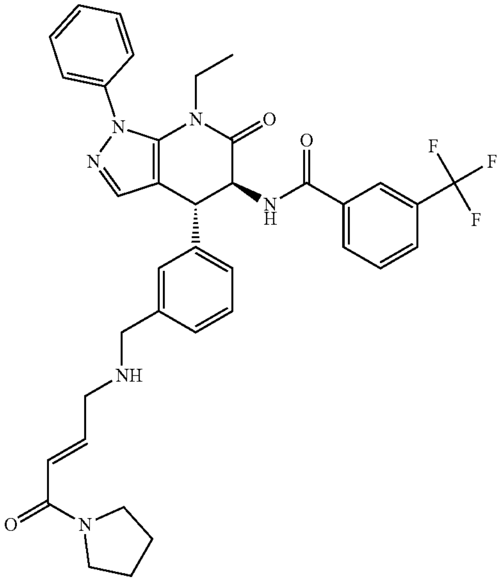 [SMILES: CCN1C(=O)[C@@H](NC(=O)c2cccc(C(F)(F)F)c2)[C@H](c2cccc(CNC/C=C/C(=O)N3CCCC3)c2)c2cnn(-c3ccccc3)c21] |
| I-308 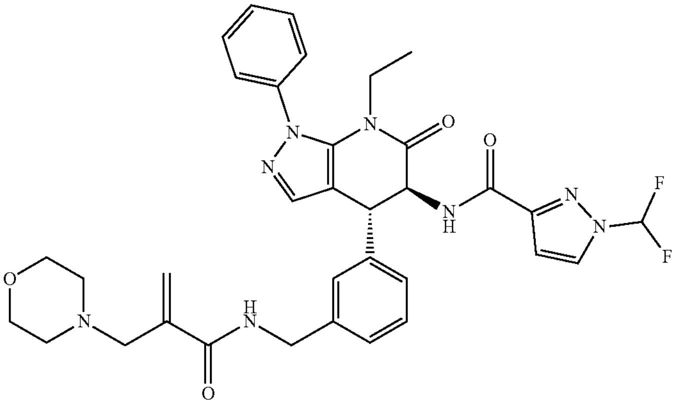 [SMILES: C=C(CN1CCOCC1)C(=O)NCc1cccc([C@@H]2c3cnn(-c4ccccc4)c3N(CC)C(=O)[C@H]2NC(=O)c2ccn(C(F)F)n2)c1] |

TABLE 1-continued
| Exemplary Compounds |
| --- |
I-309
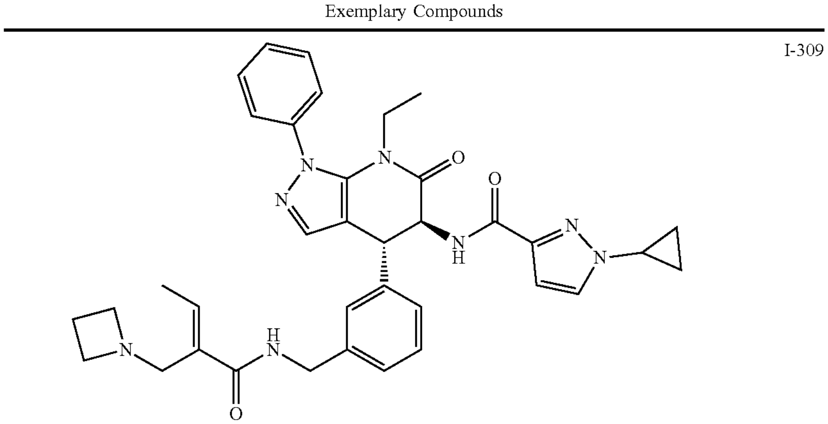
I-310
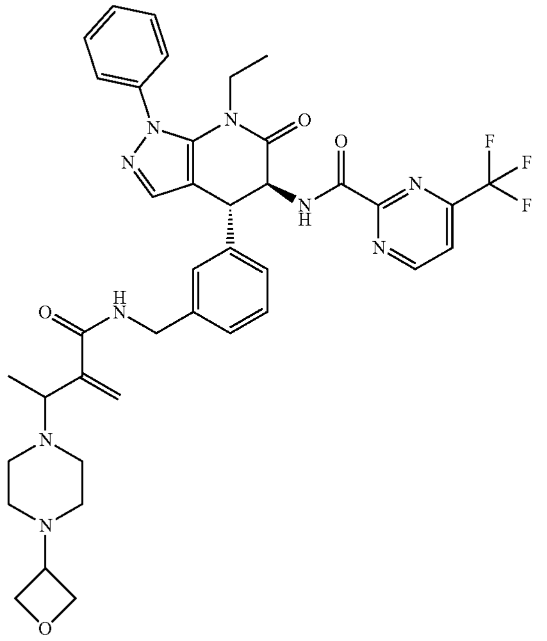 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N1CCN(C2COC2)CC1]
I-311
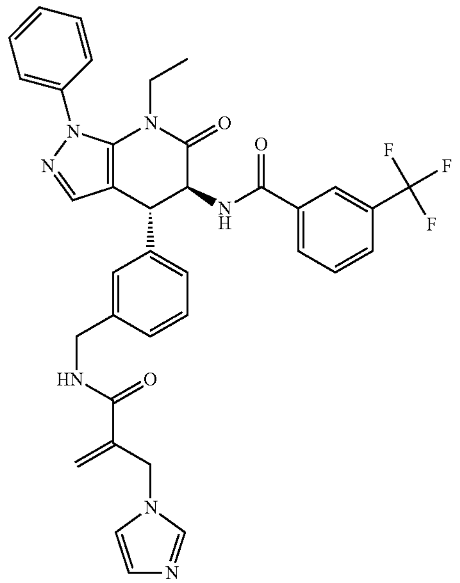 [SMILES: C=C(Cn1ccnc1)C(=O)NCc1cccc([C@@H]2c3cnn(-c4ccccc4)c3N(CC)C(=O)[C@H]2NC(=O)c2cccc(C(F)(F)F)c2)c1]

TABLE 1-continued
| Exemplary Compounds |
|---|
I-312
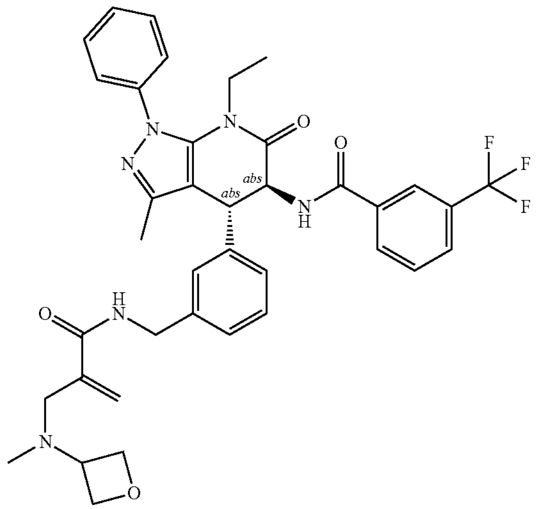 [SMILES: C=C(CN(C)C1COC1)C(=O)NCc1cccc([C@@H]2c3c(C)nn(-c4ccccc4)c3N(CC)C(=O)[C@H]2NC(=O)c2cccc(C(F)(F)F)c2)c1]
I-313
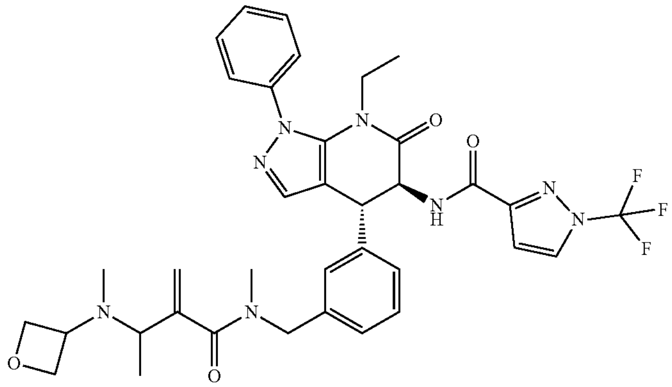 [SMILES: C=C(C(=O)N(C)Cc1cccc([C@@H]2c3cnn(-c4ccccc4)c3N(CC)C(=O)[C@H]2NC(=O)c2ccn(C(F)(F)F)n2)c1)C(C)N(C)C1COC1]
I-314
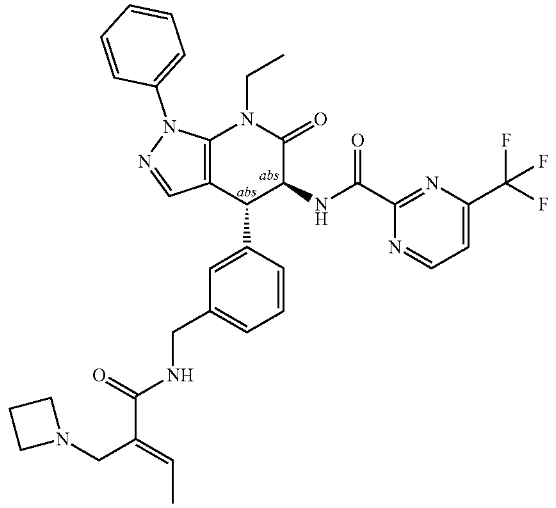 [SMILES: C/C=C(\CN1CCC1)C(=O)NCc1cccc([C@@H]2c3cnn(-c4ccccc4)c3N(CC)C(=O)[C@H]2NC(=O)c2nccc(C(F)(F)F)n2)c1]

TABLE 1-continued
| Exemplary Compounds |
|---|
I-315
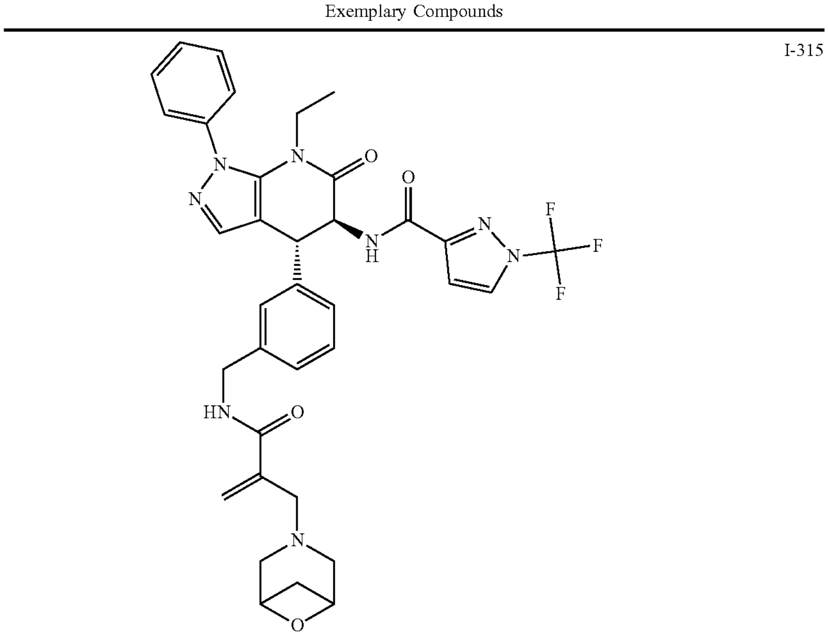
I-316
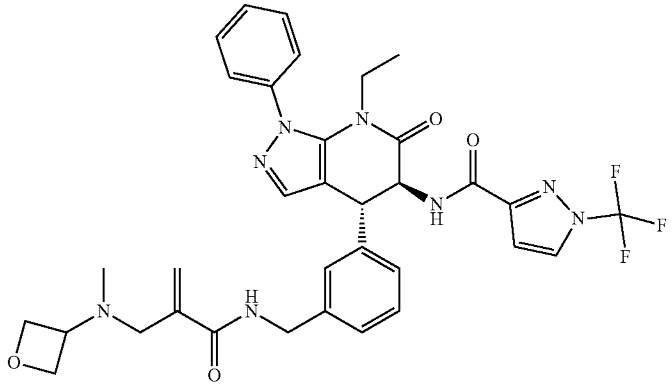 [SMILES: C=C(CN(C)C1COC1)C(=O)NCc1cccc([C@@H]2c3cnn(-c4ccccc4)c3N(CC)C(=O)[C@H]2NC(=O)c2ccn(C(F)(F)F)n2)c1]
I-317
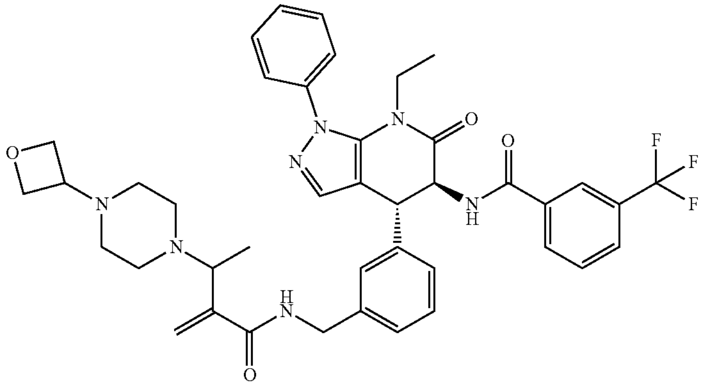 [SMILES: C=C(C(=O)NCc1cccc([C@@H]2c3cnn(-c4ccccc4)c3N(CC)C(=O)[C@H]2NC(=O)c2cccc(C(F)(F)F)c2)c1)C(C)N1CCN(C2COC2)CC1]

TABLE 1-continued
| Exemplary Compounds |
|---|
I-318
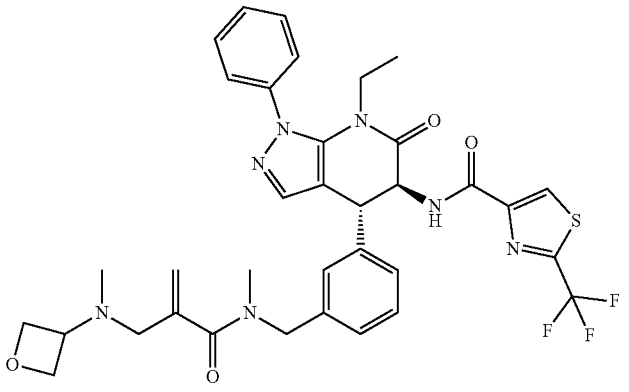 [SMILES: C=C(CN(C)C1COC1)C(=O)N(C)Cc1cccc([C@@H]2c3cnn(-c4ccccc4)c3N(CC)C(=O)[C@H]2NC(=O)c2csc(C(F)(F)F)n2)c1]
I-319
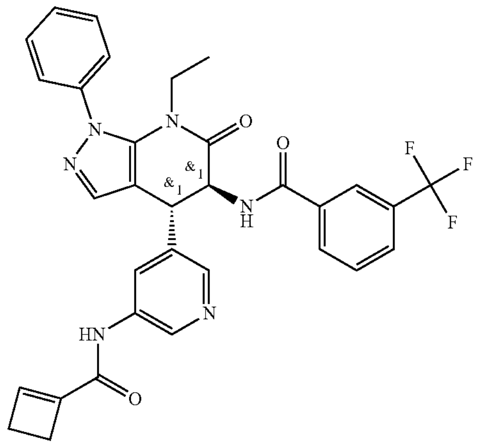 [SMILES: CCN1C(=O)[C@@H](NC(=O)c2cccc(C(F)(F)F)c2)[C@H](c2cncc(NC(=O)C3=CCC3)c2)c2cnn(-c3ccccc3)c21]
I-320
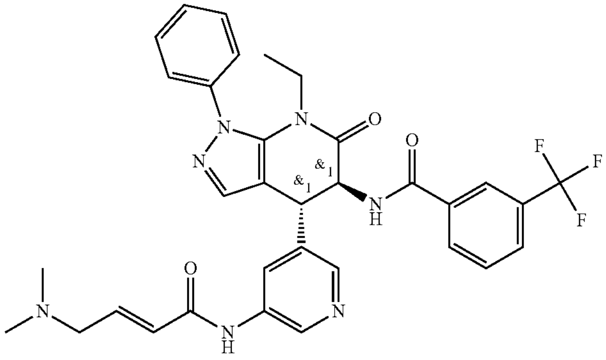 [SMILES: CCN1C(=O)[C@@H](NC(=O)c2cccc(C(F)(F)F)c2)[C@H](c2cncc(NC(=O)/C=C/CN(C)C)c2)c2cnn(-c3ccccc3)c21]

TABLE 1-continued
| Exemplary Compounds |
| --- |
| I-321<br>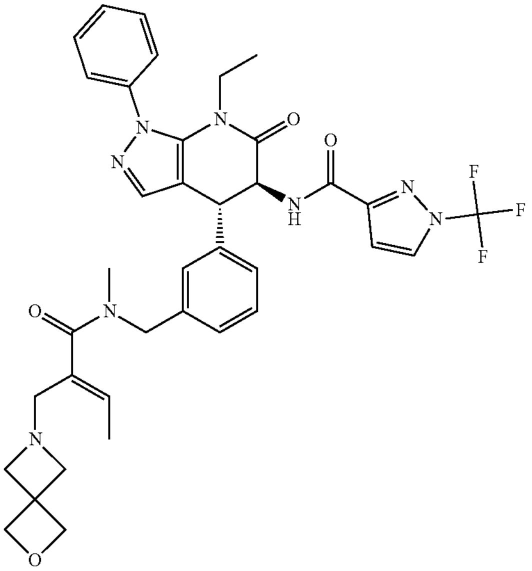 [SMILES: C/C=C(\CN1CC2(COC2)C1)C(=O)N(C)Cc1cccc([C@@H]2c3cnn(-c4ccccc4)c3N(CC)C(=O)[C@H]2NC(=O)c2ccn(C(F)(F)F)n2)c1] |
| I-322<br>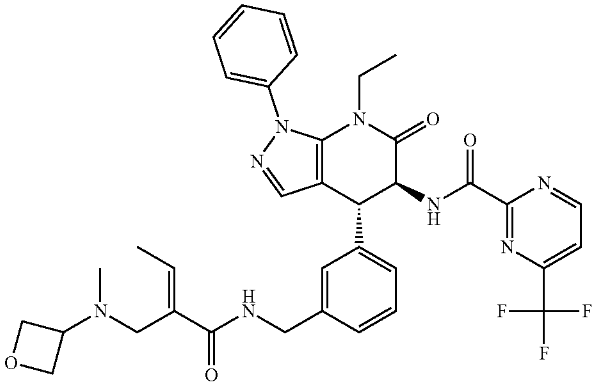 [SMILES: C/C=C(\CN(C)C1COC1)C(=O)NCc1cccc([C@@H]2c3cnn(-c4ccccc4)c3N(CC)C(=O)[C@H]2NC(=O)c2nccc(C(F)(F)F)n2)c1] |
| I-323<br>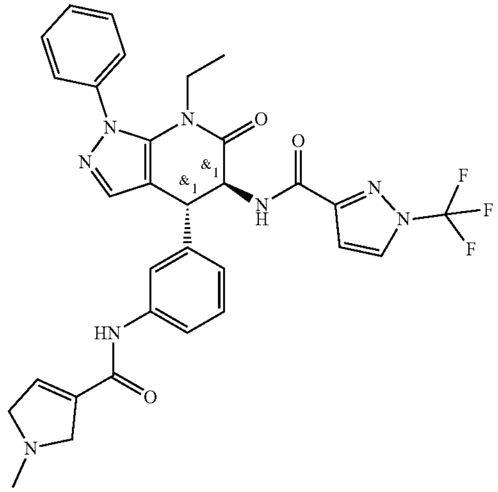 [SMILES: CCN1C(=O)[C@@H](NC(=O)c2ccn(C(F)(F)F)n2)[C@H](c2cccc(NC(=O)C3=CCN(C)C3)c2)c2cnn(-c3ccccc3)c21] |

TABLE 1-continued
| Exemplary Compounds |
| --- |
| I-324 |
| 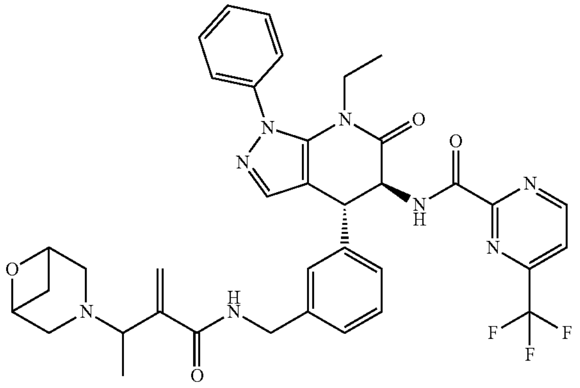 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N1CC2CC(C1)O2] |
| I-325 |
| 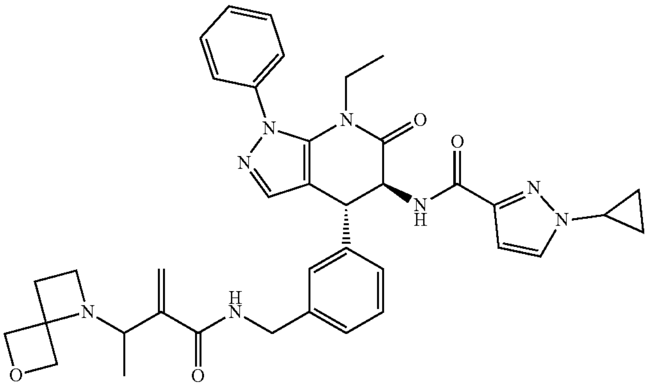 |
| I-326 |
| 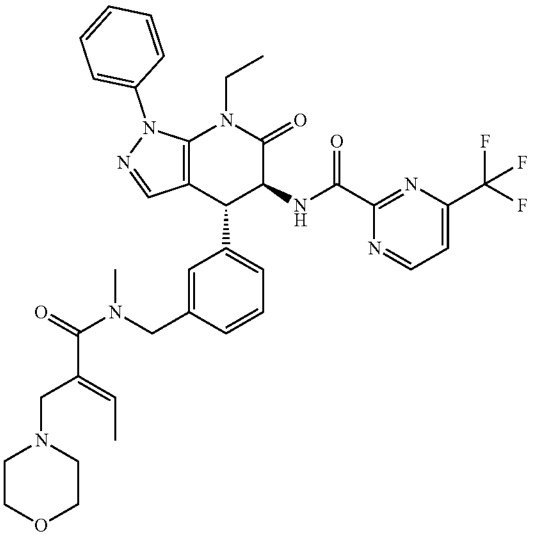 [SMILES: C/C=C(\CN1CCOCC1)C(=O)N(C)Cc1cccc([C@@H]2c3cnn(-c4ccccc4)c3N(CC)C(=O)[C@H]2NC(=O)c2nccc(C(F)(F)F)n2)c1] |

TABLE 1-continued
| Exemplary Compounds |
|---|
I-327
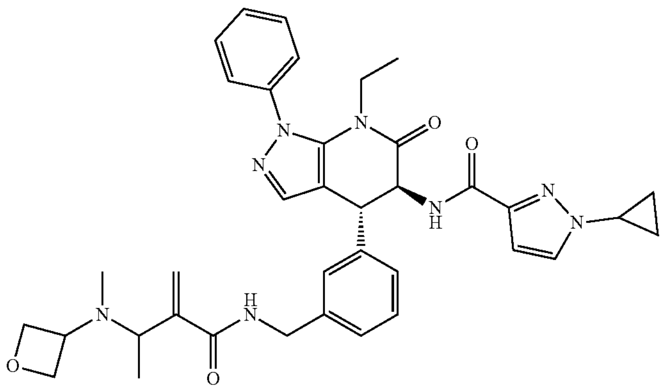 [SMILES: C=C(C(=O)NCc1cccc([C@@H]2c3cnn(-c4ccccc4)c3N(CC)C(=O)[C@H]2NC(=O)c2ccn(C3CC3)n2)c1)C(C)N(C)C1COC1]
I-328
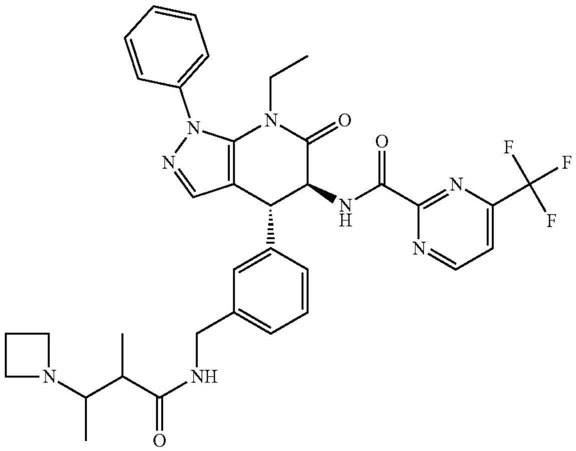 [SMILES: CCN1C(=O)[C@@H](NC(=O)c2nccc(C(F)(F)F)n2)[C@H](c2cccc(CNC(=O)C(C)C(C)N3CCC3)c2)c2cnn(-c3ccccc3)c21]
I-329
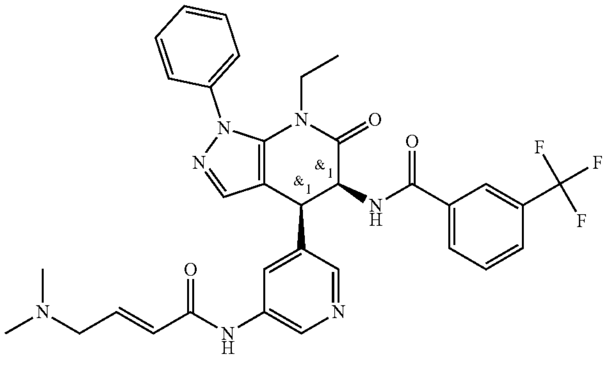 [SMILES: CCN1C(=O)[C@@H](NC(=O)c2cccc(C(F)(F)F)c2)[C@@H](c2cncc(NC(=O)/C=C/CN(C)C)c2)c2cnn(-c3ccccc3)c21]

TABLE 1-continued
| Exemplary Compounds |
|---|
I-330
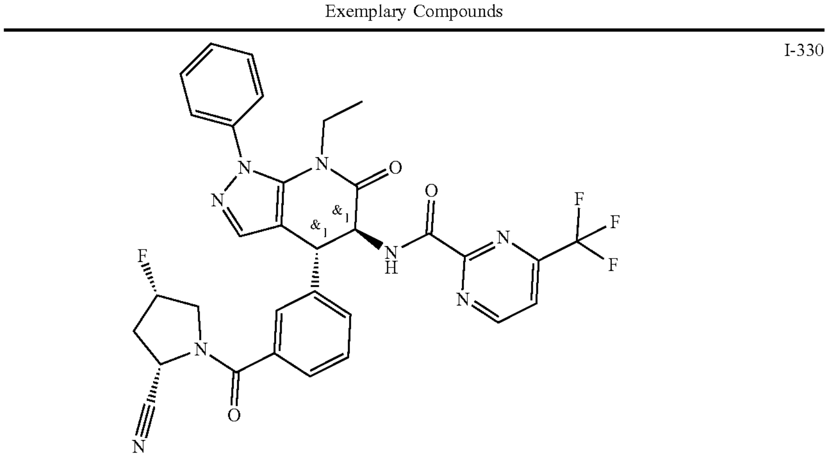
I-331
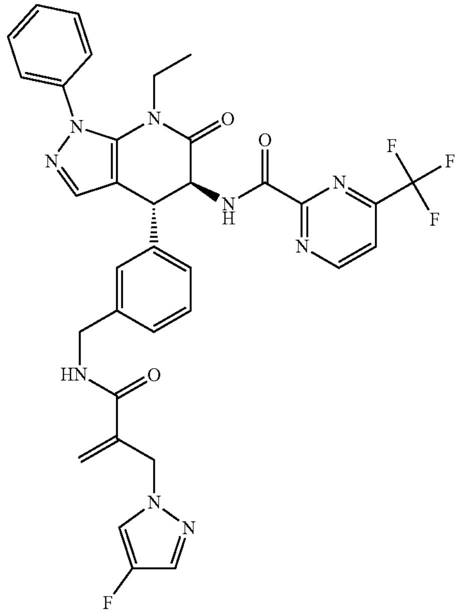 [SMILES: C=C(Cn1cc(F)cn1)C(=O)NCc1cccc([C@@H]2c3cnn(-c4ccccc4)c3N(CC)C(=O)[C@H]2NC(=O)c2nccc(C(F)(F)F)n2)c1]
I-332
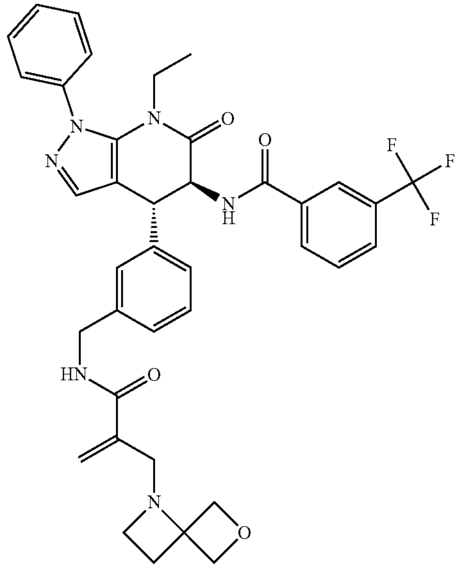 [SMILES: C=C(CN1CCC12COC2)C(=O)NCc1cccc([C@@H]2c3cnn(-c4ccccc4)c3N(CC)C(=O)[C@H]2NC(=O)c2cccc(C(F)(F)F)c2)c1]

TABLE 1-continued
| Exemplary Compounds |
| --- |
| 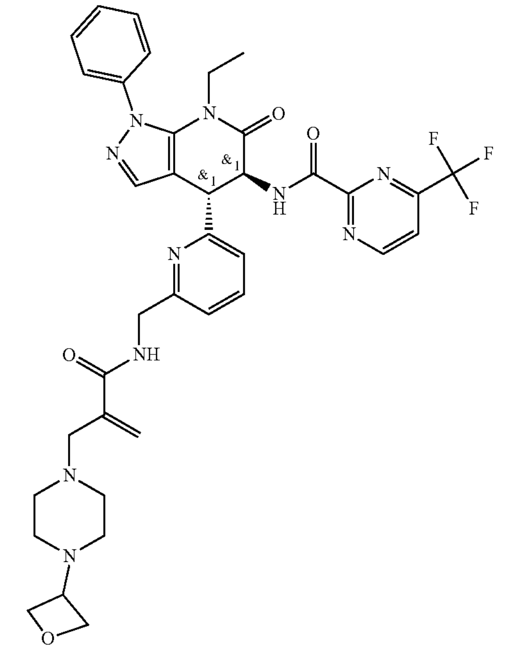 [SMILES: C=C(CN1CCN(C2COC2)CC1)C(=O)NCc1cccc([C@@H]2c3cnn(-c4ccccc4)c3N(CC)C(=O)[C@H]2NC(=O)c2nccc(C(F)(F)F)n2)n1] I-333 |
| 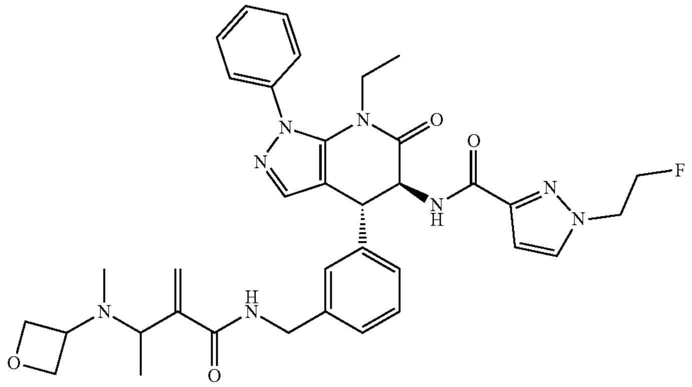 [SMILES: C=C(C(=O)NCc1cccc([C@@H]2c3cnn(-c4ccccc4)c3N(CC)C(=O)[C@H]2NC(=O)c2ccn(CCF)n2)c1)C(C)N(C)C1COC1] I-334 |
| 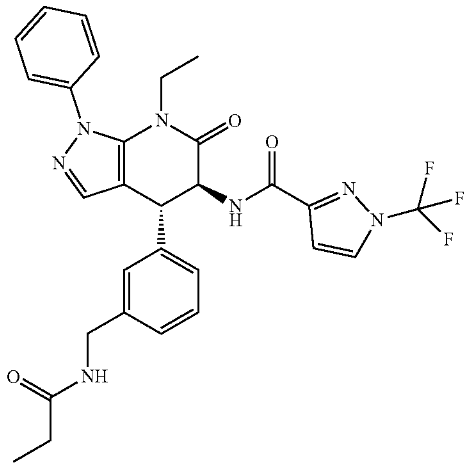 [SMILES: CCC(=O)NCc1cccc([C@@H]2c3cnn(-c4ccccc4)c3N(CC)C(=O)[C@H]2NC(=O)c2ccn(C(F)(F)F)n2)c1] I-335 |

TABLE 1-continued
| Exemplary Compounds |
| --- |
| I-336 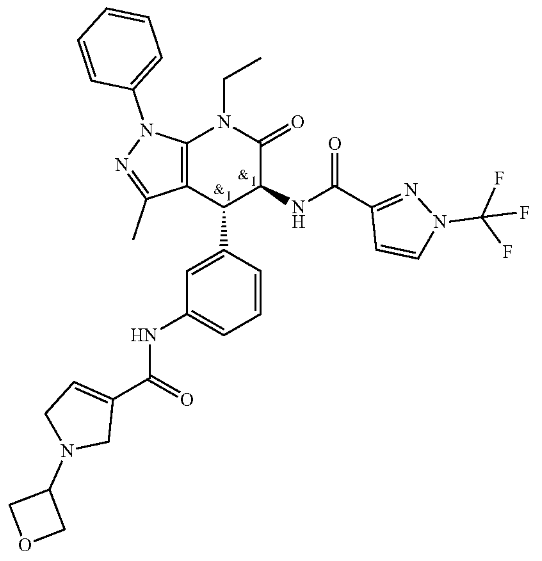 [SMILES: CCN1C(=O)[C@@H](NC(=O)c2ccn(C(F)(F)F)n2)[C@H](c2cccc(NC(=O)C3=CCN(C4COC4)C3)c2)c2c(C)nn(-c3ccccc3)c21] |
| I-337 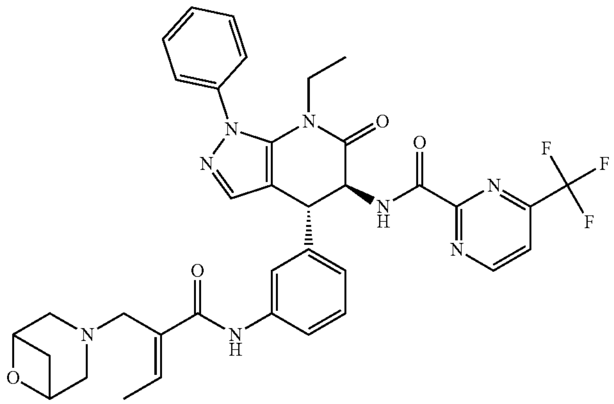 [SMILES: C/C=C(\CN1CC2CC(C1)O2)C(=O)Nc1cccc([C@@H]2c3cnn(-c4ccccc4)c3N(CC)C(=O)[C@H]2NC(=O)c2nccc(C(F)(F)F)n2)c1] |
| I-338 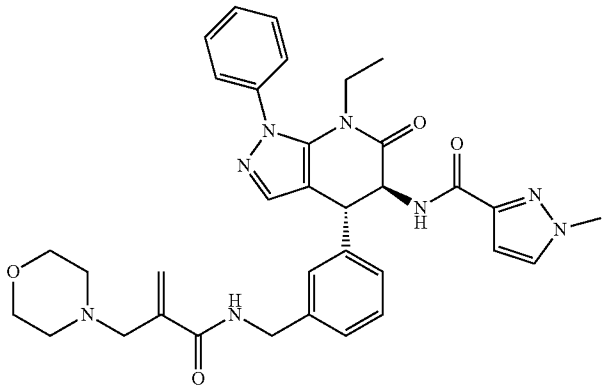 [SMILES: C=C(CN1CCOCC1)C(=O)NCc1cccc([C@@H]2c3cnn(-c4ccccc4)c3N(CC)C(=O)[C@H]2NC(=O)c2ccn(C)n2)c1] |

TABLE 1-continued
| Exemplary Compounds |
| --- |
| 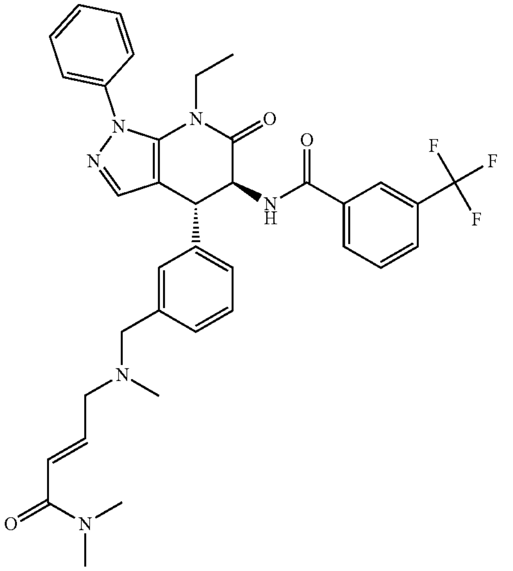 [SMILES: CCN1C(=O)[C@@H](NC(=O)c2cccc(C(F)(F)F)c2)[C@H](c2cccc(CN(C)C/C=C/C(=O)N(C)C)c2)c2cnn(-c3ccccc3)c21] I-339 |
| 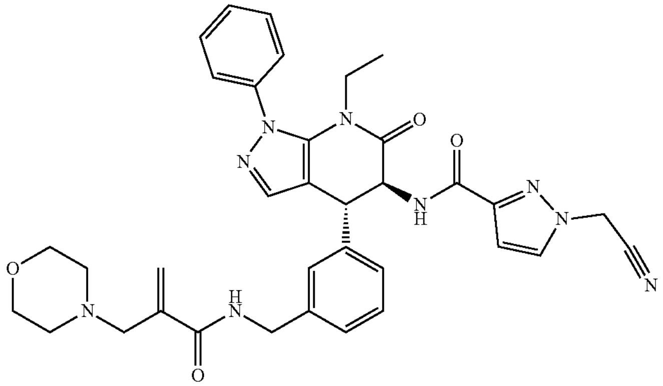 [SMILES: C=C(CN1CCOCC1)C(=O)NCc1cccc([C@@H]2c3cnn(-c4ccccc4)c3N(CC)C(=O)[C@H]2NC(=O)c2ccn(CC#N)n2)c1] I-340 |
| 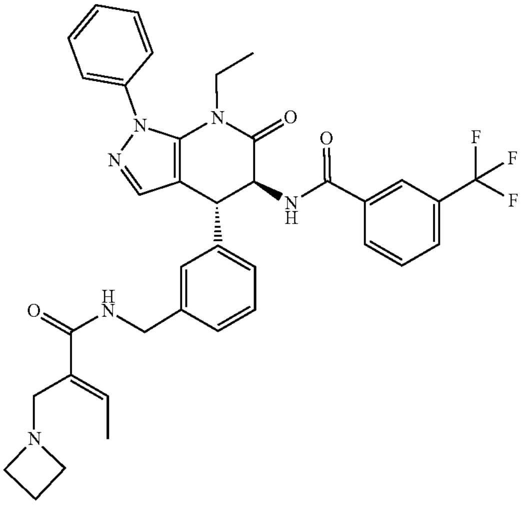 [SMILES: C/C=C(\CN1CCC1)C(=O)NCc1cccc([C@@H]2c3cnn(-c4ccccc4)c3N(CC)C(=O)[C@H]2NC(=O)c2cccc(C(F)(F)F)c2)c1] I-341 |

TABLE 1-continued
Exemplary Compounds
I-342
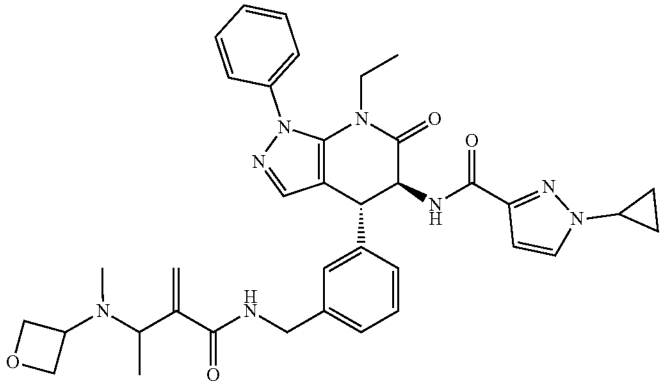 [SMILES: C=C(C(=O)NCc1cccc([C@@H]2c3cnn(-c4ccccc4)c3N(CC)C(=O)[C@H]2NC(=O)c2ccn(C3CC3)n2)c1)C(C)N(C)C1COC1]
I-343
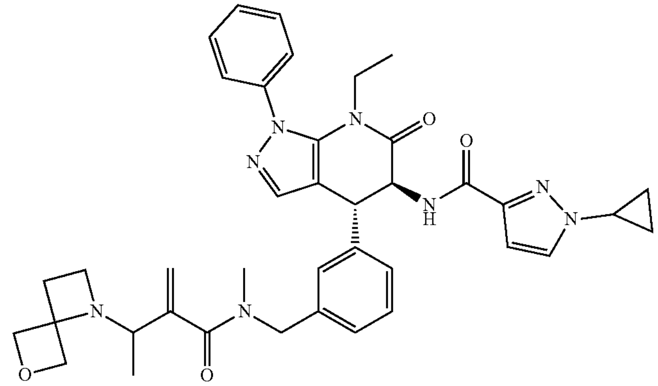 [SMILES: C=C(C(=O)N(C)Cc1cccc([C@@H]2c3cnn(-c4ccccc4)c3N(CC)C(=O)[C@H]2NC(=O)c2ccn(C3CC3)n2)c1)C(C)N1CCC12COC2]
I-344
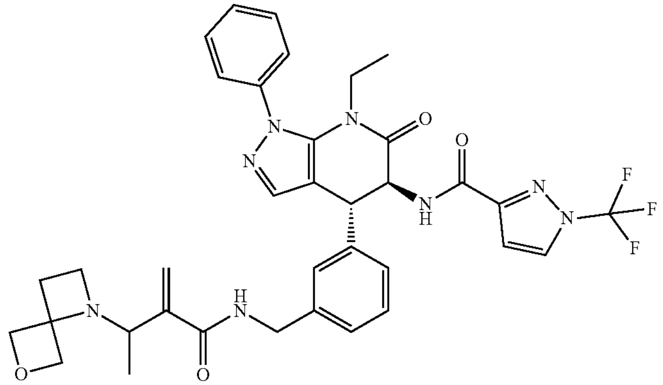 [SMILES: C=C(C(=O)NCc1cccc([C@@H]2c3cnn(-c4ccccc4)c3N(CC)C(=O)[C@H]2NC(=O)c2ccn(C(F)(F)F)n2)c1)C(C)N1CCC12COC2]
I-345
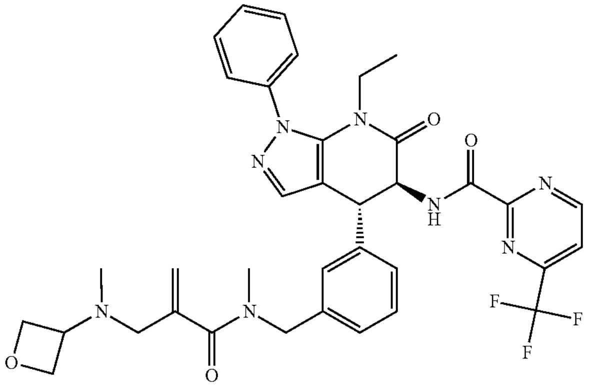 [SMILES: C=C(CN(C)C1COC1)C(=O)N(C)Cc1cccc([C@@H]2c3cnn(-c4ccccc4)c3N(CC)C(=O)[C@H]2NC(=O)c2nccc(C(F)(F)F)n2)c1]

TABLE 1-continued
| Exemplary Compounds |
| --- |
I-346
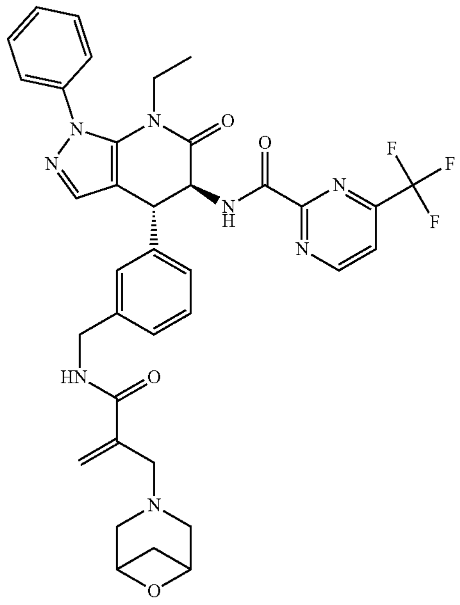 [SMILES: C=C(CN1CC2CC(C1)O2)C(=O)NCc1cccc([C@@H]2c3cnn(-c4ccccc4)c3N(CC)C(=O)[C@H]2NC(=O)c2nccc(C(F)(F)F)n2)c1]
I-347
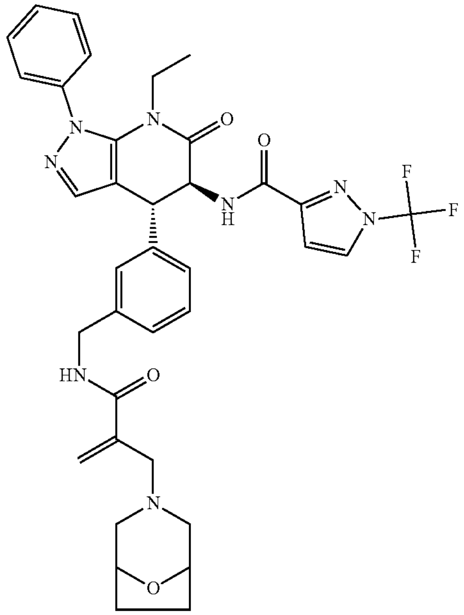 [SMILES: C=C(CN1CC2CCC(C1)O2)C(=O)NCc1cccc([C@@H]2c3cnn(-c4ccccc4)c3N(CC)C(=O)[C@H]2NC(=O)c2ccn(C(F)(F)F)n2)c1]

TABLE 1-continued
| Exemplary Compounds |
|---|
I-348
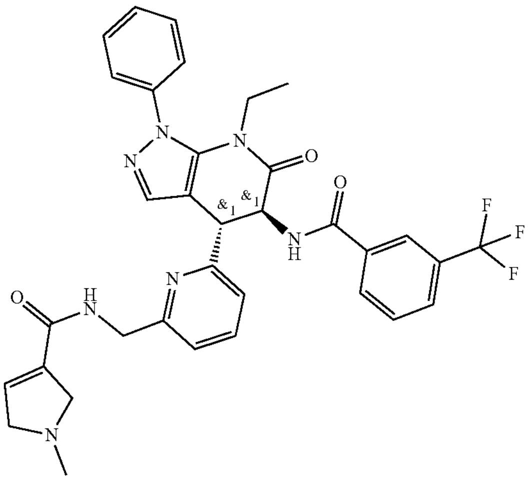 [SMILES: CCN1C(=O)[C@@H](NC(=O)c2cccc(C(F)(F)F)c2)[C@H](c2cccc(CNC(=O)C3=CCN(C)C3)n2)c2cnn(-c3ccccc3)c21]
I-349
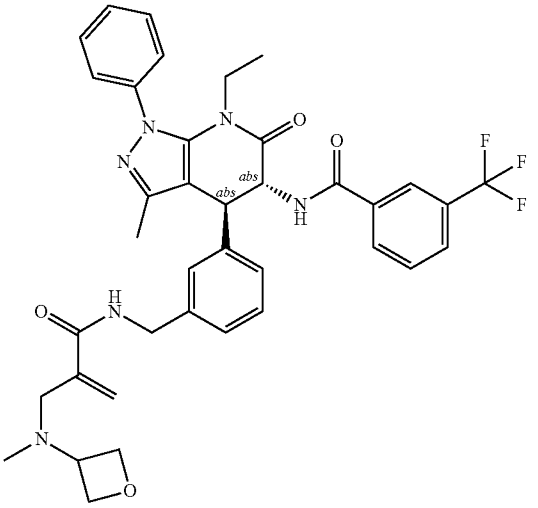 [SMILES: C=C(CN(C)C1COC1)C(=O)NCc1cccc([C@H]2c3c(C)nn(-c4ccccc4)c3N(CC)C(=O)[C@@H]2NC(=O)c2cccc(C(F)(F)F)c2)c1]
I-350
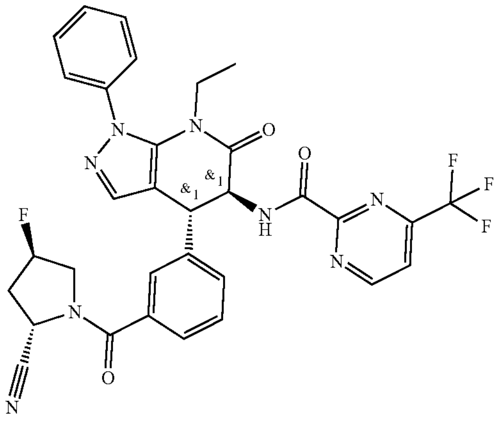 [SMILES: CCN1C(=O)[C@@H](NC(=O)c2nccc(C(F)(F)F)n2)[C@H](c2cccc(C(=O)N3C[C@H](F)C[C@H]3C#N)c2)c2cnn(-c3ccccc3)c21]

TABLE 1-continued
| Exemplary Compounds |
| --- |
| I-351 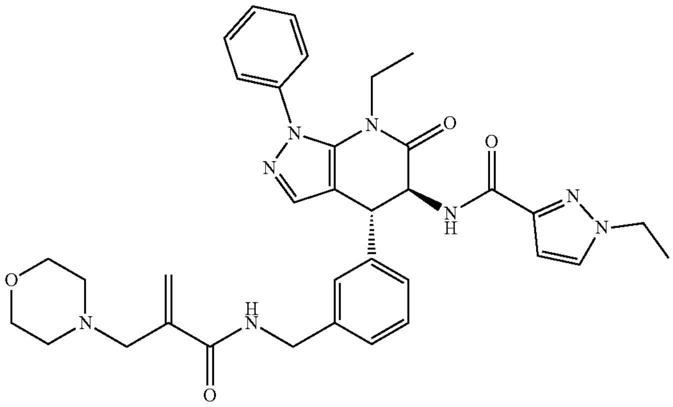 [SMILES: C=C(CN1CCOCC1)C(=O)NCc1cccc([C@@H]2c3cnn(-c4ccccc4)c3N(CC)C(=O)[C@H]2NC(=O)c2ccn(CC)n2)c1] |
| I-352 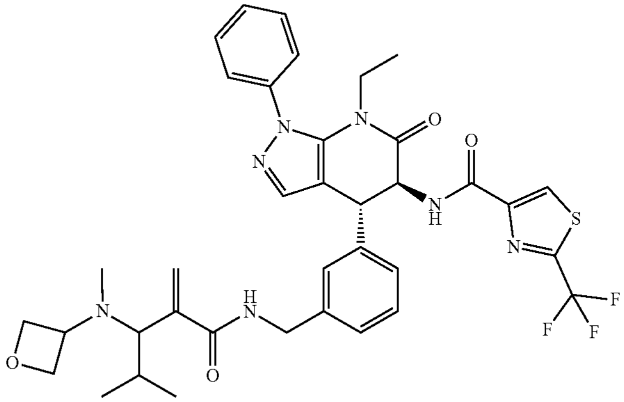 [SMILES: C=C(C(=O)NCc1cccc([C@@H]2c3cnn(-c4ccccc4)c3N(CC)C(=O)[C@H]2NC(=O)c2csc(C(F)(F)F)n2)c1)C(C(C)C)N(C)C1COC1] |
| I-353 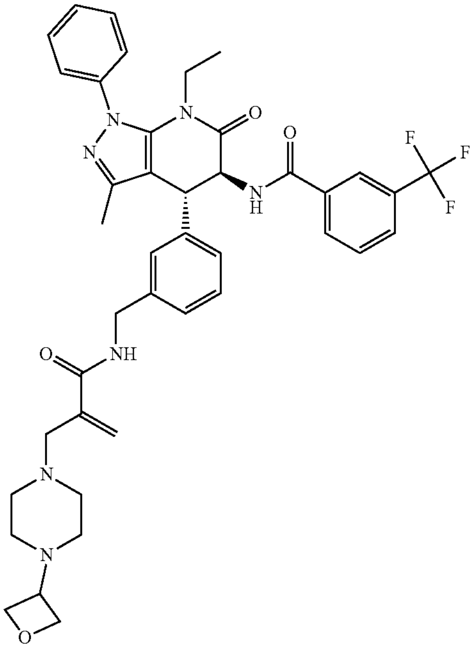 [SMILES: C=C(CN1CCN(C2COC2)CC1)C(=O)NCc1cccc([C@@H]2c3c(C)nn(-c4ccccc4)c3N(CC)C(=O)[C@H]2NC(=O)c2cccc(C(F)(F)F)c2)c1] |

TABLE 1-continued
| Exemplary Compounds |
| --- |
| 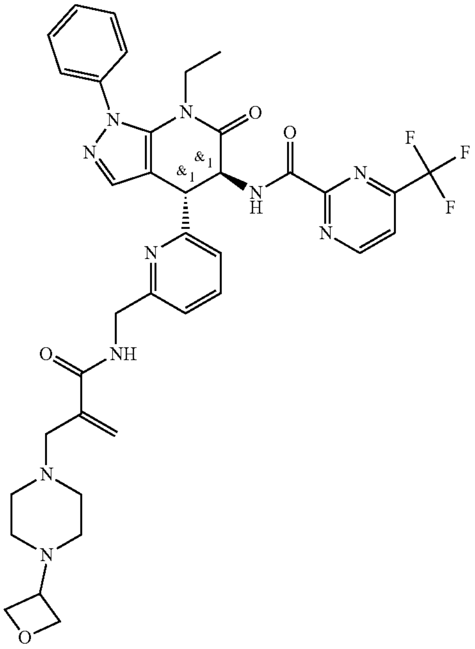 [SMILES: C=C(CN1CCN(C2COC2)CC1)C(=O)NCc1cccc([C@@H]2c3cnn(-c4ccccc4)c3N(CC)C(=O)[C@H]2NC(=O)c2nccc(C(F)(F)F)n2)n1] I-354 |
| 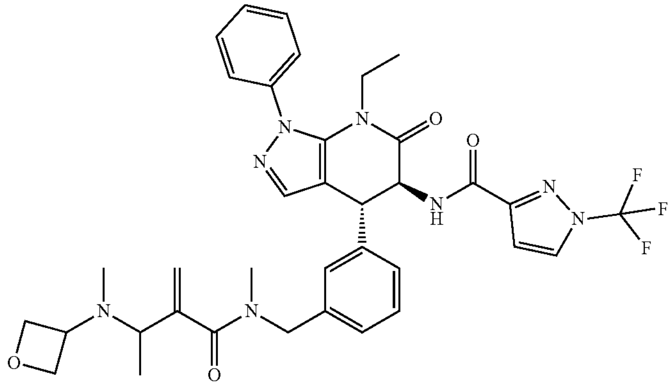 [SMILES: C=C(C(=O)N(C)Cc1cccc([C@@H]2c3cnn(-c4ccccc4)c3N(CC)C(=O)[C@H]2NC(=O)c2ccn(C(F)(F)F)n2)c1)C(C)N(C)C1COC1] I-355 |
| 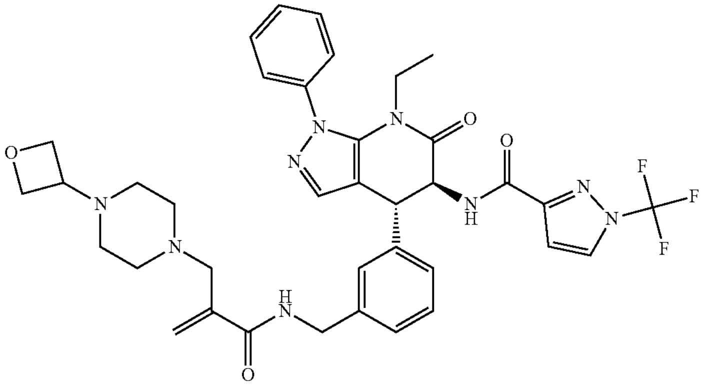 [SMILES: C=C(CN1CCN(C2COC2)CC1)C(=O)NCc1cccc([C@@H]2c3cnn(-c4ccccc4)c3N(CC)C(=O)[C@H]2NC(=O)c2ccn(C(F)(F)F)n2)c1] I-356 |

TABLE 1-continued
| Exemplary Compounds |
|---|
| 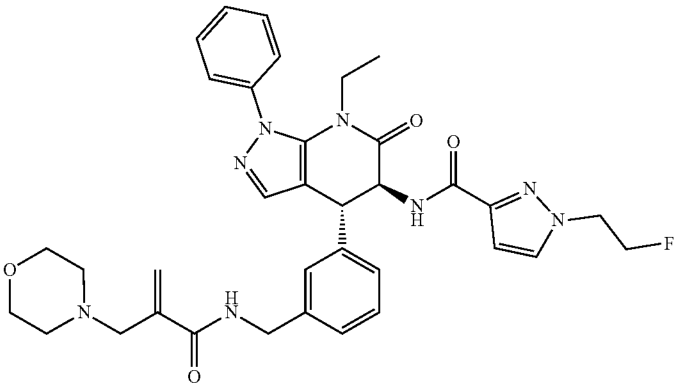 [SMILES: C=C(CN1CCOCC1)C(=O)NCc1cccc([C@@H]2c3cnn(-c4ccccc4)c3N(CC)C(=O)[C@H]2NC(=O)c2ccn(CCF)n2)c1] I-357 |
| 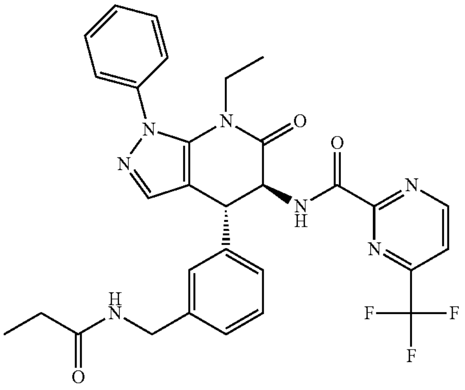 [SMILES: CCC(=O)NCc1cccc([C@@H]2c3cnn(-c4ccccc4)c3N(CC)C(=O)[C@H]2NC(=O)c2nccc(C(F)(F)F)n2)c1] I-358 |
| 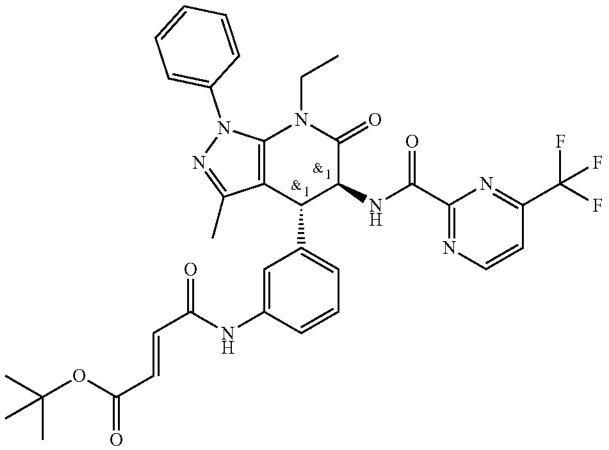 [SMILES: CCN1C(=O)[C@@H](NC(=O)c2nccc(C(F)(F)F)n2)[C@H](c2cccc(NC(=O)/C=C/C(=O)OC(C)(C)C)c2)c2c(C)nn(-c3ccccc3)c21] I-359 |

TABLE 1-continued
| Exemplary Compounds |
| --- |
| I-360 |
| 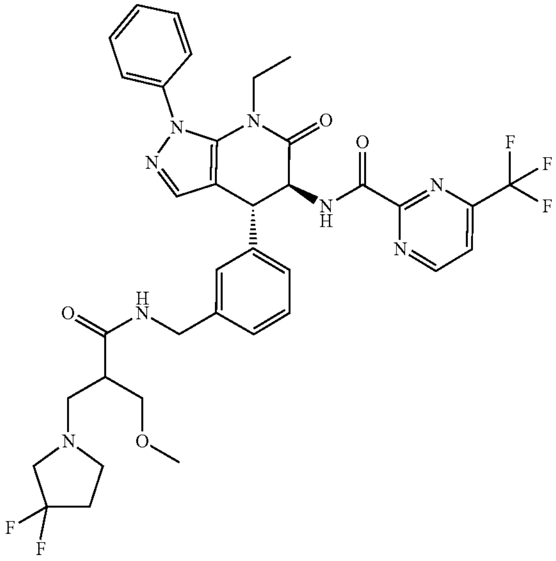 [SMILES: CCN1C(=O)[C@@H](NC(=O)c2nccc(C(F)(F)F)n2)[C@H](c2cccc(CNC(=O)C(COC)CN3CCC(F)(F)C3)c2)c2cnn(-c3ccccc3)c21] |
| I-361 |
| 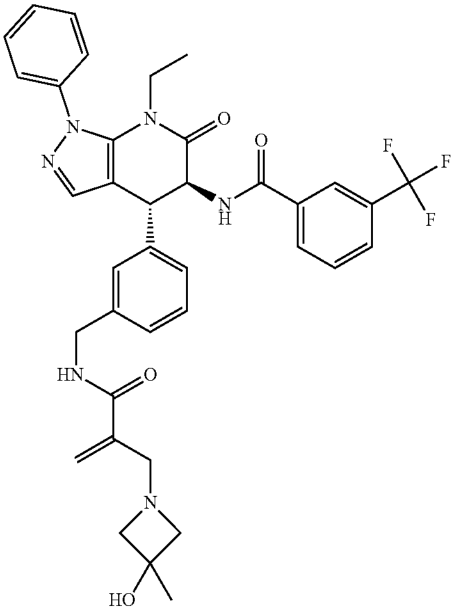 [SMILES: C=C(CN1CC(C)(O)C1)C(=O)NCc1cccc([C@@H]2c3cnn(-c4ccccc4)c3N(CC)C(=O)[C@H]2NC(=O)c2cccc(C(F)(F)F)c2)c1] |

TABLE 1-continued
| Exemplary Compounds |
| --- |
| I-362 |
| 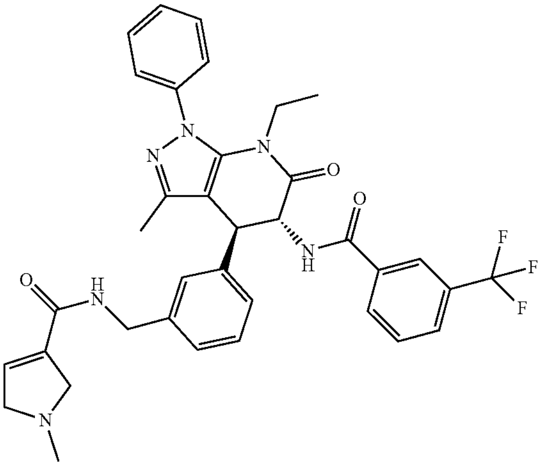 [SMILES: CCN1C(=O)[C@H](NC(=O)c2cccc(C(F)(F)F)c2)[C@@H](c2cccc(CNC(=O)C3=CCN(C)C3)c2)c2c(C)nn(-c3ccccc3)c21] |
| I-363 |
| 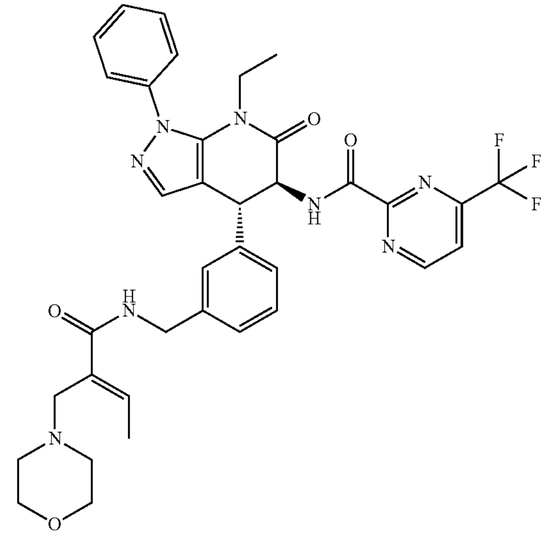 |
| I-364 |
| 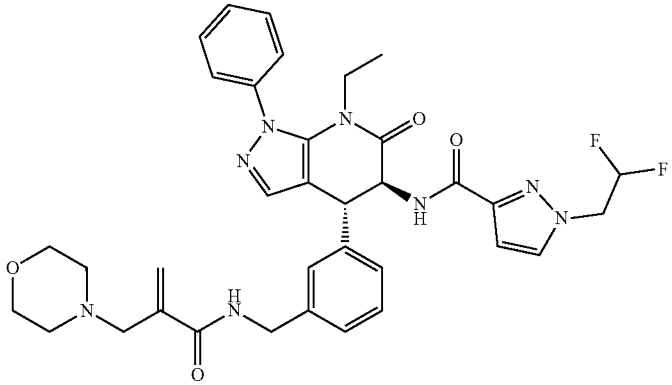 |

TABLE 1-continued
Exemplary Compounds
I-365
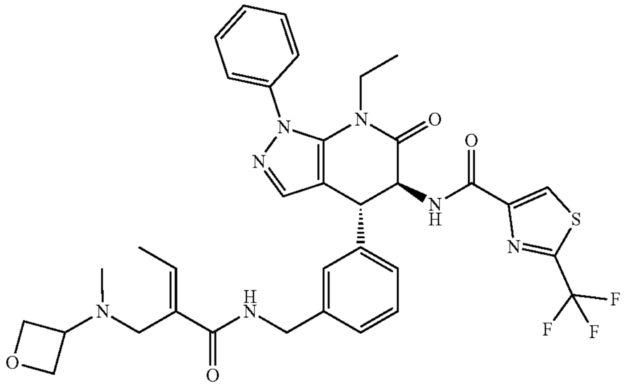 [SMILES: C/C=C(\CN(C)C1COC1)C(=O)NCc1cccc([C@@H]2c3cnn(-c4ccccc4)c3N(CC)C(=O)[C@H]2NC(=O)c2csc(C(F)(F)F)n2)c1]
I-366
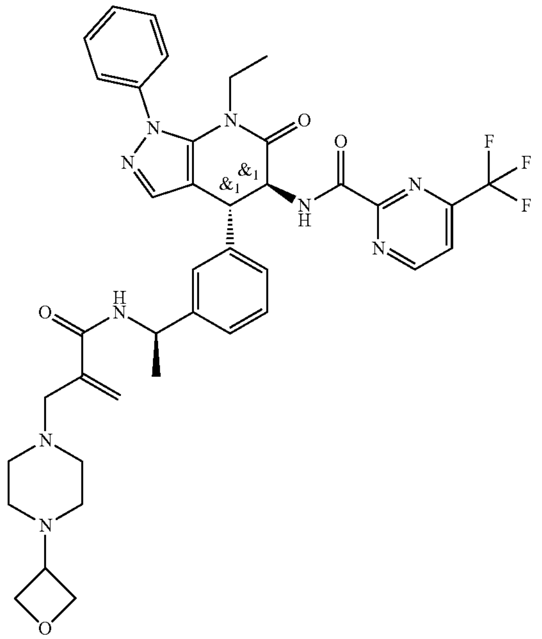 [SMILES: C=C(CN1CCN(C2COC2)CC1)C(=O)N[C@H](C)c1cccc([C@@H]2c3cnn(-c4ccccc4)c3N(CC)C(=O)[C@H]2NC(=O)c2nccc(C(F)(F)F)n2)c1]
I-367
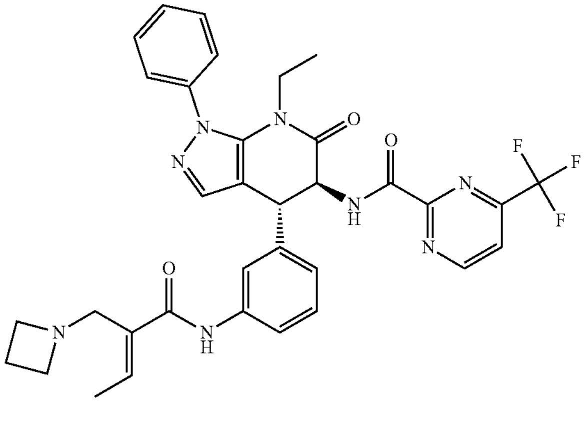 [SMILES: C/C=C(\CN1CCC1)C(=O)Nc1cccc([C@@H]2c3cnn(-c4ccccc4)c3N(CC)C(=O)[C@H]2NC(=O)c2nccc(C(F)(F)F)n2)c1]

TABLE 1-continued
| Exemplary Compounds |
|---|
I-368
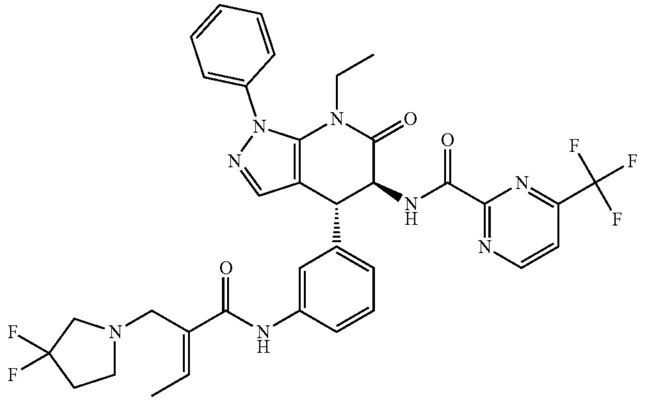 [SMILES: C/C=C(\CN1CCC(F)(F)C1)C(=O)Nc1cccc([C@@H]2c3cnn(-c4ccccc4)c3N(CC)C(=O)[C@H]2NC(=O)c2nccc(C(F)(F)F)n2)c1]
I-369
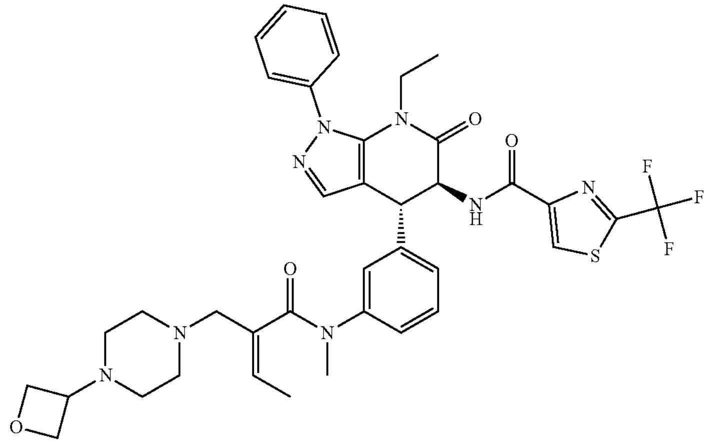 [SMILES: C/C=C(/CN1CCN(C2COC2)CC1)C(=O)N(C)c1cccc([C@@H]2c3cnn(-c4ccccc4)c3N(CC)C(=O)[C@H]2NC(=O)c2csc(C(F)(F)F)n2)c1]
I-370
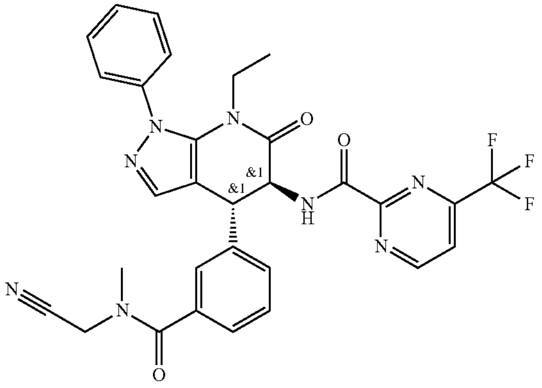 [SMILES: CCN1C(=O)[C@@H](NC(=O)c2nccc(C(F)(F)F)n2)[C@H](c2cccc(C(=O)N(C)CC#N)c2)c2cnn(-c3ccccc3)c21]

TABLE 1-continued
| Exemplary Compounds |
| --- |
I-371
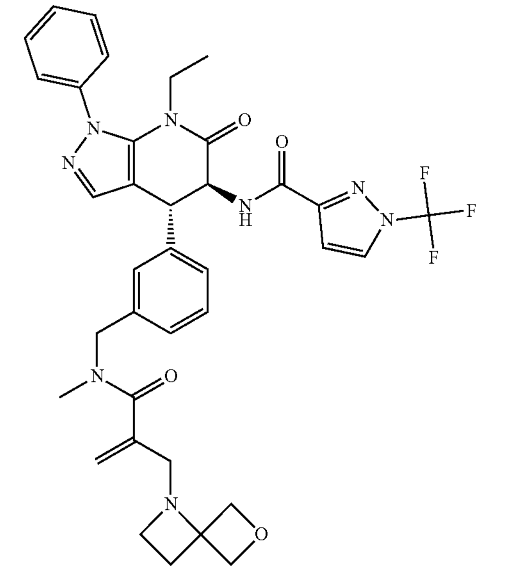 [SMILES: C=C(CN1CCC12COC2)C(=O)N(C)Cc1cccc([C@@H]2c3cnn(-c4ccccc4)c3N(CC)C(=O)[C@H]2NC(=O)c2ccn(C(F)(F)F)n2)c1]
I-372
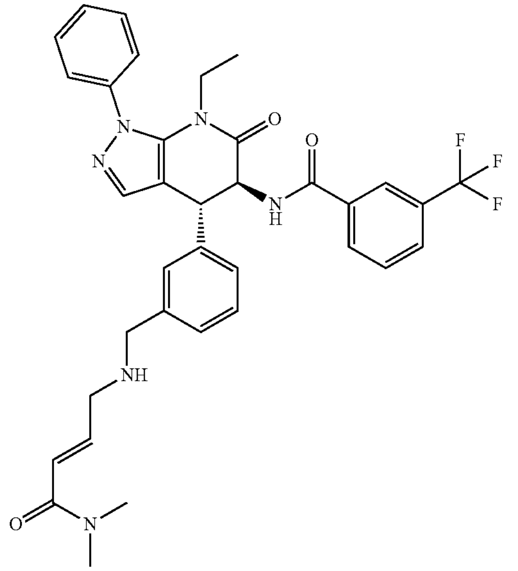 [SMILES: CCN1C(=O)[C@@H](NC(=O)c2cccc(C(F)(F)F)c2)[C@H](c2cccc(CNC/C=C/C(=O)N(C)C)c2)c2cnn(-c3ccccc3)c21]
I-373
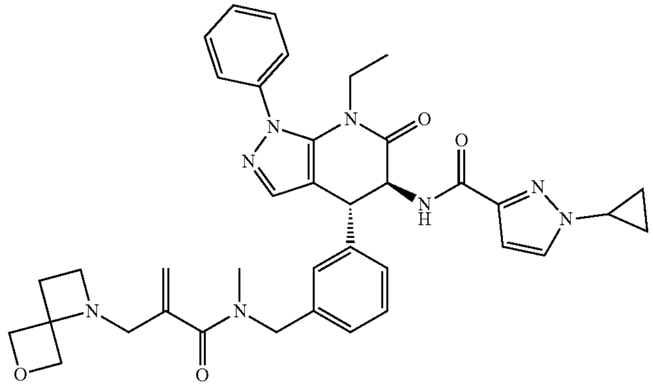 [SMILES: C=C(CN1CCC12COC2)C(=O)N(C)Cc1cccc([C@@H]2c3cnn(-c4ccccc4)c3N(CC)C(=O)[C@H]2NC(=O)c2ccn(C3CC3)n2)c1]

TABLE 1-continued
| Exemplary Compounds |
| --- |
| I-374 |
| 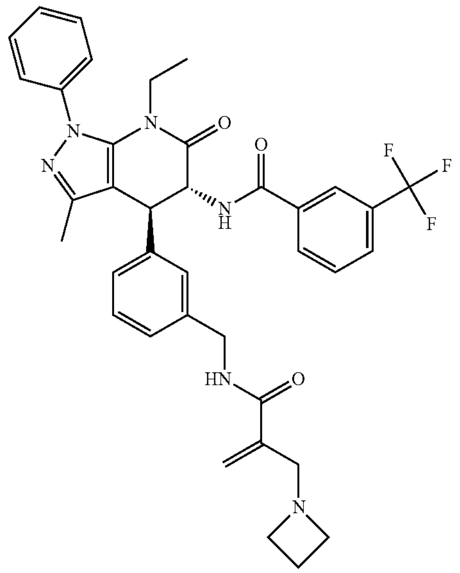 [SMILES: C=C(CN1CCC1)C(=O)NCc1cccc([C@H]2c3c(C)nn(-c4ccccc4)c3N(CC)C(=O)[C@@H]2NC(=O)c2cccc(C(F)(F)F)c2)c1] |
| I-375 |
| 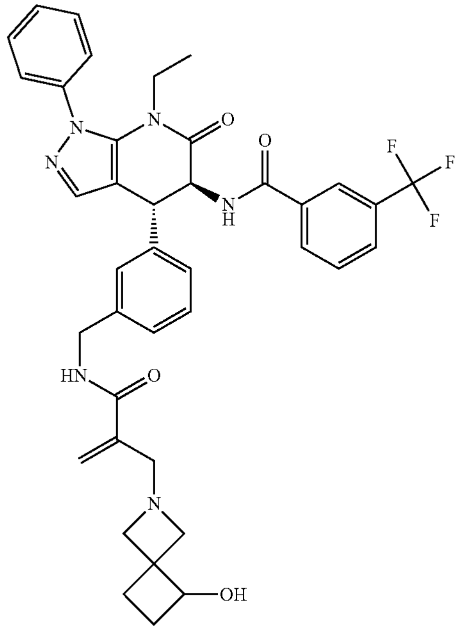 [SMILES: C=C(CN1CC2(CCC2O)C1)C(=O)NCc1cccc([C@@H]2c3cnn(-c4ccccc4)c3N(CC)C(=O)[C@H]2NC(=O)c2cccc(C(F)(F)F)c2)c1] |

TABLE 1-continued
| Exemplary Compounds |
| --- |
I-376
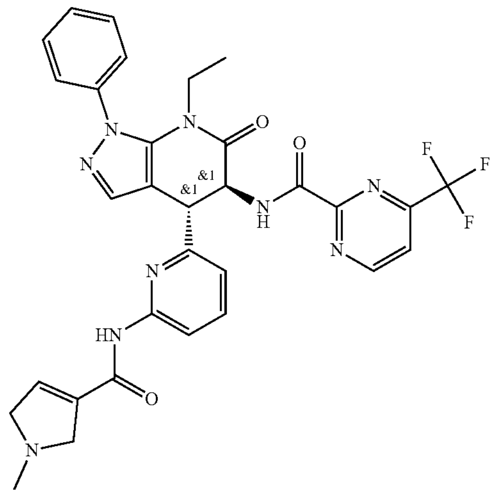 [SMILES: CCN1C(=O)[C@@H](NC(=O)c2nccc(C(F)(F)F)n2)[C@H](c2cccc(NC(=O)C3=CCN(C)C3)n2)c2cnn(-c3ccccc3)c21]
I-377
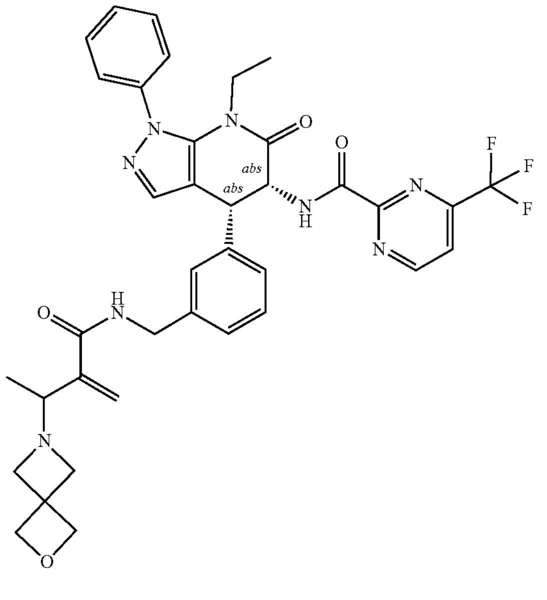 [SMILES: C=C(C(=O)NCc1cccc([C@@H]2c3cnn(-c4ccccc4)c3N(CC)C(=O)[C@@H]2NC(=O)c2nccc(C(F)(F)F)n2)c1)C(C)N1CC2(COC2)C1]

TABLE 1-continued
| Exemplary Compounds |
| --- |
| I-377' |
| 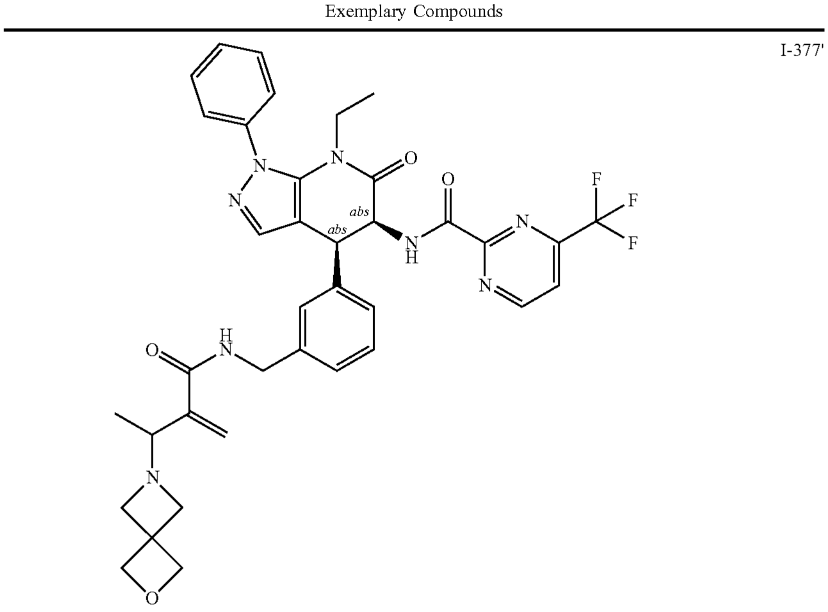 |
| I-378 |
| 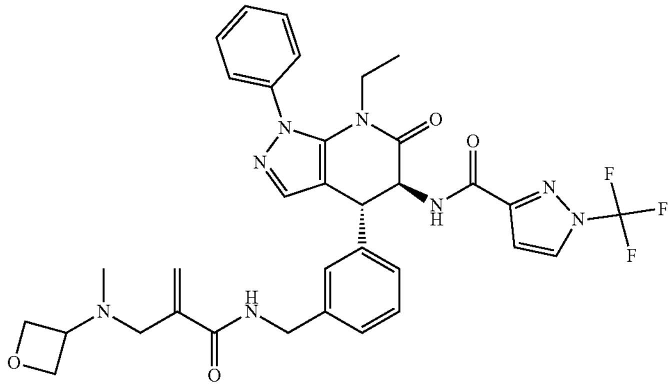 [SMILES: C=C(CN(C)C1COC1)C(=O)NCc1cccc([C@@H]2c3cnn(-c4ccccc4)c3N(CC)C(=O)[C@H]2NC(=O)c2ccn(C(F)(F)F)n2)c1] |
| I-379 |
| 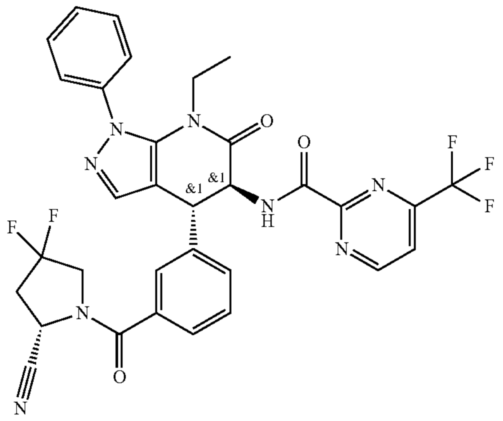 [SMILES: CCN1C(=O)[C@@H](NC(=O)c2nccc(C(F)(F)F)n2)[C@H](c2cccc(C(=O)N3CC(F)(F)C[C@H]3C#N)c2)c2cnn(-c3ccccc3)c21] |

TABLE 1-continued
| Exemplary Compounds |
|---|
| I-380<br>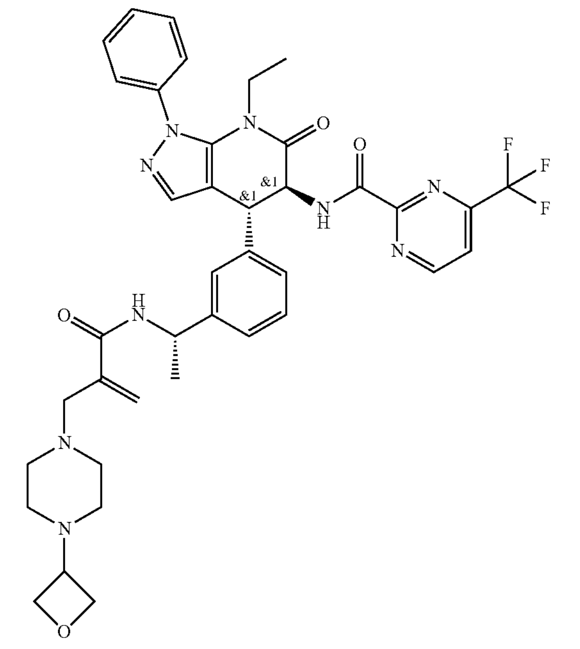 [SMILES: C=C(CN1CCN(C2COC2)CC1)C(=O)N[C@@H](C)c1cccc([C@@H]2c3cnn(-c4ccccc4)c3N(CC)C(=O)[C@H]2NC(=O)c2nccc(C(F)(F)F)n2)c1] |
| I-381<br>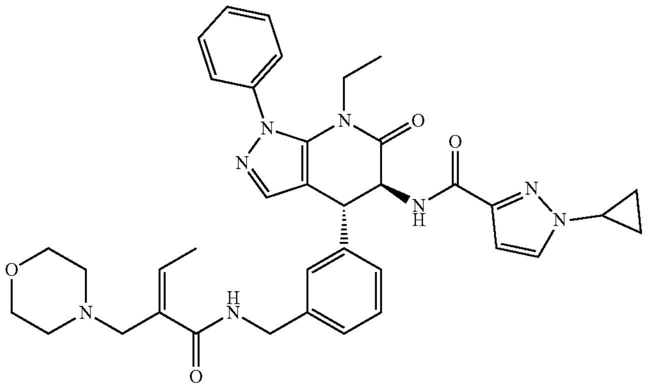 [SMILES: C/C=C(/CN1CCOCC1)C(=O)NCc1cccc([C@@H]2c3cnn(-c4ccccc4)c3N(CC)C(=O)[C@H]2NC(=O)c2ccn(C3CC3)n2)c1] |
| I-382<br>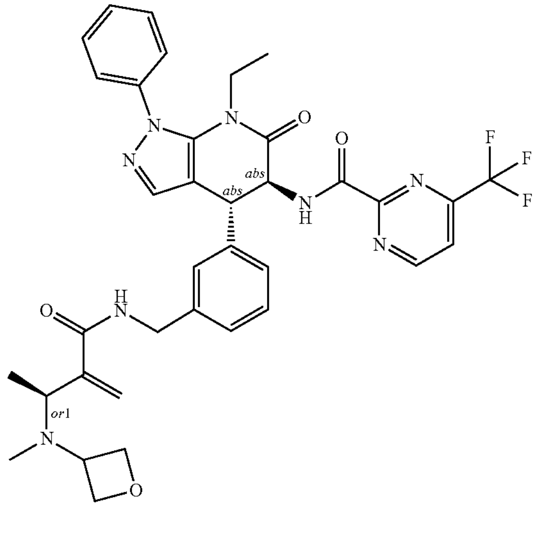 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)[C@H](C)N(C)C1COC1] |

TABLE 1-continued
| Exemplary Compounds |
| --- |
| I-383 |
| 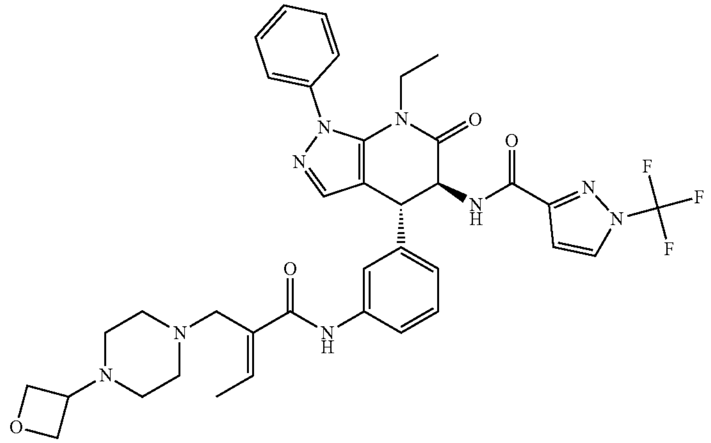 [SMILES: C/C=C(\CN1CCN(C2COC2)CC1)C(=O)Nc1cccc([C@@H]2c3cnn(-c4ccccc4)c3N(CC)C(=O)[C@H]2NC(=O)c2ccn(C(F)(F)F)n2)c1] |
| I-384 |
| 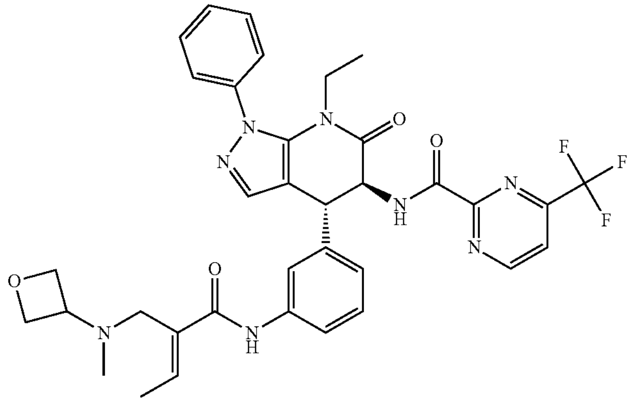 [SMILES: C/C=C(\CN(C)C1COC1)C(=O)Nc1cccc([C@@H]2c3cnn(-c4ccccc4)c3N(CC)C(=O)[C@H]2NC(=O)c2nccc(C(F)(F)F)n2)c1] |
| I-385 |
| 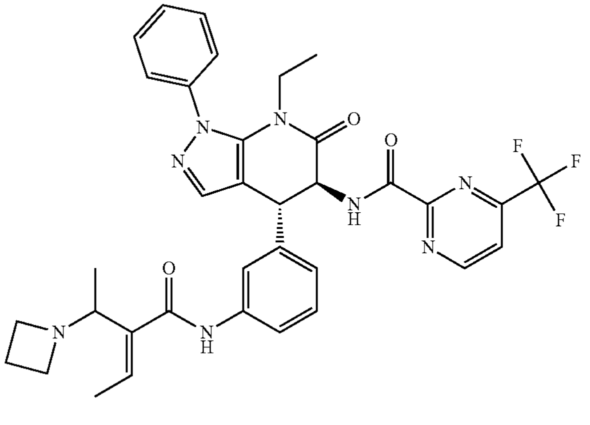 [SMILES: C/C=C(/C(=O)Nc1cccc([C@@H]2c3cnn(-c4ccccc4)c3N(CC)C(=O)[C@H]2NC(=O)c2nccc(C(F)(F)F)n2)c1)C(C)N1CCC1] |

TABLE 1-continued
| Exemplary Compounds |
| --- |
| I-386 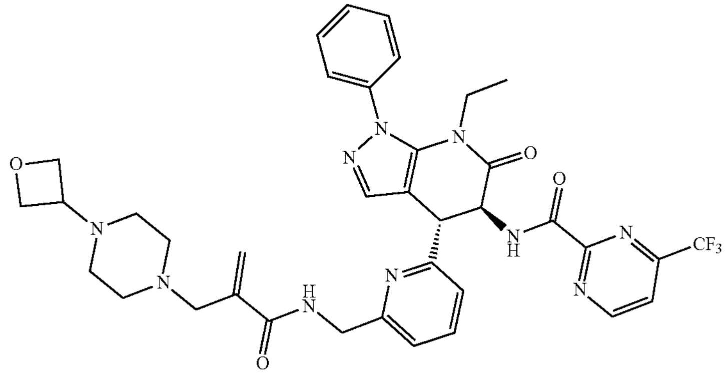 [SMILES: C=C(CN1CCN(C2COC2)CC1)C(=O)NCc1cccc([C@@H]2c3cnn(-c4ccccc4)c3N(CC)C(=O)[C@H]2NC(=O)c2nccc(C(F)(F)F)n2)n1] |
| I-387 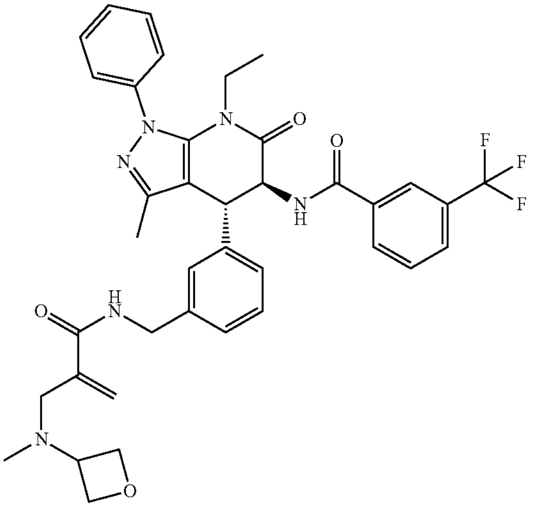 [SMILES: C=C(CN(C)C1COC1)C(=O)NCc1cccc([C@@H]2c3c(C)nn(-c4ccccc4)c3N(CC)C(=O)[C@H]2NC(=O)c2cccc(C(F)(F)F)c2)c1] |
| I-388 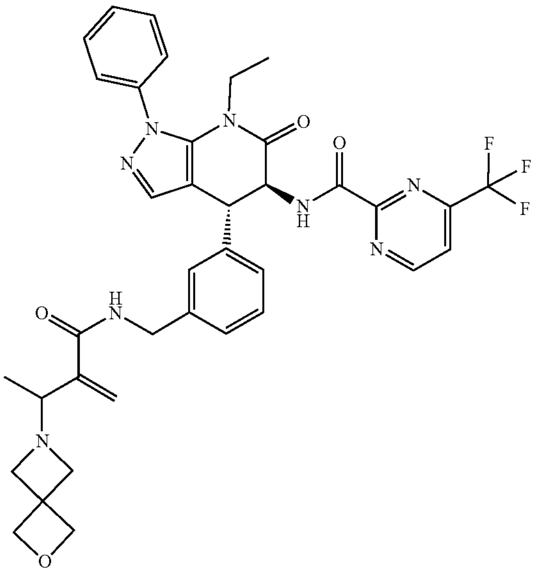 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N1CC2(COC2)C1] |

TABLE 1-continued

| Exemplary Compounds |
| --- |
| 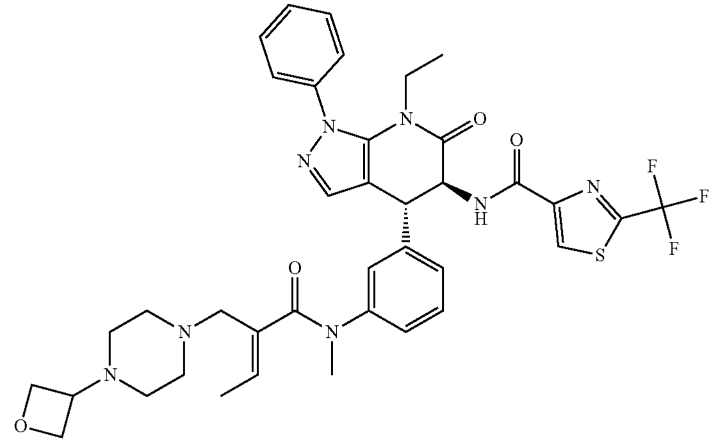 [SMILES: C/C=C(\CN1CCN(C2COC2)CC1)C(=O)N(C)c1cccc([C@@H]2c3cnn(-c4ccccc4)c3N(CC)C(=O)[C@H]2NC(=O)c2csc(C(F)(F)F)n2)c1] I-234a |
| 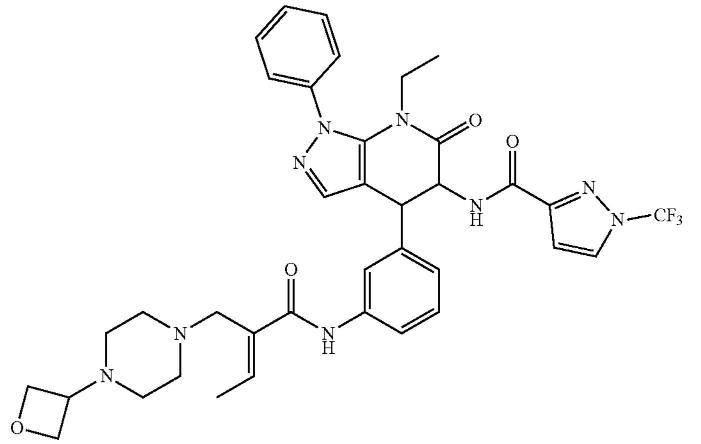 [SMILES: C/C=C(\CN1CCN(C2COC2)CC1)C(=O)Nc1cccc(C2c3cnn(-c4ccccc4)c3N(CC)C(=O)C2NC(=O)c2ccn(C(F)(F)F)n2)c1] I-383a |

2. Compounds and Related Definitions

As described generally above, the present invention provides a compound of Formula I:

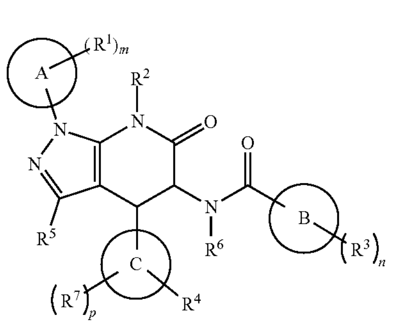

I or a pharmaceutically acceptable salt thereof, wherein the variables are as described above.

Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in *Organic Chemistry*, Thomas Sorrell, University Science Books, Sausalito: 1999, and *March's Advanced Organic Chemistry: Reactions, Mechanisms, and Structure*, M. B. Smith and J. March, $7^{th}$ Edition, John Wiley & Sons: 2013; the entire contents of each of which are hereby incorporated by reference.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms.

In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated, or having one or more units of unsaturation, having one or more atoms in common between the two rings of the ring system. Thus, the term includes any permissible ring fusion, such as ortho-fused or spirocyclic. As used herein, the term "spirocyclic" refers to organic compounds that contain at least two rings with one common atom, generally a quaternary carbon. Generally, the number of carbon atoms linked to the spiro atom in each ring is indicated in ascending order in brackets placed between the spiro prefix and the hydrocarbon name. For example,

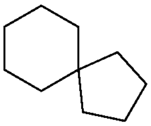

can be represented as spiro[4.5]decane.

As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, and sulfur. As used herein, the term "bridged bicyclic" refers to any bicyclic ring system, i.e. carbocyclic or heterocyclic, saturated, or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, and sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally, or alternatively, any substitutable nitrogen of a bridged bicyclic group is optionally substituted. Exemplary bicyclic rings include

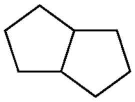
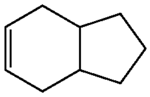
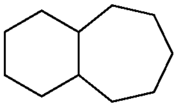

-continued

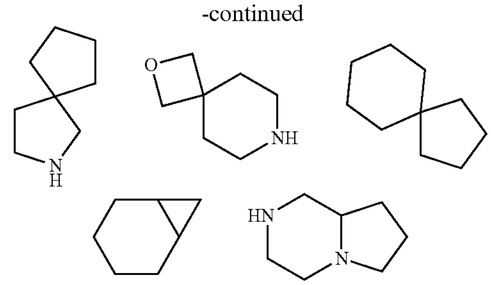

Exemplary bridged bicyclics include:

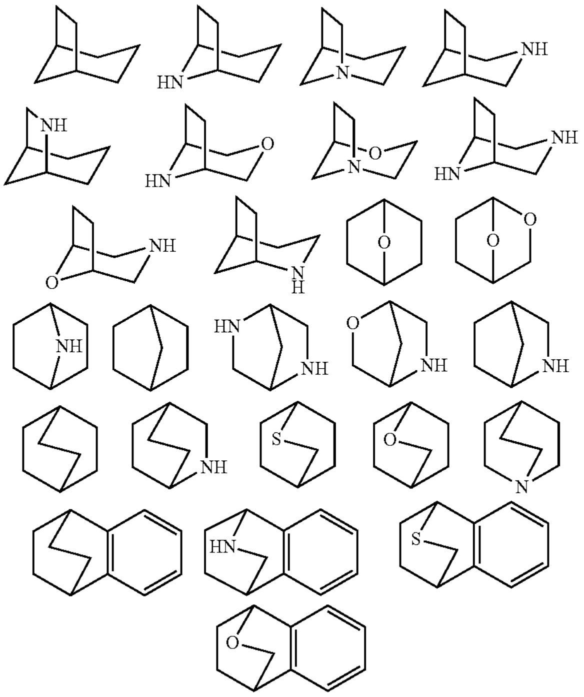

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain," refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3.

A substituted alkylene chain is a polymethylene group in which one or more methylene hydrogen atoms are replaced with a substituent. Suitable substituents include those described below for a substituted aliphatic group.

The term “alkenylene” refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term “halogen” means F, Cl, Br, or I.

The term “aryl” used alone or as part of a larger moiety as in “aralkyl,” “aralkoxy,” or “aryloxyalkyl,” refers to monocyclic or bicyclic ring systems having a total of five to fourteen ring members, wherein at least one ring in the system is aromatic and wherein each ring in the system contains 3 to 7 ring members. The term “aryl” may be used interchangeably with the term “aryl ring.” In certain embodiments of the present invention, “aryl” refers to an aromatic ring system which includes, but not limited to, phenyl, biphenyl, naphthyl, anthracyl and the like, which may bear one or more substituents. Also included within the scope of the term “aryl,” as it is used herein, is a group in which an aromatic ring is fused to one or more non-aromatic rings, such as indanyl, phthalimidyl, naphthimidyl, phenanthridinyl, or tetrahydronaphthyl, and the like. The term “phenylene” refers to a multivalent phenyl group having the appropriate number of open valences to account for groups attached to it. For example, “phenylene” is a bivalent phenyl group when it has two groups attached to it (e.g.,

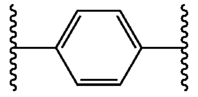 [SMILES: *c1ccc(*)cc1]

); “phenylene” is a trivalent phenyl group when it has three groups attached to it (e.g.,

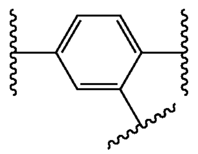 [SMILES: *c1ccc(*)c(*)c1]

). The term “arylene” refers to a bivalent aryl group.

The terms “heteroaryl” and “heteroar-,” used alone or as part of a larger moiety, e.g., “heteroaralkyl,” or “heteroaralkoxy,” refer to groups having 5 to 10 ring atoms, preferably 5, 6, or 9 ring atoms; having 6, 10, or 14 $\pi$ electrons shared in a cyclic array; and having, in addition to carbon atoms, from one to five heteroatoms. The term “heteroatom” refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms “heteroaryl” and “heteroar-,” as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term “heteroaryl” may be used interchangeably with the terms “heteroaryl ring,” “heteroaryl group,” or “heteroaromatic,” any of which terms include rings that are optionally substituted. The term “heteroaralkyl” refers to an alkyl group substituted with a heteroaryl, wherein the alkyl and heteroaryl portions independently are optionally substituted.

The term “heteroarylene” refers to a multivalent heteroaryl group having the appropriate number of open valences to account for groups attached to it. For example, “heteroarylene” is a bivalent heteroaryl group when it has two groups attached to it; “heteroarylene” is a trivalent heteroaryl group when it has three groups attached to it. The term “pyridinylene” refers to a multivalent pyridine radical having the appropriate number of open valences to account for groups attached to it. For example, “pyridinylene” is a bivalent pyridine radical when it has two groups attached to it (e.g.,

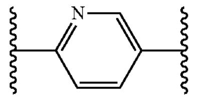 [SMILES: *c1ccc(*)nc1]

); “pyridinylene” is a trivalent pyridine radical when it has three groups attached to it (e.g.,

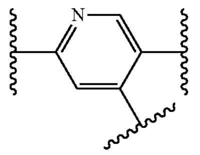 [SMILES: *c1cc(*)c(*)cn1]

).

As used herein, the terms “heterocycle,” “heterocyclyl,” “heterocyclic radical,” and “heterocyclic ring” are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term “nitrogen” includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted. The term "oxo-heterocyclyl" refers to a heterocyclyl substituted by an oxo group. The term "heterocyclylene" refers to a multivalent heterocyclyl group having the appropriate number of open valences to account for groups attached to it. For example, "heterocyclylene" is a bivalent heterocyclyl group when it has two groups attached to it; "heterocyclylene" is a trivalent heterocyclyl group when it has three groups attached to it.

As used herein, the term "partially unsaturated" refers to a ring moiety that includes at least one double or triple bond. The term "partially unsaturated" is intended to encompass rings having multiple sites of unsaturation but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent ("optional substituent") at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; —CH═CHPh, which may be substituted with $R^\circ$; $—(CH_2)_{0-4}O(CH_2)_{0-1}$-pyridyl which may be substituted with $R^\circ$; $—NO_2$; —CN; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR—$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—SC(S)SR^\circ$, $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched alkylene)$O—N(R^\circ)_2$; or $—(C_{1-4}$ straight or branched alkylene)$C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, and sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, $-(haloR^\bullet)$, $—(CH_2)_{0-2}OH$, $—(CH_2)_{0-2}OR^\bullet$, $—(CH_2)_{0-2}CH(OR^\bullet)_2$; $—O(haloR^\bullet)$, —CN, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene)$C(O)OR^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R^\circ$ include ═O and ═S.

Suitable divalent substituents on a saturated carbon atom of an "optionally substituted" group include the following: ═O, ═S, $═NNR^*_2$, $═NNHC(O)R^*$, $═NNHC(O)OR^*$, $═NNHS(O)_2R^*$, $═NR^*$, $═NOR^*$, $—O(C(R^*_2))_{2-3}O—$, or $—S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: $—O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of $R^*$ include halogen, $—R^\bullet$, $-(haloR^\bullet)$, —OH, $—OR^\bullet$, $—O(haloR^\bullet)$, —CN, —C(O)OH, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include $—R^\dagger$, $—NR^\dagger_2$, $—C(O)R^\dagger$, $—C(O)OR^\dagger$, $—C(O)C(O)R^\dagger$, $—C(O)CH_2C(O)R^\dagger$, $—S(O)_2R^\dagger$, $—S(O)_2NR^\dagger_2$, $—C(S)NR^\dagger_2$, $—C(NH)NR^\dagger_2$, or $—N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of RT are independently halogen, —R•, -(haloR•), —OH, —OR•, —O(haloR•), —CN, —C(O)OH, —C(O)OR•, —$NH_2$, —NHR•, —NR•$_2$, or —$NO_2$, wherein each R• is unsubstituted or where preceded by "halo" is substituted only with one or more halogens, and is independently $C_{1-4}$ aliphatic, —$CH_2$Ph, —O($CH_2$)$_{0-1}$Ph, or a 5-6-membered saturated, partially unsaturated, or aryl ring having 0-4 heteroatoms independently selected from nitrogen, oxygen, and sulfur.

As used herein, the term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66 (1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Salts derived from appropriate bases include alkali metal, alkaline earth metal, ammonium, and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

Compounds containing one or more stereocenters are a mixture of stereoisomers, unless otherwise stated or described (for example, with use of dashed or wedged bonds denoting stereochemistry). Generally, enhanced stereochemical representation introduces three types of identifiers that can be attached to a stereogenic center. A stereochemical group label is composed from an identifier and a group number. Each stereogenic center marked with wedge bonds belongs to one (and only one) stereochemical group. Grouping allows to specify relative relationships among stereogenic centers.

ABS denotes a stereogenic center where the absolute configuration is known. As used herein, "or" denotes a stereogenic center where the relative configuration is known, but the absolute configuration is not known. The structure represents one stereoisomer that is either the structure as drawn (R,S) or the epimer in which the stereogenic centers have the opposite configuration (S,R). One of skill in the art would understand that if a single stereogenic center is present, the designation "or" represents a single isomer for which the absolute configuration is not known. As used herein, "or1", "or2" denote stereogenic centers where the relative configuration is known, but the absolute configuration is not known when applied to a multi-center stereogroup. The designations "and" and "&" are used interchangeably and denote a mixture of stereoisomers. It can be a pair of enantiomers or all the diastereomers.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as an atropisomer (e.g., substituted biaryls), all forms of such atropisomers are considered part of this invention.

Chemical names, common names, and chemical structures may be used interchangeably to describe the same structure. If a chemical compound is referred to using both a chemical structure and a chemical name, and an ambiguity exists between the structure and the name, the structure predominates. It should also be noted that any carbon as well as heteroatom with unsatisfied valences in the text, schemes, examples, and tables herein is assumed to have the sufficient number of hydrogen atom(s) to satisfy the valences.

The terms "a" and "an" as used herein mean "one or more" and include the plural unless the context is inappropriate.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl. The term "cycloalkylene" refers to a bivalent cycloalkyl group.

The term "haloalkyl" refers to an alkyl group that is substituted with at least one halogen. Exemplary haloalkyl groups include $—CH_2F$, $—CHF_2$, $—CF_3$, $—CH_2CF_3$, $—CF_2CF_3$, and the like. The term "haloalkylene" refers to a bivalent haloalkyl group.

The term "hydroxyalkyl" refers to an alkyl group that is substituted with at least one hydroxyl. Exemplary hydroxyalkyl groups include $—CH_2CH_2OH$, $—C(H)(OH)CH_3$, $—CH_2C(H)(OH)CH_2CH_2OH$, and the like.

The terms "alkenyl" and "alkynyl" are art-recognized and refer to unsaturated aliphatic groups analogous in length and possible substitution to the alkyls described above, but that contain at least one double or triple bond, respectively.

The term "carbocyclylene" refers to a multivalent carbocyclyl group having the appropriate number of open valences to account for groups attached to it. For example, "carbocyclylene" is a bivalent carbocyclyl group when it has two groups attached to it; "carbocyclylene" is a trivalent carbocyclyl group when it has three groups attached to it.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. The term "haloalkoxyl" refers to an alkoxyl group that is substituted with at least one halogen. Exemplary haloalkoxyl groups include $—OCH_2F$, $—OCHF_2$, $—OCF_3$, $—OCH_2CF_3$, $—OCF_2CF_3$, and the like. The term "hydroxyalkoxyl" refers to an alkoxyl group that is substituted with at least one hydroxyl. Exemplary hydroxyalkoxyl groups include $—OCH_2CH_2OH$, $—OCH_2C(H)(OH)CH_2CH_2OH$, and the like. The term "alkoxylene" refers to a bivalent alkoxyl group.

The term "oxo" is art-recognized and refers to a "=O" substituent. For example, a cyclopentane substituted with an oxo group cyclopentanone.

The symbol "" indicates a point of attachment. The point of attachment can be drawn at the end of the bond in a chemical structure, for example,

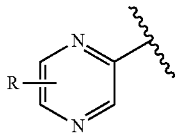

or at the center of the bond in a chemical structure, for example,

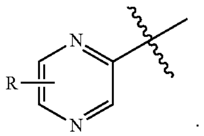

When a chemical structure containing a ring is depicted with a substituent having a bond that crosses a ring bond, the substituent may be attached at any available position on the ring. For example, the chemical structure

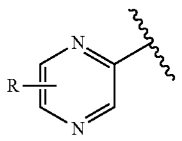

encompasses

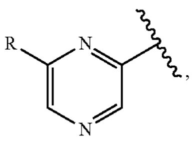, 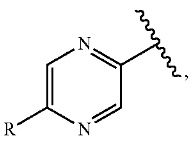, and

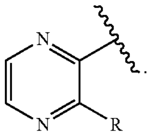

In the context of a polycyclic fused ring, when a chemical structure containing a polycyclic fused ring is depicted with one or more substituent(s) having a bond that crosses multiple rings, the one or more substituent(s) may be independently attached to any of the rings crossed by the bond. To illustrate, the chemical structure

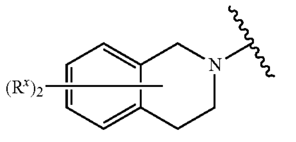

encompasses, for example,

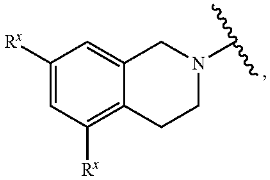
,

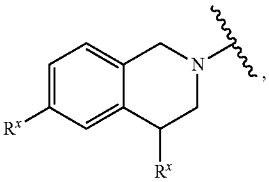
, and

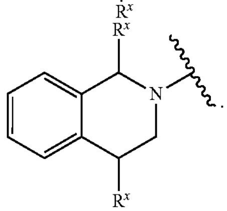
.

When any substituent or variable occurs more than one time in any constituent or the compound of the invention, its definition on each occurrence is independent of its definition at every other occurrence, unless otherwise indicated.

The term "warhead" or "warhead group" as used herein refers to a functional group present on a compound wherein that functional group is capable of reversibly or irreversibly participating in a reaction with a protein. Warheads may, for example, form covalent bonds with the protein. For example, the warhead moiety can be a functional group on an inhibitor that can participate in a bond-forming reaction, wherein a new covalent bond is formed between a portion of the warhead and a donor, for example an amino acid residue of a protein. In some embodiments, the warhead is an electrophile and the "donor" is a nucleophile such as the side chain of a cysteine residue.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

As used herein, the terms "subject" and "patient" are used interchangeably and refer to organisms to be treated by the methods of the present invention. Such organisms preferably include, but are not limited to, mammals (e.g., murines, simians, equines, bovines, porcines, canines, felines, and the like), and, most preferably, includes humans.

The term "$IC_{50}$" is art-recognized and refers to the concentration of a compound that is required to achieve 50% inhibition of the target. The potency of an inhibitor is usually defined by its $IC_{50}$ value. The lower the $IC_{50}$ value the greater the potency of the antagonist and the lower the concentration that is required to inhibit the maximum biological response. In certain embodiments, an inhibitor has an $IC_{50}$ and/or binding constant of less than about 100 μM, less than about 50 μM, less than about 1 μM, less than about 500 nM, less than about 100 nM, less than about 10 nM, or less than about 1 nM.

As used herein, the term "inhibitor" is defined as a compound that binds to and/or inhibits the target with measurable affinity. In some embodiments, inhibition in the presence of the inhibitor is observed in a dose-dependent manner. In some embodiments, the measured signal (e.g., signaling activity or biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or at least about 100% lower than the signal measured with a negative control under comparable conditions.

The terms "measurable affinity" and "measurably inhibit," as used herein, means a measurable change or inhibition in target activity between a sample comprising a compound of the present invention, or composition thereof an equivalent sample comprising target, in the absence of said compound, or composition thereof.

As used herein, the term "effective amount" refers to the amount of a compound sufficient to effect beneficial or desired results (e.g., a therapeutic, ameliorative, inhibitory, or preventative result). An effective amount can be administered in one or more administrations, applications, or dosages and is not intended to be limited to a particular formulation or administration route.

As used herein, the term "treating" includes any effect, e.g., lessening, reducing, modulating, ameliorating, or eliminating, that results in the improvement of the condition, disease, disorder, and the like, or ameliorating a symptom thereof. In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment can also be continued after symptoms have resolved, for example, to prevent or delay their recurrence.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers, and adjuvants, see e.g., Martin, Remington's Pharmaceutical Sciences, 15th Ed., Mack Publ. Co., Easton, PA [1975].

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified.

3. Methods of Use

It has now been found that the compounds and compositions of the disclosure can modulate DCN-1 (also referred to herein as DCN1) and are useful in treating disorders, diseases, and conditions associated with DCN-1. In some embodiments, modulating DCN-1 is inhibiting or reducing the activity of DCN-1. Without being limited to a specific mechanism, as shown herein, inhibiting or reducing the activity of DCN-1 results in reduced neddylation and other downstream effects. It has also been found that the compounds and compositions of the disclosure can modulate DCN-2 (also referred to herein as DCN2) and are useful in treating disorders, diseases, and conditions associated with DCN-2. In some embodiments, modulating DCN-2 is inhibiting or reducing the activity of DCN-2. Without being limited to a specific mechanism, as shown herein, inhibiting or reducing the activity of DCN-2 results in reduced neddylation and other downstream effects.

In one aspect, the present disclosure provides a method of modulating the activity of DCN-1 in vitro or in vivo, comprising contacting DCN-1 with a compound or composition thereof disclosed herein, or a pharmaceutically acceptable salt thereof. In one aspect, the present disclosure provides a method of modulating the activity of DCN-2 in vitro or in vivo, comprising contacting DCN-2 with a compound or composition thereof disclosed herein, or a pharmaceutically acceptable salt thereof.

In some embodiments, the present disclosure provides a method of modulating the activity of DCN-1 and/or DCN-2 in a subject, comprising administering to the subject a compound or composition thereof disclosed herein, or a pharmaceutically acceptable salt thereof.

In one aspect, the disease, disorder, or condition associated with DCN-1 or DCN-2 is a hemoglobinopathy such as sickle cell disorder or disease, or thalassemia disorder or disease.

In some embodiments, the disease, disorder, or condition associated with DCN-1 or DCN-2 is selected from one of those described in He et al. (Int Journal of Biological Macromolecules 227, 2024, 134541). In some embodiments, the disease, disorder, or condition associated with DCN-1 or DCN-2 is cancer (e.g., non-small cell lung cancer or gastric cancer), liver injury (e.g., non-alcoholic fatty liver disease), cardiac remodeling (e.g., atherosclerosis) or neurodegenerative disease (e.g., frontotemporal lobar degeneration). In some embodiments, the disease, disorder, or condition associated with DCN-1 or DCN-2 is characterized by overexpression of DCN-1 and/or DCN-2. In some embodiments, the disease, disorder, or condition associated with DCN-1 and/or DCN-2 overexpression is cancer (e.g., non-small cell lung cancer or gastric cancer).

In one aspect, the disclosure provides compounds and compositions for the treatment of of hemoglobinopathies such as sickle cell disorder or disease or thalassemia disorder or disease. In one aspect, the compounds and compositions described herein induce HbF (fetal hemoglobin; expressed by the gamma globin genes HBG1 and HBG2). It should be appreciated that induction of HbF allows for the treatment of hemoglobinopathies such as sickle cell disorder or disease or thalassemia disorder or disease. Thus, in one aspect, the disclosure provides compounds and compositions for the treatment of sickle cell disease.

In one aspect, the disclosure provides compounds and compositions for the treatment of of hemoglobinopathies such as sickle cell disorder or disease or thalassemia disorder or disease In one aspect, the compounds and compositions described herein induce HbF (fetal hemoglobin; expressed by the gamma globin genes HBG1 and HBG2) and reduce HbA (adult hemoglobin; expressed by the beta globin gene HBB), thus inducing production of fetal hemoglobin and reducing the expression of the hemoglobin beta gene. It should be appreciated that induction of HbF and reduction of HbA allows for the treatment of hemoglobinopathies such as sickle cell disorder or disease or thalassemia disorder or disease. Thus, in one aspect, the disclosure provides compounds and compositions for the treatment of sickle cell disease.

In some embodiments, a compound described herein is an irreversible covalent inhibitor of DCN-1 and/or DCN-2. In some embodiments, an irreversible covalent inhibitor of DCN-1 and/or DCN-2 provided herein can be used to treat diseases associated with DCN-1 and/or DCN-2. In some embodiments, an irreversible covalent inhibitor of DCN-1 and/or DCN-2 provided herein can be used to treat sickle cell disease. In some embodiments, a compound described herein is a reversible covalent inhibitor of DCN-1 and/or DCN-2. In some embodiments, a reversible covalent inhibitor of DCN-1 and/or DCN-2 provided herein can be used to treat diseases associated with DCN-1 and/or DCN-2. In some embodiments, a reversible covalent inhibitor of DCN-1 and/or DCN-2 provided herein can be used to treat sickle cell disease. In some embodiments, a compound described herein is a reversible inhibitor of DCN-1 and/or DCN-2. In some embodiments, a reversible inhibitor of DCN-1 and/or DCN-2 provided herein can be used to treat diseases associated with DCN-1 and/or DCN-2. In some embodiments, a reversible covalent of DCN-1 and/or DCN-2 provided herein can be used to treat sickle cell disease.

In one aspect, the disclosure provides irreversible covalent inhibitors of DCN-1 and/or DCN-2 for the treatment of a disease, disorder, or condition associated with DCN-1 and/or DCN-2. In some embodiments, the disclosure provides irreversible covalent inhibitors of DCN-1 and/or DCN-2 for the treatment of sickle cell disease. In some embodiments, the irreversible covalent inhibitors of DCN-1 and/or DCN-2 irreversibly covalently modify a cysteine of DCN-1 and/or DCN-2. In some embodiments, the irreversible covalent inhibitors of DCN-1 and/or DCN-2 irreversibly covalently modify Cys115 of DCN-1 and/or DCN-2.

In one aspect, the disclosure provides reversible covalent inhibitors of DCN-1 and/or DCN-2 for the treatment of a disease, disorder, or condition associated with DCN-1 and/or DCN-2. In some embodiments, the disclosure provides reversible covalent inhibitors of DCN-1 and/or DCN-2 for the treatment of sickle cell disease. In some embodiments, the reversible covalent inhibitors of DCN-1 and/or DCN-2 reversibly covalently modify a cysteine of DCN-1 and/or DCN-2. In some embodiments, the reversible covalent inhibitors of DCN-1 and/or DCN-2 reversibly covalently modify Cys115 of DCN-1 and/or DCN-2.

In one aspect, the disclosure provides reversible inhibitors of DCN-1 and/or DCN-2 for the treatment of a disease, disorder, or condition associated with DCN-1 or DCN-2. In one aspect, the disclosure provides reversible inhibitors of DCN-1 and/or DCN-2 for the treatment of sickle cell disease.

In some embodiments, the disclosure provides irreversible covalent inhibitors of DCN-1 and/or DCN-2, wherein the compound has a warhead that can irreversible covalently modify a cysteine of DCN-1 and/or DCN-2. In some embodiments, the cysteine is Cys115 of DCN-1 and/or DCN-2. In some embodiments, the disclosure provides reversible covalent inhibitors of DCN-1 and/or DCN-2, wherein the compound has a warhead that can reversible covalently modify a cysteine of DCN-1 and/or DCN-2. In some embodiments, the cysteine is Cys115 of DCN-1 and/or DCN-2.

In one aspect, the disclosure provides a DCN-1 that is covalently modified at Cys115. In some embodiments, the disclosure provides methods and compositions for covalently modifying DCN-1 in a subject. In some embodiments, the disclosure provides methods and compositions for covalently modifying DCN-1 Cys-115 in a subject. In some embodiments, the disclosure provides methods and compositions for covalently modifying DCN-1 Cys-115 in a subject for the treatment of sickle cell disease.

In one aspect, the disclosure provides a DCN-2 that is covalently modified at Cys115. In some embodiments, the disclosure provides methods and compositions for covalently modifying DCN-2 in a subject. In some embodiments, the disclosure provides methods and compositions for covalently modifying DCN-2 Cys-115 in a subject. In some embodiments, the disclosure provides methods and compositions for covalently modifying DCN-2 Cys-115 in a subject for the treatment of sickle cell disease.

In one aspect, the present disclosure provides a method of treating a hemoglobinopathy disorder or disease, comprising administering to a subject in need thereof a compound or composition thereof disclosed herein, or a pharmaceutically acceptable salt thereof. In another aspect, the present disclosure provides a method of inducing or increasing production of fetal hemoglobin. Such methods are useful, for example, in treating hemoglobin-related disorders including sickle cell disorders, diseases and conditions and thalassemia.

In some embodiments, the hemoglobinopathy is a sickle cell disorder or disease.

In some embodiments, the hemoglobinopathy is a thalassemia disorder or disease.

In one aspect, the present disclosure provides a method to increase red blood cell levels and/or hemoglobin levels in a subject in need thereof, treat or prevent an anemia in a subject in need thereof, treat sickle-cell disease in a subject in need thereof, or treat one or more complications of sickle-cell disease in a subject in need thereof, comprising administering to a subject in need thereof a compound disclosed herein, or a pharmaceutically acceptable salt thereof, in combination with hydroxyurea or a pharmaceutically acceptable salt thereof.

In one aspect, the present disclosure provides a method to increase fetal hemoglobin levels in a subject in need thereof, treat or prevent an anemia in a subject in need thereof, treat sickle-cell disease in a subject in need thereof, or treat one or more complications of sickle-cell disease in a subject in need thereof, comprising administering to a subject in need thereof a compound disclosed herein, or a pharmaceutically acceptable salt thereof, in combination with hydroxyurea or a pharmaceutically acceptable salt thereof.

In some embodiments, the present disclosure provides a method for the treatment of a DCN-1 associated disease. In some embodiments, the present disclosure provides a method for the treatment of a DCN-2 associated disease. In some embodiments, the present disclosure provides a method for the treatment of cancers, premalignant conditions (e.g., hyperplasia, metaplasia, and dysplasia), benign tumors, hyperproliferative disorders, and benign dysproliferative disorders. Such methods comprise the step of administering to a subject in need thereof a compound disclosed herein, or a pharmaceutically acceptable salt thereof. In some embodiments, the cancer is characterized by overexpression of DCN-1 and/or DCN-2.

In some embodiments, cancers and related disorders that can be treated or prevented by methods disclosed herein include, but are not limited, to the following: a squamous cell carcinoma, a metastatic squamous cell carcinoma, a non-small cell lung carcinoma, a uterine carcino-sarcoma, an embryonal rhabdomyosarcoma, a glioblastoma, a medulloblastoma, an osteosarcoma, or an adrenocortical tumor. In some embodiments, the cancer and related disorders include a cancer of the lung, cervix, ovary, uterus, esophagus, prostate, or head and neck.

In some embodiments, the cancer of the lung includes a non-small cell lung cancer, including, but not limited to a squamous cell carcinoma, adenocarcinoma, or large cell-undifferentiated carcinoma.

In some embodiments, cancers and related disorders include a hematological malignancy such as a leukemia, a lymphoma, a myeloma, a multiple lymphoma, a B-cell non-Hodgkin's lymphoma, or an acute myeloid leukemia.

In some embodiments, the present disclosure provides a method for the treatment of a cancer, including, but not limited to, leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, polycythemia vera, Lymphoma, Hodgkin's disease, non-Hodgkin's disease, multiple myeloma, Waldenstrom's macroglobulinemia, heavy chain disease, solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In some embodiments, the present disclosure provides a method for the treatment of leukemia, including, but not limited to, acute leukemia, acute lymphocytic leukemia; acute myelocytic leukemia, including, but not limited to, myeloblastic, promyelocytic, myelomonocytic, monocytic, erythroleukemia and myelodysplastic syndrome; chronic leukemia, including, but not limited to, chronic myelocytic (granulocytic) leukemia, chronic lymphocytic leukemia, hairy cell leukemia; polycythemia vera; lymphomas, including, but not limited to, Hodgkin's lymphoma, non-Hodgkin's lymphoma; myeloma, including, but not limited, to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumor, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer, including, but not limited to, papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers, including, but not limited to, Cushing's disease, prolactin-secreting tumor, acromegaly, and diabetes insipius; eye cancer, including, but not limited to, ocular melanoma such as iris melanoma, choroidal melanoma, and cilliary body melanoma, and retinoblastoma; vaginal cancer, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancer, including, but not limited to, squamous cell carcinoma, and adenocarcinoma; uterine cancer, including, but not limited to, endometrial carcinoma and uterine sarcoma; ovarian cancers, including, but not limited to, ovarian epithelial carcinoma, borderline tumor, germ cell tumor, and stromal tumor; esophageal cancer, including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancer, including, but not limited to, adenocarcinoma, fungating (polypoid), ulcerating, superficial spreading, diffusely spreading, malignant lymphom, liposarcoma, fibrosarcoma, and carcinosarcoma; colon cancer; rectal cancer; liver cancer, including, but not limited to, hepatocellular carcinoma and hepatoblastoma, gallbladder cancer, including, but not limited to, adenocarcinoma; cholangiocarcinoma, including, but not limited to, pappillary, nodular, and diffuse; lung cancer, including, but not limited to, non-small cell lung cancer, squamous cell carcinoma (epidermoid carcinoma), adenocarcinoma, large-cell carcinoma and small-cell lung cancer; testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor); prostate cancer, including, but not limited to, adenocarcinoma, leiomyosarcoma, and rhabdomyosarcoma; penal cancers; oral cancer, including, but not limited to, squamous cell carcinoma; basal cancers; salivary gland cancer, including, but not limited to, adenocarcinoma, mucoepidermoid carcinoma, and adenoidcystic carcinoma; pharynx cancer, including, but not limited to, squamous cell cancer, and verrucous; skin cancer, including, but not limited to, basal cell carcinoma, squamous cell carcinoma and melanoma, superficial spreading melanoma, nodular melanoma, lentigo malignant melanoma, and acral lentiginous melanoma; kidney cancer, including, but not limited to, renal cell cancer, adenocarcinoma, hypernephroma, fibrosarcoma, and transitional cell cancer (renal pelvis and/or uterer); Wilms' tumor; bladder cancer, including, but not limited to, transitional cell carcinoma, squamous cell cancer, adenocarcinoma, carcinosarcoma. In addition, cancer includes myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In some embodiments, the present disclosure provides a method for the treatment of liver injury. Without being limited to a specific mechanism, targeting neddylation provides a method for the treatment of liver fibrosis and liver injury. (See e.g., Zubiete-Franco et al. Hepatology 65 (2) 2017, 694-709). Thus, in some embodiments, the present disclosure provides a method for the treatment of hepatitis, Non-alcoholic fatty liver disease (NAFLD), alcoholic liver disease, cirrhosis, hemochromatosis, jaundice, autoimmune liver disorders, liver cancer, galactosemia, alpha-1 antitrypsin deficiency, Wilson disease, oxalosis, liver adenoma, Alagille syndrome, primary biliary cholangitis (PBC), and lysosomal acid lipase deficiency (LAL-D).

In some embodiments, the present disclosure provides a method for the treatment of heart disease. Without being limited to a specific mechanism, targeting neddylation, provides a method for the treatment of heart disease (See e.g., Kandala et al., Am. J. Cardiovasc. Dis 4, 2014, 140). Thus, in some embodiments, the present disclosure provides a method for the treatment of arrhythmia. heart failure, coronary artery disease, heart valve disease, congenital heart disease, angina, cardiomyopathy, pericarditis, peripheral artery disease, aortic aneurysm, aortic stenosis, deep vein thrombosis, Mlarfan syndrome and rheumatic heart disease.

In some embodiments, the present disclosure provides a method for the treatment of neurodegenerative diseases (See e.g., Villa et al., Eur J. Neurol. 16 (7) 2009, 870. Thus, in some embodiments, the present disclosure provides a method for the treatment of amyotrophic lateral sclerosis, multiple sclerosis, Parkinson's disease, Alzheimer's disease, Huntington's disease, multiple system atrophy, tauopathies and prion diseases.

In some embodiments, the method optionally comprises co-administration of a second therapeutic agent. In some embodiments, the second therapeutic agent is hydroxyurea or a pharmaceutically acceptable salt thereof.

In one aspect, the present disclosure provides a method of treating a hemoglobinopathy disorder or disease, comprising administering to a subject in need thereof a compound disclosed herein, or a pharmaceutically acceptable salt thereof, in combination with a second agent such as hydroxyurea or a pharmaceutically acceptable salt thereof.

In some embodiments, the hemoglobinopathy is a sickle cell disorder or disease.

In some embodiments, the hemoglobinopathy is a thalassemia disorder or disease.

In some embodiments, the compound or pharmaceutically acceptable salt thereof and the hydroxyurea or a pharmaceutically acceptable salt thereof act synergistically.

In some embodiments, the compound or pharmaceutically acceptable salt thereof is selected from one of those shown in Table 1, or a pharmaceutically acceptable salt thereof.

In one aspect, the present disclosure provides a method of increasing efficacy and/or reducing toxicity of hydroxyurea treatment in a subject undergoing said treatment, comprising administering to the subject a compound disclosed herein, or a pharmaceutically acceptable salt thereof. In some embodiments, the hydroxyurea treatment is for a hemoglobinopathy. In some embodiments, the hydroxyurea treatment is for sickle cell disease. In some embodiments, the hydroxyurea treatment is for a thalassemia disorder.

In some embodiments, the method further comprises the step of decreasing an amount of hydroxyurea being administered to the subject.

In some embodiments, the amount of hydroxyurea being administered is decreased by 10-90%.

In one aspect, the present disclosure provides a method of decreasing the dose of hydroxyurea or a pharmaceutically acceptable salt thereof needed for effective treatment of a hemoglobinopathy disorder or disease, comprising administering to a subject in need thereof a compound disclosed herein, or a pharmaceutically acceptable salt thereof, in combination with hydroxyurea or a pharmaceutically acceptable salt thereof, wherein the dose of hydroxyurea or a pharmaceutically acceptable salt thereof needed for effective treatment of the hemoglobinopathy disorder or disease is less than the dose needed for treatment in the subject using hydroxyurea or a pharmaceutically acceptable salt thereof as a monotherapy.

In some embodiments, the dose of hydroxyurea or a pharmaceutically acceptable salt thereof co-administered with the compound or pharmaceutically acceptable salt thereof is reduced by at least 10%, at least 20%, at least 30%, at least 40%, at least 50%, at least 60%, at least 70%, at least 80%, or at least 90% relative to the dose needed for treatment in the subject using hydroxyurea or a pharmaceutically acceptable salt thereof as a monotherapy.

In some embodiments, the compound or pharmaceutically acceptable salt thereof is selected from one of those shown in Table 1, or a pharmaceutically acceptable salt thereof.

In some embodiments, the present disclosure provides a method to treat or prevent one or more complications of sickle cell disease including, for example, anemia, anemia crisis, splenomegaly, pain crisis, chest syndrome, acute chest syndrome, blood transfusion requirement, organ damage, pain medicine (management) requirement, splenic sequestration crises, hyperhemolytic crisis, vaso-occlusion, vaso-occlusion crisis, acute myocardial infarction, sickle-cell chronic lung disease, thromboemboli, hepatic failure, hepatomegaly, hepatic sequestration, iron overload and complications of iron overload (e.g., congestive heart failure, cardiac arrhythmia, myocardial infarction, other forms of cardiac disease, diabetes mellitus, dyspnea, hepatic disease and adverse effects of iron chelation therapy), splenic infarction, acute and/or chronic D renal failure, pyelonephritis, aneurysm, ischemic stroke, intraparenchymal hemorrhage, subarachnoid hemorrhage, intraventricular hemorrhage, peripheral retinal ischemia, proliferative sickle retinopathy, vitreous hemorrhage, and/or priapism; comprising administering to a subject in need thereof a disclosed compound or pharmaceutically acceptable salt thereof, optionally in combination with a second therapeutic agent such as hydroxyurea or a pharmaceutically acceptable salt thereof.

In some embodiments, the compound or pharmaceutically acceptable salt thereof acts synergistically in combination with the second therapeutic agent, e.g., hydroxyurea or a pharmaceutically acceptable salt thereof.

4. Combination Therapies

In one aspect, the compounds of the present disclosure are used advantageously in combination with a second therapeutic agent. Such a second therapeutic agent includes, in some embodiments, hydroxyurea or a pharmaceutically acceptable salt thereof.

In some embodiments, the disclosure provides methods for using a compound or combination therapy (for example, a disclosed compound or pharmaceutically acceptable salt thereof in combination with hydroxyurea or a pharmaceutically acceptable salt thereof) to treat or prevent vascular occlusion (vaso-occlusion) in a sickle-cell disease patient in need thereof as well as various complications associated with vaso-occlusion in a sickle-cell disease patient (e.g., vaso-occlusion crisis, pain crisis, etc.). In some embodiments, the disclosure provides methods for using a disclosed compound or combination therapy to treat or prevent anemia in a sickle-cell disease patient in need thereof as well as various complications associated with anemia in a sickle-cell disease patient (e.g., aplastic crisis, hyperhemolytic crisis, etc.). In such methods, a disclosed compound or combination therapy can be used to increase red blood cell levels while reducing the need for red blood cell transfusions and/or iron chelation therapy, and thereby reduce morbidity and mortality associated with iron accumulation in vulnerable tissues/organs. In such methods, a disclosed compound or combination therapy can also be used to reduce the need for other supportive therapies for treating sickle-cell disease [e.g., treatment with hydroxyurea, treatment with an EPO or other EPO agonist, and/or pain management (e.g., treatment with one or more of opioid analgesic agents, non-steroidal anti-inflammatory drugs, and/or corticosteroids)]. In part, a disclosed compound or combination therapy can be used in combination with existing supportive therapies for sickle-cell disease including, for example, transfusion of red blood cells, iron chelation therapy, hydroxyurea therapy, EPO or EPO agonist therapy, and/or pain management therapy. Optionally, a disclosed compound or combination therapy can be used to reduce the amount, duration, etc. of an existing supportive therapy for sickle-cell disease. For example, while transfusion of red blood cells and iron chelation therapy may help treat certain complications of sickle-cell disease, they sometimes result in adverse side effects. Therefore, in certain aspects, a disclosed compound or combination therapy can be used to reduce the amount of a second supportive therapy, e.g., reduce blood cell transfusion burden or reduce the dosage of a chelation therapeutic. In certain aspects, the disclosure provides uses of a disclosed compound or combination therapy (optionally in combination with one or more supportive therapies for sickle-cell disease) for making a medicament for the treatment or prevention of sickle-cell disease, particularly one or more complications of sickle-cell disease as disclosed herein.

5. Compositions

The present disclosure also provides compositions that comprise or deliver a compound as provided herein. In some embodiments, the present disclosure provides compositions comprising a compound provided herein with one or more other components.

In some embodiments, provided compositions comprise and/or deliver a compound described herein. In some embodiments, a provided composition is a pharmaceutical composition that comprises and/or delivers a compound provided herein and further comprises a pharmaceutically acceptable carrier.

Pharmaceutical compositions typically contain an active agent (e.g., a compound described herein) in an amount effective to achieve a desired therapeutic effect while avoiding or minimizing adverse side effects. In some embodiments, provided pharmaceutical compositions comprise a compound described herein and one or more carriers or excipients (e.g., fillers, disintegrants, lubricants, glidants, anti-adherents, and/or anti-statics, etc.) Provided pharmaceutical compositions can be in a variety of forms including oral dosage forms, topical creams, topical patches, iontophoresis forms, suppository, nasal spray and/or inhaler, eye drops, intraocular injection forms, depot forms, as well as injectable and infusible solutions.

Provided pharmaceutical compositions can be prepared with any appropriate available technologies.

In some embodiments, provided compounds are formulated in a unit dosage form for ease of administration and uniformity of dosage. The expression "unit dosage form" as used herein refers to a physically discrete unit of an active agent (e.g., a compound described herein) for administration to a subject. Typically, each such unit contains a predetermined quantity of active agent. In some embodiments, a unit dosage form contains an entire single dose of the agent. In some embodiments, more than one unit dosage form is administered to achieve a total single dose. In some embodiments, administration of multiple unit dosage forms is required, or expected to be required, in order to achieve an intended effect. A unit dosage form may be, for example, a liquid pharmaceutical composition containing a predetermined quantity of one or more active agents, a solid pharmaceutical composition (e.g., a tablet, a capsule, or the like) containing a predetermined amount of one or more active agents, a sustained release formulation containing a predetermined quantity of one or more active agents, or a drug delivery device containing a predetermined amount of one or more active agents, etc.

Provided compositions may be administered in accordance with a dosing regimen (i.e., that includes a single dose or multiple doses separated from one another in time, administered via a particular route of administration) that is (e.g., has been demonstrated to be) effective for treating (e.g., delaying onset of and/or decreasing incidence and/or intensity of) a disease or disorder, for example as described herein.

The present disclosure also provides methods of preparing pharmaceutical compositions provided herein. In some embodiments, provided methods comprise (i) providing a provided compound or a pharmaceutically acceptable salt thereof, and (ii) formulating the compound with suitable excipients to give a pharmaceutical composition.

6. General Methods of Providing the Present Compounds

The compounds of this invention may be prepared or isolated in general by synthetic and/or semi-synthetic methods known to those skilled in the art for analogous compounds and by methods described in detail in the Examples and Figures, herein.

In the schemes and chemical reactions depicted in the detailed description, Examples, and Figures, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, $7^{th}$ Edition, John Wiley & Sons, 2013, *Comprehensive Organic Transformations*, R. C. Larock, $3^{rd}$ Edition, John Wiley & Sons, 2018, and *Protective Groups in Organic Synthesis*, P. G. M. Wuts, $5^{th}$ edition, John Wiley & Sons, 2014, the entirety of each of which is hereby incorporated herein by reference.

As used herein, the phrase "leaving group" (LG) includes, but is not limited to, halogens (e.g., fluoride, chloride, bromide, iodide), sulfonates (e.g., mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protective Groups in Organic Synthesis*, P. G. M. Wuts, $5^{th}$ edition, John Wiley & Sons, 2014, and Philip Kocienski, in Protecting Groups, Georg Thieme Verlag Stuttgart, New York, 1994, the entireties of which are incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protective Groups in Organic Synthesis*, P. G. M. Wuts, $5^{th}$ edition, John Wiley & Sons, 2014, and Philip Kocienski, in Protecting Groups, Georg Thieme Verlag Stuttgart, New York, 1994, the entireties of which are incorporated herein by reference. Suitable amino protecting groups include, but are not limited to, aralkylamines, carbamates, cyclic imides, allyl amines, amides, and the like. Examples of such groups include t-butyloxycarbonyl (Boc), ethyloxycarbonyl, methyloxycarbonyl, trichloroethyloxycarbonyl, allyloxycarbonyl (Alloc), benzyloxocarbonyl (Cbz), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

One of skill in the art will appreciate that various functional groups present in compounds of the invention such as aliphatic groups, alcohols, carboxylic acids, esters, amides, aldehydes, halogens, and nitriles can be interconverted by techniques well known in the art including, but not limited to reduction, oxidation, esterification, hydrolysis, partial oxidation, partial reduction, halogenation, dehydration, partial hydration, and hydration. See, for example, *March's Advanced Organic Chemistry: Reactions, Mechanisms, and Structure*, M. B. Smith, and J. March, $7^{th}$ Edition, John Wiley & Sons, 2013, *Comprehensive Organic Transformations*, R. C. Larock, $3^{rd}$ Edition, John Wiley & Sons, 2018, the entirety of each of which is incorporated herein by reference. Such interconversions may require one or more of the aforementioned techniques, and certain methods for synthesizing compounds of the invention are described below.

One of skill in the art will appreciate that various functional groups present in compounds of the invention such as aliphatic groups, alcohols, carboxylic acids, esters, amides, aldehydes, halogens, and nitriles can be interconverted by techniques well known in the art including, but not limited to reduction, oxidation, esterification, hydrolysis, partial oxidation, partial reduction, halogenation, dehydration, partial hydration, and hydration. Such groups and transformations are described in detail in *March's Advanced Organic Chemistry: Reactions, Mechanisms, and Structure*, M. B. Smith and J. March, $7^{th}$ Edition, John Wiley & Sons, 2013, *Comprehensive Organic Transformations*, R. C. Larock, $3^{rd}$ Edition, John Wiley & Sons, 2018, and *Protective Groups in Organic Synthesis*, P. G. M. Wuts, $5^{th}$ edition, John Wiley & Sons, 2014, the entirety of each of which is hereby incorporated herein by reference. Such interconversions may require one or more of the aforementioned techniques, and certain methods for synthesizing compounds of the invention are described below in the Exemplification and Figures.

7. Enumerated Embodiments

The disclosure herein is further presented as a non-limiting list of numbered embodiments.

1. A compound of Formula Ta:

Ia

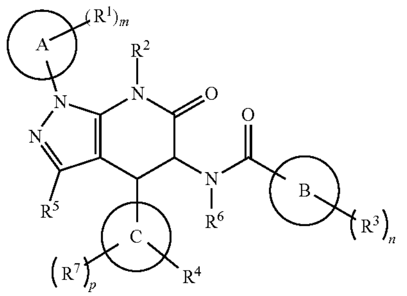

or a pharmaceutically acceptable salt thereof, wherein:

Ring A is phenyl, 3-8 membered saturated or partially unsaturated monocyclic carbocyclic ring, and a 5-6 membered monocyclic heteroaromatic ring having 1-4 heteroatoms independently selected from nitrogen, oxygen, and sulfur;

Ring B is phenyl, or a 5-6 membered monocyclic heteroaromatic ring having 1-4 heteroatoms independently selected from nitrogen, oxygen, and sulfur;

Ring C is phenyl, or a 5-6 membered monocyclic heteroaromatic ring having 1-4 heteroatoms independently selected from nitrogen, oxygen, and sulfur;

each occurrence of $R^1$ is independently an optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, or —NRS(O)$_2$R; or two instances of $R^1$ together form a 4-6 membered optionally substituted heterocyclic ring having 1-4 heteroatoms selected from nitrogen, oxygen, and sulfur, or two instances of $R^1$ together form a 4-6 membered optionally substituted carbocyclic ring;

$R^2$ is an optionally substituted group selected from $C_{1-6}$ aliphatic, or a 3-8 membered saturated or partially unsaturated monocyclic carbocyclic ring;

each occurrence of $R^3$ is independently an optionally substituted $C_{1-6}$ aliphatic, $C_{3-6}$ cycloalkyl, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, or —NRS(O)$_2$R;

$R^4$ is a substituent comprising a warhead group;

$R^5$ is hydrogen; or an optionally substituted group selected from $C_{1-6}$ aliphatic;

$R^6$ is hydrogen or an optionally substituted $C_{1-6}$ aliphatic group;

each occurrence of $R^7$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, —NRS(O)$_2$R, phenyl, or a 5-6 membered heteroaromatic ring having 1-3 heteroatoms selected from nitrogen, sulfur, and oxygen;

each occurrence of R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

m is 0, 1, 2, 3, 4, or 5;

n is 0, 1, 2, 3, 4, or 5; and p is 0, 1, 2, 3, 4, or 5.

2. A compound of Formula I:

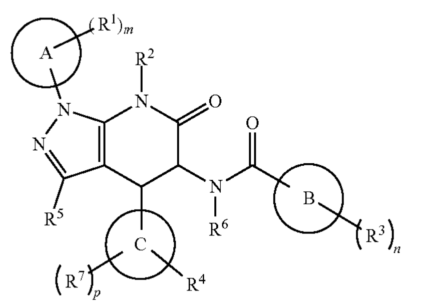

I or a pharmaceutically acceptable salt thereof, wherein:

Ring A is phenyl, 3-8 membered saturated or partially unsaturated monocyclic carbocyclic ring, and a 5-6 membered monocyclic heteroaromatic ring having 1-4 heteroatoms independently selected from nitrogen, oxygen, and sulfur;

Ring B is phenyl, or a 5-6 membered monocyclic heteroaromatic ring having 1-4 heteroatoms independently selected from nitrogen, oxygen, and sulfur;

Ring C is phenyl, or a 5-6 membered monocyclic heteroaromatic ring having 1-4 heteroatoms independently selected from nitrogen, oxygen, and sulfur;

each occurrence of $R^1$ is independently an optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, or —NRS(O)$_2$R;

$R^2$ is an optionally substituted group selected from $C_{1-6}$ aliphatic, or a 3-8 membered saturated or partially unsaturated monocyclic carbocyclic ring;

each occurrence of $R^3$ is independently an optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, or —NRS(O)$_2$R;

$R^4$ is a substituent comprising a warhead group;

$R^5$ is hydrogen; or an optionally substituted group selected from $C_{1-6}$ aliphatic;

$R^6$ is hydrogen or an optionally substituted $C_{1-6}$ aliphatic group;

each occurrence of $R^7$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, —NRS(O)$_2$R, phenyl, or a 5-6 membered heteroaromatic ring having 1-3 heteroatoms selected from nitrogen, sulfur, and oxygen;

each occurrence of R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

m is 0, 1, 2, 3, 4, or 5;

n is 0, 1, 2, 3, 4, or 5; and p is 0, 1, 2, 3, 4, or 5.

3. The compound of enumerated embodiment 1 or 2, wherein $R^4$ is $L^2$-Y, wherein $L^2$ is a covalent bond or a bivalent $C_{2-8}$ straight or branched, hydrocarbon chain wherein one or two methylene units of $L^2$ are optionally and independently replaced by —NRC(O)—, —C(O)NR—, —N(R)SO$_2$—, SO$_2$N(R)—, —S—, —O—, —NR—, S(O)—, —SO$_2$—, —C(O)—, —OC(O)—, or —C(O)O—; and additionally one methylene unit of $L^2$ is optionally replaced by an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur; and Y is hydrogen, halogen, —COOR, —CN, —CON(R)$_2$, —NRCN, NO$_2$—, —N(R)$_2$, optionally substituted $C_{1-8}$ aliphatic, or an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, and an 8-10 membered bicyclic heteroaromatic ring having 1-5 heteroatoms independently selected from nitrogen, oxygen, and sulfur;

wherein -$L^2$-Y comprises an alpha, beta-unsaturated carbonyl moiety, amide, cyano group, halogen, carbonyl, alkynyl group, sulfonyl group, or epoxide.

4. The compound of any one of enumerated embodiments 1 to 3, wherein $R^4$ is $L^2$-Y, wherein $L^2$ is a covalent bond or a bivalent $C_{2-8}$ straight or branched, hydrocarbon chain wherein one or two methylene units of $L^2$ are optionally and independently replaced by —NRC(O)—, —C(O)NR—, —N(R)$SO_2$—, —$SO_2N$(R)—, —S—, —O—, —NR—, —S(O)—, —$SO_2$—, —C(O)—, —OC(O)—, or —C(O)O—; and additionally one methylene unit of $L^2$ is optionally replaced by an optionally substituted ring selected from a 3-8 membered saturated or partially unsaturated monocyclic carbocyclic ring, or a 3-8 membered saturated or partially unsaturated monocyclic heterocyclic ring having 1-2 heteroatoms independently selected from nitrogen, oxygen, and sulfur; and Y is hydrogen, halogen, —$COOR^f$, —CN, —$CONR_2$, —$NR^f$CN, $NO_2$, —$NR_2$, $C_{1-8}$ aliphatic optionally substituted with halogen, $NO_2$—, or CN, or an optionally substituted ring selected from a 3-8 membered saturated or partially unsaturated monocyclic carbocyclic ring, phenyl, a 3-8 membered saturated or partially unsaturated monocyclic heterocyclic ring having 1-2 heteroatoms independently selected from nitrogen, oxygen, and sulfur, and a 5-10 membered bicyclic heterocyclic ring having 1-4 heteroatoms independently selected from nitrogen, oxygen, and sulfur; wherein -$L^2$-Y comprises an alpha, beta-unsaturated carbonyl moiety, amide, cyano group, halogen, carbonyl, alkynyl group, sulfonyl group, or epoxide; and wherein each occurrence of R is independently H, or straight or branched $C_{1-6}$ alkyl, $C_{2-6}$ alkenyl, or $C_{2-6}$ alkynyl group optionally substituted with 1, 2 or 3 halogen atoms.

5. The compound of any one of enumerated embodiments 1 to 4, wherein $R^4$ is $L^2$-Y, wherein $L^2$ is a covalent bond or a bivalent $C_{2-8}$ straight or branched, hydrocarbon chain wherein one or two methylene units of $L^2$ are optionally and independently replaced by —NRC(O)—, C(O)NR—, —N(R)$SO_2$—, $SO_2N$(R)—, —S—, S(O)—, —$SO_2$—, —C(O)—, —OC(O)—, or —C(O)O—; and additionally one methylene unit of $L^2$ is optionally replaced by a ring selected from,

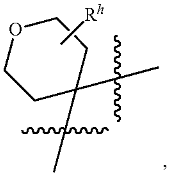, 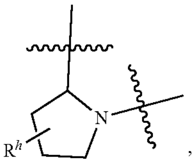, 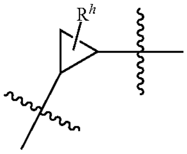, 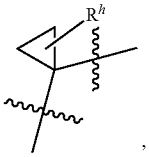, 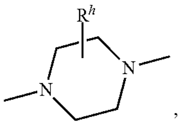, 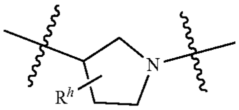, 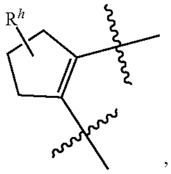, 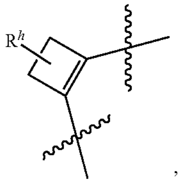, 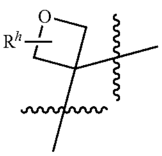, and -continued

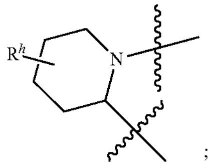;

and Y is hydrogen, halogen, —$COOR^f$, —CN, —$CONR_2$, —$NR^f$CN, $NO_2$, —$NR^f_2$, epoxide, $C_{1-8}$ aliphatic optionally substituted with halogen, $NO_2$, or CN, or a ring selected from

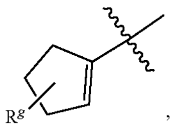, 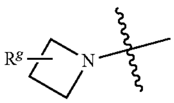, 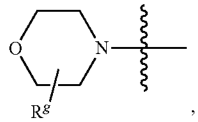, 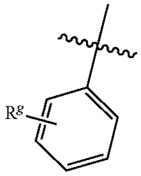, 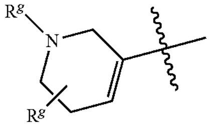, 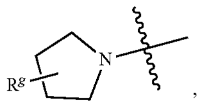, 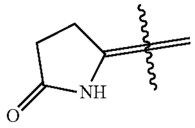, 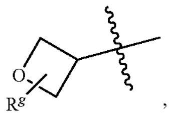, 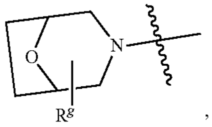, 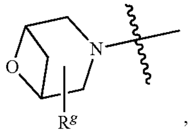, 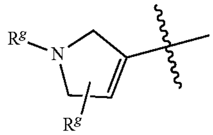, 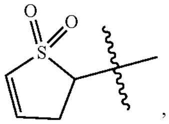, 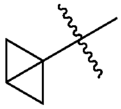, 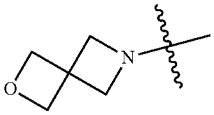, 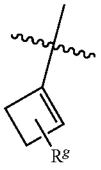, 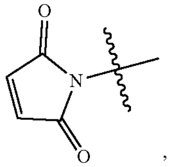, 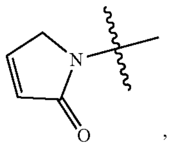, 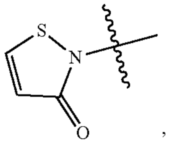, 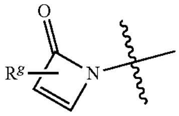, 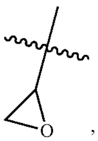, 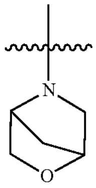, 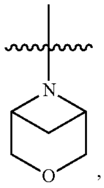, 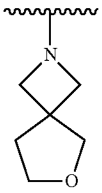, 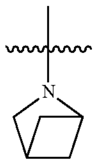, -continued

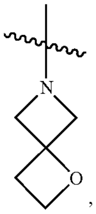, 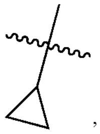, and 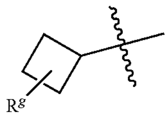, wherein $-L^2-Y$ comprises an alpha, beta-unsaturated carbonyl moiety, amide, cyano group, halogen, carbonyl, $C_{2-6}$ alkynyl group, sulfonyl group, or epoxide; wherein each occurrence of $R^f$ is independently H, or straight or branched $C_{1-6}$ alkyl, $C_{2-6}$ alkenyl, or $C_{2-6}$ alkynyl group optionally substituted with 1, 2 or 3 halogen atoms; and wherein each occurrence of $R^g$ and $R^h$ is independently H, halogen, OH, or straight or branched $C_{1-6}$ alkyl, $C_{2-6}$ alkenyl, or $C_{2-6}$ alkynyl group optionally substituted with 1, 2 or 3 halogen atoms.

6. The compound of any one of enumerated embodiments 1 to 5, wherein $R^4$ is selected from Table 1c, Table 1d or Table 1e.

7. The compound of any one of enumerated embodiments 1 to 6, wherein Ring A is phenyl.

8. The compound of any one of enumerated embodiments 1 to 7, wherein Ring B, taken together with $R^3$, is selected from

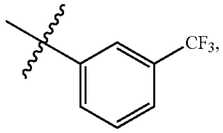 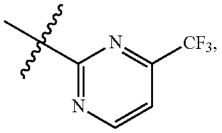

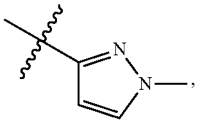 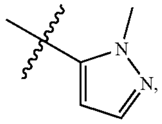 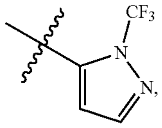

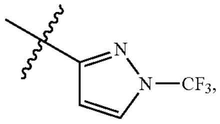 and 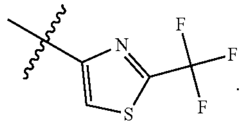.

9. The compound of any one of enumerated embodiments 1 to 8, wherein Ring C is phenyl.

10. The compound of any one of enumerated embodiments 1 to 9, wherein $R^2$ is selected from ethyl,

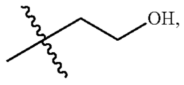 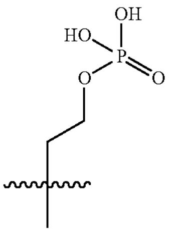 and

-continued

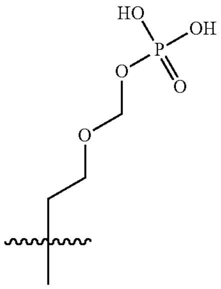

and or a pharmaceutically acceptable salt thereof.

11. The compound of any one of enumerated embodiments 1 to 10, wherein $R^3$ is $—CF_3$.

12. The compound of any one of enumerated embodiments 1 to 11, wherein $R^5$ is selected from hydrogen, ethyl,

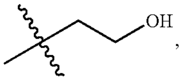, 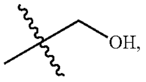 and 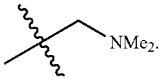

13. The compound of any one of enumerated embodiments 1 to 12, wherein $R^6$ is selected from hydrogen and

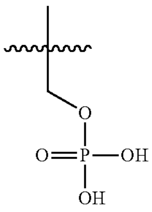 [SMILES: *COP(=O)(O)O]

or a pharmaceutically acceptable salt thereof.

14. The compound of any one of enumerated embodiments 1 to 13, wherein $R^7$ is F.

15. The compound of any one of enumerated embodiments 1 to 6, wherein the compound is of Formula II:

II

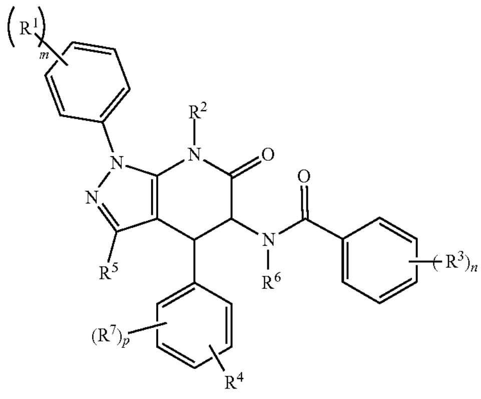

or a pharmaceutically acceptable salt thereof.-

16. The compound of any one of enumerated embodiments 1 to 6, wherein the compound is of Formula III:

III

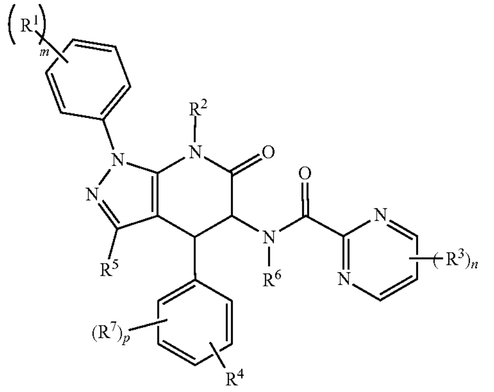

or a pharmaceutically acceptable salt thereof.

17. The compound of any one of enumerated embodiments 1 to 6, wherein the compound is of Formula IVa, Formula IVb, Formula IVc or Formula IVd:

IVa

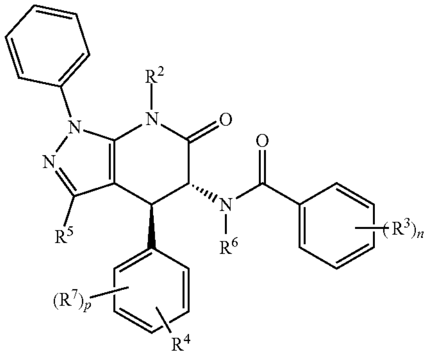

IVb

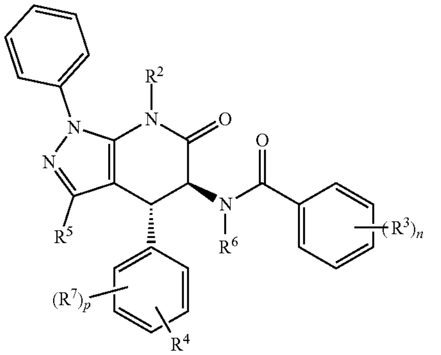

-continued

IVc

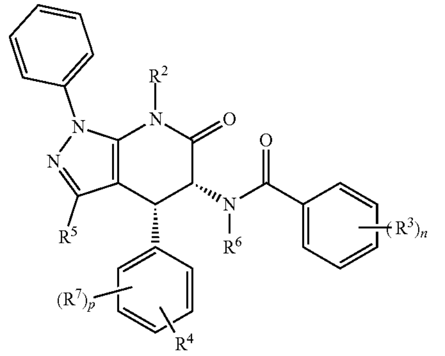

IVd

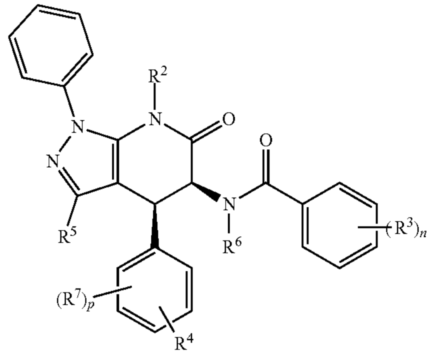

or a pharmaceutically acceptable salt thereof.

18. The compound of any one of enumerated embodiments 1 to 6, wherein the compound is of Formula Va, Formula Vb, Formula Vc or Formula Vd:

Va

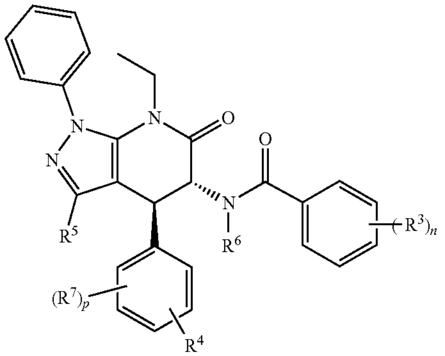

Vb

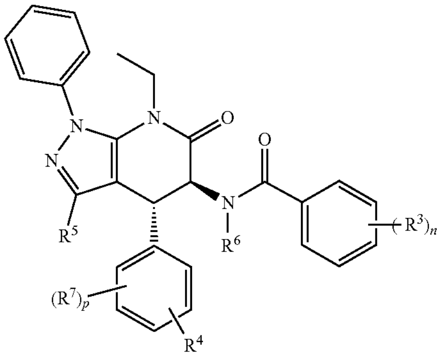

-continued

Vc

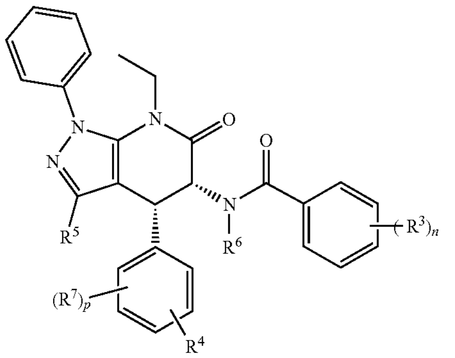

Vd

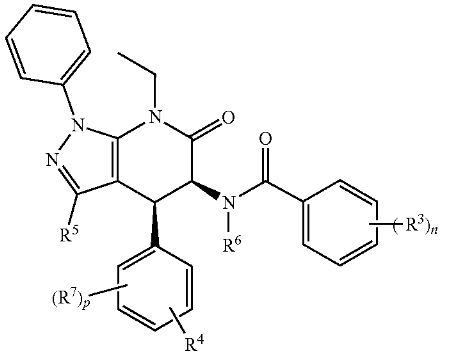

or a pharmaceutically acceptable salt thereof.

19. The compound of any one of enumerated embodiments 1 to 6, wherein the compound is of Formula Va-i, Formula Vb-i, Formula Vc-i or Formula Vd-i:

Va-i

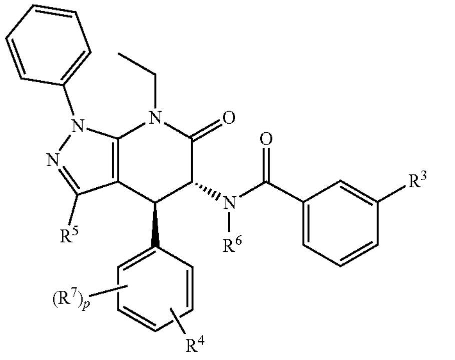

Vb-i

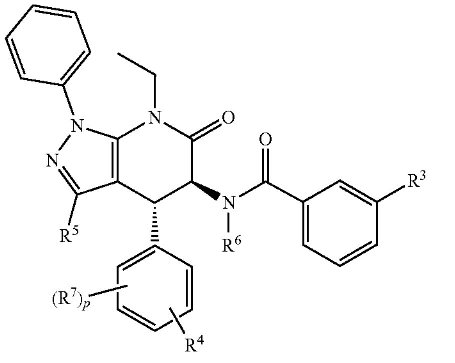

-continued

Vc-i

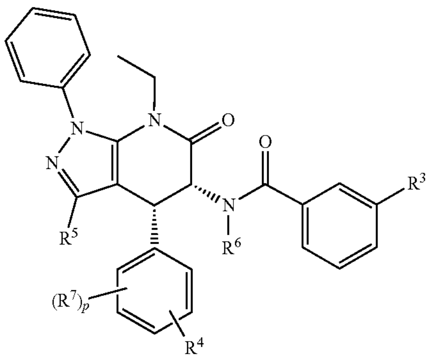

Vd-i

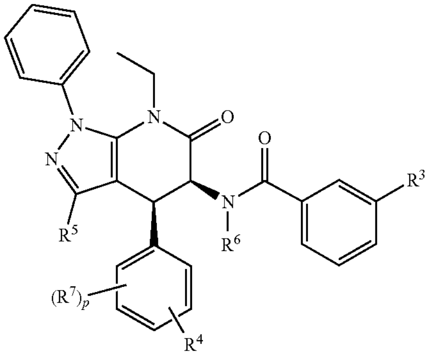

or a pharmaceutically acceptable salt thereof.

20. The compound of any one of enumerated embodiments 1 to 6, wherein the compound is of Formula VIa, Formula VIb, Formula VIc or Formula VId:

VIa

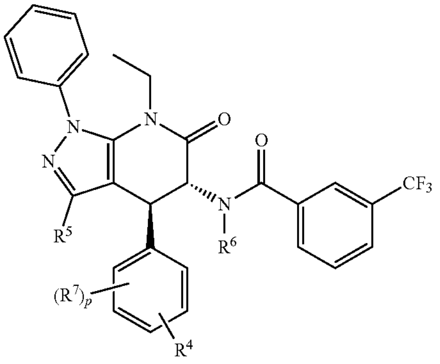

VIb

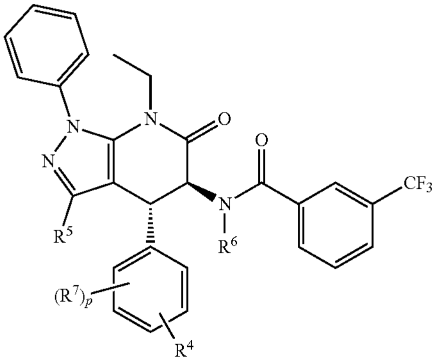

-continued

VIc

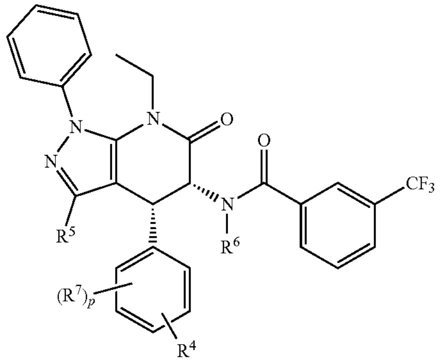

VId

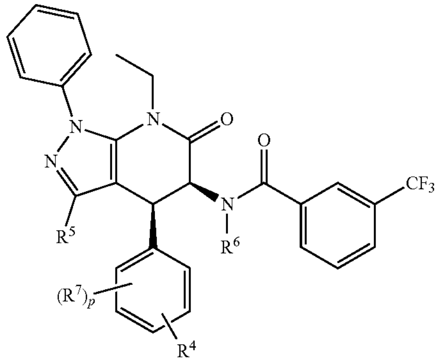

or a pharmaceutically acceptable salt thereof.

21. The compound of any one of enumerated embodiments 1 to 6, wherein the compound is of Formula VIIa, Formula VIIb, Formula VIIc or Formula VIId:

VIIa

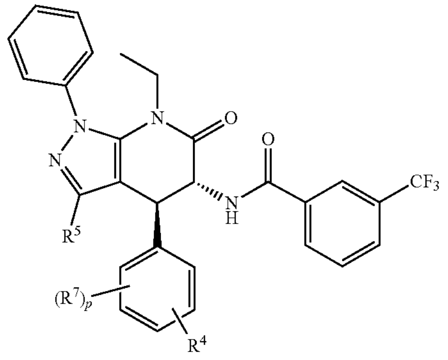

VIIb

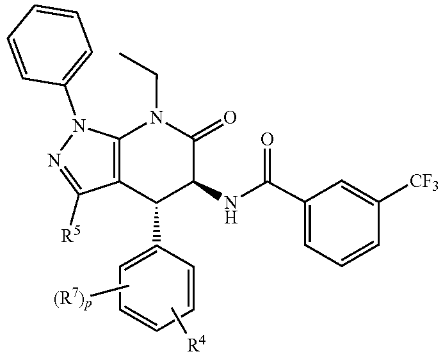

-continued

VIIc

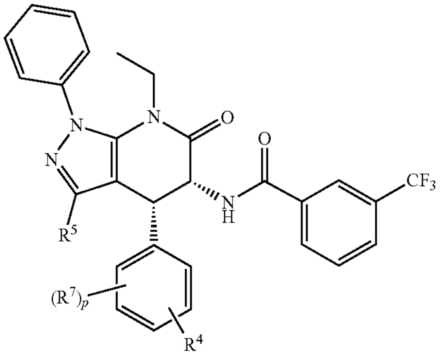

VIId

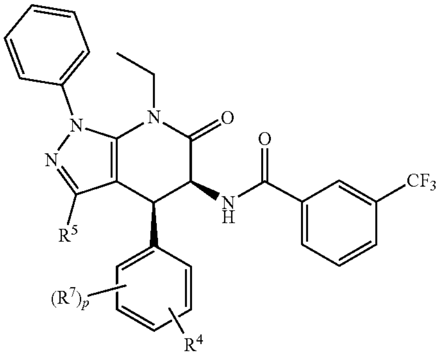

or a pharmaceutically acceptable salt thereof.

22. The compound of any one of enumerated embodiments 1 to 6, wherein the compound is of Formula VIIIa, Formula VIIIb, Formula VIIIc or Formula VIIId:

VIIIa

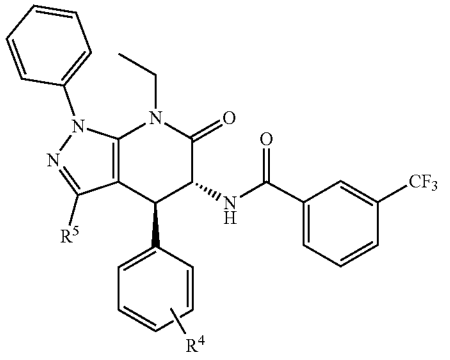

VIIIb

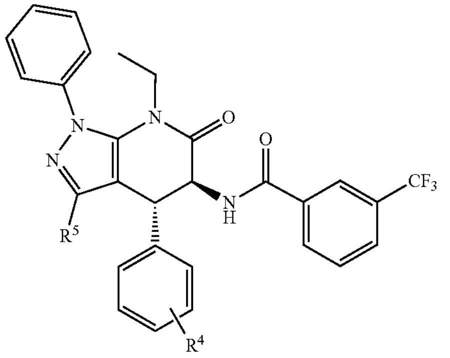

-continued

VIIIc

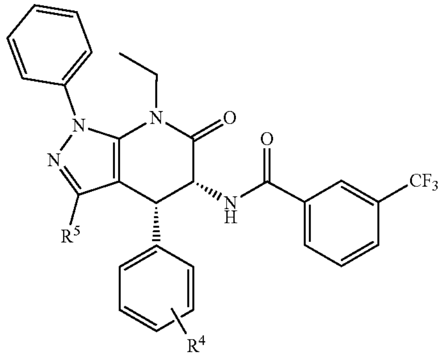

VIIId

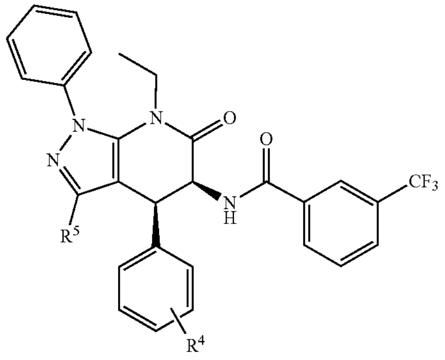

or a pharmaceutically acceptable salt thereof.

23. The compound of any one of enumerated embodiments 1 to 6, wherein the compound is of Formula IXa, Formula IXb, Formula IXc or Formula IXd:

IXa

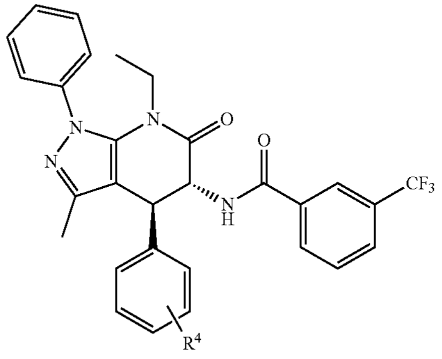

IXb

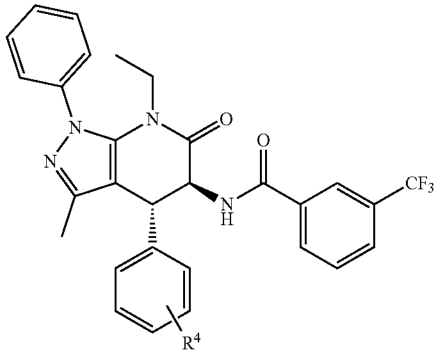

-continued

IXc

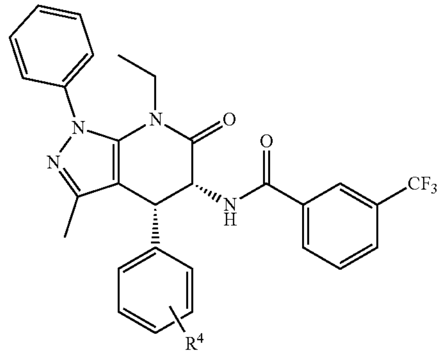

IXd

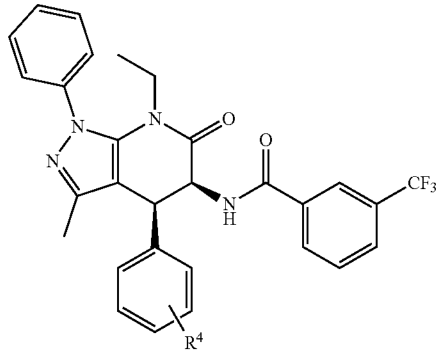

or a pharmaceutically acceptable salt thereof.

24. The compound of any one of enumerated embodiments 1 to 6, wherein the compound is of Formula IXa-i, Formula IXb-i, Formula IXc-i or Formula IXd-i:

IXa-i

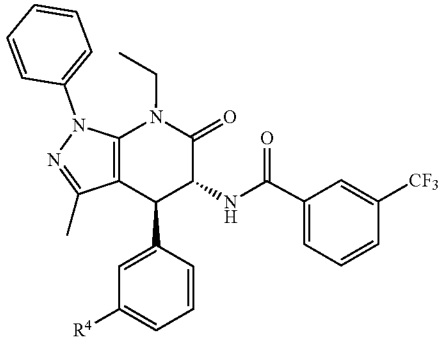

IXb-i

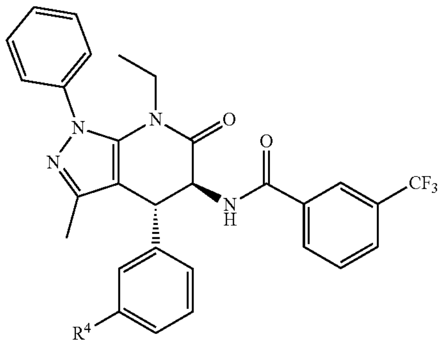

-continued

IXc-i

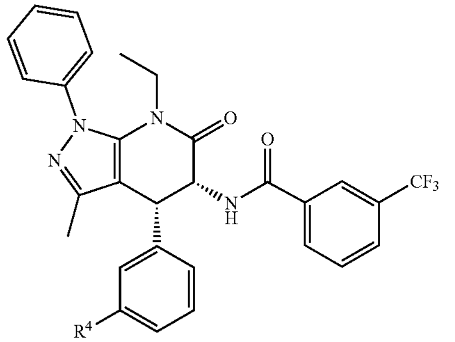

IXd-i

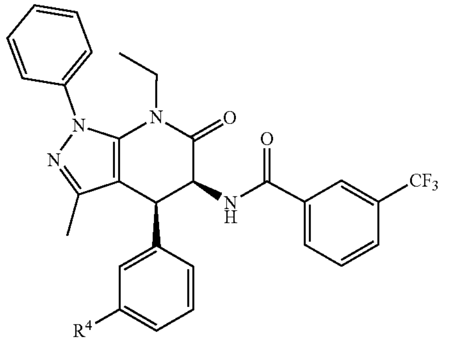

or a pharmaceutically acceptable salt thereof.

25. The compound of any one of enumerated embodiments 1 to 6, wherein the compound is of Formula Xa, Formula Xb, Formula Xc or Formula Xd:

Xa

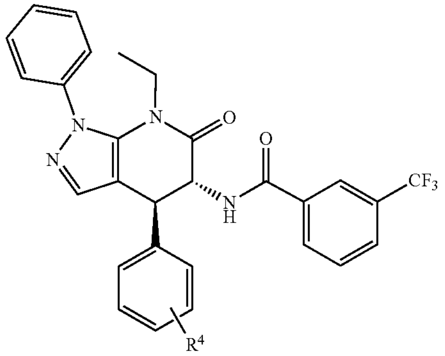

Xb

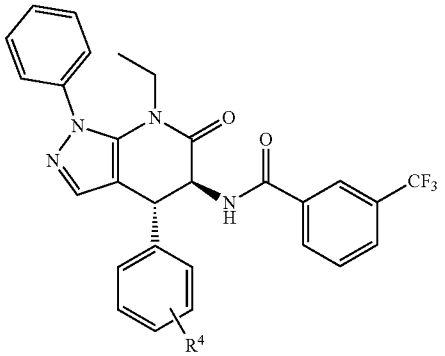

-continued

Xc

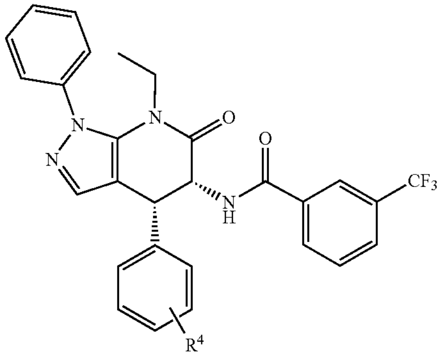

Xd

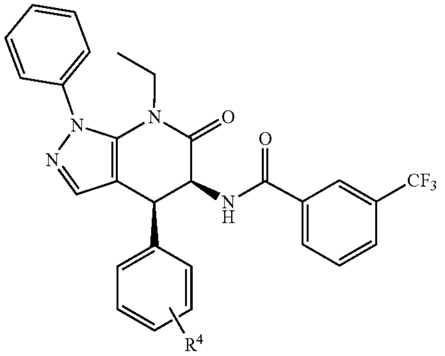

or a pharmaceutically acceptable salt thereof.

26. The compound of any one of enumerated embodiments 1 to 6, wherein the compound is of Formula Xa-i, Formula Xb-i, Formula Xc-i or Formula Xd-i:

Xa-i

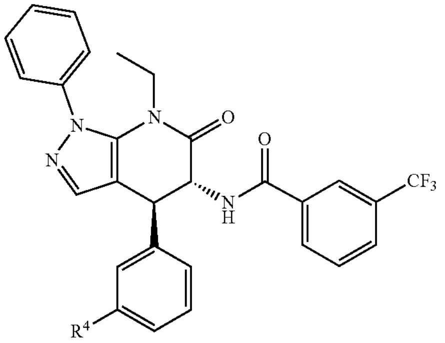

Xb-i

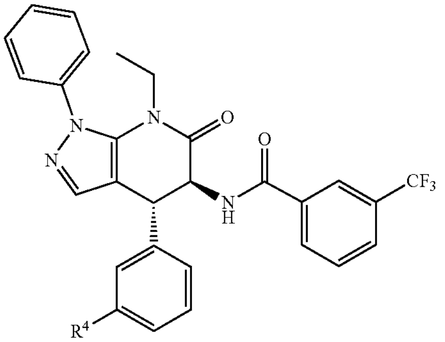

-continued

Xc-i

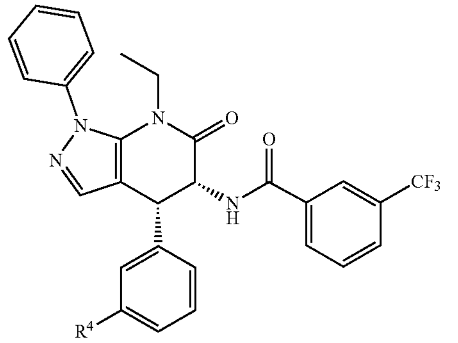

Xd-i

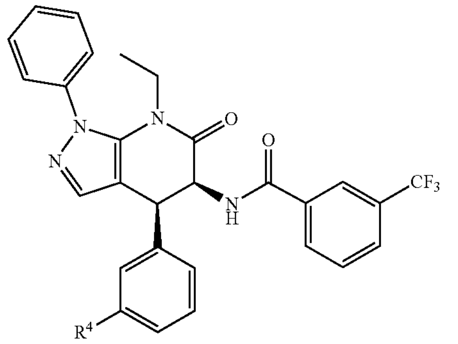

or a pharmaceutically acceptable salt thereof.

27. The compound of any one of enumerated embodiments 1 to 6, wherein the compound is of Formula XIa, Formula XIb, Formula XIc or Formula XId:

XIa

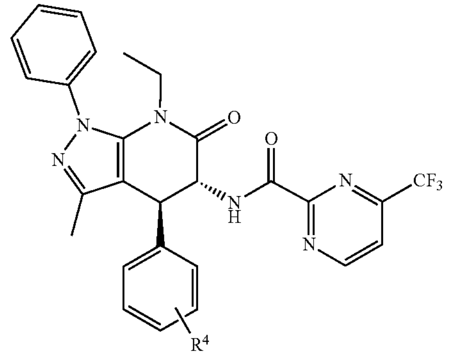

XIb

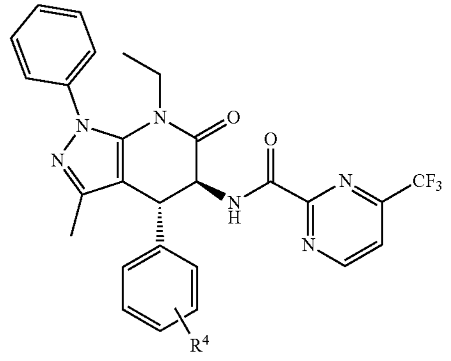

-continued

XIc

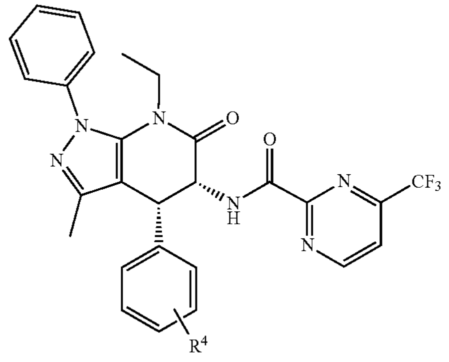

XId

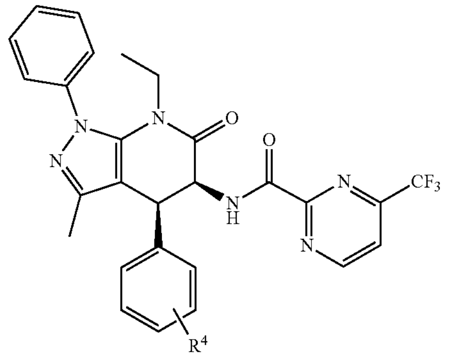

or a pharmaceutically acceptable salt thereof.

28. The compound of any one of enumerated embodiments 1 to 6, wherein the compound is of Formula Xia-i, Formula XIb-i, Formula XIc-i or Formula XId-i:

XIa-i

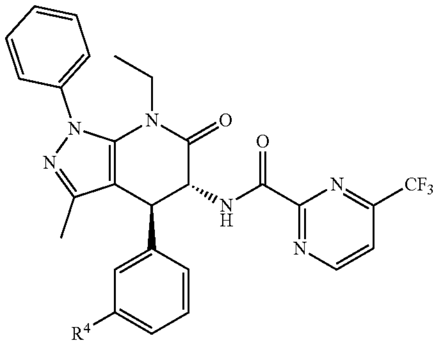

XIb-i

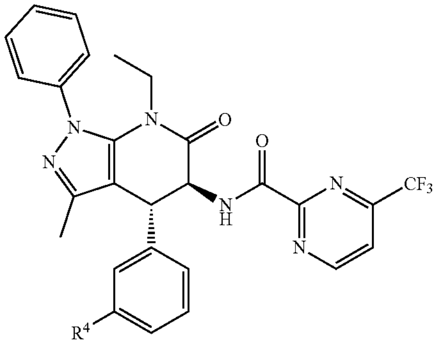

-continued

XIc-i

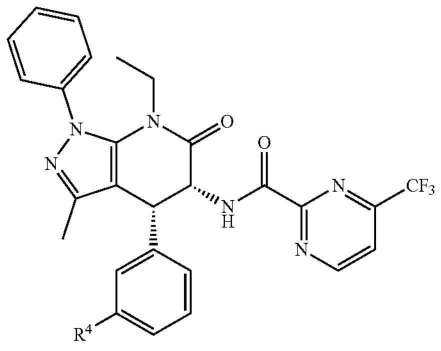

XId-i

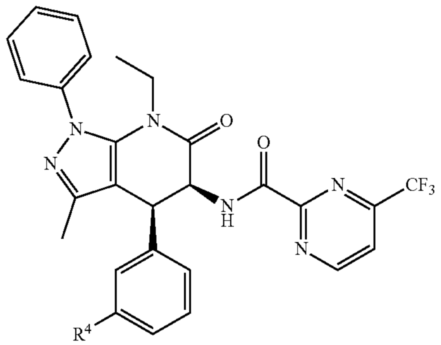

or a pharmaceutically acceptable salt thereof.

29. The compound of any one of enumerated embodiments 1 to 6, wherein the compound is of Formula XIIa, Formula XIIb, Formula XIIc, or Formula XIId:

XIIa

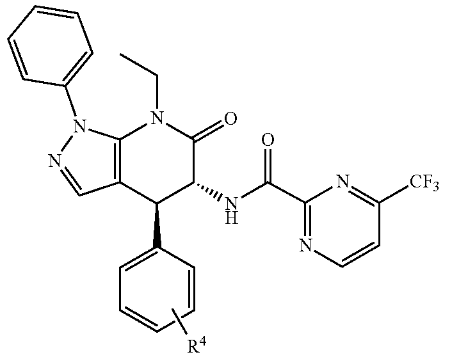

XIIb

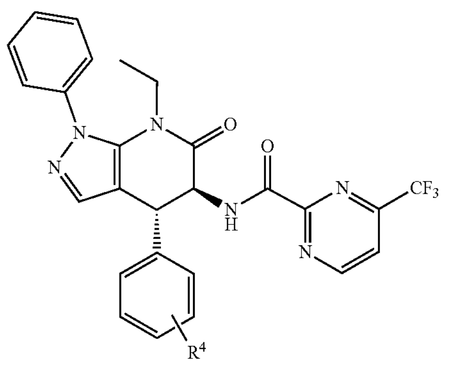

-continued

XIIc

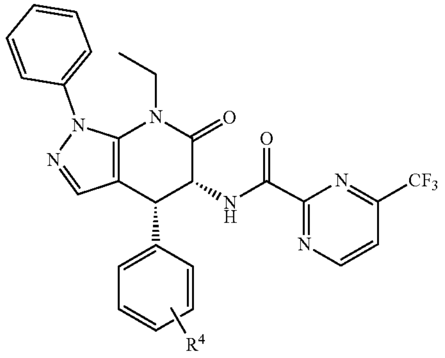

XIId

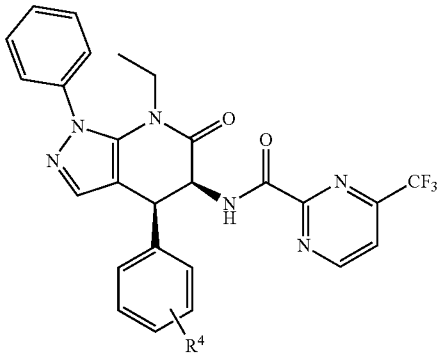

or a pharmaceutically acceptable salt thereof.

30. The compound of any one of enumerated embodiments 1 to 6, wherein the compound is of Formula XIIIa, Formula XIIIb, Formula XIIIc or Formula XIIId:

XIIIa

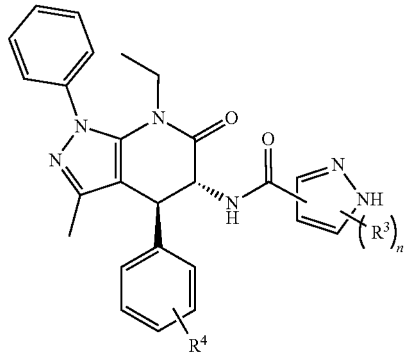

XIIIb

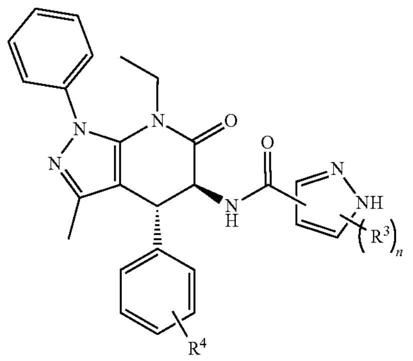

-continued
XIIIc
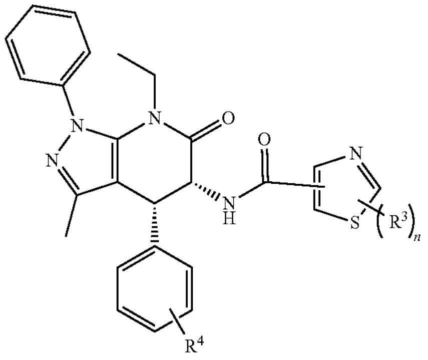
XIIId
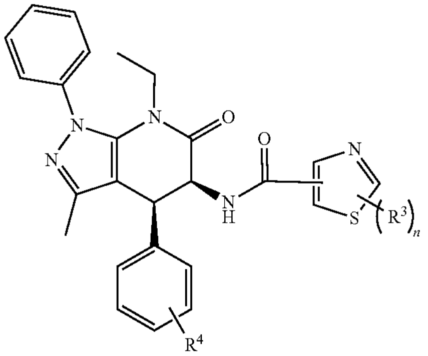
or a pharmaceutically acceptable salt thereof.
31. A compound selected from one of the following:
I-9a
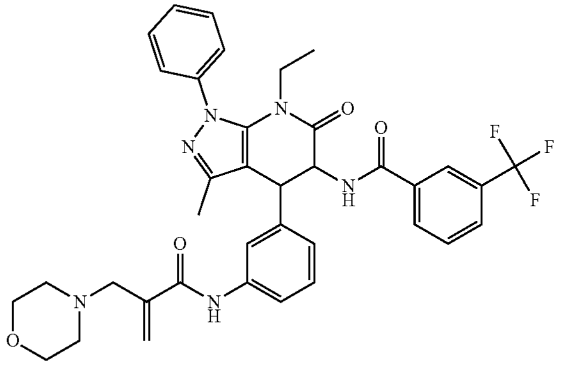
I-15a
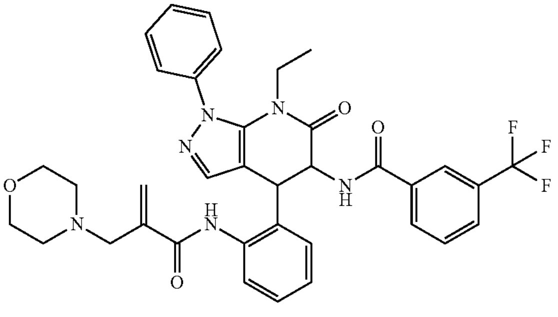
-continued
I-66a
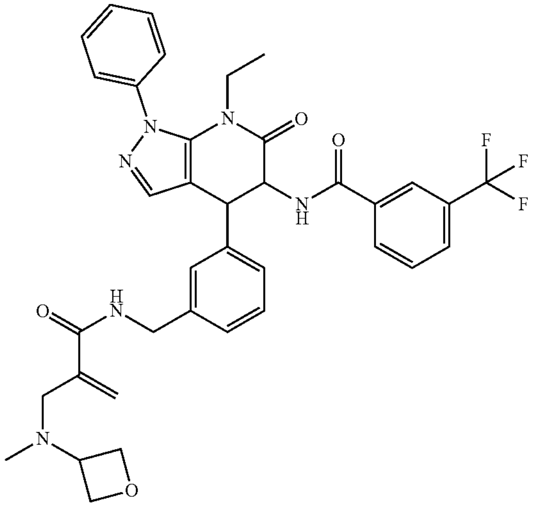
I-153a
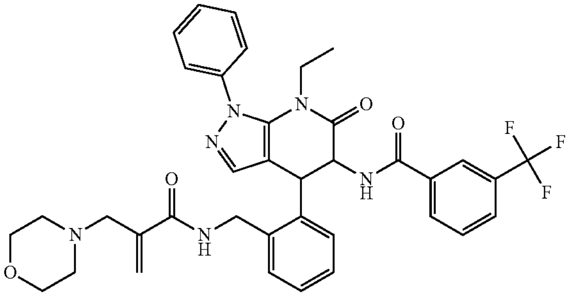
I-160a
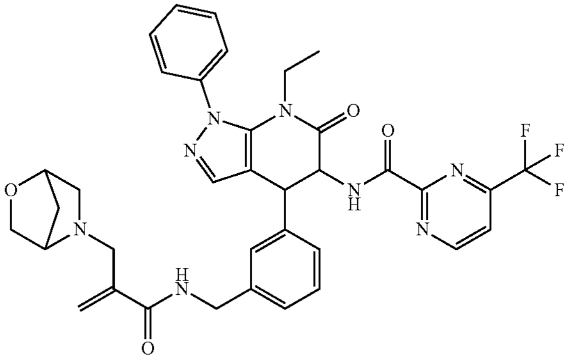
I-161a
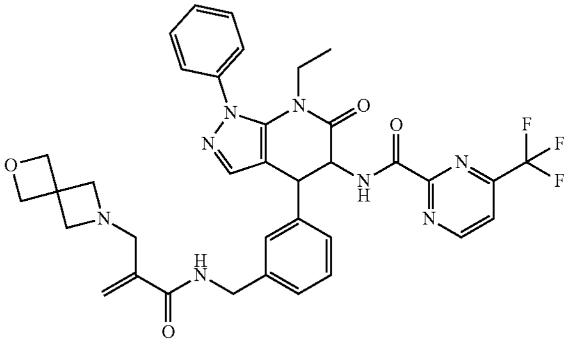

-continued
I-162a
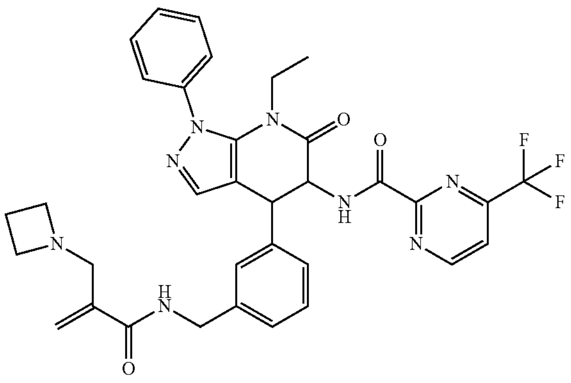
I-163a
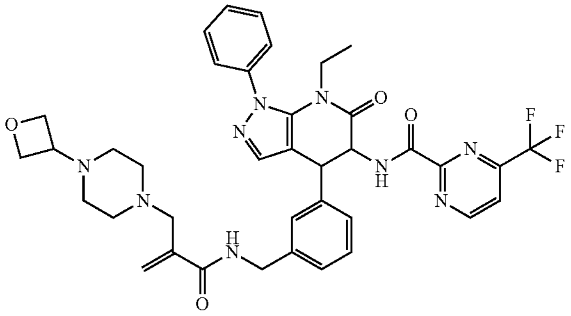
I-177a
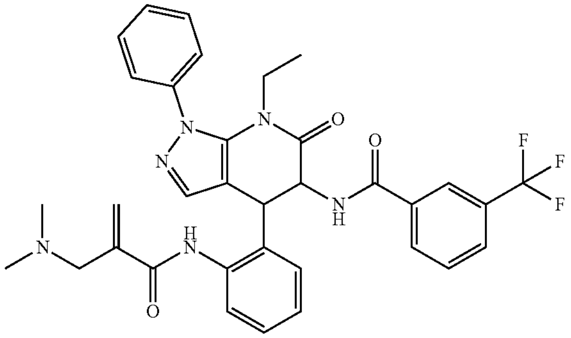
I-234a
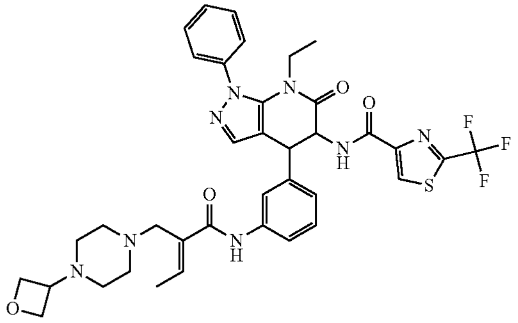
and
-continued
I-383a
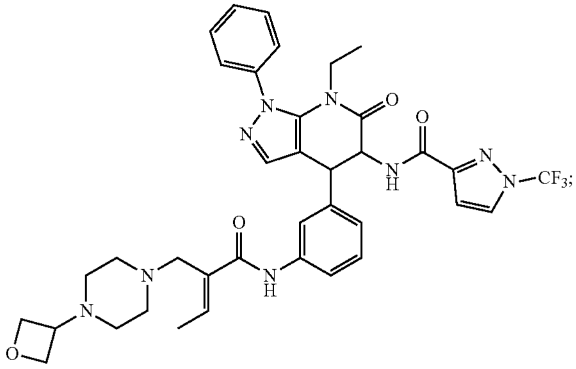
or a pharmaceutically acceptable salt thereof.
32. A compound selected from one of the following.
I-9
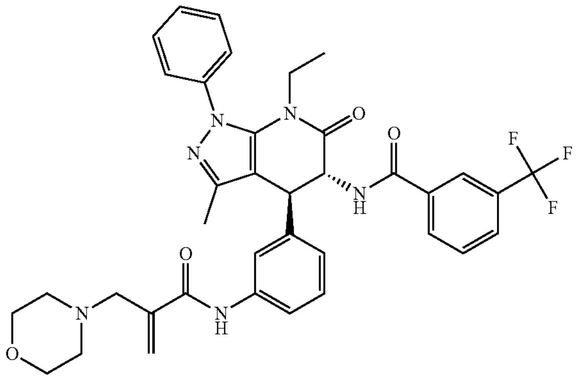
I-2
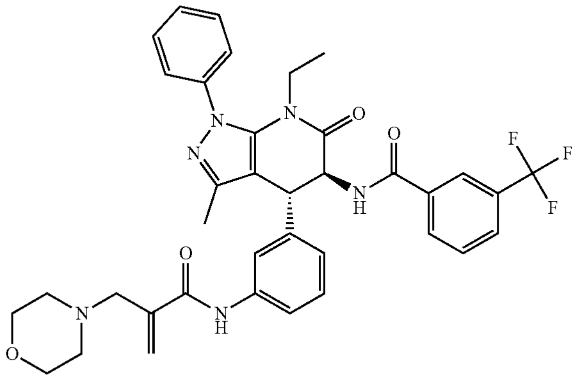
I-15
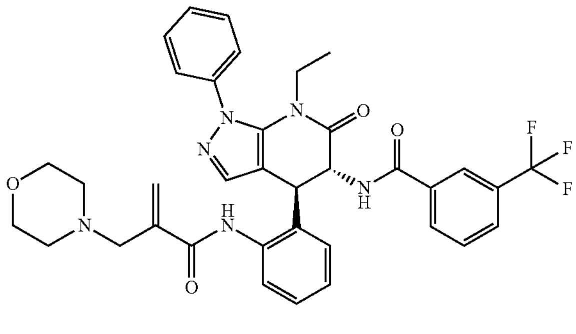

-continued
I-15b
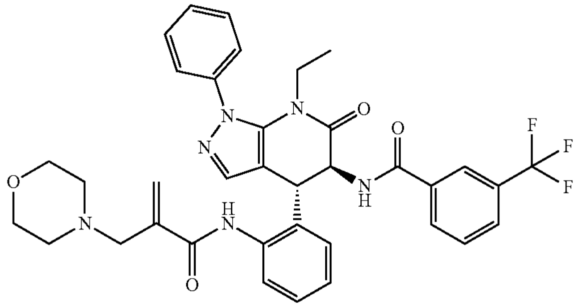
I-66
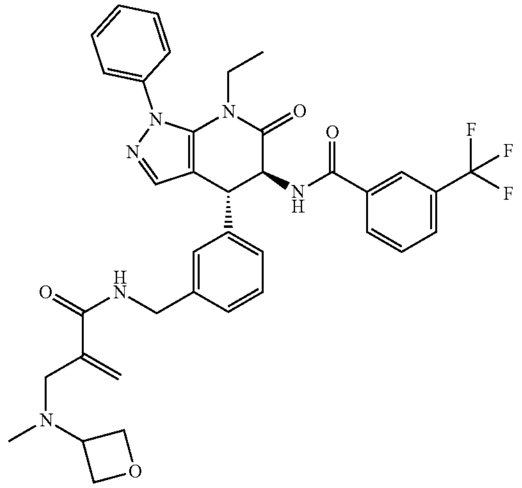
I-154
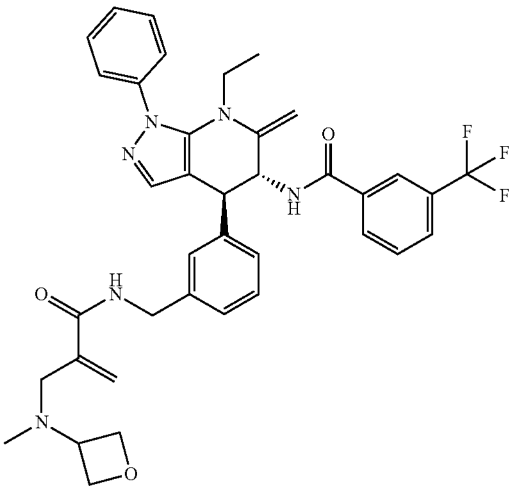
-continued
I-153
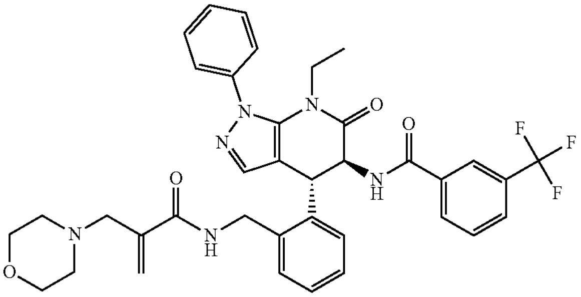
I-153b
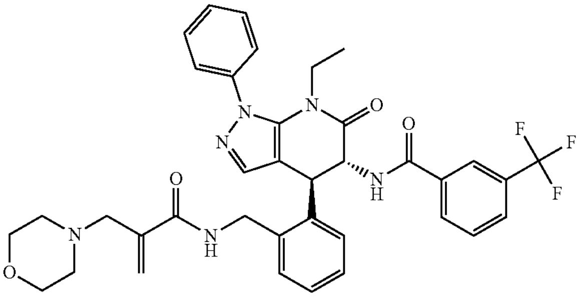
I-160
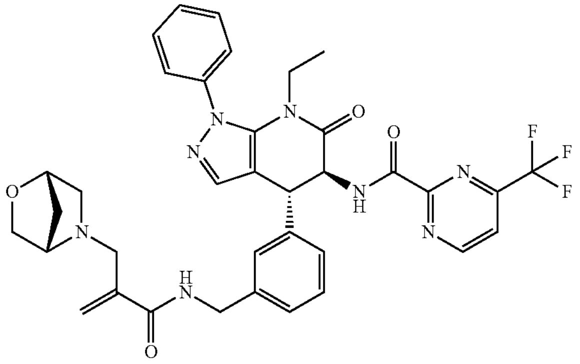
I-160b
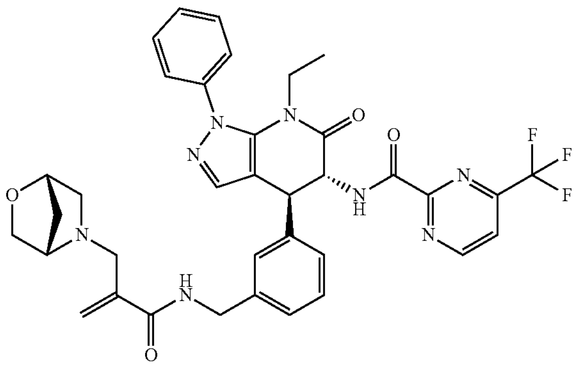

I-160c
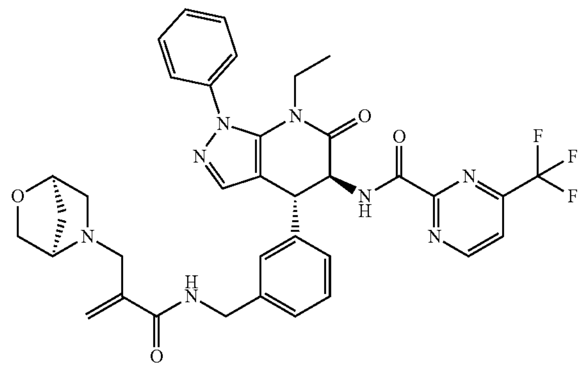
I-160d
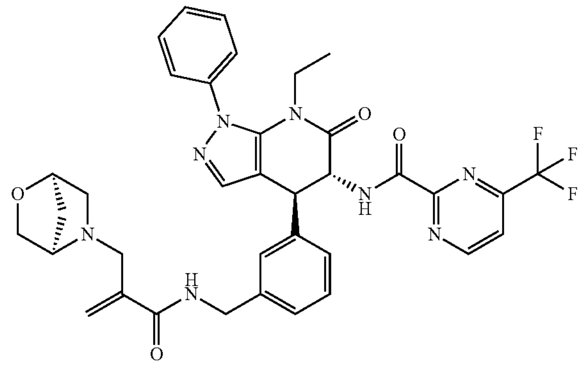
I-161
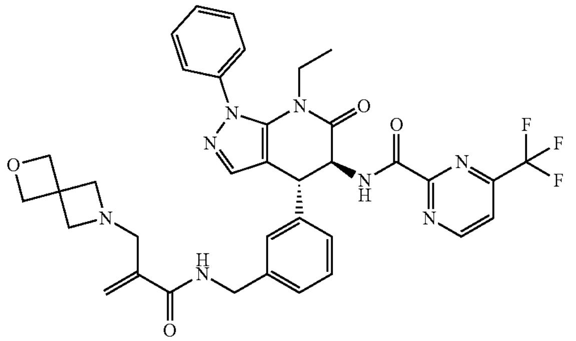
I-161b
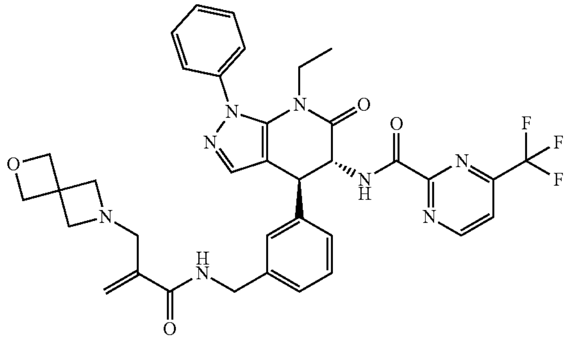
I-162
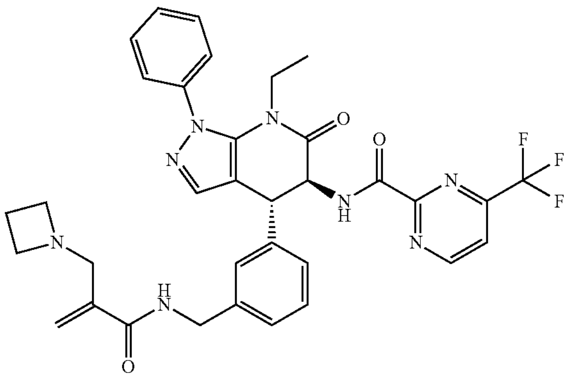
I-162b
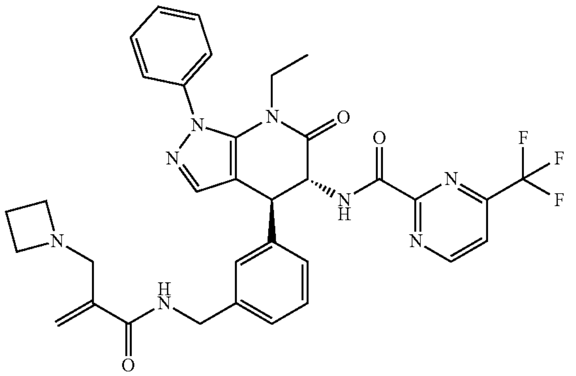
I-163
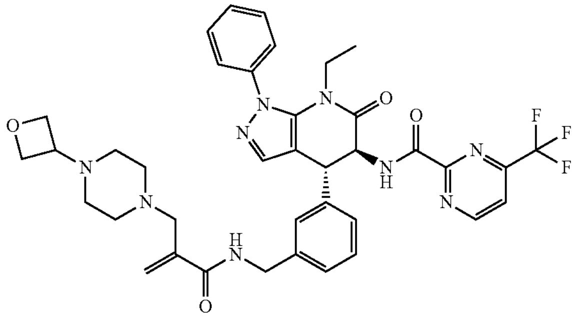
I-163b
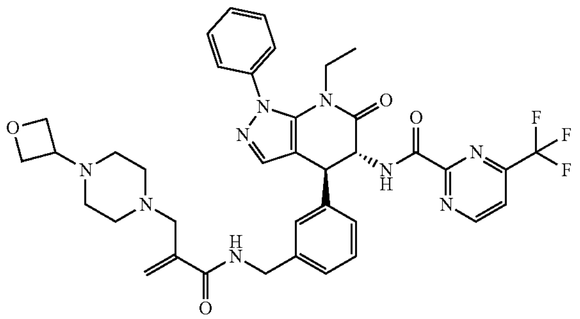

-continued
I-177
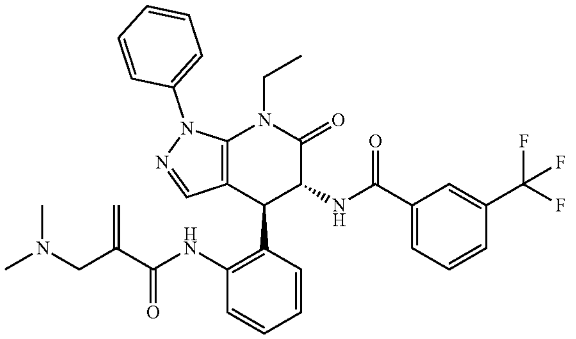
I-177b
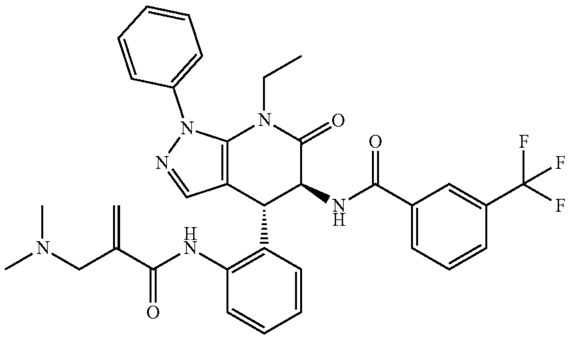
I-234
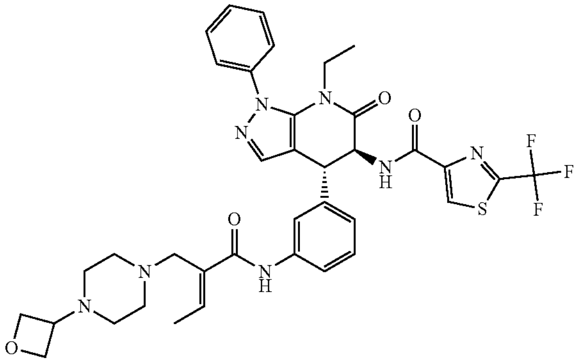
I-234b
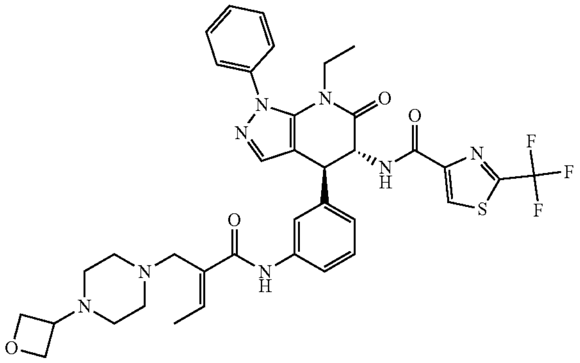
-continued
I-383
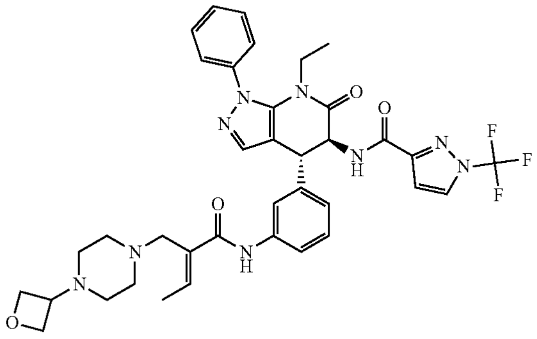
and
I-383b
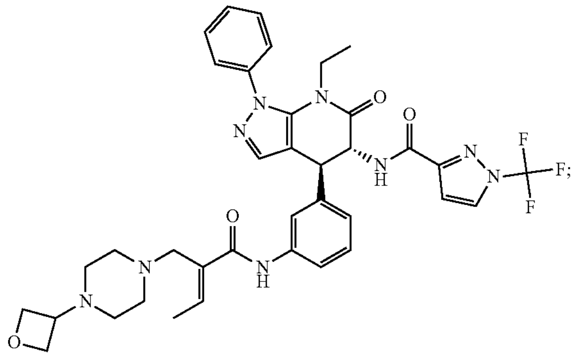
or a pharmaceutically acceptable salt thereof.
33. The compound of enumerated embodiment 31, wherein the compound is of the following structure:
I-9a
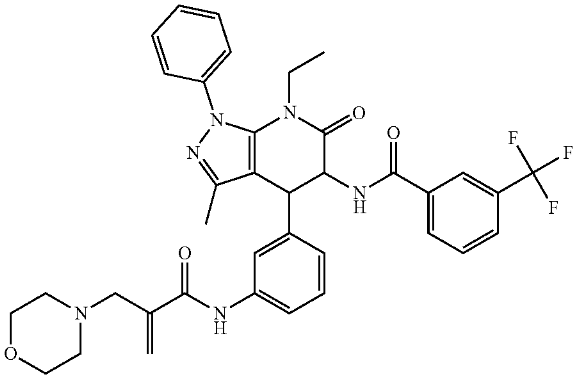
or a pharmaceutically acceptable salt thereof.

34. The compound of enumerated embodiment 31, wherein the compound is of the following structure:

I-15a

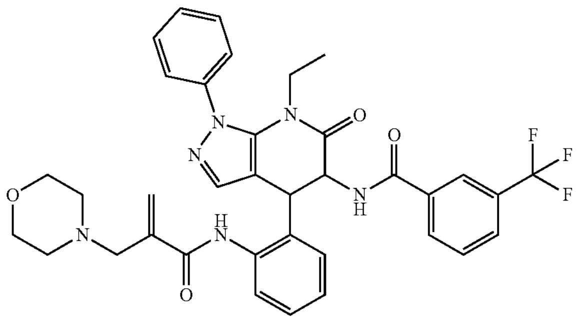

or a pharmaceutically acceptable salt thereof.

35. The compound of enumerated embodiment 31, wherein the compound is of the following structure:

I-66a

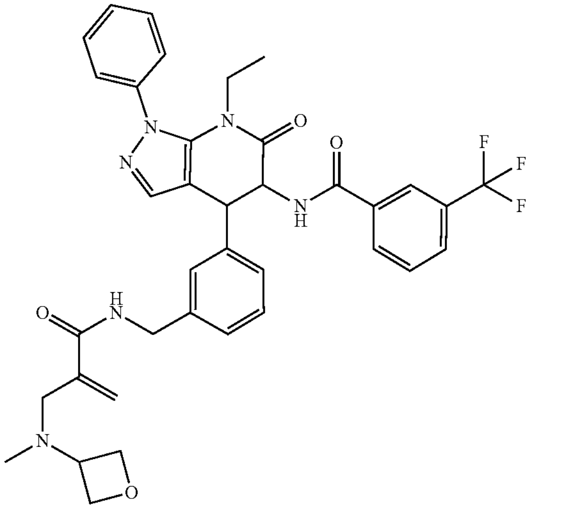

or a pharmaceutically acceptable salt thereof.

36. The compound of enumerated embodiment 31, wherein the compound is of the following structure:

I-153a

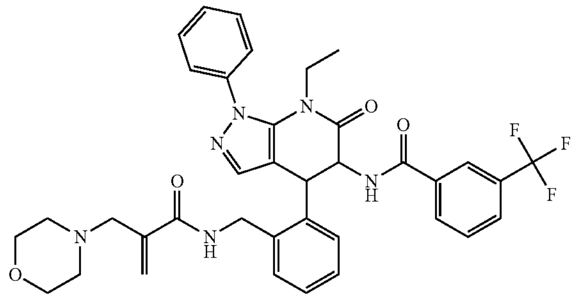

or a pharmaceutically acceptable salt thereof.

37. The compound of enumerated embodiment 31, wherein the compound is of the following structure:

I-160a

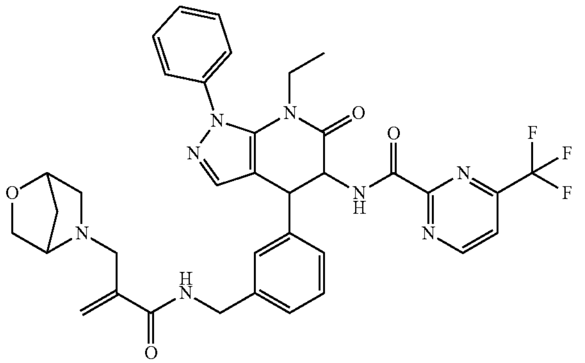

or a pharmaceutically acceptable salt thereof.

38. The compound of enumerated embodiment 31, wherein the compound is of the following structure:

I-161a

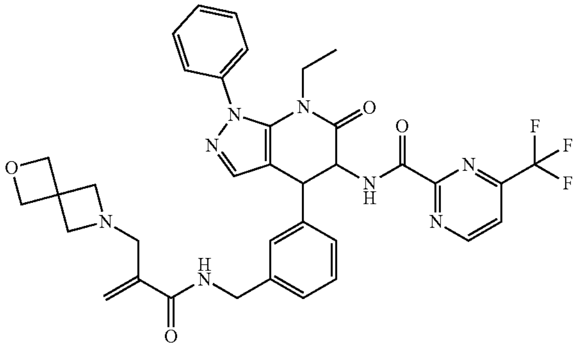

or a pharmaceutically acceptable salt thereof.

39. The compound of enumerated embodiment 31, wherein the compound is of the following structure:

I-162a

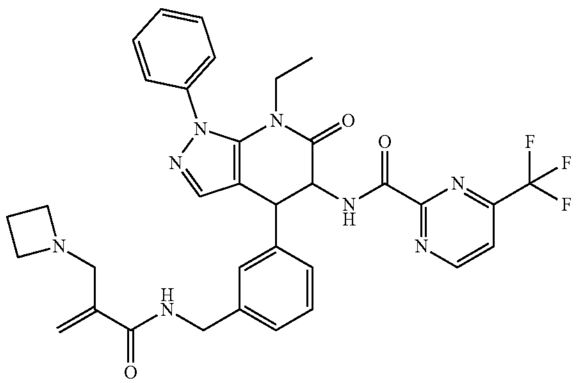

or a pharmaceutically acceptable salt thereof.

40. The compound of enumerated embodiment 31, wherein the compound is of the following structure:

I-163a

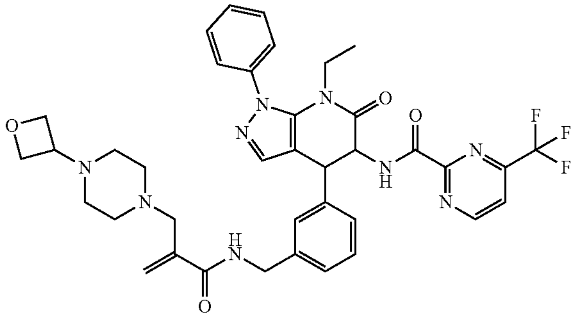

or a pharmaceutically acceptable salt thereof.

41. The compound of enumerated embodiment 31, wherein the compound is of the following structure:

I-177a

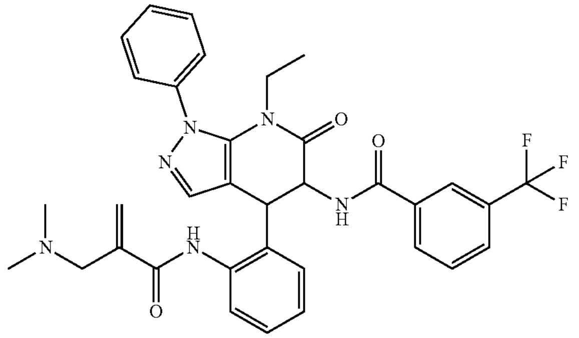

or a pharmaceutically acceptable salt thereof.

42. The compound of enumerated embodiment 31, wherein the compound is of the following structure:

I-234a

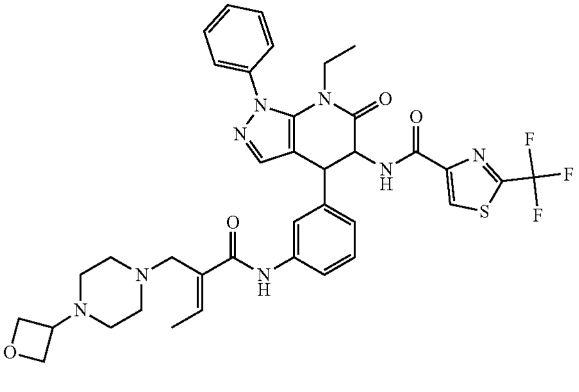

or a pharmaceutically acceptable salt thereof.

43. The compound of enumerated embodiment 31, wherein the compound is of the following structure:

I-383a

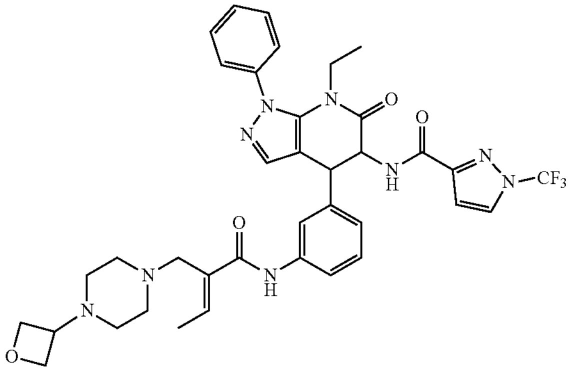

or a pharmaceutically acceptable salt thereof.

44. The compound of enumerated embodiment 32, wherein the compound is of the following structure:

I-9

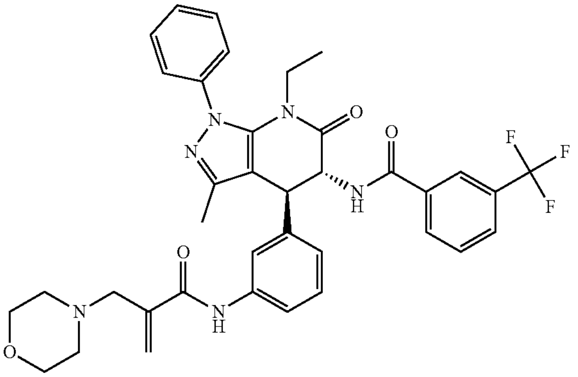

I-2

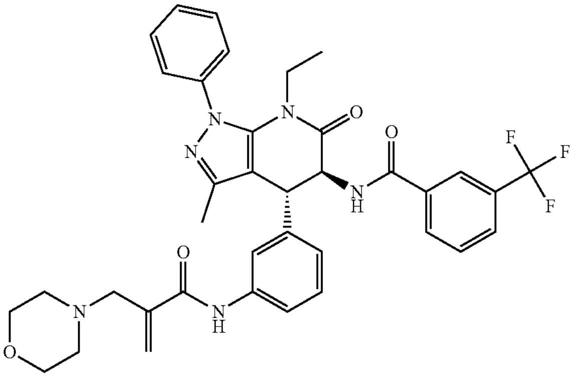

or a pharmaceutically acceptable salt thereof.

45. The compound of enumerated embodiment 32, wherein the compound is of the following structure:

I-15

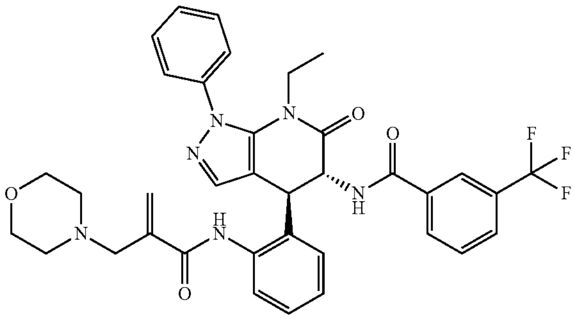

I-15b

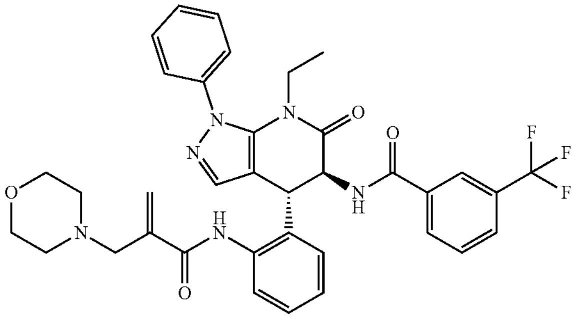

or a pharmaceutically acceptable salt thereof.

46. The compound of enumerated embodiment 32, wherein the compound is of the following structure:

I-66

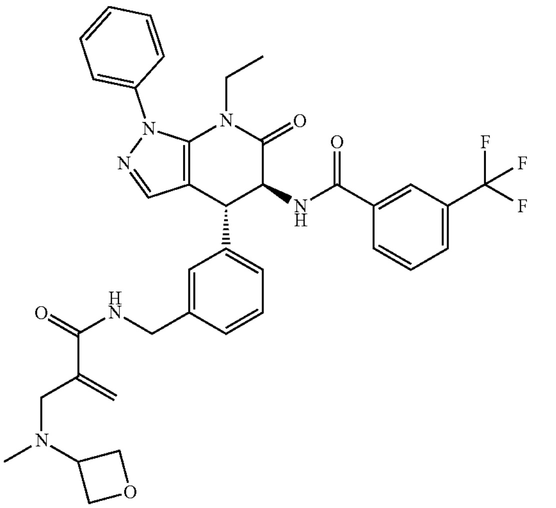

-continued

I-154

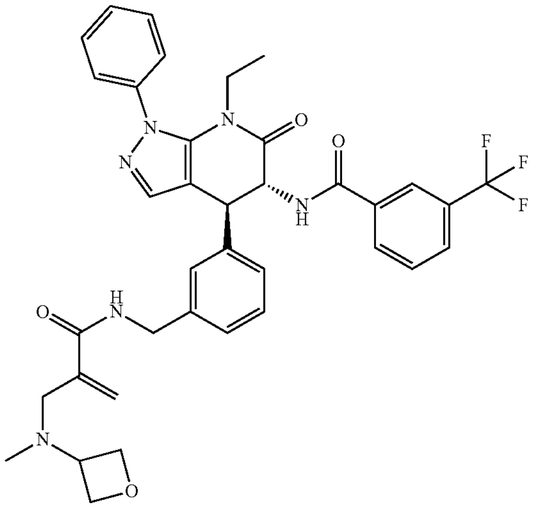

or a pharmaceutically acceptable salt thereof.

47. The compound of enumerated embodiment 32, wherein the compound is of the following structure:

I-153

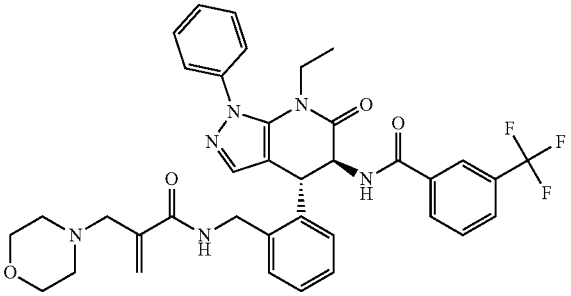

I-153b

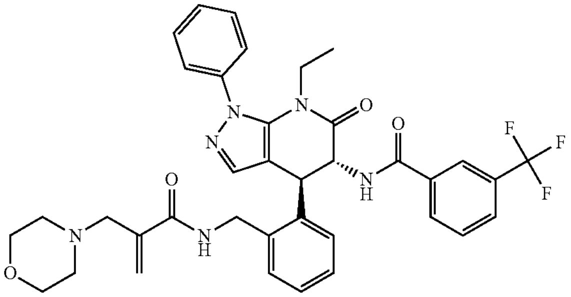

or a pharmaceutically acceptable salt thereof.

48. The compound of enumerated embodiment 32, wherein the compound is of the following structure:

I-160

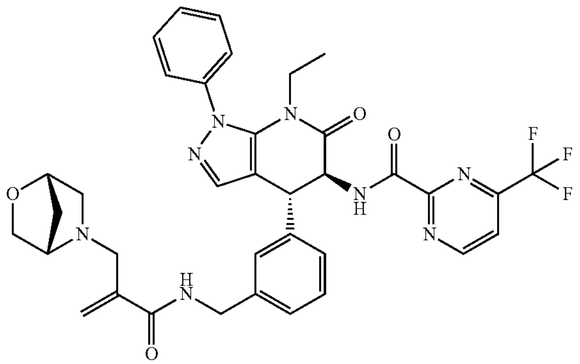

I-160b

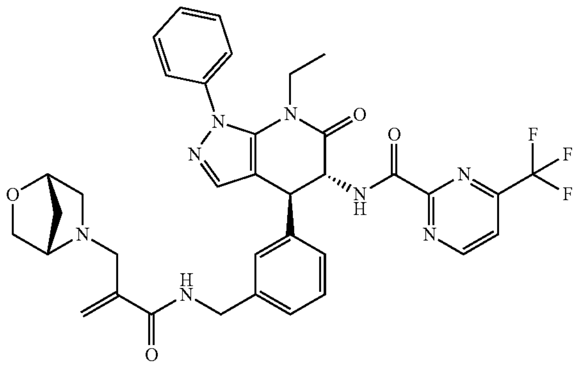

or a pharmaceutically acceptable salt thereof.

49. The compound of enumerated embodiment 32, wherein the compound is of the following structure:

I-160c

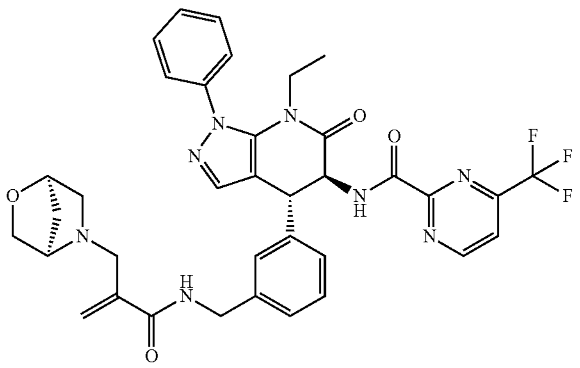

-continued

I-160d

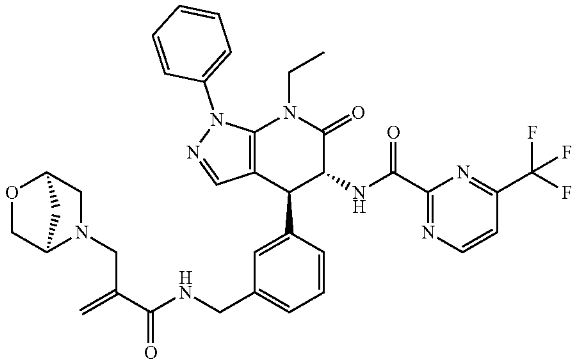

or a pharmaceutically acceptable salt thereof.

50. The compound of enumerated embodiment 32, wherein the compound is of the following structure:

I-161

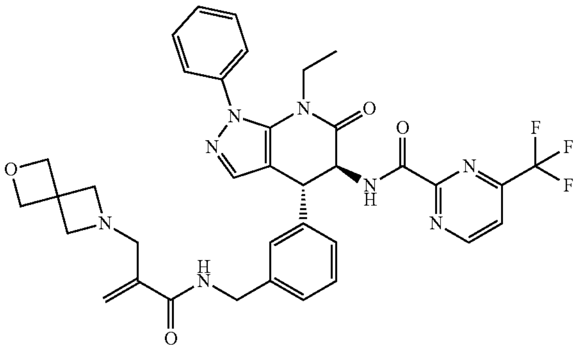

I-161b

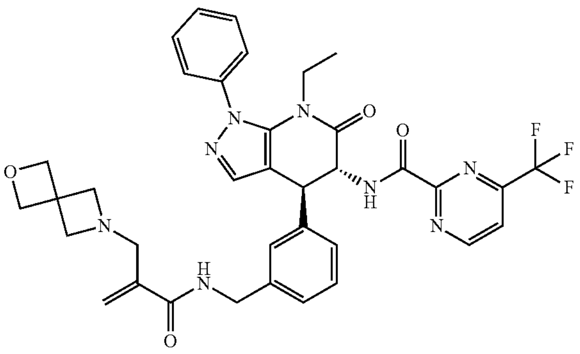

or a pharmaceutically acceptable salt thereof.

51. The compound of enumerated embodiment 32, wherein the compound is of the following structure:

I-162

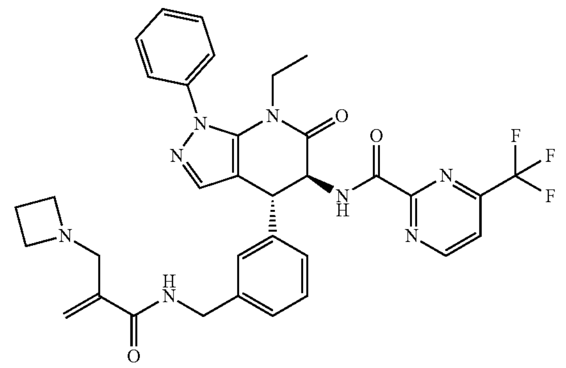

I-162b

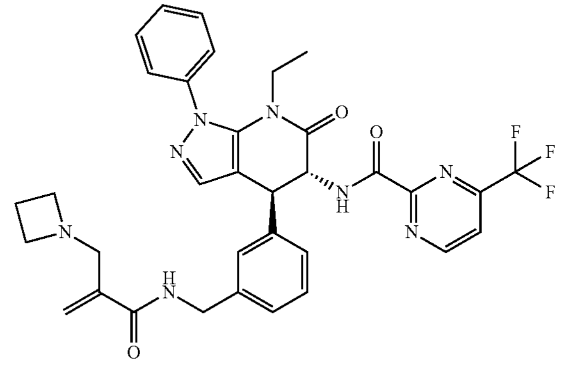

or a pharmaceutically acceptable salt thereof.

52. The compound of enumerated embodiment 32, wherein the compound is of the following structure:

I-163

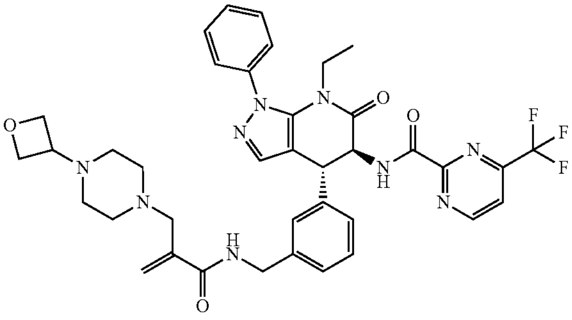

-continued

I-163b

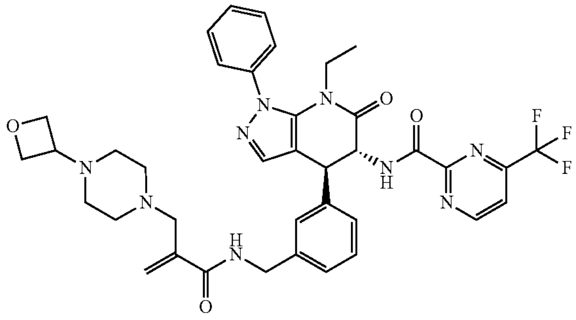

or a pharmaceutically acceptable salt thereof.

53. The compound of enumerated embodiment 32, wherein the compound is of the following structure:

I-177

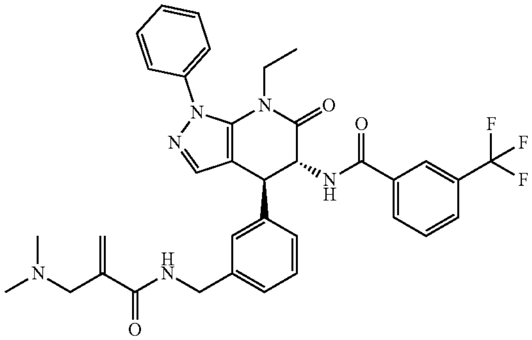

I-177b

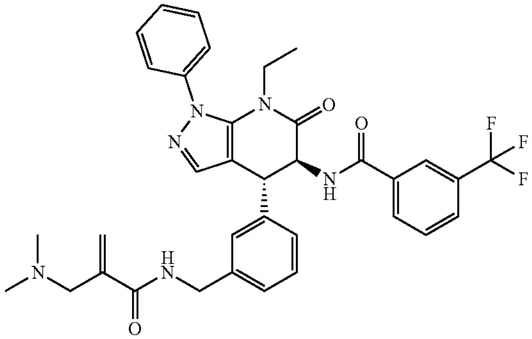

or a pharmaceutically acceptable salt thereof.

54. The compound of enumerated embodiment 32, wherein the compound is of the following structure:

I-234

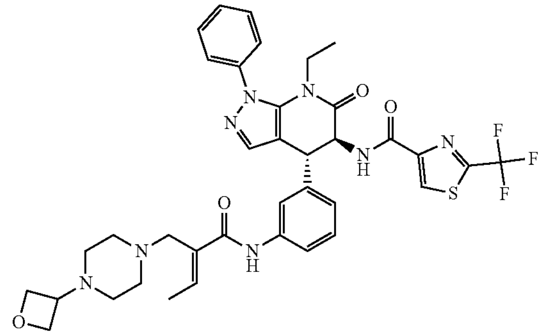

I-234b

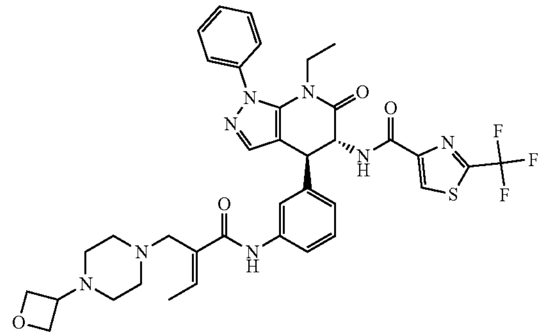

or a pharmaceutically acceptable salt thereof.

55. The compound of enumerated embodiment 32, wherein the compound is of the following structure:

I-383

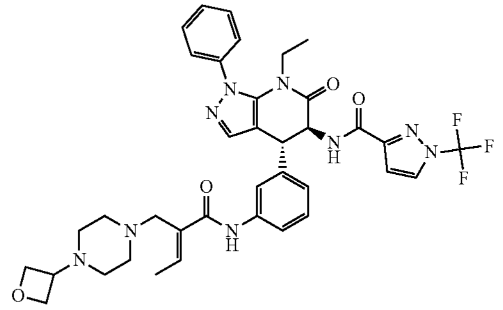

and

-continued

I-383b

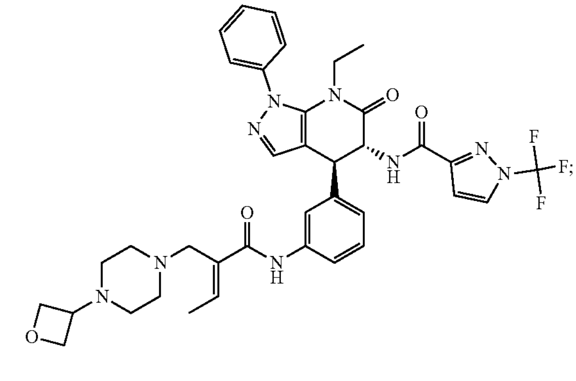

;

or a pharmaceutically acceptable salt thereof.

56. A compound selected from one of those shown in Table 1, or a pharmaceutically acceptable salt thereof.

57. A pharmaceutical composition comprising the compound of any one of enumerated embodiments 1-56, or a pharmaceutically acceptable salt thereof, and a pharmaceutically acceptable carrier.

58. A method of treating a hemoglobinopathy disorder or disease, comprising administering to a subject in need thereof the compound of any one of enumerated embodiments 1-56, or a pharmaceutically acceptable salt thereof.

59. The method of enumerated embodiment 58, wherein the hemoglobinopathy is a sickle cell disorder or disease.

60. The method of enumerated embodiment 58, wherein the hemoglobinopathy is a thalassemia disorder or disease.

61. A method of modulating the activity of DCN-1 and/or DCN-2, comprising the step of contacting DCN-1 and/or DCN-2 with the compound of any one of enumerated embodiments 1-56, or a pharmaceutically acceptable salt thereof.

EXEMPLIFICATION

As depicted in the Examples below, exemplary compounds are prepared according to the following general procedures and used in biological assays and other procedures described generally herein. It will be appreciated that, although the general methods depict the synthesis of certain compounds of the present invention, the following general methods, and other methods known to one of ordinary skill in the art, can be applied to all compounds and subclasses and species of each of these compounds, as described herein. Similarly, assays and other analyses can be adapted according to the knowledge of one of ordinary skilled in the art.

Example 1: Synthesis of Compounds I-122, I-45, I-90, I-89, I-97, and I-98

NMR:

$^1H$ NMR spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5μ.

Mobile Phase: A: 0.05% Formic acid in water: ACN (95:5) B: 0.05% Formic acid in ACN.

Inj Volume: 2.0 μL, Column oven temperature: 50 C; Flow Rate: 1.2 mL/min.

Gradient program: 0% B to 98% B in 2.0 minute, hold till 3.0 min, at 3.2 min B conc is 0% up to 4.0 min.

Method-B: Column: X-Bridge C18 (3.0*50) mm 2.5u; Mobile Phase: A: 2.5 mM Ammonium Bicarbonate in water; B: Acetonitrile; Flow Rate: 1.2 mL/min; Column oven temp. 50° C.

Gradient program: 0% B to 98% B in 2.0 minute, hold till 3.0 min, at 3.2 min B conc is 0% up to 4.0 min.

Method-C: Column: X-Select CSH C18 (50 mm*3.0 mm, 2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2

HPLC:

Method-A: Column: X Select CSH C18 (150×4.6) mm, 3.5; Mobile phase A: 0.1% FA in Water: ACN (95:05); Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: ACN; Programme/B %: 0.01/2, 2/2, 12/90, 16/90; Flow: 1.0 mL/min.; Diluent: ACN: WATER (80:20).

Method-C: Column: X SELECT CSH C18 (150×4.6 mm, 3.5μ); Mobile Phase A; 0.05% TFA IN WATER: ACN (95:05); Mobile Phase B: 0.05% TFA IN WATER: ACN(05:95); Programme: T/B %: 0.01/10, 12/90, 16/90; Flow: 1 mL/min.; Diluent: WATER:ACN (80:20).

Chiral HPLC:

Method-A: COLUMN: CHIRALPAK IA (250×4.6 mm, 5 μm), Mobile Phase A: n-Hexane, Mobile Phase B: ETOH: MEOH (50/50).

Method-B: Column: chiralpakik (250*4.6 mm, 5 μm), Mobile Phase A: n-Haxane, Mobile Phase B: IPA: MEOH (1:1) A/B: 75:25 Flow: 1.0 ml/MI.

Method-C: Column: chiralpakik (250*4.6 mm, 5 μm), Mobile Phase A: n-hexane, Mobile Phase; IPA, A/B: 50/5, Flow: 1.0 ml/MIN.

Synthesis of Intermediate Compound 6

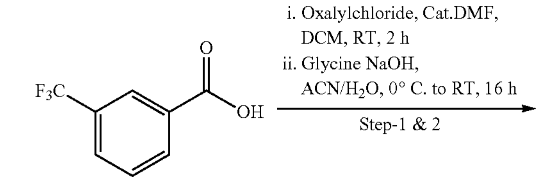

SM-1

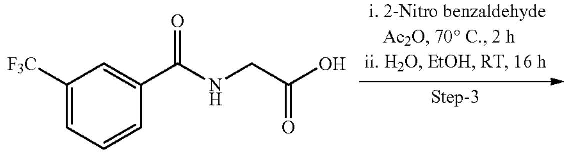

2

-continued

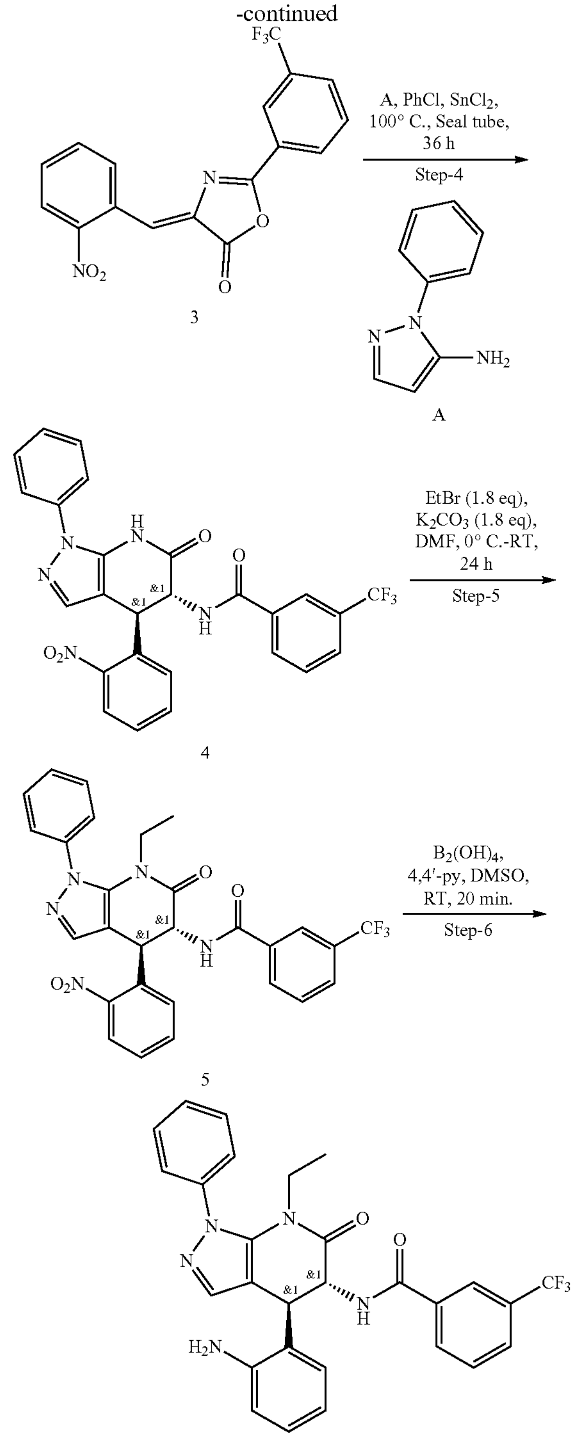

3

A

4

5

6

Step-1 & 2: Synthesis of 2-[[3-(trifluoromethyl) benzoyl]amino]acetic acid (1)

To a stirred solution of 3-(trifluoromethyl) benzoic acid (100 g, 131.56 mmol) in DCM (250 mL) at 0° C. was added dropwise oxalyl chloride (33.8 mL, 0.39 mmol) followed by DMF (1 mL). The reaction mixture was stirred at room temperature for 2 h. The reaction mixture was monitored by TLC. After completion of SM, the reaction mixture was concentrated under reduced pressure to afford crude compound. The crude compound as such taken for the next step. Glycine (10.8 g, 0.14 mmol) was dissolved in Acetonitrile (150 mL) and 50% aq. NaOH (18 g, 0.47 mmol) was added at 0° C. and followed by dropwise addition of the acid chloride in Acetonitrile at 0° C. Then the reaction mixture was stirred at room temperature for 16 h. Reaction progress was monitored by TLC. After completion of the reaction mixture was cooled to 0° C. Then the reaction mixture was acidified to pH=4 with conc. HCl and extracted with ethyl acetate (500 mL×3). The Organic layer was dried over anhydrous sodium sulphate and concentrated to afford crude compound. The obtained crude was washed with heptane and pentane to afford crude compound (2) (90 g) as an off-white solid.

$^1$H NMR (400 MHz, DMSO-d6) δ=12.6 (br s, 1H), 9.14-9.08 (m, 1H), 8.26-8.16 (m, 2H), 7.93 (d, J=6.8 Hz, 1H), 7.77-7.73 (m, 1H), 3.96-3.93 (d, 2H).

LC-MS (Method-A)=246.3 [M+H]$^+$; 65.20% at RT 1.09 min

Step-3: Synthesis of (Z)-4-(2-nitrobenzylidene)-2-(3-(trifluoromethyl) phenyl) oxazol-5 (4H)-one (3)

A stirred solution of compound (2) (5.0 g, 18.6 mmol) and 2-nitrobenzaldehyde (2.90 g, 18.6 mmol) in acetic anhydride (5.82 g, 55.8 mmol) was stirred at 70° C. for 2 h. Reaction progress was monitored by TLC. After completion of reaction, the reaction mixture was cooled to room temperature and added (1:1 ratio) ethanol (5 mL) and water (5 mL). The reaction mixture was stirred at room temperature for 16 h. Separated solid was filtered off and dried to air to afford crude. Combined crude was washed with n-heptane and n-pentane to afford pure compound (2.6 g, 37%) as an off-white solid.

$^1$H NMR (400 MHz, CDCL3-d6) δ=8.59-8.56 (m, 1H), 8.41-8.38 (m, 1H), 8.34-8.32 (m, 1H), 8.09 (m, 1H), 7.90-7.88 (m, 1H), 7.81-7.76 (m, 2H), 7.72-7.66 (m, 1H), 7.65-7.60 (m, 1H).

LC-MS (Method-B)=363.2 [M+H]$^+$; 68.20% at RT 1.93 min.

Step-4: Synthesis of rac-N-((4R,5S)-4-(2-nitrophenyl)-6-oxo-1-phenyl-4,5,6,7-tetrahydro-1H-pyrazolo [3,4-b]pyridin-5-yl)-3-(trifluoromethyl) benzamide (4)

To a stirred solution of compound (3) (7.5 g, 18 mmol) in chlorobenzene (80 mL) was added 2-phenylpyrazol-3-amine (Int.A) (4.4 g, 27 mmol) and stannous chloride (0.35 g, 1.8 mmol) at room temperature. The reaction mixture was stirred at 100° C. for 36 h. Reaction progress was monitored by TLC. After completion of reaction, the reaction mixture was cooled to room temperature and concentrated to afford crude. Combined crude was purified by column chromatography by using silica gel, eluted with 0-45% ethyl acetate/heptane to afford pure compound (4) (5.05 g, 37%) as yellow solid.

$^1$H NMR (400 MHz, DMSO-d6) δ=10.9 (s, 1H), 8.90 (d, J=8.4 Hz, 1H), 7.98-7.95 (m, 2H), 7.89-7.77 (m, 3H), 7.69 (m, 2H), 7.59-7.47 (m, 5H), 7.42-7.39 (m, 1H), 7.00 (s, 1H). 5.25-5.19 (m, 1H), 4.92 (d, J=12.8 Hz, 1H).

LC-MS (Method-B)=522.0 [M+H]$^+$; 91.10% at RT 2.37 min.

Step-5: Synthesis of rac-N-((4R,5S)-7-ethyl-4-(2-nitrophenyl)-6-oxo-1-phenyl-4,5,6,7-tetrahydro-1H-pyrazolo[3,4-b]pyridin-5-yl)-3-(trifluoromethyl) benzamide (5)

To a stirred solution of compound (4) (4.5 g, 6.0 mmol) in N,N-dimethylformamide (40 mL), potassium carbonate (1.7 g, 12 mmol) and bromoethane (1.3 g, 12 mmol) were added at 0° C. Then the reaction mixture was stirred to room temperature for 24 h. Reaction progress was monitored by TLC. After completion of reaction, the reaction mixture was diluted with water and extracted with ethyl acetate. Combined organic layer was dried over anhydrous sodium sulphate and concentrated under reduced pressure to afford crude compound (5) (1.9 g, 48%) pale yellow solid.

$^1$H NMR (400 MHz, DMSO-d6) δ=8.94 (d, J=9.2 Hz, 1H), 7.99-7.96 (m, 2H), 7.90 (d, J=8.0 Hz, 2H), 7.89-7.65 (m, 5H), 7.61-7.49 (m, 4H), 7.01 (s, 1H), 5.52-5.47 (m, 1H), 4.89 (d, J=13.2 Hz, 1H), 3.86-3.81 (m, 1H), 2.99-3.08 (m, 1H), 0.87-0.81 (m, 3H). LC-MS (Method-B)=550.0 [M+H]$^+$; 92.46% at RT 2.31 min.

Step-6: Synthesis of rac-N-((4R,5S)-4-(2-aminophenyl)-7-ethyl-6-oxo-1-phenyl-4,5,6,7-tetrahydro-1H-pyrazolo[3,4-b]pyridin-5-yl)-3-(trifluoromethyl) benzamide (6)

To a stirred solution of compound (5) (3 g, 4.36 mmol) in DMSO (20 mL) was added tetrahydroxydiboron (1.19 g, 13.10 mmol) followed by 4,4'-bipyridine (0.05 g, 0.3 mmol) at 0° C. The reaction mixture was stirred at room temperature for 20 min. Reaction progress was monitored by TLC. After completion of reaction, the reaction mixture was diluted with water and extracted with ethyl acetate. The combined organic layer was dried and concentrated to get crude. Obtained crude was purified by column chromatography by using silica gel, eluted with 0-65% of heptane/ethyl acetate to afford compound 6 (0.81 g, 34%) pale-yellow solid.

$^1$H NMR (400 MHz, DMSO-d6) δ=9.06 (d, J=8.0 Hz, 1H), 8.07-8.11 (m, 2H), 7.93 (d, J=7.6 Hz, 1H), 7.76-768 (m, 3H), 7.62-7.58 (m, 2H), 7.55-7.51 (m, 1H), 7.15 (s, 1H), 6.96-6.92 (m, 2H), 6.69 (d, J=7.4 Hz, 1H), 6.53-6.48 (m, 1H), 5.25 (s, 2H), 5.19-5.11 (m, 1H), 4.45 (d, J=10.0 Hz, 1H), 3.62-3.54 (m, 1H), 3.30-3.33 (m, 1H), 0.83 (t, J=7.2 Hz, 3H).

LC-MS (Method-B)=519.9 [M+H]$^+$; 96.02% at RT 2.24 min.

HPLC (Method-B): 92.76% at RT 8.75 min.

Synthesis of I-122:

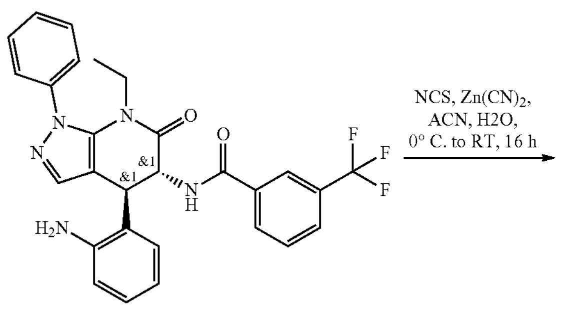

Compound 6

-continued

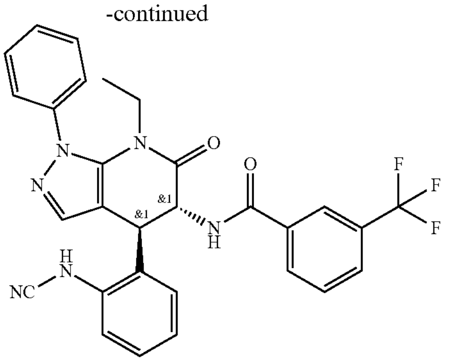

I-122

Synthesis of ~{N}—[~{rac}-(4~{S},5~{R})-4-[2-(cyanoamino)phenyl]-7-ethyl-6-oxo-1-phenyl-4,5-dihydropyrazolo[3,4-b]pyridin-5-yl]-3-(trifluoromethyl)benzamide I-122

To a stirred solution of N-chlorosuccinimide (103 mg, 0.76 mmol) and zinc cyanide (83 mg, 0.69 mmol) in mixture of ACN (4 mL) and Water (0.4 mL) at 0° C. under nitrogen. Then compound 6 (250.0 mg, 0.46 mmol) was added one portion at 0° C. and allowed to stir at room temperature for 16 h. Reaction was monitored by TLC. After completion of reaction, reaction mixture was filtered on celite bed, dried and concentrated to afford crude as brown solid. Obtained crude was purified by column chromatography by using silica gel, eluted with 0-52% of EA/heptane to afford (65 mg, 23.77%) as off white solid. Obtained pure compound was purified by prep-HPLC, product containing fractions were collected and lyophilized to afford I-122 (20 mg, 31.59%) as a white solid.

$^1$H NMR (400 MHz, DMSO-d6) δ=9.38 (m, 1H), 8.98 (d, J=8.8 Hz, 1H), 8.05-8.03 (m, 2H), 7.91 (d, J=8.0 Hz, 1H), 7.73-769 (m, 1H), 7.66-7.63 (m, 2H), 7.60-7.51 (m, 3H), 7.32-7.29 (m, 2H), 7.17-7.15 (m, 1H), 7.07-7.00 (m, 2H), 5.43 (t, J=12.0 Hz, 1H), 4.61 (d, J=12.8 Hz, 1H), 3.84-3.75 (m, 1H), 3.13-3.07 (m, 1H), 0.84 (t, J=6.8 Hz, 3H).

LC-MS (Method-B)=545.0 $[M+H]^+$; 99.47% at RT 3.63 min.

HPLC (Method-B): 99.0% at RT 6.95 min.

Chiral HPLC (Method-C)=Peak-1=49.31% at RT 4.73 min. Peak-2=50.68% at RT 6.78 min.

Synthesis of I-45:

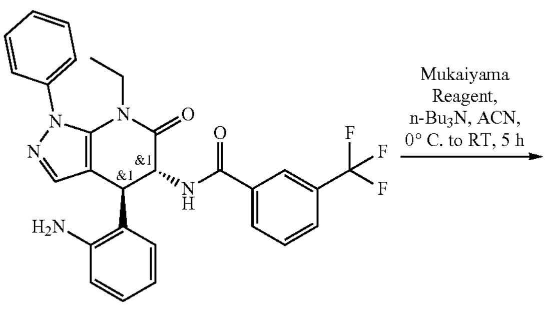

Compound 6

-continued

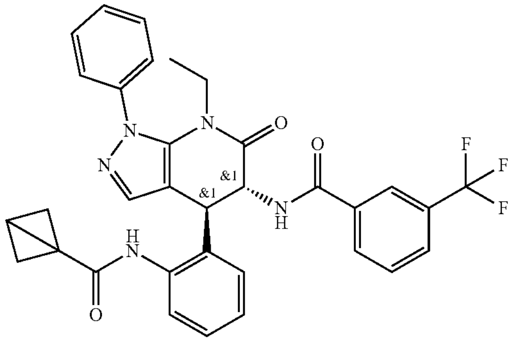

I-45

Synthesis of {N}-[2-[~{rac}-(4~{S},5~{R})-7-ethyl-6-oxo-1-phenyl-5-[[3-(trifluoromethyl)benzoyl]amino]-4,5-dihydropyrazolo[3,4-b]pyridin-4-yl]phenyl]bicyclo[1.1.0]butane-1-carboxamide I-45

To a stirred solution of compound 6 (200.0 mg, 0.38 mmol) and bicyclo[1.1.0]butane-1-carboxylic acid (57 mg, 0.57 mmol) in DMF (3 mL) was added 2-chloro-1-methylpyridinium iodide (152 mg, 0.57 mmol) followed by tributylamine (146 mg, 0.77 mmol) at 0° C. and stirred to room temperature for 5 h, reaction was monitored by TLC. After completion of reaction, added cold water to reaction mixture and filtered on Buckner funnel to afford crude yellow solid. Obtained crude was purified by column chromatography by using silica gel, eluted with 0-54% of ethyl acetate/heptane to afford racemic semi pure trans compound I-45 compound, which was further purified by prep-HPLC and lyophilized to afford I-45 (20 mg, 39.11%) as a white solid.

$^1$H NMR (400 MHz, DMSO-d6) δ=9.49 (m, 1H), 9.02 (d, J=8.0 Hz, 1H), 8.08-8.01 (m, 2H), 7.88 (d, J=7.6 Hz, 1H), 7.70-751 (m, 6H), 7.44-7.42 (m, 1H), 7.27-7.22 (m, 3H), 6.88 (s, 1H), 5.14 (dd, J=12.0 Hz, J=7.6 Hz, 1H), 4.55 (d, J=12.8 Hz, 1H), 3.76-3.71 (m, 1H), 3.17-3.11 (m, 1H), 2.44-2.41 (m, 2H), 2.21-2.19 (m, 1H), 1.08 (s, 2H), 0.82 (t, J=6.8 Hz, 3H).

LC-MS (Method-B)=600.0 $[M+H]^+$; 99.22% at RT 4.42 min.

HPLC (Method-B): 99.63% at RT 8.56 min.

Chiral HPLC (Method-A)=Peak-1=49.92% at RT 3.75 min. Peak-2=50.08% at RT 4.64 min.

Synthesis of I-90, I-98, and I-97
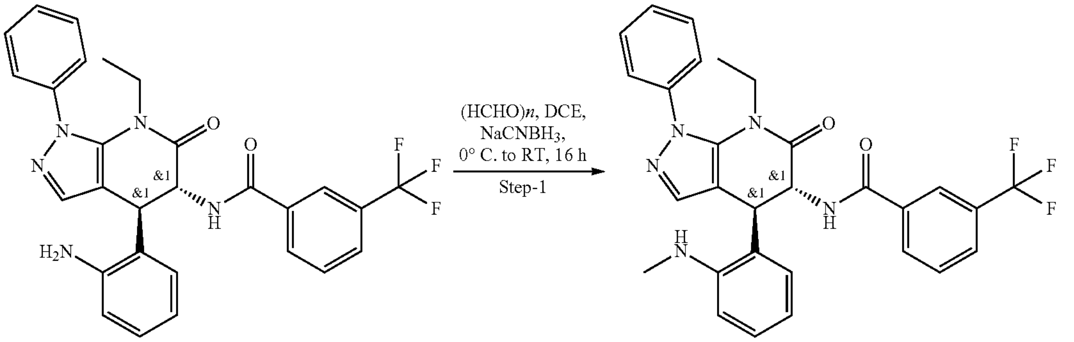
Compound 6
1
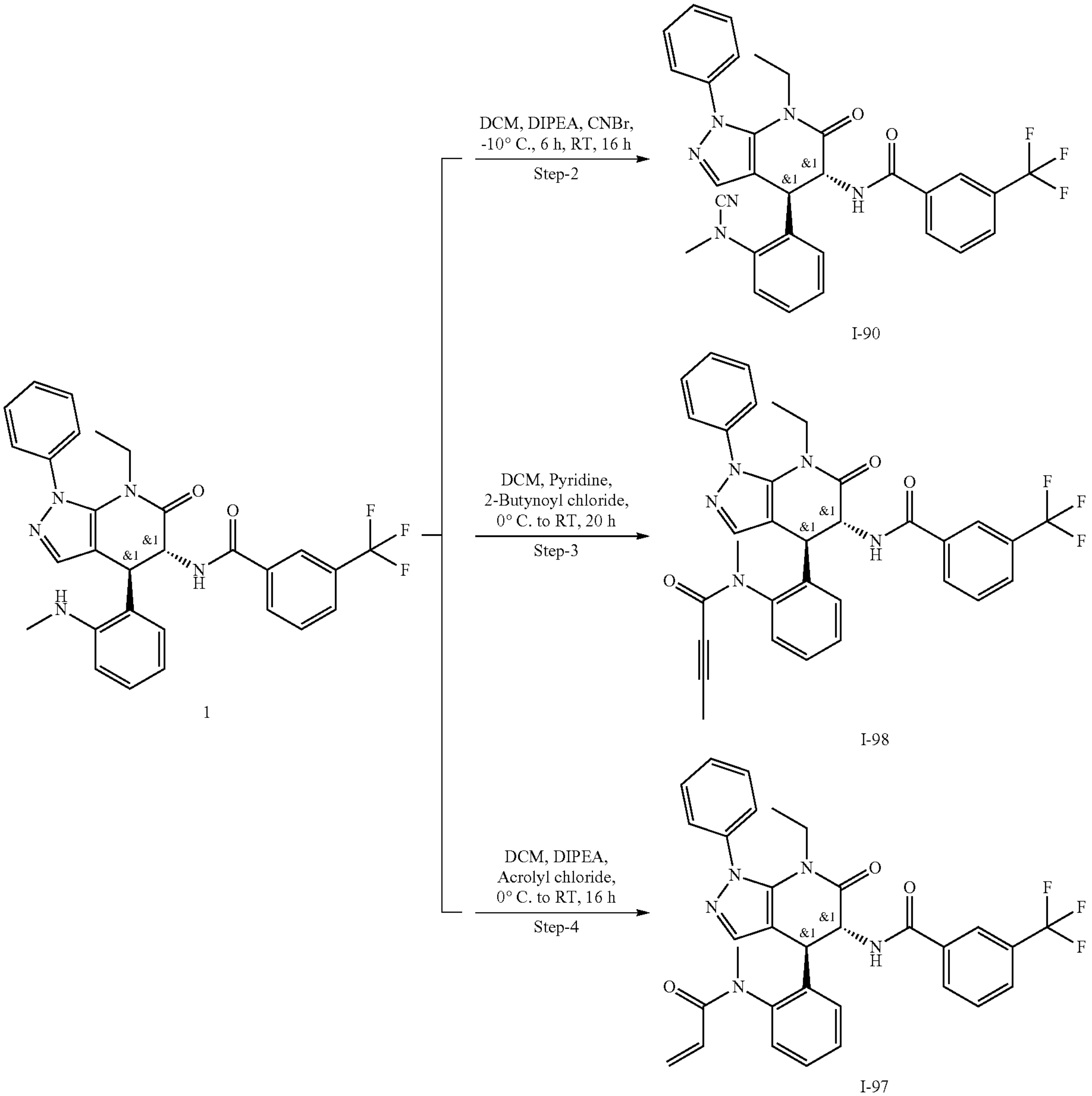
I-90
1
I-98
I-97

Step-1: Synthesis of ~{N}—[~{rac}-(4~{S}, 5~{R})-7-ethyl-4-[2-(methylamino)phenyl]-6-oxo-1-phenyl-4,5-dihydropyrazolo[3,4-b]pyridin-5-yl]-3-(trifluoromethyl)benzamide compound (1)

To a stirred solution of compound 6 (4.00 g, 7.70 mmol) in DCE (80 mL) was added Polyoxymethylene—Homopolymer (0.69 g, 7.70 mmol) at 0° C. and stirred at room temperature for 16 h. Then sodium cyanoborohydride (0.96 g, 15.4 mmol) was added at 0° C. and stirred at room temperature for 16 h. Reaction was monitored by TLC. After completion of reaction, RM was diluted with DCM and washed with cold water. Organic layer was dried and concentrated to afford crude as off white solid. Obtained crude was purified by column chromatography by using silica gel, eluted with 0-41% of ethyl acetate/heptane to afford compound (1) (1.00 g, 22.9%) as white solid.

$^1$H NMR (400 MHz, DMSO-d6) δ=9.03 (d, J=8.4 Hz, 1H), 8.06-8.04 (m, 2H), 7.92 (t, J=8.4 Hz, 1H), 7.74-7.52 (m, 7H), 7.11-6.99 (m, 3H), 6.84-6.53 (m, 2H), 6.59 (s, 1H), 5.13 (d, J=8.8 Hz, 1H), 4.46 (d, J=10.4 Hz, 1H), 3.63-3.61 (m, 1H), 2.78-2.77 (m, 3H), 0.75 (t, J=6.8 Hz, 3H).

LC-MS (Method-B)=534.0 $[M+H]^+$; 94.540% at RT 4.10 min.

Step-2: Synthesis of ~{N}—[~{rac}-(4~{S}, 5~{R})-4-[2-[cyano(methyl)amino]phenyl]-7-ethyl-6-oxo-1-phenyl-4,5-dihydropyrazolo[3,4-b]pyridin-5-yl]-3-(trifluoromethyl)benzamide I-90

To a stirred solution of Compound (1) (50.0 mg, 0.08 mmol) in Dichloromethane (1.00 mL) was added N,N-Diisopropylethylamine (6.9 mg, 0.52 mmol) followed by carbononitridic bromide (5 mmol/mL) (0.10 Ml, 0.52 mmol) 3 times portion wise for every 2 h at −10° C. and stirred at room temperature for 16 h. Reaction was monitored by TLC. After completion of reaction, RM was diluted with EtOAc and washed with cold water. Organic layer was dried and concentrated to afford crude as brown solid. Obtained crude was purified by column chromatography by using silica gel, eluted with 0-53% EtOAc/heptane to afford pure compound I-90 (17.00 mg, 33.16%) as an off white solid.

$^1$H NMR (400 MHz, DMSO-d6) δ=9.05 (d, J=9.2 Hz, 1H), 8.07-8.03 (m, 2H), 7.88 (d, J=7.6 Hz, 1H), 7.70-7.66 (m, 3H), 7.60-7.46 (m, 5H), 7.39-7.36 (m, 2H), 6.87 (s, 1H), 5.41 (dd, J=12.8 Hz, J=9.2 Hz, 1H), 4.90 (d, J=12.8 Hz, 1H), 3.86-3.81 (m, 1H), 3.23 (s, 3H), 3.11-3.06 (m, 1H), 0.85 (t, J=6.8 Hz, 3H).

LC-MS (Method-B)=559.1 $[M+H]^+$; 96.45% at RT 3.77 min.

HPLC (Method-B): 95.69% at RT 8.34 min.

Chiral HPLC (Method-A)=Peak-1=49.89% at RT 4.67 min. Peak-2=50.11% at RT 5.98 min.

Step-3: Synthesis of ~{N}—[~{rac}-(4~{S}, 5~{R})-4-[2-[but-2-ynoyl(methyl)amino]phenyl]-7-ethyl-6-oxo-1-phenyl-4,5-dihydropyrazolo[3,4-b]pyridin-5-yl]-3-(trifluoromethyl)benzamide I-98

To a stirred solution of Compound (1) (200 mg, 0.34 mmol) in Dichloromethane (4 mL) was added Pyridine (27 mg 0.34 mmol) followed by but-2-ynoyl chloride (40.1 mg, 0.38 mmol) at 0° C. and stirred at room temperature for 20 h. Reaction was monitored by TLC. After completion of reaction, the reaction mixture was diluted with water and extracted with DCM. Combined organic layer was dried and concentrated to afford a crude compound as brown solid. Obtained crude was purified by column chromatography by using silica gel, eluted with 0-43% of EtOAc/heptane to afford pure compound I-98 (27.01 mg, 22.4%) as a white solid.

VT NMR (400 MHz, DMSO-d6) δ=8.58-8.71 (m, 1H), 8.18-8.03 (m, 2H), 7.85 (d, J=6.8 Hz, 1H), 7.70-7.54 (m, 7H), 7.43-7.19 (m, 3H), 6.90-6.86 (m, 1H), 5.37 (t, J=10.8 Hz, 1H), 4.72 (d, J=12.0 Hz, 1H), 4.52-4.38 (m, 1H), 3.85-3.78 (m, 1H), 3.50-3.42 (m, 1H), 3.19-3.04 (m, 2H), 2.10 (s, 1H), 1.76 (s, 1H), 1.23 (s, 1H), 0.87 (t, J=6.8 Hz, 3H).

LC-MS (Method-B)=600.0 $[M+H]^+$; 99.24% at RT 2.29 min.

HPLC (Method-B): 99.74% at RT 8.46 min.

Chiral HPLC (Method-A)=Peak-1=50.57% at RT 4.60 min. Peak-2=49.43% at RT 5.93 min.

Step-4: Synthesis of ~{N}—[~{rac}-(4~{S}, 5~{R})-7-ethyl-4-[2-[methyl(prop-2-enoyl)amino]phenyl]-6-oxo-1-phenyl-4,5-dihydropyrazolo[3,4-b]pyridin-5-yl]-3-(trifluoromethyl)benzamide I-97

To a stirred solution of Compound (1) (150.0 mg, 0.28 mmol) in Dichloromethane (5 mL) was added N,N-Diisopropylethylamine (185 mg, 1.40 mmol) followed by prop-2-enoyl chloride (103 mg, 1.12 mmol) at 0° C. and stirred at room temperature for 16 h. The progress of the reaction was monitored by TLC and LCMS. After completion, reaction was quenched with water (30 mL), and extracted with extracted with DCM (20 mL×3). Combined organic layer was washed with brine and dried over $Na_2SO_4$ and concentrated to afford crude. Obtained Crude was purified by column chromatography using silica gel, eluted with 0-60% ethyl acetate: heptane to afford I-97 (35 mg 20.55%) as off white solid.

$^1$H NMR (400 MHz, DMSO-d6) δ=9.06-8.92 (m, 1H), 8.13-8.01 (m, 2H), 7.91-7.87 (m, 1H), 7.70-7.46 (m, 7H), 7.45-7.38 (m, 1H), 7.32-7.22 (m, 1H), 7.08-7.66 (m, 1H), 6.96-6.92 (m, 1H), 6.14-6.12 (m, 1H), 5.60-5.45 (m, 2H), 4.77 (dd, J=10.0 Hz, 2.0 Hz, 1H), 4.38 (d, J=12.8 Hz, 1H), 3.88-3.75 (m, 1H), 3.18-3.13 (m, 3H), 3.08-2.99 (m, 1H), 0.85-0.79 (m, 3H).

VT NMR (400 MHz, DMSO-d6) δ=8.85-8.72 (m, 1H), 8.09-8.00 (m, 2H), 7.84 (t, J=7.2 Hz, 1H), 7.70-7.52 (m, 7H), 7.44-7.33 (m, 1H), 7.22-7.07 (m, 1H), 6.93-6.89 (m, 1H), 6.14-6.12 (m, 1H), 597-5.90 (m, 1H), 5.80-5.40 (m, 2H), 4.82-4.69 (m, 1H), 4.82 (d, J=12.0 Hz, 1H), 3.82-3.76 (m, 1H), 3.20-3.04 (m, 4H), 0.88-0.82 (m, 3H).

LC-MS (Method-B)=588.2 $[M+H]^+$; 96.440% at RT 2.19 min.

HPLC (Method-B): 92.13% at RT 8.36 min.

Chiral HPLC (Method-A)=Peak-1=49.88% at RT 50.2 min. Peak-2=50.12% at RT 6.43 min.

Synthesis of I-89:

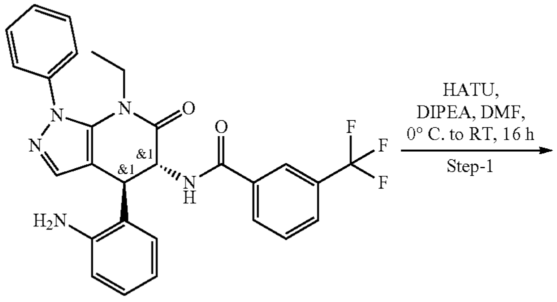

Compound 6

-continued

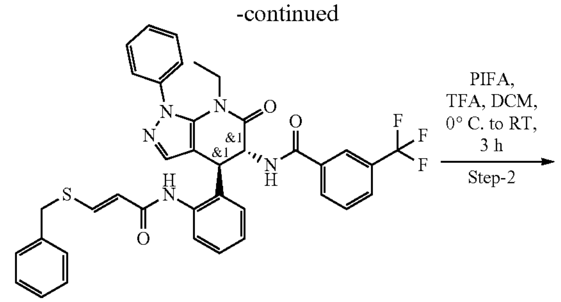

1

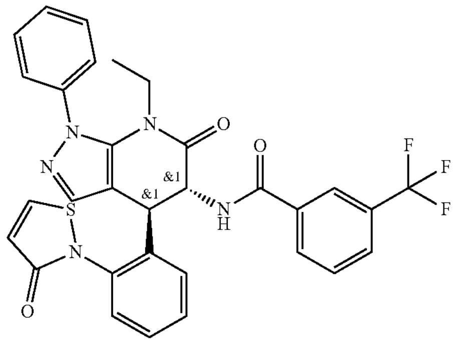

I-89

Step-1: Synthesis of ~{N}—[~{rac}-(4~{S}, 5~{R})-7-ethyl-6-oxo-1-phenyl-4-[2-[[~{rac}-(~{E})-3-benzylsulfanylprop-2-enoyl]amino]phenyl]-4,5-dihydropyrazolo[3,4-b]pyridin-5-yl]-3-(trifluoromethyl)benzamide compound (1)

To a stirred solution of compound 6 (500 mg, 0.72 mmol) and (~{E})-3-benzylsulfanylprop-2-enoic acid 230 mg, 1.06 mmol) in DMF (5 mL) was added HATU (500 mg, 1.27 mmol) followed by N,N-Diisopropylethylamine (0.5 mL, 3 mmol) at 0° C. The resulting reaction mixture was stirred at room temperature for 16 h. Progress of the reaction was monitored by LC-MS and TLC. After completion, the reaction mixture was quenched with ice-cold water (20 mL), extracted with EtOAc (2×30 mL) combined organic layer was washed with brine (2×20 mL), organic layer was dried over anhydrous $Na_2SO_4$, filtered, and concentrated under reduced pressure to afford the crude compound. The obtained crude compound was purified by combi-flash using eluted with 40% to 80% EtOAc in heptane, pure fractions were concentrated under reduced pressure and dried to afford Compound-1 (400 mg, 74.7%) as a yellow colour solid.

$^1$H NMR (400 MHz, DMSO-d6) δ=9.59 (m, 1H), 9.07-9.05 (m, 1H), 8.09-8.02 (m, 2H), 7.87 (d, J=8.4 Hz, 1H), 7.64-7.47 (m, 6H), 7.41-7.32 (m, 4H), 7.30-7.18 (m, 4H), 6.92 (s, 1H), 6.23 (d, J=9.2 Hz, 1H), 5.16-5.14 (m, 1H), 4.65-4.57 (m, 1H), 4.00 (s, 1H), 3.70-3.65 (m, 1H), 3.20-3.15 (m, 1H), 2.68 (s, 3H), 0.85-0.79 (m, 3H).

LC-MS (Method-A)=696.34 $[M+H]^+$; 93.89% at RT 2.55, 2.58 min.

Step-2: Synthesis of ~{N}—[~{rac}-(4~{S}, 5~{R})-7-ethyl-6-oxo-4-[2-(3-oxoisothiazol-2-yl) phenyl]-1-phenyl-4,5-dihydropyrazolo[3,4-b]pyridin-5-yl]-3-(trifluoromethyl)benzamide I-89

To a stirred solution of [bis(trifluoroacetoxy)iodo]benzene (290 mg, 0.65 mmol) and TFA (0.1 mL, 1 mmol) in Dichloromethane (4 mL) at 0° C., was added a solution of compound (1) (370 mg, 0.49 mmol) in Dichloromethane (4 mL) at the same temperature. The resulting reaction mixture was stirred at room temperature for 3 h. Progress of the reaction was monitored by LC-MS and TLC. Then the reaction mixture was diluted with ice-cold water (20 mL), extracted with EtOAc (2×30 mL) combined organic layer was washed with brine (2×30 mL), organic layer was dried over anhydrous Na2SO4, filtered, and concentrated under reduced pressure to afford the crude compound. The crude compound was purified by Prep-HPLC purification, after purification pure fractions were collected and lyophilized to afford I-89 (48 mg, 15.5%) as an off-white solid.

$^1$H NMR (400 MHz, DMSO-d6) δ=8.91 (d, J=7.6 Hz, 1H), 8.71 (d, J=6.0 Hz, 1H), 8.09-8.07 (m, 2H), 7.87 (d, J=8.0 Hz, 1H), 7.68-749 (m, 8H), 7.43-7.35 (m, 2H), 6.94 (s, 1H), 6.36 (s, 1H), 5.34-5.29 (m, 1H), 4.41 (s, 1H), 3.73-3.67 (m, 1H), 3.07-3.06 (m, 1H), 0.77 (t, J=6.8 Hz, 3H).

LC-MS (Method-A)=604.30 $[M+H]^+$; 99.79% at RT 2.21 min.

HPLC (Method-A): 98.31% at RT 5.92 min.

Chiral HPLC (Method-A)=Peak-1=49.81% at RT 7.97 min. Peak-2=50.18% at RT 9.93 min.

Example 2: Synthesis of Compounds I-170, I-185, I-190, I-189, I-183, I-168, I-200, I-199, I-198, I-195, I-174, I-15, I-176, I-159, I-72, I-194, I-188, I-166, I-175, I-167, I-177, I-21, I-196, and I-179

NMR:

$^1$H NMR spectrum spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5μ.

Mobile Phase: A: 0.05% Formic acid in water: ACN (95:5) B: 0.05% Formic acid in CAN.

Inj Volume: 2.0 μL, Column oven temperature: 50 C; Flow Rate: 1.2 mL/min.

Gradient program: 0% B to 98% B in 2.0 minute, hold till 3.0 min, at 3.2 min B conc is 0% up to 4.0 min.

Method-B: Column: X-Bridge C18 (3.0*50) mm 2.5u; Mobile Phase: A: 2.5 mM Ammonium Bicarbonate in water; B: Acetonitrile; Flow Rate: 1.2 mL/min; Column oven temp. 50° C.

Gradient program: 0% B to 98% B in 2.0 minute, hold till 3.0 min, at 3.2 min B conc is 0% up to 4.0 min.

Method-C: Column: X-Select CSH C18 (50 mm*3.0 mm, 2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

Method-D: Column:X-Select CSH C18 (3.0*50 mm, 2.5 μm), Mobile Phase A: 2.5 Mm Ammonium Bicarbonate in $H_2O$+5% ACN Mobile Phase B: 100% ACN, Gradient % B: 0/2, 0.3/2, 2.0/98, 2.8/98, 3.0/2, 3.7/2.

Method-E: Column: X-Bridge BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water: ACN (95:05);

Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: ACN; Programme/B %: 0.01/2, 2/2, 12/90, 16/90; Flow: 1.0 mL/min.; Diluent: ACN: WATER (80:20).

Method-C: Column: X SELECT CSH C18 (150×4.6 mm, 3.5); Mobile Phase A; 0.05% TFA IN WATER: ACN (95: 05); Mobile Phase B: 0.05% TFA IN WATER: ACN(05:95); Programme: T/B %: 0.01/10, 12/90, 16/90; Flow: 1 mL/min.; Diluent: WATER:ACN (80:20).

Method-D: Column: X-Bridge CSH C18 (4.6*150) mm 5u Mobile Phase: A—0.1% TFA in water B—Acetonitrile Inj Volume; 5.0 μL, Flow Rate: 1.2. mL/minute Gradient program: Time(min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in HEXANE Mobile Phase B: IPA A/B: 60/40 Flow: 1.0 ml/MIN PDA: OJ-H_015.

Method-F: Column: ACE Excel 2 C18-AR, 100 mm×3.0 mm Mobile Phase A: 0.05% TFA in Water; Mobile Phase B: 0.05% TFA in Acetonitrile Colum Temperature: 40° C. Flow Rate: 0.6 mL/min Gradient: 0/5, 1/5, 6/90, 8.5/90, 8.8/5, 11/5.

Method-G: Column: CHIRAL PAK-IC (250×4.6 mm, 5 μm) Mobile Phase A: 0.1% DEA in Hexane Mobile Phase B: EtOH/MEOH (50/50) A: B: 80/20 Flow: 1.0 mL/min.

Method-H: Column: ACE Excel 2 C18-AR, 100 mm×3.0 mm Mobile Phase A: 0.05% FA in Water; Mobile Phase B: 0.05% FA in Acetonitrile Colum Temperature: 40° C. Flow Rate: 0.6 mL/min Gradient: 0/5, 1/5, 6/90, 8.5/90, 8.8/5, 11/5.

Method-I: Column: X-Select CSH C18 (4.6*150) mm 5μ Mobile Phase: A—0.1% TFA in water B—Acetonitrile Inj Volume; 5.0 μL, Flow Rate: 1.2. mL/minute Gradient program: Time(min)/B Conc.: 0.01/5, 1.0/5, 8.0/100, 12.0/100, 14.0/5, 18.0/5.

Synthesis of Intermediate Compound 6

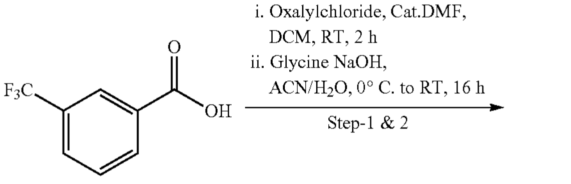

SM-1

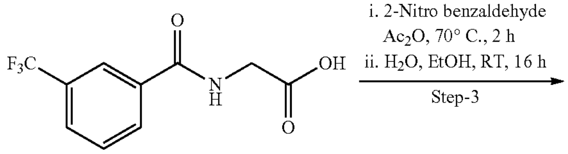

2

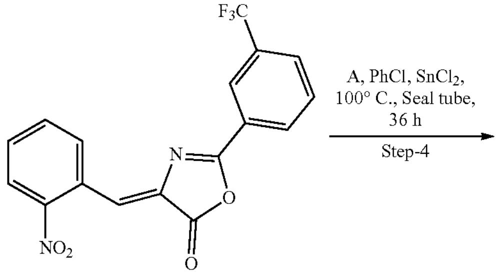

3

-continued

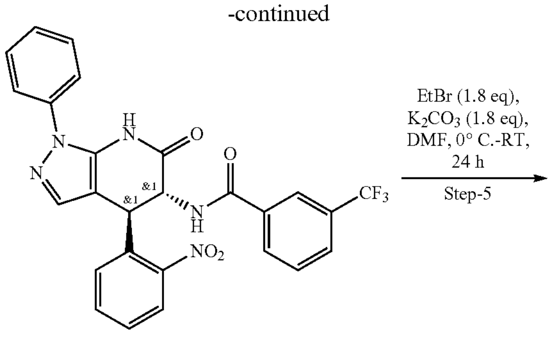

4

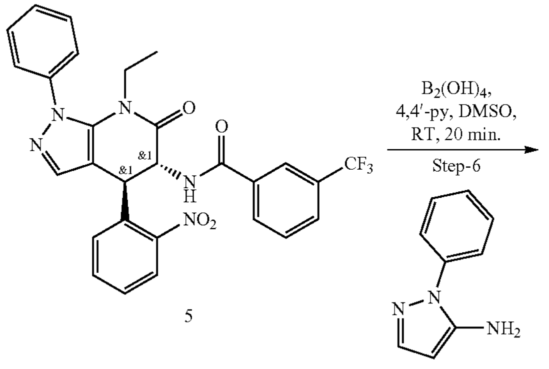

5

A

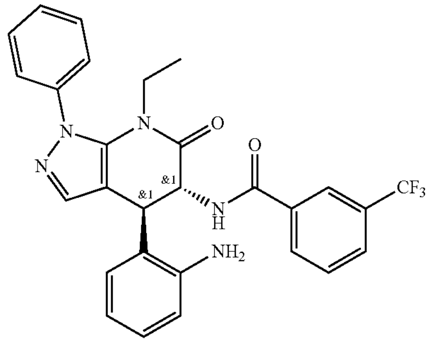

6

Step-1 & 2: Synthesis of 2-[[3-(trifluoromethyl) benzoyl]amino]acetic acid (1)

To a stirred solution of 3-(trifluoromethyl) benzoic acid (4×25 g, 131.56 mmol) in DCM (250 mL) at 0° C. was added dropwise oxalyl chloride (33.8 mL, 0.39 mmol) followed by DMF (1 mL). The reaction mixture was stirred at room temperature for 2 h. The reaction mixture was monitored by TLC. After completion of SM, the reaction mixture was concentrated under reduced pressure to afford crude compound. The crude compound as such taken for the next step. Glycine (10.8 g, 0.14 mmol) was dissolved in Acetonitrile (150 mL) and 50% aq. NaOH (18 g, 0.47 mmol) was added at 0° C. and then the above prepared acid chloride compound in Acetonitrile was slowly added in a dropwise manner at 0° C. Then the reaction mixture was stirred at room temperature for 16 h. Reaction progress was monitored by TLC. After completion of the reaction mixture was cooled to 0° C. Then the reaction mixture was acidified to pH=4 with conc. HCl and extracted with ethyl acetate (500 mL×3). The Organic layer was dried over anhydrous sodium sulphate and concentrated to afford crude compound. The obtained crude was washed with heptane and pentane to afford crude compound (2) (90 g) as an off-white solid.

$^1$H NMR (400 MHz, DMSO-d6) δ=12.6 (br s, 1H), 9.14-9.08 (m, 1H), 8.26-8.16 (m, 2H), 7.93 (d, J=6.8 Hz, 1H), 7.77-7.73 (m, 1H), 3.96-3.93 (d, 2H). LC-MS (Method-A)=246.3 [M+H]$^+$; 65.20% at RT 1.09 min.

Step-3: Synthesis of (Z)-4-(2-nitrobenzylidene)-2-(3-(trifluoromethyl) phenyl) oxazol-5 (4H)-one (3)

A stirred solution of compound (2) (5.0 g, 18.6 mmol) and 2-nitrobenzaldehyde (2.90 g, 18.6 mmol) in acetic anhydride (5.82 g, 55.8 mmol) was stirred at 70° C. for 2 h. Reaction progress was monitored by TLC. After completion of reaction, the reaction mixture was cooled to room temperature, was added (1:1 ratio) ethanol (5 mL) and (5 mL) of water and (stirred for 16 h. at room temperature. Separated solid was filtered off and dried to air to afford crude. Combined crude was washed with n-heptane and n-pentane to afford pure compound (2.6 g, 37%) as off-white solid.

$^1$H NMR (400 MHz, $CDCl_3$-d6) δ=8.59-8.56 (m, 1H), 8.41-8.38 (m, 1H), 8.34-8.32 (m, 1H), 8.09 (m, 1H), 7.90-7.88 (m, 1H), 7.81-7.76 (m, 2H), 7.72-7.66 (m, 1H), 7.65-7.60 (m, 1H).

LC-MS (Method-B)=363.2 [M+H]$^+$; 68.20% at RT 1.93 min.

Step-4: Synthesis of rac-N-((4R,5S)-4-(2-nitrophenyl)-6-oxo-1-phenyl-4,5,6,7-tetrahydro-1H-pyrazolo [3,4-b]pyridin-5-yl)-3-(trifluoromethyl) benzamide (4)

To a stirred solution of compound (3) (7.5 g, 18 mmol) in chlorobenzene (80 mL) was added 2-phenylpyrazol-3-amine (Int.A) (4.4 g, 27 mmol) and stannous chloride (0.35 g, 1.8 mmol) at room temperature. The reaction mixture was stirred at 100° C. for 36 h. Reaction progress was monitored by TLC. After completion of reaction, the reaction mixture was cooled to room temperature and concentrated to afford crude. Combined crude was purified by column chromatography by using silica gel, eluted with 0-45% ethyl acetate/heptane to afford pure compound (4) (5.05 g, 37%) as yellow solid.

$^1$H NMR (400 MHz, DMSO-d6) δ=10.9 (s, 1H), 8.90 (d, J=8.4 Hz, 1H), 7.98-7.95 (m, 2H), 7.89-7.77 (m, 3H), 7.69 (m, 2H), 7.59-7.47 (m, 5H), 7.42-7.39 (m, 1H), 7.00 (s, 1H). 5.25-5.19 (m, 1H), 4.92 (d, J=12.8 Hz, 1H).

LC-MS (Method-B)=522.0 [M+H]$^+$; 91.10% at RT 2.37 min.

Step-5: Synthesis of rac-N-((4R,5S)-7-ethyl-4-(2-nitrophenyl)-6-oxo-1-phenyl-4,5,6,7-tetrahydro-1H-pyrazolo[3,4-b]pyridin-5-yl)-3-(trifluoromethyl) benzamide (5)

To a stirred solution of compound (4) (4.5 g, 6.0 mmol) in N,N-dimethylformamide (40 mL), potassium carbonate (1.7 g, 12 mmol) and bromoethane (1.3 g, 12 mmol) were added at 0° C. Then the reaction mixture was stirred to room temperature for 24 h. Reaction progress was monitored by TLC. After completion of reaction, the reaction mixture was diluted with water and extracted with ethyl acetate. Combined organic layer was dried over anhydrous sodium sulphate and concentrated under reduced pressure to afford crude compound (4) (1.9 g, 48%) pale yellow solid.

$^1$H NMR (400 MHz, DMSO-d6) δ=8.94 (d, J=9.2 Hz, 1H), 7.99-7.96 (m, 2H), 7.90 (d, J=8.0 Hz, 2H), 7.89-7.65 (m, 5H), 7.61-7.49 (m, 4H), 7.01 (s, 1H), 5.52-5.47 (m, 1H), 4.89 (d, J=13.2 Hz, 1H), 3.86-3.81 (m, 1H), 2.99-3.08 (m, 1H), 0.87-0.81 (m, 3H).

LC-MS (Method-B)=550.0 [M+H]$^+$; 92.46% at RT 2.31 min.

Step-6: Synthesis of rac-N-((4R,5S)-4-(2-aminophenyl)-7-ethyl-6-oxo-1-phenyl-4,5,6,7-tetrahydro-1H-pyrazolo[3,4-b]pyridin-5-yl)-3-(trifluoromethyl) benzamide (compound 6)

To a stirred solution of compound (5) (3 g, 4.36 mmol) in DMSO (20 mL) was added tetrahydroxydiboron (1.19 g, 13.10 mmol) followed by 4,4'-bipyridine (0.05 g, 0.3 mmol) at 0° C. The reaction mixture was stirred at room temperature for 20 min. Reaction progress was monitored by TLC. After completion of reaction, the reaction mixture was diluted with water and extracted with ethyl acetate. The combined organic layer was dried and concentrated to get crude. Obtained crude was purified by column chromatography by using silica gel, eluted with 0-65% of heptane/ethyl acetate to afford compound 6 (0.81 g, 34%) pale-yellow solid.

$^1$H NMR (400 MHz, DMSO-d6) δ=9.06 (d, J=8.0 Hz, 1H), 8.07-8.11 (m, 2H), 7.93 (d, J=7.6 Hz, 1H), 7.76-768 (m, 3H), 7.62-7.58 (m, 2H), 7.55-7.51 (m, 1H), 7.15 (s, 1H), 6.96-6.92 (m, 2H), 6.69 (d, J=7.4 Hz, 1H), 6.53-6.48 (m, 1H), 5.25 (s, 2H), 5.19-5.11 (m, 1H), 4.45 (d, J=10.0 Hz, 1H), 3.62-3.54 (m, 1H), 3.30-3.33 (m, 1H), 0.83 (t, J=7.2 Hz, 3H).

LC-MS (Method-B)=519.9 [M+H]$^+$; 96.02% at RT 2.24 min.

HPLC (Method-B): 92.76% at RT 8.75 min.

Scaffold Analogs:

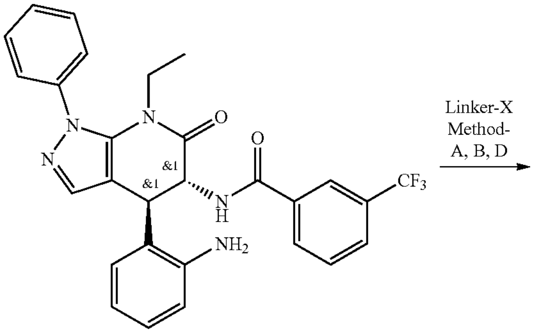

6

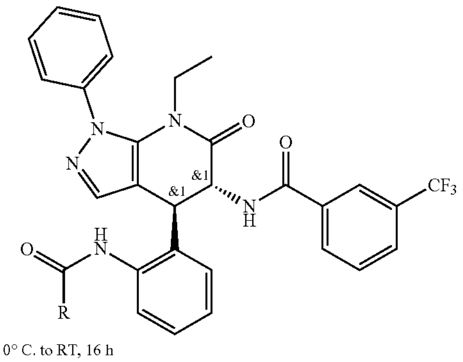

A. DIPEA, DCM, 0° C. to RT, 16 h
B. Py, DCM, 0° C. to RT, 20 h
D. Mukaiyama reagent, Tributylamine, DMF, 16 h, 70° C.

Method-A Procedure:

To a stirred solution of 6 (150.00 mg, 0.2541 mmol) in dichloromethane (2 mL) was added Linker-X(X═B, H, O) (0.50 mmol) followed by N,N-Diisopropylethylamine (0.133 mL, 0.76 mmol) at 0° C. The reaction mixture was stirred at room temperature for 16 h. The reaction was monitored by TLC. After completion of reaction, the reaction mixture was quenched with water (20 mL) and extracted with DCM (2×25 mL). Combined organic layer was dried over anhydrous sodium sulphate and concentrated under reduced pressure to afford crude. The obtained crude was purified by column chromatography using silica gel, eluted with 0-60% EA/heptane to afford the desired compound.

Method B Procedure:

To a stirred solution of 6 (100 mg, 0.1867 mmol) in dichloromethane (2 mL) was added pyridine (0.015 mL, 0.18 mmol) followed by Linker X (X=C, I, D, E, R, Y) at 0° C. The reaction mixture was stirred at room temperature for 3 h. The reaction mixture was monitored by TLC. After completion of reaction, the reaction mixture was concentrated under reduced pressure. The reaction mixture was quenched with water (20 mL) and extracted with ethyl acetate (2×25 mL). Combined organic layer was dried over anhydrous sodium sulphate and concentrated to afford crude. The obtained crude was purified by column chromatography by using silica gel, eluted with 0-82% EA/heptane to afford compound.

Method D Procedure:

To a stirred solution of 6 (200 mg, 0.385 mmol) in DMF (3 mL) were added Linker X (X=L, P, 2A, 2D, M, G, K, T, J, N, 2C) followed by 2-Chloro-1-methylpyridinium iodide (130 mg, 0.50 mmol) and tributylamine (0.19 mL, 0.77 mmol) portion wise. Then the reaction mixture was allowed to stir at 50° C. for 4 h. The reaction was monitored by TLC. After completion of the reaction, the reaction mixture was quenched with water (20 mL) and extracted with EtOAc (2×25 mL). The combined organic layer was washed with brine dried over anhydrous $Na_2SO_4$ and concentrated under reduced pressure. The crude obtained was purified by medium pressure liquid chromatography by eluting with 55% EtOAc in heptane to afford compound. The following table shows the conditions to obtain the desired compounds.

| Sr No. | Cmpd. Number | Linker | Structure (R) | Method | Compound 6 (mg) | Linker Qty (mg) | Qty (mg) & Nature of compound | Yield (%) |
|---|---|---|---|---|---|---|---|---|
| 1. | I-170 | B | 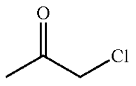 | A | 120 | 58.57 | 45 (Off-White solid) | 28.82 |
| 2. | I-185 | H | 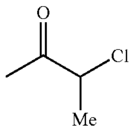 | A | 120 | 87.99 | 41 (Off-White solid) | 28.81 |
| 3. | I-190 | O | 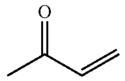 | A | 120 | 61.44 | 55.38 (Off-White solid) | 42.24 |
| 4. | I-189 | C | 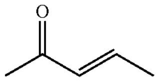 | B | 120 | 39.84 | 50 (off white solid) | 44.66 |
| 5 | I-183 | I | 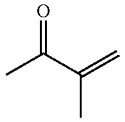 | B | 120 | 47.31 | 69 (pale-yellow solid) | 52.42 |
| 6. | I-168 | L | 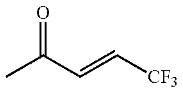 | D | 200 | 66 | 60 mg (Off-White solid) | 23.56 |
| 7. | I-200 | P | 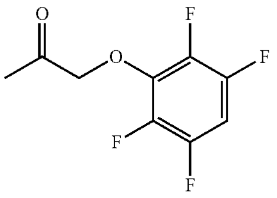 | D | 150 | 98.78 | 45 mg (Off-White solid) | 23.43 |
| 8. | I-199 | 2A | 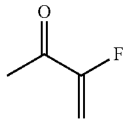 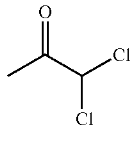 | D | 150 | 20 | 36 mg (White solid) | 25.70 |

-continued
| Sr No. | Cmpd. Number | Linker | Structure (R) | Method | Compound 6 (mg) | Linker Qty (mg) | Qty (mg) & Nature of compound | Yield (%) |
|---|---|---|---|---|---|---|---|---|
| 9. | I-198 | 2D | 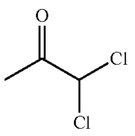 | D | 150 | 37.38 | 23 mg (White solid) | 15.26 |
| 10. | I-195 | M | 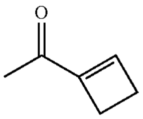 | D | 200 | 50.87 | 35 mg (White solid) | 16.71 |
| 11. | I-174 | G | 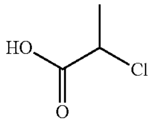 | D | 10 | 58.33 | 35 (pale-yellow solid) | 22.21 |
| 12. | I-15 | K | 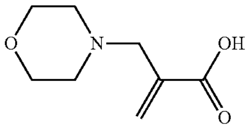 | D | 10 | 129 | 45.62 (Off-White solid) | 20 |
| 13. | I-176 | T | 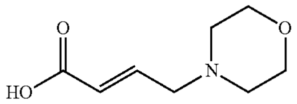 [SMILES: O=C(O)/C=C/CN1CCOCC1] | D | 200 | 87 | 47.5 | 21 |
| 14. | I-159 | D | 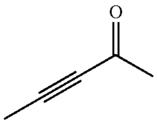 | B | 120 | 34 | 45 (White solid) | 34.31 |
| 15. | I-72 | E | 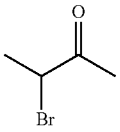 | B | 250 | 136.7 | 90 (White solid) | 32.89 |
| 16. | I-194 | J | 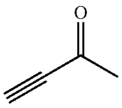 | D | 200 | 36.32 | 70 (Off-White solid) | 36.26 |
| 17. | I-188 | N | 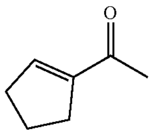 | D | 250 | 194 | 62 (Off-White solid) | 23.62 |
| 18. | I-166 | R | 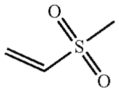 | B | 200 | 57.28 | 40 (Off-White solid) | 17.04 |
| 19. | I-175 | Y | 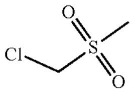 | B | 150 | 79.70 | 35 (White solid) | 21.14 |

-continued

| Sr No. | Cmpd. Number | Linker | Structure (R) | Method | Comp-ound 6 (mg) | Linker Qty (mg) | Qty (mg) & Nature of compound | Yield (%) |
|---|---|---|---|---|---|---|---|---|
| 20. | I-167 | 2C | 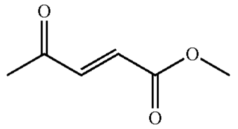 | D | 200 | 55.10 | 24.31 (Off-White solid) | 26.14 |

I-170

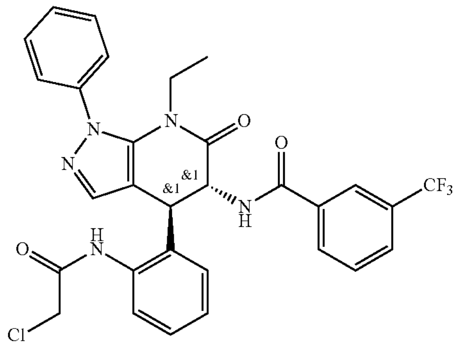 [SMILES: CCN1C(=O)[C@H](NC(=O)c2cccc(C(F)(F)F)c2)[C@@H](c2ccccc2NC(=O)CCl)c2cnn(-c3ccccc3)c21]

$^1$H NMR (400 MHz, DMSO-$d_6$) δ=9.81 (s, 1H), 8.90 (d, J=8.8 Hz, 1H), 8.01-7.99 (m, 2H), 7.89 (d, J=8.0 Hz, 1H), 7.70-7.65 (m, 3H), 7.59 (t, J=7.2 Hz, 2H), 7.55-7.53 (m, 1H), 7.42-7.40 (m, 2H), 7.28-7.23 (m, 2H), 6.98 (s, 1H), 5.22-5.17 (m, 1H), 4.68 (d, J=12.0 Hz, 1H), 4.40-4.32 (m, 2H), 3.76 (m, 1H), 3.14 (m, 1H), 0.82 (t, J=7.2 Hz, 3H). LC-MS (Method-D)=596.43 [M]$^+$; 96.93% at RT 2.02 min. HPLC (Method-B)=95.16% at RT 8.81 min.

I-185

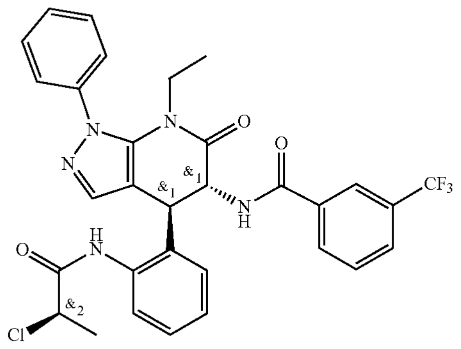 [SMILES: CCN1C(=O)[C@H](NC(=O)c2cccc(C(F)(F)F)c2)[C@@H](c2ccccc2NC(=O)[C@@H](C)Cl)c2cnn(-c3ccccc3)c21]

$^1$H NMR (400 MHz, DMSO-$d_6$) δ=9.86-9.78 (m, 1H), 8.93-8.89 (m, 1H), 8.03-7.96 (m, 2H), 7.91-7.87 (m, 1H), 7.71-7.51 (m, 6H), 7.46-7.40 (m, 2H), 7.30-7.20 (m, 2H), 6.98 (d, J=8.4 Hz, 1H), 5.23-5.17 (m, 1H), 4.85-4.79 (m, 1H), 4.72-4.58 (m, 1H), 3.82-3.75 (m, 1H), 3.17-3.08 (m, 1H), 1.65-1.54 (m, 3H), 0.82 (t, J=3.2 Hz, 3H). LC-MS (Method-D)=610.2 [M+H]$^+$; 99.15% at RT 2.27 min. HPLC (Method-B)=93.99% at RT 9.16 min.

I-190

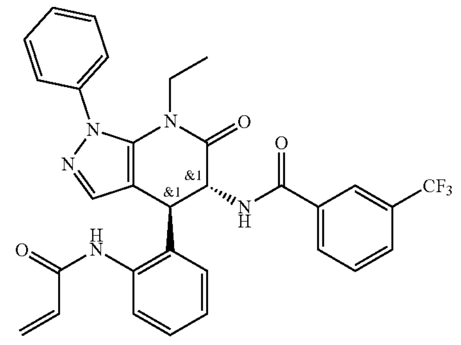 [SMILES: C=CC(=O)Nc1ccccc1[C@H]1c2cnn(-c3ccccc3)c2N(CC)C(=O)[C@@H]1NC(=O)c1cccc(C(F)(F)F)c1]

$^1$H NMR (400 MHz, DMSO-$d_6$) δ=9.76 (s, 1H), 9.03 (d, J=8.4 Hz, 1H), 8.06 (s, 1H), 8.02 (d, J=7.6 Hz, 1H), 7.89 (d, J=7.6 Hz, 1H), 7.70-7.64 (m, 3H), 7.61-7.48 (m, 4H), 7.41 (d, J=1.6 Hz, 1H), 7.29-7.20 (m, 2H), 6.96 (s, 1H), 6.60-6.53 (m, 1H), 6.28-6.23 (m, 1H), 5.78 (d, J=10.8 Hz, 1H), 5.20-5.14 (m, 1H), 4.66 (d, J=12.0 Hz, 1H), 3.75-3.69 (m, 1H), 3.18-3.12 (m, 1H), 0.81 (t, J=6.8 Hz, 3H). LC-MS (Method-D)=574.2 [M+H]$^+$; 97.75% at RT 2.21 min. HPLC (Method-B)=97.57% at RT 8.83 min.

I-189

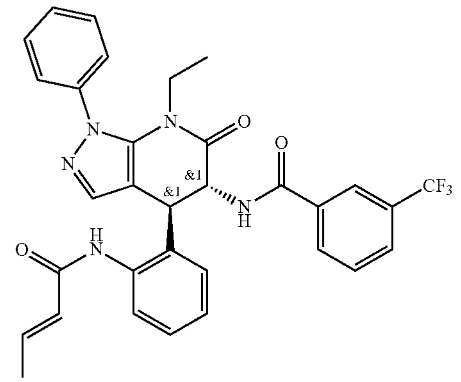 [SMILES: C/C=C/C(=O)Nc1ccccc1[C@H]1c2cnn(-c3ccccc3)c2N(CC)C(=O)[C@@H]1NC(=O)c1cccc(C(F)(F)F)c1]

$^1$H NMR (400 MHz, DMSO-$d_6$) δ=9.59 (s, 1H), 9.06 (d, J=8.0 Hz, 1H), 8.07-8.02 (m, 2H), 7.89 (d, J=7.6 Hz, 1H), 7.71-7.40 (m, 8H), 7.28-7.19 (m, 2H), 6.94 (s, 1H), 6.82-6.73 (m, 1H), 6.22-6.28 (m, 1H), 5.19-5.14 (m, 1H), 4.63 (d, J=12.0 Hz, 1H), 3.74-3.69 (m, 1H), 3.18-3.12 (m, 1H), 1.87 (d, J=6.4 Hz, 3H), 0.81 (t, J=6.8 Hz, 3H). LC-MS (Method-D)=588.2 [M+H]$^+$; 98.54% at RT 2.27 min. HPLC (Method-B)=95.23% at RT 9.06 min.

I-183

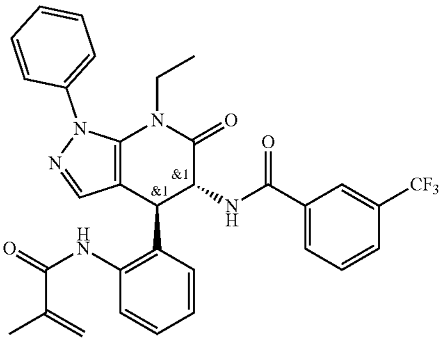 [SMILES: C=C(C)C(=O)Nc1ccccc1[C@H]1c2cnn(-c3ccccc3)c2N(CC)C(=O)[C@@H]1NC(=O)c1cccc(C(F)(F)F)c1]

$^1$H NMR (400 MHz, DMSO-$d_6$) δ=9.57 (s, 1H), 8.94 (d, J=8.4 Hz, 1H), 8.07 (s, 1H), 8.02 (d, J=8.0 Hz, 1H), 7.88 (d, J=7.6 Hz, 1H), 7.69-7.51 (m, 6H), 7.48-7.45 (m, 1H), 7.28-7.25 (m, 3H), 6.90 (s, 1H), 5.87 (s, 1H), 5.52 (s, 1H), 5.20-5.15 (m, 1H), 4.61 (d, J=12.8 Hz, 1H), 3.78-3.72 (m, 1H), 3.11-3.07 (m, 1H), 1.96 (s, 3H), 0.81 (t, J=6.8 Hz, 3H). LC-MS (Method-D)=588.2 [M+H]$^+$; 98.81% at RT 2.28 min. HPLC (Method-B)=99.72% at RT 9.12 min.

I-168

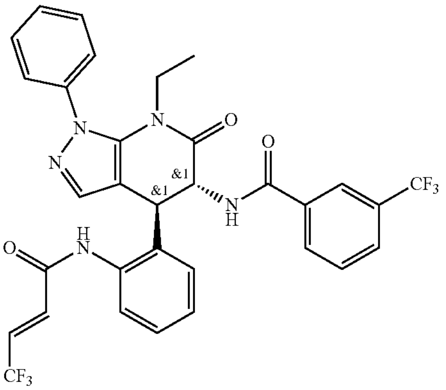 [SMILES: CCN1C(=O)[C@H](NC(=O)c2cccc(C(F)(F)F)c2)[C@@H](c2ccccc2NC(=O)/C=C/C(F)(F)F)c2cnn(-c3ccccc3)c21]

$^1$H NMR (400 MHz, DMSO-$d_6$) δ=10.10 (s, 1H), 9.00 (d, J=8.4 Hz, 1H), 8.03-7.98 (m, 2H), 7.89 (d, J=7.6 Hz, 1H), 7.69-7.65 (m, 3H), 7.61-7.52 (m, 4H), 7.43 (d, J=6.8 Hz, 1H), 7.29-7.21 (m, 2H), 7.14-7.10 (m, 1H), 7.03 (s, 1H), 6.88-6.79 (m, 1H), 5.16-5.11 (m, 1H), 4.79 (d, J=11.6 Hz, 1H), 3.77-3.71 (m, 1H), 3.19-3.14 (m, 1H), 0.82 (t, J=6.8 Hz, 3H). LC-MS (Method-D)=642.2 [M+H]$^+$. 97.64% at RT 2.32 min. HPLC (Method-B)=96.06% at RT 9.41 min.

I-200

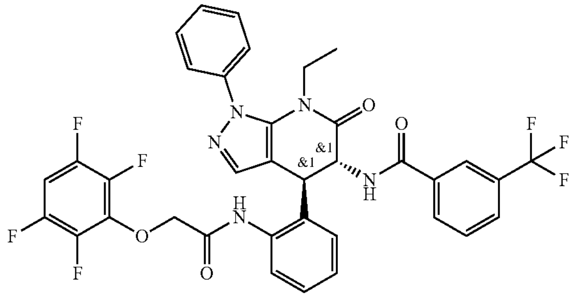 [SMILES: CCN1C(=O)[C@H](NC(=O)c2cccc(C(F)(F)F)c2)[C@@H](c2ccccc2NC(=O)COc2c(F)c(F)cc(F)c2F)c2cnn(-c3ccccc3)c21]

$^1$H NMR (400 MHz, DMSO-$d_6$) δ=9.79 (s, 1H), 8.88 (d, J=8.4 Hz, 1H), 7.98-7.96 (m, 2H), 7.88 (d, J=7.6 Hz, 1H), 7.66-7.51 (m, 7H), 7.43-7.40 (m, 2H), 7.29-7.22 (m, 2H), 6.96 (s, 1H), 5.19 (t, J=11.2 Hz, 1H), 5.10-5.00 (m, 2H), 4.67 (d, J=12.0 Hz, 1H), 3.79-3.73 (m, 1H), 3.17-3.11 (m, 1H), 0.84 (t, J=6.0 Hz, 3H). LC-MS (Method-E)=725.9 [M+H]$^+$; 97.73% at RT 2.39 min. HPLC (Method-B)=97.12% at RT 9.09 min.

I-199

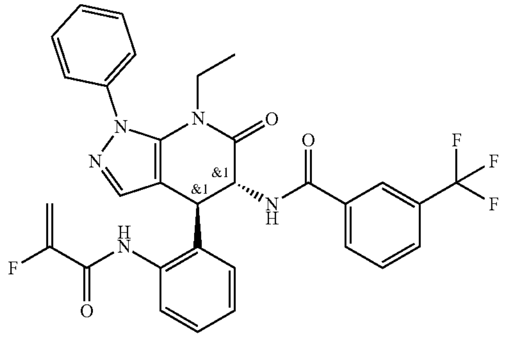 [SMILES: C=C(F)C(=O)Nc1ccccc1[C@H]1c2cnn(-c3ccccc3)c2N(CC)C(=O)[C@@H]1NC(=O)c1cccc(C(F)(F)F)c1]

$^1$H NMR (400 MHz, DMSO-$d_6$) δ=10.05 (s, 1H), 8.83 (d, J=8.4 Hz, 1H), 8.03-7.98 (m, 2H), 7.87 (d, J=7.6 Hz, 1H), 7.68-7.47 (m, 7H), 7.30-7.28 (m, 3H), 6.90 (s, 1H), 5.71-5.58 (m, 1H), 5.41-5.36 (m, 1H), 5.20-5.15 (m, 1H), 4.71 (d, J=12.8 Hz, 1H), 3.83-3.74 (m, 1H), 3.11-3.06 (m, 1H), 0.81 (t, J=6.8 Hz, 3H). LC-MS (Method-C)=592.9 [M+H]$^+$; 99.69% at RT 2.29 min. HPLC (Method-H)=99.63% at RT 6.05 min.

I-198

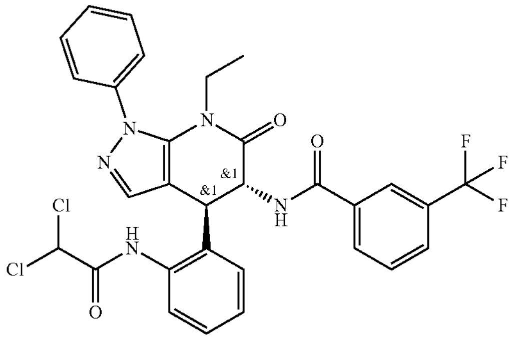 [SMILES: CCN1C(=O)[C@H](NC(=O)c2cccc(C(F)(F)F)c2)[C@@H](c2ccccc2NC(=O)C(Cl)Cl)c2cnn(-c3ccccc3)c21]

$^1$H NMR (400 MHz, DMSO-$d_6$) δ=10.09 (s, 1H), 8.92 (d, J=6.0 Hz, 1H), 7.99-7.97 (m, 2H), 7.89 (d, J=8.0 Hz, 1H), 7.69-7.51 (m, 6H), 7.44 (d, J=7.6 Hz, 2H), 7.32-7.24 (m, 2H), 7.00 (s, 1H), 6.70 (s, 1H), 5.25-5.20 (m, 1H), 4.70 (d, J=12.4 Hz, 1H), 3.84-3.75 (m, 1H), 3.13-3.08 (m, 1H), 0.81 (t, J=6.8 Hz, 3H). LC-MS (Method-C)=631.8 [M+H]$^+$; 99.73% at RT 2.35 min. HPLC (Method-H)=99.66% at RT 6.23 min.

I-195

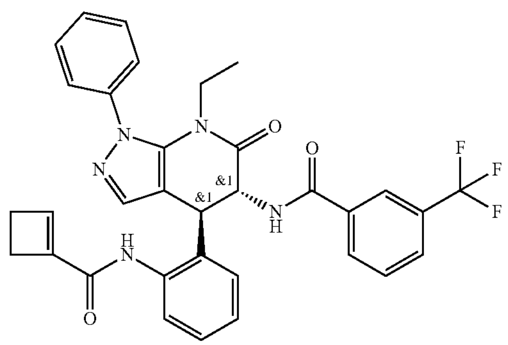 [SMILES: CCN1C(=O)[C@H](NC(=O)c2cccc(C(F)(F)F)c2)[C@@H](c2ccccc2NC(=O)C2=CCC2)c2cnn(-c3ccccc3)c21]

$^1H$ NMR (400 MHz, DMSO-$d_6$) δ=9.58 (s, 1H), 9.01 (d, J=8.0 Hz, 1H), 8.07 (s, 1H), 8.02 (d, J=7.6 Hz, 1H), 7.88 (d, J=8.0 Hz, 1H), 7.69-7.51 (m, 6H), 7.47-7.45 (m, 1H), 7.31-7.24 (m, 3H), 6.91 (s, 1H), 6.75 (br s, 1H), 5.16-5.11 (m, 1H), 4.64 (d, J=12.8 Hz, 1H), 3.77-3.68 (m, 1H), 3.17-3.08 (m, 1H), 2.70 (s, 2H), 2.41 (s, 2H), 0.81 (t, J=7.2 Hz, 3H). LC-MS (Method-D)=600.2 [M+H]$^+$; 99.76% at RT 2.47 min. HPLC (Method-B)=97.99% at RT 8.65 min.

I-174

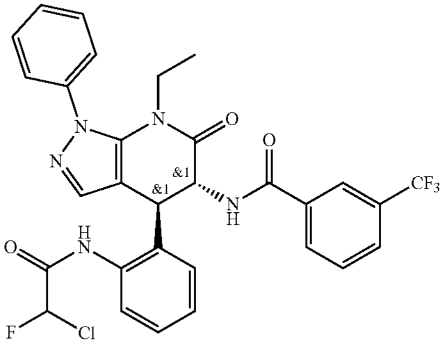 [SMILES: CCN1C(=O)[C@H](NC(=O)c2cccc(C(F)(F)F)c2)[C@@H](c2ccccc2NC(=O)C(F)Cl)c2cnn(-c3ccccc3)c21]

$^1H$ NMR (400 MHz, DMSO-$d_6$) δ=10.22 (m, 1H), 8.88-8.82 (m, 1H), 8.00-7.95 (m, 2H), 7.88 (d, J=7.6 Hz, 1H), 7.70-7.44 (m, 7H), 7.40-7.25 (m, 3H), 6.99-6.85 (m, 2H), 5.25-5.18 (m, 1H), 4.72-4.64 (m, 1H), 3.82-3.78 (m, 1H), 3.14-3.08 (m, 1H), 0.81 (t, J=7.2 Hz, 3H). LC-MS (Method-D)=614.2 [M+H]$^+$; 99.87% at RT 2.19 min. HPLC (Method-B)=99.07% at RT 8.92 min.

I-15

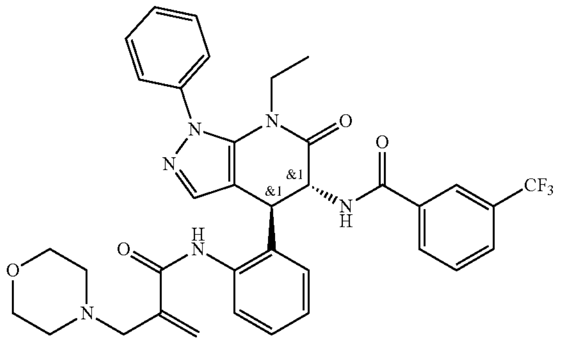 [SMILES: C=C(CN1CCOCC1)C(=O)Nc1ccccc1[C@H]1c2cnn(-c3ccccc3)c2N(CC)C(=O)[C@@H]1NC(=O)c1cccc(C(F)(F)F)c1]

$^1H$ NMR (400 MHz, DMSO-$d_6$) δ=10.5 (s, 1H), 8.93 (d, J=8.0 Hz, 1H), 8.05-7.97 (m, 2H), 7.89 (d, J=7.6 Hz, 1H), 7.70-7.52 (m, 7H), 7.46 (d, J=6.4 Hz, 1H), 7.30-7.20 (m, 2H), 6.91 (s, 1H), 6.11 (d, J=1.6 Hz, 1H), 5.62 (s, 1H), 5.27-5.21 (m, 1H), 4.76 (d, J=12.8 Hz, 1H), 3.78-3.69 (m, 1H), 3.44-3.43 (m, 4H), 3.16-3.07 (m, 1H), 2.42-2.35 (m, 4H), 2.07 (s, 2H), 0.81 (t, J=6.8 Hz, 3H). LC-MS (Method-E)=673.0 [M+H]$^+$; 99.96% at RT 2.33 min. HPLC (Method-B)=99.52% at RT 8.72 min.

I-176

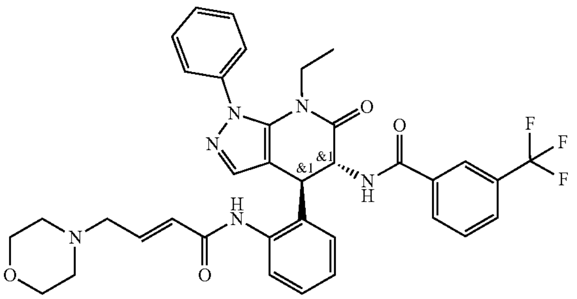 [SMILES: CCN1C(=O)[C@H](NC(=O)c2cccc(C(F)(F)F)c2)[C@@H](c2ccccc2NC(=O)/C=C/CN2CCOCC2)c2cnn(-c3ccccc3)c21]

$^1H$ NMR (400 MHz, $CDCl_3$) δ=8.59-8.57 (m, 1H), 8.28 (s, 1H), 8.11 (d, J=7.2 Hz, 1H), 7.67 (d, J=7.2 Hz, 1H), 7.53-7.46 (m, 7H), 7.38-7.31 (m, 3H), 7.26-7.23 (m, 1H), 7.14-7.07 (m, 1H), 6.89 (s, 1H), 6.26 (s, 1H), 5.33-5.28 (m, 1H), 4.41 (d, J=13.6 Hz, 1H), 3.96-3.90 (m, 1H), 3.76-3.74 (m, 4H), 3.22-3.13 (m, 3H), 2.53 (d, J=4.4 Hz, 4H), 0.89 (d, J=6.8 Hz, 3H). LC-MS (Method-E)=673.1 [M+H]$^+$; 99.67% at RT 2.15 min. HPLC (Method-B)=95.97% at RT 9.66 min.

I-159

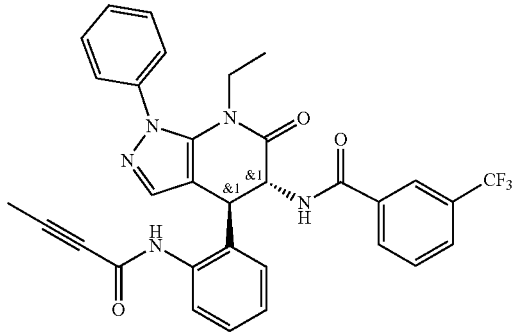 [SMILES: CC#CC(=O)Nc1ccccc1[C@H]1c2cnn(-c3ccccc3)c2N(CC)C(=O)[C@@H]1NC(=O)c1cccc(C(F)(F)F)c1]

$^1H$ NMR (400 MHz, DMSO-$d_6$) δ=10.14 (s, 1H), 8.87 (d, J=8.8 Hz, 1H), 8.00-7.98 (m, 2H), 7.89 (d, J=8.0 Hz, 1H), 7.71-7.51 (m, 6H), 7.45-7.42 (m, 1H), 7.37-7.35 (m, 1H), 7.26-7.23 (m, 2H), 6.90 (s, 1H), 5.27-5.22 (m, 1H), 4.63 (d, J=12.4 Hz, 1H), 3.80-3.74 (m, 1H), 3.14-3.09 (m, 1H), 2.04 (s, 3H), 0.84 (t, J=6.8 Hz, 3H). LC-MS (Method-D)=586.0 [M+H]$^+$; 96.97% at RT 2.25 min. HPLC (Method-B)= 96.45% at RT 8.84 min.

I-72

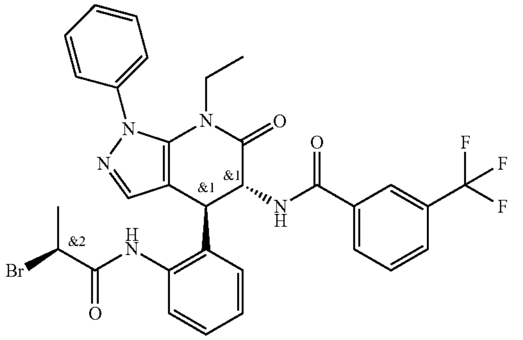 [SMILES: CCN1C(=O)[C@H](NC(=O)c2cccc(C(F)(F)F)c2)[C@@H](c2ccccc2NC(=O)[C@H](C)Br)c2cnn(-c3ccccc3)c21]

$^1$H NMR (400 MHz, DMSO-$d_6$) δ=9.96-9.78 (m, 1H), 8.92-8.83 (m, 1H), 8.05-8.02 (m, 1H), 7.99-7.96 (m, 1H), 7.91-7.87 (m, 1H), 7.72-7.52 (m, 6H), 7.45-7.38 (m, 2H), 7.30-7.20 (m, 2H), 6.99 (d, J=13.6 Hz, 1H), 5.21-5.20 (m, 1H), 4.88-4.81 (m, 1H), 4.59-4.56 (d, J=12.4 Hz, 1H), 3.82-3.76 (m, 1H), 3.14-3.06 (m, 1H), 1.78 (d, J=6.4 Hz, 3H), 0.83-0.79 (m, 3H). LC-MS (Method-D)=656.0 [M+H]$^+$; 99.63% at RT 2.34 min. HPLC (Method-B)=95.34% at RT 8.71 min.

I-194

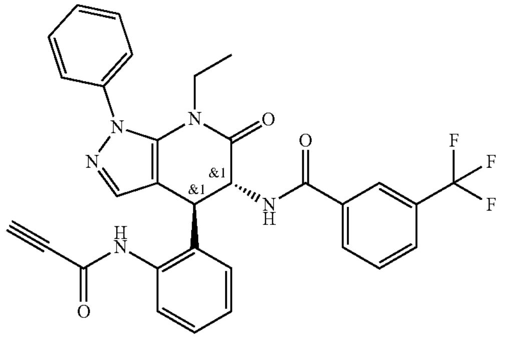 [SMILES: C#CC(=O)Nc1ccccc1[C@H]1c2cnn(-c3ccccc3)c2N(CC)C(=O)[C@@H]1NC(=O)c1cccc(C(F)(F)F)c1]

$^1$H NMR (400 MHz, DMSO-$d_6$) δ=10.35 (s, 1H), 8.88 (d, J=8.8 Hz, 1H), 8.03-7.99 (m, 2H), 7.91 (d, J=8.0 Hz, 1H), 7.81-7.52 (m, 6H), 7.49-7.47 (m, 1H), 7.38-7.31 (m, 1H), 7.29-7.36 (m, 2H), 6.92 (s, 1H), 5.29-5.24 (m, 1H), 4.68 (d, J=12.8 Hz, 1H), 4.42 (s, 1H), 3.84-3.78 (m, 1H), 3.14-3.09 (m, 1H), 0.85 (t, J=6.8 Hz, 3H). LC-MS (Method-D)=572.2 [M+H]$^+$; 97.83% at RT 4.06 min. HPLC (Method-B)=93.06% at RT 8.38 min.

I-188

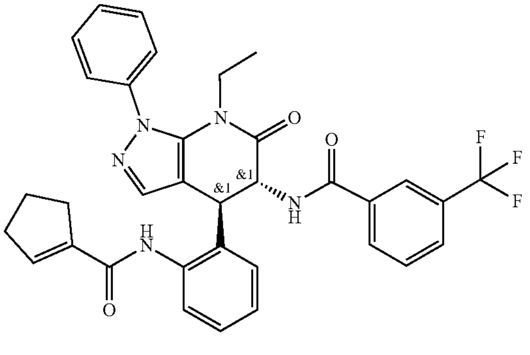 [SMILES: CCN1C(=O)[C@H](NC(=O)c2cccc(C(F)(F)F)c2)[C@@H](c2ccccc2NC(=O)C2=CCCC2)c2cnn(-c3ccccc3)c21]

$^1$H NMR (400 MHz, DMSO-$d_6$) δ=9.45 (s, 1H), 9.00 (d, J=8.0 Hz, 1H), 8.09 (s, 1H), 8.03 (d, J=7.6 Hz, 1H), 7.88 (d, J=8.0 Hz, 1H), 7.70-7.53 (m, 6H), 7.47-7.45 (m, 1H), 7.29-7.25 (m, 3H), 6.90 (s, 1H), 6.69 (s, 1H), 5.18-5.13 (m, 1H), 4.62 (d, J=12.4 Hz, 1H), 3.75-3.70 (m, 1H), 3.17-3.10 (m, 1H), 2.60-2.49 (m, 4H), 1.95-1.88 (m, 2H), 0.81 (t, J=6.8 Hz, 3H). LC-MS (Method-D)=614.2 [M+H]$^+$; 99.68% at RT 2.39 min. HPLC (Method-B)=96.38% at RT 8.93 min.

I-166

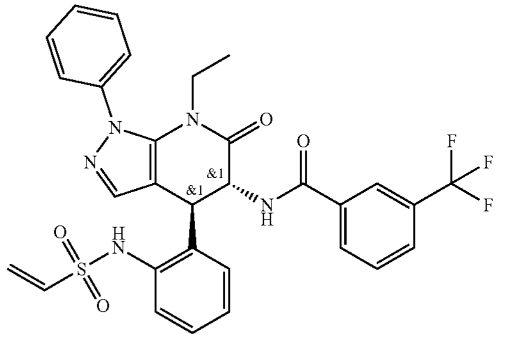 [SMILES: C=CS(=O)(=O)Nc1ccccc1[C@H]1c2cnn(-c3ccccc3)c2N(CC)C(=O)[C@@H]1NC(=O)c1cccc(C(F)(F)F)c1]

$^1$H NMR (400 MHz, DMSO-$d_6$) δ=9.34 (s, 1H), 8.74 (d, J=9.6 Hz, 1H), 8.09-7.90 (m, 3H), 7.73-7.65 (m, 3H), 7.61-7.26 (m, 4H), 7.15 (s, 3H), 6.93-6.82 (m, 2H), 5.97-5.89 (m, 2H), 5.37-5.25 (m, 1H), 4.72 (d, J=13.2 Hz, 1H), 3.82-3.76 (m, 1H), 3.17-3.08 (m, 1H), 0.85 (t, J=7.2 Hz, 3H). LC-MS (Method-A)=610.38 [M+H]$^+$; 96.61% at RT 2.03 min. HPLC (Method-H)=95.36% at RT 6.02 min.

I-175

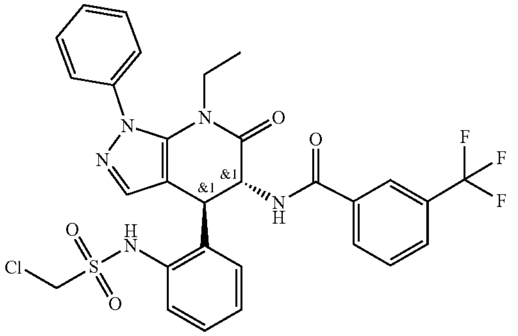 [SMILES: CCN1C(=O)[C@H](NC(=O)c2cccc(C(F)(F)F)c2)[C@@H](c2ccccc2NS(=O)(=O)CCl)c2cnn(-c3ccccc3)c21]

$^1$H NMR (400 MHz, DMSO-$d_6$) δ=9.73 (s, 1H), 7.70 (d, J=9.2 Hz, 1H), 7.95-7.90 (m, 3H), 7.73-7.65 (m, 3H), 7.60-7.50 (m, 4H), 7.38 (d, J=9.2 Hz, 1H), 7.30-7.28 (m, 2H), 7.10 (s, 1H), 5.39-5.34 (m, 1H), 5.09 (d, J=12.4 Hz, 1H), 4.86 (t, J=12.8 Hz, 2H), 3.89-3.34 (m, 1H), 3.07-3.02 (m, 1H), 0.83 (t, J=6.8 Hz, 3H). LC-MS (Method-A)=632.37 [M+H]$^+$; 95.35% at RT 2.05 min. HPLC (Method-H)=96.73% at RT 5.98 min.

I-167

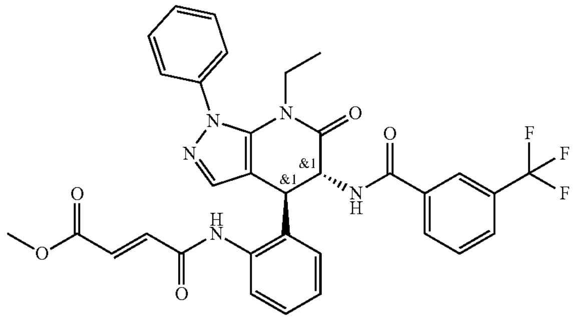 [SMILES: CCN1C(=O)[C@H](NC(=O)c2cccc(C(F)(F)F)c2)[C@@H](c2ccccc2NC(=O)/C=C/C(=O)OC)c2cnn(-c3ccccc3)c21]

$^1H$ NMR (400 MHz, DMSO-$d_6$) δ=10.08 (s, 1H), 8.98 (brs, 1H), 8.04-7.99 (m, 2H), 7.88 (d, J=7.6 Hz, 1H), 7.68-7.65 (m, 3H), 7.61-7.51 (m, 4H), 7.44 (d, J=7.6 Hz, 1H), 7.36 (d, J=15.2 Hz, 1H), 7.28-7.20 (m, 2H), 6.99 (s, 1H), 6.67 (d, J=15.6 Hz, 1H), 5.15-5.12 (m, 1H), 4.78 (d, J=12.0 Hz, 1H), 3.79-3.74 (m, 4H), 3.15-3.08 (m, 1H), 0.82 (t, J=7.2 Hz, 3H).

LC-MS (Method-D)=632.2 $[M+H]^+$; 99.71% at RT 2.31 min.

HPLC (Method-B)=99.26% at RT 8.36 min.

Synthesis of I-177:

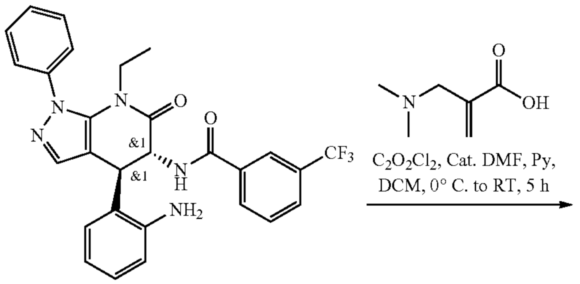

6

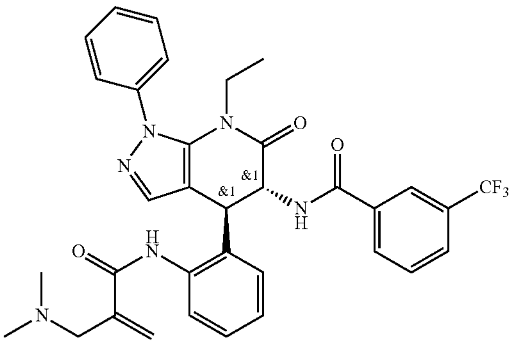

I-177

To a stirred solution of 6 (150 mg, 0.25 mmol) and 2-[(dimethyl amino)methyl]prop-2-enoic acid (55 mg, 0.38 mmol) in DCM (1 mL) was added oxalyl chloride (0.06 mL, 0.76 mmol) followed by 1 drop of DMF at 0° C. Then the reaction mixture was stirred at room temperature for 2 h. To the resulting reaction mixture was added pyridine (0.21 mL, 0.25 mmol). Then the reaction mixture was allowed to stir at room temperature for 3 h. The reaction was monitored by TLC. After completion of the reaction, the reaction mixture was quenched with ice cold water (20 mL) and extracted with DCM (2×20 mL). The combined organic layer was washed with brine solution dried over anhydrous $Na_2SO_4$ and concentrated under reduced pressure. The obtained crude was purified by prep-HPLC to afford (I-177) (12 mg, 7.11% Yield) as white solid.

$^1H$ NMR (400 MHz, DMSO-$d_6$) δ=11.34 (s, 1H), 8.92 (d, J=8.8 Hz, 1H), 8.05-8.02 (m, 2H), 7.96-7.90 (m, 2H), 7.73-7.69 (m, 1H), 7.61-7.53 (m, 5H), 7.38-7.36 (m, 1H), 7.31-7.27 (m, 1H), 7.19-7.14 (m, 1H), 6.83 (s, 1H), 6.12 (d, J=2.0 Hz, 1H), 5.59 (s, 1H), 5.56-5.41 (m, 1H), 4.60 (d, J=13.6 Hz, 1H), 3.86-3.80 (m, 1H), 3.25-3.17 (m, 2H), 3.10-3.05 (m, 1H), 2.04 (s, 6H), 0.83 (t, J=7.2 Hz, 3H). LC-MS (Method-D)=631.2 $[M+H]^+$; 95.67% at RT 2.36 min. HPLC (Method-B)=97.80% at RT 9.50 min.

Synthesis of I-21:

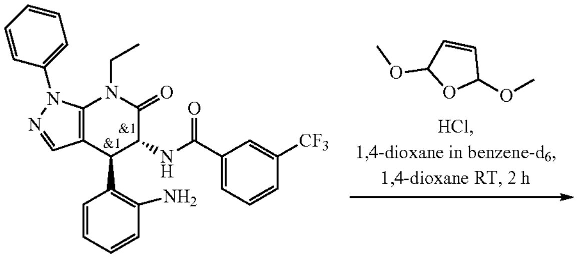

6

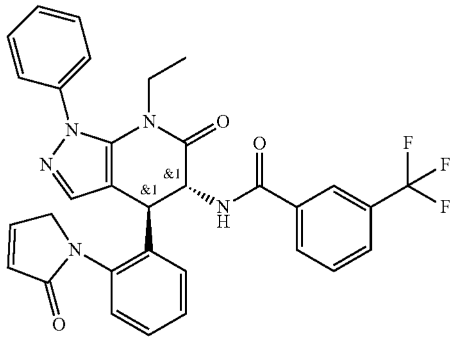

I-21

To a stirred solution of 6 (200 mg, 0.3157 mmol) in 1,4-dioxane (4 mL) was added hydrochloric acid (0.02 g, 0.63 mmol) at room temperature and stirred for 5 min. A clear solution was observed. The reaction mixture was concentrated under reduced pressure to afford solid, which was dissolved in 1,4-dioxane (2 mL) and added 2,5-dimethoxy-2,5-dihydrofuran (0.05 g, 0.38 mmol). Then the resulting reaction mixture was stirred at room temperature for 2 h. Progress of the reaction was monitored by TLC and LCMS, after compilation of reaction, the reaction mixture was extracted with ethyl acetate (40 mL) and washed with brine water (2×20 mL), concentrated organic layer purified by combi flash with 20% ethyl acetate in heptane to afford off white solid I-21 (31.2 mg, 15.6%).

$^1$H NMR (400 MHz, DMSO-$d_6$) δ=8.98 (d, J=8.0 Hz, 1H), 8.06-8.03 (d, 2H), 7.88 (d, J=7.2 Hz, 1H), 7.68-7.53 (m, 8H), 7.38-7.34 (m, 3H), 6.95 (s, 1H), 6.28 (d, J=4.4 Hz, 1H), 5.37-5.31 (m, 1H), 4.61-4.34 (m, 3H), 3.74-3.69 (m, 1H), 3.10-3.07 (m, 1H), 0.78 (m, 3H).

LC-MS (Method-A)=584.37 [M+H]$^+$; 92.50% at RT 2.24 min. HPLC (Method-H)=95.06% at RT 5.94 min.

Synthesis of I-196:

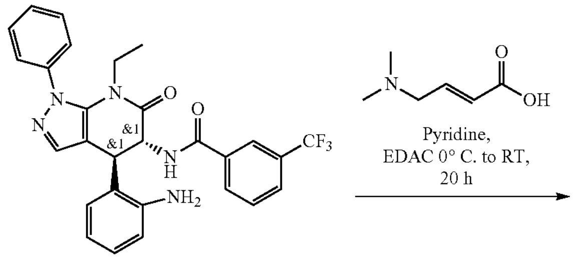

6

-continued

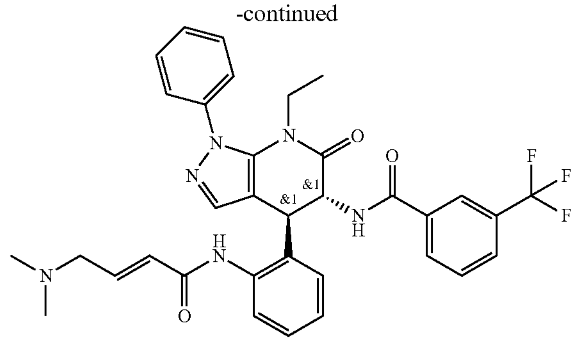

I-196

To a stirred solution of 6 (250.00 mg, 0.41 mmol) in pyridine (1 mL) was added (e)-4-(dimethylamino) but-2-enoic acid (109.1 mg, 0.83 mmol) followed by EDAC (161.9 mg, 0.83 mmol) at 0° C. and stirred at room temperature for 20 h. Reaction was monitored by TLC. After completion of reaction, the reaction mixture was diluted with DCM and washed with water. Organic layer was dried and concentrated to afford crude. Combined crude was purified by prep HPLC to afford pure compound I-196 (40 mg, 14.86%) as off-white solid.

$^1$H NMR (400 MHz, DMSO-$d_6$) δ=9.65 (s, 1H), 9.07 (d, J=8.4 Hz, 1H), 8.07-8.02 (m, 2H), 7.90 (d, J=7.6 Hz, 1H), 7.71-7.65 (m, 3H), 7.60-7.51 (m, 4H), 7.41-7.38 (m, 1H), 7.28-7.18 (m, 2H), 6.97 (s, 1H), 6.77-6.76 (m, 1H), 6.42 (d, J=15.0 Hz, 1H), 5.18-5.13 (m, 1H), 4.65 (d, J=12.0 Hz, 1H), 3.73-3.67 (m, 1H), 3.20-3.15 (m, 1H), 3.04 (d, J=5.6 Hz, 2H), 2.17 (s, 6H), 0.82 (t, J=7.2 Hz, 3H). LC-MS (Method-D)=631.3 [M+H]$^+$; 97.28% at RT 2.24 min. HPLC (Method-B)=99.71% at RT 8.01 min.

Synthesis of I-179:

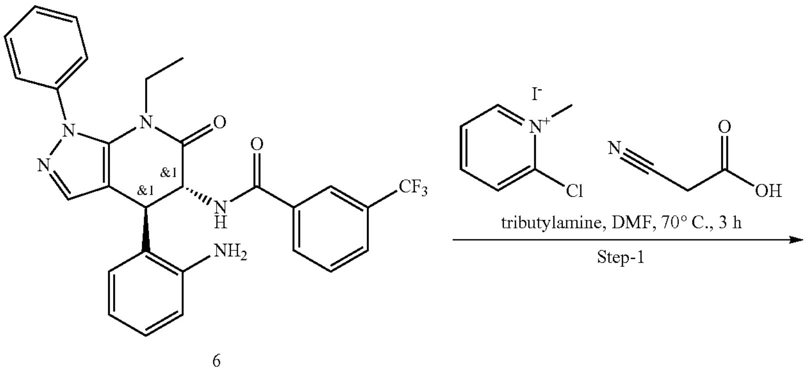

6

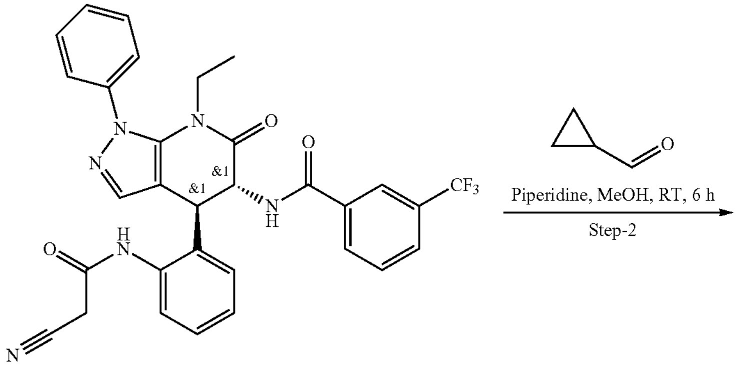

compound A

-continued

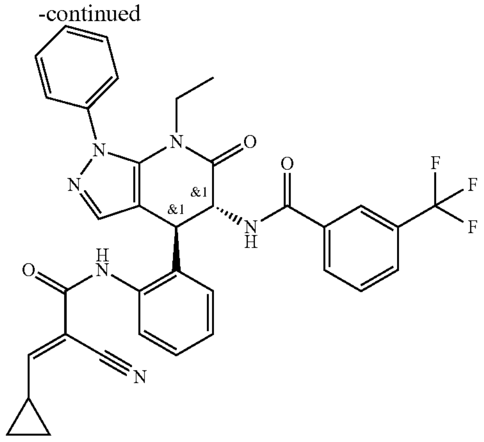

I-179

Step-1: Synthesis of Compound A:

To a stirred solution of 6 (1 g, 1.925 mmol) in DMF (5 mL) was added tributylamine (1.09 g, 5.77 mmol), 2-chloro-1-methylpyridinium iodide (0.76 g, 2.89 mmol) and 2-cyanoacetic acid (0.25 g, 2.89 mmol) at room temperature. The reaction mixture was allowed to stir at 70° C. for 3 h. Progress of the reaction was monitored by TLC and LCMS. The reaction mixture was allowed to stir room temperature. The reaction mixture was diluted with water (100 mL) and extracted with ethyl acetate (2×100 mL). Combined organic layers were dried over anhydrous sodium sulfate and concentrated to afford crude compound. Crude compound was purified by silica gel (230-400) column chromatography using ethyl acetate in heptane, eluted at 45% EA/heptane to afford pure compound A (800 mg, 68.72%) as pale white solid.

$^1$H NMR (400 MHz, DMSO-$d_6$) δ=9.85 (s, 1H), 8.88 (d, J=8.8 Hz, 1H), 8.01-7.95 (d, 2H), 7.91-7.85 (d, J=7.9 Hz, 1H), 7.69-7.65 (m, 3H), 7.61-7.52 (m, 3H), 7.42-7.38 (m, 2H), 7.28-7.20 (m, 1H), 7.00 (s, 1H), 5.20-5.15 (m, 1H), 4.69 (d, J=11.9 Hz, 1H), 4.00 (s, 2H), 3.78-3.73 (m, 1H), 3.18-3.12 (m, 1H), 0.83 (t, J=6.8 Hz, 3H). LC-MS (Method-D)=587.2 $[M+H]^+$; 99.89% at RT 2.13 min. HPLC (Method-B)=97.89% at RT 2.13 min.

Synthesis of I-179:

To a stirred solution of compound A (150 mg, 0.2557 mmol) in methanol (5 mL) was added piperidine (22.22 mg, 0.2557 mmol) and cyclopropanecarbaldehyde (32.26 mg, 0.4603 mmol). The reaction mixture was stirred at room temperature for 6 h. Progress of the reaction mixture was monitored by TLC. Then the reaction mixture was quenched with water and extracted with DCM, combined organic layers were dried over anhydrous sodium sulfate and concentrated to afford crude compound. The above crude compound was purified by silica gel (230-400) column chromatography using Ethyl acetate in heptane. Product eluted in 50% EA in Heptane to afford I-179 as an Off-white solid (35 mg, 5.573%)

$^1$H NMR (400 MHz, DMSO-$d_6$) δ=9.74 (s, 1H), 8.96-8.88 (m, 1H), 8.28-8.27 (m, 2H), 8.05-8.02 (m, 1H), 7.91-7.86 (m, 3H), 7.73-7.66 (m, 2H), 7.62-7.53 (m, 1H), 7.47-7.38 (m, 1H), 7.33-7.28 (m, 3H), 7.09-6.96 (d, 1H), 6.85 (s, 1H), 5.17-5.11 (m, 1H), 4.69 (d, J=12.0 Hz, 1H), 3.79-3.72 (m, 1H), 3.19-3.12 (m, 1H), 2.03-1.96 (m, 1H), 1.32-1.25 (m, 2H), 0.99-0.87 (m, 2H), 0.83 (t, J=7.2 Hz, 3H). LC-MS (Method-D)=639.2$[M+H]^+$; 96.42% at RT 2.77 min. HPLC (Method-A)=95.18% at RT 6.27 min.

Example 3: Synthesis of Compounds I-208, I-182, and I-165

NMR:

$^1$H NMR spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5μ; Mobile Phase: A: 0.05% Formic acid in water: ACN (95:5) B: 0.05% Formic acid in ACN Inj Volume: 2.0 μL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm, 2.5μ) Mobile Phase A: 0.05% TFA in Water Mobile Phase B: 0.05% TFA in Acetonitrile Flow rate: 1.0 mL/min.

HPLC:

Method-A: Column: X Select CSH C18 (150×4.6) mm, 3.5; Mobile phase A: 0.1% FA in Water: CAN (95:05); Mobile phase B: Acetonitrile; Gradient Programme: T/B %: 0.01/5, 1/5, 8/100, 12/100, 14/5, 18/5; Flow rate: 1.2 ml/min.

Method-B: Column: X-Bridge CSH C18 (150×4.6 mm, 3.5 μm); Mobile Phase-A: 5 mM $NH_4HCO_3$; Mobile Phase-B: ACN; Programme: T/B %: 0.01/2, 2/2, 12/90, 16/90; Flow rate: 1.0 mL/min.; Diluent: ACN: WATER (80:20).

Method-C: Column: X SELECT CSH C18 (150×4.6 mm, 3.5); Mobile Phase A; 0.05% TFA IN WATER: ACN (95:05); Mobile Phase B: 0.05% TFA IN WATER: ACN (05:95); Programme: T/B %: 0.01/10, 12/90, 16/90; Flow rate: 1 mL/min.; Diluent: WATER:ACN (80:20).

Method-D: Column: X-Bridge CSH C18 (4.6*150) mm 5μ Mobile Phase: A—0.1% TFA in water B—Acetonitrile Inj Volume; 5.0 μL, Flow Rate: 1.2 mL/minute Gradient program: Time(min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in HEXANE Mobile Phase B: IPA A/B: 60/40 Flow: 1.0 ml/MIN PDA: OJ-H_015.

Synthesis of Compound 6:

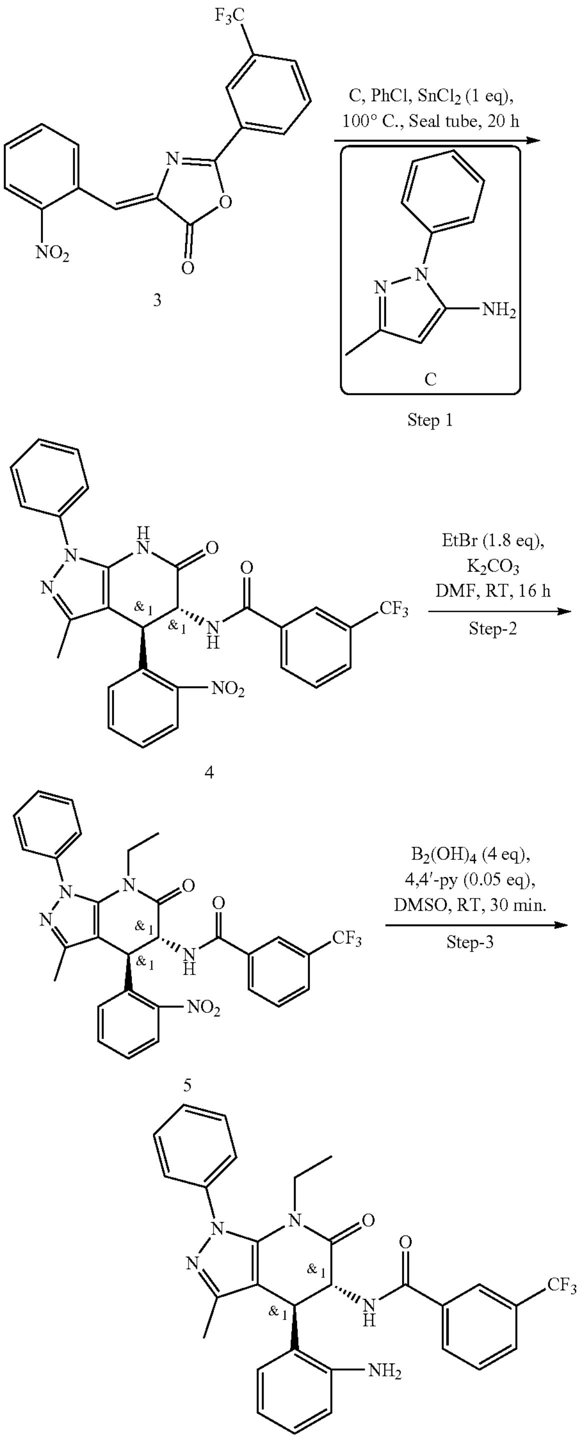

3

4

5

Compound 6

Step-1: Synthesis of rac-N-((4R,5S)-3-methyl-4-(2-nitrophenyl)-6-oxo-1-phenyl-4,5,6,7-tetrahydro-1H-pyrazolo[3,4-b]pyridin-5-yl)-3-(trifluoromethyl) benzamide (4)

To a stirred solution of Int-C(1.8 g, 10.77 mmol) in chlorobenzene (30 mL) in a sealed tube was added compound (3) (3.0 g, 8.28 mmol) followed by $SnCl_2$ (0.15 g, 0.82 mmol) at room temperature. Then the reaction mixture was stirred at 100° C. for 20 h. Reaction progress was monitored by TLC. After completion of the reaction, the reaction mixture was cooled to room temperature, quenched with water (100 mL) and extracted with ethyl acetate (2×100 mL) and then concentrated to afford crude product. Obtained crude material was purified by using column chromatography with 0-30% ethyl acetate in heptane to afford compound (4) (2.0 g, 45%) as off white solid.

$^1$H NMR (400 MHz, DMSO-$d_6$): δ=10.8 (s, 1H), 8.93 (d, J=8.8 Hz, 1H), 8.04-7.95 (m, 2H), 7.89 (d, J=7.2 Hz, 1H), 7.84-7.80 (m, 2H), 7.72-7.62 (m, 3H), 7.57-7.48 (m, 4H), 7.40-7.37 (m, 1H), 5.21-5.18 (m, 1H), 4.85 (d, J=12.8 Hz, 1H), 1.47 (s, 3H).

LC-MS (Method-A)=536.2 $[M+H]^+$; 74.15% at RT 2.06 min.

Step-2: Synthesis of rac-N-((4R,5S)-7-ethyl-3-methyl-4-(2-nitrophenyl)-6-oxo-1-phenyl-4,5,6,7-tetrahydro-1H-pyrazolo[3,4-b]pyridin-5-yl)-3-(trifluoromethyl)benzamide (5)

To a stirred solution of compound (4) (2 g, 3.70 mmol) in DMF (40 mL) was added potassium carbonate (0.92 g, 6.70 mmol) and bromoethane (0.5 mL, 6.70 mmol) at 0° C. The reaction mixture was stirred at room temperature for 16 h. Reaction progress was monitored by TLC. After completion of reaction, the reaction mixture was diluted with water (200 mL) and extracted with ethyl acetate (2×200 mL). Combined organic layer was dried over anhydrous sodium sulphate and concentrated under reduced pressure to afford crude material. Obtained crude material was purified using column chromatography with 0-40% ethyl acetate in heptane to afford compound (5) (1.03 g, 49%) as an off-white solid.

$^1$H NMR (400 MHz, DMSO-$d_6$): δ=8.93 (d, J=8.8 Hz, 1H), 7.96-7.93 (m, 2H), 7.90-7.85 (m, 2H), 7.80 (d, J=8.0 Hz, 1H), 7.73-7.68 (m, 2H), 7.66-7.62 (m, 2H), 7.58-7.54 (m, 2H), 7.52-7.49 (m, 2H), 5.52-5.56 (m, 1H), 4.81 (d, J=13.2 Hz, 1H), 3.85-3.79 (m, 1H), 3.04-2.99 (m, 1H), 1.43 (s, 3H), 0.87-0.80 (m, 3H). LC-MS (Method-B)=564.7 $[M+H]^+$; 95.99% at RT 2.06 min.

Step-3: Synthesis of rac-N-((4R,5S)-4-(2-aminophenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (5)

To a stirred solution of compound (5) (70 mg, 0.1242 mmol), dissolved in DMF (1 mL) tetrahydroxydiboron (0.03 g, 0.37 mmol) was added at 0° C., then added 2,2'-bipyridine (0.0009, 0.006 mmol) and stirred for 30 min at room temperature. The reaction progress was monitored by TLC. After completion of the reaction, the reaction mixture was diluted with water (20 mL) and extracted with ethyl acetate (2×20 mL). Combined organic layer was washed with excess of ice-cold water and dried under sodium sulphate and concentrated under vacuum to afford crude compound. Obtained crude was purified by flash column chromatography using 100-200 mesh silica gel compound was eluted with 50% ethyl acetate in heptane and concentrated under vacuum to afford a pure compound 6 (20 mg, 28.5%) as an off-white solid.

$^1$H NMR (400 MHz, —CHLOROFORM-d): δ=7.94 (s, 1H), 7.86 (d, J=7.8 Hz, 1H), 7.73 (d, J=8.0 Hz, 1H), 7.55-7.46 (m, 6H), 7.12-7.04 (m, 2H), 6.77-6.72 (m, 2H), 6.61 (d, J=8.4 Hz, 1H), 5.36 (t, J=10.0 Hz, 1H), 4.40 (d, J=10.4 Hz, 1H), 4.08 (s, 2H), 3.76-3.71 (m, 1H), 3.43-3.38 (m, 1H), 1.86 (s, 3H), 0.93 (t, J=7.2 Hz, 3H). LC-MS (Method-B)=534.2 $[M+H]^+$; 94.45% at RT 2.19 min.

Synthesis of Analogues:

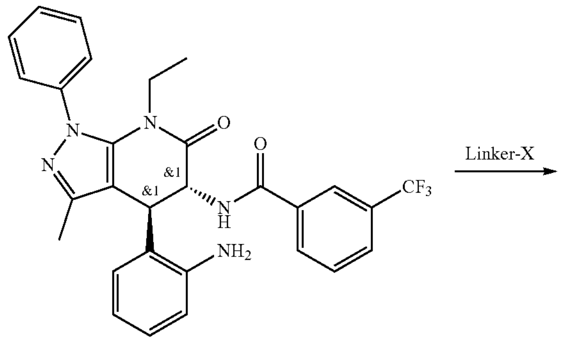

Compound 6

-continued

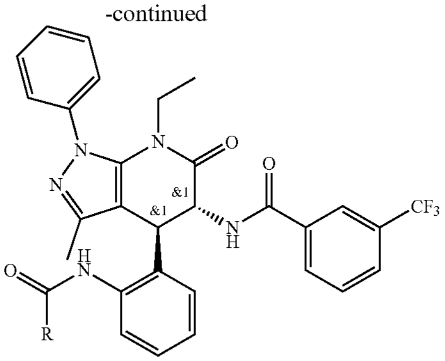

B. $K_2CO_3$, ACN, 70° C., 24 h

Method-B Procedure:

To a stirred solution of compound 6 (100.00 mg, 0.17 mmol) in ACN (2 mL) was added $K_2CO_3$ (49 mg, 0.35 mmol) at 0° C. Then to the reaction mixture was added Linker-X(X=B, H, I) (X mg). The reaction mixture was stirred at 70° C. for 24 h. Reaction was monitored by TLC. After completion of reaction, to the reaction mixture was added water and extracted with DCM. Combined organic layer was dried over anhydrous sodium sulphate and concentrated under reduced pressure to afford crude material. The obtained crude was purified by column chromatography using silica gel, eluted with 0-50% EA/heptane to afford compound. The following table shows the conditions to obtain the desired compounds.

| Sr. No | Compound Number | Linker | Structure | Method | Compound 6 Qty (mg) | Linker Qty (mg) | Qty (mg) & nature of compound | Yield (%) |
|---|---|---|---|---|---|---|---|---|
| 1. | I-208 | B | 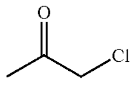 | B | 100 | 70 | 34 (white solid) | 29.8 |
| 2. | I-182 | H | 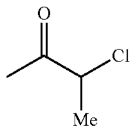 | B | 100 | 90 | 48 (white solid) | 41.3 |
| 3. | I-165 | I | 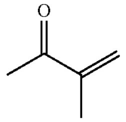 | B | 100 | 30 | 17 (white solid) | 15.71 |

I-208:

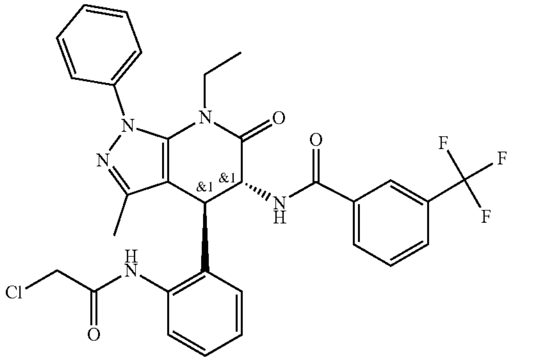 [SMILES: CCN1C(=O)[C@H](NC(=O)c2cccc(C(F)(F)F)c2)[C@@H](c2ccccc2NC(=O)CCl)c2c(C)nn(-c3ccccc3)c21]

$^1$H NMR (400 MHz, DMSO-$d_6$) δ=9.91 (s, 1H), 8.85 (d, J=8.4 Hz, 1H), 8.01-7.99 (m, 2H), 7.89 (d, J=8.0 Hz, 1H), 7.70-7.66 (m, 1H), 7.63-7.47 (m, 5H), 7.42-7.37 (m, 2H), 7.28-7.21 (m, 2H), 5.24-5.19 (m, 1H), 4.65 (d, J=11.6 Hz, 1H), 4.42-4.34 (m, 2H), 3.74-3.67 (m, 1H), 3.17-3.11 (m, 1H), 1.45 (s, 3H), 0.81 (t, J=7.2 Hz, 3H). LC-MS (Method-B)=610.2 [M+H]$^+$; 99.54% at RT 2.30 min. HPLC (Method-B): 98.29% at RT 10.09 min.

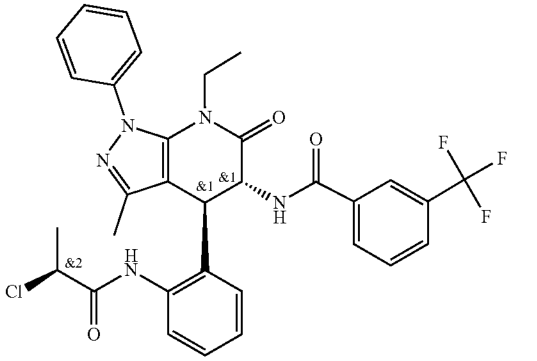 [SMILES: CCN1C(=O)[C@H](NC(=O)c2cccc(C(F)(F)F)c2)[C@@H](c2ccccc2NC(=O)[C@H](C)Cl)c2c(C)nn(-c3ccccc3)c21]

$^1$H NMR (400 MHz, DMSO-$d_6$) δ=9.98 (s, 1H), 8.89-8.83 (m, 1H), 8.02-7.96 (m, 2H), 7.90 (d, J=7.2 Hz, 1H), 7.71-7.62 (m, 1H), 7.61-7.54 (m, 4H), 7.51-7.47 (m, 1H), 7.44-7.38 (m, 2H), 7.31-7.20 (m, 2H), 5.24-5.19 (m, 1H), 4.85-4.80 (m, 1H), 4.55 (d, J=11.6 Hz, 1H), 3.75-3.70 (m, 1H), 3.16-3.09 (m, 1H), 1.67-1.62 (m, 3H), 1.46-1.45 (m, 3H), 0.83-0.78 (m, 3H). LC-MS (Method-B)=624.2 [M+H]$^+$; 97.90% at RT 2.35 min. HPLC (Method-B): 97.17% at RT 9.40 min.

I-165:

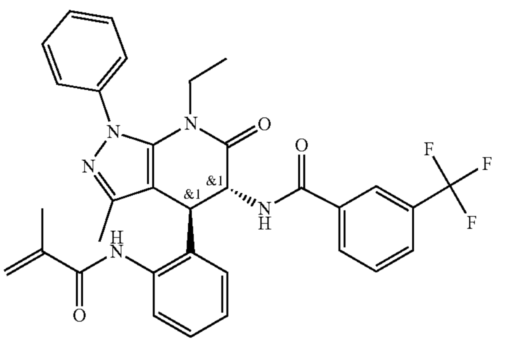 [SMILES: C=C(C)C(=O)Nc1ccccc1[C@H]1c2c(C)nn(-c3ccccc3)c2N(CC)C(=O)[C@@H]1NC(=O)c1cccc(C(F)(F)F)c1]

$^1$H NMR (400 MHz, DMSO-$d_6$) δ=9.68 (s, 1H), 8.92 (d, J=8.0 Hz, 1H), 8.07-8.01 (m, 1H), 7.89 (d, J=8.0 Hz, 2H), 7.70-7.66 (m, 1H), 7.63-7.54 (m, 5H), 7.51-7.46 (m, 2H), 7.30-7.25 (m, 2H), 5.90 (s, 1H), 5.55 (s, 1H), 5.25-5.19 (m, 1H), 4.56 (d, J=12.4 Hz, 1H), 3.76-3.69 (m, 1H), 3.17-3.06 (m, 1H), 1.98 (s, 3H), 1.43-1.37 (m, 3H), 0.81 (t, J=7.2 Hz, 3H). LC-MS (Method-A)=602.81 [M+H]$^+$; 99.62% at RT 2.47 min. HPLC (Method-B): 99.34% at RT 9.34 min.

Example 4: Synthesis of Compounds I-191 and I-181

NMR:

$^1$H NMR spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LCMS:

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

HPLC:

Method-B: Column: X-Bridge CSH C18 (150×4.6 mm, 3.5 μm); Mobile Phase-A: 5 mM $NH_4HCO_3$; Mobile Phase-B: ACN; Programme: T/B %: 0.01/2, 2/2, 12/90, 16/90; Flow rate: 1.0 mL/min.; Diluent: ACN: WATER (80:20).

Scaffold Analogs

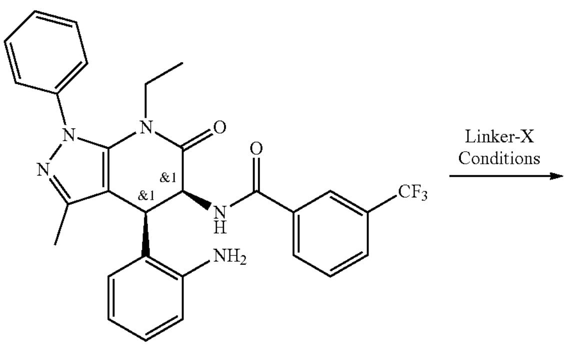

Compound 1

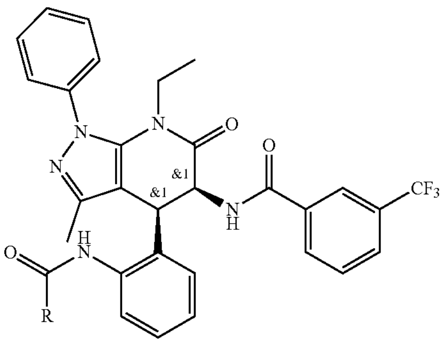

Method-A:. $K_2CO_3$, ACN, RT, 1 h and 70° C., 24 h

Method-A Procedure:

To a stirred solution of compound 1 (110.00 mg, 0.20 mmol) in ACN (2 mL) was added $K_2CO_3$ (57 mg, 0.41 mmol) at 0° C., followed by Linker-X (B&H) (1.03 mmol)

and stirred at room temperature for 1 h. Then the reaction mixture was stirred at 70° C. for 24 h. Reaction was monitored by TLC. After completion of reaction, to the reaction mixture was quenched with water (20 mL) and extracted with DCM (2×20 mL). Combined organic layer was dried over anhydrous sodium sulphate and concentrated under reduced pressure to afford crude material. The obtained crude product was purified by column chromatography using silica gel, eluted with 0-60% EA/heptane to afford compound. The following table shows the conditions to obtain the desired compounds.

| Sr No. | Compound Number | Linker | Structure (R) | Method | Compound 1 Qty (mg) | Linker Qty (mg) | Qt (mg) & Nature of compound | Yield (%) |
|---|---|---|---|---|---|---|---|---|
| 1. | I-191 | B | 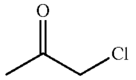 | A | 110 | 107 | 13 (white solid) | 10.5 |
| 2. | 1-181 | H | 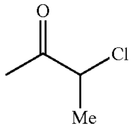 | A | 110 | 0.1 mL | 21 (white solid) | 17.0 |

I-191

$^1$H NMR (400 MHz, DMSO-$d_6$) δ=9.57 (s, 1H), 8.25 (d, J=6.8 Hz, 1H), 8.12 (s, 1H), 8.08 (d, J=7.6 Hz, 1H), 7.89 (d, J=8.0 Hz, 1H), 7.69-7.64 (m, 3H), 7.57 (t, J=7.4 Hz, 2H), 7.52-7.48 (m, 1H), 7.37 (d, J=8.0 Hz, 1H), 7.27-7.23 (m, 1H), 7.14 (t, J=8.0 Hz, 1H), 6.86-6.84 (m, 1H), 5.42 (t, J=7.2 Hz, 1H), 4.95 (d, J=7.2 Hz, 1H), 4.21 (d, J=13.6 Hz, 1H), 4.00 (d, J=13.6 Hz, 1H), 3.89-3.84 (m, 1H), 3.13-3.08 (m, 1H), 2.07 (s, 3H), 0.95 (t, J=6.8 Hz, 3H). LC-MS (Method-B)=610.2 $[M+H]^+$; 96.80% at RT 2.31 min. HPLC (Method-B): 95.10% at RT 9.43 min.

I-181

$^1$H NMR (400 MHz, DMSO-$d_6$) δ=9.58 (s, 1H), 8.28-8.02 (m, 3H), 7.91-7.87 (m, 1H), 7.71-7.64 (m, 3H), 7.58-7.41 (m, 4H), 7.29-7.25 (m, 1H), 7.19-7.13 (m, 1H), 6.89-6.86 (m, 1H), 5.50-5.40 (m, 1H), 4.93-4.79 (m, 1H), 4.62-4.56 (m, 1H), 3.88-3.83 (m, 1H), 3.13-3.09 (m, 1H), 2.08 (d, J=7.6 Hz, 3H), 1.24-1.21 (m, 3H), 0.95 (t, J=7.2 Hz, 3H).

LC-MS (Method-B)=624.36 $[M+H]^+$; 98.50% at RT 2.18 min. HPLC (Method-B): 99.89% at RT 9.55 min.

Example 5: Synthesis of Compounds I-110 and I-52

NMR:

$^1$H NMR spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5μ; Mobile Phase: A: 0.05% Formic acid in water: ACN (95:5) B: 0.05% Formic acid in ACN Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

Method-C: Column: X-Select CSH C18 (50 mm*3.0 mm, 2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water: ACN (95:05); Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: ACN; Programme/B %: 0.01/2, 2/2, 12/90, 16/90; Flow: 1.0 mL/min.; Diluent: ACN: WATER (80:20).

Method-C: Column: X SELECT CSH C18 (150×4.6 mm, 3.5); Mobile Phase A; 0.05% TFA IN WATER: ACN (95:05); Mobile Phase B: 0.05% TFA IN WATER: ACN(05:95); Programme: T/B %: 0.01/10, 12/90, 16/90; Flow: 1 mL/min.; Diluent: WATER:ACN (80:20).

Method-D: Column: X-Bridge CSH C18 (4.6*150) mm 5μ Mobile Phase: A—0.1% TFA in water B—Acetonitrile Inj Volume; 5.0 μL, Flow Rate: 1.2. mL/minute Gradient program: Time(min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in HEXANE Mobile Phase B: IPA A/B: 60/40 Flow: 1.0 ml/MIN PDA: OJ-H_015.

Method-F: Column Name: CHIRALPAK-IK (250×4.6 mm, 5 μm) Mobile phase-A: n-Hexane Mobile phase-B: ETOH/MEOH (50/50) Flow rate: 1.0 mL/min % A/B: 50/50.

Method-G: Column: X-Select CHS C18 (4.6*150) mm 5u Mobile Phase: A—5 mM Ammonium acetate B—Acetonitrile Inj Volume; 5.0 μL, Flow Rate: 1.0 mL/minute.

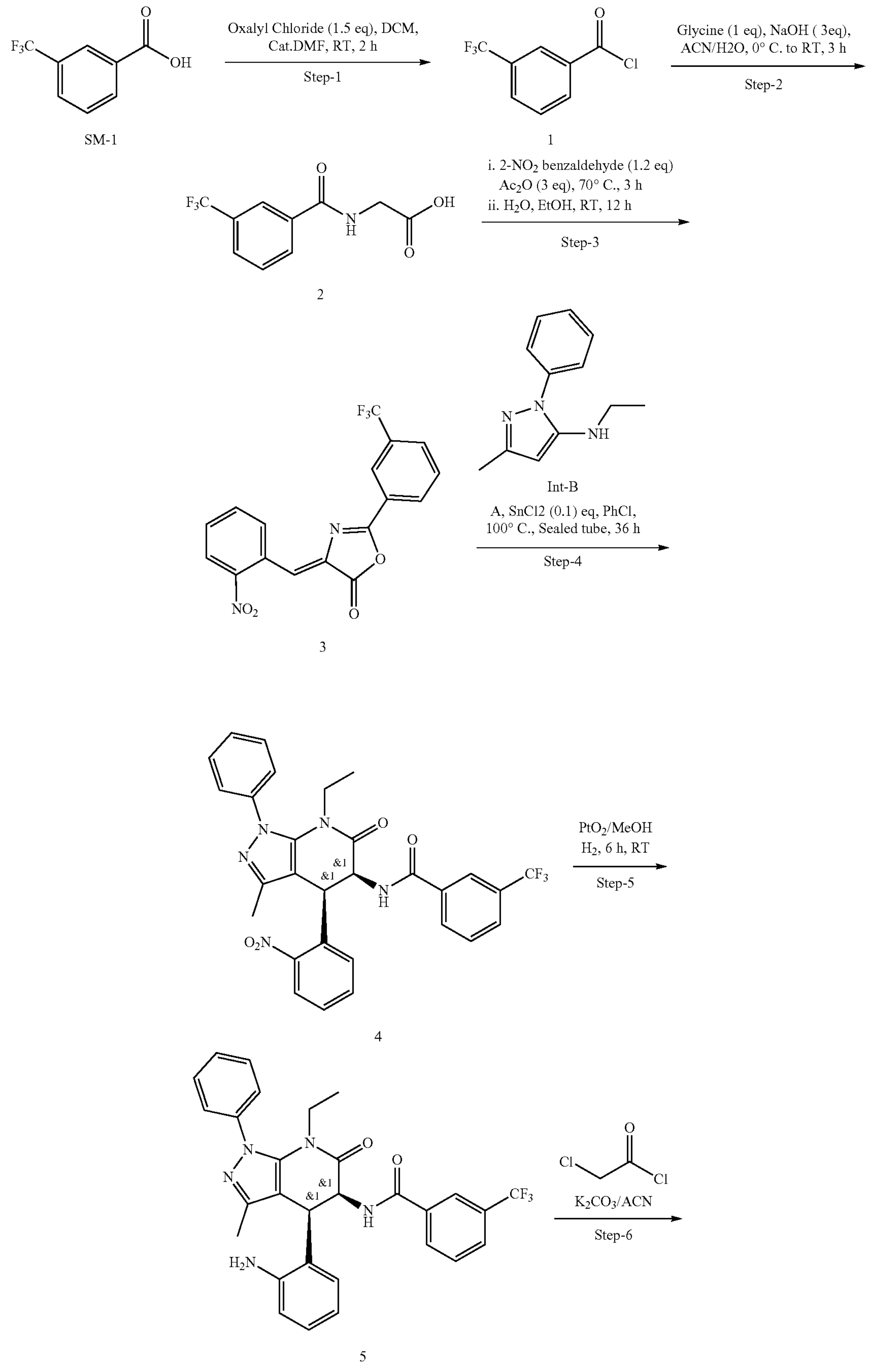
Oxalyl Chloride (1.5 eq), DCM,
Cat.DMF, RT, 2 h
Step-1
SM-1
1
Glycine (1 eq), NaOH ( 3eq),
ACN/H2O, 0° C. to RT, 3 h
Step-2
2
i. 2-$NO_2$ benzaldehyde (1.2 eq)
$Ac_2O$ (3 eq), 70° C., 3 h
ii. $H_2O$, EtOH, RT, 12 h
Step-3
Int-B
A, SnCl2 (0.1) eq, PhCl,
100° C., Sealed tube, 36 h
Step-4
3
$PtO_2$/MeOH
$H_2$, 6 h, RT
Step-5
4
$K_2CO_3$/ACN
Step-6
5

-continued

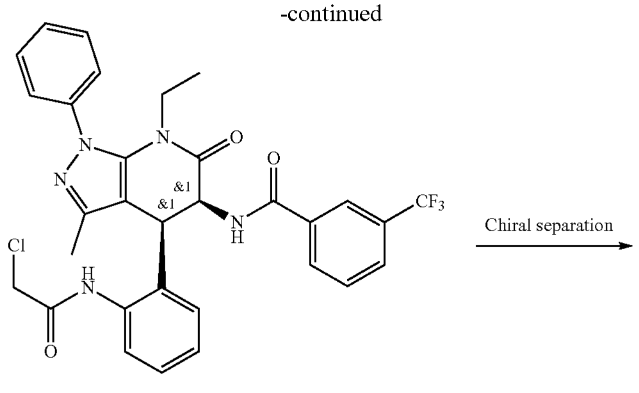

6 (racemic)

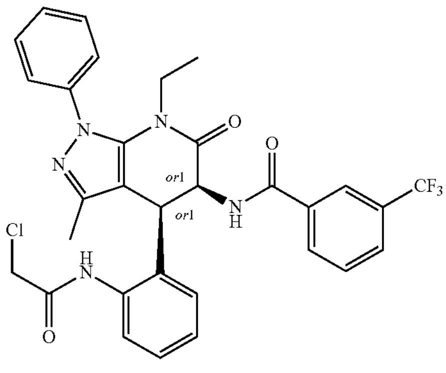

I-110

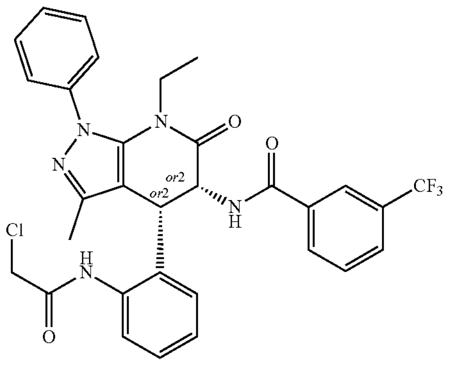

I-52

Step-1: Synthesis of 3-(trifluoromethyl)benzoyl chloride

To a stirred solution of 3-(trifluoromethyl)benzoic acid (SM-1) (100 g, 525.98 mmol) in DCM (900 mL) were added cat. amount of DMF (2 mL, 25.8 mmol) followed by oxalyl chloride (101.15 g, 788.98 mmol) at 0° C. The resulting reaction mixture was stirred at 25° C. for 3 h. The reaction was monitored by TLC; after completion of the reaction, the reaction mixture was concentrated under reduced pressure to afford compound-1 (100 g, 92%). The crude was directly used in the next step without further purification and analysis.

Step-2: Synthesis of 2-[[3-(trifluoromethyl)benzoyl]amino]acetic acid

To a stirred solution of glycine (36.35 g, 479.4 mmol) in ACN (800 mL) as added sodium hydroxide (48.42 g, 1198.7 mmol) dissolved in water (50 ml) at 0° C. and stirred for 5 min. To the resulting reaction mixture was slowly added compound-Int-1 (100 g, 479.48 mmol) dissolved in ACN. The resulting reaction mixture was stirred at 25° C. for 16 h. The reaction was monitored by TLC; after completion of the reaction, the reaction mixture was adjusted to pH=3 by using HCl and extracted by EtOAc. The combined organic layer was concentrated under reduced pressure to get crude compound. The crude compound was washed with heptane to afford compound-2 (99 g, 81% Yield) as pale yellow solid. $^1$H NMR (400 MHz, DMSO-$d_6$) δ=12.64 (br s, 1H), 9.13 (br s, 1H), 8.27-8.11 (m, 2H), 7.94 (d, J=7.3 Hz, 1H), 7.75 (t, J=7.8 Hz, 1H), 3.96 (d, J=5.9 Hz, 2H). LC-MS (Method-B)=247.8 $[M+H]^+$ 97.60% RT: 1.52 min.

Step-3: Synthesis of 4-[(2-nitrophenyl)methylene]-2-[3-(trifluoromethyl)phenyl]oxazol-5-one (3)

The solution of 2 (4.6 g, 18.6 mmol) and 2-nitro benzaldehyde (2.90 g, 18.6 mmol) in acetic anhydride (5.82 g, 55.8 mmol) was stirred at 70° C. for 2 h. Progress of the reaction was monitored by TLC. After completion of the reaction, the reaction mixture was cooled to room temperature, then 1:1 mixture of EtOH (40 mL)/water (40 mL) was added and stirred for 16 h. The obtained solid was filtered off and dried to get the crude. The crude was washed with n-heptane and n-pentane to get 3 (2.6 g, 37%) as off white solid. $^1$HNMR (400 MHz, $CDCl_3$) (δ=8.59-8.57 (m, 1H), 8.42-8.39 (m, 1H), 8.34-8.32 (m, 1H), 8.10-8.08 (m, 1H), 7.91-7.89 (m, 1H), 7.81-7.74 (m, 2H), 7.72-7.67 (m, 1H), 7.65-7.61 (m, 1H). LC-MS (Method-B)=363.2 $[M+H]^+$; 68.2% at RT 1.93 min.

Step-4: Synthesis of N-[4-(2-nitrophenyl)-6-oxo-1-phenyl-5,7-dihydro-4H-pyrazolo[3,4-b]pyridin-5-yl]-3-(trifluoromethyl)benzamide (4)

To a stirred solution of 3 (2.5 g, 6.49 mmol) in chlorobenzene (60 mL) were added B (1.81 g, 8.43 mmol) and $SnCl_2$ (0.1 g, 0.57 mmol) at room temperature and stirred at 100° C. for 36 h. Progress of the reaction was monitored by TLC. After completion of the reaction, the reaction mixture was cooled to room temperature and concentrated to get the crude. The crude was purified by column chromatography by using silica gel, eluted with 0-45% EtOAc/heptane to get 4 (0.8 g, 21%) as yellow solid. LC-MS (Method-B)=522.0 $[M+H]^+$; 86% at RT 2.20 min. $^1$HNMR (400 MHz, DMSO) (5=8.74 (d, J=7.2 Hz, 1H), 8.207-8.165 (m, 2H), 8.113-

8.077 (m, 2H), 7.90 (d, J=7.2 Hz, 2H), 7.81 (d, J=8.0 Hz, 1H), 7.687-7.495 (m, 10H), 7.098 (d, J=7.6 Hz, 1H), 5.62-5.58 (m, 1H), 5.14 (d, J=7.6 Hz, 1H), 3.86-3.81 (m, 1H), 3.07-3.02 (m, 1H), 2.0 (S, 3H), 0.97-0.94 (m, 3H).

Step-5: Synthesis of rac-N-((4R,5R)-4-(2-aminophenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (5)

To a stirred solution of 4 (800 mg. 1.363 mmol) in MeOH (24 mL) was added $PtO_2$ (0.160 g, 0.05 mmol) at RT under $H_2$ atm for 6 h. Progress of the reaction was monitored by TLC. After completion of the reaction, the reaction mixture was filtered through celite bed, then it was washed with methanol (50 mL) and concentrated to get crude. The crude was purified by column chromatography by using silica gel, eluted with 0-52% of heptane/ethyl acetate to get 5 (0.41 g, 41%) as off white solid. LC-MS (Method-B)=533 $[M+H]^+$; 90.9% at RT 2.50 min. $^1$HNMR (400 MHz, DMSO-$d_6$) (δ=8.34 (d, J=6.8 Hz, 1H), 8.08 (d, J=9.2 Hz, 2H), 7.92 (d, J=7.6 Hz, 1H), 7.73-7.50 (m, 6H), 6.97 (m, 1H), 6.71 (d, J=8.4 Hz, 1H), 6.57-6.46 (m, 2H), 5.39-5.36 (m, 1H), 5.06 (br S, 2H), 4.84 (d, J=6.8 Hz, 1H), 3.86-3.81 (m, 1H), 3.07-3.02 (m, 1H), 2.02 (S, 3H), 0.93-0.86 (m, 3H). LC-MS (Method-B)=550.0 $[M+H]^+$; 92.46% at RT 2.383 min.

Step-6: N-((4S,5R)-4-(2-(2-chloroacetamido)phenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (I-110) and N-((4R,5S)-4-(2-(2-chloroacetamido)phenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (I-52)

To a stirred solution of 5 (0.41 g, 0.67 mmol) in ACN (3 mL) were added $K_2CO_3$ (0.190 g, 1.35 mmol) and 2-chloroacetyl chloride (0.233 g, 2.0 mmol) at 0° C. and stirred at 70° C. for 36 h. Progress of the reaction was monitored by TLC. After completion of the reaction, the reaction mixture was cooled to room temperature, water was added and extracted with EtOAc. Combined organic layer was dried and concentrated to get crude. Crude was purified by column chromatography by using silica gel, eluted with 0-56% of EtOAc/heptane to get pure cis racemate compound as white solid. The cis racemate was further purified into two single enantiomers I-110 and I-52 (0.055 g, 12.8%) as white solid by chiral chromatography, using mobile phase A: n-hexane and mobile phase B: MeOH: EtOH (50:50).

I-110

$^1$HNMR (400 MHz, DMSO-$d_6$) δ=9.58 (s, 1H), 8.23-8.21 (m, 1H), 8.12 (s, 1H), 8.08 (d, J=8.0 Hz, 1H), 7.90 (d, J=7.6 Hz, 1H), 7.70-7.48 (m, 6H), 7.38-7.36 (m, 1H), 7.28-7.12 (m, 3H), 6.90-6.80 (m, 1H), 5.42 (t, J=7.2 Hz, 1H), 4.95 (d, J=7.6 Hz, 1H), 4.21 (d, J=13.6 Hz, 1H), 4.11-4.07 (m, 1H), 3.91-3.82 (m, 1H), 3.17-3.09 (m, 1H), 2.10 (s, 3H), 0.95 (t, J=7.2 Hz, 3H). LC-MS (Method-B)=610.3 $[M+H]^+$; 99.807% at RT 2.408 min. HPLC (Method-B)=95.162% at RT 8.842 min.

I-52

$^1$HNMR (400 MHz, DMSO-$d_6$) δ=9.58 (s, 1H), 8.24-8.23 (m, 1H), 8.13 (s, 1H), 8.08 (d, J=8.0 Hz, 1H), 7.90 (d, J=8.0 Hz, 1H), 7.70-7.49 (m, 6H), 7.38-7.37 (m, 1H), 7.27-7.12 (m, 2H), 6.86 (d, J=7.2 Hz, 1H), 5.42 (t, J=7.6 Hz, 1H), 4.95 (d, J=7.2 Hz, 1H), 4.21 (d, J=13.6 Hz, 1H), 4.02 (d, J=13.2 Hz, 1H), 3.89-3.84 (m, 1H), 3.14-3.07 (m, 1H), 2.08 (s, 3H), 0.95 (t, J=7.2 Hz, 3H). LC-MS (Method-B)=610.1 $[M+H]^+$; 97.74% at RT 2.407 min. HPLC (Method-C)=97.96% at RT 6.318 min.

Example 6: Synthesis of Compound I-26

NMR:

$^1$H NMR spectrum was recorded on Bruker 400 MHz and Varian 400 MHz instruments internally referenced to a tetramethyl silane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: ACN (95:5) B: 0.05% Formic acid in ACN Inj Volume: 2.0 μL, Column oven temperature: 50 C; Flow Rate: 1.2. mL/minute. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm, 2.5μ) Mobile Phase A: 0.05% TFA in Water Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water:ACN(95:05); Mobile phase B: Acetonitrile; Gradient Programme: TB %: 0.01/5, 1/5, 8/100, 12/100, 14/5, 18/5; Flow rate: 1.2 ml/min.

Method-B: Column: X-SELECT CSH C18 (150×4.6 mm, 3.5 μm); Mobile Phase-A: 5 mM NH4HCO3; Mobile Phase-B: ACN; Programme: T/B %: 0.01/2, 2/2, 12/90, 16/90; Flow: 1.0 mL/min.; Diluent: ACN:WATER (80:20).

Method-C: Column: X SELECT CSH C18 (150×4.6 mm, 3.5); Mobile Phase A; 0.05% TFA IN WATER: ACN(95:05); Mobile Phase B: 0.05% TFA IN WATER: ACN(05:95); Programme: T/B %: 0.01/10, 12/90, 16/90; Flow: 1 mL/min.; Diluent: WATER:ACN (80:20).

Method-D: Column: X-Select CSH C18 (4.6*150) mm 5u Mobile Phase: A—0.1% TFA in water B—Acetonitrile Inj Volume; 5.0 μL, Flow Rate: 1.2. mL/minute Gradient program: Time(min)/B Conc.: 0.01/5, 1.0/5, 8.0/100, 12.0/100, 14.0/5, 18.0/5.

Method-E: Column name: CHIRAL PAK-IA (250*4.6, 5 μm) mobile phase a: n-hexane mobile phase b: DCM:MEOH (50:50 program-AB 90:10 flow rate: 1.0 ml/min.

Method-F: COLUMN: CHIRAL PAK-IG (250*4.6 mm, 5 μm) Mobile phase A: 0.1% DEA in n-Hexane Mobile phase B:DCM:MEOH (50:50) A:B; 80:20 Flow: 1.0 ml/min.

Synthesis of Compound 6A:

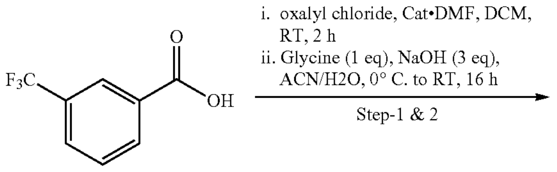

SM-1

-continued

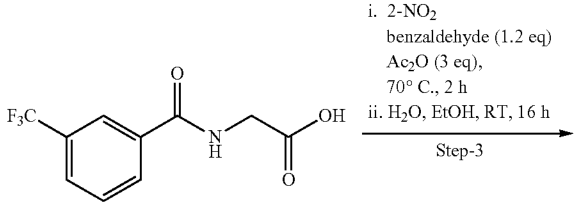

2

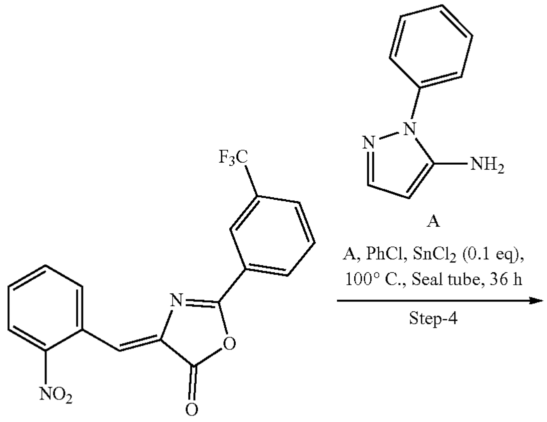

3

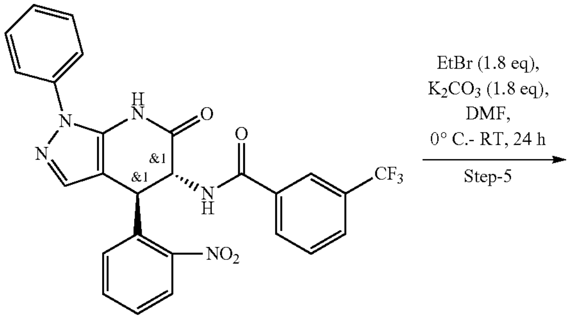

4

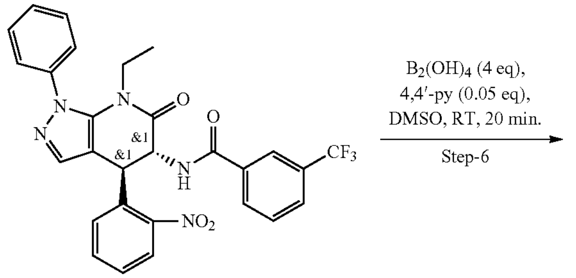

5

-continued

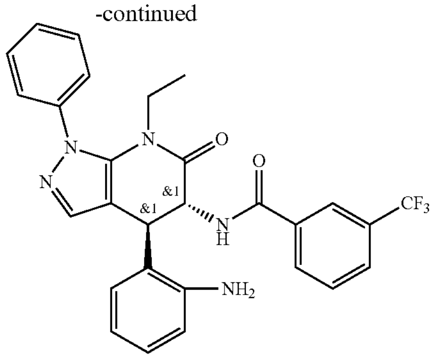

6A

Step-1 & 2: Synthesis of 2-[[3-(trifluoromethyl) benzoyl]amino]acetic acid (1)

To a stirred solution of 3-(trifluoromethyl)benzoic acid (4×25 g, 131.56 mmol) in DCM (250 mL) at 0° C. was added dropwise oxalyl chloride (33.8 mL, 0.39 mmol) followed by DMF (1 mL). The reaction mixture was stirred at room temperature for 2 h. Reaction progress was monitored by TLC. After completion of reaction, the reaction mixture was concentrated to afford crude. In another round bottom flask glycine (10.8 g, 0.14 mmol) was dissolved in acetonitrile (150 mL) and aq. NaOH (18 g, 0.47 mmol) at 0° C. and acid chloride solution was added in DCM. Then the reaction mixture was stirred at room temperature for 16 h. Reaction progress was monitored by TLC. After completion of reaction, the reaction mixture was cooled to 0° C. Then the reaction mixture was acidified with conc. HCl and extracted with ethyl acetate. The organic layer was dried over anhydrous sodium sulphate and concentrated to afford crude compound. The obtained crude was washed with heptane and pentane to afford crude compound (2) (90 g) as an off-white solid.

Step-3: Synthesis of (Z)-4-(2-nitrobenzylidene)-2-(3-(trifluoromethyl)phenyl)oxazol-5 (4H)-one (2)

To a stirred solution of compound (2) (5.0 g, 18.6 mmol) and 2-nitrobenzaldehyde (2.90 g, 18.6 mmol) in acetic anhydride (5.82 g, 55.8 mmol) was added. The reaction mixture was stirred at 70° C. for 2 h. Reaction progress was monitored by TLC. After completion of reaction, the reaction mixture was cooled to room temperature. Added 1:1 ratio of ethanol (40 mL) in water and stirred for 16 h. Separated solid was filtered off and dried to air to afford crude. Combined crude was washed with n-heptane and n-pentane to afford pure compound (2.6 g, 37%) as off-white solid. LC-MS (Method-B)=363.2 $[M+H]^+$; 68.20% at RT 1.93 min.

Step-4: Synthesis of rac-N-((4R,5S)-4-(2-nitrophenyl)-6-oxo-1-phenyl-4,5,6,7-tetrahydro-1H-pyrazolo [3,4-b]pyridin-5-yl)-3-(trifluoromethyl)benzamide (3)

To a stirred solution of compound (3) (7.5 g, 18 mmol) in chlorobenzene (80 mL) and 2-phenylpyrazol-3-amine (Int.A) (4.4 g, 27 mmol), stannous chloride (0.35 g, 1.8 mmol) was added at room temperature. Then the reaction mixture was stirred to 100° C. for 36 h. Reaction progress was monitored by TLC. After completion of reaction, the reaction mixture was cooled to room temperature and concentrated to afford crude. Combined crude was purified by column chromatography by using silica gel, eluted with 0-45% ethyl acetate/heptane to afford pure compound (4) as yellow solid. LC-MS (Method-B)=522.0 $[M+H]^+$; 70.83% at RT 2.15 min.

Step-5: Synthesis of rac-N-((4R,5S)-7-ethyl-4-(2-nitrophenyl)-6-oxo-1-phenyl-4,5,6,7-tetrahydro-1H-pyrazolo[3,4-b]pyridin-5-yl)-3-(trifluoromethyl) benzamide (5)

To a stirred solution of compound (4) (4.5 g, 6.0 mmol) in N,N-dimethylformamide (40 mL), potassium carbonate (1.7 g, 12 mmol) and bromoethane (1.3 g, 12 mmol) were added at 0° C. Then the reaction mixture was stirred to room temperature for 24 h. Reaction progress was monitored by TLC. After completion of reaction, the reaction mixture was diluted with water and extracted with ethyl acetate. Combined organic layer was dried over anhydrous sodium sulfate and concentrated under reduced pressure to afford crude compound (4) (1.9 g, 48%) pale yellow solid.

LC-MS (Method-B)=550.2 $[M+H]^+$; 86.19% at RT 2.26 min.

Step-6: Synthesis of rac-N-((4R,5S)-4-(2-aminophenyl)-7-ethyl-6-oxo-1-phenyl-4,5,6,7-tetrahydro-1H-pyrazolo[3,4-b]pyridin-5-yl)-3-(trifluoromethyl) benzamide (6A)

To a stirred solution of compound (5) (3 g, 4.36 mmol) in DMSO (20 mL) was added tetrahydroxydiboron (1.19 g, 13.10 mmol) followed by 4,4'-bipyridine (0.05 g, 0.3 mmol) at 0° C. The reaction mixture was stirred at room temperature for 20 min. Reaction progress was monitored by TLC. After completion of reaction, the reaction mixture was diluted with water and extracted with ethyl acetate. Combined organic layer was dried and concentrated to afford crude. Obtained crude was purified by column chromatography by using silica gel, eluted with 0-65% of heptane/ethyl acetate to afford compound 6A (0.81 g, 34%) pale-yellow solid. LC-MS (Method-B)=519.9 $[M+H]^+$; 96.02% at RT 2.24 min. HPLC (Method-B): 92.76% at RT 8.75 min.

Synthesis of Compound 6B:

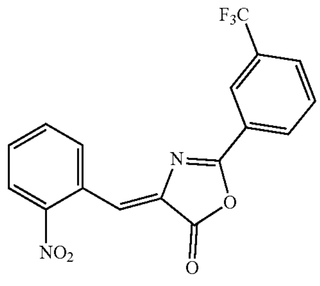

3

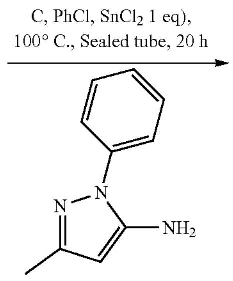

C

Step-1

-continued

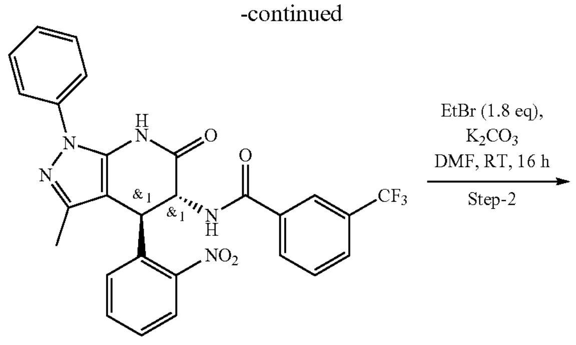

4

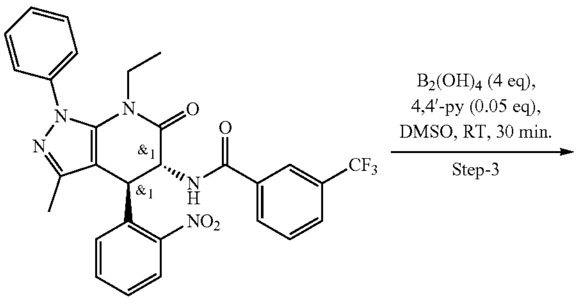

5

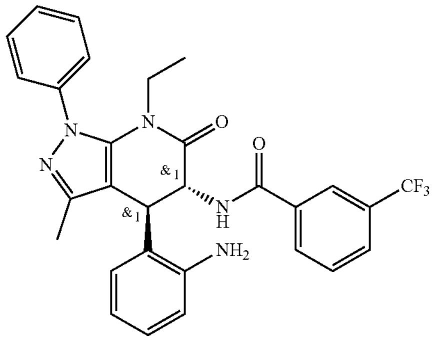

6B

Step-1: Synthesis of rac-N-((4R,5S)-3-methyl-4-(2-nitrophenyl)-6-oxo-1-phenyl-4,5,6,7-tetrahydro-1H-pyrazolo[3,4-b]pyridin-5-yl)-3-(trifluoromethyl) benzamide (4)

To a stirred solution of Int-C(1 g, 5.70 mmol) in chlorobenzene (20 mL) in a sealed tube was added compound (3) (2.09 g, 5.70 mmol) followed by $SnCl_2$ (0.10 g, 0.50 mmol) at room temperature. Then the reaction mixture was stirred at 100° C. for 20 h. Reaction progress was monitored by TLC. After completion of the reaction, the reaction mixture was cooled to room temperature and concentrated to afford crude. Obtained crude material was purified by using column chromatography with 0-45% ethyl acetate in heptane to afford crude compound (4) (0.45 g, 30.6%) as pale-yellow solid.

Step-2: Synthesis of rac-N-((4R,5S)-7-ethyl-3-methyl-4-(2-nitrophenyl)-6-oxo-1-phenyl-4,5,6,7-tetrahydro-1H-pyrazolo[3,4-b]pyridin-5-yl)-3-(trifluoromethyl)benzamide (5)

To a stirred solution of compound (4) (2 g, 3.70 mmol) in DMF (40 mL) was added potassium carbonate (0.92 g, 6.70 mmol) and bromoethane (0.5 mL, 6.70 mmol) at 0° C. The reaction mixture was stirred at room temperature for 16 h. Reaction progress was monitored by TLC. After completion of reaction, the reaction mixture was diluted with water and extracted with ethylacetate. Combined organic layer was dried over anhydrous sodium sulfate and concentrated under reduced pressure to afford crude. Obtained crude material was purified using column chromatography with 0-40% ethyl acetate in heptane to afford compound (5) (2.3 g, 49%) as off-white solid.

Step-3: Synthesis of rac-N-((4R,5S)-4-(2-aminophenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (5)

To a stirred solution of compound (5) (70 mg, 0.1242 mmol), dissolved in DMSO (1 mL) and tetrahydroxydiboron (0.03 g, 0.37 mmol) was added at 0° C., 2,2'-bipyridine (0.0009, 0.006 mmol) and stirred for 30 min at room temperature. The reaction progress was monitored by TLC. After completion of the reaction, the reaction mixture was diluted with water (10 mL) and extracted with ethyl acetate (20 mL). Combined organic layer was washed with excess of ice-cold water and dried under sodium sulphate and concentrated under vacuum to afford crude compound. Obtained crude was purified by flash column chromatography using 100-200 mesh silica gel. The compound was eluted with 50% ethyl acetate in heptane and concentrated under vacuum to afford a pure 6B (20 mg, 28.5%) as an off-white solid compound and used to next step. LC-MS (Method-B)=534.2 $[M+H]^+$; 94.45% at RT 2.19 min.

NMR:

$^1H$ NMR spectrum was recorded on Bruker 400 MHz and Varian 400 MHz instruments internally referenced to a tetramethyl silane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5µ. Mobile Phase: A: 0.05% Formic acid in water: ACN (95:5) B: 0.05% Formic acid in CAN Inj Volume: 2.0 µL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5µ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm, 2.5µ) Mobile Phase A: 0.05% TFA in Water Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

Method-D: Column:X-Select CSH C18 (3.0*50 mm, 2.5µ), Mobile Phase A: 2.5 Mm Ammonium Bicarbonate in $H_2O$+5% ACN Mobile Phase B: 100% ACN, Gradient % B: 0/2, 0.3/2, 2.0/98, 2.8/98, 3.0/2, 3.7/2.

Method-E: Column: X-Bridge BEH C18, (50 mm*3.0 mm, 2.5µ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water: ACN (95:05); Mobile phase B: Acetonitrile; Gradient Programme: T/B %: 0.01/5, 1/5, 8/100, 12/100, 14/5, 18/5; Flow rate: 1.2 ml/min.

Method-B: Column: X-Bridge CSH C18 (150×4.6 mm, 3.5 µm); Mobile Phase-A: 5 mM $NH_4HCO_3$; Mobile Phase-B: ACN; Programme: T/B %: 0.01/2, 2/2, 12/90, 16/90; Flow rate: 1.0 mL/min.; Diluent: ACN: WATER (80:20).

Method-C: Column: X SELECT CSH C18 (150×4.6 mm, 3.5µ); Mobile Phase A: 0.05% TFA IN WATER: ACN (95:05); Mobile Phase B: 0.05% TFA IN WATER: CAN (05:95); Programme: T/B %: 0.01/10, 12/90, 16/90; Flow rate: 1 mL/min.; Diluent: WATER:ACN (80:20).

Method-D: Column: X-Bridge CSH C18 (4.6*150) mm 5u Mobile Phase: A—0.1% TFA in water B—Acetonitrile Inj Volume; 5.0 µL, Flow Rate: 1.2 mL/minute Gradient program: Time(min)/B Conc.: 0.01/5, 1.0/5, 8.0/100, 12.0/100, 14.0/5, 18.0/5.

Method-E: Column: CHIRALCEL-OJ-H (250×4.6 mm, 5u) Mobile Phase A: 0.1% DEA in HEXANE Mobile Phase B: IPA A/B: 60/40 Flow: 1.0 ml/MIN PDA: OJ-H_015.

Method-F: Column: ACE Excel 2 C18-AR,100 mm×3.0 mm Mobile Phase A: 0.05% TFA in Water Mobile Phase B: 0.05% TFA in Acetonitrile Colum Temperature: 40° C. Flow Rate: 0.6 mL/min Gradient: 0/5, 1/5, 6/90, 8.5/90, 8.8/5, 11/5.

Method-G: Column: CHIRAL PAK-IC (250×4.6 mm, 5 µm) Mobile Phase A: 0.1% DEA in Hexane Mobile Phase B: ETOH/MEOH (50/50) A: B: 80/20 Flow 1.0 ml/min.

Method-H: Column: X-Bridge C18 (4.6*150) mm 5u Mobile Phase: A—5 mM Ammonium Acetate B—Acetonitrile Flow Rate: 1.0. mL/minute Gradient program: Time (min)/B Conc.: 0.01/5, 1.0/5, 8.0/100, 12.0/100, 14.0/5, 18.0/5.

Method-I: Column: CHIRALCEL-OJ-H (250×4.6 mm, 5 µm) mobile Phase A: n-HEXANE. Mobile Phase B: ETOH: MEOH (1:1) A/B: 50/50 Flow: 1.0 ml/MIN.

Method-J: Column: CHIRALCEL-OX—H Mobile Phase A: n-HEXANE Mobile Phase B: IPA Flow: 1.0 ml/MIN.

Method-K: Column Name: CHIRALPAK-IG (250×4.6 mm, 5 µm), Mobile Phase A: 0.1% DEA n-Hexane, Mobile Phase B: DCM: MEOH (50:50), Flow rate: 1.0 ml/min.

Method-L: Column IC-5 (30×250*4.6 mm, 5u) Mobile phase A N-HEXANE Mobile phase B IPA: DCM (1:1) Eluent A: B: −70-30 Total Flow rate (mL/min) 42.

Synthesis of I-26:

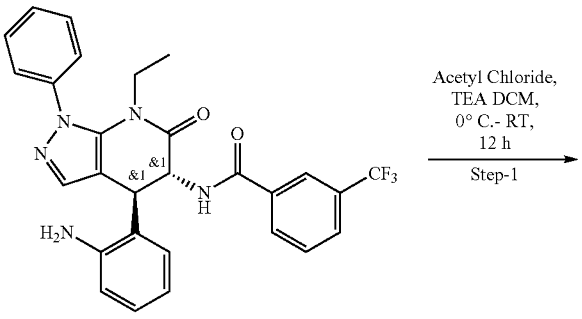

6A

-continued

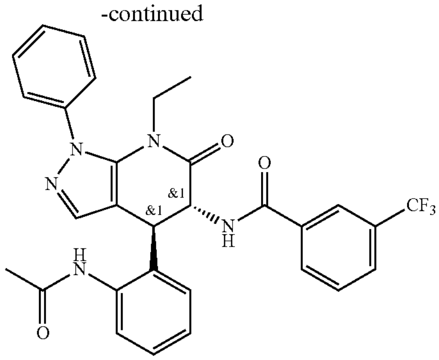

I-26

Step-1: Synthesis of rac-N-((4R,5S)-4-(2-acetamidophenyl)-7-ethyl-6-oxo-1-phenyl-4,5,6,7-tetrahydro-1H-pyrazolo[3,4-b]pyridin-5-yl)-3-(trifluoromethyl)benzamide (I-26)

To the stirred solution of 6A (150 mg, 0.28 mmol) in dichloromethane (3 mL), triethylamine (0.04 g, 0.43 mmol) was added followed by acetyl chloride (1.2 g, 15 mmol) at 0° C. Then the reaction mixture was stirred at the same temperature for 12 h. The reaction progress was monitored by TLC. After completion of starting material, the reaction mixture was diluted with water (10 mL) and extracted with EtOAc (2×20 mL). The combined organic layers were dried over sodium sulphate, concentrated under reduced pressure to afford crude. The obtained crude was purified using silica gel (230-400 mesh) by combi-flash column chromatography, eluted with 20% EtOAc/heptane to afford the title compound I-26 (80 mg, 48.5%) as an Off-White solid. $^1$H NMR (400 MHz, DMSO-$d_6$) (δ=9.60 (s, 1H), 9.12 (d, J=12.0 Hz, 1H), 8.04-8.01 (m, 2H), 7.90 (d, J=7.6 Hz, 1H), 7.71-7.65 (m, 3H), 7.59-7.51 (m, 3H), 7.43-7.38 (m, 2H), 7.25-7.16 (m, 2H), 6.95 (s, 1H), 5.19 (m, 1H), 4.66 (d, J=12.0 Hz, 1H), 3.76 (m, 1H), 3.18 (m, 1H), 2.11 (s, 3H), 0.84 (t, J=6.8 Hz, 3H). LC-MS (Method-D)=562.3 [M+H]$^+$; 98.39% at RT 2.14 min.

HPLC (Method-B)=96.54% at RT 8.04 min.

Example 7: Synthesis of Compounds I-178 and I-197

NMR:

$^1$H NMR spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: ACN (95:5) B: 0.05% Formic acid in ACN InJ Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

Method-C: Column: X-Select CSH C18 (50 mm*3.0 mm, 2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water: ACN (95:05); Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: ACN; Programme/B %: 0.01/2, 2/2, 12/90, 16/90; Flow: 1.0 mL/min.; Diluent: ACN: WATER (80:20).

Method-C: Column: X SELECT CSH C18 (150×4.6 mm, 3.5); Mobile Phase A; 0.05% TFA IN WATER: ACN (95:05); Mobile Phase B: 0.05% TFA IN WATER: ACN (05:95); Programme: T/B %: 0.01/10, 12/90, 16/90; Flow: 1 mL/min.; Diluent: WATER:ACN (80:20).

Method-D: Column: X-Bridge C18 (4.6*150) mm 5u Mobile Phase: A—5 mM Acetate in H20 B—Acetonitrile InJ Volume; 5.0 μL, Flow Rate: 1.0 mL/minute.

Chiral-HPLC:

Method-A: Column: CHIRALCEL-OX—H (250×4.6 mm, 5 μm) Mobile Phase A: n-HEXANE Mobile Phase B: ETOH: MEOH (1:1) A/B: 50/50 Flow: 1.0 ml/MIN.

Method-B: Column: CHIRALPAK IG (250×4.6 mm, 5 μm) Mobile Phase A: 0.1% DEA in n-HEXANE Mobile-Phase B: IPA A B: 60:40 Flow rate: 1.0 ml/min.

Method-C: Column Name: CHIRALPAK-IC (250×4.6 mm, 5 μm) Mobile phase-A: n-HEXANE Mobile phase-B: DCM:IPA(50:50) Flow rate: 1.0 ml/min % A/B: 50:50.

Method-D: COLUMN: CHIRALPAK IC (250×4.6 mm, 5 μm) Mobile Phase A: 0.1% TFA n-Hexane Mobile Phase B: IPA A:B: 80/20 FLOW: 1.0 ml/min.

Method-E: Column Name: CHIRALPAK-IG (250*4.6 mm, 5 μm) Mobile phase-A: 0.1% N DEA in HEXANE Mobile phase-B: ETOH:MEOH(50:50) Flow rate: 1.0 ml/min % A/B 50:50.

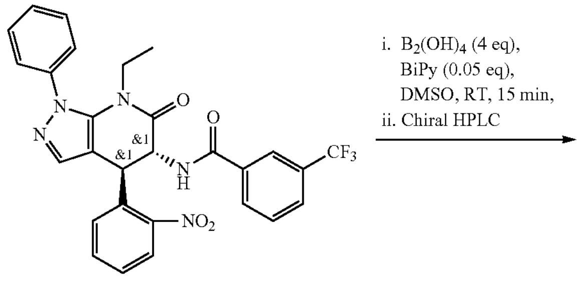

A

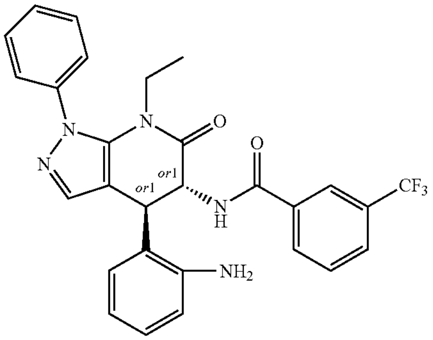

7B

-continued

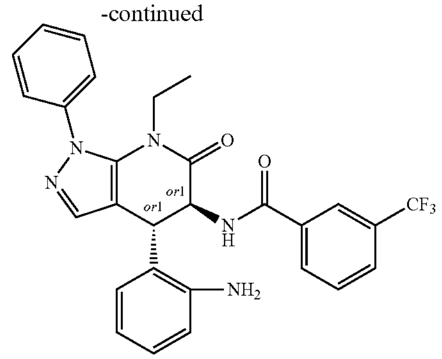

7C

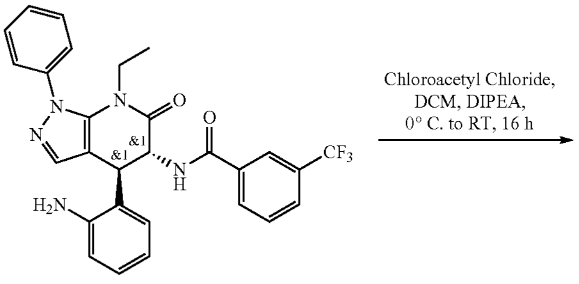

6A

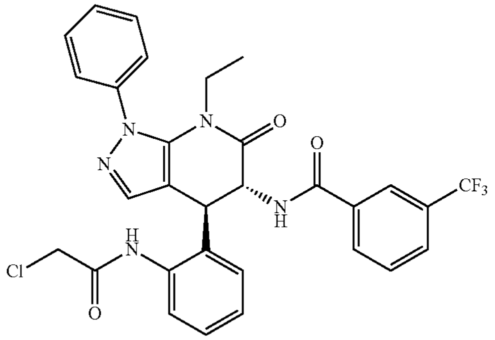

I-178

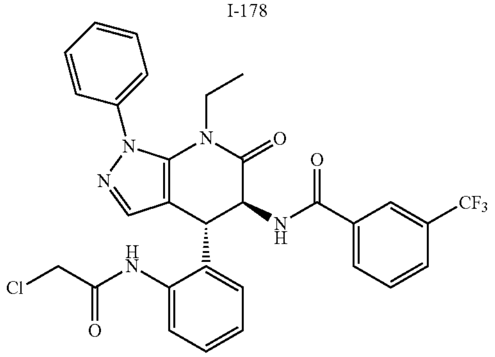

I-197

Synthesis of rel-N-((4R,5S)-4-(2-aminophenyl)-7-ethyl-6-oxo-1-phenyl-4,5,6,7-tetrahydro-1H-pyrazolo[3,4-b]pyridin-5-yl)-3-(trifluoromethyl)benzamide (7B) and rel-N-((4R,5S)-4-(2-aminophenyl)-7-ethyl-6-oxo-1-phenyl-4,5,6,7-tetrahydro-1H-pyrazolo[3,4-b]pyridin-5-yl)-3-(trifluoromethyl) benzamide (7C)

To a stirred solution of Compound (A) (1.30 g, 2.30 mmol) in DMSO (7.5 mL) were added 4-(4-pyridyl) pyridine (BiPy) (0.01 g, 0.11 mmol) and hypoboric acid (0.83 g, 9.10 mmol) at 0° C. The resulting reaction mixture was stirred for 15 minutes at room temperature. Progress of the reaction was monitored by TLC and LCMS. After completion of reaction, the reaction mass was quenched with ice water and extracted with ethyl acetate. The organic layer was dried over anhydrous $Na_2SO_4$, filtered, and concentrated under reduced pressure to afford crude was purified by combiflash at 25% ethyl acetate in heptane to afford Compound B-racemic (0.60 g, 47%) as pale-yellow solid. 300 mg of above racemic material was purified by Chiral HPLC to afford 19.34 mg 7B and 22.59 mg 7C.

7B $^1$H NMR (400 MHz, DMSO-$d_6$) δ=9.07 (d, J=8.3 Hz, 1H), 8.13-8.06 (m, 2H), 7.93 (d, J=7.9 Hz, 1H), 7.77-7.66 (m, 3H), 7.64-7.49 (m, 3H), 7.15 (s, 1H), 6.98-6.90 (m, 2H), 6.69 (d, J=7.9 Hz, 1H), 6.50 (t, J=7.2 Hz, 1H), 5.23 (s, 2H), 5.11 (t, J=9.0 Hz, 1H), 4.44 (d, J=9.7 Hz, 1H), 3.66-3.54 (m, 1H), 3.34-3.24 (m, 1H), 0.83 (t, J=6.9 Hz, 3H). LCMS (Method-A): 520.30 $[M+H]^+$; 97.44% at RT 1.49 min. HPLC(Method-B): 96.93% at RT 8.35 min. Chiral-HPLC (Method-C)=99.40% at RT 4.84 min.

7C $^1$H NMR (400 MHz, DMSO-$d_6$) δ=9.07 (d, J=8.3 Hz, 1H), 8.13-8.06 (m, 2H), 7.93 (d, J=7.9 Hz, 1H), 7.77-7.66 (m, 3H), 7.64-7.49 (m, 3H), 7.15 (s, 1H), 6.98-6.90 (m, 2H), 6.69 (d, J=7.9 Hz, 1H), 6.50 (t, J=7.2 Hz, 1H), 5.26 (s, 2H), 5.13 (t, J=9.0 Hz, 1H), 4.44 (d, J=9.7 Hz, 1H), 3.66-3.54 (m, 1H), 3.34-3.24 (m, 1H), 0.83 (t, J=6.9 Hz, 3H). LC-MS (Method-A): 520.30 $[M+H]^+$; 97.53% at RT 1.49 min. HPLC(Method-B): 97.46% at RT 8.35 min. Chiral-HPLC (Method-C)=97.65% at RT 6.64 min.

Synthesis of N-((4S,5R)-4-(2-(2-chloroacetamido) phenyl)-7-ethyl-6-oxo-1-phenyl-4,5,6,7-tetrahydro-1H-pyrazolo[3,4-b]pyridin-5-yl)-3-(trifluoromethyl) benzamide (I-178) and N-((4R,5S)-4-(2-(2-chloroacetamido)phenyl)-7-ethyl-6-oxo-1-phenyl-4,5,6,7-tetrahydro-1H-pyrazolo[3,4-b]pyridin-5-yl)-3-(trifluoromethyl)benzamide (I-197)

To a stirred solution of 6A (0.30 g, 0.56 mmol) in DCM (3 mL) was added DIPEA (0.22 g, 1.69 mmol) stirred for 5 minutes. To the reaction mixture was added chloroacetyl chloride (0.13 g, 1.13 mmol) at 0° C. The resulting reaction mixture was stirred at room temperature for 16 h. Progress of the reaction was monitored by TLC and LCMS. After completion of reaction, the reaction mass was quenched with ice water and extracted with DCM. The organic layer was dried over anhydrous $Na_2SO_4$, filtered, and concentrated under reduced pressure to afford crude which was purified by combiflash to afford 0.32 g of product as pale-yellow solid. Racemic product was further purified by Chiral HPLC to afford I-178 (0.10 g, 29.60%) as an off white solid and I-197 (0.05 g) as an off white solid.

I-178

$^1$H NMR (400 MHz, DMSO-$d_6$) δ=9.82 (s, 1H), 8.90 (d, J=8.6 Hz, 1H), 8.04-7.97 (m, 2H), 7.89 (d, J=8.0 Hz, 1H), 7.72-7.51 (m, 6H), 7.46-7.37 (m, 2H), 7.30-7.18 (m, 2H), 6.99 (s, 1H), 5.23-5.15 (m, 1H), 4.68 (d, J=12.0 Hz, 1H), 4.42-4.30 (m, 2H), 3.83-3.71 (m, 1H), 3.19-3.09 (m, 1H), 0.83 (t, J=7.0 Hz, 3H). LCMS (Method-A): 596.41 $[M+H]^+$; 98.41% at RT 2.06 min. HPLC (Method-A): 99.01% at RT 6.01 min. Chiral-HPLC (Method-C)=99.88% at RT 3.85 min.

I-197

$^1H$ NMR (400 MHz, DMSO-$d_6$) δ=9.82 (s, 1H), 8.90 (d, J=8.6 Hz, 1H), 8.04-7.97 (m, 2H), 7.89 (d, J=8.0 Hz, 1H), 7.72-7.51 (m, 6H), 7.46-7.37 (m, 2H), 7.30-7.18 (m, 2H), 6.99 (s, 1H), 5.23-5.15 (m, 1H), 4.68 (d, J=12.0 Hz, 1H), 4.42-4.30 (m, 2H), 3.83-3.71 (m, 1H), 3.19-3.09 (m, 1H), 0.83 (t, J=7.0 Hz, 3H). LCMS (Method-A): 596.41 $[M+H]^+$; 99.80% at RT 2.06 min. HPLC (Method-A): 99.60% at RT 6.01 min. Chiral-HPLC (Method-B)=Peak-1=34.38% at RT 3.85 min. Peak-2=65.62% at RT 5.72 min. Chiral HPLC Peak 1: 99% at 6.01 min. Chiral HPLC Peak 2: 100% at 5.73 min.

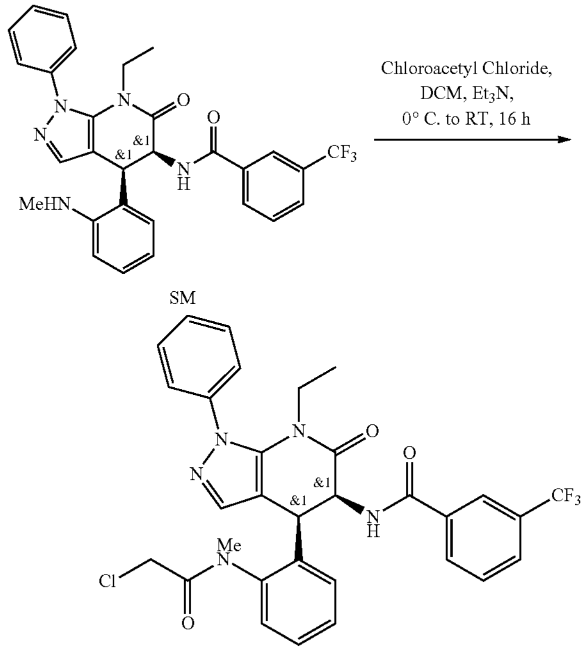

SM

7A

Synthesis of rac-N-((4R,5R)-4-(2-(2-chloro-N-methylacetamido)phenyl)-7-ethyl-6-oxo-1-phenyl-4,5,6,7-tetrahydro-1H-pyrazolo[3,4-b]pyridin-5-yl)-3-(trifluoromethyl)benzamide (7A)

To a stirred solution of the starting material (0.08 g, 0.13 mmol) in DCM (5 mL), triethylamine (0.02 g, 0.20 mmol) and chloroacetyl chloride (0.02 g, 0.17 mmol) were added at 0° C. The reaction mass was stirred at room temperature for 12 h. Reaction progress was monitored by TLC and LCMS. After completion of reaction, the reaction mixture was quenched with water and extracted with DCM. The organic layer was dried over anhydrous sodium sulphate and concentrated to afford crude. Obtained crude was purified by prep-HPLC to afford 7A (0.01 g, 11.69%) as an off-white solid.

$^1H$ NMR (400 MHz, —CHLOROFORM-d) δ=8.02 (s, 1H), 7.91-7.84 (m, 1H), 7.83-7.76 (m, 1H), 7.61-7.52 (m, 6H), 7.03-6.92 (m, 5H), 5.32-5.21 (m, 1H), 4.80 (d, J=7.3 Hz, 1H), 4.23 (d, J=13.1 Hz, 1H), 4.03-3.93 (m, 2H), 3.84 (s, 1H), 3.30-3.15 (m, 1H), 3.01 (s, 2H), 1.11-0.96 (m, 3H). LCMS(Method-D): 628.2 $[M+H]^+$; 99.92% at RT 2.40 min. HPLC(Method-B): 99.76% at RT 9.56 min. Chiral-HPLC (Method-B)=Peak-I=86.59% at RT 7.88 min. Peak-2=13.40% at RT 13.96 min.

Example 8: Synthesis of Compounds I-203, I-16, I-19, I-23, I-25, I-17, I-18, I-206, I-27, I-24, I-192, I-204, I-22, I-173, I-205, I-202, I-186 and I-172

NMR:

$^1H$ NMR spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LC-MS:

Method-A: LC-MS_X-Select (Formic acid); Column: X-Select CSH C18 (3.0*50) mm 2.5μ. Mobile Phase: A: 0.05% Formic acid in water: ACN (95:5) B: 0.05% Formic acid in ACN Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/min; Column oven temp. 50° C. Gradient program: 0% B to 98% B in 2.0 minute, hold till 3.0 min, at 3.2 min B conc is 0% up to 4.0 min.

Method-C: Column: X-Select CSH C18 (50 mm*3.0 mm, 2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

Method-D: Column:X-Select CSH C18 (3.0*50 mm, 2.5 μm), Mobile Phase A: 2.5 Mm Ammonium Bicarbonate in $H_2O$+5% ACN Mobile Phase B: 100% ACN, Gradient % B: 0/2, 0.3/2, 2.0/98, 2.8/98, 3.0/2, 3.7/2.

Method-E: Column: X-Bridge BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water: ACN (95:05); Mobile phase B: Acetonitrile; Gradient Program: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: ACN; Program/B %: 0.01/2, 2/2, 12/90, 16/90; Flow: 1.0 mL/min.; Diluent: ACN: WATER (80:20).

Method-C: Column: X SELECT CSH C18 (150×4.6 mm, 3.5); Mobile Phase A; 0.05% TFA IN WATER: ACN (95:05); Mobile Phase B: 0.05% TFA IN WATER: ACN(05:95); Program: T/B %: 0.01/10, 12/90, 16/90; Flow: 1 mL/min.; Diluent: WATER:ACN (80:20).

Method-D: Column: X-Bridge CSH C18 (4.6*150) mm 5μ Mobile Phase: A—0.1% TFA in water B—Acetonitrile Inj. Volume; 5.0 μL, Flow Rate: 1.2. mL/minute Gradient program: Time(min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in HEXANE Mobile Phase B: IPA A/B: 60/40 Flow: 1.0 ml/MIN PDA: OJ-H_015.

Method-F: Column: ACE Excel 2 C18-AR,100 mm×3.0 mm Mobile Phase A: 0.05% TFA in Water; Mobile Phase B: 0.05% TFA in Acetonitrile Colum Temperature: 40° C. Flow Rate: 0.6 mL/min Gradient: 0/5, 1/5, 6/90, 8.5/90, 8.8/5, 11/5.

Method-G: Column: CHIRAL PAK-IC (250×4.6 mm, 5 μm) Mobile Phase A: 0.1% DEA in Hexane Mobile Phase B: EtOH/MEOH (50/50) A: B: 80/20 Flow: 1.0 mL/min.

Method-H: Column: ACE Excel 2 C18-AR,100 mm×3.0 mm Mobile Phase A: 0.05% FA in Water; Mobile Phase B: 0.05% FA in Acetonitrile Colum Temperature: 40° C. Flow Rate: 0.6 mL/min Gradient: 0/5, 1/5, 6/90, 8.5/90, 8.8/5, 11/5.

Method-I: Column: X-Select CSH C18 (4.6*150) mm 5μ Mobile Phase: A—0.1% TFA in water B—Acetonitrile Inj Volume; 5.0 μL, Flow Rate: 1.2. mL/minute Gradient program: Time(min)/B Conc.: 0.01/5, 1.0/5, 8.0/100, 12.0/100, 14.0/5, 18.0/5.

Synthesis of Compound 8A:

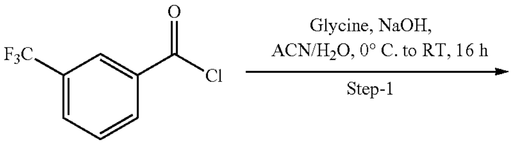

SM1

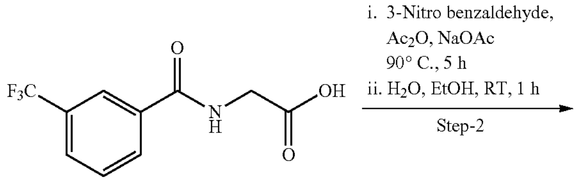

1

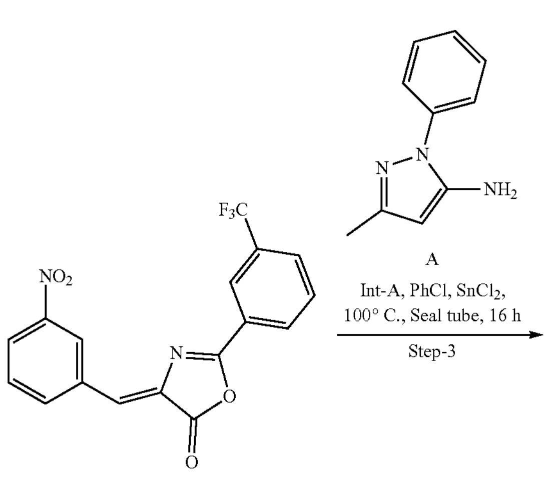

2

-continued

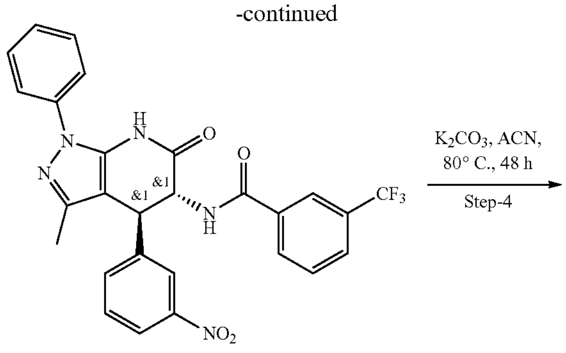

3

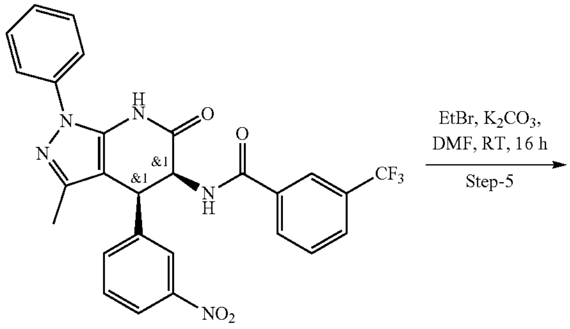

4

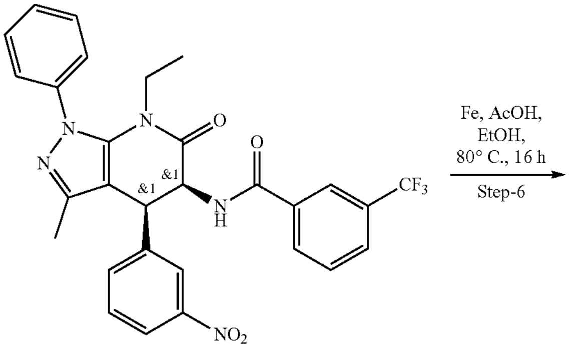

5

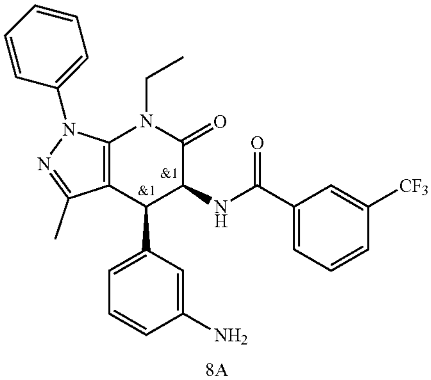

8A

Step-1: Synthesis of 2-[[3-(trifluoromethyl)benzoyl]amino]acetic acid (1)

To a stirred solution of glycine (10.8 g, 0.14 mmol) in acetonitrile (150 mL), was added NaOH (18 g, 0.47 mmol) in water (40 mL) at 0° C. and stirred for 5 min, followed by drop wise addition of 3-(trifluoromethyl)benzoyl chloride (SM1) (29 g, 0.14 mmol) in ACN (100 mL), then the reaction mixture was stirred at room temperature for 16 h. The reaction mixture was monitored by TLC and LC-MS, desired mass was observed in crude LC-MS. The reaction mixture was diluted with water and extracted with EtOAc (2×500 ml). The organic layer was dried over anhydrous $Na_2SO_4$, filtered and concentrated under reduced pressure. The crude was washed with heptane to afford a pure compound (1) (27 g, 78%). as an off white solid. $^1$H NMR (400 MHz, DMSO-$d_6$) (δ=12.6 (s, 1H), 9.14-9.08 (m, 1H), 8.26-8.16 (m, 2H), 7.93 (d, J=6.8 Hz, 1H), 7.77-7.73 (m, 1H), 3.96-3.93 (m, 2H). LC-MS (Method-A)=246.3 [M+H]$^+$; 65.20% at RT 1.09 min.

Step-2: Synthesis of (Z)-4-(3-nitrobenzylidene)-2-(3-(trifluoromethyl)phenyl)oxazol-5 (4H)-one (2)

To a stirred solution of compound (1) (5 g, 18.6 mmol) in acetic anhydride (5.82 g, 55.8 mmol) added 3-nitrobenzaldehyde (2.90 g, 18.6 mmol) and stirred at 90° C. for 5 h. The reaction mixture was monitored by TLC and LC-MS, desired mass was observed in crude LC-MS. After consumption of compound (1), (by TLC), the reaction mixture was cooled to room temperature and added (1:1 ratio) ethanol (40 mL) and (40 mL) of water and stirred for 1 h. at room temperature. Solid was filtered off and dried to afford crude. Crude was washed with n-heptane and n-pentane followed by co-distilled with toluene to afford pure compound (2.6 g, 37%) as an off-white solid. $^1$H NMR (400 MHz, CDCL3-d6) (δ=8.58 (dd, J=7.9, 1.3 Hz, 1H), 8.41-8.38 (m, 1H), 8.33 (d, J=7.9 Hz, 1H), 8.09 (dd, J=8.1, 1.3 Hz, 1H), 7.90 (d, J=7.8 Hz, 1H), 7.81-7.76 (m, 2H), 7.72-7.66 (m, 1H), 7.65-7.60 (m, 1H). LC-MS (Method-B)=363.2 [M+H]$^+$; 68.20% at RT 1.93 min.

Step-3: Synthesis of rac-N-((4R,5S)-3-methyl-4-(3-nitrophenyl)-6-oxo-1-phenyl-4,5,6,7-tetrahydro-1H-pyrazolo[3,4-b]pyridin-5-yl)-3-(trifluoromethyl) benzamide (3)

To a stirred solution of compound (2) (15 g, 41.36 mmol) and 5-methyl-2-phenyl-3,4-dihydropyrazol-3-amine (Int-A) (7.16 g, 41.36 mmol) in chlorobenzene (150 mL) was added tin(II) chloride (0.784 g, 4.13 mmol) at room temperature. Resulting reaction mixture was stirred at 100° C. in a closed sealed tube for 16 h. Progress of the reaction was monitored by TLC. After consumption of starting material (by TLC), the reaction mixture was diluted with water and extracted with EtOAc (2×100 mL). The organic layer was dried over anhydrous $Na_2SO_4$, filtered and concentrated under reduced pressure. The crude compound was purified by medium pressure liquid column chromatography by eluting with 50% EtOAc in heptane to afford compound (3) (15 g, 29%) as a pale-yellow solid. $^1$H NMR (400 MHz, DMSO-$d_6$): 10.9 (s, 1H), 8.64 (d, J=7.6 Hz, 1H), 8.15-8.12 (m, 1H), 8.09-8.07 (m, 2H), 7.90-7.85 (m, 2H), 7.68 (t, J=7.6 Hz, 1H), 7.64-7.51 (m, 5H), 7.46 (d, J=7.6 Hz, 1H), 7.39-7.37 (m, 1H), 5.13 (t, J=12.4 Hz, 1H), 4.59 (d, J=12.0 Hz, 1H), 2.03 (s, 3H). LC-MS (Method-E)=536.4[M+H]$^+$; 95.22% at RT 1.34 min.

Step-4: Synthesis of rac-N-((4R,5R)-3-methyl-4-(3-nitrophenyl)-6-oxo-1-phenyl-4,5,6,7-tetrahydro-1H-pyrazolo[3,4-b]pyridin-5-yl)-3-(trifluoromethyl) benzamide (4)

To a stirred solution of compound (3) (15 g, 28.01 mmol) in ACN (150 mL) was added potassium carbonate (11.3 g, 81.4 mmol) and heated at 80° C. for 48 h. Progress of the reaction was monitored by TLC. Reaction mixture was evaporated under vacuum. Resulting residue was purified by flash column chromatography and pure fractions were eluted at 20-25% EtOAc in heptane to afford compound (4) (10 g, 63.33%) as a yellow solid. $^1$H NMR (400 MHz, DMSO-d6): 11.2 (s, 1H), 8.64 (d, J=7.6 Hz, 1H), 8.15-8.12 (m, 1H), 8.09-8.07 (m, 2H), 7.90-7.85 (m, 2H), 7.68 (t, J=7.6 Hz, 1H), 7.64-7.51 (m, 5H), 7.46 (d, J=7.6 Hz, 1H), 7.39-7.37 (m, 1H), 5.46 (t, J=7.6 Hz, 1H), 4.73 (d, J=7.6 Hz, 1H), 2.03 (s, 3H). LC-MS (Method-B)=536.0 [M+H]$^+$; 74.95% at RT 2.29 min.

Step-5: Synthesis of rac-N-((4R,5R)-7-ethyl-3-methyl-4-(3-nitrophenyl)-6-oxo-1-phenyl-4,5,6,7-tetrahydro-1H-pyrazolo[3,4-b]pyridin-5-yl)-3-(trifluoromethyl)benzamide (5)

To a stirred solution of compound (4) (15 g, 28.01 mmol) in DMF (150.00 mL) was added potassium carbonate (7.7 g, 55 mmol) followed by bromoethane (2.5 mL) at room temperature. Resulting reaction mixture was stirred at room temperature for 16 h. Progress of the reaction was monitored by TLC. After consumption of SM, the reaction mixture was quenched with ice cold water and extracted with ethyl acetate. Organic layer was dried over $Na_2SO_4$, concentrated under vacuum to afford crude. Obtained crude was purified through flash column chromatography, eluted with the gradient of 25% ethyl acetate in heptane to afford compound (5) (8 g, 50.68%) as yellow solid. $^1$H NMR (400 MHz, DMSO-$d_6$): 8.71 (d, J=7.8 Hz, 1H), 8.15-8.09 (m, 3H), 7.91 (d, J=8.0 Hz, 1H), 7.82 (s, 1H), 7.72-7.67 (m, 3H), 7.62-7.46 (m, 5H), 5.65 (t, J=8.0 Hz 1H), 4.68 (d, J=7.2 Hz, 1H), 4.02-3.99 (m, 1H), 3.01-2.99 (m, 1H), 2.06 (s, 3H), 0.91 (t, J=7.2 Hz, 3H). LC-MS (Method-B)=564.0[M+H]$^+$; 75.93% at RT 2.46 min.

Step-6: Synthesis of rac-N-((4R,5R)-4-(3-aminophenyl)-7-ethyl-3-methyl-6-oxo-1-phenyl-4,5,6,7-tetrahydro-1H-pyrazolo[3,4-b]pyridin-5-yl)-3-(trifluoromethyl)benzamide To a stirred solution of compound (5) (8 g, 14.20 mmol) in ethanol (80 mL) was added acetic acid (7.2 mL) and iron (6.6 g, 120 mmol) at room temperature. Resulting reaction mixture was stirred at 80° C. in a closed sealed tube for 16 h. Progress of the reaction was monitored by TLC. Reaction mixture was filtered, evaporated under vacuum to afforded solid. Obtained solid was passed through flash column chromatography 230-400 mesh silica gel. Compound was eluted at 50-60% of ethyl acetate in heptane to afford compound (6) (4 g, 50.17%) as a pale-yellow solid.

$^1$H NMR (400 MHz, DMSO-$d_6$) δ=8.23 (d, J=7.0 Hz, 1H), 8.10-8.06 (m, 1H), 7.91 (d, J=7.8 Hz, 1H), 7.70 (t, J=7.8 Hz, 1H), 7.63-7.61 (m, 2H), 7.58-7.49 (m, 2H), 7.48-7.47 (m, 1H), 6.88 (t, J=7.8 Hz, 1H), 6.43 (dd, J=1.4, 7.9 Hz, 1H), 6.19 (s, 1H), 6.14 (d, J=7.6 Hz, 1H), 5.40-5.37 (m, 1H), 4.95 (d, J=8.4 Hz, 1H), 4.34 (d, J=7.2 Hz, 1H), 4.12-3.99 (m, 1H), 3.88-3.81 (m, 1H), 3.17-3.16 (m, 1H), 3.08-3.03 (m, 1H), 2.04 (s, 3H), 0.91 (d, J=6.8 Hz, 3H). LC-MS (Method-B)=534.0 [M+H]$^+$; 95.86% at RT 2.31 min.

Analogue Synthesis:

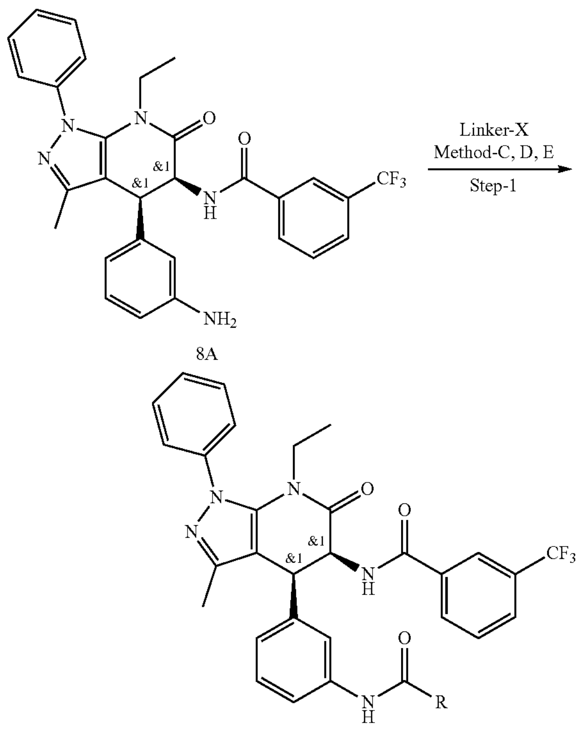

8A

Method-C:- $T_3P$ (3 eq), DIPEA (3 eq), DMF, 70° C., 14 h
Method-D:- $K_2CO_3$, ACN, 70° C., 16 h (for Acid Chlorides)
Method-E:- HATU, DIPEA, DMF, 70° C., 16 h Method-C Procedure:

To a stirred solution of Linker X (X=G, P, L, N, Q, E) (125 mg, 0.93 mmol), 8A (250 mg, 0.44 mmol) in DMF (2.5 mL) was added 1-propanephosphonic anhydride in ethyl acetate (300 mg, 0.47 mmol) and N,N-diisopropylethylamine (0.2 mL, 1 mmol) at room temperature. The resulting reaction mixture was stirred at 70° C. for 12 h. The progress of the reaction was monitored by TLC and LC-MS. The reaction mixture was quenched with water and extracted with ethyl acetate. The organic layer was dried over anhydrous sodium sulphate and concentrated under reduced pressure to afford crude. The obtained crude was purified by silica column was eluted with 50-60% ethyl acetate/hexane. The pure fraction of prep HPLC was directly lyophilized and afford compound.

Method-D Procedure:

To a stirred solution of 8A (200 mg, 0.37 mmol) in ACN (2 mL) was added potassium carbonate (102 mg, 0.72 mmol) and Linker X (X=B, H, D, C, O, I) (56 mg, 0.48 mmol) at room temperature. The reaction mixture was stirred at 70° C. for 12 h. The progress of the reaction was monitored by TLC and LC-MS. The reaction mixture was quenched with water and extracted with ethyl acetate. The organic layer was dried over anhydrous sodium sulfate and concentrated under reduced pressure to afford crude. The obtained crude was purified by prep HPLC. The pure fraction of prep HPLC was directly lyophilized and dried to afford compound.

Method E Procedure:

To a stirred solution of 8A (200 mg, 0.37 mmol) in DMF (2 mL) was added Linker X (X=J, T, M) and HATU (260 mg, 0.66 mmol) at 0° C. and added N,N-Diisopropylethylamine (0.1 mL, 0.6 mmol). Resulting reaction mixture was stirred at room temperature for 12 h. Progress of the reaction was monitored by TLC and LC-MS. Reaction mixture was quenched with water, extracted with ethyl acetate. Combined organic layer was dried over anhydrous sodium sulphate, concentrated to afford crude. Obtained crude material was purified by Prep-HPLC to afford compound. The following table shows the conditions to obtain the desired compounds.

| Sr. No. | Cpd. Number | Linker | Structure (R) | Method | 8A (mg) | Linker Qty (mg) | Qty (mg) & Nature of compound | Yield (%) |
|---|---|---|---|---|---|---|---|---|
| 1 | I-203 | B | 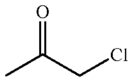 | Method-D | 200 | 56 | 48.8 (Off-White solid) | 21.1 |
| 2 | I-16 | H | 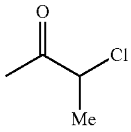 | Method-D | 200 | 56 | 70 (Off-White solid) | 29.62 |
| 3 | I-19 | D | 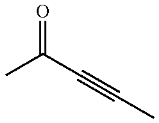 | Method-D | 200 | 46 | 90 (Off-White solid) | 39.64 |
| 4 | I-23 | C | 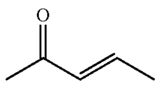 | Method-D | 200 | 46 | 36.8 (Off-White solid) | 16.2 |
| 5 | I-25 | O | 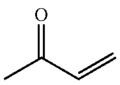 | Method-D | 200 | 65 | 32 (Off-White solid) | 16.1 |

-continued

| Sr. No. | Cpd. Number | Linker | Structure (R) | Method | 8A (mg) | Linker Qty (mg) | Qty (mg) & Nature of compound | Yield (%) |
|---|---|---|---|---|---|---|---|---|
| 6 | I-17 | I | 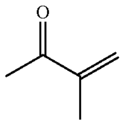 | Method-D | 200 | 46 | 40 (Off-White solid) | 19.7 |
| 7 | I-18 | G | 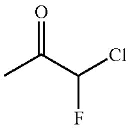 | Method-C | 200 | 84.01 | 36.10 (Off-White solid) | 15.3 |
| 8 | I-206 | P | 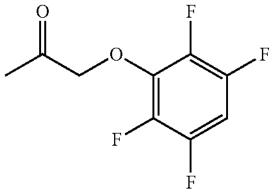 | Method-C | 200 | 159.6 | 70.30 (Pale-yellow solid) | 26.7 |
| 9 | I-27 | L | 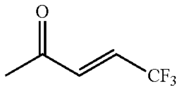 | Method-C | 200 | 99.76 | 49.61 (Pale-yellow solid) | 21.25 |
| 10 | I-24 | N | 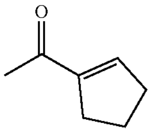 | Method-C | 200 | 79.87 | 53.72 (Pale-yellow solid) | 23.9 |
| 11 | I-192 | Q | 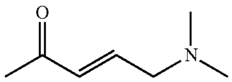 | Method-C | 250 | 125 | 4.3 (Off-White solid) | 1.4 |
| 12 | I-204 | E | 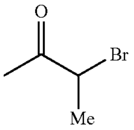 | Method-C | 200 | 114.7 | 22.7 (Off-White solid) | 9.06 |
| 13 | I-173 | J | 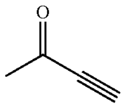 | Method-E | 200 | 682 | 18 (Off-White solid) | 8.15 |
| 14 | I-205 | T | 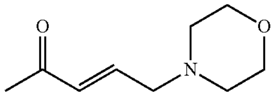 | Method-E | 200 | 120 | 17 (White solid) | 6.6 |
| 15 | I-202 | M | 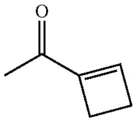 | Method-E | 200 | 100 | 8 (Off-White solid) | 3.51 |

I-203

$^1$H NMR (400 MHz, DMSO-$d_6$) δ=10.2 (s, 1H), 8.45 (d, J=7.2 Hz, 1H), 8.11-8.08 (m, 2H), 7.90 (d, J=7.6 Hz, 1H), 7.70-7.66 (m, 1H), 7.65-7.59 (m, 2H), 7.59-7.55 (m, 2H), 7.53-7.47 (m, 2H), 7.32 (s, 1H), 7.22 (t, J=8.0 Hz, 1H), 6.70 (d, J=8.0 Hz, 1H), 5.48 (t, J=7.2 Hz, 1H), 4.47 (d, J=2.4 Hz, 1H), 4.14 (s, 2H), 3.85-3.73 (m, 1H), 3.15-3.10 (m, 1H), 2.04 (s, 3H), 0.92 (t, J=7.2 Hz, 3H). LC-MS (Method-A)= 610.8 [M+H]$^+$; 99.71% at RT 2.33 min. HPLC (Method-H): 99.62% at RT 6.17 min.

I-16

$^1$H NMR (400 MHz, DMSO-$d_6$) δ=10.2 (s, 1H), 8.42 (d, J=4.4 Hz, 1H), 8.12-8.08 (m, 2H), 7.90 (d, J=7.6 Hz, 1H), 7.70-7.38 (m, 7H), 7.29-7.21 (m, 2H), 6.70 (d, J=7.2 Hz, 1H), 5.48 (t, J=7.2 Hz, 1H), 4.60-4.55 (m, 1H), 4.58 (d, J=7.6 Hz, 1H), 3.86-3.80 (m, 1H), 3.13-3.07 (m, 1H), 2.07 (s, 3H), 1.55-1.50 (m, 3H), 0.92 (t, J=7.2 Hz, 3H). LC-MS (Method-A)=622.0 $[M-H]^-$; 99.58% at RT 2.40 min. HPLC (Method-A): 98.41% at RT 9.47 min.

I-19

$^1$H NMR (400 MHz, DMSO-$d_6$) δ=10.5 (s, 1H), 8.45 (d, J=7.2 Hz, 1H), 8.11-8.08 (m, 2H), 7.90 (d, J=7.6 Hz, 1H), 7.69 (t, J=7.8 Hz, 1H), 7.64-7.62 (m, 2H), 7.59-7.55 (m, 2H), 7.50-7.44 (m, 2H), 7.37 (s, 1H), 7.19 (t, J=8.0 Hz, 1H), 6.68 (d, J=7.6 Hz, 1H), 5.46 (t, J=7.8 Hz, 1H), 4.44 (d, J=7.2 Hz, 1H), 3.80-3.75 (m, 1H), 3.17-3.10 (m, 1H), 2.04 (s, 6H), 0.90 (t, J=6.8 Hz, 3H). LC-MS (Method-A)=599.8 $[M+H]^+$; 98.76% at RT 2.33 min. HPLC (Method-H): 99.66% at RT 6.16 min.

I-23

$^1$H NMR (400 MHz, DMSO-$d_6$) δ=9.84 (s, 1H), 8.41 (d, J=6.8 Hz, 1H), 8.11-8.07 (m, 2H), 7.89 (d, J=8.0 Hz, 1H), 7.69-7.48 (m, 7H), 7.37 (s, 1H), 7.18 (t, J=8.0 Hz, 1H), 6.77-6.57 (m, 2H), 6.06-6.02 (m, 1H), 5.47 (t, J=7.2 Hz, 1H), 4.46 (d, J=7.2 Hz, 1H), 3.85-3.76 (m, 1H), 3.16-3.09 (m, 1H), 2.05 (s, 3H), 1.83-1.81 (m, 3H), 0.92 (t, J=7.0 Hz, 3H). LC-MS (Method-A)=602.8 $[M+H]^+$; 99.88% at RT 2.35 min. HPLC (Method-H): 97.92% at RT 6.23 min.

I-25

$^1$H NMR (400 MHz, DMSO-$d_6$) (δ=10.0 (s, 1H), 8.43 (d, J=6.8 Hz, 1H), 8.11-8.07 (m, 2H), 7.89 (d, J=8.0 Hz, 1H), 7.69-7.63 (m, 3H), 7.59-7.55 (m, 3H), 7.52-7.48 (m, 1H), 7.41 (s, 1H), 7.21 (t, J=8.0 Hz, 1H), 6.66 (d, J=7.6 Hz, 1H), 6.39-6.32 (m, 1H), 6.19-6.15 (m, 1H), 5.70-5.67 (m, 1H), 5.47 (t, J=7.2 Hz, 1H), 4.47 (d, J=7.2 Hz, 1H), 3.86-3.77 (m, 1H), 3.16-3.07 (m, 1H), 2.07 (s, 3H), 0.92 (t, J=6.8 Hz, 3H). LC-MS (Method-A)=588.8 $[M+H]^+$; 99.74% at RT 2.32 min. HPLC (Method-H): 99.64% at RT 6.11 min.

I-17

$^1$H NMR (400 MHz, DMSO-$d_6$) (δ=9.69 (s, 1H), 8.37 (d, J=7.2 Hz, 1H), 8.13-8.07 (m, 2H), 7.89 (d, J=7.6 Hz, 1H), 7.69-7.63 (m, 6H), 7.60-7.48 (m, 1H), 7.44 (s, 1H), 7.19 (t, J=7.6 Hz, 1H), 6.65 (d, J=7.6, Hz, 1H), 5.67 (s, 1H), 5.48-5.44 (m, 2H), 4.46 (d, J=7.6 Hz, 1H), 3.86-3.80 (m, 1H), 3.12-3.07 (m, 1H), 2.05 (s, 3H), 1.87 (s, 3H), 0.92 (t, J=7.2 Hz, 3H). LC-MS (Method-A)=601.9 $[M+H]^+$; 99.87% at RT 2.38 min. HPLC (Method-A): 98.98% at RT 9.23 min.

I-18

$^1$H NMR (400 MHz, DMSO-$d_6$) (δ=10.5 (s, 1H), 8.48 (dd, J=7.2, 2.4 Hz, 1H), 8.12-8.09 (m, 2H), 7.90 (d, J=7.6 Hz, 1H), 7.70-7.63 (m, 3H), 7.59-7.49 (m, 4H), 7.40-7.35 (m, 1H), 7.27 (t, J=7.8 Hz, 1H), 6.83-6.69 (m, 2H), 5.49 (t, J=7.2 Hz, 1H), 4.49 (d, J=7.6 Hz, 1H), 3.85-3.79 (m, 1H), 3.14-3.08 (m, 1H), 2.05 (s, 3H), 0.92 (t, J=6.8 Hz, 3H). LC-MS (Method-A)=628.25 $[M+H]^+$; 99.92% at RT 2.49 min. HPLC (Method-I): 99.52% at RT 8.55 min.

I-206

$^1$H NMR (400 MHz, DMSO-$d_6$) (δ=10.0 (s, 1H), 8.43 (d, J=7.2 Hz, 1H), 8.10-8.07 (m, 2H), 7.89 (d, J=7.8 Hz, 1H), 7.68-7.46 (m, 8H), 7.33 (s, 1H), 7.21 (t, J=8.0 Hz, 1H), 6.69 (d, J=8.0 Hz, 1H), 5.47 (t, J=7.2 Hz, 1H), 4.88 (s, 2H), 4.46 (d, J=7.2 Hz, 1H), 3.81-3.76 (m, 1H), 3.12-3.06 (m, 1H), 2.07 (s, 3H), 0.87 (t, J=7.2 Hz, 3H). LC-MS (Method-A)= 737.9 $[M-H]^-$; 99.00% at RT 2.49 min. HPLC (Method-I): 98.78% at RT 6.77 min.

I-27

$^1$H NMR (400 MHz, DMSO-$d_6$) (δ=10. (s, 1H), 8.48 (d, J=7.2, Hz, 1H), 8.12-8.08 (m, 2H), 7.88 (d, J=8.0 Hz, 1H), 7.70-7.63 (m, 3H), 7.59-7.56 (m, 3H), 7.53-7.48 (m, 1H), 7.42 (s, 1H), 7.26 (t, J=8.0 Hz, 1H), 6.91-6.79 (m, 2H), 6.71 (d, J=7.8 Hz, 1H), 5.49 (t, J=7.2 Hz, 1H), 4.48 (d, J=7.2 Hz, 1H), 3.86-3.77 (m, 1H), 3.13-3.08 (m, 1H), 2.05 (s, 3H), 0.91 (t, J=7.2 Hz, 3H). LC-MS (Method-A)=656.8 $[M-H]^+$; 99.24% at RT 2.45 min. HPLC (Method-I): 99.61% at RT 8.92 min.

I-24

$^1$H NMR (400 MHz, DMSO-$d_6$) (δ=9.53 (s, 1H), 8.39 (d, J=6.8 Hz, 1H), 8.12-8.07 (m, 2H), 7.89 (d, J=7.6 Hz, 1H), 7.69-7.48 (m, 7H), 7.42 (s, 1H), 7.18 (t, J=8.0 Hz, 1H), 6.65-6.58 (m, 2H), 5.46 (t, J=7.2 Hz, 1H), 4.46 (d, J=7.6 Hz, 1H), 3.85-3.80 (m, 1H), 3.31 (s, 1H), 3.12-3.06 (m, 1H), 2.53-2.43 (m, 3H), 2.05 (s, 3H), 1.88-1.84 (m, 2H), 0.92 (t, J=7.2 Hz, 3H).

LC-MS (Method-A)=628.2 $[M+H]^+$; 99.44% at RT 2.43 min. HPLC (Method-A): 99.62% at RT 9.46 min.

I-192

$^1$H NMR (400 MHz, DMSO-$d_6$) (δ=9.94 (s, 1H), 8.40 (d, J=6.8 Hz, 1H), 8.11-8.07 (m, 2H), 7.88 (d, J=8.0 Hz, 1H), 7.69-7.63 (m, 3H), 7.59-7.55 (m, 3H), 7.52-7.48 (m, 1H), 7.40 (s, 1H), 7.19 (t, J=8.0 Hz, 1H), 6.68-6.61 (m, 2H), 6.19 (d, J=15.2 Hz, 1H), 5.47 (t, J=7.2 Hz, 1H), 4.46 (d, J=7.2 Hz, 1H), 3.84-3.78 (m, 1H), 3.12-3.09 (m, 1H), 3.01 (d, J=4.8 Hz 2H), 2.15 (s, 6H), 2.05 (s, 3H), 0.92 (t, J=6.8 Hz, 3H). LC-MS (Method-D)=645.2 $[M+H]^+$; 97.88% at RT 2.30 min. HPLC (Method-B): 96.34% at RT 8.55 min.

I-204

$^1$H NMR (400 MHz, DMSO-$d_6$) (δ=10.2 (s, 1H), 8.42 (t, J=6.4 Hz, 1H), 8.12-8.08 (m, 2H), 7.90 (d, J=8.4 Hz, 1H), 7.70-7.63 (m, 3H), 7.59-7.49 (m, 4H), 7.43-7.39 (m, 1H), 7.24-7.20 (m, 1H), 6.69 (d, J=7.6 Hz, 1H), 5.47 (t, J=7.2 Hz, 1H), 4.62-4.58 (m, 1H), 4.48 (d, J=7.6 Hz, 1H), 3.84-3.79 (m, 1H), 3.12-3.10 (m, 1H), 2.05 (d, J=1.4 Hz, 3H), 1.69-1.64 (m, 3H), 0.92 (t, J=6.8 Hz, 3H). LC-MS (Method-A)= 668.32 $[M+H]^+$; 99.75% at RT 2.52 min. HPLC (Method-I): 98.90% at RT 8.73 min.

I-173

$^1$H NMR (400 MHz, DMSO-$d_6$) (δ=10.7 (s, 1H), 8.44 (d, J=6.8 Hz, 1H), 8.11-8.08 (m, 2H), 7.90 (d, J=7.6 Hz, 1H), 7.70-7.66 (m, 1H), 7.64-7.59 (m, 2H), 7.57-7.52 (m, 2H) 7.50-7.46 (m, 2H), 7.38 (s, 1H), 7.21 (t, J=8.0 Hz, 1H), 6.70 (d, J=7.6 Hz, 1H), 5.47 (t, J=7.2 Hz, 1H), 4.45 (d, J=7.2 Hz, 1H), 4.33 (s, 1H), 3.79-3.78 (m, 1H), 3.13-3.11 (m, 1H), 2.04 (s, 3H), 0.90 (t, J=7.2 Hz, 3H). LC-MS (Method-D)= 586.2 $[M+H]^+$; 99.49% at RT 2.24 min. HPLC (Method-B): 96.73% at RT 9.04 min.

I-205

$^1$H NMR (400 MHz, DMSO-$d_6$) (δ=9.95 (s, 1H), 8.40 (d, J=7.2 Hz, 1H), 8.11-8.07 (m, 2H), 7.88 (d, J=8.4 Hz, 1H), 7.69-7.48 (m, 6H), 7.41 (s, 1H), 7.19 (t, J=7.6 Hz, 1H), 6.67-6.60 (m, 2H), 6.19 (d, J=15.6 Hz, 1H), 5.47 (t, J=7.2 Hz, 1H), 4.46 (d, J=7.2 Hz, 1H), 3.87-3.78 (m, 1H), 3.58 (t, J=8.8 Hz, 4H), 3.16-3.00 (m, 4H), 2.36 (s, 4H), 2.05 (s, 3H), 0.91 (t, J=6.8 Hz, 3H). LC-MS (Method-A)=686.5 $[M+H]^+$; 94.40% at RT 1.77 min. HPLC (Method-H): 94.46% at RT 5.01 min.

I-202

$^1$H NMR (400 MHz, DMSO-$d_6$) (δ=9.64 (s, 1H), 8.41 (d, J=7.2 Hz, 1H), 8.12-8.07 (m, 2H), 7.89 (d, J=7.6 Hz, 1H), 7.69-7.63 (m, 3H), 7.59-7.48 (m, 3H), 7.42 (s, 1H), 7.18 (t, J=4.0 Hz, 1H), 6.69-6.64 (m, 2H), 5.46 (t, J=6.8 Hz, 1H), 4.45 (d, J=7.2 Hz, 1H), 3.85-3.79 (m, 1H), 3.12-3.07 (m, 1H), 2.63 (s, 2H), 2.37 (s, 2H), 2.04 (s, 3H), 0.92 (t, J=6.8 Hz, 3H). LC-MS (Method-D)=614.2 $[M+H]^+$; 96.50% at RT 2.31 min. HPLC (Method-A): 96.88% at RT 9.35 min.

Synthesis of I-22:

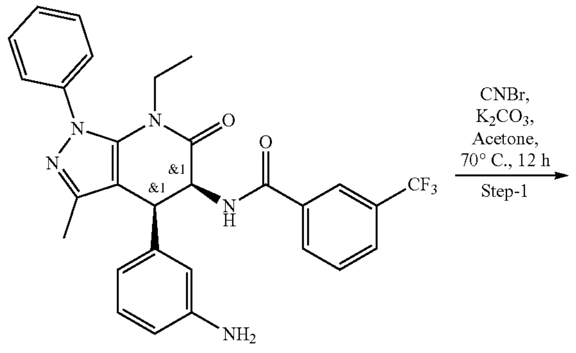

8A

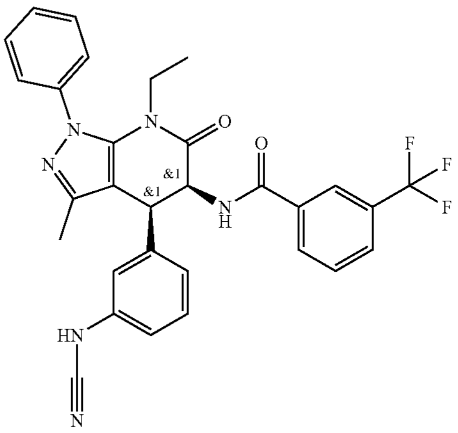

I-22

To a stirred solution of Cyanogenbromide (60 mg, 0.55 mmol) in acetone (2 mL) was added potassium carbonate (102 mg, 0.734 mmol), and 8A (200 mg, 0.35 mmol). Then the reaction mixture was stirred at 70° C. for 12 h. The progress of the reaction was monitored by TLC and LC-MS. The reaction mixture was quenched with water and extracted with ethyl acetate. The combined organic layer was dried over anhydrous sodium sulphate and concentrated under reduced pressure to afford crude. The obtained crude was purified by prep HPLC. The pure fractions of prep were directly lyophilized and dried to afford I-22 (45 mg, 22.17%) (Cis isomer) as an Off-White solid. $^1$H NMR (400 MHz, DMSO-$d_6$) (δ=10.0 (br s, 1H), 8.50 (d, J=7.2 Hz, 1H), 8.11 (d, J=8.0 Hz, 2H), 7.91 (d, J=7.6 Hz, 1H), 7.71-7.67 (m, 1H), 7.64-7.62 (m, 2H), 7.59-7.55 (m, 2H), 7.52-7.49 (m, 1H), 7.22 (t, J=8.0 Hz, 1H), 6.84-6.82 (m, 1H), 6.63 (d, J=7.6 Hz, 1H), 6.58 (s, 1H), 5.49 (t, J=7.6 Hz, 1H), 4.49 (d, J=7.2 Hz, 1H), 3.89-3.83 (m, 1H), 3.08-3.03 (m, 1H), 2.04 (s, 3H), 0.92 (t, J=7.2 Hz, 3H). LC-MS (Method-D)=559.41 $[M+H]^+$; 98.23% at RT 1.99 min. HPLC (Method-B): 97.24% at RT 9.37 min.

Synthesis of I-172:

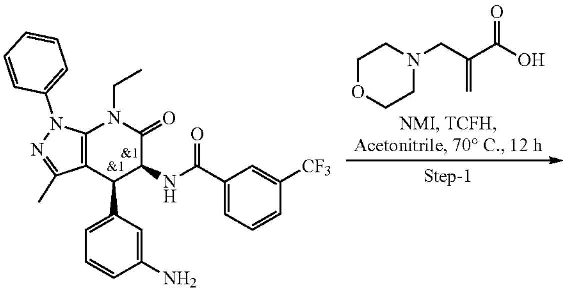

8A

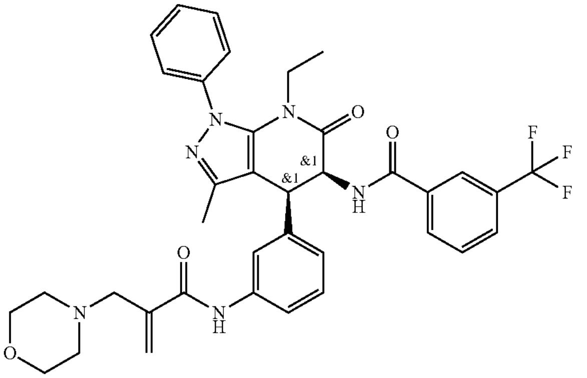

I-172

To a stirred solution of 2-(morpholinomethyl)prop-2-enoic acid (100 mg, 0.57 mmol) 8A (200 mg, 0.35 mmol) in ACN (2 mL) was added 1-methylimidazole (0.1 mL, 1 mmol) and TCFH (260 mg, 0.908 mmol) at room temperature and resulting reaction mixture was stirred at 70° C. for 12 h. Progress of the reaction was monitored by TLC and LC-MS. The reaction mixture was cooled to room temperature and quenched with water, extracted with ethyl acetate. Organic layer was washed with water, dried over sodium sulphate and concentrated to afford crude. Crude material was further purified through Prep HPLC. The pure fraction of prep was directly lyophilized and dried to afford I-172 (12 mg, 4.80%) Cis isomer as a white solid. $^1$H NMR (400 MHz, DMSO-$d_6$) (δ=10.9 (br s, 1H), 8.40 (d, J=7.2 Hz, 1H), 8.13-8.09 (m, 2H), 7.89 (d, J=7.6 Hz, 1H), 7.67 (d, J=8.0 Hz, 1H), 7.66-7.63 (m, 2H), 7.59-7.52 (m, 3H), 7.51-7.48 (m, 1H), 7.33 (s, 1H), 7.23 (t, J=8.0 Hz, 1H), 6.67 (d, J=7.6 Hz, 1H), 5.97 (s, 1H), 5.54 (s, 1H), 5.48 (t, J=7.2 Hz, 1H), 4.51 (d, J=7.2 Hz, 1H), 3.85-3.78 (m, 1H), 3.49 (t, J=4.4 Hz, 4H), 3.20-3.08 (m, 3H), 2.60-2.59 (m, 1H), 2.41-2.28 (m, 3H), 2.06 (s, 3H), 0.91 (t, J=6.8 Hz, 3H). LC-MS (Method-D)=687.6 $[M+H]^+$; 99.73% at RT 2.30 min. HPLC (Method-B): 96.93% at RT 9.46 min.

Synthesis of I-186:

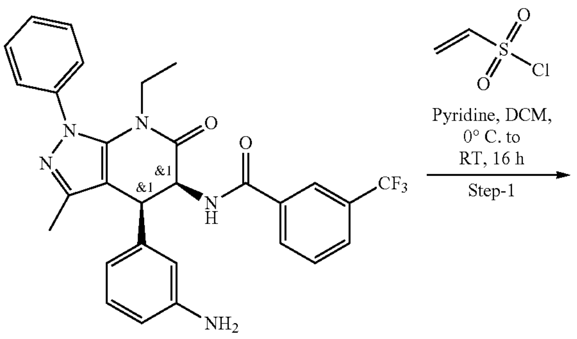

8A

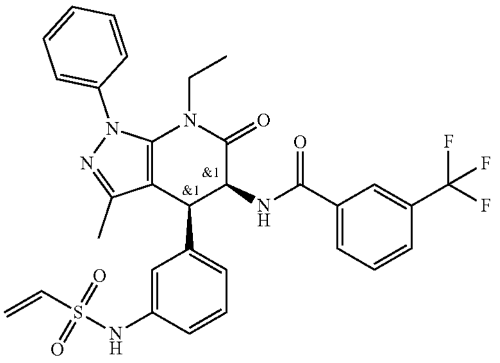

I-186

To stirred solution of 8A (200 mg, 0.36 mmol) in dichloromethane (5 mL) was added ethenesulfonyl chloride (92.99 mg, 0.73 mmol) and pyridine (58.4 mg, 0.73 mmol) at 0° C. Then the reaction mixture was stirred at room temperature for 16 h. The reaction mixture was monitored by TLC. Organic layer was washed with water, dried over sodium sulphate and concentrated to afford crude. Obtained crude was purified by prep. HPLC TFA method afforded I-186 (59.6 mg, 25.6%) as Off-white solid. $^1$H NMR (400 MHz, DMSO-$d_6$) (δ=9.90 (s, 1H), 8.51 (d, J=7.2 Hz, 1H), 8.16-8.12 (m, 2H), 7.91 (d, J=8.0 Hz, 1H), 7.70 (t, J=8.0 Hz, 1H), 7.64-7.51 (m, 5H), 7.21-7.17 (m, 1H), 7.03-7.01 (m, 1H), 6.84 (s, 1H), 6.68-6.59 (m, 2H), 5.93 (d, J=16.4 Hz, 1H), 5.77 (d, J=10.0 Hz, 1H), 5.46 (t, J=7.6 Hz, 1H), 4.45 (d, J=7.2 Hz, 1H), 3.81-3.76 (m, 1H), 3.14-3.09 (m, 1H), 2.02 (s, 3H), 0.90 (t, J=7.2 Hz, 3H). LC-MS (Method-D)=624.27 $[M+H]^+$; 99.66% at RT 2.08 min. HPLC (Method-B): 98.37% at RT 8.33 min.

Example 9: Synthesis of Compounds I-141, I-69, I-123, I-124, I-28, I-103, I-9, I-2, I-83, I-80, I-169, I-70, I-94 and I-78

NMR:

$^1$H NMR spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: ACN (95:5) B: 0.05% Formic acid in ACN Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

Method-C: Column: X-Select CSH C18 (50 mm*3.0 mm, 2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water: ACN (95:05); Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: ACN; Programme/B %: 0.01/2, 2/2, 12/90, 16/90; Flow: 1.0 mL/min.; Diluent: ACN: WATER (80:20).

Method-C: Column: X SELECT CSH C18 (150×4.6 mm, 3.5); Mobile Phase A; 0.05% TFA IN WATER: ACN (95:05); Mobile Phase B: 0.05% TFA IN WATER: ACN(05:95); Programme: T/B %: 0.01/10, 12/90, 16/90; Flow: 1 mL/min.; Diluent: WATER:ACN (80:20).

Chiral HPLC:

Method-A: Column: CHIRALCEL-OJ-H (250×4.6 mm, 5u) Mobile Phase A: 0.1% DEA in HEXANE Mobile Phase B: IPA A/B: 60/40 Flow: 1.0 ml/MIN PDA: OJ-H_015.

Method-B: Column: CHIRALCEL-OJ-H(250×4.6 mm, 5 μm) Mobile Phase A: n-HEXANE Mobile Phase B: ETOH: MEOH(1:1) A/B: 50/50 Flow: 1.0 ml/MIN.

Method-C: Column Name: CHIRALPAK IC (250×4.6 mm, 5 μm) MobilePhase A: n-HEXANE MobilePhase B: IPA:DCM(1:1)A B: 70:30 Flow rate: 1.0 ml/min.

Synthesis of 9A:

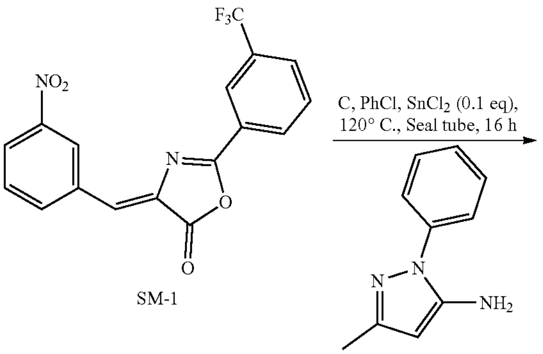

SM-1

C

Step-1

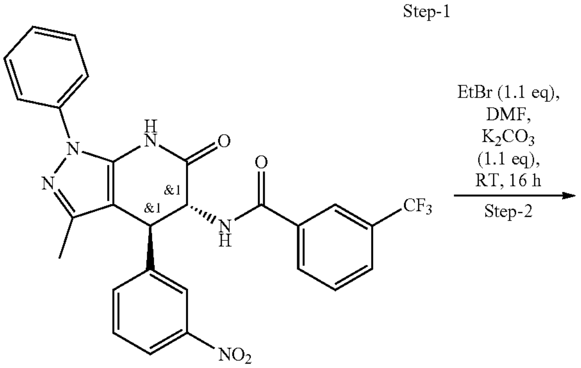

1

-continued

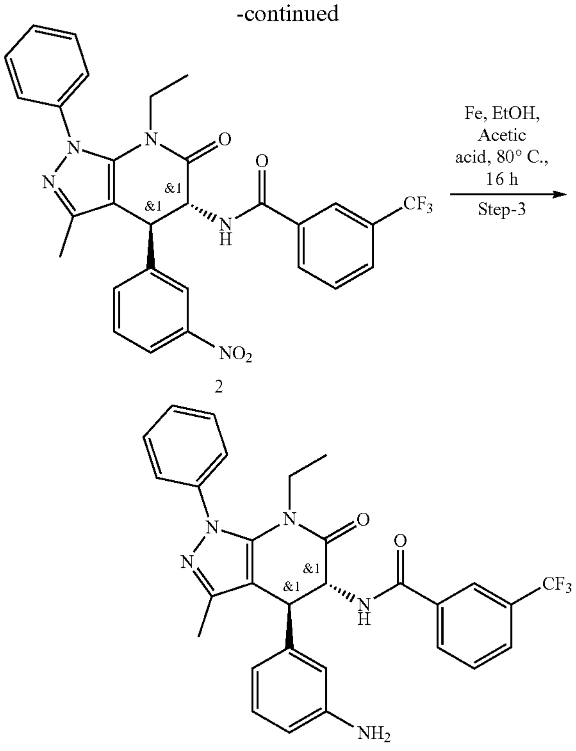

2

9A

Step-1: Synthesis of rac-N-((4R,5S)-3-methyl-4-(3-nitrophenyl)-6-oxo-1-phenyl-4,5,6,7-tetrahydro-1H-pyrazolo[3,4-b]pyridin-5-yl)-3-(trifluoromethyl) benzamide (1)

In a sealed tube, SM-1 (15 g, 41.36 mmol) in chlorobenzene (150 mL) were added Int-C (7.16 g, 41.36 mmol), and $SnCl_2$ (784 mg, 4.13 mmol) and stirred for 16 h at 120° C. After consumption of the starting material (by TLC), solvent was evaporated. Crude material was purified by using column chromatography eluted with 50% ethyl acetate in heptane and concentrated under vacuum to afford compound (1) (15 g, 67%) as a pale-yellow solid. $^1$H NMR (400 MHz, DMSO-$d_6$) (δ=10.9 (s, 1H), 9.02 (d, J=8.8 Hz, 1H), 8.28 (s, 1H), 8.14 (d, J=8.3 Hz, 1H), 8.01-7.87 (m, 2H), 7.71-7.59 (m, 5H), 7.57-7.50 (m, 2H), 7.42-7.36 (m, 2H), 5.16-5.10 (m, 1H), 4.60 (d, J=12.0 Hz, 1H), 1.49 (s, 3H). LC-MS (Method-B)=536.4 $[M+H]^+$; 95.22% at RT 1.34 min.

Step-2: Synthesis of rac-N-((4R,5S)-7-ethyl-3-methyl-4-(3-nitrophenyl)-6-oxo-1-phenyl-4,5,6,7-tetrahydro-1H-pyrazolo[3,4-b]pyridin-5-yl)-3-(trifluoromethyl)benzamide (2)

To a stirred solution of compound (1) (5 g, 9.34 mmol) in DMF (15 mL) was added potassium carbonate (1.67 g, 12.14 mmol) and bromoethane (0.76 mL) at room temperature. The reaction mixture was stirred at room temperature for 16 h. Progress of the reaction was monitored by TLC. After consumption of starting material, the reaction mixture was quenched with ice water extracted with ethyl acetate. Organic layer was dried over sodium sulphate and concentrated under vacuum to afford crude. Obtained crude was purified by flash column chromatography and eluted with 36% ethyl acetate/heptane. Pure fraction was concentrated under vacuum to afford compound (2) (2.0 g, 38%) as a pale-yellow solid. $^1$H NMR (400 MHz, DMSO-$d_6$) (δ=9.04 (d, J=8.8 Hz, 1H), 8.29 (s, 1H), 8.15-8.13 (m, 1H), 7.99 (s, 2H), 7.89 (d, J=7.2 Hz, 2H), 7.71-7.64 (m, 3H), 7.57 (t, J=6.8 Hz, 2H), 7.51-7.50 (m, 2H), 5.39-5.43 (m, 1H), 4.56 (d, J=12.4 Hz, 1H), 3.80-3.79 (m, 1H), 3.08-3.07 (m, 1H), 1.47 (s, 3H), 0.82 (t, J=6.8 Hz, 3H). LC-MS (Method-B) =564.2 $[M+H]^+$; 93.19% at RT 2.30 min.

Step-3: Synthesis of rac-N-((4R,5S)-4-(3-aminophenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (9A)

To a stirred solution of compound (2) (3 g, 5.32 mmol) and iron (1.49 g, 26.64 mmol) in ethanol (30 mL) was added acetic acid (3.19 mL) at room temperature. The reaction mixture was stirred at 80° C. in a closed sealed tube for 16 h. Progress of the reaction was monitored by TLC. After completion of reaction, the reaction mixture was filtered and diluted with saturated $NaHCO_3$ and extracted with ethyl acetate. Organic layer was dried over sodium sulphate, concentrated under vacuum, purified by column chromatography was eluting with 70% ethyl acetate/heptane to afford 9A (1.8 g, 63%) as a pale-yellow solid. $^1$H NMR (400 MHz, DMSO-d6) (δ=9.01 (d, J=8.8 Hz, 1H), 8.05-8.02 (m, 2H), 7.90 (d, J=8.0 Hz, 1H), 7.72-7.69 (m, 1H), 7.63-7.47 (m, 5H), 7.26-7.21 (m, 1H), 7.08-6.87 (m, 4H), 5.22 (dd, J=12.0, 8.8 Hz, 1H), 4.30 (d, J=12.0 Hz, 1H), 3.80-3.73 (m, 1H), 3.13-3.07 (m, 1H), 1.51 (s, 3H), 0.81 (t, J=6.8 Hz, 3H). LC-MS (Method-A)=534.1 $[M+H]^+$; 99.55% at RT 2.07 min. HPLC (Method-A): 98.91% at RT 5.51 min.

Synthesis of Analogues:

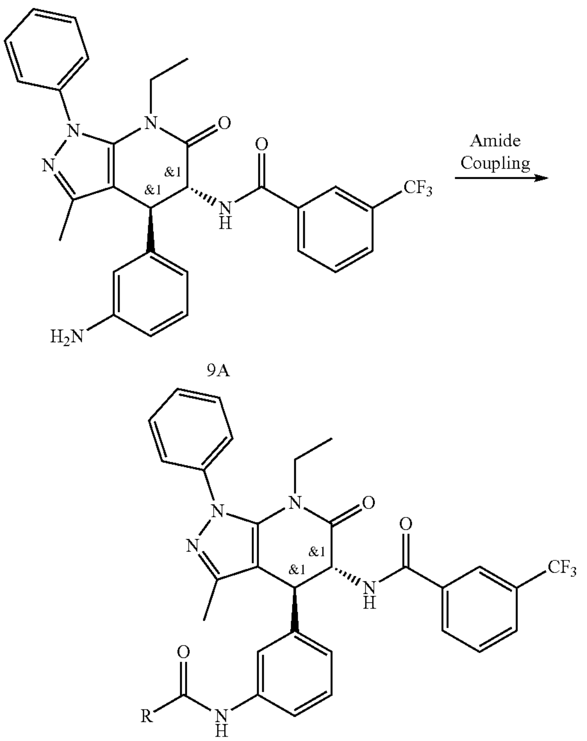

9A

A. Mukiayama reagent, TEA, DMF, 25° C., 16 h.
B. Mukaiyama reagent, DMF, tributylamine, 50° C., 16 h.
C. DCM, TEA, RT, 1 h.
D. DMF, EDAC, DPPA, HOBT, RT, 16 h.
E. ACN, NM, TCFH, 65° C., 16 h Method A Procedure:

To a stirred solution of 9A (0.3 g, 0.6 mmol) in DMF (3 mL) was added 2-chloro-1-methylpyridinium iodide (0.4 g, 1 mmol), tributylamine (0.2 g, 0.8 mmol) Linker-X (1.2 equiv.) at 0° C. The resulting reaction mixture was stirred at room temperature for 16 h. Progress of the reaction was monitored by TLC and LCMS. After consumption of starting material, the reaction mixture was quenched with ice water and extracted with ethyl acetate washed with brine and dried with $Na_2SO_4$ concentrated under reduced pressure to afford crude. The obtained crude material was purified by Prep-HPLC to afford title compound.

Method B Procedure: I-123

To a stirred solution of 9A (0.2 g, 0.4 mmol), cyclobutanecarboxylic acid (0.06 g, 0.6 mmol) in DMF (2 mL) were added tributylamine (0.1 g, 0.7 mmol) and 2-chloro-1-methylpyridinium iodide (0.1 g, 0.6 mmol) at 0° C. The reaction mixture was allowed to stirred at 50° C. for 16 h. Reaction mixture was monitored by TLC. Reaction mixture was added ice cold water and extracted with EtOAc, the organic layer was dried over sodium sulphate and concentrated under reduced pressure to afford crude. The crude compound was purified by column chromatography of 100-200 mesh silica where pure compound was eluted at 40-50% of EtOAc in heptane to afford I-123 (0.12 g, 50.00%) as an off-white solid.

Method C Procedure: I-124

To a stirred solution of 9A (0.2 g, 0.4 mmol) in dichloromethane (2 mL) was added triethylamine (0.1 g, 1 mmol) and acetyl chloride (0.03 g, 0.4 mmol) at 0° C. The reaction mixture was allowed to stir at room temperature for 1 h. After consumption of the starting material (by TLC), reaction mixture was diluted with DCM and washed with ice cold water, then extracted into DCM. The combined organic layer was dried over sodium sulphate and concentrated under reduced pressure, purified by column chromatography using 100-200 mesh silica eluting with 50-60% EtOAc in Heptane to afford I-124 (0.14 g, 60.00%) as an off-white solid.

Method D Procedure: I-103

To a stirred solution of 2-cyanoacetic acid (0.08 g, 0.94 mmol) in DMF (7.2 mL), was added 9A (0.25 g, 0.47 mmol), EDCI (0.18 g, 0.94 mmol) at 0° C. under inert atmosphere followed by the addition of N,N-Diisopropylethylamine (0.19 g, 1.4 mmol) and 1-hydroxybenzotriazole (0.13 g, 0.94 mmol). Then the reaction mixture was stirred at room temp for 16 h. After consumption of the starting material (by TLC), the reaction mixture was diluted with water and extracted by using EtOAc (20.00 mL×2). The organic layer was dried over anhydrous $Na_2SO_4$, filtered, and concentrated under reduced pressure. The obtained crude material was purified by silica gel column chromatography followed by Prep HPLC to afford I-103 (0.08 g, 30%) as a white colour solid.

Method E Procedure: I-169

To a stirring solution of 1-(morpholinomethyl)cyclopropanecarboxylic acid (0.1 g, 0.5 mmol) in ACN (4 mL, 75 mmol) was added 1-methylimidazole (0.1 g, 2 mmol) and TCFH (0.3 g, 1 mmol) under inert atmosphere followed by 9A (0.3 g, 0.5 mmol) at room temperature. The reaction mixture was stirred at 65° C. for 16 h. After consumption of the starting material (by TLC), reaction mixture was quenched with cold water then diluted and extracted with EtOAc. The crude was purified by prep HPLC to afford the I-169 (20 mg, 5%) as a white solid. The following table shows the conditions to obtain the desired compounds.

| Sr. No | Cpd. Number | Structure (R) | Method | 9A (mg) | Linker Qty (mg) | Qty (mg) & Nature of compound | Yield (%) |
|---|---|---|---|---|---|---|---|
| 1. | I-141 | 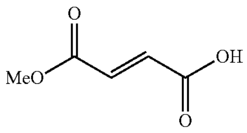 | A | 300 | 90 | 101 (Off-white) | 30 |
| 2. | I-80 | 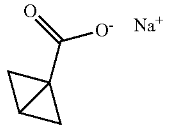 | A | 250 | 110 | 20 (Off-white) | 5.20 |
| 3. | I-123 | 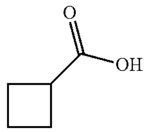 | B | 200 | 60 | 120 (Off-white) | 50 |
| 4. | I-124 | 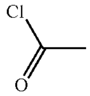 | C | 200 | 30 | 140 (Off-White) | 60 |
| 5. | I-103 | 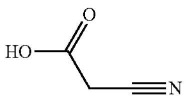 | D | 120 | 80 | 80 (white) | 30 |

-continued

| Sr. No | Cpd. Number | Structure (R) | Method | 9A (mg) | Linker Qty (mg) | Qty (mg) & Nature of compound | Yield (%) |
|---|---|---|---|---|---|---|---|
| 6. | I-169 | 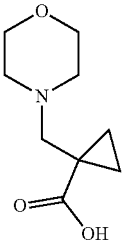 [SMILES: O=C(O)C1(CN2CCOCC2)CC1] | E | 300 | 100 | 20 (white) | 5 |

I-141

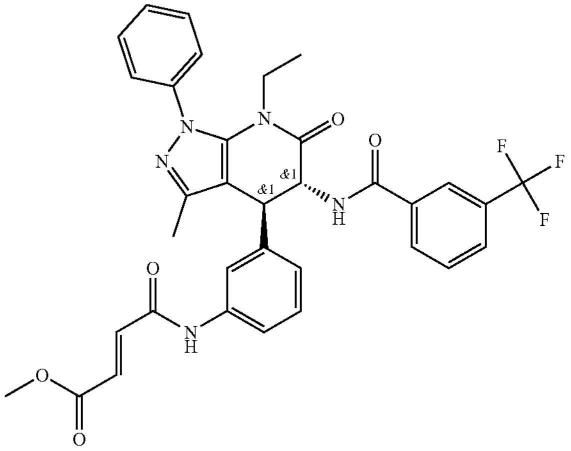 [SMILES: CCN1C(=O)[C@H](NC(=O)c2cccc(C(F)(F)F)c2)[C@@H](c2cccc(NC(=O)/C=C/C(=O)OC)c2)c2c(C)nn(-c3ccccc3)c21]

$^1$H NMR (400 MHz, DMSO-$d_6$) (δ=10.57 (s, 1H), 9.01 (d, J=8.8 Hz, 1H), 8.02-8.00 (m, 2H), 7.89 (d, J=7.6 Hz, 1H), 7.71-7.67 (m, 2H), 7.64-7.60 (m, 3H), 7.58-7.54 (m, 2H), 7.51-7.47 (m, 1H), 7.33-7.29 (m, 1H), 7.22-7.14 (m, 2H), 6.70 (d, J=15.6 Hz, 1H), 5.20-5.15 (m, 1H), 4.35 (d, J=12.0 Hz, 1H), 3.80-3.74 (m, 4H), 3.12-3.07 (m, 1H), 1.52 (s, 3H), 0.81 (t, J=6.8 Hz, 3H). LC-MS (Method-C)=646.3 [M+H]$^+$; 99.79% at RT 2.52 min. HPLC (Method-A)=99.19% at RT 6.00 min. Chiral-HPLC (Method-B)=Peak-1=51.98% at RT 4.07 min. Peak-2=48.01% at RT 5.81 min.

I-80

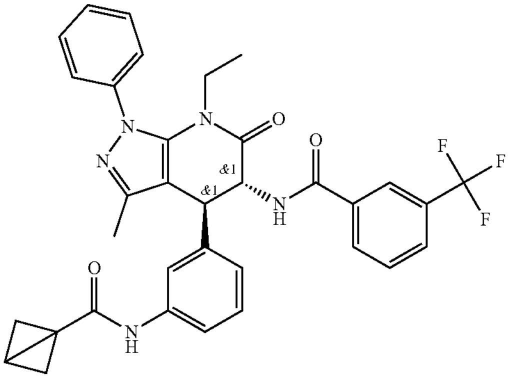 [SMILES: CCN1C(=O)[C@H](NC(=O)c2cccc(C(F)(F)F)c2)[C@@H](c2cccc(NC(=O)C34CC3C4)c2)c2c(C)nn(-c3ccccc3)c21]

$^1$H NMR (400 MHz, DMSO-$d_6$) δ=9.65 (s, 1H), 8.99 (d, J=8.8 Hz, 1H), 8.02-8.01 (m, 2H), 7.89 (d, J=7.6 Hz, 1H), 7.71-7.67 (m, 1H), 7.64-7.54 (m, 6H), 7.50-7.49 (m, 1H), 7.25-7.21 (m, 1H), 7.06-7.04 (m, 1H), 5.15-5.10 (m, 1H), 4.31 (d, J=12 Hz, 1H), 3.80-3.75 (m, 1H), 3.39-3.35 (m, 1H), 3.23-3.16 (m, 1H), 3.12-3.07 (m, 1H), 2.38 (s, 1H), 2.20-2.19 (m, 1H), 1.58-1.49 (m, 3H), 0.94-0.88 (m, 1H), 0.82-0.79 (m, 3H). LC-MS (Method-B)=614.25 [M+H]$^+$; 99.00% at RT 2.05 min. HPLC (Method-B)=97.39% at RT 8.25 min. Chiral-HPLC (Method-B)=Peak-1=50.63% at RT 3.15 min. Peak-2=49.37% at RT 3.75 min.

I-123

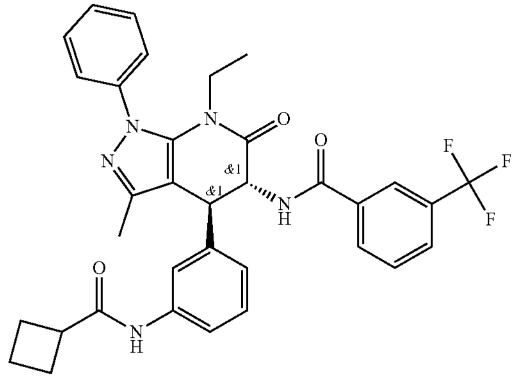 [SMILES: CCN1C(=O)[C@H](NC(=O)c2cccc(C(F)(F)F)c2)[C@@H](c2cccc(NC(=O)C3CCC3)c2)c2c(C)nn(-c3ccccc3)c21]

$^1$H NMR (400 MHz, DMSO-$d_6$) δ=9.65 (s, 1H), 8.99 (d, J=8.8 Hz, 1H), 8.02-8.00 (m, 2H), 7.89 (d, J=7.6 Hz, 1H), 7.69 (s, 1H), 7.63-7.54 (m, 6H), 7.51-7.49 (m, 1H), 7.23 (t, J=8.0 Hz, 1H), 7.04 (d, J=7.2 Hz, 1H), 5.16-5.11 (m, 1H), 4.31 (d, J=12 Hz, 1H), 3.78-3.76 (m, 1H), 3.20-3.16 (m, 1H), 3.12-3.08 (m, 1H), 2.19-2.15 (m, 2H), 2.07-2.05 (m, 2H), 1.94-1.88 (m, 1H), 1.81-1.71 (m, 1H), 1.51 (s, 3H), 0.81 (t, J=7.2 Hz, 3H). LC-MS (Method-C)=616.3 [M+H]$^+$; 97.84% at RT 2.58 min. HPLC (Method-A)=97.40% at RT 6.17 min. Chiral-HPLC (Method-B)=Peak-1=51.20% at RT 4.53 min. Peak-2=48.80% at RT 6.06 min.

I-124

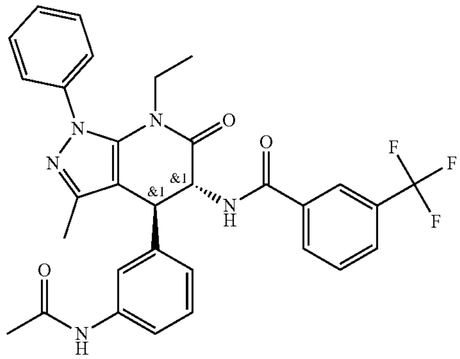 [SMILES: CCN1C(=O)[C@H](NC(=O)c2cccc(C(F)(F)F)c2)[C@@H](c2cccc(NC(C)=O)c2)c2c(C)nn(-c3ccccc3)c21]

$^1$H NMR (400 MHz, DMSO-$d_6$) δ=9.92 (s, 1H), 8.99 (d, J=8.8 Hz, 1H), 8.02-8.00 (m, 2H), 7.89 (d, J=7.2 Hz, 1H), 7.69 (t, J=7.6 Hz, 1H), 7.63-7.61 (m, 2H), 7.63-7.54 (m, 4H), 7.50-7.47 (m, 1H), 7.24 (t, J=7.6 Hz, 1H), 7.05 (d, J=7.6 Hz, 1H), 5.18-5.13 (m, 1H), 4.30 (d, J=12 Hz, 1H), 3.79-3.74 (m, 1H), 3.13-3.05 (s, 1H), 1.99 (s, 3H), 1.50 (s, 3H), 0.81 (t, J=6.8 Hz, 3H). LC-MS (Method-A)=574.34 [M−H]$^-$; 97.20% at RT 2.18 min. HPLC (Method-A)=97.26% at RT 5.69 min. Chiral-HPLC (Method-B)=Peak-1=50.32% at RT 4.80 min. Peak-2=49.68% at RT 6.82 min.

I-103

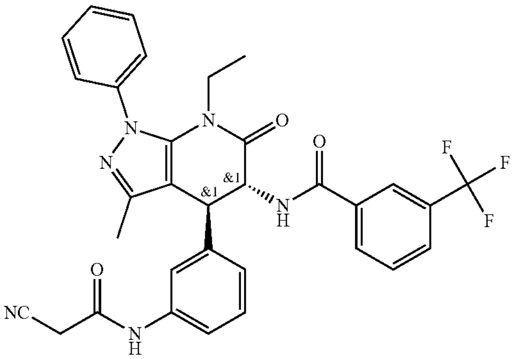 [SMILES: CCN1C(=O)[C@H](NC(=O)c2cccc(C(F)(F)F)c2)[C@@H](c2cccc(NC(=O)CC#N)c2)c2c(C)nn(-c3ccccc3)c21]

$^1$H NMR (400 MHz, DMSO-$d_6$) δ=10.32 (s, 1H), 9.01 (d, J=8.2 Hz, 1H), 8.02 (s, 2H), 7.90 (d, J=6.8 Hz, 1H), 7.70 (s, 1H), 7.63-7.51 (m, 7H), 7.29 (t, J=8.0 Hz, 1H), 7.12 (d, J=6.4 Hz, 1H), 5.17 (t, J=10.4 Hz, 1H), 4.34 (d, J=8.0 Hz, 1H), 3.85-3.76 (m, 3H), 3.17-3.06 (m, 1H), 1.52 (d, J=17.2 Hz, 3H), 0.81 (s, 3H). LC-MS (Method-A)=599.42[M−H]$^-$; 96.92% at RT 2.36 min. HPLC (Method-A)=97.15% at RT 5.70 min. Chiral-HPLC (Method-B)=Peak-1=51.87% at RT 4.29 min. Peak-2=48.13% at RT 5.00 min.

I-169

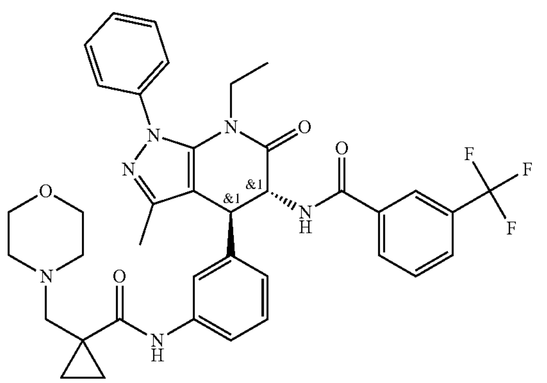 [SMILES: CCN1C(=O)[C@H](NC(=O)c2cccc(C(F)(F)F)c2)[C@@H](c2cccc(NC(=O)C3(CN4CCOCC4)CC3)c2)c2c(C)nn(-c3ccccc3)c21]

$^1$H NMR (400 MHz, DMSO-$d_6$) δ=11.07 (s, 1H), 9.03 (d, J=8.8 Hz, 1H), 8.04-8.02 (m, 2H), 7.90 (d, J=7.2 Hz, 1H), 7.69 (t, J=8.0 Hz, 1H), 7.63-7.49 (m, 7H), 7.29 (t, J=7.6 Hz, 1H), 7.08 (d, J=7.6 Hz, 1H), 5.20-5.15 (m, 1H), 4.33 (d, J=12 Hz, 1H), 3.80-3.74 (m, 1H), 3.67 (s, 4H), 3.12-3.06 (m, 1H), 2.59-2.55 (m, 2H), 2.50-2.49 (m, 4H), 1.53 (s, 3H), 1.10-1.09 (m, 2H), 0.81 (t, J=6.8 Hz, 3H), 0.62-0.61 (m, 2H). LC-MS (Method-B)=701.2 [M+H]$^+$; 98.14% at RT 2.24 min. HPLC (Method-B)=97.97% at RT 9.00 min.

Synthesis of ~{N}—[~{rac}-(4~{S},5~{R})-7-ethyl-3-methyl-4-(3-nitrophenyl)-6-oxo-1-phenyl-4,5-dihydropyrazolo[3,4-b]pyridin-5-yl]-3-(trifluoromethyl)benzamide (9B) & ~{N}—[~{rac}-(4-{S},5-{S})-7-ethyl-3-methyl-4-(3-nitrophenyl)-6-oxo-1-phenyl-4,5-dihydropyrazolo[3,4-b]pyridin-5-yl]-3-(trifluoromethyl)benzamide (9C)

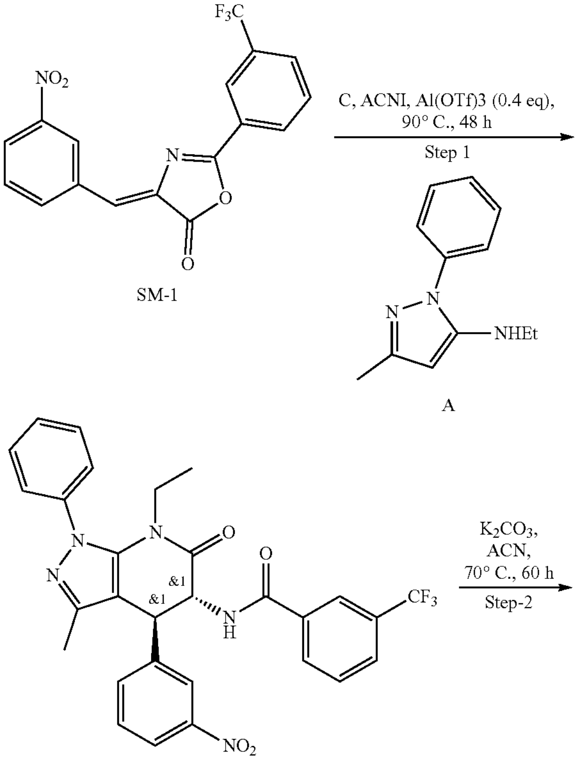

SM-1

A

9B

-continued

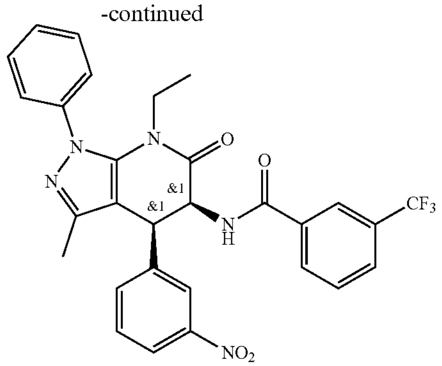

9C

Step-1: Synthesis of ~{N}—[~{rac}-(4~{S}, 5~{R})-7-ethyl-3-methyl-4-(3-nitrophenyl)-6-oxo-1-phenyl-4,5-dihydropyrazolo[3,4-b]pyridin-5-yl]-3-(trifluoromethyl)benzamide (1) (9B)

To a stirred solution of (4-{Z})-4-[(3-nitrophenyl)methylene]-2-[3-(trifluoromethyl)phenyl]oxazol-5-one (15.00 g, 41.40 mmol) in ACN (100 mL, 1910 mmol) were added ~{N}-ethyl-5-methyl-2-phenyl-pyrazol-3-amine (A) (16.67 g, 82.80 mmol), $Al(OTf)_3$ (3.96 g, 8.28 mmol) at 25° C. After completion of addition, temperature was raised to 90° C. and allowed it to stir for 16 h. Reaction mixture was monitored by TLC. If the starting material was remaining, another (0.2 eq) of $Al(OTf)_3$ was added and allowed to stir for 32 h at 90° C. The reaction mixture was cooled to RT and ice cold water was added and the precipitate solid was filtered. The obtained solid was purified by medium pressure column chromatography to afford 9B (9 g, 38.58%) as a pale brown solid. $^1$H NMR (400 MHz, DMSO-$d_6$) δ=9.04 (d, J=8.8 Hz, 1H), 8.30-8.29 (m, 1H), 8.15-8.13 (m, 1H), 7.99-7.97 (m, 2H), 7.89 (d, J=7.6 Hz, 2H), 7.70-7.63 (m, 4H), 7.59-7.55 (m, 2H), 7.51-7.48 (m, 1H), 5.39-5.34 (m, 1H), 4.56 (d, J=12.4 Hz, 1H), 3.84-3.75 (m, 1H), 3.12-3.03 (m, 1H), 1.47 (s, 3H), 0.82 (t, J=7.2 Hz, 3H). LC-MS (Method-A)=564.70 $[M+H]^+$; 97.41% at RT 2.30 min. HPLC (Method-A)=96.75% at RT 6.23 min. Chiral-HPLC (Method-B)=Peak-1=50.51% at RT 5.11 min. Peak-2=49.48% at RT 6.98 min.

Step-2: Synthesis of ~{N}—[~{rac}-(4-{S},5-{S})-7-ethyl-3-methyl-4-(3-nitrophenyl)-6-oxo-1-phenyl-4,5-dihydropyrazolo[3,4-b]pyridin-5-yl]-3-(trifluoromethyl)benzamide (9C)

To a stirred a solution of 9B (200 mg, 0.35 mmol) was added potassium carbonate (0.147 g, 1.06 mmol) in ACN (2.5 mL) and stirred at 70° C. for 60 h. After consumption of the starting material (by TLC and LCMS), the reaction mixture was diluted with EtOAC and washed with cold water. The organic layer was dried over anhydrous $Na_2SO_4$, filtered, and concentrated under reduced pressure. The resultant crude material was purified by medium-pressure liquid column chromatography by eluting with 40-50% EtOAc in heptane to afford 9C (35 mg, 17.50%) as off white solid. $^1$H NMR (400 MHz, DMSO-$d_6$) δ=8.70 (d, J=7.6 Hz, 1H), 8.16-8.13 (m, 3H), 7.91 (d, J=8.0 Hz, 1H), 7.81 (t, J=20 Hz, 1H), 7.70-7.66 (m, 3H), 7.61-7.56 (m, 3H), 7.53-7.46 (m, 2H), 5.64 (t, J=7.6 Hz, 1H), 4.67 (d, J=7.2 Hz, 1H), 4.00-3.98 (m, 1H), 3.01-2.99 (m, 1H), 2.07-2.05 (m, 3H), 0.96 (t, J=7.2 Hz, 3H). LC-MS (Method-A)=562.34 $[M-H]^-$; 98.28% at RT 2.39 min. HPLC (Method-B)=99.62% at RT 9.12 min. Chiral-HPLC (Method-B)=Peak-1=50.03% at RT 8.83 min. Peak-2=49.96% at RT 10.46 min.

Synthesis of ~{N}—[~{rac}-(4~{S},5~{R})-7-ethyl-3-methyl-6-oxo-1-phenyl-4-[3-[[~{rac}-(~{E})-2-cyano-4,4-dimethyl-pent-2-enoyl]amino]phenyl]-4,5-dihydropyrazolo[3,4-b]pyridin-5-yl]-3-(trifluoromethyl)benzamide (I-69)

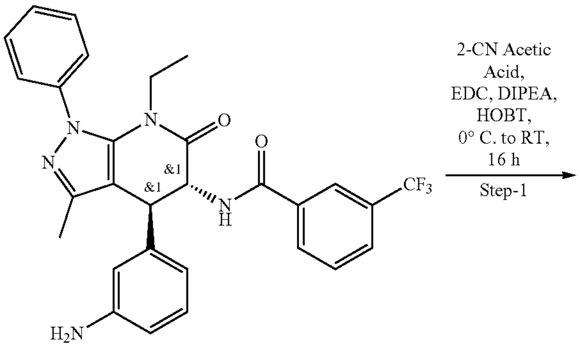

9A

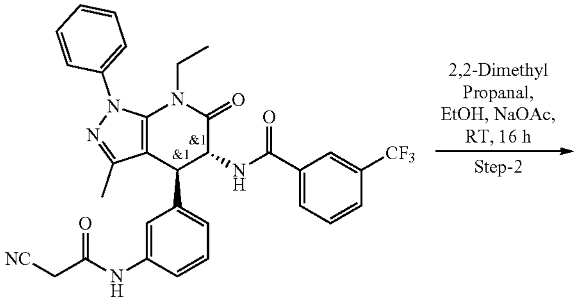

1

-continued

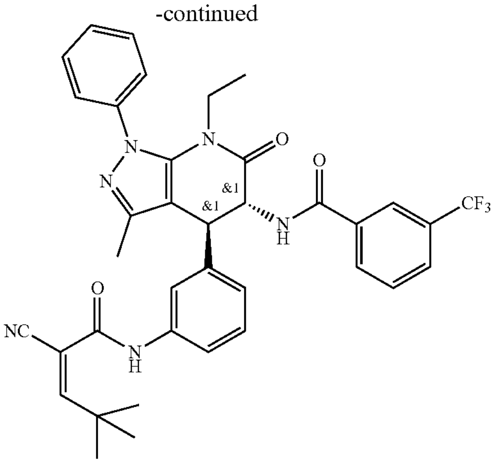

I-69

Step-1: Synthesis of ~{N}—[~{rac}-(4~{S}, 5~{R})-4-[3-[(2-cyanoacetyl)amino]phenyl]-7-ethyl-3-methyl-6-oxo-1-phenyl-4,5-dihydropyrazolo[3,4-b]pyridin-5-yl]-3-(trifluoromethyl)benzamide (1)

To a stirred solution of 2-cyanoacetic acid (0.2 g, 3 mmol) in DMF (7 mL), was added EDCI (0.4 g, 2 mmol), 9A (0.5 g, 0.9 mmol) at 0° C. under inert atmosphere followed by the addition of N,N-Diisopropylethylamine (0.4 g, 3 mmol) and 1-hydroxybenzotriazole (0.3 g, 2 mmol). Then the reaction mixture was stirred at room temp for 16 h. After consumption of the starting material (by TLC), the reaction mixture was diluted with water and extracted using EtOAc (20.00 mL×2). The organic layer was dried over anhydrous $Na_2SO_4$, filtered, and concentrated under reduced pressure. The obtained crude material was purified by silica gel column chromatography compound eluting with 45-50% EtOAc: Heptane to afford compound (1) (0.4 g, 70%) as an off-white colour solid. $^1H$ NMR (400 MHz, DMSO-$d_6$) δ=10.32 (s, 1H), 9.02 (d, J=8.8 Hz, 1H), 8.06-8.01 (m, 2H), 7.90 (d, J=8.0 Hz, 1H), 7.70 (t, J=7.2 Hz, 1H), 7.63-7.61 (m, 2H), 7.59-7.49 (m, 5H), 7.29 (t, J=7.6 Hz, 1H), 7.12 (d, J=7.6 Hz, 1H), 5.20-5.15 (m, 1H), 4.33 (d, J=12 Hz, 1H), 3.85 (s, 2H), 3.80-3.74 (m, 1H), 3.11-3.05 (m, 1H), 1.54 (s, 3H), 0.81 (t, J=6.8, 3H). LC-MS (Method-B)=601.1 $[M+H]^+$; 91.00% at RT 2.12 min.

Step-2: Synthesis of ~{N}—[~{rac}-(4~{S}, 5~{R})-7-ethyl-3-methyl-6-oxo-1-phenyl-4-[3-[[~{rac}-(~{E})-2-cyano-4,4-dimethyl-pent-2-enoyl]amino]phenyl]-4,5-dihydropyrazolo[3,4-b]pyridin-5-yl]-3-(trifluoromethyl)benzamide (2) (I-69)

To a stirred solution of compound (1) (0.2 g, 0.3 mmol) in Ethanol (6 mL), was added ammonium acetate (0.05 g, 0.7 mmol), 2,2-dimethylpropanal (0.06 g, 0.7 mmol). Then the reaction mixture was stirred at room temperature for 16 h. After consumption of the starting material (by TLC), the reaction mixture was diluted with water and extracted by using EtOAc (20.00 mL×2). The organic layer was dried over anhydrous $Na_2SO_4$, filtered, and concentrated under reduced pressure. The obtained crude material was purified by silica gel column chromatography followed by preparative HPLC to afford I-69 (0.05 g, 20%) as an off-white colour solid. $^1H$ NMR (400 MHz, DMSO-$d_6$) δ=10.21 (s, 1H), 9.00 (d, J=8.8 Hz, 1H), 8.02-8.00 (m, 2H), 7.89 (d, J=8.0 Hz, 1H), 7.69 (t, J=8.0 Hz, 1H), 7.63-7.61 (m, 3H), 6.58-6.54 (m, 3H), 7.51-7.47 (m, 1H), 7.42 (s, 1H), 7.31 (t, J=8.0 Hz, 1H), 7.16 (d, J=7.6 Hz, 1H), 5.19-5.14 (m, 1H), 4.35 (d, J=12.4 Hz, 1H), 3.81-3.76 (m, 1H), 3.11-3.06 (m, 1H), 1.52 (s, 3H), 1.26 (s, 9H), 0.81 (t, J=6.8 Hz, 3H). LC-MS (Method-C)=669.2 $[M+H]^+$; 99.84% at RT 3.74 min. HPLC (Method-C)=96.92% at RT 6.50 min. Chiral-HPLC (Method-B)=Peak-1=50.45% at RT 5.22 min. Peak-2=44.32% at RT 7.98 min. Peak-3=5.23% at RT 4.52 min.

Synthesis of ~{N}—[~{rac}-(4~{S},5~{R})-4-[3-[allyl(prop-2-enoyl)amino]phenyl]-7-ethyl-3-methyl-6-oxo-1-phenyl-4,5-dihydropyrazolo[3,4-b]pyridin-5-yl]-3-(trifluoromethyl) benzamide (I-28)

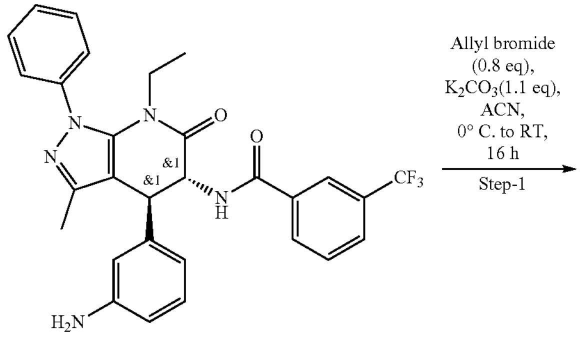

9A

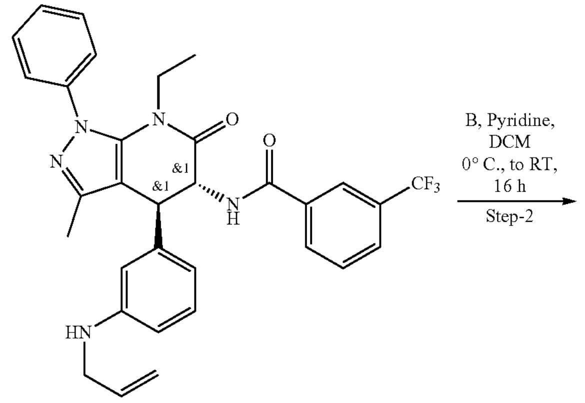

1

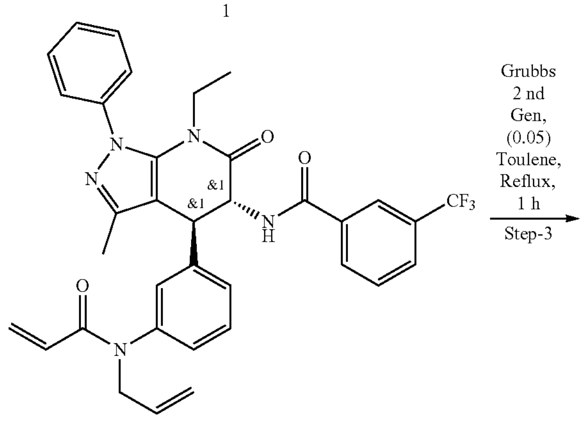

2

-continued

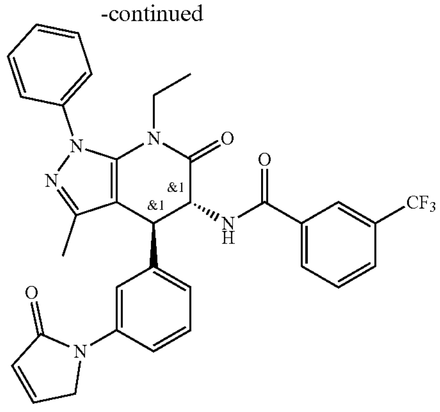

I-28

Step-1: Synthesis of ~{N}—[~{rac}-(4~{S}, 5~{R})-4-[3-(allylamino)phenyl]-7-ethyl-3-methyl-6-oxo-1-phenyl-4,5-dihydropyrazolo[3,4-b]pyridin-5-yl]-3-(trifluoromethyl) benzamide (1)

To a stirred solution of 9A (500 mg, 0.88 mmol) in DMF (10 mL) was added Potassium carbonate (200 mg, 1.45 mmol) followed by allyl bromide (100 mg, 0.81 mmol) at 0° C. The resulting reaction mixture was stirred at room temperature for 16 h. Progress of the reaction was monitored by LC-MS and TLC. Then the reaction mixture was quenched with ice-cold water (25 mL), aqueous layer was extracted with EtOAc (2×30 mL), combined organic layer was dried over $Na_2SO_4$, filtered and concentrated under reduced pressure to afford the crude compound. The crude compound was purified by combi-flash column chromatography. Compound eluted at 30% to 60% EtOAc in pet-ether, pure fractions were collected then concentrated under reduced pressure and dried to afford compound (1) (210.00 mg, 41.16%) as a pale-yellow solid. $^1$H NMR (400 MHz, DMSO-$d_6$) δ=8.97 (d, J=8.8 Hz, 1H), 8.05-8.02 (m, 2H), 7.90 (d, J=8.0 Hz, 1H), 7.70 (t, J=7.6 Hz, 1H), 7.61-7.53 (m, 4H), 7.49-7.46 (m, 1H), 7.01 (t, J=8.0 Hz, 1H), 6.58-6.53 (m, 2H), 6.43 (d, J=8.0 Hz, 1H), 5.89-5.79 (m, 2H), 5.18-5.13 (m, 2H), 5.02 (d, J=10.4 Hz, 1H), 4.20 (d, J=12 Hz, 1H), 3.86-3.73 (m, 1H), 3.70 (t, J=6.8 Hz, 2H), 3.15-3.05 (m, 1H), 1.53-1.51 (m, 3H), 0.80 (t, J=6.8 Hz, 3H). LC-MS (Method-A)=574.29 $[M+H]^+$; 95.63% at RT 1.62 min.

Step-2: Synthesis of ~{N}—[~{rac}-(4~{S}, 5~{R})-4-[3-[allyl(prop-2-enoyl)amino]phenyl]-7-ethyl-3-methyl-6-oxo-1-phenyl-4,5-dihydropyrazolo [3,4-b]pyridin-5-yl]-3-(trifluoromethyl)benzamide (2)

To the stirred solution of compound (1) (200 mg, 0.33 mmol) in dichloromethane (3 mL) was added pyridine (80 mg, 1.01 mmol) followed by acryloyl chloride (40 mg, 0.42 mmol) at 0° C. The resulting reaction mixture was stirred at room temperature for 16 h. Progress of the reaction was monitored by LC-MS and TLC. Then the reaction mixture was quenched with ice-cold water (20 mL), aqueous layer extracted with EtOAc (2×25 mL) combined organic layer was dried over $Na_2SO_4$, filtered, and concentrated under reduced pressure to afford the crude compound. The crude compound was purified by combi-flash column chromatography. Compound eluted at 20% to 50% EtOAc in pet-ether, pure fractions were collected then concentrated under reduced pressure and dried to afford compound (2) (180 mg, 34.79%) as a pale-yellow solid. $^1$H NMR (400 MHz, DMSO-$d_6$) δ=9.07-8.90 (m, 1H), 8.01 (s, 2H), 7.95-7.85 (m, 1H), 7.60-7.56 (m, 6H), 7.40 (s, 2H), 7.30-7.20 (m, 3H), 5.72-5.60 (m, 1H), 5.42-5.31 (m, 1H), 4.95-4.85 (m, 2H), 4.40-4.20 (m, 3H), 3.81-3.89 (m, 1H), 3.62-3.58 (m, 1H), 3.09-2.98 (m, 1H), 2.35-2.25 (m, 1H), 1.49-1.47 (m, 3H), 0.81 (t, J=6.8 Hz, 3H). LC-MS (Method-A)=628.38 $[M+H]^+$; 40.45% at RT 2.41 min.

Step-3: Synthesis of rac-N-((4R,5S)-7-ethyl-3-methyl-6-oxo-4-(3-(2-oxo-2,5-dihydro-1H-pyrrol-1-yl)phenyl)-1-phenyl-4,5,6,7-tetrahydro-1H-pyrazolo [3,4-b]pyridin-5-yl)-3-(trifluoromethyl)benzamide (3) (I-28)

A stirred solution of compound (2) (160 mg, 0.10 mmol) in toluene (3 mL) was purged with argon gas for 10 min, then (1,3-Bis(2,4,6-trimethylphenyl)-2-imidazolidinylidene)dichloro(phenylmethylene)(tricyclohexylphosphine)ruthenium (5 mg, 0.005 mmol) was added to the reaction mixture at room temperature. The resulting reaction mixture was stirred at 75° C. for 3 h. Progress of the reaction was monitored by LC-MS and TLC. After completion of the reaction, the reaction mixture was diluted with ice-cold water (10 mL), extracted with EtOAc (2×15 mL), combined organic layer was washed with brine solution (2×10 mL), organic layer was dried over anhydrous $Na_2SO_4$, filtered and concentrated under reduced pressure to afford the crude compound. The crude compound was purified by combi-flash column chromatography. Compound was eluted at 40% to 80% EtOAc in n-pentane, pure fractions were collected then concentrated under reduced pressure to afford compound (40 mg) with 53.28% purity by LC-MS, which was further purified by prep-HPLC to afford I-28 (12 mg, 19.26%) as an off-white solid. $^1$H NMR (400 MHz, DMSO-$d_6$) δ=8.99 (d, J=8.8 Hz, 1H), 8.01-8.00 (m, 2H), 7.89-7.86 (m, 2H), 7.70-7.54 (m, 4H), 7.50-7.43 (m, 4H), 7.34 (t, J=8.0 Hz, 1H), 7.14 (d, J=7.6 Hz, 1H), 6.23 (d, J=20 Hz, 1H), 5.28-5.23 (m, 1H), 4.57-4.52 (m, 2H), 4.36 (d, J=12 Hz, 1H), 3.81-3.74 (m, 1H), 3.13-3.04 (m, 1H), 1.51 (s, 3H), 0.81 (t, J=6.8 Hz, 3H).

LC-MS (Method-A)=598.42 $[M-H]^-$; 99.95% at RT 2.31 min. HPLC (Method-A)=97.54% at RT 5.79 min. Chiral-HPLC (Method-B)=Peak-1=50.66% at RT 6.59 min. Peak-2=49.34% at RT 8.46 min.

Synthesis of N-((4R,5S)-4-(3-(cyclobut-1-ene-1-carboxamido)phenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (I-70) & N-((4S,5R)-4-(3-(cyclobut-1-ene-1-carboxamido)phenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (I-94)

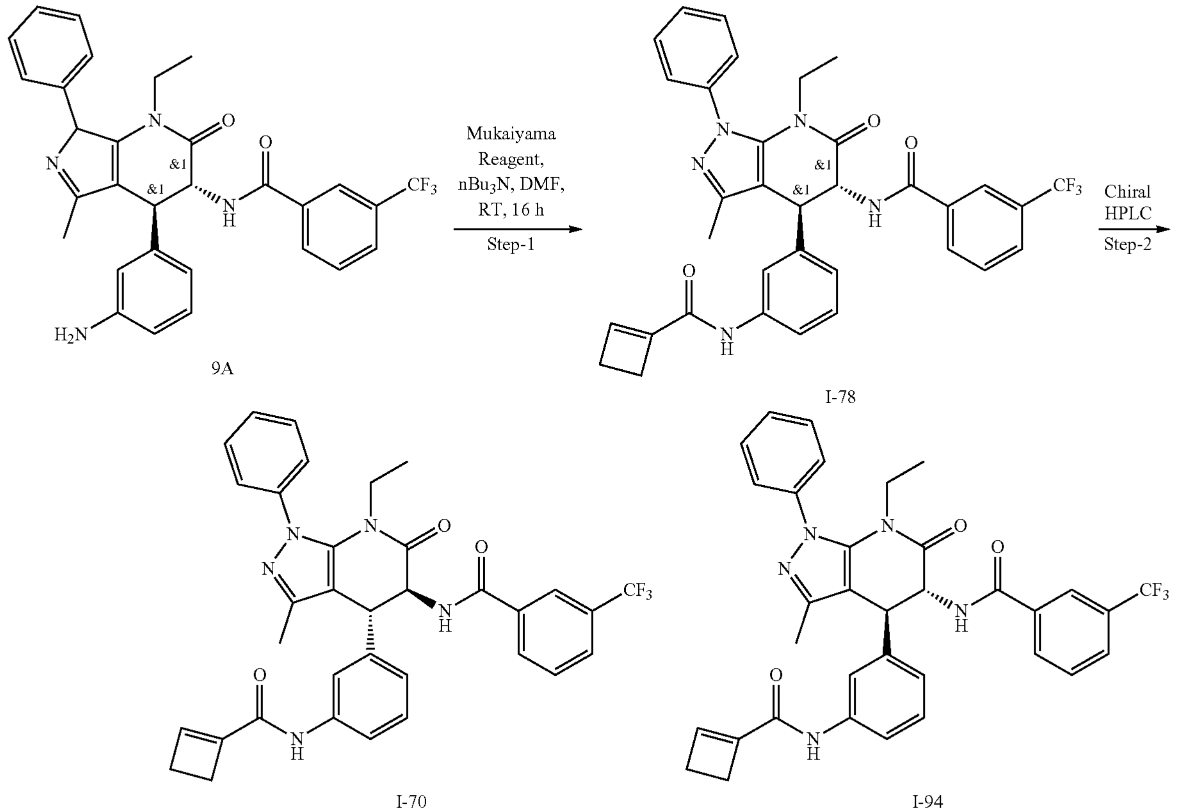

9A

I-78

I-70

I-94

Step-1: Synthesis of ~{N}—[~{rac}-(4~{S}, 5~{R})-4-[3-(cyclobutene-1-carbonylamino)phenyl]-7-ethyl-3-methyl-6-oxo-1-phenyl-4,5-dihydropyrazolo[3,4-b]pyridin-5-yl]-3-(trifluoromethyl)benzamide (1) (I-78)

To a stirred solution of cyclobutene-1-carboxylic acid (0.28 g, 2.8 mmol) in DMF (10 mL), was added 9A (1.0 g, 1.9 mmol), and tributylamine (1.4 g, 7.5 mmol) at 0° C. under inert atmosphere followed by the addition of 2-chloro-1-methylpyridinium iodide (0.74 g, 2.8 mmol). Then the reaction mixture was stirred at room temp for 16 h. After consumption of the starting material (by TLC), the reaction mixture was diluted with water and extracted by using EtOAc (20.00 mL×2). The organic layer was dried over anhydrous $Na_2SO_4$, filtered, and concentrated under reduced pressure. The obtained crude material was purified by silica gel column chromatography. A compound was eluted at 35-40% EtOAc:PE to afford I-78 (0.280 g, 24%) as an off-white colour solid. $^1H$ NMR (400 MHz, CDCL3-$d_6$) δ=7.88 (s, 1H), 7.81 (d, J=7.6 Hz, 1H), 7.71-7.69 (m, 2H), 7.52-7.43 (m, 7H), 7.33 (t, J=7.6 Hz, 1H), 7.17 (d, J=7.6 Hz, 1H), 6.74 (s, 1H), 6.51 (d, J=8.8 Hz, 1H), 5.43-5.38 (m, 1H), 4.14 (d, J=13.2 Hz, 1H), 3.96-3.91 (m, 1H), 3.18-3.13 (m, 1H), 2.80-2.78 (m, 2H), 2.52-2.50 (m, 2H), 1.63 (s, 3H), 0.92 (t, J=7.2 Hz, 3H). LC-MS (Method-B)=614.0 [M+H]$^+$; 99.94% at RT 2.24 min. HPLC (Method-B)=97.97% at RT 8.44 min. Chiral-HPLC (Method-A)=Peak-1=52.09% at RT 3.79 min. Peak-2=47.91% at RT 6.57 min.

Step-2: Synthesis of N-((4R,5S)-4-(3-(cyclobut-1-ene-1-carboxamido)phenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (I-70) & N-((4S,5R)-4-(3-(cyclobut-1-ene-1-carboxamido)phenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (2) (I-94)

I-78 was purified by chiral-prep purification then the fraction was collected and concentrated to afford the desired compound I-70 (0.065 g, 31%) as an off-white solid and I-94 (0.065 g, 31%) as a white solid.

(I-70)

$^1H$ NMR (400 MHz, DMSO-$d_6$) δ=9.75 (s, 1H), 9.00 (d, J=8.8 Hz, 1H), 8.02-8.00 (m, 2H), 7.89 (d, J=7.6 Hz, 1H), 7.71-7.54 (m, 7H), 7.51-7.47 (m, 1H), 7.26 (t, J=7.6 Hz, 1H), 7.08 (d, J=8.0 Hz, 1H), 6.75 (s, 1H), 5.18-5.12 (m, 1H), 4.33 (d, J=12.4 Hz, 1H), 3.81-3.75 (m, 1H), 3.13-3.05 (m, 1H), 2.68-2.67 (m, 2H), 2.39 (s, 2H), 1.51 (s, 3H), 0.81 (t, J=7.2 Hz, 3H). LC-MS (Method-B)=614.25 $[M+H]^+$; 96.49% at RT 2.06 min. HPLC (Method-B)=99.36% at RT 8.40 min. Chiral-HPLC (Method-C)=Peak-1=100% at RT 3.88 min.

(I-94)

$^1$H NMR (400 MHz, DMSO-$d_6$) δ=9.76 (s, 1H), 9.00 (d, J=8.8 Hz, 1H), 8.02-8.00 (m, 2H), 7.89 (d, J=7.6 Hz, 1H), 7.71-7.47 (m, 8H), 7.26 (t, J=7.6 Hz, 1H), 7.08 (d, J=8.0 Hz, 1H), 6.75 (s, 1H), 5.18-5.13 (m, 1H), 4.33 (d, J=12.0 Hz, 1H), 3.81-3.75 (m, 1H), 3.11-3.06 (m, 1H), 2.68-2.67 (m, 2H), 2.39 (s, 2H), 1.51 (s, 3H), 0.81 (t, J=7.2 Hz, 3H). LC-MS (Method-B)=612.44$[M-H]^-$; 98.05% at RT 2.05 min. HPLC (Method-B)=98.69% at RT 10.33 min. Chiral-HPLC (Method-C)=Peak-1=2.39% at RT 3.88 min. Peak-2=97.61% at RT 7.11 min.

Synthesis of N-((4R,5S)-7-ethyl-3-methyl-4-(3-(2-(morpholinomethyl)acrylamido)phenyl)-6-oxo-1-phenyl-4,5,6,7-tetrahydro-1H-pyrazolo[3,4-b]pyridin-5-yl)-3-(trifluoromethyl)benzamide & N-((4S,5R)-7-ethyl-3-methyl-4-(3-(2-(morpholinomethyl)acrylamido)phenyl)-6-oxo-1-phenyl-4,5,6,7-tetrahydro-1H-pyrazolo[3,4-b]pyridin-5-yl)-3-(trifluoromethyl)benzamide (I-2) & (I-83)

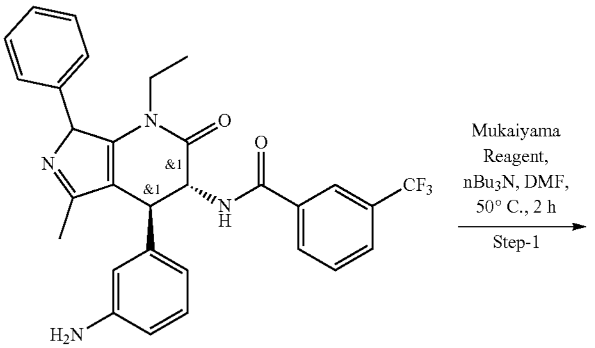

9A

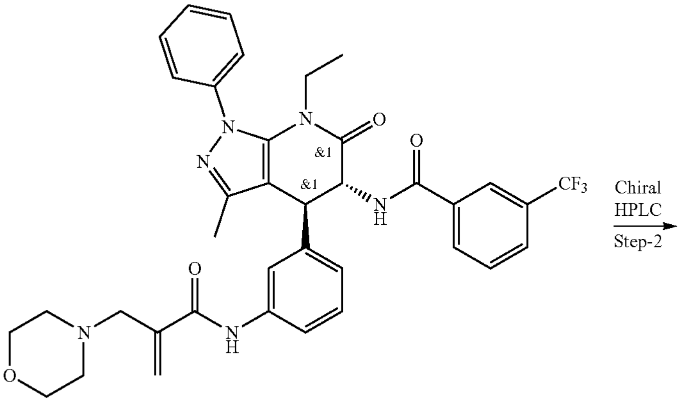

I-9

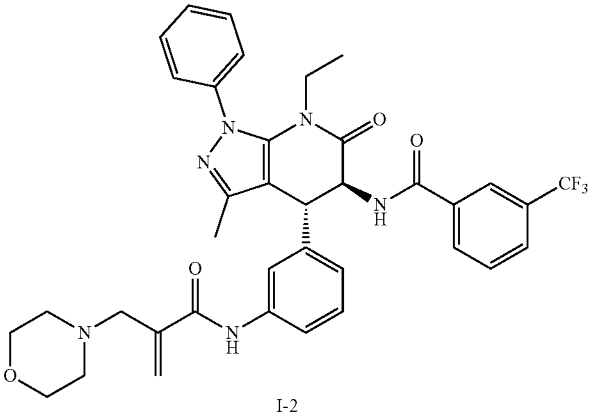

I-2

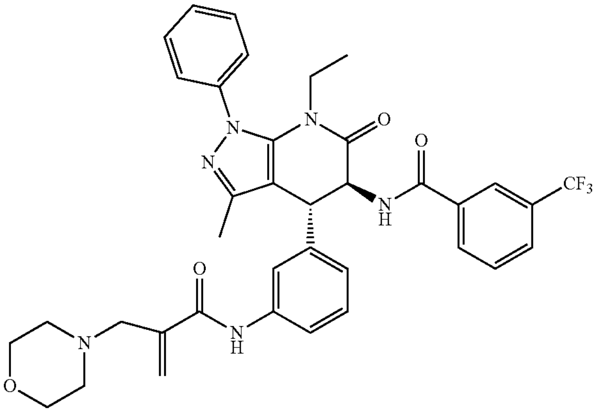

I-83

Step-1: Synthesis of N-[rac-(4S,5R)-7-ethyl-3-methyl-4-[3-[2-(morpholinomethyl)prop-2-enoylamino]phenyl]-6-oxo-1-phenyl-4,5-dihydropyrazolo[3,4-b]pyridin-5-yl]-3-(trifluoromethyl)benzamide (1): I-9

To a stirred solution of 9A (500 mg, 0.93 mmol) in DMF (10 mL) was added, 2-(morpholinomethyl) prop-2-enoic acid (0.17 g, 1.03 mmol) and 2-chloro-1-methylpyridinium iodide (0.49 g, 1.87 mmol), tributylamine (0.53 g, 2.81 mmol) at 0° C. and stirred at 50° C. for 2 h. After consumption of the starting material (by TLC), the reaction mixture was diluted with water and extracted by using EtOAc (2.00 mL×2). The organic layer was dried over anhydrous $Na_2SO_4$, filtered, and concentrated under reduced pressure. The obtained crude material was purified by flash column chromatography by using 50-60% EtOAC/Hep to afford I-9 (120 mg, 18.65%) as a white solid. $^1$H NMR (400 MHz, DMSO-$d_6$) δ=11.07 (s, 1H), 9.03 (d, J=8.8 Hz, 1H), 8.04-8.02 (m, 2H), 7.89 (t, J=7.6 Hz, 1H), 7.71-7.47 (m, 8H), 7.31 (t, J=7.6 Hz, 1H), 7.12 (d, J=8.0 Hz, 1H), 6.05 (s, 1H), 5.59 (s, 1H), 5.21-5.16 (m, 1H), 4.35 (d, J=12 Hz, 1H), 3.80-3.75 (m, 1H), 3.62 (t, J=4.4 Hz, 4H), 3.29 (s, 2H), 3.12-3.07 (m, 1H), 2.44 (s, 4H), 1.54 (s, 3H), 0.81 (t, J=7.2 Hz, 3H). LC-MS (Method-B)=687.0 $[M+H]^+$; 99.92% at RT 2.26 min. HPLC (Method-B)=99.58% at RT 8.46 min. Chiral-HPLC (Method-B)=Peak-1=50.57% at RT 4.67 min. Peak-2=49.43% at RT 5.27 min.

Step-2: Synthesis of N-((4R,5S)-7-ethyl-3-methyl-4-(3-(2-(morpholinomethyl)acrylamido)phenyl)-6-oxo-1-phenyl-4,5,6,7-tetrahydro-1H-pyrazolo[3,4-b]pyridin-5-yl)-3-(trifluoromethyl)benzamide & N-((4S,5R)-7-ethyl-3-methyl-4-(3-(2-(morpholinomethyl)acrylamido)phenyl)-6-oxo-1-phenyl-4,5,6,7-tetrahydro-1H-pyrazolo[3,4-b]pyridin-5-yl)-3-(trifluoromethyl)benzamide (I-2) & (I-83)

I-9 was purified by chiral-prep purification, collected fractions were concentrated to afford I-2 (0.22 g, 34%) as a white solid and I-83 (0.24 g, 37%) as a white solid.

(I-2)

$^1$H NMR (400 MHz, DMSO-$d_6$) δ=11.07 (s, 1H), 9.02 (d, J=8.8 Hz, 1H), 8.04-8.02 (m, 2H), 7.89 (d, J=8.0 Hz, 1H), 7.69 (t, J=7.6 Hz, 1H), 7.71-7.54 (m, 6H), 7.51-7.47 (m, 1H), 7.30 (t, J=7.6 Hz, 1H), 7.12 (d, J=7.6 Hz, 1H), 6.05 (s, 1H), 5.58 (s, 1H), 5.21-5.16 (m, 1H), 4.35 (d, J=12 Hz, 1H), 3.80-3.73 (m, 1H), 3.62 (s, 4H), 3.25 (s, 2H), 3.14-3.04 (m, 1H), 2.44 (s, 4H), 1.54 (s, 3H), 0.81 (t, J=6.8 Hz, 3H). LC-MS (Method-B)=687.29 $[M+H]^+$; 99.99% at RT 2.09 min. HPLC (Method-B)=99.98% at RT 8.46 min. Chiral-HPLC (Method-C)=Peak-1=77.73% at RT 11.53 min. Peak-2=22.27% at RT 13.93 min.

(I-83)

$^1$H NMR (400 MHz, DMSO-$d_6$) δ=11.07 (s, 1H), 9.03 (d, J=8.8 Hz, 1H), 8.04-8.02 (m, 2H), 7.89 (d, J=7.6 Hz, 1H), 7.69 (t, J=8.4 Hz, 1H), 7.63-7.49 (m, 7H), 7.30 (t, J=8.0 Hz, 1H), 7.12 (d, J=7.6 Hz, 1H), 6.05 (s, 1H), 5.58 (s, 1H), 5.21-5.15 (m, 1H), 4.35 (d, J=12 Hz, 1H), 3.80-3.74 (m, 1H), 3.62 (s, 4H), 3.29 (s, 2H), 3.12-3.07 (m, 1H), 2.44 (s, 4H), 1.53 (s, 3H), 0.81 (t, J=6.8 Hz, 3H). LC-MS (Method-B)=687.29 $[M+H]^+$; 99.94% at RT 2.09 min.

HPLC (Method-B)=99.51% at RT 8.46 min. Chiral-HPLC (Method-C)=Peak-1=98.84% at RT 13.85 min. Peak-2=1.16% at RT 11.59 min.

Example 10: Synthesis of Compounds I-150, I-48, I-180, I-171, I-193, I-207, I-164, I-201, I-75, I-77, I-78, I-20, I-5, I-209, I-47, I-38, I-146 and I-9

NMR:

$^1$H NMR spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LC-MS:

Method-A: Column: Bakerbond Q2100 C18 1.8 μm; 2.1×50 mm Mobile Phase A: 0.05% FA in Water Mobile Phase B: 0.05% FA in CAN Flow Rate: 0.6 ml Oven Temperature: 40° C. Gradient Program (Time/B %): 0_5, 0.2_5, 2.3_98, 3.3_98, 3.5_5, 4.

Method-B: X-Select CSH C18 (3.0*50 mm, 2.5 μm), Mobile Phase A: 0.05% FA in $H_2O$ Mobile Phase B: 0.05% FA in ACN Gradient % B: 0/2, 0.3/2, 2.0/98, 2.8/98, 3.0/2, 3.7/Flow Rate: 1.0 ml/min, Column Oven Temp: 40° C.

Method-C: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-D: Column: X-Select CSH C18, (50 mm*3.0 mm, 2.5μ) Mobile Phase A: 0.05% TFA in Water Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

Method-E: Column:X-Select CSH C18 (3.0*50 mm, 2.5 μm), Mobile Phase A: 2.5 mM Ammonium Bicarbonate in $H_2O$+5% ACN Mobile Phase B: 100% ACN, Gradient % B: 0/2, 0.3/2, 2.0/98, 2.8/98, 3.0/2, 3.7/2.

Method-F: Column: X-Bridge BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water: CAN (95:05); Mobile phase B: Acetonitrile; Gradient Programme: T/B %: 0.01/5, 1/5, 8/100, 12/100, 14/5, 18/5; Flow rate: 1.2 ml/min.

Method-B: Column: X-Bridge CSH C18 (150×4.6 mm, 3.5 μm); Mobile Phase-A: 5 mM $NH_4HCO_3$; Mobile Phase-B: ACN; Programme: T/B %: 0.01/2, 2/2, 12/90, 16/90; Flow rate: 1.0 mL/min.; Diluent: ACN: WATER (80:20).

Method-C: Column: X-Select CSH C18 (4.6*150) mm 5μ Mobile Phase: A—0.1% TFA in water B—Acetonitrile Inj Volume; 5.0 μL, Flow Rate: 1.2. mL/minute Gradient program: Time(min)/B Conc.: 0.01/5, 1.0/5, 8.0/100, 12.0/100, 14.0/5, 18.0/5.

Method-D: Column: ACE Excel 2 C18-AR,100 mm×3.0 mm Mobile Phase A: 0.05% TFA in Water Mobile Phase B: 0.05% TFA in Acetonitrile Colum Temperature: 40° C. Flow Rate: 0.6 mL/min Gradient: 0/5, 1/5, 6/90, 8.5/90, 8.8/5, 11/5.

Method-E: Column: CHIRALCEL-OJ-H (250×4.6 mm, 5μ) Mobile Phase A: 0.1% DEA in HEXANE Mobile Phase B: IPA A/B: 60/40 Flow: 1.0 ml/MIN PDA: OJ-H_015.

Method-F: Column: CHIRALPAK IG (250×4.6 mm, 5 μm) MobilePhase A: n-HEXANE MobilePhase B: DCM: IPA (1:1) A B: 60:40 Flow rate: LOML/MIN.

Method-G: Column: CHIRALPAK-IA (250×4.6 mm, 5 μm) A B: 70/30 MobilePhase A: n-Hexane MobilePhase B: ETOH:MEOH(1:1) Flow rate: 1.00 ml/min.

Method-H: Column: X-Bridge C18 (4.6*150) mm 5μ Mobile Phase: A—5 mM Ammonium Acetate B—Acetonitrile Flow Rate: 1.0. mL/minute Gradient program: Time (min)/B Conc.: 0.01/5, 1.0/5, 8.0/100, 12.0/100, 14.0/5, 18.0/5.

Synthesis of 10A:

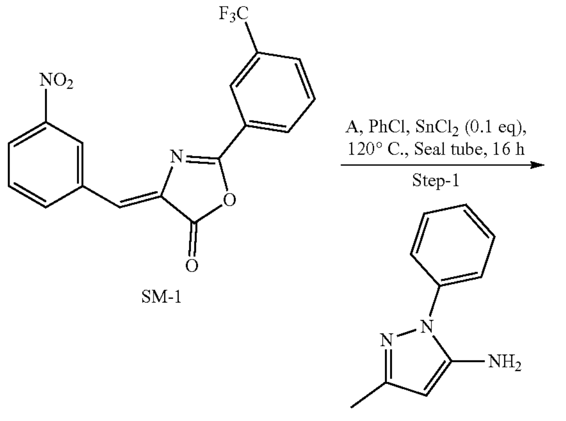

SM-1

A

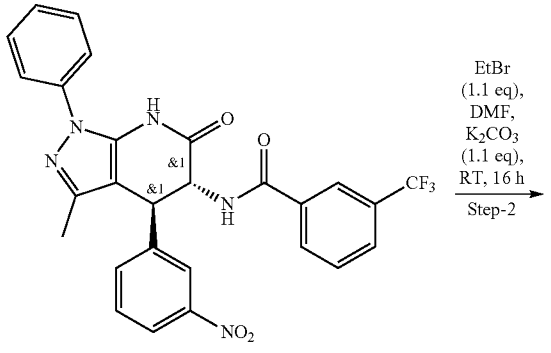

1

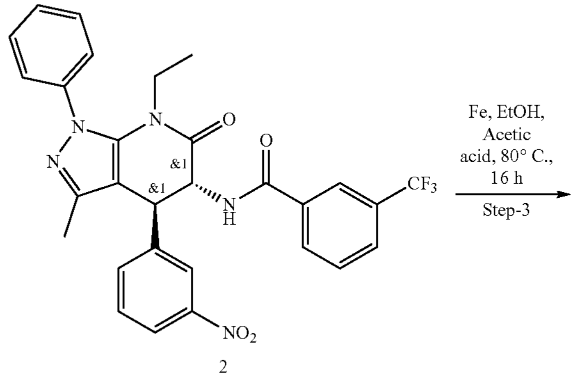

2

-continued

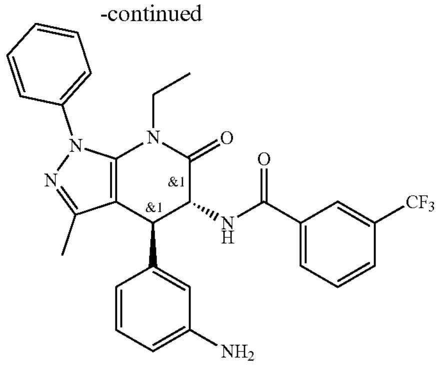

10A

Step-1: Synthesis of rac-N-((4R,5S)-3-methyl-4-(3-nitrophenyl)-6-oxo-1-phenyl-4,5,6,7-tetrahydro-1H-pyrazolo[3,4-b]pyridin-5-yl)-3-(trifluoromethyl) benzamide (1)

In a sealed tube, SM-1 (15 g, 41.36 mmol) in chlorobenzene (150 mL) were added Int-A (7.16 g, 41.36 mmol), and $SnCl_2$ (784 mg, 4.13 mmol) stirred for 16 h at 120° C. After consumption of the starting material (by TLC), the reaction mixture was purified by using column chromatography eluted with 50% ethyl acetate in heptane. Collected the fraction and concentrated in vacuum to afford compound (4) (15 g, 67%) as a pale-yellow solid. $^1H$ NMR (400 MHz, DMSO-$d_6$) (δ=10.9 (s, 1H), 9.02 (d, J=8.8 Hz, 1H), 8.28 (s, 1H), 8.14 (d, J=8.3 Hz, 1H), 8.01-7.87 (m, 2H), 7.71-7.59 (m, 5H), 7.57-7.50 (m, 2H), 7.42-7.36 (m, 2H), 5.16-5.10 (m, 1H), 4.60 (d, J=12.0 Hz, 1H), 1.49 (s, 3H). LC-MS (Method-B)=536.4 $[M+H]^+$; 95.22% at RT 1.34 min.

Step-2: Synthesis of rac-N-((4R,5S)-7-ethyl-3-methyl-4-(3-nitrophenyl)-6-oxo-1-phenyl-4,5,6,7-tetrahydro-1H-pyrazolo[3,4-b]pyridin-5-yl)-3-(trifluoromethyl)benzamide (2)

To a stirred solution of compound (4) (5 g, 9.34 mmol) in DMF (15 mL) was added potassium carbonate (1.67 g, 12.14 mmol) and bromoethane (0.76 mL) at room temperature. The reaction mixture was stirred at room temperature for 16 h. Progress of the reaction was monitored by TLC. After consumption of reaction, the reaction mixture was quenched with ice water extracted with ethyl acetate. Organic layer was dried over sodium sulfate and concentrated under vacuum to afford crude. The crude was purified by flash column chromatography and eluted with 36% ethyl acetate/heptane. Pure fraction was concentrated under vacuum to afford compound (5) (2.0 g, 38%) as a pale-yellow solid. $^1H$ NMR (400 MHz, DMSO-$d_6$) (δ=9.04 (d, J=8.8 Hz, 1H), 8.29 (s, 1H), 8.15-8.13 (m, 1H), 7.99 (s, 2H), 7.89 (d, J=7.2 Hz, 2H), 7.71-7.64 (m, 3H), 7.57 (t, J=6.8 Hz, 2H), 7.51-7.50 (m, 2H), 5.39-5.43 (m, 1H), 4.56 (d, J=12.4 Hz, 1H), 3.80-3.79 (m, 1H), 3.08-3.07 (m, 1H), 1.47 (s, 3H), 0.82 (t, J=6.8 Hz, 3H). LC-MS (Method-B)=564.2 $[M+H]^+$; 93.19% at RT 2.30 min.

Step-3: Synthesis of rac-N-((4R,5S)-4-(3-aminophenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (10A)

To a stirred solution of compound (2) (3 g, 5.32 mmol) and iron (1.49 g, 26.64 mmol) in ethanol (30 mL) was added acetic acid (3.19 mL) at room temperature. The reaction mixture was stirred at 80° C. in a closed sealed tube for 16 h. Progress of the reaction was monitored by TLC. After completion of reaction, the reaction mixture was filtered, and diluted with saturated $NaHCO_3$ and extracted with ethyl acetate. Organic layer was dried over sodium sulfate, concentrated under vacuum to afford crude. The crude was purified by column chromatography and was eluted with 70% ethyl acetate/heptane. Pure fraction was concentrated under vacuum to afford 10A (1.8 g, 63%) as a pale-yellow solid. $^1H$ NMR (400 MHz, DMSO-$d_6$) (δ=9.01 (d, J=8.8 Hz, 1H), 8.05-8.02 (m, 2H), 7.90 (d, J=8.0 Hz, 1H), 7.72-7.69 (m, 1H), 7.63-7.47 (m, 5H), 7.26-7.21 (m, 1H), 7.08-6.87 (m, 4H), 5.22 (dd, J=12.0, 8.8 Hz, 1H), 4.30 (d, J=12.0 Hz, 1H), 3.80-3.73 (m, 1H), 3.13-3.07 (m, 1H), 1.51 (s, 3H), 0.81 (t, J=6.8 Hz, 3H). LC-MS (Method-A)=534.1 $[M+H]^+$; 99.55% at RT 2.07 min. HPLC (Method-A): 98.91% at RT 5.51 min.

Synthesis of Analogues:

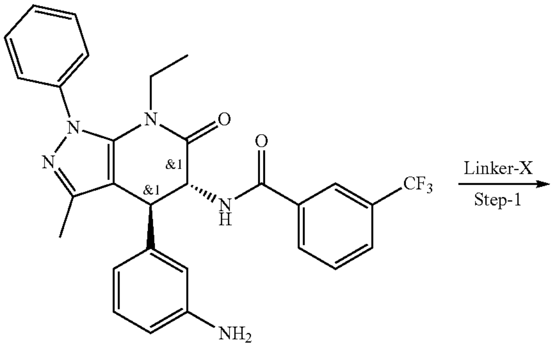

10A

-continued

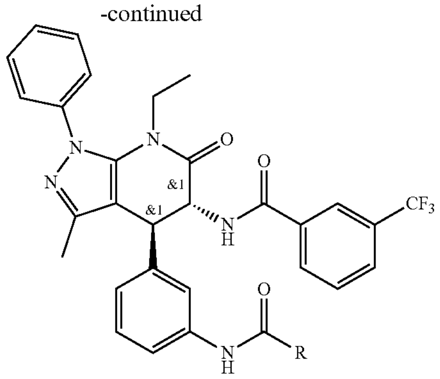

A. Py, DCM, RT, 16 h
B. $T_3P$ (3 eq), DIPEA(3 eq), DMF, 70° C., 16 h
C. $K_2CO_3$, ACN, 90° C., 16 h

Method-A Procedure:

To the stirred solution of 10A (200 mg, 0.36 mmol) in dichloromethane (5 mL) was added pyridine (58.4 mg, 0.73 mmol) and Linker X (X=R, Y) (2.0 equiv.) at 0° C. Then the reaction mixture was stirred at room temperature for 16 h. The reaction mass was monitored by TLC. Reaction mass was partitioned between DCM (10 mL) and water (10 mL). The organic layer was separated and concentrated in vacuum. The crude was purified by prep. HPLC to afford compound.

Method-B Procedure:

To the stirred solution of Linker X (X=G, E, P, D, J, C, L, M, N, Q, K) (2.0 equiv.) in DMF (1.0 mL) was added 1-propanephosphonic anhydride in ethyl acetate (3.0 equiv.) and N, N-Diisopropylethylamine (3.0 equiv.) at 0° C. Then the reaction mixture was stirred at 0° C. for 15 min. Then 10A (200 mg, 0.36 mmol) was added and temperature was raised to 70° C. and stirred for 16 h. The reaction mass was monitored by TLC. The reaction mass was partitioned between ethyl acetate (10 mL) and water (10 mL), the organic layer was separated and concentrated in vacuum. The crude was purified by Prep. HPLC.

Method-C Procedure:

To the stirred solution of 10A (1.0 equiv.) were added acetonitrile (2 mL), $K_2CO_3$ (2.0 equiv.) and Linker X (X=B, H, I, O) (1.0 equiv.). Then the reaction mixture was stirred at 90° C. for 16 h. The reaction mass was monitored by TLC. The organic layer was dried over anhydrous $Na_2SO_4$ and concentrated under reduced pressure. The crude material was purified by medium pressure liquid chromatography and eluted with 40% ethyl acetate in heptane to afford compound. The following table shows the conditions to obtain the desired compounds.

| Sr. No | Cpd. Number | Linker | Structure | Method | 10A (mg) | Linker Qty (mg) | Qty (mg) & nature of compound | Yield (%) |
|---|---|---|---|---|---|---|---|---|
| 1. | I-5 | R | 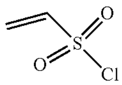 | Method-A | 200 | 92.99 | 41 (Off-white solid) | 17.72 |
| 2. | I-209 | Y | 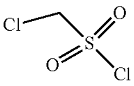 | Method-A | 200 | 109.5 | 35 (Off-white solid) | 14.51 |

-continued

| Sr. No | Cpd. Number | Linker | Structure | Method | 10A (mg) | Linker Qty (mg) | Qty (mg) & nature of compound | Yield (%) |
|---|---|---|---|---|---|---|---|---|
| 3. | I-150 | G | 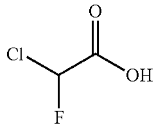 | Method-B | 200 | 82.65 | 12.10 (Pale-yellow solid) | 5.02 |
| 4. | I-180 | E | 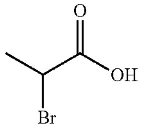 | Method-B | 200 | 112.4 | 22.46 (Off-white solid) | 8.78 |
| 5. | I-171 | P | 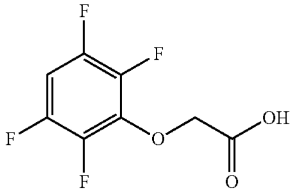 [SMILES: O=C(O)COc1c(F)c(F)cc(F)c1F] | Method-B | 200 | 164.7 | 62.35 (Off-white solid) | 22.90 |
| 6. | I-193 | D | 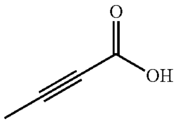 | Method-B | 200 | 61.77 | 40 (Off-white solid) | 18.16 |
| 7. | I-207 | J | 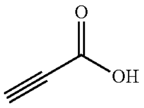 | Method-B | 200 | 51.47 | 17.56 (light brown solid) | 7.97 |
| 8. | I-164 | C | 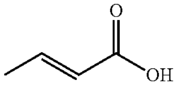 | Method-B | 200 | 63.26 | 75.35 (Off-white solid) | 33.98 |
| 9. | I-75 | L | 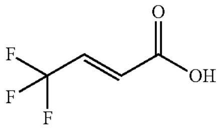 | Method-B | 200 | 102.9 | 53.27 (Off-white solid) | 21.97 |
| 10. | I-78 | M | 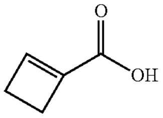 | Method-B | 150 | 36.76 | 172 (Off-white solid) | 11 |
| 11. | I-20 | N | 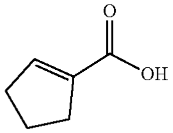 | Method-B | 150 | 42 | 176 (Off-white solid) | 22 |
| 12. | I-38 | Q | 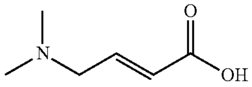 | Method-B | 200 | 94.90 | 24.20 (Off-white solid) | 10.20 |
| 13. | I-9 | K | 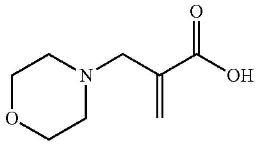 | Method-B | 200 | 128.4 | 16.37 (Off-white solid) | 6.34 |

-continued

| Sr. No | Cpd. Number | Linker | Structure | Method | 10A (mg) | Linker Qty (mg) | Qty (mg) & nature of compound | Yield (%) |
|---|---|---|---|---|---|---|---|---|
| 14. | I-210 | B | 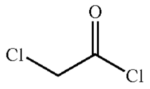 | Method-C | 100 | 21.2 | 114.4 (Off-white solid) | 20.9 |
| 15. | I-48 | H | 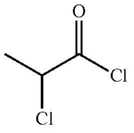 | Method-C | 100 | 23.74 | 116.88 (Off-white solid) | 23 |
| 16. | I-201 | I | 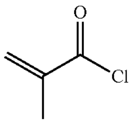 | Method-C | 100 | 19.54 | 112.75 (Off-white solid) | 39.9 |
| 17. | I-77 | O | 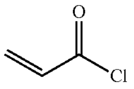 | Method-C | 100 | 16.98 | 110.13 (Off-white solid) | 40.86 |

I-5

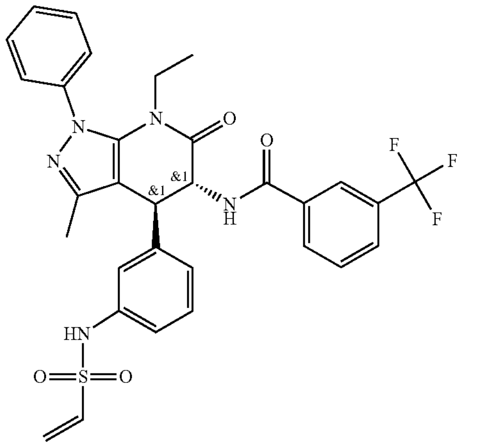 [SMILES: C=CS(=O)(=O)Nc1cccc([C@H]2c3c(C)nn(-c4ccccc4)c3N(CC)C(=O)[C@@H]2NC(=O)c2cccc(C(F)(F)F)c2)c1]

$^1$H NMR (400 MHz, DMSO-d$_6$) δ 9.94 (s, 1H), 9.00 (d, J=8.8 Hz, 1H), 8.04-8.01 (m, 2H), 7.90 (d, J=8.0 Hz, 1H), 7.70 (t, J=8.0 Hz, 1H), 7.63-7.61 (m, 2H), 7.56 (t, J=7.6 Hz, 2H), 7.50-7.47 (m, 1H), 7.28-7.24 (m, 1H), 7.21 (s, 1H), 7.12 (d, J=7.6 Hz, 1H), 7.06-6.94 (m, 1H), 6.65 (dd, J=16.4, 10.0 Hz, 1H), 5.97 (d, J=16.4 Hz, 1H), 5.80 (d, J=10 Hz, 1H), 5.20 (dd, J=12.0, 8.8 Hz, 1H), 4.31 (d, J=12.4 Hz, 1H), 3.81-3.73 (m, 1H), 3.12-3.04 (m, 1H), 1.45 (s, 3H), 0.80 (t, J=7.2 Hz, 3H). LC-MS-(Method-A)=624.31[M+H]$^+$; 99.33% at RT 2.31 min. HPLC (Method-C): 99.28% at RT 8.02 min.

I-209

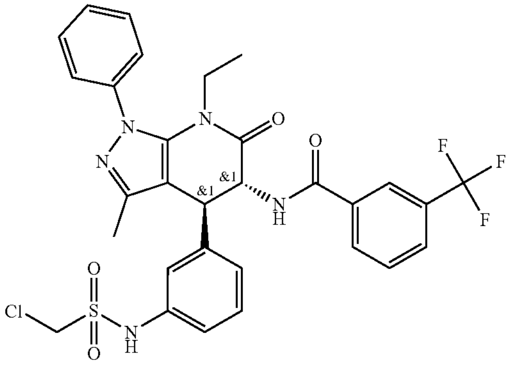 [SMILES: CCN1C(=O)[C@H](NC(=O)c2cccc(C(F)(F)F)c2)[C@@H](c2cccc(NS(=O)(=O)CCl)c2)c2c(C)nn(-c3ccccc3)c21]

$^1$H NMR (400 MHz, DMSO-d$_6$) δ=10.3 (s, 1H), 9.03 (d, J=9.2 Hz, 1H), 8.02-8.01 (m, 2H), 7.89 (d, J=7.6 Hz, 1H), 7.70-7.67 (m, 1H), 7.64-7.61 (m, 2H), 7.55 (t, J=7.2 Hz, 2H), 7.50-7.47 (m, 1H), 7.28 (t, J=8.0 Hz, 2H), 7.14 (d, J=8.0 Hz, 1H), 7.10-7.07 (m, 1H), 5.25 (dd, J=12.0, 8.8 Hz, 1H), 4.98-4.91 (m, 2H), 4.31 (d, J=12.4 Hz, 1H), 3.85-3.76 (m, 1H), 3.12-3.04 (m, 1H), 1.49 (s, 3H), 0.81 (t, J=7.2 Hz, 3H). LC-MS-(Method-A)=646.32 [M+H]$^+$; 98.54% at RT 2.35 min. HPLC (Method-C): 99.66% at RT 8.14 min.

I-150

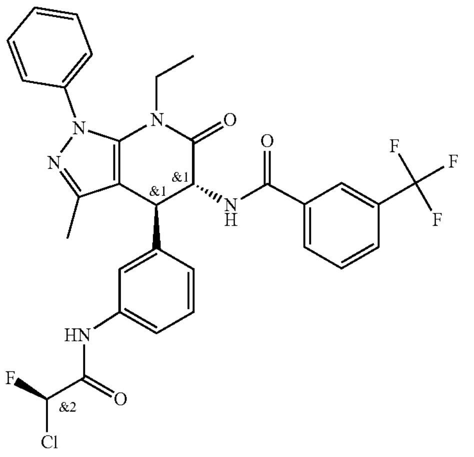 [SMILES: CCN1C(=O)[C@H](NC(=O)c2cccc(C(F)(F)F)c2)[C@@H](c2cccc(NC(=O)[C@H](F)Cl)c2)c2c(C)nn(-c3ccccc3)c21]

$^1$H NMR (400 MHz, DMSO-$d_6$) δ=10.6 (s, 1H), 9.02 (d, J=9.2 Hz, 1H), 8.02-7.98 (m, 2H), 7.89 (d, J=8.0 Hz, 1H), 7.69 (t, J=8.0 Hz, 1H), 7.63-7.47 (m, 7H), 7.33 (t, J=8.0 Hz, 1H), 7.18 (d, J=8.0 Hz, 1H), 5.17 (dd, J=12.0, 8.8 Hz, 1H), 4.36 (d, J=12 Hz, 2H), 3.85-3.76 (m, 1H), 3.13-3.05 (m, 1H), 1.51 (s, 3H), 0.81 (t, J=6.8 Hz, 3H). LC-MS-(Method-A)=628.33 $[M+H]^+$ 98.24% at RT 2.38 min. HPLC (Method-D): 95.78% at RT 6.10 min.

I-180

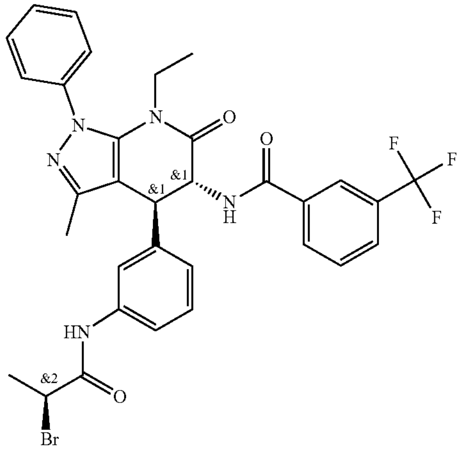 [SMILES: CCN1C(=O)[C@H](NC(=O)c2cccc(C(F)(F)F)c2)[C@@H](c2cccc(NC(=O)[C@H](C)Br)c2)c2c(C)nn(-c3ccccc3)c21]

$^1$H NMR (400 MHz, DMSO-$d_6$) δ=10.3 (s, 1H), 9.02 (d, J=8.8 Hz, 1H), 8.03-8.01 (m, 2H), 7.90 (d, J=7.6 Hz, 1H), 7.69 (t, J=8.0 Hz, 1H), 7.64-7.62 (m, 2H), 7.58-7.54 (m, 4H), 7.51-7.47 (m, 1H), 7.29 (t, J=8.0 Hz, 1H), 7.12 (d, J=7.6 Hz, 1H), 5.16 (dd, J=12.0, 8.8 Hz, 1H), 4.69-4.64 (m, 1H), 4.34 (d, J=12.4 Hz, 1H), 3.79-3.74 (m, 1H), 3.12-3.07 (m, 1H), 1.73-1.71 (m, 3H), 1.51 (s, 3H), 0.81 (t, J=7.2 Hz, 3H). LC-MS-(Method-B)=668.0 $[M+H]^+$; 98.92% at RT 2.33 min. HPLC (Method-C): 96.11% at RT 8.36 min.

I-171

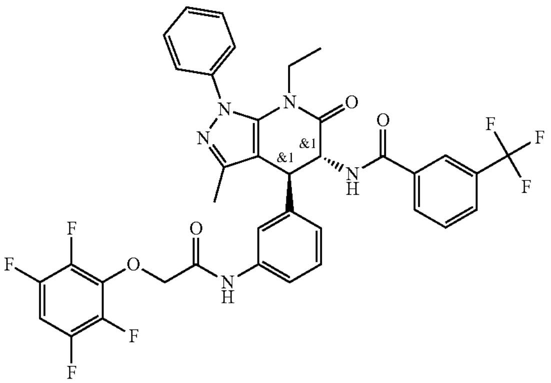 [SMILES: CCN1C(=O)[C@H](NC(=O)c2cccc(C(F)(F)F)c2)[C@@H](c2cccc(NC(=O)COc3c(F)c(F)cc(F)c3F)c2)c2c(C)nn(-c3ccccc3)c21]

$^1$H NMR (400 MHz, DMSO-$d_6$) (δ=10.1 (s, 1H), 9.01 (d, J=8.8 Hz, 1H), 8.02-8.00 (m, 2H), 7.89 (d, J=7.6 Hz, 1H), 7.68 (t, J=8.4 Hz, 1H), 7.70-7.50 (m, 8H), 7.49-7.28 (m, 2H), 5.17 (dd, J=12.0, 8.8 Hz, 1H), 4.93 (s, 2H), 4.33 (d, J=12 Hz, 1H), 3.78-3.73 (m, 1H), 3.11-3.06 (m, 1H), 1.50 (s, 3H), 0.80 (t, J=6.8 Hz, 3H). LC-MS-(Method-A)=740.38 [M+H]; 99.95% at RT 2.55 min. HPLC (Method-A): 95.24% at RT 8.74 min.

I-193

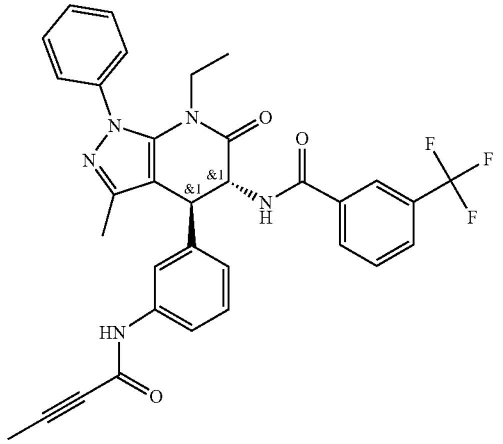 [SMILES: CC#CC(=O)Nc1cccc([C@H]2c3c(C)nn(-c4ccccc4)c3N(CC)C(=O)[C@@H]2NC(=O)c2cccc(C(F)(F)F)c2)c1]

$^1$H NMR (400 MHz, DMSO-$d_6$) δ=10.6 (s, 1H), 9.01 (d, J=8.8 Hz, 1H), 8.02-8.00 (m, 2H), 7.89 (d, J=7.6 Hz, 1H), 7.69 (t, J=8.0 Hz, 1H), 7.63-7.50 (m, 5H), 7.49-7.47 (m, 2H), 7.26 (t, J=7.6 Hz, 1H), 7.10 (d, J=7.6 Hz, 1H), 5.15 (dd, J=12.0, 8.8 Hz, 1H), 4.31 (d, J=12 Hz, 1H), 4.33 (d, J=12 Hz, 1H), 3.80-3.72 (m, 1H), 3.14-3.05 (m, 1H), 2.02 (s, 3H), 1.49 (s, 3H), 0.80 (t, J=7.2 Hz, 3H). LC-MS-(Method-A)=740.38 $[M+H]^+$; 99.95% at RT 2.55 min. HPLC (Method-A): 95.24% at RT 8.74 min.

I-207

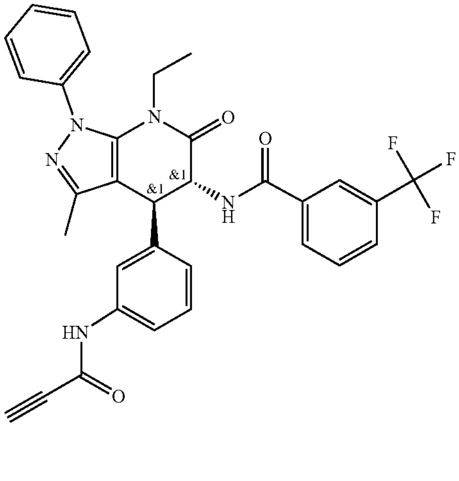 [SMILES: C#CC(=O)Nc1cccc([C@H]2c3c(C)nn(-c4ccccc4)c3N(CC)C(=O)[C@@H]2NC(=O)c2cccc(C(F)(F)F)c2)c1]

$^1$H NMR (400 MHz, DMSO-$d_6$) δ=10.8 (s, 1H), 9.01 (d, J=8.8 Hz, 1H), 8.02-8.00 (m, 2H), 7.89 (d, J=7.6 Hz, 1H), 7.69 (t, J=8.0 Hz, 1H), 7.63-7.61 (m, 3H), 7.58-7.47 (m, 4H), 7.28 (t, J=7.6 Hz, 1H), 7.13 (d, J=7.6 Hz, 1H), 5.15 (dd, J=12.0, 8.8 Hz, 1H), 4.37-4.31 (m, 2H), 3.79-3.74 (m, 1H), 3.11-3.04 (m, 1H), 1.50 (s, 3H), 0.81 (t, J=7.2 Hz, 3H). LC-MS-(Method-A)=586.37 [M+H]$^+$ 99.39% at RT 2.29 min. HPLC (Method-C): 98.90% at RT 7.95 min.

I-164

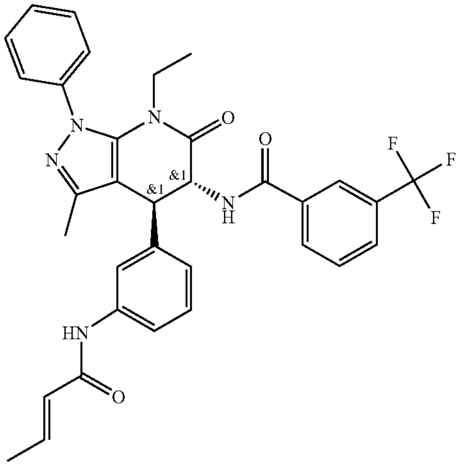 [SMILES: C/C=C/C(=O)Nc1cccc([C@H]2c3c(C)nn(-c4ccccc4)c3N(CC)C(=O)[C@@H]2NC(=O)c2cccc(C(F)(F)F)c2)c1]

$^1$H NMR (400 MHz, DMSO-$d_6$) (δ=9.95 (s, 1H), 9.01 (d, J=8.8 Hz, 1H), 8.02-8.01 (m, 2H), 7.89 (d, J=8.0 Hz, 1H), 7.69 (t, J=7.2 Hz, 1H), 7.71-7.47 (m, 5H), 7.25 (t, J=7.6 Hz, 1H), 7.06 (d, J=7.6 Hz, 1H), 6.78-6.75 (m, 1H), 6.11-6.07 (m, 1H), 5.16 (dd, J=12.0, 8.8 Hz, 1H), 4.33 (d, J=12 Hz, 1H), 3.81-3.74 (m, 3H), 3.16-3.07 (m, 1H), 1.85-1.83 (m, 3H), 1.51 (s, 3H), 0.81 (t, J=6.8 Hz, 3H). LC-MS-(Method-A)=602.39 [M+H]$^+$; 99.93% at RT 2.36 min. HPLC (Method-C): 99.70% at RT 8.15 min.

I-75

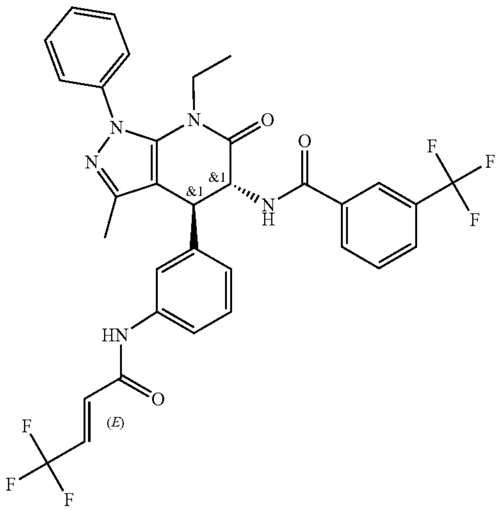 [SMILES: CCN1C(=O)[C@H](NC(=O)c2cccc(C(F)(F)F)c2)[C@@H](c2cccc(NC(=O)/C=C/C(F)(F)F)c2)c2c(C)nn(-c3ccccc3)c21]

$^1$H NMR (400 MHz, DMSO-$d_6$) δ=10.5 (s, 1H), 9.03 (d, J=8.8 Hz, 1H), 8.02-8.00 (m, 2H), 7.89 (d, J=8.0 Hz, 1H), 7.69 (t, J=7.2 Hz, 1H), 7.64-7.47 (m, 7H), 7.32 (t, J=8.0 Hz, 1H), 7.17-7.15 (m, 1H), 6.96-6.90 (m, 2H), 5.18 (dd, J=12.0, 8.8 Hz, 1H), 4.35 (d, J=12 Hz, 1H), 3.80-3.75 (m, 1H), 3.12-3.06 (m, 1H), 1.51 (s, 3H), 0.81 (t, J=6.8 Hz, 3H). LC-MS-(Method-A)=656.39 [M+H]$^+$; 99.52% at RT 2.49 min. HPLC (Method-D): 99.49% at RT 6.29 min.

I-78

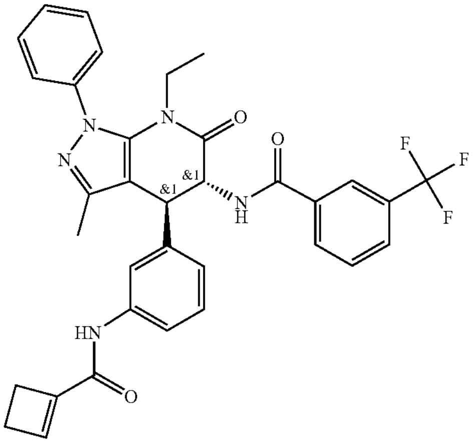 [SMILES: CCN1C(=O)[C@H](NC(=O)c2cccc(C(F)(F)F)c2)[C@@H](c2cccc(NC(=O)C3=CCC3)c2)c2c(C)nn(-c3ccccc3)c21]

$^1$H NMR (400 MHz, DMSO-$d_6$) (δ=9.95 (s, 1H), 9.00 (d, J=8.8 Hz, 1H), 8.02-8.00 (m, 2H), 7.89 (d, J=8.0 Hz, 1H), 7.71-7.60 (m, 5H), 7.58-7.54 (m, 2H), 7.51-7.49 (m, 1H), 7.26 (t, J=8.0 Hz, 1H), 7.08 (d, J=7.2 Hz, 1H), 6.74 (s, 1H), 5.15 (dd, J=12.0, 8.8 Hz, 1H), 4.33 (d, J=12.4 Hz, 1H), 3.81-3.75 (m, 1H), 3.16-3.07 (m, 1H), 2.68-2.66 (m, 2H), 2.29 (s, 2H), 1.51 (s, 3H), 0.81 (t, J=7.2 Hz, 3H). LC-MS-(Method-B)=613.8 [M+H]$^+$; 98.19% at RT 2.27 min. HPLC (Method-A): 99.11% at RT 8.73 min. Chiral HPLC (Method-F): Peak-1=52.09% at RT 3.79 min. Peak-2=47.91% at RT 6.57 min.

I-20

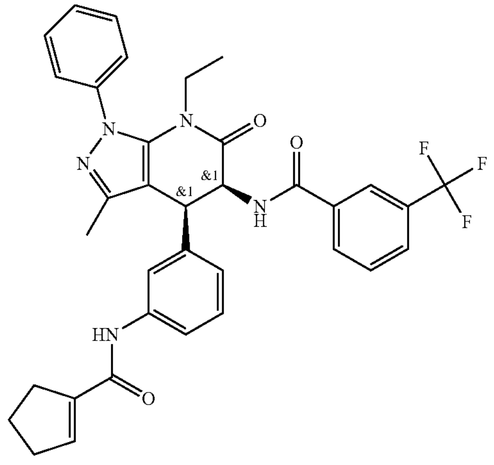 [SMILES: CCN1C(=O)[C@@H](NC(=O)c2cccc(C(F)(F)F)c2)[C@@H](c2cccc(NC(=O)C3=CCCC3)c2)c2c(C)nn(-c3ccccc3)c21]

$^1H$ NMR (400 MHz, DMSO-$d_6$) (δ=9.95 (s, 1H), 9.00 (d, J=8.8 Hz, 1H), 8.02-8.00 (m, 2H), 7.89 (d, J=8.0 Hz, 1H), 7.71-7.67 (m, 2H), 7.63-7.47 (m, 6H), 7.25 (t, J=7.2 Hz, 1H), 7.07 (d, J=8.0 Hz, 1H), 6.67 (t, J=2.0 Hz, 1H), 5.15 (dd, J=12.0, 8.8 Hz, 1H), 4.33 (d, J=12.4 Hz, 1H), 3.80-3.75 (m, 1H), 3.13-3.07 (m, 1H), 2.56-2.49 (m, 4H), 1.92-1.84 (m, 2H), 1.52 (s, 3H), 0.81 (t, J=7.2 Hz, 3H). LC-MS-(Method-B)=627.8 [M+H]$^+$; 99.57% at RT 2.33 min. HPLC (Method-A): 99.88% at RT 9.03 min.

I-38

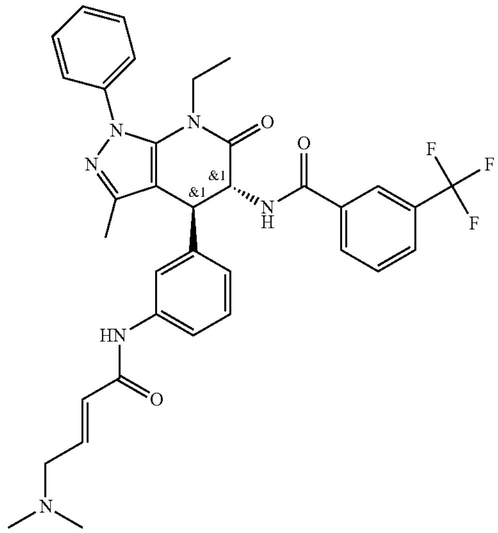 [SMILES: CCN1C(=O)[C@H](NC(=O)c2cccc(C(F)(F)F)c2)[C@@H](c2cccc(NC(=O)/C=C/CN(C)C)c2)c2c(C)nn(-c3ccccc3)c21]

$^1H$ NMR (400 MHz, DMSO-$d_6$) δ=10.0 (s, 1H), 9.01 (d, J=8.8 Hz, 1H), 8.02-8.00 (m, 2H), 7.89 (d, J=8.0 Hz, 1H), 7.71-7.51 (m, 7H), 7.49-7.47 (m, 1H), 7.26 (t, J=7.6 Hz, 1H), 7.08 (d, J=7.2 Hz, 1H), 6.73-6.66 (m, 1H), 6.25-6.21 (m, 1H), 5.16 (dd, J=12.0, 8.8 Hz, 1H), 4.33 (d, J=12 Hz, 1H), 3.80-3.75 (m, 1H), 3.12-3.03 (m, 3H), 2.16 (s, 6H), 1.51 (s, 3H), 0.81 (t, J=7.2 Hz, 3H). LC-MS-(Method-A)=645.39 [M+H]$^+$; 99.44% at RT 1.83 min. HPLC (Method-C): 95.95% at RT 6.33 min.

I-9

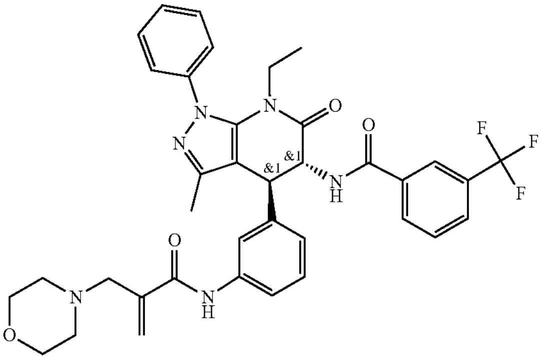 [SMILES: C=C(CN1CCOCC1)C(=O)Nc1cccc([C@H]2c3c(C)nn(-c4ccccc4)c3N(CC)C(=O)[C@@H]2NC(=O)c2cccc(C(F)(F)F)c2)c1]

$^1H$ NMR (400 MHz, DMSO-$d_6$) (δ=11.1 (s, 1H), 9.03 (d, J=8.8 Hz, 1H), 8.04-8.02 (m, 2H), 7.89 (d, J=8.0 Hz, 1H), 7.69 (t, J=7.6 Hz, 1H), 7.63-7.61 (m, 3H), 7.56 (t, J=7.6 Hz, 3H), 7.51-7.47 (m, 1H), 7.30 (t, J=7.6 Hz, 1H), 7.12-7.11 (m, 1H), 6.05 (s, 1H), 5.58 (s, 1H), 5.18 (dd, J=12.0, 8.8 Hz, 1H), 4.35 (d, J=12 Hz, 1H), 3.80-3.74 (m, 1H), 3.62 (t, J=12 Hz, 4H), 3.32-3.29 (m, 2H), 3.12-3.07 (m, 1H), 2.45 (s, 4H), 1.53 (s, 3H), 0.81 (t, J=7.2 Hz, 3H). LC-MS-(Method-A)=687.46 [M+H]$^+$; 99.58% at RT 1.89 min. HPLC (Method-D): 99.67% at RT 5.33 min. Chiral HPLC (Method-G): Peak-1=50.57% at RT 4.67 min. Peak-2=49.43% at RT 5.27 min.

I-210

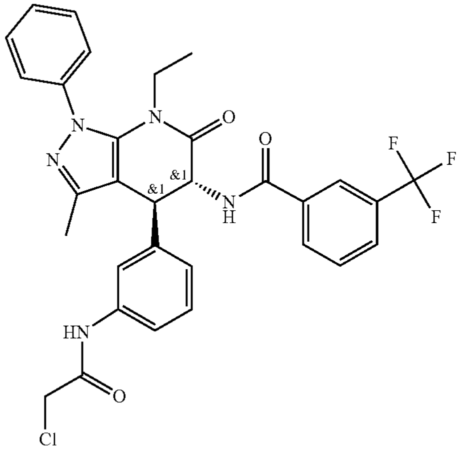 [SMILES: CCN1C(=O)[C@H](NC(=O)c2cccc(C(F)(F)F)c2)[C@@H](c2cccc(NC(=O)CCl)c2)c2c(C)nn(-c3ccccc3)c21]

$^1H$ NMR (400 MHz, DMSO-$d_6$) δ=10.3 (s, 1H), 9.01 (d, J=9.2 Hz, 1H), 8.02 (d, J=7.2 Hz, 2H), 7.90 (d, J=7.2 Hz, 1H), 7.69 (t, J=7.6 Hz, 1H), 7.63-7.54 (m, 6H), 7.51-7.47 (m, 1H), 7.29 (t, J=7.6 Hz, 1H), 7.12 (d, J=7.6 Hz, 1H), 5.17 (dd, J=12.0, 8.8 Hz, 1H), 4.34 (d, J=12 Hz, 1H), 4.21 (s, 2H), 3.80-3.68 (m, 1H), 3.17-3.04 (m, 1H), 1.50 (s, 3H), 0.81 (t, J=6.8 Hz, 3H). LC-MS(Method-A)=610.3 [M+H]$^+$; 96.86% at RT 2.38 min. HPLC (Method-C): 99.82% at RT 8.76 min.

I-48

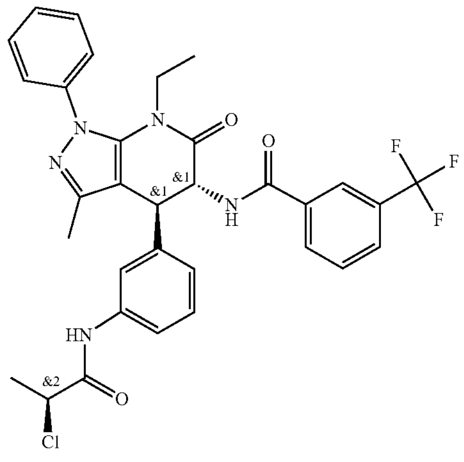

$^1$H NMR (400 MHz, DMSO-$d_6$) δ=10.3 (d, J=2.8 Hz, 1H), 9.02 (d, J=9.2 Hz, 1H), 8.03-8.01 (m, 2H), 7.89 (d, J=8.0 Hz, 1H), 7.69 (t, J=8.0 Hz, 1H), 7.64-7.47 (m, 7H), 7.29 (t, J=7.6 Hz, 1H), 7.12 (d, J=8.0 Hz, 1H), 5.16 (dd, J=12.0, 8.8 Hz, 1H), 4.66-4.61 (m, 1H), 4.34 (d, J=12 Hz, 1H), 3.81-3.72 (m, 1H), 3.14-3.05 (m, 1H), 1.59-1.57 (m, 3H), 1.52 (d, J=7.6 Hz, 3H), 0.81 (t, J=6.8 Hz, 3H). LC-MS(Method-B)=600.2[M+H]$^+$; 99.82% at RT 2.25 min. HPLC (Method-C): 99.69% at RT 8.03 min.

I-201

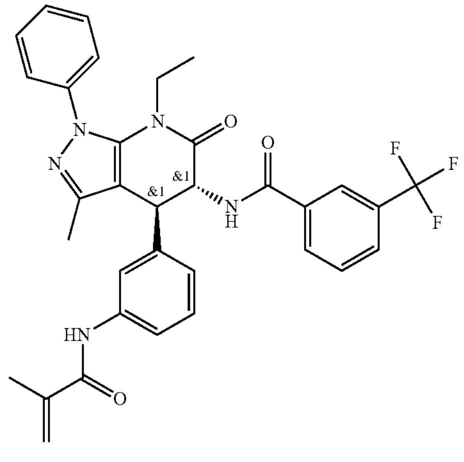 [SMILES: C=C(C)C(=O)Nc1cccc([C@H]2c3c(C)nn(-c4ccccc4)c3N(CC)C(=O)[C@@H]2NC(=O)c2cccc(C(F)(F)F)c2)c1]

$^1$H NMR (400 MHz, DMSO-$d_6$) δ=9.80 (s, 1H), 9.00 (d, J=8.8 Hz, 1H), 8.02-8.01 (m, 2H), 7.89 (d, J=8.4 Hz, 1H), 7.72-7.67 (m, 2H), 7.63-7.54 (m, 5H), 7.50-7.47 (m, 1H), 7.26 (t, J=8.0 Hz, 1H), 7.09 (d, J=7.2 Hz, 1H), 5.77 (s, 1H), 5.48 (s, 1H), 5.15 (dd, J=12.0, 8.8 Hz, 1H), 4.33 (d, J=12 Hz, 1H), 3.80-3.75 (m, 1H), 3.12-3.07 (m, 1H), 1.92 (s, 3H), 1.53 (s, 3H), 0.81 (t, J=6.8 Hz, 3H). LC-MS(Method-B)=602.2 [M+H]$^+$; 96.65% at RT 2.28 min. HPLC (Method-C): 95.15% at RT 8.25 min.

I-77

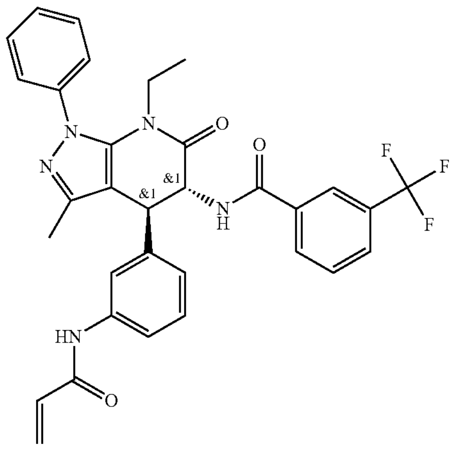 [SMILES: C=CC(=O)Nc1cccc([C@H]2c3c(C)nn(-c4ccccc4)c3N(CC)C(=O)[C@@H]2NC(=O)c2cccc(C(F)(F)F)c2)c1]

$^1$H NMR (400 MHz, DMSO-$d_6$) δ=10.1 (s, 1H), 9.01 (d, J=8.8 Hz, 1H), 8.02-8.00 (m, 2H), 7.89 (d, J=8.4 Hz, 1H), 7.71-7.61 (m, 5H), 7.58-7.54 (m, 2H), 7.51-7.47 (m, 1H), 7.28 (t, J=8.0 Hz, 1H), 7.10 (d, J=7.6 Hz, 1H), 6.44-6.37 (m, 1H), 6.25-6.20 (m, 1H), 5.74-5.71 (m, 1H), 5.16 (dd, J=12.0, 8.8 Hz, 1H), 4.33 (d, J=12.4 Hz, 1H), 3.82-3.73 (m, 1H), 3.12-3.06 (m, 1H), 1.51 (s, 3H), 0.81 (t, J=6.8 Hz, 3H). LC-MS(Method-B)=588.2[M+H]$^+$; 99.53% at RT 2.22 min. HPLC (Method-C): 99.74% at RT 7.99 min.

Synthesis of I-47:

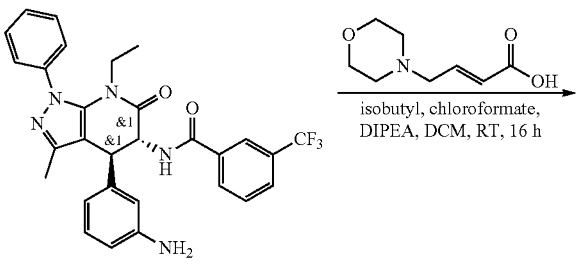

10A

-continued

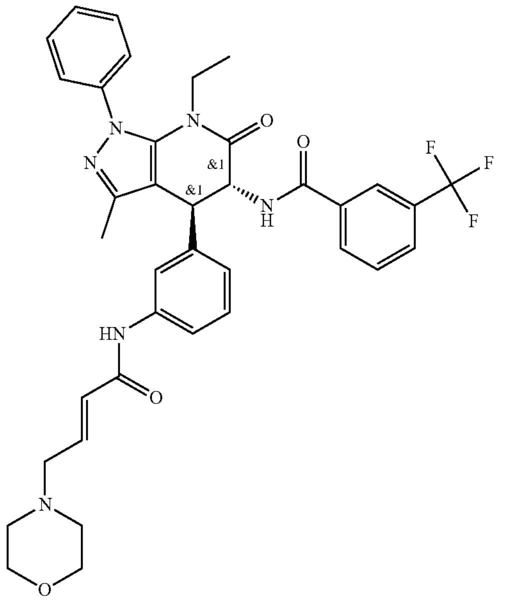

I-47

To a stirred solution of (E)-4-morpholinobut-2-enoic acid (125.8 mg, 0.73 mmol) in dichloromethane (4 mL) was added isobutyl chloroformate (153.6 mg, 1.10 mmol) and N,N-diisopropylethylamine (145 mg, 1.10 mmol) at 0° C. Then the reaction mixture was stirred at 0° C. for 15 min. Then added 10A (200 mg, 0.36 mmol) and temperature was raised to room temperature and stirred for 16 h. The reaction mass was monitored by TLC. Reaction mass was partitioned between DCM (10 mL) and water (10 mL). Separated the organic layer and concentrated in vacuum. Then the obtained crude was purified by prep. HPLC and afforded I-47 (66.37 mg, 25.8%) as off white solid. $^1$H NMR (400 MHz, DMSO-d$_6$) (δ=10.0 (s, 1H), 9.02-8.99 (m, 1H), 8.97-8.00 (m, 2H), 7.89 (d, J=8.0 Hz, 1H), 7.71-7.47 (m, 8H), 7.28-7.01 (m, 2H), 6.72-6.23 (m, 2H), 5.16 (dd, J=12.0, 8.8 Hz, 1H), 4.34-4.19 (m, 1H), 3.80-3.74 (m, 1H), 3.58 (t, J=4.4 Hz, 3H), 3.49-3.41 (m, 1H), 3.11-3.06 (m, 3H), 2.49-2.24 (m, 4H), 1.51 (s, 3H), 0.81 (t, J=7.2 Hz, 3H). LC-MS (Method-B)=687.4[M+H]$^+$; 98.79% at RT 1.79 min. HPLC (Method-C): 98.32% at RT 6.41 min.

Synthesis of I-146:

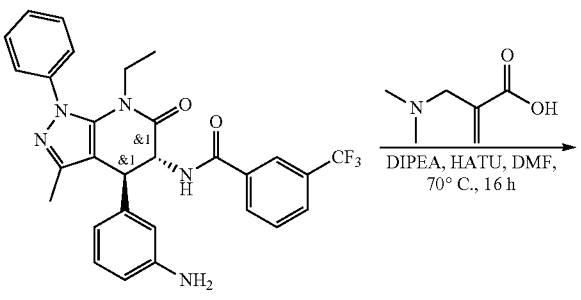

10A

-continued

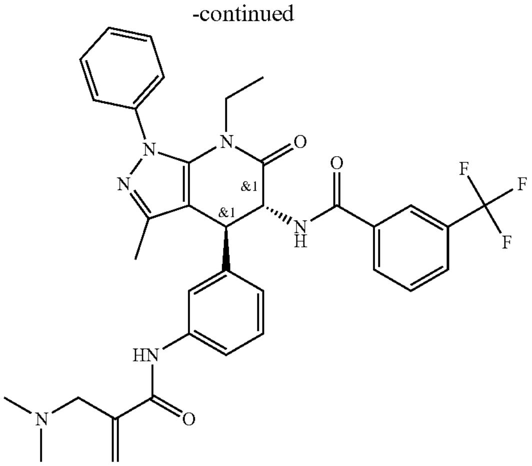

I-146

To a stirred solution of 2-[(dimethylamino)methyl]prop-2-enoic acid (53.26 mg, 0.41 mmol) in DMF (2 mL) N,N-diisopropylethylamine (148 mg, 1.12 mmol) was added, cooled and HATU (220.4 mg, 0.56 mmol) was added. The reaction mixture was stirred for 10 min and 10A (200 mg, 0.37 mmol) was added. Then the reaction mixture was stirred at 70° C. for 16 h. The reaction mass was quenched by ice water and extracted with ethyl acetate (100 mL). The organic layer was dried over anhydrous $Na_2SO_4$ and concentrated under reduced pressure. The crude material was purified by prep HPLC to afford I-146 (31.00 mg, 12.83%) as an off-white solid. $^1$H NMR (400 MHz, DMSO-d$_6$) (δ=11.0 (s, 1H), 9.01 (d, J=8.8 Hz, 1H), 8.03-8.02 (m, 2H), 7.89 (d, J=8.0 Hz, 1H), 7.71-7.44 (m, 8H), 7.28 (t, J=7.6 Hz, 1H), 7.10 (d, J=8.0 Hz, 1H), 5.98 (s, 1H), 5.54 (s, 1H), 5.16 (dd, J=12.0, 8.8 Hz, 1H), 4.34 (d, J=12.4 Hz, 1H), 3.81-3.73 (m, 1H), 3.19 (s, 2H), 3.16-3.07 (m, 1H), 2.21 (s, 6H), 1.53 (s, 3H), 0.81 (t, J=7.2 Hz, 3H). LC-MS (Method-B)=645.81 [M+H]$^+$; 97.77% at RT 1.53 min. HPLC (Method-C): 98.49% at RT 6.35 min.

Example 11: Synthesis of Compounds I-84, I-74, I-91, I-99, and I-39

NMR:

$^1$H NMR spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LC-MS:

Method-A: Column: Bakerbond Q2100 C18 1.8 μm; 2.1×50 mm Mobile Phase A: 0.05% FA in Water Mobile Phase B: 0.05% FA in CAN Flow Rate: 0.6 ml Oven Temperature: 40° C. Gradient Program (Time/B %): 0_5, 0.2_5, 2.3_98, 3.3_98, 3.5_5, 4.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm, 2.5μ) Mobile Phase A: 0.05% TFA in Water Mobile Phase B: 0.05% TFA in Acetonitrile Flow rate: 1.0 mL/min.

Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water: CAN (95:05); Mobile phase B: Acetonitrile; Gradient Programme: T/B %: 0.01/5, 1/5, 8/100, 12/100, 14/5, 18/5; Flow rate: 1.2 ml/min.

Method-B: Column: X-Bridge CSH C18 (150×4.6 mm, 3.5 μm); Mobile Phase-A: 5 mM $NH_4HCO_3$; Mobile Phase-B: ACN; Programme: T/B %: 0.01/2, 2/2, 12/90, 16/90; Flow rate: 1.0 mL/min.; Diluent: ACN: WATER (80:20).

Method-C: Column: X-Select CSH C18 (4.6*150) mm 5μ Mobile Phase: A—0.1% TFA in water B—Acetonitrile Inj Volume; 5.0 μL, Flow Rate: 1.2. ML/minute Gradient program: Time(min)/B Conc.: 0.01/5, 1.0/5, 8.0/100, 12.0/100, 14.0/5, 18.0/5.

Chiral HPLC:

Method-A: Column: CHIRALCEL-OJ-H (250×4.6 mm, 5μ) Mobile Phase A: 0.1% DEA in HEXANE Mobile Phase B: IPA A/B: 60/40 Flow: 1.0 ml/MIN PDA: OJ-H_015.

Method-B: Column: CHIRALPAK IG (250×4.6 mm, 5 μm) Mobile Phase A: n-HEXANE Mobile Phase B: DCM: IPA (1:1) A B: 60:40 Flow rate: 1.0 ML/MIN.

Method-C: Column: CHIRALPAK-IA (250×4.6 mm, 5 μm) A B: 70/30 Mobile Phase A: n-Hexane Mobile Phase B: ETOH: MEOH(1:1) Flow rate: 1.00 ml/min.

Synthesis of 11A, and 11B:

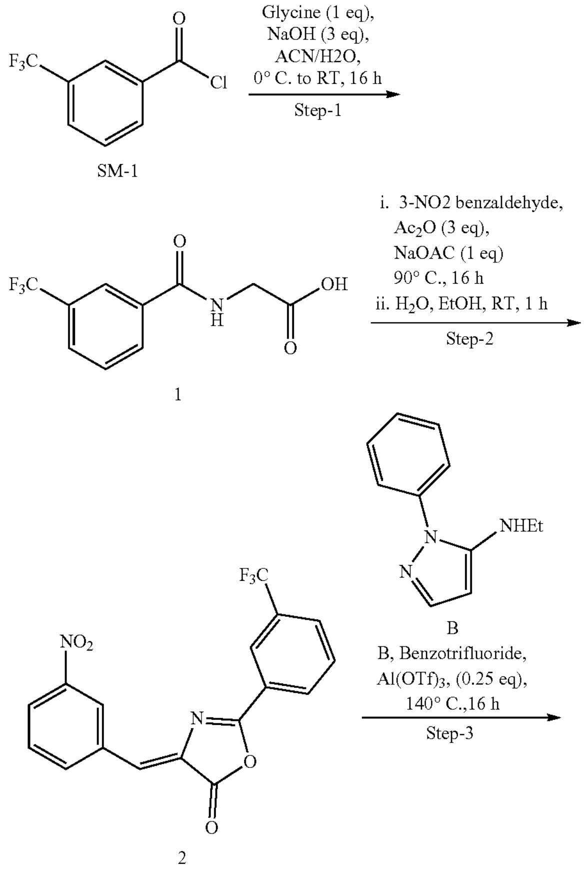

SM-1

1

2

-continued

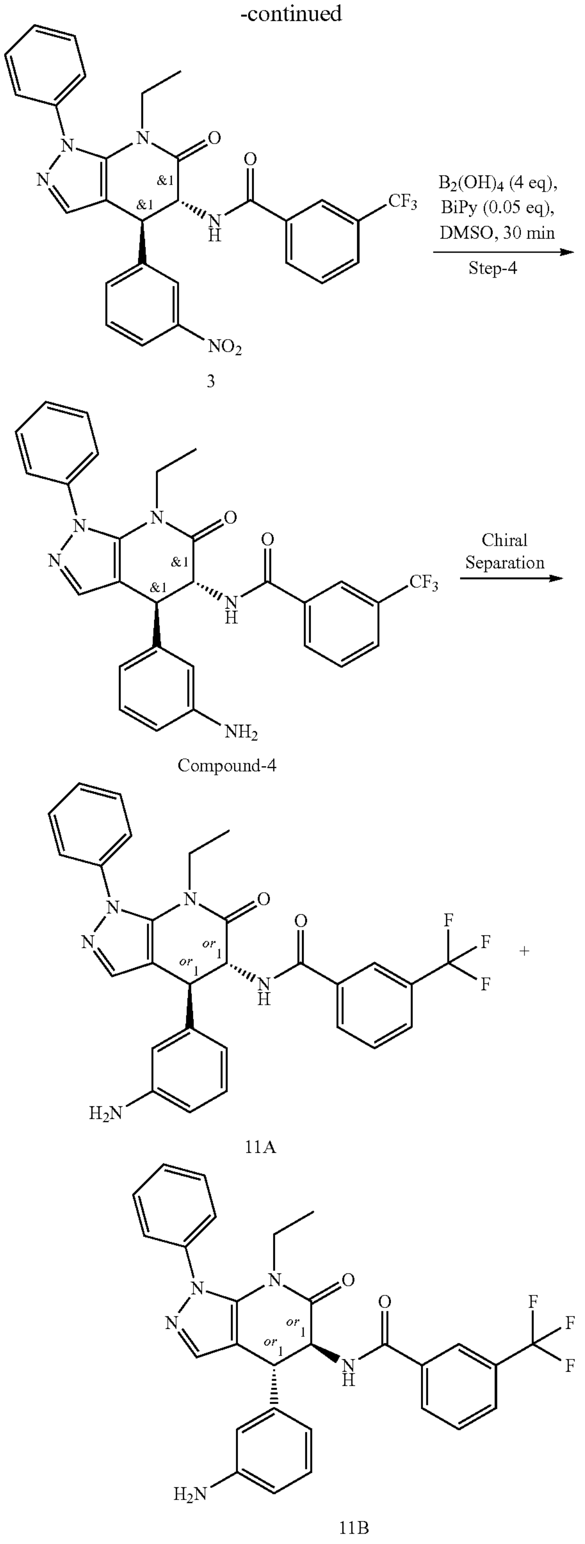

3

Compound-4

11A

11B

Step-1: Synthesis of 2-[[3-(trifluoromethyl)benzoyl] amino]acetic acid Compound (1)

A stirred solution of 3-(trifluoromethyl)benzoyl chloride (100 g, 469.8 mmol) in ACN (200 mL) was cooled to 0° C. then sodium hydroxide (49 g, 1212.8 mmol) in water (60 mL) solution was added to the reaction mixture and stirred for 5-10 minutes. Then Glycine (37 g, 487.9 mmol) in ACN (200 mL) was added drop wise at same temperature. The resulting reaction mixture was stirred at 0° C. to ambient temperature for 16 h. Progress of the reaction was monitored by TLC. After completion of reaction, the reaction mixture was quenched with HCl solution and extracted with ethyl acetate and dried over sodium sulfate, concentrated under vacuum to afford crude. The crude material was triturated with heptane and dried to afford compound (1) (90 g, 76.71%) as a white solid. $^1$H NMR (400 MHz, DMSO-$d_6$) (δ=8.92 (t, J=5.2 Hz, 1H), 8.20-8.15 (s, 2H), 7.91 (d, J=7.6 Hz, 1H), 7.73 (t, J=7.6 Hz, 1H), 3.86 (d, J=5.6 Hz, 2H). LC-MS (Method-A)=248.1 [M+H]$^+$; 99.14% at RT 1.12 min.

Step-2: Synthesis of (4-{Z})-4-[(3-nitrophenyl) methylene]-2-[3-(trifluoromethyl)phenyl]oxazol-5-one compound (2)

To a stirred solution of compound (1) (84 g, 336.4 mmol) in acetic anhydride (104 g, 1009.3 mmol), was added 3-nitrobenzaldehyde (51.9 g, 336.4 mmol) in sealed tube and stirred at 90° C. for 16 h. Progress of the reaction was monitored by TLC. After completion of reaction, the reaction mixture was quenched with EtOH: Water (1:1) and stirred for 1 h, filtered to afford solid compound. Obtained solid compound was triturated with heptane and co distilled with toluene and dried under vacuum pump to afford pure Compound (2) (70 g, 48.81%) as a yellow solid. $^1$H NMR (400 MHz, $CDCl_3$) (δ=9.15 (m, 1H), 8.47-8.30 (s, 4H), 7.91 (d, J=7.6 Hz, 1H), 7.75-7.68 (m, 2H), 7.26 (m, 1H). LC-MS (Method-A)=363.1 [M+H]$^+$; 85.10% at RT 2.59 min.

Step-3: Synthesis of rac-N-((4R,5S)-7-ethyl-4-(3-nitrophenyl)-6-oxo-1-phenyl-4,5,6,7-tetrahydro-1H-pyrazolo[3,4-b]pyridin-5-yl)-3-(trifluoromethyl) benzamide (3)

To a stirred solution of Compound (2) (1 g, 2.34 mmol) and (Compound B) ~{N}-ethyl-2-phenyl-pyrazol-3-amine (0.60 g, 3.05 mmol) in benzotrifluoride (10 mL), was added aluminium trifluoromethanesulfonate (0.28 g, 0.58 mmol) and the reaction mixture was stirred at 140° C. for 16 h. Progress of the reaction was monitored by TLC & LCMS. After completion of reaction, the reaction mixture was cooled to ambient temperature, quenched with water, and extracted with ethyl acetate. Organic layer was washed with brine solution and dried over anhydrous sodium sulphate, evaporated under vacuum to afford a crude compound. Obtained crude compound was purified through Flash column chromatography. The compound was eluted in 50-55% ethyl acetate/heptane. The pure fractions were concentrated under vacuum pump and dried to afford Compound (3) (600 mg, 46.54%) as a yellow solid. $^1$H NMR (400 MHz, DMSO-d6) (δ=9.04 (d, J=9.2 Hz, 1H), 8.31 (s, 1H), 8.14 (d, J=7.6 Hz, 1H), 8.00 (d, J=7.2 Hz, 2H), 7.89 (d, J=7.6 Hz, 1H), 7.71-7.53 (m, 7H), 7.14 (s, 1H), 5.75 (s, 1H), 5.32 (dd, J=12.8 Hz, 9.2 Hz, 1H), 4.58 (d, J=12.8 Hz, 1H), 3.85-3.84 (m, 1H), 3.08-3.04 (m, 1H), 0.83 (t, J=6.8 Hz, 3H). LC-MS (Method-C)=550.3 [M+H]$^+$; 87.09% at RT 2.16 min.

Step-4: Synthesis of rac-N-((4R,5S)-4-(3-aminophenyl)-7-ethyl-6-oxo-1-phenyl-4,5,6,7-tetrahydro-1H-pyrazolo[3,4-b]pyridin-5-yl)-3-(trifluoromethyl) benzamide (Compound-4)

A solution of compound (3) (1.5 g, 2.53 mmol) in DMSO (15 mL) was cooled to 0° C. and 2,2'-Bipyridine (0.9 g, 0.12 mmol) was added followed by BBA (0.94 g, 10.15 mmol) and the reaction mixture was stirred at ambient temperature for 30 min. Progress of the reaction was monitored by TLC. After completion of reaction, the reaction mixture was quenched with water and extracted with ethyl acetate. The combined organic layer was washed with water, dried over anhydrous sodium sulfate, and concentrated to afford crude compound. Obtained crude material was purified through triturating with n-pentane and diethyl ether (9:1) and dried under vacuum to afford compound (4) (900 mg, 65.51%) as a yellow solid. The compound was submitted to chiral separation. After evaporation fractions were lyophilized to afford 11A (410.0 mg, 45.56%) and 11B (370 mg, 41.54%) as a yellow solid.

11A

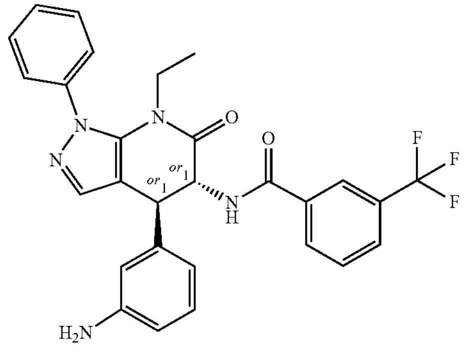 [SMILES: CCN1C(=O)[C@H](NC(=O)c2cccc(C(F)(F)F)c2)[C@@H](c2cccc(N)c2)c2cnn(-c3ccccc3)c21]

$^1$H NMR (400 MHz, DMSO-$d_6$) δ=9.96 (d, J=8.8 Hz, 1H), 8.07-8.04 (m, 2H), 7.90 (d, J=8.0 Hz, 1H), 7.71 (t, J=8.0 Hz, 1H), 7.65-7.63 (m, 2H), 7.59-7.50 (m, 3H), 7.06 (s, 1H), 6.95 (t, J=7.6 Hz, 1H), 6.59-6.53 (m, 2H), 6.43 (dd, J=8.0 Hz, J=1.2 Hz 1H), 5.09-5.03 (m, 3H), 4.22 (d, J=12.8 Hz, 1H), 3.83-3.78 (m, 1H), 3.08-3.03 (m, 1H), 0.81 (t, J=6.8 Hz, 3H). LC-MS (Method-C)=520.0 [M+H]$^+$; 96.27% at RT 2.87 min. HPLC (Method-A)=96.74% at RT 5.37 min. Chiral HPLC (Method-C)=Peak-1=99.57% at RT 10.84 min.

11B

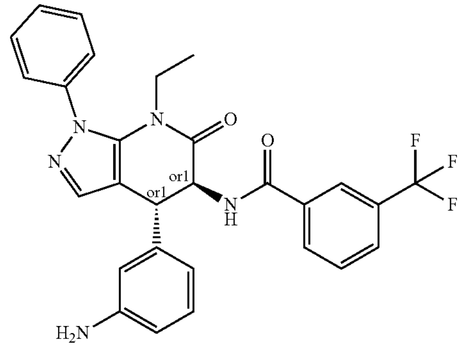 [SMILES: CCN1C(=O)[C@@H](NC(=O)c2cccc(C(F)(F)F)c2)[C@H](c2cccc(N)c2)c2cnn(-c3ccccc3)c21]

$^1$H NMR (400 MHz, DMSO-$d_6$) δ=9.96 (d, J=8.8 Hz, 1H), 8.07-8.04 (m, 2H), 7.90 (d, J=7.6 Hz, 1H), 7.71 (t, J=8.0 Hz, 1H), 7.64-7.50 (m, 5H), 7.05 (s, 1H), 6.95 (t, J=7.6 Hz, 1H), 6.58-6.53 (m, 2H), 6.43-6.41 (m, 1H), 5.09-5.03 (m, 3H), 4.22 (d, J=12.8 Hz, 1H), 3.85-3.75 (m, 1H), 3.08-3.03 (m, 1H), 0.81 (t, J=6.8 Hz, 3H). LC-MS (Method-C)=520.1 [M+H]$^+$; 96.62% at RT 2.88 min. HPLC (Method-C)=96.92% at RT 4.70 min. Chiral HPLC (Method-C)= Peak-1=99.98% at RT 8.27 min.

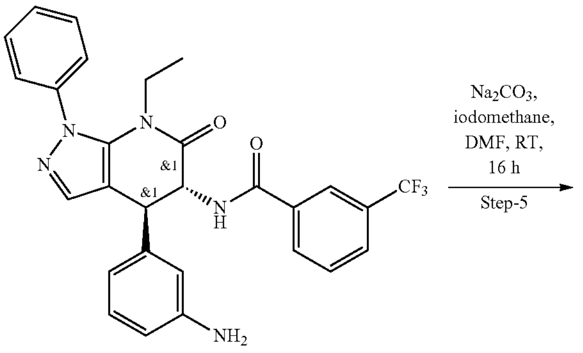

Compound 4

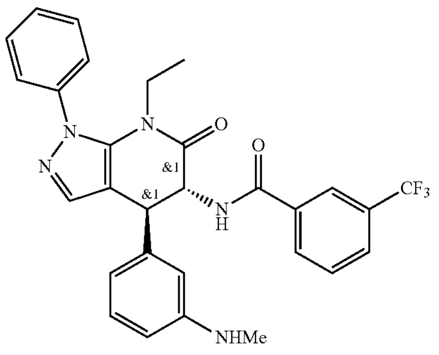

Compound-5

Step-5: Synthesis of rac-N-((4R,5S)-7-ethyl-4-(3-(methylamino)phenyl)-6-oxo-1-phenyl-4,5,6,7-tetrahydro-1H-pyrazolo[3,4-b]pyridin-5-yl)-3-(trifluoromethyl)benzamide Compound (5)

To a stirred solution of Compound-4 (7 g, 12.4 mmol) in DMF (120 mL) was added, sodium carbonate (1.97 g, 18.5 mmol) followed by iodomethane (1.6 g, 11.1 mmol) and the reaction mixture was stirred at ambient temperature for 16 h. Progress of the reaction was monitored by TLC & LCMS. After completion of reaction, the reaction mixture was quenched with ice cold water and extracted with ethyl acetate. The organic layer was washed with brine solution and dried over anhydrous sodium sulfate, evaporated under vacuum to afford desired crude product. Obtained crude was purified through flash column chromatography, the pure fractions were eluted in 35-40% ethyl acetate/heptane. Pure fractions were concentrated to afford pure compound (5) (1.6 g, 21%) as a yellow solid. $^1$H NMR (400 MHz, DMSO-$d_6$) (δ=9.01 (d, J=8.8 Hz, 1H), 8.06-8.02 (m, 2H), 7.90 (d, J=8.0 Hz, 1H), 7.72-7.50 (m, 6H), 7.05-6.95 (m, 2H), 6.55-6.53 (m, 2H), 6.43-6.41 (m, 3H), 5.09-5.03 (m, 2H), 4.22 (d, J=12.8 Hz, 1H), 3.83-3.78 (m, 1H), 3.08-3.03 (m, 1H), 2.60 (d, J=4.4 Hz, 1H), 0.80 (t, J=6.8 Hz, 3H). LC-MS (Method-C)=534.28 $[M+H]^+$; 85.20% at RT 1.74 min.

Synthesis of Analogues

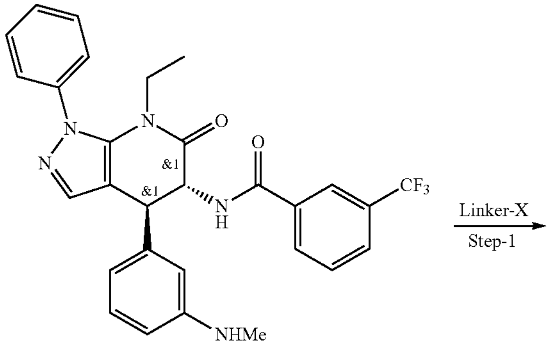

Compound-5

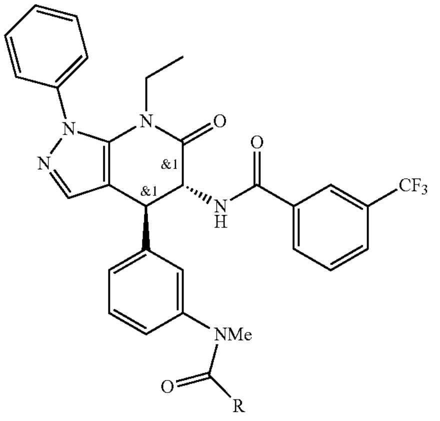

a. Mukaiyama reagent (1.5 eq), Tributylamine (2.5 eq), DMF, 70° C., 16 h R
b. HATU (1.5 eq), DIPEA (3 eq), DMF, RT 16 h, 2-(morpholinomethyl) prop-2-enoic acid
c. EDC, HOBT, DIPEA, DMF, RT, 16 h
d. DIPEA (3 eq), Acryloyl chloride, DMF, RT 16 h Synthesis of I-84 (Method-B):

To a stirred solution of Compound (1) (250 mg, 0.421 mmol) and 2-(morpholinomethyl) prop-2-enoic acid (0.06 g, 0.37 mmol) in DMF (5 mL) was added HATU (260 mg, 0.66 mmol) followed by N,N-Diisopropylethylamine (0.16 g, 1.26 mmol) at 0° C. Resulting reaction mixture was stirred at ambient temperature for 16 h. Progress of the reaction was monitored by TLC and LCMS. After completion of reaction, the reaction mixture was quenched with ice cold water, extracted with ethyl acetate. Organic layer was washed with brine solution, dried over anhydrous sodium sulfate, concentrated under vacuum to afford crude compound. Obtained crude compound was purified by prep-HPLC, product containing fractions were collected and lyophilized to afford I-84 (32 mg, 10.94%) as a white solid.

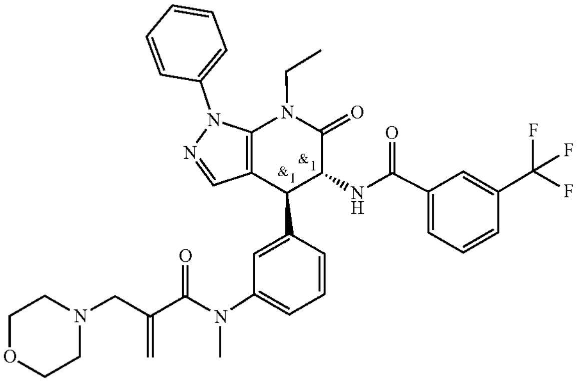 [SMILES: C=C(CN1CCOCC1)C(=O)N(C)c1cccc([C@H]2c3cnn(-c4ccccc4)c3N(CC)C(=O)[C@@H]2NC(=O)c2cccc(C(F)(F)F)c2)c1]

$^1$H NMR (400 MHz, DMSO-$d_6$) δ=8.97 (d, J=9.2 Hz, 1H), 8.07-8.03 (m, 2H), 7.90 (d, J=7.6 Hz, 1H), 7.72-7.63 (m, 3H), 7.60-7.52 (m, 3H), 7.12 (d, J=8.0 Hz, 1H), 7.02 (s, 1H), 6.75 (s, 1H), 6.68 (d, J=7.6 Hz, 1H), 6.58 (dd, J=8.4 Hz, 2.4 Hz, 1H), 5.4-5.20 (m, 2H), 5.03 (s, 2H), 4.30 (d, J=12.8 Hz, 1H), 4.08 (s, 2H), 3.86-3.81 (m, 1H), 3.39-3.16 (m, 7H), 3.07-3.02 (m, 1H), 2.88 (s, 3H), 0.81 (t, J=6.8 Hz, 3H). LC-MS (Method-A)=685.43 $[M-H]^-$; 99.90% at RT 2.22 min. HPLC (Method-A)=99.78% at RT 5.55 min.

Synthesis of I-74 (Method-D):

To a stirred solution of compound (5) (250 mg, 0.40 mmol) in DMF (3 mL) was added N,N-Diisopropylethylamine (0.10 g, 0.80 mmol), and acryloyl chloride (0.037 g, 0.40 mmol) at ambient temperature. Resulting reaction mixture was stirred at ambient temperature for 16 h. Progress of the reaction was monitored by TLC and LCMS. After completion of reaction, the reaction mixture was quenched with ice cold water, and extracted with ethyl acetate. Organic layer was washed with brine solution, dried over anhydrous sodium sulfate, concentrated under vacuum to afford desired crude compound. Obtained crude compound was purified by prep-HPLC. Product containing fractions were collected and lyophilized to afford I-74 (92 mg, 38.07%) as a fluffy white solid.

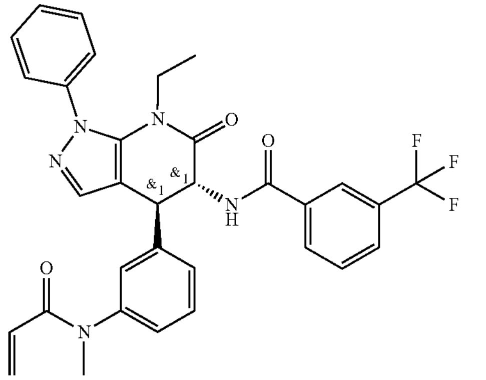 [SMILES: C=CC(=O)N(C)c1cccc([C@H]2c3cnn(-c4ccccc4)c3N(CC)C(=O)[C@@H]2NC(=O)c2cccc(C(F)(F)F)c2)c1]

$^1$H NMR (400 MHz, DMSO-$d_6$) δ=9.02 (d, J=9.2 Hz, 1H), 8.05-8.01 (m, 2H), 7.90 (d, J=8.0 Hz, 1H), 7.72-7.65 (m, 3H), 7.60-7.51 (m, 3H), 7.41 (d, J=4.8 Hz, 2H), 7.29 (s, 1H), 7.16-7.14 (m, 2H), 6.21-5.75 (m, 2H), 5.29-5.22 (m, 2H), 4.40 (d, J=13.2 Hz, 1H), 3.88-3.83 (m, 1H), 3.16 (s, 3H), 3.06-3.00 (m, 1H), 0.82 (t, J=7.2 Hz, 3H). LC-MS (Method-A)=586.34 $[M-H]^-$; 98.87% at RT 2.19 min. HPLC (Method-A)=97.81% at RT 5.44 min.

Synthesis of Analogues:

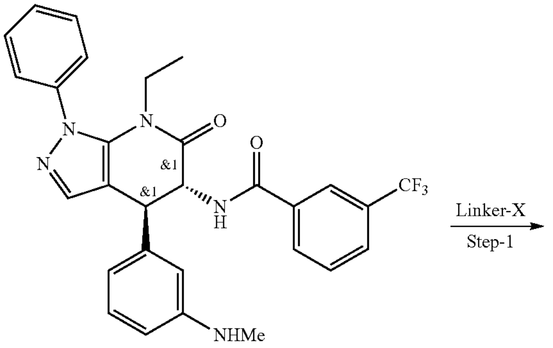

Compound-5

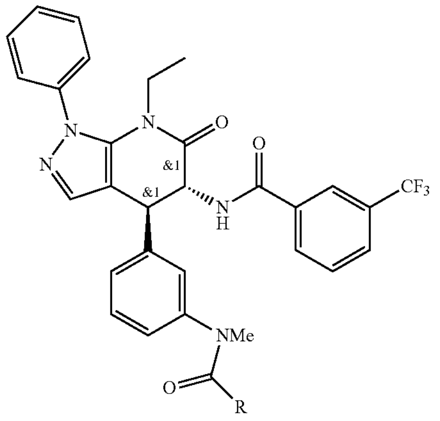

a. Mukaiyama reagent (1.5 eq), Tributylamine (2.5 eq), DMF, 60° C., 16 h, R
b. HATU (1.5 eq), DIPEA (3 eq), DMF, RT 16 h
c. EDC, HOBT, DIPEA, DMF, RT, 16 h
d. DIPEA (3 eq), Acryloyl chloride, DMF, RT 16 h Method-A To a stirred solution of compound (1) (250 mg, 0.41 mmol), and Linker-X (0.04 g, 0.41 mmol) in DMF (5 mL) was added tributylamine (0.31 g, 1.64 mmol), and 2-chloro-1-methylpyridinium iodide (0.22 g, 0.82 mmol) and the reaction mixture was stirred at 70° C. for 16 h. Progress of the reaction was monitored by TLC&LCMS. After completion of reaction, the reaction mixture was cooled to ambient temperature, and quenched with ice cold water, extracted with ethyl acetate. Organic layer was washed with brine solution, dried over anhydrous sodium sulfate, and concentrated under vacuum to afford desired crude compound. Obtained crude compound was purified by prep-HPLC, product containing fractions were collected and lyophilized to afford its corresponding analogues.

Data of I-91:

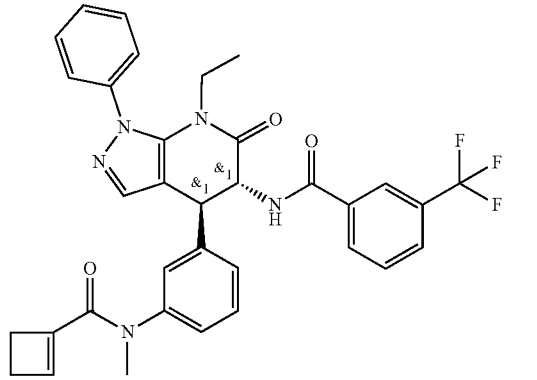 [SMILES: CCN1C(=O)[C@H](NC(=O)c2cccc(C(F)(F)F)c2)[C@@H](c2cccc(N(C)C(=O)C3=CCC3)c2)c2cnn(-c3ccccc3)c21]

$^1$H NMR (400 MHz, DMSO-$d_6$) (δ=9.02 (d, J=9.2 Hz, 1H), 8.05-8.03 (m, 2H), 7.90 (d, J=7.6 Hz, 1H), 7.72-7.65 (m, 3H), 7.60-7.47 (m, 3H), 7.45-7.39 (m, 2H), 7.35 (s, 1H), 7.20-7.17 (m, 2H), 5.40 (s, 1H), 5.31 (dd, J=13.2, Hz, 9.2 Hz, 1H), 4.42 (d, J=13.2 Hz, 1H), 3.88-3.82 (m, 1H), 3.13 (s, 3H), 3.07-3.00 (m, 1H), 1.92 (s, 2H), 1.74-1.64 (m, 2H), 0.82 (t, J=6.8 Hz, 3H). LC-MS (Method-A)=612.39 $[M-H]^-$; 99.48% at RT 2.23 min. HPLC (Method-A)=99.84% at RT 5.63 min.

Data of I-99:

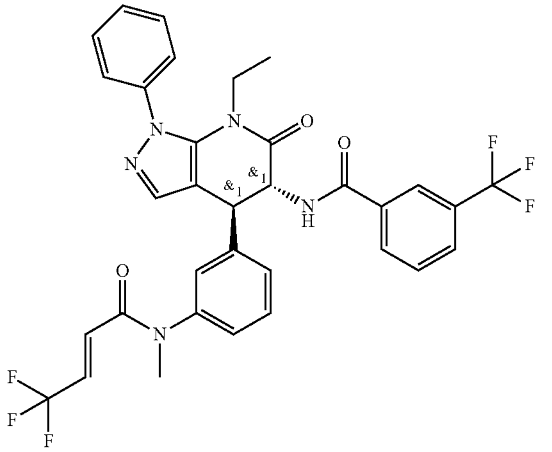 [SMILES: CCN1C(=O)[C@H](NC(=O)c2cccc(C(F)(F)F)c2)[C@@H](c2cccc(N(C)C(=O)/C=C/C(F)(F)F)c2)c2cnn(-c3ccccc3)c21]

$^1$H NMR (400 MHz, DMSO-$d_6$) δ=8.99 (d, J=9.2 Hz, 1H), 8.02-8.00 (m, 2H), 7.87 (d, J=7.6 Hz, 1H), 7.69-7.51 (m, 6H), 7.44-7.40 (m, 3H), 7.19-7.17 (m, 1H), 7.08 (s, 1H), 6.77-6.68 (m, 1H), 6.29 (d, J=15.2 Hz, 1H), 5.30 (dd, J=12.8 Hz, 9.2 Hz, 1H), 4.41 (d, J=12.8 Hz, 1H), 3.89-3.83 (m, 1H), 3.22 (s, 3H), 3.07-2.98 (m, 1H), 0.82 (t, J=6.8 Hz, 3H). LC-MS (Method-A)=656.40 $[M+H]^+$; 99.41% at RT 2.46 min. HPLC (Method-C)=98.40% at RT 5.99 min.

Synthesis of I-39:

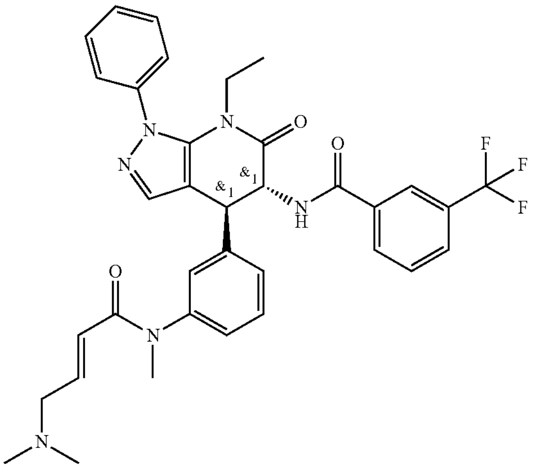 [SMILES: CCN1C(=O)[C@H](NC(=O)c2cccc(C(F)(F)F)c2)[C@@H](c2cccc(N(C)C(=O)/C=C/CN(C)C)c2)c2cnn(-c3ccccc3)c21]

$^1$H NMR (400 MHz, DMSO-$d_6$) (δ=9.01 (d, J=9.2 Hz, 1H), 8.20 (s, 1H), 8.03-8.01 (m, 2H), 7.90 (d, J=7.6 Hz, 1H), 7.72-7.64 (m, 3H), 7.60-7.51 (m, 3H), 7.40-7.31 (m, 3H), 7.16-7.12 (m, 2H), 5.73 (d, J=14.8 Hz, 1H), 5.26 (dd, J=13.2 Hz, 9.2 Hz, 1H), 4.39 (d, J=12.8 Hz, 1H), 3.89-3.80 (m, 1H), 3.15 (s, 3H), 3.05-3.00 (m, 1H), 2.70-2.65 (m, 2H), 1.93 (s, 6H), 0.82 (t, J=7.2 Hz, 3H). LC-MS (Method-A)=643.39 $[M-H]^-$; 98.60% at RT 1.83 min. HPLC (Method-C)=97.09% at RT 4.77 min.

The following table shows the conditions to obtain the desired compounds.

| Sr No. | Cpd. Number | Structure (R) | Method | Compound-5 (mg) | Linker (mg) | Qty (mg) & Nature of compound | Yield (%) |
|---|---|---|---|---|---|---|---|
| 1. | I-91 | 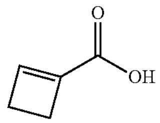 | A | 250 | 40 | 33 (white solid) | 12.9 |
| 2. | I-99 | 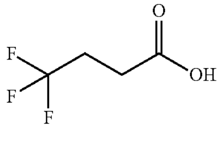 | A | 250 | 59 | 123 (fluffy white solid) | 45.2 |

-continued

| Sr No. | Cpd. Number | Structure (R) | Method | Compound-5 (mg) | Linker (mg) | Qty (mg) & Nature of compound | Yield (%) |
|---|---|---|---|---|---|---|---|
| 3. | I-39 | 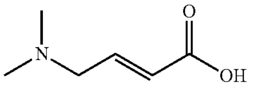 | A | 250 | 53 | 23 (white solid) | 8.73 |

Synthesis of 11C & 11D:

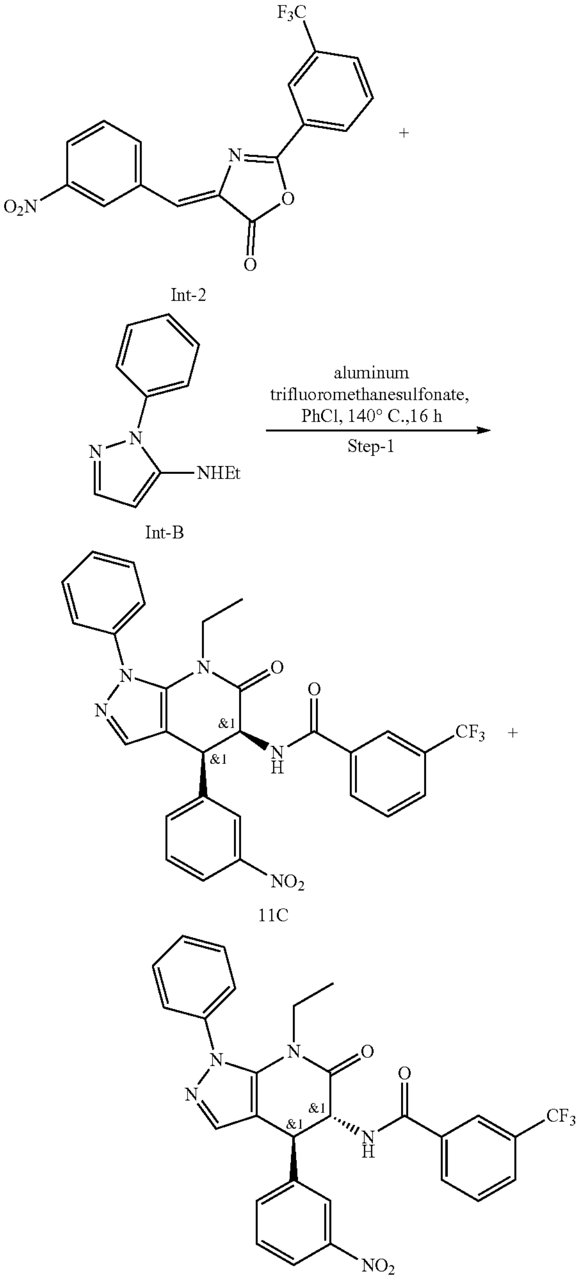

To a stirred solution of Int-2 (50 g, 131.1 mmol) and Int-B (32.2 g, 170.4 mmol) in chlorobenzene (500 mL) was added aluminum trifluoromethanesulfonate (15.7 g, 32.7 mmol) and the reaction mixture was stirred at 140° C. for 16 h. Progress of the reaction was monitored by TLC & LCMS. After completion of reaction, the reaction mixture was quenched with water and extracted with ethyl acetate. The combined organic layer was washed with brine solution and dried over anhydrous sodium sulfate, concentrated under vacuum to afford crude compound. The obtained crude compound was purified by flash column chromatography and product eluted in 50-55% in ethyl acetate in heptane. Product containing fractions were collected and concentrated to afford pure compound (25 g, 30.54%) as a yellow solid. Obtained crude material was submitted to prep HPLC purification. Both isomers were separated through prep HPLC. The pure fraction of peak-1 was directly lyophilized and dried to afford 11C (40 mg, 9.97%) as a yellow solid. The pure fraction of Peak 2 was directly lyophilized and dried to afford 11D (110.00 mg, 26.67%) as a yellow solid.

11C

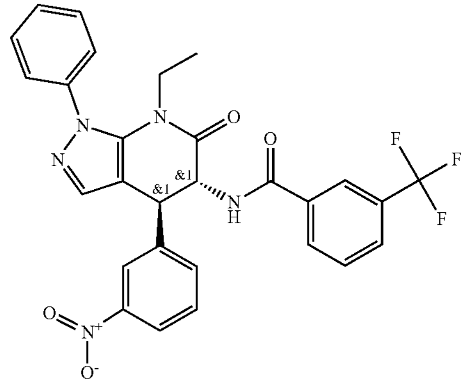 [SMILES: CCN1C(=O)[C@H](NC(=O)c2cccc(C(F)(F)F)c2)[C@@H](c2cccc([N+](=O)[O-])c2)c2cnn(-c3ccccc3)c21]

$^1$H NMR (400 MHz, DMSO-$d_6$) δ=9.05 (d, J=8.8 Hz, 1H), 8.32-8.31 (m, 1H), 8.15-8.12 (m, 1H), 8.00 (d, J=7.6 Hz, 2H), 7.89 (d, J=8.0 Hz, 2H), 7.71-7.53 (m, 7H), 7.14 (s, 1H), 5.32 (dd, J=13.2 Hz, 9.2 Hz, 1H), 4.59 (d, J=13.2 Hz, 1H), 3.87-3.80 (m, 1H), 3.08-3.03 (m, 1H), 0.83 (t, J=6.8 Hz, 3H). LC-MS (Method-A)=550.27 [M+H]$^+$; 98.54% at RT 2.30 min. HPLC (Method-A)=99.10% at RT 5.83 min.

11D

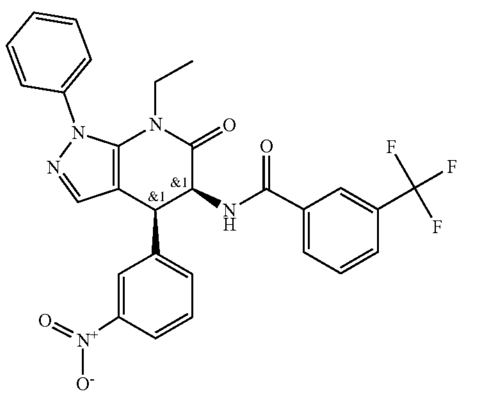 [SMILES: CCN1C(=O)[C@@H](NC(=O)c2cccc(C(F)(F)F)c2)[C@@H](c2cccc([N+](=O)[O-])c2)c2cnn(-c3ccccc3)c21]

$^1$H NMR (400 MHz, DMSO-$d_6$) (δ=8.72 (d, J=7.6 Hz, 1H), 8.15-8.13 (m, 3H), 7.91 (d, J=7.6 Hz, 1H), 7.80 (s, 1H), 7.72-7.67 (m, 4H), 7.62-7.53 (m, 4H), 7.44 (d, J=8.0 Hz, 1H), 5.62 (t, J=7.6 Hz, 1H), 4.76 (d, J=7.2 Hz, 1H), 4.00-3.95 (m, 1H), 3.07-2.98 (m, 1H), 0.95 (t, J=7.2 Hz, 3H). LC-MS (Method-A)=550.34 $[M+H]^+$; 99.72% at RT 2.38 min. HPLC (Method-C)=96.07% at RT 6.20 min.

Example 12: Synthesis of Compounds 12A, 12B and 12C

NMR:

$^1$H NMR spectrum was recorded on Bruker 400 MHz and Varian 400 MHz instruments internally referenced to a tetramethyl silane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5µ. Mobile Phase: A: 0.05% Formic acid in water: ACN (95:5) B: 0.05% Formic acid in CAN. Inj Volume: 2.0 µL, Column oven temperature: 50 C; Flow Rate: 1.2. mL/minute. Gradient program: 0% B to 98% B in 2.0 minute, hold till 3.0 min, at 3.2 min B conc is 0% up to 4.0 min.

Method-B: Column: X-Bridge C18 (3.0*50) mm 2.5µ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm, 2.5µ) Mobile Phase A: 0.05% TFA in Water Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

HPLC:

Method-D: Column: X-Select CSH C18 (4.6*150) mm 5µ Mobile Phase: A—0.1% TFA in water B—Acetonitrile Inj Volume; 5.0 µL, Flow Rate: 1.2. mL/minute Gradient program: Time(min)/B Conc.: 0.01/5, 1.0/5, 8.0/100, 12.0/100, 14.0/5, 18.0/5.

Method-E: Column name: CHIRAL PAK-IA (250*4.6, 5 µm) mobile phase a: n-hexane mobile phase b: DCM: MEOH (50:50 program-AB 90:10 flow rate: 1.0 ml/min.

Method-F: COLUMN: CHIRAL PAK-IG (250*4.6 mm, 5 µm) Mobile phase A: 0.1% DEA in n-Hexane Mobile phase B:DCM:MEOH (50:50) A:B; 80:20 Flow: 1.0 ml/min.

Method-G: Column: X-Bridge C18 (4.6*150) mm 5.0 µm Mobile Phase: A—5 mM ABC in Water B—Acetonitrile Flow Rate: 1.0 mL/minute Gradient program: Time(min)/B Conc.: 0.01 Pumps Pump B Conc. 5 1.00 Pumps Pump B Conc. 5 8.00 Pumps Pump B Conc. 100 12.00 Pumps Pump B Conc. 100 14.00 Pumps Pump B Conc. 5 18.00 Pumps Pump B Conc. 5.

Synthesis of 12A:

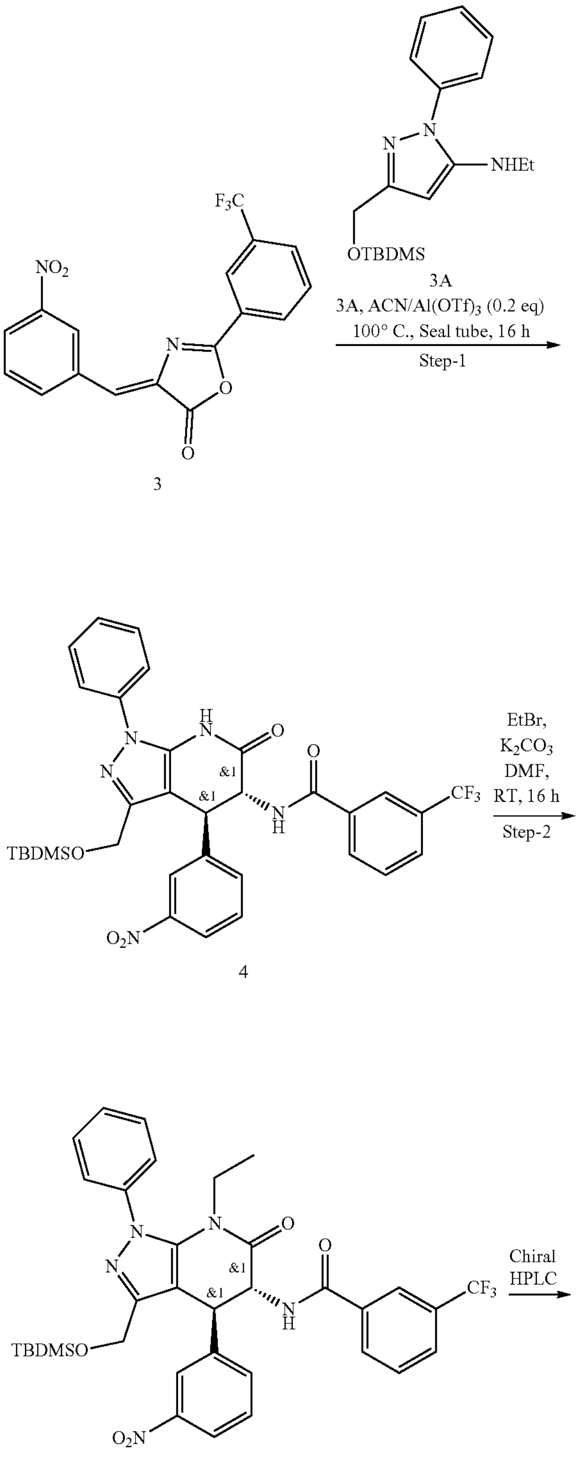

3A

3

4

12A

-continued

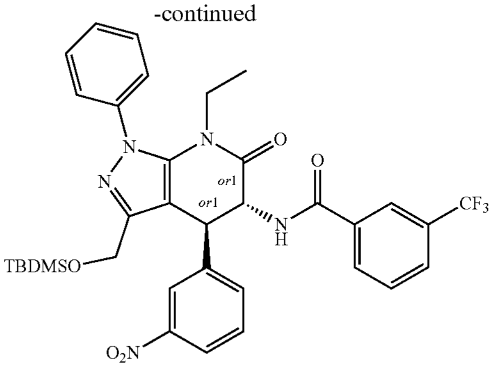

12B

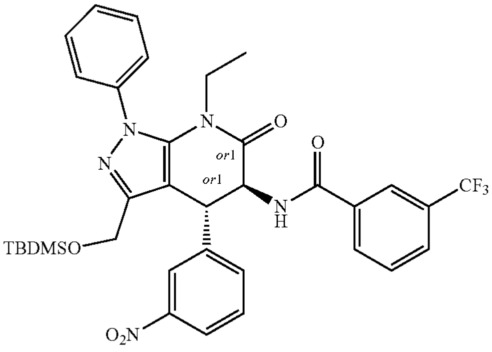

12C

Step-1: Synthesis of N-[rac-(4S,5R)-3-[[tert-butyl (dimethyl)silyl]oxymethyl]-4-(3-nitrophenyl)-6-oxo-1-phenyl-5,7-dihydro-4H-pyrazolo[3,4-b]pyridin-5-yl]-3-(trifluoromethyl)benzamide To a stirred solution of (4Z)-4-[(3-nitrophenyl)methylene]-2-[3-(trifluoromethyl) phenyl]oxazol-5-one (75 g, 186.3 mmol) and 5-[[tert-butyl(dimethyl)silyl]oxymethyl]-2-phenyl-pyrazol-3-amine (75.3 g, 223.6 mmol) in ACN (750 mL) was added aluminum trifluoromethanesulfonate (18.0 g, 37.26 mmol) at room temperature. The resulting reaction mixture was stirred at 90° C. for 16 h. The reaction was monitored by TLC; after completion of the reaction, the reaction mixture was quenched with water (750 mL). Precipitated solid was filtered and dried. The crude compound was purified by medium pressure liquid chromatography eluting with 0-30% EtOAC in heptane to afford compound-4 (30 g, 23.47% yield) as pale yellow solid. $^1$H NMR (400 MHz, DMSO-$d_6$) δ=10.99 (s, 1H), 9.01 (d, J=8.8 Hz, 1H), 8.24 (s, 1H), 8.14 (dd, J=1.6, 8.2 Hz, 1H), 8.04-7.98 (m, 2H), 7.96-7.83 (m, 2H), 7.71 (t, J=7.7 Hz, 1H), 7.66-7.59 (m, 3H), 7.58-7.52 (m, 2H), 7.45-7.39 (m, 1H), 5.08 (dd, J=8.8, 11.7 Hz, 1H), 4.59 (d, J=11.6 Hz, 1H), 4.17 (d, J=12.0 Hz, 1H), 3.81 (d, J=12.0 Hz, 1H), 0.71 (s, 9H), −0.15--0.27 (m, 6H). LC-MS (Method-B)=666.2 [M+H]$^+$ 94.75% RT: 2.67 min.

Step-2: Synthesis of (N)-[(rac)-(4 (S),5(R))-3-[[~{tert}-butyl(dimethyl)silyl]oxymethyl]-7-ethyl-4-(3-nitrophenyl)-6-oxo-1-phenyl-4,5-dihydropyrazolo [3,4-b]pyridin-5-yl]-3-(trifluoromethyl)benzamide (12A)

To a stirred solution of compound-4 (75 g, 112.7 mmol) in ACN (750 mL) was added potassium phosphate tribasic (2 equiv., 225.3 mmol), tetrabutylammonium bromide (2 equiv., 225.3 mmol) followed by bromoethane (2 equiv., 225.3 mmol, 99 mass %) at 0° C. The resulting reaction mixture was stirred at room temperature for 16 hours. Progress of the reaction was monitored by LCMS. After completion, reaction mixture was added water (700 mL) and extracted with EtOAc (700 mL×2). The combined organic layer was dried over sodium sulphate, filtered and concentrated under reduced pressure to get crude compound. The crude material was purified by column chromatography (Silica gel 60:120 mesh, 0-20% EtOAc in Heptane as eluent) to afford 12A (34 g, 40.02%) as an off white solid. $^1$H NMR (400 MHz, DMSO-$d_6$) δ=9.04 (d, J=8.8 Hz, 1H), 8.24 (s, 1H), 8.14 (d, J=7.8 Hz, 1H), 8.03-7.96 (m, 2H), 7.94-7.84 (m, 2H), 7.73-7.64 (m, 4H), 7.60 (t, J=7.6 Hz, 2H), 7.54 (d, J=6.8 Hz, 1H), 5.30 (t, J=10.0 Hz, 1H), 4.57 (d, J=11.2 Hz, 1H), 4.18 (d, J=12.2 Hz, 1H), 3.86-3.67 (m, 2H), 3.19 (dd, J=6.8, 14.2 Hz, 1H), 0.82 (t, J=6.6 Hz, 3H), 0.78-0.64 (m, 9H), −0.19 (d, J=8.3 Hz, 6H). LC-MS (Method-B)=694.2 [M+H]$^+$ 97.34% RT: 2.76 min. HPLC (Method-G)=98.4% at RT: 10.32 min.

Chiral separation of 12A:

The following target compound was purified by chiral HPLC to afford peak-1 as 12B and peak-2 as 12C. Chiral prep Method Information: Column: Chiral pack IG (30×250*mm, 5μ); Mobile Phase A: 0.05% DEA in n-Hexane; Mobile Phase B: EtOH:MeOH(1:1)

12B:

$^1$H NMR (400 MHz, DMSO-$d_6$) δ=9.06 (d, J=8.8 Hz, 1H), 8.24 (s, 1H), 8.14 (dd, J=1.5, 8.1 Hz, 1H), 8.02-7.97 (m, 2H), 7.90 (t, J=7.1 Hz, 2H), 7.73-7.64 (m, 4H), 7.64-7.58 (m, 2H), 7.56-7.52 (m, 1H), 5.31 (dd, J=8.8, 11.3 Hz, 1H), 4.57 (d, J=11.4 Hz, 1H), 4.17 (d, J=12.3 Hz, 1H), 3.83-3.68 (m, 2H), 3.22-3.13 (m, 1H), 0.81 (t, J=7.0 Hz, 3H), 0.71 (s, 9H), −0.19 (d, J=9.0 Hz, 6H). LC-MS (Method-C)=694.27 [M+H]$^+$ 99.09% RT: 2.48 min; HPLC: 100% at RT: 4.0 min.

12C:

$^1$H NMR (400 MHz, DMSO-$d_6$) δ=9.05 (d, J=8.8 Hz, 1H), 8.24 (s, 1H), 8.14 (dd, J=1.5, 8.1 Hz, 1H), 8.02-7.97 (m, 2H), 7.90 (t, J=6.6 Hz, 2H), 7.74-7.57 (m, 6H), 7.57-7.50 (m, 1H), 5.31 (dd, J=8.8, 11.3 Hz, 1H), 4.57 (d, J=11.3 Hz, 1H), 4.17 (d, J=12.4 Hz, 1H), 3.82-3.79 (m, 1H), 3.25-3.12 (m, 2H), 0.82 (t, J=7.0 Hz, 3H), 0.71 (s, 9H), −0.19 (d, J=8.9 Hz, 6H). LC-MS (Method-C)=694.31 [M+H]$^+$ 99.15% RT: 2.48 min. HPLC: 99.22% at RT: 6.57 min.

Preparation of Int-3:

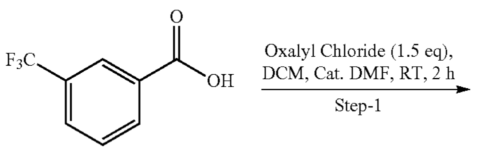

SM-1

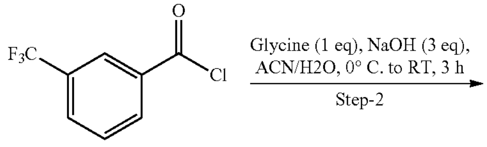

1

-continued

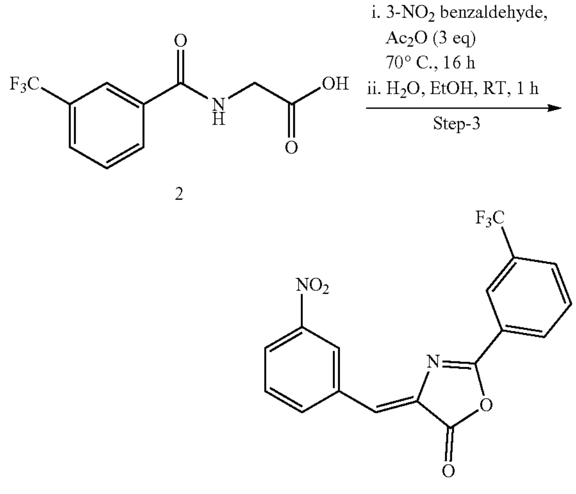

2

3

Step-1: Synthesis of 3-(trifluoromethyl)benzoyl chloride

To a stirred solution of 3-(trifluoromethyl)benzoic acid (100 g, 525.98 mmol) in DCM (900 mL) were added cat. amount of DMF (2 mL, 25.8 mmol) followed by oxalyl chloride (101.15 g, 788.98 mmol) at 0° C. The resulting reaction mixture was stirred at 25° C. for 3 h. The reaction was monitored by TLC; after completion of the reaction, the reaction mixture was econcentrated under reduced pressure to afford compound-1 (100 g, 92%). The crude was directly used in the next step without further purification and analysis.

Step-2: Synthesis of 2-[[3-(trifluoromethyl)benzoyl] amino]acetic acid

To a stirred solution of glycine (36.35 g, 479.4 mmol) in ACN (800 mL) was added sodium hydroxide (48.42 g, 1198.7 mmol) dissolved in water (50 ml) at 0° C. and stirred for 5 min. To the resulting reaction mixture was slowly added compound-1 (100 g, 479.48 mmol) dissolved in ACN. The resulting reaction mixture was stirred at 25° C. for 16 h. The reaction was monitored by TLC; after completion of the reaction, the reaction mixture was adjusted to pH=3 by using HCl and extracted by EtOAc. The combined organic layer was concentrated under reduced pressure to get crude compound. The crude compound was washed with heptane to afford compound-2 (99 g, 81% Yield) as pale yellow solid. $^1$H NMR (400 MHz, DMSO-$d_6$) δ=12.64 (br s, 1H), 9.13 (br s, 1H), 8.27-8.11 (m, 2H), 7.94 (d, J=7.3 Hz, 1H), 7.75 (t, J=7.8 Hz, 1H), 3.96 (d, J=5.9 Hz, 2H). LC-MS (Method-B)=247.8 [M+H]$^+$ 97.60% RT: 1.52 min.

Step-3: Synthesis of (4(Z))-4-[(3-nitrophenyl)methylene]-2-[3-(trifluoromethyl) phenyl]oxazol-5-one (Int-3)

To a stirred solution of compound-2 (40 g, 161.83 mmol) were added acetic anhydride (50.1 g, 485.50 mmol) followed by 3-nitrobenzaldehyde (25 g, 161.83 mmol) at 25° C. The resulting reaction mixture was stirred at 70° C. for 16 h. The reaction was monitored by TLC. After completion of the reaction, the reaction mixture was cooled to 0° C., added EtOH: $H_2O$(1:1) and stirred for 1 h. The resulting reaction mixture was filtered to afford Int-3 (35 g, 60% yield) as pale yellow solid. $^1$H NMR (400 MHz, DMSO-$d_6$) δ=9.23 (t, J=1.8 Hz, 1H), 8.71 (d, J=7.8 Hz, 1H), 8.43 (d, J=7.8 Hz, 1H), 8.37-8.32 (m, 2H), 8.15 (d, J=7.9 Hz, 1H), 7.94 (t, J=7.9 Hz, 1H), 7.85 (t, J=8.1 Hz, 1H), 7.63 (s, 1H).

Synthesis of Int-3A:

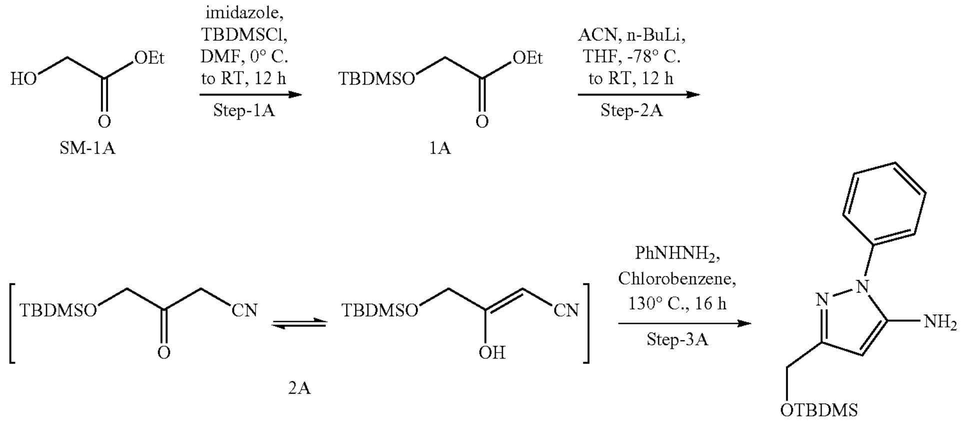

SM-1A 1A 2A 3A

Step-1: Synthesis of ethyl 2-[(tert)-butyl(dimethyl) silyl]oxyacetate

To a stirred solution of ethyl 2-hydroxyacetate (500 g, 4707.0 mmol) in DMF (2.5 L) was added imidazole (420.79 g, 6119.1 mmol) at 0° C. The reaction mixture was Stirred for 10 minutes at same temperature. To the resulting reaction mixture was added tert-Butyldimethylchlorosilane (950.82 g, 6119.1 mmol) slowly by maintaining reaction temperature below 10° C. The resulting reaction mixture was stirred at room temperature for 12 h. Reaction progress was monitored by TLC. The reaction was monitored by TLC; after completion of the reaction, the reaction mixture was quenched with ice cold water (5 L) and extracted with EtOAc (2 L×2). The organic layer was washed with ice cold water. The combined organic layer were dried over anhydrous sodium sulfate and concentrated under vacuum to afford compound-1A (1000 g, 97.293% Yield) as colourless liquid. $^1H$ NMR (400 MHz, DMSO-$d_6$) δ=4.23 (s, 2H), 4.11 (q, J=6.8 Hz, 2H), 1.19 (t, J=7.1 Hz, 3H), 0.87 (s, 9H), 0.06 (s, 6H). LC-MS (Method-C)=236.1 $[M+H_2O]^+$87.36% RT: 2.43 min.

Step-2: Synthesis of (Z)-4-((tert-butyldimethylsilyl) oxy)-3-hydroxybut-2-enenitrile To a stirred solution of acetonitrile (112.8 g, 2747.8 mmol) in THE (4 L) was added Butyl lithium (1.5 mol/L) in cyclohexane (1100 mL, 2747.8 mmol) at −78° C. for 30 min. To the resulting reaction mixture was added compound-1A (400 g, 1831.8 mmol) and diluted with 500 mL THF solvent. After addition, the reaction temperature gradually rised to room temperature. The resulting reaction mixture was stirred at room temperature for 2.5 h. The reaction was monitored by TLC; after completion of the reaction, the reaction mixture was charged with $KMNO_4$, quenched with 2N HCl at 10° C. to adjust pH to 4 and extracted with ethyl acetate. The combined organic layer was washed with brine water 2 times and dried over anhydrous sodium sulphate and concentrated under reduced pressure to afford compound-2A (391 g, crude) as brick red colored syrup. The crude was directly used in next step without any further purification and analysis.

Step-3: Synthesis of 3-(((tert-butyldimethylsilyl) oxy)methyl)-1-phenyl-1H-pyrazol-5-amine (Int-3A)

To a stirred solution of compound-2A (480 g, 2249.8 mmol) and phenylhydrazine (319.49 g, 2924.8 mmol) in chlorobenzene (2.4 L) was heated for 130° C. for 16 h. The reaction was monitored by TLC. After completion of the reaction, the reaction mixture was concentrated under reduced pressure to get crude compound. The crude material was purified by medium pressure liquid chromatography by eluting with 0-10% EtOAc in heptane to afford Int-3A (200 g, 25.78% yield) as pale yellow solid. $^1H$ NMR (400 MHz, DMSO-$d_6$) δ=7.56 (d, J=7.8 Hz, 2H), 7.46 (t, J=7.8 Hz, 2H), 7.37-7.21 (m, 1H), 5.47 (s, 1H), 5.29 (s, 2H), 4.50 (s, 2H), 0.89 (s, 9H), 0.073 (s, 6H). LC-MS (Method-C)=304.1 $[M+H]^+$ 88.11% RT: 2.30 min.

Example 13: Synthesis of Compounds I-132, and I-92

NMR:

$^1H$ NMR spectrum was recorded on Bruker 400 MHz and Varian 400 MHz instruments internally referenced to a tetramethyl silane (TMS) signal. Chemical shifts (6) and coupling constants (J) were expressed in parts per million and hertz, respectively.

LCMS:

Method-A: LCMS, X-Select (Formic acid); Column: X-Select CSH C18 (3.0*50) mm 2.5μ. Mobile Phase: A: 0.05% Formic acid in water: ACN (95:5) B: 0.05% Formic acid in ACN Inj Volume: 2.0 μL, Column oven temperature: 50° C.; Flow Rate: 1.2 mL/min. Gradient Program (B %): 0.0/2, 0.3/2, 2.0/98, 2.8/98, 3.0/2, 3.7/2.

Method-B: Column: X-Bridge BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

Method-D: Column: X-Select CSH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

Method-E: Column: CORTECS UPLC C18 (3×30 mm, 1.6 m) Mobile Phase: A: 0.05% FA in Water B: 0.05% FA in ACN, Flow rate: 0.85 mL/min (Gradient), Column Oven Temp: 45° C., Gradient Program (B %): 0/3, 0.1/3, 1.4/97, 2/97, 2.05/3, 2.5/3.

Method-F: Column: Poroshell 120 EC-C18 (3×100 mm, 2.7 m) Mobile Phase: A: 0.05% TFA in Water B: 0.05% TFA in ACN, Flow rate: 0.80 mL/min (Gradient), Column Oven Temp: 40° C., Gradient Program (B %): 0.01/2, 0.2/2, 3/98, 5/98, 5.2/2, 7/2.

Method-H: Column: BAKERBOND Q2100 C18 (2.1×50 mm, 1.8 m) Mobile Phase: A: 0.05% FA in Water, Mobile Phase B: 0.05% FA in Acetonitrile, Colum Temperature: 40° C., Flow Rate: 0.6 mL/min, Gradient: 0.0/2, 0.3/2, 2.0/98, 2.8/98, 3.0/2, 3.7/2, Diluent: ACN: Water.

Method-I: Column: Poroshell 120 EC-C18 (3×100 mm, 2.7 μm) Mobile Phase: A: 0.05% TFA in Water B: 0.05% TFA in ACN, Flow rate: 0.70 mL/min (Gradient), Column Oven Temp: 40° C., Gradient Program (B %): 0.01/10, 0.2/10, 6/90, 8/90, 8.1/10, 10/10.

HPLC:

Method-A: Column: X Select CSH C18 (150×4.6) mm, 3.5; Mobile phase A: 0.1% FA in Water: ACN (95:05); Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: ACN; Programme/B %: 0.01/5, 1.0/5, 8.0/100, 12.0/100, 14.0/5, 18.0/5; Flow: 1.0 mL/min.

Method-C: Column: X SELECT CSH C18 (150×4.6 mm, 3.5); Mobile Phase A; 0.05% TFA IN WATER: ACN (95: 05); Mobile Phase B: 0.05% TFA IN WATER: ACN (05:95); Programme: T/B %: 0.01/10, 12/90, 16/90; Flow: 1 mL/min.; Diluent: WATER:ACN (80:20).

Method-D: Column: X-Bridge CSH C18 (4.6*150) mm 5μ Mobile Phase: A—0.1% TFA in water B—Acetonitrile Inj Volume; 5.0 μL, Flow Rate: 1.2. mL/minute Gradient program: Time(min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in HEXANE Mobile Phase B: IPA A/B: 60/40 Flow: 1.0 ml/MIN PDA: OJ-H_015.

Method-F: Column Name: CHIRALPAK-IK (250×4.6 mm, 5 μm) Mobile phase-A: n-Hexane Mobile phase-B: ETOH/MEOH (1:1) Flow rate: 1.0 mL/min % A/B: 50/50.

Method-H: Column: X-Bridge CSH C18 (150×4.6 mm, 3.5 μm); Mobile Phase-A: 5 mM $NH_4HCO_3$ in water; Mobile Phase-B: ACN; Programme/B %: Time(min)/B Conc.: 0.01/5, 1.0/5, 8.0/100, 12.0/100, 14.10/5, 18.0/5; Flow: 1.0 mL/min.; Diluent: ACN: WATER (80:20).

Method-I: Column Name: CHIRALPAK-IC (250×4.6 mm, 5 μm) Mobile phase-A: 0.1% TFA in n-HEXANE, Mobile phase-B: DCM: IPA (50:50), Flow rate: 1.0 mL/min % A/B: 60/40.

Method-L: Column Name: CHIRALPAK-IA (150*4.6 mm, 3 μm)) Mobile phase-A: n-hexane, Mobile phase-B: ETOH:MEOH (1:1), Flow rate: 1.0 mL/min, % A/B: 70:30.

Method-N: Column: BAKERBOND 1.7μ or 1.8μ C18 100 mm×2.1 mm Mobile Phase A: 0.05% FA in Water, Mobile Phase B: 0.05% FA in Acetonitrile, Colum Temperature: 40° C., Flow Rate: 0.5 mL/min, Gradient: 0/5, 3/5, 6/95, 8.5/95, 8.8/5, 11/5, Diluent: ACN: Water.

Method-T: Column Name: CHIRALPAK-IC (250×4.6 mm, 5 μm) Mobile phase-A: n-HEXANE, Mobile phase-B: IPA: MeOH (50:50), Flow rate: 1.0 mL/min % A/B: 50/50.

Method-X: Column Name: CHIRALPAK-TK (250×4.6 mm, 5 μm) Mobile phase-A: n-Hexane Mobile phase-B: ETOH/MEOH (1:1) Flow rate: 1.0 mL/min % A/B: 50/50.

Method-Y: Column Name: CHIRALPAK-IK (250×4.6 mm, 5 μm) Mobile phase-A: n-Hexane Mobile phase-B: IPA/MEOH (1:1) Flow rate: 1.0 mL/min %.

Method-Z: Column Name: CHIRALPAK-IA (150*4.6 mm, 3 μm)) Mobile phase-A: n-hexane, Mobile phase-B: IPA, Flow rate: 1.0 mL/min, % A/B: 70:30.

Method-Z-1: Column Name: CHIRALPAK-IE (250×4.6 mm, 5 μm) Mobile phase-A: n-Hexane/DEA/TFA (100/0.1/0.1%) Mobile phase-B: ETOH/MEOH (1:1) Flow rate: 1.0 mL/min % A/B: 60/40.

Synthesis of I-132:

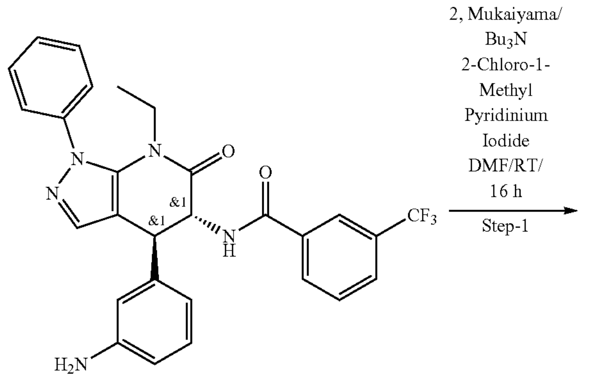

1

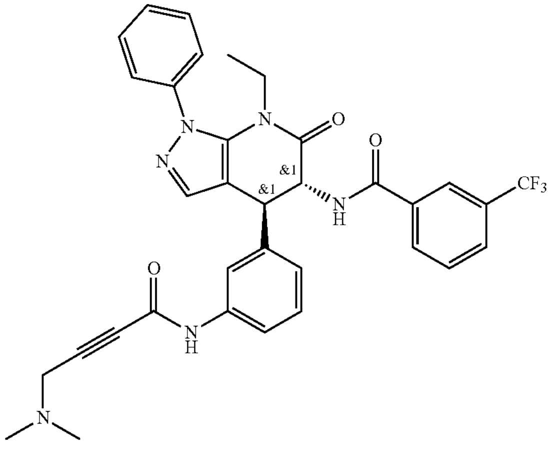

I-132

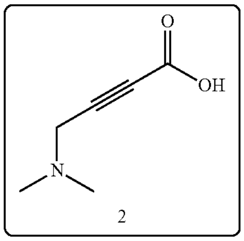

2

Step-1: rac-N-((4R,5S)-4-(3-(4-(dimethylamino)but-2-ynamido)phenyl)-7-ethyl-6-oxo-1-phenyl-4,5,6,7-tetrahydro-1H-pyrazolo[3,4-b]pyridin-5-yl)-3-(trifluoromethyl)benzamide (I-132)

To a stirred solution rac-N-((4R,5S)-4-(3-aminophenyl)-7-ethyl-6-oxo-1-phenyl-4,5,6,7-tetrahydro-1H-pyrazolo[3,4-b]pyridin-5-yl)-3-(trifluoromethyl)benzamide (250 mg, 0.433 mmol) in DMF (5 mL) was added 4-(dimethyl amino) but-2-ynoic acid (57.96 mg, 0.433 mmol), tributylamine (328 mg, 1.732 mmol) followed by 2-chloro-1-methylpyridinium iodide (228 mg, 0.866 mmol) at room temperature. The resulting reaction mixture was stirred at 70° C. for 12 h. The progress of the reaction was monitored by TLC & LCMS. After completion, the reaction mixture was quenched with ice water (20 mL), extracted with ethyl acetate (3×30 mL). The combined organic layer was washed with brine solution, dried over anhydrous sodium sulfate, concentrated under vacuum. The crude purified by Prep HPLC followed by lyophilization to afford the title compound I-132 (35 mg, 12.21%) as a pale light brown solid. $^1$H NMR (400 MHz, DMSO-$d_6$) (δ=10.66 (s, 1H), 9.01 (d, J=9.0 Hz, 1H), 8.05-8.01 (m, 2H), 7.90 (d, J=7.9 Hz, 1H), 7.72-7.64 (m, 4H), 7.62-7.52 (m, 4H), 7.27 (t, J=7.9 Hz, 1H), 7.14 (d, J=7.6 Hz, 1H), 7.10 (s, 1H), 5.11 (dd, J=9.0, 12.7 Hz, 1H), 4.37 (d, J=13.0 Hz, 1H), 3.88-3.79 (m, 1H), 3.43 (s, 2H), 3.06 (dd, J=7.0, 14.1 Hz, 1H), 2.23 (s, 6H), 0.82 (t, J=7.0 Hz, 3H). LC-MS (Method-I)=629.2 [M+H]$^+$; 96.61% at RT 4.76 min. HPLC (Method-N)=96.46% at RT 4.21 min.

Synthesis of I-92:

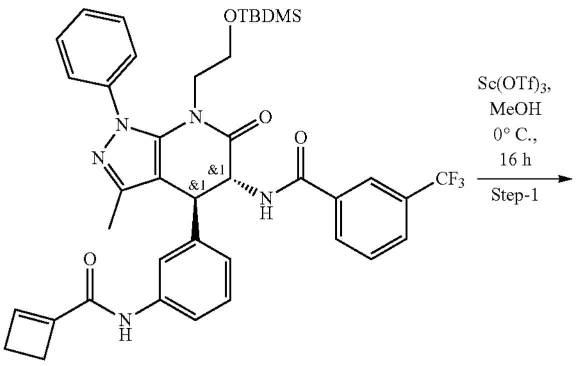

1

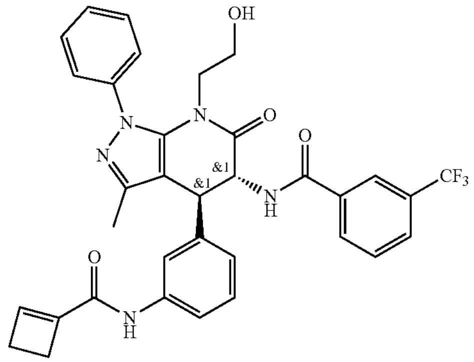

I-92

Step-1: Synthesis of rac-N-((4R,5S)-4-(3-(cyclobut-1-ene-1-carboxamido)phenyl)-7-(2-hydroxyethyl)-3-methyl-6-oxo-1-phenyl-4,5,6,7-tetrahydro-1H-pyrazolo[3,4-b]pyridin-5-yl)-3-(trifluoromethyl) benzamide (1-92)

To a stirred solution of rac-N-((4R,5S)-7-(2-((tert-butyldimethylsilyl)oxy)ethyl)-4-(3-(cyclobut-1-ene-1-carboxamido)phenyl)-3-methyl-6-oxo-1-phenyl-4,5,6,7-tetrahydro-1H-pyrazolo[3,4-b]pyridin-5-yl)-3-(trifluoromethyl) benzamide (220 mg, 0.30 mmol) in Methanol (10 mL) was added $Sc(OTf)_3$ (150 mg, 0.30 mmol) at 0° C. Then the reaction mixture was stirred at room temperature for 16 h. The progress of the reaction mixture checked by TLC. The reaction mixture was concentrated under vacuum to obtain the crude compound. The crude was purified by column chromatography to afford the title compound I-92 (47 mg, 25%) as an off-White solid. $^1H$ NMR (400 MHz, $CD_3D-d_4$) (δ=7.94 (s, 1H), 7.88 (d, J=7.8 Hz, 1H), 7.80-7.77 (m, 2H), 7.61-7.53 (m, 7H), 7.33 (t, J=7.9 Hz, 1H), 7.20 (d, J=7.6 Hz, 1H), 6.77 (s, 1H), 5.34 (d, J=12.8 Hz, 1H), 4.41 (d, J=12.9 Hz, 1H), 4.18-4.11 (m, 1H), 3.50-3.43 (m, 1H), 3.38-3.32 (m, 1H), 3.14-3.11 (m, 1H), 2.81-2.77 (m, 2H), 2.51-2.47 (m, 2H), 1.60 (s, 3H). LC-MS (Method-D)=630.0 $[M+H]^+$; 96.93% at RT 2.01 min. HPLC (Method-H)=97.47% at RT 8.10 min. Chiral HPLC (Method-Z)=Peak-I=50.12% at RT 6.70 min. Peak-2=49.88% at RT 8.05 min.

Example 14: Synthesis of Compounds I-147, and I-55

NMR:

$^1H$ NMR spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: ACN (95:5) B: 0.05% Formic acid in ACN Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

Method-C: Column: X-Select CSH C18 (50 mm*3.0 mm, 2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water: ACN (95:05); Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: ACN; Programme/B %: 0.01/2, 2/2, 12/90, 16/90; Flow: 1.0 mL/min.; Diluent: ACN: WATER (80:20).

Method-C: Column: X SELECT CSH C18 (150×4.6 mm, 3.5); Mobile Phase A; 0.05% TFA IN WATER: ACN (95:05); Mobile Phase B: 0.05% TFA IN WATER: ACN (05:95); Programme: T/B %: 0.01/10, 12/90, 16/90; Flow: 1 mL/min.; Diluent: WATER:ACN (80:20).

Method-D: Column: X-Bridge CSH C18 (4.6*150) mm 5μ Mobile Phase: A—0.1% TFA in water B—Acetonitrile Inj Volume; 5.0 μL, Flow Rate: 1.2. mL/minute Gradient program: Time(min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in HEXANE Mobile Phase B: IPA A/B: 60/40 Flow: 1.0 ml/MIN PDA: OJ-H_015.

Method-F: Column Name: CHIRALPAK-IK (250×4.6 mm, 5 μm) Mobile phase-A: n-Hexane Mobile phase-B: ETOH/MEOH (50/50) Flow rate: 1.0 mL/min % A/B: 50/50.

Method-G: Column: X-Select CHS C18 (4.6*150) mm 5μ Mobile Phase: A—5 mM Ammonium acetate B—Acetonitrile Inj Volume; 5.0 μL, Flow Rate: 1.0 mL/minute.

Synthesis of I-211:

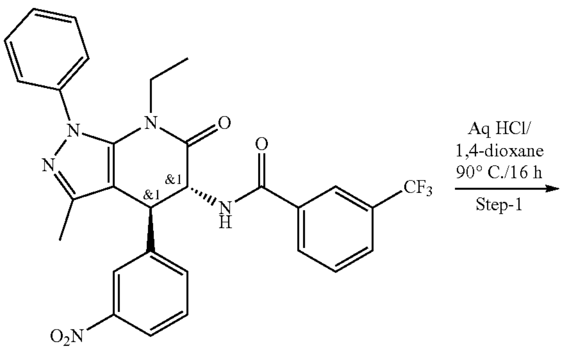

SM-1

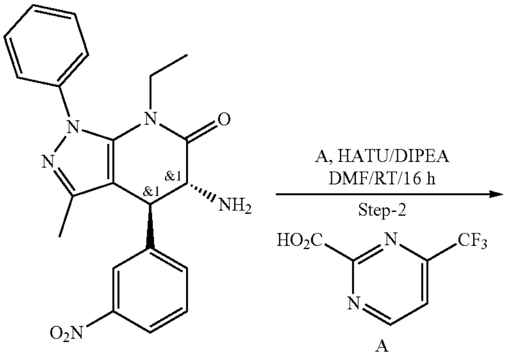

1

A

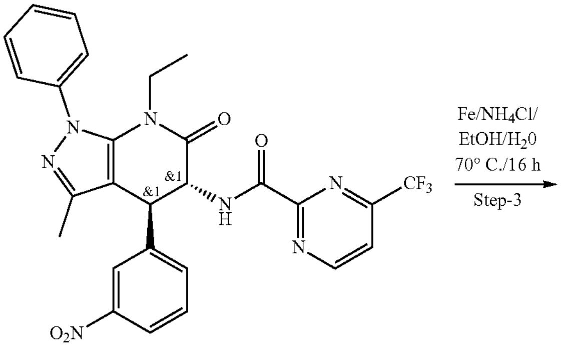

2

-continued

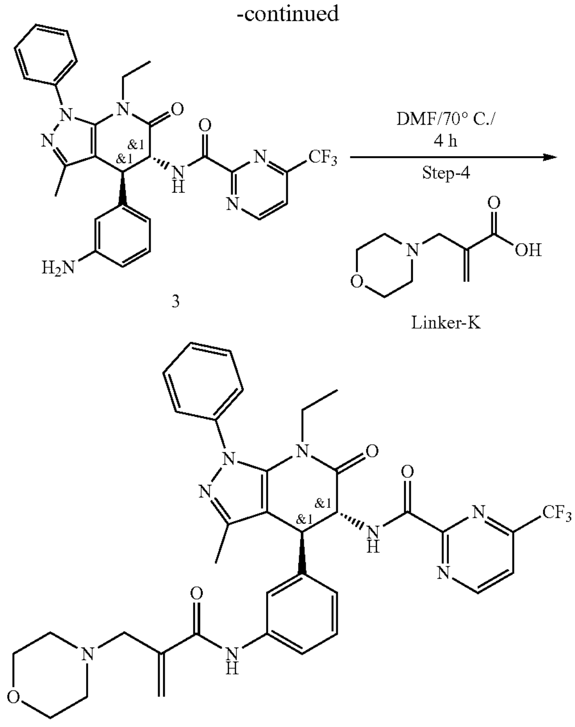

3

Linker-K

I-211

Step 1: rac-(4R,5S)-5-amino-7-ethyl-3-methyl-4-(3-nitrophenyl)-1-phenyl-1,4,5,7-tetrahydro-6H-pyrazolo[3,4-b]pyridin-6-one (1)

To a stirred solution of SM-1 (3.0 g, 5.32 mmol) in 1,4-dioxane (30 mL) and aq HCl (30 mL). The reaction mixture was stirred at 90° C. for 16 h. Progress of the reaction was monitored by TLC. The reaction mixture was diluted with ice cold water (1×10 mL) and basified with 2 N NaOH (100 mL), then extracted with ethyl acetate (3×100 mL). The combined organic layer was washed with ice cold water (3×10 mL) followed by brine wash. The organic layer dried over anhydrous sodium sulphate, filtered, and evaporated in vacuo to get the crude. The crude compound was purified by flash column chromatography and compound was eluted in 80% EtOAc in heptane to afford 1 (1.1 g, 53%) as off white solid.

$^{1}$HNMR (400 MHz, DMSO-$d_6$) δ=8.17 (d, J=7.6 Hz, 1H), 8.11 (bs, 1H), 7.80 (d, J=7.2 Hz, 1H), 7.7 (d, J=7.6 Hz, 1H), 7.56-7.49 (m, 5H), 4.12 (d, J=9.2 Hz, 1H), 3.89 (d, J=8.8 Hz, 1H), 3.58-3.53 (m, 1H), 3.30-3.22 (m, 1H), 1.97 (bs, 2H), 1.57 (s, 3H), 0.83 (t, J=6.0 Hz, 3H). LC-MS (Method-B)=311 $[M+H]^+$; 99.908% at RT 1.871 min.

Step 2: Synthesis of N-[rac-(4S,5R)-7-ethyl-3-methyl-4-(3-nitrophenyl)-6-oxo-1-phenyl-4,5-dihydropyrazolo[3,4-b]pyridin-5-yl]-4-(trifluoromethyl)pyrimidine-2-carboxamide (2)

To a stirred solution of 1 (0.2 g, 0.51 mmol) in DMF (1 mL) were added A (0.098 g, 0.51 mmol), HATU (0.40 g, 1.02 mmol) and followed by N,N-Diisopropylethylamine (0.26 mL, 1.53 mmol) at room temperature under nitrogen atmosphere. The reaction mixture was stirred at 25° C. for 16 h. Progress of the reaction was monitored by TLC. The reaction mixture was diluted with ice cold water (1×10 mL) and extracted with ethyl acetate (3×10 mL). The combined organic layer was washed with ice cold water (3×10 mL) followed by brine wash. The organic layer dried over anhydrous sodium sulphate, filtered, and evaporated in vacuo to get the crude. The crude compound was purified by flash column chromatography and compound was eluted in 60% EtOAc in heptane to afford 2 (0.09 g, 31%) as off white solid.

$^{1}$HNMR (400 MHz, DMSO-$d_6$) δ=9.35 (d, J=9.2 Hz, 1H), 9.30 (d, J=5.2 Hz, 1H), 8.27 (bs, 1H), 8.19 (d, J=4.8 Hz, 1H), 8.15-8.13 (m, 1H), 7.88 (d, J=8.0 Hz, 1H), 7.66-7.62 (m, 3H), 7.59-7.55 (m, 2H), 7.51-7.48 (m, 1H), 5.43-5.38 (m, 1H), 4.77 (d, J=12.4 Hz, 1H), 3.84-3.78 (m, 1H), 3.09-3.04 (m, 1H), 2.89 (s, 1H), 2.73 (s, 1H), 1.43 (s, 3H), 0.83 (t, J=7.2 Hz, 3H). LC-MS (Method-B)=566.0 $[M+H]^+$; 95.941% at RT 2.097 min.

Step 3: Synthesis of N-[rac-(4S,5R)-4-(3-aminophenyl)-7-ethyl-3-methyl-6-oxo-1-phenyl-4,5-dihydro-pyrazolo[3,4-b]pyridin-5-yl]-4-(trifluoromethyl) pyrimidine-2-carboxamide (3)

To a stirred solution of 2 (0.090 g, 0.159 mmol) in ethanol (4 mL) were added Iron (0.052 g, 0.79 mmol), and $NH_4Cl$ (0.085 g, 1.59 mmol) in water (1 mL) at room temperature, then the reaction mixture stirred at 70° C. for 16 h. Progress of the reaction was monitored by TLC. After the completion of the reaction, the reaction mixture was cooled to room temperature, filtered on celite, diluted with water (1×10 mL), extracted with ethyl acetate (3×10 mL). The combined organic layer was dried over anhydrous sodium sulphate, filtered, and evaporated in vacuo to get the crude. The crude compound was purified by flash column chromatography, compound eluted in 50% EtOAc in heptane to afford 3 (0.052 g, 57%) as an off white solid.

$^{1}$HNMR (400 MHz, DMSO-$d_6$) δ=9.29-9.18 (m, 2H), 8.18-8.17 (m, 1H), 7.58-7.44 (m, 4H), 6.91-6.80 (m, 1H), 6.52-6.38 (m, 3H), 5.20-5.12 (m, 1H), 4.99 (s, 2H), 4.36-4.33 (m, 1H), 1.48 (s, 3H), 0.77 (t, J=6.8 Hz, 3H). LC-MS (Method-B)=536.3 $[M+H]^+$; 89.28% at RT 1.79 min.

Step 4: Synthesis of N-[rac-(4S,5R)-7-ethyl-3-methyl-4-[3-[2-(morpholinomethyl)prop-2-enoylamino]phenyl]-6-oxo-1-phenyl-4,5-dihydropyrazolo [3,4-b]pyridin-5-yl]-4-(trifluoromethyl)pyrimidine-2-carboxamide (I-211)

To a stirred solution of 3 (0.045 g, 0.084 mmol) in DMF (2 mL) were added linker-K (0.018 g, 0.10 mmol), 2-chloro-1-methylpyridinium iodide (0.044 g, 0.16 mmol), and n-$Bu_3N$ (0.10 mL, 0.42 mmol) at room temperature. Then, the reaction mixture stirred at 70° C. for 4 h. Progress of the reaction was monitored by TLC and LCM. The reaction mixture diluted with water (1×10 mL) and extracted with Ethyl acetate (3×10 mL) and the combined organic layer washed with ice cold water (3×10 mL), followed by brine solution (1×10 mL) dried over sodium sulphate and evaporated in vacuo to get the crude, which then was purified by prep-HPLC to get I-211 (0.008 g, 13.8%).

$^{1}$HNMR (400 MHz, DMSO-$d_6$) δ=11.07 (s, 1H), 9.33 (m, 2H), 8.20 (d, J=4.8 Hz, 1H), 7.64-7.61 (m, 3H), 7.57-7.54 (m, 3H), 7.51-7.47 (m, 1H), 7.29 (t, J=7.6 Hz, 1H), 7.11 (d, J=8.0 Hz, 1H), 6.04 (s, 1H), 5.58 (s, 1H), 5.24-5.19 (m, 1H), 4.57 (d, J=12.0 Hz, 1H), 3.81-3.76 (m, 1H), 3.61 (bs, 4H), 3.28-3.25 (m, 2H), 3.11-3.06 (m, 1H), 2.44 (bs, 4H), 1.50 (s, 3H), 0.82 (t, J=7.2 Hz, 3H). LC-MS (Method-B)=689.0 $[M+H]^+$; 99.493% at RT 2.145 min. HPLC (Method-B)=

99.492% at RT 8.265 min. HPLC (Method-F)=49.734% at RT 9.112 min, 50.266% at RT 11.527 min.

Synthesis of I-147 (peak-1) and I-55 (peak-2):

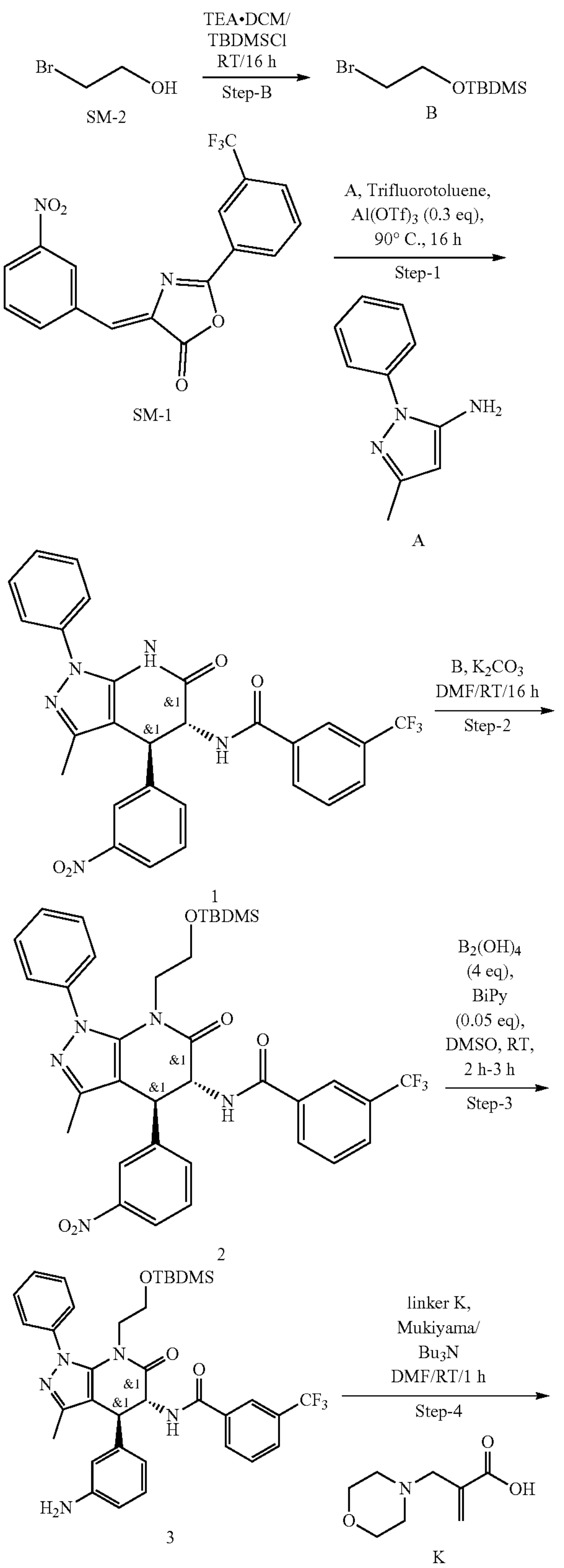

-continued

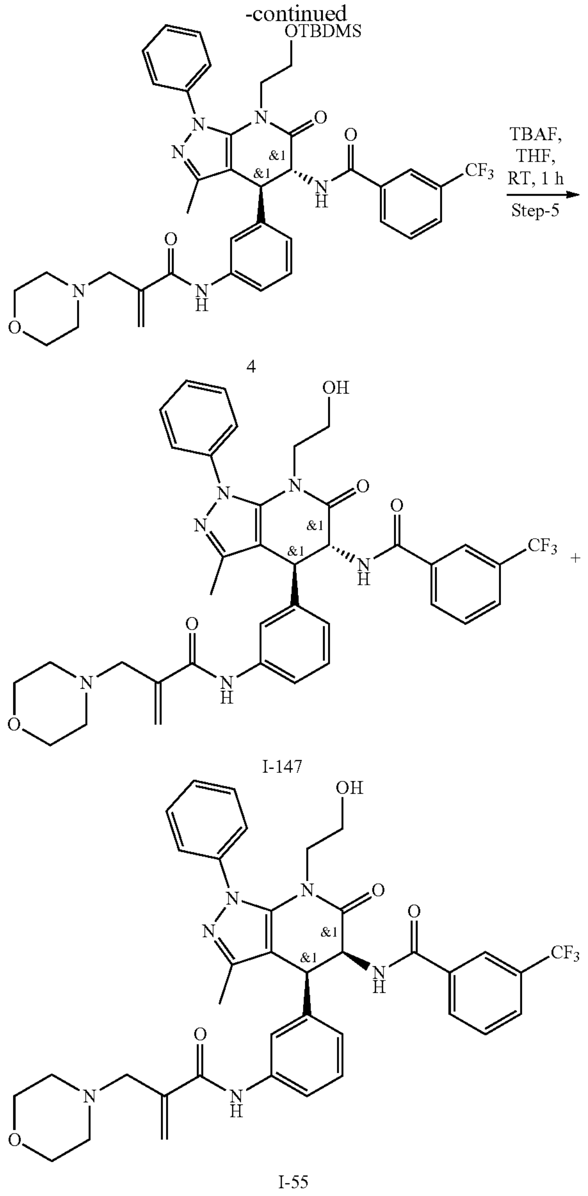

Step-1: Synthesis of ~{N}—[~{rac}-(4~{S}, 5~{R})-3-methyl-4-(3-nitrophenyl)-6-oxo-1-phenyl-5,7-dihydro-4-{H}-pyrazolo[3,4-b]pyridin-5-yl]-3-(trifluoromethyl)benzamide (1)

To a stirred solution of SM-1 (10 g, 27.60 mmol) in ACN (50.00 mL, 956 mmol) were added A (9.56 g, 55.20 mmol), and $Al(OTf)_3$ (2.64 g, 5.52 mmol). Then, the reaction mixture was stirred at 90° C. for 16 h. After consumption of the starting material (by TLC), the reaction mixture was diluted with water and the resultant solid was filtered and washed twice with acetone to get pure compound 1 (9.5 g, 64%).

$^1$HNMR (400 MHz, DMSO-$d_6$) δ=10.90 (s, 1H), 9.02-9.00 (m, 1H), 8.28 (s, 1H), 8.14 (d, J=7.6 Hz, 1H), 8.01 (bs, 2H), 7.91-7.87 (m, 2H), 7.72-7.63 (m, 6H), 7.40-7.37 (m, 1H), 5.16-5.11 (m, 1H), 4.59 (d, J=12.4 Hz, 1H), 1.50 (s, 3H). LC-MS (Method-A)=536.1 [M+H]$^+$; 88.44% at RT 1.783 min.

Step-B: Synthesis of 2-bromoethoxy-~{tert}-butyl-dimethyl-silane (B)

To the stirred solution of 2-bromoethanol (4 g, 32.0 mmol) in DCM (20 mL) were added TBDMSCI (4.5 g, 32.0 mmol) and triethylamine (8.97 mL, 64 mmol) and DMAP (0.032 g, 0.25 mmol) was added at 0° C. temperature under $N_2$ atmosphere, then reaction mixture was stirred at room temperature for 16 h. The reaction progress was monitored by TLC, after completion of reaction, the reaction mixture was diluted with ice cold water and extracted with diethyl ether. Then the organic layer was dried over sodium sulphate and concentrated to afford B (4.5 g, 58%) as colourless liquid.

$^1$HNMR (400 MHz, $CDCl_3$) δ=3.89 (t, J=6.0 Hz, 2H), 3.39 (t, J=6.4 Hz, 2H), 1.00 (s, 9H), 0.09 (s, 6H).

Step-2: Synthesis of ~{N}—[~{rac}-(4~{S}, 5~{R})-7-[2-[~{tert}-butyl(dimethyl)silyl]oxyethyl]-3-methyl-4-(3-nitrophenyl)-6-oxo-1-phenyl-4,5-dihydropyrazolo[3,4-b]pyridin-5-yl]-3-(trifluoromethyl)benzamide (2)

To a stirred solution of 1 (1 g, 1.86 mmol) in DMF (5 mL) were added B (0.67 g, 2.80 mmol) and potassium carbonate (1.5 equiv., 2.80 mmol) at 0° C. After completion of addition, reaction mixture was stirred at room temperature for 16 h. Reaction progress was monitored by TLC, after completion of the reaction, reaction mixture was poured into ice cold water, extracted with ethyl acetate, and concentrated to afford crude compound. The obtained crude was purified by column chromatography using silica 100-200 mesh. and eluted with 5-30% of ethyl acetate in heptane to afford 2 (0.2 g, 15%) as a white solid.

$^1$HNMR (400 MHz, DMSO-$d_6$) δ=9.00-8.97 (m, 1H), 8.24 (s, 1H), 8.13-8.11 (m, 1H), 7.94-7.83 (m, 5H), 7.66-7.44 (m, 6H), 5.40-5.25 (m, 1H), 4.60-4.53 (m, 1H), 3.85-3.80 (m, 1H), 3.60-3.45 (m, 1H), 3.20-3.05 (m, 1H), 1.39 (s, 3H), 0.70 (s, 12H), −0.13 (s, 6H). LC-MS (Method-B)=692.38 $[M-H]^+$; 96.08% at RT 2.586 min.

Step-3: Synthesis of ~{N}—[~{rac}-(4~{S}, 5~{R})-4-(3-aminophenyl)-7-[2-[~{tert}-butyl(dimethyl)silyl]oxyethyl]-3-methyl-6-oxo-1-phenyl-4,5-dihydropyrazolo[3,4-b]pyridin-5-yl]-3-(trifluoromethyl)benzamide (3)

To the solution of 2 (0.8 g, 1.15 mmol) in DMSO (10 mL) were added BBA (0.544 g, 5.76 mmol), and 2,2'-bipyridine (0.0018 g, 0.011 mmol) at 0° C. and stirred for 15 minutes. After completion of the addition, reaction mixture was stirred 25° C. for 2 h-3 h. Reaction progress was monitored by TLC. After completion of reaction, reaction mixture was diluted with ice cold water, extracted with ethyl acetate, dried over sodium sulphate, and concentrated to afford the crude compound. The obtained crude was further purified by flash column using silica-gel with 230-400 mesh and eluted with 5-60% of ethyl acetate in heptane to afford 3 (0.5 g, 60%) as a pale-yellow colour solid.

$^1$HNMR (400 MHz, DMSO-$d_6$) δ=8.94 (d, J=8.8 Hz, 1H), 8.03 (bs, 2H), 7.90 (d, J=7.2 Hz, 1H), 7.70 (t, J=7.6 Hz, 1H), 7.55-7.54 (m, 4H), 7.45-7.44 (m, 1H), 6.96 (t, J=7.6 Hz, 1H), 6.56 (s, 1H), 6.50 (d, J=7.2 Hz, 1H), 6.43 (d, J=7.6 Hz, 1H), 5.14 (t, J=12.4 Hz, 1H), 4.17 (d, J=12.4 Hz, 1H), 3.90-3.86 (m, 1H), 3.60-3.56 (m, 1H), 3.43-3.42 (m, 1H), 3.16-3.13 (m, 1H), 1.48 (s, 3H), 0.73 (s, 9H), −0.11 (s, 6H). LC-MS (Method-A)=664.95 $[M+H]^+$; 70.54% at RT 2.54 min.

Step-4: Synthesis of ~{N}-[(4~{S},5~{R})-7-[2-[~{tert}-butyl(dimethyl)silyl]oxyethyl]-3-methyl-4-[3-[2-(morpholinomethyl)prop-2-enoylamino]phenyl]-6-oxo-1-phenyl-4,5-dihydropyrazolo[3,4-b]pyridin-5-yl]-3-(trifluoromethyl)benzamide (4)

To a stirred solution of 3 (0.2 g, 0.30 mmol) in DMF (1 mL) were added linker-K (0.103 g, 0.60 mmol), 2-chloro-1-methylpyridinium iodide (0.158 g, 0.60 mmol) and tributylamine (0.22 mL, 0.90 mmol) at 0° C. After completion of the addition, the reaction mixture was stirred at room temperature for 1 h. Reaction progress was monitored by TLC. After completion of the reaction, the reaction mixture was diluted with water, extracted with ethyl acetate, dried over sodium sulphate, and concentrated to afford the crude compound. The obtained crude was purified by flash column using silica 230-400 mesh and eluted with 5-70% of ethyl acetate in heptane to afford 4 (0.16 g, 65%) as a white solid.

$^1$H NMR (400 MHz, DMSO-$d_6$) δ=11.08 (s, 1H), 9.01 (d, J=8.4 Hz, 1H), 8.02-7.98 (m, 2H), 7.90-7.88 (m, 1H), 7.70-7.69 (m, 1H), 7.62-7.57 (m, 6H), 7.50-7.46 (m, 1H), 7.30-7.25 (m, 1H), 7.11-7.09 (m, 1H), 6.05 (s, 1H), 5.59 (s, 1H), 5.22 (t, J=10.0 Hz, 1H), 4.34 (d, J=12.8 Hz, 1H), 3.90 (d, J=14.0 Hz, 1H), 3.63 (bs, 1H), 3.45-3.43 (m, 1H), 3.20-3.16 (m, 1H), 2.45 (bs, 3H), 1.47 (s, 3H), 1.24 (bs, 1H), 0.86-0.82 (m, 2H), 0.73 (s, 9H), −0.10 (s, 6H). LC-MS (Method-A)=815.71 $[M-H]^+$; 77.78% at RT 1.593 min.

Step-5: Synthesis of rac-N-((4R,5S)-7-(2-hydroxyethyl)-3-methyl-4-(3-(2-(morpholinomethyl)acrylamido)phenyl)-6-oxo-1-phenyl-4,5,6,7-tetrahydro-1H-pyrazolo[3,4-b]pyridin-5-yl)-3-(trifluoromethyl)benzamide (I-147) and rac-N-((4R,5R)-7-(2-hydroxyethyl)-3-methyl-4-(3-(2-(morpholinomethyl)acrylamido)phenyl)-6-oxo-1-phenyl-4,5,6,7-tetrahydro-1H-pyrazolo[3,4-b]pyridin-5-yl)-3-(trifluoromethyl)benzamide (I-55)

To a stirred solution of 4 (0.15 g, 0.18 mmol) in THF (1.5 mL) was added tetrabutylammonium fluoride in THE (0.18 mL, 0.18 mmol, 1 mol/L) at 0° C. After completion of addition, the reaction mixture was stirred at room temperature for 1 h. Reaction progress was monitored by TLC. After completion of reaction, the reaction mixture was diluted with water, extracted with ethyl acetate, dried over sodium sulphate, and concentrated to afford crude compound. The obtained crude was purified by prep. HPLC to afford I-147 (peak-1) (0.022 g, 17.8%) and I-55 (peak-2) (0.015 g, 12%) as a white solid.

Data for I-147 (peak-1)

$^1$HNMR (400 MHz, $CD_3OD$) δ=7.94-7.90 (m, 2H), 7.80-7.79 (m, 2H), 7.62-7.57 (m, 5H), 7.55-7.50 (m, 2H), 7.37 (t, J=8.0 Hz, 1H), 7.24-7.22 (m, 1H), 6.21 (s, 1H), 5.63 (s, 1H), 5.36 (d, J=12.4 Hz, 1H), 4.44 (d, J=12.8 Hz, 1H), 4.18-4.14 (m, 1H), 3.73 (t, J=4.8 Hz, 4H), 3.49-3.45 (m, 1H), 3.39-3.11 (m, 6H), 2.55 (bs, 4H), 1.62 (s, 3H), 1.43-1.41 (m, 1H), 1.03 (t, J=7.6 Hz, 1H). LC-MS (Method-B)=703.1 $[M+H]^+$; 93.129% at RT 2.066 min. HPLC (Method-B)=97.062% at RT 7.845 min. HPLC-Chiral (Method-F)=47.503% at RT 6.283 min, 48.092% at RT 7.381 min.

Data for I-55 (peak-2)

$^1$HNMR (400 MHz, $CD_3OD$) δ=8.08 (s, 1H), 8.02 (d, J=8.0 Hz, 1H), 7.85 (d, J=8.0 Hz, 1H), 7.66 (t, J=8.0 Hz,

1H), 7.61-7.54 (m, 5H), 7.52-7.49 (m, 1H), 7.45 (bs, 1H), 7.29 (t, J=8.0 Hz, 1H), 7.00 (d, J=7.6 Hz, 1H), 6.14 (s, 1H), 5.59 (s, 1H), 5.45 (d, J=7.6 Hz, 1H), 4.72 (d, J=7.6 Hz, 1H), 4.06-4.03 (m, 1H), 3.65-3.55 (m, 5H), 3.48-3.45 (m, 1H), 3.27-3.24 (m, 3H), 2.48-2.40 (m, 4H), 2.14 (s, 3H). LC-MS (Method-B)=703.1 $[M+H]^+$; 99.176% at RT 2.171 min. HPLC (Method-B)=97.579% at RT 8.400 min. HPLC-Chiral (Method-F)=49.67% at RT 11.768 min, 50.33% at RT 13.669 min.

Example 15: Synthesis of Compounds I-212, and I-213

NMR:

$^1$H NMR spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5μ; Mobile Phase: A: 0.05% Formic acid in water: ACN (95:5) B: 0.05% Formic acid in ACN; Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

Method-C: Column: X-Select CSH C18 (50 mm*3.0 mm, 2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water: ACN (95:05); Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: ACN; Programme/B %: 0.01/2, 2/2, 12/90, 16/90; Flow: 1.0 mL/min.; Diluent: ACN: water (80:20).

Method-C: Column: X SELECT CSH C18 (150×4.6 mm, 3.5); Mobile Phase A; 0.05% TFA in water: ACN (95:05); Mobile Phase B: 0.05% TFA in water: ACN(05:95); Programme: T/B %: 0.01/10, 12/90, 16/90; Flow: 1 mL/min.; Diluent: water:ACN (80:20).

Method-D: Column: X-Bridge CSH C18 (4.6*150) mm 5u Mobile Phase: A—0.1% TFA in water B—Acetonitrile Inj Volume; 5.0 μL, Flow Rate: 1.2. mL/minute Gradient program: Time(min)/B Conc.: 0.01/5, 1.0/5, 8.0/100, 12.0/100, 14.0/5, 18.0/5.

Method-E: Column: CHIRALPAK IG (250×4.6 mm, 5 μm) Mobile Phase A 0.10% DEA in n-Hexane Mobile Phase B: ETOH:MEOH(1:1) A/B: 50:50 Flow: 1.0 ml/min.

Chiral HPLC:

Method-A: Column: CHIRALCEL-OX—H (250×4.6 mm, 5 μm) Mobile Phase A: n-hexane Mobile Phase B: ETOH: MEOH (1:1) A/B: 50/50 Flow: 1.0 ml/min.

Method-B: Column: CHIRALPAK IG (250×4.6 mm, 5 μm) Mobile Phase A: 0.1% DEA in n-hexane, Mobile Phase B: IPA, A/B: 60:40 Flow rate: 1.0 ml/min.

Method-C: Column: CHIRAL PAK IA (250×4.6 mm, 5 μm) Mobile Phase A: n-Hexane, Mobile Phase B: IPA, A/B: 70:30 Flow rate: 1.0 ml/min.

Method-D: COLUMN: CHIRALPAK-IK (250×4.6 mm, 5 μm) Mobile Phase-A: n-hexane, Mobile Phase-B: IPA: MEOH (50:50) B: 50:50 Flow: 1.0 mL/min Synthesis of I-212:

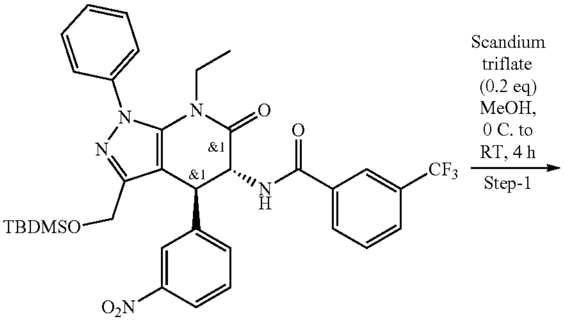

A-1

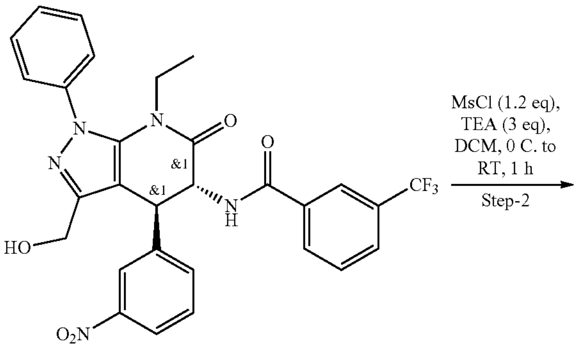

1

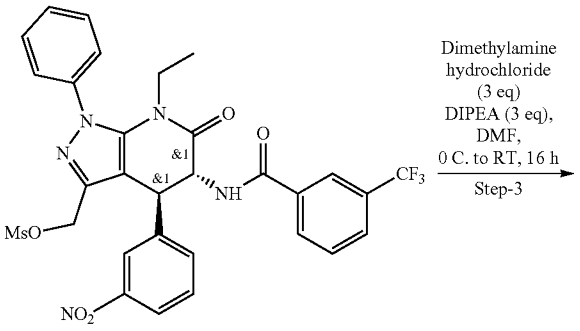

2

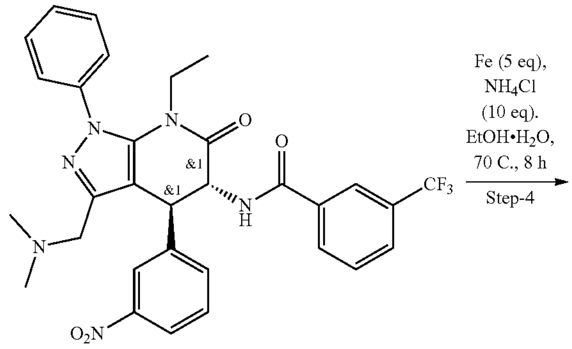

3

-continued

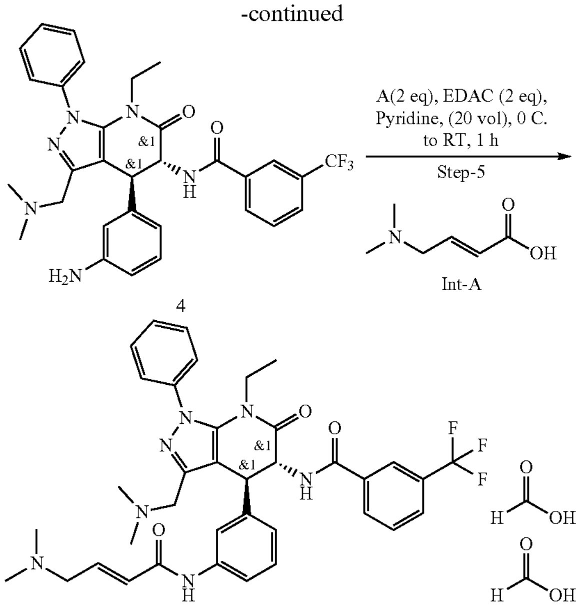

4

I-212

Step 1: Synthesis of ~{N}—[~{rac}-(4~{S}, 5~{R})-7-ethyl-3-(hydroxymethyl)-4-(3-nitro phenyl)-6-oxo-1-phenyl-4,5-dihydropyrazolo[3,4-b] pyridin-5-yl]-3-(trifluoromethyl)benzamide (1)

To a stirred solution of A-1 (500 mg, 0.66 mmol) in Methanol (5 mL) was added Scandium(III)trifluoromethanesulfonate (66 mg, 0.13 mmol) at 0° C. and the resulting reaction mixture was stirred at room temperature for 4 h. Reaction progress was monitored by TLC (50% EtOAc/Heptane) and LCMS. After completion of starting material by TLC, reaction mixture was concentrated under reduced pressure. Obtained crude material was diluted with water (10 mL) and extracted with EtOAc (2×20 mL). The combined organic layers were dried over anhydrous $Na_2SO_4$, filtered, and concentrated under reduced pressure to afford compound (1) (380 mg, 96.92%) as a brown solid.

$^1$H NMR (400 MHz, DMSO-$d_6$) δ=9.07 (d, J=8.4 Hz, 1H), 8.25 (s, 1H), 8.12 (d, J=8.0 Hz, 1H), 7.98 (s, 2H), 7.88 (t, J=9.2 Hz, 2H), 7.72-7.50 (m, 7H), 5.33 (t, J=10.4 Hz, 1H), 4.61-4.56 (m, 2H), 3.91-3.87 (m, 1H), 3.78-3.80 (m, 1H), 3.55-3.58 (m, 1H), 3.17-3.20 (m, 1H), 0.84 (t, J=6.8 Hz, 3H). LC-MS (Method-D): 580.0 $(M+H)^+$, 98.03% at RT 1.87 min.

Step 2: Synthesis of [~{rac}-(4~{S},5~{R})-7-ethyl-4-(3-nitrophenyl)-6-oxo-1-phenyl-5-[[3-(trifluoromethyl)benzoyl]amino]-4,5-dihydropyrazolo[3,4-b]pyridin-3-yl]methyl methanesulfonate To a stirred solution of compound (1) (380 mg, 0.65 mmol) in Dichloromethane (5 mL) was added Triethylamine (0.20 g, 1.96 mmol) followed by Methanesulfonyl chloride (0.09 g, 0.78 mmol) at 0° C. and the resulting reaction mixture was stirred at room temperature for 2 h. Reaction progress was monitored by TLC (50% EtOAc/Heptane). After completion of starting material by TLC, reaction mixture was diluted with water (10 mL) and extracted with DCM (2×10 mL). The combined organic layer was washed with saturated $NaHCO_3$ solution, dried over anhydrous $Na_2SO_4$, filtered, and concentrated under reduced pressure to afford compound (2) (400 mg, 92.76%) as brown solid.

$^1$HNMR (400 MHz, DMSO-$d_6$) δ=9.04 (d, J=8.8 Hz, 1H), 8.34 (d, J=9.6 Hz, 1H), 8.15 (d, J=8.4 Hz, 1H), 7.97 (s, 2H), 7.90 (d, J=7.2 Hz, 2H), 7.74-7.57 (m, 6H), 5.47 (t, J=9.2 Hz, 1H), 4.65 (d, J=11.6 Hz, 2H), 4.32 (d, J=11.6 Hz, 1H), 3.79-3.71 (m, 2H), 3.13 (t, J=7.2 Hz, 1H), 2.91 (s, 2H), 2.31 (s, 1H), 0.84 (t, J=6.8 Hz, 3H).

Step 3: Synthesis of ~{N}—[~{rac}-(4~{S}, 5~{R})-3-[(dimethylamino)methyl]-7-ethyl-4-(3-nitrophenyl)-6-oxo-1-phenyl-4,5-dihydropyrazolo[3, 4-b]pyridin-5-yl]-3-(trifluoromethyl)benzamide To a stirred solution of compound (2) (400 mg, 0.60 mmol) in DMF (5 mL) was added N,N-Diisopropylethylamine (0.23 g, 1.82 mmol) followed by Dimethylamine hydrochloride (0.15 g, 1.82 mmol) at 0° C. and the resulting reaction mixture was stirred at room temperature for 16 h. Reaction progress was monitored by TLC and LCMS. After completion of starting material by TLC, reaction mixture was diluted with water (10 mL), solid precipitated was filtered and dried thoroughly to afford compound (3) (320 mg, 78.92% Yield) as brown solid.

$^1$HNMR (400 MHz, DMSO-$d_6$) δ=9.04 (d, J=8.8 Hz, 1H), 8.24 (s, 1H), 8.13 (d, J=8.4 Hz, 1H), 7.97 (s, 2H), 7.91 (q, J=17.8 Hz, 2H), 7.71-7.49 (m, 6H), 5.35-5.30 (m, 1H), 4.55 (d, J=11.6 Hz, 1H), 4.32 (d, J=11.6 Hz, 1H), 3.19 (q, J=14.2 Hz, 1H), 2.72 (t, J=12.4 Hz, 1H), 1.75 (s, 6H), 0.94 (d, J=6.4 Hz, 2H), 0.83 (t, J=6.4 Hz, 3H). LCMS (Method-D): 607.2 $(M+H)^+$, 91.54% at RT 2.01 min.

Step 4: Synthesis of ~{N}—[~{rac}-(4~{S}, 5~{R})-4-(3-aminophenyl)-3-[(dimethylamino) methyl]-7-ethyl-6-oxo-1-phenyl-4,5-dihydropyrazolo[3,4-b]pyridin-5-yl]-3-(trifluoromethyl) benzamide To a stirred solution of compound (3) (300 mg, 0.45 mmol) in Ethanol (5 mL) and Water (1.2 mL) was added Iron (127 mg, 2.25 mmol) followed by Ammonium chloride (243.2 mg, 4.50 mmol) at room temperature and the resulting reaction mixture was stirred at 70° C. for 16 h. Reaction progress was monitored by TLC (5% MeOH in DCM). After completion of starting material by TLC, reaction mixture was filtered through celite bed and the filtrate was concentrated under reduced pressure. Obtained crude compound was diluted with water (10 mL) and extracted with 10% MeOH/DCM (20 mL×2). The combined organic layers were dried over anhydrous $Na_2SO_4$, filtered, and concentrated under reduced pressure to afford compound (4) (230.00 mg, 62.93%) as brown solid.

$^1$HNMR (400 MHz, DMSO-$d_6$) δ=10.02 (s, 1H), 9.07 (d, J=8.0 Hz, 1H), 8.05 (s, 2H), 7.92 (d, J=7.2 Hz, 1H), 7.71 (d, J=8.0 Hz, 2H), 7.62-7.53 (m, 4H), 7.02 (t, J=8.0 Hz, 1H), 6.59-6.46 (m, 3H), 5.18 (t, J=10.0 Hz, 2H), 4.35 (d, J=11.2 Hz, 1H), 4.05 (q, J=14.2 Hz, 1H), 3.67 (q, J=14.0 Hz, 1H), 2.41 (s, 3H), 1.98 (s, 1H), 1.23 (s, 2H), 1.18 (t, J=7.2 Hz, 2H), 0.82 (t, J=7.2 Hz, 3H). LC-MS (Method-D): 577.2 $(M+H)^+$, 71.60% at RT 1.81 min.

Step 5: Synthesis of ~{N}—[~{rac}-(4~{S}, 5~{R})-3-[(dimethylamino)methyl]-7-ethyl-6-oxo-1-phenyl-4-[3-[[~{rac}-(~{E})-4-(dimethylamino)but-2-enoyl]amino]phenyl]-4,5-dihydropyrazolo[3,4-b] pyridin-5-yl]-3-(trifluoromethyl)benzamide To a stirred solution of compound (4) (200 mg, 0.34 mmol) in Pyridine (5 mL) was added EDAC (134 mg, 0.69 mmol) followed by (~{E})-4-(dimethylamino)but-2-enoic acid; hydrochloride (115 mg, 0.69 mmol) at 0° C. and the resulting reaction mixture was stirred at room temperature for 1 h. Reaction progress was monitored by TLC (10% MeOH in DCM) and LCMS. After completion of the starting material by TLC, reaction mixture was directly concentrated under reduced pressure to obtain crude compound. Obtained crude compound purified by Prep. HPLC purification and lyophilized to afford I-212 (60 mg, 25.15%) as brown solid as a formate salt.

$^1$HNMR (400 MHz, DMSO-$d_6$) δ=10.05 (s, 1H), 9.05 (d, J=8.4 Hz, 1H), 8.27 (s, 2H), 8.01 (s, 2H), 7.90 (d, J=8.0 Hz, 1H), 7.72-7.50 (m, 8H), 7.27 (t, J=8.0 Hz, 1H), 7.04 (d, J=7.6 Hz, 1H), 6.71-6.66 (m, 1H), 6.25 (d, J=15.2 Hz, 1H), 5.11 (q, J=10.6 Hz, 1H), 4.38 (d, J=10.8 Hz, 1H), 3.68 (q, J=14.2 Hz, 1H), 3.25 (q, J=14.2 Hz, 1H), 3.03 (d, J=4.8 Hz, 1H), 2.70 (s, 2H), 2.16 (s, 7H), 1.84 (s, 6H), 0.82 (t, J=6.8 Hz, 3H). LCMS (Method-C): 688.3 $(M+H)^+$, 96.27% at RT 4.34 min. HPLC (Method-A): 99.10% at RT 3.451 min. Chiral-HPLC (Method-E): Peak-1=57.41% at RT 6.51 min, Peak-1=42.59% at RT 12.86 min.

Synthesis of I-213

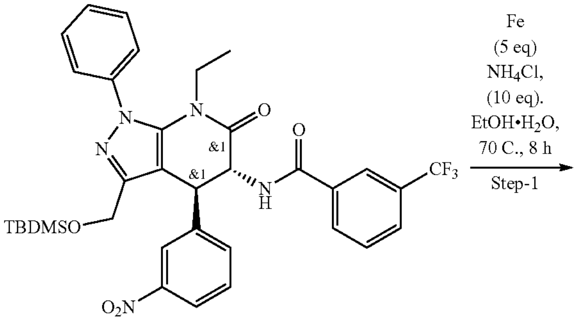

A-1

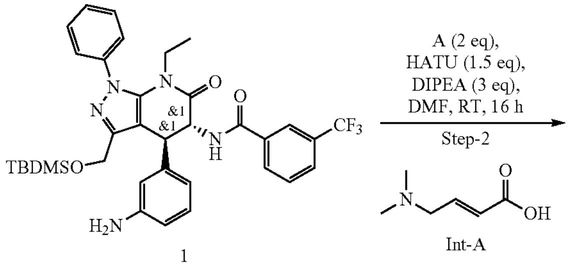

1

Int-A

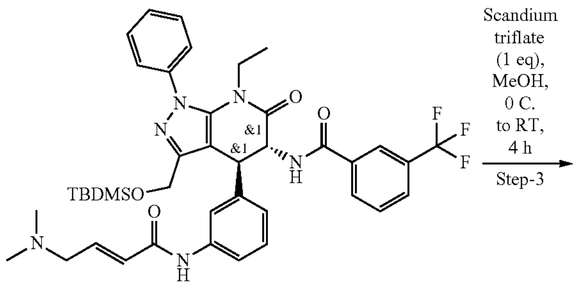

2

-continued

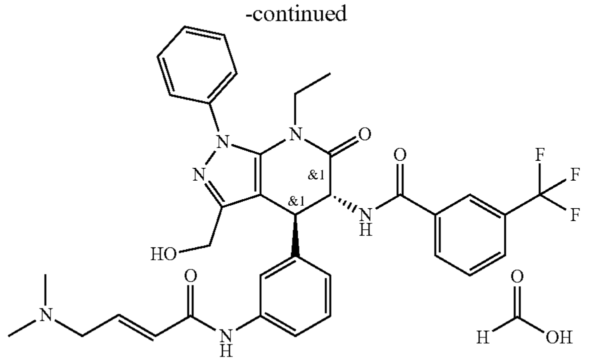

I-213

Step-1: Synthesis of ~{N}—[~{rac}-(4~{S}, 5~{R})-4-(3-aminophenyl)-3-[[~{tert}-butyl (dimethyl)silyl]oxymethyl]-7-ethyl-6-oxo-1-phenyl-4,5-dihydropyrazolo[3,4-b]pyridin-5-yl]-3-(trifluoromethyl)benzamide (1)

To a stirred solution of A-1 (5 g, 6.77 mmol) in Ethanol (90 mL) and Water (10 mL) was added Iron (1.91 g, 33.87 mmol) followed by Ammonium chloride (3.66 g, 67.74 mmol) at room temperature and the resulting reaction mixture was stirred at 70° C. for 16 h. Reaction progress was monitored by TLC (40% EtOAc/Heptane). After completion of starting material by TLC, reaction mixture was filtered through celite bed, and the filtrate was concentrated under reduced pressure. Obtained residue was diluted with water (50 mL) and extracted with EtOAc (2×50 mL). The combined organic layers were dried over anhydrous $Na_2SO_4$, filtered, and concentrated under reduced pressure to obtain crude compound. Obtained crude was purified by 230:400 silica gel flash column chromatography, eluted at 0-30% EtOAc/Heptane, to afford compound (1) (3.3 g, 64%) as an off-white solid.

$^1$HNMR (400 MHz, DMSO-$d_6$) δ=9.08 (d, J=8.0 Hz, 1H), 8.06 (s, 2H), 7.92 (d, J=8.0 Hz, 1H), 7.73-7.65 (m, 4H), 7.60 (t, J=7.6 Hz, 2H), 7.53 (d, J=7.6 Hz, 1H), 6.94 (t, J=8.0 Hz, 1H), 6.52 (s, 1H), 6.47 (q, J=18.0 Hz, 2H), 5.02 (t, J=8.4 Hz, 3H), 4.25 (q, J=15.4 Hz, 2H), 4.03 (d, J=12.4 Hz, 1H), 3.55-3.53 (m, 1H), 0.81 (t, J=7.2 Hz, 3H), 0.73 (s, 9H), −0.11 (s, 6H. LCMS (Method-M): 664.4 $(M+H)^+$, 86.90% at RT 1.76 min Step-2: Synthesis of ~{N}—[~{rac}-(4~{S}, 5~{R})-3-[[~{tert}-butyl(dimethyl)silyl]oxy methyl]-7-ethyl-6-oxo-1-phenyl-4-[3-[[~{rac}-(~{E})-4-(dimethylamino)but-2-enoyl]amino]phenyl]-4,5-dihydropyrazolo[3,4-b]pyridin-5-yl]-3-(trifluoromethyl)benzamide (2)

To a stirred solution of compound (1) (2 g, 2.62 mmol) in DMF (20 mL) was added N,N-Diisopropylethylamine (1.83 mL, 10.49 mmol), HATU (2.01 g, 5.24 mmol) followed by (~{E})-4-(dimethylamino)but-2-enoic acid. Hydrochloride (0.86 g, 5.24 mmol) at 0° C. and the resulting reaction mixture was stirred at room temperature for 16 h. Reaction progress was monitored by TLC and LCMS. After completion of starting material by TLC, reaction mixture was diluted with water (20 mL), solid was precipitated, filtered, and dried to obtain crude. Obtained crude was purified by 230:400 silica gel flash column chromatography, eluted at 6% MeOH/DCM to afford compound (2) (800 mg, 32.69%) as brown solid.

$^1$HNMR (400 MHz, DMSO-$d_6$) δ=10.24 (s, 1H), 9.11 (d, J=8.8 Hz, 1H), 8.03 (s, 2H), 7.92 (d, J=8.0 Hz, 1H), 7.73-7.51 (m, 7H), 7.27 (t, J=7.6 Hz, 1H), 7.07 (d, J=7.6 Hz, 1H), 6.73-6.66 (m, 1H), 6.40 (d, J=15.6 Hz, 1H), 5.10 (t, J=9.6 Hz, 1H), 4.40 (d, J=10.0 Hz, 1H), 4.21 (d, J=12.4 Hz, 1H), 3.99 (d, J=12.0 Hz, 1H), 3.74-3.62 (m, 2H), 2.99-2.93 (m, 1H), 2.87-2.78 (m, 2H), 2.66 (s, 4H), 1.27 (t, J=5.6 Hz, 2H), 0.82 (t, J=6.4 Hz, 3H), 0.71 (s, 9H), −0.16 (s, 6H). LCMS (Method-M): 775.5 $(M+H)^+$, 83.28% at RT 1.36 min.

Step-3: Synthesis of ~{N}—[~{rac}-(4~{S}, 5~{R})-7-ethyl-3-(hydroxymethyl)-6-oxo-1-phenyl-4-[3-[[~{rac}-(~{E})-4-(dimethylamino)but-2-enoyl]amino]phenyl]-4,5-dihydro pyrazolo[3,4-b]pyridin-5-yl]-3-(trifluoromethyl)benzamide (3)

To a stirred solution of compound (2) (200 mg, 0.21 mmol) in Methanol (5 mL) was added Scandium (III) trifluoromethanesulfonate (106 mg, 0.21 mmol) at 0° C. and the resulting reaction mixture was stirred at room temperature for 16 h. Reaction progress was monitored by TLC (10% MeOH in DCM) and LCMS. After completion of starting by TLC, reaction mixture was directly concentrated under reduced pressure. Obtained crude compound was diluted with water (10 mL) and extracted with 10% MeOH/DCM (10 mL×2). The combined organic layers were dried over anhydrous $Na_2SO_4$, filtered and concentrated under reduced pressure to obtain crude compound (200 mg) as brown solid. The crude compound was purified by Prep. HPLC and lyophilized to afford I-213 (15 mg, 2.65%) as an off-white solid in the formate salt form.

$^1$H NMR (400 MHz, DMSO-$d_6$) δ=10.07 (s, 1H), 9.06 (d, J=8.4 Hz, 1H), 8.13 (s, 2H), 8.03 (d, J=6.0 Hz, 2H), 7.90 (d, J=7.6 Hz, 1H), 7.72-7.51 (m, 8H), 7.26 (t, J=8.0 Hz, 1H), 7.07 (d, J=7.6 Hz, 1H), 6.71-6.66 (m, 1H), 6.27 (d, J=15.2 Hz, 1H), 5.13 (q, J=11.0 Hz, 1H), 4.59 (s, 1H), 4.40 (d, J=10.8 Hz, 1H), 3.93 (d, J=12.4 Hz, 1H), 3.71-3.65 (m, 2H), 3.17 (s, 1H), 3.11 (d, J=5.6 Hz, 2H), 2.21 (s, 6H), 0.83 (t, J=6.8 Hz, 3H). LC-MS (Method-B)=661.1 $(M+H)^+$, 99.02% at RT 2.14 min. Chiral-HPLC (Method-A): Peak-1=49.53% at RT 5.26 min, Peak-2=50.46% at RT 5.936 min.

Example 16: Synthesis of Compounds I-133 and I-139

NMR:

$^1$H NMR spectrum was recorded on Bruker 400 MHz and Varian 400 MHz instruments internally referenced to a tetramethylsilane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: ACN (95:5) B: 0.05% Formic acid in ACN Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

Method-C: Column: X-Select CSH C18 (50 mm*3.0 mm, 2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water: ACN (95:05); Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: ACN; Programme/B %: 0.01/2, 2/2, 12/90, 16/90; Flow: 1.0 mL/min.; Diluent: ACN: water (80:20).

Method-C: Column: X SELECT CSH C18 (150×4.6 mm, 3.5); Mobile Phase A; 0.05% TFA in water: ACN (95:05); Mobile Phase B: 0.05% TFA in water: ACN(05:95); Programme: T/B %: 0.01/10, 12/90, 16/90; Flow: 1 mL/min.; Diluent: water:ACN (80:20).

Method-D: Column: X-Bridge CSH C18 (4.6*150) mm 5μ Mobile Phase: A—0.1% TFA in water B—Acetonitrile Inj Volume; 5.0 μL, Flow Rate: 1.2. mL/minute Gradient program: Time(min)/B Conc.: 0.01/5, 1.0/5, 8.0/100, 12.0/100, 14.0/5, 18.0/5.

Method-E: Column: CHIRALCEL-OJ-H (250×4.6 mm, 5u) Mobile Phase A: 0.1% DEA in hexane, Mobile Phase B: IPA A/B: 60/40 Flow: 1.0 ml/MIN PDA: OJ-H_015.

Method-F: Column Name: CHIRALPAK-IK (250×4.6 mm, 5 μm) Mobile phase-A: n-Hexane, Mobile phase-B: EtOH/MeOH (50/50) Flow rate: 1.0 mL/min % A/B: 50/50.

Method-G: Column: X-Select CHS C18 (4.6*150) mm 5u Mobile Phase: A—5 mM Ammonium acetate B—Acetonitrile Inj Volume; 5.0 μL, Flow Rate: 1.0 mL/min.

Synthesis of I-133:

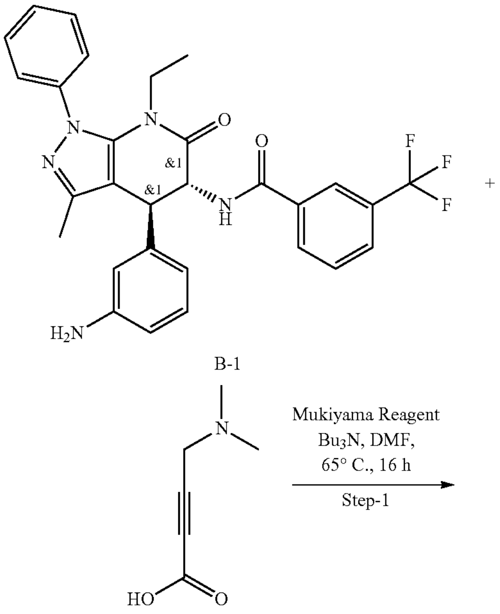

B-1

2

-continued

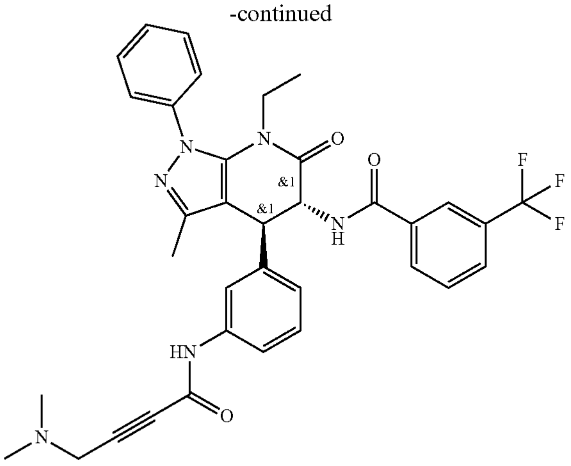

I-133

Step 1: Synthesis of rac-N-((4R,5S)-4-(3-(4-(dimethylamino)but-2-ynamido)phenyl)-7-ethyl-3-methyl-6-oxo-1-phenyl-4,5,6,7-tetrahydro-1H-pyrazolo[3,4-b]pyridin-5-yl)-3-(trifluoromethyl) benzamide (I-133)

To a stirred solution of B-1 (0.15 g, 0.28 mmol) in DMF (1.5 mL) were added tributylamine (0.14 mL, 0.56 mmol), 4-(dimethylamino)but-2-ynoic acid (0.055 g, 0.42 mmol), and 2-chloro-1-methylpyridinium iodide (0.11 g, 0.42 mmol) at 0° C. After completion of addition, raise the temperature to 65° C. and allow it to stir for 16 h. Reaction progress was monitored by TLC and LCMS. After completion of the reaction, diluted the mixture with ice cold water and extracted into DCM to obtain the crude compound. The crude compound was submitted to prep-achiral purification to get I-133 (0.035 g, 19%).

$^1$HNMR (400 MHz, $CDCl_3$) δ=7.88 (s, 1H), 7.81 (d, J=7.6 Hz, 1H), 7.71 (d, J=7.6 Hz, 1H), 7.63 (s, 1H), 7.55 (s, 1H), 7.52-7.43 (m, 8H), 7.34 (t, J=7.6 Hz, 1H), 7.21 (d, J=7.6 Hz, 1H), 6.55 (d, J=8.8 Hz, 1H), 5.45-5.40 (m, 1H), 4.15 (d, J=12.8 Hz, 1H), 3.97-3.91 (m, 1H), 3.42 (s, 2H), 3.18-3.13 (m, 1H), 2.35 (s, 6H), 1.67 (s, 3H), 0.92 (t, J=6.8 Hz, 3H). LC-MS (Method-C)=643.2 $[M+H]^+$; 96.788% at RT 4.617 min. HPLC (Method-B)=95.638% at RT 8.248 min. HPLC-Chiral (Method-F)=54.593% at RT 4.058 min, 45.407% at RT 6.083 min.

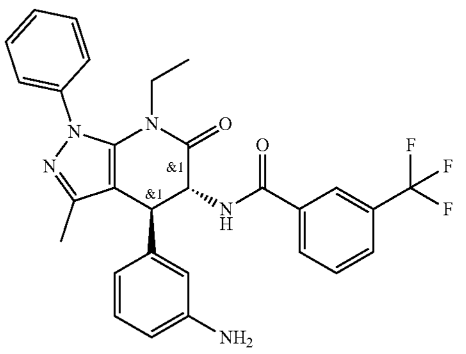

B-1

+

-continued

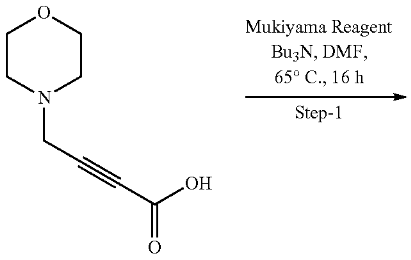

2

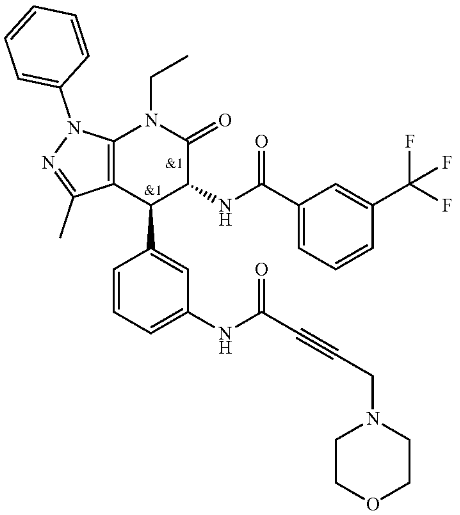

I-139

Step 1: Synthesis of rac-N-((4R,5S)-7-ethyl-3-methyl-4-(3-(4-morpholinobut-2-ynamido)phenyl)-6-oxo-1-phenyl-4,5,6,7-tetrahydro-1H-pyrazolo[3,4-b]pyridin-5-yl)-3-(trifluoromethyl)benzamide (I-139)

To a stirred solution of B-1 (0.15 g, 0.28 mmol) in DMF (1.50 mL) were added tributylamine (0.14 mL, 0.56 mmol), 2-chloro-1-methylpyridinium iodide (0.11 g, 0.42 mmol) and 4-(4-morpholinyl)-2-butynoic acid (0.073 g, 0.42 mmol) at 0° C. After completion of addition, raise the temperature to 65° C. and allow it to stir for 16 h. Reaction progress was monitored by TLC and LCMS. After the completion of reaction, add ice cold water to the reaction and extract with EtOAc. The organic layer was dried over sodium sulphate and concentrated under reduced pressure to afford crude compound. The crude compound was submitted to prep-achiral HPLC for further purification to get I-139 (0.04 g, 20.7%).

$^1$HNMR (400 MHz, DMSO-$d_6$) δ=9.01 (d, J=8.8 Hz, 1H), 8.02-8.01 (m, 2H), 7.90 (d, J=7.6 Hz, 1H), 7.70 (t, J=7.6 Hz, 1H), 7.63-7.49 (m, 7H), 7.28 (t, J=8.0 Hz, 1H), 7.12 (d, J=7.6 Hz, 1H), 5.20-5.10 (m, 1H), 4.32 (d, J=12.0 Hz, 1H), 3.80-3.70 (m, 1H), 3.61-3.59 (m, 4H), 3.50 (s, 2H), 3.15-3.08 (m, 1H), 2.52-2.50 (m, 4H), 1.50 (s, 3H), 0.81 (t, J=7.2 Hz, 3H). LC-MS (Method-B)=685.1 $[M+H]^+$; 99.922% at RT 2.014 min. HPLC (Method-B)=99.329% at RT 8.137 min. HPLC-Chiral (Method-F)=50.21% at RT 5.381 min, 49.79% at RT 6.870 min.

Example 17: Synthesis of Compound I-92

NMR:

$^1$H NMR 1H NMR spectrum was recorded on Bruker 400 MHz and Varian 400 MHz instruments internally referenced to a tetramethyl silane (TMS) signal. Chemical shifts (6) and coupling constants (J) were expressed in parts per million and hertz, respectively.

LCMS:

Method-A: LCMS, X-Select (Formic acid); Column: X-Select CSH C18 (3.0*50) mm 2.5μ. Mobile Phase: A: 0.05% Formic acid in water: ACN (95:5) B: 0.05% Formic acid in ACN Inj Volume: 2.0 μL, Column oven temperature: 50° C.; Flow Rate: 1.2 mL/min. Gradient Program (B %): 0.0/2, 0.3/2, 2.0/98, 2.8/98, 3.0/2, 3.7/2.

Method-B: Column: X-Bridge BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

Method-C: Column: X-Select CSH C18 (50 mm*3.0 mm, 2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

Method-D: Column: X-Select CSH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

Method-E: Column: CORTECS UPLC C18 (3×30 mm, 1.6 m) Mobile Phase: A: 0.05% FA in Water B: 0.05% FA in ACN, Flow rate: 0.85 mL/min (Gradient), Column Oven Temp: 45° C., Gradient Program (B %): 0/3, 0.1/3, 1.4/97, 2/97, 2.05/3, 2.5/3.

Method-F: Column: Poroshell 120 EC-C18 (3×100 mm, 2.7 m) Mobile Phase: A: 0.05% TFA in Water B: 0.05% TFA in ACN, Flow rate: 0.80 mL/min (Gradient), Column Oven Temp: 40° C., Gradient Program (B %): 0.01/2, 0.2/2, 3/98, 5/98, 5.2/2, 7/2.

Method-G: Column: X-Select BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2.

Method-H: Column: BAKERBOND Q2100 C18 (2.1×50 mm, 1.8 m) Mobile Phase: A: 0.05% FA in Water, Mobile Phase B: 0.05% FA in Acetonitrile, Colum Temperature: 40° C., Flow Rate: 0.6 mL/min, Gradient: 0.0/2, 0.3/2, 2.0/98, 2.8/98, 3.0/2, 3.7/2, Diluent: ACN: Water.

Method-I: Column: Poroshell 120 EC-C18 (3×100 mm, 2.7 m) Mobile Phase: A: 0.05% TFA in Water B: 0.05% TFA in ACN, Flow rate: 0.70 mL/min (Gradient), Column Oven Temp: 40° C., Gradient Program (B %): 0.01/10, 0.2/10, 6/90, 8/90, 8.1/10, 10/10.

Method-J: Column: BAKERBOND Q2100 (2.1×50 mm, 1.8 m) Mobile Phase: A: 0.05% TFA in Water, Mobile Phase B: 0.05% TFA in Acetonitrile, Colum Temperature: 40° C., Flow Rate: 0.6 mL/min, Gradient: 0.01/2, 0.5/4/98, 6/98, 6.1/2, 7/2, Diluent: ACN: Water.

HPLC:

Method-A: Column: X Select CSH C18 (150×4.6) mm, 3.5; Mobile phase A: 0.1% FA in Water: ACN (95:05); Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: ACN; Programme/B %: 0.01/5, 1.0/5, 8.0/100, 12.0/100, 14.0/5, 18.0/5; Flow: 1.0 mL/min.

Method-C: Column: X SELECT CSH C18 (150×4.6 mm, 3.5); Mobile Phase A; 0.05% TFA IN WATER: ACN (95:05); Mobile Phase B: 0.05% TFA IN WATER: ACN (05:95); Programme: T/B %: 0.01/10, 12/90, 16/90; Flow rate: 1.0 mL/min.; Diluent: water:ACN (80:20).

Method-D: Column: X-Bridge CSH C18 (4.6*150) mm 5μ Mobile Phase: A—0.1% TFA in water B—Acetonitrile Inj Volume; 5.0 μL, Flow Rate: 1.2 mL/min Gradient program: Time(min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in hexane, Mobile Phase B: IPA A/B: 60/40 Flow: 1.0 mL/min, PDA: OJ-H-015.

Method-F: Column Name: CHIRALPAK-IK (250×4.6 mm, 5 μm) Mobile phase-A: n-Hexane, Mobile phase-B: EtOH/MeOH (1:1) Flow rate: 1.0 mL/min, % A/B: 50/50.

Method-G: Column: X-Select CHS C18 (4.6*150) mm 5μ Mobile Phase: A—5 mM Ammonium acetate B—Acetonitrile Inj Volume; 5.0 μL, Flow Rate: 1.0 mL/min.

Method-H: Column: X-Bridge CSH C18 (150×4.6 mm, 3.5 μm); Mobile Phase-A: 5 mM $NH_4HCO_3$ in water; Mobile Phase-B: ACN; Programme/B %: Time(min)/B Conc.: 0.01/5, 1.0/5, 8.0/100, 12.0/100, 14.10/5, 18.0/5; Flow: 1.0 mL/min.; Diluent: ACN: water (80:20).

Method-I: Column Name: CHIRALPAK-IC (250×4.6 mm, 5 μm) Mobile phase-A: 0.1% TFA in n-hexane, Mobile phase-B: DCM: IPA (50:50), Flow rate: 1.0 mL/min % A/B 60/40.

Method-J: Column Name: CHIRALPAK-IA (150*4.6 mm, 3 μm)) Mobile phase-A: n-hexane, Mobile phase-B: EtOH: MeOH(1:1), Flow rate: 1.0 mL/min % A/B: 90:10.

Method-K: Column: CHIRALCEL-OX—H (250×4.6 mm, 5μ) Mobile Phase A: n-hexane, Mobile Phase B: IPA, A/B: 50/50 Flow: 1.0 mL/min.

Method-L: Column Name: CHIRALPAK-IA (150*4.6 mm, 3 μm)) Mobile phase-A: n-hexane, Mobile phase-B: ETOH: MEOH (1:1), Flow rate: 1.0 mL/min, % A/B: 70:30.

Method-M: Column: ACE Excel 2 C18-AR (100 mm×3.0 mm, 2.5 μm) Mobile Phase A: 0.05% FA in Water, Mobile Phase B: 0.05% FA in Acetonitrile, Column Temperature: 40° C. Flow Rate: 0.6 mL/min. Gradient: 0/5, 1/5, 6/90, 8.5/90, 8.8/5, 11/5. Diluent: ACN: Water.

Method-N: Column: BAKERBOND 1.7μ or 1.8μ C18 100 mm×2.1 mm Mobile Phase A: 0.05% FA in Water, Mobile Phase B: 0.05% FA in Acetonitrile, Colum Temperature: 40° C., Flow Rate: 0.5 mL/min, Gradient: 0/5, 3/5, 6/95, 8.5/95, 8.8/5, 11/5, Diluent: ACN: Water.

Method-O: Column Name: CHIRALPAK-IG (250×4.6 mm, 5 μm) Mobile phase-A: n-Hexane, Mobile phase-B: EtOH/MeOH (50/50) Flow rate: 1.0 mL/min % A/B: 50/50.

Method-P: Column Name: CHIRALPAK-IG (250×4.6 mm, 5 μm) Mobile phase-A: 0.1% DEA in n-Hexane Mobile phase-B: EtOH/MeOH (50/50) Flow rate: 1.0 mL/min % A/B: 70/30.

Method-Q: Column: BAKERBOND 1.7μ C18 100 mm×2.1 mm Mobile Phase A: 0.05% TFA in Water, Mobile Phase B: 0.05% TFA in Acetonitrile, Colum Temperature: 40° C., Flow Rate: 0.5 mL/min, Gradient: 0/5, 3/5, 6/95, 8.5/95, 8.8/5, 11/5, Diluent: ACN: Water.

Method-R: Column Name: CHIRALPAK-IC (250×4.6 mm, 5 μm) Mobile phase-A: n-hexane, Mobile phase-B: IPA: MeOH (1:1), Flow rate: 1.0 mL/min % A/B: 50/50.

Method-S: Column: CHIRALCEL-OJ-H (250×4.6 mm, 5u) Mobile Phase A: n-hexane Mobile Phase B: EtOH/MeOH (1:1) A/B: 50/50 Flow: 1.0 mL/min.

Method-T: Column Name: CHIRALPAK-IC (250×4.6 mm, 5 μm) Mobile phase-A: n-hexane, Mobile phase-B: IPA: MeOH (50:50), Flow rate: 1.0 mL/min % A/B: 50/50.

Method-U: Column Name: CHIRALPAK-IC (250×4.6 mm, 5 μm) Mobile phase-A: n-hexane, Mobile phase-B: EtOH: MeOH (50:50), Flow rate: 0.7 mL/min % A/B: 50/50.

Method-V: Column Name: CHIRALPAK-IK (250×4.6 mm, 5 μm) Mobile phase-A: n-Hexane, Mobile phase-B: EtOH/MeOH (1:1) Flow rate: 1.0 mL/min, % A/B: 70/30.

Method-W: Column Name: CHIRALPAK-IK (250×4.6 mm, 5 μm) Mobile phase-A: 0.1% DEA in n-Hexane Mobile phase-B: EtOH/MeOH (1:1) Flow rate: 1.0 mL/min, % A/B: 50/50.

Method-X: Column Name: CHIRALPAK-IK (250×4.6 mm, 5 μm) Mobile phase-A: n-Hexane, Mobile phase-B: ETOH/MEOH (1:1) Flow rate: 1.0 mL/min, % A/B: 50/50.

Method-Y: Column Name: CHIRALPAK-IK (250×4.6 mm, 5 μm) Mobile phase-A: n-Hexane, Mobile phase-B: IPA/MEOH (1:1) Flow rate: 1.0 mL/min.

Method-Z: Column Name: CHIRALPAK-IA (150*4.6 mm, 3 μm)) Mobile phase-A: n-hexane, Mobile phase-B: IPA, Flow rate: 1.0 mL/min, % A/B: 70:30.

Method-Z-1: Column Name: CHIRALPAK-IE (250×4.6 mm, 5 μm) Mobile phase-A: n-Hexane/DEA/TFA (100/0.1/0.1%) Mobile phase-B: ETOH/MEOH (1:1) Flow rate: 1.0 mL/min, % A/B: 60/40.

Synthesis of I-92:

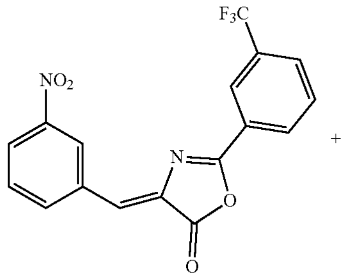

SM-1

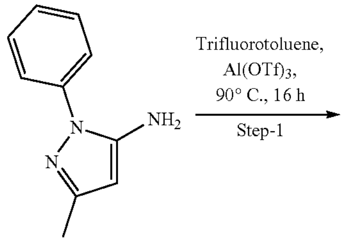

SM-2

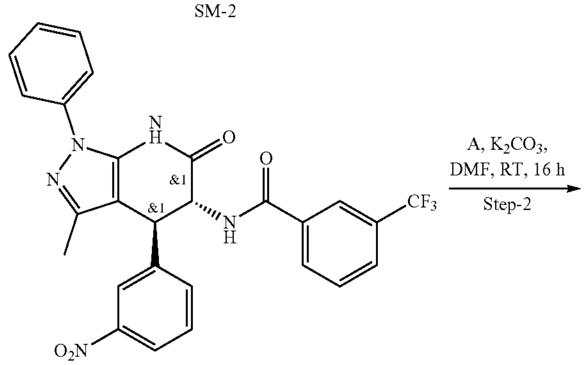

1

-continued

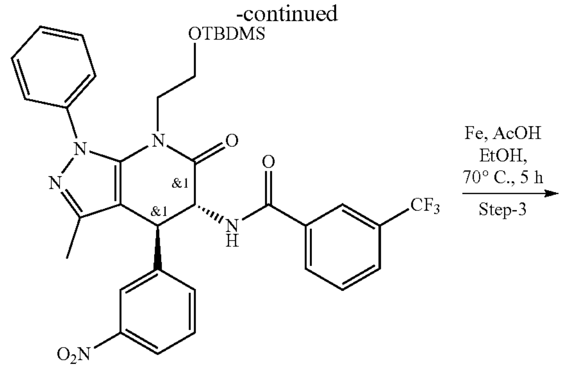

2

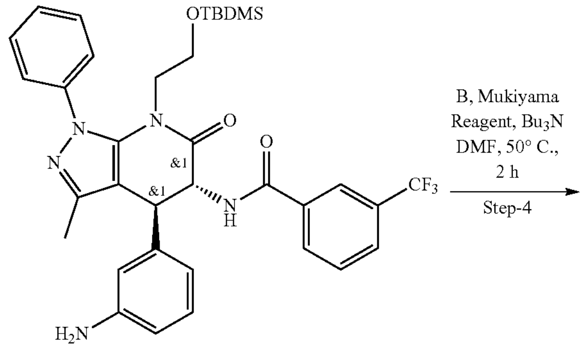

3

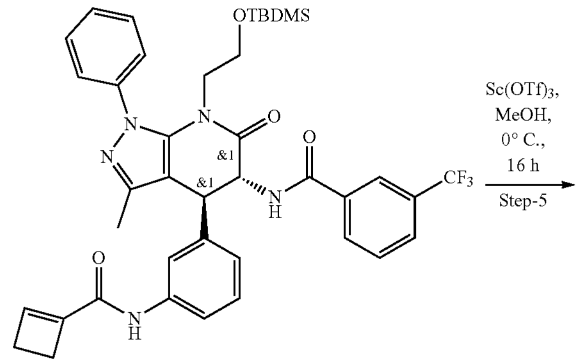

4

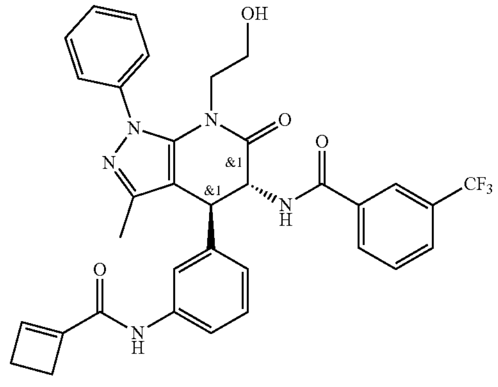

I-92

Step 1: Synthesis of N-[rac-(4S,5R)-3-methyl-4-(3-nitro phenyl)-6-oxo-1-phenyl-5,7-dihydro-4H-pyrazolo[3,4-b]pyridin-5-yl]-3-(trifluoro methyl) benzamide (1)

To a stirred solution of (4Z)-4-[(3-nitro phenyl) methylene]-2-[3-(trifluoromethyl) phenyl]oxazol-5-one (SM-1) (10 g, 27.60 mmol) in ACN (50 mL) were added 5-methyl-2-phenyl-pyrazol-3-amine (SM-2) (9.56 g, 55.20 mmol), Aluminium trifluoro methane sulfonate (2.64 g, 5.52 mmol) at room temperature. Then the reaction mixture was stirred at 90° C. for 16 h. After consumption of the starting material (by TLC), the reaction mixture was diluted with water (100 mL) and the resultant solid was filtered and washed twice with acetone. The solid was dried under vacuum to afford the compound (3) (9.5 g, 64%) as an Off-White solid.

$^1$H NMR (400 MHz, DMSO-$d_6$) (δ=10.90 (br s, 1H), 9.01 (d, J=8.8 Hz, 1H), 8.28 (s, 1H), 8.14 (d, J=8.8 Hz, 1H), 8.01 (s, 2H), 7.90-7.87 (m, 2H), 7.72-7.50 (m, 6H), 7.41-7.37 (m, 1H), 5.13 (dd, J=9.0, 12.0 Hz, 1H), 4.60 (d, J=12.2 Hz, 1H), 1.50 (s, 3H). LC-MS (Method-E)=536.1 [M+H]$^+$; 88.44% at RT 1.77 min.

Step-2: Synthesis of N-[rac-(4S,5R)-7-[2-[tert-butyl (dimethyl)silyl]oxyethyl]-3-methyl-4-(3-nitrophenyl)-6-oxo-1-phenyl-4,5-dihydropyrazolo[3,4-b]pyridin-5-yl]-3-(trifluoro methyl) benzamide (2)

To a stirred solution of N-[rac}-(4S,5R)-3-methyl-4-(3-nitrophenyl)-6-oxo-1-phenyl-5,7-dihydro-4H-pyrazolo[3,4-b]pyridin-5-yl]-3-(trifluoro methyl) benzamide (2.5 g, 4.7 mmol) in DMF (5 mL) were added Potassium carbonate (970 mg, 7.0 mmol) and followed by 2-bromoethoxy-tert-butyl-dimethyl-silane (1.7 g, 7.0 mmol) was added at 0° C. The reaction mixture stirred at room temperature for 16 h. The reaction progress was monitored by TLC. After completion of reaction, the reaction mass was quenched with ice cold water (20 mL), extracted with ethyl acetate (3×30 mL). The combined organic layer washed with brine, dried over sodium sulphate and concentrated to afford crude compound. The crude material was purified by flash column using silica 100-200 mesh and eluted with 5-30% of ethyl acetate in heptane to afford the compound (2) (1.4 g, 43%) as a white solid.

$^1$H NMR (400 MHz, DMSO-$d_6$) (δ=9.01 (d, J=8.7 Hz, 1H), 8.27 (s, 1H), 8.15 (d, J=7.9 Hz, 1H), 7.94 (d, J=6.6 Hz, 2H), 7.90-7.85 (m, 2H), 7.71-7.64 (m, 2H), 7.62-7.54 (m, 4H), 7.47 (d, J=6.2 Hz, 1H), 5.42-5.36 (m, 1H), 4.53 (d, J=12.4 Hz, 1H), 3.93-3.85 (m, 1H), 3.58 (d, J=5.4 Hz, 1H), 3.47-3.40 (m, 1H), 3.15-3.13 (m, 1H), 1.42 (s, 3H), 0.73 (s, 9H), −0.12 (m, 6H). LC-MS (Method-B)=694.1 [M+H]$^+$; 99.48% at RT 2.41 min.

Step-3: Synthesis of N-[rac-(4S,5R)-4-(3-aminophenyl)-7-[2-[tert-butyl (dimethyl) silyl]oxyethyl]-3-methyl-6-oxo-1-phenyl-4,5-dihydropyrazolo[3,4-b]pyridin-5-yl]-3-(trifluoro methyl) benzamide (3)

To a stirred solution of N-[rac-(4S,5R)-7-[2-[tert-butyl (dimethyl)silyl]oxyethyl]-3-methyl-4-(3-nitrophenyl)-6-oxo-1-phenyl-4,5-dihydropyrazolo[3,4-b]pyridin-5-yl]-3-(trifluoromethyl) benzamide (1.40 g, 2.01 mmol) in DMSO (10 mL) were added BBA (951 mg, 10.1 mmol), 2,2'-bipyridine (3.2 mg, 0.0201 mmol) at 0° C. The reaction mixture stirred at 25° C. for 2-3 h. The progress of the reaction was monitored by TLC. After completion of reaction, the reaction mass was diluted with ice cold water (20 mL) and extracted with ethyl acetate (3×30 mL) dried over sodium sulphate concentrated to afford crude compound. The crude was purified by flash column using silica with 230-400 mesh and eluted with 5-60% of ethyl acetate in heptane to afford the compound (3) (1.0 g, 68.8%) as a pale yellow solid.

$^1$H NMR (400 MHz, DMSO-$d_6$) (δ=8.94 (d, J=8.3 Hz, 1H), 8.03 (s, 2H), 7.89 (d, J=7.0 Hz, 1H), 7.73-7.66 (m, 1H), 7.54 (d, J=3.7 Hz, 4H), 7.44 (d, J=3.7 Hz, 1H), 6.97-6.93 (m, 1H), 6.56 (s, 1H), 6.49 (d, J=7.0 Hz, 1H), 6.42 (d, J=7.5 Hz, 1H), 5.15 (dd, J=8.9, 11.8 Hz, 1H), 5.02 (d, J=8.3 Hz, 1H), 4.17 (d, J=12.9 Hz, 1H), 3.91-3.81 (m, 1H), 3.56 (d, J=4.6 Hz, 1H), 3.43-3.39 (m, 1H), 3.17-3.11 (m, 1H), 1.47 (br s, 3H), 0.72 (s, 9H), −0.12 (br s, 6H). LC-MS (Method-B)=664.2 [M+H]$^+$; 95.76% at RT 2.31 min.

Step-4: Synthesis of N-[rac-(4S,5R)-7-[2-[tert-butyl (dimethyl) silyl]oxy ethyl]-4-[3-(cyclo butene-1-carbonyl amino) phenyl]-3-methyl-6-oxo-1-phenyl-4,5-dihydro pyrazolo[3,4-b]pyridin-5-yl]-3-(trifluoro methyl) benzamide (4)

To a stirred solution of compound cyclobutene-1-carboxylic acid (Int-B) (100 mg, 1 mmol) in DMF (5 mL) was added N-[rac-(4S,5R)-4-(3-amino phenyl)-7-[2-[tert-butyl (dimethyl) silyl]oxyethyl]-3-methyl-6-oxo-1-phenyl-4,5-dihydropyrazolo[3,4-b]pyridin-5-yl]-3-(trifluoromethyl) benzamide (3)(500 mg, 0.8 mmol), N, N-Diisopropylethylamine (0.4 mL, 2 mmol) and HATU (600 mg, 2 mmol) at 0° C. Then the reaction mixture was stirred at RT for 1 h. After consumption of the starting material (by TLC), the reaction mixture was diluted with water (10 mL) and extracted by using EtOAc (3×30 mL). The organic layer was dried over anhydrous $Na_2SO_4$, filtered and concentrated under reduced pressure to get the crude compound. The crude material was purified by silica gel column chromatography and eluted at 35-40% EtOAc:PE to afford the compound (4) (126 mg, 20%) as an Off-White solid.

$^1$H NMR (400 MHz, DMSO-$d_6$) δ=9.76 (s, 1H), 9.01 (d, J=8.7 Hz, 1H), 8.03-7.96 (m, 2H), 7.89 (d, J=7.9 Hz, 1H), 7.71-7.63 (m, 3H), 7.56 (d, J=3.7 Hz, 4H), 7.46 (s, 1H), 7.27 (t, J=8.1 Hz, 1H), 7.07 (d, J=7.5 Hz, 1H), 6.75 (s, 1H), 5.18 (dd, J=8.9, 12.2 Hz, 1H), 4.32 (d, J=12.9 Hz, 1H), 3.94-3.86 (m, 1H), 3.62-3.54 (m, 1H), 3.46-3.40 (m, 1H), 3.18-3.13 (m, 1H), 2.68 (d, J=4.1 Hz, 2H), 2.39 (s, 2H), 1.46 (s, 3H), 0.73 (s, 9H), −0.11 (s, 6H). LC-MS (Method-B)=741.2 [M−H]$^+$; 94.12% at RT 2.41 min.

Step-5: Synthesis of N-[rac-(4S,5R)-4-[3-(cyclobutene-1-carbonylamino) phenyl]-7-(2-hydroxyethyl)-3-methyl-6-oxo-1-phenyl-4,5-dihydropyrazolo[3,4-b]pyridin-5-yl]-3-(trifluoromethyl) benzamide (I-92)

To a stirred solution of N-[rac-(4S,5R)-7-[2-[tert-butyl (dimethyl) silyl]oxy ethyl]-4-[3-(cyclo butene-1-carbonyl amino) phenyl]-3-methyl-6-oxo-1-phenyl-4,5-dihydro pyrazolo[3,4-b]pyridin-5-yl]-3-(trifluoro methyl) benzamide (220 mg, 0.30 mmol) in Methanol (10 mL) was added $Sc(OTf)_3$ (150 mg, 0.30 mmol) at 0° C. Then the reaction mixture was stirred at room temperature for overnight. The progress of the reaction mixture checked by TLC. The reaction mixture was concentrated under vacuum to obtain the crude compound. The crude was purified by column chromatography to afford the title compound I-92 (47 mg, 25%) as an Off-White solid.

$^1$H NMR (400 MHz, $CD_3OD$-d4) (=7.94 (s, 1H), 7.88 (d, J=7.8 Hz, 1H), 7.80-7.77 (m, 2H), 7.61-7.53 (m, 7H), 7.33 (t, J=7.9 Hz, 1H), 7.20 (d, J=7.6 Hz, 1H), 6.77 (s, 1H), 5.34 (d, J=12.8 Hz, 1H), 4.41 (d, J=12.9 Hz, 1H), 4.18-4.11 (m, 1H), 3.50-3.43 (m, 1H), 3.38-3.32 (m, 1H), 3.14-3.11 (m, 1H), 2.81-2.77 (m, 2H), 2.51-2.47 (m, 2H), 1.60 (s, 3H). LC-MS (Method-D)=630.0 $[M+H]^+$; 96.93% at RT 2.01 min. HPLC (Method-H)=97.47% at RT 8.10 min. Chiral HPLC (Method-Z)=Peak-1=50.12% at RT 6.70 min. Peak-2=49.88% at RT 8.05 min.

Step-6: Synthesis of 2-bromoethoxy-tert-butyl-dimethyl-silane (4)

To a stirred solution of 2-bromoethanol (9) (10 g, 80.026 mmol) in DCM (25 mL) were added Triethylamine (22.4 mL, 160.05 mmol) and 4-Dimethylaminopyridine (101.4 mg, 0.80 mmol) followed by tert-butyl dimethyl chlorosilane (12.43 g, 80.026 mmol) at 0° C. under $N_2$ atmosphere. The reaction mixture was stirred at room temperature for 16 h. The reaction progress was monitored by TLC. After completion of reaction, the reaction mass was diluted with ice cold water (50 mL) and extracted with ethyl acetate (3×30 mL). organic layer was dried over sodium sulphate. concentrated to afford crude compound. The crude purified by flash column and eluted with 1-15% of ethyl acetate in heptane to afford compound (4) (12 g, 62.68%) as a colourless liquid.

$^1$H NMR (400 MHz, $CDCl_3$) (=3.89 (t, J=6.2 Hz, 2H), 3.39 (t, J=6.2 Hz, 2H), 0.91 (s, 9H), 0.09 (s, 6H).

Step-7: Synthesis of 2-bromoethoxy-tert-butyl-dimethyl-silane (7)

A solution of potassium hydroxide (2.2 g, 39 mmol) in toluene (30 mL) was heated at 110° C. for 1 h, then added ethyl 1-bromocyclobutanecarboxylate (10) (2.0 g, 9.7 mmol) in toluene (10 mL) was added. The resulting reaction mixture was heated at 110° C. for 1 h. After completion of the reaction (TLC: DCM/MeOH 95:5), the reaction mixture was cooled to room temperature and diluted with water (20 mL). Then aqueous layer was washed with EtOAc (40 mL). The aqueous phase was then acidified to pH=2 using HCl solution (2 M). Then the compound extracted was extracted from the aqueous layer with EtOAc (2×50 mL), dried over $Na_2SO_4$, and concentrated under vacuum to afford compound (10) (1.0 g, crude) as a yellow semi-solid.

$^1$H NMR (400 MHz, DMSO-$d_6$) (δ=12.30 (br s, 1H), 6.74 (s, 1H), 2.60-2.56 (m, 2H), 2.39-2.35 (m, 2H).

Example 18: Synthesis of Compounds I-140, I-130, I-42, I-68, I-46, and I-184

NMR:

$^1$H NMR spectrum was recorded on Bruker 400 MHz and Varian 400 MHz instruments internally referenced to a tetramethyl silane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: ACN (95:5) B: 0.05% Formic acid in ACN Inj Volume: 2.0 μL, Column oven temperature: 50 C; Flow Rate: 1.2. mL/minute. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm, 2.5μ) Mobile Phase A: 0.05% TFA in Water Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5; Mobile phase A: 0.1% FA in Water:ACN(95:05); Mobile phase B: Acetonitrile; Gradient Programme: T/B %: 0.01/5, 1/5, 8/100, 12/100, 14/5, 18/5; Flow rate: 1.2 ml/min.

Method-B: Column: X-SELECT CSH C18 (150×4.6 mm, 3.5 μm); Mobile Phase-A: 5 mM $NH_4HCO_3$; Mobile Phase-B: ACN; Programme: T/B %: 0.01/2, 2/2, 12/90, 16/90; Flow: 1.0 mL/min.; Diluent: ACN:water (80:20).

Method-C: Column: X SELECT CSH C18 (150×4.6 mm, 3.5); Mobile Phase A; 0.05% TFA IN water: ACN(95:05); Mobile Phase B: 0.05% TFA IN water: ACN(05:95); Programme: T/B %: 0.01/10, 12/90, 16/90; Flow: 1 mL/min.; Diluent: water:ACN (80:20).

Method-D: Column: X-Select CSH C18 (4.6*150) mm 5μ Mobile Phase: A—0.1% TFA in water B—Acetonitrile Inj Volume; 5.0 μL, Flow Rate: 1.2. mL/minute Gradient program: Time(min)/B Conc.: 0.01/5, 1.0/5, 8.0/100, 12.0/100, 14.0/5, 18.0/5.

Method-E: Column: CHIRAL PAK-IA (250*4.6, 5 um) mobile phase a: n-hexane mobile phase b: DCM:MEOH(50:50 program-AB 90:10 flow rate: 1.0 ml/min.

Method-F: Column: CHIRAL PAK-IG (250*4.6 mm, 5 um) Mobile phase A: 0.10% DEA in n-Hexane, Mobile phase B: DCM:MEOH (50:50) A:B; 80:20 Flow: 1.0 ml/min.

Synthesis of C-1:

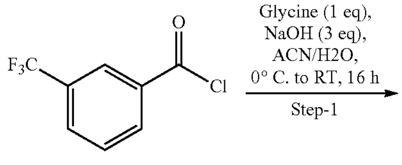

SM1

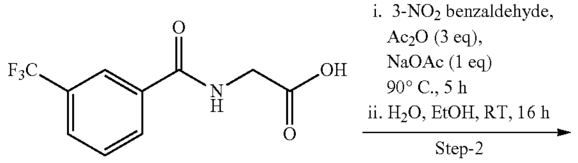

1

-continued

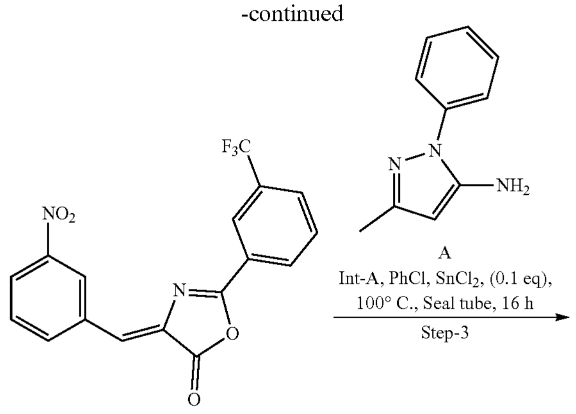

2

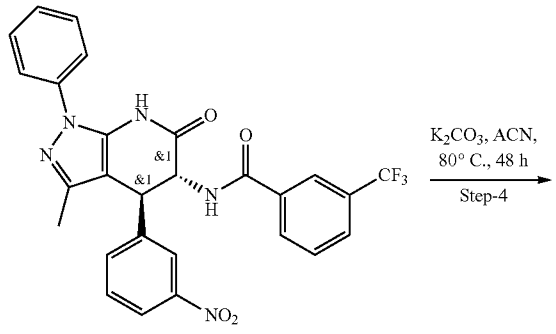

3

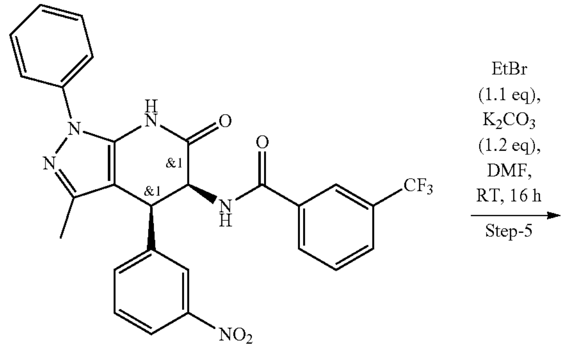

4

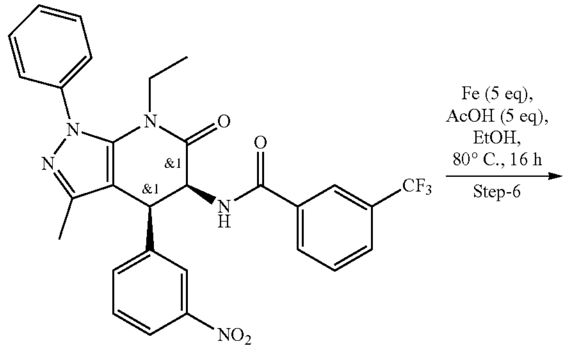

5

-continued

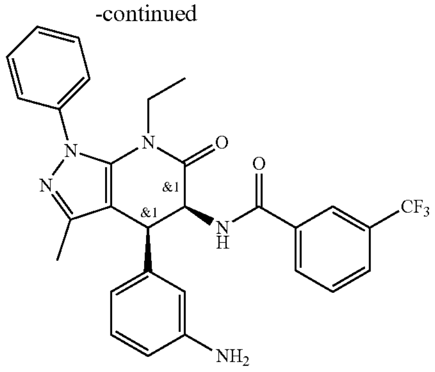

C-1

Step-1: Synthesis of 2-[[3-(trifluoromethyl)benzoyl] amino]acetic acid (1)

To a stirred solution of glycine (10.8 g, 0.14 mmol) in acetonitrile (150 mL) was added NaOH (18 g, 0.47 mmol) in water (40 mL) at 0° C. and stirred for 5 min, followed by drop wise addition of 3-(trifluoromethyl)benzoyl chloride (SM1) (29 g, 0.14 mmol) in ACN (100 mL). Then the reaction mixture was stirred at room temperature for 16 h. Reaction progress was monitored by TLC. The reaction mixture was diluted with water and extracted with EtOAc (2×500 mL). The organic layer was dried over anhydrous $Na_2SO_4$, filtered, and concentrated under reduced pressure. The obtained crude was washed with heptane to afford compound (1) (9 g, 31%) as an off white solid.

Step-2: Synthesis of (Z)-4-(3-nitrobenzylidene)-2-(3-(trifluoromethyl)phenyl)oxazol-5 (4H)-one (2)

To a stirred solution of compound (1) (5 g, 18.6 mmol) and 3-nitrobenzaldehyde (2.90 g, 18.6 mmol) in acetic anhydride (5.82 g, 55.8 mmol) was stirred at 90° C. for 5 h. Reaction was monitored by TLC. After completion of reaction, the reaction mixture was cooled to room temperature and added 1:1 ratio of ethanol (40 mL) in water and stirred for 16 h. Solid was filtered off and dried to afford crude. Crude was washed with n-heptane and n-pentane followed by co-distilled with toluene to afford pure compound (2.6 g, 37%) as off-white solid. LC-MS (Method-B)=363.2 $[M+H]^+$; 68.20% at RT 1.93 min.

Step-3: Synthesis of rac-N-((4R,5S)-3-methyl-4-(3-nitrophenyl)-6-oxo-1-phenyl-4,5,6,7-tetrahydro-1H-pyrazolo[3,4-b]pyridin-5-yl)-3-(trifluoromethyl) benzamide (3)

To a stirred solution of compound (2) (24 g, 59.62 mmol) and 5-methyl-2-phenyl-3,4-dihydropyrazol-3-amine (Int-A) (15.6 g, 84.6 mmol) in chlorobenzene (240 mL) was added tin(II) chloride (1.3 g, 6.5 mmol) at room temperature. Resulting reaction mixture was stirred at 100° C. in a closed sealed tube for 16 h. Progress of the reaction was monitored by TLC. After consumption of starting material (by TLC), the reaction mixture was diluted with water and extracted with EtOAc (2×100 mL). The organic layer was dried over anhydrous $Na_2SO_4$ filtered and concentrated under reduced pressure. The crude compound was purified by medium pressure liquid column chromatography by eluting with 30-35% EtOAc in heptane to afford compound (3) (15 g, 42.8%) as a pale-yellow solid. LC-MS (Method-B)=536.0 $[M+H]^+$; 50.71% at RT 2.22 min.

Step-4: Synthesis of rac-N-((4R,5R)-3-methyl-4-(3-nitrophenyl)-6-oxo-1-phenyl-4,5,6,7-tetrahydro-1H-pyrazolo[3,4-b]pyridin-5-yl)-3-(trifluoromethyl) benzamide (4)

To a stirred solution of compound (3) (15 g, 28.01 mmol) in ACN (150 mL) was added potassium carbonate (11.3 g, 81.4 mmol) and heated at 80° C. for 48 h. Progress of the reaction was monitored by TLC. Reaction mass was evaporated under vacuum. Resulting residue was purified by flash column chromatography and pure fractions were eluted at 20-25% EtOAc/heptane to afford compound (4) (10 g, 63.33%) as a yellow solid. LC-MS (Method-B)=536.0 $[M+H]^+$; 74.95% at RT 2.29 min.

Step-5: Synthesis of rac-N-((4R,5R)-7-ethyl-3-methyl-4-(3-nitrophenyl)-6-oxo-1-phenyl-4,5,6,7-tetrahydro-1H-pyrazolo[3,4-b]pyridin-5-yl)-3-(trifluoromethyl)benzamide (5)

To a stirred solution of compound (4) (15 g, 28.01 mmol) in DMF (150.00 ml) was added potassium carbonate (7.7 g, 55 mmol) followed by bromoethane (2.5 mL) at room temperature. Resulting reaction mixture was stirred at room temperature for 16 h. Progress of the reaction was monitored by TLC. After consumption of reaction, reaction mixture was quenched with ice water extracted with ethyl acetate. Organic layer was dried over $Na_2SO_4$, concentrated under vacuum to afford crude. Obtained crude was purified through flash column chromatography eluted with the gradient of 25% ethyl acetate/heptane. to afford compound (5) (8 g, 50.68%) as yellow solid. LC-MS (Method-B)=564.0 $[M+H]^+$; 75.93% at RT 2.46 min

Step-6: Synthesis of rac-N-((4R,5R)-4-(3-aminophenyl)-7-ethyl-3-methyl-6-oxo-1-phenyl-4,5,6,7-tetrahydro-1H-pyrazolo[3,4-b]pyridin-5-yl)-3-(trifluoromethyl)benzamide To a stirred solution of compound (5) (8 g, 14.20 mmol) and iron (6.6 g, 120 mmol) in ethanol (80 mL) was added acetic acid (7.2 mL) at room temperature. Resulting reaction mixture was stirred at 80° C. in a closed sealed tube for 16 h. Progress of the reaction was monitored by TLC. After 16 h. Reaction mixture was filtered, evaporated under vacuum to afforded solid. Obtained solid was passed through flash column chromatography 230-400 mesh silica gel. Compound was eluted at 50-60% of ethyl acetate/heptane to afford compound (6) (4 g, 50.17%) as a pale-yellow solid. LC-MS (Method-B)=564.0$[M+H]^+$; 75.93% at RT 2.46 min.

Synthesis of C-2:

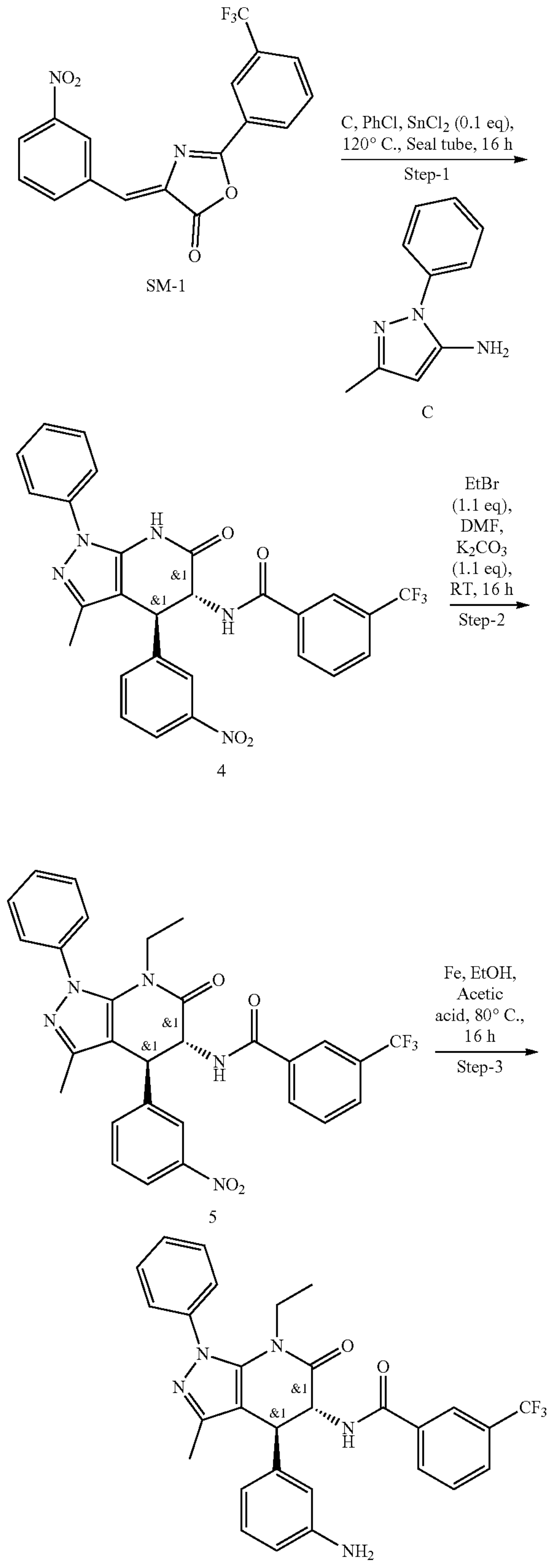

SM-1

C

4

5

C-2

Step-1: Synthesis of rac-N-((4R,5S)-3-methyl-4-(3-nitrophenyl)-6-oxo-1-phenyl-4,5,6,7-tetrahydro-1H-pyrazolo[3,4-b]pyridin-5-yl)-3-(trifluoromethyl) benzamide (4)

In a sealed tube, Int (C) (15 mg, 41.36 mmol) in chlorobenzene (150 mL) were added SM-1 (7.16 g, 41.36 mmol), and $SnCl_2$ (784 mg, 4.13 mmol) stirred for 16 h at 120° C. After consumption of the starting material (by TLC), the reaction mixture was purified by using column chromatography eluted with 50% ethyl acetate in heptane. Collected the fraction and concentrated in vacuum to afford compound (4) (15 g, 29%). LC-MS (Method-B)=536.4 $[M+H]^+$; 95.22% at RT 1.34 min 355314.

Step-2: Synthesis of rac-N-((4R,5S)-7-ethyl-3-methyl-4-(3-nitrophenyl)-6-oxo-1-phenyl-4,5,6,7-tetrahydro-1H-pyrazolo[3,4-b]pyridin-5-yl)-3-(trifluoromethyl)benzamide (5)

To a stirred solution of compound (4) (5 g, 9.34 mmol) in DMF (15 mL) was added potassium carbonate (1.67 g, 12.14 mmol) and bromoethane (0.76 mL) at room temperature. The reaction mixture was stirred at room temperature for 16 h. Progress of the reaction was monitored by TLC. After consumption of reaction, the reaction mixture was quenched with ice water extracted with ethyl acetate. Organic layer was dried over sodium sulfate and concentrated under vacuum to afford crude. Obtained crude was purified by flash column chromatography was eluted with 36% ethyl acetate/heptane. Pure fraction was concentrated under vacuum to afford compound (5) (2.0 g, 38%) as a pale-yellow solid. LC-MS (Method-B)=564.2 $[M+H]^+$; 93.19% at RT 2.30 min 376836

Step-3: Synthesis of rac-N-((4R,5S)-4-(3-aminophenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (C-2)

To a stirred solution of compound (2) (3 g, 5.32 mmol) and iron (1.49 g, 26.64 mmol) in ethanol (30 mL) was added acetic acid (3.19 mL) at room temperature. The reaction mixture was stirred at 80° C. in a closed sealed tube for 16 h. Progress of the reaction was monitored by TLC. After completion of reaction, the reaction mixture was filtered, and diluted with saturated $NaHCO_3$ and extracted with ethyl acetate. Organic layer was dried over sodium sulfate, concentrated under vacuum to afford crude. Obtained crude was purified by column chromatography was eluted with 70% ethyl acetate/heptane. Pure fraction was concentrated under vacuum to afford C-2 (1.8 g, 63%) as a pale-yellow solid. LC-MS (Method-B)=535.0 $[M+H]^+$; 98.21% at RT 2.39 min.

NMR:

$^1H$ NMR spectrum was recorded on Bruker 400 MHz and Varian 400 MHz instruments internally referenced to a tetramethyl silane (TMS) signal. Chemical shifts (6) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: ACN (95:5) B: 0.05% Formic acid in ACN Inj Volume: 2.0 μL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm, 2.5μ) Mobile Phase A: 0.05% TFA in Water Mobile Phase B: 0.05% TFA in Acetonitrile Flow rate: 1.0 mL/min. Column temperature: 40° C. Gradient Program (B %): 0.0/2, 0.3/2, 2.0/98, 2.8/98, 3.0/2, 3.7/2.

Method-D: Column:X-Select CSH C18 (3.0*50 mm, 2.5 μm), Mobile Phase A: 2.5 Mm Ammonium Bicarbonate in $H_2O$+5% ACN Mobile Phase B: 100% ACN, Gradient % B: 0/2, 0.3/2, 2.0/98, 2.8/98, 3.0/2, 3.7/2.

Method-E: Column: X-Bridge BEH C18, (50 mm*3.0 mm, 2.5μ) Mobile Phase A: 2.5 mM Ammonium Bicarbonate in Water+5% ACN Mobile Phase B: 100% ACN Flow rate: 1.0 mL/min. Column temperature: 40° C. Gradient Program (B %): 0.0/2, 0.3/2, 2.0/98, 2.8/98, 3.0/2, 3.7/2

HPLC:

Method-A: Column: X Select CSH C18 (150×4.6) mm, 3.5; Mobile phase A: 0.1% FA in Water: ACN (95:05); Mobile phase B: Acetonitrile; Gradient Programme: T/B %: 0.01/5, 1/5, 8/100, 12/100, 14/5, 18/5; Flow rate: 1.2 ml/min.

Method-B: Column: X-Bridge CSH C18 (150×4.6 mm, 3.5 μm); Mobile Phase-A: 5 mM $NH_4HCO_3$; Mobile Phase-B: ACN; Programme: T/B %: 0.01/2, 2/2, 12/90, 16/90; Flow rate: 1.0 mL/min.; Diluent: ACN: water (80:20)

Method-C: Column: X SELECT CSH C18 (150×4.6 mm, 3.5); Mobile Phase A: 0.05% TFA in water: ACN (95:05); Mobile Phase B: 0.05% TFA in water: ACN (05:95); Programme: T/B %: 0.01/10, 12/90, 16/90; Flow rate: 1 mL/min.; Diluent: water:ACN (80:20).

Method-D: Column: X-Bridge CSH C18 (4.6*150) mm 5μ Mobile Phase: A—0.1% TFA in water, B—Acetonitrile Inj Volume; 5.0 μL, Flow Rate: 1.2 mL/minute Gradient program: Time(min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in hexane, Mobile Phase B: IPA A/B: 60/40 Flow: 1.0 ml/MIN PDA: OJ-H_015.

Method-F: Column: ACE Excel 2 C18-AR,100 mm×3.0 mm Mobile Phase A: 0.05% TFA in Water, Mobile Phase B: 0.05% TFA in Acetonitrile, Colum Temperature: 40° C., Flow Rate: 0.6 mL/min Gradient: 0/5, 1/5, 6/90, 8.5/90, 8.8/5, 11/5.

Method-G: Column: CHIRAL PAK-IC (250×4.6 mm, 5 μm) Mobile Phase A: 0.1% DEA in Hexane, Mobile Phase B: EtOH/MeOH (50/50) A: B: 80/20 Flow 1.0 ml/min.

Method-H: Column: X-Bridge C18 (4.6*150) mm 5μ Mobile Phase: A—5 mM Ammonium Acetate, B—Acetonitrile Flow Rate: 1.0. mL/minute, Gradient program: Time (min)/B Conc.: 0.01/5, 1.0/5, 8.0/100, 12.0/100, 14.0/5, 18.0/5.

Method-I: Column: CHIRALCEL-OJ-H (250×4.6 mm, 5 μm) mobile Phase A: n-hexane, Mobile Phase B: EtOH: MeOH (1:1) A/B: 50/50 Flow: 1.0 ml/min.

Method-J: Column: CHIRALCEL-OX—H Mobile Phase A: n-hexane, Mobile Phase B: IPA Flow: 1.0 ml/min.

Method-K: Column Name: CHIRALPAK-IG (250×4.6 mm, 5 μm), Mobile Phase A: 0.1% DEA n-Hexane, Mobile Phase B: DCM: MeOH (50:50), Flow rate: 1.0 ml/min.

Method-L: Column IC-5 (30×250*4.6 mm, 5μ) Mobile phase A n-hexane, Mobile phase B IPA: DCM (1:1) Eluent A: B: −70-30 Total Flow rate (mL/min) 42.

Synthesis of I-140:

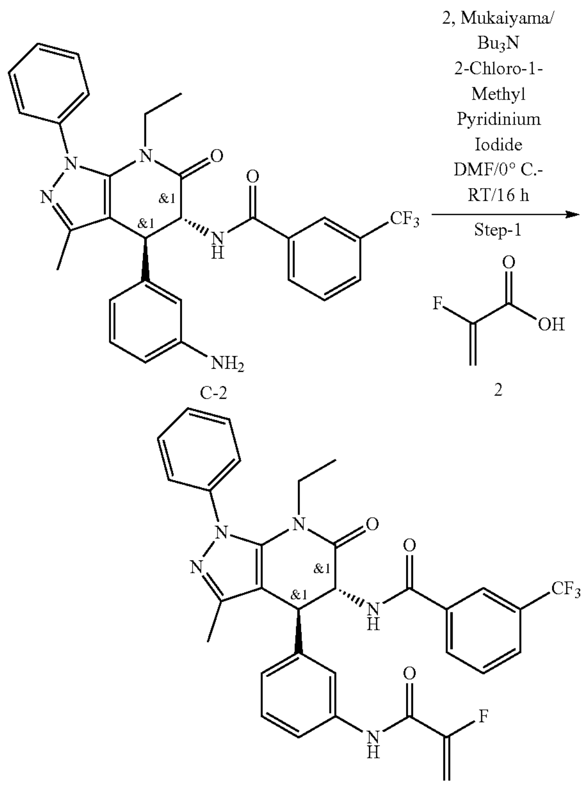

C-2

2

I-140

Step-1: Synthesis of N-((4S,5R)-7-ethyl-4-(3-(2-fluoroacrylamido)phenyl)-3-methyl-6-oxo-1-phenyl-4,5,6,7-tetrahydro-1H-pyrazolo[3,4-b]pyridin-5-yl)-3 (trifluoromethyl) benzamide (I-140)

To a stirred solution of C-2 (300 mg, 0.6 mmol) in DMF (3 mL) were added 2-chloro-1-methylpyridinium iodide (0.2 g, 0.9 mmol) and tributylamine (0.3 g, 1 mmol) and then 2-fluoroacrylic acid (2) (0.05 g, 0.6 mmol) was added at 0° C. and stirred for 16 hours at room temperature. The reaction progress was monitored by TLC. After completion, then the reaction mixture was quenched with ice water (20 mL) and extracted into ethyl acetate (3×20 mL) washed with brine water. The combined organic layers were dried over sodium sulphate, concentrated under reduced pressure to obtain crude compound. The crude obtained was purified by silica gel flash column chromatography and eluted at 25% EtOAc/heptane to afford the title compound I-140 (105 mg, 30%) as a pale-yellow solid.

$^1H$ NMR (400 MHz, DMSO-$d_6$) δ=10.32 (s, 1H), 9.02 (d, J=8.8 Hz, 1H), 8.02-8.00 (m, 2H), 7.90 (d, J=7.6 Hz, 1H), 7.76 (s, 1H), 7.71 (t, J=7.6 Hz, 1H), 7.63-7.61 (m, 3H), 7.58 (t, J=7.2 Hz, 2H), 7.51-7.47 (m, 1H), 7.32 (t, J=7.6 Hz, 1H), 7.17 (d, J=7.6 Hz, 1H), 5.78-5.61 (m, 1H), 5.42-5.37 (m, 1H), 5.19-5.13 (m, 1H), 4.36 (d, J=12 Hz, 1H), 3.81 (m, 1H), 3.13-3.04 (m, 1H), 1.52 (s, 3H), 0.83 (t, J=6.8 Hz, 3H). LC-MS (Method-A)=604.42 [M−H]$^-$; 99.38% at RT 2.27 min. HPLC (Method-A)=99.47% at RT 6.05 min. Chiral HPLC (Method-G): Peak-1 50.12% at RT 4.58 min, Peak-2 49.88% at RT 5.37 min.

Synthesis of I-130:

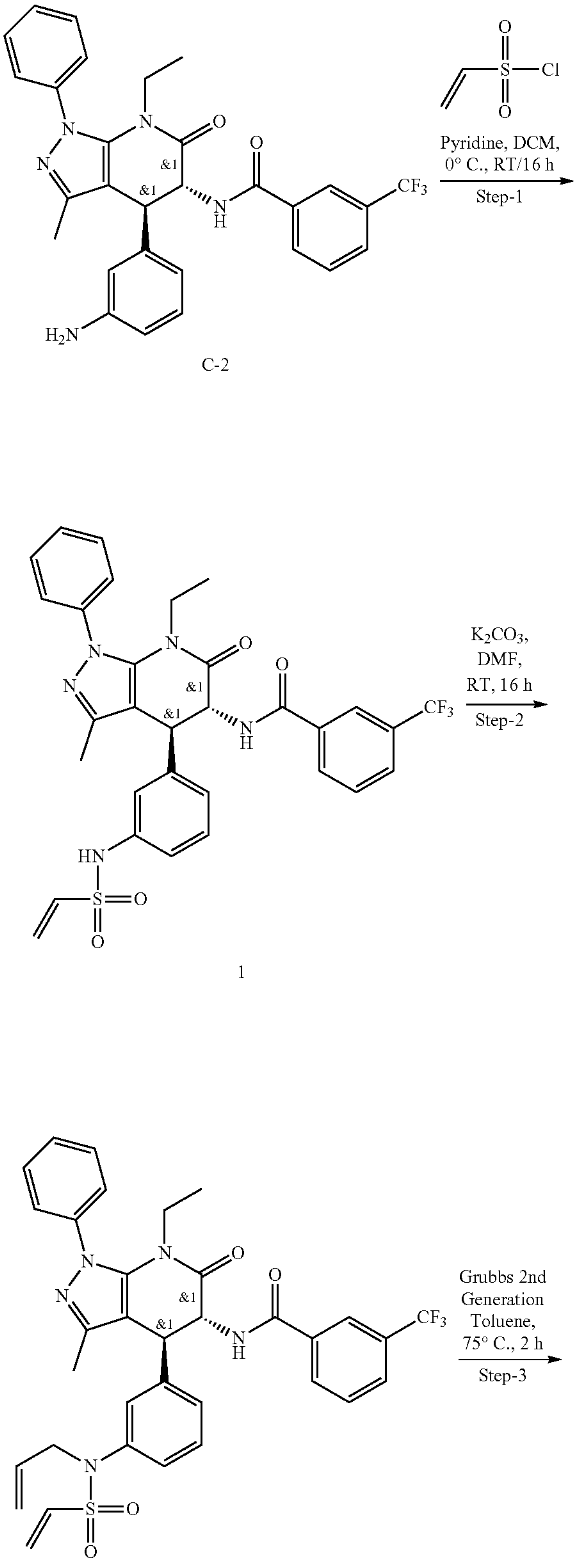

C-2

1

2

-continued

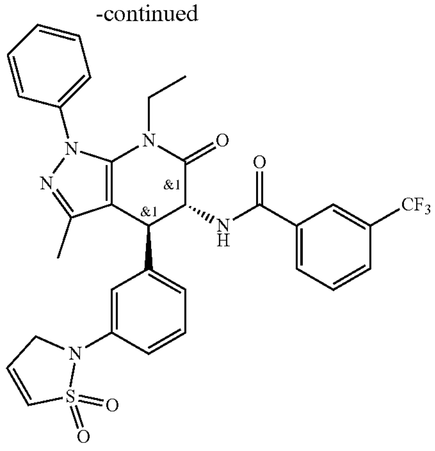

I-130

Step-1: Synthesis of rac-N-((4R,5S)-7-ethyl-3-methyl-6-oxo-1-phenyl-4-(3-(vinylsulfonamido)phenyl)-4,5,6,7-tetrahydro-1[1]H-pyrazolo[3,4-b]pyridin-5-yl)-3-(trifluoromethyl)benzamide (1)

To the stirred solution of C-2 (250 mg, 0.44 mmol) in dichloromethane (4.5 mL) was added pyridine (40 mg, 0.50 mmol) followed by ethene sulfonyl chloride (60 mg, 0.45 mmol) at 0° C. The resulting reaction mixture was stirred at room temperature for 16 h. The progress of the reaction was monitored by LC-MS and TLC (50% ethyl acetate in pet-ether). Then the reaction mixture was quenched with ice-cold water (25 mL), aqueous layer extracted with DCM (2×30 mL) combined organic layer was dried over $Na_2SO_4$, filtered, and concentrated under reduced pressure to afford the crude compound. The crude compound was purified by combi-flash using (12 g Column) and eluted at 20% to 60% EtOAc in pet-ether to obtain the compound (1) (130 mg, 42.94%) as an Off-White solid.

$^1$H NMR (400 MHz, DMSO-$d_6$) (δ=9.95 (s, 1H), 9.00 (d, J=8.8 Hz, 1H), 8.04-8.01 (m, 2H), 7.90 (t, J=8.0 Hz, 1H), 7.71 (t, J=8.0 Hz, 1H), 7.63-7.61 (m, 2H), 7.57-7.54 (m, 2H), 7.50-7.47 (m, 1H), 7.28-7.21 (m, 2H), 7.12 (d, J=7.6 Hz, 1H), 7.02 (d, J=7.6 Hz, 1H), 6.68-6.62 (m, 1H), 5.97 (d, J=16.8 Hz, 1H), 5.81 (d, J=10.0 Hz, 1H), 5.23-5.18 (m, 1H), 4.31 (d, J=12.4 Hz, 1H), 3.80-3.75 (m, 1H), 3.10-3.05 (m, 1H), 1.45 (s, 3H), 0.80 (t, J=6.8 Hz, 3H). LC-MS (Method-A)=624.3 $[M+H]^+$; 91.59% at RT 1.50 min.

Step-2: Synthesis of rac-N-((4R,5S)-4-(3-(N-allylvinylsulfonamido)phenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (2)

To the stirred solution of compound (1) (130 mg, 0.190 mmol) in DMF (2 mL) was added Potassium carbonate (40 mg, 0.28 mmol) followed by allyl bromide (35 mg, 0.28 mmol) at 0° C. The resulting reaction mixture was stirred at room temperature for 16 h. The progress of the reaction was monitored by LC-MS and TLC (30% ethyl acetate in pet-ether). After starting material completion, the reaction mixture was quenched with ice-cold water (20 mL), aqueous layer extracted with EtOAc (2×25 mL). The combined organic layer was dried over $Na_2SO_4$, filtered, and concentrated under reduced pressure to afford the crude compound. The crude compound was purified by combi-flash using (12 g Column) and the compound eluted at 20% to 50% EtOAc in pet-ether to obtain the compound (2) (140 mg, 88.87%) as a pale-yellow solid.

$^1$H NMR (400 MHz, DMSO-$d_6$) (δ=8.97 (d, J=8.8 Hz, 1H), 8.01-7.97 (m, 1H), 7.88 (d, J=7.6 Hz, 1H), 7.70-7.66 (m, 1H), 7.62 (d, J=7.6 Hz, 2H), 7.58-7.54 (m, 2H), 7.50-7.47 (m, 1H), 7.35-7.33 (m, 2H), 7.17 (s, 1H), 6.90-6.83 (m, 1H), 6.01 (d, J=10.4 Hz, 1H), 5.91 (d, J=16.0 Hz, 1H), 5.59-5.58 (m, 1H), 5.37-5.32 (m, 1H), 5.94 (d, J=17.2 Hz, 1H), 4.77 (d, J=10.0 Hz, 1H), 4.35 (d, J=13.2 Hz, 1H), 4.97 (s, 2H), 3.85-3.80 (m, 1H), 3.06-3.01 (m, 1H), 2.88 (s, 1H), 2.72 (s, 1H), 1.40 (s, 3H), 0.85-0.79 (m, 3H). LC-MS (Method-A)=664.8 $[M+H]^+$; 80.44% at RT 2.34 min.

Step-3: Synthesis of rac-N-((4R,5S)-4-(3-(1,1-dioxidoisothiazol-2 (3H)-yl)phenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (I-130)

To a stirred solution of compound (2) (150 mg, 0.18 mmol) in Toluene (2.5 mL) purged with argon gas for 10 min, (1,3-Bis(2,4,6-trimethyl phenyl)-2-imidazolidinylidene) dichloro (phenyl methylene) (tricyclo hexyl phosphine) ruthenium (10 mg, 0.01 mmol) was added to the reaction mixture at room temperature. The resulting reaction mixture was stirred at 75° C. for 2 h. The reaction progress was monitored by LC-MS and TLC. After completion of starting material, the reaction mixture was diluted with ice-cold water (15 mL), extracted with EtOAc (2×20 mL). The combined organic layers were washed with brine (2×20 mL) and dried over sodium sulphate, concentrated under reduced pressure to obtain crude compound. The crude obtained was purified by silica gel combi-flash column chromatography and eluted with 40-80% EtOAc/heptane to get the solid compound. Further the obtained solid was washed with n-pentane (3×5 mL) and dried to afford the title compound I-130 (65 mg, 55.31%) as an off-white solid.

$^1$H NMR (400 MHz, DMSO-$d_6$) δ=9.01 (d, J=13.2 Hz, 1H), 8.03 (d, J=8.0 Hz, 2H), 7.89 (d, J=7.6 Hz, 1H), 7.70 (t, J=7.6 Hz, 1H), 7.63 (d, J=1.2 Hz, 2H), 7.57 (t, J=7.2 Hz, 2H), 7.50-7.47 (m, 1H), 7.39-7.31 (m, 4H), 7.21-7.14 (m, 2H), 5.29 (m, 1H), 4.53 (s, 2H), 4.40 (d, J=12.4 Hz, 1H), 3.81 (m, 1H), 3.11 (m, 1H), 1.51 (s, 3H), 0.83 (t, J=6.8 Hz, 3H). LC-MS (Method-C)=636.0 $[M+H]^+$; 99% at RT 2.47 min. HPLC (Method-A)=98.34% at RT 5.86 min. Chiral HPLC (Method-G)=Peak-1=49.22% at RT 5.28 min, Peak-2=50.78% at RT 6.32 min.

Synthesis of I-42:

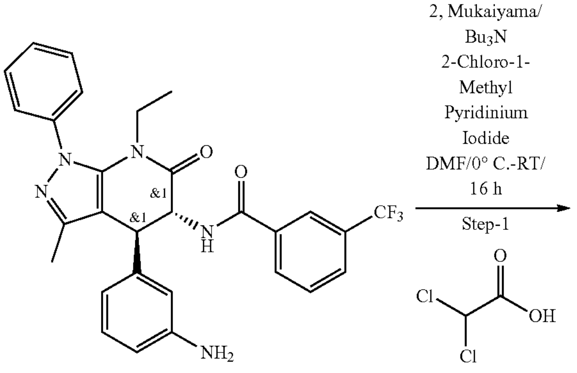

C-2

2

-continued

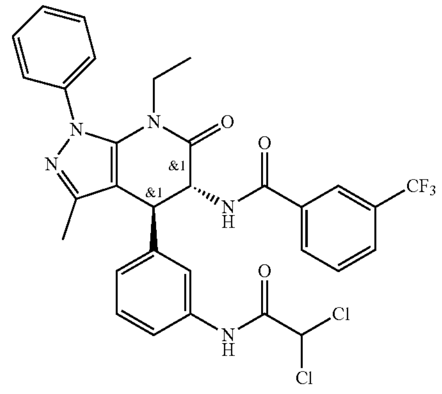

I-42

Step-1: Synthesis of N-((4S,5R)-4-(3-(2,2-dichloroacetamido)phenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (I-42)

To the stirred solution of C-2 (0.15 g, 0.28 mmol) in DMF (2 mL), 2-chloro-1-methyl pyridinium iodide (0.11 g, 0.42 mmol) was added followed by Tributylamine (0.13 g, 0.70 mmol) and Dichloroacetic acid (2) (0.04 g, 0.34 mmol) at 0° C. The resulting reaction mixture was stirred at room temperature for 16 h. Reaction progress was monitored by LC-MS and TLC. After completion of starting material by TLC, reaction mixture was quenched with ice water and extracted with ethyl acetate washed with brine water. The combined organic layers were dried over sodium sulphate, concentrated under reduced pressure to afford crude compound. Obtained crude was purified by silica gel combi-flash column chromatography, eluted with 50-60% EtOAc/heptane to afford the title compound I-42 (36 mg, 20%) as a white solid.

$^{1}$H NMR (400 MHz, DMSO-$d_6$) (δ=10.7 (s, 1H), 9.03 (d, J=8.8 Hz, 1H), 8.02 (d, J=6.4 Hz, 2H), 7.90 (d, J=8.0 Hz, 1H), 7.71 (t, J=8.4 Hz, 1H), 7.64 (d, J=1.6 Hz, 2H), 7.62-7.54 (m, 4H), 7.51-7.47 (m, 1H), 7.35 (t, J=7.6 Hz, 1H), 7.19 (d, J=7.6 Hz, 1H), 6.55 (s, 1H), 5.21 (m, 1H), 4.37 (d, J=12.0 Hz, 1H), 3.79 (m, 1H), 3.12 (m, 1H), 1.51 (s, 3H), 0.83 (t, J=6.8 Hz, 3H). LC-MS (Method-C)=643.7 $[M+H]^+$; 99.01% at RT 2.59 min. HPLC (Method-C)=99.08% at RT 6.20 min. Chiral HPLC (Method-G)=Peak-1=50.87% at RT 7.02 min, Peak-2=49.13% at RT 8.21 min.

Synthesis of I-68, and I-46:

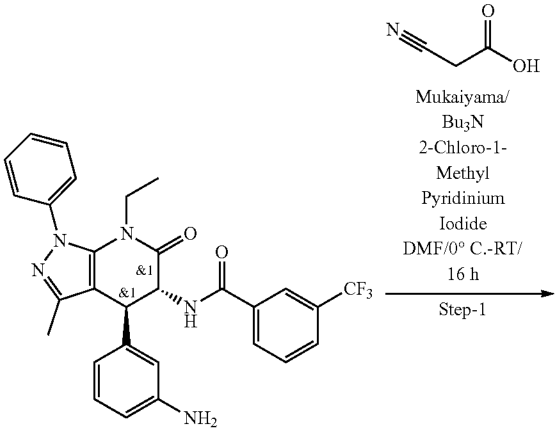

C-2

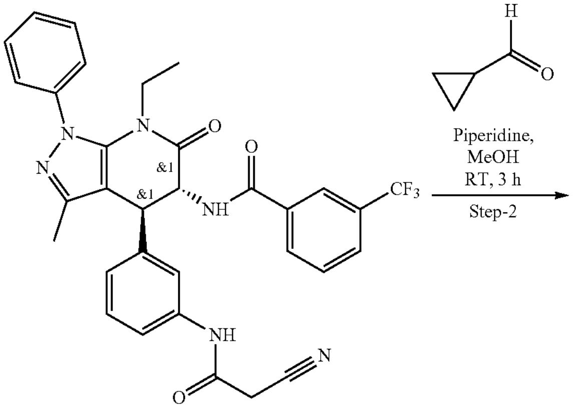

1

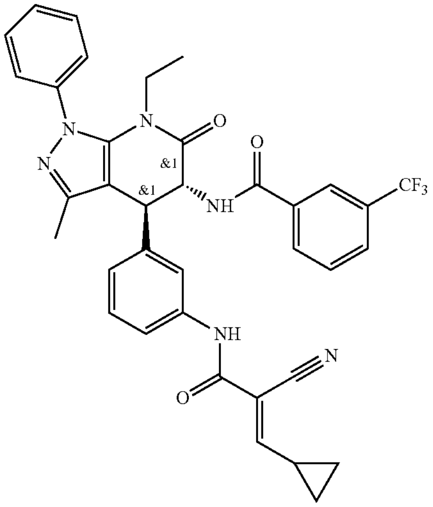

I-68

-continued

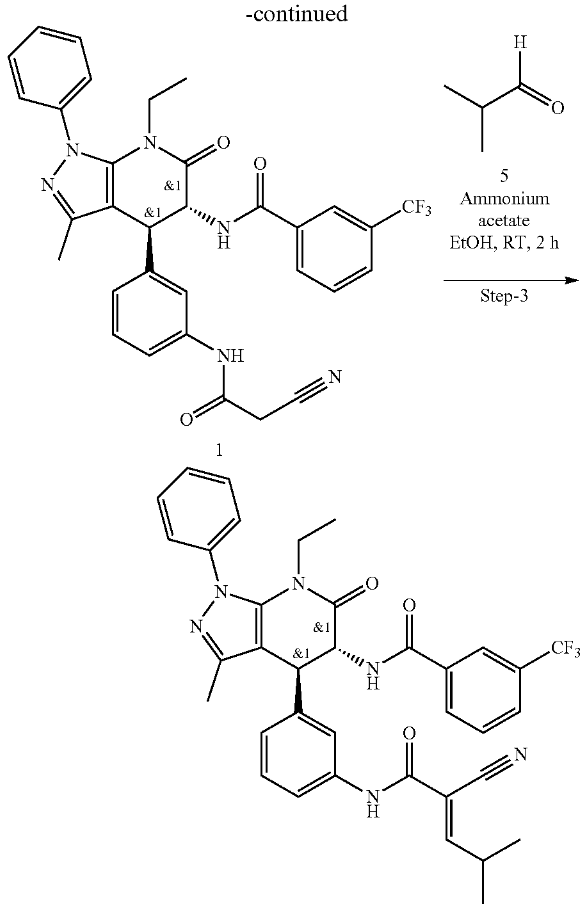

1

I-46

Step-1: Synthesis of rac-N-((4R,5S)-4-(3-(2-cyano-acetamido)phenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (1)

To a stirred solution of 2-cyano acetic acid (0.24 g, 2.8 mmol) in DMF (14 mL) was added EDAC (0.73 g, 3.7 mmol)C-2 (1.0 g, 1.9 mmol) at 0° C. under inert atmosphere followed by the addition of N, N-diisopropylethylamine (0.99 mL, 5.6 mmol), 1-hydroxy benzotriazole (0.52 g, 3.7 mmol). Then the reaction mixture was stirred at room temperature for 16 h. The progress of the reaction checked by TLC. After consumption of the starting material, the reaction mixture was diluted with water (20 mL) and extracted by using EtOAc (20 mL×2). The organic layer was dried over anhydrous $Na_2SO_4$, filtered and concentrated under reduced pressure. The obtained crude material was purified by silica gel column chromatography and eluted at 45-50% EtOAc:PE to afford the compound (1) (0.9 g, 80%) as an Off-White colour solid.

$^1$H NMR (400 MHz, DMSO-$d_6$) δ=10.32 (s, 1H), 9.02 (d, J=8.8 Hz, 1H), 8.02 (d, J=7.6 Hz, 2H), 7.95-7.89 (m, 1H), 7.70 (t, J=7.2 Hz, 1H), 7.63-7.56 (m, 2H), 7.54-7.47 (m, 5H), 7.31-7.27 (m, 1H), 7.12 (d, J=7.6 Hz, 1H), 5.20-5.15 (m, 1H), 4.33 (d, J=12 Hz, 1H), 3.85 (s, 2H), 3.80-3.75 (m, 1H), 3.11-3.06 (m, 1H), 1.54 (s, 3H), 0.81 (t, J=6.8 Hz, 3H). LC-MS (Method-A)=601.7 [M+H]$^+$; 86.83% at RT 2.18 min.

Step-2: Synthesis of rac-N-((4R,5S)-4-(3-((E)-2-cyano-3-cyclopropylacrylamido)phenyl)-7-ethyl-3-methyl-6-oxo-1-phenyl-4,5,6,7-tetrahydro-1H-pyrazolo[3,4-b]pyridin-5-yl)-3-(trifluoromethyl) benzamide (2)

To the stirred solution of compound (1) (0.2 g, 0.3 mmol) in MeOH (1 mL), was added Piperidine (0.06 g, 0.7 mmol) and cyclopropane carbaldehyde (0.05 g, 0.7 mmol). Then the reaction mixture was stirred at room temperature for 3 h. The reaction progress was monitored by TLC. After completion of starting material, the reaction mixture was distilled and then diluted with water (20 mL) and extracted with DCM (2×20 mL). The combined organic layer was dried over sodium sulphate, concentrated under reduced pressure to afford crude. The obtained crude was purified by silica gel combi-flash column chromatography and eluted with 45-50% EtOAc/heptane to afford I-68 (120 mg, 60%) as a white solid.

$^1$H NMR (400 MHz, DMSO-$d_6$) δ=10.06 (s, 1H), 9.02 (d, J=8.8 Hz, 1H), 8.02 (d, J=7.6 Hz, 2H), 7.90 (d, J=7.6 Hz, 1H), 7.71 (t, J=7.6 Hz, 1H), 7.63-7.60 (m, 3H), 7.58-7.54 (m, 3H), 7.51-7.47 (m, 1H), 7.31 (t, J=8.0 Hz, 1H), 7.14 (d, J=7.6 Hz, 1H), 7.05 (d, J=10.8 Hz, 1H), 5.18 (m, 1H), 4.35 (d, J=12.4 Hz, 1H), 3.81 (m, 1H), 3.10 (m, 1H), 1.95-1.91 (m, 1H), 1.51 (s, 3H), 1.28-1.23 (m, 2H), 1.00-0.97 (m, 2H), 0.83 (t, J=6.8 Hz, 3H). LC-MS (Method-C)=653.5 [M+H]$^+$; 97.47% at RT 2.60 min. HPLC (Method-A)=96.29% at RT 6.25 min. Chiral HPLC (Method-G)=Peak-1=49.01% at RT 5.45 min, Peak-2=49.79% at RT 6.76 min.

Step-3: Synthesis of rac-N-((4R,5S)-4-(3-((E)-2-cyano-4-methylpent-2-enamido)phenyl)-7-ethyl-3-methyl-6-oxo-1-phenyl-4,5,6,7-tetrahydro-1H-pyrazolo[3,4-b]pyridin-5-yl)-3-(trifluoromethyl) benzamide To the stirred solution of compound (1) (0.2 g, 0.3 mmol) in EtOH (10 mL) was added ammonium acetate (5 mg, 0.07 mmol), 2-methyl propanal (5) (0.05 g, 0.7 mmol). Then the reaction mixture was stirred at room temperature for 2 h. The reaction progress was monitored by TLC. After completion of starting material by TLC, the reaction mixture was distilled and then diluted with water (20 mL) and extracted with EtOAc (2×20 mL). The combined organic layer was dried over sodium sulphate, concentrated under reduced pressure to afford crude. The obtained Crude was purified by mixing with previous batch (2×0.2 g) by silica gel combi-flash column chromatography and eluted with 45-50% EtOAc/heptane to afford I-46 (60 mg, 30%) as an off-white solid.

$^1$H NMR (400 MHz, DMSO-$d_6$) δ=10.20 (s, 1H), 9.01 (d, J=8.8 Hz, 1H), 8.02 (d, J=7.2 Hz, 2H), 7.90 (d, J=7.6 Hz, 1H), 7.71 (t, J=7.6 Hz, 1H), 7.62-7.54 (m, 6H), 7.51-7.47 (m, 1H), 7.42 (d, J=10.0 Hz, 1H), 7.33 (t, J=8.0 Hz, 1H), 7.17 (d, J=8.0 Hz, 1H), 5.19 (m, 1H), 4.37 (d, J=12.4 Hz, 1H), 3.81 (m, 1H), 3.11 (m, 1H), 2.85-2.79 (m, 1H), 1.52 (s, 3H), 1.13 (d, J=6.4 Hz, 6H), 0.83 (t, J=7.2 Hz, 3H). LC-MS (Method-A)=655.35 [M+H]$^+$; 92.98% at RT 2.40 min. HPLC (Method-A)=97.93% at RT 6.41 min. Chiral HPLC (Method-G)=Peak-1=50.50% at RT 4.94 min, Peak-2=43.67% at RT 6.92 min.

Synthesis of I-184:

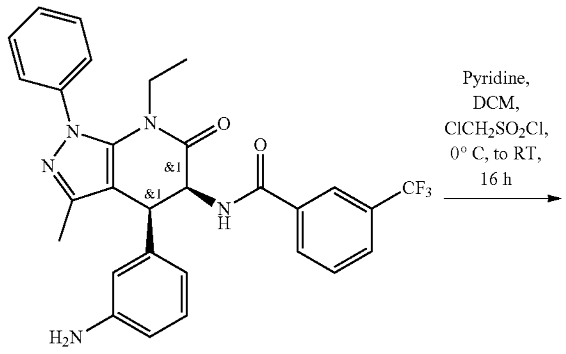

C-1

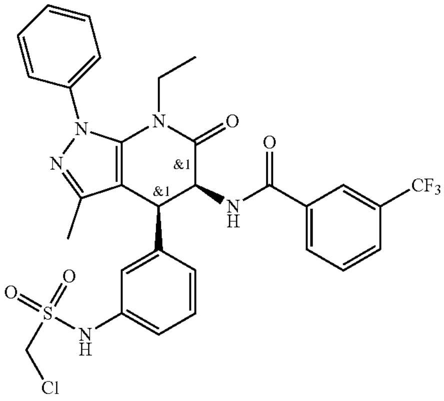

I-184

To a stirred solution of C-1 (200 mg, 0.35 mmol) in dichloromethane (5 mL) was added chloromethanesulfonyl chloride (0.05 g, 0.35 mmol) and pyridine (0.05 g, 0.71 mmol) at 0° C. The temperature of reaction mixture was raised to room temperature and stirred for 16 h. The reaction mass was monitored by TLC. Reaction mass was diluted with water (10 mL) and extracted with DCM (10 mL). The combined organic layer was dried over sodium sulphate and concentrated under reduced pressure, to afford crude compound (A) (180 mg) as a brown solid which is purified by Prep. HPLC to afford I-184 (99.74 mg, 42.91%) as off-white solid.

$^1$H NMR (400 MHz, DMSO-$d_6$) δ=10.23 (s, 1H), 8.67 (d, J=7.6 Hz, 1H), 8.16-8.14 (m, 2H), 7.91 (d, J=7.6 Hz, 1H), 7.71 (t, J=7.6 Hz, 1H), 7.64 (d, J=7.6 Hz, 2H), 7.59-7.55 (m, 2H), 7.52-7.50 (m, 1H), 7.24 (t, J=8.0 Hz, 1H), 7.09 (d, J=8.0 Hz, 1H), 6.97 (s, 1H), 6.70 (d, J=7.6 Hz, 1H), 5.50 (t, J=7.6 Hz, 1H), 4.80 (d, J=12.4 Hz, 1H), 4.46-4.41 (m, 2H), 3.88-3.76 (m, 1H), 3.11-3.06 (m, 1H), 2.03 (s, 3H), 0.91 (t, J=7.2 Hz, 3H). LCMS: (Method-A)=646.32 $[M+H]^+$; 99.27% at RT 2.11 min. HPLC(Method-C): 99.55% at RT 8.41 min.

Epimerization with $K_2CO_3$/ACN:

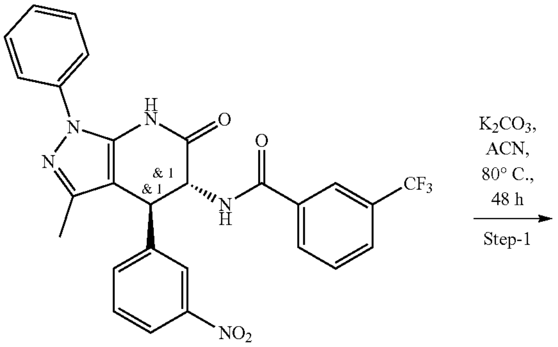

1

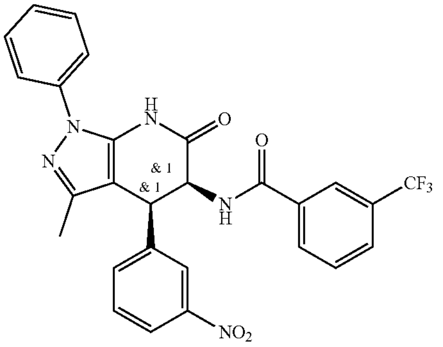

2

Step-1: Synthesis of rac-N-((4R,5R)-3-methyl-4-(3-nitrophenyl)-6-oxo-1-phenyl-4,5,6,7-tetrahydro-1H-pyrazolo[3,4-b]pyridin-5-yl)-3-(trifluoromethyl) benzamide (2)

To a stirred solution of trans (rac) compound 1 (15 g, 28.01 mmol) in ACN (150 mL) was added potassium carbonate (11.3 g, 81.4 mmol) and heated at 80° C. for 48 h. Progress of the reaction was monitored by TLC. Reaction mass was evaporated under vacuum. Resulting residue was purified by flash column chromatography and pure fractions were eluted at 20-25% EtOAc/heptane to afford cis (rac) compound 2 (10 g, 63.33%) as a yellow solid.

$^1$H NMR (400 MHz, DMSO-$d_6$): 8.64 (d, J=7.6 Hz, 1H), 8.14 (dd, J=8.2, 2.3, 1.1 Hz, 1H), 8.07-8.10 (m, 2H), 7.83-7.91 (m, 2H), 7.69 (t, J=7.7 Hz, 2H), 7.49-7.65 (m, 5H), 7.46 (d, J=7.8 Hz, 1H), 7.36-7.43 (m, 1H), 5.46 (t, J=7.6 Hz, 1H), 4.73 (d, J=7.5 Hz, 1H), 2.03 (s, 3H). LC-MS (Method-B)=536.0 $[M+H]^+$; 74.95% at RT 2.29 min.

LCMS:

Method-A (LCMS-25): Column: L-column3 C18 3.0*30 mm 3 um, Mobile Phase: A: 5 mM $NH_4HCO_3$ in water; B: Acetonitrile, Flow Rate: 1.2 mL/min. Oven Temperature: 40 C, Gradient program (B %): 0.00/10.0, 1.4/95, 1.9/95, 1.91/10

Method-B (LCMS-10/24): Column: HALO C18, 30*3.0 mm, 2 um, Mobile Phase: A: Water/0.05% TFA; B: Acetonitrile, Flow Rate: 1.5 mL/min. Oven Temperature: 40 C, Gradient program (B %): 0.01/5, 1.5/95, 1.9/95, 1.91/5

Method-C(LCMS-10): Column: CORTECS C18+, 30*3.0 mm, 2.7 um, Mobile Phase: A: Water/0.05% TFA; B: Acetonitrile, Flow Rate: 1.5 mL/min. Oven Temperature: 40 C, Gradient program (B %): 0.01/5, 1.5/95, 1.9/95, 1.91/5

Method-D (LCMS-13): Column: HPH—C18, 50*3.0 mm, 2.7 um, Mobile Phase: A: Water/0.05% ammonia water; B: Acetonitrile, Flow Rate: 1.2 mL/min. Oven Temperature: 40 C, Gradient program (B %): 0.50/55, 3.50/70, 4.00/95, 4.80/95, 4.81/5.

Method-E (LCMS-29): Column: SB-Aq 4.6*50 mm 1.8 um, Mobile Phase: A: Water/0.02% FA; B: Acetonitrile 0.02% FA, Flow Rate: 1.5 mL/min. Oven Temperature: 40 C, Gradient program (B %): 0.00/5.0, 2.00/95.0, 2.90/95.0, 2.91/5.0.

Method-F (LCMS-10): Column: CORTECS C18+, 30*3.0 mm, 2.7 um, Mobile Phase: A: Water/0.05% TFA; B: Acetonitrile, Flow Rate: 1.5 mL/min. Oven Temperature: 40 C, Gradient program (B %): 0.30/30, 1.80/60, 2.20/95, 2.80/95, 2.81/5.

Method-G (LCMS-24): Column: SB-Aq 4.6*50 mm 1.8 um, Mobile Phase: A: Water/0.05% TFA; B: Acetonitrile, Flow Rate: 1.5 mL/min. Oven Temperature: 40 C, Gradient program (B %): 0.00/5, 0.30/40, 1.80/80, 2.20/95, 2.80/95, 2.81/5.

Method-H (LCMS-10): Column: SB-Aq 4.6*50 mm 1.8 um, Mobile Phase: A: Water/0.05% TFA; B: Acetonitrile, Flow Rate: 1.5 mL/min. Oven Temperature: 40 C, Gradient program (B %): 0.00/5, 0.40/40, 3.20/70, 4.10/95, 4.80/95, 4.81/5.

Method-I (LCMS-13): Column: HPH—C18, 50*3.0 mm, 2.7 um, Mobile Phase: A: Water/0.05% ammonia water; B: Acetonitrile, Flow Rate: 1.2 mL/min. Oven Temperature: 40 C, Gradient program (B %): 0.01/5, 0.50/50, 2.10/80, 2.60/95, 3.30/95, 3.31/5.

Method-J (LCMS-13): Column: HPH—C18, 50*3.0 mm, 2.7 um, Mobile Phase: A: Water/0.05% ammonia water; B: Acetonitrile, Flow Rate: 1.2 mL/min. Oven Temperature: 40 C, Gradient program (B %): 0.01/5, 2.00/95, 2.80/95, 2.81/5.

Method-K (LCMS-29): Column: CORTECS C18+, 30*3.0 mm, 2.7 um, Mobile Phase: A: Water/0.02% FA; B: Acetonitrile 0.02% FA, Flow Rate: 1.5 mL/min. Oven Temperature: 40 C, Gradient program (B %): 0.00/5.0, 1.50/95.0, 1.90/95.0, 1.91/5.0.

Method-L (LCMS-13): Column: Atlantis Premiser BEH C18 AX, 50*4.6 mm, 2.5 um, Mobile Phase: A: Water/0.05% ammonia water; B: Acetonitrile, Flow Rate: 1.2 mL/min. Oven Temperature: 40 C, Gradient program (B %): 0.01/50, 2.00/95, 2.80/95, 2.81/50.

Method-M (LCMS-13): Column: YMC-Triart C18, 50*3.0 mm, 3 um, Mobile Phase: A: Water/0.05% ammonia water; B: Acetonitrile, Flow Rate: 1.2 mL/min. Oven Temperature: 40 C, Gradient program (B %): 0.01/50, 2.00/95, 2.80/95, 2.81/30.

Method-N(LCMS-13): Column: L-column3 C18, 50*3.0 mm, 3 um, Mobile Phase: A: Water/0.05% ammonia water; B: Acetonitrile, Flow Rate: 1.2 mL/min. Oven Temperature: 40 C, Gradient program (B %): 0.01/5, 2.00/95, 2.80/95, 2.81/5.

Method-O (LCMS-13): Column: HPH—C18, 100*4.6 mm, 2.7 um, Mobile Phase: A: Water/0.05% ammonia water; B: Acetonitrile, Flow Rate: 1.2 mL/min. Oven Temperature: 40 C, Gradient program (B %): 0.01/40, 5.50/70, 6.5/95, 7.50/95, 7.51/40, Method-P (LCMS-13): Column: L-column3 C18, 50*3.0 mm, 3 um, Mobile Phase: A: Water/0.05% ammonia water; B: Acetonitrile, Flow Rate: 1.2 mL/min. Oven Temperature: 40 C, Gradient program (B %): 0.01/5, 0.50/50, 2.10/80, 2.60/95, 3.30/95, 3.31/5.

Method-Q (LCMS-13): Column: HPH—C18, 50*3.0 mm, 2.7 um, Mobile Phase: A: Water/0.05% ammonia water; B: Acetonitrile, Flow Rate: 1.2 mL/min. Oven Temperature: 40 C, Gradient program (B %): 0.01/5, 0.50/50, 2.10/80, 2.60/95, 3.30/95, Method-R (LCMS-29): Column: HALO 90A, PCS C18 30*3 mm 2.7 um, Mobile Phase: A: Water/0.02% FA; B: Acetonitrile 0.02% FA, Flow Rate: 1.5 mL/min. Oven Temperature: 40 C, Gradient program (B %): 0.00/5.0, 1.50/95.0, 1.90/95.0, 1.91/5.0.

Method-S(LCMS-13): Column: YMC-Triart C18, 50*3.0 mm, 3 um, Mobile Phase: A: Water/0.05% ammonia water; B: Acetonitrile, Flow Rate: 1.2 mL/min. Oven Temperature: 40 C, Gradient program (B %): 0.01/30, 3.50/95, 4.80/95, 4.81/30.

Method-T (LCMS-10): Column: SB-Aq, 50*4.6 mm, 1.8 um, Mobile Phase: A: Water/0.05% TFA; B: Acetonitrile, Flow Rate: 1.5 mL/min. Oven Temperature: 40 C, Gradient program (B %): 0.30/30, 1.80/60, 2.20/95, 2.80/95, 2.81/5.

Method-U (LCMS-13): Column: Atlantis Premiser BEH C18 AX, 50*4.6 mm, 2.5 um, Mobile Phase: A: Water/0.05% ammonia water; B: Acetonitrile, Flow Rate: 1.2 mL/min. Oven Temperature: 40 C, Gradient program (B %): 0.01/50, 3.50/80, 4.00/95, 4.80/95, 4.81/50.

Method-V (LCMS-13): Column: HPH—C18, 50*3.0 mm, 2.7 um, Mobile Phase: A: Water/0.05% ammonia water; B: Acetonitrile, Flow Rate: 1.2 mL/min. Oven Temperature: 40 C, Gradient program (B %): 0.01/5, 2.00/95, 2.80/95, 2.81/5.

Method-W (LCMS-13): Column: YMC-Triart C18, 50*3.0 mm, 3 um, Mobile Phase: A: Water/0.05% ammonia water; B: Acetonitrile, Flow Rate: 1.2 mL/min. Oven Temperature: 40 C, Gradient program (B %): 0.01/5, 2.00/95, 2.80/95, 2.81/5.

Method-X (LCMS-25): Column: L-column3 C18 3.0*30 mm 3 um, Mobile Phase: A: 5 mM $NH_4HCO_3$ in water; B: Acetonitrile, Flow Rate: 1.2 mL/min. Oven Temperature: 40 C, Gradient program (B %): 0.00/10.0, 0.30/40, 1.80/70, 2.20/95, 2.90/95, 2.91/10

Method-Y (LCMS-10/24): Column: HALO C18, 30*3.0 mm, 2 um, Mobile Phase: A: Water/0.05% TFA; B: Acetonitrile, Flow Rate: 1.5 mL/min. Oven Temperature: 40 C, Gradient program (B %): 0.01/5, 2.00/40, 2.50/95, 2.80/95, 2.81/5

Method-Z (LCMS-13): Column: HPH—C18, 50*3.0 mm, 2.7 um, Mobile Phase: A: Water/0.05% ammonia water; B: Acetonitrile, Flow Rate: 1.2 mL/min. Oven Temperature: 40 C, Gradient program (B %): 0.01/5, 0.50/30, 2.10/60, 2.50/95, 2.80/95, 2.81/5.

Method-AA (LCMS-10): Column: CORTECS C18+, 30*3.0 mm, 2.7 um, Mobile Phase: A: Water/0.05% TFA; B: Acetonitrile, Flow Rate: 1.5 mL/min. Oven Temperature: 40 C, Gradient program (B %): 0.00/5, 1.80/45, 2.20/95, 2.80/95, 2.81/5.

Method-AB (LCMS-29): Column: CORTECS C18+, 30*3.0 mm, 2.7 um, Mobile Phase: A: Water/0.02% FA; B: Acetonitrile 0.02% FA, Flow Rate: 1.5 mL/min. Oven Temperature: 40 C, Gradient program (B %): 0.00/5.0, 1.80/40, 2.30/95.0, 2.80/95.0, 2.81/5.0.

Method-AC (LCMS-13): Column: HPH—C18, 50*3.0 mm, 2.7 um, Mobile Phase: A: Water/0.05% ammonia water; B: Acetonitrile, Flow Rate: 1.2 mL/min. Oven Temperature: 40 C, Gradient program (B %): 0.01/5, 0.50/40, 2.10/70, 2.50/95, 2.80/95, 2.81/5.

Method-AD (LCMS-10): Column: CORTECS C18+, 30*3.0 mm, 2.7 um, Mobile Phase: A: Water/0.05% TFA; B: Acetonitrile, Flow Rate: 1.5 mL/min. Oven Temperature: 40 C, Gradient program (B %): 0.30/20, 1.80/50, 2.20/95, 2.80/95, 2.81/5.

Method-AE (LCMS-10): Column: Cortecs T3, 50*3.0 mm, 2.7 um, Mobile Phase: A: Water/0.05% TFA; B: Acetonitrile, Flow Rate: 1.5 mL/min. Oven Temperature: 40 C, Gradient program (B %): 0.01/5, 2.20/95, 2.80/95, 2.81/5.

Method-AF (LCMS-29): Column: SB-Aq 4.6*50 mm 1.8 um, Mobile Phase: A: Water/0.02% FA; B: Acetonitrile 0.02% FA, Flow Rate: 1.5 mL/min. Oven Temperature: 40 C, Gradient program (B %): 0.00/5.0, 3.00/50, 4.00/95.0, 4.80/95.0, 4.81/5.0.

Method-AG (LCMS-13): Column: HPH—C18, 50*3.0 mm, 2.7 um, Mobile Phase: A: Water/0.05% ammonia water; B: MeOH, Flow Rate: 1.0 mL/min. Oven Temperature: 40 C, Gradient program (B %): 0.00/40, 4.00/95, 5.80/95, 5.81/40.

Method-AH (LCMS-13): Column: HPH—C18, 50*3.0 mm, 2.7 um, Mobile Phase: A: Water/0.05% ammonia water; B: Acetonitrile, Flow Rate: 1.2 mL/min. Oven Temperature: 40 C, Gradient program (B %): 0.01/5, 0.80/40, 3.60/70, 4.00/95, 4.80/95, 4.81/5.

Method-AI (LCMS-10): Column: SB-Aq 4.6*50 mm 1.8 um, Mobile Phase: A: Water/0.05% TFA; B: Acetonitrile/0.05% TFA, Flow Rate: 1.5 mL/min. Oven Temperature: 40 C, Gradient program (B %): 0.00/5, 0.30/30, 1.80/60, 2.20/95, 2.80/95, 2.81/5.

Method-AJ (LCMS-10): Column: CORTECS C18+, 30*3.0 mm, 2.7 um, Mobile Phase: A: Water/0.05% TFA; B: Acetonitrile, Flow Rate: 1.5 mL/min. Oven Temperature: 40 C, Gradient program (B %): 0.01/5, 1.60/40, 2.20/95, 2.80/95, 2.81/5

Method-AK (LCMS-29): Column: SB-Aq 4.6*50 mm 1.8 um, Mobile Phase: A: Water/0.02% FA; B: Acetonitrile 0.02% FA, Flow Rate: 1.5 mL/min. Oven Temperature: 40 C, Gradient program (B %): 0.00/5.0, 0.40/20, 3.00/50, 4.00/95.0, 4.80/95.0, 4.81/5.0.

Method-AL (LCMS-25): Column: L-column3 C18 3.0*30 mm 3 um, Mobile Phase: A: 5 mM $NH_4HCO_3$ in water; B: Acetonitrile, Flow Rate: 1.2 mL/min. Oven Temperature: 40 C, Gradient program (B %): 0.00/10.0, 1.80/50, 2.30/95, 2.90/95, 2.91/10

Method-AM (LCMS-10): Column: ZORBAX SB-Aq, 50*4.6 mm, 1.8 um, Mobile Phase: A: Water/0.05% TFA; B: Acetonitrile, Flow Rate: 1.5 mL/min. Oven Temperature: 40 C, Gradient program (B %): 0.01/5, 2.00/95, 2.80/95, 2.81/5.

Method-AN (LCMS-13): Column: Atlantis Premier BEH C18 AX, 4.6*50 mm, 2.5 um, Mobile Phase: A: Water/0.05% ammonia water; B: Acetonitrile, Flow Rate: 1.2 mL/min. Oven Temperature: 40 C, Gradient program (B %): 0.01/5, 0.50/40, 2.10/70, 2.50/95, 2.80/95, 2.81/5.

Method-AO (LCMS-24): Column: HALO C18, 30*3.0 mm, 2 um, Mobile Phase: A: Water/0.05% TFA; B: Acetonitrile, Flow Rate: 1.5 mL/min. Oven Temperature: 40 C, Gradient program (B %): 0.01/5, 0.30/40, 1.80/70, 2.20/95, 2.80/95, 2.81/5.

Method-AP (LCMS-13): Column: YMC-Triart C18, 50*3.0 mm, 3 um, Mobile Phase: A: Water/0.05% ammonia water; B: Acetonitrile, Flow Rate: 1.2 mL/min. Oven Temperature: 40 C, Gradient program (B %): 0.01/5, 0.50/65, 2.10/90, 2.60/95, 3.30/95, 3.31/5.

Method-AQ (LCMS-13): Column: YMC-Triart C18, 50*3.0 mm, 3 um, Mobile Phase: A: Water/0.05% ammonia water; B: Acetonitrile, Flow Rate: 1.2 mL/min. Oven Temperature: 40 C, Gradient program (B %): 0.01/5, 0.80/45, 3.60/75, 4.00/90, 4.80/95, 4.81/5.

Method-AR (LCMS-29): Column: Kinetex XB—C18, 30*3.0 mm, 1.7 um; Mobile Phase: A: Water/0.1% FA; B: Acetonitrile 0.07% FA, Flow Rate: 1.5 mL/min. Oven Temperature: 40 C, Gradient program (B %): 0.00/5.0, 1.50/95.0, 1.90/95.0, 1.91/5.0.

Method-AS (LCMS-10): Column: SB-Aq, 30*3.0 mm, 1.8 um, Mobile Phase: A: Water/0.05% TFA; B: Acetonitrile, Flow Rate: 1.5 mL/min. Oven Temperature: 40 C, Gradient program (B %): 0.01/5, 1.5/95, 1.9/95, 1.91/5

Method-AT (LCMS-13): Column: L-column3 C18, 50*3.0 mm, 3 um, Mobile Phase: A: Water/0.05% ammonia water; B: Acetonitrile, Flow Rate: 1.2 mL/min. Oven Temperature: 40 C, Gradient program (B %): 0.01/5, 0.80/50, 3.60/80, 4.00/95, 4.80/95, 4.81/5.

Method-AU (LCMS-24): Column: Xbridge BEH Phenyl, C18, 50*3.0 mm, 2.5 um; Mobile Phase: A: Water/0.05% TFA; B: Acetonitrile, Flow Rate: 1.5 mL/min. Oven Temperature: 40 C, Gradient program (B %): 0.01/5, 3.00/60, 4.00/95, 4.80/95, 4.81/5.

Method-AV (LCMS-13): Column: EVO C18, 50*3.0 mm, 2.6 um; Mobile Phase: A: Water/0.05% ammonia water; B: Acetonitrile, Flow Rate: 1.5 mL/min. Oven Temperature: 40 C, Gradient program (B %): 0.01/5, 2.00/95, 2.80/95, 2.81/5.

Method-AW (LCMS-10): Column: HALO C18, 30*3.0 mm, 2 um, Mobile Phase: A: Water/0.05% TFA; B: Acetonitrile, Flow Rate: 1.5 mL/min. Oven Temperature: 40 C, Gradient program (B %): 0.40/50, 3.20/80, 4.10/95, 4.80/95, 4.81/5.

Method-AX (LCMS-24): Column: Xselect CSH Fluoro-Phenyl, 50*3.0 mm, 2.5 um, Mobile Phase: A: Water/0.05% TFA; B: Acetonitrile/0.05% TFA, Flow Rate: 1.5 mL/min. Oven Temperature: 40 C, Gradient program (B %): 0.00/5, 0.40/20, 3.00/50, 4.00/95, 4.80/95, 4.81/5.

Chiral HPLC:

Method-A: CHIRALPAK IF-3, 50*4.6 mm, 3 um IF30CB—CP002; Mobile Phase: A: n-Hexane/DCM=5/1 B: IPA(0.1% DEA); Conc. Of Pump B: 30.0%; Flow rate: 1.0 ml/min; Column Temperature: 25 C.

Method-B: CHIRALPAK IH-3, 100*4.6 mm, 3 um IH30CC-BT002; Mobile Phase: A: n-Hexane/THF=4/1 B: MeOH; Conc. Of Pump B: 2.0%; Flow rate: 1.0 ml/min; Column Temperature: 25 C.

Method-C: CHIRALPAK IH-3, 50*4.6 mm, 3 um IH30CB—BX008; Mobile Phase: A: n-Hexane B: EtOH; Conc. Of Pump B: 20%; Flow rate: 1.0 ml/min; Column Temperature: 25 C.

Method-D: CHIRALPAK IG-3, 50*4.6 mm, 3 um IG30CB—BW008; Mobile Phase: A: n-Hexane/DCM=5/1 B: EtOH (0.1% MIPA); Conc. Of Pump B: 50%; Flow rate: 1.0 ml/min; Column Temperature: 25 C.

Method-E: Column: XA-RP-CHIRALPAK IB N-3 4.6*50 mm, 3 um; IBN3CC-XD006; Mobile Phase A: Water(0.05% TFA), Mobile Phase B: Acetonitrile, Conc. Of Pump B: 10.0%; Flow rate: 1.0 ml/min; Oven Temperature: 25 C.

Method-F: Column: CHIRALPAK IH-3, 50*4.6 mm, 3 μm 30CC—WHO04; Mobile Phase A: n-Hexane/THF=4/1, Mobile Phase B: MeOH (0.5% FA), Conc. Of Pump B: 5.0%; Flow rate: 1.0 ml/min; Oven Temperature: 25 C.

Method-G: Column: (R,R)-WHELK-01 100*4.6 mm, 3.5 um 71749; Mobile Phase A: n-Hexane/DCM=3/1, Mobile Phase B: EtOH (0.1% EDA), Conc. Of Pump B: 20.0%; Flow rate: 1.0 ml/min; Oven Temperature: 25 C.

Method-H: Column: CHIRALPAK IH-3, 100*4.6 mm, 3 um IH30CC-BT002; Mobile Phase A: n-Hexane/DCM=5/1, Mobile Phase B: EtOH, Conc. Of Pump B: 5.0%; Flow rate: 1.0 ml/min; Oven Temperature: 25 C.

Method-I (Chiral-HPLC): Column: CHIRALPAK IE-3, 50*4.6 mm, 3 um IE30CB—BV004; Mobile Phase A:

n-Hexane/DCM=3/1, Mobile Phase B: EtOH, Conc. Of Pump B: 5.0%; Flow rate: 1.0 ml/min; Oven Temperature: 25 C.

Chiral SFC:

Method-A: Column: CHIRALPAK IG-3, 50*3.0 mm, 3 um; Co-Solvent: MeOH/DCM=1/1 (20 mM NH3); Gradient (B): 10% to 50% in 2.0 min, hold 1.0 min at 50%. Flow rate: 3.0 ml/min; Column Temperature: 35 C.

Method-B: Column: (R,R)-WHELK CORE 50*3.0 mm, 2.7 um; Co-Solvent: MeOH/DCM=1/1 (10 mM NH3); Gradient (B): 10% to 50% in 2.0 min, hold 1.0 min at 50%. Flow rate: 3.0 ml/min; Column Temperature: 35 C.

Method-C: Column: CHIRALPAK IG-U, 50*3.0 mm, 1.6 um; Co-Solvent: MeOH/DCM=1/1 (20 mM NH3); Gradient (B): 10% to 50% in 2.0 min, hold 1.0 min at 50%. Flow rate: 3.0 ml/min; Column Temperature: 35 C.

Method-D: Column: Cellulose-SC 100×4.6 mm 3.0 um; Co-Solvent: MeOH+50% DCM+10 mM NH3; Gradient (B): 0.01/10, 2.50/50, 3.70/50, 3.71/10; Flow rate: 3.0 ml/min; Column Temperature: 40 C.

Method-E: Column: CHIRALPAK IA-U, 50*3 mm, 1.6 um; Co-Solvent: MeOH/DCM=1/1 (10 mM NH3); Gradient (B): 10% to 50% in 2.0 min, hold 1.0 min at 50%. Flow rate: 1.0 ml/min; Column Temperature: 35 C.

Method-F: Column: CHIRALPAK IH—U, 50*3 mm, 1.6 um; Co-Solvent: MeOH/DCM=1/1 (10 mM NH3); Gradient (B): 10% to 50% in 2.0 min, hold 1.0 min at 50%. Flow rate: 1.0 ml/min; Column Temperature: 35 C.

Method-G: Column: (R,R)-WHELK-01 CORE 50*4.6 mm, 3.5 um; Co-Solvent: MeOH/DCM=1/1 (20 mM NH3); Gradient (B): 10% to 50% in 2.5 min, hold 1.2 min at 50%. Flow rate: 3.0 ml/min; Column Temperature: 35 C.

Method-H: Column: CHIRALPAK IM-3, 50*3 mm, 3 um; Co-Solvent: IPA+50% Hex=20 mM NH3; Gradient (B): 10% to 50% in 2.0 min, hold 1.0 min at 50%. Flow rate: 3.0 ml/min; Column Temperature: 35 C.

Method-I: Column: CHIRALPAK IG-3, 50*3.0 mm, 3 um; Co-Solvent: IPA+50% Hex+20 mM NH3; Gradient (B): 10% to 50% in 2.0 min, hold 1.0 min at 50%. Flow rate: 3.0 ml/min; Column Temperature: 35 C.

1. Synthesis of rac-N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-3-(trifluoromethyl)benzamide intermediate

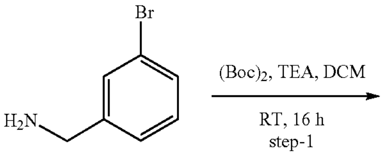

1

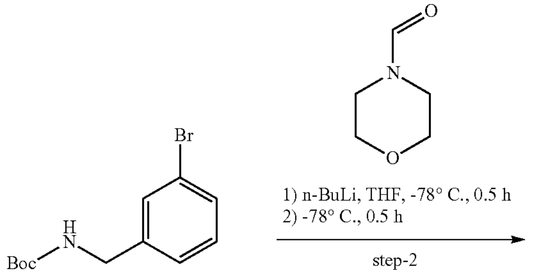

2

-continued

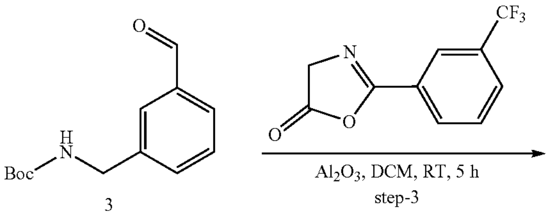

3

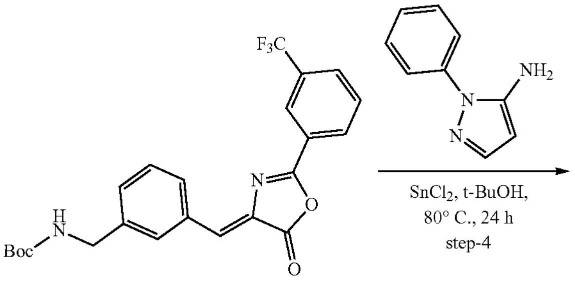

4

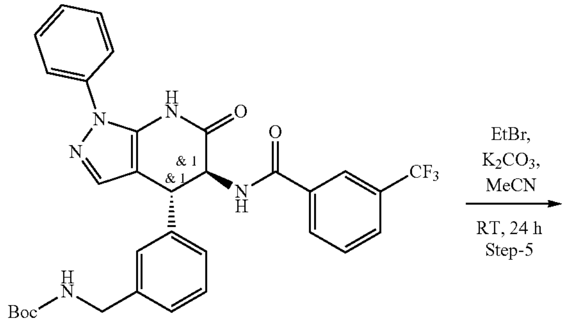

5

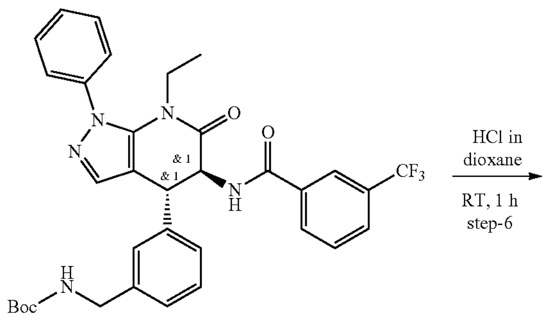

6

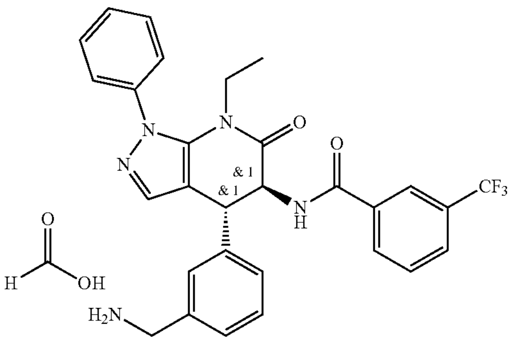

tert-butyl N-[(3-bromophenyl)methyl]carbamate (2)

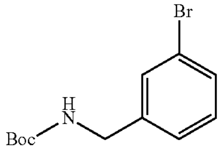 [SMILES: CC(C)(C)OC(=O)NCc1cccc(Br)c1]

A solution of 1-(3-bromophenyl)methanamine (70.0 g, 376 mmol, 1.00 equiv), TEA(79.2 g, 752 mmol, 2.00 equiv) in DCM (1000 mL) at 0° C., followed by the addition of $(Boc)_2O$ (90.3 g, 413 mmol, 1.10 equiv) dropwise at 0° C. The resulting mixture was stirred for 16 hours at room temperature. The reaction was quenched with water (200 mL) at 0° C. The resulting mixture was extracted with DCM (2×500 mL). The combined organic layers were washed with sat brine (200 mL), dried over anhydrous $Na_2SO_4$. After filtration, the filtrate was concentrated under reduced pressure. The residue was purified by silica gel column chromatography, eluted with ethyl acetate/petroleum ether (0-30%, 20 min) to afford tert-butyl N-[(3-bromophenyl) methyl]carbamate (90.0 g, 84%) as an off-white oil.

LCMS Calculated for $C_{12}H_{16}BrNO_2$: 285.04; Observed: 286.1 $[M+H]^+$.

tert-butyl (3-formylbenzyl)carbamate (3)

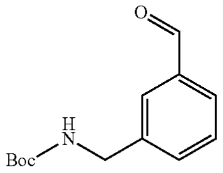 [SMILES: CC(C)(C)OC(=O)NCc1cccc(C=O)c1]

To a stirred solution of tert-butyl N-[(3-bromophenyl) methyl]carbamate (50.0 g, 175 mmol, 1.00 equiv) in THF (500 mL) was added n-BuLi (154 mL, 384 mmol, 2.10 equiv) dropwise at −78° C. under $N_2$. The resulting mixture was stirred for 0.5 hours at −78° C. under $N_2$. To the above mixture was added formyl morpholine (21.9 g, 190 mmol, 1.10 equiv in THF (100 mL), dropwise over 15 min at −78° C. The resulting mixture was stirred for additional 0.5 hour at −78° C. The reaction was quenched by the addition of water (500 ml), the mixture was adjusted pH-3-4 with 1N HCl. The resulting mixture was extracted with ethyl acetate (2×500 ml). The combined organic layers were washed with sat. brine (500 mL), dried over anhydrous $Na_2SO_4$. After filtration, the filtrate was concentrated under reduced pressure. The residue was purified by silica gel column chromatography, eluted with ethyl acetate/petroleum ether (0-50%, 20 min) to afford tert-butyl tert-butyl (3-formylbenzyl)carbamate (25.0 g, 61%) as a white solid.

tert-butyl (Z)-(3-((5-oxo-2-(3-(trifluoromethyl)phenyl)oxazol-4 (5H)-ylidene)methyl)benzyl)carbamate (4)

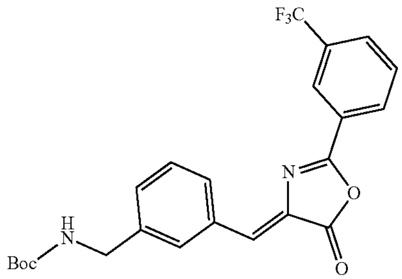 [SMILES: CC(C)(C)OC(=O)NCc1cccc(/C=C2\N=C(c3cccc(C(F)(F)F)c3)OC2=O)c1]

To a stirred solution of tert-butyl tert-butyl (3-formylbenzyl)carbamate (25.0 g, 106 mmol, 1.00 equiv) and 2-[3-(trifluoromethyl)phenyl]-4H-1,3-oxazol-5-one (48.7 g, 212 mmol, 2.00 equiv) in DCM (300 mL) was added $Al_2O_3$ (216 g, 2.12 mol, 20.0 equiv) in portions at room temperature. The resulting mixture was stirred for 5 hours at room temperature. The resulting mixture was filtered, the filter cake was washed with DCM (2×100 mL). The filtrate was concentrated under reduced pressure. To above residue was added n-hexane (100 mL), the precipitated solids were collected by filtration and washed with n-hexane (2×20 mL). This resulted in tert-butyl (Z)-(3-((5-oxo-2-(3-(trifluoromethyl)phenyl)oxazol-4 (5H)-ylidene)methyl)benzyl)carbamate (20.0 g, 38%) as a white solid.

LCMS Calculated for $C_{23}H_{21}F_3N_2O_4$: 446.15; Observed: 447.3 $[M+H]^+$.

rac-tert-butyl (3-((4R,5S)-6-oxo-1-phenyl-5-(3-(trifluoromethyl)benzamido)-4,5,6,7-tetrahydro-1H-pyrazolo[3,4-b]pyridin-4-yl)benzyl)carbamate (5)

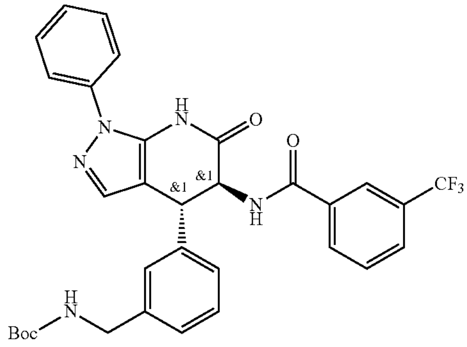 [SMILES: CC(C)(C)OC(=O)NCc1cccc([C@@H]2c3cnn(-c4ccccc4)c3NC(=O)[C@H]2NC(=O)c2cccc(C(F)(F)F)c2)c1]

A solution of tert-butyl (Z)-(3-((5-oxo-2-(3-(trifluoromethyl)phenyl)oxazol-4 (5H)-ylidene)methyl)benzyl)carbamate (20.0 g, 44.8 mmol, 1.00 equiv), 1-phenyl-1H-pyrazol-5-amine(10.7 g, 67.2 mmol, 1.5 equiv), $SnCl_2$ (0.847 g, 0.045 mmol, 0.10 equiv) in t-BuOH (300 mL) at room temperature. The resulting mixture was stirred for 24 hours at 80° C. The resulting mixture was concentrated under vacuum. The residue was purified by silica gel column chromatography, eluted with ethyl acetate/DCM (0-30%, 30 min) to afford rac-tert-butyl (3-((4R,5S)-6-oxo-1-phenyl-5-(3-(trifluoromethyl)benzamido)-4,5,6,7-tetrahydro-1H-pyrazolo[3,4-b]pyridin-4-yl)benzyl)carbamate (20.0 g, 70%) as a yellow solid.

LCMS Calculated for $C_{32}H_{30}F_3N_5O_4$: 605.22; Observed: 606.3 $[M+H]^+$.

rac-tert-butyl (3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)carbamate (6)

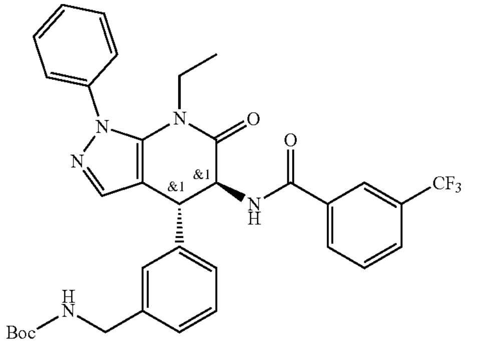 [SMILES: CCN1C(=O)[C@@H](NC(=O)c2cccc(C(F)(F)F)c2)[C@H](c2cccc(CNC(=O)OC(C)(C)C)c2)c2cnn(-c3ccccc3)c21]

A solution of rac-tert-butyl (3-((4R,5S)-6-oxo-1-phenyl-5-(3-(trifluoromethyl)benzamido)-4,5,6,7-tetrahydro-1H-pyrazolo[3,4-b]pyridin-4-yl)benzyl)carbamate (270 mg, 0.426 mmol, 1.00 equiv) in MeCN (5.0 mL) was added $K_2CO_3$ (6.85 g, 49.5 mmol, 1.50 equiv), bromoethane (10.8 g, 99.0 mmol, 3.00 equiv) at room temperature. The resulting mixture was stirred for 24 hours at room temperature. The resulting mixture was filtered, the filter cake was washed with MeCN (2×10 mL). The residue was purified by reversed-phase flash chromatography with the following conditions: column, C18 silica gel; mobile phase, water (0.1% $NH_3 \cdot H_2O$) in (MeCN:MeOH=1:1), 30% to 100% gradient in 20 min; detector, UV 254 nm. This resulted in rac-tert-butyl (3-((4R,5S)-7-ethyl-6-oxo-1-phenyl-5-(3-(trifluoromethyl)benzamido)-4,5,6,7-tetrahydro-1H-pyrazolo [3,4-b]pyridin-4-yl)benzyl)carbamate (12.7 g, 55%) as white solid.

LCMS Calculated for $C_{34}H_{34}F_3N_5O_4$: 633.26; Observed: 634.4 $[M+H]^+$.

rac-N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-3-(trifluoromethyl)benzamide

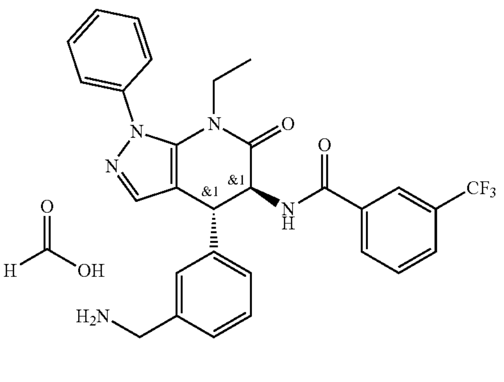

A solution of tert-butyl N-((3-[(4R,5S)-7-ethyl-6-oxo-1-phenyl-5-[3-(trifluoromethyl)benzamido]-4H,5H-pyrazolo [3,4-b]pyridin-4-yl]phenylmethyl)carbamate (2.60 g, 4.10 mmol, 1.00 equiv) 4M HCl in 1,4-dioxane (50.0 mL). The resulting mixture was stirred for 1.0 hour at room temperature. The resulting mixture was concentrated under reduced pressure. The residue was purified by Pre-HPLC (0.01% formic acid solution). This resulted in rac-N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-3-(trifluoromethyl)benzamide (2.0 g, 85%) as white solid.

LCMS Calculated for $C_{29}H_{26}F_3N_5O_2$: 579.21; Observed (Method-AJ): 534.1 $[M-HCOOH+H]^+$, 99.6% at RT 1.583 min.

$^1H$ NMR (300 MHz, DMSO-$d_6$) δ 9.07 (d, J=8.9 Hz, 1H), 8.36 (s, 1H), 8.05 (d, J=9.3 Hz, 2H), 7.91 (d, J=7.8 Hz, 1H), 7.76-7.50 (m, 6H), 7.46 (s, 1H), 7.37-7.27 (m, 3H), 7.10 (s, 1H), 5.18 (dd, J=12.9, 8.9 Hz, 1H), 4.42 (d, J=12.8 Hz, 1H), 3.92-3.78 (m, 1H), 3.07 (dq, J=13.8, 6.8 Hz, 1H), 0.83 (t, J=7.0 Hz, 3H).

2. Synthesis of tert-butyl (3-((4S,5R)-7-ethyl-6-oxo-1-phenyl-5-(3-(trifluoromethyl)benzamido)-4,5,6,7-tetrahydro-1H-pyrazolo[3,4-b]pyridin-4-yl)benzyl) carbamate & tert-butyl (3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl) carbamate

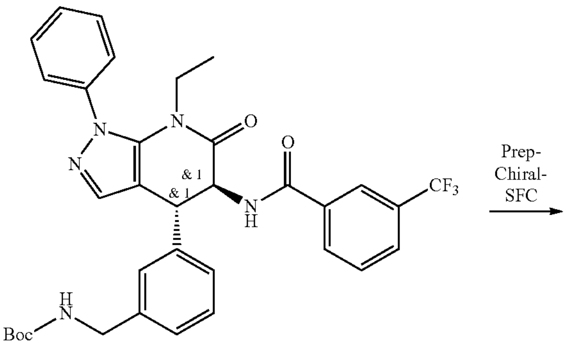

6

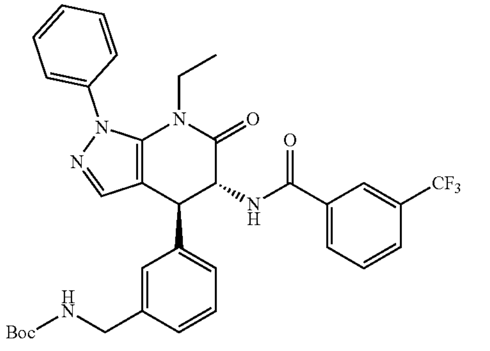 [SMILES: CCN1C(=O)[C@H](NC(=O)c2cccc(C(F)(F)F)c2)[C@@H](c2cccc(CNC(=O)OC(C)(C)C)c2)c2cnn(-c3ccccc3)c21]

+

-continued

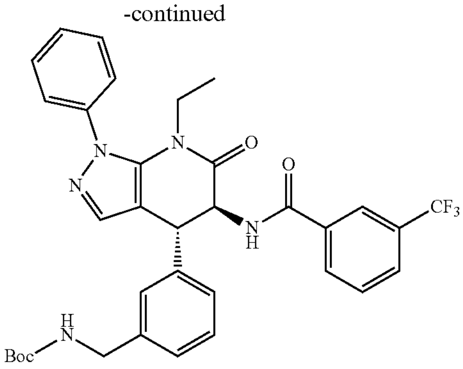

The crude product rac-tert-butyl (3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)carbamate (7.00 g, 10.5 mmol, 1.0 equiv) was purified by CHIRAL-SFC flash with the following conditions (Column: XA-CHIRAL ART Cellulose-SC, 3*25 cm Sum; Mobile Phase A: $CO_2$, Mobile Phase B: MEOH:DCM=2:1 (0.1% 2M $NH_3$-MeOH); Flow rate: 80 mL/min; Gradient: isocratic 25% B; Column Temperature (° C.): 35; Back Pressure(bar): 100; Wave Length: 220 nm; RT1 (min): 3.8; RT2 (min): 4.6; Sample Solvent: MeOH:DCM=2:1; Injection Volume: 1 mL) to afford tert-butyl (3-((4S,5R)-7-ethyl-6-oxo-1-phenyl-5-(3-(trifluoromethyl)benzamido)-4,5,6,7-tetrahydro-1H-pyrazolo[3,4-b]pyridin-4-yl)benzyl)carbamate (2.60 g, 38.8%) and tert-butyl (3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)carbamate (2.50 g, 38.0%) as a white solid.

The following intermediate compounds were accordingly prepared:

| | |
|---|---|
| 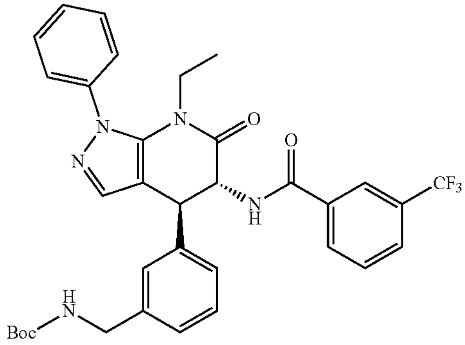 | $^1$H NMR (300 MHz, DMSO-$d_6$) δ 9.01 (d, J = 9.0 Hz, 1H), 8.09-8.01 (m, 2H), 7.91 (dd, J = 7.7, 1.7 Hz, 1H), 7.75-7.49 (m, 6H), 7.36-7.26 (m, 4H), 7.17-7.10 (m, 1H), 7.05 (s, 1H), 5.16 (dd, J = 12.8, 8.9 Hz, 1H), 4.41 (d, J = 12.8 Hz, 1H), 4.10 (d, J = 6.1 Hz, 2H), 3.84 (dq, J = 14.2, 7.1 Hz, 1H), 3.08 (dq, J = 13.8, 6.8 Hz, 1H), 1.37 (s, 9H), 0.83 (t, J = 7.0 Hz, 3H); 99.3 % at RT 2.04 min. LCMS Calculated for $C_{34}H_{34}F_3N_5O_4$: 633.26; Observed (Method-AR): 634.5 [M + H]$^+$, 99.3% at RT 2.046 min. Chiral SFC (Method-A): 99.8% at RT 1.221 min. |
| 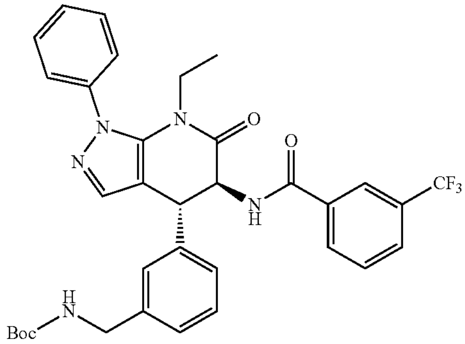 [SMILES: CCN1C(=O)[C@@H](NC(=O)c2cccc(C(F)(F)F)c2)[C@H](c2cccc(CNC(=O)OC(C)(C)C)c2)c2cnn(-c3ccccc3)c21] | $^1$H NMR (300 MHz, DMSO-$d_6$) δ 9.01 (d, J = 8.9 Hz, 1H), 8.09-8.01 (m, 2H), 7.91 (d, J = 7.8 Hz, 1H), 7.76-7.50 (m, 6H), 7.36-7.26 (m, 4H), 7.17-7.10 (m, 1H), 7.05 (s, 1H), 5.16 (dd, J= 12.8, 8.9 Hz, 1H), 4.41 (d, J = 12.8 Hz, 1H), 4.14-4.05 (m, 2H), 3.83 (dq, J = 14.2, 7.0 Hz, 1H), 3.08 (dq, J = 13.8, 6.8 Hz, 1H), 1.37 (s, 9H), 0.83 (t, J = 7.0 Hz, 3H); 99.3 % at RT 2.05 min. LCMS Calculated for $C_{34}H_{34}F_3N_5O_4$: 633.26; Observed (Method-AR): 634.5 [M + H]$^+$, 99.8% at RT 2.044 min. Chiral SFC (Method-A): 98.4% at RT 1.336 min. |
| 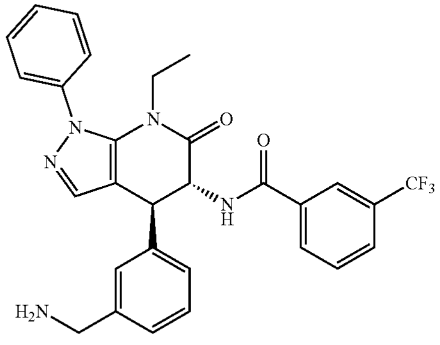 [SMILES: CCN1C(=O)[C@H](NC(=O)c2cccc(C(F)(F)F)c2)[C@@H](c2cccc(CN)c2)c2cnn(-c3ccccc3)c21] | $^1$H NMR (300 MHz, DMSO-$d_6$) δ 9.09 (d, J = 9.0 Hz, 1H), 8.07 (d, J = 7.8 Hz, 2H), 7.92 (d, J = 7.8 Hz, 1H), 7.72 (t, J = 7.8 Hz, 1H), 7.68-7.50 (m, 6H), 7.50-7.33 (m, 3H), 7.13 (s, 1H), 5.19 (dd, J = 12.9, 9.0 Hz, 1H), 4.47 (d, J = 12.9 Hz, 1H), 4.00 (q, J = 6.0 Hz, 2H), 3.86 (dq, J = 14.2, 7.1 Hz, 1H), 3.07 (dq, J = 13.8, 6.8 Hz, 1H), 0.84 (t, J = 7.0 Hz, 3H); LCMS Calculated for $C_{29}H_{26}F_3N_5O_2$: 533.20; Observed (Method-E): 534.5 [M + H]$^+$, 98.9% at 1.235 min. Optical rotation: a = +138, (c = 0.08 g/100 mL in MeOH, T = 25° C.) |

-continued

| | |
|---|---|
| 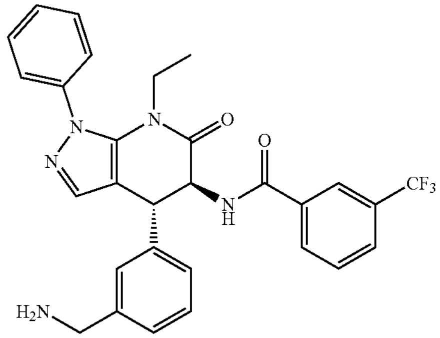 [SMILES: CCN1C(=O)[C@@H](NC(=O)c2cccc(C(F)(F)F)c2)[C@H](c2cccc(CN)c2)c2cnn(-c3ccccc3)c21] | $^1$H NMR (300 MHz, DMSO-$d_6$) δ 9.11 (d, J = 8.9 Hz, 1H), 8.07 (d, J = 7.1 Hz, 2H), 7.92 (d, J = 7.8 Hz, 1H), 7.72 (t, J = 7.9 Hz, 1H), 7.68-7.63 (m, 2H), 7.60 (dd, J = 8.5, 6.4 Hz, 2H), 7.57-7.50 (m, 1H), 7.48-7.36 (m, 3H), 7.13 (s, 1H), 5.19 (dd, J = 12.9, 8.9 Hz, 1H), 4.48 (d, J = 12.9 Hz, 1H), 3.99 (q, J = 6.1 Hz, 2H), 3.85 (dq, J = 14.2, 7.1 Hz, 1H), 3.07 (dq, J = 13.9, 6.8 Hz, 1H), 0.84 (t, J = 7.0 Hz, 3H); 99.5 % at RT 1.23 min. LCMS Calculated for $C_{29}H_{26}F_3N_5O_2$: 533.20; Observed (Method-E): 534.5 $[M + H]^+$, 99.5% at RT 1.231 min. Optical rotation: a = −129, (c = 0.08 g/100 mL in MeOH, T = 25° C.) |

3. Synthesis of rac-N-((4R,5S)-4-(2-(aminomethyl) phenyl)-7-ethyl-6-oxo-1-phenyl-4,5,6,7-tetrahydro-1H-pyrazolo[3,4-b]pyridin-5-yl)-3-(trifluoromethyl) benzamide

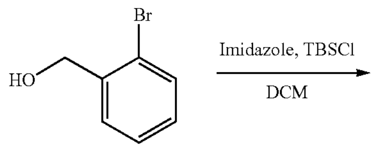

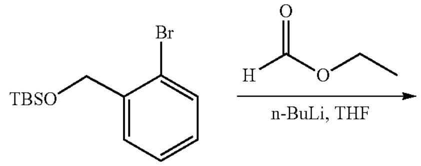

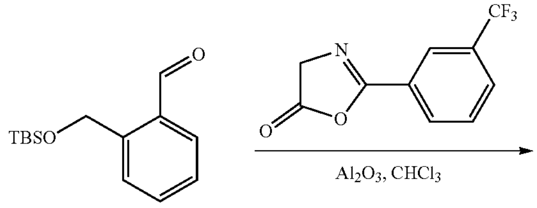

8

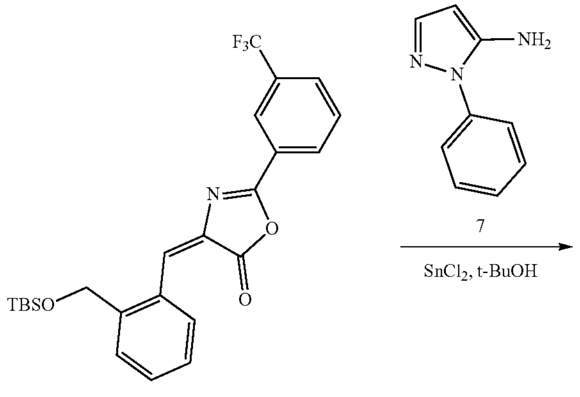

9

-continued

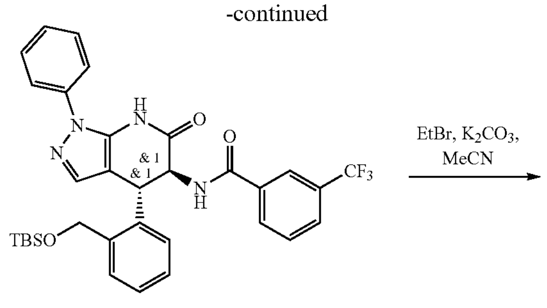

10

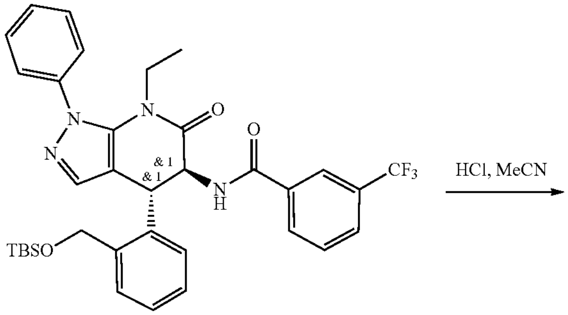

11

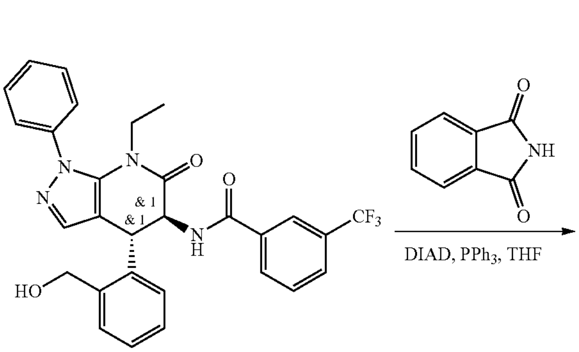

12

-continued

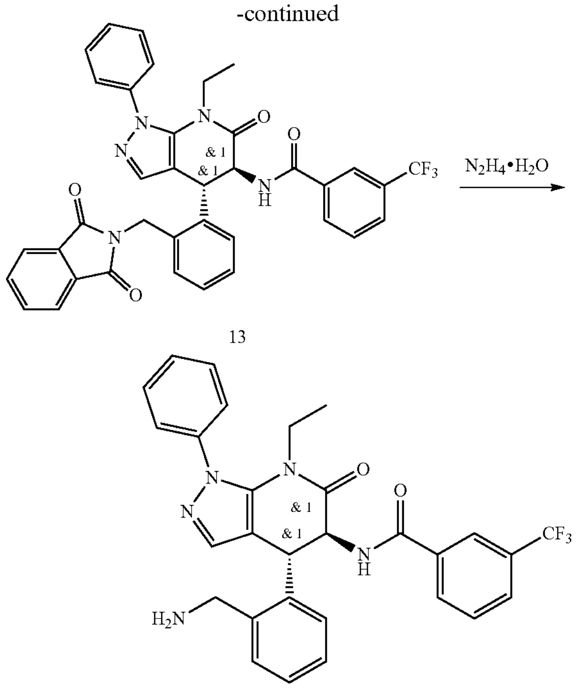

13

(2-bromobenzyl)oxy)(tert-butyl)dimethylsilane (7)

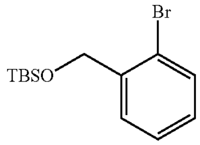 [SMILES: CC(C)(C)[Si](C)(C)OCc1ccccc1Br]

A solution of (2-bromophenyl)methanol (50.0 g, 267 mmol, 1.00 equiv) in DCM (500 mL) was treated with imidazole (27.3 g, 401 mmol, 1.50 equiv) for 0.5 h at 0° C. followed by the addition of TBSCl (48.4 g, 321 mmol, 1.20 equiv). The mixture was stirred for 2 h at 0° C. under $N_2$ atmosphere. The resulting mixture were washed with water (500 mL). The organic layer was dried over anhydrous $Na_2SO_4$. After filtration, the filtrate was concentrated under reduced pressure. The residue was purified by silica gel column chromatography, eluted with petroleum ether: ethyl acetate (10:1) to afford ((2-bromobenzyl)oxy)(tert-butyl) dimethylsilane (60 g, 74%) as a colorless oil.

2-(((tert-butyldimethylsilyl)oxy)methyl)benzaldehyde (8)

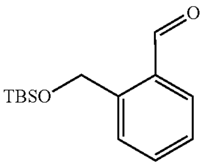 [SMILES: CC(C)(C)[Si](C)(C)OCc1ccccc1C=O]

To a stirred solution of ((2-bromobenzyl)oxy)(tert-butyl) dimethylsilane (60 g, 199 mmol, 1.00 equiv) in THF (600 mL) was added n-BuLi (96 mL, 38.3 mmol) dropwise at −78° C. under nitrogen atmosphere. The mixture was stirred for 1 h at −78° C. To the mixture was added ethyl formate (17.7 g, 239 mmol, 1.20 equiv) dropwise over 10 min at −78° C. The resulting mixture was stirred for additional 1 h at −78° C. The reaction was quenched by the addition of water (500 mL) at room temperature. The resulting mixture was extracted with EtOAc (2*500 mL). The combined organic layers were washed with brine (500 mL), dried over anhydrous $Na_2SO_4$. After filtration, the filtrate was concentrated under reduced pressure. The residue was purified by silica gel column chromatography, eluted with PE/EA (5:1) to afford 2-(((tert-butyldimethylsilyl)oxy)methyl)benzaldehyde (30 g, 60%) as a colorless oil.

(E)-4-(2-(((tert-butyldimethylsilyl)oxy)methyl)benzylidene)-2-(3-(trifluoromethyl)phenyl)oxazol-5 (4H)-one (9)

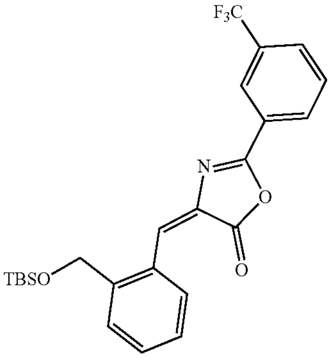 [SMILES: CC(C)(C)[Si](C)(C)OCc1ccccc1/C=C1/N=C(c2cccc(C(F)(F)F)c2)OC1=O]

A solution of 2-(((tert-butyldimethylsilyl)oxy)methyl) benzaldehyde (30 g, 120 mmol, 1.00 equiv), 2-(3-(trifluoromethyl)phenyl)oxazol-5 (4H)-one (27.4 g, 120 mmol, 1.00 equiv) and $AlCl_3$ (244 g, 2.40 mol, 20.0 equiv) in $CHCl_3$ (300 mL) was stirred for 4 h at room temperature. The resulting mixture was filtered, the filter cake was washed with $CHCl_3$ (50 mL). The filtrate was concentrated under reduced pressure. The product was precipitated by the addition of hexane (50 mL). The precipitated solids were collected by filtration and washed with hexane (10 mL). The crude product (E)-4-(2-(((tert-butyldimethylsilyl)oxy) methyl)benzylidene)-2-(3-(trifluoromethyl)phenyl)oxazol-5 (4H)-one (12 g, 21.70%) as a yellow solid, which was used in the next step directly without further purification.

LCMS Calculated for $C_{24}H_{26}F_3NO_3Si$: 461.16; Observed: 462.2 $[M+H]^+$.

rac-N-((4R,5S)-4-(2-(((tert-butyldimethylsilyl)oxy)methyl)phenyl)-6-oxo-1-phenyl-4,5,6,7-tetrahydro-1H-pyrazolo[3,4-b]pyridin-5-yl)-3-(trifluoromethyl)benzamide (10)

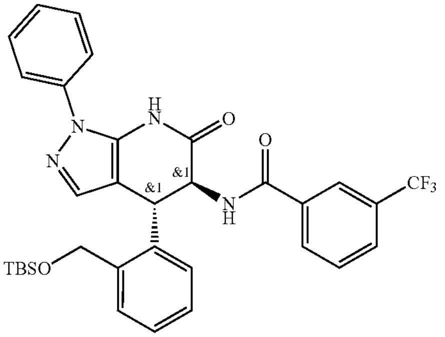 [SMILES: CC(C)(C)[Si](C)(C)OCc1ccccc1[C@@H]1c2cnn(-c3ccccc3)c2NC(=O)[C@H]1NC(=O)c1cccc(C(F)(F)F)c1]

A solution of (E)-4-(2-(((tert-butyldimethylsilyl)oxy)methyl)benzylidene)-2-(3-(trifluoromethyl)phenyl)oxazol-5(4H)-one (5.00 g, 10.8 mmol, 1.00 equiv), 1-phenyl-1H-pyrazol-5-amine (2.59 g, 16.3 mmol, 1.50 equiv) and $SnCl_2$ (0.21 g, 1.09 mmol, 0.10 equiv) in t-BuOH (50 mL) was stirred for 48 hours at 80° C. The resulting mixture was concentrated under reduced pressure. The residue was purified by silica gel column chromatography, eluted with ethyl acetate/petroleum ether (1:1) to afford rac-N-((4R,5S)-4-(2-(((tert-butyldimethylsilyl)oxy)methyl)phenyl)-6-oxo-1-phenyl-4,5,6,7-tetrahydro-1H-pyrazolo[3,4-b]pyridin-5-yl)-3-(trifluoromethyl)benzamide (2 g, 29%) as a yellow solid.

LCMS Calculated for $C_{33}H_{35}F_3N_4O_3Si$: 620.24; Observed: 621.2 $[M+H]^+$.

rac-N-((4R,5S)-4-(2-(((tert-butyldimethylsilyl)oxy)methyl)phenyl)-7-ethyl-6-oxo-1-phenyl-4,5,6,7-tetrahydro-1H-pyrazolo[3,4-b]pyridin-5-yl)-3-(trifluoromethyl)benzamide (11)

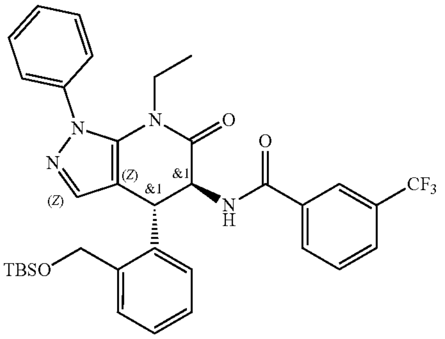 [SMILES: CCN1C(=O)[C@@H](NC(=O)c2cccc(C(F)(F)F)c2)[C@H](c2ccccc2CO[Si](C)(C)C(C)(C)C)c2cnn(-c3ccccc3)c21]

A solution of rac-N-((4R,5S)-4-(2-(((tert-butyldimethylsilyl)oxy)methyl)phenyl)-6-oxo-1-phenyl-4,5,6,7-tetrahydro-1H-pyrazolo[3,4-b]pyridin-5-yl)-3-(trifluoromethyl)benzamide (2.00 g, 3.22 mmol, 1.00 equiv) and $K_2CO_3$ (1.26 g, 3.87 mmol, 1.20 equiv) in MeCN (20 mL) was stirred for 10 min at 0° C. To the above mixture was added bromoethane (0.70 g, 6.44 mmol, 2.00 equiv) dropwise over 5 min at 0° C. The resulting mixture was stirred 16 hour at room temperature. The resulting mixture was concentrated under reduced pressure. The residue was purified by silica gel column chromatography, eluted with petroleum ether: ethyl acetate (3:1) to afford rac-N-((4R,5S)-4-(2-(((tert-butyldimethylsilyl)oxy)methyl)phenyl)-7-ethyl-6-oxo-1-phenyl-4,5,6,7-tetrahydro-1H-pyrazolo[3,4-b]pyridin-5-yl)-3-(trifluoromethyl)benzamide (1.5 g, 71%) as a yellow solid.

LCMS Calculated for $C_{35}H_{39}F_3N_4O_3Si$: 648.27; Observed: 649.3 $[M+H]^+$.

rac-N-((4R,5S)-7-ethyl-4-(2-(hydroxymethyl)phenyl)-6-oxo-1-phenyl-4,5,6,7-tetrahydro-1H-pyrazolo[3,4-b]pyridin-5-yl)-3-(trifluoromethyl)benzamide (12)

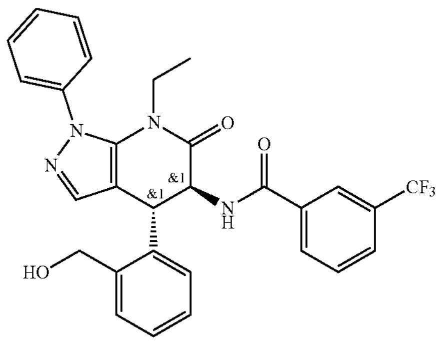 [SMILES: CCN1C(=O)[C@@H](NC(=O)c2cccc(C(F)(F)F)c2)[C@H](c2ccccc2CO)c2cnn(-c3ccccc3)c21]

A solution of rac-N-((4R,5S)-4-(2-(((tert-butyldimethylsilyl)oxy)methyl)phenyl)-7-ethyl-6-oxo-1-phenyl-4,5,6,7-tetrahydro-1H-pyrazolo[3,4-b]pyridin-5-yl)-3-(trifluoromethyl)benzamide (1.50 g, 2.31 mmol, 1.00 equiv) in conc HCl (1.5 mL) and MeCN (15 mL) was stirred for 16 hours at room temperature under air atmosphere. The resulting mixture was concentrated under reduced pressure. The residue was purified by silica gel column chromatography, eluted with ethyl acetate/petroleum ether (1:1) to afford rac-N-((4R,5S)-7-ethyl-4-(2-(hydroxymethyl)phenyl)-6-oxo-1-phenyl-4,5,6,7-tetrahydro-1H-pyrazolo[3,4-b]pyridin-5-yl)-3-(trifluoromethyl)benzamide (1.1 g, 89%) as a yellow solid.

LCMS Calculated for $C_{29}H_{25}F_3N_4O_3$: 534.19; Observed: 535.3 $[M+H]^+$.

rac-N-((4R,5S)-4-(2-((1,3-dioxoisoindolin-2-yl)methyl)phenyl)-7-ethyl-6-oxo-1-phenyl-4,5,6,7-tetrahydro-1H-pyrazolo[3,4-b]pyridin-5-yl)-3-(trifluoromethyl)benzamide (13)

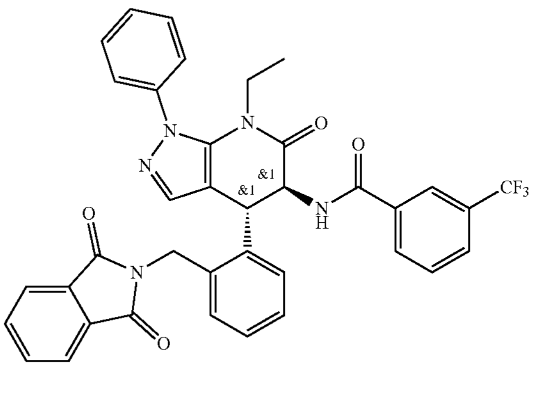 [SMILES: CCN1C(=O)[C@@H](NC(=O)c2cccc(C(F)(F)F)c2)[C@H](c2ccccc2CN2C(=O)c3ccccc3C2=O)c2cnn(-c3ccccc3)c21]

A solution of rac-N-((4R,5S)-7-ethyl-4-(2-(hydroxymethyl)phenyl)-6-oxo-1-phenyl-4,5,6,7-tetrahydro-1H-pyrazolo[3,4-b]pyridin-5-yl)-3-(trifluoromethyl)benzamide (1.10 g, 2.06 mmol, 1.00 equiv), isoindoline-1,3-dione (0.36 g, 2.47 mmol, 1.20 equiv) and $PPh_3$ (0.81 g, 3.09 mmol, 1.50 equiv) in THE (12 mL) was stirred for 1 h at 0° C. under nitrogen atmosphere. To the above mixture was added DIAD (0.62 g, 3.09 mmol, 1.50 equiv) dropwise over 5 minutes at 0° C. The resulting mixture was stirred overnight at room temperature. The resulting mixture was concentrated under reduced pressure. The residue was purified by silica gel column chromatography, eluted with ethyl acetate/petroleum ether (1:1) to afford rac-N-((4R,5S)-4-(2-((1,3-dioxoisoindolin-2-yl)methyl)phenyl)-7-ethyl-6-oxo-1-phenyl-4,5,6,7-tetrahydro-1H-pyrazolo[3,4-b]pyridin-5-yl)-3-(trifluoromethyl)benzamide (0.9 g, 65.%) as a yellow solid.

LCMS Calculated for: $C_{37}H_{28}F_3N_5O_4$: 663.21; Observed: 664.2 $[M+H]^+$.

rac-N-((4R,5S)-4-(2-(aminomethyl)phenyl)-7-ethyl-6-oxo-1-phenyl-4,5,6,7-tetrahydro-1H-pyrazolo[3,4-b]pyridin-5-yl)-3-(trifluoromethyl)benzamide

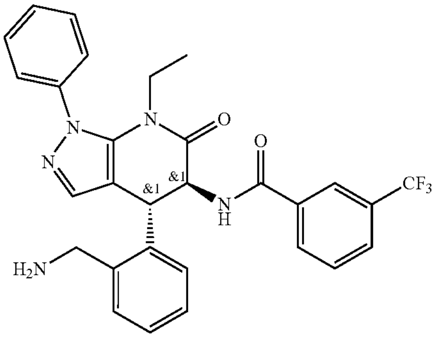 [SMILES: CCN1C(=O)[C@@H](NC(=O)c2cccc(C(F)(F)F)c2)[C@H](c2ccccc2CN)c2cnn(-c3ccccc3)c21]

A solution of rac-N-((4R,5S)-4-(2-((1,3-dioxoisoindolin-2-yl)methyl)phenyl)-7-ethyl-6-oxo-1-phenyl-4,5,6,7-tetrahydro-1H-pyrazolo[3,4-b]pyridin-5-yl)-3-(trifluoromethyl) benzamide (900 mg, 1.36 mmol, 1.00 equiv) and $N_2H_4H_2O$ (272 mg, 5.42 mmol, 4.00 equiv) in MeOH (10 mL) was stirred overnight at room temperature under air atmosphere. To the above mixture was added DCM (100 mL), the resulting mixture was washed with water (100 mL) and brine (100 mL). The organic layer was dried over anhydrous $Na_2SO_4$. After filtration, the filtrate was concentrated under reduced pressure. The residue was purified by prep-HPLC ($NH_3H_2O$ buffer) to afford rac-N-((4R,5S)-4-(2-(aminomethyl)phenyl)-7-ethyl-6-oxo-1-phenyl-4,5,6,7-tetrahydro-1H-pyrazolo[3,4-b]pyridin-5-yl)-3-(trifluoromethyl)benzamide (650 mg, 89%) as a white solid.

$^1H$ NMR (300 MHz, DMSO-$d_6$) δ 9.69 (d, J=7.9 Hz, 1H), 8.80-7.93 (m, 2H), 7.88 (d, J=7.9 Hz, 1H), 7.71-7.61 (m, 3H), 7.60-7.48 (m, 3H), 7.39 (d, J=7.5 Hz, 1H), 7.32 (d, J=7.3 Hz, 1H), 7.28-7.15 (m, 2H), 6.88 (s, 1H), 5.28-5.14 (m, 1H), 4.76-4.65 (m, 1H), 3.88 (d, J=6.5 Hz, 2H), 3.85-3.73 (m, 1H), 3.13-2.99 (m, 1H), 0.82 (t, J=6.9 Hz, 3H).

LCMS Calculated for $C_{29}H_{26}F_3N_5O_2$: 533.20; Observed (Method-E): 534.4 $[M+H]^+$, 97.2% at RT 1.269 min.

4. Synthesis of N-(3-((4S,5R)-7-ethyl-3-methyl-6-oxo-1-phenyl-5-(3-(trifluoromethyl)benzamido)-4,5,6,7-tetrahydro-1H-pyrazolo[3,4-b]pyridin-4-yl)benzyl)-1-methyl-2,5-dihydro-1H-pyrrole-3-carboxamide I-362. Compound 17 was Prepared According to tert-butyl (3-((4S,5R)-7-ethyl-6-oxo-1-phenyl-5-(3-(trifluoromethyl)benzamido)-4,5,6,7-tetrahydro-1H-pyrazolo[3,4-b]pyridin-4-yl)benzyl) carbamate

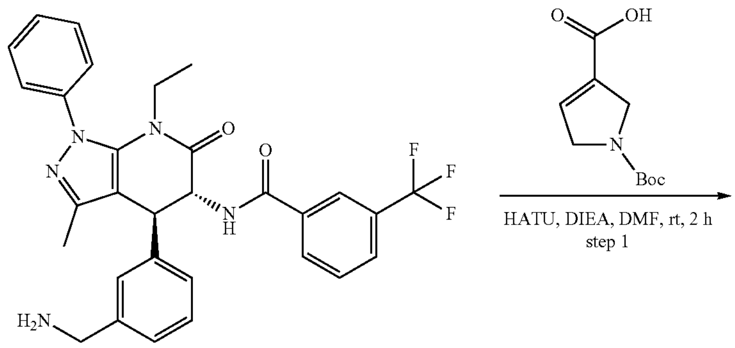

17

-continued
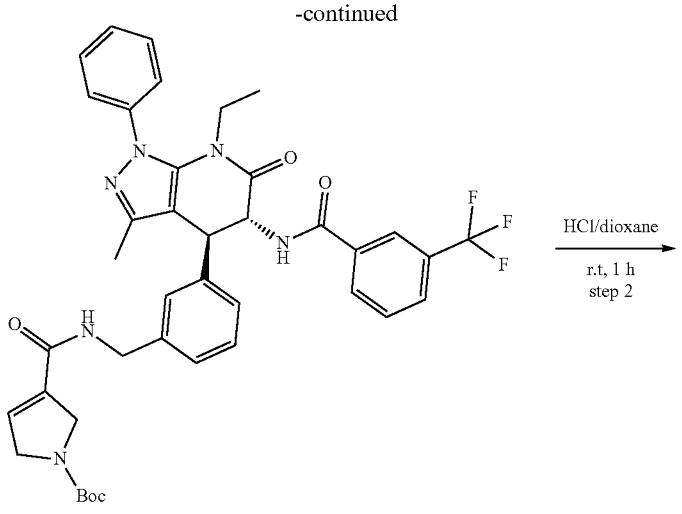
18
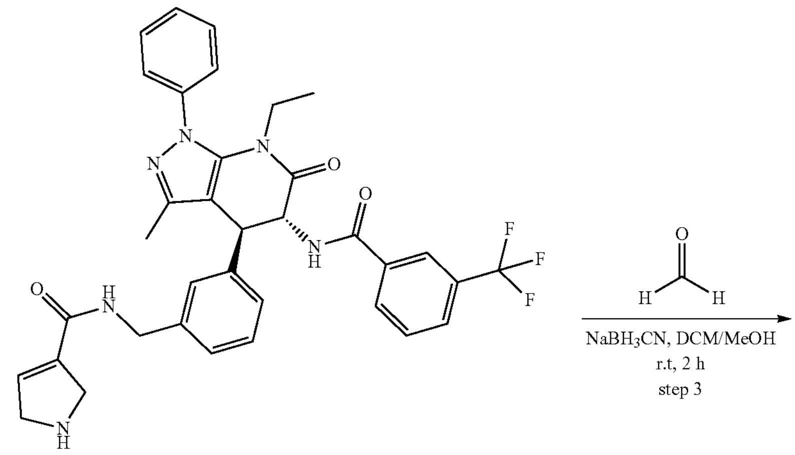
19
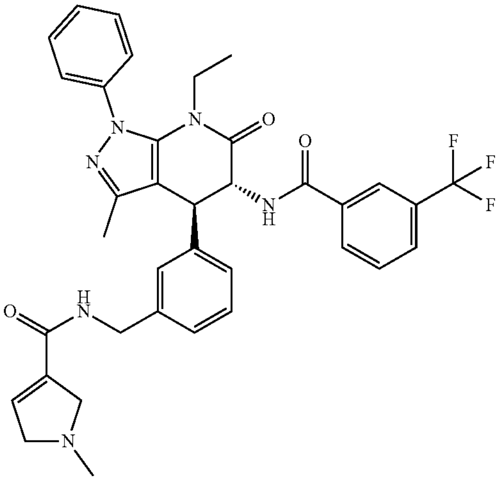
I-362 tert-butyl 3-((3-((4S,5R)-7-ethyl-3-methyl-6-oxo-1-phenyl-5-(3-(trifluoromethyl)benzamido)-4,5,6,7-tetrahydro-1H-pyrazolo[3,4-b]pyridin-4-yl)benzyl) carbamoyl)-2,5-dihydro-1H-pyrrole-1-carboxylate (18)

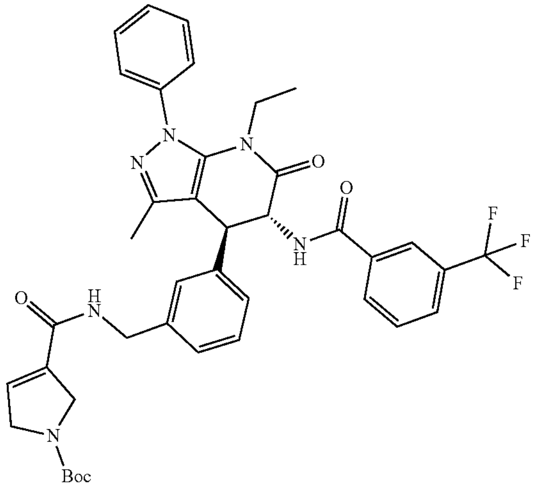 [SMILES: CCN1C(=O)[C@H](NC(=O)c2cccc(C(F)(F)F)c2)[C@@H](c2cccc(CNC(=O)C3=CCN(C(=O)OC(C)(C)C)C3)c2)c2c(C)nn(-c3ccccc3)c21]

Into a 8 mL vial were added N-((4S,5R)-4-(3-(aminomethyl)phenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (150 mg, 0.274 mmol, 1.00 equiv), 1-(tert-butoxycarbonyl)-2,5-dihydro-1H-pyrrole-3-carboxylic acid (58.4 mg, 0.274 mmol, 1.00 equiv), DIEA (106 mg, 0.822 mmol, 3.00 equiv) and HATU (125 mg, 0.329 mmol, 1.20 equiv) in DMF (2 mL) at room temperature. The mixture was stirred at room temperature for 2 hour. The reaction was purified by Column: XBridge Prep RP C18 Column, 30*150 mm, 5 m; Mobile Phase A: Water(10 mmol/L $NH_{40}H$), Mobile Phase B: ACN; Flow rate: 35 mL/min; Gradient: 36% B to 56% B in 10 min; Wave Length: 254 nm/220 nm; RT1 (min): 6.82. This resulted in tert-butyl 3-((3-((4S,5R)-7-ethyl-3-methyl-6-oxo-1-phenyl-5-(3-(trifluoromethyl) benzamido)-4,5,6,7-tetrahydro-1H-pyrazolo[3,4-b]pyridin-4-yl)benzyl)carbamoyl)-2,5-dihydro-1H-pyrrole-1-carboxylate (200 mg, 94.5%) as a white solid.

LCMS Calculated for $C_{40}H_{41}F_3N_6O_5$: 742.31; Observed: 743.22 $[M+H]^+$.

N-(3-((4S,5R)-7-ethyl-3-methyl-6-oxo-1-phenyl-5-(3-(trifluoromethyl)benzamido)-4,5,6,7-tetrahydro-1H-pyrazolo[3,4-b]pyridin-4-yl)benzyl)-2,5-dihydro-1H-pyrrole-3-carboxamide (19)

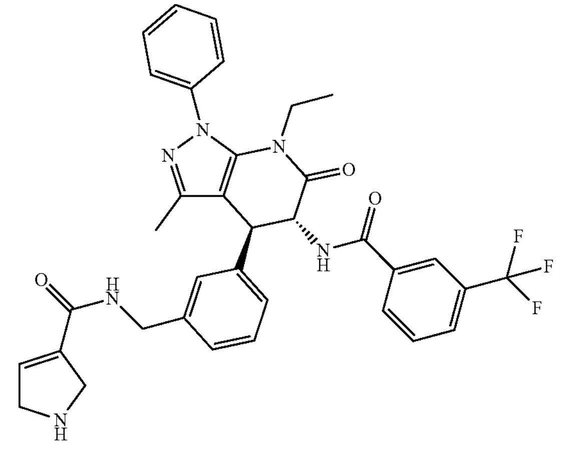 [SMILES: CCN1C(=O)[C@H](NC(=O)c2cccc(C(F)(F)F)c2)[C@@H](c2cccc(CNC(=O)C3=CCNC3)c2)c2c(C)nn(-c3ccccc3)c21]

A solution of tert-butyl 3-((3-((4S,5R)-7-ethyl-3-methyl-6-oxo-1-phenyl-5-(3-(trifluoromethyl)benzamido)-4,5,6,7-tetrahydro-1H-pyrazolo[3,4-b]pyridin-4-yl)benzyl)carbamoyl)-2,5-dihydro-1H-pyrrole-1-carboxylate (100 mg, 0.135 mmol, 1.00 equiv) 4M HCl in 1,4-dioxane (2 mL) at room temperature. The reaction mixture was stirred for 1 hour at room temperature. The resulting mixture was concentrated in vacuum to afford N-(3-((4S,5R)-7-ethyl-3-methyl-6-oxo-1-phenyl-5-(3-(trifluoromethyl)benzamido)-4,5,6,7-tetrahydro-1H-pyrazolo[3,4-b]pyridin-4-yl)benzyl)-2,5-dihydro-1H-pyrrole-3-carboxamide (80 mg, 86.1%) as a white solid, which was used for next step directly.

LCMS Calculated for $C_{35}H_{33}F_3N_6O_3$: 642.26; Observed: 643.11 $[M+H]^+$.

N-(3-((4S,5R)-7-ethyl-3-methyl-6-oxo-1-phenyl-5-(3-(trifluoromethyl)benzamido)-4,5,6,7-tetrahydro-1H-pyrazolo[3,4-b]pyridin-4-yl)benzyl)-1-methyl-2,5-dihydro-1H-pyrrole-3-carboxamide I-362

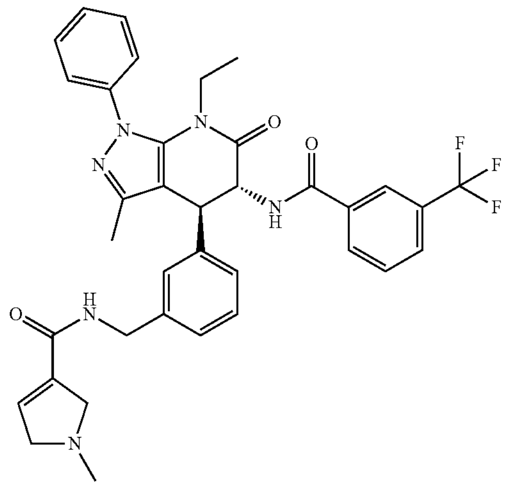 [SMILES: CCN1C(=O)[C@H](NC(=O)c2cccc(C(F)(F)F)c2)[C@@H](c2cccc(CNC(=O)C3=CCN(C)C3)c2)c2c(C)nn(-c3ccccc3)c21]

Into a 8 mL vial were added N-(3-((4S,5R)-7-ethyl-3-methyl-6-oxo-1-phenyl-5-(3-(trifluoromethyl)benzamido)-4,5,6,7-tetrahydro-1H-pyrazolo[3,4-b]pyridin-4-yl)benzyl)-2,5-dihydro-1H-pyrrole-3-carboxamide (80 mg, 0.124 mmol, 1.00 equiv), formaldehyde (4.49 mg, 0.149 mmol, 1.20 equiv), $NaBH_3CN$ (23.47 mg, 0.372 mmol, 3.00 equiv) in DCM (1 mL) and MeOH (1 mL) at room temperature. And react at room temperature for 1 hour. The reaction was purified by Column: Uitimate-AQ-C18 Column, 50*250 mm, 10 m; Mobile Phase A: Water (0.1% FA), Mobile Phase B: ACN; Flow rate: 90 mL/min; Gradient: isocratic 10%-60% 12 min; Wave Length: 254 nm/220 nm nm; RT1 (min): 11. This resulted in the desired compound (15 mg, 17.4%) as a white solid.

$^1$H NMR (400 MHz, DMSO-$d_6$) δ 9.02 (d, J=8.8 Hz, 1H), 8.45 (t, J=6.2 Hz, 1H), 8.07-7.99 (m, 2H), 7.91 (d, J=7.7 Hz, 1H), 7.74-7.61 (m, 3H), 7.60-7.48 (m, 3H), 7.34-7.22 (m, 3H), 7.15 (d, J=7.3 Hz, 1H), 6.47 (s, 1H), 5.21 (dd, J=11.8, 8.8 Hz, 1H), 4.35 (d, J=11.7 Hz, 1H), 4.30 (d, J=6.1 Hz, 2H), 3.79-3.70 (m, 1H), 3.50 (s, 4H), 3.18-3.08 (m, 1H), 2.34 (s, 3H), 1.45 (s, 3H), 0.81 (t, J=7.0 Hz, 3H).

LCMS Calculated for $C_{36}H_{35}F_3N_6O_3$: 656.27; Observed (Method-B): 657.2 $[M+H]^+$, 95.09% at RT 0.905 min.

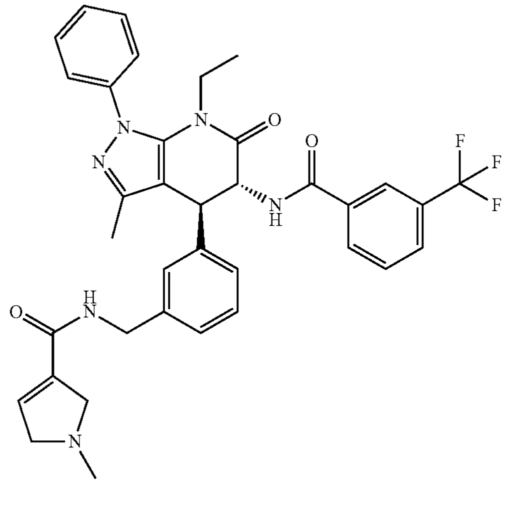 [SMILES: CCN1C(=O)[C@H](NC(=O)c2cccc(C(F)(F)F)c2)[C@@H](c2cccc(CNC(=O)C3=CCN(C)C3)c2)c2c(C)nn(-c3ccccc3)c21]

I-362

$^1$H NMR (400 MHz, DMSO-$d_6$) δ 9.02 (d, J = 8.8 Hz, 1H), 8.45 (t, J = 6.2 Hz, 1H), 8.07-7.99 (m, 2H), 7.91 (d, J = 7.7 Hz, 1H), 7.74-7.61 (m, 3H), 7.60-7.48 (m, 3H), 7.34-7.22 (m, 3H), 7.15 (d, J = 7.3 Hz, 1H), 6.47 (s, 1H), 5.21 (dd, J = 11.8, 8.8 Hz, 1H), 4.35 (d, J = 11.7 Hz, 1H), 4.30 (d, J = 6.1 Hz, 2H), 3.79-3.70 (m, 1H), 3.50 (s, 4H), 3.18-3.08 (m, 1H), 2.34 (s, 3H), 1.45 (s, 3H), 0.81 (t, J = 7.0 Hz, 3H).
LCMS Calculated for $C_{36}H_{35}F_3N_6O_3$: 656.27; Observed (Method-B): 657.2 $[M + H]^+$, 95.09% at RT 0.905 min.

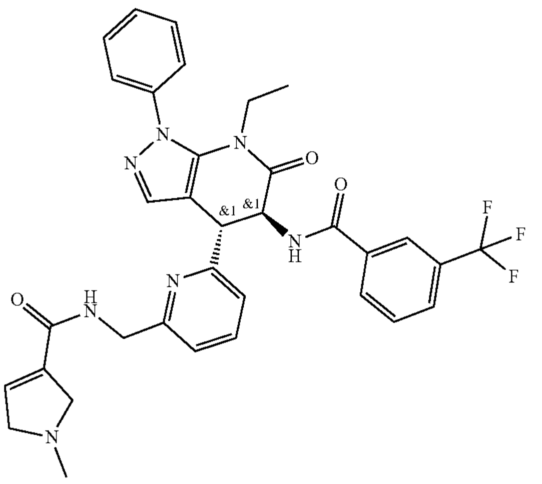 [SMILES: CCN1C(=O)[C@@H](NC(=O)c2cccc(C(F)(F)F)c2)[C@H](c2cccc(CNC(=O)C3=CCN(C)C3)n2)c2cnn(-c3ccccc3)c21]

I-348

$^1$H NMR (400 MHz, DMSO-$d_6$) δ 9.00 (d, J = 9.0 Hz, 1H), 8.64 (t, J = 6.0 Hz, 1H), 8.09-8.00 (m, 2H), 7.91 (d, J = 7.8 Hz, 1H), 7.75-7.69 (m, 1H), 7.68-7.64 (m, 2H), 7.62-7.51 (m, 3H), 7.35-7.25 (m, 3H), 7.18-7.12 (m, 2H), 7.04 (s, 1H), 5.88 (s, 1H), 5.53 (s, 1H), 5.18 (dd, J = 12.8, 8.9 Hz, 1H), 4.40 (d, J = 12.8 Hz, 1H), 4.31 (d, J = 6.0 Hz, 2H), 3.90-3.77 (m, 2H), 3.55 (s, 3H), 3.13-3.00 (m, 1H), 0.83 (t, J = 7.0 Hz, 3H).
LCMS Calculated for $C_{34}H_{32}F_3N_7O_3$: 643.25; Observed (Method-AJ): 644.3 $[M + H]^+$, 95.1% at RT 1.137 min.

-continued

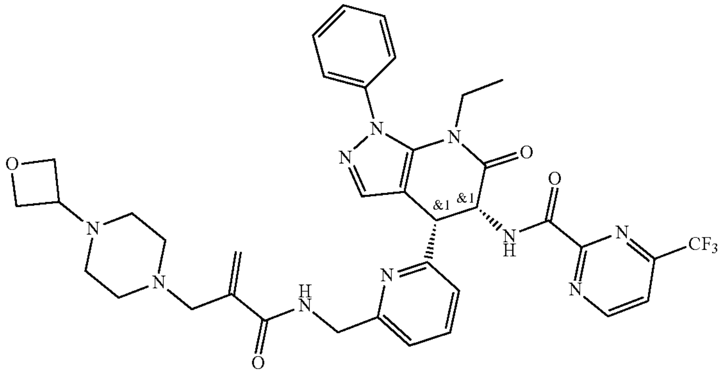 [SMILES: C=C(CN1CCN(C2COC2)CC1)C(=O)NCc1cccc([C@@H]2c3cnn(-c4ccccc4)c3N(CC)C(=O)[C@@H]2NC(=O)c2nccc(C(F)(F)F)n2)n1]

I-386

$^1$H NMR (400 MHz, DMSO-$d_6$) δ 9.31 (d, J = 5.0 Hz, 1H), 8.98 (d, J = 6.8 Hz, 1H), 8.93 (t, J = 5.8 Hz, 1H), 8.25 (d, J = 5.0 Hz, 1H), 7.71 (d, J = 5.5 Hz, 1H), 7.67 (d, J = 7.6 Hz, 1H), 7.65-7.42 (m, 5H), 7.21-7.10 (m, 2H), 5.89 (s, 1H), 5.45 (s, 1H), 5.36 (t, J = 6.7 Hz, 1H), 4.86 (d, J = 6.5 Hz, 1H), 4.48 (q, J = 6.3 Hz, 2H), 4.40-4.19 (m, 4H), 3.95-3.78 (m, 1H), 3.28 (d, J = 6.6 Hz, 1H), 3.21 (s, 2H), 3.06-2.90 (m, 1H), 2.39 (s, 4H), 2.15 (s, 4H), 0.79 (t, J = 7.0 Hz, 3H).
LCMS Calculated for $C_{37}H_{39}F_3N_{10}O_4$: 744.31; Observed (Method-V): 745.4 [M + H]$^+$, 96.2% at RT 1.434 min.

5. Synthesis of N-((4R,5S)-7-ethyl-4-(3-((2-methylene-3-(2-oxa-6-azaspiro[3.3]heptan-6-yl)butanamido)methyl)phenyl)-6-oxo-1-phenyl-4,5,6,7-tetrahydro-1H-pyrazolo[3,4-b]pyridin-5-yl)-4-(trifluoromethyl)pyrimidine-2-carboxamide I-221 & N-((4R,5R)-7-ethyl-4-(3-((2-methylene-3-(2-oxa-6-azaspiro[3.3]heptan-6-yl)butanamido)methyl)phenyl)-6-oxo-1-phenyl-4,5,6,7-tetrahydro-1H-pyrazolo[3,4-b]pyridin-5-yl)-4-(trifluoromethyl)pyrimidine-2-carboxamide I-377'

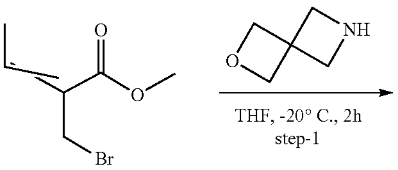

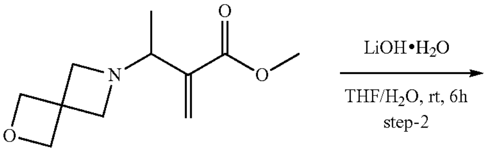

20

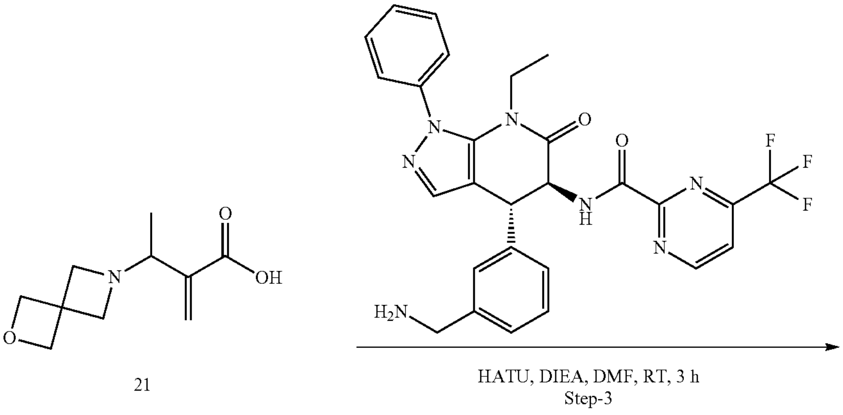

21

-continued

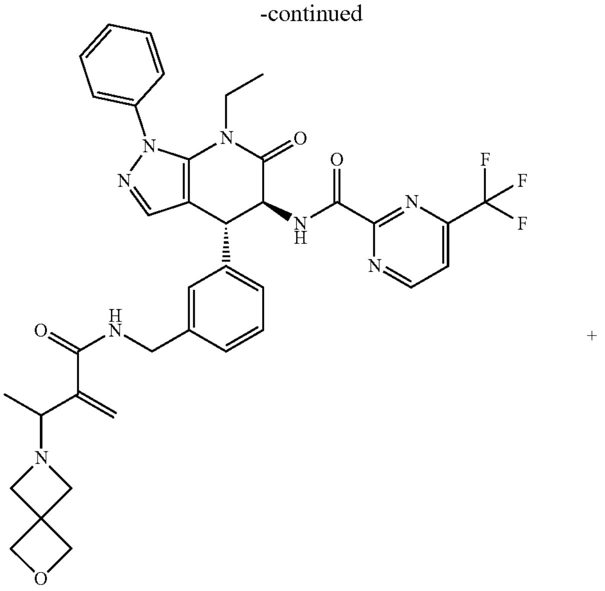

I-221

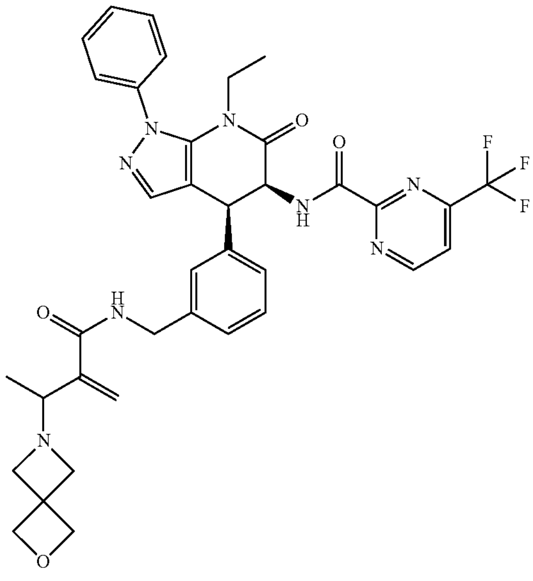

I-377'

Methyl 2-methylene-3-(2-oxa-6-azaspiro[3.3]heptan-6-yl)butanoate (20)

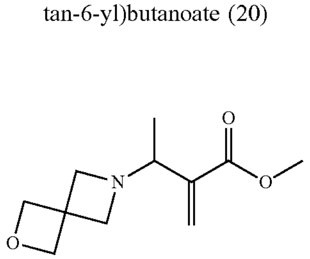

To a solution of methyl methyl 2-(bromomethyl)but-2-enoate (1.00 g, 5.18 mmol, 1.00 equiv) in THF (20 mL) was added 2-oxa-6-azaspiro[3.3]heptane (0.620 g, 6.22 mmol, 1.20 equiv) at −20° C. The mixture was stirred at −20° C. for 5 h. The reaction was quenched by the addition of water (15 mL) at −20° C. The mixture was basified to pH 8 with $Na_2CO_3$ aqueous. The resulting mixture was extracted with ethyl acetate (3×10 mL). The combined organic layers were washed with brine (2×15 mL), dried over $Na_2SO_4$. After filtration, the filtrate was concentrated under reduced pressure. The residue was purified by silica gel column chromatography, eluted with ethyl acetate/petroleum ether (0%~100%) to afford methyl 2-methylidene-3-(2-oxa-6-azaspiro[3.3]heptan-6-ylbutanoate (200 mg, 18.28%) as a colorless oil.

LCMS Calculated for $C_{11}H_{17}NO_3$: 211.12; Observed: 212.26 $[M+H]^+$.

2-methylene-3-(2-oxa-6-azaspiro[3.3]heptan-6-yl) butanoic acid (21)

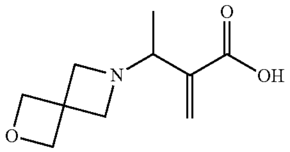

To a stirred solution of methyl 2-methylidene-3-(2-oxa-6-azaspiro[3.3]heptan-6-ylbutanoate (100 mg, 0.473 mmol, 1.00 equiv) in $H_2O$ (0.5 mL)/THF (1.5 mL)/MeOH (0.5 mL) was added $LiOH·H_2O$ (79.5 mg, 1.89 mmol, 4.00 equiv). The reaction mixture was stirred at room temperature for a period of 3 h. After completion of reaction, the reaction mixture was concentrated under reduced pressure to give crude 2-methylidene-3-(2-oxa-6-azaspiro[3.3]heptan-6-ylbutanoic acid (140 mg) which was used for next step directly.

N-((4R,5S)-7-ethyl-4-(3-((2-methylene-3-(2-oxa-6-azaspiro[3.3]heptan-6-yl)butanamido)methyl)phenyl)-6-oxo-1-phenyl-4,5,6,7-tetrahydro-1H-pyrazolo[3,4-b]pyridin-5-yl)-4-(trifluoromethyl)pyrimidine-2-carboxamide I-388 & N-((4R,5R)-7-ethyl-4-(3-((2-methylene-3-(2-oxa-6-azaspiro[3.3]heptan-6-yl)butanamido)methyl)phenyl)-6-oxo-1-phenyl-4,5,6,7-tetrahydro-1H-pyrazolo[3,4-b]pyridin-5-yl)-4-(trifluoromethyl)pyrimidine-2-carboxamide I-377

I-388

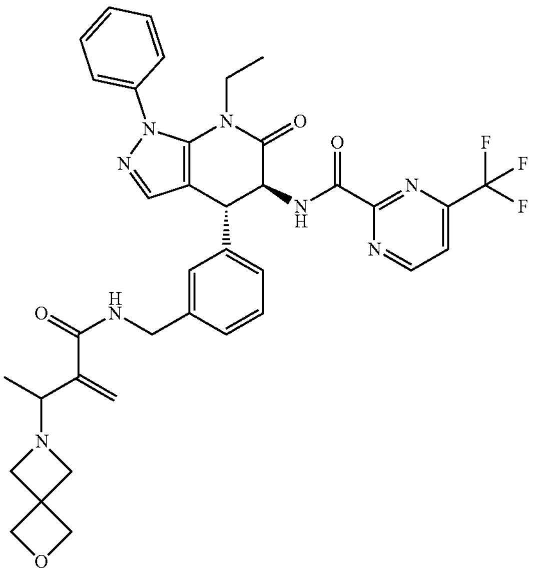 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N1CC2(COC2)C1]

-continued

I-377

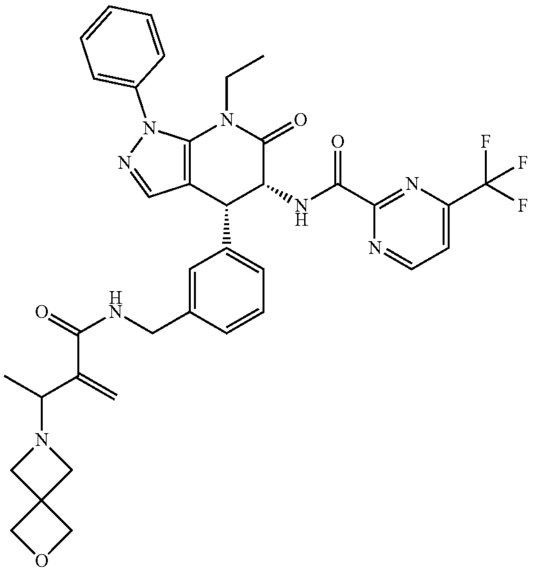

To a stirred solution of N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (168 mg, 0.314 mmol, 1.00 equiv) and 2-methylidene-3-(2-oxa-6-azaspiro[3.3]heptan-6-ylbutanoic acid (61.8 mg, 0.314 mmol, 1.00 equiv) in DMF (3 mL) was added HBTU (143 mg, 0.377 mmol, 1.20 equiv) and DIEA at room temperature. The resulting mixture was stirred for additional 2 h at room temperature. The reaction was quenched with water at room temperature. The resulting mixture was purified by reversed-phase flash chromatography with the following conditions: column, C18 silica gel; mobile phase, MeCN in Water (0.1% $NH_3·H_2O$), 10% to 90% gradient in 10 min; detector, UV 254 nm. This resulted in N-((4R,5S)-7-ethyl-4-(3-((2-methylene-3-(2-oxa-6-azaspiro[3.3]heptan-6-yl)butanamido)methyl)phenyl)-6-oxo-1-phenyl-4,5,6,7-tetrahydro-1H-pyrazolo[3,4-b]pyridin-5-yl)-4-(trifluoromethyl)pyrimidine-2-carboxamide I-388 (14.8 mg, 6.38%) as a white solid and N-((4R,5R)-7-ethyl-4-(3-((2-methylene-3-(2-oxa-6-azaspiro[3.3]heptan-6-yl)butanamido)methyl)phenyl)-6-oxo-1-phenyl-4,5,6,7-tetrahydro-1H-pyrazolo[3,4-b]pyri din-5-yl)-4-(trifluoromethyl)pyrimidine-2-carboxamide I-377 (18.3 mg 7.6%) as a white solid.

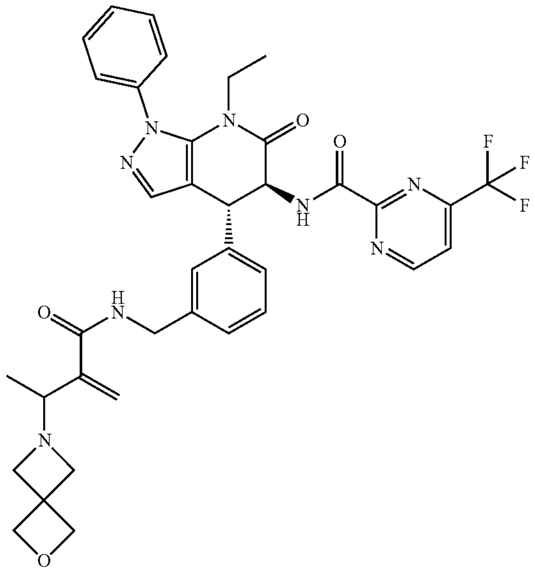

I-221

$^{1}$H NMR (400 MHz, DMSO-$d_6$) δ 9.38-9.26 (m, 2H), 9.02 (d, J = 5.2 Hz, 1H), 8.21 (d, J = 5.1 Hz, 1H), 7.65 (d, J = 7.8 Hz, 2H), 7.61-7.50 (m, 3H), 7.29 (d, J = 2.7 Hz, 3H), 7.13 (d, J = 6.1 Hz, 1H), 6.96 (s, 1H), 5.76-5.69 (m, 1H), 5.38 (s, 1H), 5.20 (dd, J = 12.7, 9.2 Hz, 1H), 4.64 (d, J = 12.7 Hz, 1H), 4.48 (qd, J = 6.6, 3.4 Hz, 4H), 4.40-4.19 (m, 2H), 3.83 (dt, J = 14.5, 7.2 Hz, 1H), 3.17 (t, J = 5.4 Hz, 4H), 3.11-3.05 (m, 2H), 0.93 (dd, J = 6.6, 2.1 Hz, 3H), 0.82 (t, J = 7.0 Hz, 3H).
LCMS Calculated for $C_{37}H_{37}F_3N_8O_4$: 714.29; Observed (Method-D): 715.3 [M + H]$^+$, 96.6% at RT 3.529 min.

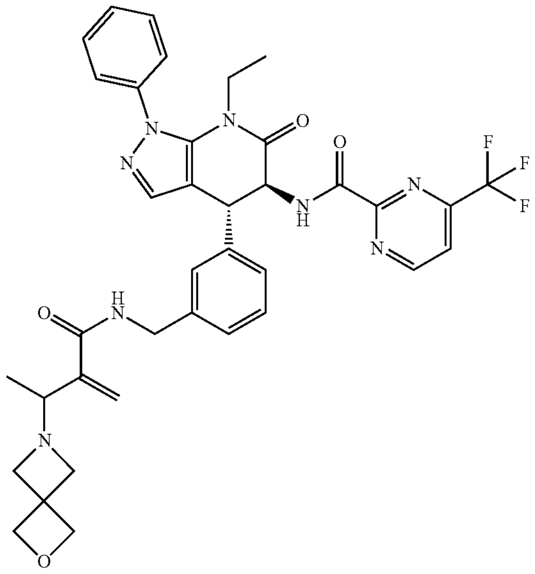 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N1CC2(COC2)C1]

I-377

$^{1}$H NMR (400 MHz, DMSO-$d_6$) δ 9.43-9.23 (m, 2H), 9.00 (d, J = 4.9 Hz, 1H), 8.22 (d, J = 5.1 Hz, 1H), 7.73-7.47 (m, 5H), 7.29 (d, J = 3.2 Hz, 3H), 7.13 (s, 1H), 6.97 (s, 1H), 5.75-5.70 (m, 1H), 5.38 (s, 1H), 5.20 (dd, J = 12.7, 9.3 Hz, 1H), 4.65 (d, J = 12.7 Hz, 1H), 4.49 (qd, J = 6.6, 3.3 Hz, 4H), 4.40-4.22 (m, 2H), 3.85 (dd, J = 14.2, 7.1 Hz, 1H), 3.23-3.12 (m, 4H), 3.12-2.91 (m, 2H), 0.93 (dd, J = 6.5, 2.2 Hz, 3H), 0.83 (t, J = 7.0 Hz, 3H).
LCMS Calculated for $C_{37}H_{37}F_3N_8O_4$: 714.29; Observed (Method-D): 715.3 [M + H]$^+$, 93.1% at RT 2.653 min.

6. Synthesis of N-(rac-(4R,5S)-4-(3-((S)-2-cyano-4,4-difluoropyrrolidine-1-carbonyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide I-379

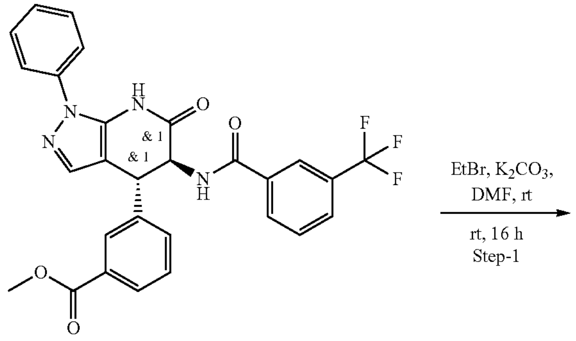

22

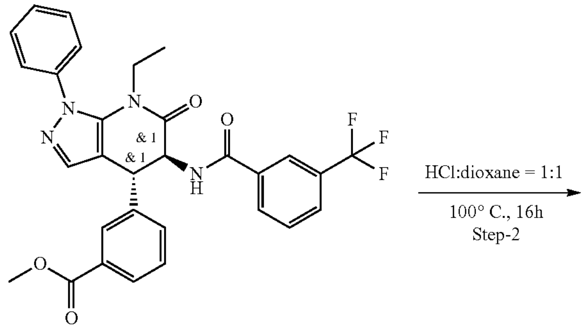

23

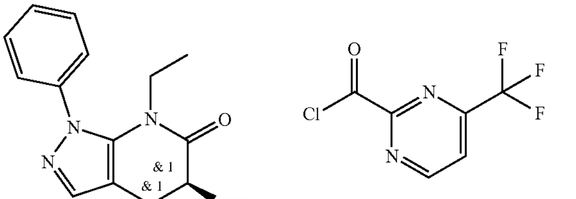

4

24

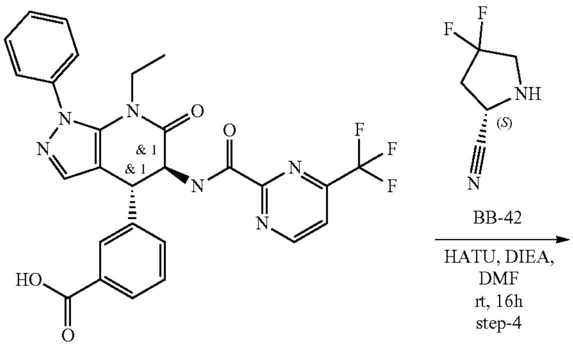

BB-42

25

-continued

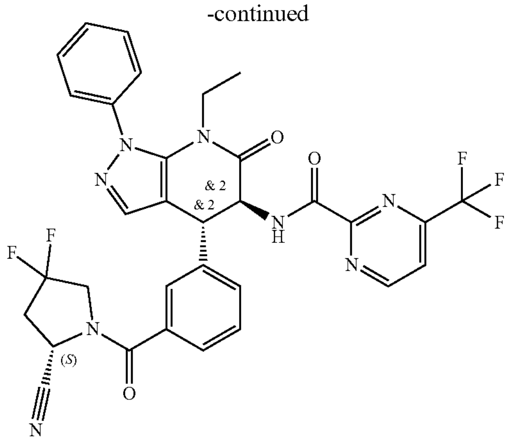

I-379

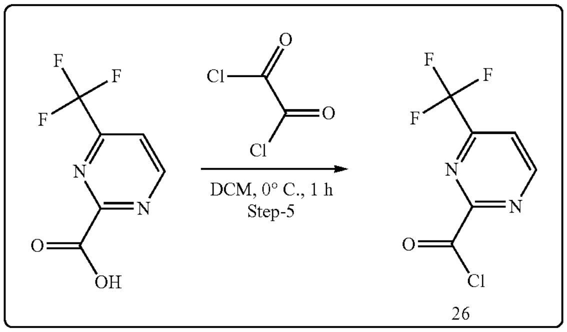

26 rac-methyl 3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzoate (23)

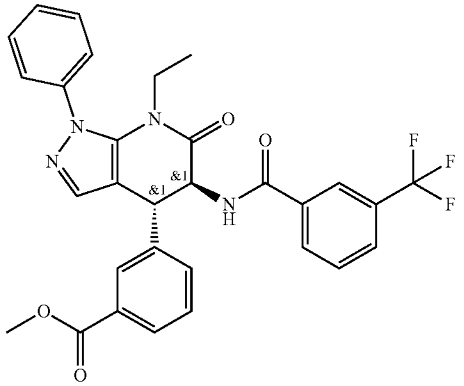 [SMILES: CCN1C(=O)[C@@H](NC(=O)c2cccc(C(F)(F)F)c2)[C@H](c2cccc(C(=O)OC)c2)c2cnn(-c3ccccc3)c21]

Into a 40-mL sealed tube, were placed rac-methyl 3-((4R,5S)-6-oxo-1-phenyl-5-(3-(trifluoromethyl)benzamido)-4,5,6,7-tetrahydro-1H-pyrazolo[3,4-b]pyridin-4-yl)benzoate (2.00 g, 3.74 mmol, 1.00 equiv), bromoethane (0.82 g, 7.48 mmol, 2.00 equiv), $K_2CO_3$ (1.03 g, 7.48 mmol, 2.00 equiv) and DMF (20 mL). The resulting solution was stirred for 16 h at room temperature. The resulting mixture was then quenched by the addition of water (60 mL). The resulting solution was extracted with ethyl acetate (2×60 mL) and washed with brine (2×60 mL) and the organic layers combined. The mixture was dried over anhydrous $Na_2SO_4$. After filtration, the filtrate was concentrated under vacuum. The residue was purified by silica gel column chromatography, eluted with ethyl acetate/petroleum ether (1:1) to afford rac-methyl 3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzoate (1 g, 47%) as a yellow solid.

LCMS Calculated for $C_{30}H_{35}F_3N_4O_4$: 562.18; Observed: 563.2 $[M+H]^+$.

rac-3-((4R,5S)-5-amino-7-ethyl-6-oxo-1-phenyl-4,5,6,7-tetrahydro-1H-pyrazolo[3,4-b]pyridin-4-yl)benzoic acid (24)

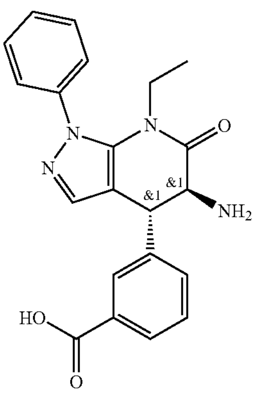 [SMILES: CCN1C(=O)[C@@H](N)[C@H](c2cccc(C(=O)O)c2)c2cnn(-c3ccccc3)c21]

A solution of rac-methyl 3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzoate (1.00 g, 1.78 mmol, 1.00 equiv) in HCl (11.9 M, 10.0 mL) and dioxane (10 mL) was stirred overnight at 100° C. The mixture was allowed to cool down to room temperature, The resulting mixture was concentrated in vacuum, diluted with $Et_2O$ (5.0 mL), filtered to afford rac-3-((4R,5S)-5-amino-7-ethyl-6-oxo-1-phenyl-4,5,6,7-tetrahydro-1H-pyrazolo[3,4-b]pyridin-4-yl)benzoic acid (500 mg, 74%) as a yellow solid, which was used for next step directly.

LCMS Calculated for $C_{21}H_{20}N_4O_3$: 376.15; Observed: 377.3 $[M+H]^+$.

rac-3-((4R,5S)-7-ethyl-6-oxo-1-phenyl-5-(4-(trifluoromethyl)pyrimidine-2-carboxamido)-4,5,6,7-tetrahydro-1H-pyrazolo[3,4-b]pyridin-4-yl)benzoic acid (25)

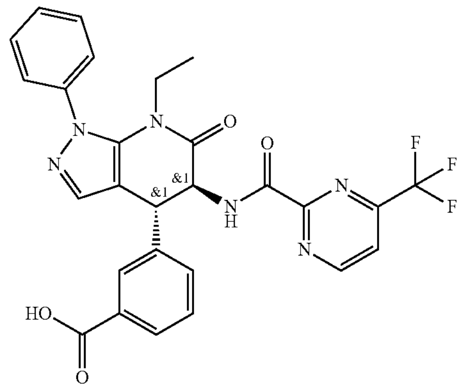 [SMILES: CCN1C(=O)[C@@H](NC(=O)c2nccc(C(F)(F)F)n2)[C@H](c2cccc(C(=O)O)c2)c2cnn(-c3ccccc3)c21]

A mixture of rac-3-((4R,5S)-5-amino-7-ethyl-6-oxo-1-phenyl-4,5,6,7-tetrahydro-1H-pyrazolo[3,4-b]pyridin-4-yl) benzoic acid (500 mg, 1.33 mmol, 1.00 equiv), TEA (269 mg, 2.66 mmol, 2.00 equiv) and DMF (5 mL) was stirred at 0° C. for 10 min. 4-(trifluoromethyl)pyrimidine-2-carbonyl chloride (335 mg, 1.59 mmol, 1.20 equiv) was then added, and the reaction mixture was stirred for 1.0 h at 0° C. The resulting mixture was concentrated in vacuum, the residue was purified by silica gel column chromatography, eluted with ethyl acetate/petroleum ether (1:1) to afford rac-3-((4R,5S)-7-ethyl-6-oxo-1-phenyl-5-(4-(trifluoromethyl)pyrimidine-2-carboxamido)-4,5,6,7-tetrahydro-1H-pyrazolo[3,4-b]pyridin-4-yl)benzoic acid (350 mg, 47.8%) as a yellow solid.

LCMS Calculated for $C_{27}H_{21}F_3N_6O_4$: 550.16; Observed: −551.3 $[M+H]^+$.

4-(trifluoromethyl)pyrimidine-2-carbonyl chloride (26)

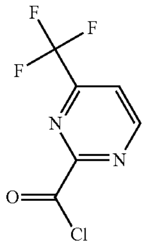 [SMILES: O=C(Cl)c1nccc(C(F)(F)F)n1]

A mixture of 4-(trifluoromethyl)pyrimidine-2-carboxylic acid (500 mg, 2.60 mmol, 1.00 equiv), DMF (19.03 mg, 0.260 mmol, 0.10 equiv) and DCM (5 mL) was stirred at 0° C. for 10 min. oxalyl chloride (396 mg, 3.12 mmol, 1.20 equiv) was then added, and the reaction mixture was stirred for 1.0 h at 0° C. The resulting mixture was concentrated in vacuum to afford 4-(trifluoromethyl)pyrimidine-2-carbonyl chloride (400 mg, 72%) as a yellow solid, which was used for next step directly.

N-(rac-(4R,5S)-4-(3-((S)-2-cyano-4,4-difluoropyrrolidine-1-carbonyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide I-379

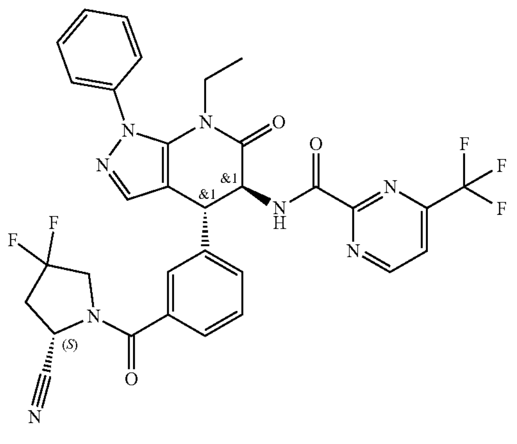

A mixture of rac-3-((4R,5S)-7-ethyl-6-oxo-1-phenyl-5-(4-(trifluoromethyl)pyrimidine-2-carboxamido)-4,5,6,7-tetrahydro-1H-pyrazolo[3,4-b]pyridin-4-yl)benzoic acid (70.0 mg, 0.127 mmol, 1.00 equiv), DIEA (49.3 mg, 0.381 mmol, 3.00 equiv) and (2S,4S)-4-fluoropyrrolidine-2-carbonitrile (14.51 mg, 0.127 mmol, 1.00 equiv) in DMF (1 mL) was stirred at room temperature for 10 min. HATU (58.0 mg, 0.152 mmol, 1.20 equiv) was then added, and the reaction mixture was stirred for 2.0 h at room temperature. The reaction was quenched with water (20 mL) at room temperature. The resulting mixture was extracted with EtOAc (2×20 mL). The combined organic layers were washed with brine (1×20 mL), dried over anhydrous $Na_2SO_4$. After filtration, the filtrate was concentrated under reduced pressure. The residue was purified by reversed-phase flash chromatography with the following conditions: Column: X Bridge Prep RP C18 Column, 30*150 mm, 5 m; Mobile Phase A: Water(0.1% $NH_3·H_2O$), Mobile Phase B: ACN; Flow rate: 35 mL/min; Gradient: 62% B to 92% B in 10 min; Wave Length: 254 nm/220 nm; RT1 (min): 6.9 to afford N-(rac-(4R,5S)-4-(3-((S)-2-cyano-4,4-difluoropyrrolidine-1-carbonyl)phenyl)-7-ethyl-6-oxo-1-phenyl-4,5,6,7-tetrahydro-1H-pyrazolo[3,4-b]pyridin-5-yl)-4-(trifluoromethyl) pyrimidine-2-carboxamide (16.4 mg, 19.9%) as a white solid. The following compounds were prepared using the intermediate 25.

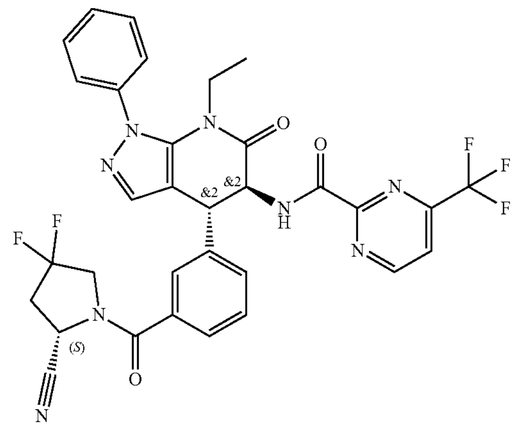

$^1$H NMR (300 MHz, Chloroform-d) δ 9.14 (dd, J = 10.1, 4.9 Hz, 1H), 8.50 (s, 1H), 7.78 (t, J = 5.7 Hz, 1H), 7.69-7.43 (m, 9H), 7.19 (d, J = 16.1 Hz, 1H), 5.46 (s, 1H), 5.11 (s, 1H), 4.27 (d, J = 11.6 Hz, 1H), 4.10-3.81 (m, 3H), 3.19 (dd, J = 14.0, 7.1 Hz, 1H), 2.75 (d, J = 13.6 Hz, 2H), 0.97 (td, J = 7.1, 2.2 Hz, 3H).
LCMS Calculated for $C_{32}H_{25}F_5N_8O_3$: 664.20; Observed (Method-T): 665.1 [M + H]$^+$, 92.9% at RT 1.772 min.

I-379

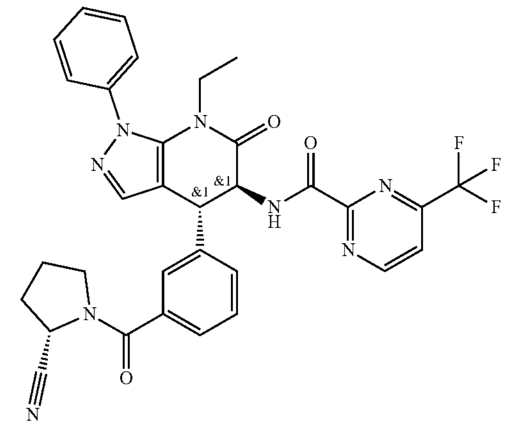 [SMILES: CCN1C(=O)[C@@H](NC(=O)c2nccc(C(F)(F)F)n2)[C@H](c2cccc(C(=O)N3CCC[C@H]3C#N)c2)c2cnn(-c3ccccc3)c21]

$^1$H NMR (300 MHz, DMSO-d$_6$) δ 9.31 (dt, J = 7.4, 4.5 Hz, 2H), 8.19 (dd, J = 5.2, 2.8 Hz, 1H), 7.65 (d, J = 7.5 Hz, 2H), 7.62-7.48 (m, 5H), 7.42 (d, J = 4.7 Hz, 2H), 7.03 (d, J = 9.2 Hz, 1H), 5.37-5.20 (m, 1H), 4.87-4.77 (m, 1H), 4.67 (d, J = 12.9 Hz, 1H), 3.85 (dd, J = 14.2, 7.3 Hz, 1H), 3.49-3.43 (m, 1H), 3.40-3.36 (m, 1H), 3.02 (dd, J = 14.1, 7.1 Hz, 1H), 2.29-2.23 (m, 1H), 2.13 (dd, J = 12.2, 5.9 Hz, 1H), 1.94-1.69 (m, 2H), 0.82 (t, J = 7.0 Hz, 3H).
LCMS Calculated for $C_{32}H_{27}F_3N_8O_3$: 628.22; Observed (Method-B): 629.10 [M + H]$^+$, 99.5% at RT 1.087 min.

I-249

-continued

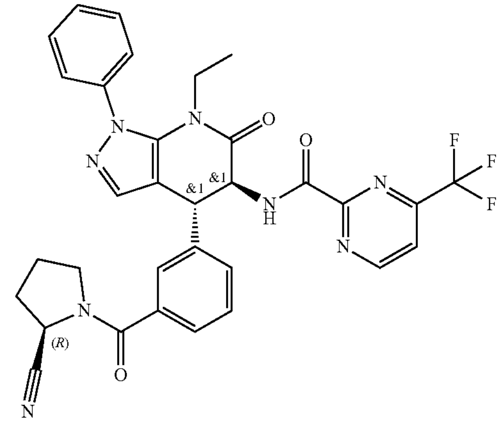

$^1$H NMR (300 MHz, DMSO-$d_6$) δ 9.38-9.24 (m, 2H), 8.19 (dd, J = 5.2, 2.8 Hz, 1H), 7.65 (d, J = 7.6 Hz, 2H), 7.61-7.49 (m, 5H), 7.42 (d, J = 5.4 Hz, 2H), 7.03 (d, J = 9.2 Hz, 1H), 5.36-5.18 (m, 1H), 4.90-4.76 (m, 1H), 4.67 (d, J = 12.9 Hz, 1H), 3.98-3.73 (m, 1H), 3.59-3.34 (m, 2H), 3.13-2.90 (m, 1H), 2.36-2.03 (m, 2H), 1.95-1.64 (m, 2H), 0.82 (t, J = 7.0 Hz, 3H).
LCMS Calculated for $C_{32}H_{27}F_3N_8O_3$: 628.22; Observed (Method-B): 629.10 $[M + H]^+$, 98.8% at RT 1.078 min.

I-250

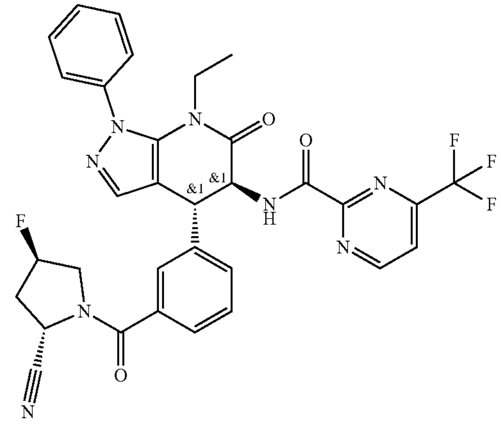 [SMILES: CCN1C(=O)[C@@H](NC(=O)c2nccc(C(F)(F)F)n2)[C@H](c2cccc(C(=O)N3C[C@H](F)C[C@H]3C#N)c2)c2cnn(-c3ccccc3)c21]

$^1$H NMR (400 MHz, Chloroform-d) δ 9.19-9.08 (m, 1H), 8.48-8.33 (m, 1H), 7.83-7.74 (m, 1H), 7.71-7.42 (m, 10H), 7.17 (d, J = 14.5 Hz, 1H), 5.55-5.11 (m, 1H), 5.07-4.97 (m, 1H), 4.48-4.21 (m, 1H), 4.11-3.51 (m, 2H), 3.29-3.14 (m, 1H), 2.91-2.68 (m, 1H), 2.51 (d, J = 37.8 Hz, 1H), 0.98 (t, J = 6.8 Hz, 3H).
LCMS Calculated for $C_{32}H_{26}F_4N_8O_3$: 646.21; Observed (Method-T): 647.10 $[M + H]^+$, 96.1% at RT 1.271 min.

I-350

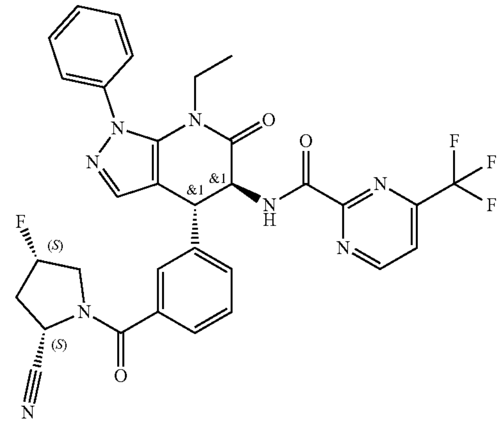

$^1$H NMR (300 MHz, Chloroform-d) δ 9.14 (s, 1H), 8.49 (s, 1H), 7.79 (t, J = 5.3 Hz, 1H), 7.66 (s, 1H), 7.66-7.30 (m, 9H), 7.17 (s, 1H), 5.40 (d, J = 48.9 Hz, 2H), 5.13 (s, 1H), 4.42-3.85 (m, 3H), 3.19 (dd, J = 14.1, 7.0 Hz, 1H), 2.69 (t, J = 14.9 Hz, 1H), 2.41 (d, J = 36.4 Hz, 1H), 0.97 (td, J = 7.0, 2.5 Hz, 3H).
LCMS Calculated for $C_{32}H_{26}F_4N_8O_3$: 646.21; Observed (Method-B): 647.1 $[M + H]^+$, 98.6% at RT 1.065 min.

I-330

-continued
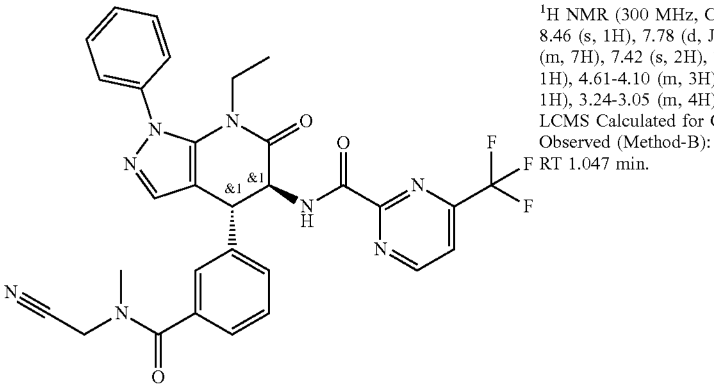
I-370
$^1$H NMR (300 MHz, Chloroform-d) δ 9.14 (s, 1H), 8.46 (s, 1H), 7.78 (d, J = 4.3 Hz, 1H), 7.61-7.47 (m, 7H), 7.42 (s, 2H), 7.16 (s, 1H), 5.50-5.30 (m, 1H), 4.61-4.10 (m, 3H), 3.97 (dd, J = 14.3, 7.1 Hz, 1H), 3.24-3.05 (m, 4H), 0.95 (t, J = 7.0 Hz, 3H). LCMS Calculated for $C_{30}H_{25}F_3N_8O_3$: 602.20; Observed (Method-B): 603.10 [M + H]$^+$, 98.6% at RT 1.047 min.
7. Synthesis of N-((4R,5S)-4-(3-((1,1-dioxidoisothiazol-2 (3H)-yl)methyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide I-263
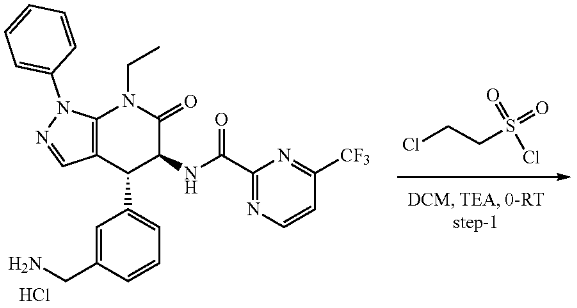
-continued
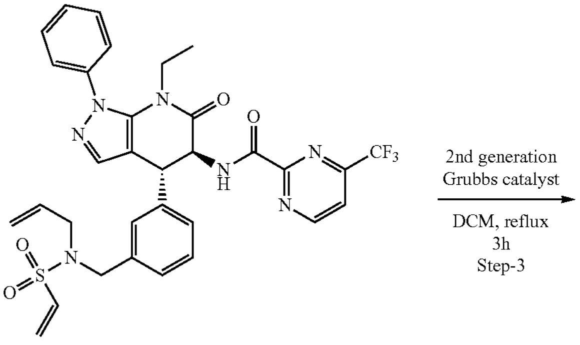
28
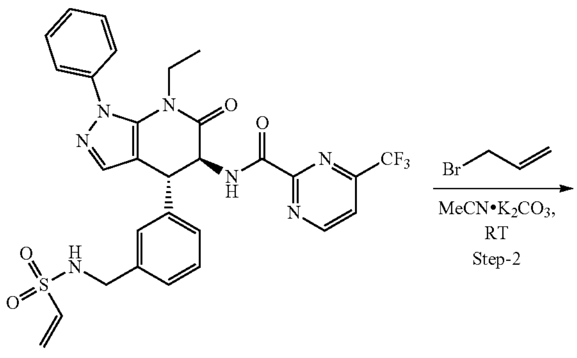
27
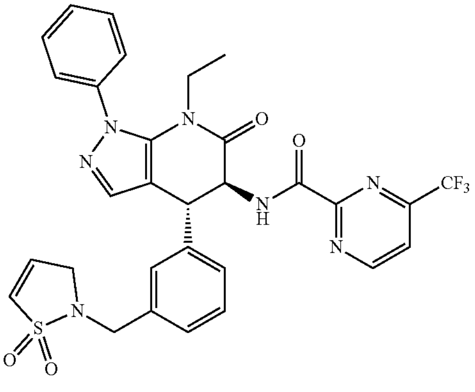
I-263

N-((4R,5S)-7-ethyl-6-oxo-1-phenyl-4-(3-(vinylsulfonamidomethyl)phenyl)-4,5,6,7-tetrahydro-1H-pyrazolo[3,4-b]pyridin-5-yl)-4-(trifluoromethyl)pyrimidine-2-carboxamide (27)

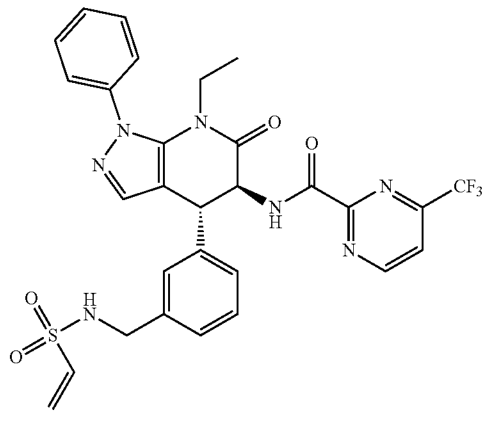 [SMILES: C=CS(=O)(=O)NCc1cccc([C@@H]2c3cnn(-c4ccccc4)c3N(CC)C(=O)[C@H]2NC(=O)c2nccc(C(F)(F)F)n2)c1]

To a solution of N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide hydrochloride (500 mg, 0.934 mmol, 1.00 equiv) and DIEA (603 mg, 4.67 mmol, 5.00 equiv) in DCM (5 mL) was added 2-chloroethanesulfonyl chloride (182.63 mg, 1.121 mmol, 1.2 equiv). The mixture was stirred for 3 h at RT. The reaction was quenched by the addition of $H_2O$ (5 mL) at 0° C. The aqueous layer was extracted with DCM (3×3 mL). The combined organic layers were dried over anhydrous $Na_2SO_4$. After filtration, the filtrate was concentrated under reduced pressure. The residue was purified by silica gel column chromatography, eluted with ethyl acetate/petroleum ether from 40% to 95% to afford N-((4R,5S)-7-ethyl-6-oxo-1-phenyl-4-(3-(vinylsulfonamidomethyl)phenyl)-4,5,6,7-tetrahydro-1H-pyrazolo[3,4-b]pyridin-5-yl)-4-(trifluoromethyl)pyrimidine-2-carboxamide (280 mg, 43.6%) as a white solid.

N-((4R,5S)-4-(3-((N-allylvinylsulfonamido)methyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (28)

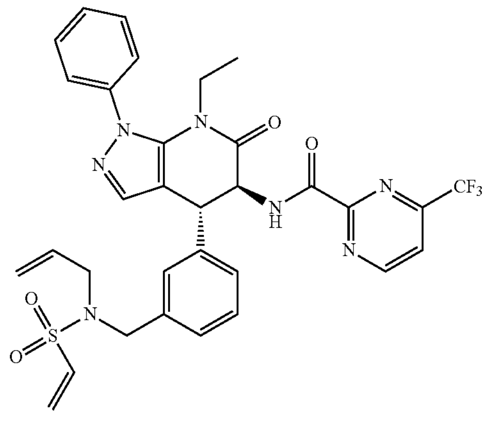 [SMILES: C=CCN(Cc1cccc([C@@H]2c3cnn(-c4ccccc4)c3N(CC)C(=O)[C@H]2NC(=O)c2nccc(C(F)(F)F)n2)c1)S(=O)(=O)C=C]

To a stirred solution of N-((4R,5S)-7-ethyl-6-oxo-1-phenyl-4-(3-(vinylsulfonamidomethyl)phenyl)-4,5,6,7-tetrahydro-1H-pyrazolo[3,4-b]pyridin-5-yl)-4-(trifluoromethyl)pyrimidine-2-carboxamide (270 mg, 0.406 mmol, 1.00 equiv) in anhydrous MeCN (5.4 mL) was added $K_2CO_3$ (79.5 mg, 0.576 mmol, 2.00 equiv) and allyl bromide (41.8 mg, 0.346 mmol, 1.20 equiv). The reaction mixture was stirred at RT for 16 h. After completion of reaction, the resulting mixture was filtered, the filter cake was washed with MeCN (5 mL). The filtrate was concentrated under reduced pressure. The residue was purified by silica gel column chromatography, eluted with ethyl acetate/petroleum ether (10%-40%) to afford N-((4R,5S)-4-(3-((N-allylvinylsulfonamido)methyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (180 mg, 70.9%) as a white solid.

N-((4R,5S)-4-(3-((1,1-dioxidoisothiazol-2 (3H)-yl)methyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide I-263

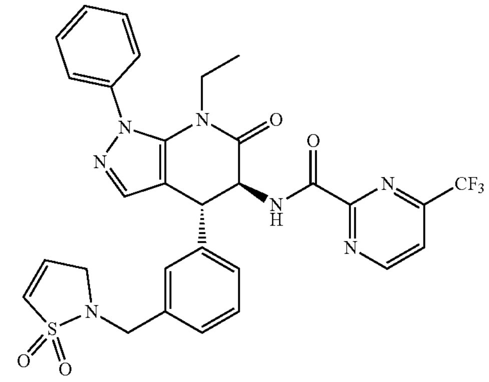 [SMILES: CCN1C(=O)[C@@H](NC(=O)c2nccc(C(F)(F)F)n2)[C@H](c2cccc(CN3CC=CS3(=O)=O)c2)c2cnn(-c3ccccc3)c21]

To a stirred solution of N-((4R,5S)-4-(3-((N-allylvinylsulfonamido)methyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (180 mg, 0.270 mmol, 1.00 equiv) in anhydrous DCM (4 mL) was added [1,3-bis-(2,4,6-trimethylphenyl)-2-imidazolidinylidene]dichloro (O-isopropoxyphenylmethylene) ruthenium (23.0 mg, 0.027 mmol, 0.100 equiv) under $N_2$ protecting and stirred at 40° C. for 3 h. The reaction progress was monitored by TLC. After completion of reaction, the reaction mixture was concentrated under reduced pressure to give crude product which was further purified by Pre-HPLC with follow condition: Column: XBridge Prep C18 Column, 19*250 mm, 5 m; Mobile Phase A: Water(0.1% $NH_3 \cdot H_2O$), Mobile Phase B: ACN; Flow rate: 25 mL/min; Gradient: 40% B to 65% B in 10 min; Wave Length: 254 nm/220 nm; This resulted in N-((4R,5S)-4-(3-((1,1-dioxidoisothiazol-2 (3H)-yl)methyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (40 mg, 23.2%) as a white solid.

$^1H$ NMR (300 MHz, DMSO-$d_6$) δ 9.38-9.27 (m, 2H), 8.21 (d, J=5.1 Hz, 1H), 7.70-7.64 (m, 2H), 7.63-7.49 (m, 3H), 7.42 (s, 1H), 7.34 (d, J=4.8 Hz, 2H), 7.26 (s, 1H), 7.19 (d, J=7.1 Hz, 1H), 7.08-7.01 (m, 2H), 5.25 (dd, J=12.8, 9.3

Hz, 1H), 4.64 (d, J=12.9 Hz, 1H), 4.22 (s, 2H), 3.96-3.68 (m, 3H), 3.03 (dd, J=14.3, 7.2 Hz, 1H), 0.83 (t, J=7.0 Hz, 3H).

LCMS Calculated for $C_{30}H26F_3N_{704}S$: 637.17; Observed (Method-V): 638.3 $[M+H]^+$, 91.9% at RT 1.562 min.

8. Synthesis of rac-N-((4R,5S)-4-(2-((E)-2-cyanovinyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide I-259 and rac-N-((4R,5S)-4-(2-((Z)-2-cyanovinyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide I-260

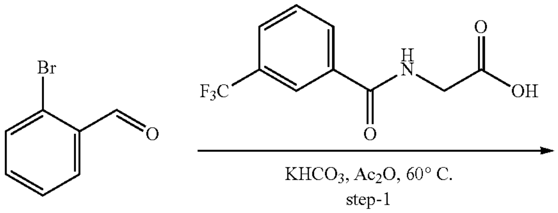

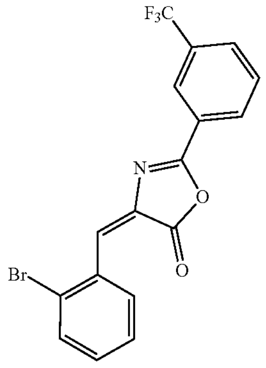

29

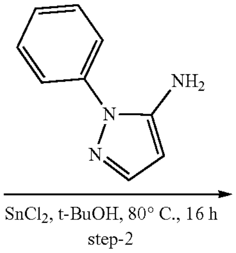

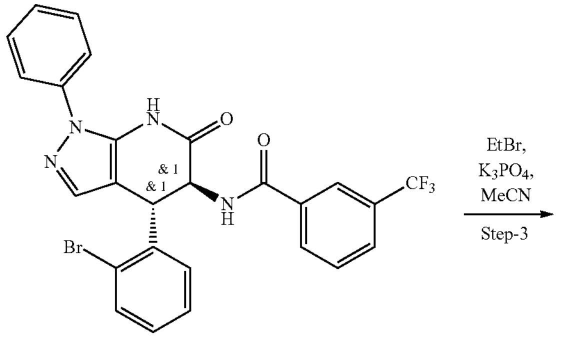

30

-continued

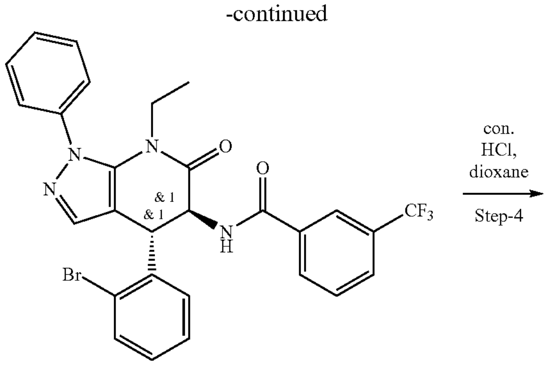

31

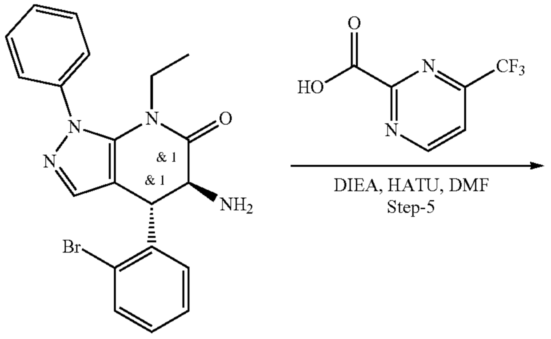

32

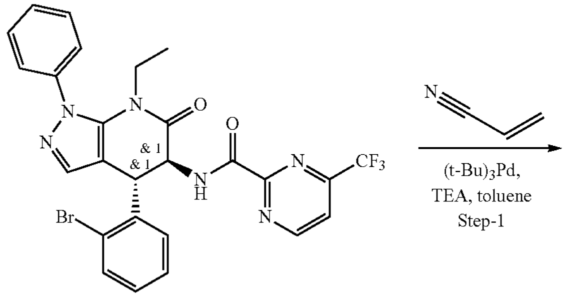

33

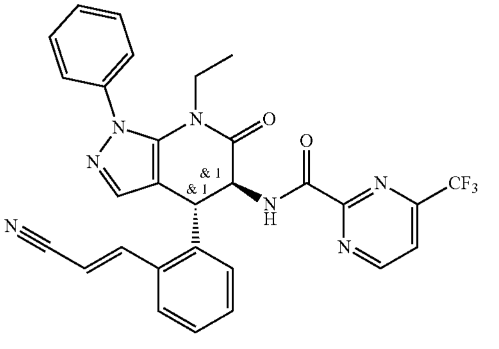

I-259

-continued

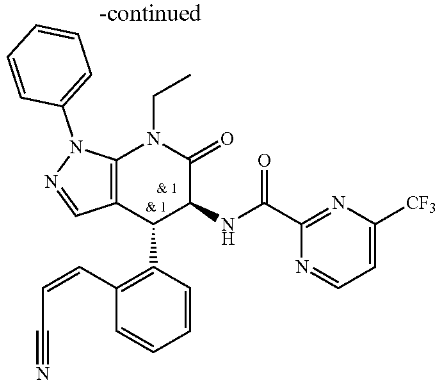

I-260

(4E)-4-[(2-bromophenyl)methylidene]-2-[3-(trifluoromethyl)phenyl]-1,3-oxazol-5-one (29)

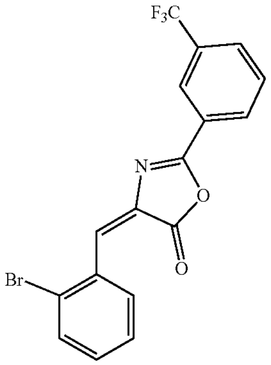 [SMILES: O=C1OC(c2cccc(C(F)(F)F)c2)=N/C1=C/c1ccccc1Br]

A mixture of 2-bromobenzaldehyde (36.0 g, 194 mmol, 1.00 equiv), ([3-(trifluoromethyl)phenyl]formamidoacetic acid (48.0 g, 195 mmol, 1.00 equiv) and $KHCO_3$ (1.95 g, 19.4 mmol, 0.100 equiv) in $Ac_2O$ (300 mL) was stirred for 16 h at 60° C. The mixture was allowed to cool down to room temperature. The resulting mixture was diluted with $H_2O$ (1000 mL). The mixture was stirred for 1 h at room temperature. The precipitated solids were collected by filtration and washed with $H_2O$ (3×50 mL). This resulted in (4E)-4-[(2-bromophenyl)methylidene]-2-[3-(trifluoromethyl)phenyl]-1,3-oxazol-5-one (30.0 g, 31.9%) as a yellow solid.

rac-N-((4R,5R)-4-(2-bromophenyl)-6-oxo-1-phenyl-4,5,6,7-tetrahydro-1H-pyrazolo[3,4-b]pyridin-5-yl)-3-(trifluoromethyl)benzamide (30)

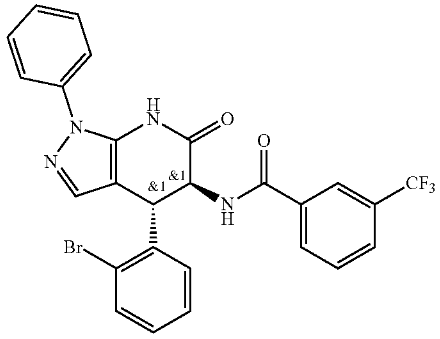 [SMILES: O=C(N[C@@H]1C(=O)Nc2c(cnn2-c2ccccc2)[C@H]1c1ccccc1Br)c1cccc(C(F)(F)F)c1]

A solution of (4E)-4-[(2-bromophenyl)methylidene]-2-[3-(trifluoromethyl)phenyl]-1,3-oxazol-5-one (30.0, 75.7 mmol, 1.00 equiv), 1-phenyl-1H-pyrazol-5-amine (12.0 g, 75.7 mmol, 1.00 equiv) and $SnCl_2$ (1.45 g, 7.57 mmol, 0.100 equiv) in t-BuOH (300 mL) was stirred for 16 h at 80° C. The mixture was allowed to cool down to room temperature. The resulting mixture was concentrated under reduced pressure. The residue was purified by silica gel column chromatography, eluted with petroleum ether/ethyl acetate (2:1) to afford rac-N-((4R,5R)-4-(2-bromophenyl)-6-oxo-1-phenyl-4,5,6,7-tetrahydro-1H-pyrazolo[3,4-b]pyridin-5-yl)-3-(trifluoromethyl)benzamide (18 g, 30.8%) as a yellow solid.

rac-N-((4R,5R)-4-(2-bromophenyl)-7-ethyl-6-oxo-1-phenyl-4,5,6,7-tetrahydro-1H-pyrazolo[3,4-b]pyridin-5-yl)-3-(trifluoromethyl)benzamide (31)

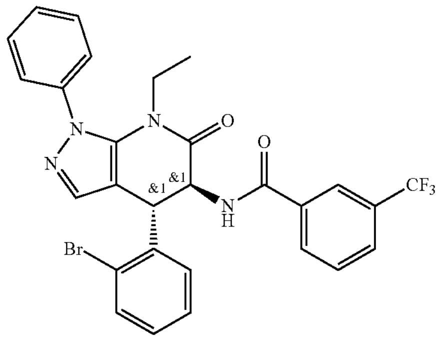 [SMILES: CCN1C(=O)[C@@H](NC(=O)c2cccc(C(F)(F)F)c2)[C@H](c2ccccc2Br)c2cnn(-c3ccccc3)c21]

A solution of rac-N-((4R,5R)-4-(2-bromophenyl)-6-oxo-1-phenyl-4,5,6,7-tetrahydro-1H-pyrazolo[3,4-b]pyridin-5-yl)-3-(trifluoromethyl)benzamide (18.0 g, 32.4 mmol, 1.00 equiv), bromoethane (4.24 g, 38.8 mmol, 1.20 equiv) and $K_3PO_4$ (10.3 g, 48.6 mmol, 1.50 equiv) in ACN (200 mL) was stirred for 20 h at 60° C. The mixture was allowed to cool down to room temperature. The resulting mixture was concentrated under reduced pressure. The residue was purified by silica gel column chromatography, eluted with PE/EA (2:1) to afford rac-N-((4R,5R)-4-(2-bromophenyl)-7-ethyl-6-oxo-1-phenyl-4,5,6,7-tetrahydro-1H-pyrazolo[3,4-b]pyridin-5-yl)-3-(trifluoromethyl)benzamide (14.0 g, 58.4%) as a yellow solid.

$^1$H NMR (400 MHz, Chloroform-d) δ 7.99 (d, J=14.8 Hz, 1H), 7.88 (t, J=8.3 Hz, 1H), 7.80-7.70 (m, 1H), 7.67-7.48 (m, 8H), 7.39 (t, J=7.6 Hz, 1H), 7.29-7.14 (m, 2H), 5.61-5.40 (m, 1H), 4.89 (d, J=13.4 Hz, 1H), 4.26-4.09 (m, 1H), 4.06-3.90 (m, 1H), 3.37-3.10 (m, 1H), 1.36-1.21 (m, 1H), 1.01-0.89 (m, 2H).

rac-(4R,5R)-5-amino-4-(2-bromophenyl)-7-ethyl-1-phenyl-4H,5H-pyrazolo[3,4-b]pyridin-6-one (32)

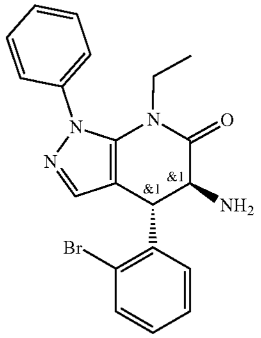 [SMILES: CCN1C(=O)[C@@H](N)[C@H](c2ccccc2Br)c2cnn(-c3ccccc3)c21]

A mixture of rac-N-((4R,5R)-4-(2-bromophenyl)-7-ethyl-6-oxo-1-phenyl-4,5,6,7-tetrahydro-1H-pyrazolo[3,4-b]pyridin-5-yl)-3-(trifluoromethyl)benzamide (14.0 g, 23.9 mmol, 1.00 equiv) and HCL (200 mL, 12 M) in dioxane (200 mL) was stirred for 16 h at 90° C. The mixture was allowed to cool down to room temperature. The resulting mixture was concentrated under reduced pressure. The mixture was basified to pH 8 with saturated $NaHCO_3$ (aq.). The resulting mixture was extracted with EtOAc (3×100 mL). The combined organic layers were washed with brine (3×100 mL), dried over anhydrous $Na_2SO_4$. The resulting mixture was filtered, the filter cake was washed with EtOAc (3×50 mL). The filtrate was concentrated under reduced pressure. The residue was purified by silica gel column chromatography, eluted with ethyl acetate/petroleum ether (1:1) to afford rac-(4R,5R)-5-amino-4-(2-bromophenyl)-7-ethyl-1-phenyl-4H,5H-pyrazolo[3,4-b]pyridin-6-one (9.50 g, 94.3%) as a yellow solid.

rac-N-((4R,5R)-4-(2-bromophenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (33)

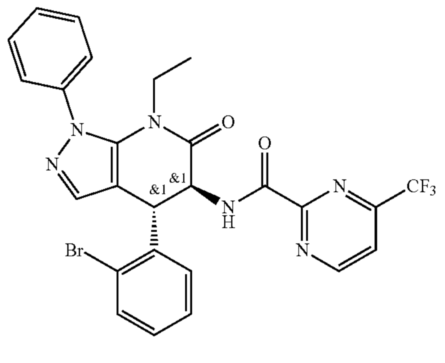 [SMILES: CCN1C(=O)[C@@H](NC(=O)c2nccc(C(F)(F)F)n2)[C@H](c2ccccc2Br)c2cnn(-c3ccccc3)c21]

A mixture of rac-(4R,5R)-5-amino-4-(2-bromophenyl)-7-ethyl-1-phenyl-4H,5H-pyrazolo[3,4-b]pyridin-6-one (2.00 g, 4.863 mmol, 1 equiv), 4-(trifluoromethyl)pyrimidine-2-carboxylic acid (1.03 g, 5.34 mmol, 1.10 equiv), DIEA (1.26 g, 9.72 mmol, 2.00 equiv) and HATU (2.22 g, 5.83 mmol, 1.20 equiv) in DMF (20 mL) was stirred for 16 h at room temperature. The resulting mixture was diluted with $H_2O$ (50 mL). The resulting mixture was extracted with EtOAc (3×50 mL). The combined organic layers were washed with brine (3×50 mL), dried over anhydrous $Na_2SO_4$. The resulting mixture was filtered, the filter cake was washed with EtOAc (3×20 mL). After filtration, the filtrate was concentrated under reduced pressure. The residue was purified by silica gel column chromatography, eluted with ethyl acetate/petroleum ether (1:1) to afford rac-N-((4R,5R)-4-(2-bromophenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (2.2 g, 63.3%) as a yellow solid. $^1$H NMR (300 MHz, DMSO-$d_6$) δ 9.32 (d, J=5.1 Hz, 1H), 8.32-8.17 (m, 1H), 7.70-7.47 (m, 7H), 7.45-7.17 (m, 2H), 6.92-6.86 (m, 1H), 5.55-5.41 (m, 1H), 5.12 (d, J=12.9 Hz, 1H), 4.10-3.97 (m, 1H), 3.92-3.74 (m, 1H), 3.16-3.00 (m, 1H), 0.97-0.76 (m, 3H).

rac-N-((4R,5S)-4-(2-((E)-2-cyanovinyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide I-259 and rac-N-((4R,5S)-4-(2-((Z)-2-cyanovinyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide I-260

I-259

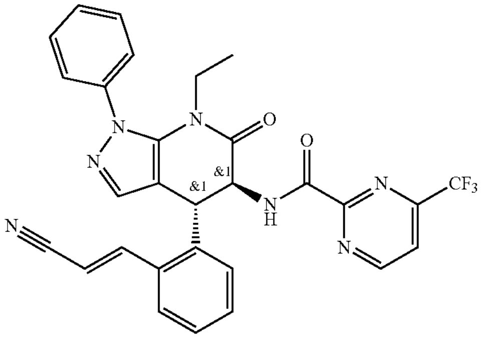

I-260

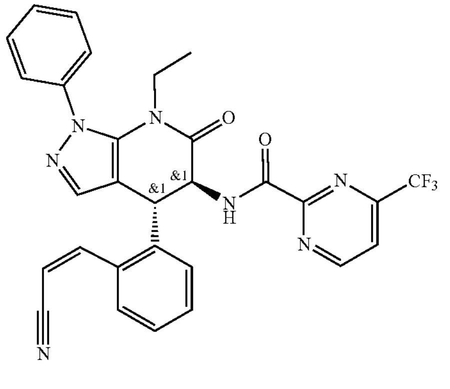

A solution of rac-N-[(4R,5R)-4-(2-bromophenyl)-7-ethyl-6-oxo-1-phenyl-4H,5H-pyrazolo[3,4-b]pyridin-5-yl]-4-(trifluoromethyl)pyrimidine-2-carboxamide (1.00 g, 1.70 mmol, 1.00 equiv), acrylonitrile (0.110 g, 2.05 mmol, 1.20 equiv), $P(T\text{-}BU)_3PDG_2$ (87.5 mg, 0.171 mmol, 0.1 equiv) and TEA (0.520 g, 5.124 mmol, 3 equiv) in toluene (10 mL) was stirred for 4 h at 100° C. under nitrogen atmosphere. The mixture was allowed to cool down to room temperature. The reaction was quenched with Water (30 ml) at room temperature. The resulting mixture was extracted with EtOAc (3×20 mL). The combined organic layers were washed with brine (3×20 mL), dried over anhydrous $Na_2SO_4$. After filtration, the filtrate was concentrated under reduced pressure. The crude product was purified by Prep-HPLC with the following conditions (Column: SunFire Prep C18 OBD Column, 30*150 mm, 5 μm; Mobile Phase A: Water(0.1% FA), Mobile Phase B: ACN; Flow rate: 35 mL/min mL/min; Gradient: isocratic 55%-85% 9 min; Wave Length: 254 nm/220 nm nm; RT1 (min): 8.5) to afford rac-N-((4R,5S)-4-(2-((E)-2-cyanovinyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (37 mg, 3.8%) and N-((4R,5S)-4-(2-((Z)-2-cyanovinyl)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (25 mg, 2.4%) as a white solid.

9. Synthesis of 1-(cyanomethyl)-N-((4R,5S)-7-ethyl-4-(3-((2-(morpholinomethyl)acrylamido)methyl)phenyl)-6-oxo-1-phenyl-4,5,6,7-tetrahydro-1H-pyrazolo[3,4-b]pyridin-5-yl)-1H-pyrazole-3-carboxamide (I-340)

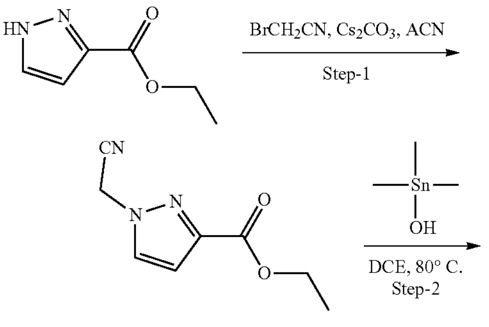

34

| | |
|---|---|
| 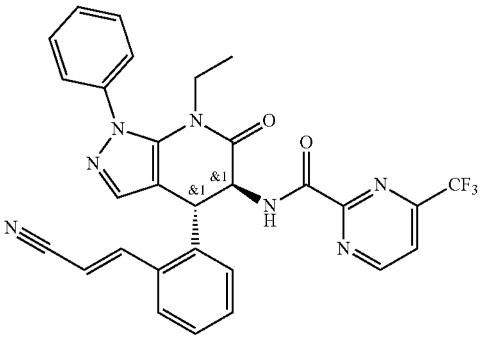 [SMILES: CCN1C(=O)[C@@H](NC(=O)c2nccc(C(F)(F)F)n2)[C@H](c2ccccc2/C=C/C#N)c2cnn(-c3ccccc3)c21] I-259 | $^1H$ NMR (300 MHz, DMSO-$d_6$) δ 9.35-9.22 (m, 2H), 8.31-8.18 (m, 2H), 7.78-7.40 (m, 8H), 7.38-7.27 (m, 1H), 6.91 (s, 1H), 6.27 (d, J = 16.3 Hz, 1H), 5.43-5.29 (m, 1H), 5.08 (d, J = 12.7 Hz, 1H), 3.95-3.80 (m, 1H), 3.11-2.98 (m, 1H), 0.86 (t, J = 6.9 Hz, 3H). LCMS Calculated for $C_{29}H_{22}F_3N_7O_2$: 557.18; Observed: (Method-D) 556.2 $[M - H]^-$, 99.2% at RT 1.678 min. |
| 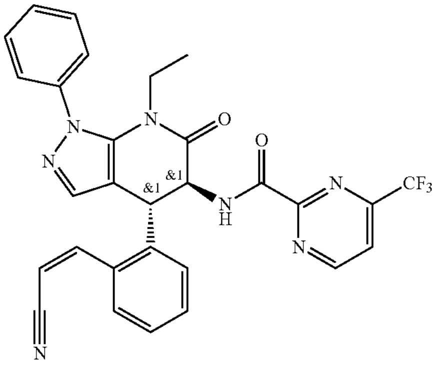 [SMILES: CCN1C(=O)[C@@H](NC(=O)c2nccc(C(F)(F)F)n2)[C@H](c2ccccc2/C=C\C#N)c2cnn(-c3ccccc3)c21] I-260 | $^1H$ NMR (300 MHz, DMSO-$d_6$) δ 9.31 (d, J = 5.1 Hz, 1H), 9.20 (d, J = 9.6 Hz, 1H), 8.22 (d, J = 5.1 Hz, 1H), 7.90 (d, J = 11.9 Hz, 1H), 7.77-7.22 (m, 9H), 7.03-6.85 (m, 1H), 5.92 (d, J = 11.7 Hz, 1H), 5.44-5.31 (m, 1H), 4.92 (d, J = 12.7 Hz, 1H), 3.93-3.80 (m, 1H), 3.20-2.69 (m, 1H), 0.86 (d, J = 6.9 Hz, 3H). LCMS Calculated for $C_{29}H_{22}F_3N_7O_2$: 557.18; Observed: (Method-D) 558.3 $[M + H]^+$, 95.0% at RT 1.644 min. |

-continued

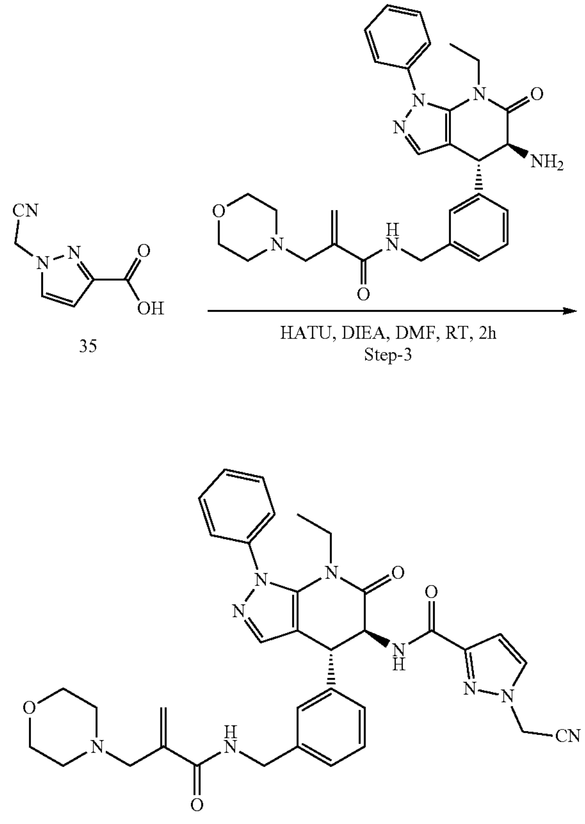

35

I-340 ethyl 1-(cyanomethyl)-1H-pyrazole-3-carboxylate (34)

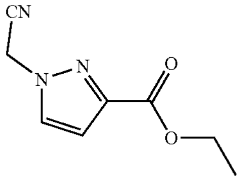

To a stirred solution of ethyl 1H-pyrazole-3-carboxylate (1.00 g, 7.14 mmol, 1.00 equiv) and $Cs_2CO_3$ (2.79 g, 8.56 mmol, 1.20 equiv) in ACN (10 mL) was added $BrCH_2CN$ (0.945 g, 7.85 mmol, 1.10 equiv) dropwise at room temperature. The resulting mixture was stirred overnight at room temperature. The reaction was monitored by LCMS and TLC. After completion of reaction, the reaction was quenched by the addition of ice water (5 mL). The resulting mixture was extracted with ethyl acetate (3x20 mL). The combined organic layers were washed with brine (3x10 mL), dried over anhydrous $Na_2SO_4$. After filtration, the filtrate was concentrated under reduced pressure. The residue was purified by silica gel column chromatography, eluted with ethyl acetate/petroleum ether=1/1 to afford ethyl 1-(cyanomethyl)-1H-pyrazole-3-carboxylate (804 mg, 67% yield) as a white solid.

1-(cyanomethyl)-1H-pyrazole-3-carboxylic acid (35)

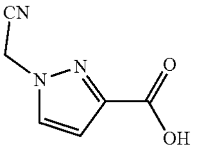 [SMILES: N#CCn1ccc(C(=O)O)n1]

To a stirred solution of ethyl 1-(cyanomethyl)-1H-pyrazole-3-carboxylate (200 mg, 1.12 mmol, 1.00 equiv) in DCE (2 mL) were added trimethyltin hydroxide (807 mg, 4.46 mmol, 4.00 equiv) at room temperature. The resulting mixture was stirred overnight at 80° C. The reaction was monitored by LCMS. After the completion of reaction, the mixture was acidified to pH 5-6 with HCl (0.5 mol/L). The resulting mixture was concentrated under reduced pressure. The residue was dissolved in DMF (2 mL). The residue was purified by reversed-phase flash chromatography with the following conditions: column, C18 silica gel; mobile phase, ACN in $NH_3H_2O$ (0.05%), 0% to 50% gradient in 10 min; detector, UV 254 nm. This resulted in 1-(cyanomethyl)-1H-pyrazole-3-carboxylic acid (130 mg, 77% yield) as a white oil.

1-(cyanomethyl)-N-((4R,5S)-7-ethyl-4-(3-((2-(morpholinomethyl)acrylamido)methyl)phenyl)-6-oxo-1-phenyl-4,5,6,7-tetrahydro-1H-pyrazolo[3,4-b]pyridin-5-yl)-1H-pyrazole-3-carboxamide

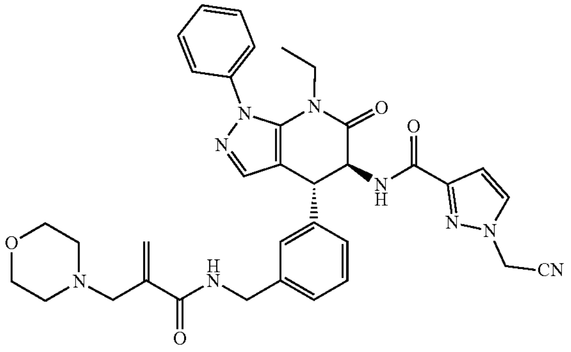 [SMILES: C=C(CN1CCOCC1)C(=O)NCc1cccc([C@@H]2c3cnn(-c4ccccc4)c3N(CC)C(=O)[C@H]2NC(=O)c2ccn(CC#N)n2)c1]

To a stirred solution of 1-(cyanomethyl)pyrazole-3-carboxylic acid (22.6 mg, 0.150 mmol, 1.10 equiv) in DMF (0.7 mL) was added HATU (103 mg, 0.272 mmol, 2.00 equiv) and DIEA (52.7 mg, 0.408 mmol, 3.00 equiv) at room temperature. The resulting mixture was stirred for 10 min. Then into the reaction mixture was added N-(3-((4R,5S)-5-amino-7-ethyl-6-oxo-1-phenyl-4,5,6,7-tetrahydro-1H-pyrazolo[3,4-b]pyridin-4-yl)benzyl)-2-(morpholinomethyl)acrylamide (70.0 mg, 0.136 mmol, 1.00 equiv). The resulting mixture was stirred for 2 h. The crude product was purified by Prep-HPLC with the following conditions (Column: XBridge Prep RP C18 Column, 30*150 mm, 5 m; Mobile Phase A: Water(10 mmol/L $NH_4HCO_3$), Mobile Phase B: ACN; Flow rate: 35 mL/min; Gradient: 38% B to 68% B in 10 min; Wave Length: 254 nm/220 nm; RT1 (min): 6) to afford 1-(cyanomethyl)-N-((4R,5S)-7-ethyl-4-(3-((2-(morpholinomethyl)acrylamido)methyl)phenyl)-6-oxo-1-phenyl-4,5,6,7-tetrahydro-1H-pyrazolo[3,4-b]pyridin-5-yl)-1H-pyrazole-3-carboxamide (20 mg, 22.2% yield, 97.6% purity) as a white solid.

$^1$H NMR (400 MHz, DMSO-$d_6$) δ 8.96 (t, J=5.9 Hz, 1H), 8.40 (d, J=9.3 Hz, 1H), 7.90 (d, J=2.4 Hz, 1H), 7.67-7.47 (m, 5H), 7.35-7.16 (m, 4H), 6.90 (s, 1H), 6.66 (d, J=2.4 Hz, 1H), 5.89 (d, J=2.0 Hz, 1H), 5.54 (d, J=1.5 Hz, 2H), 5.45 (s, 1H), 5.21-5.11 (m, 1H), 4.55 (d, J=12.8 Hz, 1H), 4.36 (t, J=5.4 Hz, 2H), 3.90-3.77 (m, 1H), 3.44 (d, J=5.3 Hz, 4H), 3.17 (s, 2H), 3.07-2.96 (m, 1H), 2.31 (s, 4H), 0.81 (t, J=7.0 Hz, 3H).

LCMS Calculated for $C_{35}H_{37}N_9O_4$:647.3 Observed (Method-I): 648.4[M+H]97.65% at RT 1.470 min.

10. Synthesis of tert-butyl ((S)-1-(3-(rac-(4R,5S)-6-oxo-1-phenyl-5-(3-(trifluoromethyl)benzamido)-4,5,6,7-tetrahydro-1H-pyrazolo[3,4-b]pyridin-4-yl)phenyl)ethyl)carbamate I-380

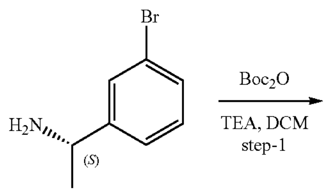

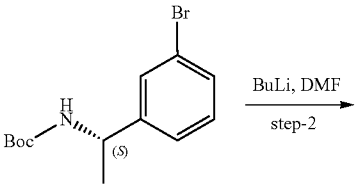

36

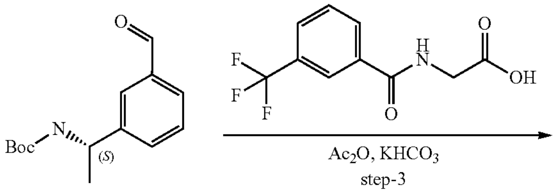

37

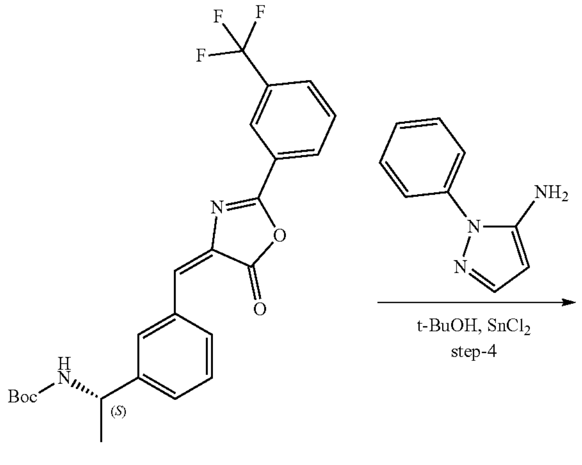

38

-continued

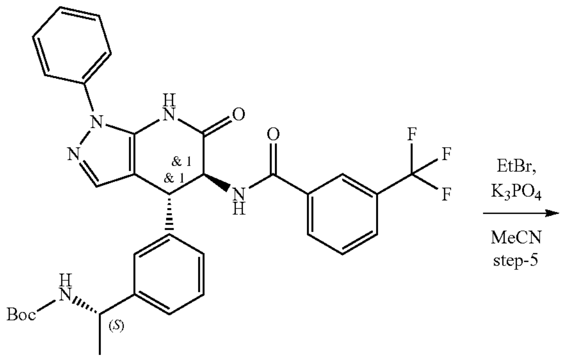

39

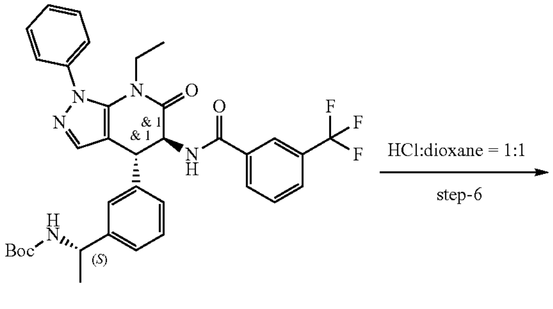

40

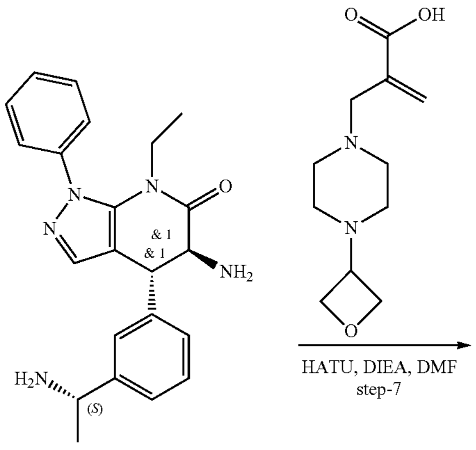

41

-continued

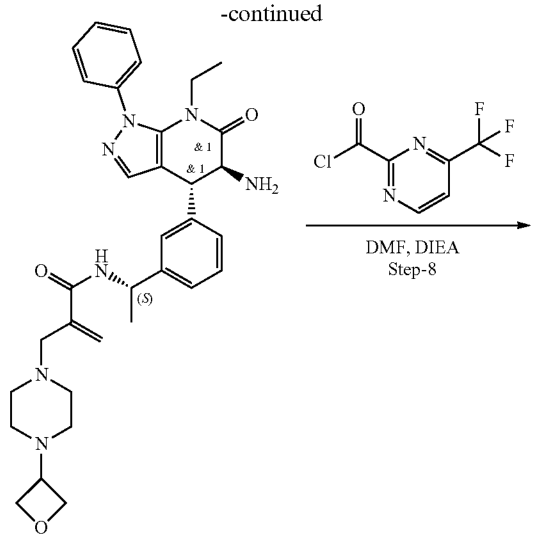

42

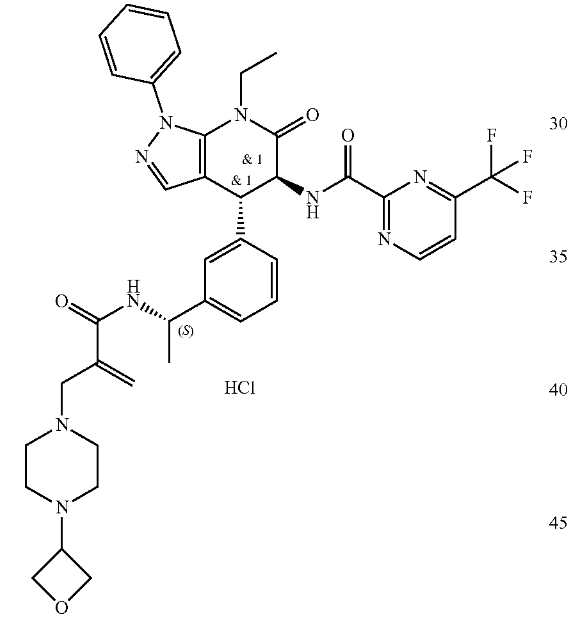

I-380 tert-butyl (S)-(1-(3-bromophenyl)ethyl)carbamate (36)

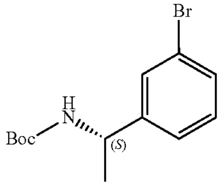

Into a 50 mL round-bottom flask were added (1S)-1-(3-bromophenyl)ethanamine (9.00 g, 45.0 mmol, 1.00 equiv), DCM (100 mL), $Boc_2O$ (11.8 g, 54.0 mmol, 1.20 equiv) and TEA (13.7 g, 135 mmol, 3.00 equiv) at room temperature. The resulting mixture was stirred for 2 h at room temperature. The reaction was quenched with Water at room temperature. The resulting mixture was extracted with DCM (2×50 mL). The combined organic layers were washed with brine (2×50 mL), dried over anhydrous $Na_2SO_4$. After filtration, the filtrate was concentrated under reduced pressure. The residue was purified by silica gel column chromatography, eluted with ethyl acetate/petroleum ether (1:1) to afford tert-butyl (S)-(1-(3-bromophenyl)ethyl)carbamate (11.2 g, 82.9%) as a yellow solid.

LCMS Calculated for $C_{13}H_{18}BrNO_2$: 299.05; Observed: 300.1 $[M+H]^+$.

tert-butyl (S)-(1-(3-formylphenyl)ethyl)carbamate (37)

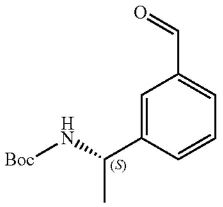

A solution of tert-butyl (S)-(1-(3-bromophenyl)ethyl)carbamate (12.0 g, 40.0 mmol, 1.00 equiv) in THF (150 mL) was treated with n-BuLi (3.84 g, 59.9 mmol, 1.50 equiv) at −78° C. for 30 min under nitrogen atmosphere followed by the addition of DMF (5.84 g, 79.9 mmol, 2.00 equiv) dropwise at −78° C. The resulting mixture was stirred at −78° C. for 4 h under $N_2$ atmosphere. The reaction was quenched with $NH_4Cl$ (aq.) (200 mL) at 0° C. The resulting mixture was extracted with EA (3×150 mL). The combined organic layers were washed with brine (1×200 mL), dried over anhydrous $Na_2SO_4$. After filtration, the filtrate was concentrated under reduced pressure. The residue was purified by silica gel column chromatography, eluted with ethyl acetate/petroleum ether (1:3) to afford tert-butyl (S)-(1-(3-formylphenyl)ethyl)carbamate (5 g, 50.1%) as a light yellow solid.

LCMS Calculated for $C_{14}H_{19}NO_3$: 249.14; Observed: 250.2 $[M+H]^+$.

tert-butyl (S,E)-(1-(3-((5-oxo-2-(3-(trifluoromethyl) phenyl)oxazol-4 (5H)-ylidene)methyl)phenyl)ethyl) carbamate (38)

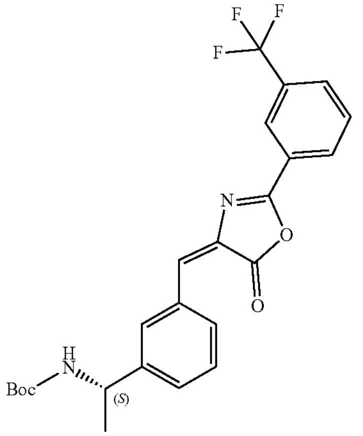

A solution of tert-butyl (S)-(1-(3-formylphenyl)ethyl)carbamate (5.00 g, 20.1 mmol, 1.00 equiv), (3-(trifluoromethyl) benzoyl)glycine (5.95 g, 24.1 mmol, 1.20 equiv), $Ac_2O$ (50 mL) and $KHCO_3$ (0.20 g, 2.01 mmol, 0.100 equiv) at room temperature. The resulting mixture was stirred at 50° C. for 4 h. The resulting mixture was diluted with EtOH (50 mL). The precipitated solids were collected by filtration and washed with EtOH (3×40 mL), to afford tert-butyl (S,E)-(1-(3-((5-oxo-2-(3-(trifluoromethyl)phenyl)oxazol-4 (5H)-ylidene)methyl)phenyl)ethyl)carbamate (3.9 g, 42.2%) as a yellow solid.

LCMS Calculated for $C_{24}H_{23}F_3N_2O_4$: 460.16; Observed: 461.3 $[M+H]^+$.

tert-butyl ((S)-1-(3-(rac-(4R,5S)-6-oxo-1-phenyl-5-(3-(trifluoromethyl)benzamido)-4,5,6,7-tetrahydro-1H-pyrazolo[3,4-b]pyridin-4-yl)phenyl)ethyl)carbamate (39)

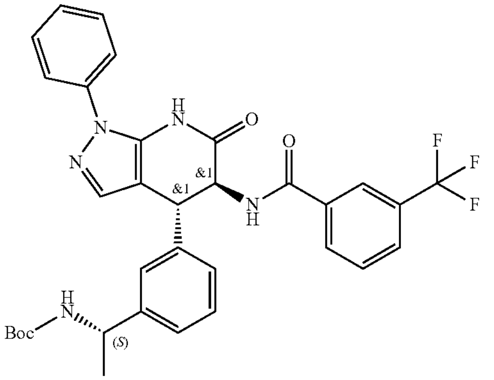

Into a 40 mL sealed tube were added tert-butyl (S,E)-(1-(3-((5-oxo-2-(3-(trifluoromethyl)phenyl)oxazol-4 (5H)-ylidene)methyl)phenyl)ethyl)carbamate (3.80 g, 8.25 mmol, 1.00 equiv), pyrazole, 1-phenyl-1H-pyrazol-5-amine (1.58 g, 9.90 mmol, 1.20 equiv), $SnCl_2$ (0.16 g, 0.825 mmol, 0.100 equiv) and t-BuOH (40 mL) at room temperature. The resulting mixture was stirred for 2 h at 100° C. The mixture was allowed to cool down to room temperature. The resulting mixture was concentrated under reduced pressure. The residue was purified by silica gel column chromatography, eluted with ethyl acetate/petroleum ether (1:1) to afford tert-butyl ((S)-1-(3-(rac-(4R,5S)-6-oxo-1-phenyl-5-(3-(trifluoromethyl)benzamido)-4,5,6,7-tetrahydro-1H-pyrazolo[3,4-b]pyridin-4-yl)phenyl)ethyl)carbamate (2.1 g, 41.07%) as a light yellow solid.

LCMS Calculated for $C_{33}H_{32}F_3N_5O_4$: 619.24; Observed: 620.3 $[M+H]^+$.

tert-butyl ((S)-1-(3-(rac-(4R,5S)-7-ethyl-6-oxo-1-phenyl-5-(3-(trifluoromethyl)benzamido)-4,5,6,7-tetrahydro-1H-pyrazolo[3,4-b]pyridin-4-yl)phenyl) ethyl)carbamate (40)

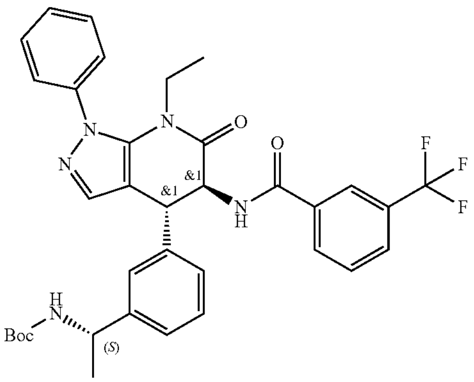

Into a 8 mL sealed tube were added tert-butyl ((S)-1-(3-(rac-(4R,5S)-6-oxo-1-phenyl-5-(3-(trifluoromethyl)benzamido)-4,5,6,7-tetrahydro-1H-pyrazolo[3,4-b]pyridin-4-yl)phenyl)ethyl)carbamate (2.00 g, 3.23 mmol, 1.00 equiv), MeCN (20 mL) were added bromoethane (0.420 g, 3.87 mmol, 1.20 equiv) and $K_3PO_4$ (1.37 g, 6.46 mmol, 2.00 equiv) at room temperature. The resulting mixture was stirred for 16 h at 50° C. The reaction was quenched with water (20 mL) at room temperature. The resulting mixture was extracted with EtOAc (2×20 mL). The combined organic layers were washed with brine (1×20 mL), dried over anhydrous $Na_2SO_4$. After filtration, the filtrate was concentrated under reduced pressure. The residue was purified by silica gel column chromatography, eluted with PE/EA (1:1) to afford tert-butyl ((S)-1-(3-(rac-(4R,5S)-7-ethyl-6-oxo-1-phenyl-5-(3-(trifluoromethyl)benzamido)-4,5,6,7-tetrahydro-1H-pyrazolo[3,4-b]pyridin-4-yl)phenyl) ethyl)carbamate (1 g, 47.8%) as a light yellow oil.

LCMS Calculated for $C_{35}H_{36}F_3N_5O_4$: 647.27; Observed: 648.4 $[M+H]^+$.

(rac-(4R,5S))-5-amino-4-(3-((S)-1-aminoethyl)phenyl)-7-ethyl-1-phenyl-1,4,5,7-tetrahydro-6H-pyrazolo[3,4-b]pyridin-6-one (41)

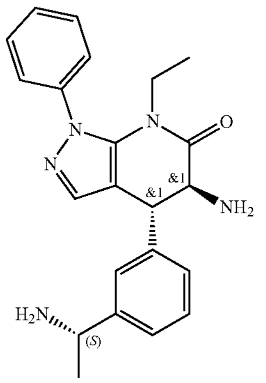

A solution of tert-butyl ((S)-1-(3-(rac-(4R,5S)-7-ethyl-6-oxo-1-phenyl-5-(3-(trifluoromethyl)benzamido)-4,5,6,7-tetrahydro-1H-pyrazolo[3,4-b]pyridin-4-yl)phenyl)ethyl)carbamate (900 mg, 1.39 mmol, 1.00 equiv) in HCl (11.9 M, 5.0 mL) and dioxane (5 mL) was stirred overnight at 100° C. The mixture was allowed to cool down to room temperature, The resulting mixture was concentrated in vacuum, diluted with $Et_2O$ (5.0 mL), filtered to afford (rac-(4R,5S))-5-amino-4-(3-((S)-1-aminoethyl)phenyl)-7-ethyl-1-phenyl-1,4,5,7-tetrahydro-6H-pyrazolo[3,4-b]pyridin-6-one (300 mg, 57.5%) as a yellow solid, which was used for next step directly.

N—((S)-1-(3-(rac-(4R,5S)-5-amino-7-ethyl-6-oxo-1-phenyl-4,5,6,7-tetrahydro-1H-pyrazolo[3,4-b]pyridin-4-yl)phenyl)ethyl)-2-((4-(oxetan-3-yl)piperazin-1-yl)methyl)acrylamide (42)

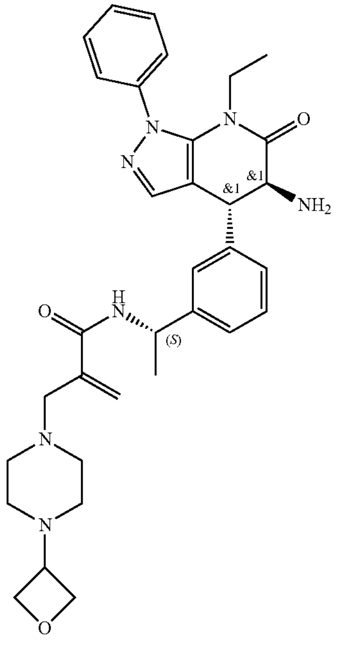

Into a 8 mL sealed tube were added (rac-(4R,5S))-5-amino-4-(3-((S)-1-aminoethyl)phenyl)-7-ethyl-1-phenyl-1,4,5,7-tetrahydro-6H-pyrazolo[3,4-b]pyridin-6-one (150 mg, 0.399 mmol, 1.00 equiv), 2-{[4-(oxetan-3-yl)piperazin-1-yl]methyl}prop-2-enoic acid (72.3 mg, 0.319 mmol, 0.800 equiv), DIEA (155 mg, 1.19 mmol, 3.00 equiv), DMF (2 mL), HATU (182 mg, 0.479 mmol, 1.20 equiv). The resulting mixture was stirred for 1 h at 0° C. The reaction was quenched with water at room temperature. The resulting mixture was extracted with EtOAc (2×20 mL). The combined organic layers were washed with brine (2×20 mL), dried over anhydrous $Na_2SO_4$. After filtration, the filtrate was concentrated under reduced pressure. The residue was purified by reversed-phase flash chromatography with the following conditions: Column: X Bridge Prep RP C18 Column, 30*150 mm, 5 m; Mobile Phase A: Water(0.1% $NH_3{\cdot}H_2O$), Mobile Phase B: ACN; Flow rate: 35 mL/min; Gradient: 62% B to 92% B in 10 min; Wave Length: 254 nm/220 nm; RT1 (min): 6.9. This resulted in N—((S)-1-(3-(rac-(4R,5S)-5-amino-7-ethyl-6-oxo-1-phenyl-4,5,6,7-tetrahydro-1H-pyrazolo[3,4-b]pyridin-4-yl)phenyl)ethyl)-2-((4-(oxetan-3-yl)piperazin-1-yl)methyl)acrylamide (77 mg, 33.%) as a white solid.

LCMS Calculated for $C_{33}H_{41}N_7O_3$: 583.33; Observed: 584.4 $[M+H]^+$.

tert-butyl ((S)-1-(3-(rac-(4R,5S)-6-oxo-1-phenyl-5-(3-(trifluoromethyl)benzamido)-4,5,6,7-tetrahydro-1H-pyrazolo[3,4-b]pyridin-4-yl)phenyl)ethyl)carbamate I-380

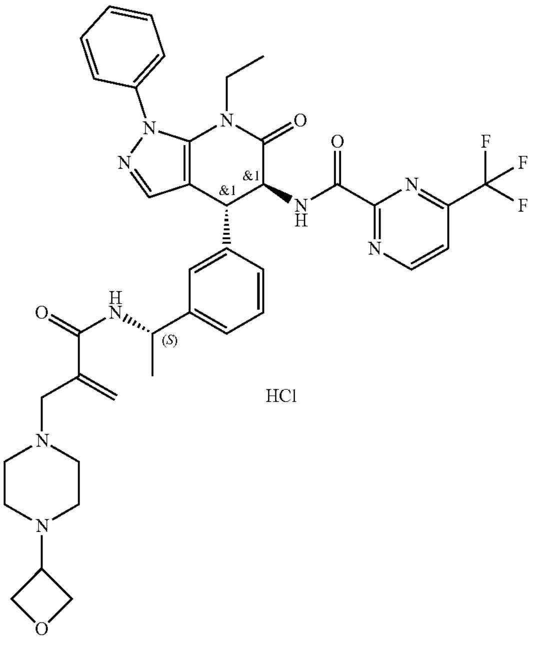

A mixture of N—((S)-1-(3-(rac-(4R,5S)-5-amino-7-ethyl-6-oxo-1-phenyl-4,5,6,7-tetrahydro-1H-pyrazolo[3,4-b]pyridin-4-yl)phenyl)ethyl)-2-((4-(oxetan-3-yl)piperazin-1-yl)methyl)acrylamide (60.0 mg, 0.103 mmol, 1.00 equiv), TEA (20.8 mg, 0.206 mmol, 2.00 equiv) and DMF (2 mL) was stirred at 0° C. for 10 min. 4-(trifluoromethyl)pyrimidine-2-carbonyl chloride (26.0 mg, 0.124 mmol, 1.20 equiv was then added, and the reaction mixture was stirred for 1 h at room temperature. The resulting mixture was concentrated in vacuum. The residue was purified by reversed-phase flash chromatography with the following conditions: Column: SunFire Prep C18 OBD Column, 30*150 mm, 5 μm; Mobile Phase A: Water(0.1% FA), Mobile Phase B: ACN; Flow rate: 35 mL/min; Gradient: isocratic 30%-60% 9 min; Wave Length: 254 nm/220 nm; RT1 (min): 7.3. This resulted in tert-butyl ((S)-1-(3-(rac-(4R,5S)-6-oxo-1-phenyl-5-(3-(trifluoromethyl)benzamido)-4, 5, 6,7-tetrahydro-1H-pyrazolo[3,4-b]pyridin-4-yl)phenyl)ethyl)carbamate (2.1 mg, 2.50%) as a yellow solid.

The following compounds were prepared using the above methodology.

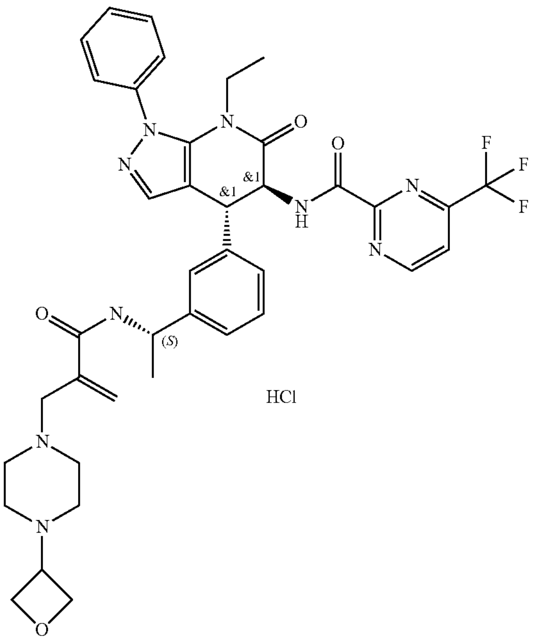

I-380

$^1$H NMR (300 MHz, DMSO-$d_6$) δ 10.45-10.25 (m, 1H), 9.69-9.12 (m, 2H), 8.83 (s, 1H), 8.21 (d, J = 5.1 Hz, 1H), 7.57-7.50 (m, 5H), 7.44-7.15 (m, 4H), 6.98 (s, 1H), 6.38-5.39 (m, 2H), 5.20 (dd, J = 12.7, 9.3 Hz, 1H), 5.00-4.77 (m, 1H), 4.63 (d, J = 12.6 Hz, 1H), 4.50 (t, J = 6.7 Hz, 2H), 4.35 (s, 1H), 3.83 (dt, J = 14.2, 7.1 Hz, 2H), 3.46 (s, 2H), 3.12-2.64 (m, 5H), 2.45-2.05 (m, 2H), 1.32 (d, J = 6.9 Hz, 3H), 0.81 (t, J = 7.0 Hz, 3H).
LCMS Calculated for $C_{39}H_{43}ClF_3N_9O_4$: 793.31; Observed (Method-B): 758.3 [M − HCl + H]$^+$, 99.7%
at RT 0.748 min.

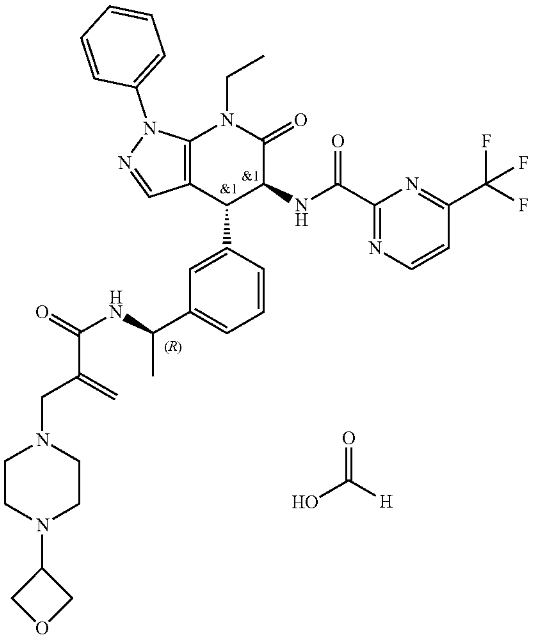

I-366 as formic acid salt

$^1$H NMR (300 MHz, DMSO-$d_6$) δ 9.43-9.21 (m, 3H), 8.33 (s, 1H), 8.20 (d, J = 5.0 Hz, 1H), 7.76-7.45 (m, 5H), 7.39-7.26 (m, 3H), 7.20 (s, 1H), 6.99 (s, 1H), 5.89 (d, J = 2.2 Hz, 1H), 5.40 (s, 1H), 5.19 (dd, J = 12.6, 9.2 Hz, 1H), 4.88 (t, J = 7.3 Hz, 1H), 4.66 (d, J = 12.7 Hz, 1H), 4.43 (t, J = 6.5 Hz, 1H), 4.39-4.23 (m, 3H), 3.89 (dd, J = 14.2, 7.1 Hz, 1H), 3.24 (s, 1H), 3.18 (s, 2H), 3.08-2.99 (m, 1H), 2.34 (s, 4H), 2.14 (s, 4H), 1.26 (d, J = 6.9 Hz, 3H), 0.84 (t, J = 7.0 Hz, 3H).
LCMS Calculated for $C_{40}H_{44}F_3N_9O_6$: 803.34; Observed (Method-C): 758.3 [M − HCOOH + H]$^+$, 99.4% at RT 0.857 min.

-continued

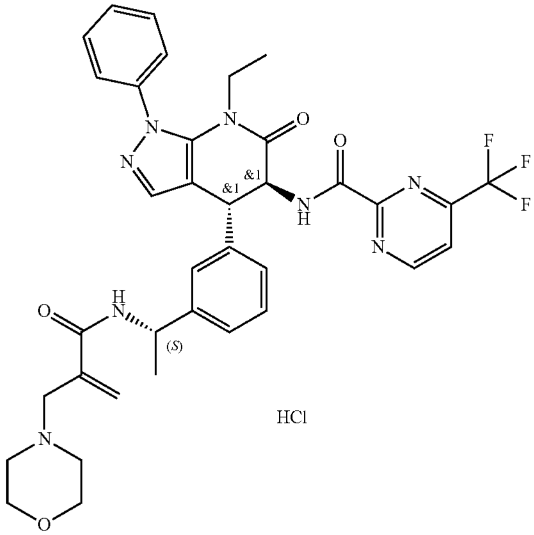

HCl

I-299

$^1$H NMR (300 MHz, DMSO-$d_6$) δ 10.10-10.05 (m, 1H), 9.55-9.18 (m, 2H), 8.87 (s, 1H), 8.22 (d, J = 5.0 Hz, 1H), 7.65-7.61 (m, 2H), 7.57-7.53 (m, 6.8 Hz, 3H), 7.37 (s, 1H), 7.32-7.18 (m, 3H), 6.98 (s, 1H), 6.31 (s, 1H), 6.06 (s, 1H), 5.21 (dd, J = 12.7, 9.3 Hz, 1H), 4.93 (t, J = 7.3 Hz, 1H), 4.64 (d, J = 12.7 Hz, 1H), 3.85 (dt, J = 13.9, 7.0 Hz, 6H), 3.19 (s, 3H), 3.03 (dt, J = 15.0, 7.6 Hz, 3H), 1.35 (d, J = 6.9 Hz, 3H), 0.82 (t, J = 7.0 Hz, 3H). LCMS Calculated for $C_{36}H_{38}ClF_3N_8O_4$: 738.27; Observed (Method-C): 703.2 [M − HCl + H]$^+$, 98.6% at RT 0.963 min.

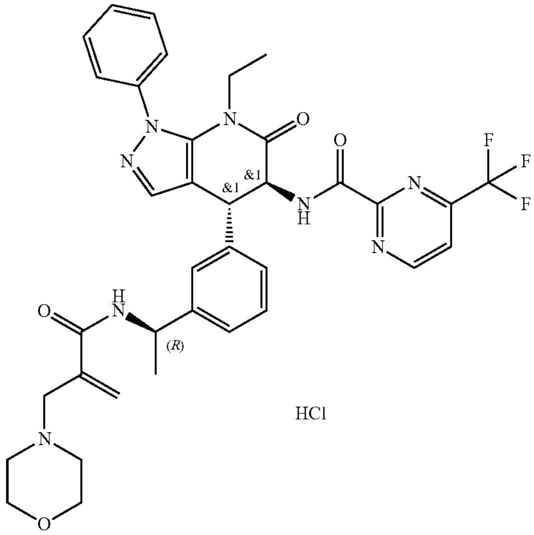

HCl

I-281

$^1$HNMR (300 MHz, DMSO-$d_6$) δ 10.67-10.65 (m, 1H), 9.50-9.14 (m, 2H), 8.90 (s, 1H), 8.20 (d, J = 5.0 Hz, 1H), 7.75-7.45 (m, 5H), 7.43-7.10 (m, 4H), 6.97 (s, 1H), 6.19 (d, J = 52.0 Hz, 2H), 5.20 (dd, J = 12.7, 9.3 Hz, 1H), 4.91 (p, J = 7.1 Hz, 1H), 4.63 (d, J = 12.6 Hz, 1H), 3.83 (tt, J = 18.9, 9.5 Hz, 6H), 3.21-2.11 (m, 3H), 3.10-2.75 (m, 3H), 1.33 (d, J = 6.9 Hz, 3H), 0.81 (t, J = 6.9 Hz, 3H). LCMS Calculated for $C_{36}H_{38}ClF_3N_8O_4$: 738.27; Observed (Method-B): 703.2 [M − HCl + H]$^+$, 99.3% at RT 0.772 min.

11. Synthesis of rac-N-((4R,5S)-4-(2-cyanoisoindolin-4-yl)-7-ethyl-6-oxo-1-phenyl-4,5,6,7-tetrahydro-1H-pyrazolo[3,4-b]pyridin-5-yl)-3-(trifluoromethyl)benzamide I-282

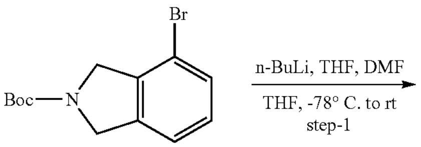

-continued

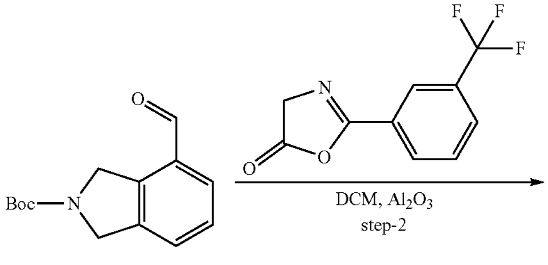

42

-continued

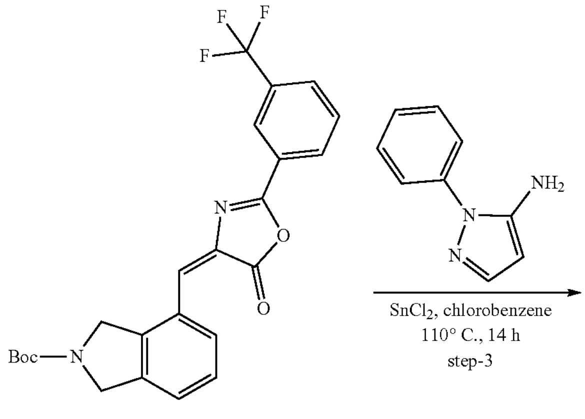

43

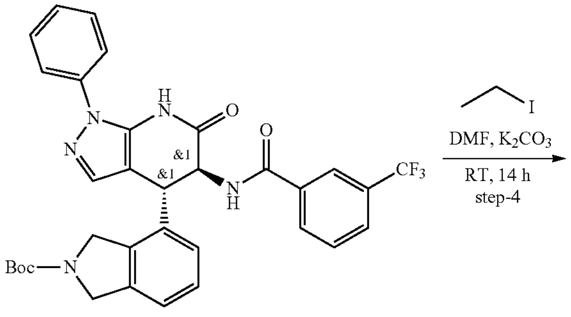

44

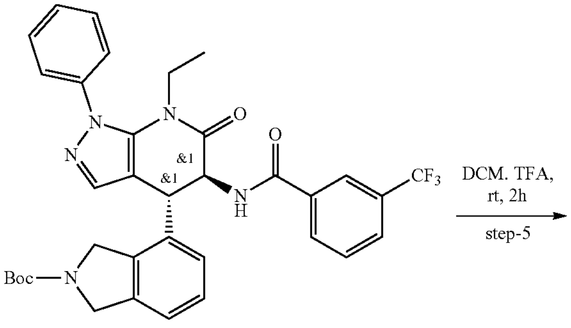

45

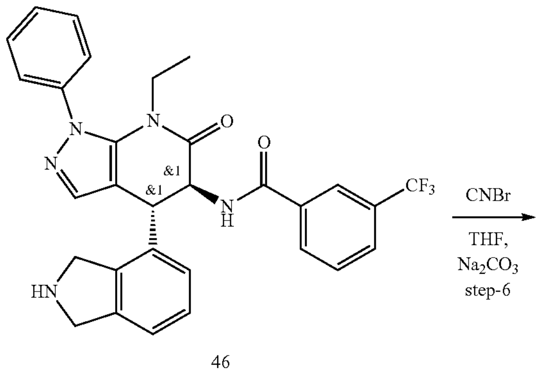

46

-continued

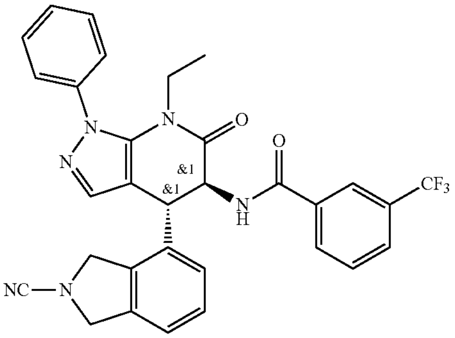

I-282

Synthesis of tert-butyl 4-formyl-1,3-dihydroisoindole-2-carboxylate (42)

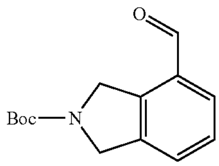 [SMILES: CC(C)(C)OC(=O)N1Cc2cccc(C=O)c2C1]

In a 500-mL round bottom flask, to a solution of tert-butyl 4-bromo-1,3-dihydroisoindole-2-carboxylate (20.0 g, 67.1 mmol, 1.00 equiv) in THF (200 mL) was added dropwise n-butyllithium solution (2.5 M in hexane, 32.2 mL, 80.5 mmol) at −78° C. under $N_2$ atmosphere. The reaction mixture was stirred at −78° C. for 30 mins. Then a solution of DMF (9.81 g, 134 mmol, 2.00 equiv) in 20 mL THF was added dropwise and the mixture was stirred for another 30 mins. The reaction was quenched with water/sat. $NH_4Cl$ (200 mL), and then the mixture was extracted with EtOAc (2×200 mL). The combined organic extracts were washed with brine (200 mL), dried over anhydrous $Na_2SO_4$, and concentrated under vacuum to yield a crude product which was directly purified by flash chromatography (EA:PE=1:1) mixture to yield tert-butyl 4-formyl-1,3-dihydroisoindole-2-carboxylate (5.3 g, 31.9%) as a light-yellow solid.

tert-butyl (E)-4-((5-oxo-2-(3-(trifluoromethyl)phenyl)oxazol-4 (5H)-ylidene)methyl) isoindoline-2-carboxylate (43)

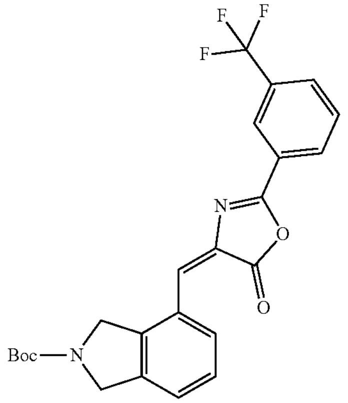 [SMILES: CC(C)(C)OC(=O)N1Cc2cccc(/C=C3/N=C(c4cccc(C(F)(F)F)c4)OC3=O)c2C1]

To a stirred mixture of 2-[3-(trifluoromethyl)phenyl]-4H-1,3-oxazol-5-one (4.91 g, 21.4 mmol, 1.00 equiv) and tert-butyl 4-formyl-1,3-dihydroisoindole-2-carboxylate (5.3 g, 21.4 mmol, 1.00 equiv) in $CHCl_3$ (100 mL) was added aluminum oxide (44.1 g, 428 mmol, 20.0 equiv) in portions at room temperature. The resulting mixture was stirred at room temperature for 2 h. The resulting mixture was filtered, the filter cake was washed with MeOH (2×200 mL). The filtrate was concentrated under reduced pressure. The crude product was re-crystallized from $Et_2O$/ethyl acetate (1:1.10 mL) to afford tert-butyl (E)-4-((5-oxo-2-(3-(trifluoromethyl) phenyl)oxazol-4 (5H)-ylidene)methyl)isoindoline-2-carboxylate (1.8 g, 18.3%) as a light yellow solid.

rac-tert-butyl 4-((4R,5S)-6-oxo-1-phenyl-5-(3-(trifluoromethyl)benzamido)-4,5,6,7-tetrahydro-1H-pyrazolo[3,4-b]pyridin-4-yl)isoindoline-2-carboxylate (44)

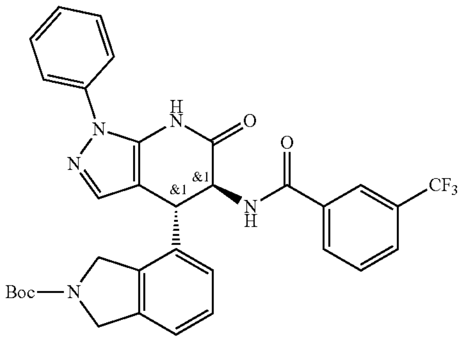 [SMILES: CC(C)(C)OC(=O)N1Cc2cccc([C@@H]3c4cnn(-c5ccccc5)c4NC(=O)[C@H]3NC(=O)c3cccc(C(F)(F)F)c3)c2C1]

Into a 40 mL vial were added pyrazole, 5-amino-1-phenyl- (0.42 g, 2.62 mmol, 1.00 equiv), tert-butyl (E)-4-((5-oxo-2-(3-(trifluoromethyl)phenyl)oxazol-4 (5H)-ylidene)methyl)isoindoline-2-carboxylate (1.20 g, 2.61 mmol, 1.00 equiv), chlorobenzene (12.0 mL) and $SnCl_2$ (0.05 g, 0.262 mmol, 0.100 equiv) at room temperature. The resulting mixture was stirred at 110° C. for 14 h. The mixture was allowed to cool down to room temperature. The resulting mixture was concentrated under reduced pressure. The residue was purified by silica gel column chromatography, eluted with ethyl acetate/petroleum ether (1:1) to afford rac-tert-butyl 4-((4R,5S)-6-oxo-1-phenyl-5-(3-(trifluoromethyl)benzamido)-4,5,6,7-tetrahydro-1H-pyrazolo[3,4-b]pyridin-4-yl)isoindoline-2-carboxylate (260 mg, 16.0%) as a yellow solid.

rac-tert-butyl 4-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)isoindoline-2-carboxylate (45)

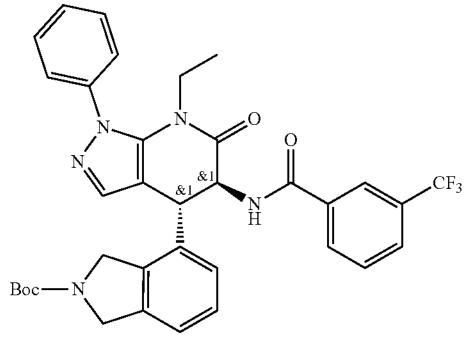 [SMILES: CCN1C(=O)[C@@H](NC(=O)c2cccc(C(F)(F)F)c2)[C@H](c2cccc3c2CN(C(=O)OC(C)(C)C)C3)c2cnn(-c3ccccc3)c21]

To a 8 mL vial were added rac-tert-butyl 4-((4R,5S)-6-oxo-1-phenyl-5-(3-(trifluoromethyl)benzamido)-4,5,6,7-tetrahydro-1H-pyrazolo[3,4-b]pyridin-4-yl)isoindoline-2-carboxylate (240 mg, 0.389 mmol, 1.00 equiv), DMF (3 mL), $K_2CO_3$ (107 mg, 0.778 mmol, 2.00 equiv) and ethyl iodide (72.7 mg, 0.467 mmol, 1.20 equiv) at room temperature. The resulting mixture was stirred at room temperature for 14 h. The resulting mixture was diluted with water (3 mL). The resulting mixture was extracted with EtOAc (2×5 mL). The combined organic layers were washed with brine (2×5 mL), dried over anhydrous $Na_2SO_4$. After filtration, the filtrate was concentrated under reduced pressure. The residue was purified by silica gel column chromatography, eluted with petroleum ether/ethyl acetate (2:1) to afford rac-tert-butyl 4-((4R,5S)-7-ethyl-6-oxo-1-phenyl-5-(3-(trifluoromethyl) benzamido)-4,5,6,7-tetrahydro-1H-pyrazolo[3,4-b]pyridin-4-yl)isoindoline-2-carboxylate (80 mg, 31.8%) as a yellow solid.

rac-N-((4R,5S)-7-ethyl-4-(isoindolin-4-yl)-6-oxo-1-phenyl-4,5,6,7-tetrahydro-1H-pyrazolo[3,4-b]pyridin-5-yl)-3-(trifluoromethyl)benzamide (46)

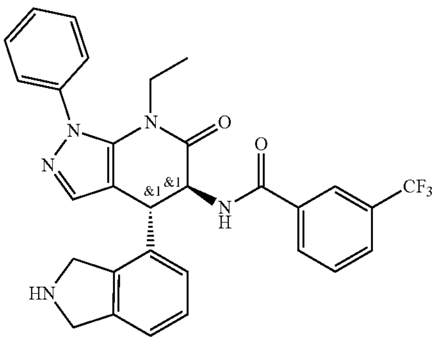 [SMILES: CCN1C(=O)[C@@H](NC(=O)c2cccc(C(F)(F)F)c2)[C@H](c2cccc3c2CNC3)c2cnn(-c3ccccc3)c21]

Into a 8 mL vial were added rac-tert-butyl 4-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)isoindoline-2-carboxylate (80.0 mg, 0.124 mmol, 1.00 equiv), DCM (1 mL) and TFA (0.3 mL) at room temperature. The resulting mixture was stirred at room temperature for 2 h. The resulting mixture was concentrated under reduced pressure. The residue was purified by silica gel column chromatography, eluted with PE/EA (0:1) to afford rac-N-((4R,5S)-7-ethyl-4-(isoindolin-4-yl)-6-oxo-1-phenyl-4,5,6,7-tetrahydro-1H-pyrazolo[3,4-b]pyridin-5-yl)-3-(trifluoromethyl)benzamide (50 mg, 73.9%) as a light yellow solid.

rac-N-((4R,5S)-4-(2-cyanoisoindolin-4-yl)-7-ethyl-6-oxo-1-phenyl-4,5,6,7-tetrahydro-1H-pyrazolo[3,4-b]pyridin-5-yl)-3-(trifluoromethyl)benzamide

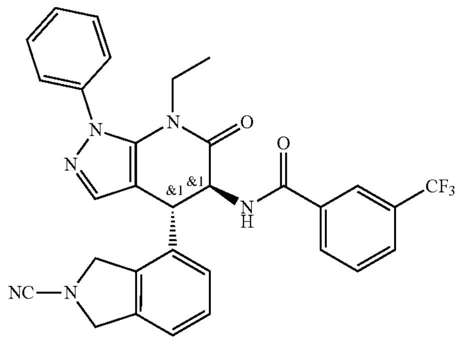 [SMILES: CCN1C(=O)[C@@H](NC(=O)c2cccc(C(F)(F)F)c2)[C@H](c2cccc3c2CN(C#N)C3)c2cnn(-c3ccccc3)c21]

Into a 8 mL vial were added rac-N-((4R,5S)-7-ethyl-4-(isoindolin-4-yl)-6-oxo-1-phenyl-4,5,6,7-tetrahydro-1H-pyrazolo[3,4-b]pyridin-5-yl)-3-(trifluoromethyl)benzamide (50.0 mg, 0.092 mmol, 1.00 equiv), THE (1 mL), $Na_2CO_3$ (19.4 mg, 0.184 mmol, 2.00 equiv) and cyanogen bromide (11.6 mg, 0.110 mmol, 1.20 equiv) at room temperature. The resulting mixture was stirred at room temperature for 2 h. The resulting mixture was concentrated under reduced pressure. The residue was purified by reversed-phase flash chromatography with the following conditions: column, C18 silica gel; mobile phase, MeCN in Water (0.1% FA), 10% to 50% gradient in 10 min; detector, UV 254 nm. This resulted in rac-N-((4R,5S)-4-(2-cyanoisoindolin-4-yl)-7-ethyl-6-oxo-1-phenyl-4,5,6,7-tetrahydro-1H-pyrazolo[3,4-b]pyridin-5-yl)-3-(trifluoromethyl)benzamide (25 mg, 47.8%) as a white solid.

$^1$H NMR (400 MHz, DMSO-$d_6$) δ 9.01 (d, J=9.1 Hz, 1H), 8.05-7.99 (m, 2H), 7.92 (d, J=7.8 Hz, 1H), 7.73 (d, J=8.0 Hz, 1H), 7.70-7.65 (m, 2H), 7.64-7.50 (m, 3H), 7.32 (d, J=6.8 Hz, 2H), 7.27-7.19 (m, 1H), 7.02 (s, 1H), 5.37 (dd, J=12.8, 9.1 Hz, 1H), 4.93 (s, 2H), 4.80 (d, J=13.0 Hz, 1H), 4.75 (d, J=12.9 Hz, 1H), 4.36 (d, J=12.8 Hz, 1H), 3.82 (dq, J=14.2, 7.0 Hz, 1H), 3.09 (dq, J=13.8, 6.7 Hz, 1H), 0.84 (t, J=7.0 Hz, 3H).

LCMS Calculated for $C_{31}H_{25}F_3N_6O_2$: 570.20; Observed (Method-AP): 571.3 $[M+H]^+$, 96.8% at RT 1.709 min.

12. Synthesis of N-((4R,5S)-7-ethyl-4-(3-((3-methyl-3-(methyl(oxetan-3-yl)amino)-2-methylenebutanamido)methyl)phenyl)-6-oxo-1-phenyl-4,5,6,7-tetrahydro-1H-pyrazolo[3,4-b]pyridin-5-yl)-2-(trifluoromethyl)thiazole-4-carboxamide I-231

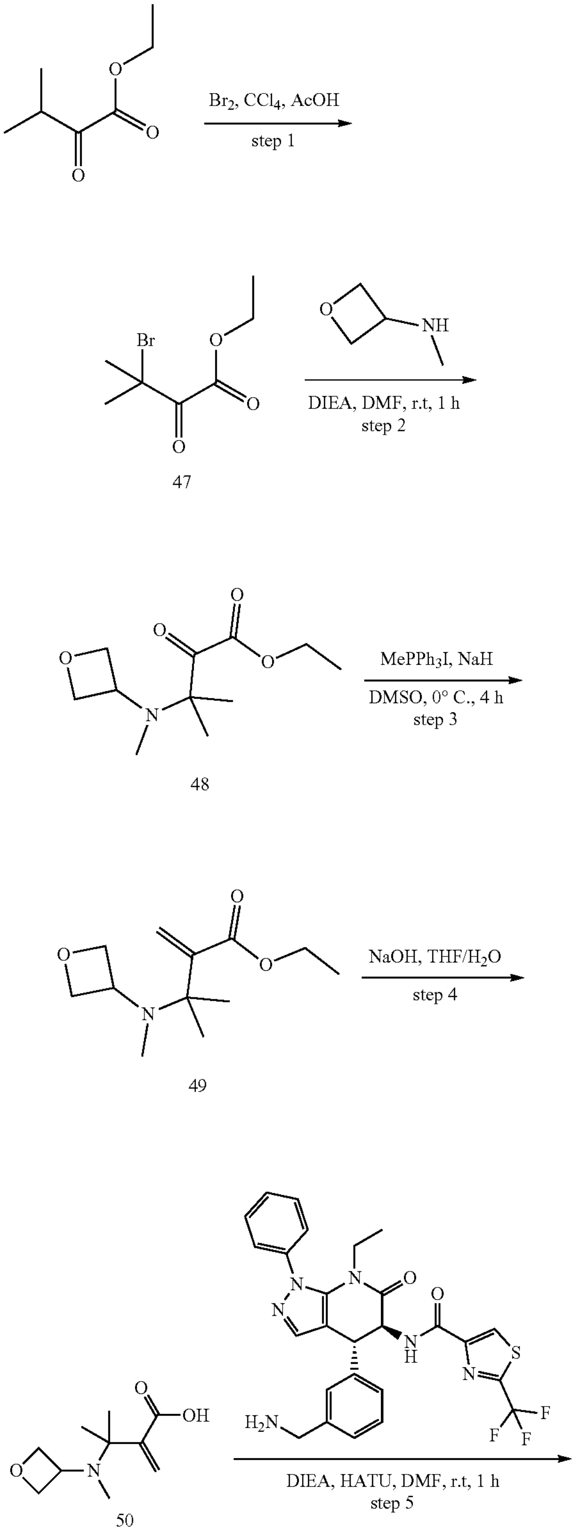

-continued

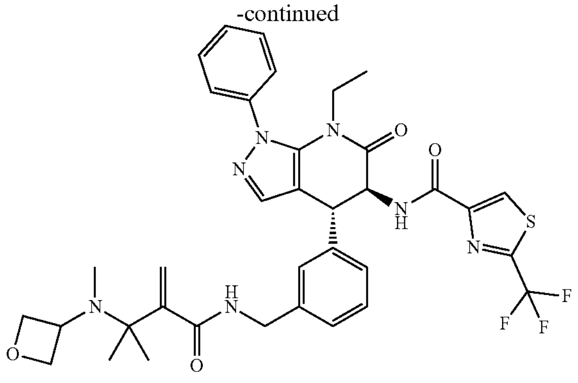

I-231 ethyl 3-bromo-3-methyl-2-oxobutanoate (47)

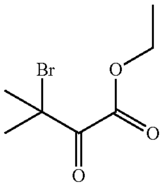

Into a 50 ml three-necked flask, 15 mL of $CCl_4$ were placed. Thereto, ethyl 3-methyl-2-oxobutanoate (6.00 g, 41.6 mmol, 1.00 equiv) was added, followed by $Br_2$ (6.65 g, 41.6 mmol, 1.00 equiv). Then AcOH (2.50 g, 41.6 mmol, 1.00 equiv) was used for acidification. After decoloring the solution, the reaction was quenched using 30 ml of sat. $NaHCO_3$ solution, and the mixture was transferred into a separating funnel. There, 100 ml diethyl ether and another 20 ml of $NaHCO_3$ were added. The aqueous layer was discarded, and the organic layer was re-extracted with 50 ml of $NaHCO_3$. The ether layer was washed with sat. NaCl, dried over anhydrous $Na_2SO_4$. After filtration, the filtrate was concentrated under reduced pressure to afford ethyl 3-bromo-3-methyl-2-oxobutanoate (6.2 g, 99.1% purity) as a colorless oil.

ethyl 3-methyl-3-(methyl(oxetan-3-yl)amino)-2-oxobutanoate (48)

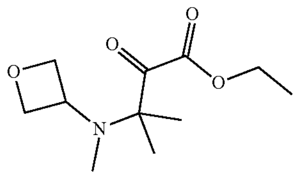 [SMILES: CCOC(=O)C(=O)C(C)(C)N(C)C1COC1]

To a stirred solution DMF (15 mL) of ethyl 3-bromo-3-methyl-2-oxobutanoate (1.00 g, 4.48 mmol, 1.00 equiv) and N-methyloxetan-3-amine (0.47 g, 5.38 mmol, 1.20 equiv), DIEA (1.74 g, 13.4 mmol, 3.00 equiv) at room temperature. The resulting mixture was stirred for 2 hours at room temperature. The mixture was diluted with water (30.0 mL) and the mixture was extracted with EtOAc (30 mL×2). The combined organic phase was washed with brine (50 mL), dried over anhydrous sodium sulfate, filtered and concentrated in vacuum. The residue was purified by silica gel chromatography, eluted with PE:EA=3:1 to afford ethyl 3-methyl-3-(methyl(oxetan-3-yl)amino)-2-oxobutanoate (800 mg, 95.3% purity) as a colorless oil.

LCMS Calculated for $C_{11}H_9NO_4$: 229.13. Observed: 230.2 $[M+H]^+$.

ethyl 3-methyl-3-(methyl(oxetan-3-yl)amino)-2-methylenebutanoate (49)

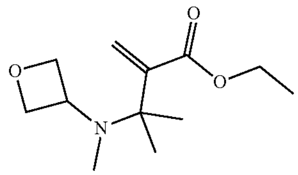 [SMILES: C=C(C(=O)OCC)C(C)(C)N(C)C1COC1]

To a stirred solution of DMSO (20 mL) were added NaH (183 mg, 4.58 mmol, 1.50 equiv, 60%), ethyl 3-methyl-3-[methyl(oxetan-3-yl)amino]-2-oxobutanoate (700 mg, 3.05 mmol, 1.00 equiv) at room temperature. The resulting mixture was at room temperature for 30 min, methyltriphenylphosphanium iodide (1.85 g, 4.58 mmol, 1.50 equiv) was added. The resulting mixture was at room temperature for 16 h. The mixture was diluted with water (30.0 mL) and the mixture was extracted with EtOAc (30 mL×2). The combined organic phase was washed with brine (100 mL), dried over anhydrous sodium sulfate, filtered and concentrated in vacuum. The residue was purified by silica gel chromatography, eluted with petroleum ether/ethyl acetate=3:1 to afford ethyl 3-methyl-3-[methyl(oxetan-3-yl)amino]-2-methylidenebutanoate (180 mg, 96.3% purity) as a white solid.

LCMS Calculated for $C_{12}H_{21}NO_3$: 227.15. Observed: 228.2 $[M+H]^+$.

3-methyl-3-(methyl(oxetan-3-yl)amino)-2-methylenebutanoic acid (50)

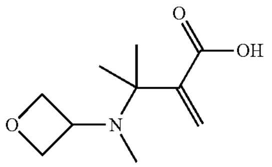

To a solution of THF $H_2O$=(4:1, 5 mL) were added ethyl 3-methyl-3-[methyl(oxetan-3-yl)amino]-2-methylidenebutanoate (100 mg, 0.440 mmol, 1.00 equiv) and NaOH (70.3 mg, 1.760 mmol, 4.00 equiv) at room temperature. The resulting mixture was stirred for 1 hour at room temperature. The mixture was acidified neutralized to pH 2-3 with 1 N HCl. The precipitated solids were collected by filtration and washed with water (50 mL). This resulted in 3-methyl-3-[methyl(oxetan-3-yl)amino]-2-methylidenebutanoic acid (52 mg crude) as a white solid.

N-((4R,5S)-7-ethyl-4-(3-((3-methyl-3-(methyl (oxetan-3-yl)amino)-2-methylenebutanamido) methyl)phenyl)-6-oxo-1-phenyl-4,5,6,7-tetrahydro-1H-pyrazolo[3,4-b]pyridin-5-yl)-2-(trifluoromethyl) thiazole-4-carboxamide I-231

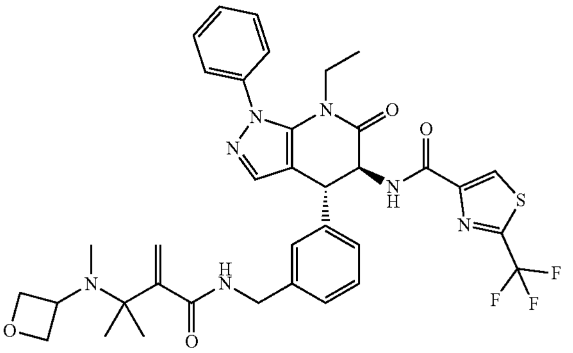 [SMILES: C=C(C(=O)NCc1cccc([C@@H]2c3cnn(-c4ccccc4)c3N(CC)C(=O)[C@H]2NC(=O)c2csc(C(F)(F)F)n2)c1)C(C)(C)N(C)C1COC1]

Into a 8 mL vial were added 3-methyl-3-[methyl(oxetan-3-yl)amino]-2-methylidenebutanoic acid (66.3 mg, 0.332 mmol, 1.20 equiv), DIEA (107 mg, 0.831 mmol, 3.00 equiv) and HATU (126 mg, 0.332 mmol, 1.20 equiv) in DMF (1 mL) at room temperature. The mixture was stirred at 0° C. for 10 minute, N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-2-(trifluoromethyl)thiazole-4-carboxamide (150 mg, 0.277 mmol, 1.00 equiv) was added and the mixture was allowed to stirred for 1 hour at 0° C. The reaction was purified by Column: YMC-Actus Triart C18 Column, 50*250 mm, 5 m; Mobile Phase A: Water (10 mmol/L $NH_4HCO_3$), Mobile Phase B: ACN; Flow rate: 90 mL/min; Gradient: 45% B to 75% B in 16 min; Wave Length: 254 nm/220 nm; RT1 (min): 10. This resulted in N-((4R,5S)-7-ethyl-4-(3-((3-methyl-3-(methyl(oxetan-3-yl) amino)-2-methylenebutanamido)methyl)phenyl)-6-oxo-1-phenyl-4,5,6,7-tetrahydro-1H-pyrazolo[3,4-b]pyridin-5-yl)-2-(trifluoromethyl)thiazole-4-carboxamide (7.00 mg, 91.6% purity) as a white solid.

$^1$H NMR (400 MHz, DMSO-$d_6$) δ 9.54 (t, J=5.8 Hz, 1H), 8.82 (d, J=9.3 Hz, 1H), 8.62 (s, 1H), 8.41 (s, 2H), 7.66-7.48 (m, 4H), 7.35-7.24 (m, 3H), 7.21-7.14 (m, 1H), 6.90 (s, 1H), 5.81 (d, J=1.3 Hz, 1H), 5.34 (d, J=1.4 Hz, 1H), 5.20 (dd, J=13.0, 9.3 Hz, 1H), 4.60 (d, J=12.8 Hz, 1H), 4.44-4.35 (m, 2H), 4.35-4.27 (m, 3H), 4.11-4.01 (m, 1H), 3.90-3.80 (m, 1H), 3.06-2.96 (m, 1H), 2.14 (s, 3H), 1.06 (s, 6H), 0.82 (t, J=7.0 Hz, 3H).

LCMS Calculated for: $C_{36}H_{38}F_3N_7O_4S$: 721.27; Observed (Method-A): 722.2[M+H]$^+$, 91.64% at RT 1.275 min.

The following compounds were prepared using the above methodology.

| | |
|---|---|
| 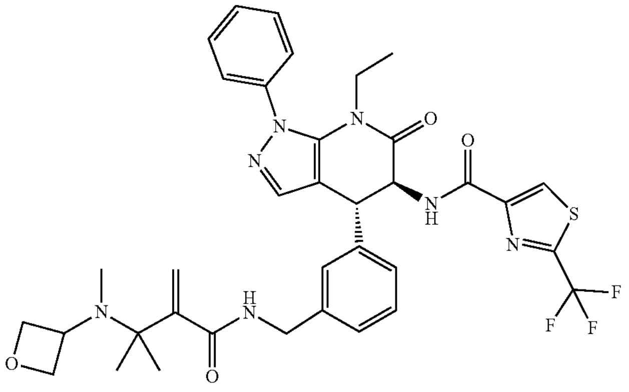 [SMILES: C=C(C(=O)NCc1cccc([C@@H]2c3cnn(-c4ccccc4)c3N(CC)C(=O)[C@H]2NC(=O)c2csc(C(F)(F)F)n2)c1)C(C)(C)N(C)C1COC1]<br>I-231 | $^1$H NMR (400 MHz, DMSO-$d_6$) δ 9.54 (t, J = 5.8 Hz, 1H), 8.82 (d, J = 9.3 Hz, 1H), 8.62 (s, 1H), 8.41 (s, 2H), 7.66-7.48 (m, 4H), 7.35-7.24 (m, 3H), 7.21-7.14 (m, 1H), 6.90 (s, 1H), 5.81 (d, J = 1.3 Hz, 1H), 5.34 (d, J = 1.4 Hz, 1H), 5.20 (dd, J= 13.0, 9.3 Hz, 1H), 4.60 (d, J = 12.8 Hz, 1H), 4.44-4.35 (m, 2H), 4.35-4.27 (m, 3H), 4.11-4.01 (m, 1H), 3.90-3.80 (m, 1H), 3.06-2.96 (m, 1H), 2.14 (s, 3H), 1.06 (s, 6H), 0.82 (t, J = 7.0 Hz, 3H).<br>LCMS Calculated for $C_{36}H_{38}F_3N_7O_4S$: 721.27; Observed (Method-A): 722.2 [M + H]$^+$, 91.64% at RT 1.275min. |
| 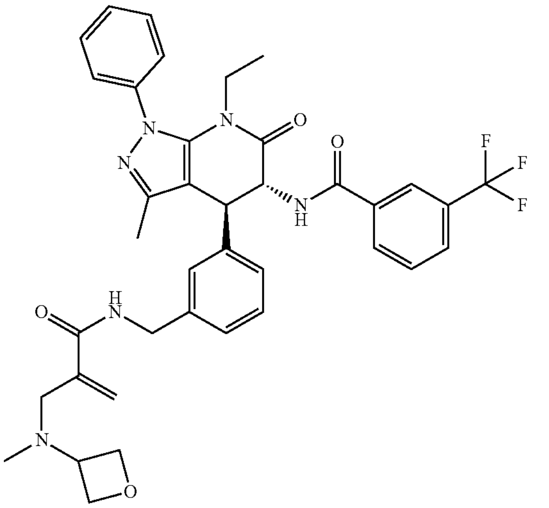 | $^1$H NMR (400 MHz, DMSO-$d_6$) δ 9.00 (d, J = 8.9 Hz, 1H), 8.87-8.81 (m, 1H), 8.08-8.00 (m, 2H), 7.91 (d, J = 8.0 Hz, 1H), 7.74-7.69 (m, 1H), 7.67-7.63 (m, 2H), 7.62-7.57 (m, 2H), 7.56-7.53 (m, 1H), 7.36 (s, 1H), 7.33-7.28 (m, 2H), 7.24-7.20 (m, 1H), 7.04 (s, 1H), 5.81 (s, 1H), 5.44 (s, 1H), 5.23-5.14 (m, 1H), 4.48-4.31 (m, 7H), 3.92-3.76 (m, 1H), 3.54-3.46 (m, 1H), 3.04 (s, 3H), 1.97 (s, 3H), 0.82 (t, J = 7.0 Hz, 3H).<br>LCMS Calculated for: $C_{37}H_{37}F_3N_6O_4$: 686.28; Observed (Method-B): 687.5 [M + H]$^+$, 97.06% at RT 0.850 min.<br>Chiral HPLC (Method-F): 100% at RT 0.44 min. |

-continued

I-154

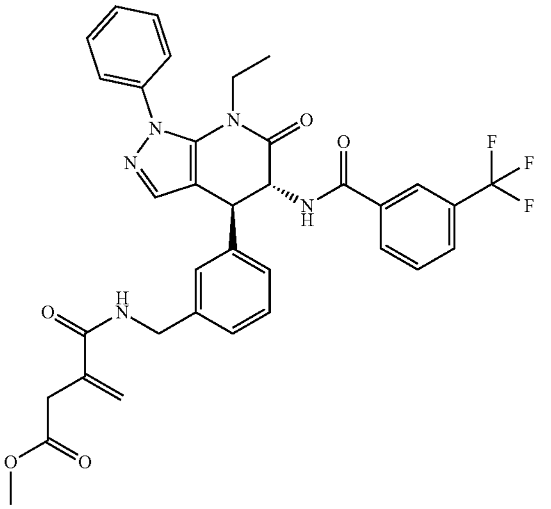 [SMILES: C=C(CC(=O)OC)C(=O)NCc1cccc([C@H]2c3cnn(-c4ccccc4)c3N(CC)C(=O)[C@@H]2NC(=O)c2cccc(C(F)(F)F)c2)c1]

$^1H$ NMR (400 MHz, DMSO-$d_6$) δ 9.00 (d, J = 9.0 Hz, 1H), 8.64 (t, J = 6.0 Hz, 1H), 8.09-8.00 (m, 2H), 7.91 (d, J = 7.8 Hz, 1H), 7.75-7.69 (m, 1H), 7.68-7.64 (m, 2H), 7.62-7.51 (m, 3H), 7.35-7.25 (m, 3H), 7.18-7.12 (m, 2H), 7.04 (s, 1H), 5.88 (s, 1H), 5.53 (s, 1H), 5.18 (dd, J = 12.8, 8.9 Hz, 1H), 4.40 (d, J = 12.8 Hz, 1H), 4.31 (d, J = 6.0 Hz, 2H), 3.90-3.77 (m, 2H), 3.55 (s, 3H), 3.13-3.00 (m, 1H), 0.83 (t, J = 7.0 Hz, 3H).
LCMS Calculated for: $C_{35}H_{32}F_3N_5O_5$: 659.24; Observed (Method-AJ): 660.2 $[M + H]^+$, 99.96% at RT 1.454 min.
Chiral HPLC (Method-F): 99.73% at RT 0.942 min.

I-121

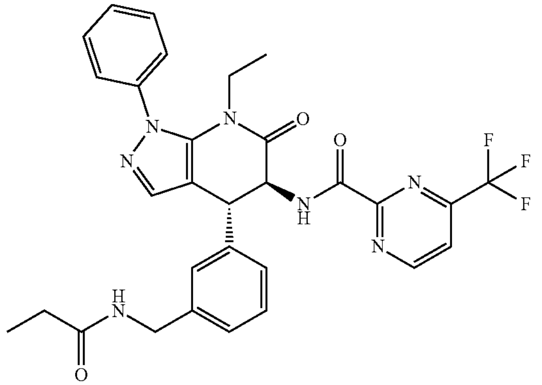 [SMILES: CCC(=O)NCc1cccc([C@@H]2c3cnn(-c4ccccc4)c3N(CC)C(=O)[C@H]2NC(=O)c2nccc(C(F)(F)F)n2)c1]

$^1H$ NMR (300 MHz, $CDCl_3$) δ 9.14 (d, J = 5.1 Hz, 1H), 8.38 (d, J = 7.2 Hz, 1H), 7.78 (d, J = 4.8 Hz, 1H), 7.76-7.45 (m, 6H), 7.31-7.15 (m, 3H), 6.18-6.08 (m, 1H), 5.54-5.48 (m, 1H), 4.53-4.46 (m, 2H), 4.44-4.23 (m, 1H), 4.06-3.92 (m, 1H), 3.23-3.18 (m, 1H), 2.45-2.33 (m, 2H), 1.28-1.23 (m, 3H), 0.99-0.95 (m, 3H).
LCMS Calculated for $C_{30}H_{28}F_3N_7O_3$: 591.22; Observed (Method-B): 592.1 $[M + H]^+$, 96.4% at RT 1.022 min.

I-350

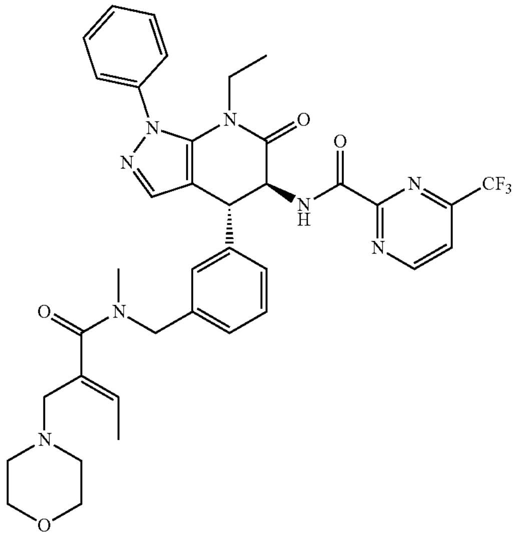 [SMILES: C/C=C(\CN1CCOCC1)C(=O)N(C)Cc1cccc([C@@H]2c3cnn(-c4ccccc4)c3N(CC)C(=O)[C@H]2NC(=O)c2nccc(C(F)(F)F)n2)c1]

$^1H$ NMR (300 MHz, DMSO-$d_6$) δ 9.35-9.28 (m, J = 5.8 Hz, 2H), 8.24-8.18 (m, J = 5.1 Hz, 1H), 7.70-7.48 (m, J = 25.1, 8.7 Hz, 5H), 7.28 (d, J = 13.9 Hz, 3H), 7.18 (s, 1H), 7.03-6.96 (m, J = 6.9 Hz, 1H), 5.74 (d, J = 7.0 Hz, 1H), 5.40-4.94 (m, 1H), 4.63 (d, J = 12.8 Hz, 1H), 4.52 (s, 2H), 3.94-3.74 (m, 1H), 3.53-3.42 (m, 4H),3.17-2.97 (m, 3H), 2.73 (s, 3H), 2.33 (s,4H), 1.81-1.35 (m, 3H), 0.83 (t, J = 7.0 Hz, 3H).
LCMS Calculated for $C_{37}H_{39}F_3N_8O_4$: 716.30; Observed (Method-J): 717.4 $[M + H]^+$, 96.1% at RT 1.631.

I-326

-continued

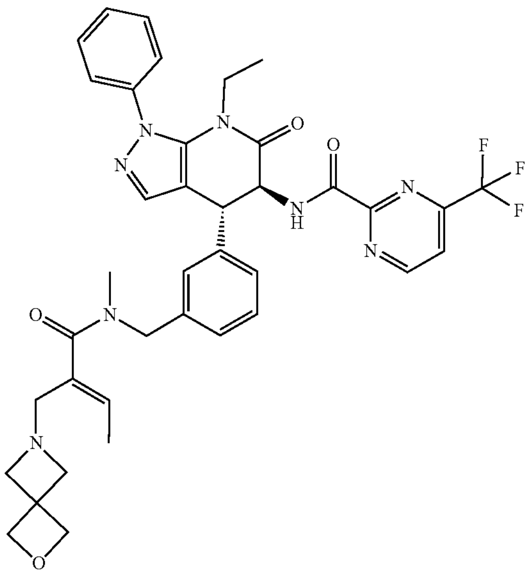 [SMILES: C/C=C(\CN1CC2(COC2)C1)C(=O)N(C)Cc1cccc([C@@H]2c3cnn(-c4ccccc4)c3N(CC)C(=O)[C@H]2NC(=O)c2nccc(C(F)(F)F)n2)c1]

I-235

$^1$H NMR (300 MHz, DMSO-$d_6$) δ 9.36-9.26 (m, 2H), 8.22 (d, J = 5.1 Hz, 1H), 7.73-7.50 (m, 5H), 7.33-7.23 (m, 3H), 7.20-7.14 (m, 1H), 7.01 (s, 1H), 5.67-5.56 (m, 1H), 5.23 (dd, J = 12.8, 9.3 Hz, 1H), 4.62 (d, J = 12.8 Hz, 1H), 4.55-4.47 (m, 6H), 3.94-3.81 (m, 1H), 3.25-3.11 (m, 7H), 2.80-2.53 (m, 3H), 1.32-1.18 (m, 3H), 0.82 (t, J = 7.1 Hz, 3H). Calculated for $C_{38}H_{39}F_3N_8O_4$: 728.30; Observed (Method-J): 729.4 $[M + H]^+$, 95.3% at RT 1.335 min.

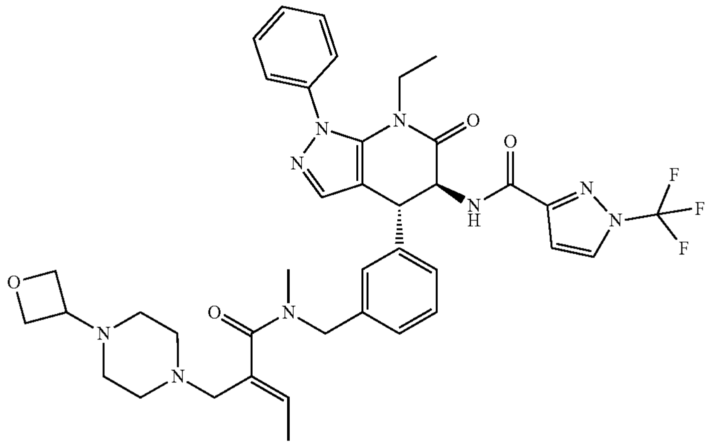 [SMILES: C/C=C(\CN1CCN(C2COC2)CC1)C(=O)N(C)Cc1cccc([C@@H]2c3cnn(-c4ccccc4)c3N(CC)C(=O)[C@H]2NC(=O)c2ccn(C(F)(F)F)n2)c1]

I-237

$^1$H NMR (300 MHz, DMSO-$d_6$) δ 8.78 (d, J = 9.2 Hz, 1H), 8.58 (d, J = 2.9 Hz, 1H), 7.68-7.50 (m, 5H), 7.35-7.15 (m, 4H), 6.97 (s, 1H), 6.89 (d, J = 2.8 Hz, 1H), 5.74 (d, J = 7.1 Hz, 1H), 5.24-5.11 (m, 1H), 4.59-4.31 (m, 6H), 3.98-3.75 (m, 1H), 3.24-2.91 (m, 2H), 2.84-2.68 (m, 2H), 2.64-2.54 (m, 1H), 2.45-2.01 (m, 8H), 1.79-1.61 (m, 3H), 1.28-1.21 (m, 3H), 0.82 (t, J = 7.0 Hz, 3H). LCMS Calculated for $C_{39}H_{44}F_3N_9O_4$: 759.84; Observed (Method-C): 760.85 $[M + H]^+$, 90.6% at RT 0.856 min.

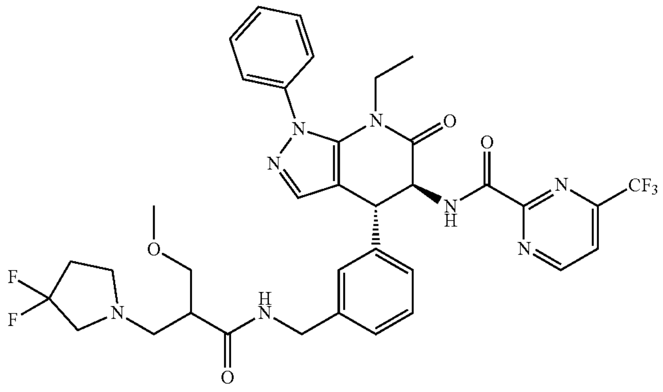 [SMILES: CCN1C(=O)[C@@H](NC(=O)c2nccc(C(F)(F)F)n2)[C@H](c2cccc(CNC(=O)C(COC)CN3CCC(F)(F)C3)c2)c2cnn(-c3ccccc3)c21]

I-360

$^1$H NMR (300 MHz, DMSO-$d_6$) δ 9.36-9.23 (m, 2H), 8.44-8.36 (m, 1H), 8.21 (d, J = 5.1 Hz, 1H), 7.69-7.47 (m, 5H), 7.32-7.16 (m, 4H), 6.97 (d, J = 1.6 Hz, 1H), 5.22 (dd, J = 12.8, 9.2 Hz, 1H), 4.63 (d, J = 12.8 Hz, 1H), 4.42-4.28 (m, 1H), 4.26-4.12 (m, 1H), 3.86 (dd, J = 14.2, 7.1 Hz, 1H), 3.49-3.37 (m, 1H), 3.19 (d, J = 2.2 Hz, 3H), 3.12-2.87 (m, 2H), 2.76-2.63 (m, 6H), 2.41-2.35 (m, 1H), 2.25-2.08 (m, 2H), 0.83 (t, J = 6.9 Hz, 3H). Calculated for: $C_{36}H_{37}F_5N_8O_4$: 740.29; Observed (Method-J): 741.4 $[M + H]^+$, 100.0% at RT 1.677 min.

-continued

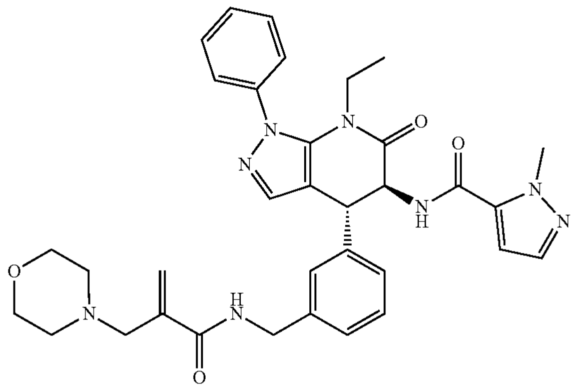 [SMILES: C=C(CN1CCOCC1)C(=O)NCc1cccc([C@@H]2c3cnn(-c4ccccc4)c3N(CC)C(=O)[C@H]2NC(=O)c2ccnn2C)c1]

$^1$H NMR (400 MHz, DMSO-$d_6$) δ 9.01 (t, J = 5.9 Hz, 1H), 8.78 (d, J = 9.1 Hz, 1H), 7.69-7.49 (m, 5H), 7.47-7.18 (m, 15H), 7.00 (s, 1H), 6.78 (d, J = 2.1 Hz, 1H), 5.91 (d, J = 1.9 Hz, 1H), 5.46 (s, 1H), 5.10 (dd, J = 12.8, 9.0 Hz, 1H), 4.43-4.29 (m, 3H), 3.91 (s, 3H), 3.86-3.76 (m, 1H), 3.50-3.41 (m, 4H), 3.17 (s, 2H), 3.05 (dq, J = 13.9, 6.8 Hz, 1H), 2.31 (t, J = 4.4 Hz, 4H), 0.81 (t, J = 7.0 Hz, 3H). LCMS Calculated for $C_{34}H_{38}N_8O_4$: 622.3; Observed (Method-J): 623.4 [M + H]$^+$, 99.4% at RT 1.465 min.

I-266

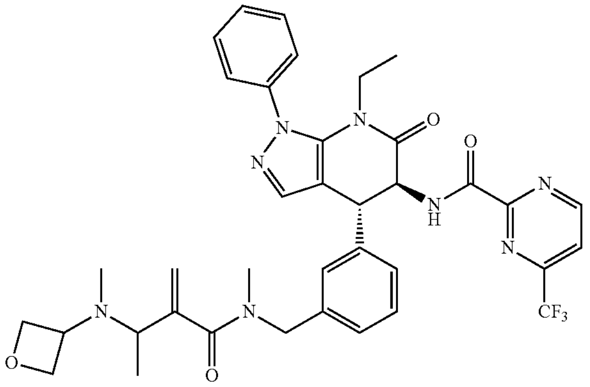 [SMILES: C=C(C(=O)N(C)Cc1cccc([C@@H]2c3cnn(-c4ccccc4)c3N(CC)C(=O)[C@H]2NC(=O)c2nccc(C(F)(F)F)n2)c1)C(C)N(C)C1COC1]

$^1$H NMR (400 MHz, DMSO-$d_6$) δ 9.31-9.24 (m, 2H), 8.29 (s, 2H), 8.19 (d, J = 4.9 Hz, 1H), 7.64 (d, J = 7.7 Hz, 2H), 7.56-7.52 (m, 3H), 7.35-7.11 (m, 4H), 6.98 (d, J = 4.2 Hz, 1H), 5.26-5.20 (m, 2H), 4.71-4.27 (m, 6H), 3.94-3.70 (m, 1H), 3.49 (d, J = 6.8 Hz, 1H), 3.01 (s, 1H), 2.70 (dd, J = 32.8, 7.1 Hz, 2H), 2.58 (d, J = 24.3 Hz, 1H), 2.03-1.86 (m, 3H), 1.67 (s, 1H), 1.01-0.94 (m, 3H), 0.81 (t, J = 7.0 Hz, 3H). LCMS Calculated for $C_{37}H_{39}F_3N_8O_4$: 716.30; Observed (Method-A): 717.1 [M + H]$^+$, 99.0% at RT 1.582 min.

I-345

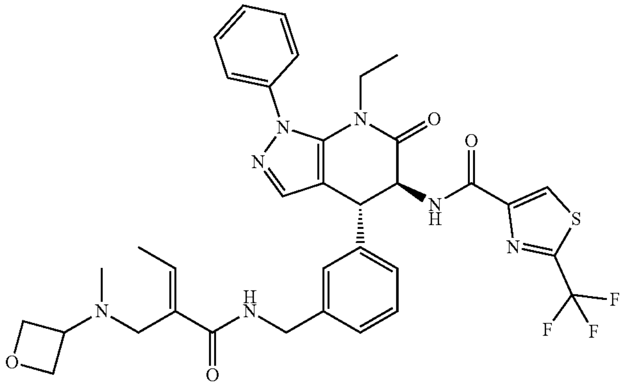 [SMILES: C/C=C(\CN(C)C1COC1)C(=O)NCc1cccc([C@@H]2c3cnn(-c4ccccc4)c3N(CC)C(=O)[C@H]2NC(=O)c2csc(C(F)(F)F)n2)c1]

$^1$H NMR (300 MHz, DMSO-$d_6$) δ 8.83 (d, J = 8.9 Hz, 2H), 8.62 (s, 1H), 7.60 (q, J = 8.3 Hz, 5H), 7.38-7.09 (m, 4H), 6.94 (s, 1H), 5.19 (dd, J = 13.0, 9.3 Hz, 1H), 4.60 (d, J = 12.8 Hz, 2H), 4.37 (s, 5H), 3.94-3.78 (m, 1H), 3.52 (s, 1H), 3.15-2.91 (m, 2H), 2.10-1.67 (m, 6H), 0.82 (t, J = 6.9 Hz, 3H). LCMS Calculated for $C_{35}H_{36}F_3N_7O_4S$: 707.2; Observed (Method A): 708.4 [M + H]$^+$, 98.6% at RT 1.906 min.

I-365

-continued

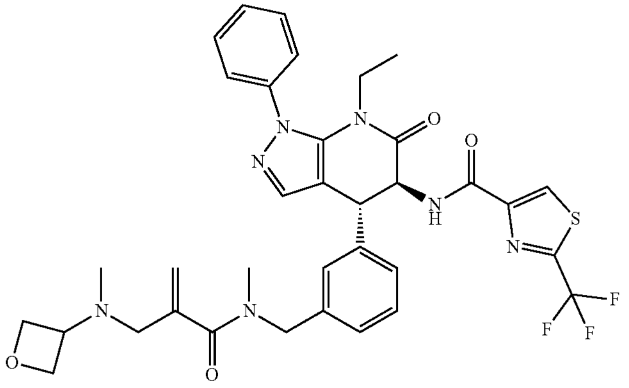 [SMILES: C=C(CN(C)C1COC1)C(=O)N(C)Cc1cccc([C@@H]2c3cnn(-c4ccccc4)c3N(CC)C(=O)[C@H]2NC(=O)c2csc(C(F)(F)F)n2)c1]

I-318

$^1$H NMR (300 MHz, DMSO-$d_6$) δ 8.61 (d, J = 9.2 Hz, 1H), 8.53 (s, 1H), 7.64-7.45 (m, 5H), 7.37-7.20 (m, 3H), 7.18 (t, J = 4.8 Hz, 1H), 6.98 (s, 1H), 5.74 (s, 1H), 5.56 (s, 1H), 5.21-5.03 (m, 1H), 4.72-4.49 (m, 7H), 4.22 (s, 1H), 3.90-3.79 (m, 1H), 3.14-3.03 (m, 1H), 2.81 (s, 3H), 2.51 (d, J = 10.2 Hz, 3H), 0.84 (t, J = 7.0 Hz, 3H).
LCMS Calculated for $C_{35}H_{36}F_3N_7O_4S$: 707.3; Observed (Method B): 708.4 $[M + H]^+$, 91.1% at RT 1.881 min.

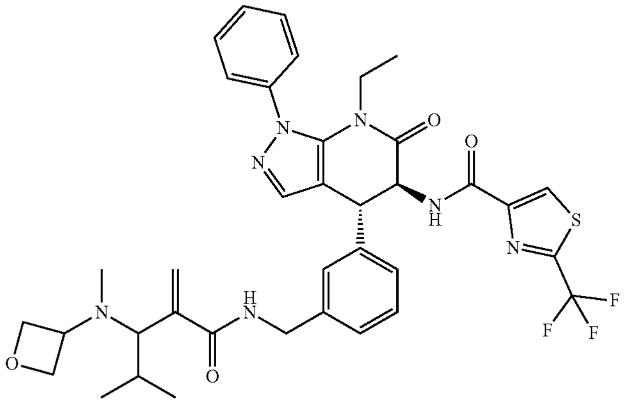 [SMILES: C=C(C(=O)NCc1cccc([C@@H]2c3cnn(-c4ccccc4)c3N(CC)C(=O)[C@H]2NC(=O)c2csc(C(F)(F)F)n2)c1)C(C(C)C)N(C)C1COC1]

I-352

$^1$H NMR (400 MHz, DMSO-$d_6$) δ 8.83 (dd, J = 9.3, 3.5 Hz, 1H), 8.63 (s, 1H), 8.57 (q, J = 6.2 Hz, 1H), 7.66-7.49 (m, 5H), 7.35-7.23 (m, 3H), 7.17 (d, J = 7.2 Hz, 1H), 6.96 (d, J = 1.9 Hz, 1H), 5.85 (d, J = 4.9 Hz, 1H), 5.24 (s, 1H), 5.21-5.14 (m, 1H), 4.61 (d, J = 12.9 Hz, 1H), 4.41-4.16 (m, 6H), 3.91-3.82 (m, 1H), 3.58 (q, J = 7.0 Hz, 1H), 3.08-2.96 (m, 2H), 2.05-1.94 (m, 1H), 1.91 (d, J = 7.5 Hz, 3H), 0.95 (t, J = 6.5 Hz, 3H), 0.86-0.79 (m, 3H), 0.74 (d, J = 6.4 Hz, 3H).
LCMS Calculated for $C_{37}H_{40}F_3N_7O_4S$: 735.28; Observed (Method-D): 736.4 $[M + H]^+$, 99.2% at RT 1.791 min.

13. Synthesis of N-((4R,5S)-7-ethyl-4-(3-((E)-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)-4-(trifluoromethyl)pyrimidine-2-carboxamide I-232

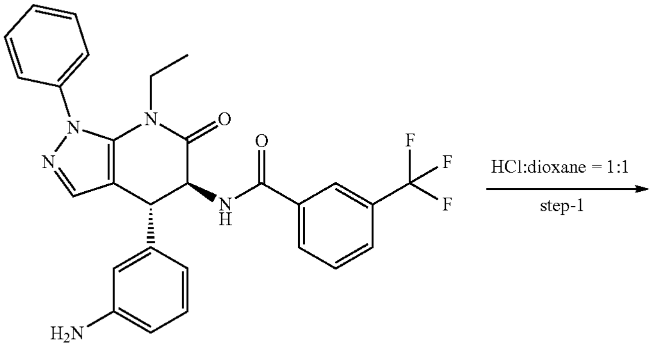

CY-2011325

-continued
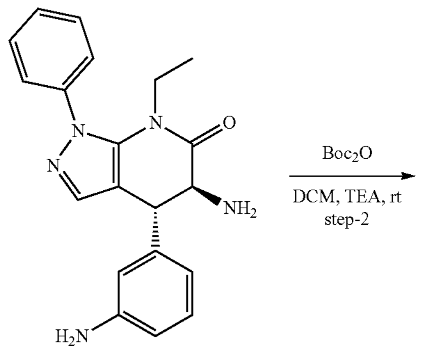
51
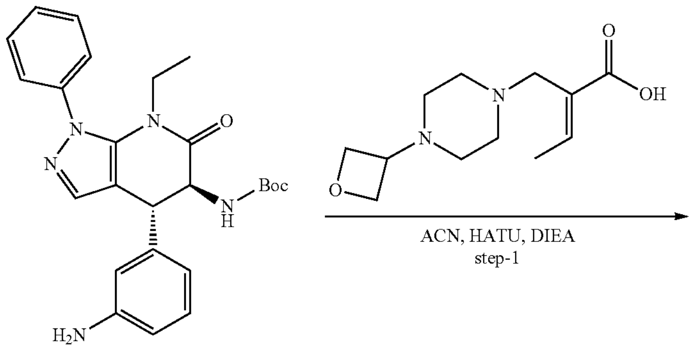
52
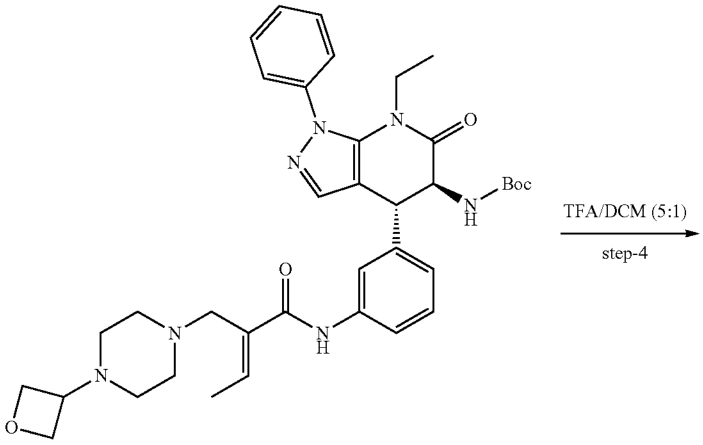
53

-continued

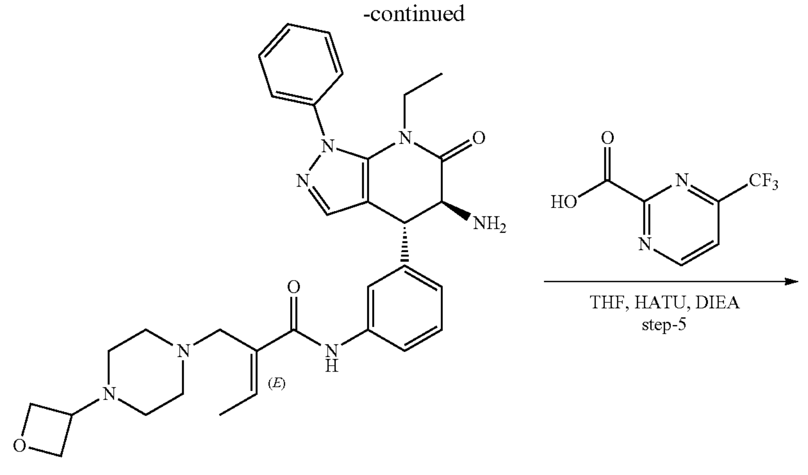

54

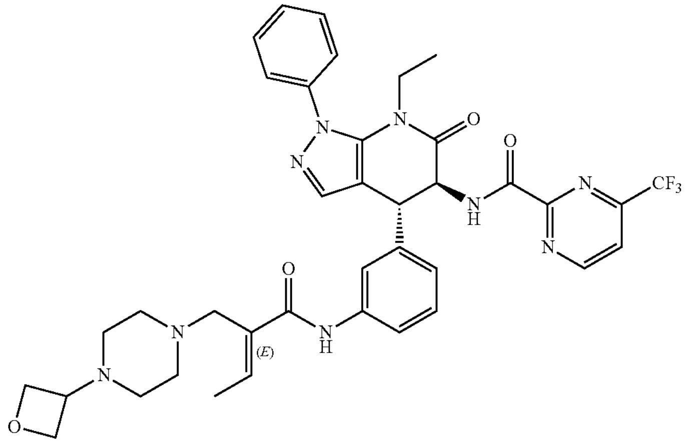

I-232

(4R,5S)-5-amino-4-(3-aminophenyl)-7-ethyl-1-phenyl-1,4,5,7-tetrahydro-6H-pyrazolo[3,4-b]pyridin-6-one (51)

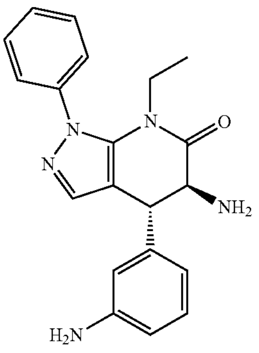 [SMILES: CCN1C(=O)[C@@H](N)[C@H](c2cccc(N)c2)c2cnn(-c3ccccc3)c21]

A solution of N-((4R,5S)-4-(3-aminophenyl)-7-ethyl-6-oxo-1-phenyl-4,5,6,7-tetrahydro-1H-pyrazolo[3,4-b]pyridin-5-yl)-3-(trifluoromethyl)benzamide (5.00 g, 1.71 mmol, 1.00 equiv) in HCl (50 mL) and dioxane (50 mL) was stirred at 100° C. for 48 h. The mixture was allowed to cool down to room temperature. The resulting mixture was concentrated in vacuum, diluted with $Et_2O$ (50 mL), filtered to afford (4R,5S)-5-amino-4-(3-aminophenyl)-7-ethyl-1-phenyl-1,4,5,7-tetrahydro-6H-pyrazolo[3,4-b]pyridin-6-one (5 g, curde) as a yellow solid, which was used for next step directly.

LCMS Calculated for $C_{20}H_{21}N_5O$: 347.1; Observed (Method B): 348.2 [M+H], 64.6% at RT 1.298 min.

tert-butyl ((4R,5S)-4-(3-aminophenyl)-7-ethyl-6-oxo-1-phenyl-4,5,6,7-tetrahydro-1H-pyrazolo[3,4-b]pyridin-5-yl)carbamate (52)

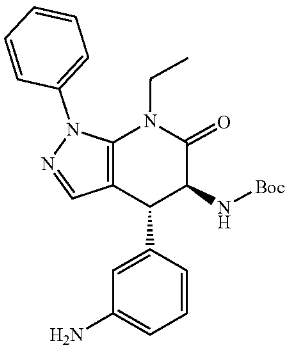 [SMILES: CCN1C(=O)[C@@H](NC(=O)OC(C)(C)C)[C@H](c2cccc(N)c2)c2cnn(-c3ccccc3)c21]

Into a 50 mL round-bottom flask was added (4R,5S)-5-amino-4-(3-aminophenyl)-7-ethyl-1-phenyl-1,4,5,7-tetrahydro-6H-pyrazolo[3,4-b]pyridin-6-one (2.00 g, curde), DCM (20 mL), $Boc_2O$ (0.75 g, 3.45 mmol, 1.20 equiv) and TEA (0.87 g, 8.65 mmol, 3.00 equiv) at room temperature. The resulting mixture was stirred for 2 h at room temperature. The reaction was quenched with Water (100 mL) at room temperature. The resulting mixture was extracted with DCM (2×50 mL). The combined organic layers were washed with brine (2×50 mL), dried over anhydrous $Na_2SO_4$. After filtration, the filtrate was concentrated under reduced pressure. The residue was purified by silica gel column chromatography, eluted with ethyl acetate/petroleum ether (1:1) to afford tert-butyl ((4R,5S)-4-(3-aminophenyl)-7-ethyl-6-oxo-1-phenyl-4,5,6,7-tetrahydro-1H-pyrazolo[3,4-b]pyridin-5-yl)carbamate (700 mg, 34.9%) as a yellow solid.

LCMS Calculated for $C_{25}H_{29}N_5O_3$: 447.2; Observed (Method B): 448.2 $[M+H]^+$, 83.6% at RT 1.435 min.

tert-butyl ((4R,5S)-7-ethyl-4-(3-((E)-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)carbamate (53)

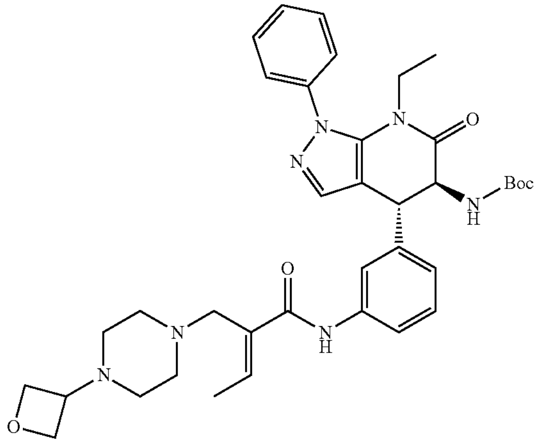 [SMILES: C/C=C(\CN1CCN(C2COC2)CC1)C(=O)Nc1cccc([C@@H]2c3cnn(-c4ccccc4)c3N(CC)C(=O)[C@H]2NC(=O)OC(C)(C)C)c1]

Into a 40 mL vial were added tert-butyl ((4R,5S)-4-(3-aminophenyl)-7-ethyl-6-oxo-1-phenyl-4,5,6,7-tetrahydro-1H-pyrazolo[3,4-b]pyridin-5-yl)carbamate (400 mg, 0.89 mmol, 1.00 equiv), ACN (10 mL), HATU (510 mg, 1.34 mmol, 1.50 equiv), (E)-2-((4-(oxetan-3-yl)piperazin-1-yl)methyl)but-2-enoic acid (1.10 g, 4.47 mmol, 5.00 equiv) and DIEA (231 mg, 1.79 mmol, 2.00 equiv) at room temperature. The reaction was quenched by the addition of water (20 mL) at room temperature. The resulting mixture was extracted with EtOAc (3×10 mL). The combined organic layers were washed with brine (2×20 mL), dried over anhydrous $Na_2SO_4$. After filtration, the filtrate was concentrated under reduced pressure. The residue was purified by silica gel column chromatography, eluted with PE/EA (1:1) to afford tert-butyl ((4R,5S)-7-ethyl-4-(3-((E)-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)carbamate (120 mg, 20% yield, 99.3% purity) as a white solid.

LCMS Calculated for $C_{37}H_{47}N_7O_5$: 669.36; Observed (Method B): 670.3 $[M+H]^+$, 99.39% at RT 0.758 min.

(E)-N-(3-((4R,5S)-5-amino-7-ethyl-6-oxo-1-phenyl-4,5,6,7-tetrahydro-1H-pyrazolo[3,4-b]pyridin-4-yl)phenyl)-2-((4-(oxetan-3-yl)piperazin-1-yl)methyl)but-2-enamide (54)

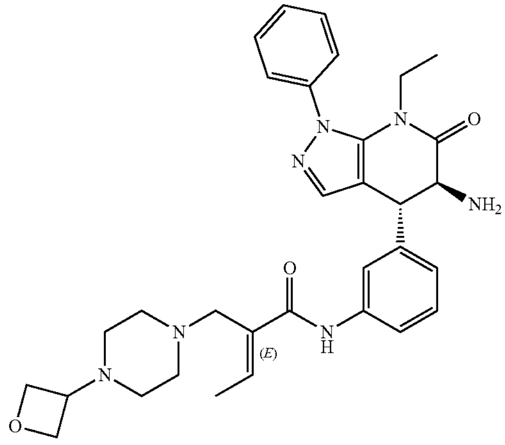 [SMILES: C/C=C(\CN1CCN(C2COC2)CC1)C(=O)Nc1cccc([C@@H]2c3cnn(-c4ccccc4)c3N(CC)C(=O)[C@H]2N)c1]

Into a 8 mL vial were added tert-butyl ((4R,5S)-7-ethyl-4-(3-((E)-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)carbamate (120 mg, 0.18 mmol, 1.0 equiv) and DCM (1 mL) at room temperature. To the above mixture was added trifluoroacetic acid (0.2 mL) dropwise over 1 min at 0° C. The resulting mixture was stirred at 0° C. for additional 2 h. The resulting mixture was concentrated under reduced pressure. This resulted in (E)-N-(3-((4R,5S)-5-amino-7-ethyl-6-oxo-1-phenyl-4,5,6,7-tetrahydro-1H-pyrazolo[3,4-b]pyridin-4-yl)phenyl)-2-((4-(oxetan-3-yl)piperazin-1-yl)methyl)but-2-enamide (100 mg) as an off-white solid.

LCMS Calculated for $C_{32}H_{39}N_7O_3$: 569.31; Observed (Method-B): 570.3 $[M+H]^+$, 100% at RT 0.525 min.

N-((4R,5S)-7-ethyl-4-(3-((E)-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)-4-(trifluoromethyl)pyrimidine-2-carboxamide

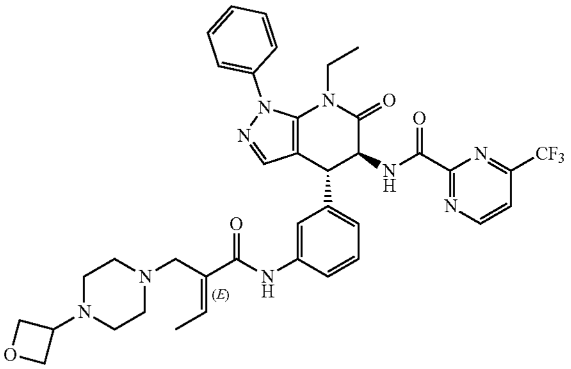 [SMILES: C/C=C(\CN1CCN(C2COC2)CC1)C(=O)Nc1cccc([C@@H]2c3cnn(-c4ccccc4)c3N(CC)C(=O)[C@H]2NC(=O)c2nccc(C(F)(F)F)n2)c1]

A solution of (E)-N-(3-((4R,5S)-5-amino-7-ethyl-6-oxo-1-phenyl-4,5,6,7-tetrahydro-1H-pyrazolo[3,4-b]pyridin-4-yl)phenyl)-2-((4-(oxetan-3-yl)piperazin-1-yl)methyl)but-2-enamide (30.0 mg, 0.05 mmol, 1.00 equiv), 4-(trifluoromethyl)pyrimidine-2-carboxylic acid (10.0 mg, 0.050 mmol, 1.00 equiv), DIEA (14 mg, 0.11 mmol, 2.0 equiv) and HATU (24 mg, 0.06 mmol, 1.2 equiv) in THE (1 mL) was stirred at room temperature for 2 h. The reaction was quenched by the addition of Water (1 mL) at room temperature. The residue was purified by reversed-phase flash chromatography with the following conditions: Column: Xselsect CSH OBD F-Phenyl Column, 30*150 mm, 5 μm; Mobile Phase A: Water(0.1% FA), Mobile Phase B: ACN; Flow rate: 35 mL/min; Gradient: isocratic 20%-35% 10 min; Wave Length: 254 nm/220 nm; RT1 (min): 9.4, to afford N-((4R,5S)-7-ethyl-4-(3-((E)-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)-4-(trifluoromethyl)pyrimidine-2-carboxamide (12 mg, 30% yield, 99.8% purity) as a white solid.

The following compounds were prepared using the above methodology

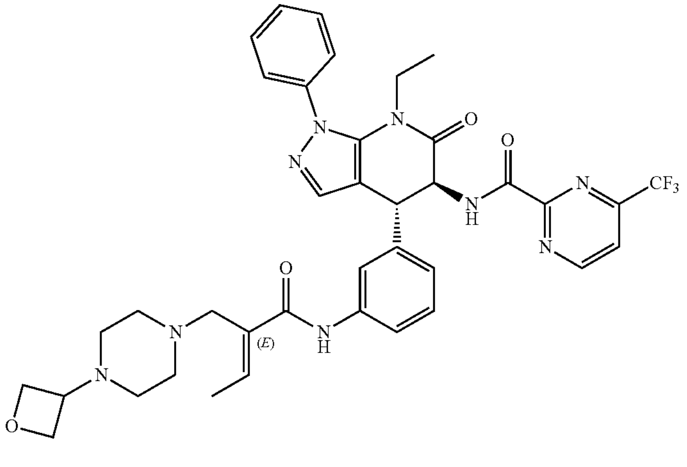 [SMILES: C/C=C(\CN1CCN(C2COC2)CC1)C(=O)Nc1cccc([C@@H]2c3cnn(-c4ccccc4)c3N(CC)C(=O)[C@H]2NC(=O)c2nccc(C(F)(F)F)n2)c1]

I-232

$^1$H NMR (400 MHZ, Acetonitrile-$d_3$) δ 11.64 (s, 1H), 9.16 (d, J = 5.0 Hz, 1H), 8.50 (d, J = 9.5 Hz, 1H), 7.92 (d, J = 5.1 Hz, 1H), 7.69-7.44 (m, 7H), 7.26 (t, J = 8.2 Hz, 1H), 7.17-7.04 (m, 2H), 6.91 (q, J = 7.2 Hz, 1H), 5.26 (dd, J = 12.9, 9.6 Hz, 1H), 4.52-4.29 (m, 5H), 3.95 (dq, J = 14.3, 7.2 Hz, 1H), 3.43-3.35 (m, 1H), 3.33 (s, 2H), 3.11 (dq, J = 13.9, 6.9 Hz, 1H), 2.93-2.40 (m, 8H), 1.83 (d, J = 7.2 Hz, 3H), 0.89 (t, J = 7.0 Hz, 3H).
LCMS Calculated for $C_{38}H_{40}F_3N_9O_4$: 743.32; Observed (Method-B): 744.3 $[M + H]^+$, 99.8% at RT 0.861 min.

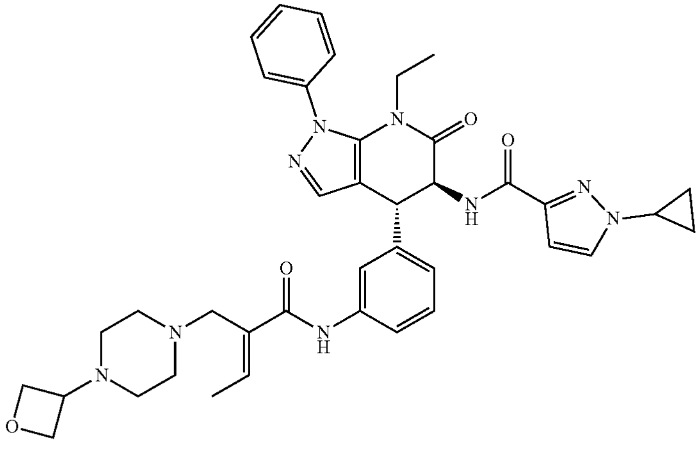 [SMILES: C/C=C(\CN1CCN(C2COC2)CC1)C(=O)Nc1cccc([C@@H]2c3cnn(-c4ccccc4)c3N(CC)C(=O)[C@H]2NC(=O)c2ccn(C3CC3)n2)c1]

I-233

$^1$H NMR (400 MHZ, Acetonitrile-$d_3$) δ 11.64 (s, 1H), 7.68-7.44 (m, 8H), 7.36 (d, J = 9.6 Hz, 1H), 7.28 (t, J = 7.8 Hz, 1H), 7.08 (dt, J = 7.7, 1.4 Hz, 1H), 7.05 (s, 1H), 6.94 (d, J = 7.2 Hz, 1H), 6.52 (d, J = 2.4 Hz, 1H), 5.19 (dd, J = 13.0, 9.6 Hz, 1H), 4.49-4.23 (m, 5H), 3.92 (dd, J = 14.3, 7.1 Hz, 1H), 3.67 (tt, J = 7.4, 3.8 Hz, 1H), 3.39 (p, J = 6.3 Hz, 1H), 3.34 (s, 2H), 3.09 (dd, J = 14.1, 7.0 Hz, 1H), 2.79-2.24 (m, 8H), 1.84 (d, J = 7.2 Hz, 3H), 1.14-1.08 (m, 2H), 1.04-0.96 (m, 2H), 0.87 (t, J = 7.0 Hz, 3H).
LCMS Calculated for $C_{39}H_{45}N_9O_4$: 703.36; Observed (Method-E): 704.5 $[M + H]^+$, 97.5% at RT 0.639 min.

-continued

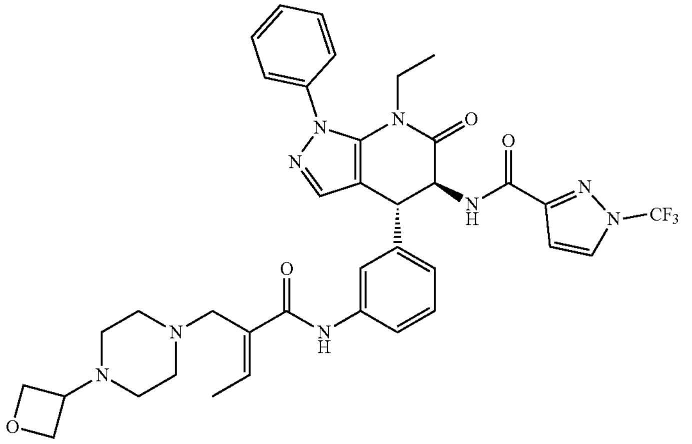 [SMILES: C/C=C(\CN1CCN(C2COC2)CC1)C(=O)Nc1cccc([C@@H]2c3cnn(-c4ccccc4)c3N(CC)C(=O)[C@H]2NC(=O)c2ccn(C(F)(F)F)n2)c1]

$^1$H NMR (400 MHZ, Acetonitrile-$d_3$) δ 11.65 (s, 1H), 8.08 (d, J = 2.8 Hz, 1H), 7.66-7.47 (m, 8H), 7.29 (t, J = 7.8 Hz, 1H), 7.08 (d, J = 12.1 Hz, 2H), 6.94 (d, J = 7.3 Hz, 1H), 6.80 (d, J = 2.8 Hz, 1H), 5.21 (dd, J = 13.0, 9.5 Hz, 1H), 4.50-4.32 (m, 5H), 3.93 (dd, J = 14.3, 7.2 Hz, 1H), 3.39 (q, J = 6.2 Hz, 1H), 3.34 (s, 2H), 3.09 (dd, J = 14.1, 7.0 Hz, 1H), 2.85-2.19 (m, 8H), 1.84 (d, J = 7.2 Hz, 3H), 0.88 (t, J = 7.0 Hz, 3H).
LCMS Calculated for $C_{37}H_{40}F_3N_9O_4$: 731.32; Observed (Method B): 732.3 [M + H]$^+$, 99.4% at RT 1.478 min.

I-383

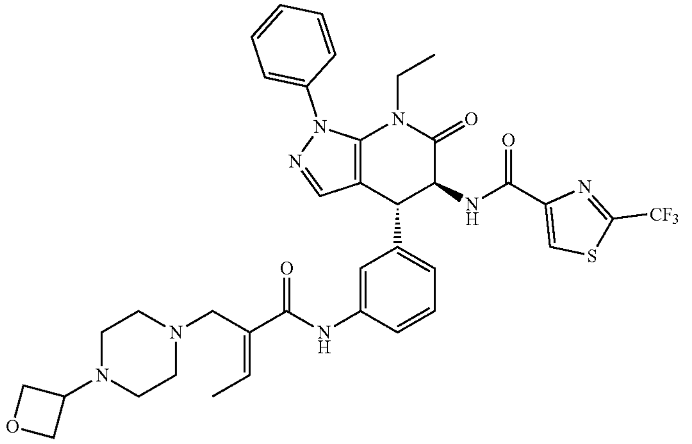 [SMILES: C/C=C(\CN1CCN(C2COC2)CC1)C(=O)Nc1cccc([C@@H]2c3cnn(-c4ccccc4)c3N(CC)C(=O)[C@H]2NC(=O)c2csc(C(F)(F)F)n2)c1]

$^1$H NMR (400 MHZ, Acetonitrile-$d_3$) δ 11.64 (s, 1H), 8.25 (s, 1H), 7.94 (d, J = 9.5 Hz, 1H), 7.70-7.46 (m, 7H), 7.29 (t, J = 7.8 Hz, 1H), 7.16-7.02 (m, 2H), 6.93 (d, J = 7.2 Hz, 1H), 5.19 (dd, J = 13.0, 9.5 Hz, 1H), 4.54-4.31 (m, 5H), 3.94 (dd, J = 14.3, 7.2 Hz, 1H), 3.39 (p, J = 6.2 Hz, 1H), 3.34 (s, 2H), 3.10 (dd, J = 14.2, 7.0 Hz, 1H), 2.81-2.26 (m, 8H), 1.83 (d, J = 7.3 Hz, 3H), 0.89 (t, J = 7.1 Hz, 3H).
LCMS Calculated for $C_{37}H_{39}F_3N_8O_4S$: 748.28; Observed (Method B): 749.2 [M + H]$^+$, 99.1% at RT 1.377 min.

I-234

14. Synthesis of N-((4R,5S)-4-(3-((E)-2-((6-oxa-3-azabicyclo[3.1.1]heptan-3-yl)methyl)but-2-enamido)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide I-337

-continued

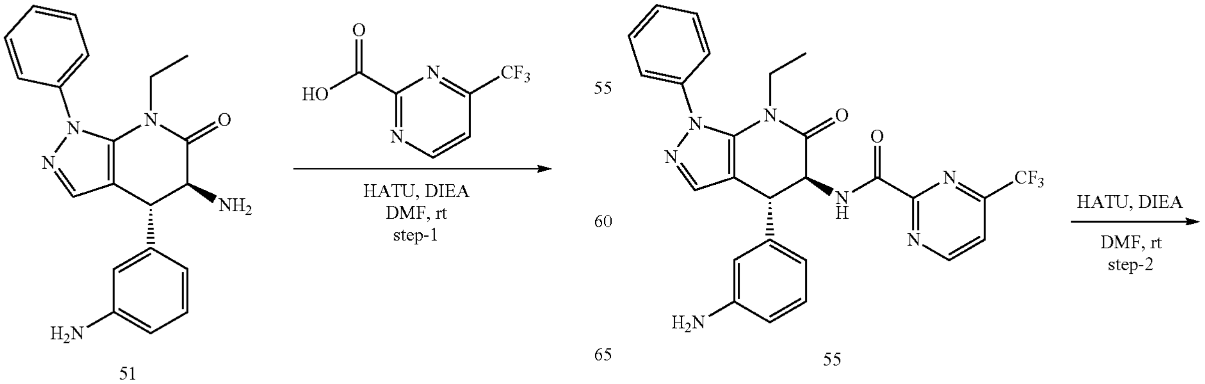

51

55

-continued

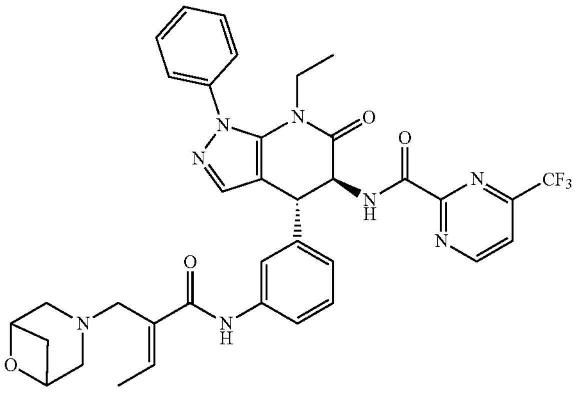

I-337

N-((4R,5S)-4-(3-aminophenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (55)

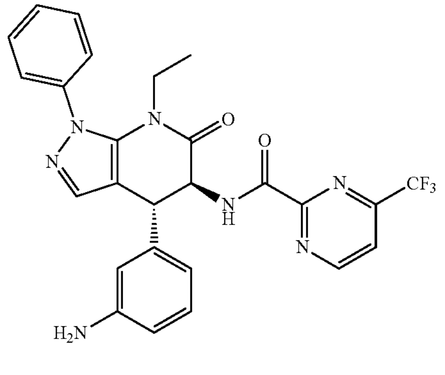 [SMILES: CCN1C(=O)[C@@H](NC(=O)c2nccc(C(F)(F)F)n2)[C@H](c2cccc(N)c2)c2cnn(-c3ccccc3)c21]

Into a 100 mL round-bottom flask were added (4R,5S)-5-amino-4-(3-aminophenyl)-7-ethyl-1-phenyl-1,4,5,7-tetrahydro-6H-pyrazolo[3,4-b]pyridin-6-one (3.00 g, crude, 1.00 equiv), DMF (40 mL), 4-(trifluoromethyl)pyrimidine-2-carboxylic acid (1.66 g, 8.65 mmol, 2.00 equiv), DIEA (0.66 g, 5.18 mmol, 3.00 equiv), HATU (1.64 g, 4.32 mmol, 1.20 equiv) at room temperature. The resulting mixture was stirred for 2 h at room temperature. The reaction was quenched with water (50 mL) at room temperature. The resulting mixture was extracted with EtOAc (2×50 mL). The combined organic layers were washed with brine (2×50 mL), dried over anhydrous $Na_2SO_4$. After filtration, the filtrate was concentrated under reduced pressure. The residue was purified by silica gel column chromatography, eluted with ethyl acetate/petroleum ether (1:1) to afford N-((4R,5S)-4-(3-aminophenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (900 mg, 33.4%) as a light yellow solid.

LCMS Calculated for $C_{26}H_{22}F_3N_7O_2$: 521.1; Observed (Method-B): 522.2 $[M+H]^+$, 84.6% at RT 1.326 min.

N-((4R,5S)-4-(3-((E)-2-((6-oxa-3-azabicyclo[3.1.1]heptan-3-yl)methyl)but-2-enamido)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide

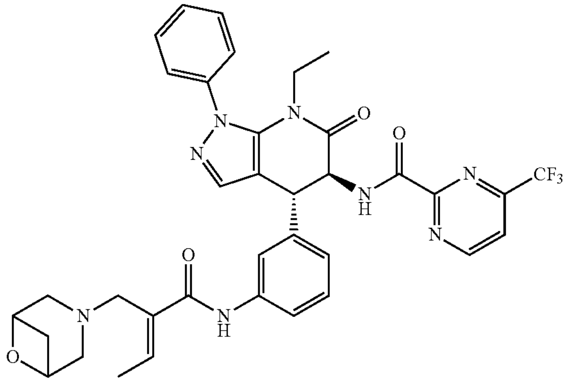 [SMILES: C/C=C(\CN1CC2CC(C1)O2)C(=O)Nc1cccc([C@@H]2c3cnn(-c4ccccc4)c3N(CC)C(=O)[C@H]2NC(=O)c2nccc(C(F)(F)F)n2)c1]

A mixture of N-((4R,5S)-4-(3-aminophenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (50.0 mg, 0.096 mmol, 1.00 equiv), DIEA (36.5 mg, 0.288 mmol, 3.00 equiv) and (E)-2-((6-oxa-3-azabicyclo[3.1.1]heptan-3-yl)methyl)but-2-enoic acid (37.8 mg, 0.192 mmol, 2.00 equiv) in DMF (2 mL) was stirred at room temperature for 10 min. HATU (47.5 mg, 0.125 mmol, 1.30 equiv) was then added, and the reaction mixture was stirred for 2 h at room temperature. The reaction was quenched with water (20 mL) at room temperature. The resulting mixture was extracted with EtOAc (2×20 mL). The combined organic layers were washed with brine (1×20 mL), dried over anhydrous $Na_2SO_4$. After filtration, the filtrate was concentrated under reduced pressure. The residue was purified by reversed-phase flash chromatography with the following conditions: Column: X Bridge Prep RP C18 Column, 30*150 mm, 5 m; Mobile Phase A: Water(0.1% $NH_3{\cdot}H_2O$), Mobile Phase B: ACN; Flow rate: 35 mL/min; Gradient: 62% B to 92% B in 10 min; Wave Length: 254 nm/220 nm; RT1 (min): 6.9. This resulted in N-((4R,5S)-4-(3-((E)-2-((6-oxa-3-azabicyclo[3.1.1]heptan-3-yl)methyl)but-2-enamido)phenyl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (12.2 mg, 18.3%) as a white solid.

$^1H$ NMR (300 MHz, DMSO-$d_6$) δ 10.87 (s, 1H), 9.40-9.21 (m, 2H), 8.21 (d, J=5.1 Hz, 1H), 7.65 (t, J=6.6 Hz, 3H), 7.60-7.41 (m, 4H), 7.25 (t, J=7.8 Hz, 1H), 7.13-6.98 (m, 2H), 6.76 (q, J=7.1 Hz, 1H), 5.17 (dd, J=12.8, 9.2 Hz, 1H), 4.61 (d, J=12.7 Hz, 1H), 4.44 (d, J=5.9 Hz, 2H), 3.85 (dq, J=14.2, 7.0 Hz, 1H), 3.52 (s, 2H), 3.08 (ddd, J=24.5, 13.5, 8.9 Hz, 3H), 2.88 (q, J=7.0 Hz, 1H), 2.69 (dd, J=11.3, 4.5 Hz, 2H), 2.08 (d, J=8.2 Hz, 1H), 1.87 (d, J=7.1 Hz, 3H), 0.82 (t, J=7.0 Hz, 3H).

LCMS Calculated for $C_{36}H_{35}F_3N_8O_4$: 700.2; Observed (Method G): 701.2 $[M+H]^+$, 95.5% at RT 1.480 min.

The following compounds were prepared using the above methodology.

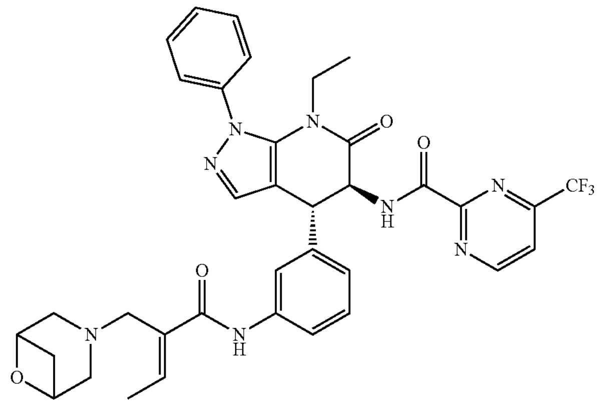 [SMILES: C/C=C(\CN1CC2CC(C1)O2)C(=O)Nc1cccc([C@@H]2c3cnn(-c4ccccc4)c3N(CC)C(=O)[C@H]2NC(=O)c2nccc(C(F)(F)F)n2)c1]

$^1H$ NMR (300 MHz, DMSO-$d_6$) δ 10.87 (s, 1H), 9.40-9.21 (m, 2H), 8.21 (d, J = 5.1 Hz, 1H), 7.65 (t, J = 6.6 Hz, 3H), 7.60-7.41 (m, 4H), 7.25 (t, J = 7.8 Hz, 1H), 7.13-6.98 (m, 2H), 6.76 (q, J = 7.1 Hz, 1H), 5.17 (dd, J = 12.8, 9.2 Hz, 1H), 4.61 (d, J = 12.7 Hz, 1H), 4.44 (d, J = 5.9 Hz, 2H), 3.85 (dq, J = 14.2, 7.0 Hz, 1H), 3.52 (s, 2H), 3.19-3.02 (m, 3H), 2.88 (q, J = 7.0 Hz, 1H), 2.69 (dd, J = 11.3, 4.5 Hz, 2H), 2.08 (d, J = 8.2 Hz, 1H), 1.87 (d, J = 7.1 Hz, 3H), 0.82 (t, J = 7.0 Hz, 3H).
LCMS Calculated for $C_{36}H_{35}F_3N_8O_4$: 700.2; Observed (Method-G): 701.2 $[M + H]^+$, 95.5% at RT 1.480 min.

I-337

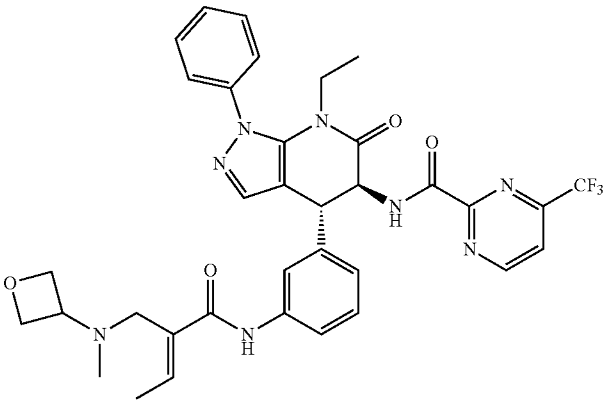 [SMILES: C/C=C(\CN(C)C1COC1)C(=O)Nc1cccc([C@@H]2c3cnn(-c4ccccc4)c3N(CC)C(=O)[C@H]2NC(=O)c2nccc(C(F)(F)F)n2)c1]

$^1H$ NMR (300 MHz, DMSO-$d_6$) δ 10.87 (s, 1H), 9.40-9.21 (m, 2H), 8.21 (d, J = 5.1 Hz, 1H), 7.65 (t, J = 6.6 Hz, 3H), 7.60-7.41 (m, 4H), 7.25 (t, J = 7.8 Hz, 1H), 7.13-6.98 (m, 2H), 6.76 (q, J = 7.1 Hz, 1H), 5.17 (dd, J = 12.8, 9.2 Hz, 1H), 4.61 (d, J = 12.7 Hz, 1H), 4.44 (d, J = 5.9 Hz, 2H), 3.85 (dq, J = 14.2, 7.0 Hz, 1H), 3.52 (s, 2H), 3.08 (ddd, J = 24.5, 13.5, 8.9 Hz, 3H), 2.88 (q, J = 7.0 Hz, 1H), 2.69 (dd, J = 11.3, 4.5 Hz, 2H), 2.08 (d, J = 8.2 Hz, 1H), 1.87 (d, J = 7.1 Hz, 3H), 0.82 (t, J = 7.0 Hz, 3H).
LCMS Calculated for $C_{35}H_{35}F_3N_8O_4$: 688.2; Observed (Method-G): 689.2 $[M + H]^+$, 95.5% at RT 1.480 min.

I-384

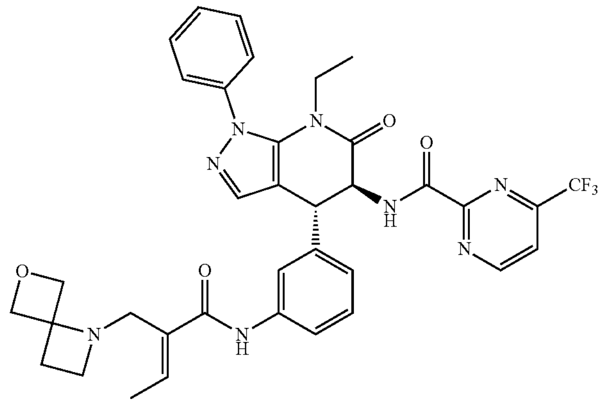 [SMILES: C/C=C(\CN1CCC12COC2)C(=O)Nc1cccc([C@@H]2c3cnn(-c4ccccc4)c3N(CC)C(=O)[C@H]2NC(=O)c2nccc(C(F)(F)F)n2)c1]

$^1H$ NMR (300 MHz, DMSO-$d_6$) δ 10.69 (s, 1H), 9.43-9.19 (m, 2H), 8.21 (d, J = 5.1 Hz, 1H), 7.69-7.50 (m, 7H), 7.25 (t, J = 7.8 Hz, 1H), 7.16-6.99 (m, 2H), 6.59 (q, J = 7.0 Hz, 1H), 5.18 (dd, J = 12.7, 9.3 Hz, 1H), 4.84 (t, J = 6.7 Hz, 2H), 4.72-4.65 (m, 3H), 3.85 (dd, J = 14.2, 7.2 Hz, 1H), 3.58 (s, 2H), 3.03 (dt, J = 13.9, 7.0 Hz, 3H), 2.32 (t, J = 7.0 Hz, 2H), 1.85 (d, J = 7.1 Hz, 3H), 0.83 (t, J = 7.0 Hz, 3H).
LCMS Calculated for $C_{36}H_{35}F_3N_8O_4$: 700.2; Observed (Method G): 701.2 $[M + H]^+$, 98.5% at RT 1.478 min.

I-251

-continued

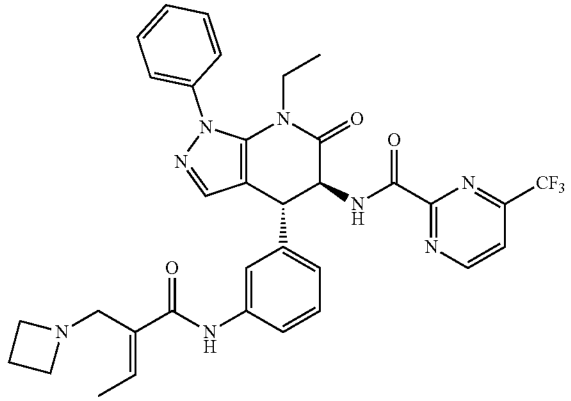 [SMILES: C/C=C(\CN1CCC1)C(=O)Nc1cccc([C@@H]2c3cnn(-c4ccccc4)c3N(CC)C(=O)[C@H]2NC(=O)c2nccc(C(F)(F)F)n2)c1]

$^1$H NMR (300 MHz, DMSO-$d_6$) δ 11.16 (s, 1H), 9.39-9.18 (m, 2H), 8.21 (d, J = 5.1 Hz, 1H), 7.66 (d, J = 5.1 Hz, 3H), 7.62-7.46 (m, 4H), 7.26 (t, J = 7.8 Hz, 1H), 7.06-7.01 (m, 2H), 6.61 (d, J = 7.2 Hz, 1H), 5.21 (dd, J = 12.7, 9.3 Hz, 1H), 4.63 (d, J = 12.7 Hz, 1H), 3.86 (dd, J = 14.2, 7.2 Hz, 1H), 3.61-3.52 (m, 2H), 3.19-3.02 (m, 5H), 2.02 (t, J = 7.0 Hz, 2H), 1.84 (d, J = 7.2 Hz, 3H), 0.83 (t, J = 7.0 Hz, 3H).
LCMS Calculated for $C_{33}H_{33}F_3N_8O_3$: 658.2; Observed (Method-G): 659.2 [M + H]$^+$, 95.2% at RT 1.491 min.

I-367

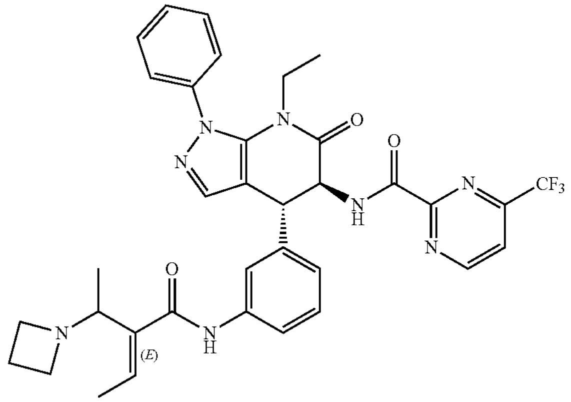 [SMILES: C/C=C(/C(=O)Nc1cccc([C@@H]2c3cnn(-c4ccccc4)c3N(CC)C(=O)[C@H]2NC(=O)c2nccc(C(F)(F)F)n2)c1)C(C)N1CCC1]

$^1$H NMR (400 MHz, DMSO-$d_6$) δ 12.12-11.91 (m, 1H), 9.32 (q, J = 6.1, 5.2 Hz, 2H), 8.21 (dd, J = 5.2, 2.6 Hz, 1H), 7.67 (d, J = 7.6 Hz, 2H), 7.63-7.50 (m, 5H), 7.34-7.25 (m, 1H), 7.11 (d, J = 7.7 Hz, 1H), 7.07 (d, J = 3.5 Hz, 1H), 6.71-6.60 (m, 1H), 5.27-5.17 (m, 1H), 4.65 (d, J = 12.7 Hz, 1H), 3.91-3.81 (m, 1H), 3.61 (d, J = 6.6 Hz, 1H), 3.25-2.96 (m, 6H), 2.10-1.98 (m, 1H), 1.84 (d, J = 7.2 Hz, 3H), 0.99 (dd, J = 12.7, 6.6 Hz, 3H), 0.84 (t, J = 7.0 Hz, 3H).
LCMS Calculated for $C_{35}H_{35}F_3N_8O_3$: 672.2; Observed (Method-M): 673.2 [M + H]$^+$, 99.2% at RT 1.707 min.

I-385

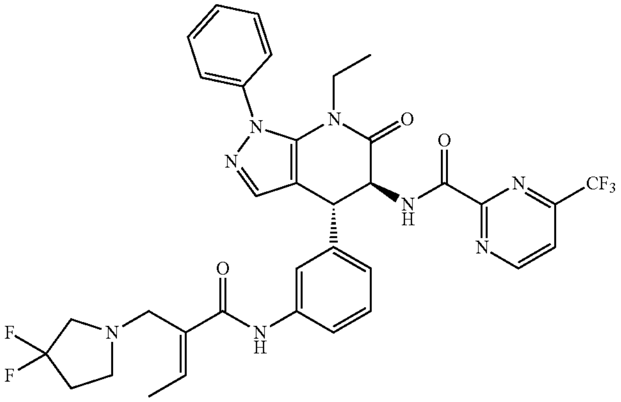 [SMILES: C/C=C(\CN1CCC(F)(F)C1)C(=O)Nc1cccc([C@@H]2c3cnn(-c4ccccc4)c3N(CC)C(=O)[C@H]2NC(=O)c2nccc(C(F)(F)F)n2)c1]

$^1$H NMR (300 MHz, DMSO-$d_6$) δ 10.48 (s, 1H), 9.35-9.26 (m, 2H), 8.21 (d, J = 5.1 Hz, 1H), 7.73-7.63 (m, 3H), 7.63-7.51 (m, 3H), 7.46 (dd, J = 7.9, 1.9 Hz, 1H), 7.25 (t, J = 7.8 Hz, 1H), 7.09 (d, J = 7.7 Hz, 1H), 7.04 (s, 1H), 6.68-6.55 (m, 1H), 5.17 (dd, J = 12.8, 9.2 Hz, 1H), 4.62 (d, J = 12.7 Hz, 1H), 3.94-3.77 (m, 1H), 3.43 (s, 2H), 3.12-3.02 (m, 1H), 2.95 (t, J = 13.1 Hz, 2H), 2.78 (t, J = 7.0 Hz, 2H), 2.38-2.17 (m, 2H), 1.84 (d, J = 7.1 Hz, 3H), 0.83 (t, J = 7.0 Hz, 3H).
LCMS Calculated for $C_{35}H_{33}F_5N_8O_3$: 708.26; Observed (Method-F): 709.10 [M + H]$^+$, 99.9% at RT 0.938 min.

I-368

15. Synthesis of N-((4R,5S)-7-ethyl-4-(3-((E)-N-methyl-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)-2-(trifluoromethyl)thiazole-4-carboxamide I-301'

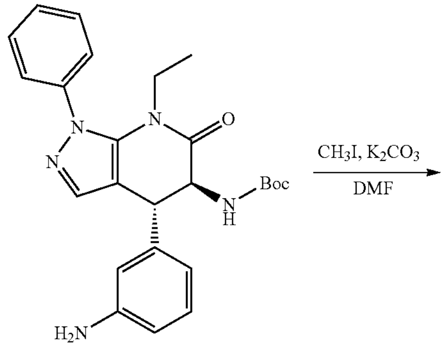

52

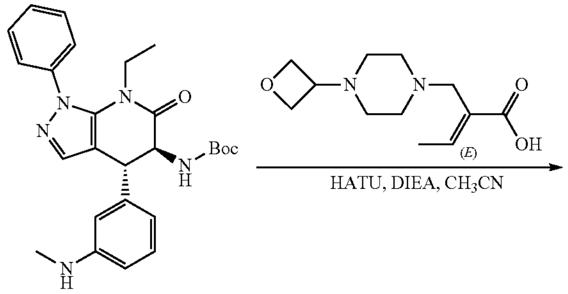

56

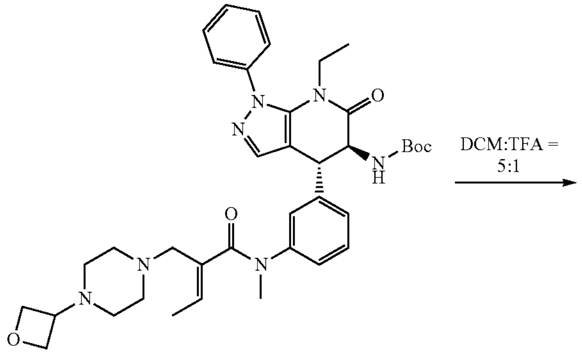

57

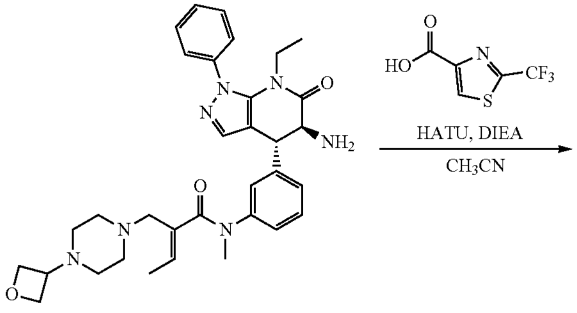

58

-continued

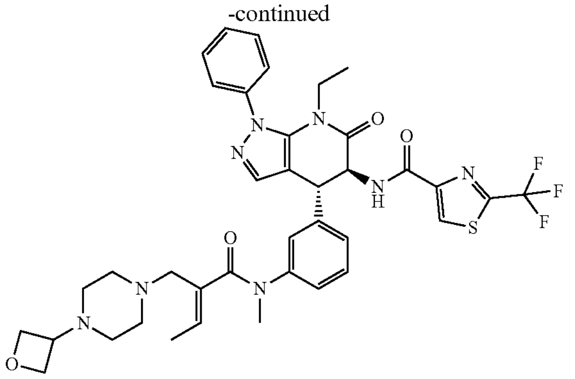

I-301′ (trans isomer)

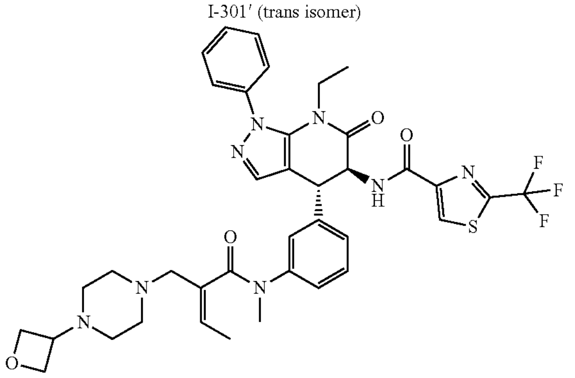

I-301 tert-butyl ((4R,5S)-7-ethyl-4-(3-(methylamino)phenyl)-6-oxo-1-phenyl-4,5,6,7-tetrahydro-1H-pyrazolo[3,4-b]pyridin-5-yl)carbamate (56)

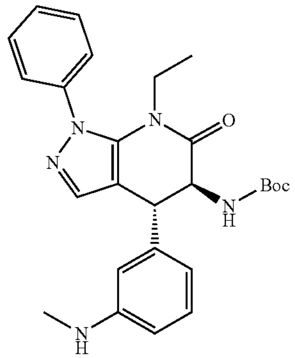 [SMILES: CCN1C(=O)[C@@H](NC(=O)OC(C)(C)C)[C@H](c2cccc(NC)c2)c2cnn(-c3ccccc3)c21]

Into a 50 mL sealed tube were added tert-butyl N-[(4R,5S)-4-(3-aminophenyl)-7-ethyl-6-oxo-1-phenyl-4H,5H-pyrazolo[3,4-b]pyridin-5-yl]carbamate (300 mg, 0.670 mmol, 1.00 equiv), DMF (3 mL), $K_2CO_3$ (278 mg, 2.01 mmol, 3.00 equiv) at 0° C. To the above mixture was added iodomethane (114 mg, 0.804 mmol, 1.20 equiv) dropwise over 5 mins at 0° C. The resulting mixture was stirred for 1 h at room temperature. The resulting mixture was diluted with $H_2O$ (50 mL). The resulting mixture was extracted with EtOAc (3×30 mL). The combined organic layers were washed with brine (3×30 mL), dried over anhydrous $Na_2SO_4$. After filtration, the filtrate was concentrated under reduced pressure. The residue was purified by silica gel column chromatography, eluted with PE/EA (1:1) to afford tert-butyl ((4R,5S)-7-ethyl-4-(3-(methylamino)phenyl)-6-oxo-1-phenyl-4,5,6,7-tetrahydro-1H-pyrazolo[3,4-b]pyridin-5-yl)carbamate (150 mg, 48.48%) as a yellow solid.

LCMS Calculated for $C_{26}H_{31}N_5O_3$: 461.24; Observed (Method-B): 462.24 $[M+H]^+$, 75.2% at RT 0.829 min.

tert-butyl ((4R,5S)-7-ethyl-4-(3-((E)-N-methyl-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)carbamate (57)

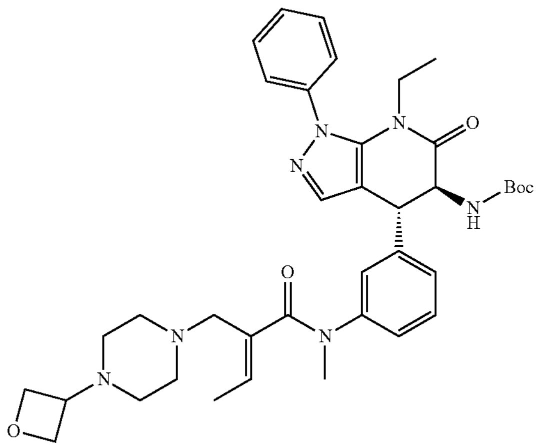 [SMILES: C/C=C(\CN1CCN(C2COC2)CC1)C(=O)N(C)c1cccc([C@@H]2c3cnn(-c4ccccc4)c3N(CC)C(=O)[C@H]2NC(=O)OC(C)(C)C)c1]

Into a 100 mL round-bottom flask were added tert-butyl ((4R,5S)-7-ethyl-4-(3-(methylamino)phenyl)-6-oxo-1-phenyl-4,5,6,7-tetrahydro-1H-pyrazolo[3,4-b]pyridin-5-yl)carbamate (100 mg, 0.217 mmol, 1.00 equiv), acetonitrile (1.5 mL), (2E)-2-{[4-(oxetan-3-yl)piperazin-1-yl]methyl}but-2-enoic acid (260 mg, 1.08 mmol, 5.00 equiv), DIEA (84.0 mg, 0.651 mmol, 3.00 equiv), HATU (98.9 mg, 0.260 mmol, 1.20 equiv) at room temperature. The resulting mixture was stirred for 2 h at 35° C. The reaction was quenched with water (20 mL) at room temperature. The resulting mixture was extracted with EtOAc (2×20 mL). The combined organic layers were washed with brine (2×20 mL), dried over anhydrous $Na_2SO_4$. After filtration, the filtrate was concentrated under reduced pressure. The residue was purified by silica gel column chromatography, eluted with DCM/MeOH (10:1) to afford tert-butyl ((4R,5S)-7-ethyl-4-(3-((E)-N-methyl-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)carbamate (70 mg, 47.2%) as a light yellow solid.

(E)-N-(3-((4R,5S)-5-amino-7-ethyl-6-oxo-1-phenyl-4,5,6,7-tetrahydro-1H-pyrazolo[3,4-b]pyridin-4-yl)phenyl)-N-methyl-2-((4-(oxetan-3-yl)piperazin-1-yl)methyl)but-2-enamide (58)

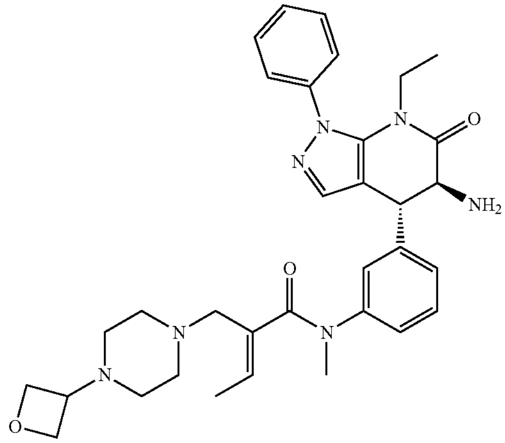 [SMILES: C/C=C(\CN1CCN(C2COC2)CC1)C(=O)N(C)c1cccc([C@@H]2c3cnn(-c4ccccc4)c3N(CC)C(=O)[C@H]2N)c1]

Into a 50 mL round-bottom flask were added tert-butyl ((4R,5S)-7-ethyl-4-(3-((E)-N-methyl-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)carbamate (70 mg, 0.102 mmol, 1.00 equiv) and DCM (1 mL) at 0° C. To the above mixture was added trifluoroacetic acid (0.2 mL) dropwise over 2 mins at 0° C. The resulting mixture was stirred for 2 h at 0° C. The resulting mixture was concentrated under reduced pressure. This resulted in (E)-N-(3-((4R,5S)-5-amino-7-ethyl-6-oxo-1-phenyl-4,5,6,7-tetrahydro-1H-pyrazolo[3,4-b]pyridin-4-yl)phenyl)-N-methyl-2-((4-(oxetan-3-yl)piperazin-1-yl)methyl)but-2-enamide (50 mg crude) as a light yellow solid.

LCMS Calculated for $C_{33}H_{41}N_7O_3$: 583.38; Observed (Method-B): 584.38 $[M+H]^+$, 90.1% at RT 0.529 min.

N-((4R,5S)-7-ethyl-4-(3-((E)-N-methyl-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)-2-(trifluoromethyl)thiazole-4-carboxamide

I-301′

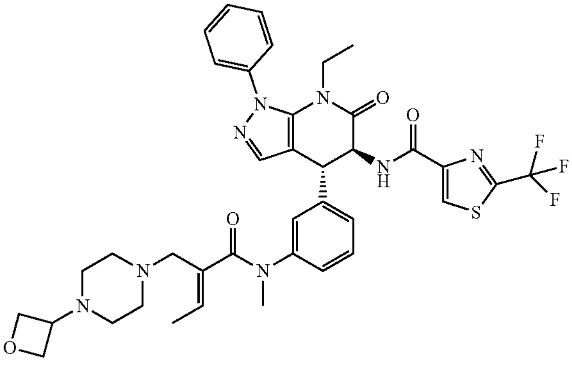

Into a 8 mL vial were added (E)-N-(3-((4R,5S)-5-amino-7-ethyl-6-oxo-1-phenyl-4,5,6,7-tetrahydro-1H-pyrazolo[3,4-b]pyridin-4-yl)phenyl)-N-methyl-2-((4-(oxetan-3-yl)piperazin-1-yl)methyl)but-2-enamide (100 mg, 0.171 mmol, 1.00 equiv), acetonitrile (1 mL), 2-(trifluoromethyl)-1,3-thiazole-4-carboxylic acid (33.8 mg, 0.171 mmol, 1.00 equiv) and DIEA (66.4 mg, 0.513 mmol, 3.00 equiv), HATU (78.2 mg, 0.205 mmol, 1.20 equiv) at room temperature. The resulting mixture was stirred for 1 h at 35° C. The reaction was quenched with water (20 mL) at room temperature. The resulting mixture was extracted with EtOAc (2×20 mL). The combined organic layers were washed with brine (2×20 mL), dried over anhydrous $Na_2SO_4$. After filtration, the filtrate was concentrated under reduced pressure. The residue was purified by reversed-phase flash chromatography with the following conditions: Column: YMC-Actus Triart C18 Column, 50*250 mm, 5 μm; Mobile Phase A: Water (10 mmol/L $NH_4HCO_3$+0.05% $NH_3 \cdot H_2O$), Mobile Phase B: ACN; Flow rate: 90 mL/min; Gradient: 32% B to 58% B in 16 min; Wave Length: 254 nm/220 nm; RT1 (min): 10 to afford N-[(4R,5S)-7-ethyl-4-{3-[(2E)-N-methyl-2-{[4-(oxetan-3-yl)piperazin-1-yl]methyl}but-2-enamido]phenyl}-6-oxo-1-phenyl-4H,5H-pyrazolo[3,4-b]pyridin-5-yl]-2-(trifluoromethyl)-1,3-thiazole-4-carboxamide (12 mg, 9.18%) as a white solid

| | |
|---|---|
| 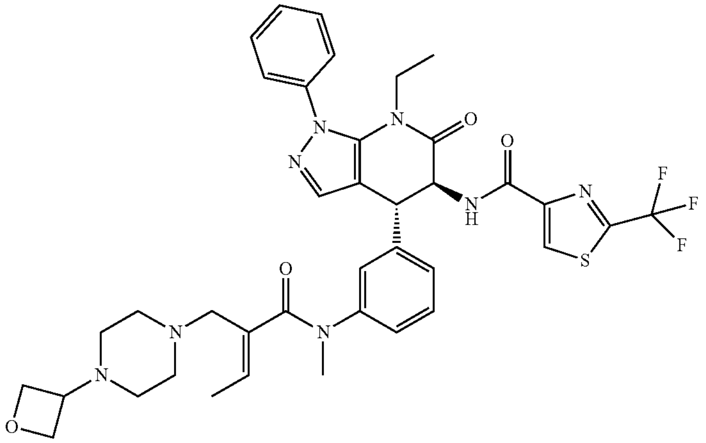 [SMILES: C/C=C(\CN1CCN(C2COC2)CC1)C(=O)N(C)c1cccc([C@@H]2c3cnn(-c4ccccc4)c3N(CC)C(=O)[C@H]2NC(=O)c2csc(C(F)(F)F)n2)c1]<br>I-301' | $^1$H NMR (400 MHz, DMSO-$d_6$) δ 9.29-9.22 (m, 1H), 8.79 (s, 1H), 7.68-7.50 (m, 5H), 7.34-7.23 (m, 3H), 7.13-7.06 (m, 1H), 6.92 (s, 1H), 5.60 (q, J = 6.9 Hz, 1H), 5.29-5.19 (m, 1H), 4.59 (d, J = 13.1 Hz, 1H), 4.53-4.43 (m, 2H), 4.37 (t, J = 6.0 Hz, 2H), 3.96-3.83 (m, 1H), 3.41-3.32 (m, 1H), 3.15 (s, 3H), 3.07-2.93 (m, 1H), 2.86 (q, J = 12.9 Hz, 2H), 2.23-2.19 (m, 8H), 1.36 (d, J = 7.0 Hz, 3H), 0.83 (t, J = 7.0 Hz, 3H). LCMS Calculated for $C_{38}H_{41}F_3N_8O_4S$: 762.29; Observed (Method-M): 763.4 [M + H]$^+$, 99.5% at RT 1.813 min. |

The following compounds were prepared according to I-214.

| | |
|---|---|
| 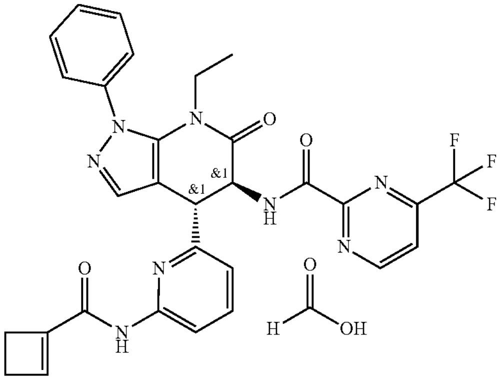<br>I-279 | $^1$H NMR (400 MHz, DMSO-$d_6$) δ 9.46-9.17 (m, 2H), 8.49 (s, 1H), 8.21 (d, J = 5.1 Hz, 1H), 7.82 (t, J = 7.9 Hz, 1H), 7.65 (d, J = 7.7 Hz, 2H), 7.62-7.46 (m, 4H), 7.30 (d, J = 7.4 Hz, 1H), 7.04 (d, J = 5.3 Hz, 2H), 5.61-5.43 (m, 1H), 5.32 (dd, J = 8.1, 4.2 Hz, 1H), 4.80 (d, J = 12.3 Hz, 1H), 3.84 (dd, J = 14.4, 7.3 Hz, 1H), 3.08 (dd, J = 14.1, 7.2 Hz, 1H), 2.71-2.53 (m, 1H), 2.48-2.41 (m, 2H),2.34 (s, 2H), 0.84 (q, J = 7.1 Hz, 3H). LCMS Calculated for $C_{31}H_{27}F_3N_8O_5$: 648.21; Observed (Method-AB): 603.4 [M + H − FA]$^+$, 95.4% at RT 1.750 min. |

-continued
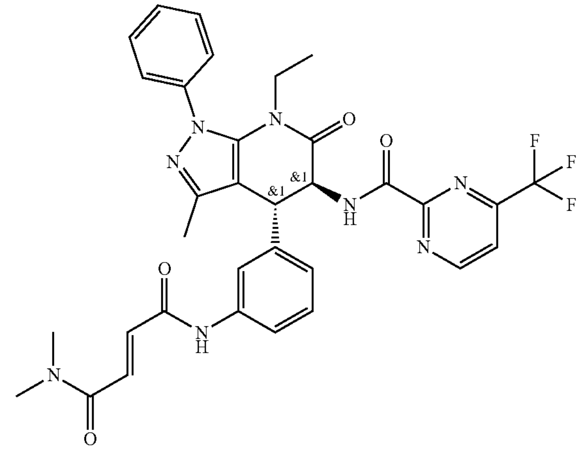 [SMILES: CCN1C(=O)[C@@H](NC(=O)c2nccc(C(F)(F)F)n2)[C@H](c2cccc(NC(=O)/C=C/C(=O)N(C)C)c2)c2c(C)nn(-c3ccccc3)c21]
$^1$H NMR (300 MHz, DMSO-$d_6$) δ 10.48 (s, 1H), 9.35-9.26 (m, 2H), 8.21 (d, J = 5.0 Hz, 1H), 7.66 (s, 4H), 7.60 (d, J = 16.8 Hz, 3H), 7.55-7.47 (m, 2H), 7.41-7.24 (m, 1H), 7.12 (d, J = 7.8 Hz, 1H), 7.00 (d, J = 15.0 Hz, 1H), 5.29-5.16 (m, 1H), 4.58 (d, J = 12.0 Hz, 1H), 3.10 (s, 4H), 2.93 (s, 3H), 1.49 (s, 3H), 0.83 (t, J = 7.0 Hz, 3H). LCMS Calculated for $C_{33}H_{31}F_3N_8O_4$: 660.24; Observed (Method-K): 661.24 $[M + H]^+$, 99.4% at RT 0.915 min.
I-245
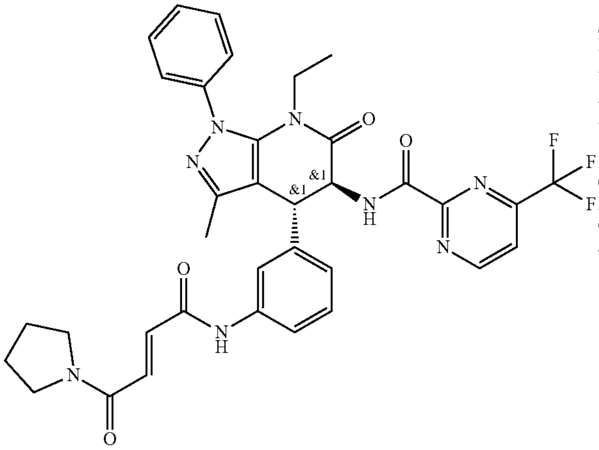
$^1$H NMR (300 MHz, DMSO-$d_6$) δ 10.50 (s, 1H), 9.36-9.27 (m, 2H), 8.21 (d, J = 5.1 Hz, 1H), 7.69-7.47 (m, 4H), 7.29 (t, J = 7.8 Hz, 3H), 7.23-7.09 (m, 1H), 7.05 (d, J = 15.0 Hz, 3H), 5.23 (dd, J = 12.0, 9.3 Hz, 1H), 4.58 (d, J = 12.1 Hz, 1H), 3.87-3.73 (m, 1H), 3.60 (t, J = 6.7 Hz, 2H), 3.39 (t, J = 6.7 Hz, 2H), 3.16-3.03 (m, 1H), 1.98-1.86 (m, 2H), 1.89-1.73 (m, 2H), 1.49 (s, 3H), 0.83 (t, J = 6.9 Hz, 3H). LCMS Calculated for $C_{35}H_{33}F_3N_8O_4$: 686.26; Observed (Method-AK): 687.2 $[M + H]^+$, 96.8% at RT 2.939 min.
I-262

The following compounds were prepared according to I-10.

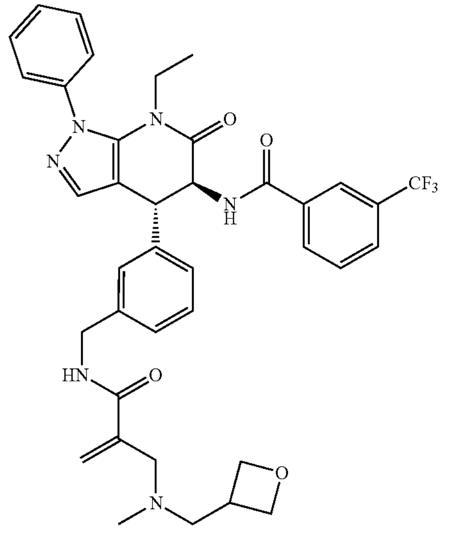 [SMILES: C=C(CN(C)CC1COC1)C(=O)NCc1cccc([C@@H]2c3cnn(-c4ccccc4)c3N(CC)C(=O)[C@H]2NC(=O)c2cccc(C(F)(F)F)c2)c1]

$^1$H NMR (400 MHz, DMSO-$d_6$) δ 9.01 (d, J = 9.0 Hz, 1H), 8.92 (t, J = 5.9 Hz, 1H), 8.08-8.01 (m, 2H), 7.91 (d, J = 7.8 Hz, 1H), 7.76-7.50 (m, 6H), 7.34-7.28 (m, 3H), 7.20-7.14 (m, 1H), 7.03 (s, 1H), 5.89 (d, J = 2.0 Hz, 1H), 5.46-5.41 (m, 1H), 5.18 (dd, J = 12.9, 8.9 Hz, 1H), 4.47-4.37 (m, 3H), 4.36-4.25 (m, 2H), 4.07 (td, J = 6.1, 1.9 Hz, 2H), 3.84 (dd, J = 14.2, 7.2 Hz, 1H), 3.14 (s, 2H), 3.06 (tt, J = 13.4, 7.0 Hz, 2H), 2.57 (d, J = 7.5 Hz, 2H), 2.01 (s, 3H), 0.83 (t, J = 7.0 Hz, 3H).
LCMS Calculated for $C_{38}H_{39}F_3N_6O_4$: 700.30; Observed (Method-A): 701.4 $[M + H]^+$, 99.5% at RT 1.104 min.

I-61

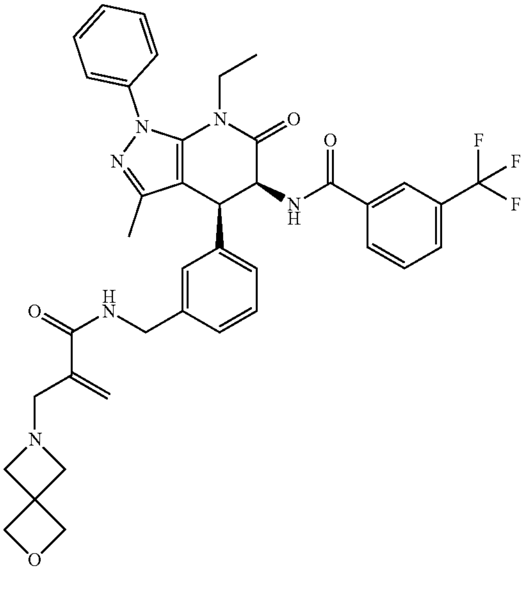 [SMILES: C=C(CN1CC2(COC2)C1)C(=O)NCc1cccc([C@H]2c3c(C)nn(-c4ccccc4)c3N(CC)C(=O)[C@H]2NC(=O)c2cccc(C(F)(F)F)c2)c1]

$^1$H NMR (400 MHz, DMSO-$d_6$) δ 9.02 (d, J = 8.8 Hz, 1H), 8.94 (t, J = 5.9 Hz, 1H), 8.06-7.99 (m, 2H), 7.91 (d, J = 7.8 Hz, 1H), 7.71 (t, J = 7.8 Hz, 1H), 7.65-7.53 (m, 4H), 7.50 (t, J = 7.0 Hz, 1H), 7.39-7.24 (m, 3H), 7.18 (d, J = 7.2 Hz, 1H), 5.77 (s, 1H), 5.39 (s, 1H), 5.23 (dd, J = 12.0, 8.8 Hz, 1H), 4.40-4.26 (m, 3H), 3.77 (dq, J = 13.9, 6.9 Hz, 1H), 3.19-3.00 (m, 6H), 1.90 (p, J = 7.0 Hz, 2H), 1.45 (s, 3H), 0.81 (t, J = 7.0 Hz, 3H).
LCMS Calculated for $C_{39}H_{39}F_3N_6O_4$: 712.30; Observed (Method-J): 713.4 $[M + H]^+$, 98.2% at RT 1.679 min.

I-304

I—NMR:

II—$^1$H NMR spectrum was recorded on Bruker 400 MHz and 300 MHz instruments internally referenced to a tetramethylsilane (TMS) signal. Chemical shifts (6) and coupling constants (J) were expressed in parts per million and hertz, respectively.

III—LCMS

IV—Method-A (LCMS-25): Column: L-column3 C18 3.0*30 mm 3 um, Mobile Phase: A: 5 mM $NH_4HCO_3$ in water; B: Acetonitrile, Flow Rate: 1.2 mL/min. Oven Temperature: 40 C, Gradient program (B %): 0.00/10.0, 1.4/95, 1.9/95, 1.91/10

V—HPLC:

VI—Method-A: Cortecs C18+, 100*4.6 mm, 2.7 um, Mobile Phase: A: 0.10% MSA in water; B: Acetonitrile, Flow Rate: 1.5 mL/min. Oven Temperature: 40 C, Gradient program (B %): 0.00/10.0, 1.50/40, 8.50/70, 10.0/95, 12.0/95

VII—Chiral-HPLC:

VIII—Method-J: Column: CHIRALPAK ID-3, 50*4.6 mm, 3 um IE30CB—BV004; Mobile Phase A: n-Hexane/DCM=3/1, Mobile Phase B: EtOH (0.1% DEA), Conc. of Pump B: 30.0%; Flow rate: 1.0 ml/min; Oven Temperature: 25 C.

Synthesis of N-((4R,5S)-7-ethyl-4-(3-((E)-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)-1-(trifluoromethyl)-1H-pyrazole-3-carboxamide I-383
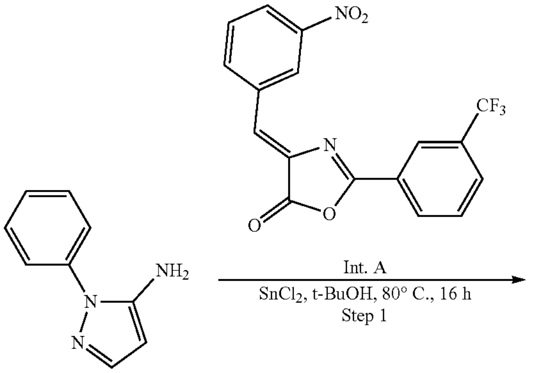
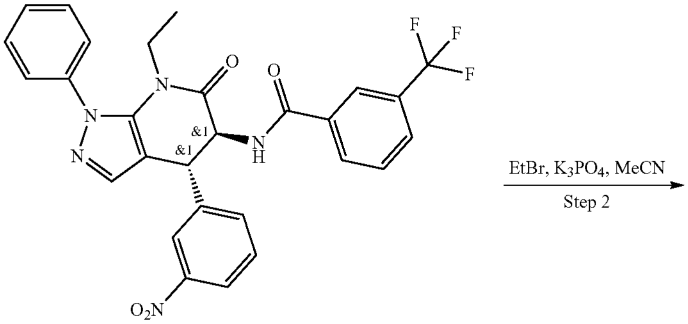
1
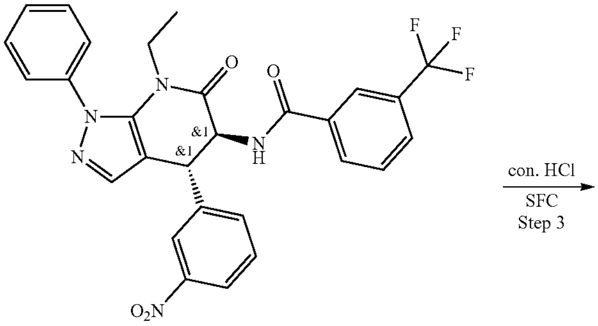
2
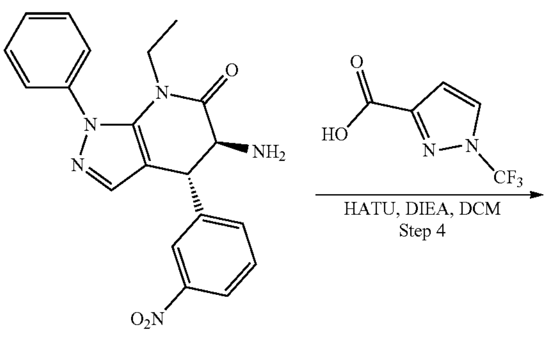
3A -continued
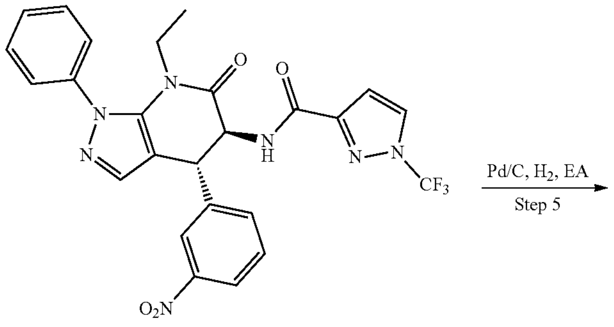
4
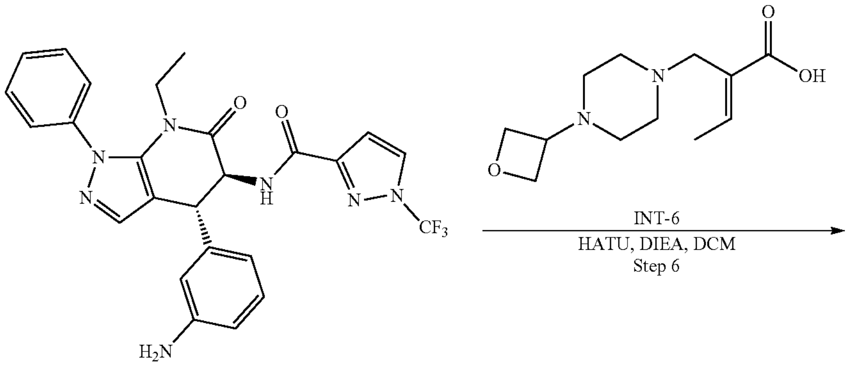
5
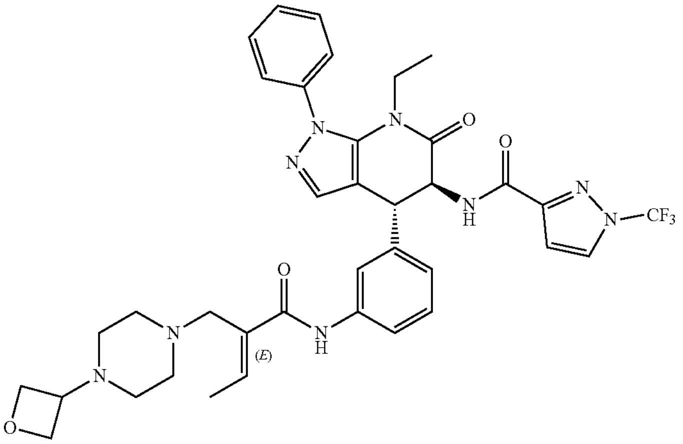
I-383
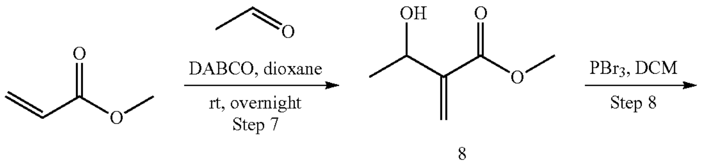
8
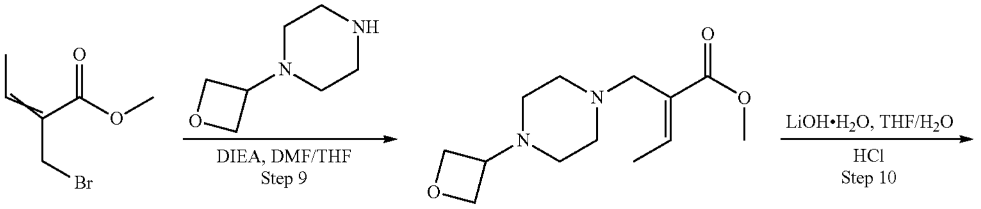
9
10

-continued

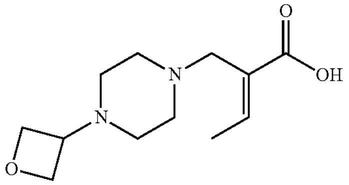

INT-6 rac-N-((4R,5S)-4-(3-nitrophenyl)-6-oxo-1-phenyl-4,5,6,7-tetrahydro-1H-pyrazolo[3,4-b]pyridin-5-yl)-3-(trifluoromethyl)benzamide (1)

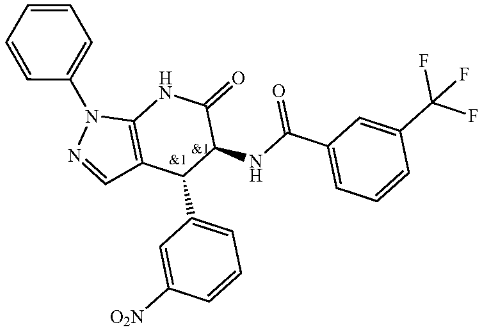 [SMILES: O=C(N[C@@H]1C(=O)Nc2c(cnn2-c2ccccc2)[C@H]1c1cccc([N+](=O)[O-])c1)c1cccc(C(F)(F)F)c1]

A solution of (4Z)-4-[(3-nitrophenyl)methylidene]-2-[3-(trifluoromethyl)phenyl]-1,3-oxazol-5-one (75.0 g, 207 mmol, 1.00 equiv), 1-phenyl-1H-pyrazol-5-amine (36.2 g, 227 mmol, 1.10 equiv) and $SnCl_2$ (3.93 g, 20.7 mmol, 0.100 equiv) in t-BuOH (750 mL) was stirred at 80° C. for 16 h. The mixture was allowed to cool down to room temperature. The resulting mixture was concentrated under reduced pressure. The residue was purified by silica gel column chromatography, eluted with petroleum ether/ethyl acetate (2:1) to afford rac-N-((4R,5S)-4-(3-nitrophenyl)-6-oxo-1-phenyl-4,5,6,7-tetrahydro-1H-pyrazolo[3,4-b]pyridin-5-yl)-3-(trifluoromethyl)benzamide (54.7 g, 50.6% yield, 88% purity) as a yellow solid.

LCMS Calculated for $C_{26}H_{18}F_3N_5O_4$: 521.13; Observed: 522.3 $[M+H]^+$ rac-N-((4R,5S)-7-ethyl-4-(3-nitrophenyl)-6-oxo-1-phenyl-4,5,6,7-tetrahydro-1H-pyrazolo[3,4-b]pyridin-5-yl)-3-(trifluoromethyl)benzamide (2)

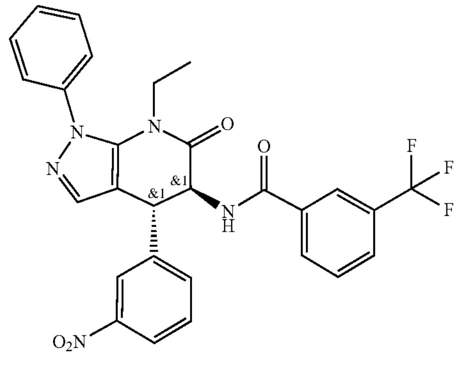 [SMILES: CCN1C(=O)[C@@H](NC(=O)c2cccc(C(F)(F)F)c2)[C@H](c2cccc([N+](=O)[O-])c2)c2cnn(-c3ccccc3)c21]

A solution of rac-N-((4R,5S)-4-(3-nitrophenyl)-6-oxo-1-phenyl-4,5,6,7-tetrahydro-1H-pyrazolo[3,4-b]pyridin-5-yl)-3-(trifluoromethyl)benzamide (54.7 g, 104 mmol, 1.00 equiv), $K_3PO_4$ (44.5 g, 209 mmol, 2.00 equiv) and bromoethane (13.7 g, 125 mmol, 1.20 equiv) in MeCN (600 mL) was stirred at 70° C. for 16 h. The mixture was allowed to cool down to room temperature. The resulting mixture was filtered, the filter cake was washed with MeCN (3×100 mL). The filtrate was concentrated under reduced pressure. The residue was purified by silica gel column chromatography, eluted with petroleum ether/THF (3:1) to afford rac-N-((4R,5S)-7-ethyl-4-(3-nitrophenyl)-6-oxo-1-phenyl-4,5,6,7-tetrahydro-1H-pyrazolo[3,4-b]pyridin-5-yl)-3-(trifluoromethyl)benzamide (46 g, 79.8% yield, 92% purity) as a yellow solid.

LCMS Calculated for $C_{28}H_{22}F_3N_5O_4$: 549.16; Observed: 550.3 $[M+H]^+$ (4R,5S)-5-amino-7-ethyl-4-(3-nitrophenyl)-1-phenyl-1,4,5,7-tetrahydro-6H-pyrazolo[3,4-b]pyridin-6-one (3A)

3A

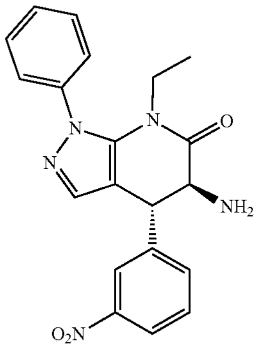

A solution of rac-N-((4R,5S)-7-ethyl-4-(3-nitrophenyl)-6-oxo-1-phenyl-4,5,6,7-tetrahydro-1H-pyrazolo[3,4-b]pyridin-5-yl)-3-(trifluoromethyl)benzamide (46.0 g, 83.7 mmol, 1.00 equiv) in con.HCl (500 mL) was stirred at 110° C. for 16 h. The mixture was allowed to cool down to room temperature. The mixture was diluted with water (500 mL) and the resulting mixture was neutralized to pH 7 with saturated $NaHCO_3$ (aq.). The resulting mixture was extracted with EtOAc (3×500 mL). The combined organic layers were washed with brine (1×600 mL), dried over anhydrous $Na_2SO_4$. After filtration, the filtrate was concentrated under reduced pressure. The residue was purified by silica gel column chromatography, eluted with petroleum ether/THE (1:1) to afford rac-(4R,5S)-5-amino-7-ethyl-4-(3-nitrophenyl)-1-phenyl-1,4,5,7-tetrahydro-6H-pyrazolo[3,4-b]pyridin-6-one (26.1 g, 82.6% yield, 88% purity) as a yellow solid. The crude product rac-(4R,5S)-5-amino-7-ethyl-4-(3-nitrophenyl)-1-phenyl-4H,5H-pyrazolo[3,4-b]pyridin-6-one (26.1 g) was purified by PREP_CHIRAL_SFC with the following conditions (Column: XA-CHIRAL ART Cellulose-SC, 5*25 cm, 5 μm; Mobile Phase A: $CO_2$—, Mobile Phase B: MEOH:DCM=3:1 (0.1% 7M $NH_3$-MeOH); Flow rate: 150 mL/min; Gradient: isocratic 55% B; Column Temperature (° C.): 35; Back Pressure(bar): 100; Wave Length: 220 nm; RT1 (min): 5.7; RT2 (min): 6.86; Sample Solvent: MeOH:DCM=4:1; Injection Volume: 2.0 mL) to afford (4R,5S)-5-amino-7-ethyl-4-(3-nitrophenyl)-1-phenyl-4H,5H-pyrazolo[3,4-b]pyridin-6-one (3A, desired) (13 g, 49.8% yield, 99% purity) as a yellow solid and (4S,5R)-5-amino-7-ethyl-4-(3-nitrophenyl)-1-phenyl-1,4,5,7-tetrahydro-6H-pyrazolo[3,4-b]pyridin-6-one (3B, undesired) (13.0 g, 49.8% yield, 99% purity) as a yellow solid.

LCMS Calculated for $C_{20}H_{19}N_5O_3$: 377.15; Observed: 378.3 $[M+H]^+$ Optical rotation: a=−48, (c=0.1 g/100 mL in MeOH, T=25° C.)

N-((4R,5S)-7-ethyl-4-(3-nitrophenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (4)

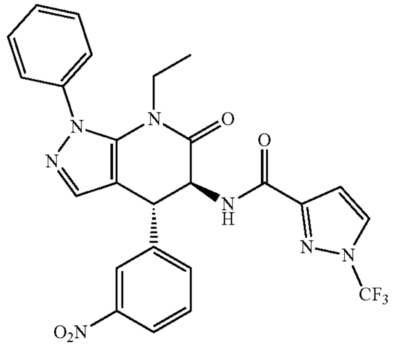 [SMILES: CCN1C(=O)[C@@H](NC(=O)c2ccn(C(F)(F)F)n2)[C@H](c2cccc([N+](=O)[O-])c2)c2cnn(-c3ccccc3)c21]

A solution of 1-(trifluoromethyl)pyrazole-3-carboxylic acid (5.00 g, 27.7 mmol, 1.00 equiv), HATU (60.3 g, 158 mmol, 1.20 equiv) in DCM (60 mL) was treated with DIEA (51.2 g, 396 mmol, 3.00 equiv) at room temperature for 20 min followed by the addition of (4R,5S)-5-amino-7-ethyl-4-(3-nitrophenyl)-1-phenyl-4H,5H-pyrazolo[3,4-b]pyridin-6-one (9.90 g, 132 mmol, 1.00 equiv) in portions at room temperature. The resulting mixture was stirred at room temperature for 3 h. The resulting mixture was diluted with $H_2O$ (40 mL). The resulting mixture was extracted with $CH_2Cl_2$ (3×100 mL). The combined organic layers were washed with brine (200 mL), dried over anhydrous $Na_2SO_4$. After filtration, the filtrate was concentrated under reduced pressure. The residue was purified by silica gel column chromatography, eluted with petroleum ether/EtOAc (1:1) to afford N-((4R,5S)-7-ethyl-4-(3-nitrophenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (6.20 g, 8.69% yield, 99% purity) as a yellow solid.

LCMS Calculated for $C_{25}H_{20}F_3N_7O_4$: 539.15; Observed: 540.3 $[M+H]^+$

N-((4R,5S)-4-(3-aminophenyl)-7-ethyl-6-oxo-1-phenyl-4,5,6,7-tetrahydro-1H-pyrazolo[3,4-b]pyridin-5-yl)-1-(trifluoromethyl)-1H-pyrazole-3-carboxamide (5)

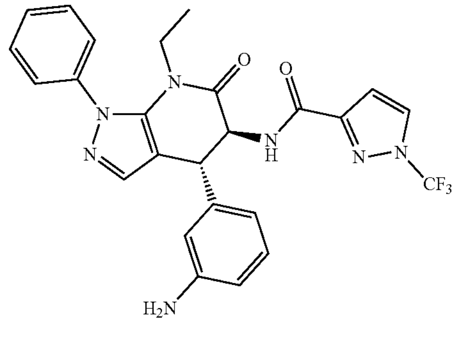 [SMILES: CCN1C(=O)[C@@H](NC(=O)c2ccn(C(F)(F)F)n2)[C@H](c2cccc(N)c2)c2cnn(-c3ccccc3)c21]

A solution of N-((4R,5S)-7-ethyl-4-(3-nitrophenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (6.20 g, 11.5 mmol, 1.00 equiv), and Pd/C (0.61 g, 10%) in ethyl acetate (70 mL) was stirred at room temperature for 10 h under hydrogen gas. The resulting mixture was filtered, the filter cake was washed with ethyl acetate (3×20 mL). The filtrate was concentrated under reduced pressure. The residue was purified by silica gel column chromatography, eluted with petroleum ether/ethyl acetate (1:2) to afford N-((4R,5S)-4-(3-aminophenyl)-7-ethyl-6-oxo-1-phenyl-4,5,6,7-tetrahydro-1H-pyrazolo[3,4-b]pyridin-5-yl)-1-(trifluoromethyl)-1H-pyrazole-3-carboxamide (5.20 g, 88.8% yield, 96% purity) as a yellow solid.

LCMS Calculated for $C_{25}H_{22}F_3N_7O_2$: 509.18; Observed: 510.3 $[M+H]^+$ methyl 3-hydroxy-2-methylenebutanoate (7)

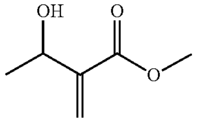

To a stirred solution of methyl acrylate (100 g, 1.10 mol, 1.00 equiv) in dioxane (800 mL) were added acetaldehyde (102 g, 2.20 mol, 2.00 equiv) and 1,4-diazabicyclo[2.2.2]octane (13.1 g, 0.10 mol, 0.10 equiv) in portions at room temperature. The resulting mixture was stirred at room temperature overnight. The reaction was monitored by LCMS and TLC. After completion of reaction, the resulting mixture was concentrated under reduced pressure. The residue was purified by silica gel column chromatography, eluted with petroleum ether/ethyl acetate=1/1 to afford methyl 3-hydroxy-2-methylidenebutanoate (73 g, 48.3% yield, 95% purity) as a colorless oil.

$^1H$ NMR (400 MHz, DMSO-$d_6$) δ 6.10-6.04 (m, 1H), 5.91-5.84 (m, 1H), 5.10 (s, 1H), 4.52-4.43 (m, 1H), 3.69 (s, 3H), 1.19 (d, J=6.5 Hz, 3H).

methyl 2-(bromomethyl)but-2-enoate (8)

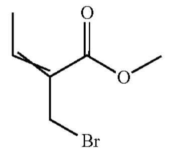

To a solution of methyl 3-hydroxy-2-methylidenebutanoate (25.0 g, 192 mmol, 1.00 equiv) in DCM (500 mL) under nitrogen atmosphere was added phosphorus tribromide (26.0 g, 96.0 mmol, 0.500 equiv) dropwise at 0° C. The reaction mixture was stirred at 0° C. for 1 h. The reaction was quenched by the addition of water (300 mL) at 0° C. The resulting mixture was extracted with $CH_2Cl_2$ (2×300 mL). The combined organic layers were washed with brine (1×100 mL), dried over anhydrous $Na_2SO_4$. After filtration, the filtrate was concentrated under reduced pressure. This resulted in methyl 2-(bromomethyl)but-2-enoate (18.9 g, 50.9% yield, 91.4% purity) as a light green liquid.

LCMS Calculated for $C_6H_9BrO_2$: 191.98; Observed: 193.0, 195.0 $[M+H]^+$ methyl (E)-2-((4-(oxetan-3-yl)piperazin-1-yl) methyl)but-2-enoate (9)

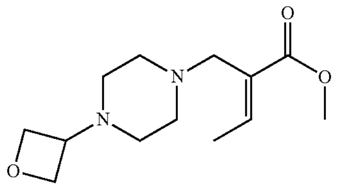 [SMILES: C/C=C(\CN1CCN(C2COC2)CC1)C(=O)OC]

A solution of 1-(oxetan-3-yl)piperazine (16.7 g, 117 mmol, 1.20 equiv) in DMF (180 mL) was treated with DIEA (25.3 g, 196 mmol, 2.00 equiv) at 0° C. for 5 min under nitrogen atmosphere followed by the addition of methyl 2-(bromomethyl)but-2-enoate (18.9 g, 97.9 mmol, 1.00 equiv) dropwise at 0° C. The reaction mixture was stirred at 20° C. for 2 h. The crude product was purified by reverse phase flash with the following conditions (0.05% $NH_3 \cdot H_2O$ solution) to afford methyl-2-((4-(oxetan-3-yl)piperazin-1-yl)methyl)but-2-enoate (E:Z=7:1) (23.7 g, 95.1% yield, 98.9% purity) as a green liquid. The mixture (23.7 g) was separated by Chiral-SFC with follow conditions: Column: XA-CHIRAL ART Cellulose-SC, 3*25 cm Sum; Mobile Phase A: $CO_2$, Mobile Phase B: MeOH(0.1% 2M $NH_3$-MeOH); Flow rate: 100 mL/min; Gradient (B %): isocratic 12% B; Column Temperature (° C.): 35; Back Pressure(bar): 100; Wave Length: 220 nm; RT1 (min): 3.8; RT2 (min): 4.4; Sample Solvent: MEOH; Injection Volume: 0.5 mL to afford methyl (E)-2-((4-(oxetan-3-yl)piperazin-1-yl)methyl)but-2-enoate (12.8 g, 54.0% yield, 97.4% purity).

LCMS Calculated for $C_{13}H_{22}N_2O_3$: 254.16; Observed: 255.2 $[M+H]^1$H NMR (300 MHz, DMSO-$d_6$) δ 6.91 (q, J=7.2 Hz, 1H), 4.50 (t, J=6.6 Hz, 2H), 4.39 (t, J=6.0 Hz, 2H), 3.65 (s, 3H), 3.41-3.33 (m, 1H), 3.16 (s, 2H), 2.46-2.04 (m, 8H), 1.84 (d, J=7.2 Hz, 3H).

(E)-2-((4-(oxetan-3-yl)piperazin-1-yl)methyl)but-2-enoic acid (INT-6)

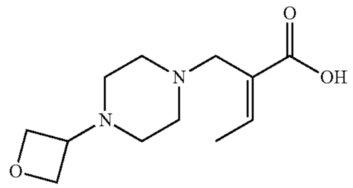 [SMILES: C/C=C(\CN1CCN(C2COC2)CC1)C(=O)O]

A solution of methyl (E)-2-((4-(oxetan-3-yl)piperazin-1-yl)methyl)but-2-enoate (10.5 g, 41.3 mmol, 1.00 equiv) and $LiOH \cdot H_2O$ (6.93 g, 165 mmol, 4.00 equiv) in $H_2O$ (50 mL) and THF (50 mL) was stirred at 60° C. for 3 h under nitrogen atmosphere. The mixture was allowed to cool down to room temperature. The resulting mixture was neutralized to with con.HCl (13.9 mL, 165 mmol, 4.00 equiv). The resulting mixture was concentrated under reduced pressure to afford (E)-2-((4-(oxetan-3-yl)piperazin-1-yl)methyl)but-2-enoic acid (20.0 g, 40% purity (included salt)) as a white solid. LCMS Calculated for $C_{12}H_{20}N_2O_3$: 240.15; Observed: 239.1$[M-H]^-$ $^1$H NMR (300 MHz, DMSO-$d_6$) δ 6.62 (q, J=7.2 Hz, 1H), 4.51 (t, J=6.3 Hz, 2H), 4.40 (t, J=6.0 Hz, 2H), 3.37-3.27 (m, 1H), 3.10 (s, 2H), 2.45-2.03 (m, 8H), 1.69 (d, J=7.2 Hz, 3H).

N-((4R,5S)-7-ethyl-4-(3-((E)-2-((4-(oxetan-3-yl) piperazin-1-yl)methyl)but-2-enamido)phenyl)-6-oxo-1-phenyl-4,5,6,7-tetrahydro-1H-pyrazolo[3,4-b] pyridin-5-yl)-1-(trifluoromethyl)-1H-pyrazole-3-carboxamide

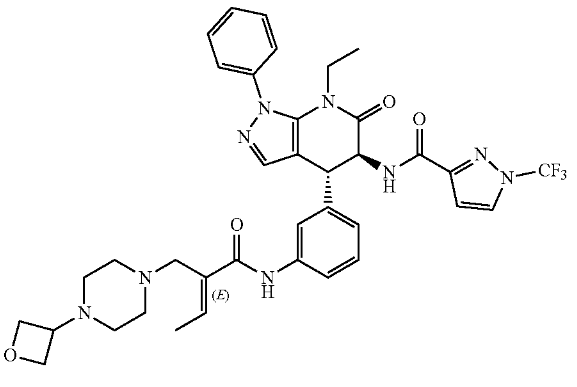 [SMILES: C/C=C(\CN1CCN(C2COC2)CC1)C(=O)Nc1cccc([C@@H]2c3cnn(-c4ccccc4)c3N(CC)C(=O)[C@H]2NC(=O)c2ccn(C(F)(F)F)n2)c1]

A solution of (E)-2-((4-(oxetan-3-yl)piperazin-1-yl) methyl)but-2-enoic acid (40% purity, 10.4 g, 17.3 mmol, 1.60 equiv), DIEA (5.59 g, 43.2 mmol, 4.00 equiv) and HATU (8.23 g, 21.6 mmol, 2.00 equiv) in DCM (60 mL) was stirred at room temperature for 20 min. To the above mixture was added N-((4R,5S)-4-(3-aminophenyl)-7-ethyl-6-oxo-1-phenyl-4,5,6,7-tetrahydro-1H-pyrazolo[3,4-b]pyridin-5-yl)-1-(trifluoromethyl)-1H-pyrazole-3-carboxamide (5.51 g, 10.8 mmol, 1.00 equiv) in portions. The resulting mixture was stirred at room temperature for 2 h. The reaction was quenched by the addition of water (150 mL) at room temperature. The resulting mixture was extracted with $CH_2Cl_2$ (3×100 mL). The combined organic layers were washed with brine (1×100 mL), dried over anhydrous $Na_2SO_4$. The crude product was purified by Prep-HPLC with the following conditions (Column: YMC-Triart-$C_{18-10}$ um 50*150 mm; Mobile Phase A: Water(0.05% $NH_4HCO_3$), Mobile Phase B: ACN; Flow rate: 90 mL/min; Gradient: isocratic 20%-78% 15 min; Wave Length: 254 nm/220 nm; RT1 (min): 9.6) to afford N-((4R,5S)-7-ethyl-4-(3-((E)-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (4.00 g, 50.5% yield, 99.9% purity) as a white solid.

| | |
|---|---|
| 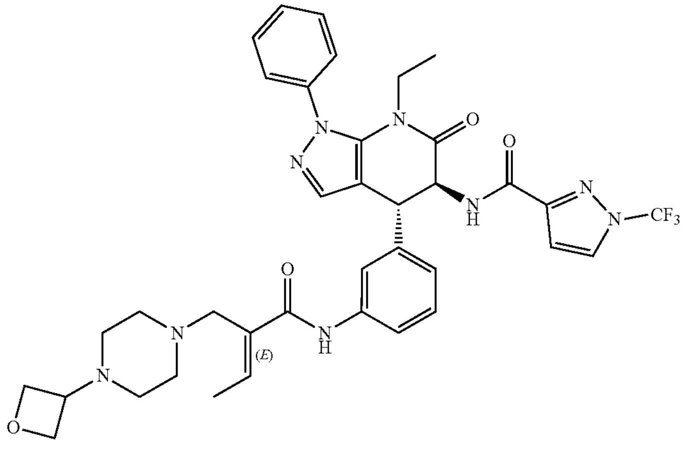 [SMILES: C/C=C(\CN1CCN(C2COC2)CC1)C(=O)Nc1cccc([C@@H]2c3cnn(-c4ccccc4)c3N(CC)C(=O)[C@H]2NC(=O)c2ccn(C(F)(F)F)n2)c1]<br>I-383 | $^1H$ NMR (400 MHz, DMSO-$d_6$) δ 11.39 (s, 1H), 8.79 (d, J = 9.2 Hz, 1H), 8.58 (d, J = 2.8 Hz, 1H), 7.71-7.64 (m, 2H), 7.63-7.49 (m, 5H), 7.27 (t, J = 7.8 Hz, 1H), 7.06 (d, J = 10.2 Hz, 2H), 6.91 (d, J = 2.8 Hz, 1H), 6.79 (q, J = 7.1 Hz, 1H), 5.09 (dd, J = 12.8, 9.2 Hz, 1H), 4.52 (d, J = 12.7 Hz, 1H), 4.45-4.27 (m, 4H), 3.86 (dq, J = 14.2, 7.0 Hz, 1H), 3.36 (q, J = 6.2 Hz, 1H), 3.31 (s, 2H), 3.06 (dq, J = 13.6, 6.8 Hz, 1H), 2.76-2.50 (m, 4H), 2.45-2.10 (m, 4H), 1.82 (d, J = 7.2 Hz, 3H), 0.83 (t, J = 7.0 Hz, 3H).LCMS Calculated for $C_{37}H_{40}F_3N_9O_4$: 731.32; Observed (Method-A): 732.4 [M + H]$^+$, 99.5% at RT 1.042 min. HPLC (Method-A): 99.95% at RT 5.14 min. CHIRAL-HPLC (Method-J): 99.85% at RT 1.68 min. Optical rotation: a = −134.99, (c = 0.1 g/100 mL in MeOH, T = 25° C.) |

NMR:

IX—$^1H$ NMR spectrum was recorded on Bruker 400 MHz and 300 MHz instruments internally referenced to a tetramethylsilane (TMS) signal. Chemical shifts (6) and coupling constants (J) were expressed in parts per million and hertz, respectively.

LCMS:

X—Method-N: Column: L-column3 C18, 50*3.0 mm, 3 um, Mobile Phase: A: Water/0.05% ammonia water; B: Acetonitrile, Flow Rate: 1.2 mL/min. Oven Temperature: 40 C, Gradient program (B %): 0.01/5, 2.00/95, 2.80/95, 2.81/5.

HPLC:

XI—Method-A: Cortecs C18+, 100*4.6 mm, 2.7 um, Mobile Phase: A: 0.1% MSA in water; B: Acetonitrile, Flow Rate: 1.5 mL/min. Oven Temperature: 40 C, Gradient program (B %): 0.00/10.0, 1.50/40, 8.50/70, 10.0/95, 12.0/95

Chiral-HPLC:

XII—Method-J: Column: CHIRALPAK ID-3, 50*4.6 mm, 3 um IE30CB—BV004; Mobile Phase A: n-Hexane/DCM=3/1, Mobile Phase B: EtOH (0.1% DEA), Conc. of Pump B: 30.0%; Flow rate: 1.0 ml/min; Oven Temperature: 25 C.

Synthesis of N-((4R,5S)-7-ethyl-4-(3-((E)-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)-2-(trifluoromethyl)thiazole-4-carboxamide I-234

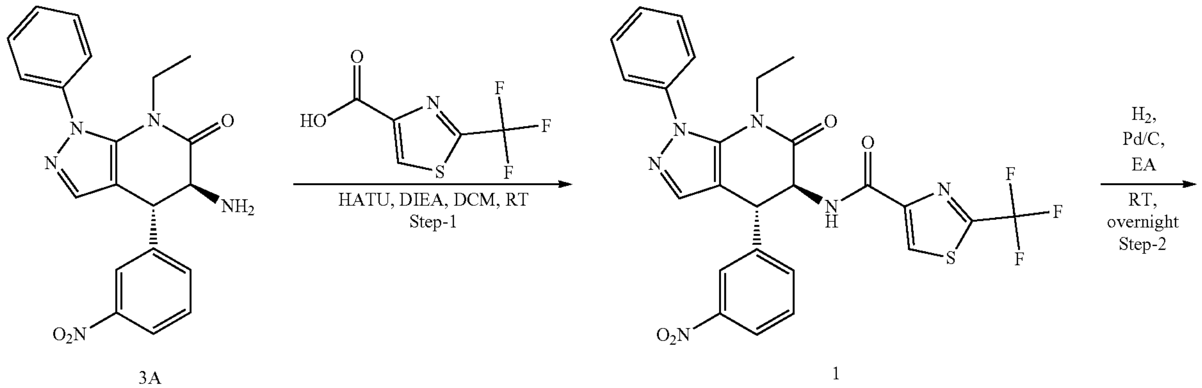

3A 1

-continued

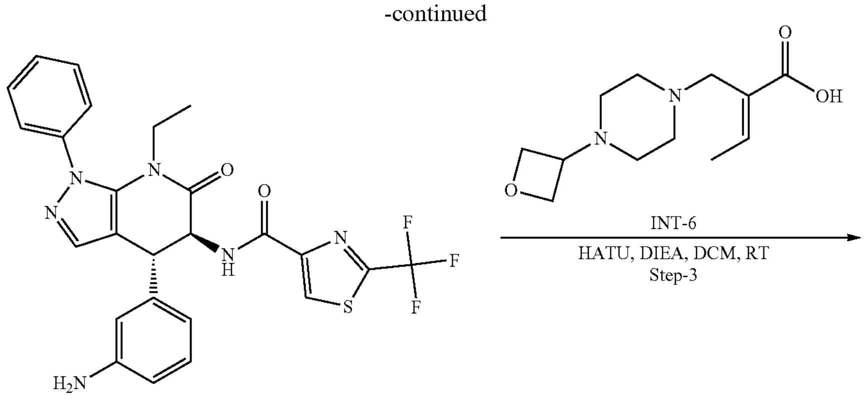

2

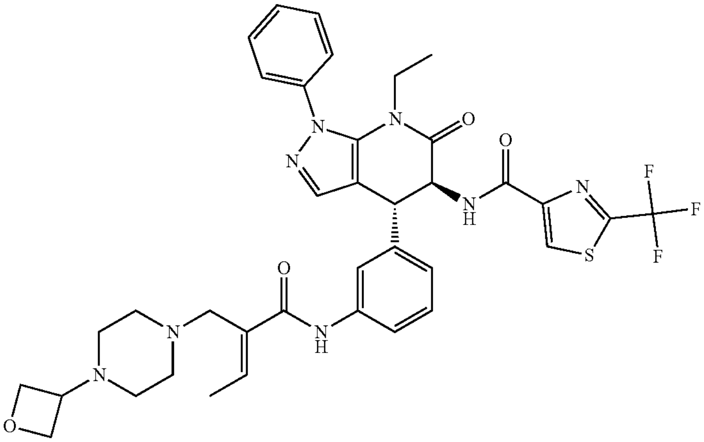

I-234

N-((4R,5S)-7-ethyl-4-(3-nitrophenyl)-6-oxo-1-phenyl-4,5,6,7-tetrahydro-1H-pyrazolo[3,4-b]pyridin-5-yl)-2-(trifluoromethyl)thiazole-4-carboxamide (1)

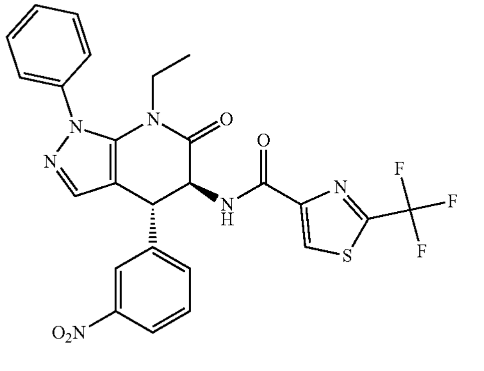 [SMILES: CCN1C(=O)[C@@H](NC(=O)c2csc(C(F)(F)F)n2)[C@H](c2cccc([N+](=O)[O-])c2)c2cnn(-c3ccccc3)c21]

A solution of 2-(trifluoromethyl)-1,3-thiazole-4-carboxylic acid (3.13 g, 15.9 mmol, 1.20 equiv) in DCM (100 mL) was treated with HATU (7.56 g, 19.9 mmol, 1.50 equiv) and DIEA (3.42 g, 26.5 mmol, 2.00 equiv) at room temperature for 10 min by the addition of (4R,5S)-5-amino-7-ethyl-4-(3-nitrophenyl)-1-phenyl-4H,5H-pyrazolo[3,4-b]pyridin-6-one (5.00 g, 13.2 mmol, 1.00 equiv) in portions at room temperature. The resulting mixture was stirred at room temperature for 3 h. The reaction was monitored by LCMS and TLC. After completion of reaction, the resulting mixture was concentrated under reduced pressure. The residue was purified by silica gel column chromatography, eluted with petroleum ether/ethyl acetate=1/1 to afford N-((4R,5S)-7-ethyl-4-(3-nitrophenyl)-6-oxo-1-phenyl-4,5,6,7-tetrahydro-1H-pyrazolo[3,4-b]pyridin-5-yl)-2-(trifluoromethyl)thiazole-4-carboxamide (6 g, 81.4% yield, 96% purity) as a light yellow solid. LCMS Calculated for $C_{25}H_{19}F_3N_6O_4S$: 556.11; Observed: 557.1 $[M+H]^+$, N-((4R,5S)-4-(3-aminophenyl)-7-ethyl-6-oxo-1-phenyl-4,5,6,7-tetrahydro-1H-pyrazolo[3,4-b]pyridin-5-yl)-2-(trifluoromethyl)thiazole-4-carboxamide (2)

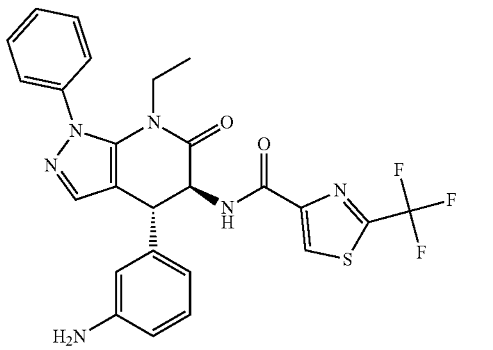 [SMILES: CCN1C(=O)[C@@H](NC(=O)c2csc(C(F)(F)F)n2)[C@H](c2cccc(N)c2)c2cnn(-c3ccccc3)c21]

To a solution of N-((4R,5S)-7-ethyl-4-(3-nitrophenyl)-6-oxo-1-phenyl-4,5,6,7-tetrahydro-1H-pyrazolo[3,4-b]pyridin-5-yl)-2-(trifluoromethyl)thiazole-4-carboxamide (5.80 g, 10.4 mmol, 1.00 equiv) in ethyl acetate (60 mL) was added Pd/C (10%, 1 g) under nitrogen atmosphere. The mixture was hydrogenated at room temperature overnight under hydrogen atmosphere using a hydrogen balloon. The reaction was monitored by TLC and LCMS. After completion of reaction, filtered through a Celite pad, the filter cake was washed with EA (4×10 mL). The filtrate was concentrated under reduced pressure. The residue was purified by silica gel column chromatography, eluted with petroleum ether/ethyl acetate=1/1 to afford N-((4R,5S)-4-(3-aminophenyl)-7-ethyl-6-oxo-1-phenyl-4,5,6,7-tetrahydro-1H-pyrazolo[3,4-b]pyridin-5-yl)-2-(trifluoromethyl)thiazole-4-carboxamide (4.8 g, 87.5% yield, 88% purity) as a yellow solid. LCMS Calculated for $C_{25}H_{21}F_3N_6O_2S$: 526.14; Observed: 527.2 $[M+H]^+$.

N-((4R,5S)-7-ethyl-4-(3-((E)-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)-2-(trifluoromethyl)thiazole-4-carboxamide I-234

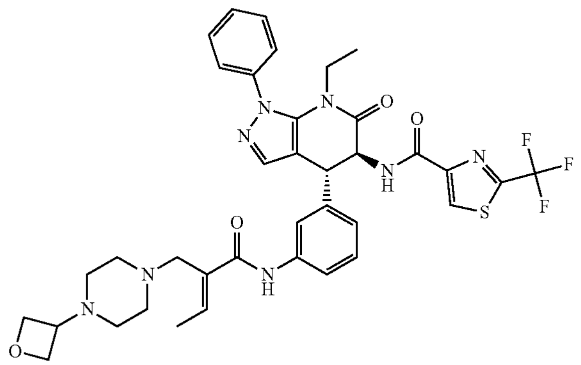 [SMILES: C/C=C(\CN1CCN(C2COC2)CC1)C(=O)Nc1cccc([C@@H]2c3cnn(-c4ccccc4)c3N(CC)C(=O)[C@H]2NC(=O)c2csc(C(F)(F)F)n2)c1]

A solution of (E)-2-((4-(oxetan-3-yl)piperazin-1-yl)methyl)but-2-enoic acid (40% purity, 8.22 g, 13.7 mmol, 1.5 equiv) in DCM (100 mL) was treated with HATU (5.12 g, 13.7 mmol, 1.5 equiv) and DIEA (2.36 g, 18.2 mmol, 2.0 equiv) at room temperature for 10 min followed by the addition of N-((4R,5S)-4-(3-aminophenyl)-7-ethyl-6-oxo-1-phenyl-4,5,6,7-tetrahydro-1H-pyrazolo[3,4-b]pyridin-5-yl)-2-(trifluoromethyl)thiazole-4-carboxamide (4.8 g, 9.12 mmol, 1.00 equiv) in portions at room temperature. The resulting mixture was stirred at room temperature for 3 h. The reaction was monitored by LCMS and TLC. After completion of reaction, the residue was purified by silica gel column chromatography, eluted with dichloromethane/MeOH (10/1) to afford crude product (6.2 g, 84% yield, 92% purity) as a yellow solid. The crude product was purified by DAC (0.05% $NH_3H_2O$ solution) to afford N-((4R,5S)-7-ethyl-4-(3-((E)-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)-2-(trifluoromethyl)thiazole-4-carboxamide as a white solid (2.8 g, 99.9% purity for HPLC, 97.3% purity for chiral HPLC). The crude product was purified by SFC with the following conditions (Column: XA-(R, R)-WHELK-O, 3*25 cm, 5 μm; Mobile Phase A: $CO_2$, Mobile Phase B: MeOH:DCM=2:1 (0.1% 2M $NH_3$-MeOH); Flow rate: 80 mL/min; Gradient: isocratic 50% B; Column Temperature (° C.): 35; Back Pressure(bar): 100; Wave Length: 254 nm; RT1 (min): 5.29; RT2 (min): 5.69; Sample Solvent: MeOH:DCM=1:1; Injection Volume: 0.5 mL) to afford N-((4R,5S)-7-ethyl-4-(3-((E)-2-((4-(oxetan-3-yl)piperazin-1-yl)methyl)but-2-enamido)phenyl)-6-oxo-1-phenyl-4,5,6,7-tetrahydro-1H-pyrazolo[3,4-b]pyridin-5-yl)-2-(trifluoromethyl)thiazole-4-carboxamide as a white solid (2.3 g, 33.7% yield, 99.5% purity). LCMS Calculated for $C_{37}H_{39}F_3N_8O_4S$: 748.28; Observed (Method-N): 749.4 $[M+H]^+$, 99.56% at RT 1.825 min. $^1H$ NMR (400 MHz, DMSO-$d_6$) δ 11.39 (s, 1H), 8.86 (d, J=9.3 Hz, 1H), 8.61 (s, 1H), 7.70-7.63 (m, 2H), 7.63-7.49 (m, 5H), 7.26 (t, J=7.8 Hz, 1H), 7.10-7.02 (m, 2H), 6.78 (q, J=7.1 Hz, 1H), 5.17-5.07 (m, 1H), 4.59 (d, J=12.9 Hz, 1H), 4.42-4.30 (m, 4H), 3.94-3.81 (m, 1H), 3.36 (d, J=6.3 Hz, 1H), 3.28 (s, 2H), 3.11-2.98 (m, 1H), 2.70-2.55 (s, 4H), 2.41-2.10 (m, 4H), 1.82 (d, J=7.2 Hz, 3H), 0.84 (t, J=7.0 Hz, 3H). HPLC (Method-A): 99.53% at RT 5.49 min. CHIRAL-HPLC (Method-J): 99.852% at RT 1.944 min.

1. Synthesis of tert-butyl (3-((4R,5S)-5-amino-7-ethyl-6-oxo-1-phenyl-4,5,6,7-tetrahydro-1H-pyrazolo[3,4-b]pyridin-4-yl)benzyl)carbamate

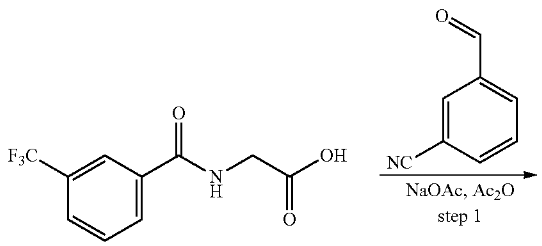

-continued

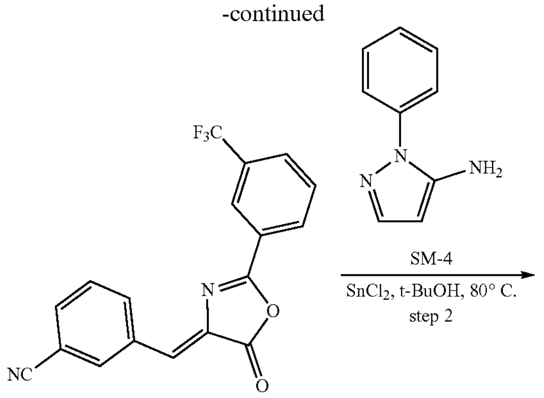

6

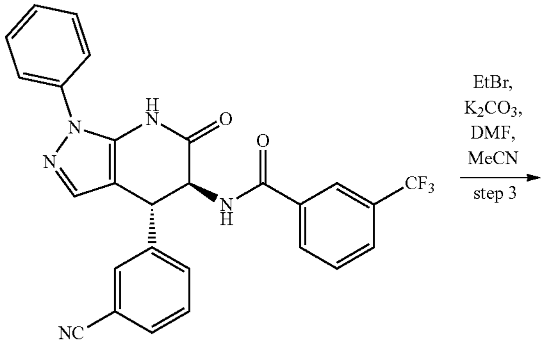

7

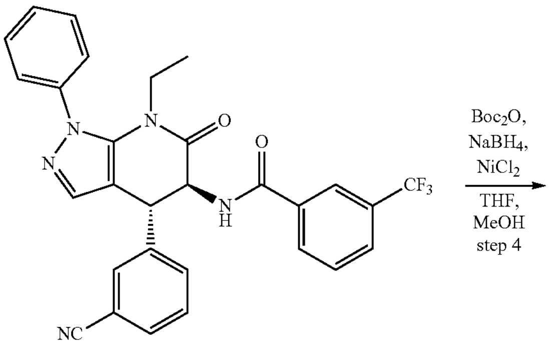

8

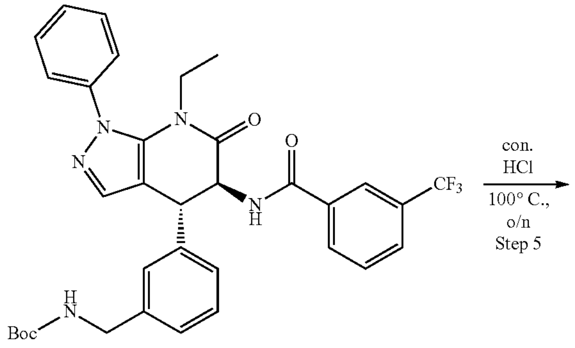

9

-continued

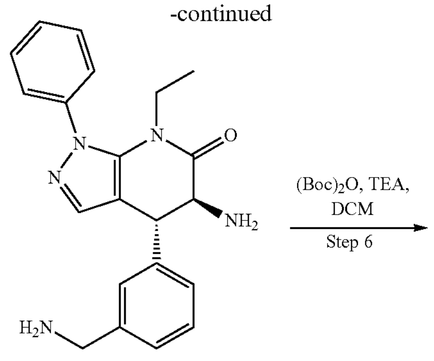

10

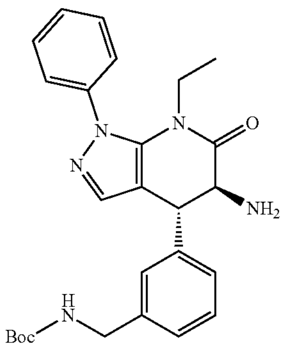

(Z)-3-((5-oxo-2-(3-(trifluoromethyl)phenyl)oxazol-4 (5H)-ylidene)methyl)benzonitrile (6)

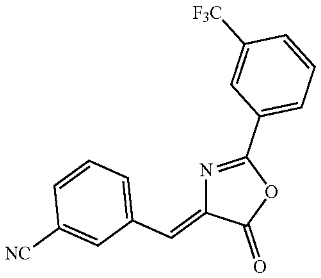 [SMILES: N#Cc1cccc(/C=C2\N=C(c3cccc(C(F)(F)F)c3)OC2=O)c1]

To a solution of $Ac_2O$ (28 μL, 4 V) in 50 L reactor was added (3-(trifluoromethyl)benzoyl)glycine (7.0 kg, 1.0 eq) and 3-formylbenzonitrile (3.71 kg, 1.0 eq) at room temperature. To the above mixture was added NaOAc (2.32 kg, 1.0 eq) and the resulting mixture was stirred at 80° C. for 4 h. The mixture was cooled to room temperature and stirred overnight. Hexane (21 μL, 3 V) was added into the reaction and the solution was stirred for additional 1 h at room temperature. The solid was collected by filtration and washed with hexane (7 μL, 1 V). The solid was dissolved with THF/EtOAc (1/1, 8V) and the solution was filtered through a silicone pad. The filtrate was concentrated under vacuum. 6.5 kg of crude product was obtained. Slurry with petroleum ether (2.5 V, 17 L), stirred for 50 min. The slurry was treated with petroleum ether (2.5 V, 17 L) for 50 min. The solid was collected by filtration. This resulted in (Z)-3-((5-oxo-2-(3-(trifluoromethyl)phenyl)oxazol-4 (5H)-ylidene)methyl)benzonitrile (6.3 kg, IY=56.2%, 98.2%) as an off-white solid.

N-((4R,5S)-4-(3-cyanophenyl)-6-oxo-1-phenyl-4,5,6,7-tetrahydro-1H-pyrazolo[3,4-b]pyridin-5-yl)-3-(trifluoromethyl)benzamide (7)

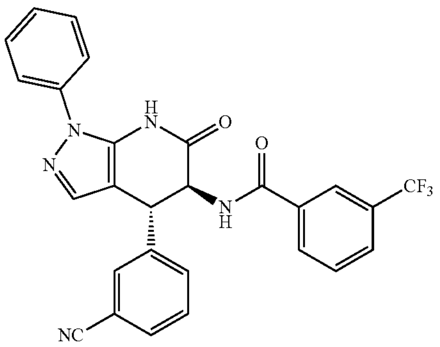 [SMILES: N#Cc1cccc([C@@H]2c3cnn(-c4ccccc4)c3NC(=O)[C@H]2NC(=O)c2cccc(C(F)(F)F)c2)c1]

To a solution of t-BuOH (47.7 μL, 9 V) in the reactor was added (Z)-3-((5-oxo-2-(3-(trifluoromethyl)phenyl)oxazol-4(5H)-ylidene)methyl)benzonitrile (5.30 kg, 1.00 eq), 1-phenyl-1H-pyrazol-5-amine (3.2 kg, 1.30 eq) and $SnCl_2$ (294 g, 0.100 eq) at room temperature. The mixture was heated to 80° C. within 2 hours and stirred for 12 hours at this temperature. The solution was filtered at 80° C., the filter cake was washed with t-BuOH (3.15 μL, 0.5 V) and heptane (6.30 μL, 1 V); The solid was dried. This resulted in N-((4R,5 S)-4-(3-cyanophenyl)-6-oxo-1-phenyl-4,5,6,7-tetrahydro-1H-pyrazolo[3,4-b]pyridin-5-yl)-3-(trifluoromethyl)benzamide (3.70 kg, 97.6% purity, 37.3% yield) as an off-white solid.

N-((4R,5S)-4-(3-cyanophenyl)-7-ethyl-6-oxo-1-phenyl-4,5,6,7-tetrahydro-1H-pyrazolo[3,4-b]pyridin-5-yl)-3-(trifluoromethyl)benzamide (8)

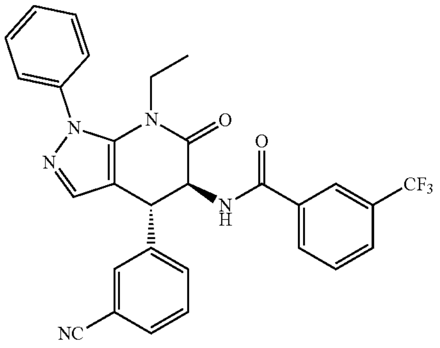 [SMILES: CCN1C(=O)[C@@H](NC(=O)c2cccc(C(F)(F)F)c2)[C@H](c2cccc(C#N)c2)c2cnn(-c3ccccc3)c21]

To a stirred solution of DMF (25.6 L, 8 V) and MeCN (9.6 L, 3 V) was added N-((4R,5S)-4-(3-cyanophenyl)-6-oxo-1-phenyl-4,5,6,7-tetrahydro-1H-pyrazolo[3,4-b]pyridin-5-yl)-3-(trifluoromethyl)benzamide (3.20 kg, 1.00 eq) and anhydrous $K_2CO_3$ (1.36 kg, 1.55 eq) at room temperature. To the above mixture was added EtBr (2.07 kg, 3.00 eq) dropwise at 0° C. The mixture was stirred for 20 hours at 30° C. The reaction mixture was quenched by additional of water (128 L, 40 V) and MTBE/EtOAc=2/1 (32 L, 10 V), the mixture was stirred for 1 hour at room temperature. The organic phase was separated, the aqueous phase was extracted with MTBE (2*16 L). The combined organic phase was washed with 15% wt NaCl aq (1*18.5 L, 5 V). The solution was concentrated to 5~6 V remained, the residue was stirred for 5 hours, the solid was collected by filtration. This resulted in N-((4R,5S)-4-(3-cyanophenyl)-7-ethyl-6-oxo-1-phenyl-4,5,6,7-tetrahydro-1H-pyrazolo[3,4-b]pyridin-5-yl)-3-(trifluoromethyl)benzamide (2.38 kg, 99.2% HPLC purity, 60% yield) as a white solid.

tert-butyl (3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)carbamate (9)

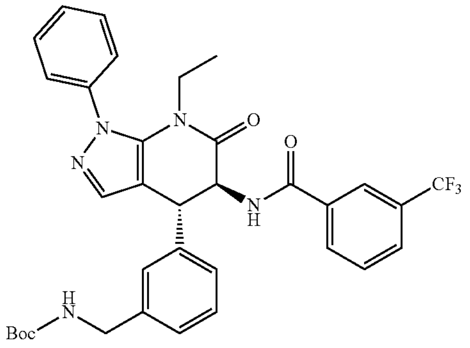 [SMILES: CCN1C(=O)[C@@H](NC(=O)c2cccc(C(F)(F)F)c2)[C@H](c2cccc(CNC(=O)OC(C)(C)C)c2)c2cnn(-c3ccccc3)c21]

To a stirred solution of anhydrous THE (30.3 L, 15 V) and MeOH (10.1 L, 5 V) was added N-((4R,5S)-4-(3-cyanophenyl)-7-ethyl-6-oxo-1-phenyl-4,5,6,7-tetrahydro-1H-pyrazolo[3,4-b]pyridin-5-yl)-3-(trifluoromethyl)benzamide (2.02 kg, 1.00 eq), $Boc_2O$ (1.24 kg, 1.50 eq) and $NiCl_2.6H_2O$ (0.90 kg, 1.00 eq) at room temperature. The temperature was allowed to cool down to −5±5° C. To the above mixture was added $NaBH_4$ (0.43 kg, 3 eq) portions within 4 hours, kept the temperature at 0±5° C. The mixture was stirred for 12 hours at 20° C. The resulting mixture was allowed to cool down to −5±5° C. The reaction mixture was quenched by additional of 1M HCl aq. (30.3 L, 15 V) and stirred for 1 hour at room temperature. The organic phase was separated, the aqueous phase was extracted with EtOAc (2*30 L). The combined organic phase was washed with 15% wt NaCl aq and dried with $Na_2SO_4$, concentrated under vacuum to afford tert-butyl (3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)carbamate (2.5 kg, 77% in LCMS). The crude product was used in next step without purification.

(4R,5S)-5-amino-4-(3-(aminomethyl)phenyl)-7-ethyl-1-phenyl-1,4,5,7-tetrahydro-6H-pyrazolo[3,4-b]pyridin-6-one (10)

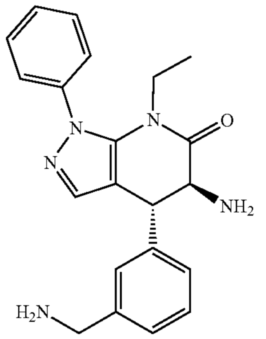 [SMILES: CCN1C(=O)[C@@H](N)[C@H](c2cccc(CN)c2)c2cnn(-c3ccccc3)c21]

To a stirred solution of conc. HCl (12.5 L, 10 V) and dioxane (1.25 L, 1 V) was added tert-butyl (3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl) carbamate (1.25 kg, crude) in portions at room temperature. The mixture was heated to 100±5° C. and stirred for 24 h. The mixture was allowed to cool down to room temperature and concentrated under vacuum. The residue was diluted with water (7.5 L, 3 V) and extracted with DCM (2*25 L), the aqueous phase was adjusted PH to 7-8 with ammonium hydroxide and extracted with DCM/propan-2-ol=4/1 (4*25 L). The organic phase was combined and concentrated under vacuum to afford 1.5 kg crude. The slurry was treated with petroleum ether/EtOAc=4/1 (4 V, 6 L) for 50 min. The solid was collected by filtration to afford (4R,5S)-5-amino-4-(3-(aminomethyl)phenyl)-7-ethyl-1-phenyl-1,4,5,7-tetrahydro-6H-pyrazolo[3,4-b]pyridin-6-one (1.2 kg, 92% purity in LCMS) as a light green solid.

tert-butyl (3-((4R,5S)-5-amino-7-ethyl-6-oxo-1-phenyl-4,5,6,7-tetrahydro-1H-pyrazolo[3,4-b]pyridin-4-yl)benzyl)carbamate

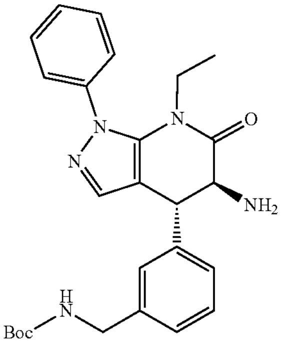 [SMILES: CCN1C(=O)[C@@H](N)[C@H](c2cccc(CNC(=O)OC(C)(C)C)c2)c2cnn(-c3ccccc3)c21]

To a solution of (4R,5S)-5-amino-4-(3-(aminomethyl) phenyl)-7-ethyl-1-phenyl-1,4,5,7-tetrahydro-6H-pyrazolo [3,4-b]pyridin-6-one (1.2 kg, crude) and TEA (424 g) in DCM was added $(Boc)_2O$ (549 g) at 0° C. The mixture was stirred for 4 h. The resulting mixture was quenched by the addition of water (24 L, 20 V) at room temperature. The organic phase was separated and the aqueous phase was extracted with DCM (12 L, 10 V). The combined organic phase was dried with $Na_2SO_4$ and concentrated under vacuum. The residue was purified by column chromatogram (DCM/THF=1/0~2/1) to afford tert-butyl (3-((4R,5S)-5-amino-7-ethyl-6-oxo-1-phenyl-4,5,6,7-tetrahydro-1H-pyrazolo[3,4-b]pyridin-4-yl)benzyl)carbamate (880 g, 96.1% HPLC purity) as a white solid. Optical rotation: [a]=−52.6 (C=0.10 g/100 ml in MeOH, T=25° C.)

1. Synthesis of N-((4R,5S)-7-ethyl-4-(3-((2-((3-hydroxy-3-methylpyrrolidin-1-yl)methyl)acrylamido)methyl)phenyl)-6-oxo-1-phenyl-4,5,6,7-tetrahydro-1H-pyrazolo[3,4-b]pyridin-5-yl)-3-(trifluoromethyl)benzamide I-10

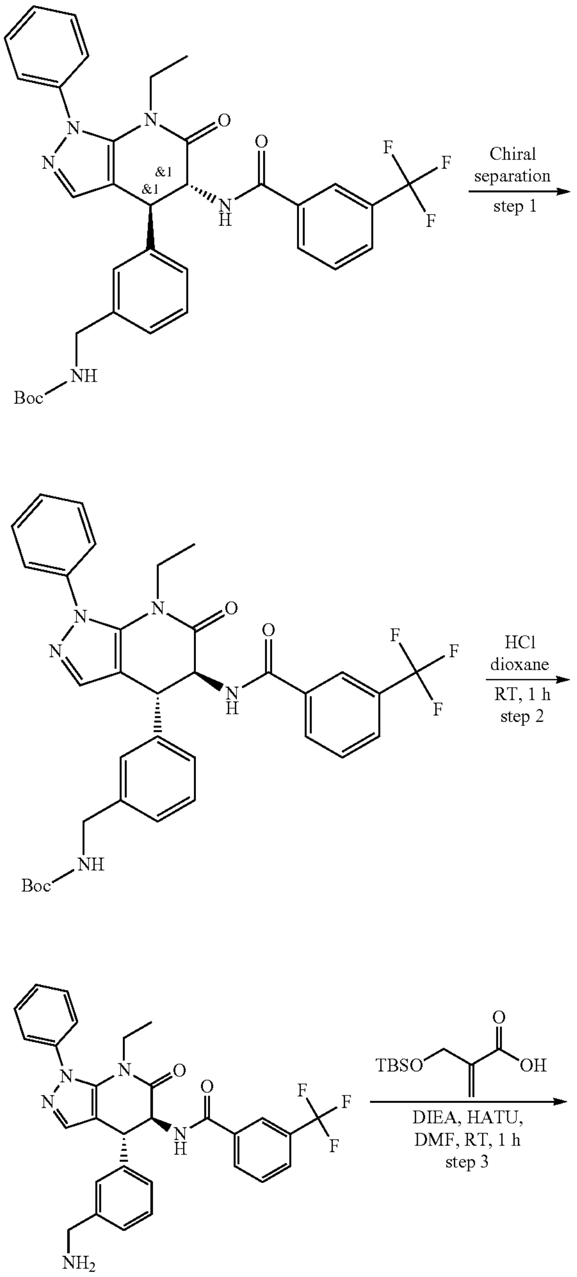

-continued

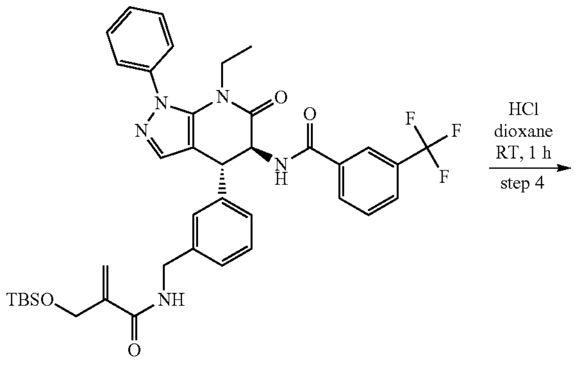

1

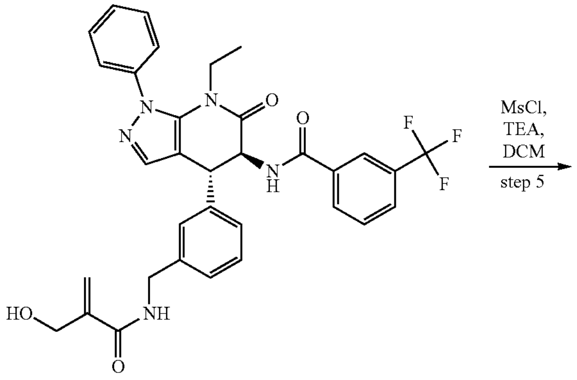

2

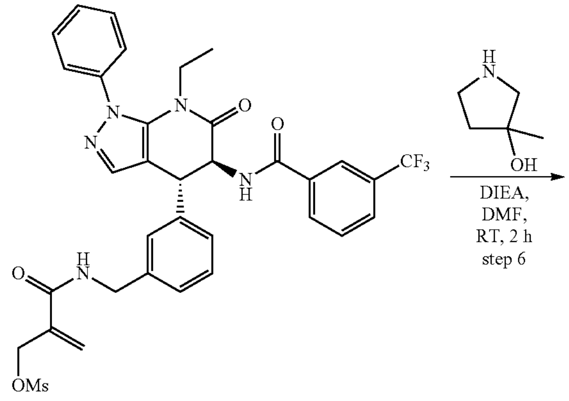

3

-continued

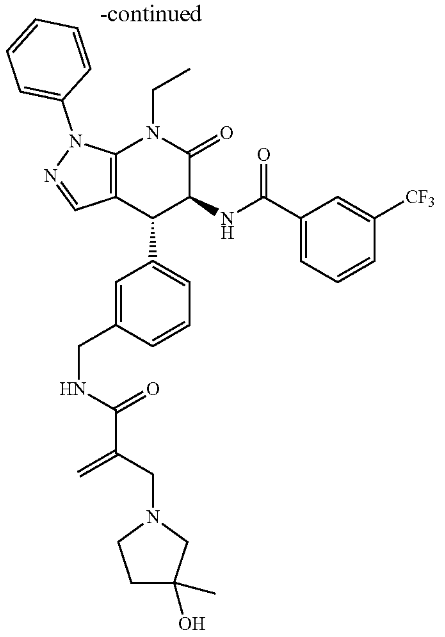

I-10 tert-butyl (3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)carbamate

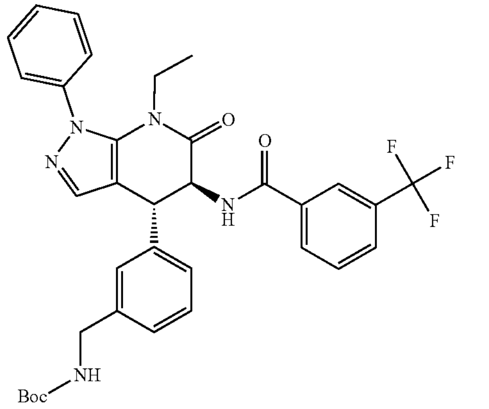 [SMILES: CCN1C(=O)[C@@H](NC(=O)c2cccc(C(F)(F)F)c2)[C@H](c2cccc(CNC(=O)OC(C)(C)C)c2)c2cnn(-c3ccccc3)c21]

The mixture product was separated by chiral-SFC flash with the following conditions (Column: XA-CHIRAL ART Cellulose-SC, 3*25 cm 5 um; Mobile Phase A: $CO_2$; Flow rate: 100 mL/min; Gradient: isocratic 20% B; Column Temperature: 35° C.; Back Pressure(bar): 100; Wave Length: 220 nm; RT1 (min): 4; RT2 (min): 5; Injection Volume: 1.5 mL) to afford tert-butyl (3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)carbamate (5.0 g, 33.93%) as a white solid.

N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-3-(trifluoromethyl)benzamide

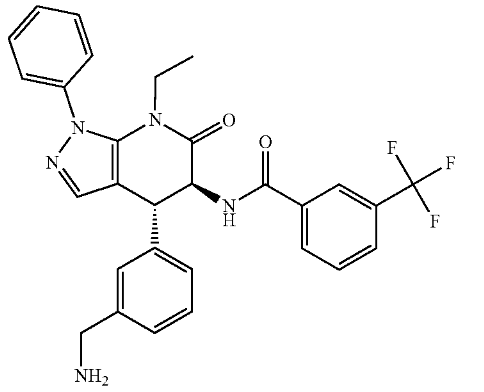 [SMILES: CCN1C(=O)[C@@H](NC(=O)c2cccc(C(F)(F)F)c2)[C@H](c2cccc(CN)c2)c2cnn(-c3ccccc3)c21]

A solution of tert-butyl (3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)carbamate (2.50 g, 3.95 mmol, 1.00 equiv) in HCl(gas) in 1,4-dioxane (1.83 mL, 60.3 mmol) was stirred for 2 hours at room temperature. The resulting mixture was concentrated under reduced pressure. The crude product was lyophilization under vacuum. Vacuum to afford N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-3-(trifluoromethyl)benzamide (2.20 g, 83.6%) was used in the next step directly without further purification.

N-((4R,5S)-4-(3-((2-(((tert-butyldimethylsilyl)oxy)methyl)acrylamido)methyl)phenyl)-7-ethyl-6-oxo-1-phenyl-4,5,6,7-tetrahydro-1H-pyrazolo[3,4-b]pyridin-5-yl)-3-(trifluoromethyl)benzamide (1)

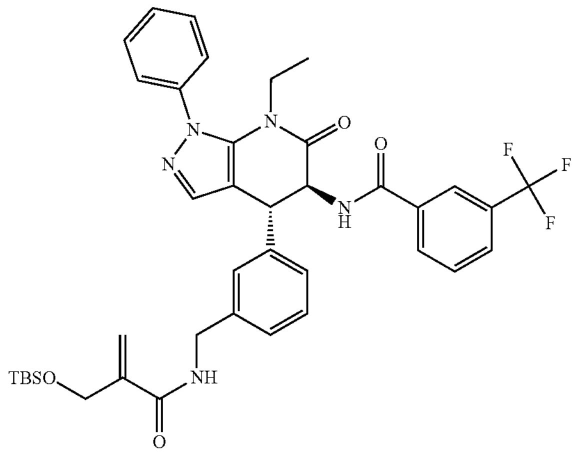 [SMILES: C=C(CO[Si](C)(C)C(C)(C)C)C(=O)NCc1cccc([C@@H]2c3cnn(-c4ccccc4)c3N(CC)C(=O)[C@H]2NC(=O)c2cccc(C(F)(F)F)c2)c1]

To a stirred solution of N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-3-(trifluoromethyl)benzamide (2.10 g, 3.94 mmol, 1.00 equiv) and DIEA (1.53 g, 11.8 mmol, 3.00 equiv), 2-([(tert-butyldimethylsilyl)oxy]methyl-prop-2-enoic acid (1.02 g, 4.72 mmol, 1.20 equiv) in DMF (50 mL) were added HATU (1.80 g, 4.72 mmol, 1.20 equiv) in portions at room temperature. The resulting mixture was stirred for 1 hour at room temperature. The reaction was quenched with water (300 ml) at ice bath. The precipitated solids were collected by filtration and washed with water (2×100 ml). This resulted in N-((4R,5S)-4-(3-((2-(((tert-butyldimethylsilyl)oxy)methyl)acrylamido)methyl)phenyl)-7-ethyl-6-oxo-1-phenyl-4,5,6,7-tetrahydro-1H-pyrazolo[3,4-b]pyridin-5-yl)-3-(trifluoromethyl)benzamide (2.10 g, 61.9%) as a yellow solid. LCMS Calculated for $C_{39}H_{44}F_3N_5O_4Si$: 731.31; Observed: 732.3 $[M+H]^+$ N-((4R,5S)-7-ethyl-4-(3-((2-(hydroxymethyl)acrylamido)methyl)phenyl)-6-oxo-1-phenyl-4,5,6,7-tetrahydro-1H-pyrazolo[3,4-b]pyridin-5-yl)-3-(trifluoromethyl)benzamide (2)

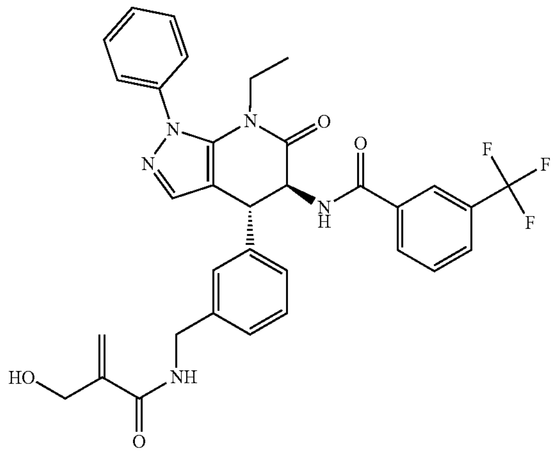 [SMILES: C=C(CO)C(=O)NCc1cccc([C@@H]2c3cnn(-c4ccccc4)c3N(CC)C(=O)[C@H]2NC(=O)c2cccc(C(F)(F)F)c2)c1]

A solution of N-((4R,5S)-4-(3-((2-(((tert-butyldimethylsilyl)oxy)methyl)acrylamido)methyl)phenyl)-7-ethyl-6-oxo-1-phenyl-4,5,6,7-tetrahydro-1H-pyrazolo[3,4-b]pyridin-5-yl)-3-(trifluoromethyl)benzamide (1.70 g, 2.32 mmol, 1.00 equiv) and conc. HCl (5 mL) in MeCN (20 mL) was stirred for 2 hours at room temperature. The resulting mixture was diluted with water (50 ml). The resulting mixture was extracted with EtOAc (2×100 ml). The combined organic layers were washed with sat brine (2×50 ml), dried over anhydrous $Na_2SO_4$. After filtration, the filtrate was concentrated under reduced pressure. The crude product N-((4R,5S)-7-ethyl-4-(3-((2-(hydroxymethyl)acrylamido)methyl)phenyl)-6-oxo-1-phenyl-4,5,6,7-tetrahydro-1H-pyrazolo[3,4-b]pyridin-5-yl)-3-(trifluoromethyl)benzamide (1.50 g, 83.6%) was used in the next step directly without further purification.

2-((3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)carbamoyl)allyl methanesulfonate (15)

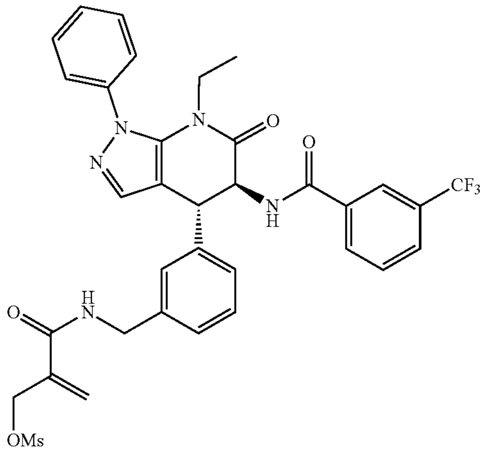 [SMILES: C=C(COS(C)(=O)=O)C(=O)NCc1cccc([C@@H]2c3cnn(-c4ccccc4)c3N(CC)C(=O)[C@H]2NC(=O)c2cccc(C(F)(F)F)c2)c1]

To a stirred mixture of N-((4R,5S)-7-ethyl-4-(3-((2-(hydroxymethyl)acrylamido)methyl)phenyl)-6-oxo-1-phenyl-4,5,6,7-tetrahydro-1H-pyrazolo[3,4-b]pyridin-5-yl)-3-(trifluoromethyl)benzamide (160 mg, 0.259 mmol, 1.00 equiv) and $Et_3N$ (78.6 mg, 0.777 mmol, 3.00 equiv) in THF (2 mL) was added methanesulfonyl chloride (44.5 mg, 0.389 mmol, 1.50 equiv) dropwise at 0° C. under $N_2$ atmosphere. The resulting mixture was stirred for 1 h at room temperature. The reaction was quenched with water. The resulting mixture was extracted with EtOAc (3x8 mL). The combined organic layers were washed with brine (1x5 mL), dried over anhydrous $Na_2SO_4$. After filtration, the filtrate was concentrated under reduced pressure. This resulted in 2-((3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)carbamoyl)allyl methanesulfonate (160 mg, 88%) as a white solid. LCMS Calculated for $C_{34}H_{32}F_3N_5O_6S$: 695.7; Observed: 696.7 $[M+H]^+$ N-((4R,5S)-7-ethyl-4-(3-((2-((3-hydroxy-3-methylpyrrolidin-1-yl)methyl)acrylamido)methyl)phenyl)-6-oxo-1-phenyl-4,5,6,7-tetrahydro-1H-pyrazolo[3,4-b]pyridin-5-yl)-3-(trifluoromethyl)benzamide I-10

I-10

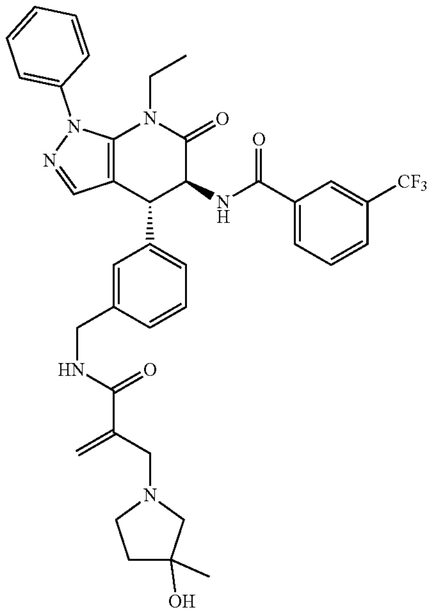

A mixture of 2-((3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)carbamoyl)allyl methanesulfonate (100 mg, 0.144 mmol, 1.0 equiv) and DIEA (37.2 mg, 0.288 mmol, 2.00 equiv), 3-methylpyrrolidin-3-ol (15.9 mg, 0.158 mmol, 1.1 equiv) in DMF (2 mL) was stirred at room temperature for 2 hours. The resulting mixture was purified by Column: XBridge Prep OBD C18 Column, 30*150 mm, 5 m; Mobile Phase A: Water(10 mmol/L $NH_4HCO_3$), Mobile Phase B: ACN; Flow rate: 60 mL/min; Gradient: isocratic 40%-55% 11 min; Wave Length: 254 nm/220 nm nm; RT1 (min): 6.45 to give N-((4R,5S)-7-ethyl-4-(3-((2-((3-hydroxy-3-methylpyrrolidin-1-yl)methyl)acrylamido)methyl)phenyl)-6-oxo-1-phenyl-4,5,6,7-tetrahydro-1H-pyrazolo[3,4-b]pyridin-5-yl)-3-(trifluoromethyl)benzamide (25.0 mg, 24.1%) as a white solid. I-10. $^1H$ NMR (400 MHz, DMSO-$d_6$): 8.03-7.91 (m, 2H), 7.87 (d, J=7.8 Hz, 1H), 7.67 (t, J=7.8 Hz, 1H), 7.64-7.47 (m, 5H), 7.28-7.19 (m, 3H), 7.17-7.02 (m, 1H), 6.97 (s, 1H), 5.83 (s, 1H), 5.43 (s, 1H), 5.12 (dd, J=13.0, 1.7 Hz, 1H), 4.49-4.19 (m, 3H), 3.80-3.75 (m, 1H), 3.20 (s, 2H), 3.02-2.97 (m, 1H), 2.50-2.39 (m, 1H), 2.35 (d, J=3.6 Hz, 2H), 1.69-1.56 (m, 1H), 1.52-1.44 (m, 1H), 1.06 (s, 3H), 0.79 (t, J=7.0 Hz, 3H). LCMS Calculated for $C_{38}H_{39}F_3N_6O_4$: 700.33; Observed (Method-A): 701.3 $[M+H]^+$, 99.25% at RT 1.053 min.

Compounds Below Prepared Using Mesylate Intermediate Like I-10

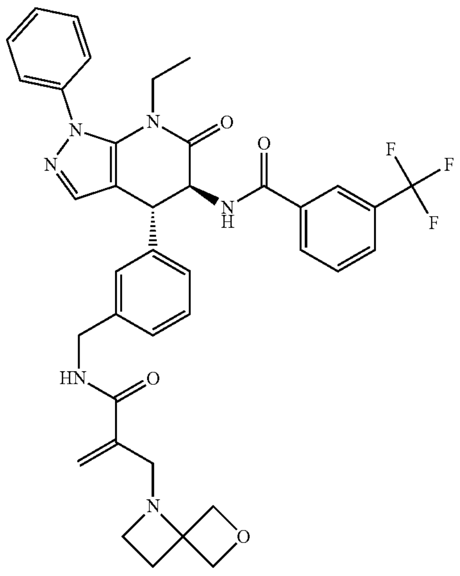 [SMILES: C=C(CN1CCC12COC2)C(=O)NCc1cccc([C@@H]2c3cnn(-c4ccccc4)c3N(CC)C(=O)[C@H]2NC(=O)c2cccc(C(F)(F)F)c2)c1]

I-332

$^1$H NMR (400 MHz, DMSO-$d_6$) δ 9.02 (d, J = 8.8 Hz, 1H), 8.73 (s, 1H), 8.08-8.00 (m, 2H), 7.91 (d, J = 8.0 Hz, 1H), 7.74-7.69 (m, 1H), 7.67-7.64 (m, 2H), 7.62-7.51 (m, 3H), 7.37-7.28 (m, 3H), 7.21-7.16 (m, 1H), 7.03 (s, 1H), 5.80 (s, 1H), 5.48 (s, 1H), 5.18 (dd, J = 12.9, 9.0 Hz, 1H), 4.78 (d, J = 7.0 Hz, 2H), 4.44-4.24 (m, 5H), 3.89-3.79 (m, 1H), 3.47 (s, 1H), 3.40 (s, 1H), 3.12-3.02 (m, 1H), 2.95-2.82 (m, 2H), 2.35-2.20 (m, 2H), 0.83 (t, J = 7.0 Hz, 3H).
LCMS Calculated for $C_{38}H_{37}F_3N_6O_4$: 698.28; Observed (Method-B): 699.2 [M + H]$^+$, 98.84% at RT 0.935 min.

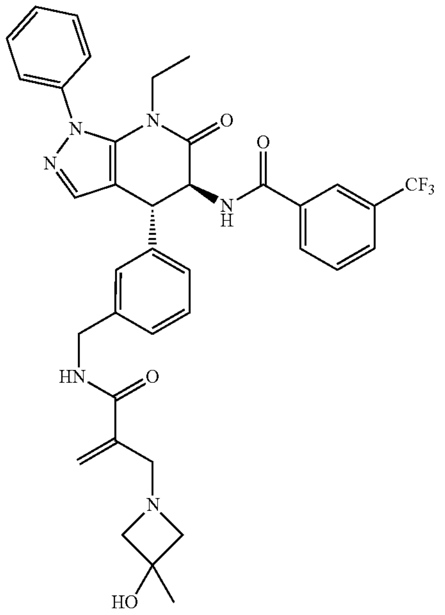 [SMILES: C=C(CN1CC(C)(O)C1)C(=O)NCc1cccc([C@@H]2c3cnn(-c4ccccc4)c3N(CC)C(=O)[C@H]2NC(=O)c2cccc(C(F)(F)F)c2)c1]

I-361

$^1$H NMR (400 MHz, DMSO-$d_6$) δ 9.05-8.94 (m, 2H), 8.38 (s, 1H), 8.04 (d, J = 12.1 Hz, 2H), 7.91 (d, J = 7.8 Hz, 1H), 7.75-7.68 (m, 1H), 7.68-7.63 (m, 2H), 7.63-7.50 (m, 3H), 7.33 (s, 1H), 7.30 (d, J = 5.1 Hz, 2H), 7.20-7.15 (m, 1H), 7.02 (s, 1H), 5.81 (d, J = 1.9 Hz, 1H), 5.40 (s, 1H), 5.18 (dd, J = 12.8, 9.0 Hz, 1H), 4.40 (d, J = 12.9 Hz, 1H), 4.37-4.25 (m, 2H), 3.88-3.78 (m, 1H), 3.24 (s, 2H), 3.13-3.02 (m, 3H), 2.81 (d, J = 6.9 Hz, 2H), 1.23 (s, 3H), 0.83 (t, J = 7.0 Hz, 3H).
LCMS Calculated for $C_{37}H_{37}F_3N_6O_4$: 686.28; Observed (Method-B): 687.3 [M + H]$^+$, 97.89% at RT 0.797 min.

-continued

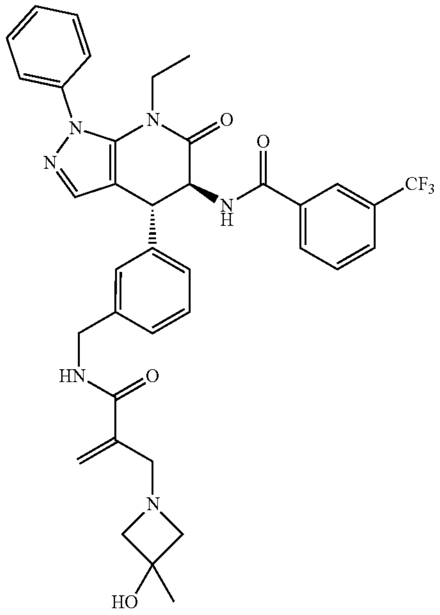 [SMILES: C=C(CN1CC(C)(O)C1)C(=O)NCc1cccc([C@@H]2c3cnn(-c4ccccc4)c3N(CC)C(=O)[C@H]2NC(=O)c2cccc(C(F)(F)F)c2)c1]

$^1$H NMR (400 MHz, DMSO-$d_6$) δ 9.05-8.95 (m, 2H), 8.05-7.98 (m, 2H), 7.89 (d, J = 7.8 Hz, 1H), 7.73-7.65 (m, 1H), 7.65-7.60 (m, 2H), 7.60-7.53 (m, 2H), 7.55-7.47 (m, 1H), 7.33-7.25 (m, 3H), 7.18-7.12 (m, 1H), 7.01 (d, J = 1.6 Hz, 1H), 5.77 (s, 1H), 5.36 (s, 1H), 5.15 (dd, J = 12.8, 9.0 Hz, 1H), 5.08 (dd, J = 6.3, 3.0 Hz, 1H), 4.38 (d, J = 12.8 Hz, 1H), 4.33-4.29 (m, 2H), 3.86-3.78 (m, 1H), 3.77-3.69 (m, 1H), 3.42-3.36 (m, 1H), 3.15 (s, 2H), 3.08-3.01 (m, 1H), 3.00-2.95 (m, 1H), 2.93-2.86 (m, 2H), 1.91 (s, 1H), 1.62 (d, J = 15.3 Hz, 1H), 1.43 (s, 2H), 0.80 (t, J = 7.0 Hz, 3H).
LCMS Calculated for $C_{39}H_{39}F_3N_6O_4$: 712.30; Observed (Method-B): 713.3 $[M + H]^+$, 99.72% at RT 0.817 min.

I-375

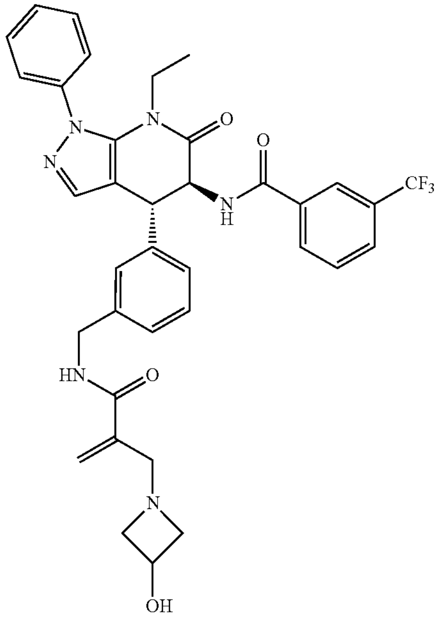 [SMILES: C=C(CN1CC(O)C1)C(=O)NCc1cccc([C@@H]2c3cnn(-c4ccccc4)c3N(CC)C(=O)[C@H]2NC(=O)c2cccc(C(F)(F)F)c2)c1]

$^1$H NMR (400 MHz, DMSO-$d_6$) δ 9.01 (d, J = 8.9 Hz, 1H), 8.83 (t, J = 6.1 Hz, 1H), 8.08-8.00 (m, 2H), 7.91 (d, J = 7.8 Hz, 1H), 7.74-7.69 (m, 1H), 7.67-7.64 (m, 2H), 7.62-7.51 (m, 3H), 7.35-7.26 (m, 3H), 7.19-7.13 (m, 1H), 7.04 (s, 1H), 5.78 (s, 1H), 5.40 (s, 1H), 5.32-5.28 (m, 1H), 5.17 (dd, J = 12.9, 8.9 Hz, 1H), 4.40 (d, J = 12.9 Hz, 1H), 4.33 (t, J = 5.9 Hz, 2H), 4.18-4.11 (m, 1H), 3.88-3.78 (m, 1H), 3.51-3.41 (m, 2H), 3.22 (s, 2H), 3.11-3.02 (m, 1H), 2.71 (t, J = 6.6 Hz, 2H), 0.83 (t, J = 7.0 Hz, 3H).
LCMS Calculated for $C_{36}H_{35}F_3N_6O_4$: 672.27; Observed (Method-Y): 673.2 $[M + H]^+$, 95.73% at RT 1.877 min.

I-291

-continued

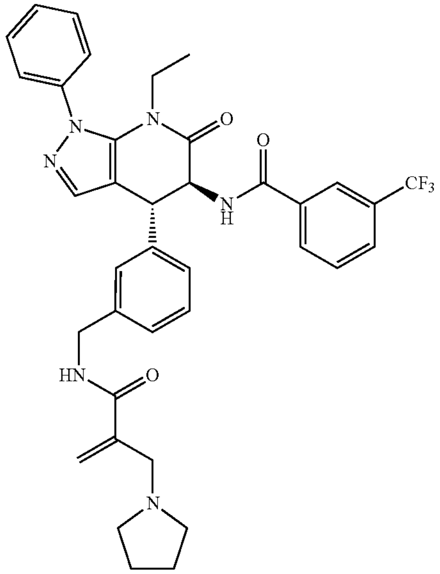 [SMILES: C=C(CN1CCCC1)C(=O)NCc1cccc([C@@H]2c3cnn(-c4ccccc4)c3N(CC)C(=O)[C@H]2NC(=O)c2cccc(C(F)(F)F)c2)c1]

I-264

$^1H$ NMR (400 MHz, DMSO-$d_6$) δ 9.13 (s, 1H), 9.02 (d, J = 9.0 Hz, 1H), 8.04 (d, J = 10.3 Hz, 2H), 7.91 (d, J = 7.8 Hz, 1H), 7.75-7.69 (m, 1H), 7.67-7.64 (m, 2H), 7.62-7.51 (m, 3H), 7.35-7.28 (m, 3H), 7.17 (s, 1H), 7.02 (s, 1H), 5.87-5.83 (m, 1H), 5.47-5.42 (m, 1H), 5.23-5.13 (m, 1H), 4.46-4.29 (m, 3H), 3.89-3.79 (m, 1H), 3.33-3.20 (m, 3H), 3.11-3.02 (m, 1H), 2.44-2.30 (m, 4H), 1.61-1.57 (m, 3H), 0.83 (t, J = 7.0 Hz, 3H).
LCMS Calculated for $C_{37}H_{37}F_3N_6O_3$: 670.29; Observed (Method-B): 671.2 [M + H]$^+$, 98.94% at RT 0.971 min.

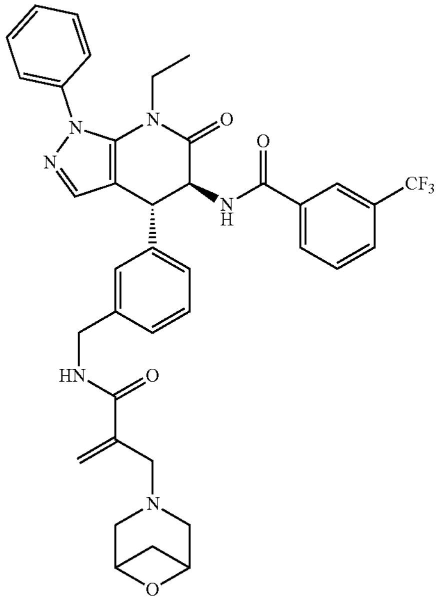 [SMILES: C=C(CN1CC2CC(C1)O2)C(=O)NCc1cccc([C@@H]2c3cnn(-c4ccccc4)c3N(CC)C(=O)[C@H]2NC(=O)c2cccc(C(F)(F)F)c2)c1]

I-290

$^1H$ NMR (400 MHz, DMSO-$d_6$) δ 9.00 (d, J = 9.0 Hz, 1H), 8.91 (t, J = 5.9 Hz, 1H), 8.04 (d, J = 10.7 Hz, 2H), 7.91 (d, J = 7.9 Hz, 1H), 7.74-7.69 (m, 1H), 7.68-7.64 (m, 2H), 7.63-7.51 (m, 3H), 7.34-7.24 (m, 3H), 7.19-7.13 (m, 1H), 6.99 (s, 1H), 5.92 (d, J = 2.1 Hz, 1H), 5.52 (s, 1H), 5.17 (dd, J = 12.9, 8.9 Hz, 1H), 4.44-4.28 (m, 2H), 4.26 (d, J = 6.1 Hz, 2H), 3.89-3.79 (m, 1H), 3.40 (s, 2H), 3.22-3.02 (m, 1H), 2.95-2.86 (m, 2H), 2.67-2.58 (m, 1H), 2.55 (s, 1H), 1.78 (d, J = 8.1 Hz, 1H), 1.26 (q, J = 7.4, 6.6 Hz, 2H), 0.83 (t, J = 7.0 Hz, 3H).
LCMS Calculated for $C_{38}H_{37}F_3N_6O_4$: 698.28; Observed (Method-B): 699.2 [M + H]$^+$, 99.41% at RT 0.943 min.

-continued

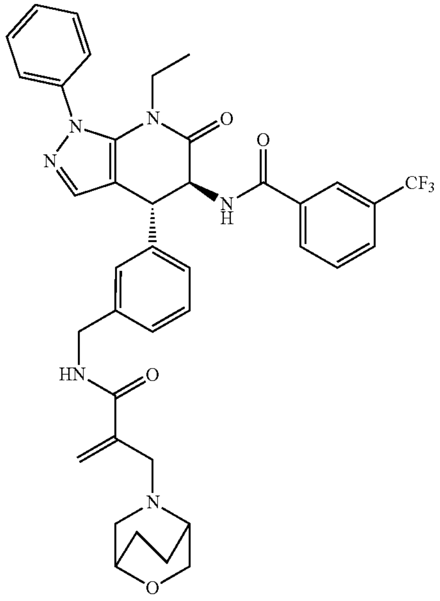 [SMILES: C=C(CN1CC2CCC1CO2)C(=O)NCc1cccc([C@@H]2c3cnn(-c4ccccc4)c3N(CC)C(=O)[C@H]2NC(=O)c2cccc(C(F)(F)F)c2)c1]

$^1$H NMR (400 MHz, DMSO-$d_6$) δ 9.23 (d, J = 6.7 Hz, 1H), 9.00 (d, J = 8.6 Hz, 1H), 8.04 (d, J = 11.6 Hz, 2H), 7.91 (d, J = 7.8 Hz, 1H), 7.71 (t, J = 7.7 Hz, 1H), 7.65 (d, J = 7.7 Hz, 2H), 7.60 (t, J = 7.5 Hz, 2H), 7.54 (t, J = 7.2 Hz, 1H), 7.37-7.29 (m, 3H), 7.21 (s, 1H), 7.01 (d, J = 2.3 Hz, 1H), 5.90 (s, 1H), 5.49 (s, 1H), 5.20 (dd, J = 13.0, 9.0 Hz, 1H), 4.43-4.33 (m, 2H), 4.00-3.91 (m, 1H), 3.87-3.79 (m, 1H), 3.58-3.52 (m, 2H), 3.43-3.36 (m, 2H), 3.11-3.01 (m, 1H), 2.85-2.74 (m, 1H), 2.71-2.64 (m, 1H), 1.73-1.68 (m, 3H), 1.49-1.27 (m, 3H), 0.83 (t, J = 7.0 Hz, 3H).
LCMS Calculated for $C_{39}H_{39}F_3N_6O_4$: 712.30; Observed (Method-B): 713.2 [M + H]$^+$, 99.27% at RT 0.959 min.

I-293

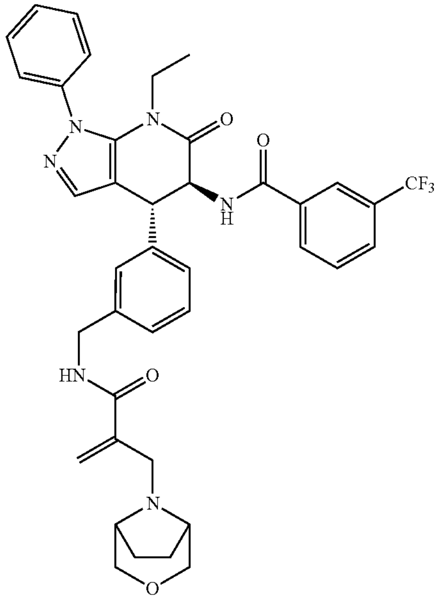 [SMILES: C=C(CN1C2CCC1COC2)C(=O)NCc1cccc([C@@H]2c3cnn(-c4ccccc4)c3N(CC)C(=O)[C@H]2NC(=O)c2cccc(C(F)(F)F)c2)c1]

$^1$H NMR (400 MHz, DMSO-$d_6$) δ 9.36 (t, J = 5.7 Hz, 1H), 9.01 (d, J = 9.0 Hz, 1H), 8.04 (d, J = 11.5 Hz, 2H), 7.91 (d, J = 7.9 Hz, 1H), 7.71 (t, J = 7.8 Hz, 1H), 7.65 (d, J = 7.3 Hz, 2H), 7.63-7.50 (m, 3H), 7.36 (s, 1H), 7.32 (d, J = 4.6 Hz, 2H), 7.27-7.21 (m, 1H), 7.01 (s, 1H), 5.91 (d, J = 2.2 Hz, 1H), 5.46 (s, 1H), 5.18 (dd, J = 12.9, 9.0 Hz, 1H), 4.44-4.30 (m, 3H), 3.89-3.79 (m, 1H), 3.28-3.26 (m, 4H), 3.11-3.02 (m, 3H), 2.93-2.88 (m, 2H), 1.84-1.77 (m, 2H), 1.63 (d, J = 7.4 Hz, 2H), 0.83 (t, J = 7.0 Hz, 3H).
LCMS Calculated for $C_{39}H_{39}F_3N_6O_4$: 712.30; Observed (Method-B): 713.2 [M + H]$^+$, 98.64% at RT 0.971 min.

I-289

-continued
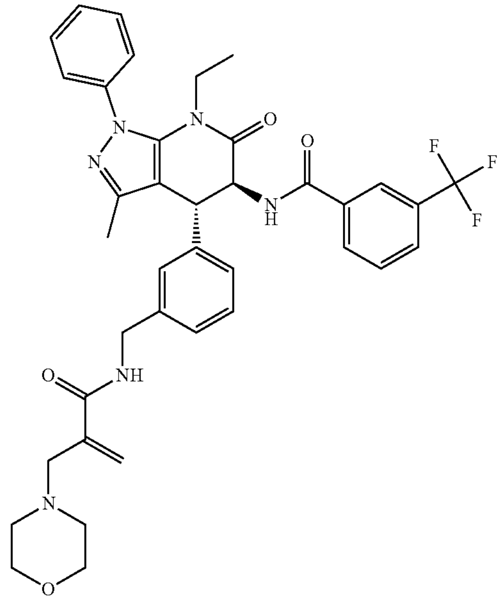 [SMILES: C=C(CN1CCOCC1)C(=O)NCc1cccc([C@@H]2c3c(C)nn(-c4ccccc4)c3N(CC)C(=O)[C@H]2NC(=O)c2cccc(C(F)(F)F)c2)c1]
1H NMR (300 MHz, DMSO-$d_6$) δ 9.01-8.88 (m, 2H), 8.02 (d, J = 8.7 Hz, 2H), 7.91 (d, J = 7.8 Hz, 1H), 7.70 (t, J = 7.8 Hz, 1H), 7.66-7.44 (m, 5H), 7.30-7.22 (m, 3H), 7.22 (d, J = 7.0 Hz, 1H), 5.90 (d, J = 2.0 Hz, 1H), 5.44 (s, 1H), 5.23-5.14 (m, 1H), 4.43-4.21 (m, 3H), 3.96-3.59 (m, 1H), 3.42-3.34 (m, 4H), 3.12 (d, J = 16.7 Hz, 3H), 2.29-2.21 (m, 4H), 1.44 (s, 3H), 0.81 (t, J = 7.0 Hz, 3H). LCMS Calculated for $C_{38}H_{39}F_3N_6O_4$: 700.30; Observed (Method-B): 701.2 $[M + H]^+$, 99.72% at RT 0.955 min.
I-215
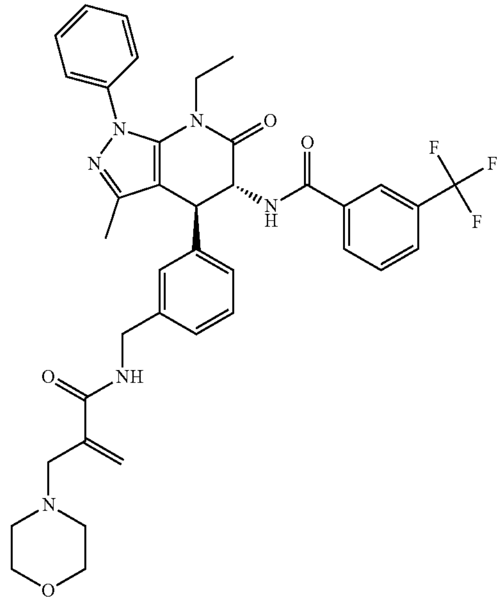 [SMILES: C=C(CN1CCOCC1)C(=O)NCc1cccc([C@H]2c3c(C)nn(-c4ccccc4)c3N(CC)C(=O)[C@@H]2NC(=O)c2cccc(C(F)(F)F)c2)c1]
$^1$H NMR (400 MHz, DMSO-$d_6$) δ 9.01 (d, J = 9.1 Hz, 2H), 8.02 (d, J = 10.3 Hz, 2H), 7.90 (d, J = 7.8 Hz, 1H), 7.75-7.66 (m, 1H), 7.65-7.60 (m, 2H), 7.60-7.54 (m, 2H), 7.53-7.47 (m, 1H), 7.36-7.25 (m, 3H), 7.22 (d, J = 7.3 Hz, 1H), 5.90 (s, 1H), 5.44 (s, 1H), 5.28-5.18 (m, 1H), 4.40-4.32 (m, 3H), 3.84-3.72 (m, 1H), 3.43 (d, J = 5.1 Hz, 4H), 3.15 (s, 2H), 3.13-3.06 (m, 1H), 2.31-2.26 (m, 4H), 1.44 (s, 3H), 0.82 (t, J = 7.0 Hz, 3H). LCMS Calculated for $C_{38}H_{39}F_3N_6O_4$: 700.30; Observed (Method-B): 701.2 $[M + H]^+$, 99.59% at RT 0.824 min.
I-285

-continued

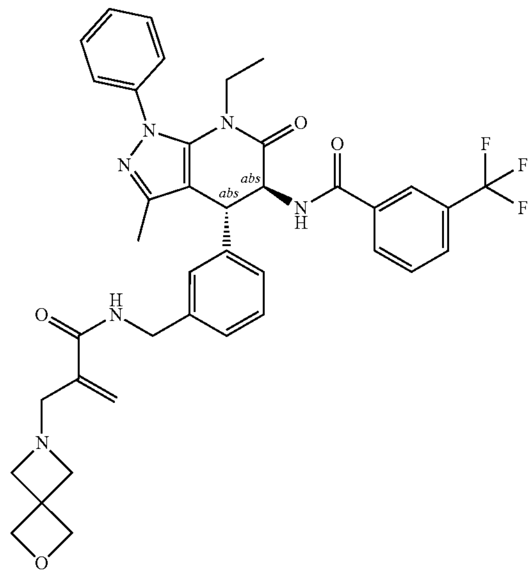 [SMILES: C=C(CN1CC2(COC2)C1)C(=O)NCc1cccc([C@@H]2c3c(C)nn(-c4ccccc4)c3N(CC)C(=O)[C@H]2NC(=O)c2cccc(C(F)(F)F)c2)c1]

$^1$H NMR (400 MHz, DMSO-$d_6$) δ 9.01 (d, J = 8.8 Hz, 1H), 8.77 (t, J = 6.0 Hz, 1H), 8.02 (d, J = 9.5 Hz, 2H), 7.91 (d, J = 7.8 Hz, 1H), 7.71 (t, J = 7.8 Hz, 1H), 7.67-7.44 (m, 5H), 7.29 (d, J = 7.6 Hz, 3H), 7.15 (d, J = 6.9 Hz, 1H), 5.76 (d, J = 1.6 Hz, 1H), 5.37 (s, 1H), 5.22 (dd, J = 12.0, 8.8 Hz, 1H), 4.52-4.42 (m, 4H), 4.43-4.23 (m, 3H), 3.76 (dd, J = 14.1, 7.1 Hz, 1H), 3.21-3.17 (m, 4H), 3.14-3.11 (m, 3H), 1.44 (s, 3H), 0.81 (t, J = 7.0 Hz, 3H).
LCMS Calculated for $C_{39}H_{39}F_3N_6O_4$: 712.30; Observed (Method-J): 713.4 [M + H]$^+$, 98.81% at RT 1.682 min.

I-283

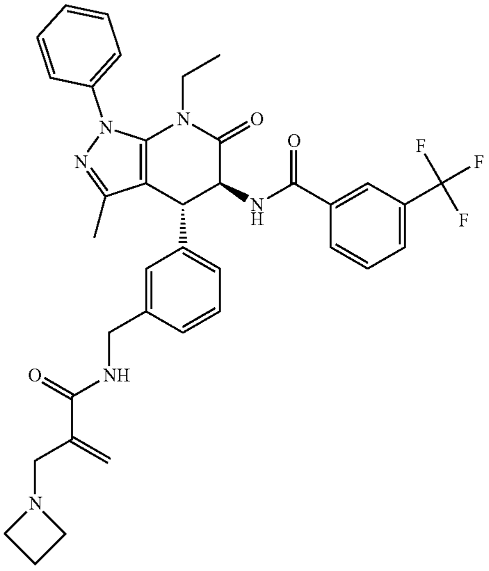 [SMILES: C=C(CN1CCC1)C(=O)NCc1cccc([C@@H]2c3c(C)nn(-c4ccccc4)c3N(CC)C(=O)[C@H]2NC(=O)c2cccc(C(F)(F)F)c2)c1]

$^1$H NMR (400 MHz, DMSO-$d_6$) $^1$H NMR (300 MHz, DMSO-$d_6$) δ 9.01 (d, J = 8.8 Hz, 1H), 8.94 (t, J = 5.9 Hz, 1H), 8.02 (d, J = 9.0 Hz, 2H), 7.91 (d, J = 7.8 Hz, 1H), 7.70
(t, J = 7.7 Hz, 1H), 7.65-7.44 (m, 5H), 7.31 (t, J = 7.6 Hz, 3H), 7.17 (d, J = 7.0 Hz, 1H), 5.77 (d, J = 1.9 Hz, 1H), 5.39
(s, 1H), 5.23 (dd, J = 11.9, 8.8 Hz, 1H), 4.41-4.29 (m, 3H), 3.76 (dd, J = 14.2, 7.2 Hz, 1H), 3.19-2.99 (m, 6H), 1.89 (m, 2H), 1.44 (s, 3H), 0.81 (t, J = 6.9 Hz, 3H).
LCMS Calculated for $C_{37}H_{37}F_3N_6O_3$: 670.29; Observed (Method-J): 671.4 [M + H]$^+$, 99.35% at RT 1.884 min.

I-303

-continued

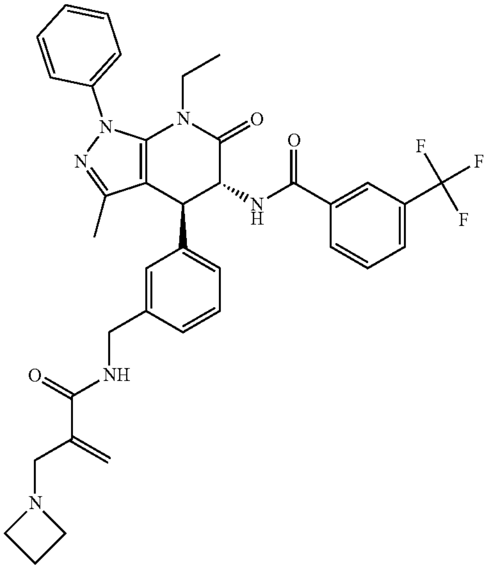 [SMILES: C=C(CN1CCC1)C(=O)NCc1cccc([C@H]2c3c(C)nn(-c4ccccc4)c3N(CC)C(=O)[C@@H]2NC(=O)c2cccc(C(F)(F)F)c2)c1]

$^1$H NMR (400 MHz, DMSO-d6): δ 9.01 (d, J = 8.8 Hz, 1H), 8.94 (t, J = 5.9 Hz, 1H), 8.07-8.00 (m, 2H), 7.90 (d, J = 7.8 Hz, 1H), 7.70 (t, J = 7.8 Hz, 1H), 7.64-7.53 (m, 4H), 7.52-7.46 (m, 1H), 7.33-7.24 (m, 3H), 7.17 (d, J = 7.2 Hz, 1H), 5.77 (s, 1H), 5.38 (s, 1H), 5.22 (dd, J = 12.0, 8.8 Hz, 1H), 4.46-4.25 (m, 3H), 3.86-3.70 (m, 1H), 3.16 (s, 2H), 3.14-3.07 (m, 1H), 3.04 (t, J = 7.0 Hz, 4H), 1.95-1.82 (m, 2H), 1.44 (s, 3H), 0.81 (t, J = 7.0 Hz, 3H). LCMS Calculated for $C_{37}H_{37}F_3N_6O_3$: 670.29; Observed (Method-J): 671.4 $[M + H]^+$, 99.01% at RT 1.883 min.

I-374

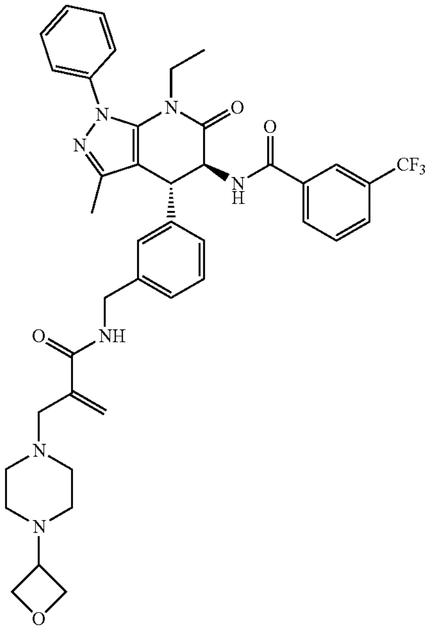 [SMILES: C=C(CN1CCN(C2COC2)CC1)C(=O)NCc1cccc([C@@H]2c3c(C)nn(-c4ccccc4)c3N(CC)C(=O)[C@H]2NC(=O)c2cccc(C(F)(F)F)c2)c1]

$^1$H NMR (400 MHz, DMSO-$d_6$) δ 9.10 (t, J = 5.7 Hz, 1H), 9.00 (d, J = 8.8 Hz, 1H), 8.02 (d, J = 7.6 Hz, 2H), 7.91 (d, J = 7.8 Hz, 1H), 7.76-7.44 (m, 5H), 7.30-7.21 (m, 3H), 7.20 (d, J = 6.7 Hz, 1H), 5.90 (d, J = 2.1 Hz, 1H), 5.43 (s, 1H), 5.23 (dd, J = 12.1, 8.8 Hz, 1H), 4.47-4.35 (m, 4H), 4.35-4.24 (m, 3H), 3.77 (dd, J = 14.2, 7.1 Hz, 1H), 3.27-3.04 (m, 4H), 2.32-2.24 (m, 4H), 2.09-2.04 (m, 4H), 1.44 (s, 3H), 0.82 (t, J = 7.0 Hz, 3H). LCMS Calculated for $C_{41}H_{44}F_3N_7O_4$: 755.34; Observed (Method-J): 756.4 $[M + H]^+$, 97.90% at RT 1.644 min.

I-353

-continued
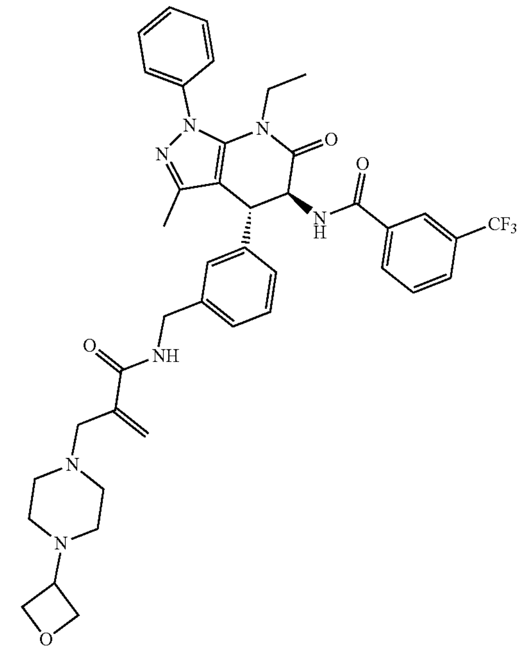 [SMILES: C=C(CN1CCN(C2COC2)CC1)C(=O)NCc1cccc([C@@H]2c3c(C)nn(-c4ccccc4)c3N(CC)C(=O)[C@H]2NC(=O)c2cccc(C(F)(F)F)c2)c1]
$^1$H NMR (300 MHz, DMSO-$d_6$) δ 9.09 (t, J = 5.8 Hz, 1H), 8.99 (d, J = 8.9 Hz, 1H), 8.04-7.96 (m, 2H), 7.89 (d, J = 7.6 Hz, 1H), 7.69 (t, J = 7.8 Hz, 1H), 7.63-7.53 (m, 4H), 7.52-7.44 (m, 1H), 7.35-7.24 (m, 3H), 7.22-7.15 (m, 1H), 5.88 (s, 1H), 5.41 (s, 1H), 5.22 (dd, J = 12.1, 8.8 Hz, 1H), 4.45-4.37 (m, 2H), 4.36-4.23 (m, 5H), 3.82-3.68 (m, 1H), 3.26-2.99 (m, 4H), 2.42-2.18 (m, 4H), 2.17-1.90 (m, 4H), 1.41 (s, 3H), 0.80 (t, J = 7.0 Hz, 3H). LCMS Calculated for $C_{41}H_{44}F_3N_7O_4$: 755.34; Observed (Method-J): 756.4 [M + H]$^+$, 98.35% at RT 1.638 min.
I-252
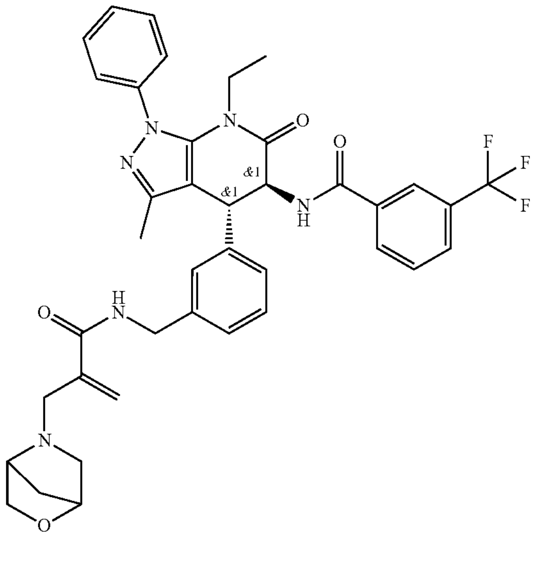 [SMILES: C=C(CN1CC2CC1CO2)C(=O)NCc1cccc([C@@H]2c3c(C)nn(-c4ccccc4)c3N(CC)C(=O)[C@H]2NC(=O)c2cccc(C(F)(F)F)c2)c1]
$^1$H NMR (400 MHz, DMSO-$d_6$) δ 9.14 (s, 1H), 9.01 (d, J = 8.8 Hz, 1H), 8.02 (d, J = 8.7 Hz, 2H), 7.91 (d, J = 7.8 Hz, 1H), 7.76-7.46 (m, 5H), 7.32 (d, J = 7.9 Hz, 1H), 7.29 (s, 2H), 7.18 (d, J = 7.0 Hz, 1H), 5.84 (s, 1H), 5.46 (s, 1H), 5.29-5.16 (m, 1H), 4.35 (d, J = 11.7 Hz, 2H), 4.25-4.18 (m, 2H), 3.84-3.67 (m, 2H), 3.30-3.21 (m, 4H), 3.17-3.04 (m, 1H), 2.58-2.51 (m, 1H), 2.42-2.31 (m, 1H), 1.63 (d, J = 9.6 Hz, 1H), 1.44 (s, 3H), 0.81 (t, J = 6.9 Hz, 3H). LCMS Calculated for $C_{39}H_{39}F_3N_6O_4$: 712.30; Observed (Method-J): 713.4 [M + H]$^+$, 98.72% at RT 1.733 min.
I-236

-continued

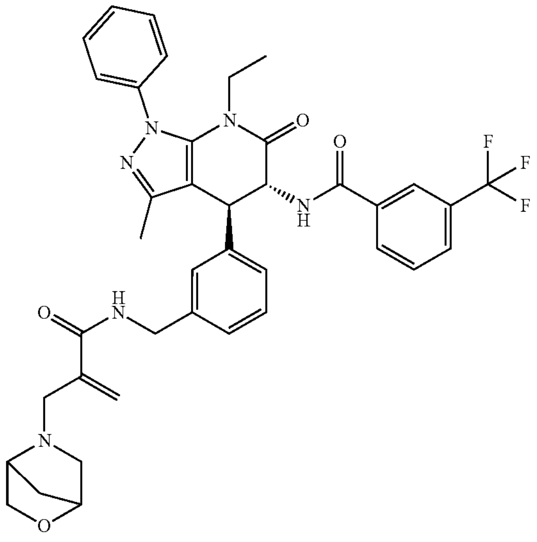 [SMILES: C=C(CN1CC2CC1CO2)C(=O)NCc1cccc([C@H]2c3c(C)nn(-c4ccccc4)c3N(CC)C(=O)[C@@H]2NC(=O)c2cccc(C(F)(F)F)c2)c1]

$^1$H NMR (300 MHz, DMSO-d$_6$): δ 9.13 (t, J = 6.0 Hz, 1H), 9.00 (d, J = 8.8 Hz, 1H), 8.05-7.95 (m, 2H), 7.93-7.84 (m, 1H), 7.68 (t, J = 7.7 Hz, 1H), 7.64-7.43 (m, 5H), 7.36-7.21 (m, 3H), 7.20-7.12 (m, 1H), 5.81 (s, 1H), 5.44 (s, 1H), 5.27-5.14 (m, 1H), 4.38-4.26 (m, 2H), 4.25-4.19 (m, 1H), 3.82-3.65 (m, 2H), 3.42-3.35 (m, 1H), 3.30-3.18 (m, 1H), 3.15-3.02 (m, 1H), 2.75-2.52 (m, 2H), 2.40-2.28 (m, 1H), 1.66-1.56 (m, 1H), 1.49-1.45 (m, 1H), 1.42 (s, 3H), 0.79 (t, J = 7.0 Hz, 3H). LCMS Calculated for $C_{39}H_{39}F_3N_6O_4$: 712.30; Observed (Method-J): 713.4 [M + H]$^+$, 98.66% at RT 1.733 min.

I-294

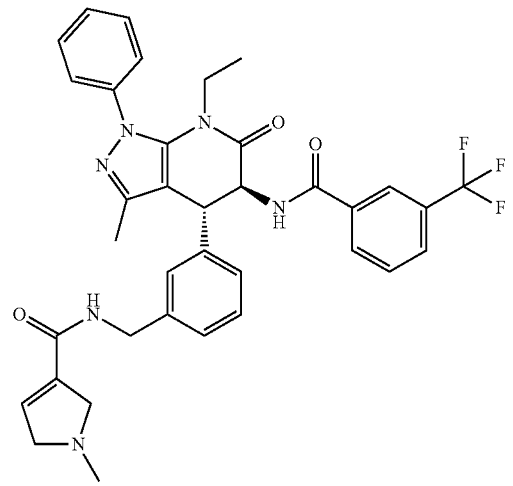 [SMILES: CCN1C(=O)[C@@H](NC(=O)c2cccc(C(F)(F)F)c2)[C@H](c2cccc(CNC(=O)C3=CCN(C)C3)c2)c2c(C)nn(-c3ccccc3)c21]

$^1$H NMR (400 MHz, DMSO-d$_6$) δ 9.01 (d, J = 8.8 Hz, 1H), 8.45 (t, J = 6.1 Hz, 1H), 8.03 (d, J = 10.8 Hz, 2H), 7.91 (d, J = 7.8 Hz, 1H), 7.71 (t, J = 7.8 Hz, 1H), 7.66-7.45 (m, 5H), 7.35-7.20 (m, 3H), 7.14 (d, J = 6.8 Hz, 1H), 6.47 (d, J = 1.8 Hz, 1H), 5.21 (dd, J = 11.7, 8.8 Hz, 1H), 4.43-4.20 (m, 3H), 3.74 (dd, J = 14.2, 7.2 Hz, 1H), 3.51-3.42 (m, 4H), 3.13 (dd, J = 14.1, 7.0 Hz, 1H), 2.35 (s, 3H), 1.45 (s, 3H), 0.81 (t, J = 7.0 Hz, 3H). LCMS Calculated for $C_{36}H_{35}F_3N_6O_3$: 656.27; Observed (Method-J): 657.3 [M + H]$^+$, 93.32% at RT 1.638 min.

I-244

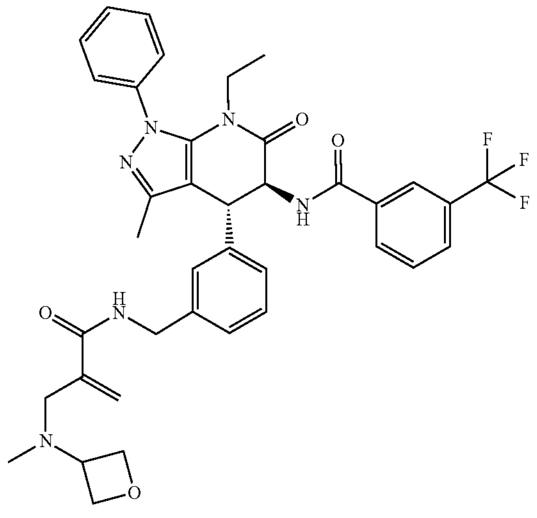 [SMILES: C=C(CN(C)C1COC1)C(=O)NCc1cccc([C@@H]2c3c(C)nn(-c4ccccc4)c3N(CC)C(=O)[C@H]2NC(=O)c2cccc(C(F)(F)F)c2)c1]

$^1$H NMR (400 MHz, DMSO-d$_6$) δ 9.01 (d, J = 8.8 Hz, 1H), 8.87 (t, J = 5.9 Hz, 1H), 8.02 (d, J = 9.1 Hz, 2H), 7.90 (d, J = 7.9 Hz, 1H), 7.70 (t, J = 7.7 Hz, 1H), 7.65-7.51 (m, 5H), 7.35-7.24 (m, 3H), 7.21 (d, J = 6.8 Hz, 1H), 5.80 (s, 1H), 5.43 (s, 1H), 5.23 (dd, J = 12.1, 8.8 Hz, 1H), 4.43-4.37 (m, 2H), 4.40-4.31 (m, 5H), 3.83-3.70 (m, 1H), 3.51 (q, J = 6.4 Hz, 1H), 3.17-3.05 (m, 1H), 3.03 (s, 2H), 1.95 (s, 3H), 1.44 (s, 3H), 0.81 (t, J = 7.0 Hz, 3H). LCMS Calculated for $C_{38}H_{39}F_3N_6O_4$: 700.30; Observed (Method-J): 701.4 [M + H]$^+$, 98.72% at RT 1.739 min.

I-312

-continued

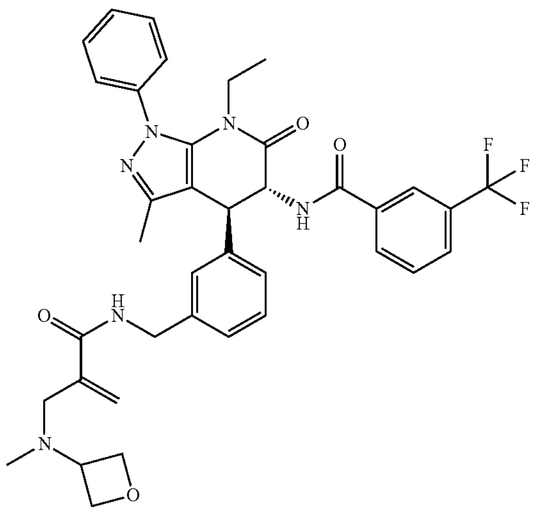 [SMILES: C=C(CN(C)C1COC1)C(=O)NCc1cccc([C@H]2c3c(C)nn(-c4ccccc4)c3N(CC)C(=O)[C@@H]2NC(=O)c2cccc(C(F)(F)F)c2)c1]

$^{1}H$ NMR (400 MHz, DMSO-$d_6$) δ 9.01 (d, J = 8.8 Hz, 1H), 8.88 (t, J = 5.9 Hz, 1H), 8.03 (d, J = 11.7 Hz, 2H), 7.91 (d, J = 7.9 Hz, 1H), 7.73-7.68 (m, 1H), 7.64-7.54 (m, 4H), 7.50 (d, J = 7.2 Hz, 1H), 7.34-7.25 (m, 3H), 7.21 (d, J = 7.4 Hz, 1H), 5.80 (s, 1H), 5.44 (s, 1H), 5.23 (dd, J = 12.0, 8.8 Hz, 1H), 4.48-4.40 (m, 2H), 4.40-4.33 (m, 5H), 3.82-3.72 (m, 1H), 3.54-3.46 (m, 1H), 3.15-3.05 (m, 1H), 3.03 (s, 2H), 1.95 (s, 3H), 1.44 (s, 3H), 0.81 (t, J = 7.0 Hz, 3H).
LCMS Calculated for $C_{38}H_{39}F_3N_6O_4$: 700.30; Observed (Method-B): 701.2 $[M + H]^+$, 95.04% at RT 0.952 min.

I-349

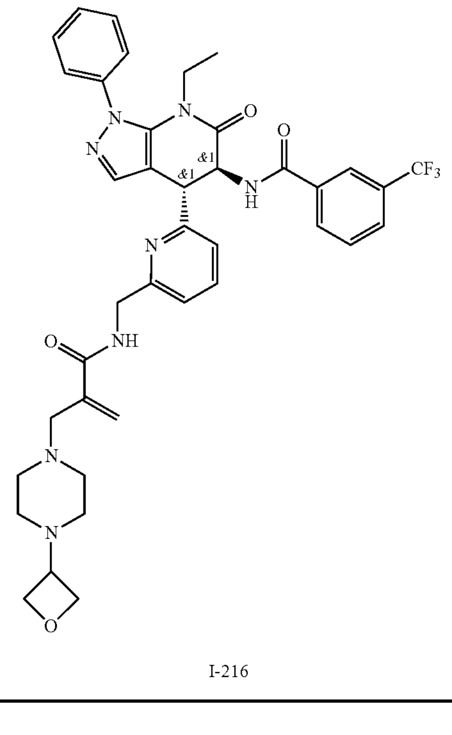

$^{1}H$ NMR (300 MHz, DMSO-$d_6$) δ 9.05 (d, J = 8.3 Hz, 2H), 8.05 (d, J = 9.0 Hz, 2H), 7.92 (d, J = 7.9 Hz, 1H), 7.83-7.48 (m, 7H), 7.35 (d, J = 7.7 Hz, 1H), 7.26 (d, J = 7.7 Hz, 1H), 7.04 (s, 1H), 5.92 (s, 1H), 5.49-5.35 (m, 2H), 4.58 (d, J = 12.5 Hz, 1H), 4.50-4.40 (m, 4H), 4.34 (q, J = 5.9 Hz, 2H), 3.84 (dd, J = 14.2, 7.1 Hz, 1H), 3.21 (s, 2H), 3.17-3.04 (m, 1H), 2.39 (s, 4H), 2.18 (s, 4H), 0.84 (t, J = 7.0 Hz, 3H).
LCMS Calculated for $C_{39}H_{41}F_3N_8O_4$: 742.3; Observed (Method-J): 743.4 $[M + H]^+$, 97.40% at RT 1.515 min.

I-216

2. Synthesis of N-((4R,5S)-7-ethyl-4-(3-(((E)-N-methyl-2-((4-(oxetan-3-yl)piperazin-1-yl)methyl)but-2-enamido)methyl)phenyl)-6-oxo-1-phenyl-4,5,6,7-tetrahydro-1H-pyrazolo[3,4-b]pyridin-5-yl)-1-(trifluoromethyl)-1H-pyrazole-3-carboxamide I-237

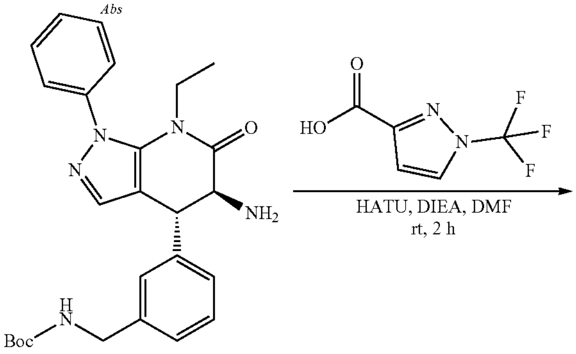

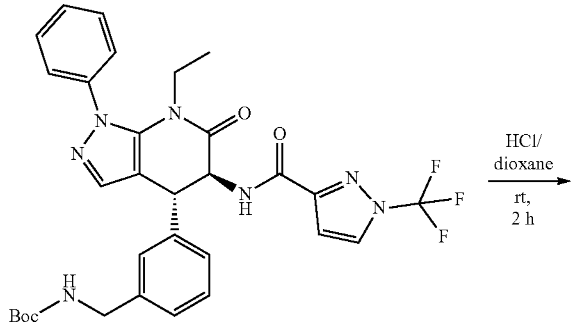

4

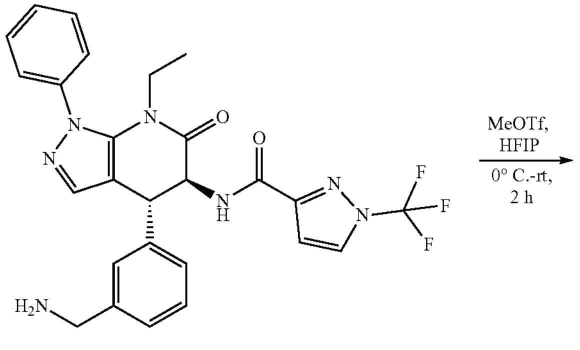

5

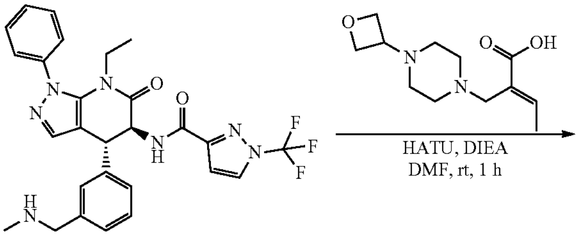

6

-continued

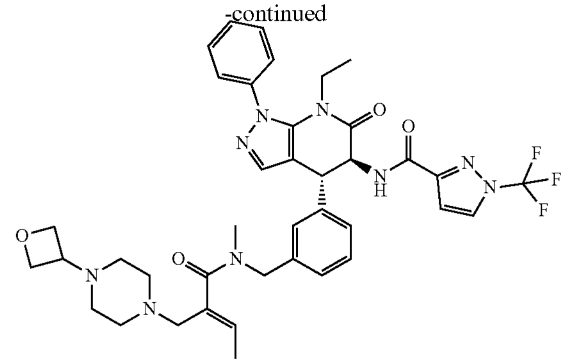

I-237 tert-butyl (3-((4R,5S)-7-ethyl-6-oxo-1-phenyl-5-(1-(trifluoromethyl)-1H-pyrazole-3-carboxamido)-4,5,6,7-tetrahydro-1H-pyrazolo[3,4-b]pyridin-4-yl)benzyl) carbamate (4)

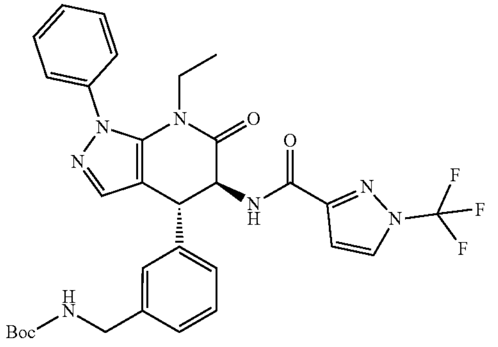 [SMILES: CCN1C(=O)[C@@H](NC(=O)c2ccn(C(F)(F)F)n2)[C@H](c2cccc(CNC(=O)OC(C)(C)C)c2)c2cnn(-c3ccccc3)c21]

Into a 100 mL round-bottom flask were added tert-butyl (3-((4R,5S)-5-amino-7-ethyl-6-oxo-1-phenyl-4,5,6,7-tetrahydro-1H-pyrazolo[3,4-b]pyridin-4-yl)benzyl) carbamate (4.0 g, 8.67 mmol, 1.00 equiv), DMF (50 mL), 1-(trifluoromethyl)-1H-pyrazole-3-carboxylic acid (3.12 g, 17.3 mmol, 2.00 equiv), DIEA (3.36 g, 26.0 mmol, 3.00 equiv), HATU (3.95 g, 10.4 mmol, 1.20 equiv) at room temperature. The resulting mixture was stirred for 2 h at room temperature. The reaction was quenched with water (50 mL) at room temperature. The resulting mixture was extracted with EtOAc (2×50 mL). The combined organic layers were washed with brine (2×50 mL), dried over anhydrous $Na_2SO_4$. After filtration, the filtrate was concentrated under reduced pressure. The residue was purified by silica gel column chromatography, eluted with PE/EtOAc (1:1) to afford tert-butyl (3-((4R,5S)-7-ethyl-6-oxo-1-phenyl-5-(1-(trifluoromethyl)-1H-pyrazole-3-carboxamido)-4,5,6,7-tetrahydro-1H-pyrazolo[3,4-b]pyridin-4-yl)benzyl)carbamate (4.5 g, 83.2%) as a light yellow solid. LCMS Calculated for $C_{31}H_{32}F_3N_7O_4$: 623.64; Observed: 624.25 $[M+H]^+$ N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-1-(trifluoromethyl)-1H-pyrazole-3-carboxamide (5)

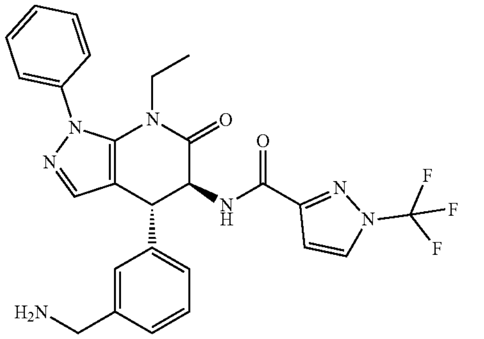 [SMILES: CCN1C(=O)[C@@H](NC(=O)c2ccn(C(F)(F)F)n2)[C@H](c2cccc(CN)c2)c2cnn(-c3ccccc3)c21]

Into a 100 mL round-bottom flask were added tert-butyl (3-((4R,5S)-7-ethyl-6-oxo-1-phenyl-5-(1-(trifluoromethyl)-1H-pyrazole-3-carboxamido)-4,5,6,7-tetrahydro-1H-pyrazolo[3,4-b]pyridin-4-yl)benzyl)carbamate (4.5 g, 7.22 mmol, 1.0 equiv), 4M HCl in 1,4-dioxane (50 mL) at room temperature. The resulting mixture was stirred for 2 h at room temperature. The resulting mixture was concentrated under reduced pressure. The mixture was basified to pH=10 with $NaHCO_3$(aq.). The resulting mixture was extracted with EtOAc (2×50 mL). The combined organic layers were washed with brine (2×50 mL), dried over anhydrous $Na_2SO_4$. After filtration, the filtrate was concentrated under reduced pressure. This resulted in N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-1-(trifluoromethyl)-1H-pyrazole-3-carboxamide (3.5 g crude) as a light yellow solid. LCMS Calculated for $C_{26}H_{24}F_3N_7O_2$: 523.52; Observed: 524.52 $[M+H]^+$.

N-((4R,5S)-7-ethyl-4-(3-((methylamino)methyl)phenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (6)

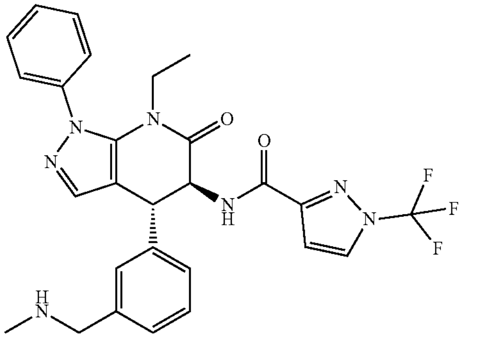 [SMILES: CCN1C(=O)[C@@H](NC(=O)c2ccn(C(F)(F)F)n2)[C@H](c2cccc(CNC)c2)c2cnn(-c3ccccc3)c21]

Into a 100 mL round-bottom flask were added N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-1-(trifluoromethyl)-1H-pyrazole-3-carboxamide (3.5 g, 6.69 mmol, 1.0 equiv) and HFIP (40 mL) at 0° C. To the above mixture was added methyl trifluoromethanesulfonate (1.32 g, 8.02 mmol, 1.20 equiv) dropwise over 10 min at 0° C. The resulting mixture was stirred for 2 h at room temperature. The reaction was quenched by the addition of water (50 mL) and extracted with EtOAc (3×50 mL). The combined organic layers were washed with brine (2×50 mL), dried over anhydrous $Na_2SO_4$. After filtration, the filtrate was concentrated under reduced pressure. The crude residue was applied onto a silica gel column and eluted with DCM/MeOH=5:1 to give N-((4R,5S)-7-ethyl-4-(3-((methylamino)methyl)phenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (1.5 g, 41.7%) as a light yellow solid. LCMS Calculated for $C_{27}H_{26}F_3N_7O_2$: 537.55; Observed: 538.55 $[M+H]^+$.

N-((4R,5S)-7-ethyl-4-(3-(((E)-N-methyl-2-((4-(oxetan-3-yl)piperazin-1-yl)methyl)but-2-enamido)methyl)phenyl)-6-oxo-1-phenyl-4,5,6,7-tetrahydro-1H-pyrazolo[3,4-b]pyridin-5-yl)-1-(trifluoromethyl)-1H-pyrazole-3-carboxamide

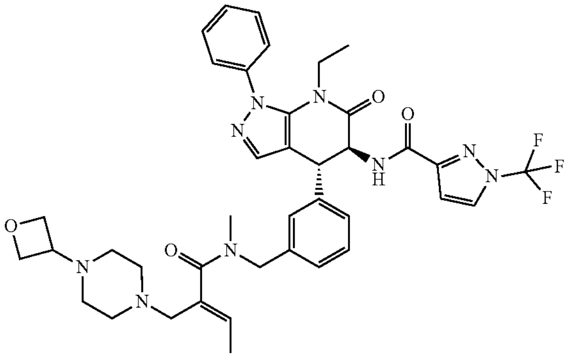 [SMILES: C/C=C(\CN1CCN(C2COC2)CC1)C(=O)N(C)Cc1cccc([C@@H]2c3cnn(-c4ccccc4)c3N(CC)C(=O)[C@H]2NC(=O)c2ccn(C(F)(F)F)n2)c1]

Into an 8 mL vial were added N-((4R,5S)-7-ethyl-4-(3-((methylamino)methyl)phenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (100 mg, 0.186 mmol, 1.0 equiv), (E)-2-((4-(oxetan-3-yl)piperazin-1-yl)methyl)but-2-enoic acid (67.1 mg, 0.279 mmol, 1.50 equiv), DIEA (72.13 mg, 0.558 mmol, 3.0 equiv), DMF (1 mL) and HATU (84.9 mg, 0.223 mmol, 1.20 equiv) at room temperature. The resulting mixture was stirred for 1 h at room temperature. The reaction was quenched by the addition of water (20 mL) and extracted with EtOAc (2×50 mL). The combined organic layers were washed with brine (2×50 mL), dried over anhydrous $Na_2SO_4$. After filtration, the filtrate was concentrated under reduced pressure. The residue was purified by reversed-phase flash chromatography with the following conditions: Column: Sunfire Prep C18 OBD Column, 19*150 mm, 5 m; Mobile Phase A: Water(0.1% FA), Mobile Phase B: ACN; Flow rate: 30 mL/min; Gradient: 50% B to 70% B in 9 min; Wave Length: 254 nm/220 nm; RT1 (min): 7.57; This resulted in N-((4R,5S)-7-ethyl-4-(3-(((E)-N-methyl-2-((4-(oxetan-3-yl)piperazin-1-yl)methyl)but-2-enamido)methyl)phenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (15 mg, 10.6%) as a white solid. $^1H$ NMR (300 MHz, DMSO-$d_6$) δ 8.78 (d, J=9.2 Hz, 1H), 8.58 (d, J=2.9 Hz, 1H), 7.68-7.50 (m, 5H), 7.35-7.15 (m, 4H), 6.97 (s, 1H), 6.89 (d, J=2.8 Hz, 1H), 5.74 (d, J=7.1 Hz, 1H), 5.24-5.11 (m, 1H), 4.59-4.31 (m, 6H), 3.98-3.75 (m, 1H), 3.24-2.91 (m, 2H), 2.84-2.68 (m, 2H), 2.64-2.54 (m, 1H), 2.45-2.01 (m, 8H), 1.79-1.61 (m, 3H), 1.28-1.21 (m, 3H), 0.82 (t, J=7.0 Hz, 3H). LCMS Calculated for $C_{39}H_{44}F_3N_9O_4$: 759.84; Observed (Method-C): 760.2 $[M+H]^+$, 90.67% at RT 0.856 min.

3. Synthesis of N-((4R,5S)-7-ethyl-4-(3-(((E)-2-((4-(oxetan-3-yl)piperazin-1-yl)methyl)but-2-enamido)methyl)phenyl)-6-oxo-1-phenyl-4,5,6,7-tetrahydro-1H-pyrazolo[3,4-b]pyridin-5-yl)-1-(trifluoromethyl)-1H-pyrazole-3-carboxamide I-230A

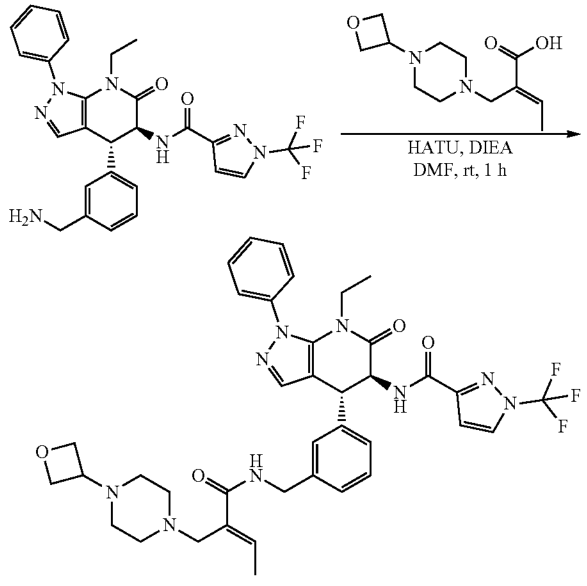

I-230A

Into a 8 mL vial were added N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-1-(trifluoromethyl)-1H-pyrazole-3-carboxamide (100 mg, 0.191 mmol, 1.00 equiv), (E)-2-((4-(oxetan-3-yl)piperazin-1-yl)methyl)but-2-enoic acid (68.9 mg, 0.286 mmol, 1.50 equiv), DIEA (74.1 mg, 0.573 mmol, 3.00 equiv), DMF (1 mL) and HATU (87.2 mg, 0.229 mmol, 1.20 equiv) at room temperature. The resulting mixture was stirred for 1 h at room temperature. The reaction was quenched by the addition of water (20 mL) and extracted with EtOAc (2×50 mL). The combined organic layers were washed with brine (2×50 mL), dried over anhydrous $Na_2SO_4$. After filtration, the filtrate was concentrated under reduced pressure. The residue was purified by reversed-phase flash chromatography with the following conditions: Column: XBridge Prep RP C18 Column, 30*150 mm, 5 μm; Mobile Phase A: Water(0.1% $NH_3 \cdot H_2O$), Mobile Phase B: ACN; Flow rate: 35 mL/min; Gradient: 62% B to 92% B in 10 min; Wave Length: 254 nm/220 nm; RT1 (min): 6.9 to afford N-((4R,5S)-7-ethyl-4-(3-(((E)-2-((4-(oxetan-3-yl)piperazin-1-yl)methyl)but-2-enamido)methyl)phenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (15 mg, 10.5%) as a white solid. $^1H$ NMR (300 MHz, DMSO-$d_6$) δ 9.04 (t, J=5.7 Hz, 1H), 8.76 (d, J=9.2 Hz, 1H), 8.59 (d, J=2.8 Hz, 1H), 7.67-7.51 (m, 5H), 7.33-7.25 (m, 3H), 7.20 (d, J=7.1 Hz, 1H), 6.91 (d, J=4.1 Hz, 2H), 6.70-6.61 (m, 1H), 5.17 (dd, J=12.9, 9.2 Hz, 1H), 4.54 (d, J=12.9 Hz, 1H), 4.46-4.28 (m, 6H), 3.85 (dd, J=14.2, 7.2 Hz, 1H), 3.26-3.17 (m, 3H), 3.04 (dd, J=14.1, 7.0 Hz, 1H), 2.45-1.96 (m, 8H), 1.75 (d, J=7.1 Hz, 3H), 0.82 (t, J=7.0 Hz, 3H). LCMS Calculated for $C_{38}H_{42}F_3N_9O_4$: 745.33; Observed (Method-C): 746.2 $[M+H]^+$, 91.96% at RT 0.829 min.

---

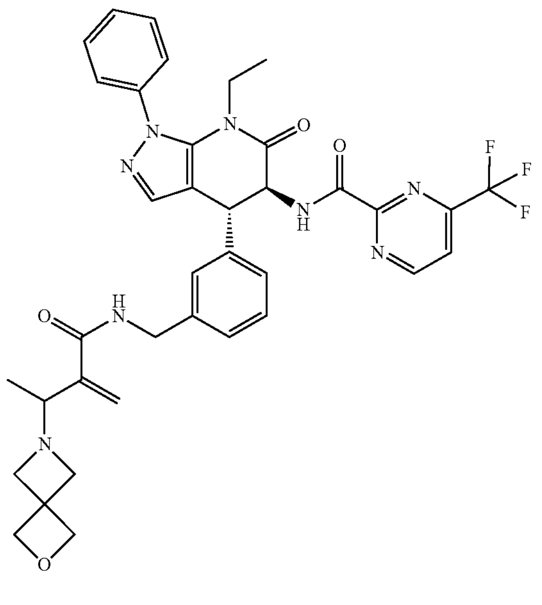 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N1CC2(COC2)C1]

I-388

$^1H$ NMR (400 MHz, DMSO-$d_6$) δ 9.38-9.26 (m, 2H), 9.02 (d, J = 5.2 Hz, 1H), 8.21 (d, J = 5.1 Hz, 1H), 7.65 (d, J = 7.8 Hz, 2H), 7.56 (dt, J = 21.8, 7.2 Hz, 3H), 7.29 (d, J = 2.7 Hz, 3H), 7.13 (d, J = 6.1 Hz, 1H), 6.96 (s, 1H), 5.76-5.69 (m, 1H), 5.38 (s, 1H), 5.20 (dd, J = 12.7, 9.2 Hz, 1H), 4.64 (d, J = 12.7 Hz, 1H), 4.48 (qd, J = 6.6, 3.4 Hz, 4H), 4.40-4.19 (m, 2H), 3.83 (dt, J = 14.5, 7.2 Hz, 1H), 3.17-(t, J = 5.4 Hz, 4H), 3.11-3.05 (m, 2H), 0.93 (dd, J = 6.6, 2.1 Hz, 3H), 0.82 (t, J = 7.0 Hz, 3H). LCMS Calculated for $C_{37}H_{37}F_3N_8O_4$: 714.29; Observed (Method-D): 715.3 $[M + H]^+$, 96.69% at RT 3.529 min.

-continued

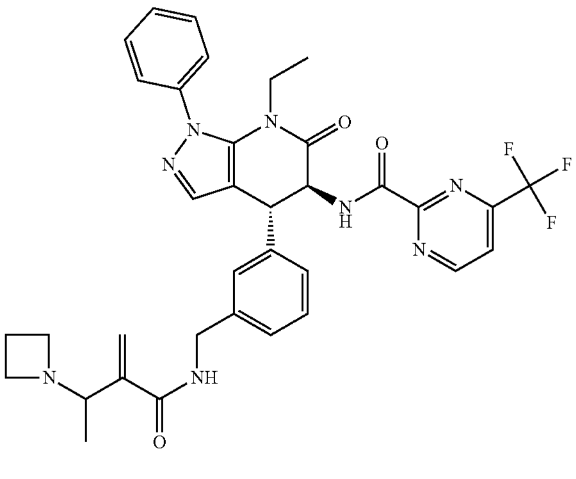 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N1CCC1]

$^1$H NMR (400 MHz, DMSO-$d_6$) δ 9.45-9.13 (m, 3H), 8.20 (d, J = 5.1 Hz, 1H), 7.70-7.50 (m, J = 22.3, 14.1, 7.4 Hz, 5H), 7.35-7.24 (m, 3H), 7.16 (d, J = 3.6 Hz, 1H), 6.97 (s, 1H), 5.74 (s, 1H), 5.40 (s, 1H), 5.20 (dd, J = 12.6, 9.2 Hz, 1H), 4.65 (d, J = 12.7 Hz, 1H), 4.36 (d, J = 5.8 Hz, 2H), 3.20-3.09 (m, 1H), 3.02 (t, J = 7.4 Hz, 4H), 1.84 (q, J = 7.1 Hz, 2H), 0.94 (d, J = 6.5 Hz, 3H), 0.83 (t, J = 7.0 Hz, 3H).
LCMS Calculated for $C_{35}H_{35}F_3N_8O_3$: 672.28; Observed (Method-J): 673.71 [M + H]$^+$, 90.86% at RT 1.766 min.

I-328

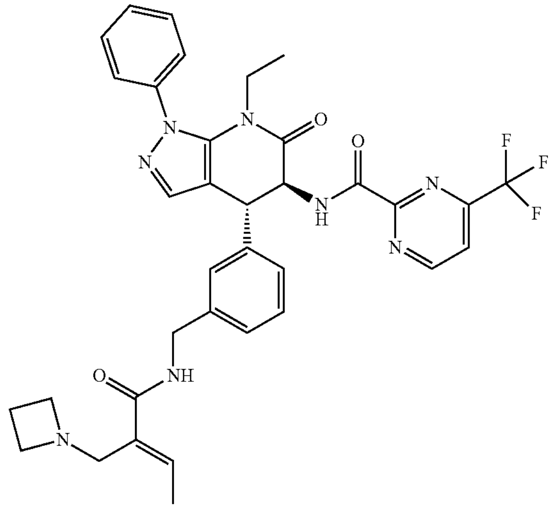 [SMILES: C/C=C(\CN1CCC1)C(=O)NCc1cccc([C@@H]2c3cnn(-c4ccccc4)c3N(CC)C(=O)[C@H]2NC(=O)c2nccc(C(F)(F)F)n2)c1]

$^1$H NMR (400 MHz, DMSO-$d_6$) $^1$H NMR (400 MHz, DMSO-$d_6$) δ 9.31 (t, J = 6.9 Hz, 2H), 9.06 (d, J = 6.2 Hz, 1H), 8.21 (d, J = 5.1 Hz, 1H), 7.63-7.49 (m, J = 22.8, 14.8, 7.3 Hz, 5H), 7.38-7.10 (m, 4H), 6.98 (s, 1H), 6.54 (q, J = 6.9 Hz, 1H), 5.27-5.14 (m, 1H), 4.65 (d, J = 12.7 Hz, 1H), 4.34 (t, J = 5.3 Hz, 2H), 3.93-3.74 (m, 1H), 3.22 (s, 2H), 3.06 (t, J = 7.0 Hz, 5H), 1.87 (t, J = 7.0 Hz, 2H), 1.78 (d, J = 7.1 Hz, 3H), 0.83 (t, J = 7.0 Hz, 3H).
LCMS Calculated for $C_{35}H_{35}F_3N_8O_3$: 672.28; Observed (Method-J): 673.71 [M + H]$^+$, 91.73% at RT 1.777 min.

I-314

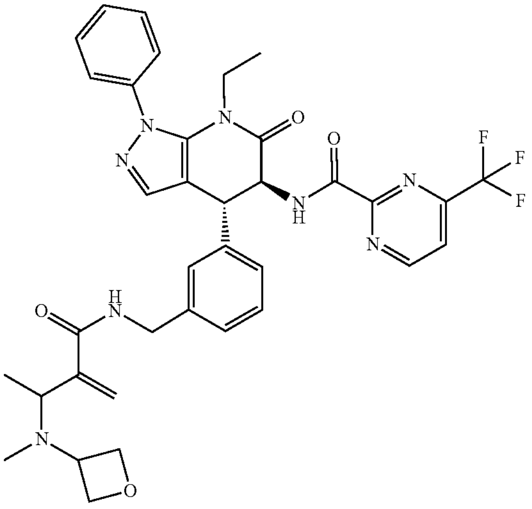 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N(C)C1COC1]

$^1$H NMR (400 MHz, DMSO-$d_6$) δ 9.29 (t, J = 5.5 Hz, 2H), 8.86 (q, J = 6.4 Hz, 1H), 8.18 (d, J = 5.0 Hz, 1H), 7.64-7.47 (m, J = 23.4, 17.7, 7.3 Hz, 5H), 7.31-7.22 (m, 3H), 7.20-7.13 (m, 1H), 6.95 (s, 1H), 5.71 (d, J = 4.2 Hz, 1H), 5.28 (s, 1H), 5.20 (d, J = 12.9 Hz, 1H), 4.62 (dd, J = 12.8, 2.3 Hz, 1H), 4.43-4.24 (m, J = 16.6, 13.3, 6.5 Hz, 6H), 3.88-3.69 (m, J = 32.3, 13.2, 6.9 Hz, 2H), 3.54 (p, J = 6.4 Hz, 1H), 3.02 (ddt, J = 14.2, 7.3, 3.8 Hz, 1H), 1.96 (d, J = 3.3 Hz, 3H), 0.95 (d, J = 6.7 Hz, 3H), 0.80 (t, J = 7.0 Hz, 3H).
LCMS Calculated for $C_{36}H_{37}F_3N_8O_4$: 702.29; Observed (Method-Z): 703.4 [M + H]$^+$, 98.77% at RT 2.017 min.

I-217

-continued

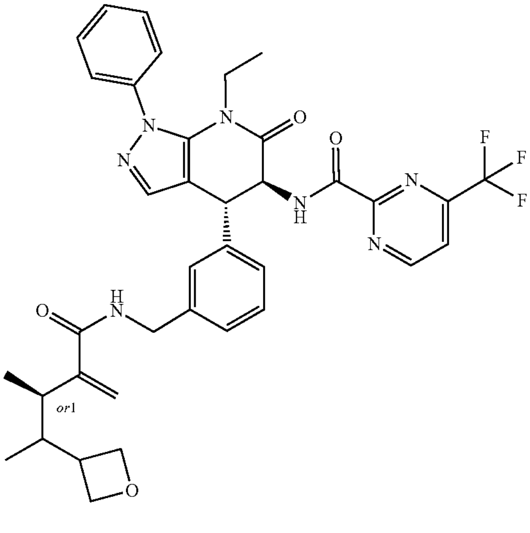 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)[C@H](C)C(C)C1COC1]

I-382

$^1$H NMR (400 MHz, DMSO-$d_6$) δ 9.34-9.25 (m, 2H), 8.86 (d, J = 6.5 Hz, 1H), 8.21 (d, J = 5.1 Hz, 1H), 7.66-7.61 (m, 2H), 7.62-7.50 (m, 3H), 7.33-7.25 (m, 3H), 7.20 (s, 1H), 6.97 (s, 1H), 5.73 (s, 1H), 5.30 (s, 1H), 5.21 (dd, J = 12.7, 9.2 Hz, 1H), 4.64 (d, J = 12.7 Hz, 1H), 4.49-4.30 (m, 6H), 3.89-3.73 (m, 2H), 3.59-3.52 (m, 1H), 3.09-2.99 (m, 1H), 1.98 (s, 3H), 0.97 (d, J = 6.8 Hz, 3H), 0.82 (t, J = 7.0 Hz, 3H).
LCMS Calculated for $C_{37}H_{38}F_3N_7O_4$: 702.29; Observed (Method-AA): 703.2 [M + H]$^+$, 99.54% at RT 1.523 min.
Chiral HPLC (Method-E): 100% at RT 4.361 min.

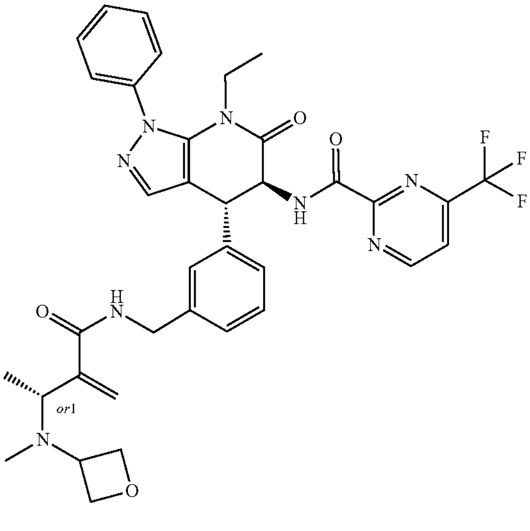 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)[C@@H](C)N(C)C1COC1]

I-300

$^1$H NMR (400 MHz, DMSO-$d_6$) δ 9.34-9.25 (m, 2H), 8.85 (t, J = 6.0 Hz, 1H), 8.21 (d, J = 5.1 Hz, 1H), 7.68-7.62 (m, 2H), 7.55 (dt, J = 22.4, 7.2 Hz, 3H), 7.34-7.24 (m, 3H), 7.23-7.16 (m, 1H), 6.97 (s, 1H), 5.72 (s, 1H), 5.29 (s, 1H), 5.22 (dd, J = 12.8, 9.3 Hz, 1H), 4.63 (d, J = 12.8 Hz, 1H), 4.44-4.25 (m, 6H), 3.91-3.70 (m, 2H), 3.62-3.52 (m, 1H), 3.10-2.97 (m, 1H), 1.97 (s, 3H), 0.97 (d, J = 6.8 Hz, 3H), 0.82 (t, J = 7.0 Hz, 3H).
LCMS Calculated for $C_{37}H_{38}F_3N_7O_4$: 702.29; Observed (Method-AA): 703.2 [M + H]$^+$, 96.86% at RT 1.518 min.
Chiral HPLC (Method-E): 100% at RT 5.102 min.

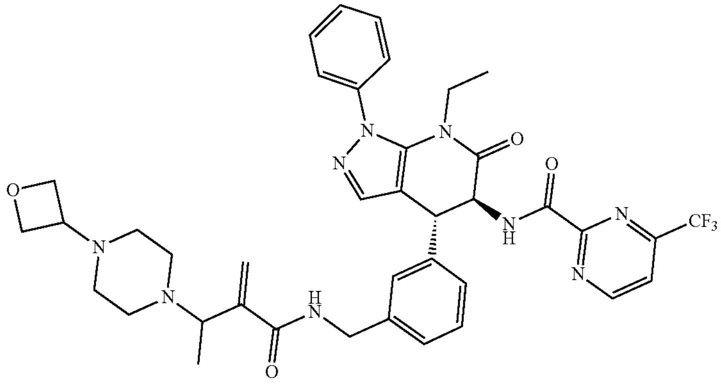 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N1CCN(C2COC2)CC1]

I-310

$^1$H NMR (300 MHz, DMSO-$d_6$) δ 9.36-9.23 (m, 3H), 8.22 (d, J = 5.1 Hz, 1H), 7.69-7.48 (m, 5H), 7.37-7.14 (m, 4H), 6.94 (s, 1H), 5.86 (s, 1H), 5.36 (s, 1H), 5.27-5.14 (m, 1H), 4.65 (dd, J = 12.7, 2.2 Hz, 1H), 4.44-4.24 (m, 6H), 3.85 (dd, J = 14.2, 7.2 Hz, 1H), 3.39-3.33 (m, 1H), 3.22 (q, J = 6.4 Hz, 1H), 3.06 (dd, J = 14.2, 7.1 Hz, 1H), 2.38 (d, J = 28.1 Hz, 4H), 2.19-1.98 (m, 4H), 1.10 (dd, J = 6.7, 4.4 Hz, 3H), 0.83 (t, J = 7.0 Hz, 3H).
LCMS Calculated for $C_{39}H_{42}F_3N_9O_4$: 757.33; Observed (Method-Z): 758.4 [M + H]$^+$, 99.74% at RT 1.815 min.

-continued

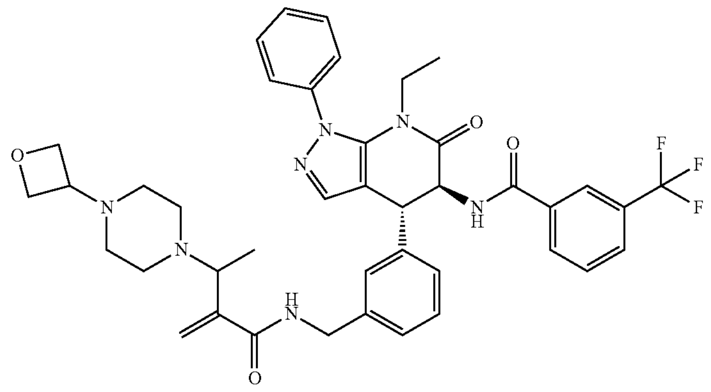 [SMILES: C=C(C(=O)NCc1cccc([C@@H]2c3cnn(-c4ccccc4)c3N(CC)C(=O)[C@H]2NC(=O)c2cccc(C(F)(F)F)c2)c1)C(C)N1CCN(C2COC2)CC1]

$^1$H NMR (400 MHz, DMSO-$d_6$) δ 9.31 (d, J = 5.8 Hz, 1H), 9.00 (d, J = 9.0 Hz, 1H), 8.07-8.00 (m, 2H), 7.91 (d, J = 7.8 Hz, 1H), 7.72 (t, J = 7.8 Hz, 1H), 7.68-7.50 (m, 5H), 7.37-7.29 (m, 3H), 7.22 (d, J = 5.8 Hz, 1H), 7.00 (s, 1H), 5.88 (d, J = 3.2 Hz, 1H), 5.37 (s, 1H), 5.23-5.13 (m, 1H), 4.45-4.25 (m, 7H), 3.84 (dd, J = 14.2, 7.2 Hz, 1H), 3.24-3.00 (m, 3H), 2.48-2.19 (m, 4H), 2.03 (s, 4H), 1.10 (t, J = 6.4 Hz, 3H), 0.83 (t, J = 7.0 Hz, 3H). LCMS Calculated for $C_{41}H_{44}F_3N_7O_4$: 755.34; Observed (Method-V): 756.4 [M + H]$^+$, 95.04% at RT 1.520 min.

I-317

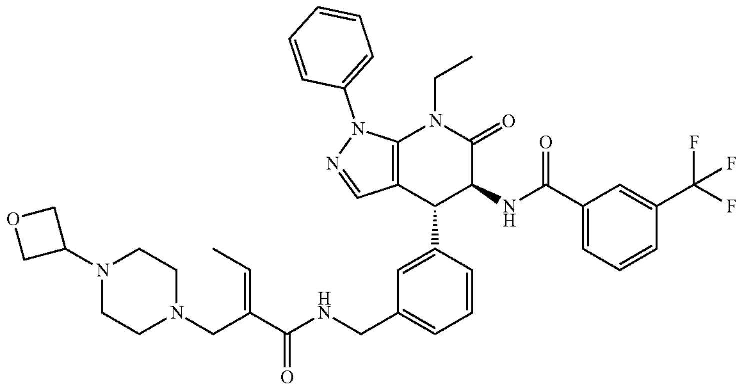 [SMILES: C/C=C(\CN1CCN(C2COC2)CC1)C(=O)NCc1cccc([C@@H]2c3cnn(-c4ccccc4)c3N(CC)C(=O)[C@H]2NC(=O)c2cccc(C(F)(F)F)c2)c1]

$^1$H NMR (400 MHz, DMSO-$d_6$) δ 9.09-8.97 (m, 2H), 8.03 (d, J = 9.1 Hz, 2H), 7.91 (d, J = 7.8 Hz, 1H), 7.71 (t, J = 7.8 Hz, 1H), 7.65 (d, J = 7.8 Hz, 2H), 7.60 (t, J = 7.5 Hz, 2H), 7.56-7.49 (m, 1H), 7.32 (d, J = 3.8 Hz, 3H), 7.20 (d, J = 4.8 Hz, 1H), 7.00 (s, 1H), 6.66 (q, J = 7.0 Hz, 1H), 5.19 (dd, J = 12.9, 8.9 Hz, 1H), 4.44-4.33 (m, 4H), 4.32-4.23 (m, 3H), 3.85 (dq, J = 14.3, 7.1 Hz, 1H), 3.17 (d, J = 10.0 Hz, 3H), 3.06 (dq, J = 14.3, 7.1 Hz, 1H), 2.56-1.86 (m, 8H), 1.74 (d, J = 7.1 Hz, 3H), 0.83 (t, J = 7.0 Hz, 3H). LCMS Calculated for $C_{41}H_{44}F_3N_7O_4$: 755.34; Observed (Method-B): 756.2 [M + H]$^+$, 99.96% at RT 0.975 min.

I-222

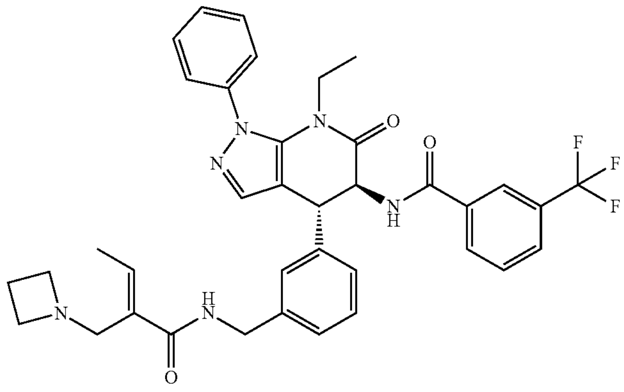 [SMILES: C/C=C(\CN1CCC1)C(=O)NCc1cccc([C@@H]2c3cnn(-c4ccccc4)c3N(CC)C(=O)[C@H]2NC(=O)c2cccc(C(F)(F)F)c2)c1]

$^1$H NMR (400 MHz, DMSO-d6) δ 9.07 (t, J = 6.0 Hz, 1H), 9.02 (d, J = 9.0 Hz, 1H), 8.08-8.00 (m, 2H), 7.91 (d, J = 7.8 Hz, 1H), 7.71 (t, J = 7.8 Hz, 1H), 7.66-7.56 (m, 4H), 7.55-7.50 (m, 1H), 7.33 (s, 1H), 7.30 (d, J = 6.3 Hz, 2H), 7.16 (d, J = 6.3 Hz, 1H), 7.03 (s, 1H), 6.55 (q, J = 7.0 Hz, 1H), 5.17 (dd, J = 12.9, 8.9 Hz, 1H), 4.45-4.26 (m, 3H), 3.83 (dd, J = 14.2, 7.1 Hz, 1H), 3.21 (s, 2H), 3.08-3.00 (m, 5H), 1.86 (p, J = 6.8 Hz, 2H), 1.78 (d, J = 7.2 Hz, 3H), 0.82 (t, J = 7.0 Hz, 3H). LCMS Calculated for $C_{37}H_{37}F_3N_6O_3$: 670.29; Observed (Method-J): 671.4 [M + H]$^+$, 98.84% at RT 1.924 min.

I-341

-continued

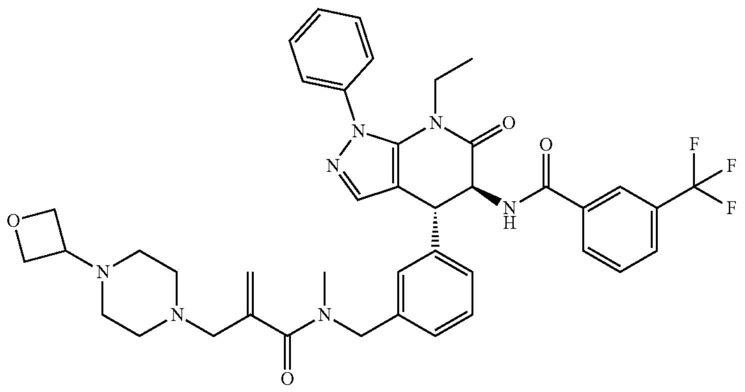 [SMILES: C=C(CN1CCN(C2COC2)CC1)C(=O)N(C)Cc1cccc([C@@H]2c3cnn(-c4ccccc4)c3N(CC)C(=O)[C@H]2NC(=O)c2cccc(C(F)(F)F)c2)c1]

I-218

$^1$H NMR (400 MHz, DMSO-$d_6$) δ 9.03 (d, J = 9.1 Hz, 1H), 8.10-8.00 (m, 2H), 7.90 (d, J = 7.8 Hz, 1H), 7.77-7.49 (m, 6H), 7.40-7.22 (m, 3H), 7.24-7.11 (m, 1H), 7.10-7.00 (m, 1H), 5.36-5.10 (m, 3H), 4.70-4.26 (m, 7H), 4.00-3.78 (m, 1H), 3.25-2.91 (m, 4H), 2.75 (s, 2H), 2.62 (s, 1H), 2.46-2.01 (m, 8H), 0.84 (t, J = 7.0 Hz, 3H). LCMS Calculated for $C_{41}H_{44}F_3N_7O_4$: 755.34; Observed (Method-J): 756.5 $[M + H]^+$, 96.76% at RT 1.601 min.

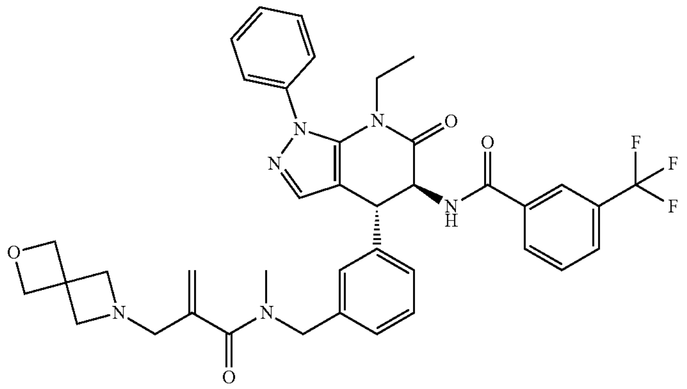 [SMILES: C=C(CN1CC2(COC2)C1)C(=O)N(C)Cc1cccc([C@@H]2c3cnn(-c4ccccc4)c3N(CC)C(=O)[C@H]2NC(=O)c2cccc(C(F)(F)F)c2)c1]

I-219

$^1$H NMR (400 MHz, DMSO-d6) δ 9.02 (d, J = 9.0 Hz, 1H), 8.06-7.96 (m, 2H), 7.91 (d, J = 7.8 Hz, 1H), 7.76-7.65 (m, 3H), 7.65-7.48 (m, 2H), 7.36-7.30 (m, 2H), 7.26 (s, 1H), 7.18-7.12 (m, 1H), 7.06 (s, 1H), 5.35-5.17 (m, 1H), 5.14-5.03 (m, 1H), 4.60-4.49 (m, 6H), 4.38 (d, J = 13.0 Hz, 1H), 3.93-3.81 (m, 1H), 3.35-3.30 (m, 1H), 3.28-3.17 (m, 4H), 3.12-2.99 (m, 3H), 2.73 (s, 2H), 2.61 (s, 2H), 0.88-0.78 (m, 3H). LCMS Calculated for $C_{39}H_{39}F_3N_6O_4$: 712.30; Observed (Method-K): 713.4 $[M + H]^+$, 93.16% at RT 0.736 min.

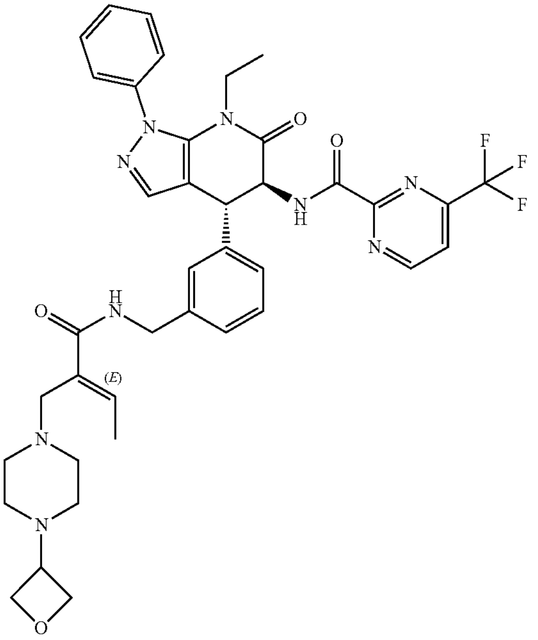 [SMILES: C/C=C(\CN1CCN(C2COC2)CC1)C(=O)NCc1cccc([C@@H]2c3cnn(-c4ccccc4)c3N(CC)C(=O)[C@H]2NC(=O)c2nccc(C(F)(F)F)n2)c1]

I-220

$^1$H NMR (300 MHz, DMSO-$d_6$) δ 9.36-9.26 (m, 2H), 9.02 (s, 1H), 8.23 (d, J = 5.1 Hz, 1H), 7.67-7.50 (m, J = 19.0, 12.1, 7.2 Hz, 5H), 7.28 (s, 3H), 7.18 (s, 1H), 6.93 (s, 1H), 6.63 (d, J = 7.1 Hz, 1H), 5.28-5.13 (m, 1H), 4.64 (d, J = 12.8 Hz, 1H), 4.45-4.26 (m, 6H), 3.85 (s, 1H), 3.20 (d, J = 14.4 Hz, 3H), 2.73 (s, 1H), 2.41-1.98 (m, 8H), 1.75 (d, J = 7.1 Hz, 3H), 0.83 (t, J = 7.0 Hz, 3H). LCMS Calculated for $C_{39}H_{42}F_3N_9O_4$: 757.33; Observed (Method-V): 758.4 $[M + H]^+$, 97.33% at RT 1.521 min.

-continued

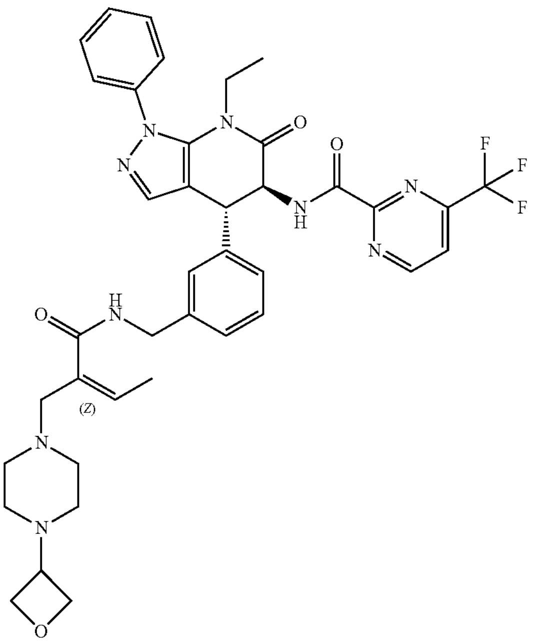 [SMILES: C/C=C(/CN1CCN(C2COC2)CC1)C(=O)NCc1cccc([C@@H]2c3cnn(-c4ccccc4)c3N(CC)C(=O)[C@H]2NC(=O)c2nccc(C(F)(F)F)n2)c1]

$^1$H NMR (400 MHz, DMSO-$d_6$) δ 9.36-9.26 (m, 2H), 8.75 (s, 1H), 8.23 (d, J = 5.1 Hz, 1H), 7.74-7.68 (m, 1H), 7.65 (d, J = 7.7 Hz, 2H), 7.59 (t, J = 7.5 Hz, 2H), 7.54 (t, J = 7.0 Hz, 1H), 7.36-7.27 (m, 3H), 7.24 (s, 1H), 6.95 (s, 1H), 5.23 (dd, J = 12.7, 9.4 Hz, 1H), 4.65 (d, J = 12.7 Hz, 1H), 4.52-4.23 (m, 6H), 4.14 (dd, J = 5.6, 3.5 Hz, 1H), 3.86 (dd, J = 14.3, 7.2 Hz, 1H), 3.15-2.98 (m, 2H), 2.93 (s, 1H), 2.34-2.09 (m, 4H), 1.97-1.55 (m, 4H), 1.43-1.16 (m, 3H), 0.94-0.79 (m, 3H). LCMS Calculated for $C_{39}H_{42}F_3N_9O_4$: 757.33; Observed (Method-Z): 758.4 [M + H]$^+$, 99.40% at RT 1.760 min.

I-257

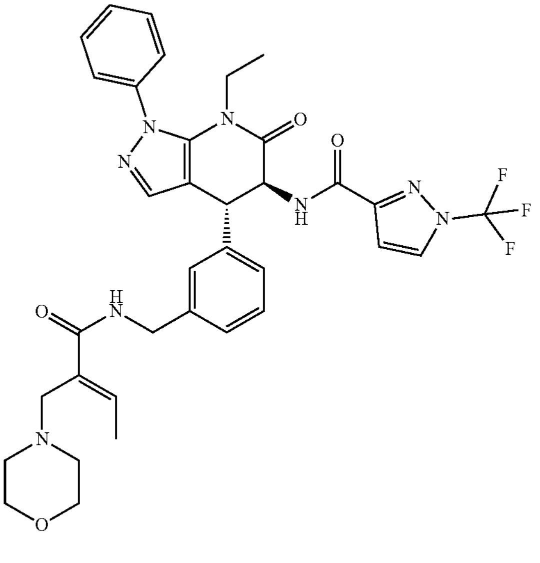 [SMILES: C/C=C(\CN1CCOCC1)C(=O)NCc1cccc([C@@H]2c3cnn(-c4ccccc4)c3N(CC)C(=O)[C@H]2NC(=O)c2ccn(C(F)(F)F)n2)c1]

$^1$H NMR (400 MHz, DMSO-$d_6$) δ 8.93 (t, J = 5.8 Hz, 1H), 8.77 (d, J = 9.2 Hz, 1H), 8.58 (d, J = 2.8 Hz, 1H), 7.64 (d, J = 8.6 Hz, 2H), 7.61-7.55 (m, 2H), 7.55-7.49 (m, 1H), 7.37-7.23 (m, 3H), 7.20 (d, J = 7.4 Hz, 1H), 6.92 (d, J = 3.3 Hz, 2H), 6.65 (q, J = 7.1 Hz, 1H), 5.17 (dd, J = 12.9, 9.1 Hz, 1H), 4.55 (d, J = 12.9 Hz, 1H), 4.41-4.25 (m, 2H), 3.85 (dq, J = 14.0, 7.0 Hz, 1H), 3.43 (d, J = 4.6 Hz, 4H), 3.18 (s, 2H), 3.11-2.91 (m, 1H), 2.33 (s, 4H), 1.76 (d, J = 7.1 Hz, 3H), 0.82 (t, J = 6.9 Hz, 3H). LCMS Calculated for $C_{35}H_{37}F_3N_8O_4$: 690.29; Observed (Method-AB): 691.5 [M + H]$^+$, 93.49% at RT 1.470 min.

I-284

-continued

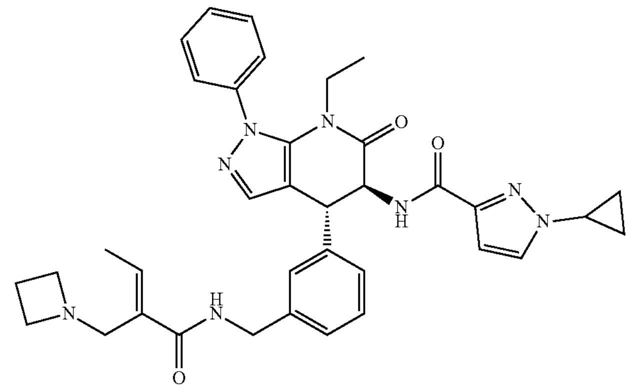 [SMILES: C/C=C(\CN1CCC1)C(=O)NCc1cccc([C@@H]2c3cnn(-c4ccccc4)c3N(CC)C(=O)[C@H]2NC(=O)c2ccn(C3CC3)n2)c1]

$^{1}$H NMR (400 MHz, DMSO-$d_6$) δ 9.07 (t, J = 5.9 Hz, 1H), 8.27 (d, J = 9.3 Hz, 1H), 7.81 (d, J = 2.4 Hz, 1H), 7.67-7.45 (m, 5H), 7.35-7.20 (m, 3H), 7.16 (d, J = 7.4 Hz, 1H), 6.92 (s, 1H), 6.64-6.40 (m, 2H), 5.13 (dd, J = 12.8, 9.3 Hz, 1H), 4.55 (d, J = 12.8 Hz, 1H), 4.44-4.24 (m, 2H), 3.97-3.61 (m, 2H), 3.24 (s, 2H), 3.06-2.93 (m, 5H), 1.97-1.83 (m, 2H), 1.79 (d, J = 7.2 Hz, 3H), 1.12-0.92 (m, 2H), 1.03-0.93 (m, 2H), 0.81 (t, J = 7.0 Hz, 3H). LCMS Calculated for $C_{36}H_{40}N_8O_3$: 632.32; Observed (Method-AC): 633.4 [M + H]$^+$, 94.47% at RT 1.798 min.

I-309

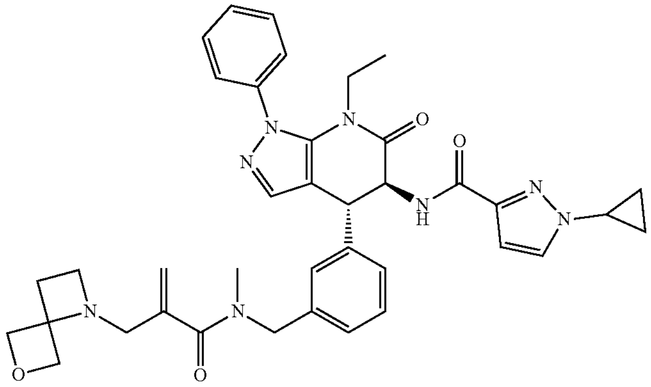 [SMILES: C=C(CN1CCC12COC2)C(=O)N(C)Cc1cccc([C@@H]2c3cnn(-c4ccccc4)c3N(CC)C(=O)[C@H]2NC(=O)c2ccn(C3CC3)n2)c1]

$^{1}$H NMR (400 MHz, DMSO-$d_6$) δ 8.25 (d, J = 9.4 Hz, 1H), 7.78 (d, J = 2.3 Hz, 1H), 7.68-7.44 (m, 5H), 7.40-7.25 (m, 3H), 7.14 (d, J = 6.9 Hz, 1H), 6.93 (s, 1H), 6.48 (s, 1H), 5.29 (d, J = 6.9 Hz, 1H), 5.15-5.02 (m, 2H), 4.73 (d, J = 7.2 Hz, 2H), 4.63-4.47 (m, 3H), 4.42 (dd, J = 7.3, 4.5 Hz, 2H), 3.82 (dt, J = 14.3, 7.2 Hz, 1H), 3.73 (tt, J = 7.4, 3.9 Hz, 1H), 3.53-3.34 (m, 2H), 3.09-2.84 (m, 3H), 2.70 (d, J = 10.9 Hz, 3H), 2.28-2.16 (m, 2H), 1.15-0.91 (m, 4H), 0.79 (t, J = 7.0 Hz, 3H). LCMS Calculated for $C_{38}H_{42}N_8O_4$: 674.33; Observed (Method-K): 675.6 [M + H]$^+$, 97.50% at RT 0.693 min.

I-373

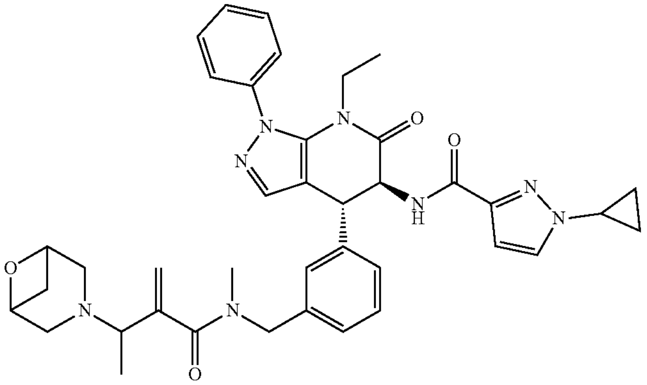 [SMILES: C=C(C(=O)N(C)Cc1cccc([C@@H]2c3cnn(-c4ccccc4)c3N(CC)C(=O)[C@H]2NC(=O)c2ccn(C3CC3)n2)c1)C(C)N1CC2CC(C1)O2]

$^{1}$H NMR (400 MHz, DMSO-$d_6$) δ 9.08 (t, J = 5.7 Hz, 1H), 8.22 (d, J = 9.3 Hz, 1H), 7.79 (d, J = 2.4 Hz, 1H), 7.62-7.48 (m, 5H), 7.30-7.19 (m, 3H), 7.18-7.06 (m, 1H), 6.84 (s, 1H), 6.51 (d, J = 2.4 Hz, 1H), 5.86 (d, J = 1.8 Hz, 1H), 5.44 (d, J = 1.6 Hz, 1H), 5.09 (ddd, J = 12.2, 9.3, 2.4 Hz, 1H), 4.50 (d, J = 12.7 Hz, 1H), 4.44-4.17 (m, 4H), 3.88-3.65 (m, 2H), 3.53 (tt, J = 6.6, 3.9 Hz, 1H), 3.01 (dq, J = 13.9, 6.7 Hz, 1H), 2.87 (ddd, J = 11.3, 4.9, 2.3 Hz, 1H), 2.79 (dd, J = 11.6, 2.2 Hz, 1H), 2.70-2.53 (m, 3H), 1.65 (dd, J = 8.2, 1.9 Hz, 1H), 1.20 (d, J = 6.7 Hz, 3H), 1.12-1.02 (m, 2H), 1.02-0.94 (m, 2H), 0.79 (t, J = 7.0 Hz, 3H). LCMS Calculated for $C_{38}H_{42}N_8O_4$: 674.33; Observed- (Method-I): 675.4. [M + H]$^+$, 99.93 at RT 1.472 min.

I-240

-continued

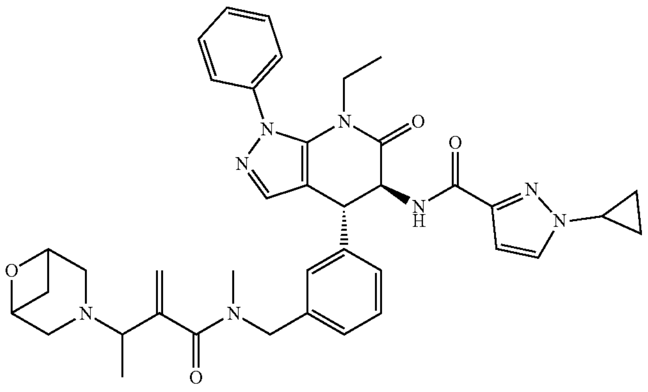 [SMILES: C=C(C(=O)N(C)Cc1cccc([C@@H]2c3cnn(-c4ccccc4)c3N(CC)C(=O)[C@H]2NC(=O)c2ccn(C3CC3)n2)c1)C(C)N1CC2CC(C1)O2]

$^1$H NMR (400 MHz, DMSO-$d_6$) δ 8.24 (d, J = 9.4 Hz, 1H), 7.77 (d, J = 2.4 Hz, 1H), 7.66-7.48 (m, 5H), 7.39-7.20 (m, 3H), 7.15-7.08 (m, 1H), 6.94 (d, J = 7.3 Hz, 1H), 6.47 (d, J = 2.3 Hz, 1H), 5.33 (d, J = 9.6 Hz, 1H), 5.23-5.03 (m, 2H), 4.65-4.40 (m, 3H), 4.33 (d, J = 6.1 Hz, 2H), 3.92-3.76 (m, 1H), 3.73 (td, J = 7.2, 3.7 Hz, 1H), 3.37 (d, J = 4.3 Hz, 2H), 3.00 (dd, J = 14.0, 8.5 Hz, 3H), 2.85-2.54 (m, 6H), 2.20-2.02 (m, 1H), 1.15-0.90 (m, 4H), 0.79 (t, J = 7.0 Hz, 3H).
LCMS Calculated for $C_{38}H_{42}N_8O_4$: 674.33; Observed (Method-E): 675.7 [M + H]$^+$, 98.19% at RT 1.250 min.

I-258

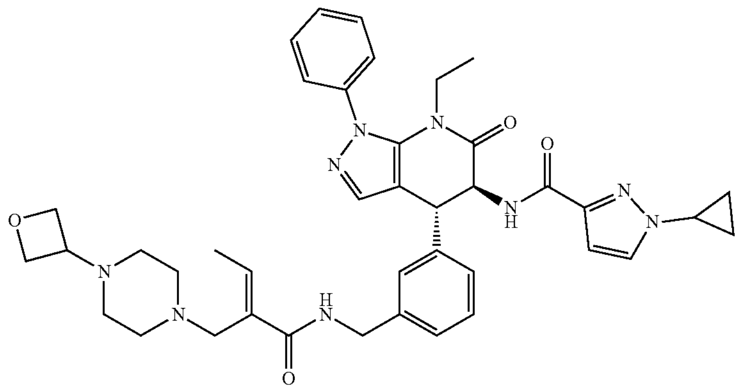 [SMILES: C/C=C(\CN1CCN(C2COC2)CC1)C(=O)NCc1cccc([C@@H]2c3cnn(-c4ccccc4)c3N(CC)C(=O)[C@H]2NC(=O)c2ccn(C3CC3)n2)c1]

$^1$H NMR (300 MHz, DMSO-$d_6$) δ 9.04 (t, J = 5.7 Hz, 1H), 8.25 (d, J = 9.4 Hz, 1H), 7.81 (d, J = 2.3 Hz, 1H), 7.67-7.47 (m, 5H), 7.36-7.22 (m, 3H), 7.18 (d, J = 7.0 Hz, 1H), 6.88 (s, 1H), 6.66 (q, J = 7.1 Hz, 1H), 6.52 (d, J = 2.3 Hz, 1H), 5.13 (dd, J = 12.8, 9.3 Hz, 1H), 4.54 (d, J = 12.8 Hz, 1H), 4.46-4.22 (m, 6H), 3.92-3.70 (m, 2H), 3.23 (t, J = 6.3 Hz, 1H), 3.19 (s, 2H), 3.04 (dq, J = 13.7, 6.8 Hz, 1H), 2.48-2.32 (m, 4H), 2.21-1.90 (s, 4H), 1.76 (d, J = 7.1 Hz, 3H), 1.13-0.94 (m, 4H), 0.82 (t, J = 7.0 Hz, 3H).
LCMS Calculated for $C_{40}H_{47}N_9O_4$: 717.38; Observed (Method-C): 718.30 [M + H]$^+$, 99.48% at RT 0.800 min.

I-288

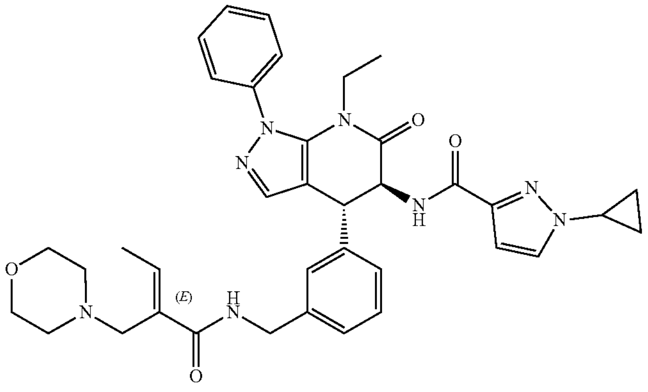 [SMILES: C/C=C(\CN1CCOCC1)C(=O)NCc1cccc([C@@H]2c3cnn(-c4ccccc4)c3N(CC)C(=O)[C@H]2NC(=O)c2ccn(C3CC3)n2)c1]

$^1$H NMR for 0545-0(400 MHz, DMSO-$d_6$) δ 8.93 (t, J = 5.8 Hz, 1H), 8.27 (d, J = 9.4 Hz, 1H), 7.81 (d, J = 2.4 Hz, 1H), 7.67-7.49 (m, 5H), 7.27 (q, J = 7.4 Hz, 3H), 7.19 (d, J = 7.2 Hz, 1H), 6.90 (s, 1H), 6.66 (t, J = 7.2 Hz, 1H), 6.53 (d, J = 2.4 Hz, 1H), 5.13 (dd, J = 12.8, 9.3 Hz, 1H), 4.54 (d, J = 12.7 Hz, 1H), 4.35 (t, J = 4.7 Hz, 2H), 4.09-3.56 (m, 2H), 3.42 (t, J = 4.6 Hz, 4H), 3.18 (s, 2H), 3.03 (dd, J = 14.1, 7.1 Hz, 1H), 2.33 (s, 4H), 1.76 (d, J = 7.2 Hz, 3H), 1.11-1.05 (m, 2H), 1.05-0.94 (m, 2H), 0.81 (d, J = 7.0 Hz, 3H).
LCMS Calculated for $C_{37}H_{42}N_8O_4$: 662.33; Observed (Method-AD): 663.3 [M + H]$^+$, 99.84% at RT 1.195 min.

I-241

-continued

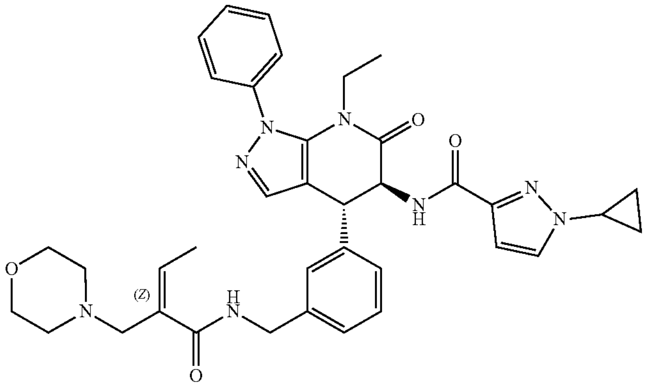 [SMILES: C/C=C(/CN1CCOCC1)C(=O)NCc1cccc([C@@H]2c3cnn(-c4ccccc4)c3N(CC)C(=O)[C@H]2NC(=O)c2ccn(C3CC3)n2)c1]

$^{1}H$ NMR (400 MHz, DMSO-$d_6$) δ 8.68 (t, J = 5.9 Hz, 1H), 8.27 (d, J = 9.4 Hz, 1H), 7.81 (d, J = 2.4 Hz, 1H), 7.71-7.47 (m, 5H), 7.38-7.16 (m, 4H), 6.90 (s, 1H), 6.53 (d, J = 2.4 Hz, 1H), 5.73 (q, J = 6.7 Hz, 1H), 5.14 (dd, J = 12.8, 9.3 Hz, 1H), 4.55 (d, J = 12.8 Hz, 1H), 4.45-4.27 (m, 2H), 4.03-3.59 (m, 2H), 3.54-3.44 (m, 4H), 3.08-2.95 (m, 3H), 2.30 (d, J = 5.8 Hz, 4H), 1.78 (d, J = 6.9 Hz, 3H), 1.10-1.05 (m, 2H), 1.01-0.93 (m, 2H), 0.82 (q, J = 7.5, 7.0 Hz, 3H).
LCMS Calculated for $C_{37}H_{42}N_8O_4$: 662.33; Observed (Method-AD): 663.3 $[M + H]^+$, 98.86% at RT 1.182 min.

I-381

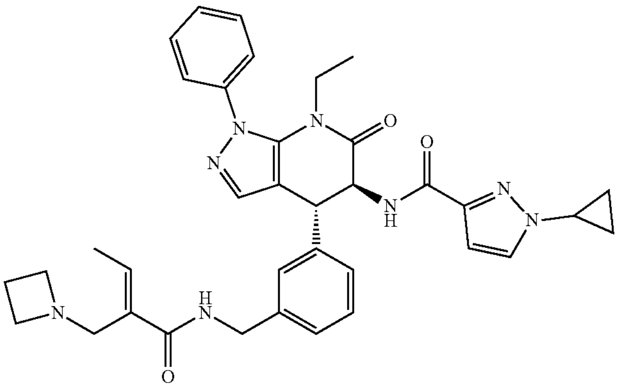 [SMILES: C/C=C(\CN1CCC1)C(=O)NCc1cccc([C@@H]2c3cnn(-c4ccccc4)c3N(CC)C(=O)[C@H]2NC(=O)c2ccn(C3CC3)n2)c1]

$^{1}H$ NMR (400 MHz, DMSO-$d_6$) δ 9.07 (t, J = 5.9 Hz, 1H), 8.27 (d, J = 9.3 Hz, 1H), 7.81 (d, J = 2.4 Hz, 1H), 7.67-7.45 (m, 5H), 7.35-7.20 (m, 3H), 7.16 (d, J = 7.4 Hz, 1H), 6.92 (s, 1H), 6.64-6.40 (m, 2H), 5.13 (dd, J = 12.8, 9.3 Hz, 1H), 4.55 (d, J = 12.8 Hz, 1H), 4.44-4.24 (m, 2H), 3.97-3.61 (m, 2H), 3.24 (s, 2H), 3.06-2.93 (m, 5H), 1.97-1.83 (m, 2H), 1.79 (d, J = 7.2 Hz, 3H), 1.12-0.92 (m, 2H), 1.03-0.93 (m, 2H), 0.81 (t, J = 7.0 Hz, 3H).
LCMS Calculated for $C_{36}H_{40}N_8O_3$: 632.32; Observed (Method-AC): 633.4 $[M + H]^+$, 94.47% at RT 1.798 min.

I-309

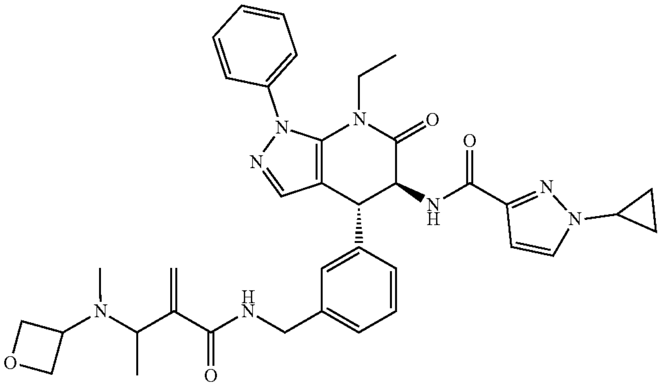

$^{1}H$ NMR (300 MHz, DMSO-$d_6$) δ 8.24 (t, J = 8.2 Hz, 1H), 7.79 (d, J = 2.4 Hz, 1H), 7.68-7.51 (m, 4H), 7.51 (dd, J = 8.2, 5.2 Hz, 1H), 7.26 (d, J = 9.8 Hz, 4H), 6.96 (s, 1H), 6.49 (t, J = 2.4 Hz, 1H), 5.31-5.19 (m, 1H), 5.19-5.05 (m, 1H), 4.69 (dd, J = 14.7, 9.3 Hz, 1H), 4.54 (s, 2H), 4.52-4.34 (m, 5H), 3.82 (td, J = 15.2, 8.2 Hz, 3H), 3.52 (d, J = 7.0 Hz, 1H), 3.07-2.94 (m, 1H), 2.79 (s, 2H), 2.02 (s, 2H), 1.96 (d, J = 6.3 Hz, 1H), 1.13-0.92 (m, 8H), 0.81 (t, J = 7.0 Hz, 3H).
LCMS Calculated for $C_{28}H_{44}N_8O_4$: 676.35; Observed (Method-B): 677.3 $[M + H]^+$, 99.28% at RT 0.728 min.

I-342

-continued

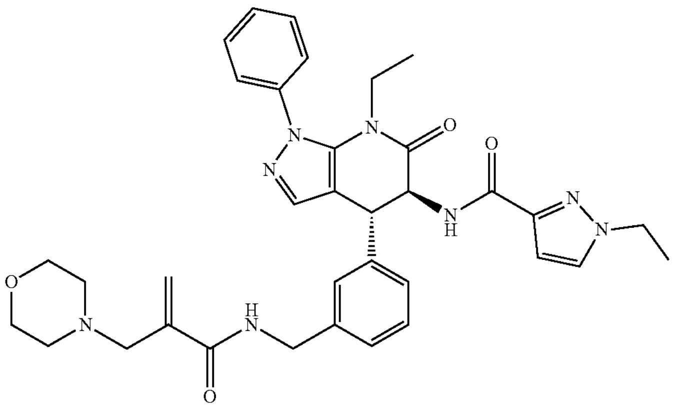 [SMILES: C=C(CN1CCOCC1)C(=O)NCc1cccc([C@@H]2c3cnn(-c4ccccc4)c3N(CC)C(=O)[C@H]2NC(=O)c2ccn(CC)n2)c1]

$^1$H NMR (300 MHz, DMSO-$d_6$) δ 8.95 (t, J = 5.8 Hz, 1H), 8.21 (d, J = 9.3 Hz, 1H), 7.79-7.74 (m, 1H), 7.66-7.45 (m, 5H), 7.33-7.22 (m, 3H), 7.18 (t, J = 7.3 Hz, 1H), 6.89 (s, 1H), 6.56-6.50 (m, 1H), 5.91-5.85 (m, 1H), 5.43 (s, 1H), 5.13 (dd, J = 12.7, 9.3 Hz, 1H), 4.57-4.44 (m, 1H), 4.38-4.30 (m, 2H), 4.15 (q, J = 7.3 Hz, 2H), 3.88-3.72 (m, 1H), 3.48-3.37 (m, 2H), 3.15 (s, 3H), 3.10-2.93 (m, 1H), 2.36-2.24 (m, 4H), 1.37 (t, J = 7.3 Hz, 3H), 0.79 (t, J = 7.0 Hz, 3H).
LCMS Calculated for $C_{35}H_{40}N_8O_4$: 636.32; Observed (Method-Z): 637.4 $[M + H]^+$, 99.62% at RT 1.815 min.

I-351

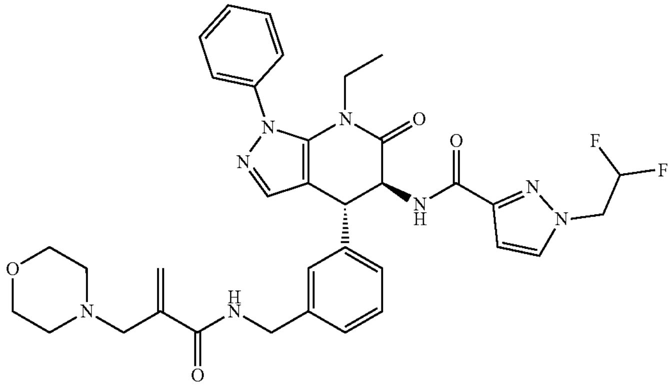 [SMILES: C=C(CN1CCOCC1)C(=O)NCc1cccc([C@@H]2c3cnn(-c4ccccc4)c3N(CC)C(=O)[C@H]2NC(=O)c2ccn(CC(F)F)n2)c1]

$^1$H NMR (300 MHz, DMSO-$d_6$) δ 8.95 (t, J = 5.9 Hz, 1H), 8.29 (d, J = 9.3 Hz, 1H), 7.82 (d, J = 2.4 Hz, 1H), 7.67-7.43 (m, 5H), 7.27 (dd, J = 7.6, 5.3 Hz, 3H), 7.19 (t, J = 8.2 Hz, 1H), 6.89 (s, 1H), 6.62 (d, J = 2.4 Hz, 1H), 6.58-6.15 (m, 1H), 5.88 (d, J = 2.0 Hz, 1H), 5.43 (s, 1H), 5.14 (dd, J = 12.7, 9.3 Hz, 1H), 4.76-4.57 (m, 2H), 4.52 (d, J = 12.8 Hz, 1H), 4.44-4.24 (m, 2H), 3.82 (dt, J = 14.2, 6.9 Hz, 1H), 3.50-3.36 (m, 4H), 3.16 (s, 2H), 3.02 (dd, J = 14.2, 7.1 Hz, 1H), 2.37-2.23 (m, 4H), 0.79 (t, J = 7.0 Hz, 3H).
LCMS Calculated for $C_{35}H_{38}F_2N_8O_4$: 672.30; Observed (Method-J): 673.4 $[M + H]^+$, 99.85% at RT 1.525 min.

I-364

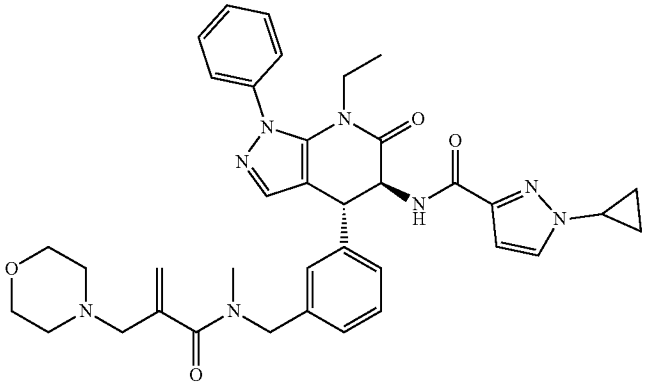 [SMILES: C=C(CN1CCOCC1)C(=O)N(C)Cc1cccc([C@@H]2c3cnn(-c4ccccc4)c3N(CC)C(=O)[C@H]2NC(=O)c2ccn(C3CC3)n2)c1]

$^1$H NMR (300 MHz, DMSO-$d_6$) δ 8.97 (t, J = 5.7 Hz, 1H), 8.28 (d, J = 9.3 Hz, 1H), 7.80 (d, J = 2.3 Hz, 1H), 7.65-7.45 (m, 5H), 7.28 (q, J = 7.1 Hz, 3H), 7.19 (t, J = 8.3 Hz, 1H), 6.88 (s, 1H), 6.51 (d, J = 2.3 Hz, 1H), 5.88 (d, J = 2.0 Hz, 1H), 5.43 (s, 1H), 5.12 (dd, J = 12.8, 9.3 Hz, 1H), 4.53 (d, J = 12.8 Hz, 1H), 4.42-4.26 (m, 2H), 3.87-3.68 (m, 2H), 3.48-3.38 (m, 4H), 3.15 (s, 2H), 3.00 (dd, J = 14.2, 7.2 Hz, 1H), 2.37-2.20 (m, 4H), 1.11-1.02 (m, 2H), 1.01-0.92 (m, 2H), 0.78 (t, J = 7.0 Hz, 3H).
LCMS Calculated for $C_{36}H_{40}N_8O_4$: 648.32; Observed (Method-J): 649.4 $[M + H]^+$, 97.47% at RT 1.557 min.

I-280

-continued

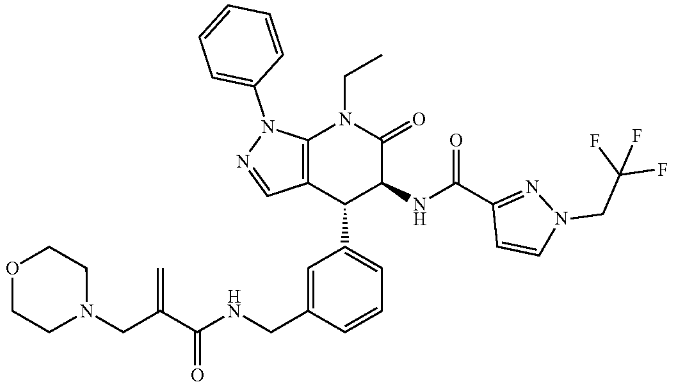

$^1$H NMR (300 MHz, DMSO-$d_6$): δ 8.96 (t, J = 5.9 Hz, 1H), 8.34 (d, J = 9.3 Hz, 1H), 7.89 (d, J = 2.4 Hz, 1H), 7.66-7.45 (m, 5H), 7.33-7.22 (m, 3H), 7.18 (d, J = 7.2 Hz, 1H), 6.89 (s, 1H), 6.67 (d, J = 2.4 Hz, 1H), 5.88 (s, 1H), 5.43 (s, 1H), 5.26-5.07 (m, 3H), 4.53 (d, J = 12.8 Hz, 1H), 4.42-4.24 (m, 2H), 3.82 (dd, J = 14.2, 7.2 Hz, 1H), 3.48-3.38 (m, 4H), 3.15 (s, 2H), 3.00 (dd, J = 14.2, 7.1 Hz, 1H), 2.37-2.23 (m, 4H), 0.79 (t, J = 7.0 Hz, 3H). LCMS Calculated for $C_{35}H_{37}F_3N_8O_4$: 690.29; Observed (Method-J): 691.4 $[M + H]^+$, 97.21% at RT 1.600 min.

I-297

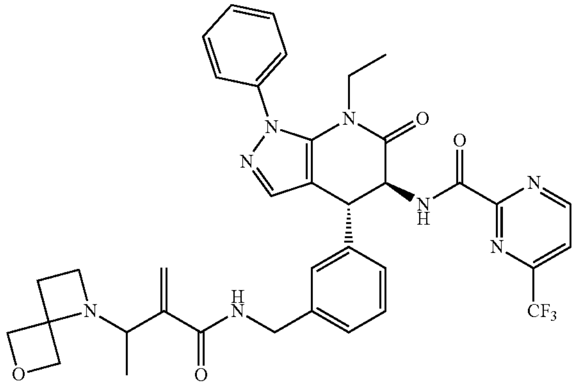 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N1CCC12COC2]

$^1$H NMR (400 MHz, DMSO-$d_6$) δ 9.30 (dd, J = 13.5, 7.2 Hz, 2H), 8.98 (d, J = 6.1 Hz, 1H), 8.21 (d, J = 5.1 Hz, 1H), 7.64 (d, J = 7.6 Hz, 2H), 7.61-7.49 (m, 3H), 7.34-7.25 (m, 3H), 7.16 (s, 1H), 6.96 (s, 1H), 5.85 (s, 1H), 5.53 (s, 1H), 5.24-5.16 (m, 1H), 4.82 (d, J = 7.3 Hz, 1H), 4.73 (d, J = 7.5 Hz, 1H), 4.65 (d, J = 12.6 Hz, 1H), 4.45 (s, 1H), 4.41-4.33 (m, 3H), 3.84 (dd, J = 14.3, 7.2 Hz, 1H), 3.65 (d, J = 6.8 Hz, 1H), 3.06 (dd, J = 14.3, 7.4 Hz, 1H), 2.95-2.88 (m, 1H), 2.88-2.79 (m, 1H), 2.14 (s, 2H), 1.16 (d, J = 6.4 Hz, 3H), 0.83 (t, J = 7.0 Hz, 3H). LCMS Calculated for $C_{37}H_{37}F_3N_8O_4$: 714.29; Observed (Method-B): 715.2 $[M + H]^+$, 0.740 min.

I-256

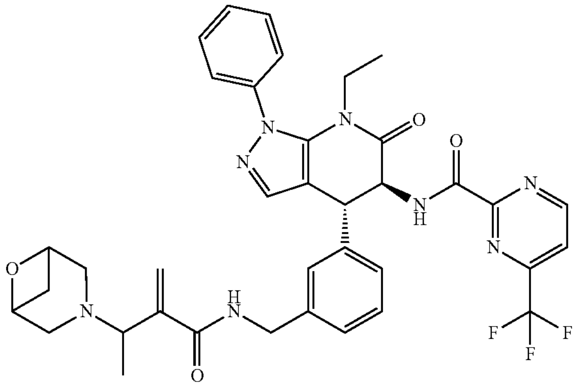 [SMILES: C=C(C(=O)NCc1cccc([C@@H]2c3cnn(-c4ccccc4)c3N(CC)C(=O)[C@H]2NC(=O)c2nccc(C(F)(F)F)n2)c1)C(C)N1CC2CC(C1)O2]

$^1$H NMR (400 MHz, DMSO-$d_6$) δ 9.35-9.26 (m, 2H), 9.07 (s, 1H), 8.22 (d, J = 5.1 Hz, 1H), 7.67-7.62 (m, 2H), 7.56 (dt, J = 22.4, 7.2 Hz, 3H), 7.32-7.25 (m, 3H), 7.15 (d, J = 5.5 Hz, 1H), 6.92 (s, 1H), 5.86 (d, J = 1.8 Hz, 1H), 5.44 (s, 1H), 5.19 (dd, J = 12.4, 9.4 Hz, 1H), 4.63 (d, J = 12.7 Hz, 1H), 4.41-4.25 (m, 4H), 3.85 (dd, J = 14.2, 7.3 Hz, 1H), 3.55 (q, J = 6.8 Hz, 1H), 3.06 (dd, J = 14.1, 6.9 Hz, 1H), 2.89 (t, J = 11.3 Hz, 1H), 2.81 (t, J = 10.2 Hz, 1H), 2.69-2.56 (m, 3H), 1.71 (dd, J = 8.1, 4.1 Hz, 1H), 1.21 (dd, J = 6.7, 3.9 Hz, 3H), 0.83 (t, J = 7.0 Hz, 3H). LCMS Calculated for $C_{37}H_{37}F_3N_8O_4$: 714.29; Observed (Method-E): 715.6 $[M + H]^+$, 99.44% at RT 1.275 min.

I-324

-continued

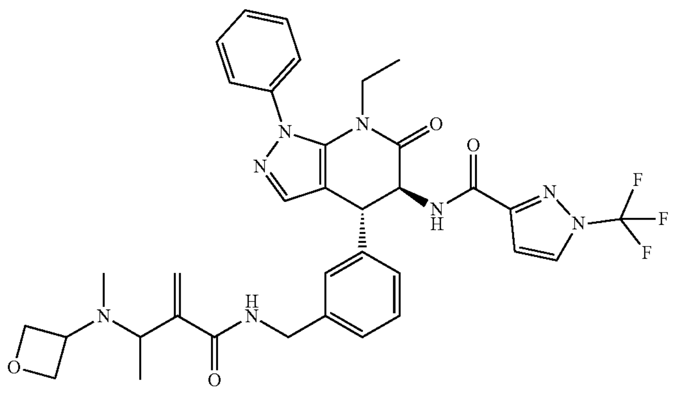

$^1H$ NMR (300 MHz, DMSO-$d_6$) δ 8.89 (d, J = 5.2 Hz, 1H), 8.76 (d, J = 9.2 Hz, 1H), 8.57 (d, J = 2.8 Hz, 1H), 7.68-7.47 (m, 5H), 7.36-7.18 (m, 4H), 6.99-6.89 (m, 2H), 5.74 (s, 1H), 5.31 (s, 1H), 5.24-5.10 (m, 1H), 4.59-4.44 (m, 1H), 4.48-4.31 (m, 6H), 3.91-3.74 (m, 2H), 3.62-3.56 (m, 1H), 3.10-2.94 (m, 1H), 1.99 (d, J = 3.0 Hz, 3H), 0.98 (d, J = 6.7 Hz, 3H), 0.82 (t, J = 7.0 Hz, 3H). LCMS Calculated for $C_{35}H_{37}F_3N_8O_4$: 690.29; Observed (Method-C): 691.20 [M + H]$^+$, 98.19% at RT 0.861 min.

I-355

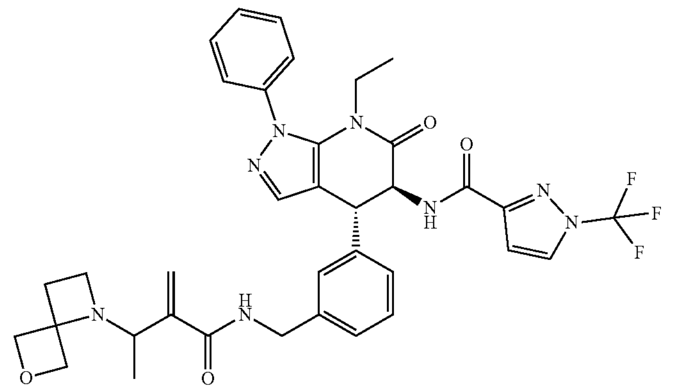 [SMILES: C=C(C(=O)NCc1cccc([C@@H]2c3cnn(-c4ccccc4)c3N(CC)C(=O)[C@H]2NC(=O)c2ccn(C(F)(F)F)n2)c1)C(C)N1CCC12COC2]

$^1H$ NMR (400 MHz, DMSO-$d_6$) δ 8.97 (q, J = 5.6 Hz, 1H), 8.74 (d, J = 9.2 Hz, 1H), 8.55 (d, J = 2.8 Hz, 1H), 7.64-7.46 (m, 5H), 7.33-7.21 (m, 3H), 7.18-7.12 (m, 1H), 6.93-6.86 (m, 2H), 5.84 (s, 1H), 5.51 (s, 1H), 5.13 (dd, J = 12.8, 9.2 Hz, 1H), 4.81 (d, J = 7.3 Hz, 1H), 4.71 (d, J = 7.2 Hz, 1H), 4.52 (d, J = 12.8 Hz, 1H), 4.43 (dd, J = 7.3, 3.7 Hz, 1H), 4.37 (dd, J = 9.8, 6.6 Hz, 3H), 3.81 (dq, J = 14.2, 7.0 Hz, 1H), 3.63 (q, J = 6.4 Hz, 1H), 3.08-2.95 (m, 1H), 2.90 (q, J = 6.7 Hz, 1H), 2.86-2.76 (m, 1H), 2.21-2.05 (m, 2H), 1.15 (d, J = 6.4 Hz, 3H), 0.79 (t, J = 7.0 Hz, 3H). LCMS Calculated for $C_{36}H_{37}F_3N_8O_4$: 702.29; Observed (Method-AC): 703.40 [M + H]$^+$, 97.38% at RT 1.652 min.

I-344

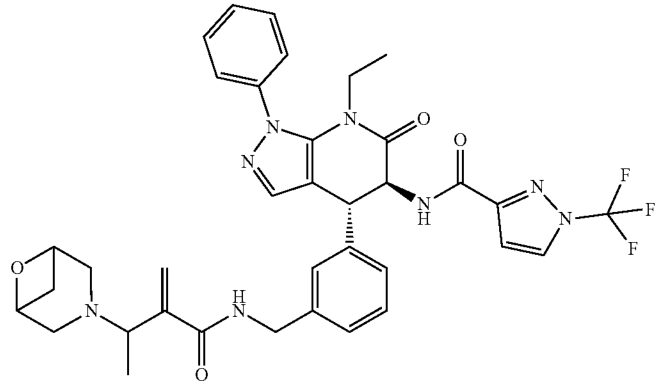 [SMILES: C=C(C(=O)NCc1cccc([C@@H]2c3cnn(-c4ccccc4)c3N(CC)C(=O)[C@H]2NC(=O)c2ccn(C(F)(F)F)n2)c1)C(C)N1CC2CC(C1)O2]

$^1H$ NMR (400 MHz, DMSO-$d_6$) δ 9.10 (t, J = 5.8 Hz, 1H), 8.75 (d, J = 9.2 Hz, 1H), 8.58 (d, J = 2.8 Hz, 1H), 7.67-7.49 (m, 5H), 7.28 (d, J = 6.2 Hz, 3H), 7.16 (d, J = 6.9 Hz, 1H), 6.95-6.87 (m, 2H), 5.88 (s, 1H), 5.46 (s, 1H), 5.15 (ddd, J = 12.3, 9.2, 2.5 Hz, 1H), 4.53 (d, J = 12.8 Hz, 1H), 4.46-4.24 (m, 4H), 3.89-3.78 (m, 1H), 3.60-3.51 (m, 1H), 3.10-2.99 (m, 1H), 2.94-2.85 (m, 1H), 2.82 (d, J = 11.5 Hz, 1H), 2.69-2.56 (m, 3H), 1.70 (d, J = 8.1 Hz, 1H), 1.21 (d, J = 6.7 Hz, 3H), 0.82 (t, J = 7.0 Hz, 3H). LCMS Calculated for $C_{36}H_{37}F_3N_8O_4$: 702.29; Observed (Method-AC): 703.40 [M + H]$^+$, 98.76% at RT 1.643 min.

I-287

-continued

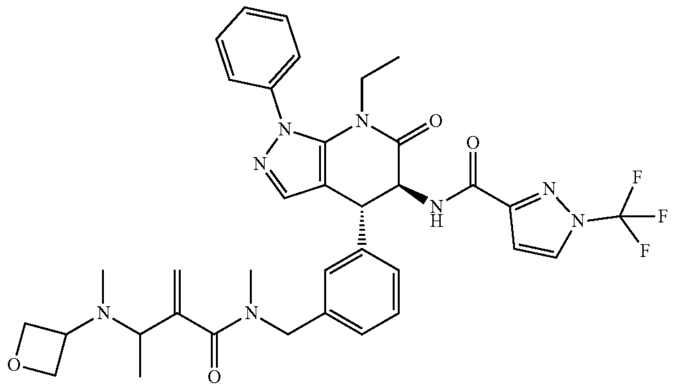 [SMILES: C=C(C(=O)N(C)Cc1cccc([C@@H]2c3cnn(-c4ccccc4)c3N(CC)C(=O)[C@H]2NC(=O)c2ccn(C(F)(F)F)n2)c1)C(C)N(C)C1COC1]

$^1$H NMR (300 MHz, DMSO-$d_6$) δ 8.75 (t, J = 8.1 Hz, 1H), 8.57 (d, J = 2.8 Hz, 1H), 7.69-7.50 (m, 5H), 7.40-7.18 (m, 4H), 7.00 (s, 1H), 6.92-6.85 (m, 1H), 5.35-5.08 (m, 3H), 4.73-4.30 (m, 7H), 3.91-3.76 (m, 2H), 3.56-3.50 (m, 1H), 3.06-3.00 (m, 1H), 2.82-2.76 (m, 2H), 2.70-2.57 (m, 1H), 2.05-1.90 (m, 3H), 0.99-0.93 (m, 3H), 0.82 (t, J = 6.9 Hz, 3H).
LCMS Calculated for $C_{36}H_{39}F_3N_8O_4$: 704.30; Observed (Method-AA): 705.10 [M + H]$^+$, 95.68% at RT 1.625 min.

I-313

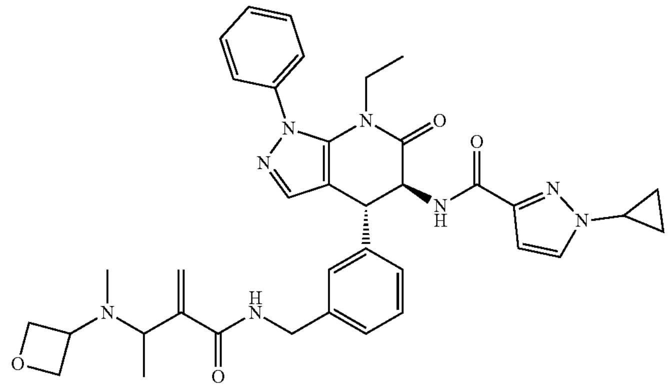

$^1$H NMR (300 MHz, DMSO-$d_6$) δ 8.88 (q, J = 5.6 Hz, 1H), 8.26 (d, J = 9.3 Hz, 1H), 7.81 (d, J = 2.4 Hz, 1H), 7.65-7.49 (m, 5H), 7.35-7.19 (m, 4H), 6.93 (s, 1H), 6.54 (d, J = 2.4 Hz, 1H), 5.75 (s, 1H), 5.32 (s, 1H), 5.14 (ddd, J = 12.9, 9.3, 1.9 Hz, 1H), 4.55 (d, J = 12.8 Hz, 1H), 4.48-4.31 (m, 6H), 3.90-3.71 (m, 3H), 3.64-3.54 (m, 1H), 3.11-2.96 (m, 1H), 2.00 (d, J = 2.9 Hz, 3H), 1.11-0.94 (m, 7H), 0.81 (t, J = 7.0 Hz, 3H).
LCMS Calculated for $C_{37}H_{42}N_8O_4$: 662.33; Observed (Method-AE): 663.30 [M + H]$^+$, 99.04% at RT 1.194 min.

I-327

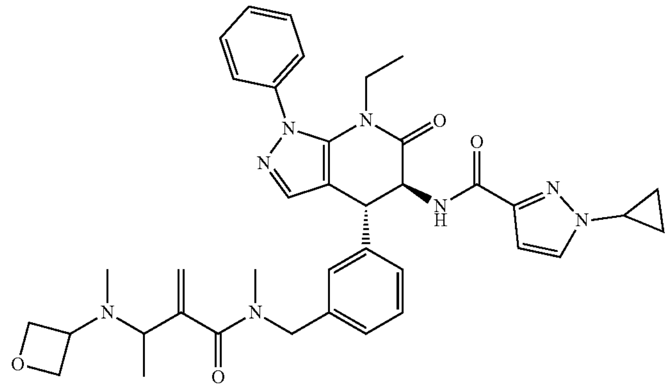 [SMILES: C=C(C(=O)N(C)Cc1cccc([C@@H]2c3cnn(-c4ccccc4)c3N(CC)C(=O)[C@H]2NC(=O)c2ccn(C3CC3)n2)c1)C(C)N(C)C1COC1]

$^1$H NMR (400 MHz, DMSO-$d_6$) δ 8.22 (d, J = 9.4 Hz, 1H), 7.78 (d, J = 2.4 Hz, 1H), 7.67-7.40 (m, 5H), 7.42-7.01 (m, 4H), 6.94 (s, 1H), 6.48 (d, J = 2.4 Hz, 1H), 5.47-4.93 (m, 3H), 4.66-4.40 (m, 5H), 4.33 (t, J = 6.1 Hz, 2H), 3.82 (dt, J = 14.2, 7.1 Hz, 1H), 3.74 (tt, J = 7.4, 3.9 Hz, 1H), 3.51 (p, J = 6.4 Hz, 1H), 3.10-2.90 (m, 3H), 2.78-2.63 (m, 3H), 2.01 (d, J = 22.5 Hz, 3H), 1.13-1.01 (m, 2H), 0.98 (dd, J = 7.1, 4.7 Hz, 2H), 0.79 (t, J = 7.0 Hz, 3H).
LCMS Calculated for $C_{37}H_{42}N_8O_4$: 662.33; Observed (Method-K): 663.6 [M + H]$^+$, 99.05% at RT 0.710 min.

I-239

-continued

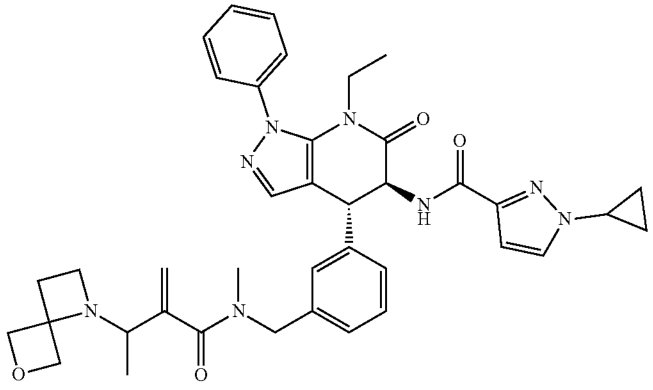

$^1$H NMR (300 MHz, DMSO-$d_6$) δ 8.98 (q, J = 5.5 Hz, 1H), 8.25 (d, J = 9.3 Hz, 1H), 7.79 (d, J = 2.4 Hz, 1H), 7.65-7.45 (m, 5H), 7.34-7.19 (m, 3H), 7.18-7.10 (m, 1H), 6.89 (s, 1H), 6.51 (d, J = 2.4 Hz, 1H), 5.85 (s, 1H), 5.52 (s, 1H), 5.10 (dd, J = 12.8, 9.3 Hz, 1H), 4.82 (d, J = 7.3 Hz, 1H), 4.72 (d, J = 7.2 Hz, 1H), 4.58-4.32 (m, 5H), 3.89-3.69 (m, 2H), 3.64 (q, J = 6.4 Hz, 1H), 3.08-2.76 (m, 3H), 2.22-2.03 (m, 2H), 1.16 (d, J = 6.4 Hz, 3H), 1.10-1.02 (m, 2H), 1.01-0.93 (m, 2H), 0.79 (t, J = 7.0 Hz, 3H).
LCMS Calculated for $C_{38}H_{42}N_8O_4$: 674.33; Observed (Method-AF): 675.70 $[M + H]^+$, 95.80% at RT 2.508 min.

I-325

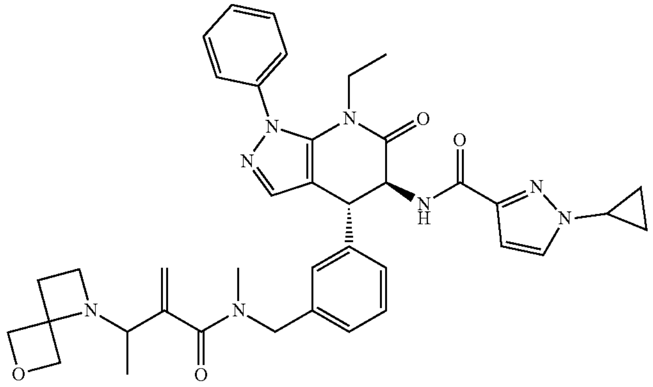

$^1$H NMR (300 MHz, DMSO-$d_6$) δ 8.25 (d, J = 9.4 Hz, 1H), 7.78 (d, J = 2.4 Hz, 1H), 7.66-7.44 (m, 5H), 7.31-7.25 (m, 2H), 7.24-7.18 (m, 1H), 7.19-7.08 (m, 1H), 7.02-6.86 (m, 1H), 6.47 (d, J = 2.4 Hz, 1H), 5.48-5.39 (m, 1H), 5.19-5.03 (m, 2H), 4.89 (d, J = 7.1 Hz, 1H), 4.73 (d, J = 7.0 Hz, 1H), 4.57-4.39 (m, 5H), 3.89-3.67 (m, 2H), 3.46 (t, J = 6.1 Hz, 1H), 3.06-3.00 (m, 2H), 2.85-2.60 (m, 4H), 2.28-2.10 (m, 2H), 1.19 (d, J = 6.4 Hz, 3H), 1.08-1.03 (m, 2H), 0.97 (d, J = 6.7, 2.9 Hz, 2H), 0.79 (t, J = 7.0 Hz, 3H).
LCMS Calculated for $C_{39}H_{44}N_8O_4$: 688.35; Observed (Method-AG): 689.50 $[M + H]^+$, 97.54% at RT 2.314 min.

I-343

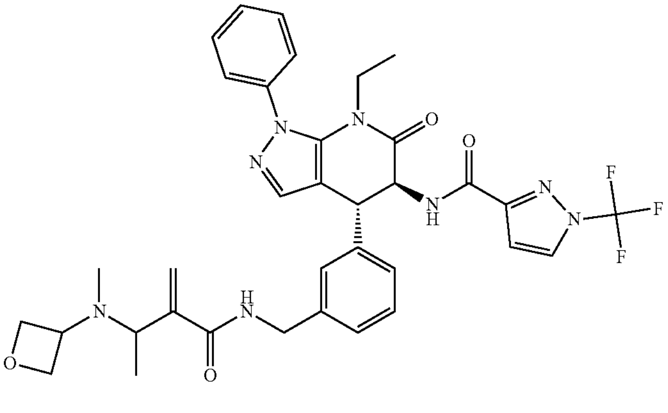 [SMILES: C=C(C(=O)NCc1cccc([C@@H]2c3cnn(-c4ccccc4)c3N(CC)C(=O)[C@H]2NC(=O)c2ccn(C(F)(F)F)n2)c1)C(C)N(C)C1COC1]

$^1$H NMR (300 MHz, DMSO-$d_6$) δ 8.83 (t, J = 6.0 Hz, 1H), 8.73 (d, J = 9.2 Hz, 1H), 8.55 (d, J = 2.9 Hz, 1H), 7.64-7.59 (m, 2H), 7.59-7.47 (m, 3H), 7.32-7.25 (m, 2H), 7.25-7.21 (m, 1H), 7.21-7.16 (m, 1H), 6.98-6.79 (m, 2H), 5.79 (d, J = 1.7 Hz, 1H), 5.42 (d, J = 1.7 Hz, 1H), 5.15 (dd, J = 12.9, 9.2 Hz, 1H), 4.52 (d, J = 12.9 Hz, 1H), 4.45-4.38 (m, 2H), 4.34-4.29 (m, 4H), 3.82 (dq, J = 14.1, 7.0 Hz, 1H), 3.51-3.40 (m, 1H), 3.08-2.96 (m, 3H), 1.96 (s, 3H), 0.79 (t, J = 7.0 Hz, 3H).
LCMS Calculated for $C_{34}H_{35}F_3N_8O_4$: 676.27; Observed (Method-Y): 677.2 $[M + H]^+$, 90.15% at RT 1.765 min.

I-378

-continued

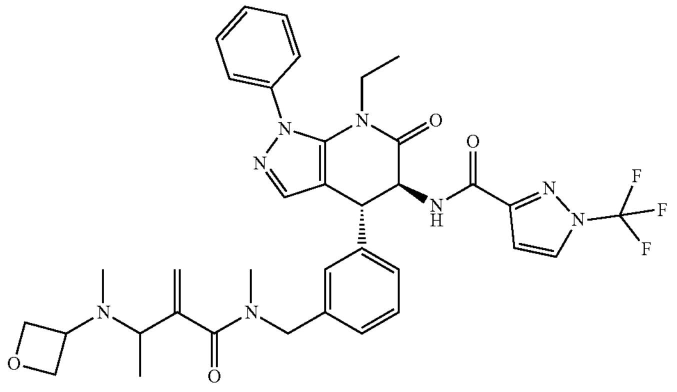 [SMILES: C=C(C(=O)N(C)Cc1cccc([C@@H]2c3cnn(-c4ccccc4)c3N(CC)C(=O)[C@H]2NC(=O)c2ccn(C(F)(F)F)n2)c1)C(C)N(C)C1COC1]

I-316

$^1$H NMR (300 MHz, DMSO-$d_6$) δ 8.52 (d, J = 9.2 Hz, 1H), 8.46 (d, J = 2.8 Hz, 1H), 7.68-7.49 (m, 5H), 7.39-7.28 (m, 3H), 7.26-7.19 (m, 1H), 7.00 (s, 1H), 6.86 (d, J = 2.8 Hz, 1H), 5.46 (s, 1H), 5.30 (s, 1H), 5.15 (dd, J = 12.7, 9.2 Hz, 1H), 4.62-4.48 (m, 5H), 4.52-4.42 (m, 2H), 3.94-3.74 (m, 3H), 3.17-3.01 (m, 2H), 2.80 (s, 3H), 2.22 (s, 3H), 0.86 (t, J = 7.0 Hz, 3H).
LCMS Calculated for $C_{35}H_{37}F_3N_8O_4$: 690.29; Observed (Method-AC): 691.40 $[M + H]^+$, 97.98% at RT 1.603 min.

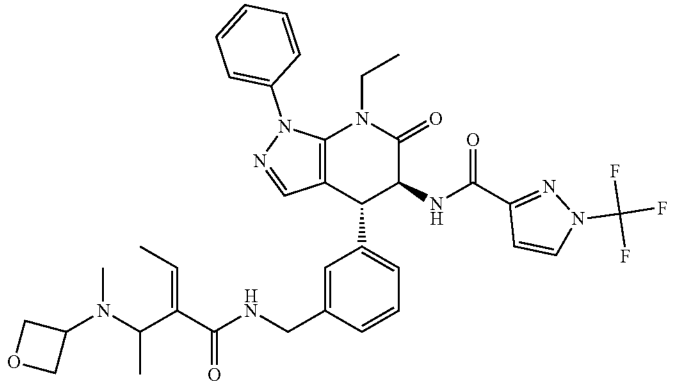 [SMILES: C/C=C(/C(=O)NCc1cccc([C@@H]2c3cnn(-c4ccccc4)c3N(CC)C(=O)[C@H]2NC(=O)c2ccn(C(F)(F)F)n2)c1)C(C)N(C)C1COC1]

I-248

$^1$H NMR (300 MHz, DMSO-$d_6$) δ 8.85-8.69 (m, 2H), 8.55 (d, J = 2.8 Hz, 1H), 7.64-7.43 (m, 5H), 7.35-7.14 (m, 4H), 6.95-6.86 (m, 2H), 6.52 (q, J = 7.0 Hz, 1H), 5.15 (dd, J = 12.9, 9.2 Hz, 1H), 4.52 (d, J = 12.9 Hz, 1H), 4.47-4.25 (m, 6H), 3.91-3.73 (m, 1H), 3.56-3.42 (m, 1H), 3.06-2.85 (m, 3H), 1.94 (s, 3H), 1.73 (d, J = 7.1 Hz, 3H), 0.79 (t, J = 7.0 Hz, 3H).
LCMS Calculated for $C_{35}H_{37}F_3N_8O_4$: 690.29; Observed (Method-AC): 691.40 $[M + H]^+$, 98.14% at RT 1.632 min.

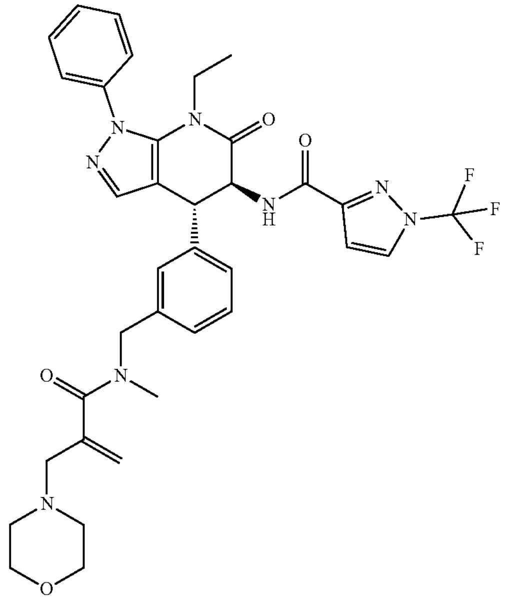 [SMILES: C=C(CN1CCOCC1)C(=O)N(C)Cc1cccc([C@@H]2c3cnn(-c4ccccc4)c3N(CC)C(=O)[C@H]2NC(=O)c2ccn(C(F)(F)F)n2)c1]

I-295

$^1$H NMR (400 MHz, DMSO-$d_6$) δ 8.77 (d, J = 9.3 Hz, 1H), 8.57 (d, J = 2.8 Hz, 1H), 7.65 (d, J = 7.1 Hz, 2H), 7.61-7.49 (m, 3H), 7.36-7.15 (m, 4H), 6.99 (s, 1H), 6.91-6.86 (m, 1H), 5.47-5.08 (m, 3H), 4.60-4.49 (m, 3H), 3.87 (dq, J = 14.2, 7.0 Hz, 1H), 3.58-3.42 (m, 4H), 3.18-2.96 (m, 3H), 2.80 (s, 2H), 2.66 (s, 1H), 2.37-2.33 (m, 4H), 0.82 (t, J = 7.0 Hz, 3H).
LCMS Calculated for $C_{35}H_{37}F_3N_8O_4$: 690.29; Observed (Method-AC): 691.40 $[M + H]^+$, 99.42% at RT 1.608 min.

-continued

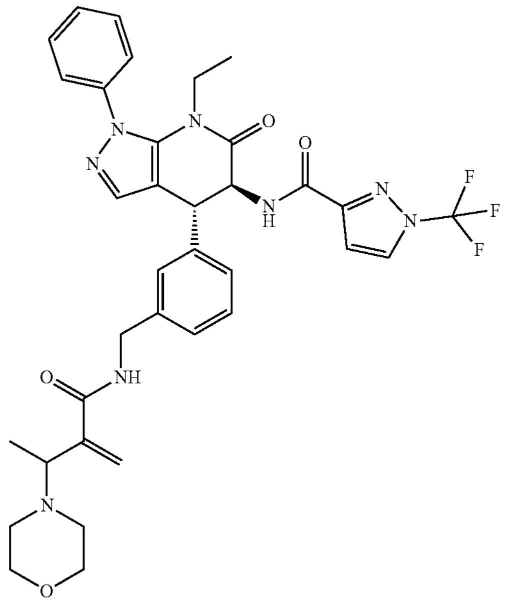 [SMILES: C=C(C(=O)NCc1cccc([C@@H]2c3cnn(-c4ccccc4)c3N(CC)C(=O)[C@H]2NC(=O)c2ccn(C(F)(F)F)n2)c1)C(C)N1CCOCC1]

$^1$H NMR (300 MHz, DMSO-$d_6$) δ 9.20 (q, J = 5.3 Hz, 1H), 8.75 (d, J = 9.2 Hz, 1H), 8.55 (d, J = 2.8 Hz, 1H), 7.66-7.45 (m, 5H), 7.36-7.23 (m, 3H), 7.20 (d, J = 7.1 Hz, 1H), 6.89 (d, J = 1.8 Hz, 2H), 5.84 (s, 1H), 5.36 (s, 1H), 5.15 (ddd, J = 12.8, 9.2, 3.5 Hz, 1H), 4.53 (d, J = 12.9 Hz, 1H), 4.43-4.24 (m, 2H), 3.82 (dq, J = 14.2, 7.0 Hz, 1H), 3.39 (d, J = 3.7 Hz, 4H), 3.28 (d, J = 6.7 Hz, 1H), 3.00 (dt, J = 13.7, 6.9 Hz, 1H), 2.42-2.20 (m, 4H), 1.08 (dd, J = 6.7, 2.4 Hz, 3H), 0.79 (t, J = 7.0 Hz, 3H). LCMS Calculated for $C_{35}H_{37}F_3N_8O_4$: 690.29; Observed (Method-AC): 691.40 [M + H]$^+$, 97.91% at RT 1.693 min.

I-296

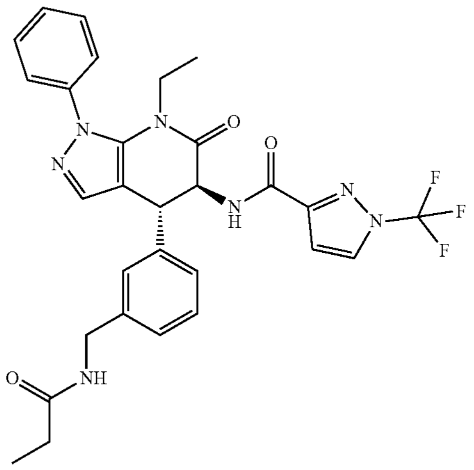 [SMILES: CCC(=O)NCc1cccc([C@@H]2c3cnn(-c4ccccc4)c3N(CC)C(=O)[C@H]2NC(=O)c2ccn(C(F)(F)F)n2)c1]

$^1$H NMR (400 MHz, DMSO-$d_6$) δ 8.76 (d, J = 9.2 Hz, 1H), 8.58 (d, J = 2.8 Hz, 1H), 8.22 (t, J = 5.9 Hz, 1H), 7.65 (d, J = 8.1 Hz, 2H), 7.61-7.49 (m, 3H), 7.33-7.21 (m, 3H), 7.14 (d, J = 7.3 Hz, 1H), 7.01-6.89 (m, 2H), 5.15 (dd, J = 12.8, 9.2 Hz, 1H), 4.54 (d, J = 12.8 Hz, 1H), 4.23 (d, J = 5.9 Hz, 2H), 3.84 (dq, J = 14.1, 7.0 Hz, 1H), 3.04 (dq, J = 13.7, 6.7 Hz, 1H), 2.12 (q, J = 7.6 Hz, 2H), 1.01 (dd, J = 8.2, 6.9 Hz, 3H), 0.82 (t, J = 7.0 Hz, 3H). LCMS Calculated for $C_{29}H_{28}F_3N_7O_3$: 579.22; Observed (Method-A): 580.3 [M + H]$^+$, 97.59% at RT 0.991 min.

I-335

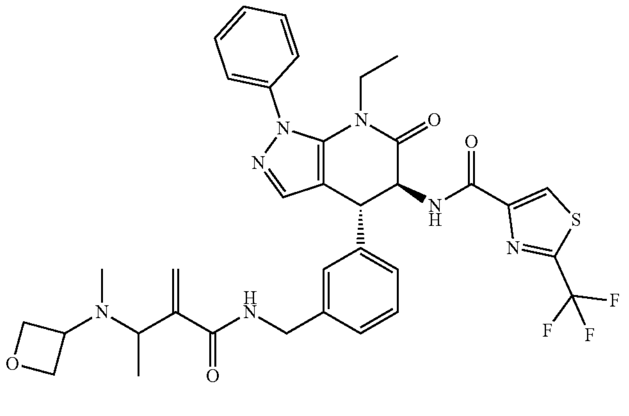 [SMILES: C=C(C(=O)NCc1cccc([C@@H]2c3cnn(-c4ccccc4)c3N(CC)C(=O)[C@H]2NC(=O)c2csc(C(F)(F)F)n2)c1)C(C)N(C)C1COC1]

$^1$H NMR (300 MHz, DMSO-$d_6$) δ 8.93-8.76 (m, 2H), 8.63 (s, 1H), 7.74-7.45 (m, 5H), 7.41-7.15 (m, 4H), 6.94 (s, 1H), 5.74 (d, J = 3.3 Hz, 1H), 5.31 (s, 1H), 5.27-5.09 (m, 1H), 4.61 (d, J = 12.8 Hz, 1H), 4.50-4.25 (m, 6H), 3.94-3.71 (m, 2H), 3.58 (d, J = 7.0 Hz, 1H), 3.12-2.91 (m, 1H), 1.99 (d, J = 3.0 Hz, 3H), 0.98 (d, J = 6.8 Hz, 3H), 0.82 (t, J = 7.0 Hz, 3H). LCMS Calculated for $C_{35}H_{36}F_3N_7O_4S$: 707.2; Observed (Method-AH): 708.4 [M + H]$^+$, 97.02% at RT 2.354 min.

I-305

-continued

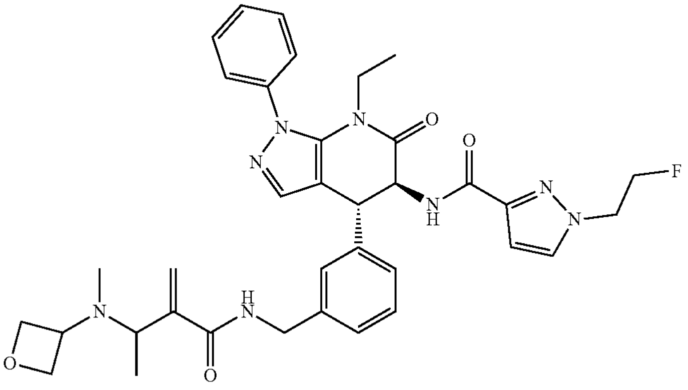 [SMILES: C=C(C(=O)NCc1cccc([C@@H]2c3cnn(-c4ccccc4)c3N(CC)C(=O)[C@H]2NC(=O)c2ccn(CCF)n2)c1)C(C)N(C)C1COC1]

$^1$H NMR (300 MHz, DMSO-$d_6$) δ 8.87 (s, 1H), 8.26 (d, J = 9.4 Hz, 1H), 7.82 (d, J = 2.4 Hz, 1H), 7.69-7.46 (m, 6H), 7.34-7.12 (m, 5H), 6.93 (s, 1H), 6.60 (d, J = 2.3 Hz, 1H), 5.74 (s, 1H), 5.31 (s, 1H), 5.19-5.11 (m, 1H), 4.87 (t, J = 4.8 Hz, 1H), 4.72 (t, J = 4.7 Hz, 1H), 4.58-4.50 (m, 2H), 4.48-4.22 (m, 8H), 3.87-3.74 (m, 2H), 3.59 (d, J = 7.1 Hz, 1H), 3.30 (s, 3H), 3.03 (d, J = 8.0 Hz, 1H), 2.00 (d, J = 2.8 Hz, 3H), 0.98 (d, J = 6.7 Hz, 3H), 0.81 (t, J = 7.0 Hz, 3H).
LCMS Calculated for $C_{36}H_{41}FN_8O_4$: 668.3; Observed (Method-V): 669.5 [M + H]$^+$, 99.01% at RT 1.499 min.

I-334

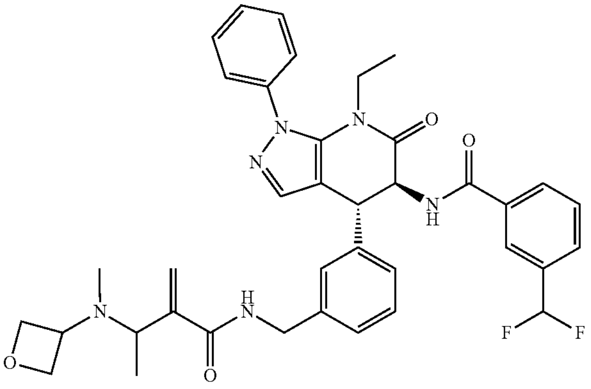 [SMILES: C=C(C(=O)NCc1cccc([C@@H]2c3cnn(-c4ccccc4)c3N(CC)C(=O)[C@H]2NC(=O)c2cccc(C(F)F)c2)c1)C(C)N(C)C1COC1]

$^1$H NMR (300 MHz, DMSO-$d_6$) δ 8.90 (t, J = 8.2 Hz, 2H), 8.00-7.84 (m, 2H), 7.73 (d, J = 7.7 Hz, 1H), 7.68-7.50 (m, 6H), 7.38-6.91 (m, 6H), 5.75 (d, J = 4.4 Hz, 1H), 5.31 (s, 1H), 5.26-5.10 (m, 1H), 4.50-4.22 (m, 7H), 3.91-3.70 (m, 2H), 3.57 (t, J = 5.6 Hz, 1H), 3.14-2.98 (m, 1H), 1.98 (s, 3H), 0.97 (d, J = 6.8 Hz, 3H), 0.82 (t, J = 7.0 Hz, 3H).
LCMS Calculated for $C_{38}H_{40}F_2N_6O_4$: 682.31; Observed (Method-AH): 683.31 [M + H]$^+$, 98.39% at RT 2.105 min.

I-277

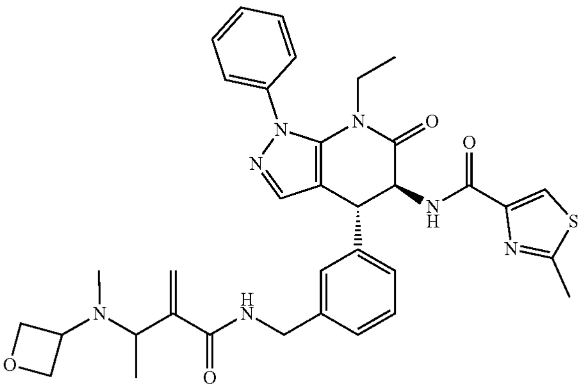 [SMILES: C=C(C(=O)NCc1cccc([C@@H]2c3cnn(-c4ccccc4)c3N(CC)C(=O)[C@H]2NC(=O)c2csc(C)n2)c1)C(C)N(C)C1COC1]

$^1$H NMR (400 MHz, DMSO-$d_6$) δ 8.87 (d, J = 5.7 Hz, 1H), 8.50 (d, J = 9.5 Hz, 1H), 8.03 (s, 1H), 7.70-7.45 (m, 5H), 7.33-7.14 (m, 4H), 6.92 (s, 1H), 5.75 (d, J = 4.7 Hz, 1H), 5.32 (s, 1H), 5.17 (t, J = 11.2 Hz, 1H), 4.59 (d, J = 12.8 Hz, 1H), 4.51-4.24 (m, 6H), 3.91-3.72 (m, 2H), 3.59 (d, J = 7.9 Hz, 1H), 3.08-2.98 (m, 1H), 2.70 (s, 3H), 2.00 (d, J = 3.9 Hz, 3H), 0.99 (d, J = 6.9, 1.6 Hz, 3H), 0.81 (t, J = 7.0 Hz, 3H).
LCMS Calculated for $C_{35}H_{39}N_7O_4S$: 653.28; Observed (Method-W): 654.40 [M + H]$^+$, 98.34% at RT 1.736 min.

I-278

-continued

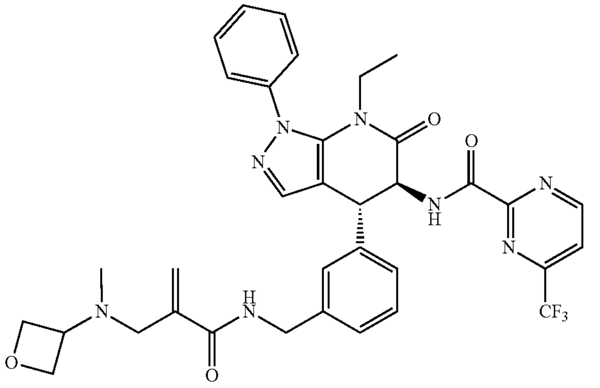 [SMILES: C=C(CN(C)C1COC1)C(=O)NCc1cccc([C@@H]2c3cnn(-c4ccccc4)c3N(CC)C(=O)[C@H]2NC(=O)c2nccc(C(F)(F)F)n2)c1]

I-254

$^1$H NMR (300 MHz, DMSO-$d_6$) δ 9.35-9.23 (m, 2H), 8.21 (d, J = 5.1 Hz, 1H), 7.72-7.48 (m, 5H), 7.38-7.17 (m, 4H), 7.01 (s, 1H), 5.45-5.07 (m, 3H), 4.73-4.39 (m, 5H), 4.34 (t, J = 6.0 Hz, 2H), 3.87 (dd, J = 14.4, 7.2 Hz, 1H), 3.51 (t, J = 6.3 Hz, 1H), 3.16-2.90 (m, 3H), 2.79 (s, 2H), 2.60 (s, 1H), 2.00 (d, J = 19.5 Hz, 3H), 0.82 (t, J = 6.9 Hz, 3H). LCMS Calculated for $C_{36}H_{37}F_3N_8O_4$: 702.3; Observed (Method-V): 703.4 $[M + H]^+$, 91.65% at RT 1.580 min.

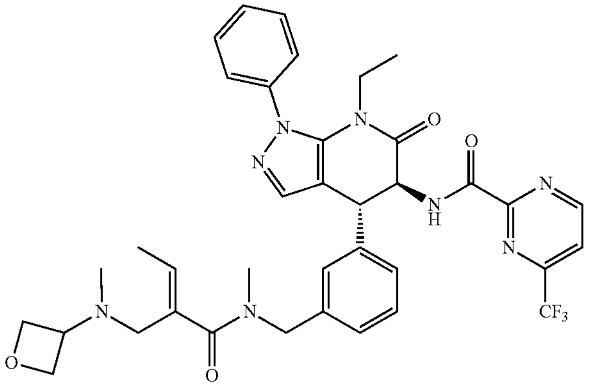 [SMILES: C/C=C(\CN(C)C1COC1)C(=O)N(C)Cc1cccc([C@@H]2c3cnn(-c4ccccc4)c3N(CC)C(=O)[C@H]2NC(=O)c2nccc(C(F)(F)F)n2)c1]

I-322

$^1$H NMR (300 MHz, DMSO-$d_6$) δ 9.33-9.22 (m, 2H), 8.78 (d, J = 6.3 Hz, 1H), 8.19 (d, J = 5.1 Hz, 1H), 7.62 (d, J = 7.6 Hz, 2H), 7.62-7.47 (m, 3H), 7.33-7.22 (m, 3H), 7.19-7.15 (m, 1H), 6.95-6.94 (m, 1H), 6.50-6.45 (m, 1H), 5.20 (dd, J = 12.7, 9.2 Hz, 1H), 4.62 (d, J = 12.7 Hz, 1H), 4.45-4.30 (m, 1H), 3.83 (dd, J = 14.2, 7.2 Hz, 1H), 3.48 (t, J = 6.5 Hz, 1H), 3.04-3.00 (m, 3H), 1.94 (s, 3H), 1.72 (d, J = 7.1 Hz, 3H), 0.80 (t, J = 7.0 Hz, 3H). LCMS Calculated for $C_{36}H_{37}F_3N_8O_4$: 702.29; Observed (Method-C): 703.1 $[M + H]^+$, 99.36% at RT 0.822 min.

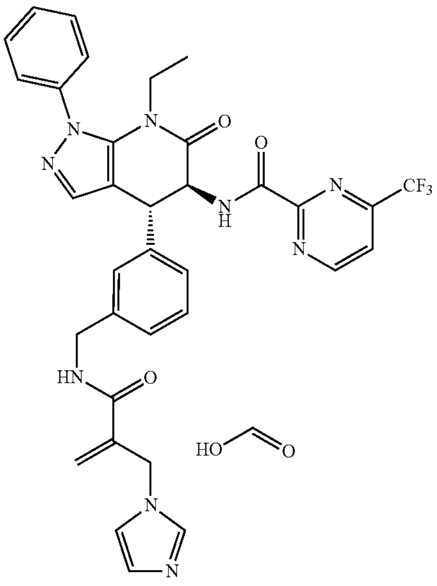 [SMILES: C=C(Cn1ccnc1)C(=O)NCc1cccc([C@@H]2c3cnn(-c4ccccc4)c3N(CC)C(=O)[C@H]2NC(=O)c2nccc(C(F)(F)F)n2)c1 ; O=CO]

I-311

$^1$H NMR (400 MHz, DMSO-$d_6$) δ 9.34 (dd, J = 16.3, 7.2 Hz, 2H), 8.73 (t, J = 6.0 Hz, 1H), 8.33 (s, 1H), 8.20 (s, 1H), 7.66 (d, J = 7.7 Hz, 2H), 7.62-7.49 (m, 4H), 7.29-7.18 (m, 3H), 7.11-7.01 (m, 2H), 6.98 (s, 1H), 6.87 (s, 1H), 5.85 (s, 1H), 5.30-5.17 (m, 2H), 4.84 (s, 2H), 4.61 (d, J = 12.7 Hz, 1H), 4.30 (d, J = 5.9 Hz, 2H), 3.85 (dq, J = 14.3, 7.1 Hz, 1H), 3.06 (dq, J = 13.9, 6.8 Hz, 1H), 0.84 (t, J = 7.0 Hz, 3H). LCMS Calculated for $C_{34}H_{30}F_3N_9O_3$: 669.24; Observed (Method-AI): 670.1 $[M + H]^+$, 99.61% at RT 1.499 min.

-continued

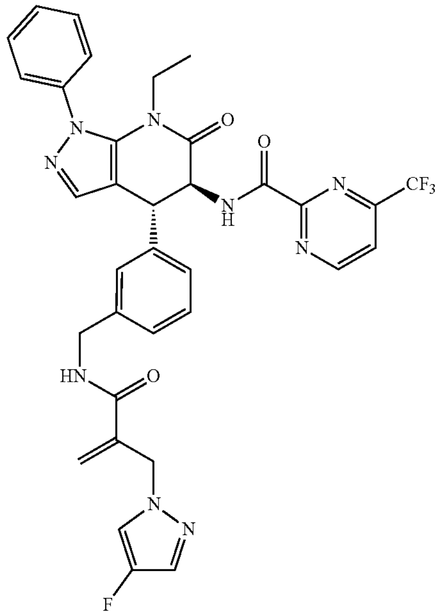 [SMILES: C=C(Cn1cc(F)cn1)C(=O)NCc1cccc([C@@H]2c3cnn(-c4ccccc4)c3N(CC)C(=O)[C@H]2NC(=O)c2nccc(C(F)(F)F)n2)c1]

I-331

$^1$H NMR (300 MHz, DMSO-$d_6$) δ 9.35-9.28 (m, 2H), 8.70 (t, J = 5.8 Hz, 1H), 8.22 (d, J = 5.0 Hz, 1H), 7.83 (d, J = 4.6 Hz, 1H), 7.66 (d, J = 7.7 Hz, 2H), 7.56 (dt, J = 22.2, 7.3 Hz, 3H), 7.48 (d, J = 4.2 Hz, 1H), 7.30-7.23 (m, 3H), 7.07 (s, 1H), 6.98 (s, 1H), 5.84 (s, 1H), 5.21 (dd, J = 12.7, 9.3 Hz, 1H), 5.15 (s, 1H), 4.88 (s, 2H), 4.64 (d, J = 12.7 Hz, 1H), 4.30 (d, J = 6.0 Hz, 2H), 3.85 (dd, J = 14.4, 7.4 Hz, 1H), 3.04 (dt, J = 14.5, 7.0 Hz, 1H), 0.83 (t, J = 7.0 Hz, 3H).
LCMS Calculated for $C_{34}H_{29}F_4N_9O_3$: 687.23; Observed (Method-B): 688.1 $[M + H]^+$, 99.79% at RT 1.104 min.

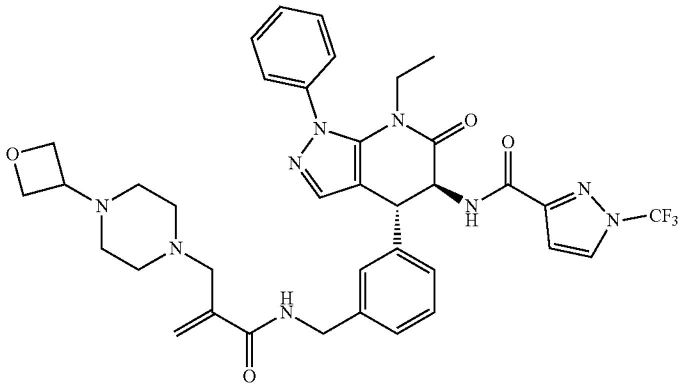 [SMILES: C=C(CN1CCN(C2COC2)CC1)C(=O)NCc1cccc([C@@H]2c3cnn(-c4ccccc4)c3N(CC)C(=O)[C@H]2NC(=O)c2ccn(C(F)(F)F)n2)c1]

I-356

$^1$H NMR (300 MHz, DMSO-d6) δ 9.08 (t, J = 5.7 Hz, 1H), 8.76 (d, J = 9.2 Hz, 1H), 8.59 (d, J = 2.8 Hz, 1H), 7.67-7.49 (m, 5H), 7.38-7.24 (m, 3H), 7.21 (d, J = 7.1 Hz, 1H), 6.95-6.88 (m, 2H), 5.91 (d, J = 2.1 Hz, 1H), 5.44 (s, 1H), 5.18 (dd, J = 12.8, 9.2 Hz, 1H), 4.55 (d, J = 12.9 Hz, 1H), 4.45-4.39 (m, 2H), 4.38-4.27 (m, 4H), 3.91-3.76 (m, 1H), 3.28-3.21 (m, 1H), 3.19 (s, 2H), 3.12-2.95 (m, 1H), 2.45-2.27 (m, 4H), 2.15-2.09 (m, 4H), 0.82 (t, J = 7.0 Hz, 3H).
LCMS Calculated for $C_{37}H_{40}F_3N_9O_4$: 731.32; Observed (Method-V): 732.40 $[M + H]^+$, 98.84% at RT 1.430 min.

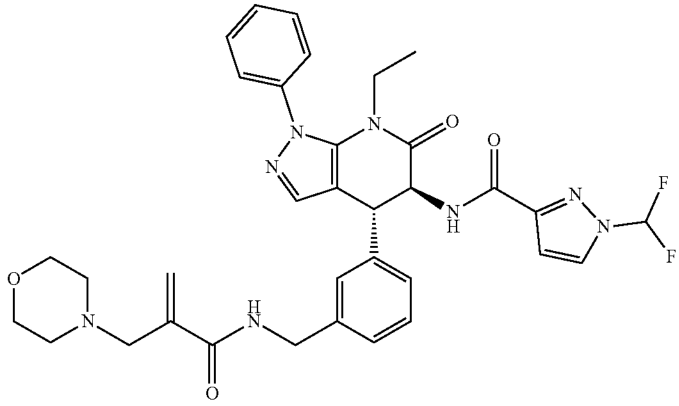 [SMILES: C=C(CN1CCOCC1)C(=O)NCc1cccc([C@@H]2c3cnn(-c4ccccc4)c3N(CC)C(=O)[C@H]2NC(=O)c2ccn(C(F)F)n2)c1]

I-308

$^1$H NMR (400 MHz, DMSO-$d_6$) δ 8.97 (t, J = 5.8 Hz, 1H), 8.63 (d, J = 9.2 Hz, 1H), 8.30 (d, J = 2.7 Hz, 1H), 8.02-7.80 (m, 1H), 7.66-7.62 (m, 2H), 7.61-7.50 (m, 3H), 7.36-7.28 (m, 2H), 7.28-7.23 (m, 1H), 7.23-7.18 (m, 1H), 6.92 (s, 1H), 6.80 (d, J = 2.7 Hz, 1H), 5.90 (d, 1H), 5.45 (d, 1H), 5.17 (dd, J = 12.9, 9.2 Hz, 1H), 4.55 (d, J = 12.8 Hz, 1H), 4.44-4.29 (m, 2H), 3.91-3.77 (m, 1H), 3.45 (t, J = 4.7 Hz, 4H), 3.17 (s, 2H), 3.10-2.98 (m, 1H), 2.31 (s, 4H), 0.81 (t, J = 7.0 Hz, 3H).
LCMS Calculated for $C_{34}H_{36}F_2N_8O_4$: 658.28; Observed (Method-V): 659.4 $[M + H]^+$, 99.86% at RT 1.526 min.

-continued

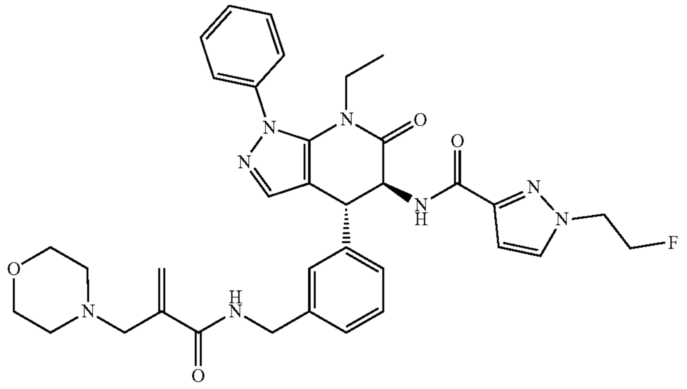 [SMILES: C=C(CN1CCOCC1)C(=O)NCc1cccc([C@@H]2c3cnn(-c4ccccc4)c3N(CC)C(=O)[C@H]2NC(=O)c2ccn(CCF)n2)c1]

$^1$H NMR (400 MHz, DMSO-$d_6$) δ 8.97 (t, J = 5.5 Hz, 1H), 8.28 (d, J = 9.4 Hz, 1H), 7.82 (d, J = 2.2 Hz, 1H), 7.66-7.50 (m, 5H), 7.34-7.23 (m, 3H), 7.20 (d, J = 7.4 Hz, 1H), 6.91 (s, 1H), 6.60 (d, J = 2.3 Hz, 1H), 5.90 (s, 1H), 5.45 (s, 1H), 5.21-5.11 (m, 1H), 4.86 (t, J = 4.9 Hz, 1H), 4.74 (t, J = 4.8 Hz, 1H), 4.58-4.49 (m, 2H), 4.45 (d, J = 4.9 Hz, 1H), 4.36 (t, J = 5.5 Hz, 2H), 3.87-3.78 (m, 1H), 3.48-3.42 (m, 4H), 3.18 (s, 2H), 3.09-2.99 (m, 1H), 2.34-2.30 (m, 4H), 0.81 (t, J = 7.0 Hz, 3H). LCMS Calculated for $C_{35}H_{39}FN_8O_4$: 654.31; Observed (Method-B): 655.2 [M + H]$^+$, 99.52% at RT 0.827 min.

I-357

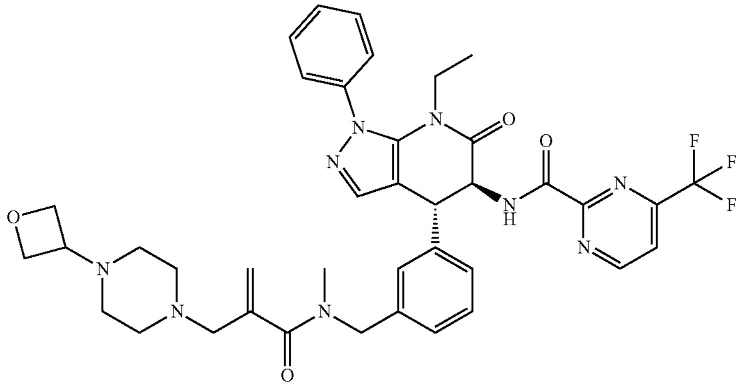

$^1$H NMR (300 MHz, DMSO-$d_6$) δ 9.32 (d, J = 5.2 Hz, 2H), 8.22 (d, J = 5.1 Hz, 1H), 7.72-7.50 (m 5H), 7.36-7.23 (m, 3H), 7.19-7.13 (m, 1H), 7.00 (s, 1H), 5.39-5.10 (m, 3H), 4.69-4.35 (m, 7H), 3.91-3.85 (m, 1H), 3.22-2.90 (m, 4H), 2.76 (s, 2H), 2.57 (s, 1H), 2.43-2.37 (m, 4H), 2.21-2.15 (m, 4H), 0.84 (t, J = 7.0 Hz, 3H). LCMS Calculated for $C_{39}H_{42}F_3N_9O_4$: 757.33; Observed (Method-V): 758.41 [M + H]$^+$, 96.96% at RT 1.488 min.

I-223

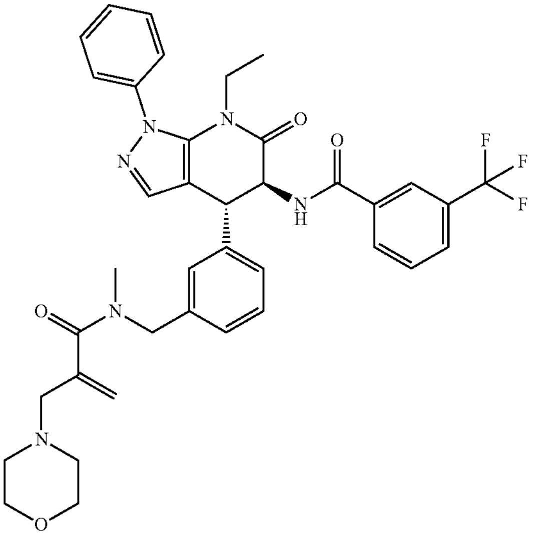 [SMILES: C=C(CN1CCOCC1)C(=O)N(C)Cc1cccc([C@@H]2c3cnn(-c4ccccc4)c3N(CC)C(=O)[C@H]2NC(=O)c2cccc(C(F)(F)F)c2)c1]

$^1$H NMR (400 MHz, DMSO-$d_6$) δ 9.02 (d, J = 9.0 Hz, 1H), 8.02 (d, J = 10.2 Hz, 2H), 7.90 (d, J = 7.8 Hz, 1H), 7.75-7.63 (m, 3H), 7.64-7.51 (m, 3H), 7.35-7.31 (m, 2H), 7.28 (s, 1H), 7.20-7.16 (m, 1H), 7.06 (s, 1H), 5.35 (s, 1H), 5.29-5.14 (m, 2H), 4.54 (s, 2H), 4.39 (d, J = 13.0 Hz, 1H), 3.92-3.82 (m, 1H), 3.50-3.45 (m, 4H), 3.15-2.94 (m, 3H), 2.75 (s, 2H), 2.64 (s, 1H), 2.31 (d, J = 25.5 Hz, 4H), 0.84 (t, J = 6.6 Hz, 3H). LCMS Calculated for $C_{38}H_{39}F_3N_6O_4$: 700.30; Observed (Method-B): 701.2 [M + H]$^+$, 97.88% at RT 0.980 min.

I-298

-continued

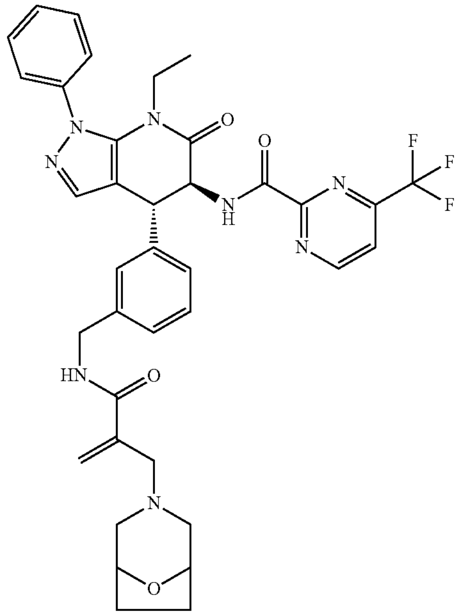 [SMILES: C=C(CN1CC2CCC(C1)O2)C(=O)NCc1cccc([C@@H]2c3cnn(-c4ccccc4)c3N(CC)C(=O)[C@H]2NC(=O)c2nccc(C(F)(F)F)n2)c1]

I-292

$^1$H NMR (400 MHz, DMSO-$d_6$) δ 9.36-9.27 (m, 2H), 8.96 (t, J = 6.0 Hz, 1H), 8.22 (d, J = 5.1 Hz, 1H), 7.69-7.63 (m, 2H), 7.63-7.50 (m, 3H), 7.36-7.28 (m, 3H), 7.24-7.18 (m, 1H), 6.94 (s, 1H), 5.91 (s, 1H), 5.43 (s, 1H), 5.27-5.17 (m, 1H), 4.65 (d, J = 12.6 Hz, 1H), 4.35 (t, J = 5.7 Hz, 2H), 4.06 (s, 2H), 3.89-3.79 (m, 1H), 3.11 (s, 2H), 3.09-3.01 (m, 1H), 2.44 (d, J = 12.2 Hz, 2H), 2.08 (d, J = 10.9 Hz, 2H), 1.49-1.33 (m, 4H), 0.83 (t, J = 7.0 Hz, 3H).
LCMS Calculated for $C_{37}H_{37}F_3N_8O_4$: 714.29; Observed (Method-C): 715.1 $[M + H]^+$, 99.31% at RT 0.857 min.

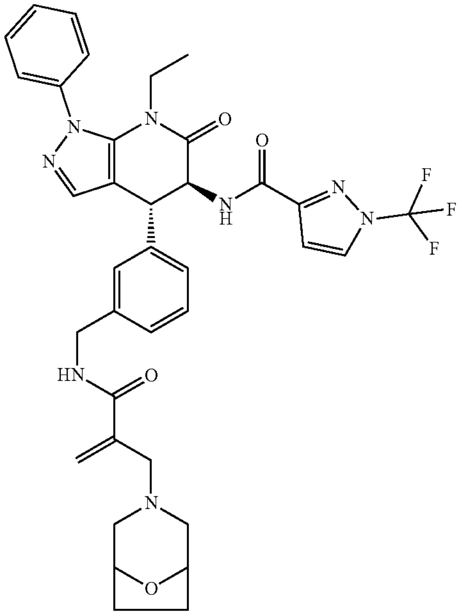 [SMILES: C=C(CN1CC2CCC(C1)O2)C(=O)NCc1cccc([C@@H]2c3cnn(-c4ccccc4)c3N(CC)C(=O)[C@H]2NC(=O)c2ccn(C(F)(F)F)n2)c1]

I-347

$^1$H NMR (400 MHz, DMSO-$d_6$) δ 8.97 (t, J = 5.8 Hz, 1H), 8.75 (d, J = 9.2 Hz, 1H), 8.58 (d, J = 2.8 Hz, 1H), 7.64 (d, J = 7.2 Hz, 2H), 7.61-7.49 (m, 3H), 7.31 (dd, J = 9.8, 2.7 Hz, 3H), 7.23 (t, J = 4.2 Hz, 1H), 7.01-6.80 (m, 2H), 5.93 (d, J = 2.2 Hz, 1H), 5.44 (s, 1H), 5.18 (dd, J = 12.8, 9.2 Hz, 1H), 4.55 (d, J = 12.8 Hz, 1H), 4.37 (d, J = 5.6 Hz, 2H), 4.06 (d, J = 4.5 Hz, 2H), 3.84 (dq, J = 14.3, 7.0 Hz, 1H), 3.11 (s, 2H), 3.04 (dd, J = 14.1, 7.1 Hz, 1H), 2.46 (t, J = 10.4 Hz, 2H), 2.09 (dd, J = 11.2, 2.4 Hz, 2H), 1.47 (dd, J = 7.9, 4.2 Hz, 2H), 1.37 (q, J = 7.3, 6.1 Hz, 2H), 0.82 (t, J = 7.0 Hz, 3H).
LCMS Calculated for $C_{36}H_{37}F_3N_8O_4$: 702.29; Observed (Method-X): 703.3 $[M + H]^+$, 99.58% at RT 1.595 min.

-continued

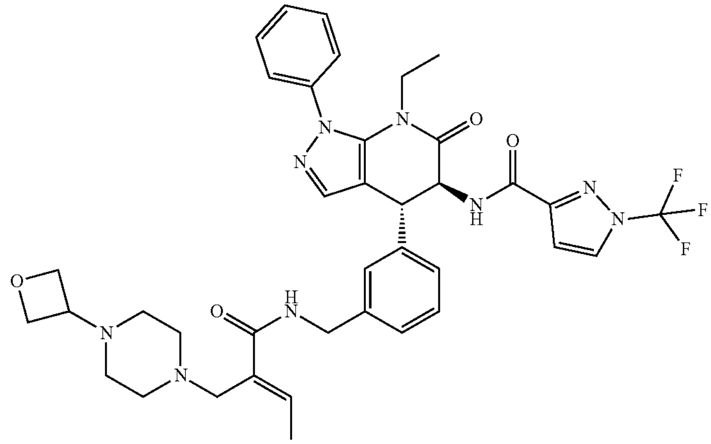 [SMILES: C/C=C(\CN1CCN(C2COC2)CC1)C(=O)NCc1cccc([C@@H]2c3cnn(-c4ccccc4)c3N(CC)C(=O)[C@H]2NC(=O)c2ccn(C(F)(F)F)n2)c1]

$^1$H NMR (300 MHz, DMSO-$d_6$) δ 9.04 (t, J = 5.7 Hz, 1H), 8.76 (d, J = 9.2 Hz, 1H), 8.59 (d, J = 2.8 Hz, 1H), 7.67-7.51 (m, 5H), 7.33-7.25 (m, 3H), 7.20 (d, J = 7.1 Hz, 1H), 6.91 (d, J = 4.1 Hz, 2H), 6.70-6.61 (m, 1H), 5.17 (dd, J = 12.9, 9.2 Hz, 1H), 4.54 (d, J = 12.9 Hz, 1H), 4.46-4.28 (m, 6H), 3.85 (dd, J = 14.2, 7.2 Hz, 1H), 3.26-3.17 (m, 3H), 3.04 (dd, J = 14.1, 7.0 Hz, 1H), 2.45-1.96 (m, 8H), 1.75 (d, J = 7.1 Hz, 3H), 0.82 (t, J = 7.0 Hz, 3H). LCMS Calculated for $C_{38}H_{42}F_3N_9O_4$: 745.81; Observed (Method-C): 746.81 $[M + H]^+$, 91.96% at RT 0.829 min.

I-230A

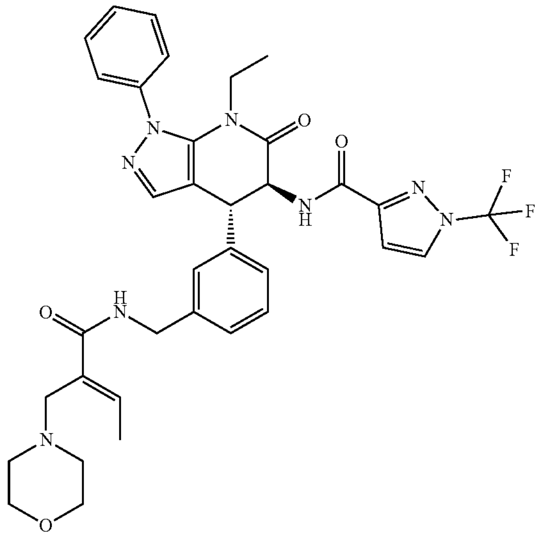 [SMILES: C/C=C(\CN1CCOCC1)C(=O)NCc1cccc([C@@H]2c3cnn(-c4ccccc4)c3N(CC)C(=O)[C@H]2NC(=O)c2ccn(C(F)(F)F)n2)c1]

$^1$H NMR (400 MHz, DMSO-$d_6$) δ 8.93 (t, J = 5.8 Hz, 1H), 8.77 (d, J = 9.2 Hz, 1H), 8.58 (d, J = 2.8 Hz, 1H), 7.64 (d, J = 8.6 Hz, 2H), 7.61-7.55 (m, 2H), 7.55-7.49 (m, 1H), 7.37-7.23 (m, 3H), 7.20 (d, J = 7.4 Hz, 1H), 6.92 (d, J = 3.3 Hz, 2H), 6.65 (q, J = 7.1 Hz, 1H), 5.17 (dd, J = 12.9, 9.1 Hz, 1H), 4.55 (d, J = 12.9 Hz, 1H), 4.41-4.25 (m, 2H), 3.85 (dq, J = 14.0, 7.0 Hz, 1H), 3.43 (d, J = 4.6 Hz, 4H), 3.18 (s, 2H), 3.11-2.91 (m, 1H), 2.33 (s, 4H), 1.76 (d, J = 7.1 Hz, 3H), 0.82 (t, J = 6.9 Hz, 3H). LCMS Calculated for $C_{35}H_{37}F_3N_8O_4$: 690.29; Observed (Method-AB): 691.5 $[M + H]^+$, 93.49% at RT 1.470 min.

I-284

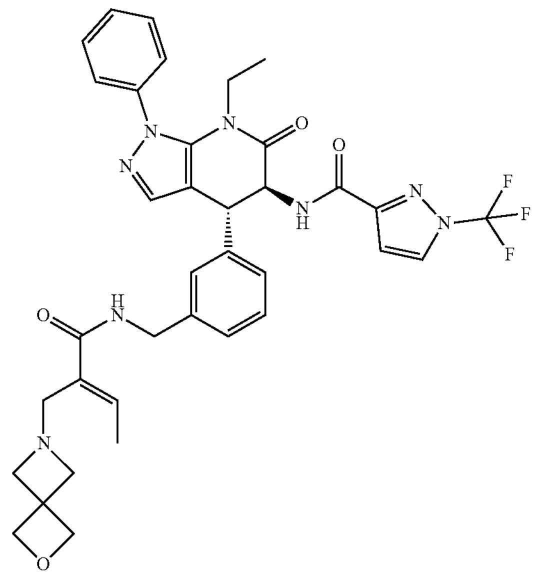 [SMILES: C/C=C(\CN1CC2(COC2)C1)C(=O)NCc1cccc([C@@H]2c3cnn(-c4ccccc4)c3N(CC)C(=O)[C@H]2NC(=O)c2ccn(C(F)(F)F)n2)c1]

$^1$H NMR (300 MHz, DMSO-$d_6$) δ 8.85-8.78 (m, 1H), 8.75 (d, J = 9.2 Hz, 1H), 8.56 (d, J = 2.8 Hz, 1H), 7.65-7.47 (m, 5H), 7.32-7.20 (m, 3H), 7.13 (d, J = 7.3 Hz, 1H), 6.92-6.87 (m, 2H), 6.57-6.45 (m, 1H), 5.19-5.08 (m, 1H), 4.59-4.42 (m, 4H), 4.31 (t, J = 5.5 Hz, 1H), 3.83 (dd, J = 14.2, 7.3 Hz, 1H), 3.23-3.11 (m, 4H), 3.01 (dd, J = 14.2, 7.1 Hz, 1H), 1.75 (d, J = 7.1 Hz, 3H), 1.37-1.07 (m, 4H), 0.90-0.73 (m, 3H). LCMS Calculated for $C_{36}H_{37}F_3N_8O_4$: 702.74; Observed (Method-AJ): 703.75 $[M + H]^+$, 97.88% at RT 1.623 min.

-continued

I-302

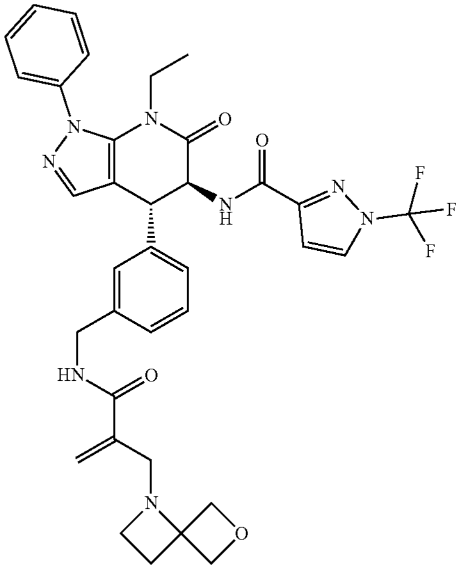 [SMILES: C=C(CN1CCC12COC2)C(=O)NCc1cccc([C@@H]2c3cnn(-c4ccccc4)c3N(CC)C(=O)[C@H]2NC(=O)c2ccn(C(F)(F)F)n2)c1]

$^1H$ NMR (400 MHz, DMSO-$d_6$) δ 8.84-8.67 (m, 2H), 8.58 (d, J = 2.8 Hz, 1H), 7.71-7.46 (m, 5H), 7.30 (d, J = 7.3 Hz, 2H), 7.25 (d, J = 7.7 Hz, 1H), 7.18 (d, J = 7.4 Hz, 1H), 7.05-6.79 (m, 2H), 5.80 (s, 1H), 5.48 (s, 1H), 5.17 (dd, J = 12.8, 9.2 Hz, 1H), 4.78 (dd, J = 7.3, 4.1 Hz, 2H), 4.55 (d, J = 12.8 Hz, 1H), 4.42 (d, J = 7.3 Hz, 2H), 4.36 (d, J = 6.0 Hz, 2H), 3.85 (dq, J = 14.1, 6.9 Hz, 1H), 3.48 (s, 2H), 3.03 (dq, J = 14.1, 6.9 Hz, 1H), 2.94 (t, J = 6.8 Hz, 2H), 2.23 (t, J = 6.9 Hz, 2H), 0.82 (t, J = 7.0 Hz, 3H).
LCMS Calculated for $C_{35}H_{35}F_3N_8O_4$: 688.27; Observed (Method-K): 689.4 $[M + H]^+$, 97.99% at RT 0.706 min.

I-247

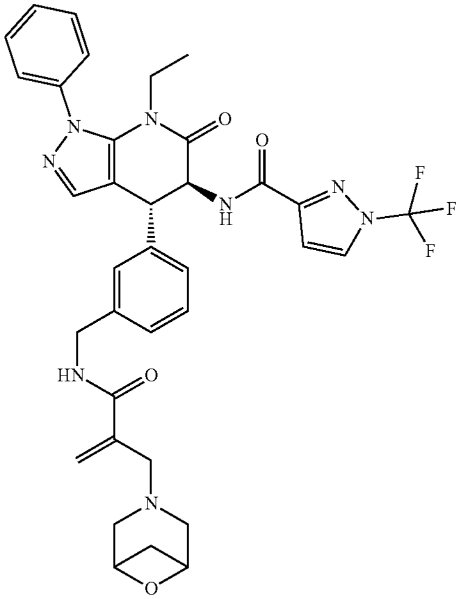 [SMILES: C=C(CN1CC2CC(C1)O2)C(=O)NCc1cccc([C@@H]2c3cnn(-c4ccccc4)c3N(CC)C(=O)[C@H]2NC(=O)c2ccn(C(F)(F)F)n2)c1]

$^1H$ NMR (400 MHz, DMSO-$d_6$) δ 8.93 (t, J = 5.8 Hz, 1H), 8.76 (d, J = 9.2 Hz, 1H), 8.59 (d, J = 2.8 Hz, 1H), 7.64 (d, J = 8.5 Hz, 2H), 7.56 (dt, J = 22.2, 7.3 Hz, 3H), 7.26 (dd, J = 9.2, 6.8 Hz, 3H), 7.16 (d, J = 7.0 Hz, 1H), 7.01-6.81 (m, 2H), 5.91 (d, J = 2.1 Hz, 1H), 5.53 (s, 1H), 5.16 (dd, J = 12.8, 9.2 Hz, 1H), 4.53 (d, J = 12.9 Hz, 1H), 4.39-4.27 (m, 4H), 3.84 (dq, J = 14.2, 6.9 Hz, 1H), 3.41 (s, 2H), 3.03 (dq, J = 14.1, 6.9 Hz, 1H), 2.94 (d, J = 11.4 Hz, 2H), 2.66 (q, J = 6.7 Hz, 1H), 2.56 (d, J = 11.4 Hz, 2H), 1.82 (d, J = 8.0 Hz, 1H), 0.82 (t, J = 7.0 Hz, 3H).
LCMS Calculated for $C_{35}H_{35}F_3N_8O_4$: 688.27; Observed (Method-AK): 689.5 $[M + H]^+$, 96.17% at RT 2.282 min.

I-315

-continued

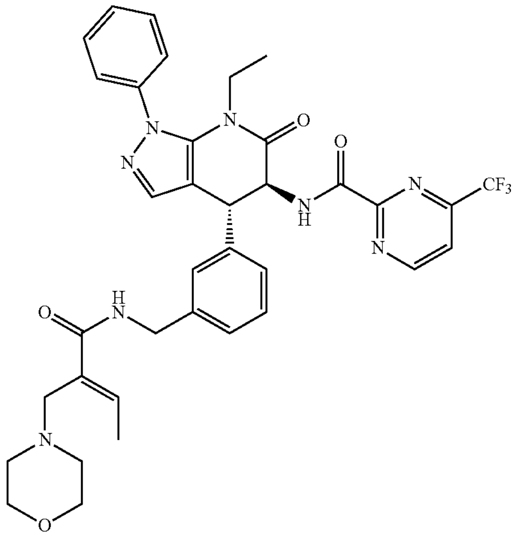 [SMILES: C/C=C(\CN1CCOCC1)C(=O)NCc1cccc([C@@H]2c3cnn(-c4ccccc4)c3N(CC)C(=O)[C@H]2NC(=O)c2nccc(C(F)(F)F)n2)c1]

$^1$H NMR (300 MHz, DMSO-$d_6$) δ 9.38-9.23 (m, 2H), 8.98-8.89 (m, J = 6.4 Hz, 1H), 8.22 (d, J = 5.1 Hz, 1H), 7.69-7.47 (m, 5H), 7.29 (d, J = 4.8 Hz, 3H), 7.22-7.16 (m, J = 3.3 Hz, 1H), 6.95 (s, 1H), 6.63 (q, J = 6.9 Hz, 1H), 5.22 (dd, J = 12.7, 9.2 Hz, 1H), 4.65 (d, J = 12.8 Hz, 1H), 4.44-4.20 (m, 2H), 3.85 (dd, J = 14.2, 7.3 Hz, 1H), 3.41 (s, 4H), 3.17 (s, 2H), 3.05 (dd, J = 14.1, 7.0 Hz, 1H), 2.32 (s, 4H), 1.75 (d, J = 7.1 Hz, 3H), 1.36 (s, 0H), 1.24 (s, 0H), 0.83 (t, J = 7.0 Hz, 3H).
LCMS Calculated for $C_{36}H_{37}F_3N_8O_4$: 702.29; Observed (Method-V): 703.4 $[M + H]^+$, 96.85% at RT 1.648 min.

I-363

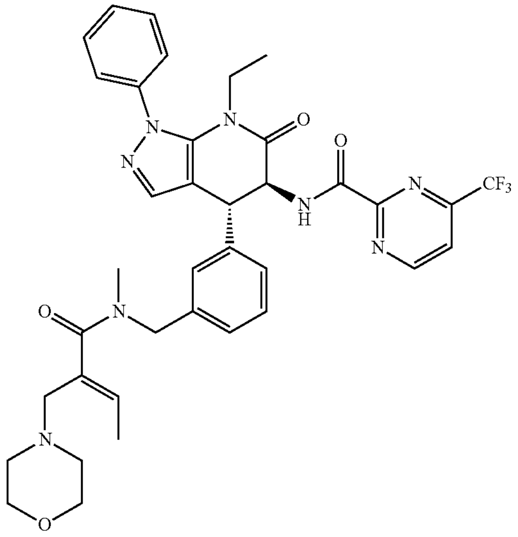 [SMILES: C/C=C(\CN1CCOCC1)C(=O)N(C)Cc1cccc([C@@H]2c3cnn(-c4ccccc4)c3N(CC)C(=O)[C@H]2NC(=O)c2nccc(C(F)(F)F)n2)c1]

$^1$H NMR (300 MHz, DMSO-$d_6$) δ 9.35-9.28 (m, J = 5.8 Hz, 2H), 8.24-8.18 (m, J = 5.1 Hz, 1H), 7.70-7.48 (m, J = 25.1, 8.7 Hz, 5H), 7.28 (d, J = 13.9 Hz, 3H), 7.18 (s, 1H), 7.03-6.96 (m, J = 6.9 Hz, 1H), 5.74 (d, J = 7.0 Hz, 1H), 5.40-4.94 (m, 1H), 4.63 (d, J = 12.8 Hz, 1H), 4.52 (s, 2H), 3.94-3.74 (m, 1H), 3.53-3.42 (m, 4H), 3.17-2.97 (m, 3H), 2.73 (s, 3H), 2.33 (s, 4H), 1.81-1.35 (m, 3H), 0.83 (t, J = 7.0 Hz, 3H).
LCMS Calculated for $C_{37}H_{39}F_3N_8O_4$: 716.30; Observed (Method-V): 717.4 $[M + H]^+$, 96.11% at RT 1.631 min.

I-242

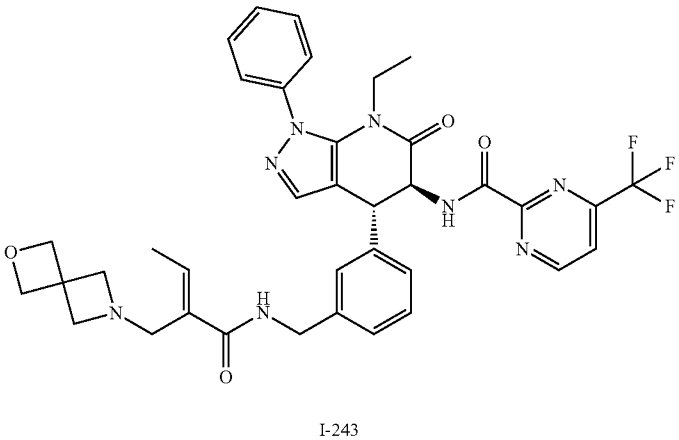

$^1$H NMR (300 MHz, DMSO-$d_6$) δ 9.36-9.27 (m, 2H), 8.84 (t, J = 5.8 Hz, 1H), 8.22 (d, J = 5.1 Hz, 1H), 7.75-7.63 (m, 3H), 7.62-7.49 (m, 3H), 7.32-7.25 (m, 2H), 7.17-7.11 (m, 1H), 6.97 (s, 1H), 6.59-6.46 (m, 1H), 5.22 (dd, J = 12.7, 9.3 Hz, 1H), 4.65 (d, J = 12.7 Hz, 1H), 4.49 (s, 4H), 4.41-4.21 (m, 2H), 4.15 (dd, J = 5.8, 2.0 Hz, 1H), 3.92-3.79 (m, 1H), 3.22 (d, J = 4.6 Hz, 5H), 3.12-2.98 (m, 1H), 1.77 (d, J = 7.1 Hz, 3H), 0.83 (t, J = 6.9 Hz, 3H).
LCMS Calculated for $C_{37}H_{37}F_3N_8O_4$: 714.29; Observed (Method-V): 715.4 $[M + H]^+$, 90.17% at RT 1.530 min.

I-243

-continued

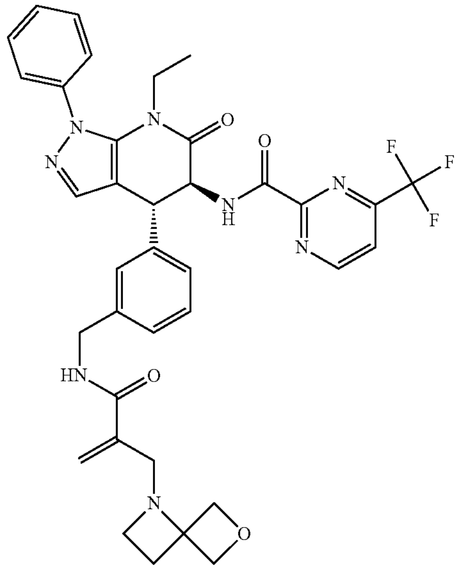 [SMILES: C=C(CN1CCC12COC2)C(=O)NCc1cccc([C@@H]2c3cnn(-c4ccccc4)c3N(CC)C(=O)[C@H]2NC(=O)c2nccc(C(F)(F)F)n2)c1]

$^1$H NMR (400 MHz, DMSO-$d_6$) δ 9.35-9.28 (m, 2H), 8.73 (t, J = 6.0 Hz, 1H), 8.22 (d, J = 5.1 Hz, 1H), 7.68-7.63 (m, 2H), 7.62-7.51 (m, 3H), 7.32 (s, 1H), 7.31-7.26 (m, 2H), 7.20-7.14 (m, 1H), 6.97 (s, 1H), 5.79 (s, 1H), 5.47 (s, 1H), 5.22 (dd, J = 12.5, 9.4 Hz, 1H), 4.81-4.73 (m, 2H), 4.65 (d, J = 12.8 Hz, 1H), 4.45-4.38 (m, 2H), 4.34 (d, J = 5.9 Hz, 2H), 3.91-3.81 (m, 1H), 3.47 (s, 2H), 3.10-3.00 (m, 1H), 2.94 (t, J = 6.9 Hz, 2H), 2.23 (t, J = 6.7 Hz, 2H), 0.83 (t, J = 7.0 Hz, 3H). LCMS Calculated for $C_{36}H_{35}F_3N_8O_4$: 700.27; Observed (Method-C): 701.1 $[M + H]^+$, 96.06% at RT 0.817 min.

I-246

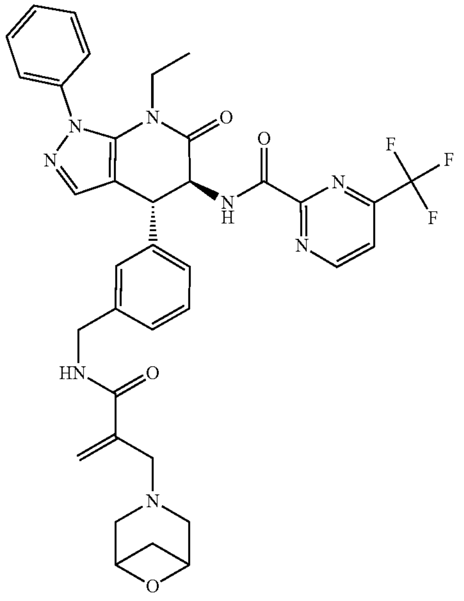 [SMILES: C=C(CN1CC2CC(C1)O2)C(=O)NCc1cccc([C@@H]2c3cnn(-c4ccccc4)c3N(CC)C(=O)[C@H]2NC(=O)c2nccc(C(F)(F)F)n2)c1]

$^1$H NMR (400 MHz, DMSO-$d_6$) δ 9.36-9.27 (m, 2H), 8.91 (t, J = 5.9 Hz, 1H), 8.22 (d, J = 5.0 Hz, 1H), 7.69-7.63 (m, 2H), 7.62-7.51 (m, 3H), 7.31-7.22 (m, 3H), 7.18-7.12 (m, 1H), 6.93 (s, 1H), 5.89 (d, J = 2.1 Hz, 1H), 5.52 (d, J = 1.7 Hz, 1H), 5.20 (dd, J = 12.7, 9.2 Hz, 1H), 4.63 (d, J = 12.7 Hz, 1H), 4.42-4.28 (m, 4H), 3.90-3.80 (m, 1H), 3.41 (s, 2H), 3.10-3.00 (m, 1H), 2.98-2.89 (m, 2H), 2.69-2.61 (m, 1H), 2.57 (s, 1H), 2.54 (s, 1H), 1.83 (d, J = 8.1 Hz, 1H), 0.83 (t, J = 7.0 Hz, 3H). LCMS Calculated for $C_{36}H_{35}F_3N_8O_4$: 700.27; Observed (Method-C): 701.2 $[M + H]^+$, 99.43% at RT 0.824 min.

I-346

-continued
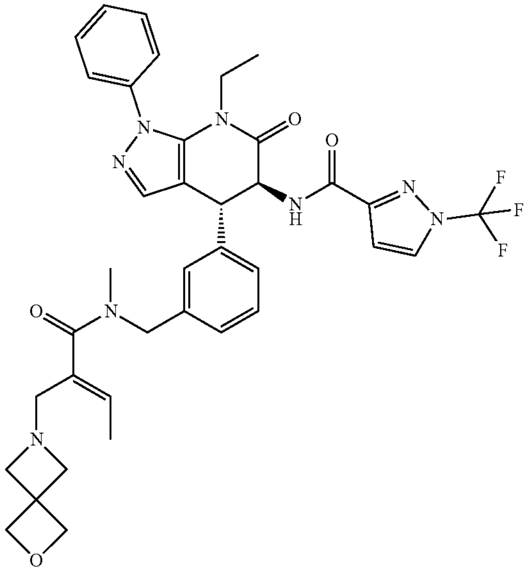 [SMILES: C/C=C(\CN1CC2(COC2)C1)C(=O)N(C)Cc1cccc([C@@H]2c3cnn(-c4ccccc4)c3N(CC)C(=O)[C@H]2NC(=O)c2ccn(C(F)(F)F)n2)c1]
I-321
$^1$H NMR (300 MHz, DMSO-$d_6$) δ 8.74 (d, J = 9.2 Hz, 1H), 8.55 (d, J = 2.8 Hz, 1H), 7.66-7.45 (m, 5H), 7.38-7.10 (m, 5H), 6.95 (d, J = 9.9 Hz, 1H), 6.87 (s, 1H), 5.63-5.53 (m, 1H), 5.15 (dd, J = 12.9, 9.2 Hz, 1H), 4.56-4.38 (m, 4H), 3.96-3.73 (m, 1H), 3.20 (d, J = 2.6 Hz, 3H), 3.16-3.11 (m, 4H), 3.06-2.91 (m, 1H), 2.81-2.63 (m, 4H), 1.72-1.34 (m, 3H), 0.80 (t, J = 7.0 Hz, 3H).
LCMS Calculated for $C_{37}H_{39}F_3N_8O_4$: 716.77; Observed (Method-AJ): 717.77 $[M + H]^+$, 96.14% at RT 1.679 min.
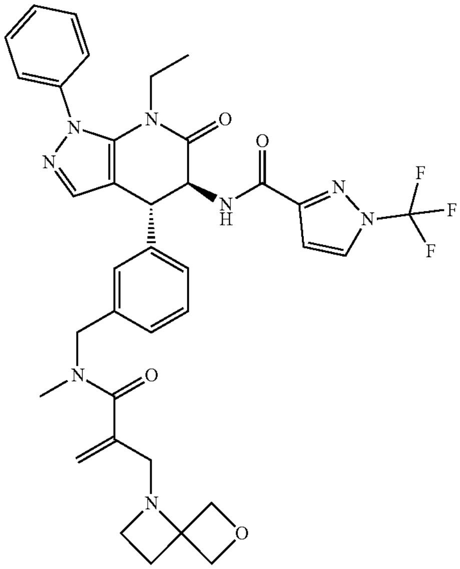 [SMILES: C=C(CN1CCC12COC2)C(=O)N(C)Cc1cccc([C@@H]2c3cnn(-c4ccccc4)c3N(CC)C(=O)[C@H]2NC(=O)c2ccn(C(F)(F)F)n2)c1]
I-371
$^1$H NMR (400 MHz, DMSO-$d_6$) δ 8.78 (d, J = 9.1 Hz, 1H), 8.57 (d, J = 2.8 Hz, 1H), 7.70-7.60 (m, 2H), 7.59-7.40 (m, 3H), 7.35-7.28 (m, 3H), 7.22-7.05 (m, 1H), 6.99 (s, 1H), 6.89 (s, 1H), 5.48-4.99 (m, 3H), 4.80-4.75 (m, 2H), 4.56-4.50 (m, 3H), 4.44 (t, J = 6.4 Hz, 2H), 3.87 (dq, J = 14.3, 7.1 Hz, 1H), 3.56-3.38 (m, 2H), 3.10-2.87 (m, 3H), 2.75-2.55 (m, 3H), 2.28-2.12 (m, 2H), 0.82 (t, J = 7.0 Hz, 3H).
LCMS Calculated for $C_{36}H_{37}F_3N_8O_4$: 702.29; Observed (Method-K): 703.5 $[M + H]^+$, 99.61% at RT 0.727 min.

-continued

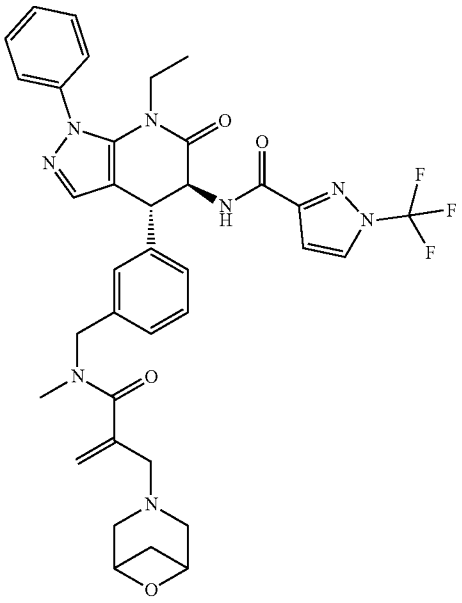 [SMILES: C=C(CN1CC2CC(C1)O2)C(=O)N(C)Cc1cccc([C@@H]2c3cnn(-c4ccccc4)c3N(CC)C(=O)[C@H]2NC(=O)c2ccn(C(F)(F)F)n2)c1]

$^1H$ NMR (400 MHz, DMSO-$d_6$) δ 8.77 (d, J = 9.3 Hz, 1H), 8.57 (d, J = 2.8 Hz, 1H), 7.70-7.61 (m, 2H), 7.61-7.48 (m, 3H), 7.38-7.21 (m, 3H), 7.20-7.07 (m, 1H), 6.99 (d, J = 4.9 Hz, 1H), 6.88 (d, J = 2.8 Hz, 1H), 5.47-5.25 (m, 1H), 5.23-5.06 (m, 2H), 4.66-4.42 (m, 3H), 4.35 (d, J = 6.1 Hz, 2H), 3.96-3.77 (m, 1H), 3.41-3.37 (m, 1H), 3.09-2.90 (m, 3H), 2.86-2.70 (m, 3H), 2.71-2.56 (m, 3H), 2.20-1.99 (m, 1H), 0.82 (t, J = 7.0 Hz, 3H). LCMS Calculated for $C_{36}H_{37}F_3N_8O_4$: 702.29; Observed (Method-X): 703.3 [M + H]$^+$, 97.74% at RT 1.484 min.

I-253

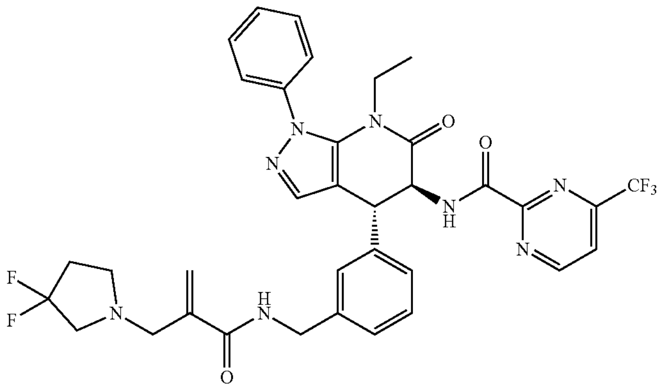 [SMILES: C=C(CN1CCC(F)(F)C1)C(=O)NCc1cccc([C@@H]2c3cnn(-c4ccccc4)c3N(CC)C(=O)[C@H]2NC(=O)c2nccc(C(F)(F)F)n2)c1]

$^1H$ NMR (300 MHz, DMSO-$d_6$) δ 9.30 (dd, J = 10.7, 7.2 Hz, 2H), 8.64 (t, J = 6.0 Hz, 1H), 8.21 (d, J = 5.1 Hz, 1H), 7.70-7.48 (m, 5H), 7.33-7.23 (m, 3H), 7.16 (d, J = 5.3 Hz, 1H), 6.97 (s, 1H), 5.80 (d, J = 1.7 Hz, 1H), 5.47 (s, 1H), 5.21 (dd, J = 12.7, 9.3 Hz, 1H), 4.64 (d, J = 12.7 Hz, 1H), 4.33 (d, J = 5.9 Hz, 2H), 3.91-3.76 (m, 1H), 3.31-3.29 (m, 2H),, 3.12-2.99 (m, 1H), 2.85 (t, J = 13.4 Hz, 2H), 2.68 (t, J = 7.0 Hz, 2H), 2.29-2.08 (m, 2H), 0.83 (t, J = 7.0 Hz, 3H). LCMS Calculated for $C_{35}H_{33}F_5N_8O_3$: 708.26; Observed (Method-V): 709.3 [M + H]$^+$, 100% at RT 1.727 min.

I-230B

-continued

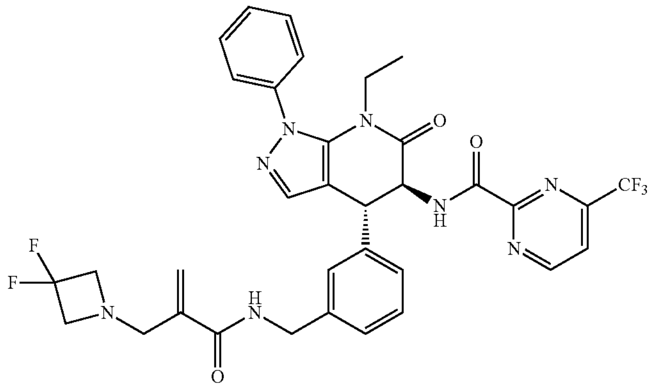 [SMILES: C=C(CN1CC(F)(F)C1)C(=O)NCc1cccc([C@@H]2c3cnn(-c4ccccc4)c3N(CC)C(=O)[C@H]2NC(=O)c2nccc(C(F)(F)F)n2)c1]

I-261

$^{1}H$ NMR (300 MHz, DMSO-$d_6$) δ 9.36-9.25 (m, 2H), 8.58 (t, J = 5.8 Hz, 1H), 8.22 (d, J = 5.1 Hz, 1H), 7.69-7.50 (m, 5H), 7.34-7.24 (m, 3H), 7.18-7.12 (m, 1H), 6.98 (s, 1H), 5.79 (d, J = 1.3 Hz, 1H), 5.47 (d, J = 1.4 Hz, 1H), 5.21 (dd, J = 12.7, 9.3 Hz, 1H), 4.64 (d, J = 12.6 Hz, 1H), 4.32 (d, J = 6.0 Hz, 2H), 3.91-3.78 (m, 1H), 3.57 (t, J = 12.6 Hz, 4H), 3.39 (s, 2H), 3.12-2.99 (m, 1H), 0.83 (t, J = 7.0 Hz, 3H).
LCMS Calculated for $C_{34}H_{31}F_5N_8O_3$: 694.24; Observed (Method-V): 695.3 $[M + H]^+$, 98.52% at RT 1.638 min.

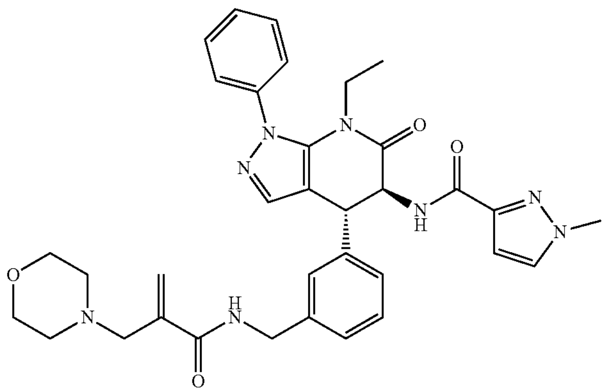 [SMILES: C=C(CN1CCOCC1)C(=O)NCc1cccc([C@@H]2c3cnn(-c4ccccc4)c3N(CC)C(=O)[C@H]2NC(=O)c2ccn(C)n2)c1]

I-338

$^{1}H$ NMR (400 MHz, DMSO-$d_6$) δ 8.97 (s, 1H), 8.24 (d, J = 9.4 Hz, 1H), 7.73 (d, J = 2.2 Hz, 1H), 7.58 (ddd, J = 22.5, 15.5, 7.3 Hz, 5H), 7.34-7.17 (m, 4H), 6.91 (s, 1H), 6.54 (d, J = 2.3 Hz, 1H), 5.91 (s, 1H), 5.46 (s, 1H), 5.14 (dd, J = 12.7, 9.4 Hz, 1H), 4.54 (d, J = 12.7 Hz, 1H), 4.37 (d, J = 5.4 Hz, 2H), 3.88 (s, 3H), 3.80 (dt, J = 14.2, 7.2 Hz, 1H), 3.45 (t, J = 4.8 Hz, 4H), 3.18 (s, 2H), 3.04 (dd, J = 14.0, 7.1 Hz, 1H), 2.33 (d, J = 5.4 Hz, 4H), 0.81 (t, J = 7.1 Hz, 3H).
LCMS Calculated for $C_{34}H_{38}N_8O_4$: 622.3; Observed (Method-V): 623.4 $[M + H]^+$, 99.99% at RT 1.406 min.

-continued

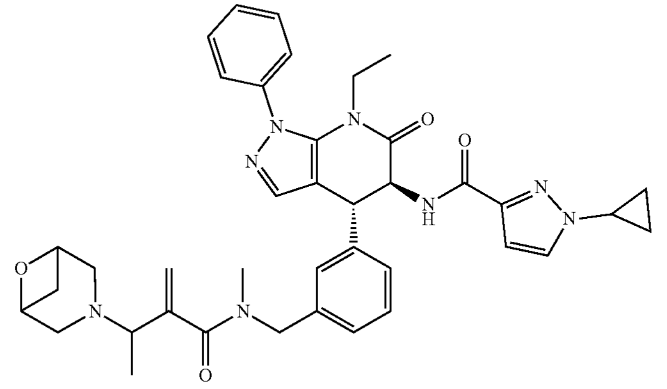 [SMILES: C=C(C(=O)N(C)Cc1cccc([C@@H]2c3cnn(-c4ccccc4)c3N(CC)C(=O)[C@H]2NC(=O)c2ccn(C3CC3)n2)c1)C(C)N1CC2CC(C1)O2]

I-286

$^1$H NMR (300 MHz, DMSO-$d_6$) δ 8.28 (s, 1H), 7.99 (d, J = 9.2 Hz, 1H), 7.74 (d, J = 2.4 Hz, 1H), 7.65-7.47 (m, 5H), 7.37-7.23 (m, 3H), 7.15 (s, 1H), 6.97 (d, J = 2.9 Hz, 1H), 6.49 (d, J = 2.4 Hz, 1H), 5.38-5.04 (m, 3H), 4.60-4.48 (m, 3H), 4.37 (d, J = 6.2 Hz, 2H), 3.90-3.56 (m, 4H), 2.95-2.86 (m, 4H), 2.79 (s, 4H), 2.09 (d, J = 7.6 Hz, 1H), 1.23 (d, J = 6.9 Hz, 3H), 1.08 (td, J = 3.7, 2.3 Hz, 2H), 1.05-0.96 (m, 2H), 0.85 (t, J = 7.0 Hz, 3H). LCMS Calculated for $C_{39}H_{44}N_8O_4$: 688.35; Observed (Method-B): 689.3 $[M + H]^+$, 98.17% at RT 0.742 min.

4. Synthesis of tert-butyl (E)-4-((3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)amino)but-2-enoate I-306

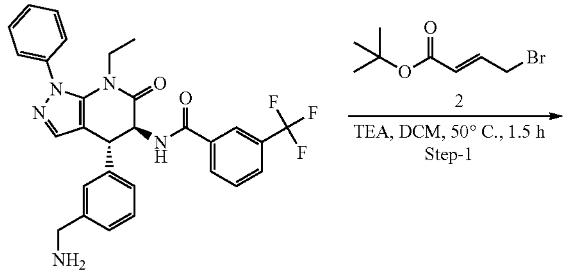

-continued

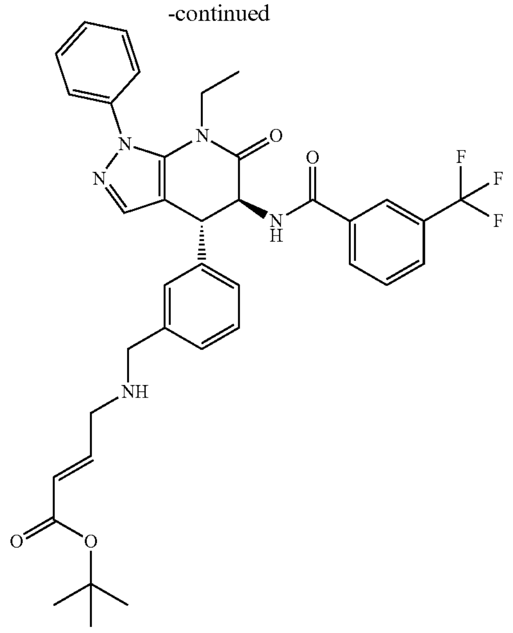

I-306

To a stirred mixture of N-((4R,5S)-4-(3-(aminomethyl)phenyl)-7-ethyl-6-oxo-1-phenyl-4,5,6,7-tetrahydro-1H-pyrazolo[3,4-b]pyridin-5-yl)-3-(trifluoromethyl)benzamide (300 mg, 0.562 mmol, 1.00 equiv) and TEA (85.4 mg, 0.843 mmol, 1.50 equiv) in DMF (5 ml) was added tert-butyl (2E)-4-bromobut-2-enoate (112 mg, 0.506 mmol, 0.9 equiv) in portions at room temperature. The resulting mixture was stirred for 1.5 h at 50° C. The resulting mixture was purified by reversed-phase flash chromatography with the following conditions: column, C18 silica gel; mobile phase, MeCN in Water (0.1% FA), 10% to 80% gradient in 10 min; detector, UV 254 nm. This resulted in tert-butyl (E)-4-((3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)amino)but-2-enoate (200 mg, 52%) as a white solid.

$^1$H NMR (300 MHz, DMSO-$d_6$) δ 9.01 (d, J=9.0 Hz, 1H), 8.03 (d, J=7.8 Hz, 2H), 7.89 (d, J=7.8 Hz, 1H), 7.75-7.48 (m, 6H), 7.37 (s, 1H), 7.35-7.25 (m, 2H), 7.22 (d, J=4.1 Hz, 1H), 7.06 (s, 1H), 6.78-6.64 (m, 1H), 5.81 (d, J=15.7 Hz, 1H), 5.21 (dd, J=12.9, 8.9 Hz, 1H), 4.38 (d, J=12.9 Hz, 1H), 3.92-3.79 (m, 1H), 3.64 (s, 2H), 3.17-3.00 (m, 3H), 1.42 (s, 9H), 0.83 (t, J=7.0 Hz, 3H).

LCMS Calculated for $C_{37}H_{38}F_3N_5O_4$. 673.3; Observed (Method-V): 674.3 [M+H]$^+$, 98.96% at RT 2.003 min.

$^1$H NMR (300 MHz, DMSO-$d_6$) δ 9.01 (d, J = 9.0 Hz, 1H), 8.02 (d, J = 9.2 Hz, 2H), 7.90 (d, J = 7.8 Hz, 1H), 7.71 (d, J = 7.7 Hz, 1H), 7.71-7.48 (m, 5H), 7.39 (s, 1H), 7.32-7.19 (m, 3H), 7.07 (s, 1H), 6.67-6.52 (m, 1H), 6.46 (s, 1H), 5.20 (dd, J = 12.9, 9.0 Hz, 1H), 4.38 (d, J = 12.9 Hz, 1H), 3.91-3.78 (m, 1H), 3.65 (s, 2H), 3.17 (dd, J = 5.5, 1.4 Hz, 2H), 3.12-3.00 (m, 1H), 2.98 (s, 3H), 2.84 (s, 3H), 0.83 (t, J = 7.0 Hz, 3H). LCMS Calculated for $C_{35}H_{35}F_3N_6O_3$: 644.3; Observed (Method-V): 645.4 [M + H]$^+$, 96.73% at RT 1.607 min.

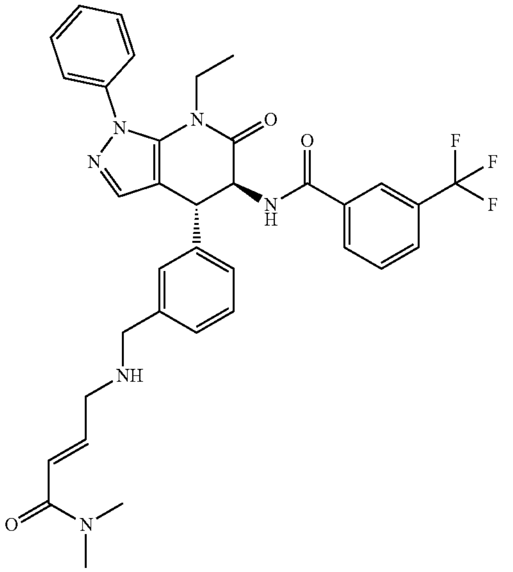 [SMILES: CCN1C(=O)[C@@H](NC(=O)c2cccc(C(F)(F)F)c2)[C@H](c2cccc(CNC/C=C/C(=O)N(C)C)c2)c2cnn(-c3ccccc3)c21]

-continued

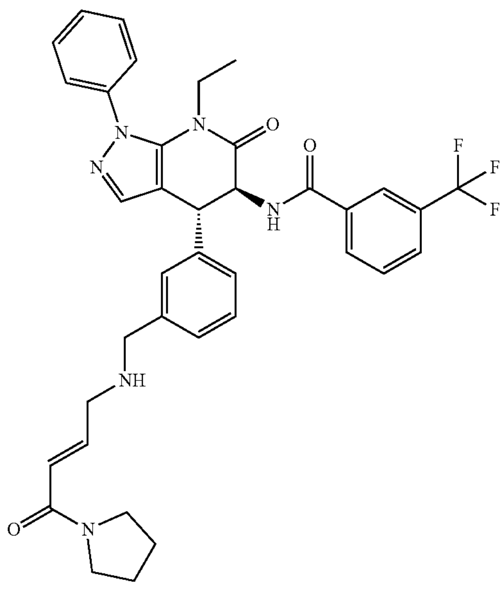 [SMILES: CCN1C(=O)[C@@H](NC(=O)c2cccc(C(F)(F)F)c2)[C@H](c2cccc(CNC/C=C/C(=O)N3CCCC3)c2)c2cnn(-c3ccccc3)c21]

I-307

$^1$H NMR (300 MHz, DMSO-$d_6$) δ 9.03 (d, J = 9.0 Hz, 1H), 8.19 (s, 1H), 8.02 (d, J = 8.9 Hz, 2H), 7.90 (d, J = 7.8 Hz, 1H), 7.76-7.48 (m, 6H), 7.41 (s, 1H), 7.29 (d, J = 4.7 Hz, 2H), 7.23 (d, J = 4.3 Hz, 1H), 7.08 (s, 1H), 6.69-6.54 (m, 1H), 6.30 (d, J = 15.3 Hz, 1H), 5.20 (dd, J = 12.9, 9.0 Hz, 1H), 4.38 (d, J = 12.9 Hz, 1H), 3.92-3.79 (m, 1H), 3.43 (t, J = 6.5 Hz, 2H), 3.31 (t, J = 6.6 Hz, 2H), 3.24-3.16 (m, 2H), 3.12-2.99 (m, 1H), 1.86-1.69 (m, 4H), 0.83 (t, J = 7.0 Hz, 3H).

LCMS Calculated for $C_{37}H_{37}F_3N_6O_3$: 607.3; Observed (Method-V): 671.3 [M + H]$^+$, 99.44% at RT 1.667 min.

5. Synthesis of tert-butyl (E)-4-((3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)(methyl)amino)but-2-enoate I-238

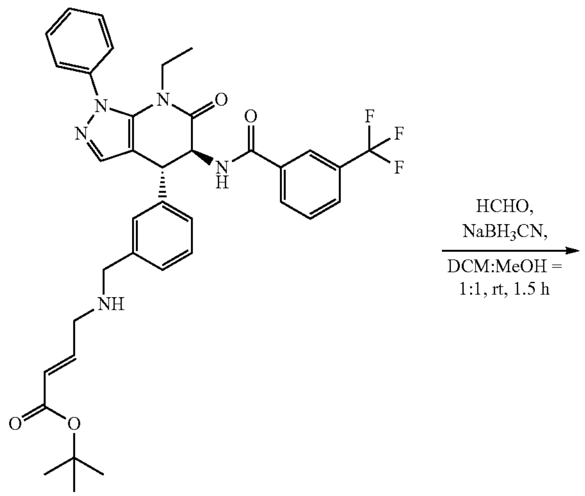

-continued

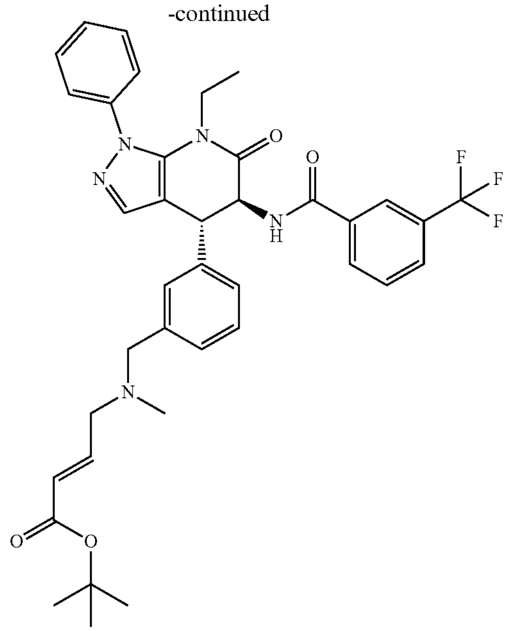

I-238

A solution of tert-butyl (E)-4-((3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)amino)but-2-enoate (80 mg, 0.119 mmol, 1.00 equiv) in DMF (2 ml) was treated with HCHO (12.5 mg, 0.416 mmol, 3.50 equiv) for 30 min at room temperature followed by the addition of $NaBH_3CN$ (22.4 mg, 0.357 mmol, 3.00 equiv) in portions at room temperature. The reaction was monitored by LCMS. The residue was purified by reversed-phase flash chromatography with the following conditions: column, C18 silica gel; mobile phase, MeCN in Water (10 mmol/L $NH_4HCO_3$), 10% to 90% gradient in 10 min; detector, UV 254 nm. This resulted in tert-butyl (E)-4-((3-((4R,5S)-7-ethyl-6-oxo-1-phenyl-5-(3-(trifluoromethyl)benzamido)-4,5,6,7-tetrahydro-1H-pyrazolo[3,4-b]pyridin-4-yl)benzyl)(methyl)amino)but-2-enoate (40 mg, 48%) as a white solid.

$^1$H NMR (300 MHz, DMSO-$d_6$) δ 9.02 (d, J=9.1 Hz, 1H), 8.02 (d, J=7.9 Hz, 2H), 7.88 (d, J=7.8 Hz, 1H), 7.68 (d, J=6.6 Hz, 3H), 7.63-7.47 (m, 3H), 7.36-7.24 (m, 3H), 7.17 (s, 1H), 7.06 (s, 1H), 6.73-6.53 (m, 1H), 5.83 (d, J=15.7 Hz, 1H), 5.30-5.10 (m, 1H), 4.38 (d, J=13.0 Hz, 1H), 3.95-3.77 (m, 1H), 3.44 (s, 2H), 3.10-2.89 (m, 3H), 1.96 (s, 3H), 1.42 (s, 9H), 0.83 (t, J=7.0 Hz, 3H).

LCMS Calculated for $C_{38}H_{40}F_3N_5O_4$: 687.3; Observed (Method-V): 688.3 [M+H]$^+$, 99.58% at RT 1.794 min.

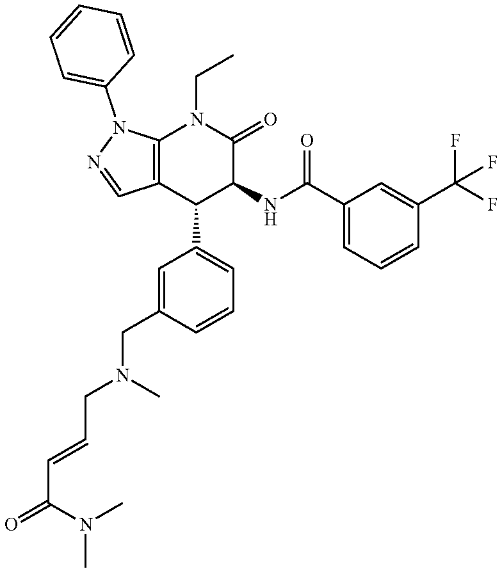 [SMILES: CCN1C(=O)[C@@H](NC(=O)c2cccc(C(F)(F)F)c2)[C@H](c2cccc(CN(C)C/C=C/C(=O)N(C)C)c2)c2cnn(-c3ccccc3)c21]

I-339

$^1$H NMR (300 MHz, DMSO-$d_6$) δ 9.01 (d, J = 9.0 Hz, 1H), 8.01 (d, J = 8.8 Hz, 2H), 7.88 (d, J = 7.9 Hz, 1H), 7.74-7.65 (m, 3H), 7.65-7.44 (m, 3H), 7.36 (s, 1H), 7.33-7.24 (m, 2H), 7.18 (d, J = 4.7 Hz, 1H), 7.05 (s, 1H), 6.63-6.46 (m, 2H), 5.20 (dd, J = 13.0, 9.0 Hz, 1H), 4.38 (d, J = 12.9 Hz, 1H), 3.93-3.72 (m, 1H), 3.44 (s, 2H), 3.09-2.92 (m, 5H), 2.85 (s, 3H), 1.98 (s, 3H), 0.83 (t, J = 7.0 Hz, 3H).

LCMS Calculated for $C_{36}H_{37}F_3N_6O_3$: 658.3; Observed (Method-V): 659.4 [M + H]$^+$, 92.87% at RT 1.706 min.

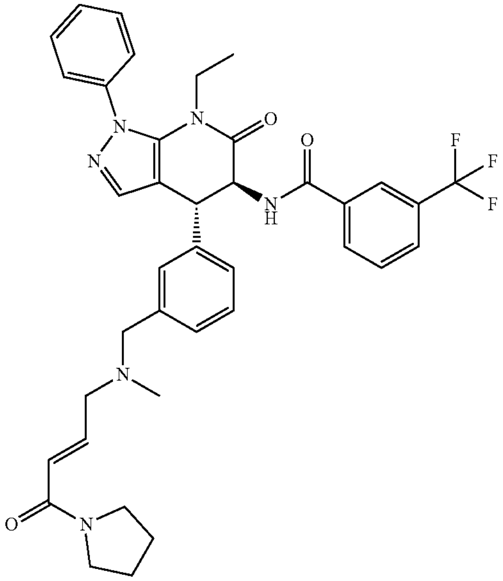 [SMILES: CCN1C(=O)[C@@H](NC(=O)c2cccc(C(F)(F)F)c2)[C@H](c2cccc(CN(C)C/C=C/C(=O)N3CCCC3)c2)c2cnn(-c3ccccc3)c21]

I-255

$^1$H NMR (300 MHz, DMSO-$d_6$) δ 9.00 (d, J = 9.0 Hz, 1H), 8.01 (d, J = 8.6 Hz, 2H), 7.88 (d, J = 7.9 Hz, 1H), 7.74-7.48 (m, 6H), 7.38 (s, 1H), 7.30 (d, J = 4.8 Hz, 2H), 7.18 (s, 1H), 7.06 (s, 1H), 6.69-6.48 (m, 1H), 6.33 (d, J = 15.1 Hz, 1H), 5.20 (dd, J = 12.9, 9.0 Hz, 1H), 4.38 (d, J = 12.9 Hz, 1H), 3.92-3.79 (m, 1H), 3.49-3.39 (m, 4H), 3.32 (d, J = 13.4 Hz, 1H), 3.07 (s, 3H), 2.01 (s, 3H), 1.88-1.70 (m, 4H), 0.83 (t, J = 7.0 Hz, 3H).

LCMS Calculated for $C_{38}H_{39}F_3N_6O_3$: 684.3; Observed (Method-V): 685.4 [M + H]$^+$, 97.92% at RT 1.791 min.

Synthesis of rac-N-((4R,5S)-7-ethyl-4-(6-(1-methyl-2,5-dihydro-1H-pyrrole-3-carboxamido)pyridin-2-yl)-6-oxo-1-phenyl-4,5,6,7-tetrahydro-1H-pyrazolo[3,4-b]pyridin-5-yl)-4-(trifluoromethyl)pyrimidine-2-carboxamide I-376
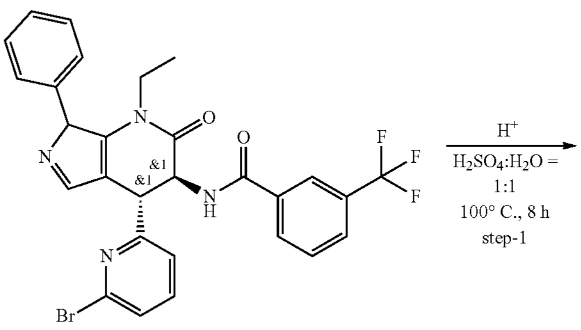
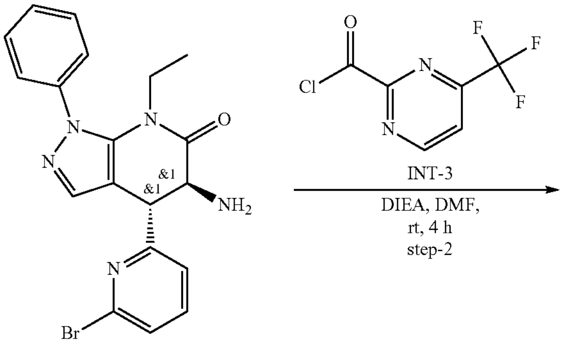
7
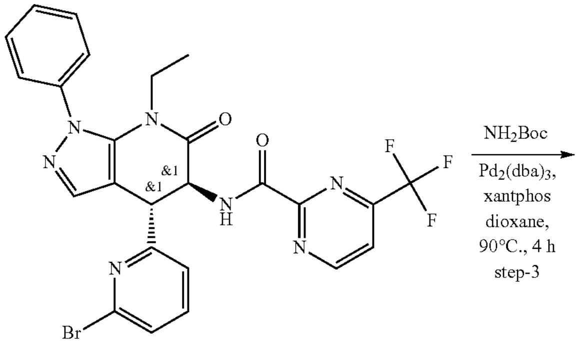
8
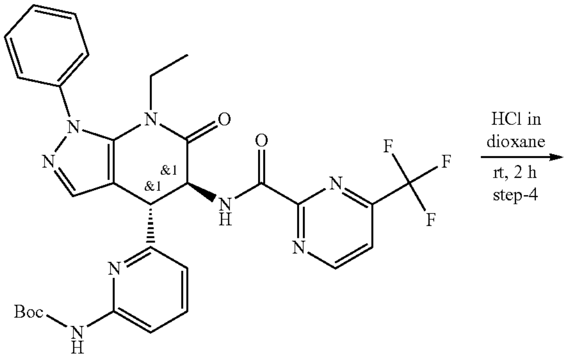
9
-continued
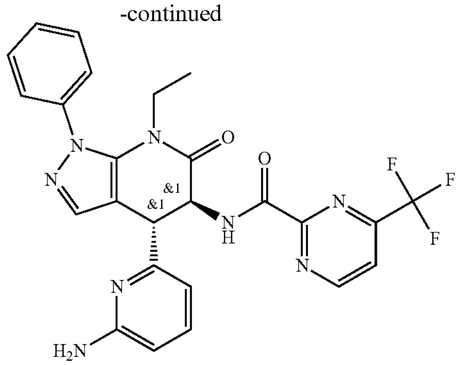
10
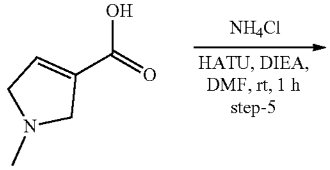
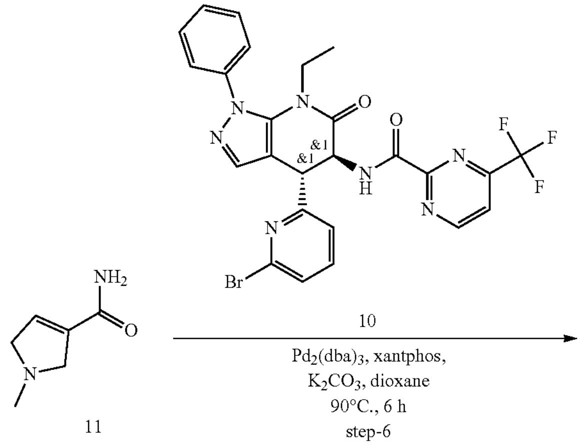
11
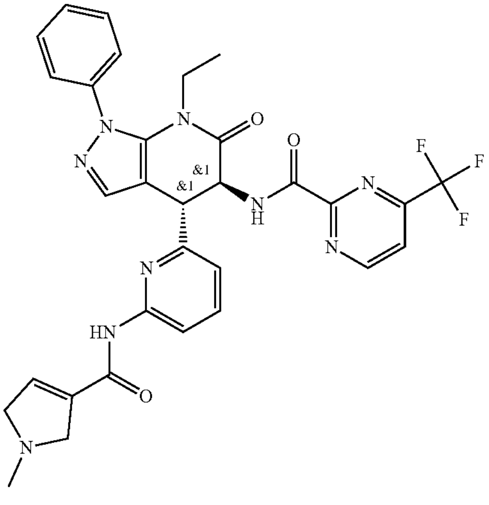
I-376 rac-(4R,5S)-5-amino-4-(6-bromopyridin-2-yl)-7-ethyl-1-phenyl-1,4,5,7-tetrahydro-6H-pyrazolo[3,4-b]pyridin-6-one (7)

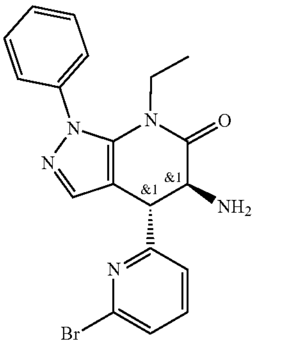 [SMILES: CCN1C(=O)[C@@H](N)[C@H](c2cccc(Br)n2)c2cnn(-c3ccccc3)c21]

A solution of rac-N-((3R,4S)-4-(6-bromopyridin-2-yl)-1-ethyl-2-oxo-7-phenyl-2,3,4,7-tetrahydro-1H-pyrrolo[3,4-b]pyridin-3-yl)-3-(trifluoromethyl)benzamide (1.00 g, 1.71 mmol, 1.00 equiv) (n $H_2SO_4$ (5 mL) and $H_2O$ (5 mL) was stirred at 100° C. for 8 h. The mixture was allowed to cool down to room temperature. The resulting mixture was concentrated in vacuum, diluted with $Et_2O$ (5.0 mL), filtered to afford rac-(4R,5S)-5-amino-4-(6-bromopyridin-2-yl)-7-ethyl-1-phenyl-1,4,5,7-tetrahydro-6H-pyrazolo[3,4-b]pyridin-6-one (400 mg, 56.7%) as a yellow solid, which was used for next step directly.

LCMS Calculated for: $C_{19}H_{18}BrN_5O$: 411.07; Observed: 412.2 $[M+H]^+$.

rac-N-((4R,5S)-4-(6-bromopyridin-2-yl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (8)

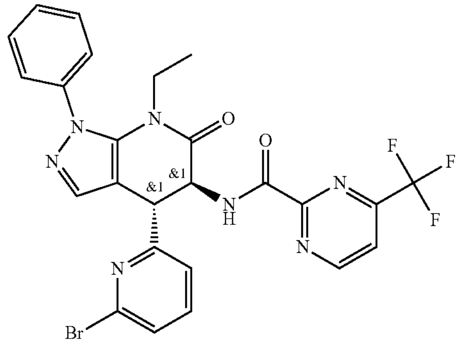 [SMILES: CCN1C(=O)[C@@H](NC(=O)c2nccc(C(F)(F)F)n2)[C@H](c2cccc(Br)n2)c2cnn(-c3ccccc3)c21]

A mixture of rac-(4R,5S)-5-amino-4-(6-bromopyridin-2-yl)-7-ethyl-1-phenyl-1,4,5,7-tetrahydro-6H-pyrazolo[3,4-b]pyridin-6-one (400 mg, 0.970 mmol, 1.00 equiv), TEA (196 mg, 1.94 mmol, 2.00 equiv) and DMF (5 mL) was stirred at 0° C. for 10 min. 4-(trifluoromethyl)pyrimidine-2-carbonyl chloride (245 mg, 1.16 mmol, 1.20 equiv) was then added, and the reaction mixture was stirred for 4 h at room temperature. The resulting mixture was concentrated in vacuum, the residue was purified by silica gel column chromatography, eluted with EtOAc:PE (1:1) to afford rac-N-((4R,5S)-4-(6-bromopyridin-2-yl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (300 mg, 52.7%) as a yellow solid.

LCMS Calculated for: $C_{25}H_{19}BrF_3N_7O_2$: 585.07; Observed: 586.3 $[M+H]^+$.

tert-butyl (6-(rac-(4R,5S)-7-ethyl-6-oxo-1-phenyl-5-(4-(trifluoromethyl)pyrimidine-2-carboxamido)-4,5,6,7-tetrahydro-1H-pyrazolo[3,4-b]pyridin-4-yl)pyridin-2-yl)carbamate (9)

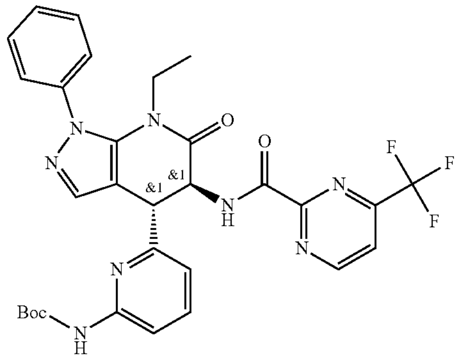 [SMILES: CCN1C(=O)[C@@H](NC(=O)c2nccc(C(F)(F)F)n2)[C@H](c2cccc(NC(=O)OC(C)(C)C)n2)c2cnn(-c3ccccc3)c21]

A mixture of rac-N-((4R,5S)-4-(6-bromopyridin-2-yl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (300 mg, 0.512 mmol, 1.00 equiv), $BocNH_2$ (120 mg, 1.02 mmol, 2.00 equiv), $Pd_2(dba)_3$ (29.4 mg, 0.051 mmol, 0.10 equiv), XantPhos (29.6 mg, 0.051 mmol, 0.10 equiv), dioxane (5 mL) was stirred at room temperature. The resulting mixture was stirred for 4 h at 90° C. under $N_2$ atmosphere. The reaction was quenched with water (20 mL) at room temperature. The resulting mixture was extracted with EtOAc (2×20 mL). The combined organic layers were washed with brine (1×20 mL), dried over anhydrous $Na_2SO_4$. After filtration, the filtrate was concentrated under reduced pressure. The residue was purified by reversed-phase flash chromatography with the following conditions: Column: X Bridge Prep RP C18 Column, 30*150 mm, 5 m; Mobile Phase A: Water(0.1% $NH_3 \cdot H_2O$), Mobile Phase B: ACN; Flow rate: 35 mL/min; Gradient: 62% B to 92% B in 10 min; Wave Length: 254 nm/220 nm; RT1 (min): 6.9 to afford tert-butyl (6-(rac-(4R,5S)-7-ethyl-6-oxo-1-phenyl-5-(4-(trifluoromethyl)pyrimidine-2-carboxamido)-4,5,6,7-tetrahydro-1H-pyrazolo[3,4-b]pyridin-4-yl)pyridin-2-yl)carbamate (150 mg, 39.6%) as a white solid.

LCMS Calculated for $C_{30}H29F_3N_8O_4$: 622.23; Observed: 623.3 $[M+H]^+$.

rac-N-((4R,5S)-4-(6-aminopyridin-2-yl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (10)

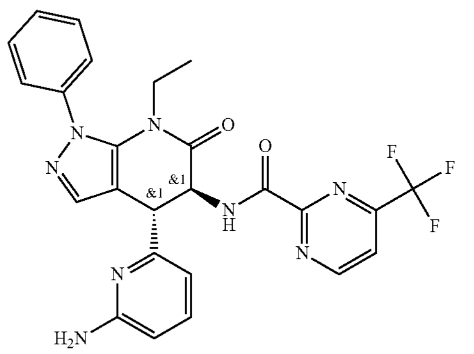 [SMILES: CCN1C(=O)[C@@H](NC(=O)c2nccc(C(F)(F)F)n2)[C@H](c2cccc(N)n2)c2cnn(-c3ccccc3)c21]

Into a 8 mL flask were added tert-butyl (6-(rac-(4R,5S)-7-ethyl-6-oxo-1-phenyl-5-(4-(trifluoromethyl)pyrimidine-2-carboxamido)-4,5,6,7-tetrahydro-1H-pyrazolo[3,4-b]pyridin-4-yl)pyridin-2-yl)carbamate (150 mg, 0.241 mmol, 1.00 equiv), HCl(gas) in 1,4-dioxane (4M, 2 mL) at room temperature. The resulting mixture was stirred for 2 h at room temperature. The resulting mixture was concentrated under reduced pressure. The mixture basified to pH=10 with $NaHCO_3$(aq.). The resulting mixture was extracted with EtOAc (2×10 mL). The combined organic layers were washed with brine (2×10 mL), dried over anhydrous $Na_2SO_4$. After filtration, the filtrate was concentrated under reduced pressure. This resulted in rac-N-((4R,5S)-4-(6-aminopyridin-2-yl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (100 mg, 79.4%) as a light yellow solid.

LCMS Calculated for: $C_{25}H_{21}F_3N_8O_2$: 522.17; Observed: 523.3 $[M+H]^+$.

1-methyl-2,5-dihydro-1H-pyrrole-3-carboxamide (11)

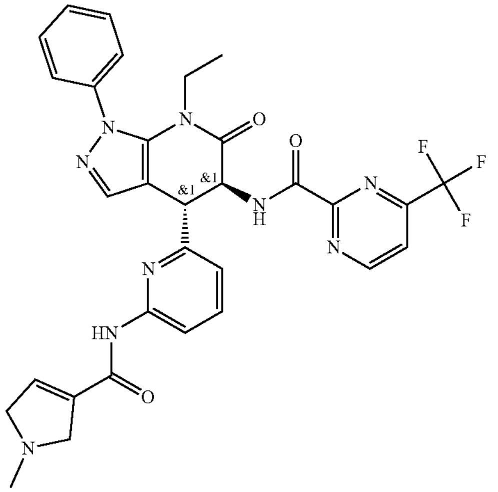 [SMILES: CCN1C(=O)[C@@H](NC(=O)c2nccc(C(F)(F)F)n2)[C@H](c2cccc(NC(=O)C3=CCN(C)C3)n2)c2cnn(-c3ccccc3)c21]

A mixture of ammonium chloride (315.53 mg, 5.900 mmol, 5 equiv), DIEA (457.45 mg, 3.540 mmol, 3 equiv) and 1-methyl-2,5-dihydro-1H-pyrrole-3-carboxylic acid (150 mg, 1.180 mmol, 1 equiv) in DMF (2 mL) was stirred at room temperature for 10 min. HATU (583.17 mg, 1.534 mmol, 1.3 equiv) was then added, and the reaction mixture was stirred for 1 h at room temperature. The reaction was quenched with water (20 mL) at room temperature. The resulting mixture was extracted with EtOAc (2×20 mL). The combined organic layers were washed with brine (1×20 mL), dried over anhydrous $Na_2SO_4$. After filtration, the filtrate was concentrated under reduced pressure. The residue was purified by reversed-phase flash chromatography with the following conditions: Column: X Bridge Prep RP C18 Column, 30*150 mm, 5 m; Mobile Phase A: Water (0.1% $NH_3 \cdot H_2O$), Mobile Phase B: ACN; Flow rate: 35 mL/min; Gradient: 62% B to 92% B in 10 min; Wave Length: 254 nm/220 nm; RT1 (min): 6.9 to afford 1-methyl-2,5-dihydro-1H-pyrrole-3-carboxamide (100 mg, 67.1%) as a white solid.

LCMS Calculated for: $C_6H_{10}N_2O$: 126.08; Observed: 127.1 $[M+H]^+$.

rac-N-((4R,5S)-7-ethyl-4-(6-(1-methyl-2,5-dihydro-1H-pyrrole-3-carboxamido)pyridin-2-yl)-6-oxo-1-phenyl-4,5,6,7-tetrahydro-1H-pyrazolo[3,4-b]pyridin-5-yl)-4-(trifluoromethyl)pyrimidine-2-carboxamide

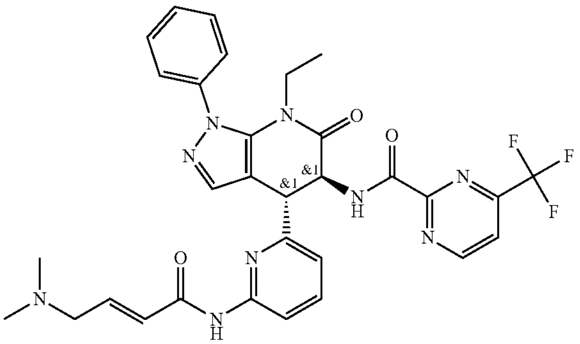 [SMILES: CCN1C(=O)[C@@H](NC(=O)c2nccc(C(F)(F)F)n2)[C@H](c2cccc(NC(=O)/C=C/CN(C)C)n2)c2cnn(-c3ccccc3)c21]

A mixture of rac-N-((4R,5S)-4-(6-aminopyridin-2-yl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (100 mg, 0.171 mmol, 1.00 equiv), 1-methyl-2,5-dihydropyrrole-3-carboxamide (43.0 mg, 0.342 mmol, 2.00 equiv), $Pd_2(dba)_3$ (9.81 mg, 0.017 mmol, 0.10 equiv), XantPhos (9.87 mg, 0.017 mmol, 0.10 equiv), $K_2CO_3$ (70.7 mg, 0.513 mmol, 3.00 equiv) and dioxane (5 mL) was stirred at room temperature. The resulting mixture was stirred for 6 h at 90° C. under $N_2$ atmosphere. The reaction was quenched with water (20 mL) at room temperature. The resulting mixture was extracted with EtOAc (2×20 mL). The combined organic layers were washed with brine (1×20 mL), dried over anhydrous $Na_2SO_4$. After filtration, the filtrate was concentrated under reduced pressure. The residue was purified by reversed-phase flash chromatography with the following conditions: Column: X Bridge Prep RP C18 Column, 30*150 mm, 5 m; Mobile Phase A: Water(0.1% $NH_3 \cdot H_2O$), Mobile Phase B: ACN; Flow rate: 35 mL/min; Gradient: 62% B to 92% B in 10 min; Wave Length: 254 nm/220 nm; RT1 (min): 6.9 to afford rac-N-((4R,5S)-7-ethyl-4-(6-(1-methyl-2,5-dihydro-1H-pyrrole-3-carboxamido)pyridin-2-yl)-6-oxo-1-phenyl-4,5,6,7-tetrahydro-1H-pyrazolo[3,4-b]pyridin-5-yl)-4-(trifluoromethyl)pyrimidine-2-carboxamide (15 mg, 13.9%) as a white solid. $^1$H NMR (300 MHz, DMSO-$d_6$) δ 10.21 (s, 1H), 9.35-9.22 (m, 2H), 8.20 (d, J=5.1 Hz, 1H), 7.94 (d, J=8.2 Hz, 1H), 7.74 (t, J=7.9 Hz, 1H), 7.66-7.46 (m, 5H), 7.17 (d, J=7.5 Hz, 1H), 7.06 (s, 1H), 6.94 (d, J=2.5 Hz, 1H), 5.44 (dd, J=12.7, 9.1 Hz, 1H), 4.78 (d, J=12.6 Hz, 1H), 3.87 (dt, J=14.3, 7.2 Hz, 1H), 3.68-3.52 (m, 4H), 3.04 (dt, J=13.7, 6.9 Hz, 1H), 2.36 (s, 3H), 0.83 (t, J=7.0 Hz, 3H).

LCMS Calculated for $C_{31}H_{28}F_3N_9O_3$: 631.23; Observed (Method-Y): 632.2 [M+H]$^+$, 82.53% at RT 1.686 min.

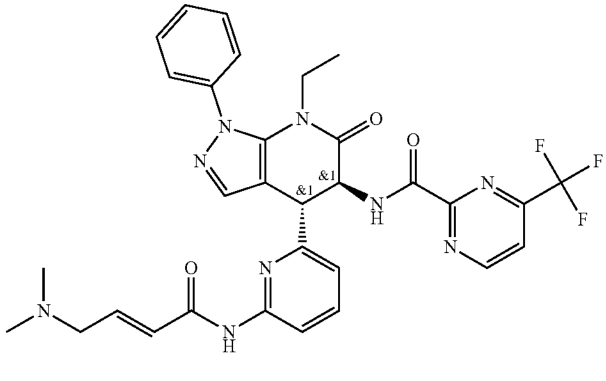 [SMILES: CCN1C(=O)[C@@H](NC(=O)c2nccc(C(F)(F)F)n2)[C@H](c2cccc(NC(=O)/C=C/CN(C)C)n2)c2cnn(-c3ccccc3)c21]

I-265

$^1$H NMR (400 MHz, DMSO-$d_6$) δ 10.58 (s, 1H), 9.41-9.20 (m, 2H), 8.21 (d, J = 5.1 Hz, 1H), 8.09 (d, J = 8.3 Hz, 1H), 7.74 (t, J = 7.9 Hz, 1H), 7.67-7.49 (m, 5H), 7.15 (d, J = 7.5 Hz, 1H), 6.76 (dt, J = 15.5, 6.1 Hz, 1H), 6.50 (d, J = 15.4 Hz, 1H), 5.41 (dd, J = 12.7, 9.2 Hz, 1H), 4.77 (d, J = 12.8 Hz, 1H), 3.89 (dt, J = 14.1, 7.1 Hz, 1H), 3.17-2.98 (m, 3H), 2.18 (s, 6H), 0.84 (t, J = 7.0 Hz, 3H). LCMS Calculated for $C_{31}H_{30}F_3N_9O_3$: 633.24; Observed (Method-AL): 634.3 [M + H]$^+$, 92.28% at RT 1.709 min.

6. Synthesis of rac-N-((4R,5S)-7-ethyl-4-(6-((2-((4-(oxetan-3-yl)piperazin-1-yl)methyl)acrylamido)methyl)pyridin-2-yl)-6-oxo-1-phenyl-4,5,6,7-tetrahydro-1H-pyrazolo[3,4-b]pyridin-5-yl)-4-(trifluoromethyl)pyrimidine-2-carboxamide I-386

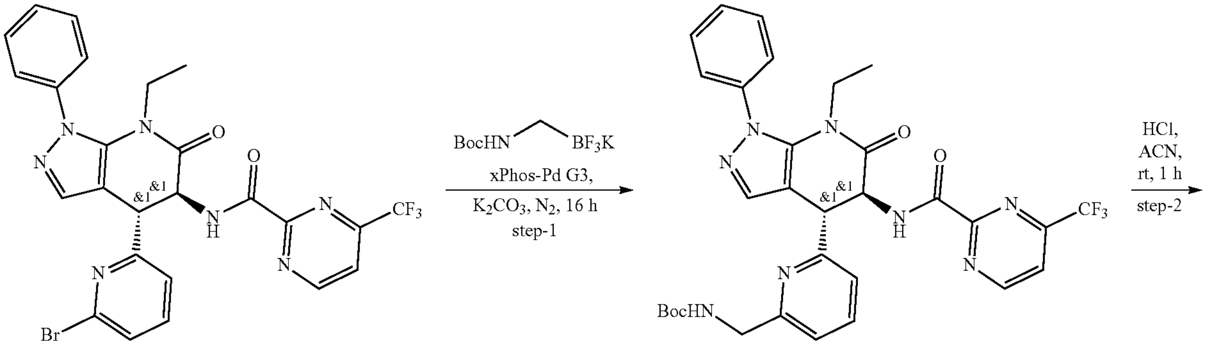

8 12

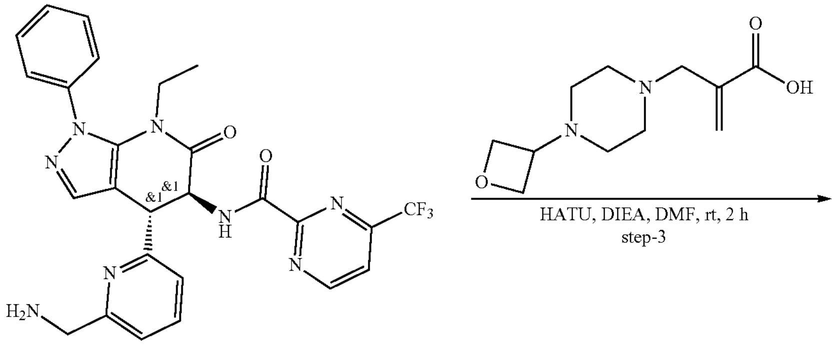

13

-continued

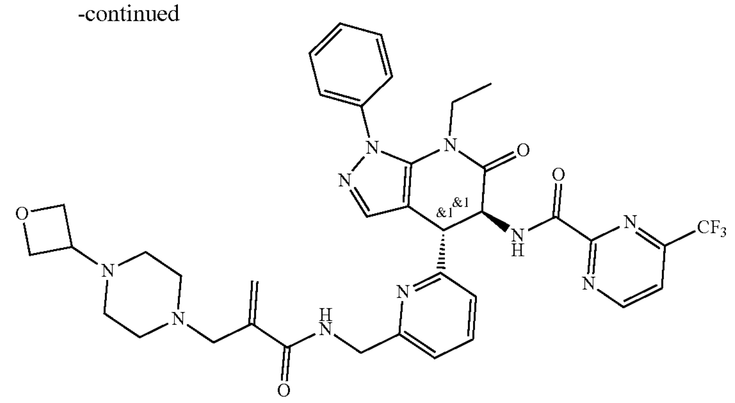

I-386 rac-tert-butyl ((6-((4R,5S)-7-ethyl-6-oxo-1-phenyl-5-(4-(trifluoromethyl)pyrimidine-2-carboxamido)-4,5,6,7-tetrahydro-1H-pyrazolo[3,4-b]pyridin-4-yl)pyridin-2-yl)methyl)carbamate (12)

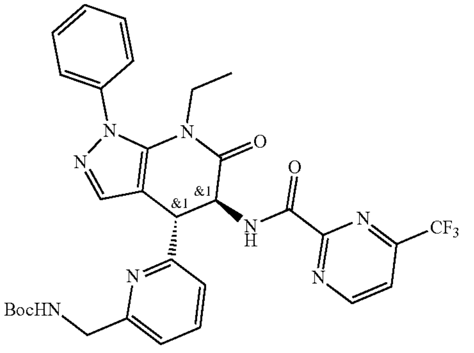 [SMILES: CCN1C(=O)[C@@H](NC(=O)c2nccc(C(F)(F)F)n2)[C@H](c2cccc(CNC(=O)OC(C)(C)C)n2)c2cnn(-c3ccccc3)c21]

To a mixture of rac-N-((4R,5S)-4-(6-bromopyridin-2-yl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (220 mg, 0.375 mmol, 1.00 equiv) and tert-butyl N-[(trifluoro-lambda4-boranyl)methyl]carbamate (149 mg, 0.750 mmol, 2.00 equiv) in 1,4-dioxane:$H_2O$=10:1 (4 ml) were added $K_2CO_3$ (156 mg, 1.13 mmol, 3.00 equiv) and XPhos Pd G3 (31.8 mg, 0.038 mmol, 0.10 equiv) in portions at room temperature under nitrogen atmosphere. The resulting mixture was stirred overnight at 80° C. under nitrogen atmosphere. The mixture was allowed to cool down to room temperature. The reaction was quenched with Water. The resulting mixture was extracted with EtOAc (3×8 mL). The combined organic layers were washed with brine (2×5 mL), dried over anhydrous $Na_2SO_4$. After filtration, the filtrate was concentrated under reduced pressure. The residue was purified by silica gel column chromatography, eluted with PE/EtOAc (6:1) to afford rac-tert-butyl ((6-((4R,5S)-7-ethyl-6-oxo-1-phenyl-5-(4-(trifluoromethyl)pyrimidine-2-carboxamido)-4,5,6,7-tetrahydro-1H-pyrazolo[3,4-b]pyridin-4-yl)pyridin-2-yl)methyl)carbamate (120 mg, 50.24%) as a white solid.

LCMS Calculated for $C_{31}H_{31}F_3N_8O_4$: 636.2; Observed: 637.2 $[M+H]^+$.

rac-N-((4R,5S)-4-(6-(aminomethyl)pyridin-2-yl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (13)

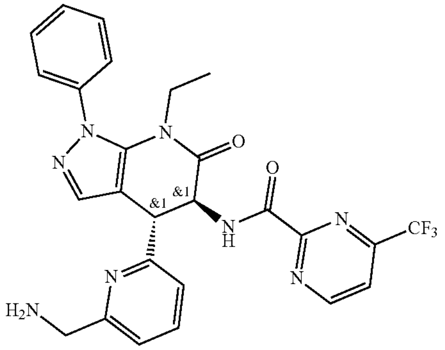 [SMILES: CCN1C(=O)[C@@H](NC(=O)c2nccc(C(F)(F)F)n2)[C@H](c2cccc(CN)n2)c2cnn(-c3ccccc3)c21]

To a stirred solution of rac-tert-butyl ((6-((4R,5S)-7-ethyl-6-oxo-1-phenyl-5-(4-(trifluoromethyl)pyrimidine-2-carboxamido)-4,5,6,7-tetrahydro-1H-pyrazolo[3,4-b]pyridin-4-yl)pyridin-2-yl)methyl)carbamate (120 mg, 0.188 mmol, 1.00 equiv) in CAN (2 ml) was added HCl (0.5 mL) dropwise at room temperature under air atmosphere. The resulting mixture was stirred for 30 min at room temperature under air atmosphere. The resulting mixture was concentrated under reduced pressure. This resulted in rac-N-((4R,5S)-4-(6-(aminomethyl)pyridin-2-yl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (100 mg, 98%) as a yellow solid. The crude product was used to the next step directly without further purification.

LCMS Calculated for $C_{26}H_{23}F_3N_8O_2$: 536.2; Observed: 537.2 $[M+H]^+$.

rac-N-((4R,5S)-7-ethyl-4-(6-((2-((4-(oxetan-3-yl)piperazin-1-yl)methyl)acrylamido)methyl)pyridin-2-yl)-6-oxo-1-phenyl-4,5,6,7-tetrahydro-1H-pyrazolo[3,4-b]pyridin-5-yl)-4-(trifluoromethyl)pyrimidine-2-carboxamide

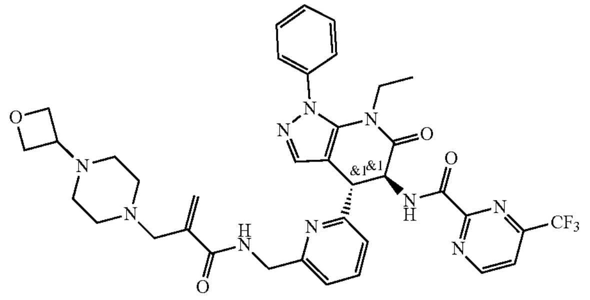 [SMILES: C=C(CN1CCN(C2COC2)CC1)C(=O)NCc1cccc([C@@H]2c3cnn(-c4ccccc4)c3N(CC)C(=O)[C@H]2NC(=O)c2nccc(C(F)(F)F)n2)n1]

To a mixture of rac-N-((4R,5S)-4-(6-(aminomethyl)pyridin-2-yl)-7-ethyl-6-oxo-1-phenyl-4,5,6,7-tetrahydro-1H-pyrazolo[3,4-b]pyridin-5-yl)-4-(trifluoromethyl)pyrimidine-2-carboxamide (150 mg, 0.242 mmol, 1.00 equiv) and HATU (138 mg, 0.363 mmol, 1.50 equiv) in DMF (2 ml) was added DIEA (78.1 mg, 0.605 mmol, 2.50 equiv) dropwise at room temperature. The resulting mixture was stirred for 2 h at room temperature. The residue was purified by reversed-phase flash chromatography with the following conditions: column, C18 silica gel; mobile phase, MeCN in Water (0.1% $NH_3 \cdot H_2O$), 30% to 90% gradient in 10 min; detector, UV 254 nm. This resulted in rac-N-((4R,5S)-7-ethyl-4-(6-((2-((4-(oxetan-3-yl)piperazin-1-yl)methyl)acrylamido)methyl)pyridin-2-yl)-6-oxo-1-phenyl-4,5,6,7-tetrahydro-1H-pyrazolo[3,4-b]pyridin-5-yl)-4-(trifluoromethyl)pyrimidine-2-carboxamide (20 mg, 11.11%) as a white solid.

$^1$H NMR (400 MHz, DMSO-$d_6$) δ 9.35-9.28 (m, 2H), 9.08 (d, J=5.8 Hz, 1H), 8.22 (d, J=4.9 Hz, 1H), 7.79-7.71 (m, 1H), 7.67-7.56 (m, 4H), 7.54 (d, J=7.0 Hz, 1H), 7.33 (d, J=7.8 Hz, 1H), 7.25 (d, J=7.7 Hz, 1H), 6.99 (s, 1H), 5.91 (s, 1H), 5.45 (s, 2H), 4.80 (d, J=12.3 Hz, 1H), 4.47-4.40 (m, 4H), 4.39-4.31 (m, 2H), 3.89-3.79 (m, 1H), 3.21 (s, 2H), 3.14-3.04 (m, 1H), 2.40-2.23 (s, 4H), 2.20 (s, 4H), 0.84 (t, J=7.0 Hz, 3H).

LCMS Calculated for $C_{37}H_{39}F_3N_{10}O_4$: 744.3; Observed (Method-V): 745.4 [M+H]$^+$, 99.70% at RT 1.395 min.

7. Synthesis of rac-tert-butyl (E)-4-((3-((4R,5S)-7-ethyl-3-methyl-6-oxo-1-phenyl-5-(4-(trifluoromethyl)pyrimidine-2-carboxamido)-4,5,6,7-tetrahydro-1H-pyrazolo[3,4-b]pyridin-4-yl)phenyl)amino)-4-oxobut-2-enoate I-359

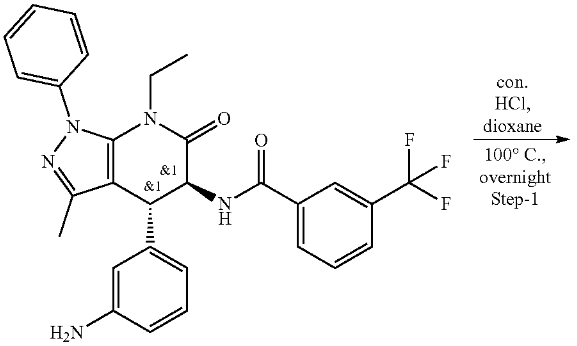

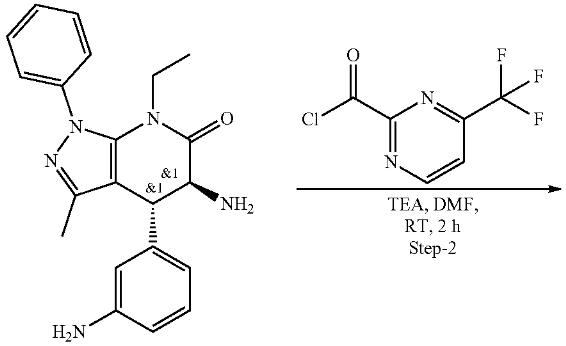

14

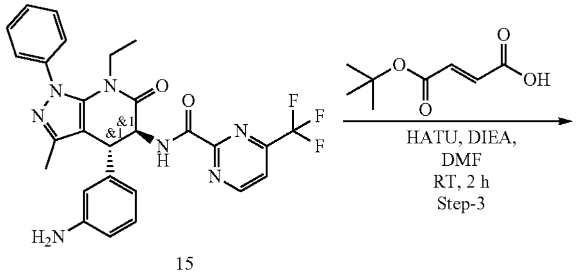

15

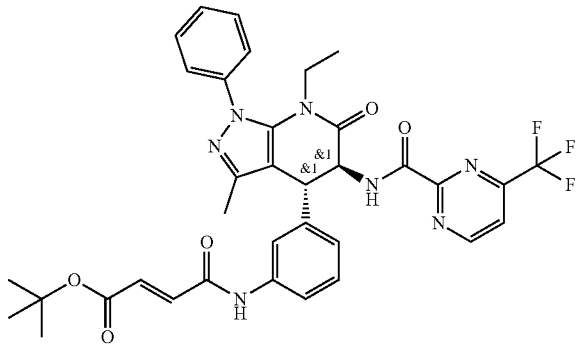

rac-(4R,5S)-5-amino-4-(3-aminophenyl)-7-ethyl-3-methyl-1-phenyl-1,4,5,7-tetrahydro-6H-pyrazolo[3,4-b]pyridin-6-one (14)

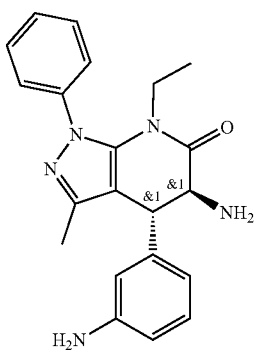 [SMILES: CCN1C(=O)[C@@H](N)[C@H](c2cccc(N)c2)c2c(C)nn(-c3ccccc3)c21]

A solution of rac-N-((4R,5S)-4-(3-aminophenyl)-7-ethyl-3-methyl-6-oxo-1-phenyl-4,5,6,7-tetrahydro-1H-pyrazolo[3,4-b]pyridin-5-yl)-3-(trifluoromethyl)benzamide (200 mg, 0.375 mmol, 1.00 equiv)(n HCl (3 mL, 55%) was stirred for 12 hours at 100° C. The mixture was allowed to cool down to room temperature, the resulting mixture was concentrated in vacuum to afford rac-(4R,5S)-5-amino-4-(3-aminophenyl)-7-ethyl-3-methyl-1-phenyl-1,4,5,7-tetrahydro-6H-pyrazolo[3,4-b]pyridin-6-one (130 mg, 90%) as a white solid, which was used for next step directly.

rac-N-((4R,5S)-4-(3-aminophenyl)-7-ethyl-3-methyl-6-oxo-1-phenyl-4,5,6,7-tetrahydro-1H-pyrazolo[3,4-b]pyridin-5-yl)-4-(trifluoromethyl)pyrimidine-2-carboxamide (15)

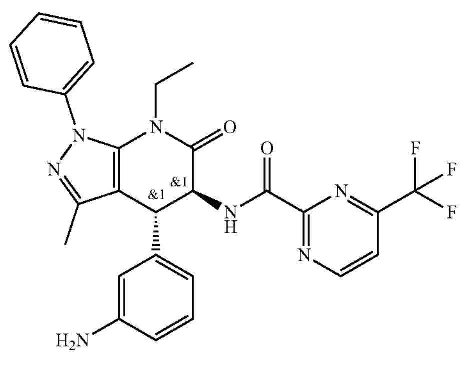 [SMILES: CCN1C(=O)[C@@H](NC(=O)c2nccc(C(F)(F)F)n2)[C@H](c2cccc(N)c2)c2c(C)nn(-c3ccccc3)c21]

A mixture of (4R,5S)-5-amino-4-(3-aminophenyl)-7-ethyl-3-methyl-1-phenyl-4H,5H-pyrazolo[3,4-b]pyridin-6-one (500 mg, 1.383 mmol, 1.0 equiv) and TEA (419 mg, 4.15 mmol, 3.0 equiv) in DMF (10.0 mL, 0.137 mmol) was stirred at 0° C. 4-(trifluoromethyl)pyrimidine-2-carbonyl chloride (349 mg, 1.66 mmol, 1.20 equiv) was then added, and the reaction mixture was stirred for 2.0 hours at room temperature. The resulting mixture was concentrated in vacuum, the residue was purified by prep-HPLC ($NH_3{\cdot}H_2O$ buffer) to give rac-N-((4R,5S)-4-(3-aminophenyl)-7-ethyl-3-methyl-6-oxo-1-phenyl-4,5,6,7-tetrahydro-1H-pyrazolo[3,4-b]pyridin-5-yl)-4-(trifluoromethyl)pyrimidine-2-carboxamide (200 mg, 25.7%) as a white solid.

rac-tert-butyl (E)-4-((3-((4R,5S)-7-ethyl-3-methyl-6-oxo-1-phenyl-5-(4-(trifluoromethyl)pyrimidine-2-carboxamido)-4,5,6,7-tetrahydro-1H-pyrazolo[3,4-b]pyridin-4-yl)phenyl)amino)-4-oxobut-2-enoate

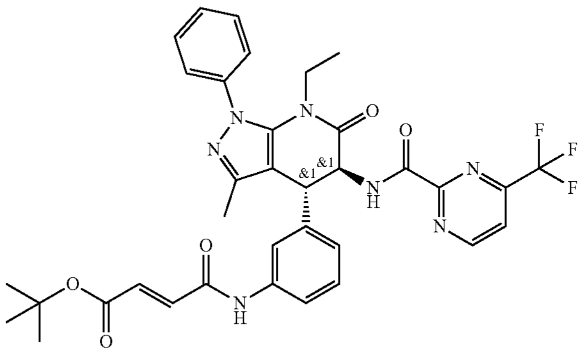 [SMILES: CCN1C(=O)[C@@H](NC(=O)c2nccc(C(F)(F)F)n2)[C@H](c2cccc(NC(=O)/C=C/C(=O)OC(C)(C)C)c2)c2c(C)nn(-c3ccccc3)c21]

A mixture of rac-N-((4R,5S)-4-(3-aminophenyl)-7-ethyl-3-methyl-6-oxo-1-phenyl-4,5,6,7-tetrahydro-1H-pyrazolo[3,4-b]pyridin-5-yl)-4-(trifluoromethyl)pyrimidine-2-carboxamide (200 mg, 0.373 mmol, 1.00 equiv), (E)-4-(tert-butoxy)-4-oxobut-2-enoic acid and DIEA (144 mg, 1.12 mmol, 3.00 equiv) in DMF (5.0 mL) was stirred at room temperature for 10 min. HATU (170 mg, 0.448 mmol, 1.2 equiv) was then added, and the reaction mixture was stirred for 1.0 hour at room temperature. The resulting mixture was concentrated in vacuum, the residue was purified by prep-HPLC ($NH_3{\cdot}H_2O$ buffer) to give rac-tert-butyl (E)-4-((3-((4R,5S)-7-ethyl-3-methyl-6-oxo-1-phenyl-5-(4-(trifluoromethyl)pyrimidine-2-carboxamido)-4,5,6,7-tetrahydro-1H-pyrazolo[3,4-b]pyridin-4-yl)phenyl)amino)-4-oxobut-2-enoate (50.0 mg, 19.4%) as a white solid.

$^1H$ NMR (300 MHz, DMSO-$d_6$) δ 10.55 (s, 1H), 9.42-9.19 (m, 2H), 8.20 (d, J=5.1 Hz, 1H), 7.70-7.60 (m, 4H), 7.61-7.44 (m, 3H), 7.30 (t, J=7.8 Hz, 1H), 7.13 (d, J=9.2 Hz, 1H), 7.07 (s, 1H), 6.58 (d, J=15.4 Hz, 1H), 5.23 (dd, J=12.0, 9.1 Hz, 1H), 4.58 (d, J=11.9 Hz, 1H), 3.79-3.72 (m, 1H), 3.08-3.01 (m, 1H), 1.48 (s, 12H), 0.82 (t, J=7.0 Hz, 3H).

LCMS Calculated for $C_{35}H_{34}F_3N_7O_5$: 689.26; Observed (Method-V): 690.3 $[M+H]^+$, 99.92% at RT 1.837 min.

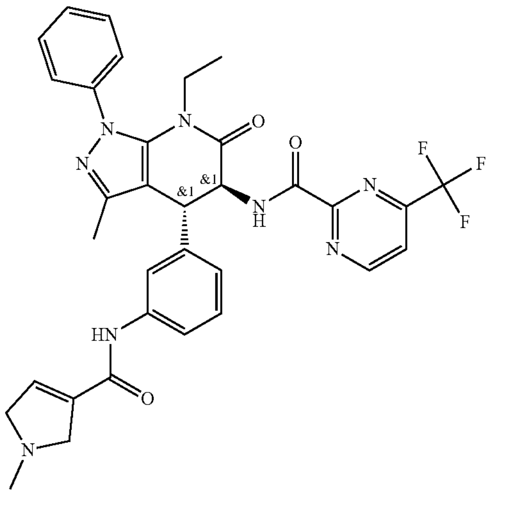 [SMILES: CCN1C(=O)[C@@H](NC(=O)c2nccc(C(F)(F)F)n2)[C@H](c2cccc(NC(=O)C3=CCN(C)C3)c2)c2c(C)nn(-c3ccccc3)c21]

I-224

$^1$H NMR (400 MHz, DMSO-d6) δ 9.78 (s, 1H), 9.33-9.26 (m, 2H), 8.21 (d, J = 5.1 Hz, 1H), 7.67-7.43 (m, 7H), 7.26 (t, J = 7.8 Hz, 1H), 7.09 (d, J = 7.6 Hz, 1H), 6.71 (s, 1H), 5.21 (dd, J = 12.0, 9.1 Hz, 1H), 4.56 (d, J = 12.0 Hz, 1H), 3.80 (dd, J = 14.2, 7.2 Hz, 1H), 3.60 (s, 4H), 3.09 (dd, J = 14.1, 7.1 Hz, 1H), 2.40 (s, 3H), 1.48 (s, 3H), 0.83 (t, J = 7.0 Hz, 3H).
LCMS Calculated for $C_{33}H_{31}F_3N_8O_3$: 644.2; Observed (Method-L): 645.5 [M + H]$^+$, 98.34% at RT 0.663 min.

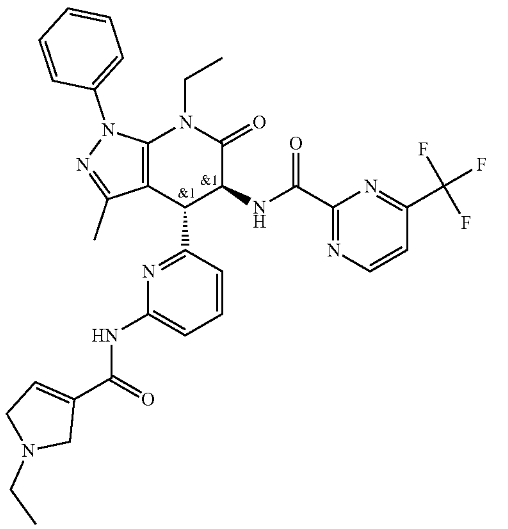 [SMILES: CCN1CC=C(C(=O)Nc2cccc([C@@H]3c4c(C)nn(-c5ccccc5)c4N(CC)C(=O)[C@H]3NC(=O)c3nccc(C(F)(F)F)n3)n2)C1]

I-225

$^1$H NMR (400 MHz, DMSO-d6) δ 9.77 (s, 1H), 9.35-9.24 (m, 2H), 8.20 (d, J = 5.1 Hz, 1H), 7.70-7.46 (m, 7H), 7.26 (t, J = 8.2 Hz, 1H), 7.09 (d, J = 7.7 Hz, 1H), 6.73 (s, 1H), 5.21 (dd, J = 12.0, 9.2 Hz, 1H), 4.56 (d, J = 12.0 Hz, 1H), 3.80 (dd, J = 14.2, 7.2 Hz, 1H), 3.59 (s, 4H), 3.16-3.02 (m, 1H), 2.59 (q, J = 7.2 Hz, 2H), 1.48 (s, 3H), 1.03 (t, J = 7.2 Hz, 3H), 0.83 (t, J = 7.0 Hz, 3H).
LCMS Calculated for $C_{34}H_{33}F_3N_8O_3$: 658.2; Observed (Method-K): 659.5 [M + H]$^+$, 97.92% at RT 0.672 min.

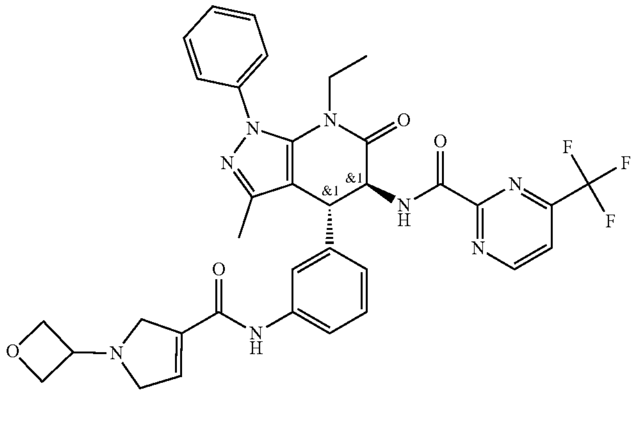 [SMILES: CCN1C(=O)[C@@H](NC(=O)c2nccc(C(F)(F)F)n2)[C@H](c2cccc(NC(=O)C3=CCN(C4COC4)C3)c2)c2c(C)nn(-c3ccccc3)c21]

I-226

$^1$H NMR (400 MHz, DMSO-d6) δ 9.82 (s, 1H), 9.35-9.23 (m, 2H), 8.21 (d, J = 5.1 Hz, 1H), 7.68-7.45 (m, 7H), 7.26 (t, J = 8.1 Hz, 1H), 7.09 (d, J = 7.7 Hz, 1H), 6.76 (s, 1H), 5.21 (dd, J = 12.0, 9.2 Hz, 1H), 4.67-4.45 (m, 5H), 3.95 (s, 1H), 3.80 (dd, J = 14.3, 7.2 Hz, 1H), 3.69 (s, 4H), 3.09 (dd, J = 14.1, 7.0 Hz, 1H), 1.48 (s, 3H), 0.83 (t, J = 7.0 Hz, 3H).
LCMS Calculated for $C_{35}H_{33}F_3N_8O_4$: 686.2; Observed (Method-V): 687.4 [M + H]$^+$, 95.57% at RT 1.465 min.

-continued

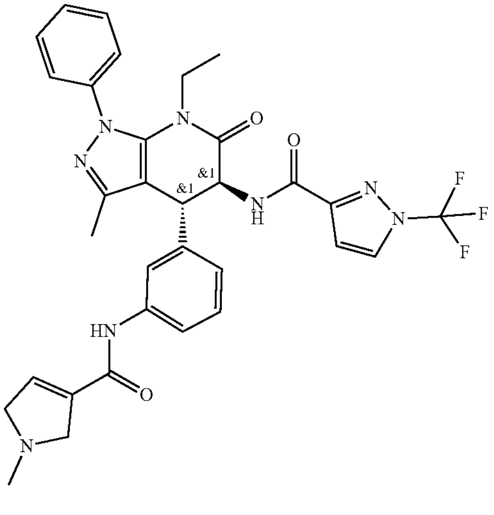 [SMILES: CCN1C(=O)[C@@H](NC(=O)c2ccn(C(F)(F)F)n2)[C@H](c2cccc(NC(=O)C3=CCN(C)C3)c2)c2c(C)nn(-c3ccccc3)c21]

$^1$H NMR (300 MHz, Chloroform-d) δ 7.79-7.70 (m, 2H), 7.67 (d, J = 8.2 Hz, 1H), 7.49 (q, J = 3.7, 3.1 Hz, 5H), 7.40 (d, J = 9.7 Hz, 1H), 7.30-7.25 (m, 1H), 7.13 (d, J = 7.6 Hz, 1H), 6.82 (d, J = 2.7 Hz, 1H), 6.51 (s, 1H), 5.37 (dd, J = 12.4, 9.3 Hz, 1H), 4.21 (d, J = 12.4 Hz, 1H), 3.91 (dq, J = 14.0, 7.0 Hz, 1H), 3.78 (t, J = 4.6 Hz, 2H), 3.69 (d, J = 4.8 Hz, 2H), 3.19 (dq, J = 13.8, 6.6 Hz, 1H), 2.52 (s, 3H), 1.60 (s, 3H), 0.92 (t, J = 7.1 Hz, 3H).
LCMS Calculated for $C_{32}H_{31}F_3N_8O_3$: 632.25; Observed (Method-Y): 633.2 [M + H]$^+$, 95.53% at RT 2.049 min.

I-323

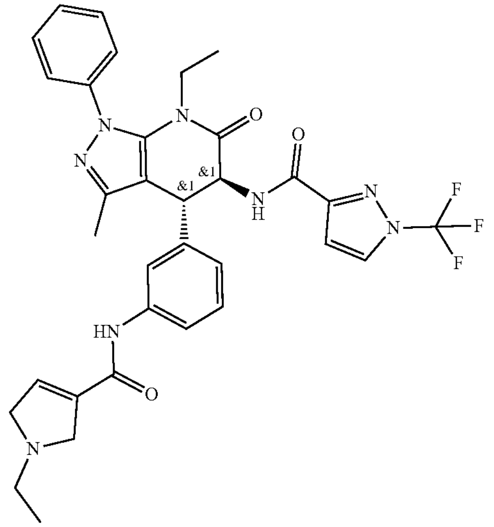 [SMILES: CCN1CC=C(C(=O)Nc2cccc([C@@H]3c4c(C)nn(-c5ccccc5)c4N(CC)C(=O)[C@H]3NC(=O)c3ccn(C(F)(F)F)n3)c2)C1]

$^1$H NMR (300 MHz, DMSO-d$_6$) δ 9.77 (s, 1H), 8.76 (d, J = 9.0 Hz, 1H), 8.56 (d, J = 2.8 Hz, 1H), 7.66-7.47 (m, 6H), 7.31-7.22 (m, 1H), 7.07 (d, J = 7.7 Hz, 1H), 6.90 (d, J = 2.8 Hz, 1H), 6.74 (d, J = 2.1 Hz, 1H), 5.15 (dd, J = 12.2, 9.0 Hz, 1H), 4.46 (d, J = 12.2 Hz, 1H), 3.80 (dd, J = 14.2, 7.2 Hz, 1H), 3.66-3.54 (m, 5H), 3.07 (dd, J = 13.9, 7.1 Hz, 1H), 2.65-2.53 (m, 2H), 1.46 (s, 3H), 1.03 (t, J = 7.2 Hz, 3H), 0.81 (t, J = 7.0 Hz, 3H).
LCMS Calculated for $C_{33}H_{33}F_3N_8O_3$: 646.68; Observed (Method-Z): 647.70 [M + H]$^+$, 95.40% at RT 1.578 min.

I-227

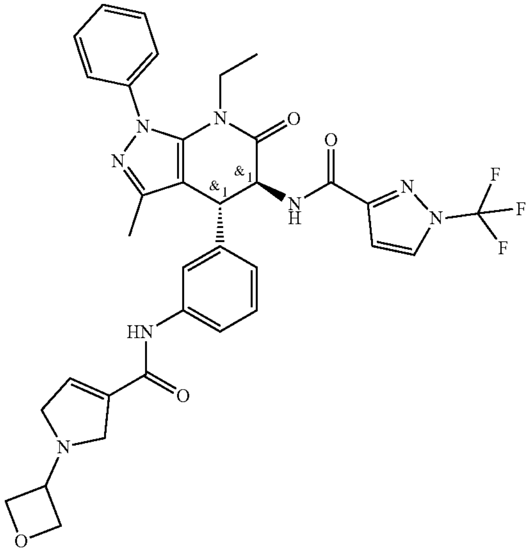 [SMILES: CCN1C(=O)[C@@H](NC(=O)c2ccn(C(F)(F)F)n2)[C@H](c2cccc(NC(=O)C3=CCN(C4COC4)C3)c2)c2c(C)nn(-c3ccccc3)c21]

$^1$H NMR (300 MHz, DMSO-d$_6$) δ 9.82 (s, 1H), 8.78 (d, J = 9.1 Hz, 1H), 8.58 (d, J = 2.8 Hz, 1H), 7.68-7.45 (m, 7H), 7.27 (t, J = 7.8 Hz, 1H), 7.08 (d, J = 7.6 Hz, 1H), 6.91 (d, J = 2.8 Hz, 1H), 6.77 (d, J = 2.4 Hz, 1H), 5.16 (dd, J = 12.3, 9.1 Hz, 1H), 4.65-4.56 (m, 2H), 4.51-4.43 (m, 3H), 3.97-3.72 (m, 2H), 3.65 (d, J = 5.0 Hz, 4H), 3.06 (dd, J = 14.1, 7.0 Hz, 1H), 1.45 (s, 3H), 0.81 (t, J = 7.0 Hz, 3H).
LCMS Calculated for $C_{34}H_{33}F_3N_8O_4$: 674.69; Observed (Method-C): 675.70 [M + H]$^+$, 97.18% at RT 0.841 min.

-continued

I-336

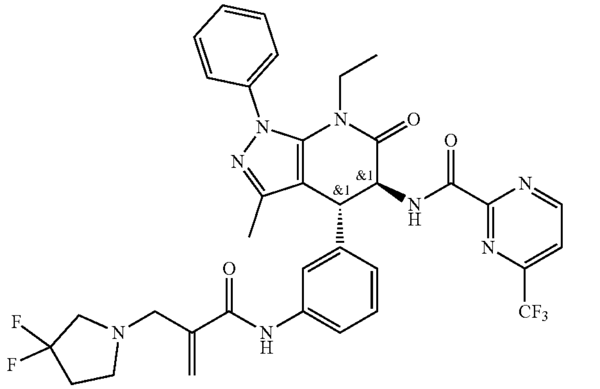 [SMILES: C=C(CN1CCC(F)(F)C1)C(=O)Nc1cccc([C@@H]2c3c(C)nn(-c4ccccc4)c3N(CC)C(=O)[C@H]2NC(=O)c2nccc(C(F)(F)F)n2)c1]

$^1$H NMR (400 MHz, DMSO-$d_6$) δ 10.39 (s, 1H), 9.30 (t, J = 7.5 Hz, 2H), 8.20 (d, J = 5.0 Hz, 1H), 7.68 (s, 1H), 7.56 (m, 6H), 7.27 (t, J = 7.8 Hz, 1H), 7.10 (d, J = 7.8 Hz, 1H), 5.94 (s, 1H), 5.62 (s, 1H), 5.25-5.15 (m, 1H), 4.56 (d, J = 11.8 Hz, 1H), 3.78 (m, 1H), 3.40 (s, 2H), 3.09 (m, 2H), 2.93 (s, 1H), 2.76 (s, 2H), 2.28 (s, 2H), 1.49 (s, 3H), 0.82 (t, J = 7.0 Hz, 3H).
LCMS Calculated for $C_{35}H_{33}F_5N_8O_3$: 708.26; Observed (Method-AM): 709.1 [M + H]+, 85.72% at RT 1.678 min.

I-228

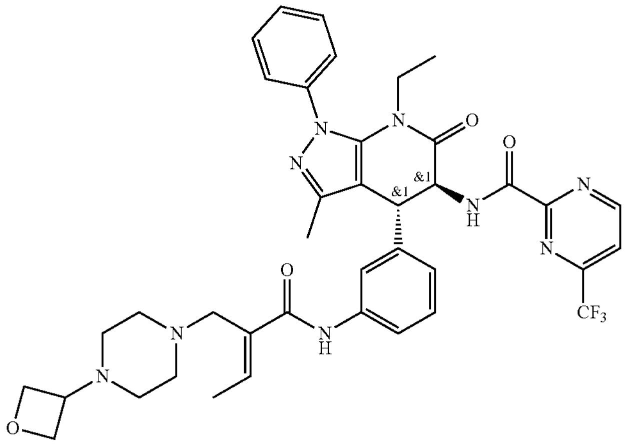 [SMILES: C/C=C(\CN1CCN(C2COC2)CC1)C(=O)Nc1cccc([C@@H]2c3c(C)nn(-c4ccccc4)c3N(CC)C(=O)[C@H]2NC(=O)c2nccc(C(F)(F)F)n2)c1]

$^1$H NMR (400 MHz, DMSO-$d_6$) δ 11.38 (s, 1H), 9.34-9.27 (m, 2H), 8.20 (d, J = 5.0 Hz, 1H), 7.64-7.49 (m, 7H), 7.25 (t, J = 7.9 Hz, 1H), 7.06 (d, J = 7.6 Hz, 1H), 6.78 (d, J = 7.3 Hz, 1H), 5.23-5.14 (m, 1H), 4.56 (d, J = 11.8 Hz, 1H), 4.39 (t, J = 6.4 Hz, 1H), 4.32 (dd, J = 16.8, 6.1 Hz, 3H), 3.78 (dd, J = 14.1, 7.2 Hz, 1H), 3.30-3.10 (m, 1H), 2.67 (s, 4H), 2.49 (s, 2H), 1.81 (d, J = 7.3 Hz, 3H), 1.65 (s, 5H), 1.50 (s, 3H), 0.82 (t, J = 7.0 Hz, 3H).
LCMS Calculated for $C_{39}H_{42}F_3N_9O_4$: 757.33; Observed (Method-AN): 758.4 [M + H]+, 97.72% at RT 1.533 min.

I-229

Example 19: TR-FRET Assay

The TR-FRET assay was designed following the Scott et al. protocol (Scott et al., Nat Chem Biol. 2017 August; 13(8): 850-857. doi:10.1038/nchembio.2386). The recombinant form of the DCN1 (DCUND1) protein PONY domain was produced using an *E. coli* expression system at Viva Biotech (China). The DCN1 protein was biotinylated (EZ sulfo-NHS-LC-biotin; Thermofisher) for labeling with streptavidin terbium (Tb) cryptate in the reaction. The probe was changed to a non-covalent DCN1 inhibitor labeled with carboxyfluorescein (FAM; Zhou et al., *Nat Commun.* 2017; 8: 1150. doi: 10.1038/s41467-017-01243-7). Buffer conditions were modified to enhance protein stability by exchanging Tween20 for TritonX and increasing NaCl to 200 mM. The compounds were screened against 5 nM DCN1 and 20 nM FAM-probe or 0.31 nM DCN1 and 900 nM total probe (100 nM FAM-labeled plus 800 nM unlabeled). The TR-FRET ratio between Tb-DCN1 and the FAM-labeled probe was measured in a 384-well opti-plate (Perkin Elmer) using a plate reader (BMG) at 1, 5, and 24 hrs after treatment with compound (final DMSO concentration of 0.1%). The ratio was normalized to the high (DCN1 and FAM-probe) and low (DCN1 and no probe) controls for a readout of % activity (=100*(x−low)/(high−low).

Example 20: Intact Protein MS Analysis with the RapidFire-TOF System

DCN1 protein, His-TEV-DCN1, were expressed in *E. Coli.* The His-tagged protein was first purified with an Ni-NTA column. The His-tag was cleaved using His-tag TEV protease and the His-tags were removed using a second Ni-NTA column. Protein purity was verified with SDS-PAGE and intact MS. DCN1 was dissolved in a buffer containing 25 mM Tris-HCl, 200 mM NaCl, and 1 mM DTT at 400 nM. 11 concentrations of compounds were added to the DCN1 solution and incubated at room temperature for 3 hours, unless otherwise specified. The reaction plates were quenched by adding 0.2% formic acid. Quenched assay plates were analyzed with an Agilent RapidFire 360 system connected to an Agilent 6545 Q-TOF mass spectrometer equipped with an AJS source. 10 μL of sample volume was loaded onto a custom packed cartridge (4 μL, PLRP-S 30 μm/1000 Å pore; Optimize Technologies) with loading buffer ($ddH_2O$ with 0.09% (vol/vol) formic acid and 0.01%

(vol/vol) trifluoroacetic acid; 1.25 ml/min) for 6 seconds before being eluted directly into the mass spectrometer in elution buffer (80% acetonitrile with 0.09% (vol/vol) formic acid and 0.01% (vol/vol) trifluoroacetic acid; 0.5 ml/min) for 7 seconds. The cartridge was re-equilibrated with loading buffer for 1 second before collection of the next sample. The Q-TOF was operated in TOF-only positive ionization mode set to the following parameters: Gas Temp=350 C, Drying Gas=7 l/min, Nebulizer=50 psi, Sheath Gas Temp=400 C, Sheath Gas Flow=12 l/min, VCap=4000 V, Nozzle Voltage=1000 V, Fragmentor=125 V, Skimmer=65 V and Oct 1 RF Vpp=750V. Raw MS data files were deconvoluted and analyzed using the Agilent MassHunter Bioconfirm software package to identify both parent protein and expected compound adduct mass signatures.

Example 21: HBG1 Nanostring Assay

A Nanostring Assay was performed to evaluate the ability of the compounds to induce expression of the fetal hemoglobin gene HBG1 in cells. The data are shown as EC50, with stronger inducers having a lower EC50 value and higher YMax.

CD34 Culture and Sample Preparation

Mobilized peripheral blood (mPB) derived CD34+ hematopoietic stem and progenitor cells (HSPCs) were thawed and plated at 500,000 cells/ml on day of cell thaw (day −4) in StemSpan (StemCell Tech, 09600) complete media supplemented with 1% StemSpan CC100 (StemCell Tech, 02690), and 0.2% human recombinant thrombopoietin (StemCell Tech, 02822). Forty eight hours later (day −2), the cells were passaged at a density of 200,000 cells/ml (100 ul/well in 96 well culture plate) in complete expantion media. The cells were plated at 200,000 cells/ml on day 0 and day 3, 400,000 cells/ml on day 5 in phase 1 erythroid differentiation containing StemSpan with 2.5 U/mL of EPO (R&D systems, 287-TC-500), 0.5 mg/mL of Holo-Transferrin (Sigma, T0665-500MG), 1× Glutamine (Gluta-Max) (Gibco, 35050-061), 5 µL/mL Lipid Mixture (Sigma, L0288-100ML), 50 ng/mL SCF (R&D Systems, 255-SV-050), 10 ng/mL IL-3 (R&D Systems, 203-ILO10) and 10 ng/mL Insulin (Sigma, I9278-5ML) all 200 µl per well in 96 well culture plate. Cells were then passaged at 500,000 cells/ml and 200 µl per well on day 7 in phase 2 Erythroid differentiation (Phase 1 erythroid differentiation removing IL-3) until collection day (Day 10). The culture conditions were used for both control DMSO as well as experimental treatments.

For all cell pasagings, cells were centrifuged at 300 g for 8 minutes at room temperature and cell number were normalized by MANTIS and Integra VIAFLO 384. All the compounds are diluted in DMSO and added to complete media by Formulatrix FAST and mixed starting from day −2. Cells were counted by Luna cell counter with AOPI Staining Solution (Nexcelom Bioscience, CS2-0106-25 mL) on day-2. Cells were counted by BD FACSCelesta Flow Cytometer with CountBright™ Plus Absolute Counting Beads (Thermal Fisher Scientific, C36995) and SYTOX AADvanced™ Ready Flow™ Reagent (Invitrogen, R37173) for other passages. Cells were cultured at 37° C. and 5% $CO_2$. DMSO concentration was kept at 0.1% to minimize any effects to the cells by the vehicle. Due to the insolubility of positive control, it was freshly made every 6 weeks with stock concentration at 3 mM while stock concentration for other compounds are 10 mM. Compound plates were kept at room temptureture to protect from light to avoid multiple freeze and thaw cycle.

On the collection day (Day10), 100K cells were collected and stored at −80° C. For direct hybridization for Nanostring, 100K cell pellet was lyzed in 25 µL of RLT (QIAGEN, 79216) with 1×β-Mercaptoethanol (Gibco, 21985-023) and shaked at 300-500 RPM for 5 minutes at room temperature. Cell lysate was stored in −80° C. after lysis.

Hybridization and Imaging

All hybridizations were done in a total volume of 15 µL (3 µL of RNA lysate added to master mix of 12 µL probe A/B, capture probe/reporter probes, proteinase K and attenuation oligos suspended in hybridization buffer). Samples were hybridized at 67° C. for 22 hr. Following hybridization, the tripartide complexes were purified, immobilized by nCounter Prep Station and imaged by Digital Analyzer (nCounter MAX/FLEX Analysis System), to generate digital counts of barcodes corresponding to each target in the multiplexed reaction. Labeled barcodes obtained from unamplified extracts were counted at 555 images or field of view (FOV). The barcode counts for each sample were recorded in Reporter Code Count (RCC) files that are imported into nSolver analysis software (provided with CodeSet by NS) for quality control evaluation.

Quality Control (QC) Metrics and Data Analysis

The quality control (QC) metric included limit of detection QC by checking for wells with less than 100 total counts for positive controls.

Hybridization signals were normalized against the ERCC positive controls and CodeSet Content (housekeeping gene). Briefly, this involved first calculating a sample-specific scaling factor by calculating arithmetic mean of geomeans of all ERCC positive controls with counts more than zero in all samples. Then this arithmetic mean was divided by the geometric mean of each lane to generate a lane-specific normalization factor. All negative controls and target-specific signal values were then normalized by multiplying counts values with their sample-specific scaling factor. The acceptable range for scaling factors is 0.3-3.0. For housekeeping gene(s) normalization, first calculating the arithmetic mean of geometric means of selected housekeeping genes for each lane for all samples. Then this arithmetic mean was divided by the geometric mean of each lane to generate a lane-specific normalization factor followed by multiplying the counts for every gene by its lane-specific normalization factor. The acceptable range for housekeeping genes normalization scaling factors is 0.1-10.

HBG1 dose-response curves, % Emax and EC50 values were generated by Dotmatic with setting control DMSO as 0% and biology control as 100%. When reporting EC50, Top will be fixed as 10000 for compounds with observed Emax>=50%. For compounds with observed Emax<50% is reporting either inactive or max observed Emax.

Compounds with an $EC_{50}$ less than or equal to 100.0 nM are designated as "+++". Compounds with an $EC_{50}$ greater than 100.0 nM and less than or equal to 1000.0 nM are designated as "C++". Compounds with an $EC_{50}$ greater than 1000.0 nM are designated as "+". The results are shown in Table 1-I below.

The Nanostring Ymax observed data is relative to a control compound, presented in 0% which is shown in Table 1-I below. Compounds with a Nanostring Ymax greater than or equal to 0.0 and less than or equal to 50.0 are designated as "+". Compounds with a Nanostring Ymax greater than 50.0 and less than or equal to 100.0 are designated as "++". Compounds with a Nanostring Ymax greater than 100.0 are designated as

TABLE 1-I

| HBG1 Nanostring Assay | | |
|---|---|---|
| Compound I-No. | Nanostring EC50 (nM) | Nanostring Ymax obs (%) |
| 1 | N/A | ++ |
| 2 | +++ | +++ |
| 5 | + | ++ |
| 6 | +++ | +++ |
| 7 | N/A | ++ |
| 9 | +++ | +++ |
| 14 | +++ | ++ |
| 15 | +++ | +++ |
| 28 | + | ++ |
| 34 | ++ | +++ |
| 38 | ++ | +++ |
| 44 | ++ | ++ |
| 46 | + | + |
| 47 | + | ++ |
| 48 | + | +++ |
| 56 | ++ | ++ |
| 58 | ++ | ++ |
| 65 | +++ | ++ |
| 68 | + | + |
| 69 | + | ++ |
| 72 | + | ++ |
| 75 | ++ | +++ |
| 77 | + | +++ |
| 78 | ++ | +++ |
| 81 | +++ | ++ |
| 82 | N/A | ++ |
| 83 | ++ | +++ |
| 86 | + | + |
| 130 | + | ++ |
| 131 | ++ | ++ |
| 133 | N/A | ++ |
| 135 | N/A | ++ |
| 141 | N/A | ++ |
| 146 | ++ | ++ |
| 147 | +++ | +++ |
| 150 | + | ++ |
| 153 | +++ | +++ |
| 166 | + | +++ |
| 167 | ++ | +++ |
| 170 | + | ++ |
| 173 | ++ | + |
| 177 | +++ | +++ |
| 180 | + | ++ |
| 181 | + | + |
| 190 | + | ++ |
| 191 | + | + |
| 193 | + | +++ |
| 194 | ++ | + |
| 197 | ++ | +++ |
| 207 | ++ | + |
| 208 | + | + |
| 212 | ++ | +++ |
| 214 | +++ | +++ |
| 215 | | ++ |
| 216 | +++ | +++ |
| 217 | +++ | +++ |
| 234 | +++ | +++ |
| 236 | | ++ |
| 264 | | ++ |
| 289 | | ++ |
| 290 | +++ | ++ |
| 291 | | +++ |
| 293 | | ++ |
| 300 | +++ | +++ |
| 305 | +++ | +++ |
| 312 | | ++ |
| 328 | +++ | ++ |
| 332 | | +++ |

TABLE 1-I-continued

| HBG1 Nanostring Assay | | |
|---|---|---|
| Compound I-No. | Nanostring EC50 (nM) | Nanostring Ymax obs (%) |
| 361 | | ++ |
| 375 | | +++ |
| 383 | +++ | +++ |

Example 22: AlphaLISA Assay

An AlphaLISA assay was performed to evaluate the ability of the compounds to suppress neddylation, which is downstream from DCN-1 and DCN-2. A stronger inhibition of DCN-1 and DCN-2 is expected to result in a suppression of neddylation as shown by a lower AlphaLISA signal.

The AlphaLISA assay for detecting Cullin-3 (CUL3) neddylation was performed according to manufacturer instructions (Revvity, Hopkinton, MA). Briefly, TF1 cells (ATCC) were plated in Iscove's Modified Dulbecco's Medium (IMDM) without supplements in 384-well plates. These cells were treated with 11 concentrations for 3 hours before lysing them with AlphaLISA lysis buffer, 5× (Revvity). To detect the level of CUL3 neddylation, biotinylated anti-NEDD8 antibody, was added followed by AlphaLISA Acceptor beads conjugated with anti-CUL3 antibody. After overnight incubation, Streptavidin-coated Alpha Donor beads were added and incubated for 1 hour. The AlphaLISA signal was then read on a VICTOR Nivo Multimode Microplate Reader (Revvity, Hopkinton, MA). The positive control was 1 μM DI-1548, which is reported to reduce CUL3 neddylation (Zhou et al. Nature Comm. 2021). The neddylation signal was normalized such that the percent inhibition is 0% for vehicle control and 100% for positive control. The dose-response curves were fitted with the Hill equation to obtain IC50 values (Graphpad Prism).

Compounds with an $IC_{50}$ less than or equal to 100.0 nM are designated as "+++". Compounds with an $IC_{50}$ greater than 100.0 nM and less than or equal to 1000.0 nM are designated as "++". Compounds with an $IC_{50}$ greater than 1000.0 nM are designated as "+". The results are shown in Table 1-II below.

TABLE 1-II

| AlphaLISA Assay | |
|---|---|
| Compound I-No. | Neddylation IC50 (nM) |
| 1 | +++ |
| 2 | +++ |
| 3 | +++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 28 | + |
| 34 | +++ |
| 37 | +++ |
| 38 | ++ |
| 44 | +++ |
| 46 | +++ |

TABLE 1-II-continued

| AlphaLISA Assay | |
|---|---|
| Compound I-No. | Neddylation IC50 (nM) |
| 47 | + |
| 48 | + |
| 56 | ++ |
| 58 | ++ |
| 60 | +++ |
| 61 | +++ |
| 62 | +++ |
| 63 | +++ |
| 64 | +++ |
| 65 | +++ |
| 66 | +++ |
| 68 | ++ |
| 69 | +++ |
| 72 | ++ |
| 75 | ++ |
| 77 | ++ |
| 78 | ++ |
| 81 | +++ |
| 82 | +++ |
| 83 | +++ |
| 86 | + |
| 103 | + |
| 130 | ++ |
| 131 | ++ |
| 133 | +++ |
| 135 | +++ |
| 136 | +++ |
| 137 | +++ |
| 141 | +++ |
| 142 | +++ |
| 146 | +++ |
| 147 | +++ |
| 150 | + |
| 153 | +++ |
| 160 | +++ |
| 161 | +++ |
| 162 | +++ |
| 163 | +++ |
| 166 | + |
| 167 | ++ |
| 170 | ++ |
| 173 | + |
| 177 | +++ |
| 178 | + |
| 180 | ++ |
| 181 | + |
| 190 | + |
| 191 | ++ |
| 193 | + |
| 194 | ++ |
| 197 | ++ |
| 207 | ++ |
| 208 | ++ |
| 212 | ++ |
| 213 | + |
| 215 | +++ |
| 216 | +++ |
| 217 | +++ |
| 218 | +++ |
| 219 | +++ |
| 220 | +++ |
| 221 | +++ |
| 222 | +++ |
| 223 | +++ |
| 224 | ++ |
| 225 | ++ |
| 226 | +++ |
| 227 | +++ |
| 228 | +++ |
| 229 | +++ |
| 230A | +++ |
| 230B | +++ |
| 231 | +++ |
| 232 | +++ |
| 233 | +++ |
| 234 | +++ |

TABLE 1-II-continued

| AlphaLISA Assay | |
|---|---|
| Compound I-No. | Neddylation IC50 (nM) |
| 235 | + |
| 236 | +++ |
| 237 | ++ |
| 238 | + |
| 239 | ++ |
| 240 | +++ |
| 241 | ++ |
| 242 | + |
| 243 | ++ |
| 244 | ++ |
| 245 | + |
| 246 | +++ |
| 247 | +++ |
| 248 | +++ |
| 249 | + |
| 250 | + |
| 251 | +++ |
| 252 | ++ |
| 253 | ++ |
| 254 | +++ |
| 255 | + |
| 256 | +++ |
| 257 | + |
| 258 | ++ |
| 259 | + |
| 260 | + |
| 261 | +++ |
| 262 | + |
| 263 | + |
| 264 | +++ |
| 265 | ++ |
| 266 | + |
| 277 | +++ |
| 278 | +++ |
| 279 | + |
| 280 | +++ |
| 281 | +++ |
| 282 | ++ |
| 283 | +++ |
| 284 | ++ |
| 285 | ++ |
| 286 | ++ |
| 287 | +++ |
| 288 | +++ |
| 289 | +++ |
| 290 | +++ |
| 291 | +++ |
| 292 | +++ |
| 293 | +++ |
| 294 | ++ |
| 295 | +++ |
| 296 | +++ |
| 297 | +++ |
| 298 | +++ |
| 299 | + |
| 300 | +++ |
| 301 | ++ |
| 302 | +++ |
| 303 | +++ |
| 304 | ++ |
| 305 | +++ |
| 306 | + |
| 307 | + |
| 308 | +++ |
| 309 | ++ |
| 310 | +++ |
| 311 | ++ |
| 312 | +++ |
| 313 | ++ |
| 314 | +++ |
| 315 | +++ |
| 316 | ++ |
| 317 | +++ |
| 318 | +++ |
| 321 | + |
| 322 | ++ |

TABLE 1-II-continued

| AlphaLISA Assay | |
|---|---|
| Compound I-No. | Neddylation IC50 (nM) |
| 323 | +++ |
| 324 | +++ |
| 325 | +++ |
| 326 | + |
| 327 | +++ |
| 328 | +++ |
| 330 | + |
| 331 | ++ |
| 332 | +++ |
| 333 | ++ |
| 338 | ++ |
| 339 | + |
| 340 | + |
| 341 | +++ |
| 342 | ++ |
| 343 | ++ |
| 344 | +++ |
| 345 | + |
| 342 | ++ |
| 346 | +++ |
| 347 | +++ |
| 348 | + |
| 349 | ++ |
| 350 | +++ |
| 351 | +++ |
| 352 | +++ |
| 353 | +++ |
| 354 | + |
| 355 | +++ |
| 356 | +++ |
| 357 | +++ |
| 359 | +++ |
| 360 | + |
| 361 | +++ |
| 362 | + |
| 363 | +++ |
| 364 | +++ |
| 365 | +++ |
| 366 | ++ |
| 367 | ++ |
| 368 | +++ |
| 369 | + |
| 370 | + |
| 371 | + |
| 372 | + |
| 373 | ++ |
| 374 | ++ |
| 375 | +++ |
| 376 | +++ |
| 377 | ++ |
| 378 | +++ |
| 379 | + |
| 380 | ++ |
| 381 | + |
| 382 | +++ |
| 383 | +++ |
| 384 | +++ |
| 385 | +++ |

Example 23: HbF HPLC Cell Culture and Analysis

A Cell Culture Assay was performed to evaluate the ability of compounds to induce fetal hemoglobin in a cell culture. The amount fetal hemoglobin protein induced was measured by HPLC.

Cell culture began on Day −4 (thaw day). Thaw buffer was prepared by sterile filtering 6 mL of Human Serum Albumin and 144 mL of PBS to make sterile 1% HSA/PBS. Cells were removed from liquid nitrogen storage and mostly thawed in a 37° C. water bath. Once the ice in the cryovials was melted, cells were transferred quickly into a 50 mL conical tube. Cryovial was rinsed once with thaw buffer and buffer was transferred over to the conical tube as well. Next, doubling volumes of thaw buffer was added to the conical and gently swirled for ~30 seconds to one minute (for example: 2 mL was added and swirled, then 4 mL, then 8 mL, and so on) until the volume in the conical is 32 mL. Cells and buffer were centrifuged at 300 G for 8 minutes, and the supernatant was aspirated. Another 32 mL of thaw buffer was added slowly, swirling the tube. The tube was again centrifuged at 300 G for 8 minutes and the supernatant was aspirated. Cells were counted by resuspending in 1 mL of expansion media and counting with AOPI to determine the concentration of cells/mL.

On day 2, Passage & Treatment Day, each cell culture well was counted. Next fresh CD34 Expansion Media was made which contained StemSpan SFEM, CC100 and TPO all from StemCell technologies. Appropriate volume of cells were collected, centrifuged at 300 g and resuspended in fresh media. Cells were plated in treatment format at a density of 200,000 cells/ml, 25,000 cells/well. Finally, they were treated with test compounds as well as positive and negative controls.

On Days 0, 3 & 5 the same process was carried out. First, each cell culture well was counted. Next Phase 1 Erythroid Differentiation Media was freshly made, which contained StemSpan SFEM, 2.5 U/ml EPO, 0.5 mg/ml Holo-TF, 1× Glutamax, 5 μl/ml chemically defined lipid mixture, 10 ng/ml insulin, 50 ng/ml SCF, 10 ng/ml IL-3. Appropriate volume of cells were collected, centrifuged at 300 g and resuspended in fresh media. Cells should now be in fresh wells at a density of 100,000 cells/ml. 60,000 cells, 60,000 cells and 100,000 cells for days 0, 3, 5 respectively. Finally, fresh compound were added to each well at each timepoint (Days 0, 3 & 5).

On Day 7 media and cell culture density changes. Each cell culture well was counted. Next, Phase 2 Erythroid Differentiation Media was freshly made, which contains StemSpan SFEM, 2.5 U/ml EPO, 0.5 mg/ml Holo-TF, 1× Glutamax, 5 μl/ml chemically defined lipid mixture, 10 ng/ml insulin, 50 ng/ml SCF. Appropriate volume of cells was collected, centrifuged at 300 g and resuspended in fresh media. Cells were plated in fresh wells at a density of 500,000 cells/ml, 300,000 cells/well. Finally, fresh compound was added to each well at Day 7 timepoint.

On Day 10 media formulation is once again changed. Each cell culture well was counted. Fresh Phase 3 Erythroid Differentiation Media was made which contains StemSpan SFEM, 2.5 U/ml EPO, 0.5 mg/ml Holo-TF, 1× Glutamax, 5 μl/ml chemically defined lipid mixture, 10 ng/ml insulin. Appropriate volume of cells was collected, centrifuged at 300 g and resuspended in fresh media. Cells were plated in fresh wells at a density of 500,000 cells/ml, 500,000 cells/well. Finally, fresh compound was added to each well at Day 10 timepoint.

On Day 12 the cell density is once again changed. Each cell culture well was counted. Fresh Phase 3 Erythroid Differentiation Media was made. Appropriate volume of cells was collected, centrifuged at 300 g and resuspended in fresh media. Cells were plated in fresh wells at a density of 1,000,000 cells/ml, 1,000,000 cells/well. Finally fresh compound was added to each well.

Day 14 ($18^{th}$ day of experiment) refers to the terminal day of culture. Each cell culture well was counted. Next between 150K and 650K cells were placed in a uniquely labeled 1.5 ml standard tube. Cells were centrifuged in media at 300 g for 8 minutes, then as much of the media as possible was removed without disturbing the pellet. The pellet was washed with 500p dPBS and once again spun at 300 g for 8 minutes. As much of the supernatant as possible was removed without disturbing the pellet and immediately frozen at −80° C. Cell pellets are now ready for HPLC lysis and analysis.

All centrifugation were run at 300×G for 8 minutes at room temperature. Cells were cultured in a standard incubator at 37° C. and 5% C). Cell culture plates were either a 96-well treated plate for Day −2 or 24-well cell culture treated plates for day 0 through 14. Culture wells were counted using a 1:1 mix of cells and AOPI. Counting was done on Nexcelom Cellaca.

Methods for assaying % HBF and % F+ cells are well known in the art. Non-limiting examples include high performance liquid chromatography (HPLC), flow cytometry, or ion-exchange chromatography. The HbF % is usually measured by HPLC. The flow cytometry assay, the standard clinical method, may be used for assaying % F+ cells by immunofluorescent techniques. In addition to flow cytometry, ion-exchange chromatography may be used to measure the fraction HbF relative to all other hemoglobin (HbF/HbA+HbF).

Compounds with an $EC_{50}$ less than or equal to 20.0 nM are designated as "+++". Compounds with an $EC_{50}$ greater than 20.0 nM and less than or equal to 60.0 nM are designated as "++". Compounds with an $EC_{50}$ greater than 60.0 nM are designated as "+". The results are shown in Table 1-III below.

The Hemoglobin HPLC Ymax observed data is relative to a control compound, presented in % which is shown in Table 1-III below. Compounds with a Hemoglobin HPLC Ymax greater than or equal to 0.0 and less than or equal to 50.0 are designated as "+". Compounds with a Hemoglobin HPLC Ymax greater than 50.0 and less than or equal to 100.0 are designated as "++". Compounds with a Hemoglobin HPLC Ymax greater than 100.0 are designated as "+++".

TABLE 1-III

HbF HPLC Cell Culture Assay

| Compound I-No. | Hemoglobin HPLC EC50 (nM) | Hemoglobin HPLC Ymax obs (%) |
|---|---|---|
| 4 | +++ | ++ |
| 9 | + | +++ |
| 15 | ++ | +++ |
| 66 | +++ | +++ |
| 81 | ++ | ++ |
| 135 | ++ | ++ |
| 160 | + | ++ |
| 161 | +++ | ++ |
| 162 | +++ | +++ |
| 163 | +++ | +++ |
| 217 | + | ++ |
| 220 | ++ | +++ |
| 223 | + | +++ |
| 246 | + | +++ |
| 292 | + | +++ |
| 300 | + | ++ |
| 305 | + | +++ |
| 346 | + | +++ |

Example 24: TR-FRET Assay

A TR-FRET assay was performed to evaluate the ability of the compounds to bind the DCN-1 protein.

The TR-FRET assay was designed following the Scott et al. protocol (Scott et al., Nat Chem Biol. 2017 August; 13(8): 850-857. Doi: 10.1038/nchembio.2386). The recombinant form of the DCNI (DCUND1) protein PONY domain was produced using an *E. coli* expression system at Viva Biotech (China). The DCN1 protein was biotinylated (EZ sulfo-NHS-LC-biotin; Thermofisher) for labeling with streptavidin terbium (Tb) cryptate in the reaction. The probe was changed to a non-covalent DCN1 inhibitor labeled with carboxyfluorescein (FAM; Zhou et al., *Nat Commun.* 2017; 8: 1150. Doi: 10.1038/s41467-017-01243-7). Buffer conditions were modified to enhance protein stability by exchanging Tween20 for TritonX and increasing NaCl to 200 mM. The compounds were screened against 5 nM DCN1 and 20 nM FAM-probe or 0.31 nM DCN1 and 900 nM total probe (100 nM FAM-labeled plus 800 nM unlabeled). The TR-FRET ratio between Tb-DCN1 and the FAM-labeled probe was measured in a 384-well opti-plate (Perkin Elmer) using a plate reader (BMG) at 1, 5, and 24 hrs after treatment with compound (final DMSO concentration of 0.1%). The ratio was normalized to the high (DCN1 and FAM-probe) and low (DCN1 and no probe) controls for a readout of % activity (=100*(x−low)/(high−low). The % activity across concentrations is used to determine the IC50.

Compounds with an $IC_{50}$ less than or equal to 200.0 nM are designated as "++++". Compounds with an $IC_{50}$ greater than 200.0 nM and less than or equal to 1000.0 nM are designated as "+++". Compounds with an $IC_{50}$ greater than 1000.0 nM and less than or equal to 3000.0 nM are designated as "++". Compounds with an $IC_{50}$ greater than 3000.0 nM are designated as "+". The results are shown in Table 2 below.

TABLE 2

TR-FRET Assay

| Compound No. | TR FRET IC50 1 hr (nM) | TR FRET IC50 24 hr (nM) |
|---|---|---|
| I-1 | ++++ | ++++ |
| I-2 | ++++ | ++++ |
| I-3 | ++++ | ++++ |
| I-4 | ++++ | ++++ |
| I-5 | ++++ | ++++ |
| I-6 | ++++ | ++++ |
| I-7 | ++++ | ++++ |
| I-8 | ++++ | ++++ |
| I-9 | ++++ | ++++ |
| I-10 | ++++ | ++++ |
| I-11 | ++++ | ++++ |
| I-12 | ++++ | ++++ |
| I-13 | ++++ | ++++ |
| I-14 | ++++ | ++++ |
| I-15 | ++++ | ++++ |
| I-16 | + | + |
| I-17 | + | + |
| I-18 | + | + |
| I-19 | + | + |
| I-20 | + | + |
| I-21 | + | + |
| I-22 | + | + |
| I-23 | + | + |
| I-24 | + | + |
| I-25 | + | + |
| I-26 | + | + |

TABLE 2-continued

| TR-FRET Assay | | |
|---|---|---|
| Compound No. | TR FRET IC50 1 hr (nM) | TR FRET IC50 24 hr (nM) |
| I-27 | + | + |
| I-28 | ++ | ++ |
| I-29 | ++ | ++ |
| I-30 | ++ | ++ |
| I-31 | ++ | ++ |
| I-32 | ++ | ++++ |
| I-33 | ++ | ++ |
| I-34 | ++++ | ++++ |
| I-35 | ++ | ++ |
| I-36 | ++ | ++ |
| I-37 | ++++ | ++++ |
| I-38 | ++ | ++++ |
| I-39 | ++ | ++ |
| I-40 | ++ | ++ |
| I-41 | ++ | ++ |
| I-42 | + | ++ |
| I-43 | ++ | ++ |
| I-44 | +++ | ++++ |
| I-45 | ++ | ++ |
| I-46 | ++++ | ++++ |
| I-47 | + | ++ |
| I-48 | + | ++ |
| I-49 | ++ | ++ |
| I-50 | ++ | ++++ |
| I-51 | ++ | ++++ |
| I-52 | ++ | ++++ |
| I-53 | ++ | ++ |
| I-54 | ++ | ++++ |
| I-55 | ++ | ++ |
| I-56 | +++ | ++++ |
| I-57 | ++ | ++ |
| I-58 | ++ | ++++ |
| I-59 | ++ | ++++ |
| I-60 | ++++ | ++++ |
| I-61 | ++++ | ++++ |
| I-62 | ++++ | ++++ |
| I-63 | ++++ | ++++ |
| I-64 | ++++ | ++++ |
| I-65 | ++++ | ++++ |
| I-66 | ++++ | ++++ |
| I-67 | ++ | ++ |
| I-68 | ++++ | +++ |
| I-69 | +++ | +++ |
| I-70 | ++ | +++ |
| I-71 | ++ | +++ |
| I-72 | ++ | +++ |
| I-73 | ++ | ++ |
| I-74 | ++ | ++ |
| I-75 | + | +++ |
| I-76 | ++ | ++ |
| I-77 | ++ | +++ |
| I-78 | ++ | +++ |
| I-79 | ++ | +++ |
| I-80 | ++ | ++ |
| I-81 | ++++ | ++++ |
| I-82 | ++++ | ++++ |
| I-83 | ++++ | ++++ |
| I-84 | ++ | ++ |
| I-85 | ++ | ++ |
| I-86 | ++ | ++ |
| I-87 | ++ | ++ |
| I-88 | ++ | ++ |
| I-89 | ++ | ++ |
| I-90 | ++ | ++ |
| I-91 | ++ | ++ |
| I-92 | ++ | ++ |
| I-93 | ++ | ++ |
| I-94 | ++ | ++ |
| I-95 | ++ | ++ |
| I-96 | ++ | ++ |
| I-97 | ++ | ++ |
| I-98 | ++ | ++ |
| I-99 | ++ | ++ |
| I-100 | ++ | ++ |
| I-101 | ++ | ++ |

TABLE 2-continued

| TR-FRET Assay | | |
|---|---|---|
| Compound No. | TR FRET IC50 1 hr (nM) | TR FRET IC50 24 hr (nM) |
| I-102 | ++ | ++ |
| I-103 | ++ | ++ |
| I-104 | ++ | ++ |
| I-105 | ++ | ++ |
| I-106 | ++ | ++ |
| I-107 | ++ | ++ |
| I-108 | ++ | ++ |
| I-109 | ++ | ++ |
| I-110 | ++ | ++ |
| I-111 | ++ | ++ |
| I-112 | ++ | ++ |
| I-113 | ++ | ++ |
| I-114 | ++ | ++ |
| I-115 | ++ | ++ |
| I-116 | ++ | ++ |
| I-117 | ++ | ++ |
| I-118 | ++ | ++ |
| I-119 | ++ | ++ |
| I-120 | ++ | ++ |
| I-121 | ++ | ++ |
| I-122 | ++ | ++ |
| I-123 | ++ | ++ |
| I-124 | ++ | ++ |
| I-125 | ++ | ++ |
| I-126 | ++ | ++ |
| I-127 | ++ | ++ |
| I-128 | ++ | ++ |
| I-129 | ++ | ++ |
| I-130 | + | +++ |
| I-131 | +++ | ++++ |
| I-132 | +++ | +++ |
| I-133 | ++++ | ++++ |
| I-134 | ++ | +++ |
| I-135 | ++++ | ++++ |
| I-136 | ++++ | ++++ |
| I-137 | ++++ | ++++ |
| I-138 | +++ | +++ |
| I-139 | ++ | +++ |
| I-140 | + | + |
| I-141 | ++++ | ++++ |
| I-142 | ++++ | ++++ |
| I-143 | ++ | +++ |
| I-144 | ++ | +++ |
| I-145 | ++ | +++ |
| I-146 | ++++ | ++++ |
| I-147 | ++++ | ++++ |
| I-148 | ++ | +++ |
| I-149 | ++ | +++ |
| I-150 | ++ | +++ |
| I-151 | ++ | ++++ |
| I-152 | ++ | ++++ |
| I-153 | ++++ | ++++ |
| I-154 | ++ | +++ |
| I-155 | ++ | ++++ |
| I-156 | ++ | +++ |
| I-157 | ++ | +++ |
| I-158 | ++ | ++++ |
| I-159 | + | + |
| I-160 | ++++ | ++++ |
| I-161 | ++++ | ++++ |
| I-162 | ++++ | ++++ |
| I-163 | ++++ | ++++ |
| I-213 | ++ | +++ |
| I-212 | +++ | ++++ |
| I-214 | +++ | ++++ |
| I-215 | ++++ | ++++ |
| I-216 | +++ | ++++ |
| I-217 | ++++ | ++++ |
| I-218 | ++++ | ++++ |
| I-219 | +++ | ++++ |
| I-220 | +++ | ++++ |
| I-221 | ++++ | ++++ |
| I-222 | +++ | ++++ |
| I-223 | ++++ | ++++ |
| I-224 | +++ | ++++ |

TABLE 2-continued

| TR-FRET Assay | | |
|---|---|---|
| Compound No. | TR FRET IC50 1 hr (nM) | TR FRET IC50 24 hr (nM) |
| I-225 | +++ | ++++ |
| I-226 | ++ | +++ |
| I-227 | +++ | ++++ |
| I-228 | ++++ | ++++ |
| I-229 | ++++ | ++++ |
| I-230A | +++ | ++++ |
| I-230B | +++ | ++++ |
| I-231 | ++++ | ++++ |
| I-232 | ++++ | ++++ |
| I-233 | ++++ | ++++ |
| I-234 | ++++ | ++++ |
| I-235 | ++ | ++ |
| I-236 | ++++ | ++++ |
| I-237 | ++ | +++ |
| I-238 | ++ | ++ |
| I-239 | ++ | ++++ |
| I-240 | ++++ | ++++ |
| I-241 | ++ | ++++ |
| I-242 | ++ | +++ |
| I-243 | +++ | ++++ |
| I-244 | ++ | ++++ |
| I-245 | ++ | ++ |
| I-246 | ++++ | ++++ |
| I-247 | +++ | ++++ |
| I-248 | +++ | ++++ |
| I-249 | ++ | ++ |
| I-250 | ++ | ++ |
| I-251 | ++ | ++++ |
| I-252 | ++ | ++++ |
| I-253 | ++ | ++++ |
| I-254 | ++ | ++++ |
| I-255 | ++ | ++ |
| I-256 | +++ | ++++ |
| I-257 | ++ | ++ |
| I-258 | ++ | ++++ |
| I-259 | ++ | ++ |
| I-260 | ++ | ++ |
| I-261 | +++ | ++++ |
| I-262 | ++ | ++ |
| I-263 | ++ | ++ |
| I-264 | ++++ | ++++ |
| I-265 | +++ | +++ |
| I-266 | ++ | ++ |
| I-277 | ++++ | ++++ |
| I-278 | ++++ | ++++ |
| I-279 | ++ | ++ |
| I-280 | ++++ | ++++ |
| I-281 | ++ | +++ |
| I-282 | ++ | ++ |
| I-283 | ++++ | ++++ |
| I-284 | ++ | ++++ |
| I-285 | ++ | ++++ |
| I-286 | ++ | ++++ |
| I-287 | ++++ | ++++ |
| I-288 | +++ | ++++ |
| I-289 | ++++ | ++++ |
| I-290 | ++++ | ++++ |
| I-291 | ++++ | ++++ |
| I-292 | ++++ | ++++ |
| I-293 | ++++ | ++++ |
| I-294 | +++ | ++++ |
| I-295 | ++ | ++++ |
| I-296 | ++++ | ++++ |
| I-297 | +++ | ++++ |
| I-298 | +++ | ++++ |
| I-299 | ++ | ++ |
| I-300 | ++++ | ++++ |
| I-301 | ++ | +++ |
| I-302 | +++ | ++++ |
| I-303 | ++++ | ++++ |
| I-304 | ++ | +++ |
| I-305 | ++++ | ++++ |

TABLE 2-continued

| TR-FRET Assay | | |
|---|---|---|
| Compound No. | TR FRET IC50 1 hr (nM) | TR FRET IC50 24 hr (nM) |
| I-306 | ++ | +++ |
| I-307 | ++ | ++ |
| I-308 | +++ | ++++ |
| I-309 | ++++ | ++++ |
| I-310 | ++++ | ++++ |
| I-311 | +++ | ++++ |
| I-312 | ++++ | ++++ |
| I-313 | ++ | ++++ |
| I-314 | +++ | ++++ |
| I-315 | ++++ | ++++ |
| I-316 | ++ | +++ |
| I-317 | ++++ | ++++ |
| I-318 | +++ | ++++ |
| I-319 | ++ | +++ |
| I-320 | ++ | +++ |
| I-321 | ++ | ++ |
| I-322 | ++ | ++++ |
| I-323 | +++ | ++++ |
| I-324 | ++++ | ++++ |
| I-325 | +++ | ++++ |
| I-326 | ++ | ++ |
| I-327 | ++++ | ++++ |
| I-328 | ++++ | ++++ |
| I-329 | ++ | ++ |
| I-330 | ++ | ++ |
| I-331 | ++ | +++ |
| I-332 | ++++ | ++++ |
| I-333 | +++ | ++++ |
| I-334 | +++ | ++++ |
| I-335 | ++ | +++ |
| I-337 | +++ | ++++ |
| I-338 | ++ | ++++ |
| I-339 | ++ | ++ |
| I-340 | ++ | +++ |
| I-341 | +++ | ++++ |
| I-342 | ++ | +++ |
| I-343 | ++ | +++ |
| I-344 | +++ | ++++ |
| I-345 | ++ | +++ |
| I-346 | ++++ | ++++ |
| I-347 | ++++ | ++++ |
| I-348 | ++ | ++ |
| I-349 | ++ | +++ |
| I-350 | ++ | ++ |
| I-351 | +++ | ++++ |
| I-352 | ++++ | ++++ |
| I-353 | ++++ | ++++ |
| I-354 | ++ | ++ |
| I-355 | ++++ | ++++ |
| I-356 | ++++ | ++++ |
| I-357 | +++ | ++++ |
| I-358 | ++ | ++ |
| I-359 | ++ | ++++ |
| I-360 | ++ | ++ |
| I-361 | ++++ | ++++ |
| I-362 | ++ | ++ |
| I-363 | +++ | ++++ |
| I-364 | +++ | ++++ |
| I-365 | +++ | ++++ |
| I-366 | ++ | ++ |
| I-367 | ++ | ++++ |
| I-368 | ++ | ++++ |
| I-369 | ++ | ++ |
| I-370 | ++ | ++ |
| I-371 | ++ | +++ |
| I-372 | ++ | +++ |
| I-373 | +++ | ++++ |
| I-374 | +++ | +++ |
| I-375 | ++++ | ++++ |
| I-376 | +++ | ++++ |
| I-377 | ++ | +++ |

TABLE 2-continued

| TR-FRET Assay | | |
|---|---|---|
| Compound No. | TR FRET IC50 1 hr (nM) | TR FRET IC50 24 hr (nM) |
| I-378 | ++++ | ++++ |
| I-379 | ++ | ++ |
| I-380 | ++ | ++ |
| I-381 | ++ | ++ |
| I-382 | +++ | ++++ |
| I-383 | ++++ | ++++ |
| I-384 | +++ | ++++ |
| I-385 | ++ | ++ |

Example 25: Intact Protein MS Analysis with the RapidFire-TOF System

An MS assay was performed to evaluate the ability of the compounds to covalently modify DCN-1.

DCN1 protein, His-TEV-DCN1, were expressed in *E. Coli*. The His-tagged protein was first purified with an Ni-NTA column. The His-tag was cleaved using His-tag TEV protease and the His-tags were removed using a second Ni-NTA column. Protein purity was verified with SDS-PAGE and intact MS. DCN1 was dissolved in a buffer containing 25 mM Tris-HCl, 200 mM NaCl, and 1 mM DTT at 400 nM. 11 concentrations of compounds were added to the DCN1 solution and incubated at room temperature for 3 hours, unless otherwise specified. The reaction plates were quenched by adding 0.2% formic acid. Quenched assay plates were analyzed with an Agilent RapidFire 360 system connected to an Agilent 6545 Q-TOF mass spectrometer equipped with an AJS source. 10 μL of sample volume was loaded onto a custom packed cartridge (4 μL, PLRP-S 30 μm/1000 Å pore; Optimize Technologies) with loading buffer ($ddH_2O$ with 0.09% (vol/vol) formic acid and 0.01% (vol/vol) trifluoroacetic acid; 1.25 ml/min) for 6 seconds before being eluted directly into the mass spectrometer in elution buffer (80% acetonitrile with 0.09% (vol/vol) formic acid and 0.01% (vol/vol) trifluoroacetic acid; 0.5 ml/min) for 7 seconds. The cartridge was re-equilibrated with loading buffer for 1 second before collection of the next sample. The Q-TOF was operated in TOF-only positive ionization mode set to the following parameters: Gas Temp=350 C, Drying Gas=7 l/min, Nebulizer=50 psi, Sheath Gas Temp=400 C, Sheath Gas Flow=12 l/min, Vcap=4000 V, Nozzle Voltage=1000 V, Fragmentor=125 V, Skimmer=65 V and Oct 1 RF Vpp=750V. Raw MS data files were deconvoluted and analyzed using the Agilent MassHunter Bioconfirm software package to identify both parent protein and expected compound adduct mass signatures.

The MS data is presented in % adduct formation which is shown in Table 3 below. The MS data is presented in % adduct formation which is shown in Table 3 below. Compounds with an MS Emax % adduct formation greater than or equal to 0.0 and less than or equal to 30.0 are designated as "+". Compounds with an MS Emax % adduct formation greater than 30.0 and less than or equal to 80.0 are designated as "++". Compounds with an MS Emax % adduct formation greater than 80.0 and less than or equal to 100.0 are designated as

TABLE 3

| Intact Protein MS Analysis | |
|---|---|
| Compound No. | % Adduct Formation |
| I-1 | +++ |
| I-2 | +++ |
| I-4 | +++ |
| I-5 | +++ |
| I-6 | +++ |
| I-9 | +++ |
| I-11 | +++ |
| I-14 | +++ |
| I-15 | +++ |
| I-16 | + |
| I-17 | + |
| I-18 | + |
| I-19 | + |
| I-20 | + |
| I-22 | + |
| I-23 | + |
| I-24 | + |
| I-25 | + |
| I-27 | + |
| I-28 | +++ |
| I-34 | +++ |
| I-38 | +++ |
| I-44 | +++ |
| I-46 | +++ |
| I-47 | + |
| I-48 | +++ |
| I-60 | +++ |
| I-62 | +++ |
| I-64 | +++ |
| I-65 | +++ |
| I-66 | +++ |
| I-68 | +++ |
| I-69 | +++ |
| I-72 | +++ |
| I-75 | +++ |
| I-77 | +++ |
| I-78 | +++ |
| I-81 | +++ |
| I-82 | +++ |
| I-83 | ++ |
| I-86 | + |
| I-103 | + |
| I-130 | + |
| I-133 | +++ |
| I-135 | +++ |
| I-137 | +++ |
| I-141 | +++ |
| I-142 | +++ |
| I-146 | +++ |
| I-150 | +++ |
| I-159 | + |
| I-164 | + |
| I-165 | + |
| I-166 | +++ |
| I-167 | +++ |
| I-168 | + |
| I-170 | +++ |
| I-171 | + |
| I-172 | + |
| I-173 | ++ |
| I-174 | + |
| I-175 | + |
| I-176 | + |
| I-177 | ++ |
| I-178 | + |
| I-179 | +++ |
| I-180 | +++ |
| I-181 | ++ |
| I-182 | + |
| I-183 | + |
| I-184 | + |
| I-185 | + |
| I-186 | ++ |
| I-187 | + |
| I-188 | + |
| I-189 | + |

TABLE 3-continued

| Intact Protein MS Analysis | |
|---|---|
| Compound No. | % Adduct Formation |
| I-190 | ++ |
| I-191 | +++ |
| I-192 | + |
| I-193 | ++ |
| I-194 | +++ |
| I-195 | + |
| I-196 | + |
| I-197 | +++ |
| I-198 | + |
| I-199 | + |
| I-200 | + |
| I-201 | + |
| I-202 | + |
| I-203 | + |
| I-204 | + |
| I-205 | + |
| I-206 | + |
| I-207 | +++ |
| I-208 | +++ |
| I-209 | + |
| I-214 | +++ |
| I-215 | +++ |
| I-216 | +++ |
| I-217 | +++ |
| I-218 | +++ |
| I-219 | +++ |
| I-220 | +++ |
| I-221 | +++ |
| I-222 | +++ |
| I-223 | +++ |
| I-224 | +++ |
| I-225 | +++ |
| I-226 | + |
| I-227 | +++ |
| I-228 | +++ |
| I-229 | +++ |
| I-230A | +++ |
| I-230B | +++ |
| I-231 | +++ |
| I-232 | +++ |
| I-233 | +++ |
| I-234 | +++ |

Example 26: Materials and Methods: NBSGW Humanized Mouse Model for HbF Induction

Animals

Female, 6-week-old NOD.Cg-KitW-41J Tyr+ Prkdcscid 112rgtm1Wjl/ThomJ (NBSGW) mice (Jackson Laboratory strain #02662) will be used for these studies. The mice will be acclimatized to laboratory conditions for 5 days prior to inoculation.

Cell Preparation and Inoculation

GCSF-mobilized human CD34+ cells will be removed from liquid nitrogen storage, thawed in a 37C water bath and transferred quickly into a 50 mL conical tube. Cryovial will be rinsed once with thaw buffer, 0.1% BSA in phosphate buffered saline (PBS), and buffer will be transferred combined with the original contents in the 50 mL conical tube. Next, doubling volumes of thaw buffer will be added to the conical and gently swirled for −30 seconds to one minute until the volume in the conical is 32 mL. Cells and buffer will be centrifuged at 300 G for 8 minutes, and the supernatants will be aspirated. Cells will be counted by resuspending in 1 mL of thawing buffer per million of cells to a target concentration range of 0.5 to 2M/ml) and counting with AOPI (1:1) on a luna cell counter to confirm the concentration of cells/mL. The cell concentration will be adjusted to 3×10^6 cells/ml. For each mouse, 300 thousand cells in 0.1 ml will be injected into the tail vein with a 25-gauge needle.

Engraftment Checkpoint

On day 56 after human cell adoptive transfer, whole blood will be collected from each mouse by submandibular bleed and a 100 μL sample of EDTA whole blood will be transferred to a 2 ml tube containing 1.8 mL ACK Lysing Buffer at room temperature (RT), and then inverted to mix. Samples will be incubated at RT for 15 min in the dark to lyse. After lysis, samples will be centrifuged at 500×g for 5 minutes at RT to enable supernatant decanting. Remaining cells will be washed with 1 mL of PBS-0.5% BSA and centrifuged at 500×g for 5 minutes at 4C. Supernatant will be decanted and cells will be stained with leukocyte markers (human and mouse CD45 antibodies; BD347464, BD557659) to confirm human cell engraftment. Mice having less than one percent, or greater than ten percent, human CD45 positive cells will be excluded from the subsequent study. The remaining mice will be then randomized into treatment groups based on percentage of human cell engraftment. Each treatment group included 10-11 mice.

Compound Administration

Compounds will be dissolved in a 5% Cremophor RH40, 20% hydroxylpropyl-b-cyclodextrin solution. Hydroxyurea will be solubilized in PBS. Formulations will be prepared fresh daily. Commencing on day 84 post human cell engraftment, mice will be treated by oral gavage with test compound, hydroxyurea or their respective vehicles, for a period of three weeks using either once daily (QD) or twice daily (BID) dosing regimens. Mice will be monitored daily for body weight and condition. Mice which lose greater than 20% body weight prior to study completion will be removed from the study and humanely euthanized.

Bone Marrow Collection and Analysis

Figure 1B:
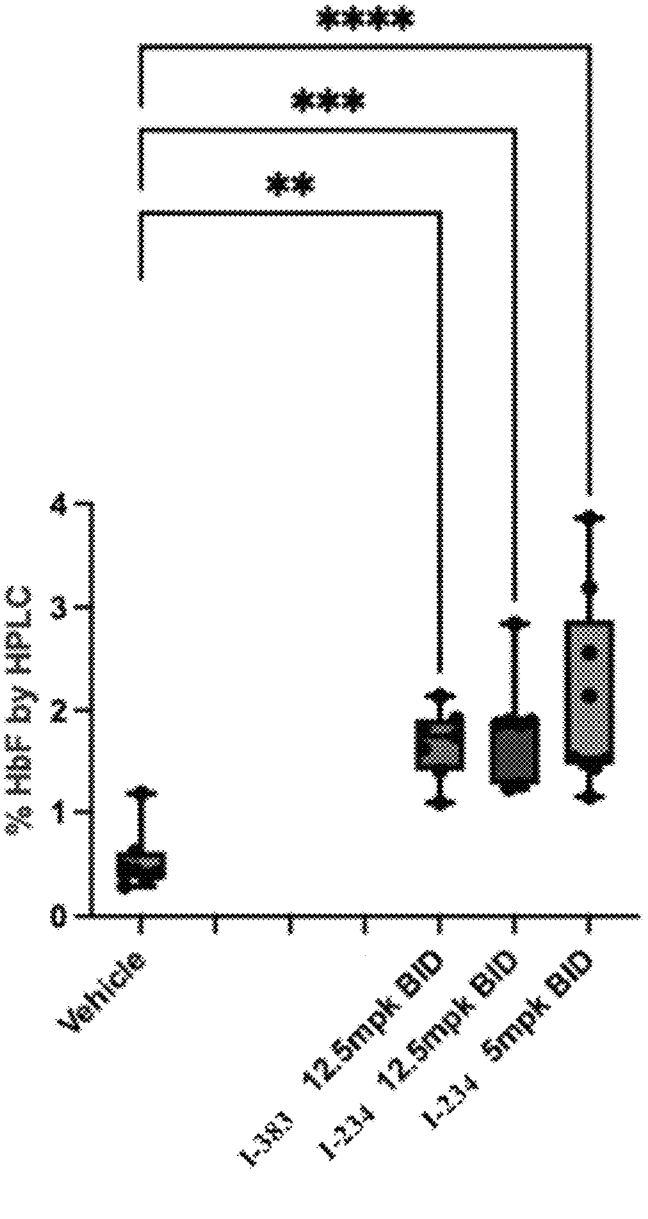
Figure 2A:
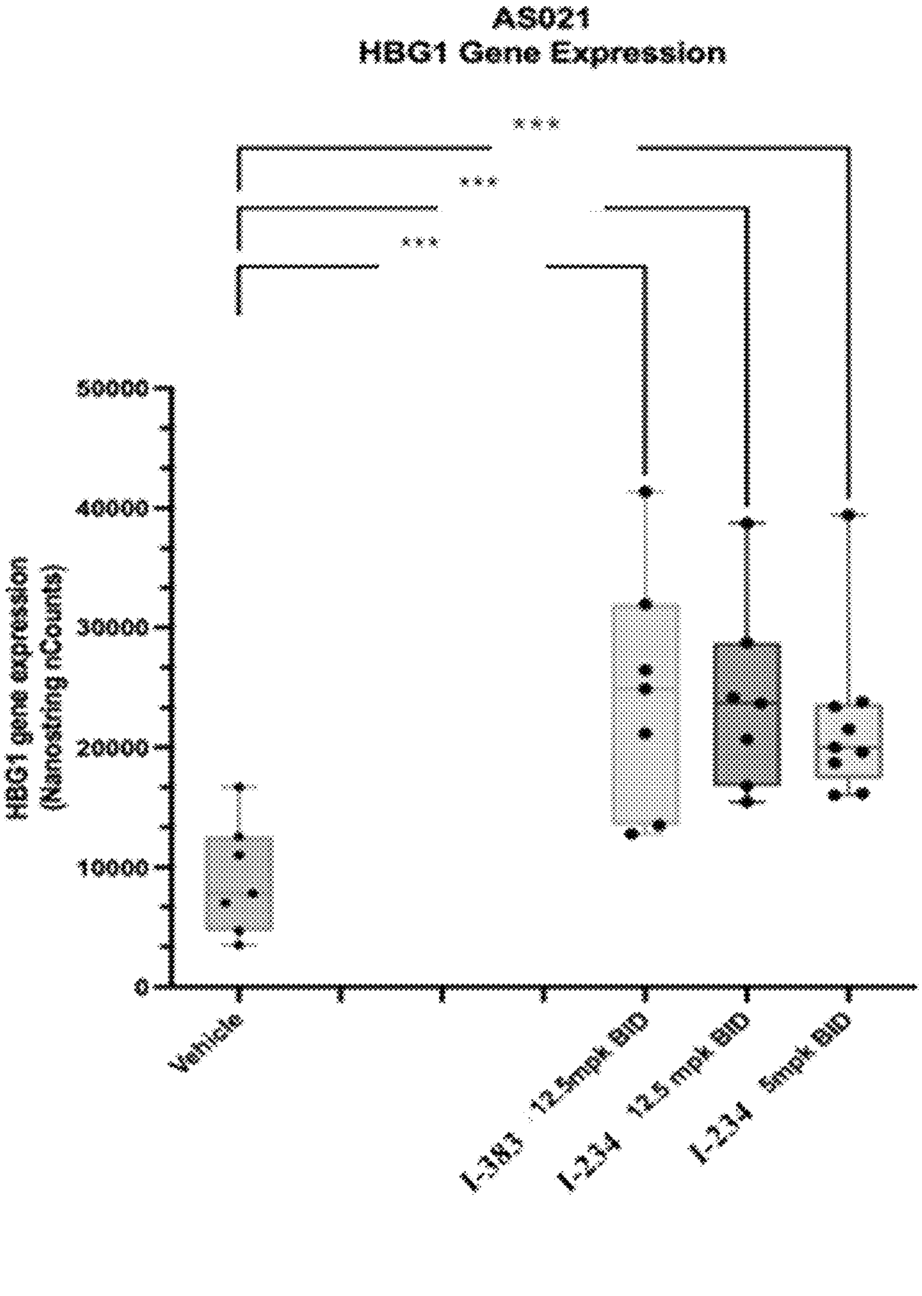
Figure 2B:
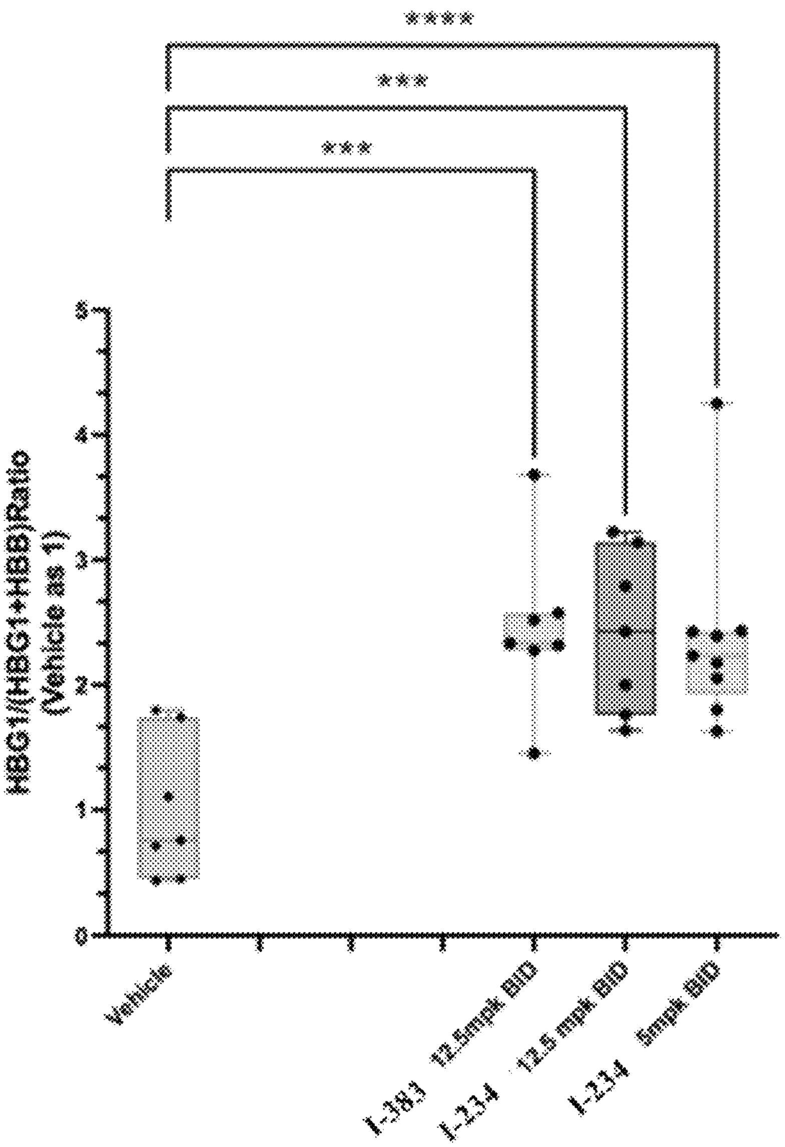
Figure 2C:
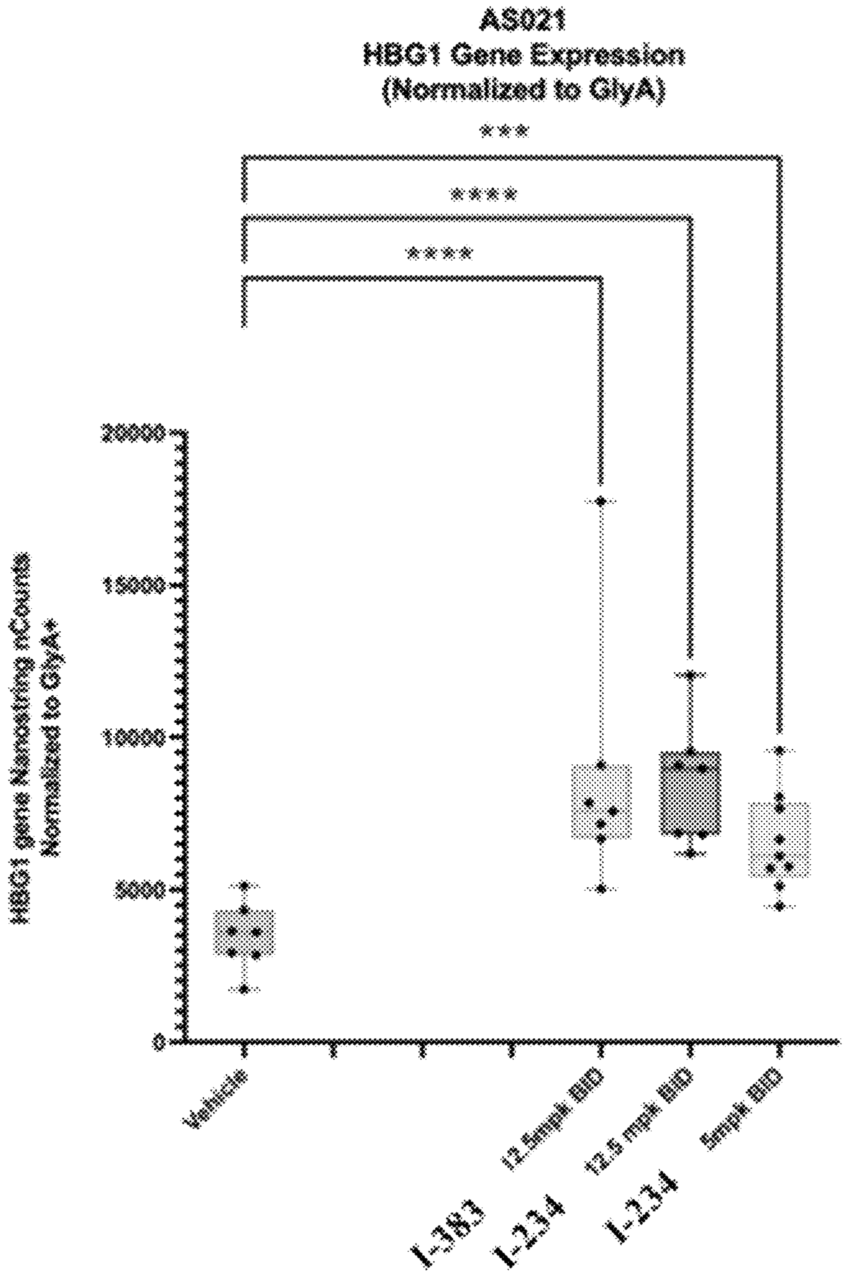

After 21 days of dosing, all mice will be euthanized and prepared for bone marrow collection. Both femurs will be collected from each mouse by first disinfecting the skin with 70% ethanol and then, using a pair of scissors and forceps, removing the limb and dissecting the muscles both above and below the femur and tibia, taking care not to damage the bone. Femurs will be placed in PBS-0.5% BSA-2 mM EDTA-containing tubes on ice during collections. Each femur will be flushed to extract marrow with 1 mL of 0.5% BSA-PBS 2 mM EDTA using a 27 gauge needle a total of three times. Extracted cells will be counted and aliquoted to prepare for analysis. Whole bone marrow cells were used to analyze the levels of HbF protein and gene levels (HBG1 and HBB). HbF protein levels were analyzed by flow cytometry (% F-cells) or by AlphaLisa. HbF gene (HBG1) expression was analyzed by Nanostring. (The details for the Nanostring and AlphaLisa assays are provided in the preceding examples). An antibody against Glycophorin A (GlyA), a marker for human red blood cells, was used to purify GlyA positive cells by magnetic sorting. Cell lysate from GlyA positive cells was used for HPLC analysis and percentage of fetal HbF and adult HbB was calculated. The data are depicted in FIGS. 1 and 2.

Example 27: Synthesis of Probe Compound
Synthesis of 2-((1E,3E)-5-((E)-1-(6-(4-(3-(3-((4R, 5S)-7-ethyl-4-(3-(2-(morpholinomethyl)acrylamido) phenyl)-6-oxo-5-(3-(trifluoromethyl)benzamido)-4, 5,6,7-tetrahydro-1H-pyrazolo[3,4-b]pyridin-1-yl) phenoxy)propyl)piperazin-1-yl)-6-oxohexyl)-3,3-dimethyl-5-sulfoindolin-2-ylidene)penta-1,3-dien-1-yl)-1,3,3-trimethyl-3H-indol-1-ium-5-sulfonate (P-1)
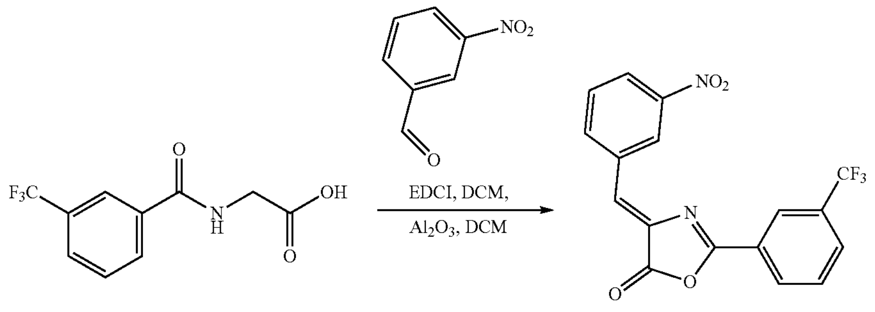
Int. A
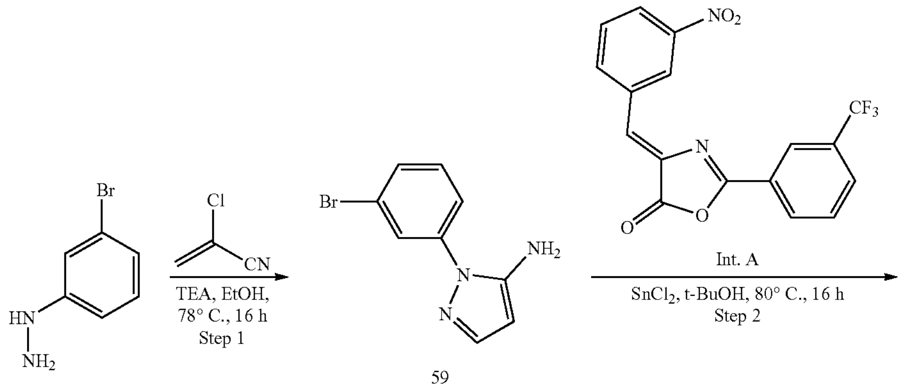
59
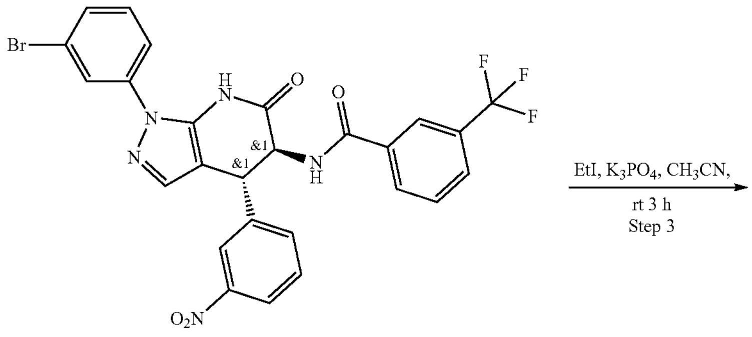
60

-continued
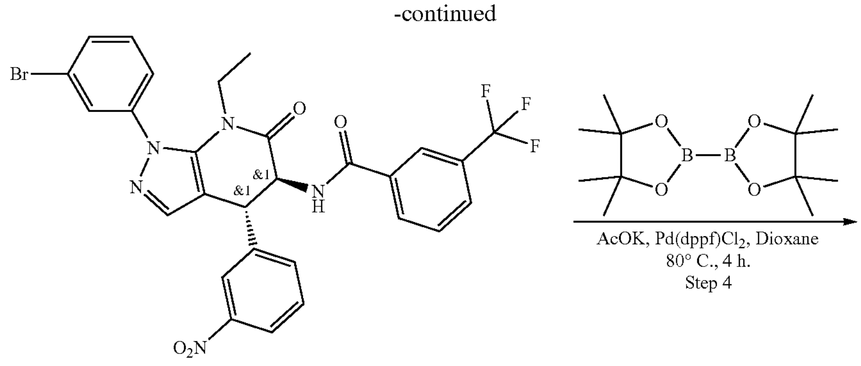
61
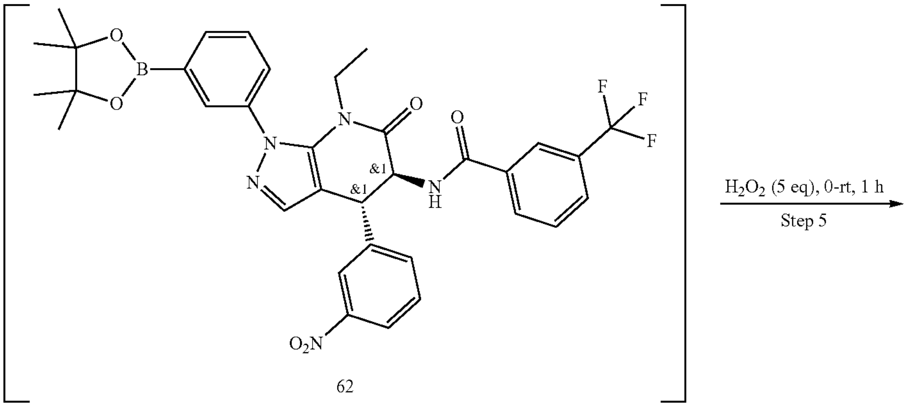
62
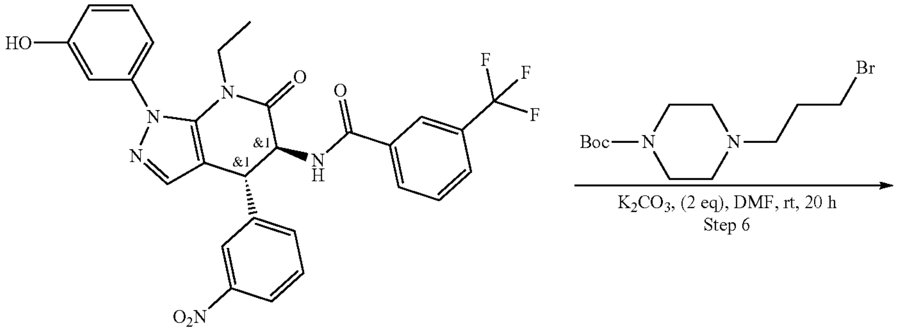
63
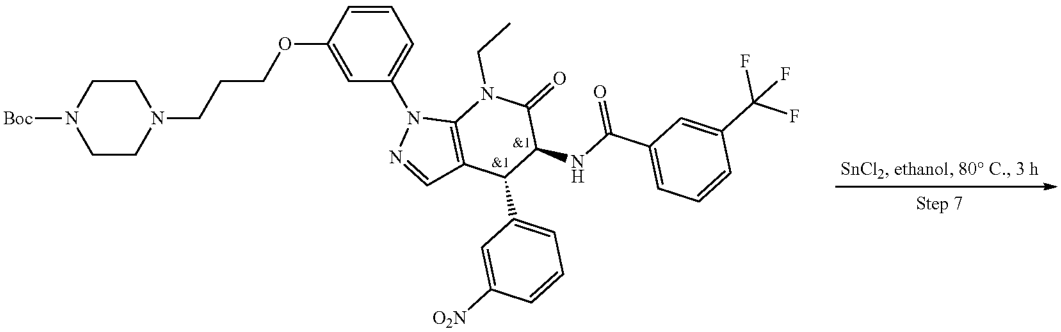
64

-continued
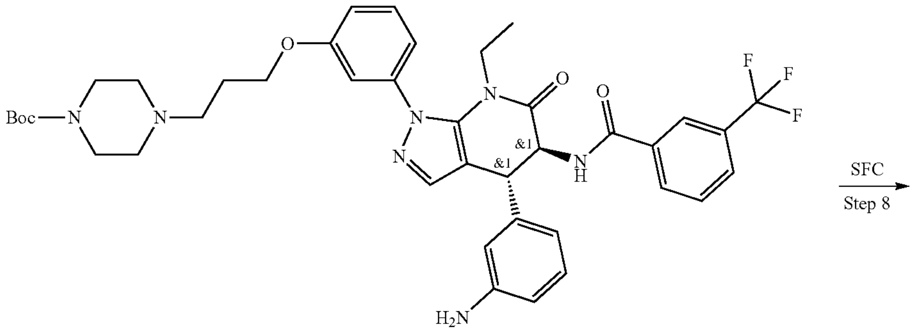
65
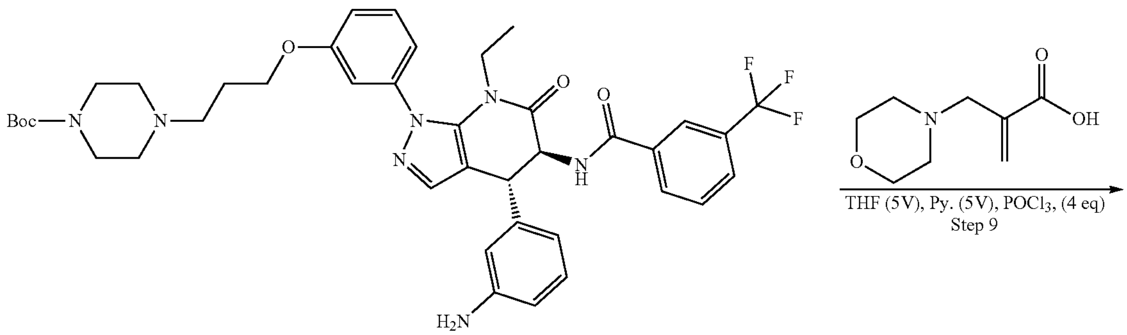
66
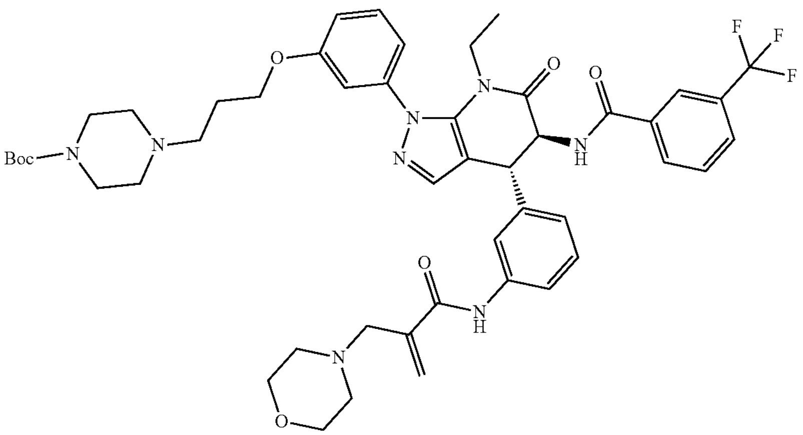
67
TMSI, 2,6-dimethylpyridine
Step 10

-continued
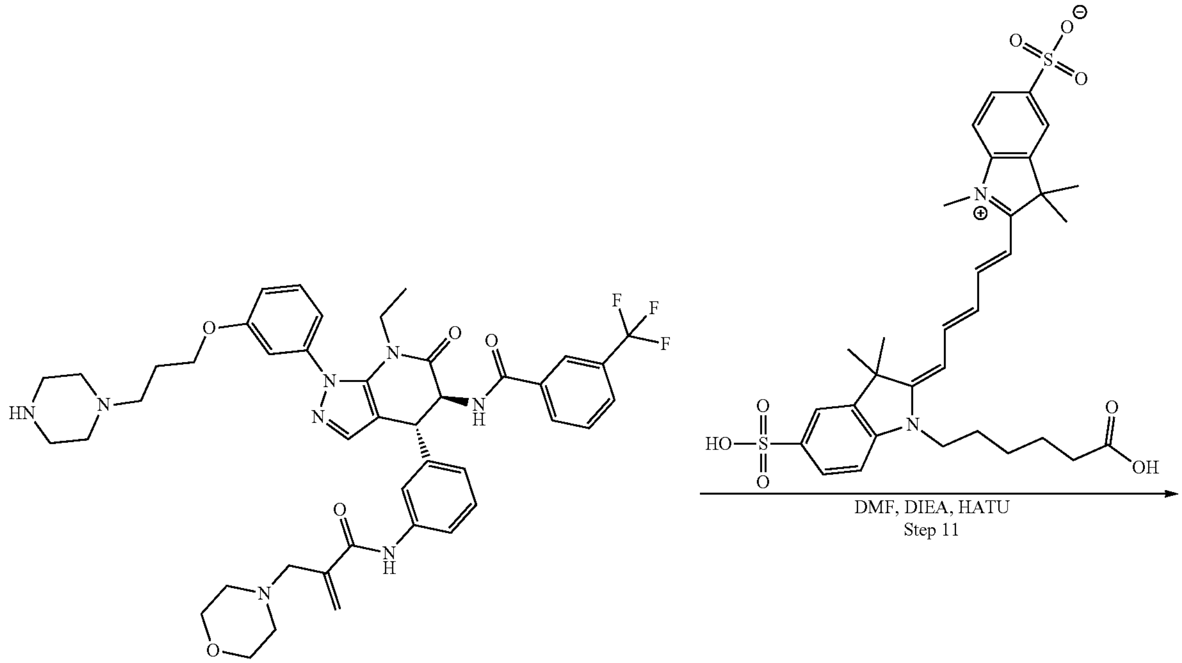
68
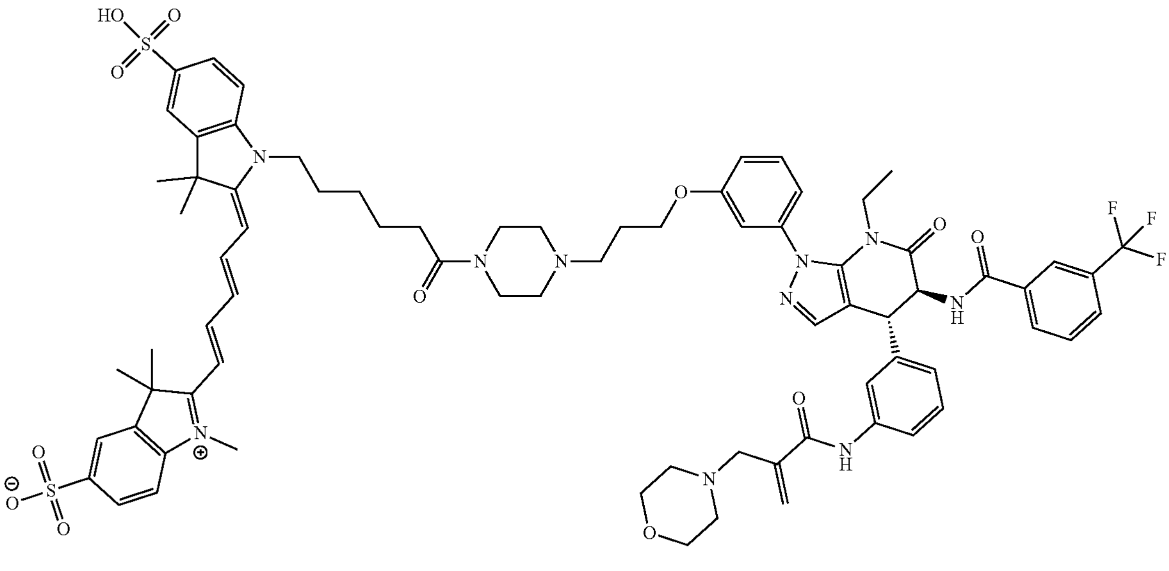
P-1

(4Z)-4-[(3-nitrophenyl)methylidene]-2-[3-(trifluoromethyl)phenyl]-1,3-oxazol-5-one (Int.A)

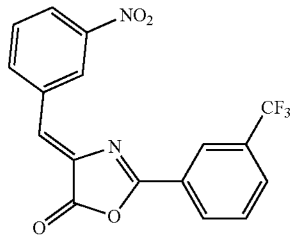 [SMILES: O=C1OC(c2cccc(C(F)(F)F)c2)=N/C1=C\c1cccc([N+](=O)[O-])c1]

A solution of {[3-(trifluoromethyl)phenyl]formamido}acetic acid (200 g, 809 mmol, 1.00 equiv) in DCM (2000 mL) was treated with EDCI (138 g, 890 mmol, 1.10 equiv) at 0° C. for 40 min under nitrogen atmosphere. The resulting mixture was washed with $H_2O$ (3×1000 mL), dried over anhydrous $Na_2SO_4$. The filtration was treated with 3-nitrobenzaldehyde (122 g, 809 mmol, 1.00 equiv) and $Al_2O_3$ (825.01 g, 8091.500 mmol, 10 equiv) at 0° C. for 40 min under nitrogen atmosphere followed. The resulting mixture was filtered, the filter cake was washed with DCM (5×500 mL). The filtrate was concentrated under reduced pressure. The residue was treated with DCM:PE=1:5 (500 mL) for 1 h. The precipitated solids were collected by filtration and washed with DCM:Petroleum ether=1:5 (3×500 mL). This resulted in (4Z)-4-[(3-nitrophenyl)methylidene]-2-[3-(trifluoromethyl)phenyl]-1,3-oxazol-5-one (190 g, 64.8% yield, 90% purity) as a yellow solid.

$^1$H NMR (300 MHz, DMSO-$d_6$) δ 9.22 (t, J=2.0 Hz, 1H), 8.70 (d, J=7.8 Hz, 1H), 8.42 (d, J=7.9 Hz, 1H), 8.33 (ddd, J=8.1, 2.4, 1.0 Hz, 2H), 8.14 (d, J=7.9 Hz, 1H), 7.93 (t, J=7.9 Hz, 1H), 7.84 (t, J=8.0 Hz, 1H), 7.62 (s, 1H).

LCMS Calculated for $C_{17}H_9F_3N_2O_4$: 362.05; Observed: 363.1[M+H]$^+$ 1-(3-bromophenyl)-1H-pyrazol-5-amine (59)

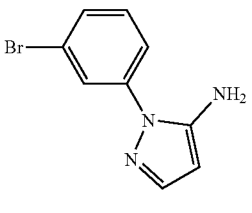 [SMILES: Nc1ccnn1-c1cccc(Br)c1]

A solution of (3-bromophenyl)hydrazine (50.0 g, 267 mmol, 1.00 equiv) in EtOH (500 mL) was treated with 2-propenenitrile, 2-chloro- (23.4 g, 267 mmol, 1.00 equiv) at room temperature for 1 h. The resulting mixture was stirred at 70° C. for 16 h under nitrogen atmosphere. The resulting mixture was concentrated under reduced pressure. The residue was purified by silica gel column chromatography, eluted with petroleum ether/ethyl acetate (4:1) to afford 2-(3-bromophenyl)pyrazol-3-amine (30 g, 47.14% yield, 90% purity) as a red solid.

$^1$H NMR (400 MHz, DMSO-$d_6$) δ 8.21 (d, J=2.6 Hz, 1H), 7.87 (t, J=2.0 Hz, 1H), 7.66 (ddd, J=8.1, 2.2, 1.1 Hz, 1H), 7.34 (t, J=8.0 Hz, 1H), 7.30-7.24 (m, 1H), 5.78 (d, J=2.6 Hz, 1H).

LCMS Calculated for $C_9H_8BrN_3$: 236.99; Observed: 238.0, 240.0 [M+H]$^+$.

rac-N-((4R,5S)-1-(3-bromophenyl)-4-(3-nitrophenyl)-6-oxo-4,5,6,7-tetrahydro-1H-pyrazolo[3,4-b]pyridin-5-yl)-3-(trifluoromethyl)benzamide (60)

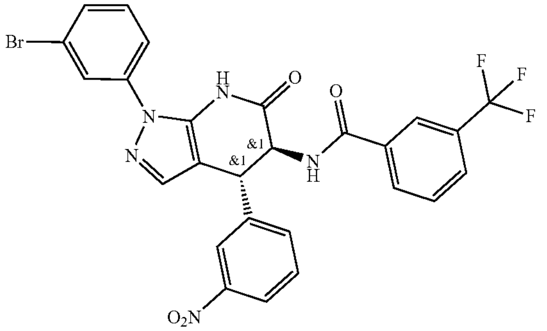 [SMILES: O=C(N[C@@H]1C(=O)Nc2c(cnn2-c2cccc(Br)c2)[C@H]1c1cccc([N+](=O)[O-])c1)c1cccc(C(F)(F)F)c1]

A solution of 2-(3-bromophenyl)pyrazol-3-amine (13.0 g, 54.6 mmol, 1.00 equiv) in t-BuOH (130 mL) was treated with $SnCl_2$ (1.04 g, 5.46 mmol, 0.10 equiv) at 80° C. for 16 h under nitrogen atmosphere. The resulting mixture was concentrated under reduced pressure. The residue was purified by silica gel column chromatography, eluted with petroleum ether/ethyl acetate (1:1) to afford rac-N-((4R,5S)-1-(3-bromophenyl)-4-(3-nitrophenyl)-6-oxo-4,5,6,7-tetrahydro-1H-pyrazolo[3,4-b]pyridin-5-yl)-3-(trifluoromethyl)benzamide (12 g, 47.14% yield, 90% purity) as a yellow solid.

$^1$H NMR (400 MHz, DMSO-$d_6$) δ 11.19 (s, 1H), 9.04 (d, J=9.0 Hz, 1H), 8.33-8.29 (m, 1H), 8.15 (ddd, J=8.2, 2.4, 1.0 Hz, 1H), 8.03 (d, J=7.3 Hz, 2H), 7.94-7.86 (m, 2H), 7.84 (t, J=1.9 Hz, 1H), 7.72 (t, J=7.9 Hz, 1H), 7.69-7.61 (m, 3H), 7.52 (t, J=8.0 Hz, 1H), 7.16 (s, 1H), 5.15 (dd, J=12.8, 8.9 Hz, 1H), 4.63 (d, J=12.8 Hz, 1H). LCMS Calculated for $C_{26}H_{17}BrF_3N_5O_4$: 599.04; Observed: 600.1, 602.1 [M+H]$^+$.

rac-N-((4R,5S)-1-(3-bromophenyl)-7-ethyl-4-(3-nitrophenyl)-6-oxo-4,5,6,7-tetrahydro-1H-pyrazolo[3,4-b]pyridin-5-yl)-3-(trifluoromethyl)benzamide (61)

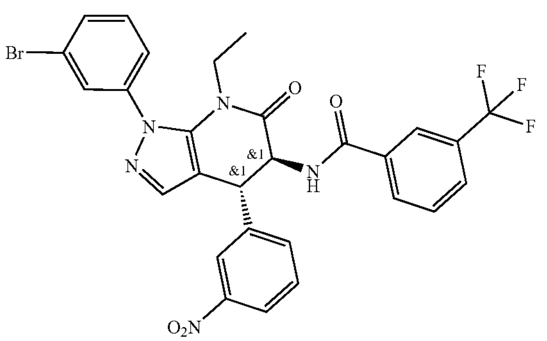 [SMILES: CCN1C(=O)[C@@H](NC(=O)c2cccc(C(F)(F)F)c2)[C@H](c2cccc([N+](=O)[O-])c2)c2cnn(-c3cccc(Br)c3)c21]

To a stirred mixture of rac-N-((4R,5S)-1-(3-bromophenyl)-4-(3-nitrophenyl)-6-oxo-4,5,6,7-tetrahydro-1H-pyrazolo[3,4-b]pyridin-5-yl)-3-(trifluoromethyl)benzamide (10.0 g, 16.7 mmol, 1.00 equiv) and iodoethane (3.12 g, 20.0 mmol, 1.20 equiv) in acetonitrile (100 mL) were added $K_3PO_4$ (10.6 g, 49.9 mmol, 3.00 equiv) at room temperature. The resulting mixture was stirred at room temperature for additional 3 h, then filtered. The filter cake was washed with acetonitrile (2×10 mL). The filtrate was concentrated under reduced pressure. The mixture was purified by silica gel column chromatography, eluted with petroleum ether/ethyl acetate (2:1) to afford rac-N-((4R,5S)-1-(3-bromophenyl)-7-ethyl-4-(3-nitrophenyl)-6-oxo-4,5,6,7-tetrahydro-1H-pyrazolo[3,4-b]pyridin-5-yl)-3-(trifluoromethyl)benzamide (7 g, 66.8% yield, 95% purity) as a yellow solid.

$^1$H NMR (400 MHz, DMSO-$d_6$) δ 9.05 (d, J=9.1 Hz, 1H), 8.35-8.29 (m, 1H), 8.15 (ddd, J=8.2, 2.3, 1.0 Hz, 1H), 8.05-7.97 (m, 3H), 7.89 (t, J=7.7 Hz, 2H), 7.78-7.62 (m, 4H), 7.57 (t, J=8.0 Hz, 1H), 7.18 (s, 1H), 5.46-5.34 (m, 1H), 4.58 (d, J=12.9 Hz, 1H), 3.84 (dq, J=14.2, 7.1 Hz, 1H), 3.12 (dq, J=13.8, 6.8 Hz, 1H), 0.89 (t, J=7.0 Hz, 3H). LCMS Calculated for $C_{28}H_{21}BrF_3N_5O_4$: 627.07; Observed: 628.1, 630.1 [M+H]$^+$.

rac-N-((4R,5S)-7-ethyl-1-(3-hydroxyphenyl)-4-(3-nitrophenyl)-6-oxo-4,5,6,7-tetrahydro-1H-pyrazolo[3,4-b]pyridin-5-yl)-3-(trifluoromethyl)benzamide (63)

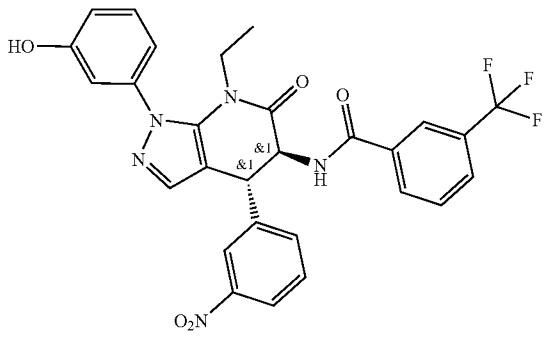 [SMILES: CCN1C(=O)[C@@H](NC(=O)c2cccc(C(F)(F)F)c2)[C@H](c2cccc([N+](=O)[O-])c2)c2cnn(-c3cccc(O)c3)c21]

To a stirred solution of rac-N-((4R,5S)-1-(3-bromophenyl)-7-ethyl-4-(3-nitrophenyl)-6-oxo-4,5,6,7-tetrahydro-1H-pyrazolo[3,4-b]pyridin-5-yl)-3-(trifluoromethyl)benzamide (7.00 g, 11.1 mmol, 1.00 equiv) and bis(pinacolato) diboron (2.83 g, 11.1 mmol, 1.00 equiv) in 1,4-dioxane (70 mL) were added AcOK (3.28 g, 33.4 mmol, 3.00 equiv) and Pd(dppf)$Cl_2$ (0.82 g, 1.11 mmol, 0.1 equiv) at room temperature under nitrogen atmosphere. The resulting mixture was stirred at 80° C. for additional 4 h. The mixture was allowed to cool down to room temperature.

To the above reaction liquid added $H_2O_2$ (2 mL) dropwise at 0° C. The resulting mixture was stirred at room temperature for 1 h. The reaction was quenched by the addition of ice water (100 mL) at room temperature. The reaction added 20 mL $Na_2S_2O_3$(aq.). The resulting mixture was extracted with EtOAc (2×100 mL). The combined organic layers were washed with saturated brine (2×100 mL), dried over anhydrous $Na_2SO_4$. The mixture was purified by reversed-phase flash chromatography with the following conditions: column, C18 silica gel; mobile phase, acetonitrile in water (0.05% $NH_3 \cdot H_2O$), 40% to 80% gradient in 30 min; detector, UV 254 nm. This resulted in rac-N-((4R,5S)-7-ethyl-1-(3-hydroxyphenyl)-4-(3-nitrophenyl)-6-oxo-4,5,6,7-tetrahydro-1H-pyrazolo[3,4-b]pyridin-5-yl)-3-(trifluoromethyl) benzamide (5 g, 95% purity) as a yellow solid.

LCMS Calculated for $C_{28}H_{22}F_3N_5O_5$: 565.16; Observed: 564.1 [M−H]$^-$.

rac-tert-butyl 4-(3-(3-((4R,5S)-7-ethyl-4-(3-nitrophenyl)-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (64)

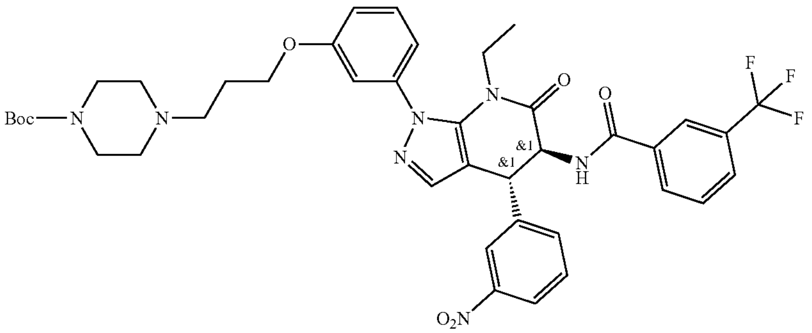

To a stirred mixture of rac-N-((4R,5S)-7-ethyl-1-(3-hydroxyphenyl)-4-(3-nitrophenyl)-6-oxo-4,5,6,7-tetrahydro-1H-pyrazolo[3,4-b]pyridin-5-yl)-3-(trifluoromethyl)benzamide (5.00 g, 8.84 mmol, 1.00 equiv) and tert-butyl 4-(3-bromopropyl)piperazine-1-carboxylate (3.26 g, 10.6 mmol, 1.20 equiv) in DMF (50 mL) was added $K_2CO_3$ (2.44 g, 17.7 mmol, 2.00 equiv) at room temperature. The resulting mixture was stirred at room temperature for 20 h. The resulting mixture was filtered, the filter cake was washed with EtOAc (2×50 mL). The filtrate was concentrated under reduced pressure. The solution was purified by reversed-phase flash chromatography with the following conditions: column, C18 silica gel; mobile phase, acetonitrile in water (0.05% $NH_3 \cdot H_2O$), 45% to 75% gradient in 25 min; detector, UV 254 nm. This resulted in rac-tert-butyl 4-(3-(3-((4R,5S)-7-ethyl-4-(3-nitrophenyl)-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (3.7 g, 52.8% yield, 95% purity) as a yellow solid.

LCMS Calculated for $C_{40}H_{44}F_3N_7O_7$: 791.33; Observed: 792.4 $[M+H]^+$ rac-tert-butyl 4-(3-(3-((4R,5S)-4-(3-aminophenyl)-7-ethyl-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (65)

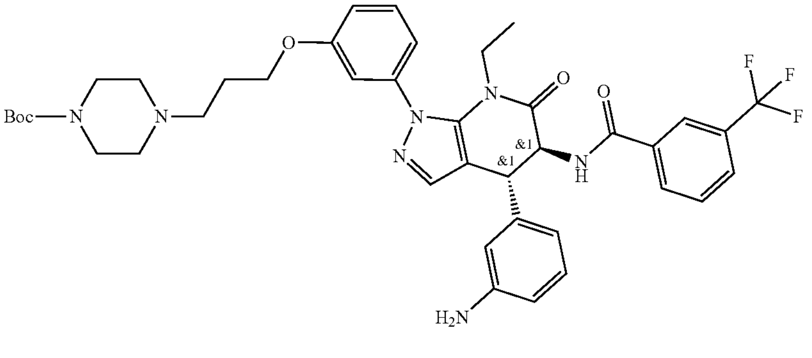 [SMILES: CCN1C(=O)[C@@H](NC(=O)c2cccc(C(F)(F)F)c2)[C@H](c2cccc([N+](=O)[O-])c2)c2cnn(-c3cccc(OCCCN4CCN(C(=O)OC(C)(C)C)CC4)c3)c21]

To a stirred mixture of rac-tert-butyl 4-(3-(3-((4R,5S)-7-ethyl-4-(3-nitrophenyl)-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (3.70 g, 4.67 mmol, 1.00 equiv) in EtOH (37 mL) were added $SnCl_2$ (4.43 g, 23.4 mmol, 5.00 equiv) at room temperature. The resulting mixture was stirred at 80° C. for 3 h. The resulting mixture was filtered and then washed with EtOH (2x5 mL). The filtrate was concentrated under reduced pressure. The residue was purified by reversed-phase flash chromatography with the following conditions: column, C18 silica gel; mobile phase, acetonitrile in water (0.05% $NH_3 \cdot H_2O$), 40% to 80% gradient in 30 min; detector, UV 254 nm. This resulted in rac-tert-butyl 4-(3-(3-((4R,5S)-4-(3-aminophenyl)-7-ethyl-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (1.5 g, 95% purity) as a yellow solid.

$^1H$ NMR (300 MHz, DMSO-$d_6$) δ 8.96 (d, J=8.9 Hz, 1H), 8.06 (d, J=9.0 Hz, 2H), 7.91 (d, J=7.8 Hz, 1H), 7.72 (t, J=7.7 Hz, 1H), 7.47 (t, J=8.1 Hz, 1H), 7.27-7.15 (m, 2H), 7.09 (d, J=8.2 Hz, 1H), 7.04 (s, 1H), 6.95 (t, J=7.8 Hz, 1H), 6.59 (s, 1H), 6.54 (d, J=7.5 Hz, 1H), 6.43 (d, J=7.8 Hz, 1H), 5.09 (dd, J=12.7, 8.9 Hz, 1H), 5.04 (s, 2H), 4.21 (d, J=12.7 Hz, 1H), 4.09 (t, J=6.5 Hz, 2H), 3.89-3.74 (m, 1H), 3.32-3.25 (m, 4H), 3.20-3.05 (m, 1H), 2.45 (t, J=7.0 Hz, 2H), 2.33 (t, J=5.0 Hz, 4H), 1.90 (t, J=6.8 Hz, 2H), 1.39 (s, 9H), 0.85 (t, J=7.0 Hz, 3H).

LCMS Calculated for $C_{40}H_{46}F_3N_7O_5$: 761.35; Observed: 762.4 $[M+H]^+$.

tert-butyl 4-(3-(3-((4R,5S)-4-(3-aminophenyl)-7-ethyl-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (66)

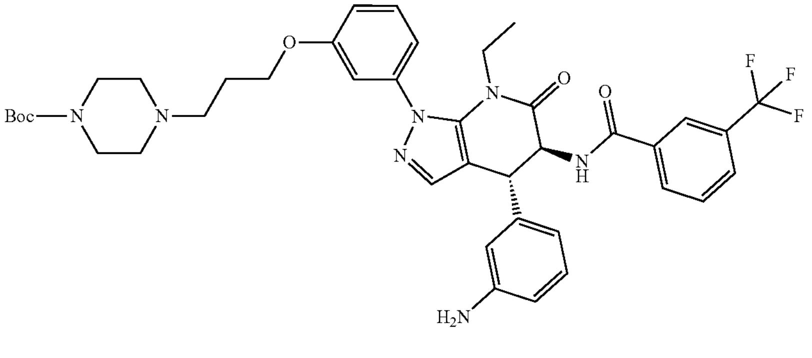

The mixture rac-tert-butyl 4-(3-(3-((4R,5S)-4-(3-aminophenyl)-7-ethyl-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (1.5 g) was separated by Prep-Chiral SFC with the following conditions: Column: CHIRALPAKIG-U50*3.0 mm, 1.6 um; Mobile Phase B: MeOH/DCM=1/1 (10 mM $NH_3$); Gradient: isocratic % B. This resulted in tert-butyl 4-(3-(3-((4R,5S)-4-(3-aminophenyl)-7-ethyl-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (650 mg, 45.6% yield, 98.5% purity) as a yellow solid.

LCMS Calculated for $C_{40}H_{46}F_3N_7O_5$: 761.35; Observed: 762.4 $[M+H]^+$.

Optical rotation value: a=−117.3 (C=0.1 g/100 mL in MeOH, T=25° C.).

Chiral-SFC (Method-A): 99.6% at RT 2.617 min tert-butyl 4-(3-(3-((4R,5S)-7-ethyl-4-(3-(2-(morpholinomethyl)acrylamido)phenyl)-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (67)

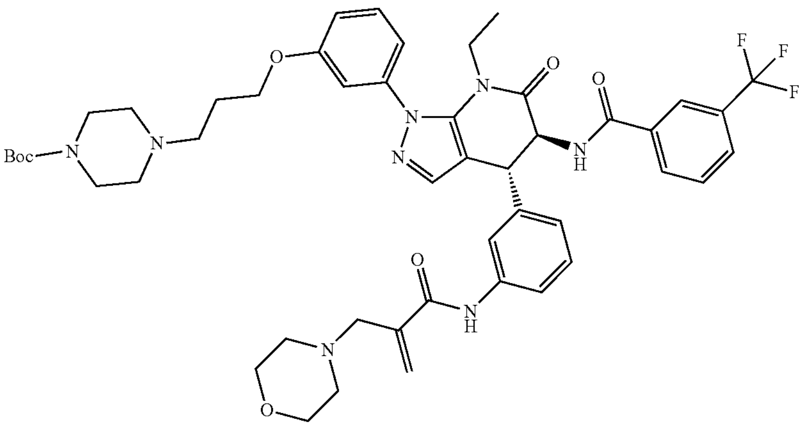 [SMILES: C=C(CN1CCOCC1)C(=O)Nc1cccc([C@@H]2c3cnn(-c4cccc(OCCCN5CCN(C(=O)OC(C)(C)C)CC5)c4)c3N(CC)C(=O)[C@H]2NC(=O)c2cccc(C(F)(F)F)c2)c1]

To a stirred mixture of 2-[(morpholin-4-yl)methyl]prop-2-enoic acid (119 mg, 0.697 mmol, 1.00 equiv) and tert-butyl 4-(3-(3-((4R,5S)-4-(3-aminophenyl)-7-ethyl-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (650 mg, 0.697 mmol, 1.00 equiv) in THE (6.5 mL) and pyridine (6.5 mL) were added phosphoroyl trichloride (267 mg, 1.74 mmol, 2.50 equiv) dropwise at 0° C. The resulting mixture was stirred at room temperature for 1 h. The reaction was quenched with water/ice (0.5 mL) at 0° C. The mixture was purified by reversed-phase flash chromatography with the following conditions: column, C18 silica gel; mobile phase, acetonitrile in water (0.05% $NH_3 \cdot H_2O$), 50% to 75% gradient in 25 min; detector, UV 254 nm. This resulted in tert-butyl 4-(3-(3-((4R,5S)-7-ethyl-4-(3-(2-(morpholinomethyl)acrylamido)phenyl)-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (170 mg, 26.6% yield, 95.0% purity) as a yellow solid.

LCMS Calculated for $C_{48}H_{57}F_3N_8O_7$: 914.43; Observed: 915.6 $[M+H]^+$.

N-((4R,5S)-7-ethyl-4-(3-(2-(morpholinomethyl)acrylamido)phenyl)-6-oxo-1-(3-(3-(piperazin-1-yl)propoxy)phenyl)-4,5,6,7-tetrahydro-1H-pyrazolo[3,4-b]pyridin-5-yl)-3-(trifluoromethyl)benzamide (68)

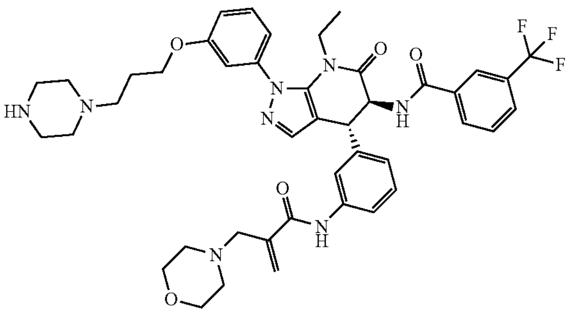 [SMILES: C=C(CN1CCOCC1)C(=O)Nc1cccc([C@@H]2c3cnn(-c4cccc(OCCCN5CCNCC5)c4)c3N(CC)C(=O)[C@H]2NC(=O)c2cccc(C(F)(F)F)c2)c1]

To a stirred mixture of tert-butyl 4-(3-(3-((4R,5S)-7-ethyl-4-(3-(2-(morpholinomethyl)acrylamido)phenyl)-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (170 mg, 0.186 mmol, 1.00 equiv) in DCM (2.5 mL) were added 2,6-dimethylpyridine (79.6 mg, 0.744 mmol, 4.00 equiv) at 0° C. After 10 min, to the above mixture was added trimethylsulfanium iodide (114 mg, 0.558 mmol, 3.00 equiv) dropwise at 0° C. The resulting mixture was stirred at 0° C. for 1 h. After completion of reaction, the mixture reaction was concentrated under pressure to give N-((4R,5S)-7-ethyl-4-(3-(2-(morpholinomethyl)acrylamido)phenyl)-6-oxo-1-(3-(3-(piperazin-1-yl)propoxy)phenyl)-4,5,6,7-tetrahydro-1H-pyrazolo[3,4-b]pyridin-5-yl)-3-(trifluoromethyl)benzamide (350 mg, crude) which was used for next step directly.

LCMS Calculated for $C_{43}H_{49}F_3N_8O_5$: 814.38; Observed: 815.4 $[M+H]^+$.

2-((1E,3E)-5-((E)-1-(6-(4-(3-(3-((4R,5S)-7-ethyl-4-(3-(2-(morpholinomethyl)acrylamido)phenyl)-6-oxo-5-(3-(trifluoromethyl)benzamido)-4,5,6,7-tetrahydro-1H-pyrazolo[3,4-b]pyridin-1-yl)phenoxy)propyl)piperazin-1-yl)-6-oxohexyl)-3,3-dimethyl-5-sulfoindolin-2-ylidene)penta-1,3-dien-1-yl)-1,3,3-trimethyl-3H-indol-1-ium-5-sulfonate (P-1)

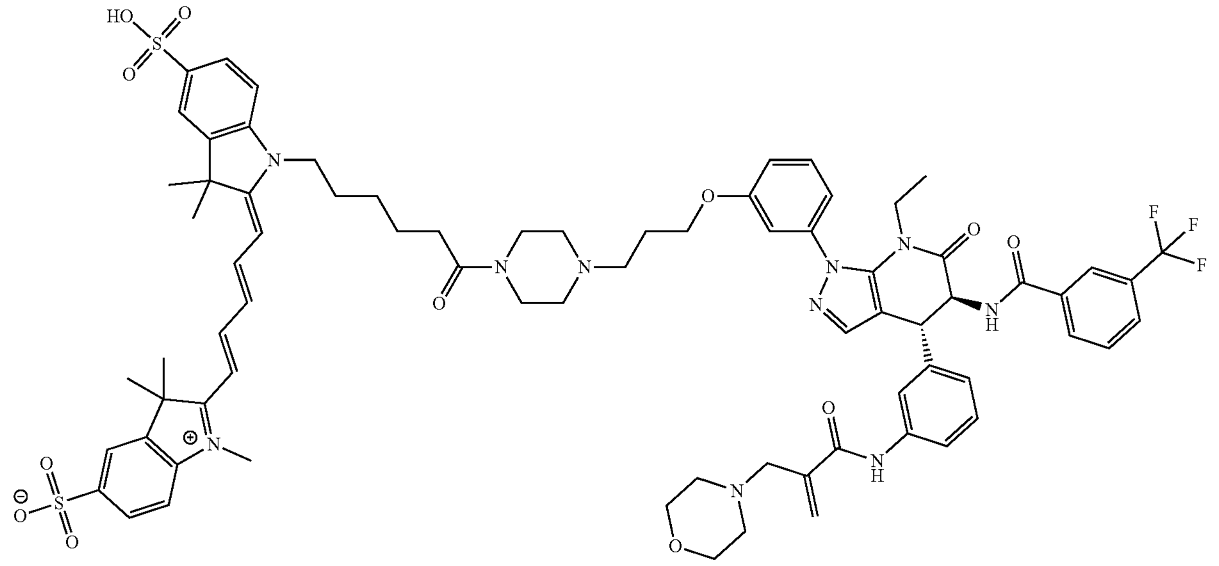 [SMILES: C=C(CN1CCOCC1)C(=O)Nc1cccc([C@@H]2c3cnn(-c4cccc(OCCCN5CCN(C(=O)CCCCCN6/C(=C/C=C/C=C/C7=[N+](C)c8ccc(S(=O)(=O)[O-])cc8C7(C)C)C(C)(C)c7cc(S(=O)(=O)O)ccc76)CC5)c4)c3N(CC)C(=O)[C@H]2NC(=O)c2cccc(C(F)(F)F)c2)c1]

To a stirred mixture of sodium 1-(5-carboxypentyl)-3,3-dimethyl-2-[(1E,3E)-5-[(2E)-1,3,3-trimethyl-5-sulfo-2,3-dihydro-1H-indol-2-ylidene]penta-1,3-dien-(1-yl]-3H-indol-1-ium-5-sulfonate (173 mg, 0.261 mmol, 1.00 equiv) in DMF (5 mL) were added DIEA (101 mg, 0.783 mmol, 3.00 equiv) and HATU (119 mg, 0.313 mmol, 1.20 equiv) at 0° C. After 5 min, to the above mixture was added N-((4R, 5S)-7-ethyl-4-(3-(2-(morpholinomethyl)acrylamido)phenyl)-6-oxo-1-(3-(3-(piperazin-1-yl)propoxy)phenyl)-4,5,6,7-tetrahydro-1H-pyrazolo[3,4-b]pyridin-5-yl)-3-(trifluoromethyl)benzamide (380 mg, crude from last step) at room temperature. The resulting mixture was stirred at room temperature for additional 1 h. The reaction was quenched by the addition of water/ice (1 mL) at room temperature. The mixture was purified by reversed-phase flash chromatography with the following conditions: column: Ultimate—XB—C18 Column, 30*150 mm, 10 m; Mobile Phase A: Water(0.05% NH3H2O), Mobile Phase B: ACN; Flow rate: 90 mL/min; Gradient: isocratic 5%-50% 12 min; Wave Length: 254 nm/220 nm; RT1 (min): 11.5. This resulted in 2-((1E,3E)-5-((E)-1-(6-(4-(3-(3-((4R,5S)-7-ethyl-4-(3-(2-(morpholinomethyl)acrylamido)phenyl)-6-oxo-5-(3-(trifluoromethyl)benzamido)-4,5,6,7-tetrahydro-1H-pyrazolo[3,4-b]pyridin-1-yl)phenoxy)propyl)piperazin-1-yl)-6-oxohexyl)-3,3-dimethyl-5-sulfoindolin-2-ylidene) penta-1,3-dien-1-yl)-1,3,3-trimethyl-3H-indol-1-ium-5-sulfonate (109 mg, 29.0% yield, 97.4% purity) as a light blue solid.

$^1$H NMR (400 MHz, DMSO-$d_6$) δ 11.07 (s, 1H), 9.02 (d, J=9.0 Hz, 1H), 8.34 (t, J=13.1 Hz, 2H), 8.03 (d, J=4.0 Hz, 2H), 7.88 (d, J=7.8 Hz, 1H), 7.79 (d, J=1.5 Hz, 2H), 7.70-7.54 (m, 5H), 7.46-7.41 (m, 1H), 7.32-7.25 (m, 3H), 7.22-7.15 (m, 2H), 7.12 (d, J=7.8 Hz, 1H), 7.05 (d, J=9.6 Hz, 2H), 6.54 (t, J=12.3 Hz, 1H), 6.33-6.21 (m, 2H), 6.03 (d, J=1.9 Hz, 1H), 5.57 (s, 1H), 5.14 (dd, J=12.8, 9.0 Hz, 1H), 4.36 (d, J=12.8 Hz, 1H), 4.07 (t, J=6.7 Hz, 4H), 3.83 (dt, J=14.1, 7.0 Hz, 1H), 3.60 (t, J=4.7 Hz, 4H), 3.58-3.54 (m, 3H), 3.42-3.35 (m, 4H), 3.28-3.23 (m, 2H), 3.14-3.02 (m, 1H), 2.46-2.36 (m, 6H), 2.34-2.22 (m, 6H), 1.86 (q, J=7.6, 7.1 Hz, 2H), 1.75-1.63 (m, 14H), 1.50 (t, J=7.5 Hz, 2H), 1.38-1.27 (m, 2H), 0.93 (d, J=6.4 Hz, 1H), 0.83 (t, J=7.0 Hz, 3H).

LCMS Calculated for $C_{75}H_{85}F_3N_{10}O_{12}S_2$: 1438.57; Observed (Method A): 1438.1 $[M-H]^-$, 97.4% at RT 1.797 min.

Chiral-HPLC: 95.3% at RT 3.082 min.

Example 28: Assay to Measure the Off-Rate of Reversible Covalent Molecules Description A TR-FRET assay was performed to classify the compounds as an irreversible covalent binder, a reversible covalent binder or a reversible binder.

An assay to measure the off-rate of reversible covalent molecules was developed. A typical covalent compound is assumed to stay bound to a protein for at least the life of that protein in the cell. In reality, there is a range of how long a covalent compounds remains bound before a reverse reaction takes place. Thus, some covalent bonds can be labeled as reversible as their reverse reaction takes place in a measurable amount of time under physiological conditions. The assay capitalizes on the range of covalent binders by using a high affinity covalent binder as a probe to displace the more reversible binders in an adaptation of the jump dilution method.

In this version of the jump dilution method, the increase in covalent probe binding over time was measured through a TR-FRET reaction between the covalent probe and the biotinylated target protein.

Methods

Target Protein Preparation

The recombinant form of the DCN1 (DCUND1) protein PONY domain was produced using an *E. coli* expression system at Viva Biotech (China). The DCN1 protein was biotinylated (EZ sulfo-NHS-LC-biotin; Thermofisher) for labeling with streptavidin terbium (Tb) cryptate in the reaction. This biotinylated protein was used in two forms of the TR-FRET assay as described below.

TR-FRET with FAM Probe

This version of the TR-FRET assay was used to measure compound potency to the target, specifically to measure the potency of the Cy5 probe (P-1). A non-covalent DCN1 inhibitor (Zhou et al., 2017) labeled with carboxyfluorescein (FAM) was used as the FRET acceptor probe. Displacement of the covalent probe, and thus decrease in the FRET signal, was indicative of compound activity on the target protein. Buffer conditions were optimized to enhance compound and protein stability (200 mM NaCl, 25 mM Tris, 0.5 mM DTT, 0.05% Tween20, 5% DMSO, 5% PEG-3350, pH 7.5) and concentrations of protein (0.31 nM) and probe (100 nM labeled, 800 nM unlabeled) were optimized for detection of potent molecules. The TR-FRET ratio between Tb-DCN1 and the FAM-labeled probe was measured in a 384-well opti-plate (Perkin Elmer) using a plate reader (BMG) at 1, 5, and 24 hrs after treatment with compound. The ratio was normalized to the high (DCN1 and FAM-probe) and low (DCN1 and no probe) controls for a readout of % activity (=100*(x−low)/(high−low)).

TR-FRET with Cy5 Probe

This version of the TR-FRET assay was used to measure both the potency of the molecules to the target and the off-rate of the compounds from the target. All potency measurements in this assay condition were used to determine the concentrations used in the off-rate assay. A covalent probe labeled with Cy5 was used as the FRET acceptor. Similar conditions were used as for the TR-FRET with FAM probe. The only differences include, 0.625 nM protein, 2.5 nM probe, and detection timepoints at 0.5, 1, 2, 4, 24 hrs. Calculations were the same.

Off-Rate Measurement

The off-rate measurement is executed in two steps based on the jump dilution method. Step one, test compounds were incubated 1 hour at room temperature with Tb and 6 nM protein at a concentration 10-fold higher than the EC50 determined in the TR-FRET with Cy5 probe assay. Step two, the mixture in Step one was diluted into a new reaction buffer containing the Cy5 probe at a concentration of 150 nM<<its Kd (EC50 23.2 nM). The degree of dilution (20, 50, or 100-fold) was dependent on the EC50 of the test compound. The greatest dilution allowed within the constraints of the assay was chosen. These factors allow a competitive advantage for the covalent probe to replace the test compound when that compound releases from the target protein. The actual measure is the rate of increased TR-FRET signal as the covalent probe replaces the test compound over time. The TR-FRET signal is measured every 0.5 minutes up to 0.5 hours; every 5 minutes up to 2 hours; every 15 minutes up to 2 hours with a BMG Labtech plate reader (Optic module: LanthaScreen 337/665/620). The resulting time dependent curve of the TR-FRET signal is fit to the following equation:

$$Y=Y0+(\text{Plateau}-Y0)*(1-\exp(-K*x))$$

K is the rate constant (1/unit of time). The residence time is defined as the inverse of K, the rate constant. The half-life is calculated as ln(2)/K.

The structures of tool compounds 1 and 2 respectively are shown below.

TABLE 4

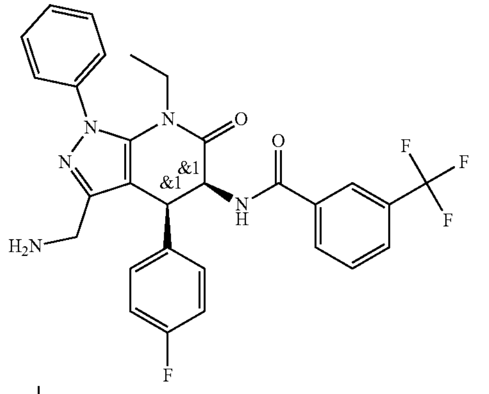

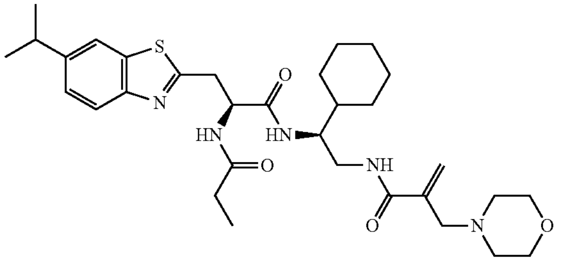

Assay

| Compound ID | Koff (min-1) | residence time (min) | half-life (min) | n | Category |
|---|---|---|---|---|---|
| Tool compound 1 | 0.344928571 | 3.32880461 | 2.30735153 | 7 | reversible |
| Tool compound 2 | ND | | | 7 | irreversible covalent |
| I-2 | ND | | | 3 | irreversible covalent |

TABLE 4-continued

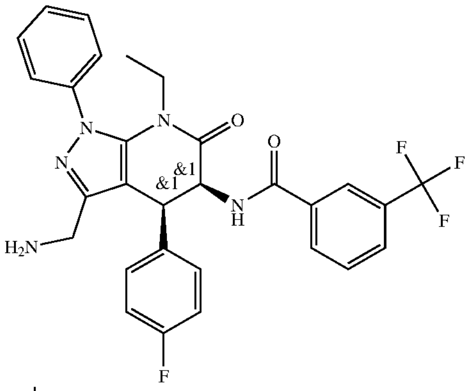

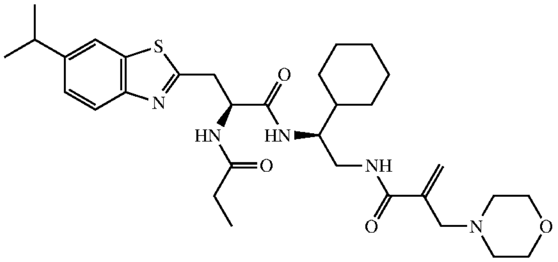

| Compound ID | Koff (min-1) | residence time (min) | half-life (min) | n | Category |
|---|---|---|---|---|---|
| | | Assay | | | |
| I-305 | ND | | | 2 | irreversible covalent |
| I-300 | ND | | | 2 | irreversible covalent |
| I-383 | ND | | | 3 | irreversible covalent |
| I-234 | ND | | | 2 | irreversible covalent |

Example 29: Measurement of Kinact/KI in the DCN2 TR-FRET Assay

Methods

A TR-FRET Assay was performed to evaluate the ability of the compounds to bind DCN-2.

The time resolved—Forster's resonance energy transfer (TR-FRET) assay was designed following the protocol established in (Scott et al., Nat Chem Biol. 2017 August; 13(8): 850-857). A recombinant form of the DCN2 (DCUND2) protein PONY domain was produced using an *E. coli* expression system at Viva Biotech China. The DCN2 protein was biotinylated (EZ sulfo-NHS-LC-biotin; Thermofisher) for labeling with 2.5 nM streptavidin terbium (Tb) cryptate in the reaction. The probe was changed to a non-covalent DCN1 inhibitor labeled with carboxyfluorescein (FAM; Zhou el al., *Nat Commun.* 2017; 8: 1150). Buffer conditions were modified to enhance protein stability by replacing TritonX with 0.05% Tween20 and increasing NaCl to 200 mM. The compounds were screened against 0.31 nM DCN1 and 40 nM FAM-labeled probe in a 40 ul reaction volume. The TR-FRET ratio between Tb-DCN1 and the FAM-labeled probe was measured in a 384-well opti-plate (Perkin Elmer) using a plate reader (BMG) at after treatment with compound (final DMSO concentration of 0.1%). The ratio was normalized to the high (DCN1 and FAM-probe) and low (DCN1 and no probe) controls for a readout of % activity (=100*(x−low)/(high−low)).

The Kinact and KI measurements were taken to allow for continuous reads over 24 hrs. Plates were read every 5 min up to 1 hr, every 15 min up to 5 hr, and every hour up to 10 hours. Kinact and KI were calculated based on the following equations (Krippendorff B F, et al. Mechanism-based inhibition: deriving K(I) and k(inact) directly from time-dependent IC(50) values. J BiomolScreen. 2009; Mons E et al. A Comprehensive Guide for Assessing Covalent Inhibition in Enzymatic Assays Illustrated with Kinetic Simulations. CurrProtoc. 2022) where the KM of the probe against DCN2 is 21.62 nM. The Kinact and KI values could be estimated from the tight curves of the IC50 values over time.

$$IC_{50}(t) = K_I\left(1 + \frac{S}{K_M}\right)\cdot\left(\frac{2 - 2e^{-\eta_{IC_{50}}\cdot k_{inact}\cdot t}}{\eta_{IC_{50}}\cdot k_{inact}\cdot t} - 1\right) \text{ with}$$

$$\eta_{IC_{50}} = \frac{IC_{50}(t)}{K_I\left(I + \frac{S}{K_M}\right) + IC_{50}(t)}.$$

The structure of $C_1$ is shown below.

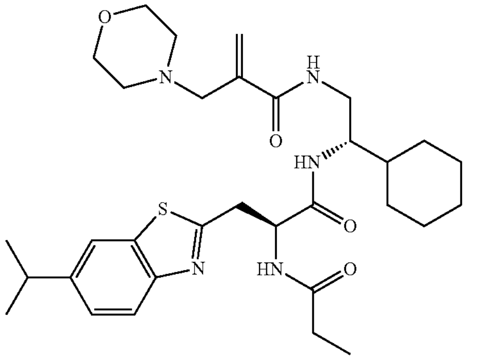 [SMILES: C=C(CN1CCOCC1)C(=O)NC[C@@H](NC(=O)[C@H](Cc1nc2ccc(C(C)C)cc2s1)NC(=O)CC)C1CCCCC1]

For the KI measurement in Table 5 below, a measurement of less than or equal to 0.1 nM is designated as "++++". 0.1 nM up to and including 0.2 nM is designated as "+++". 0.2 nM up to 0.5 nM is designated as "++". Greater than 0.5 nM is designated as "+".

For the Kinact data in Table 5 below, a measurement of between 0.1 and <0.2 min^-1 is designated as "+". A measurement of 0.2 to <0.3 min^-1 is designated as "++". A measurement of 0.3 to 0.5 min^-1 is designated as "+++".

For the Kinact/KI data in Table 5 below, a measurement of between 0.01 and <0.2 nM^-1*min^-1 is designated as "+". A measurement of 0.2 to <0.5 nM^-1*min^-1 is designated as "++". A measurement of 0.5 to 1.0 nM^-1*min^-1 is designated as

TABLE 5

| Measurement of Kinact/KI in the DCN2 TR-FRET Assay | | | |
|---|---|---|---|
| Compound ID | Kinact (min^-1) | KI (nM) | Kinact/KI (nM^-1*min^-1) |
| C1 | +++ | ++ | +++ |
| I-2 | ++ | + | ++ |
| I-305 | +++ | + | + |
| I-383 | ++ | + | + |
| I-234 | + | + | + |

The invention claimed is:

1. A compound selected from one of the following:

I-9a

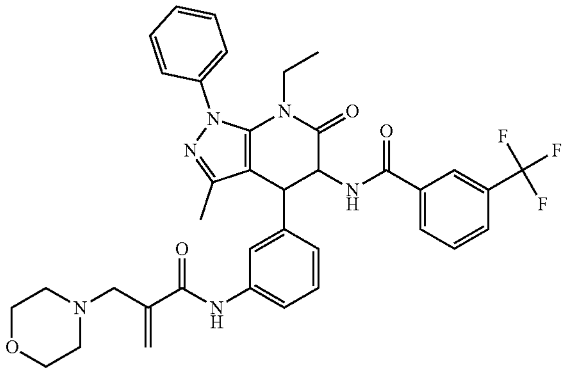

-continued

I-15a

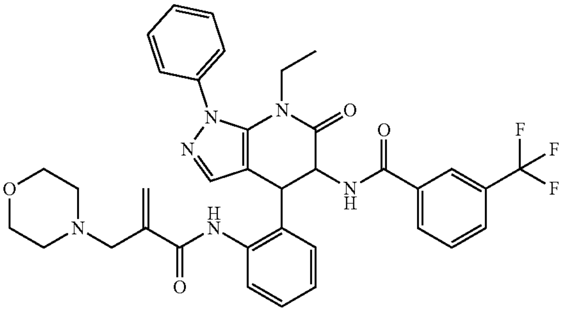

I-66a

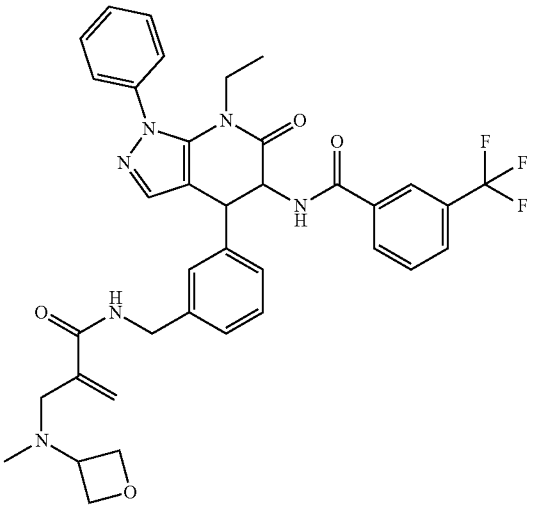

I-153a

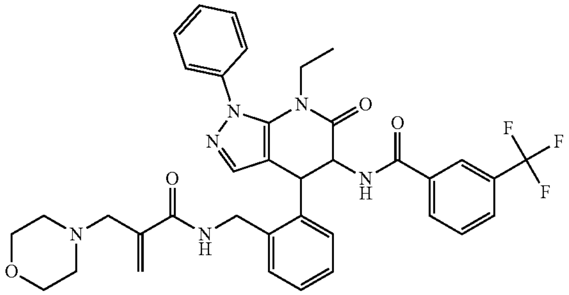

I-160a

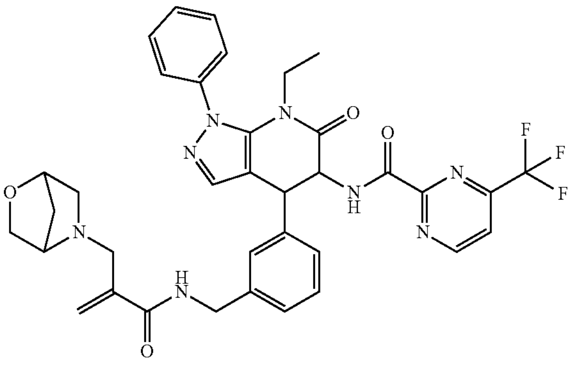

-continued
I-161a
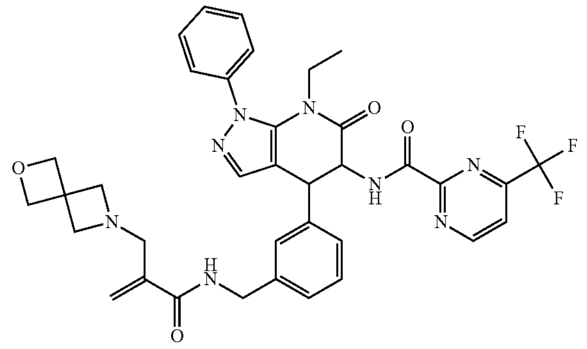
I-162a
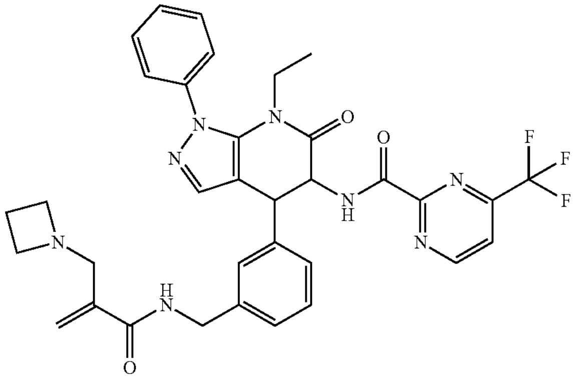
I-163a
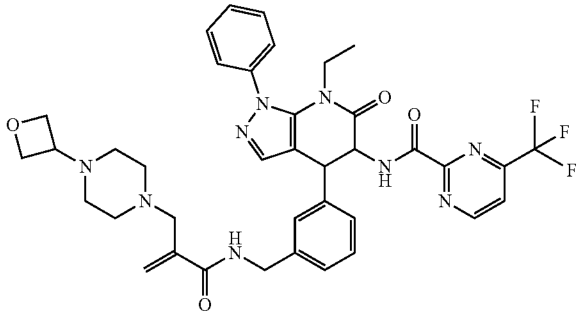
I-177a
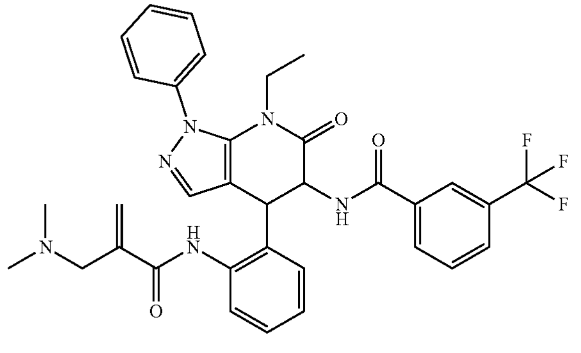
-continued
I-234a
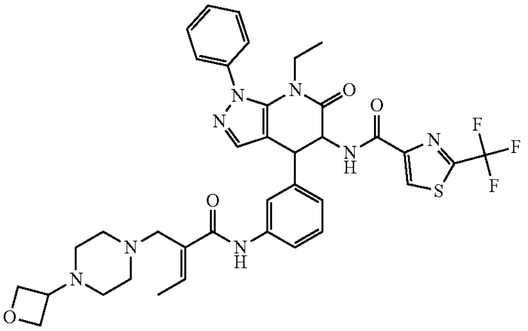
and
I-383a
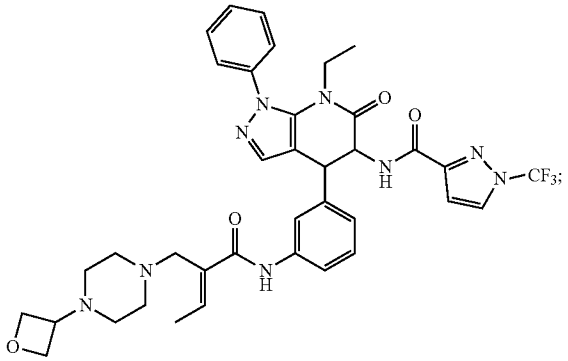
or a pharmaceutically acceptable salt thereof.
2. A compound selected from one of the following:
I-9
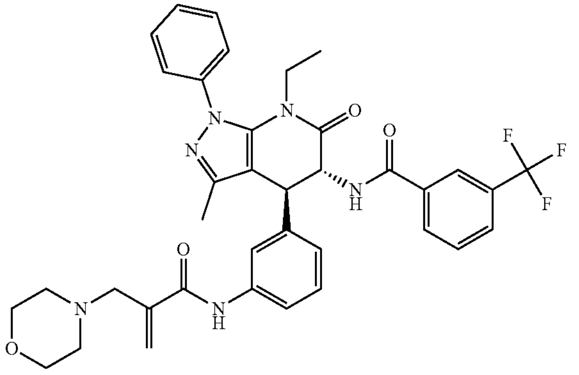

-continued
I-2
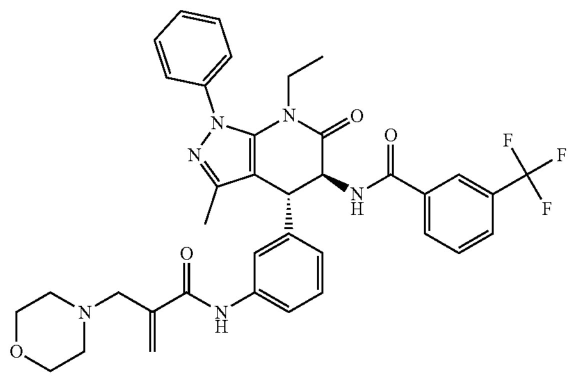
I-15
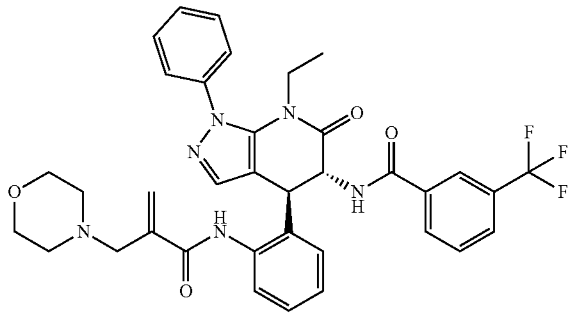
I-15b
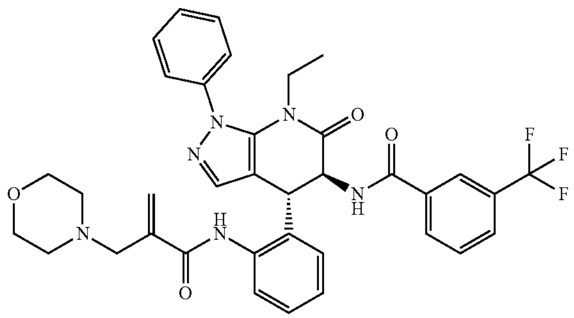
I-66
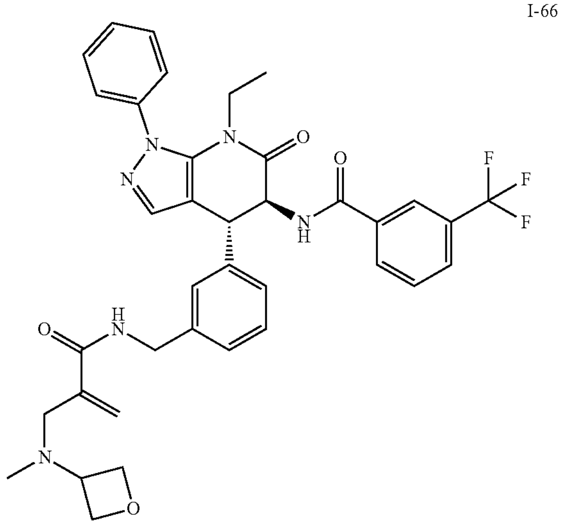
-continued
I-154
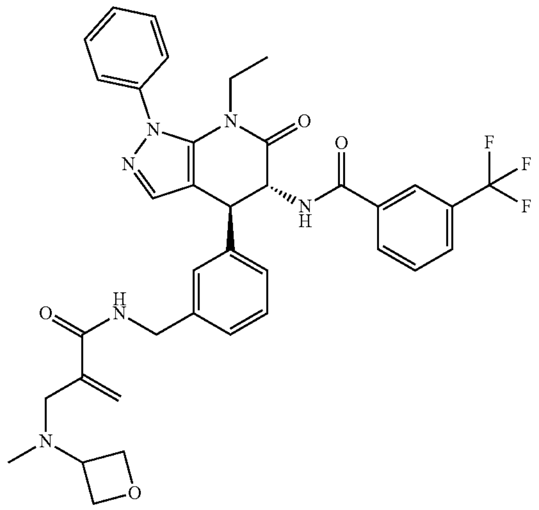
I-153
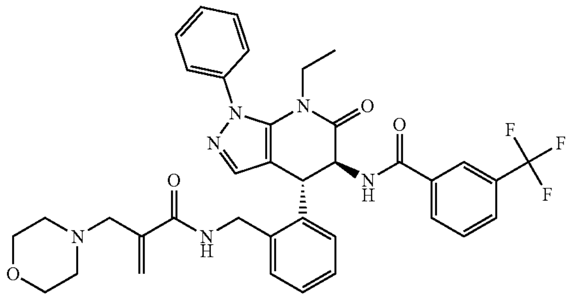
I-153b
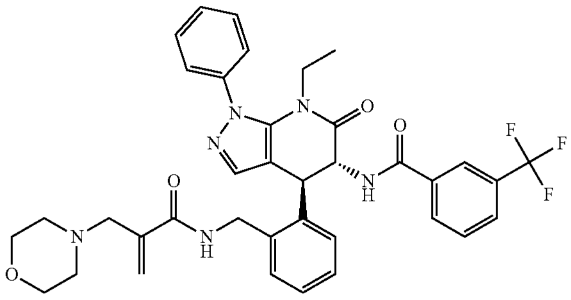
I-160
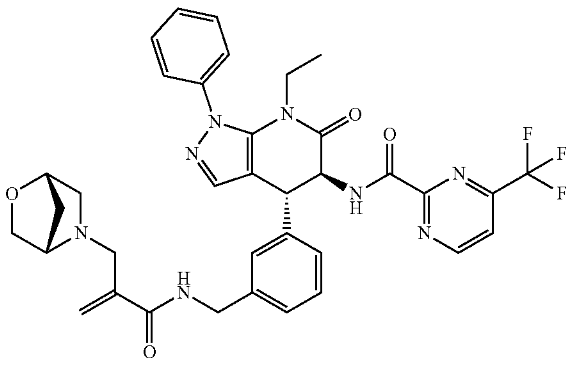

I-160b
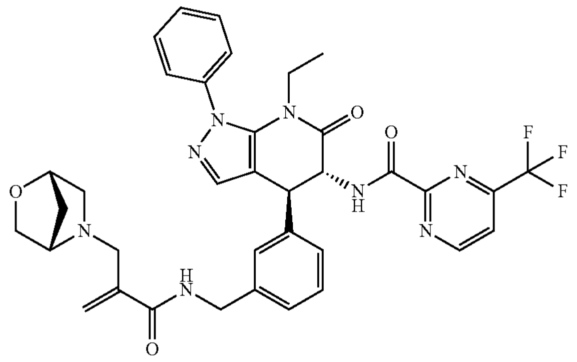
I-160c
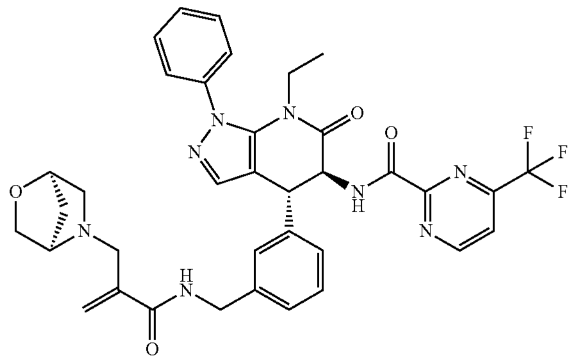
I-160d
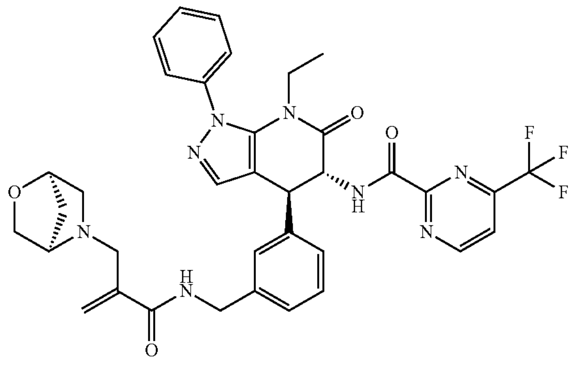
I-161
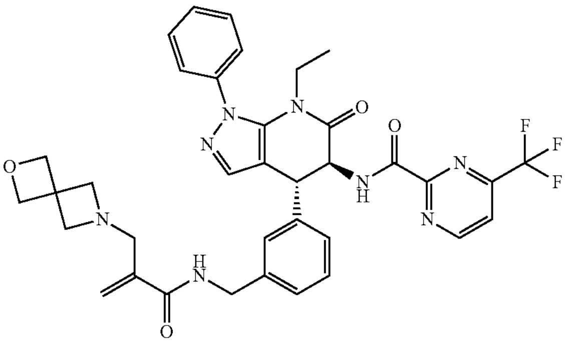
I-161b
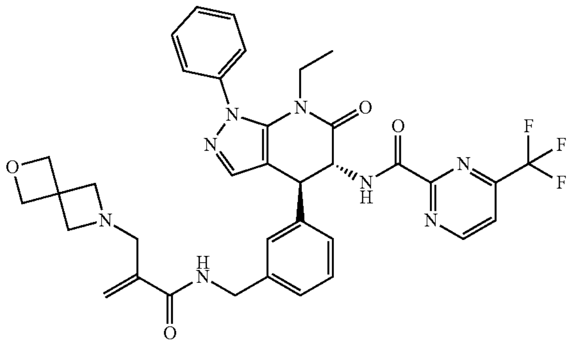
I-162
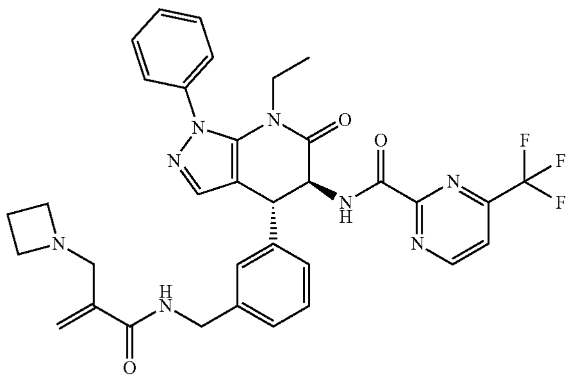
I-162b
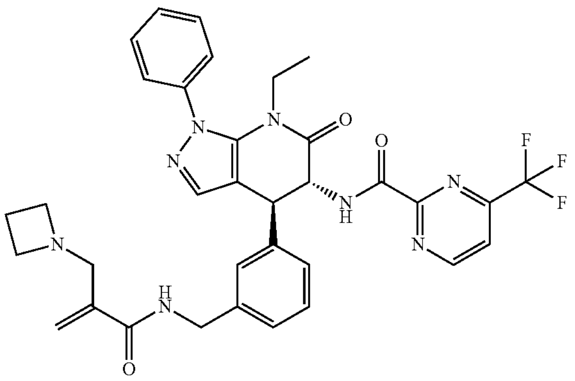
I-163
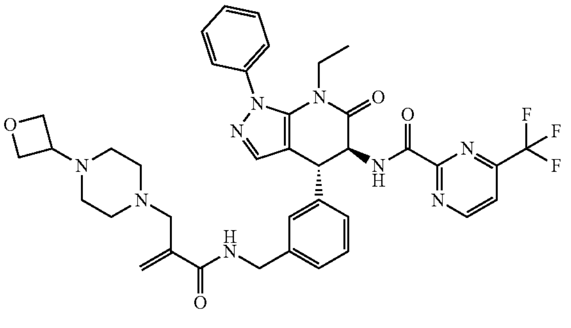

-continued
I-163b
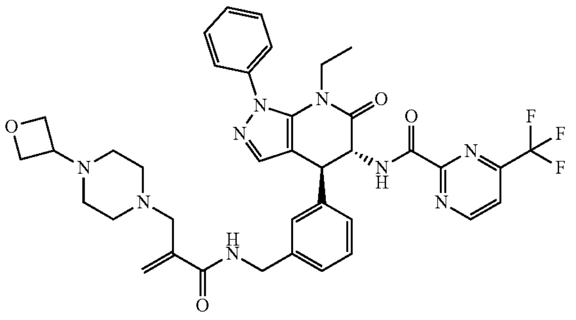
I-177
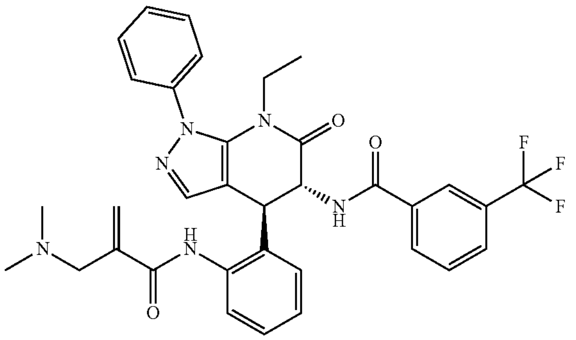
I-177b
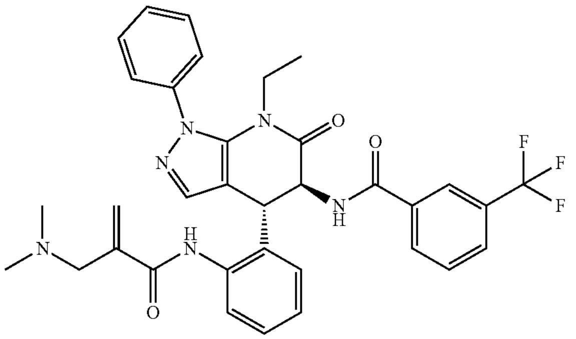
I-234
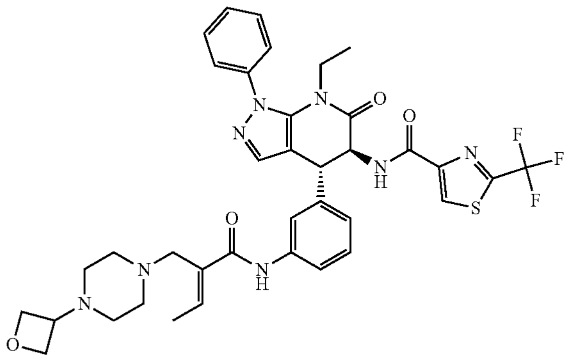
-continued
I-234b
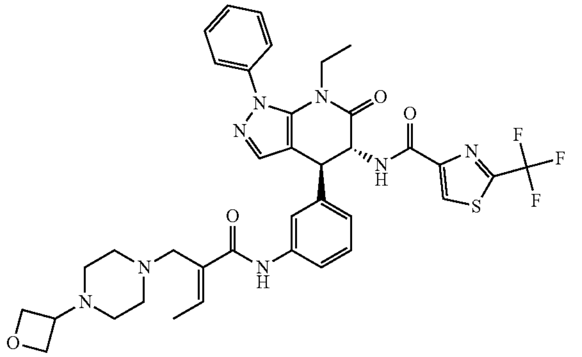
I-383
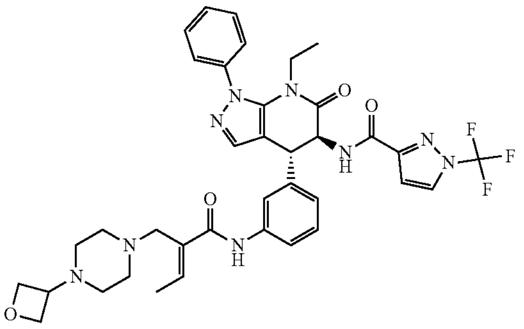
and
I-383b
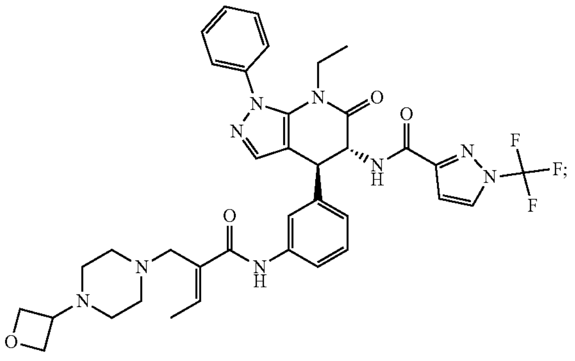
or a pharmaceutically acceptable salt thereof.

3. The compound of claim 1, wherein the compound is of the following structure:

I-9a

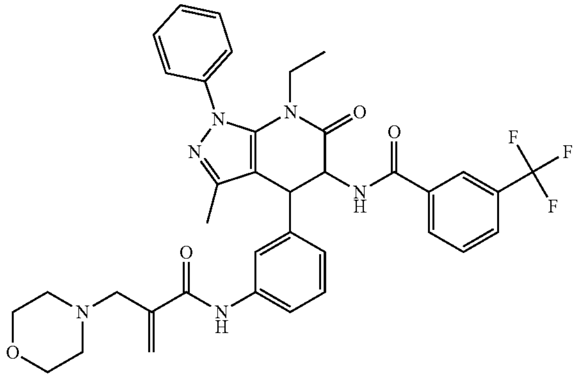

or a pharmaceutically acceptable salt thereof.

4. The compound of claim 1, wherein the compound is of the following structure:

I-15a

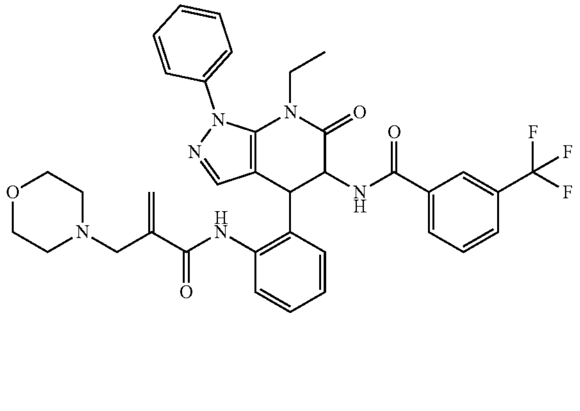

or a pharmaceutically acceptable salt thereof.

5. The compound of claim 1, wherein the compound is of the following structure:

I-66a

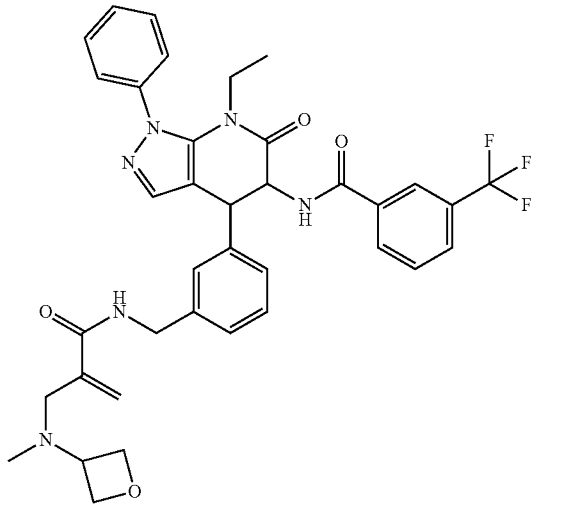

or a pharmaceutically acceptable salt thereof.

6. The compound of claim 1, wherein the compound is of the following structure:

I-153a

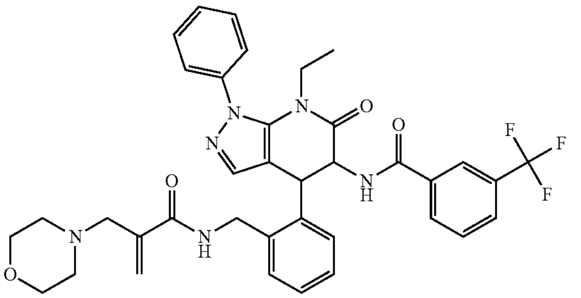

or a pharmaceutically acceptable salt thereof.

7. The compound of claim 1, wherein the compound is of the following structure:

I-160a

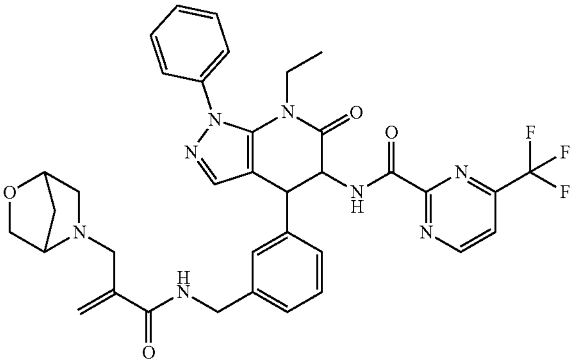

or a pharmaceutically acceptable salt thereof.

8. The compound of claim 1, wherein the compound is of the following structure:

I-161a

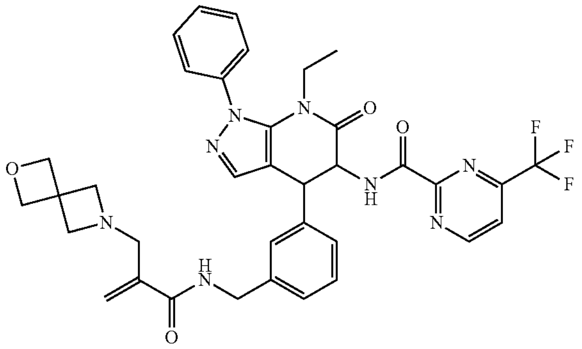

or a pharmaceutically acceptable salt thereof.

9. The compound of claim 1, wherein the compound is of the following structure:

I-162a

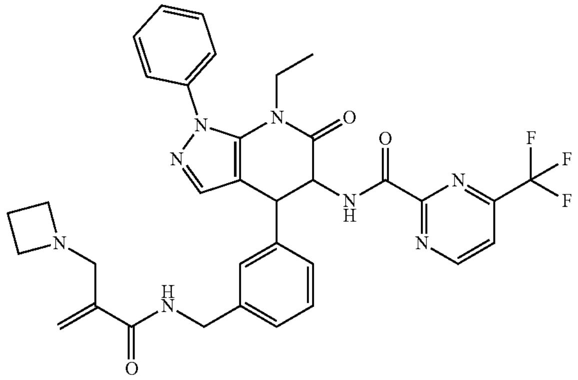

or a pharmaceutically acceptable salt thereof.

10. The compound of claim 1, wherein the compound is of the following structure:

I-163a

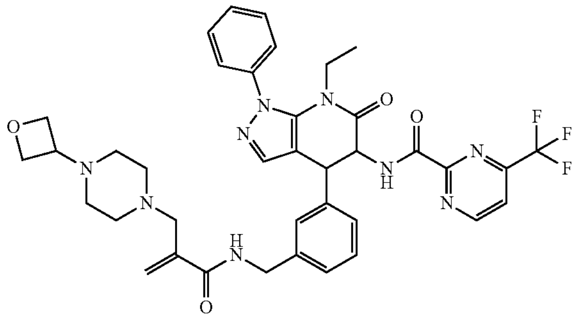

or a pharmaceutically acceptable salt thereof.

11. The compound of claim 1, wherein the compound is of the following structure:

I-177a

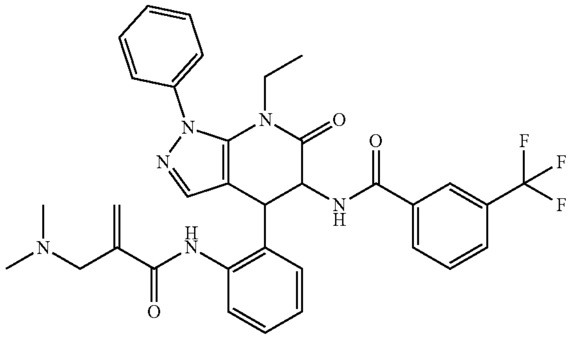

or a pharmaceutically acceptable salt thereof.

12. The compound of claim 1, wherein the compound is of the following structure:

I-234a

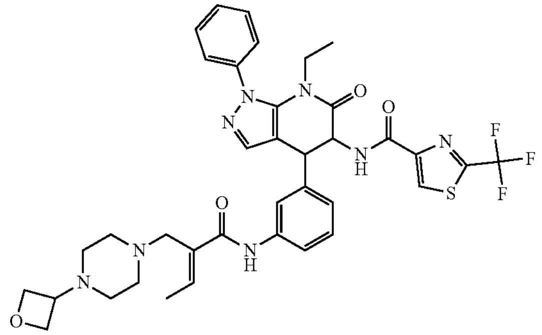

or a pharmaceutically acceptable salt thereof.

13. The compound of claim 1, wherein the compound is of the following structure:

I-383a

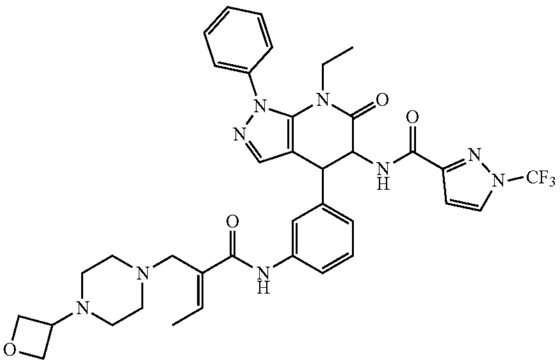

or a pharmaceutically acceptable salt thereof.

14. The compound of claim 2, wherein the compound is of the following structure:

I-9

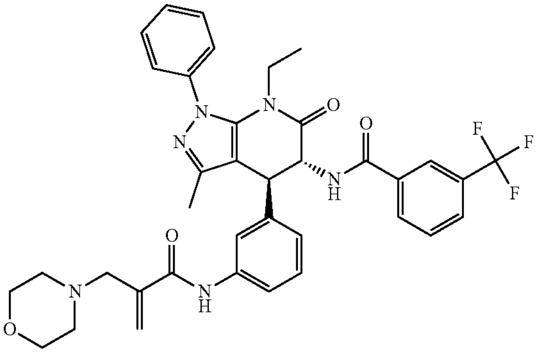

I-2

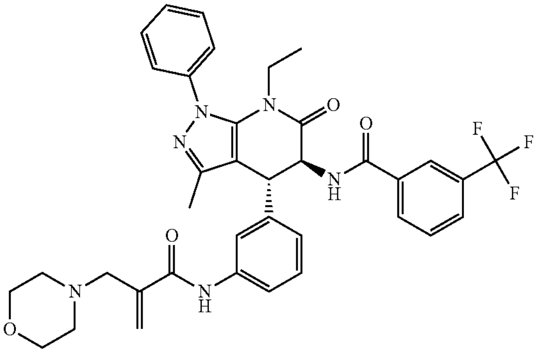

or a pharmaceutically acceptable salt thereof.

15. The compound of claim 2, wherein the compound is of the following structure:

I-15

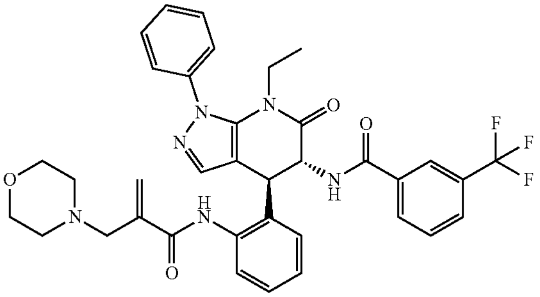

I-15b

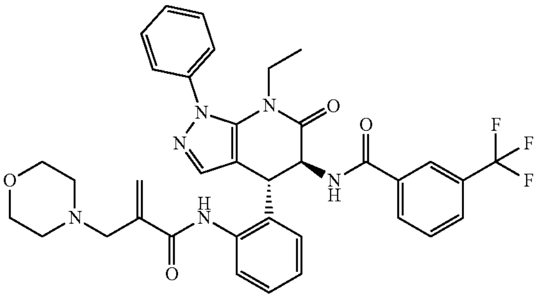

or a pharmaceutically acceptable salt thereof.

16. The compound of claim 2, wherein the compound is of the following structure:

I-66

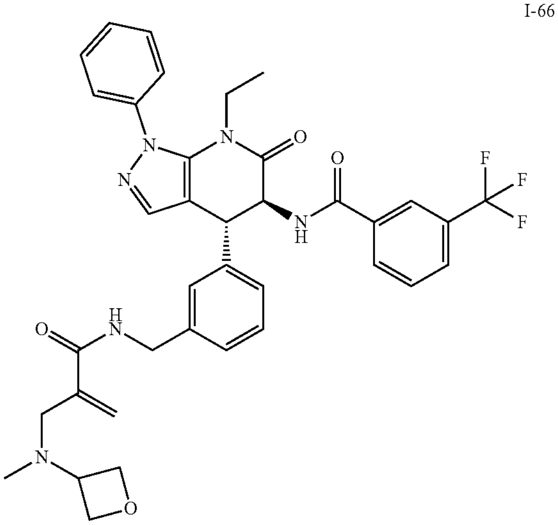

I-154

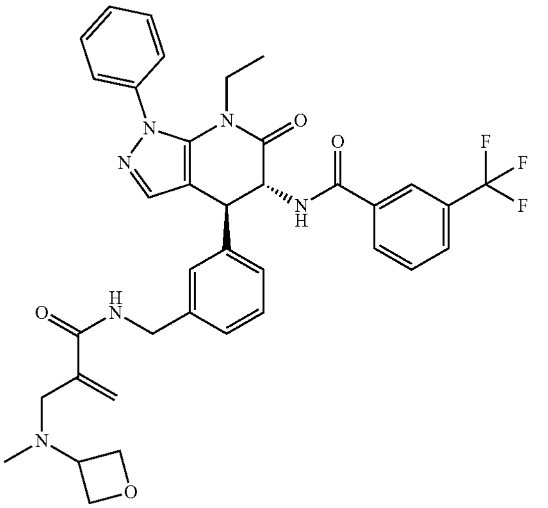

or a pharmaceutically acceptable salt thereof.

17. The compound of claim 2, wherein the compound is of the following structure:

I-153

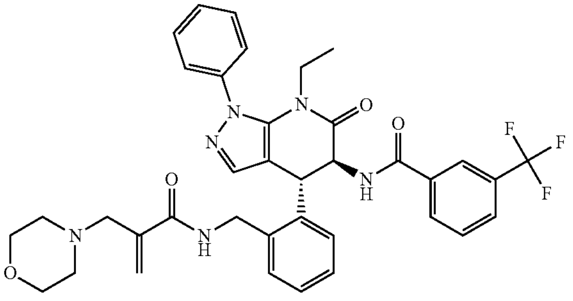

-continued

I-153b

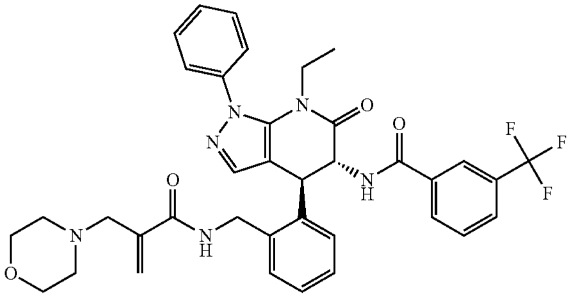

or a pharmaceutically acceptable salt thereof.

18. The compound of claim 2, wherein the compound is of the following structure:

I-160

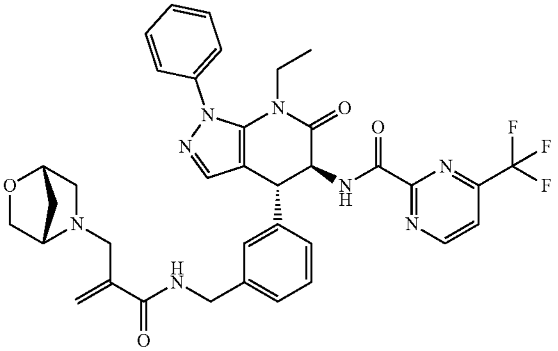

I-160b

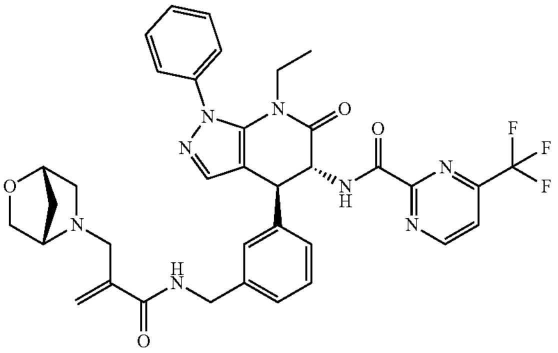

or a pharmaceutically acceptable salt thereof.

19. The compound of claim 2, wherein the compound is of the following structure:

I-160c

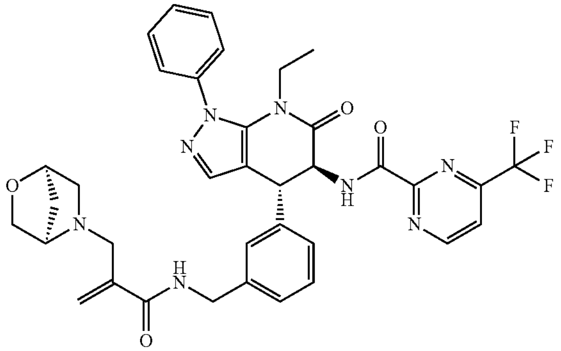

I-160d

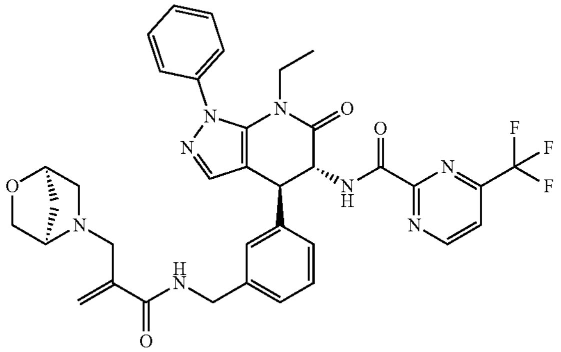

or a pharmaceutically acceptable salt thereof.

20. The compound of claim 2, wherein the compound is of the following structure:

I-161

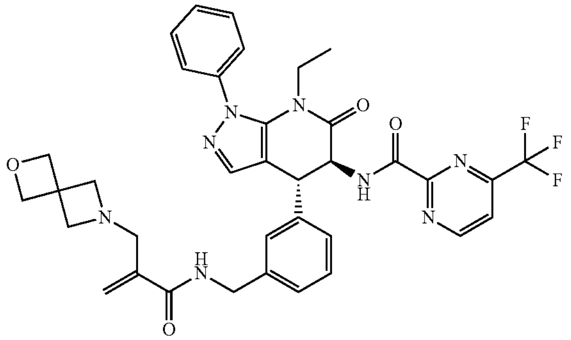

-continued

I-161b

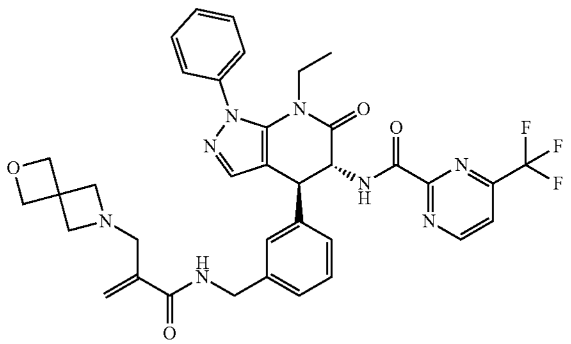

or a pharmaceutically acceptable salt thereof.

21. The compound of claim 2, wherein the compound is of the following structure:

I-162

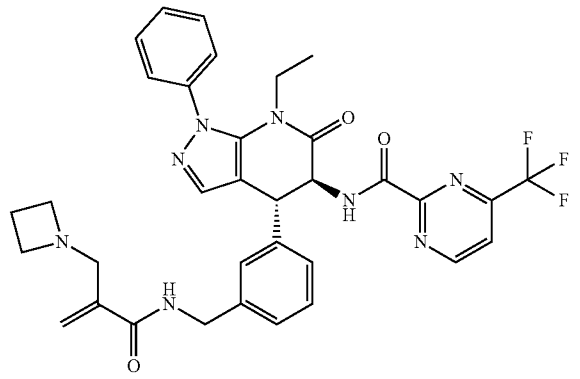

I-162b

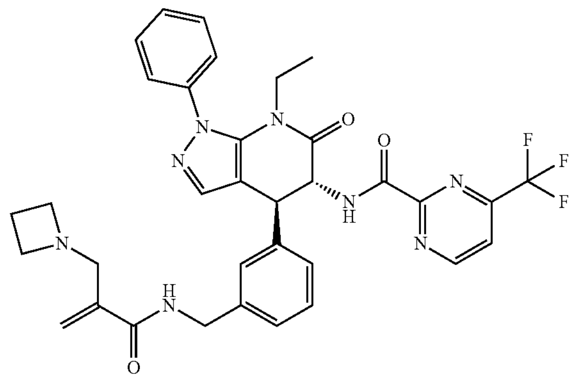

or a pharmaceutically acceptable salt thereof.

22. The compound of claim 2, wherein the compound is of the following structure:

I-163

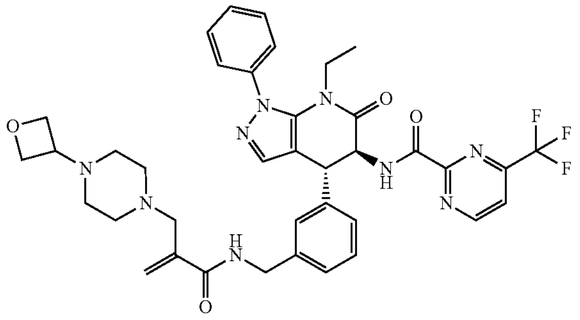

I-163b

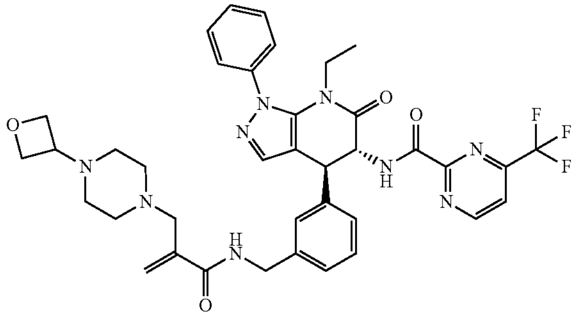

or a pharmaceutically acceptable salt thereof.

23. The compound of claim 2, wherein the compound is of the following structure:

I-177

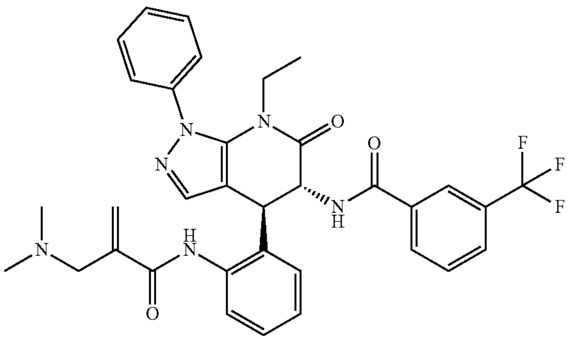

-continued

I-177b

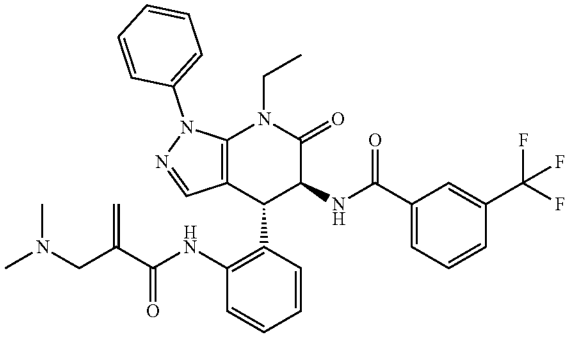

or a pharmaceutically acceptable salt thereof.

24. The compound of claim 2, wherein the compound is of the following structure:

I-234

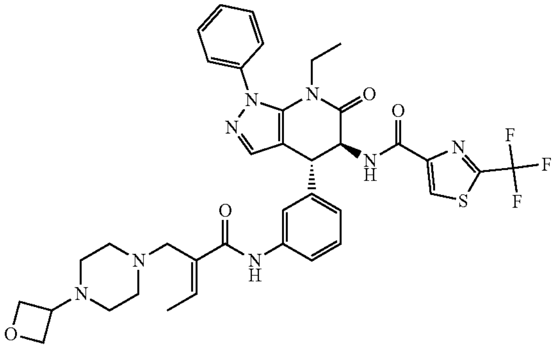

I-234b

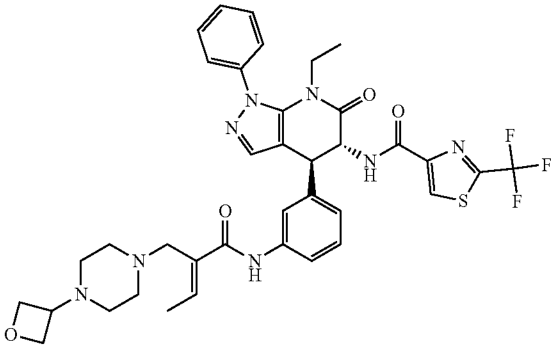

or a pharmaceutically acceptable salt thereof.

25. The compound of claim 2, wherein the compound is of the following structure:

I-383

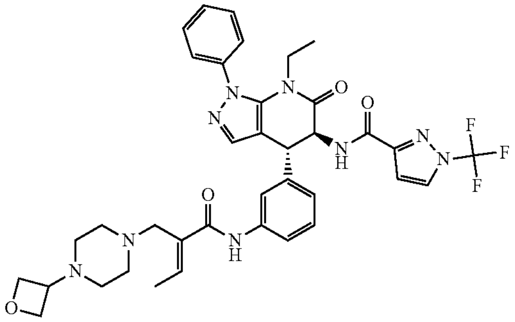

and

I-383b

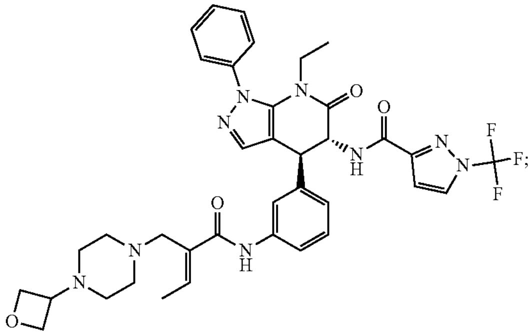

or a pharmaceutically acceptable salt thereof.

26. A pharmaceutical composition comprising the compound of claim 1, or a pharmaceutically acceptable salt thereof, and a pharmaceutically acceptable carrier.

27. A pharmaceutical composition comprising the compound of claim 2, or a pharmaceutically acceptable salt thereof, and a pharmaceutically acceptable carrier.

* * * * *